US009221827B2

(12) United States Patent
Duffy et al.

(10) Patent No.: US 9,221,827 B2
(45) Date of Patent: *Dec. 29, 2015

(54) ANTIMICROBIAL COMPOUNDS AND METHODS OF MAKING AND USING THE SAME

(75) Inventors: Erin M. Duffy, Deep River, CT (US); Ashoke Bhattacharjee, Cheshire, CT (US); Shili Chen, Cheshire, CT (US); Zoltan F. Kanyo, North Haven, CT (US); Matthew H. Scheideman, New Haven, CT (US); Yuanqing Tang, Cheshire, CT (US)

(73) Assignee: Melinta Therapeutics, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/112,027

(22) PCT Filed: Apr. 11, 2012

(86) PCT No.: PCT/US2012/032994
§ 371 (c)(1),
(2), (4) Date: Feb. 7, 2014

(87) PCT Pub. No.: WO2012/173689
PCT Pub. Date: Dec. 20, 2012

(65) Prior Publication Data
US 2014/0163049 A1    Jun. 12, 2014

Related U.S. Application Data

(60) Provisional application No. 61/476,138, filed on Apr. 15, 2011, provisional application No. 61/535,118, filed on Sep. 15, 2011, provisional application No. 61/610,363, filed on Mar. 13, 2012.

(51) Int. Cl.
*A61K 31/519* (2006.01)
*C07D 487/04* (2006.01)
*C07D 403/12* (2006.01)
*C07D 401/14* (2006.01)
*C07D 239/36* (2006.01)

(52) U.S. Cl.
CPC ............ *C07D 487/04* (2013.01); *C07D 239/36* (2013.01); *C07D 401/14* (2013.01); *C07D 403/12* (2013.01)

(58) Field of Classification Search
CPC ........................... A61K 31/519; C07D 487/04
USPC .............. 544/242, 253, 280; 514/256, 258.1, 514/265.1
See application file for complete search history.

(56) References Cited

U.S. PATENT DOCUMENTS

| 4,971,965 | A | 11/1990 | Ono et al. |
|---|---|---|---|
| 5,958,930 | A | 9/1999 | Gangjee |
| 6,110,925 | A | 8/2000 | Williams et al. |
| 6,162,925 | A | 12/2000 | Williams et al. |
| 6,617,332 | B1 | 9/2003 | Brands et al. |
| 2002/0016297 | A1 | 2/2002 | Linde et al. |
| 2002/0193385 | A1 | 12/2002 | Chambers et al. |
| 2005/0153992 | A1 | 7/2005 | Tsutsumi et al. |
| 2010/0190747 | A1 | 7/2010 | Suzuki et al. |
| 2012/0220566 | A1 | 8/2012 | Duffy et al. |

FOREIGN PATENT DOCUMENTS

| CN | 1871240 A | 11/2006 |
|---|---|---|
| CN | 101535311 A | 9/2009 |
| DE | 10061537 A1 | 6/2002 |
| DE | 10061538 A1 | 6/2002 |
| DE | 10061541 A1 | 6/2002 |
| DE | 10061542 A1 | 6/2002 |
| DE | 10133277 A1 | 1/2003 |
| DE | 10141271 A1 | 3/2003 |
| EP | 0339596 A2 | 11/1989 |
| EP | 1113008 A1 | 7/2001 |
| JP | 2008-222557 | 9/2008 |
| KR | 10-2006-0118416 | 11/2006 |
| WO | WO 98/49177 | 11/1998 |
| WO | WO-9907685 A1 | 2/1999 |
| WO | WO-0012484 A1 | 3/2000 |
| WO | WO 01/60825 | 8/2001 |
| WO | WO-03072574 A1 | 9/2003 |
| WO | WO-2004080466 A1 | 9/2004 |
| WO | WO 2007/069923 A1 | 6/2007 |
| WO | WO 2008/004796 | 1/2008 |
| WO | WO 2008/030119 | 3/2008 |
| WO | WO-2008082440 A2 | 7/2008 |
| WO | WO-2008154642 A2 | 12/2008 |
| WO | WO 2009/074812 A1 | 6/2009 |

(Continued)

OTHER PUBLICATIONS

Bondock, Samir, et al: "Synthesis and antimicrobial activity of some new heterocycles incorporating antipyrine moiety", European Journal of Medicinal Chemistry, vol. 43, No. 10, Oct. 1, 2008, pp. 2122-2129, XP055132947.
Michael C. Laufersweiler et al., 'Synthesis and evaluation of tricyclic pyrrolopyrimidinones as dipeptide mimetics: Inhibition of interleukin-1-beta-converting enzyme', Bioorganic & Medicinal Chemistry Letters, vol. 15, pp. 4322-4326 (Jul. 19, 2005).
Aguilar et al. "Toward a Library Synthesis of the Natural Dipeptide Antibiotic TAN 1057 A,B." *Molecules.* 7.6(2002):469-474.
Bandow et al. "Proteomic Approach to Understanding Antibiotic Action." *Antimicrob. Agents Chemother.* 47.3(2003):948-955.
Belov et al. "First Enantioselective Synthesis of the Novel Antiinfective TAN-1057A Via its Aminomethyl-Substituted Dihydropyrimidinone Heterocycle." *Tetrahedron.* 60.35(2004):7579-7589.

(Continued)

Primary Examiner — Golam M M Shameem
(74) Attorney, Agent, or Firm — Cooley LLP; Heidi A. Erlacher; Lian Ouyang

(57) ABSTRACT

The present invention relates generally to the field of antimicrobial compounds and to methods of making and using them. These compounds are useful for treating, preventing, and reducing the risk of microbial infections in humans and animals.

17 Claims, No Drawings

(56) References Cited

FOREIGN PATENT DOCUMENTS

| | | |
|---|---|---|
| WO | WO-2009113828 A2 | 9/2009 |
| WO | WO-2011045415 A2 | 4/2011 |
| WO | WO-2011047319 A2 | 4/2011 |
| WO | WO-2012173689 A2 | 12/2012 |

OTHER PUBLICATIONS

Berlinck. "Natural Guanidine Derivatives." *Nat. Prod. Rep.* 16.3(1999):339-365.

Brackmann et al. "Titanium-Mediated Cyclopropanation of N,N-Dibenzylcarboxamides Towards Functionally Substituted 2-(1'-Aminocyclopropyl)acetic Acids." *Synthesis*. 12(2005):2008-2014.

Brands et al. "Dihydropyrimidinones—A New Class of Anti-Staphylococcal Antibiotics." *Bioorg. Med. Chem*. 13.2(2003):241-245.

Brands et al. "Novel Antibiotics for the Treatment of Gram-Positive Bacterial Infections." *J. Med. Chem*. 45.19(2002):4246-4253.

Brands et al. "Pyrimidinone Antibiotics—Heterocyclic Analogues With Improved Antibacterial Spectrum." *Bioorg. Med. Chem. Lett*. 13.16(2003):2641-2645.

Böddeker et al. "Characterization of a Novel Antibacterial Agent That Inhibits Bacterial Translation." *RNA*. 8.9(2002):1120-1128.

Champney et al. "TAN-1057A: A Translational Inhibitor With a Specific Inhibitory Effect of 50S Ribosomal Subunit Formation." *Curr. Microbiol.* 43.5(2001):340-345.

Funabashi et al. "A New Anti-MRSA Dipeptide, TAN-1057 A." *Tetrahedron.* 49.1(1993):13-28.

Gangjee et al. "Synthesis of Classical, Three-Carbon-Bridged 5-Substituted Furo[2,3-d]pyridmidine and 6-Substituted Pyrrolo[2,3-d]pyrimidine Analogues as Antifolates." *J. Med. Chem*. 47.27(2004):6893-6901.

Gnad et al. "Synthesis and Applications of β-Aminocarboxylic Acids Containing a Cyclopropane Ring." *Chem. Rev*. 103.4(2003):1603-1623.

Hudson et al. "Fluorescent 7-Deazapurine Derivatives from 5-Iodocytosine via a Tandem Cross-Coupling-Annulation Reaction With Terminal Alkynes." *Synlett*. 13(2004):2400-2402.

Hudson et al. "Nucleobase Modified Peptide Nucleic Acid." *Nucleosides Nucleotides Nucleic Acids*. 22.5-8(2003):1029-1033.

Janeba et al. "Synthesis and Biological Evaluation of Acyclic 3-[(2-Hydroxyethoxy)methyl] Analogues of Antiviral Furo- and Pyrrolo[2,3-d]pyrimidine Nucleosides." *J. Med. Chem*. 48.14(2005):4690-4696.

Katayama et al. "TAN-1057 A~D, New Antibioics With Potent Antibacterial Activity Against Methicillin-Resistant *Staphylococcus aureus*." *J. Antibiot.* 46.4(1993):606-613.

Kawahara et al. "Computer-Aided Molecular Design of Hydrogen Bond Equivalents of Nucleobases: Theoretical Study of Substituent Effects on the Hydrogen Bond Energies of Nucleobase Pairs." *Eur. J. Org. Chem.* 2003.14(2003):2577-2584.

Kordes et al. "Preparation of Cyclopropane Analogues of the Natural Antibiotic TAN 1057 A/B." *Eur. J. Org. Chem*. 2005.14(2005):3008-3016.

Limburg et al. "Ribosomal Alterations Contribute to Bacterial Resistane Against the Dipeptide Antibiotic TAN 1057." *Antimicrob. Agents Chemother*. 48.2(2004):619-622.

Lin et al. "Assembly of the TAN-1057 A/B Heterocycle From a Dehydroalanine Precursor." *Synthesis*. 14(2000):2127-2130.

Liu et al. "Recent Advances in the Stereoselective Synthesis of β-Amino Acids." *Tetrahedron.* 58.40(2002):7991-8035.

Nett et al. "The Chemistry of Gliding Bacteria." *Nat. Prod. Rep*. 24.6(2007):1245-1261.

Orner et al. "The Guanidinium Group in Molecular Recognition: Design and Synthetic Approaches." *J. Inclusion Phenomena Macrocylic Chem*. 41.1-4(2001):141-147.

Sokolov et al. "Total Synthesis of TAN-1057 A/B, a New Dipeptide Antibiotic from *Flexibacter* sp. PK-74." *Eur. J. Org. Chem.* 1998. 5(1998):777-783.

Williams et al. "Synthesis and Antimicrobial Evaluation of TAN-1057A/B Analogs." *J. Antibiotic*. 51(1998):189-201.

Wojciechowski et al. "Exceptional Fluorescence and Hybridization Properties of a Phenylpyrrolocytosine in Peptide Nucleic Acid." *Nucleic Acids Symposium Series*. 52(2008):401-402.

Wojciechowski et al. "Fluorescence and Hybridization Properties of Peptide Nucleic Acid Containing a Substituted Phenylpyrrolocytosine Designed to Engaged Guanine with an Additional H-Bond." *J. Am. Chem. Soc.*, Web. Aug. 30, 2008.

Wojciechowski et al. "Peptide Nucleic Acid Containing a Meta-Substituted Phenylpyrrolocytosine Exhibits a Fluorescence Response and Increased Binding Affinity Toward RNA." *Org. Lett*. 11.21(2009):4878-4881.

Xu et al. "A New and Convergent Synthesis for 2,5-diaminotetrahydropyrimidones." *Tetrahedron Lett*. 44.12(2003):2601-2604.

Xu et al. "SAR Studies on Dihydropyrimidinone Antibiotics." *Bioorg. Med. Chem. Lett.* 21.6(2011):1670-1674.

Yuan et al. "Total Synthesis of the Anti Methicillin-Resistant *Staphylococcus aureus* Peptide Antibiotics TAN-1057A-D." *J. Am. Chem. Soc.* 119.49(1997):11777-11784.

Zhang et al. "A Facile Construction of the 3,6-diamino-1,2,3,4-tetrahydropryidine-4-one Scaffold: Synthesis of N-3 to Carbon Replacement Analog of TAN-1057A/B." *Tetrahedron Lett*. 48.18(2007):3273-3275.

Zhang et al. "A New Approach to the 2,5-diamino-5,6-dihyrdo-1H-pyrimidine-4-one Derivatives: Synthesis of TAN-1057A/B and Analogs." *Tetrahedron Lett.* 44.31(2003):5871-5873.

Reigan et al. "Synthesis and Enzymatic Evaluation of Xanthine Oxidase-Activated Prodrugs Based on Inhibitors of Thymidine Phosphorylase." *Bioorg. Med. Chem. Lett*. 14(2004):5247-5250.

Snaidy, Adam et al., "Zinc-Catalyzed Cycloisomerizations. Synthesis of Substituted Furans and Furopyrimidine Nucleosides," *J. Org. Chem*. 73(15), 2008, 5881-5889.

ANTIMICROBIAL COMPOUNDS AND METHODS OF MAKING AND USING THE SAME

RELATED APPLICATIONS

The present application is a national stage application, filed under 35 U.S.C. §371, of International Application No. PCT/US2012/032994, filed on Apr. 11, 2012, which claims priority to and the benefit of U.S. provisional application No. 61/476,138, filed Apr. 15, 2011, U.S. provisional application No. 61/535,118, filed Sep. 15, 2011, and U.S. provisional application No. 61/610,363, filed Mar. 13, 2012. The contents the aforementioned applications are hereby incorporated by reference in their entirety.

FIELD OF THE INVENTION

The present invention relates generally to the field of antimicrobial compounds and to methods of making and using them. These compounds are useful for treating, preventing, and reducing the risk of microbial infections in humans and animals.

BACKGROUND

Since the discovery of penicillin in the 1920s and streptomycin in the 1940s, many new compounds have been discovered or specifically designed for use as antibiotic agents. It was once thought that infectious diseases could be completely controlled or eradicated with the use of such therapeutic agents. However, such views have been challenged because strains of cells or microorganisms resistant to currently effective therapeutic agents continue to evolve. Almost every antibiotic agent developed for clinical use has ultimately encountered problems with the emergence of resistant bacteria. For example, resistant strains of Gram-positive bacteria such as methicillin-resistant staphylococci, penicillin-resistant streptococci, and vancomycin-resistant *enterococci* have developed. Resistant bacteria can cause serious and even fatal results for infected patients. See, e.g., Lowry, F. D. "Antimicrobial Resistance: The Example of *Staphylococcus aureus*," *J. Clin. Invest.*, vol. 111, no. 9, pp. 1265-1273 (2003); and Gold, H. S. and Moellering, R. C., Jr., "Antimicrobial-Drug Resistance," *N. Engl. J. Med.*, vol. 335, pp. 1445-53 (1996).

The discovery and development of new antibacterial agents have been for decades a major focus in many pharmaceutical companies. Nonetheless, in more recent years there has been an exodus of pharmaceutical companies from this area of research and drug development. As a consequence of this exodus, there have been very few new antibiotics entering the market. This lack of new antibiotics is particularly disturbing, especially at a time when bacterial resistance to current therapies is increasing both in the hospital and community settings.

In the search for new antibiotic agents, researchers have tried combining or linking various portions of antibiotic molecules to create multifunctional or hybrid compounds Other researchers have tried making derivatives of known classes of antibiotics, e.g., telithromycin, which is sold under the trade name Ketek®, is a derivative of erythromycin. However, these approaches have met with limited success.

An approach to developing new antimicrobial compounds is to design modulators, for example, inhibitors, of bacterial ribosome function. By modulating or inhibiting bacterial ribosome function such antimicrobial compounds could interfere with essential processes such as RNA translation and protein synthesis, thereby providing an antimicrobial effect. In fact, some antibiotic compounds such as erythromycin, clindamycin, and linezolid are known to bind to the ribosome.

The present invention utilizes a structure based drug design approach for discovering and developing new antimicrobial agents. This approach starts with the high resolution X-ray crystal of the ribosome to design new classes of antimicrobial compounds having specific chemical structures, ribosome binding characteristics, and antimicrobial activity. This structure based drug discovery approach is described in the following publication: Franceschi, F. and Duffy, E. M., "Structure-based drug design meets the ribosome", *Biochemical Pharmacology*, vol. 71, pp. 1016-1025 (2006).

Based on this structure based drug design approach, the present invention describes new chemical classes of antimicrobial compounds useful for treating bacterial infections in humans and animals. Without being limited by theories, these compounds are believed to inhibit bacterial ribosome function by binding to the ribosome. By taking advantage of these ribosome binding sites, the antimicrobial compounds of the present invention can provide better activity, especially against resistant strains of bacteria, than current antibiotic compounds.

The present invention therefore fills an important ongoing need for providing new antimicrobial agents, particularly for antimicrobial agents, having activity against resistant pathogenic bacterial organisms.

SUMMARY OF THE INVENTION

The present invention relates generally to the field of antimicrobial compounds and to methods of making and using them. These compounds and tautomers thereof are useful for treating, preventing, and reducing the risk of microbial infections in humans and animals. The present invention also provides pharmaceutically acceptable salts, esters, and prodrugs of these compounds and tautomers.

In one aspect, the present invention relates to a compound having the formula:

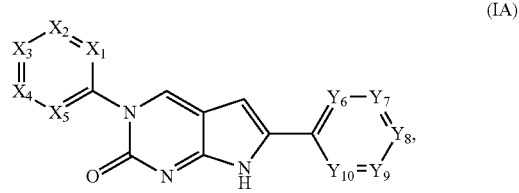

(IA)

or a tautomer thereof, or a pharmaceutically acceptable salt, ester, or prodrug of said compound or tautomer, wherein $X_1$ is $CR^1$ or N; $X_2$ is $CR^2$ or N; $X_3$ is $CR^3$ or N; $X_4$ is $CR^4$ or N; $X_5$ is $CR^5$ or N; with the proviso that $X_1$, $X_2$, $X_3$, $X_4$, and $X_5$ are not all N;

$Y_6$ is $CR^6$ or N; $Y_7$ is $CR^7$ or N; $Y_8$ is $CR^8$ or N; $Y_9$ is $CR^9$ or N; $Y_{10}$ is $CR^{10}$ or N; with the proviso that $Y_6$, $Y_7$, $Y_8$, $Y_9$, and $Y_{10}$ are not all N; wherein $R^1$, $R^2$, $R^4$, $R^5$, $R^6$, $R^7$, $R^8$ and $R^{10}$ are each independently selected from (a) hydrogen, (b) F, (c) Cl, (d) Br, (e) I, (f) —$CF_3$, (g) —$CF_2H$, (h) —$CFH_2$, (i) —$OCF_3$, (j) —$OCF_2H$, (k) —$OCFH_2$, (l) —$OCH_3$, (m) —CN, (n) —$N_3$, (o) —$NO_2$, (p) —$NR^{11}C(O)R^{11}$, (r) —$C(O)NR^{11}R^{11}$, (s) —$OR^{11}$, (t) —COH, (u) —CO($C_1$-$C_8$ alkyl), (v) —$COR^{11}$, (w) —$NR^{11}$(CNR$^{11}$)NR$^{11}$R$^{11}$, (x) —S(O)$_p$R$^{11}$, (y) —NR$^{11}$S(O)$_p$R$^{11}$, (z) —SR$^{11}$, (aa) —$SCF_3$, (bb) —C(CF$_3$)H—NH—CHR$^{11}$R$^{11}$, (cc) —COOR¹¹, (dd) —(OCH₂CH₂)ₓR¹¹, (ee) —(OCH₂CH₂)ₓOR¹¹, (ff) —C₁-C₈ alkyl, (gg) —C₂-C₈ alkenyl, (hh) —C₂-C₈ alkynyl, (ii) —(C₁-C₈ alkyl)-(3-14 membered saturated, unsaturated, or aromatic heterocycle containing one or more heteroatoms selected from the group consisting of nitrogen, oxygen, and sulfur), (jj) —(C₁-C₈ alkyl)-(3-14 membered saturated, unsaturated, or aromatic carbocycle), (kk) -haloalkyl, (ll) -3-14 membered saturated, unsaturated, or aromatic heterocycle containing one or more heteroatoms selected from the group consisting of nitrogen, oxygen, and sulfur, (mm) -3-14 membered saturated, unsaturated, or aromatic carbocycle, and (nn) —CHR¹¹—NH-(3-14 membered saturated, unsaturated, or aromatic heterocycle containing one of more heteroatoms selected from the group consisting of nitrogen, oxygen, and sulfur);

wherein each (ff) through (nn) is optionally substituted with one or more R¹²; alternatively, wherein two substituents selected from R⁶, R⁷, and R⁸ are taken together with the carbon atom to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur; wherein each (a) through (b) is optionally substituted with one or more R¹²;

each R¹¹ is independently selected from (a) hydrogen, (b) halogen, (c) —OH, (d) —SH, (e) —(C₁-C₈ alkyl)OH, (f) —OCF₃, (g) —OCF₂H, (h) —OCFH₂, (i) —OCH₃, (j) —OR¹², (k) —COR¹², (l) —CN, (m) —NO₂, (n) —CONH₂, (o) —CONR¹²R¹², (p) —COCH₃, (q) —S(O)ₚCH₃, (r) —S(O)ₚNR¹²R¹², —SR¹², (t) —C(O)OH, (u) —C(O)OR¹², (v) —N₃, (w) —NH₂, (x) —NR¹²C(O)R¹², (y) —NH(C₁-C₈ alkyl), (z) —N(C₁-C₈ alkyl)₂, (aa) —C₁-C₈ alkyl, (bb) —C₂-C₈ alkenyl, (cc) —C₂-C₈ alkynyl, (dd) -haloalkyl, (ee) —(C₁-C₈ alkyl)-(3-14 membered saturated, unsaturated, or aromatic heterocycle containing one or more heteroatoms selected from the group consisting of nitrogen, oxygen, and sulfur), (ff) —(C₁-C₈ alkyl)-(3-14 membered saturated, unsaturated, or aromatic carbocycle), (gg) -3-14 membered saturated, unsaturated, or aromatic heterocycle containing one or more heteroatoms selected from the group consisting of nitrogen, oxygen, and sulfur, (hh) -3-14 membered saturated, unsaturated, or aromatic carbocycle, and (ii) —(C=NH)NR¹²R¹²;

wherein each (y) through (hh) is optionally substituted with one or more R¹²;

alternatively two R¹¹ substituents are taken together to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur, wherein each (a) through (b) is optionally substituted with one or more R¹²;

R³ is selected from:

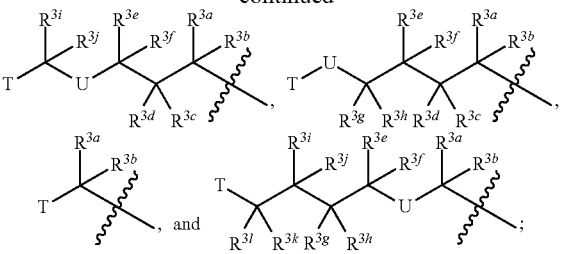

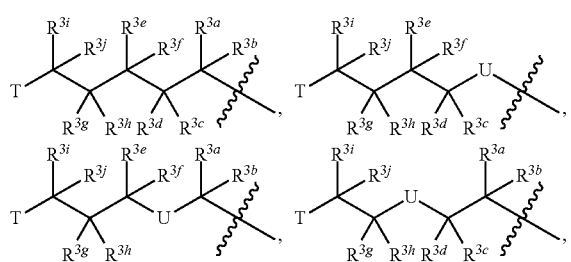

wherein R³ᵃ, R³ᵇ, R³ᶜ, R³ᵈ, R³ᵉ, R³ᶠ, R³ᵍ, R³ʰ, R³ⁱ, R³ʲ, R³ᵏ, and R³ˡ are each independently selected from (a) hydrogen, (b) halogen, (c) —CN, (d) —N₃, (e) —NO₂, (f) —OCF₃, (g) —OCF₂H, (h) —OCFH₂, (i) —OCH₃, (j) —OR¹¹, (k) —C(O)R¹¹, (l) —C(O)NR¹¹R¹¹, (m) —NH₂, (n) —NR¹¹R¹¹, (o) —NR¹¹C(O)R¹¹, (p) —S(O)ₚR¹¹, (q) —C(O)OH, (r) —C(O)OR¹¹, (s) —C₁-C₈ alkyl, (t) —C₂-C₈ alkenyl, (u) —C₂-C₈ alkynyl, (v) haloalkyl, (w) -3-14 membered saturated, unsaturated, or aromatic heterocycle containing one or more heteroatoms selected from the group consisting of nitrogen, oxygen, and sulfur, and (x) -3-14 membered saturated, unsaturated, or aromatic carbocycle;

wherein each (s) through (x) is optionally substituted with one or more R¹²;

alternatively, one or more pairs of substituents selected from R³ᵃ and R³ᵇ, R³ᶜ and R³ᵈ, R³ᵉ and R³ᶠ, R³ᵍ and R³ʰ, R³ⁱ and R³ʲ, and R³ᵏ and R³ˡ are taken together with the carbon atom to which they are attached to form (a) -3-7 membered saturated or unsaturated carbocyclic, (b) -3-7 membered saturated or unsaturated heterocyclic ring containing one or more heteroatoms selected from the group consisting of nitrogen, oxygen, and sulfur, (c) an exo carbon-carbon double bond, (d) carbonyl group, or (e) thiocarbonyl group;

wherein each (a) through (b) is optionally substituted with one or more R¹²;

alternatively, wherein two substituents selected from R³ᵃ, R³ᵇ, R³ᶜ, R³ᵈ, R³ᵉ, R³ᶠ, R³ᵍ, R³ʰ, R³ⁱ, R³ʲ, R³ᵏ, and R³ˡ on different carbon atoms are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more R¹²;

alternatively, wherein two substituents selected from R³ᵃ, R³ᵇ, R³ᶜ, R³ᵈ, R³ᵉ, R³ᶠ, R³ᵍ, R³ʰ, R³ⁱ, R³ʲ, R³ᵏ, and R³ˡ on two adjacent carbon atoms are taken together with the bond between said adjacent carbon atoms form a substituted or unsubstituted carbon-carbon double bond, or wherein four substituents selected from R³ᵃ, R³ᵇ, R³ᶜ, R³ᵈ, R³ᵉ, R³ᶠ, R³ᵍ, R³ʰ, R³ⁱ, R³ʲ, R³ᵏ, and R³ˡ on two adjacent carbon atoms are taken together with the bond between said adjacent carbon atoms form a carbon-carbon triple bond;

U is selected from —O—, —S(O)ₚ—, —NR¹¹—, —(C=O)—, —NR¹¹(C=O)—, —(C=O)NR¹¹—, —S(O)ₚNR¹¹—, —NR¹¹S(O)ₚ—, —NR¹¹S(O)ₚNR¹¹—, and —NR¹¹C(O)NR¹¹—;

T is selected from —NR¹¹R¹¹, —NR¹¹(C=O)OR¹¹, —NR¹¹(C=NR¹¹)NR¹¹R¹¹, and OR¹¹;

alternatively, one R¹¹ and one substituent selected from R³ᵃ, R³ᵇ, R³ᶜ, R³ᵈ, R³ᵉ, R³ᶠ, R³ᵍ, R³ʰ, R³ⁱ, R³ʲ, R³ᵏ, and R³ˡ are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

$R^9$ is selected from:

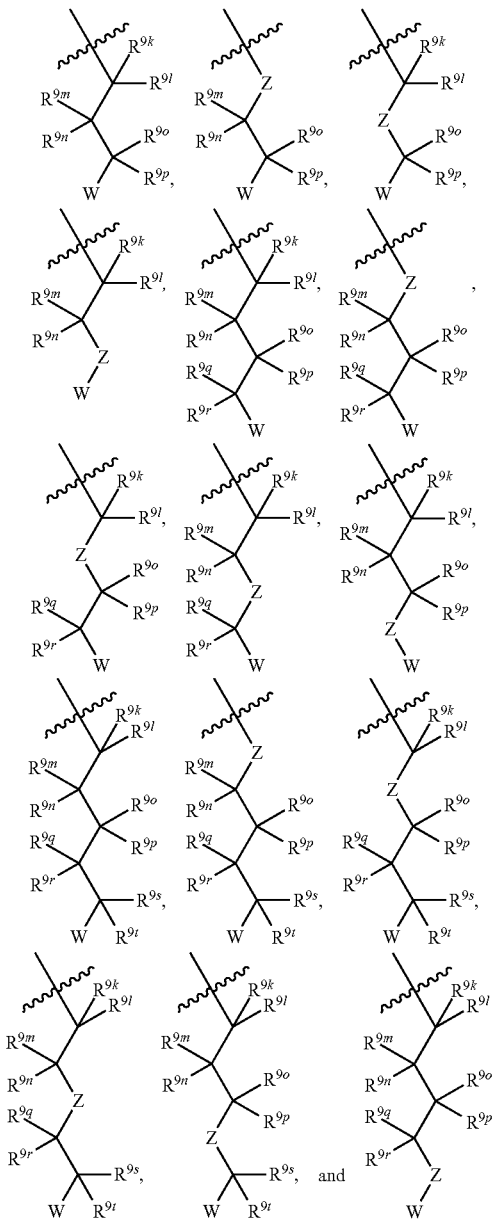

wherein $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are each independently selected from (a) hydrogen, (b) halogen, (c) —CN, (d) —N$_3$, (e) —NO$_2$, (f) —OCF$_3$, (g) —OCH$_3$, (h) —OCF$_2$H, (i) —OCFH$_2$, (j) —OR$^{11}$, (k) —NH$_2$, (l) —NR$^{11}$R$^{11}$, (m) —C(O)R$^{11}$, (n) —C(O)OR$^{11}$, (o) —C(O)NR$^{11}$R$^{11}$, (p) —NR$^{11}$C(O)R$^{11}$, (q) —S(O)$_p$R$^{11}$, (r) —C$_1$-C$_8$ alkyl, (s) —C$_2$-C$_8$ alkenyl, (t) —C$_1$-C$_8$ alkynyl, (u) haloalkyl, (v) -3-14 membered saturated, unsaturated, or aromatic heterocycle containing one or more heteroatoms selected from the group consisting of nitrogen, oxygen, and sulfur, and (w) -3-14 membered saturated, unsaturated, or aromatic carbocycle;

wherein each (r) through (w) is optionally substituted with one or more $R^{12}$;

alternatively, one or more pairs of substituents selected from $R^{9k}$ and $R^{9l}$, $R^{9m}$ and $R^{9n}$, $R^{9o}$ and $R^{9p}$, $R^{9q}$ and $R^{9r}$, and $R^{9s}$ and $R^{9t}$ are taken together with the carbon atom to which they are attached to form (a) 3-7 membered saturated or unsaturated carbocyclic, (b) 3-7 membered saturated or unsaturated heterocyclic ring containing one or more heteroatoms selected from the group consisting of nitrogen, oxygen, and sulfur, (c) an exo carbon-carbon double bond, (d) carbonyl group, or (e) thiocarbonyl group;

wherein each (a) through (c) is optionally substituted with one or more $R^{12}$;

alternatively, two substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on different carbon atoms are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

alternatively, two substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on two adjacent carbon atoms are taken together with the bond between said adjacent carbon atoms form a substituted or unsubstituted carbon-carbon double bond, or four substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on two adjacent carbon atoms are taken together with the bond between said adjacent carbon atoms form a carbon-carbon triple bond;

Z is selected from —O—, —S(O)$_p$—, —NR$^{11}$—, —(C=O)—, —NR$^{11}$(C=O)—, —(C=O)NR$^{11}$—, —S(O)$_p$ NR$^{11}$—, —NR$^{11}$S(O)$_p$—, —NR$^{11}$S(O)$_p$NR$^{11}$—, and —NR$^{11}$C(O)NR$^{11}$—;

W is selected from —NR$^{11}$R$^{11}$, —NR$^{11}$(CO)OR$^{11}$, —NR$^{11}$(C=NR$^{11}$)NR$^{11}$R$^{11}$, and —OR$^{11}$;

alternatively, one $R^{11}$ and one substituent selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

$R^{12}$ is independently selected from (a) hydrogen, (b) halogen, (c) —OH, (d) —SH, (e) —(C$_1$-C$_8$ alkyl)OH, (f) —OCF$_3$, (g) —OCH$_3$, (h) —OCF$_2$H, (i) —OCFH$_2$, (j) —O(C$_1$-C$_8$ alkyl), (k) —CN, (l) —NO$_2$, (m) —CONH$_2$, (n) C(O)NH(C$_1$-C$_8$ alkyl), (o) C(O)N(C$_1$-C$_8$ alkyl)$_2$, (p) —COH, (q) —COCH$_3$, (r) —S(O)$_p$CH$_3$, (s) —S(O)$_p$N(C$_1$-C$_8$ alkyl)$_2$, (t) —S(C$_1$-C$_8$ alkyl), (u) —C(O)OH, (v) —C(O)O(C$_1$-C$_8$ alkyl), (w) —N$_3$, (x) —NHC(O)(C$_1$-C$_8$ alkyl), (y) —N(C$_1$-C$_8$ alkyl)C(O)(C$_1$-C$_8$ alkyl), (z) —NH$_2$, (aa) —NH(C$_1$-C$_8$ alkyl), (bb) —N(C$_1$-C$_8$ alkyl)$_2$, (cc) —C$_1$-C$_8$ alkyl, (dd) —C$_2$-C$_8$ alkenyl, (ee) —C$_2$-C$_8$ alkynyl, (ff) -haloalkyl, (gg) —(C$_1$-C$_8$ alkyl)-(3-14 membered saturated, unsaturated, or aromatic heterocycle containing one or more heteroatoms selected from the group consisting of nitrogen, oxygen, and sulfur), (hh) —(C$_1$-C$_8$ alkyl)-(3-14 membered saturated, unsaturated, or aromatic carbocycle), (ii) -3-14 membered saturated, unsaturated, or aromatic heterocycle containing one or more heteroatoms selected from the group consisting of nitrogen, oxygen, and sulfur, (jj) -3-14 membered saturated, unsaturated, or aromatic carbocycle, (kk) —(C=NH)NH$_2$, (ll) —C(=NH)NH$_2$, (mm) —C(O)R$^{13}$, (nn) =O, and (oo) =NR$^{13}$;

wherein each (aa) through (jj) is optionally substituted with one or more R$^{13}$;

R$^{13}$ is independently selected from (a) hydrogen, (b) halogen, (c) —C$_1$-C$_8$ alkyl, (d) —C$_2$-C$_8$ alkenyl, (e) —C$_2$-C$_8$ alkynyl, (f) -haloalkyl, (g) —OH, (h) —OC$_1$-C$_8$ alkyl, (i) —OC$_2$-C$_8$ alkenyl, (j) —OC$_2$-C$_8$ alkynyl, (k) —OCF$_3$, (l) —OCH$_3$, (m) —OCF$_2$H, (n) —OCFH$_2$, (O) —NH$_2$, (p) —CN, (q) —N$_3$, (r) —S(O)$_p$C$_1$-C$_8$ alkyl, (s) -3-14 membered saturated, unsaturated, or aromatic heterocycle containing one or more heteroatoms selected from the group consisting of nitrogen, oxygen, and sulfur, and (t) -3-14 membered saturated, unsaturated, or aromatic carbocycle;

p is 0, 1, or 2; and t is 0, 1, or 2.

In one aspect, the present invention relates to a compound or a tautomer thereof, or a pharmaceutically acceptable salt, ester, or prodrug of said compound or tautomer, having the formula:

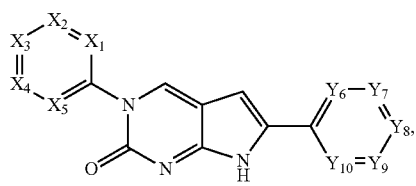

(I)

or a tautomer thereof, or a pharmaceutically acceptable salt, ester, or prodrug of said compound or tautomer, wherein X$_1$ is CR$^1$ or N; X$_2$ is CR$^2$ or N; X$_3$ is CR$^3$ or N; X$_4$ is CR$^4$ or N; X$_5$ is CR$^5$ or N; with the proviso that X$_1$, X$_2$, X$_3$, X$_4$, and X$_5$ are not all N;

Y$_6$ is CR$^6$ or N; Y$_7$ is CR$^7$ or N; Y$_8$ is CR$^8$ or N; Y$_9$ is CR$^9$ or N; Y$_{10}$ is CR$^{10}$ or N; with the proviso that Y$_6$, Y$_7$, Y$_8$, Y$_9$, and Y$_{10}$ are not all N; wherein R$^1$, R$^2$, R$^4$, R$^5$, R$^6$, R$^7$, R$^8$ and R$^{10}$ are each independently selected from (a) hydrogen, (b) F, (c) Cl, (d) Br, (e) I, (f) —CF$_3$, (g) —CF$_2$H, (h) —CFH$_2$, (i) —OCF$_3$, (j) —OCF$_2$H, (k) —OCFH$_2$, (l) —OCH$_3$, (m) —CN, (n) —N$_3$, (o) —NO$_2$, (p) NR$^{11}$R$^{11}$, (q) NR$^{11}$(CO)R$^{11}$, (r) —(CO)NR$^{11}$R$^{11}$, (s) —OR$^{11}$, (t) —COH, (u) —CO(C$_1$-C$_8$ alkyl), (v) —COR$^{11}$, (w) —NR$^{11}$(CNR$^{11}$)NR$^{11}$R$^{11}$, (x) —S(O)$_p$R$^{11}$, (y) —NR$^{11}$S(O)$_p$R$^{11}$, (z) —SR$^{11}$, (aa) —SCF$_3$, (bb) —C(CF$_3$)H—NH—CHR$^{11}$R$^{11}$, (cc) —COOR$^{11}$, (dd) —(OCH$_2$CH$_2$)$_t$R$^{11}$, (ee) —(OCH$_2$CH$_2$)$_t$OR$^{11}$, (ff) —C$_1$-C$_8$ alkyl, (gg) —C$_2$-C$_8$ alkenyl, (hh) —C$_2$-C$_8$ alkynyl, (ii) —(C$_1$-C$_8$ alkyl)-(3-14 membered saturated, unsaturated, or aromatic heterocycle containing one or more heteroatoms selected from the group consisting of nitrogen, oxygen, and sulfur), (jj) —(C$_1$-C$_8$ alkyl)-(3-14 membered saturated, unsaturated, or aromatic carbocycle), (kk) -haloalkyl, (ll) -3-14 membered saturated, unsaturated, or aromatic heterocycle containing one or more heteroatoms selected from the group consisting of nitrogen, oxygen, and sulfur, (mm) -3-14 membered saturated, unsaturated, or aromatic carbocycle, and (nn) —CHR$^1$—NH-(3-14 membered saturated, unsaturated, or aromatic heterocycle containing one of more heteroatoms selected from the group consisting of nitrogen, oxygen, and sulfur);

wherein each (ff) through (nn) is optionally substituted with one or more R$^{12}$;

each R$^{11}$ is independently selected from (a) hydrogen, (b) halogen, (c) —CF$_3$, (d) —CF$_2$H, (e) —CFH$_2$, (f) —OH, (g) —SH, (h) —(C$_1$-C$_8$ alkyl)OH, (i) —OCF$_3$, (j) —OCF$_2$H, (k) —OCFH$_2$, (l) —OCH$_3$, (m) —OR$^{12}$, (n) —COR$^{12}$, (o) —CN, (p) —NO$_2$, (q) —CONH$_2$, (r) —CONR$^{12}$R$^{12}$, (s) —C(O)CH$_3$, (t) —S(O)$_p$CH$_3$, (u) —S(O)$_p$NR$^{12}$R$^{12}$, (v) —SR$^{12}$, (w) —C(O)OH, (x) —C(O)OR$^{12}$, (y) —N$_3$, (z) —NH$_2$, (aa) —NR$^{12}$C(O)R$^{12}$, (bb) —NH(C$_1$-C$_8$ alkyl), (cc) —N(C$_1$-C$_8$ alkyl)$_2$, (dd) —C$_1$-C$_8$ alkyl, (ee) —C$_2$-C$_8$ alkenyl, (ff) —C$_2$-C$_8$ alkynyl, (gg) -haloalkyl, (hh) —(C$_1$-C$_8$ alkyl)-(3-14 membered saturated, unsaturated, or aromatic heterocycle containing one or more heteroatoms selected from the group consisting of nitrogen, oxygen, and sulfur), (ii) —(C$_1$-C$_8$ alkyl)-(3-14 membered saturated, unsaturated, or aromatic carbocycle), (jj) -3-14 membered saturated, unsaturated, or aromatic heterocycle containing one or more heteroatoms selected from the group consisting of nitrogen, oxygen, and sulfur, (kk) -3-14 membered saturated, unsaturated, or aromatic carbocycle, and (ll) —(C=NH)NR$^{12}$R$^{12}$;

wherein each (bb) through (kk) is optionally substituted with one or more R$^{12}$;

alternatively two R$^{11}$ substituents are taken together to form (a) 3-7 membered saturated or unsaturated carbocyclic or (b) 3-7 membered saturated or unsaturated heterocyclic ring containing one or more heteroatoms selected from the group consisting of nitrogen, oxygen, and sulfur, wherein each (a) through (b) is optionally substituted with one or more R$^{12}$;

R$^3$ is selected from:

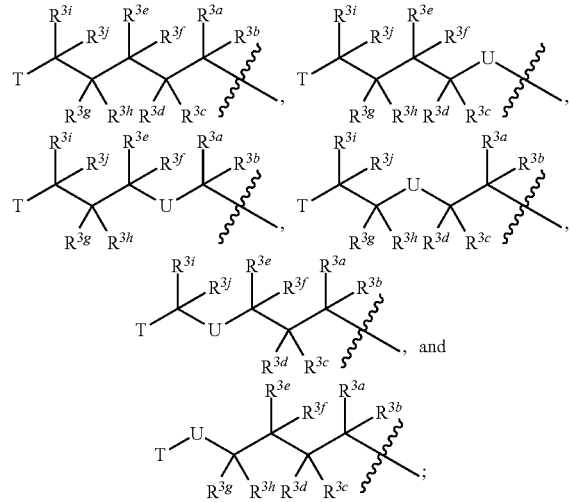

wherein R$^{3a}$, R$^{3b}$, R$^{3c}$, R$^{3d}$, R$^{3e}$, R$^{3f}$, R$^{3g}$, R$^{3h}$, R$^{3i}$, and R$^{3j}$ are each independently selected from (a) hydrogen, (b) halogen, (c) —CH$_3$, (d) —CF$_3$, (e) —CF$_2$H, (f) —CFH$_2$, (g) —OCF$_3$, (h) —OCF$_2$H, (i) —OCFH$_2$, (j) —OCH$_3$, (k) —OR$^{11}$, (l) —C$_1$-C$_8$ alkyl, (m) haloalkyl, (n) -3-14 membered saturated, unsaturated, or aromatic heterocycle containing one or more heteroatoms selected from the group consisting of nitrogen, oxygen, and sulfur, and (o) -3-14 membered saturated, unsaturated, or aromatic carbocycle;

wherein each (l) through (o) is optionally substituted with one or more R$^{12}$;

alternatively, one or more pairs of substituents selected from R$^{3a}$ and R$^{3b}$, R$^{3c}$ and R$^{3d}$, R$^{3e}$ and R$^{3f}$, R$^{3g}$ and R$^{3h}$, and R$^{3i}$ and R$^{3j}$ are taken together with the carbon atom to which they are attached to form (a) -3-7 membered saturated or unsaturated carbocyclic, (b) -3-7 membered saturated or unsaturated heterocyclic ring containing one or more heteroatoms selected from the group consisting of nitrogen, oxygen, and sulfur, (c) an exo carbon-carbon double bond, (d) carbonyl group, or (e) thiocarbonyl group;

wherein each (a) through (b) is optionally substituted with one or more $R^{12}$;

alternatively, wherein two substituents selected from $R^{3a}$, $R^{3b}$, $R^{3c}$, $R^{3d}$, $R^{3e}$, $R^{3f}$, $R^{3g}$, $R^{3h}$, $R^{3i}$, and $R^{3j}$ on different carbon atoms are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

alternatively, wherein two substituents selected from $R^{3a}$, $R^{3b}$, $R^{3c}$, $R^{3d}$, $R^{3e}$, $R^{3f}$, $R^{3g}$, $R^{3h}$, $R^{3i}$, and $R^{3j}$ on two adjacent carbon atoms are taken together with the bond between said adjacent carbon atoms form a substituted or unsubstituted carbon-carbon double bond, or wherein four substituents selected from $R^{3a}$, $R^{3b}$, $R^{3c}$, $R^{3d}$, $R^{3e}$, $R^{3f}$, $R^{3g}$, $R^{3h}$, $R^{3i}$, and $R^{3j}$ on two adjacent carbon atoms are taken together with the bond between said adjacent carbon atoms form a carbon-carbon triple bond;

U is selected from —O—, —S(O)$_p$—, —(C=O)—, —NR$^{11}$(C=O)—, —(C=O)NR$^{11}$—, —S(O)$_p$NR$^{11}$—, —NR$^{11}$S(O)$_p$— and —NR$^{11}$S(O)$_p$NR$^{11}$—;

T is selected from —NR$^{11}$R$^{11}$, —NR$^{11}$(C=P)OR$^{11}$, —N$^{11}$(C=NR$^{11}$)NR$^{11}$R$^{11}$, and OR$^{11}$;

alternatively, one $R^{11}$ and one substituent selected from $R^{3a}$, $R^{3b}$, $R^{3c}$, $R^{3d}$, $R^{3e}$, $R^{3f}$, $R^{3g}$, $R^{3h}$, $R^{3i}$, and $R^{3j}$ are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

$R^9$ is selected from:

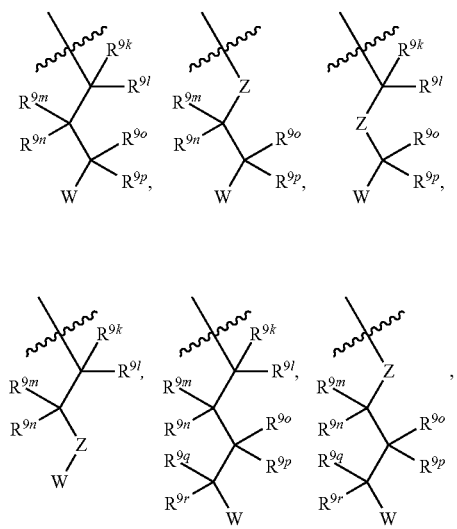

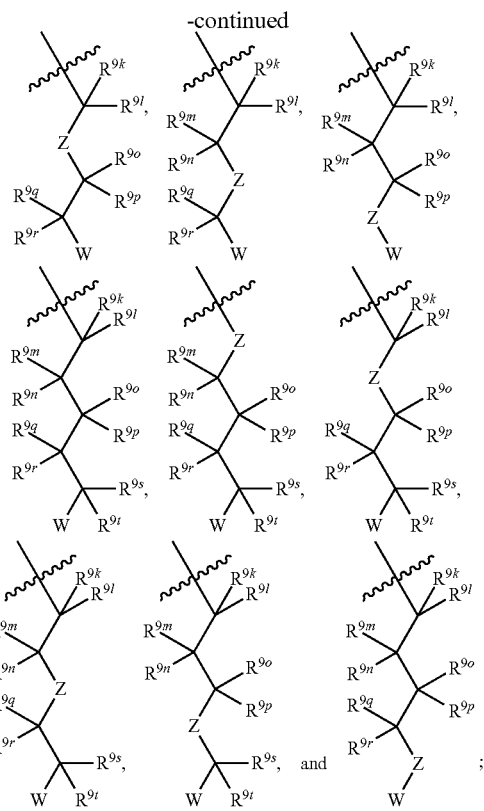

wherein $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are each independently selected from (a) hydrogen, (b) halogen, (c) —CH$_3$, (d) —CF$_3$, (e) —CF$_2$H, (f) —CFH$_2$, (g) —OCF$_3$, (h) —OCH$_3$, (i) —OCF$_2$H, (j) —OCFH$_2$, (k) —OR$_{11}$, (l) —C$_1$-C$_8$ alkyl, (m) haloalkyl, (n) -3-14 membered saturated, unsaturated, or aromatic heterocycle containing one or more heteroatoms selected from the group consisting of nitrogen, oxygen, and sulfur, and (o) -3-14 membered saturated, unsaturated, or aromatic carbocycle;

wherein each (l) through (o) is optionally substituted with one or more $R^{12}$;

alternatively, one or more pairs of substituents selected from $R^{9k}$ and $R^{9l}$, $R^{9m}$ and $R^{9n}$, $R^{9o}$ and $R^{9p}$, $R^{9q}$ and $R^{9r}$, and $R^{9s}$ and $R^{9t}$ are taken together with the carbon atom to which they are attached to form (a) -3-7 membered saturated or unsaturated carbocyclic, (b) -3-7 membered saturated or unsaturated heterocyclic ring containing one or more heteroatoms selected from the group consisting of nitrogen, oxygen, and sulfur, (c) an exo carbon-carbon double bond, (d) carbonyl group, and (e) thiocarbonyl group;

wherein each (a) through (c) is optionally substituted with one or more $R^{12}$;

alternatively, two substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on different carbon atoms are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

alternatively, two substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on two adjacent carbon atoms are taken together with the bond between said adjacent carbon atoms form a substituted or unsubstituted carbon-carbon double bond, or four substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on two adjacent carbon atoms are taken together with the bond between said adjacent carbon atoms form a carbon-carbon triple bond;

Z is selected from —O—, —S(O)$_p$—, —NR$^{11}$, —(C=O)—, —NR$^{11}$(C=O)—, —(C=O)NR$^{11}$—, —S(O)$_p$NR$^{11}$, —NR$^{11}$S(O)$_p$— and —NR$^{11}$S(O)$_p$NR$^{11}$—;

W is selected from —NR$^{11}$R$^{11}$, —NR$^{11}$(CO)OR$^{11}$, —NR$^{11}$(C=NR$^{11}$)NR$^{11}$R$^{11}$, and —OR$^{11}$;

alternatively, one $R^{11}$ and one substituent selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

$R^{12}$ is independently selected from (a) hydrogen, (b) halogen, (c) —CF$_3$, (d) —CF$_2$H, (e) —CFH$_2$, (f) —OH, (g) —SH, (h) —(C$_1$-C$_8$ alkyl)OH, (i) —OCF$_3$, (j) —OCH$_3$, (k) —OCF$_2$H, (l) —OCFH$_2$, (m) —O(C$_1$-C$_8$ alkyl), (n) —CN, (o) —NO$_2$, (p) —CONH$_2$, (q) —C(O)H, (r) —C(O)CH$_3$, (s) —S(O)$_p$CH$_3$, (t) —S(O)$_p$N(C$_1$-C$_8$ alkyl)$_2$, (u) —S(C$_1$-C$_8$ alkyl), (v) —C(O)OH, (w) —C(O)O(C$_1$-C$_8$ alkyl), (x) —N$_3$, (y) —NHC(O)(C$_1$-C$_8$ alkyl), (z) —N(C$_1$-C$_8$ alkyl)C(O)(C$_1$-C$_8$ alkyl), (aa) —NH$_2$, (bb) —NH(C$_1$-C$_8$ alkyl), (cc) —N(C$_1$-C$_8$ alkyl)$_2$, (dd) —C$_1$-C$_8$ alkyl, (ee) —C$_2$-C$_8$ alkenyl, (ff) —C$_2$-C$_8$ alkynyl, (gg) -haloalkyl, (hh) —(C$_1$-C$_8$ alkyl)-(3-14 membered saturated, unsaturated, or aromatic heterocycle containing one or more heteroatoms selected from the group consisting of nitrogen, oxygen, and sulfur), (ii) —(C$_1$-C$_8$ alkyl)-(3-14 membered saturated, unsaturated, or aromatic carbocycle), (jj) -3-14 membered saturated, unsaturated, or aromatic heterocycle containing one or more heteroatoms selected from the group consisting of nitrogen, oxygen, and sulfur, (kk) -3-14 membered saturated, unsaturated, or aromatic carbocycle, (ll) —(C=NH)NH$_2$, (mm) —C(O)NH (C$_1$-C$_8$ alkyl), (nn) —C(O)N(C$_1$-C$_8$ alkyl)$_2$, and (oo) —C(=NH)NH$_2$;

p is 0, 1, or 2; and t is 0, 1, or 2.

In addition, the invention provides methods of synthesizing the foregoing compounds and tautomers thereof, and pharmaceutically acceptable salts, esters and prodrugs of said compounds and tautomers. Following synthesis, an effective amount of one or more of the compounds or tautomers thereof, or pharmaceutically acceptable salts, esters or prodrugs of said compounds or tautomers can be formulated with a pharmaceutically acceptable carrier for administration to a human or animal for use as antimicrobial agents, particularly as antibacterial agents. In certain embodiments, the compounds of the present invention are useful for treating, preventing, or reducing the risk of microbial infections or for the manufacture of a medicament for treating, preventing, or reducing the risk of microbial infections. Accordingly, the compounds or tautomers thereof, or pharmaceutically acceptable salts, esters, or prodrugs of said compounds or tautomers or their formulations can be administered, for example, via oral, parenteral, intravenous, otic, ophthalmic, nasal, or topical routes, to provide an effective amount of the compound or tautomer thereof, or pharmaceutically acceptable salt, ester or prodrug of said compound or tautomer to the human or animal.

The foregoing and other aspects and embodiments of the invention can be more fully understood by reference to the following detailed description and claims.

DETAILED DESCRIPTION OF THE INVENTION

The present invention provides a family of compounds or tautomers thereof that can be used as antimicrobial agents, more particularly as antibacterial agents.

The present invention also includes pharmaceutically acceptable salts, esters, and prodrugs of said compounds and tautomers.

The compounds or tautomers thereof, or pharmaceutically acceptable salts, esters, or prodrugs of said compounds or tautomers described herein can have asymmetric centers. Compounds or tautomers thereof or pharmaceutically acceptable salts, esters, or prodrugs of said compounds or tautomers of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds or tautomers thereof, or pharmaceutically acceptable salts, esters, or prodrugs of said compounds or tautomers described herein, and all such stable isomers are contemplated in the present invention. Cis and trans geometric isomers of the compounds or tautomers thereof, or pharmaceutically acceptable salts, esters, or prodrugs of said compounds or tautomers of the present invention are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds or tautomers thereof, or pharmaceutically acceptable salts, esters, or prodrugs of said compounds or tautomers of the present invention and intermediates made therein are considered to be part of the present invention. All tautomers of shown or described compounds are also considered to be part of the present invention. Furthermore, the invention also includes metabolites of the compounds described herein.

The invention also comprehends isotopically-labeled compounds or tautomers thereof, or pharmaceutically acceptable salts, esters, or prodrugs of said compounds or tautomers, which are identical to those recited in formulae of the invention and following, but for the fact that one or more atoms are replaced by an atom having an atomic mass or mass number different from the atomic mass or mass number most commonly found in nature. Examples of isotopes that can be incorporated into compounds or tautomers thereof, or pharmaceutically acceptable salts, esters, or prodrugs of said compounds or tautomers of the invention include isotopes of hydrogen, carbon, nitrogen, fluorine, such as $^3$H, $^{11}$C, $^{14}$C and $^{18}$F.

Compounds or tautomers thereof, or pharmaceutically acceptable salts, esters, or prodrugs of said compounds or tautomers of the present invention that contain the aforementioned isotopes and/or other isotopes of other atoms are within the scope of the present invention. Isotopically-labeled compounds or tautomers thereof, or pharmaceutically acceptable salts, esters, or prodrugs of said compounds or tautomers of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and ⁸F isotopes are particularly useful in PET (positron emission tomography). PET is useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances, isotopically labeled compounds or tautomers thereof, or pharmaceutically acceptable salts, esters, or prodrugs of said compounds or tautomers having a formula of the invention can generally be prepared by carrying out the procedures disclosed in the Schemes and/or in the Examples below, by substituting a readily available isotopically labeled reagent for a non-isotopically labeled reagent. In one embodiment, the compounds or tautomers thereof, or pharmaceutically acceptable salts, esters, or prodrugs of said compounds or tautomers of the invention are not isotopically labelled.

When any variable (e.g., $R^{12}$) occurs more than one time in any constituent or formulae of the invention, its definition at each occurrence is independent of its definition at every other occurrence. Thus, for example, if a group is shown to be substituted with one or more $R^{12}$ moieties, then $R^{12}$ at each occurrence is selected independently from the definition of $R^{12}$. Also, combinations of substituents and/or variables are permissible, but only if such combinations result in stable compounds within a designated atom's normal valency.

A chemical structure showing a dotted line representation for a chemical bond indicates that the bond is optionally present. For example, a dotted line drawn next to a solid single bond indicates that the bond can be either a single bond or a double bond.

When a bond to a substituent is shown to cross a bond connecting two atoms in a ring, then such substituent can be bonded to any atom on the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

In cases wherein there are nitrogen atoms in the compounds or tautomers thereof, or pharmaceutically acceptable salts, esters, or prodrugs of said compounds or tautomers of the present invention, these, where appropriate, can be converted to N-oxides by treatment with an oxidizing agent (e.g., MCPBA and/or hydrogen peroxides). Thus, shown and claimed nitrogen atoms are considered to cover both the shown nitrogen and its N-oxide (N→O) derivative, as appropriate. In some embodiments, the present invention relates to N-oxides of the compounds or tautomers thereof, or pharmaceutically acceptable salts, esters, or prodrugs of said compounds or tautomers disclosed herein.

One approach to developing improved anti-proliferative and anti-infective agents is to provide modulators (for example, inhibitors) of ribosome function.

Ribosomes are ribonucleoproteins, which are present in both prokaryotes and eukaryotes. Ribosomes are the cellular organelles responsible for protein synthesis. During gene expression, ribosomes translate the genetic information encoded in a messenger RNA into protein (Garrett et al. (2000) "*The Ribosome: Structure, Function, Antibiotics and Cellular Interactions*," American Society for Microbiology, Washington, D.C.).

Ribosomes comprise two nonequivalent ribonucleoprotein subunits. The larger subunit (also known as the "large ribosomal subunit") is about twice the size of the smaller subunit (also known as the "small ribosomal subunit"). The small ribosomal subunit binds messenger RNA (mRNA) and mediates the interactions between mRNA and transfer RNA (tRNA) anticodons on which the fidelity of translation depends. The large ribosomal subunit catalyzes peptide bond formation, i.e. the peptidyl-transferase reaction of protein synthesis, and includes, at least, three different tRNA binding sites known as the aminoacyl, peptidyl, and exit sites. The aminoacyl site or A-site accommodates the incoming aminoacyl-tRNA that is to contribute its amino acid to the growing peptide chain. Also, the A space of the A-site is important. The peptidyl site or P-site accommodates the peptidyl-tRNA complex, i.e., the tRNA with its amino acid that is part of the growing peptide chain. The exit or E-site accommodates the deacylated tRNA after it has donated its amino acid to the growing polypeptide chain.

1. DEFINITIONS

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. A compound with one chiral center has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, J., *Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomers" refers to compounds whose structures differ markedly in arrangement of atoms, but which exist in easy and rapid equilibrium. It is to be understood that compounds of present invention may be depicted as different tautomers. It should also be understood that when compounds have tautomeric forms, all tautomeric forms are intended to be within the scope of the invention, and the naming of the compounds does not exclude any tautomer form.

Some compounds of the present invention can exist in a tautomeric form which is also intended to be encompassed within the scope of the present invention.

The compounds, pharmaceutically acceptable salts, esters and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers can be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs are: ketone-enol, amide-nitrile, lactam-lactim, amide-imidic acid tautomerism in heterocyclic rings (e.g. in the nucleobases guanine, thymine, and cytosine), amine-enamine and enamine-enamine. An example below is included for illustrative purposes, and the present invention is not limited to this example:

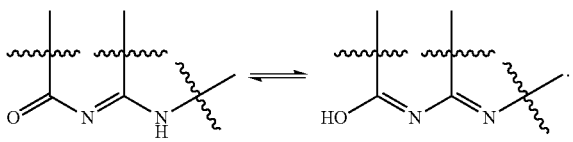

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "substituted," as used herein, means that any one or more hydrogens on the designated atom, usually a carbon, oxygen, or nitrogen atom, is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, N=N, etc.).

As used herein, the term "anomeric carbon" means the acetal carbon of a glycoside.

As used herein, the term "glycoside" is a cyclic acetal.

As used herein, "alkyl" is intended to include both branched and straight-chain saturated aliphatic hydrocarbon groups having the specified number of carbon atoms. For example $C_{1-4}$ is intended to include $C_1$, $C_2$, $C_3$, and $C_4$ $C_{1-6}$ alkyl is intended to include $C_1$, $C_2$, $C_3$, $C_4$, $C_5$, and $C_6$ alkyl groups and $C_{1-8}$ is intended to include $C_1$, $C_2$, $C_3$, $C_4$, $C_5$, $C_6$, $C_7$, and $C_8$. Some examples of alkyl include, but are not limited to, methyl, ethyl, n-propyl, i-propyl, n-butyl, s-butyl, t-butyl, n-pentyl, s-pentyl, n-hexyl, n-heptyl, and n-octyl.

As used herein, "alkenyl" is intended to include hydrocarbon chains of either straight or branched configuration and one or more unsaturated carbon-carbon bonds that can occur in any stable point along the chain, such as ethenyl and propenyl. For example $C_{2-6}$ alkenyl is intended to include $C_2$, $C_3$, $C_4$, $C_5$, and $C_6$ alkenyl groups and $C_{2-8}$ alkenyl is intended to include $C_2$, $C_3$, $C_4$, $C_5$, $C_6$, $C_7$, and $C_8$.

As used herein, "alkynyl" is intended to include hydrocarbon chains of either straight or branched configuration and one or more triple carbon-carbon bonds that can occur in any stable point along the chain, such as ethynyl and propynyl. For example, $C_{2-6}$ alkynyl is intended to include $C_2$, $C_3$, $C_4$, $C_5$, and $C_6$ alkynyl groups and $C_{2-8}$ alkynyl is intended to include $C_2$, $C_3$, $C_4$, $C_5$, $C_6$, $C_7$, and $C_8$.

Furthermore, "alkyl", "alkenyl", and "alkynyl" are intended to include moieties which are diradicals, i.e., having two points of attachment. A nonlimiting example of such an alkyl moiety that is a diradical is —CH$_2$CH$_2$—, i.e., a C$_2$ alkyl group that is covalently bonded via each terminal carbon atom to the remainder of the molecule. The alkyl diradicals are also known as "alkylenyl" radicals. The alkenyl diradicals are also known as "alkenylenyl" radicals. The alkynyl diradicals are also known as "alkynylenyl" radicals.

As used herein, "cycloalkyl" is intended to include saturated ring groups, such as cyclopropyl, cyclobutyl, or cyclopentyl. $C_{3-8}$ cycloalkyl is intended to include $C_3$, $C_4$, $C_5$, $C_6$, $C_7$, and $C_8$ cycloalkyl groups.

As used herein "counterion" is used to mean a positively or negatively charged species present in conjunction with an ion of opposite charge. A nonlimiting example of a counterion is an ion or ions present to counterbalance the charge or charges on an organic compound. Nonlimiting examples of counterions include chloride, bromide, hydroxide, acetate, sulfate, and ammonium.

As used herein, "halo" or "halogen" refers to fluoro, chloro, bromo, and iodo substituents.

As used herein, "haloalkyl" is intended to include both branched and straight-chain saturated aliphatic hydrocarbon groups having the specified number of carbon atoms, substituted with 1 or more halogen (for example —C$_v$F$_w$ wherein v=1 to 3 and w=1 to (2v+1)). Examples of haloalkyl include, but are not limited to, trifluoromethyl, trichloromethyl, pentafluoroethyl, and pentachloroethyl.

As used herein, "alkoxy" refers to an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "alkylthio" refers to an alkyl group as defined above with the indicated number of carbon atoms attached through a sulfur bridge. $C_{1-6}$ alkylthio, is intended to include $C_1$, $C_2$, $C_3$, $C_4$, $C_5$, and $C_6$ alkylthio groups. $C_{1-8}$ alkylthio, is intended to include $C_1$, $C_2$, $C_3$, $C_4$, $C_5$, $C_6$, $C_7$, and $C_8$ alkylthio groups.

As used herein, "carbocycle" or "carbocyclic ring" is intended to mean, unless otherwise specified, any stable 3, 4, 5, 6, 7, 8, 9, 10, 11, or 12-membered monocyclic, bicyclic or tricyclic ring, any of which can be saturated, unsaturated (including partially and fully unsaturated), or aromatic and said ring consists of carbon atoms in its core ring structure. Examples of such carbocycles or carbocyclic rings include, but are not limited to, cyclopropyl, cyclobutyl, cyclobutenyl, cyclopentyl, cyclopentenyl, cyclohexyl, cyclohexenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring can also be present on the bridge. Fused (e.g., naphthyl and tetrahydronaphthyl) and spiro rings are also included.

As used herein, the term "heterocycle" or "heterocyclic" ring means, unless otherwise stated, a stable 3, 4, 5, 6, 7, 8, 9, 10, 11, or 12-membered monocyclic, bicyclic or tricyclic ring which is saturated, unsaturated (including partially and fully unsaturated), or aromatic, and said ring consists of carbon atoms and one or more heteroatoms in its core ring structure, e.g., 1 or 1-2 or 1-3 or 1-4 or 1-5 or 1-6 heteroatoms, independently selected from nitrogen, oxygen, and sulfur, and including any bicyclic or tricyclic group in which any of the above-defined heterocyclic rings is fused or attached to a second ring (e.g., a benzene ring). The nitrogen and sulfur heteroatoms can optionally be oxidized (i.e., N→O and S(O)$_p$, wherein p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom can be substituted or unsubstituted (i.e., N or NR wherein R is H or another substituent, as defined). The heterocycle or heterocyclic ring can be attached to its pendant group at any heteroatom or carbon atom that results in a stable structure. The heterocycle or heterocyclic rings described herein can be substituted on carbon or on a nitrogen atom if the resulting compound is stable. A nitrogen in the heterocycle or heterocyclic ring can optionally be quaternized. Bridged rings are also included in the definition of heterocycle or heterocyclic ring. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. When a ring is bridged, the substituents recited for the ring can also be present on the bridge. Spiro and fused rings are also included.

As used herein, the term "aromatic heterocycle", "aromatic heterocylic" or "heteroaryl" ring is intended to mean a stable 5, 6, 7, 8, 9, 10, 11, or 12-membered monocyclic or bicyclic aromatic ring which consists of carbon atoms and one or more heteroatoms, e.g., 1 or 1-2 or 1-3 or 1-4 or 1-5 or 1-6 heteroatoms, independently selected from nitrogen, oxygen, and sulfur. In the case of bicyclic aromatic heterocyclic or heterocycle or heteroaryl rings, only one of the two rings needs to be aromatic (e.g., 2,3-dihydroindole), though both can be (e.g., quinoline). The second ring can also be fused or bridged as defined above for heterocycles. The nitrogen atom can be substituted or unsubstituted (i.e., N or NR wherein R is H or another substituent, as defined). The nitrogen and sulfur heteroatoms can optionally be oxidized (i.e., N→O and S(O)$_p$, wherein p=1 or 2). In certain compounds, the total number of S and O atoms in the aromatic heterocycle is not more than 1.

Examples of aromatic heterocycles, aromatic heterocyclics or heteroaryls include, but are not limited to, acridinyl, azabicyclooctanonyl, azepanyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, benzodioxoly, benzooxadiazoly, carbazolyl, 4aH-carbazolyl, carbolinyl, chromanyl, chromenyl, cinnolinyl, cycloheptyl, decahydroquinolinyl, dihydrobenzodioxinyl, 2H,6H-1,5,2-dithiazinyl, dihydrofuro[2,3-b]tetrahydrofuran, furanyl, furazanyl, imidazolidinyl, imidazolidinylimine, imidazolinyl, imidazolyl, imidazolonyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, methylbenztriazolyl, methylfuranyl, methylimidazolyl, methylthiazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolidinonyl, oxazolyl, oxindolyl, phenanthridinyl, phenanthrolinyl, phenazinyl, phenothiazinyl, phenoxathinyl, phenoxazinyl, phthalazinyl, piperazinyl, piperazinonyl, piperidinyl, piperidenyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridinonyl, pyridyl, pyrimidinyl, pyrroldionyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, thiomorpholinyldioxidyl, triazinyl, triazolopyrimidinyl, 1,2,3-triazolyl, 1,2,4-triazolyl, 1,2,5-triazolyl, 1,3,4-triazolyl, and xanthenyl.

As used herein, the phrase "pharmaceutically acceptable" refers to those compounds or tautomers thereof, or salts, esters, or prodrugs thereof, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds or tautomers thereof, wherein the parent compound or a tautomer thereof, is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound or a tautomer thereof formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present invention can be synthesized from the parent compound or a tautomer thereof that contains a basic or acidic moiety by conventional chemical methods. Generally, such pharmaceutically acceptable salts can be prepared by reacting the free acid or base forms of these compounds or tautomers thereof with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., USA, p. 1445 (1990).

Since prodrugs are known to enhance numerous desirable qualities of pharmaceuticals (e.g., solubility, bioavailability, manufacturing, etc.) the compounds or tautomers thereof of the present invention can be delivered in prodrug form. Thus, the present invention is intended to cover prodrugs of the presently claimed compounds or tautomers thereof, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound or a tautomer thereof in such a way that the modifications are cleaved, either in routine manipulation or in vivo, to the parent compound or a tautomer thereof. Prodrugs include compounds or tautomers thereof of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

As used herein, "stable compound" and "stable structure" are meant to indicate a compound that is sufficiently robust to survive isolation to a useful degree of purity from a reaction mixture, and formulation into an efficacious therapeutic agent.

As used herein, the term "patient", as used herein, means the human or animal (in the case of an animal, more typically a mammal) subject that would be subjected to a surgical or invasive medical procedure. Such patient or subject could be considered to be in need of the methods of treating, reducing the risk of or preventing the infection due to a surgical procedure or an invasive medical procedure. Such patient or subject can also be considered to be in need of peri-operative prophylaxis.

As used herein, the term "treating" means to provide a therapeutic intervention to cure or ameliorate an infection.

As used herein, the term "preventing", as used herein means, to completely or almost completely stop an infection from occurring, for example when the patient or subject is predisposed to an infection or at risk of contracting an infection. Preventing can also include inhibiting, i.e. arresting the development, of an infection.

As used herein, the term "reducing the risk of", as used herein, means to lower the likelihood or probability of an infection occurring, for example when the patient or subject is predisposed to an infection or at risk of contracting an infection.

As used herein, "unsaturated" refers to compounds having at least one degree of unsaturation (e.g., at least one multiple bond) and includes partially and fully unsaturated compounds.

As used herein, the term "effective amount" refers to an amount of a compound or a tautomer thereof, or a pharmaceutically acceptable salt, ester, or prodrug of said compound or tautomer, (including combinations of compounds and/or tautomers thereof, and/or pharmaceutically acceptable salts, esters, or prodrugs of said compound or tautomer), of the present invention that is effective when administered alone or in combination as an antimicrobial agent. For example, an effective amount refers to an amount of the compound or tautomer thereof, or a pharmaceutically acceptable salt, ester, or prodrug said compound or tautomer that is present in a composition, a formulation or on a medical device given to a recipient patient or subject sufficient to elicit biological activity, for example, anti-infective activity, such as e.g., anti-microbial activity, anti-bacterial activity, anti-fungal activity, anti-viral activity, or anti-parasitic activity.

The term "prophylactically effective amount" means an amount of a compound or a tautomer of said compound or tautomer, or a pharmaceutically acceptable salt, ester, or prodrug of said compound or tautomer (including combinations of compounds and/or tautomers thereof, and/or pharmaceutically acceptable salts, esters, or prodrugs thereof), of the present invention that is effective prophylactically when administered alone or in combination as an antimicrobial agent. For example, a prophylactically effective amount refers to an amount of the compound or tautomer thereof, or a pharmaceutically acceptable salt, ester, or prodrug of said compound or tautomer that is present in a composition, a formulation, or on a medical device given to a recipient patient or subject sufficient to prevent or reduce the risk of an infection due to a surgical procedure or an invasive medical procedure.

It is to be further understood that the representations for "Hydrogen Bond Acceptor—Hydrogen Bond Acceptor—Hydrogen Bond Donor" and "Hydrogen Bond Acceptor—Hydrogen Bond Acceptor—Hydrogen Bond Acceptor" are meant to indicate the relative orientation of the hydrogen bond acceptors and donor and not meant to limit that such groups are directly connected together as it is contemplated that additional atoms or groups of atoms can be included between such groups.

In the specification, the singular forms also include the plural, unless the context clearly dictates otherwise. Unless defined otherwise, all technical and scientific terms used herein have the same meaning as commonly understood by one of ordinary skill in the art to which this invention belongs.

In the case of conflict, the present specification will control. As used herein, "mammal" refers to human and non-human patients.

As used herein, the term "therapeutically effective amount" refers to an amount of a compound or a tautomer thereof or a pharmaceutically acceptable salt, ester, or prodrug of said compound or tautomer, (also including combinations of compounds and/or tautomers thereof, and/or pharmaceutically acceptable salts, esters, or prodrugs or said compounds or tautomers), of the present invention that is effective when administered alone or in combination as an antimicrobial agent. For example, a therapeutically effective amount refers to an amount of the compound or tautomer thereof, or a pharmaceutically acceptable salt, ester, or prodrug of said compound or tautomer that is present in a composition, a formulation, or on a medical device given to a recipient patient or subject in an amount sufficient to elicit biological activity, for example, anti-microbial activity, anti-fungal activity, anti-viral activity, anti-parasitic activity, anti-diarrheal activity, and/or anti-proliferative activity. In one aspect, the combination of compounds and/or tautomers thereof, and/or pharmaceutically acceptable salts, esters, or prodrugs or said compounds or tautomers is a synergistic combination. Synergy, as described, for example, by Chou and Talalay, Adv. Enzyme Regul. vol. 22, pp. 27-55 (1984), occurs when the effect of the compounds or tautomers thereof or pharmaceutically acceptable salts, esters, or prodrugs of said compounds or tautomers when administered in combination is greater than the additive effect of the compounds or tautomers thereof, or pharmaceutically acceptable salts, esters, or prodrugs of said compounds or tautomers when administered alone as a single agent. In general, a synergistic effect is most clearly demonstrated at sub-optimal concentrations of the compounds or tautomers thereof, or pharmaceutically acceptable salts, esters, or prodrugs of said compounds or tautomers. Synergy can be in terms of lower cytotoxicity, increased anti-proliferative and/or anti-infective effect, or some other beneficial effect of the combination compared with the individual components.

As used herein, the term "RNA microhelix binding site" refers to the ribofunctional locus of the large ribosomal subunit occupied by the RNA microhelix of Formula III. The RNA microhelix binding site defines at least a portion of or overlaps with the E-site.

As used herein, the term "A-site" refers to the ribofunctional locus occupied by an aminoacyl-tRNA molecule immediately prior to its participation in the peptide-bond forming reaction.

As used herein, the term "B-site" refers to the ribofunctional locus occupied by a deacylated tRNA molecule following its participation in the peptide-bond forming reaction.

As used herein, the term "P-site" refers to the ribofunctional locus occupied by a peptidyl-tRNA at the time it participates in the peptide-bond forming reaction.

As used herein, the term "A-space" refers to the portion of the A-site within the peptidyl transferase center in which the amino acid portion of the aminoacylated t-RNA binds, or alternatively the portion of the A-site in which the oxazolidinone ring of linezolid binds.

As used herein and in reference to a ribosome or ribosomal subunit, the terms "a portion of" or "a portion of the three-dimensional structure of" are understood to mean a portion of the three-dimensional structure of a ribosome or ribosomal subunit, including charge distribution and hydrophilicity/hydrophobicity characteristics, formed by at least three, more preferably at least three to ten, and most preferably at least ten amino acid residues and/or nucleotide residues of the ribosome or ribosomal subunit. The residues forming such a portion can be, for example, (i) contiguous residues based upon, for example, a primary sequence of a ribosomal RNA or ribosomal protein, (ii) residues which form a contiguous portion of the three-dimensional structure of the ribosome or ribosomal subunit, or (c) a combination thereof. As used herein and in reference to the RNA microhelix, the terms "a portion of" or "a portion of the three-dimensional structure of" are understood to mean a portion of the three-dimensional structure of RNA microhelix, including charge distribution and hydrophilicity/hydrophobicity characteristics, formed by at least three, more preferably at least three to ten atoms of one or more core residues of Formula III. The atoms forming such a portion can be, for example, (i) solvent inaccessible atoms buried within the core of the RNA microhelix, (ii) solvent accessible atoms of the RNA microhelix, or (iii) a combination thereof.

As used herein, the term ESBL is extended spectrum beta-lactamase. The term KPC is *Klebsiella pneumonia* carbapenemase.

As used herein, the term acute bacterial skin and skin structure infection (ABSSSI) encompasses complicated skin and skin structure infections (cSSSI) and complication skin and soft tissue infections (cSSTI), which have been used interchangeably. The terms uncomplicated skin and skin structure infections (uCSSSI) and uncomplicated skin and soft tissue infections (uCSSTI) have been used interchangeably.

As used herein, the term "spp." is the abbreviation for species.

As used herein, the term "formulae of the invention" includes one or more of the formulae:

IA, I, II, III, IV, V, VI, VII, VIII, IX, X, XI, XII, XIII, XIV, XV, XVI, XVII, XVIII, Va, VIIa, VIIa, VIIIa, IXa, Xa, XIa, XIIa, XIIIa, XIVa, XVa, XVIa, XVIIa, XVIIIa, XXa, XXa1, XXb, XXb1,

A1, A2, A3, A4, A5, A6, A7, B1, B2, B3, B4, B5, B6, B7, C1, C2, C3, C4, C5, C6, C7, D1, D2, D3, D4, D5, D6, D7, E1, E2, E3, E4, E5, E6, E7,

A1a, A2a, A3a, A4a, A5a, A6a, A7a, A8a, A9a, B1a, B2a, B3a, B4a, B5a, B6a, B7a, B8a, B9a, C1a, C2a, C3a, C4a, C5a, C6a, C7a, C8a, C9a,

D1a, D2a, D3a, D4a, D5a, D6a, D7a, D8a, D9a, E1a, E2a, E3a, E4a, E5a, E6a, E1a, E8a, F1, F2, G1, G2, G3, G4,

H1, H2, H3, H4, H5, H6, H7, H8, H9, H10, H11, H12, I1, I2, I3, I4, I5, I6, I7, I8, I9, I10, I11, and I12.

As used herein, the term "compound of the invention" includes one or more compounds of the formulae of the invention or a compound explicitly disclosed herein.

All percentages and ratios used herein, unless otherwise indicated, are by weight.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions can be conducted simultaneously.

2. COMPOUNDS OF THE INVENTION

In some embodiments, the present invention relates to a compound having the formula:

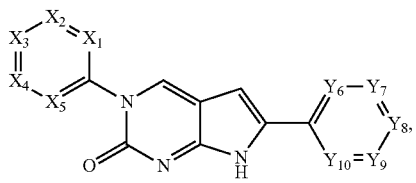

(IA)

or a tautomer thereof, or a pharmaceutically acceptable salt, ester, or prodrug of said compound or tautomer, wherein $X_1$ is $CR^1$ or N; $X_2$ is $CR^2$ or N; $X_3$ is $CR^3$ or N; $X_4$ is $CR^4$ or N; $X_5$ is $CR^5$ or N; with the proviso that $X_1$, $X_2$, $X_3$, $X_4$, and $X_5$ are not all N;

$Y_6$ is $CR^6$ or N; $Y_7$ is $CR^7$ or N; $Y_8$ is $CR^8$ or N; $Y_9$ is $CR^9$ or N; $Y_{10}$ is $CR^{10}$ or N; with the proviso that $Y_6$, $Y_7$, $Y_8$, $Y_9$, and $Y_{10}$ are not all N; wherein $R^1$, $R^2$, $R^4$, $R^5$, $R^6$, $R^7$, $R^8$ and $R^{10}$ are each independently selected from (a) hydrogen, (b) F, (c) Cl, (d) Br, (e) I, (f) —$CF_3$, (g) —$CF_2H$, (h) —$CFH_2$, (i) —$OCF_3$, (j) —$OCF_2H$, (k) —$OCFH_2$, (l) —$OCH_3$, (m) —CN, (n) —$N_3$, (o) —$NO_2$, (p) —$NR^{11}R^{11}$, (q) —$NR^{11}C(O)R^{11}$, (r) —$C(O)NR^{11}R^{11}$, (s) —$OR^{11}$, (t) —COH, (u) —$CO(C_1$-$C_8$ alkyl), (v) —$COR^{11}$, (w) —$NR^{11}(CNR^{11})NR^{11}R^{11}$, (x) —$S(O)_pR^{11}$, (y) —$NR^{11}S(O)_pR^{11}$, (z) —$SR^{11}$, (aa) —$SCF_3$, (bb) —$C(CF_3)H$—NH—$CHR^{11}R^{11}$, (cc) —$COOR^{11}$, (dd) —$(OCH_2CH_2)_tR^{11}$, (ee) —$(OCH_2CH_2)_tOR^{11}$, (ff) —$C_1$-$C_8$ alkyl, (gg) —$C_2$-$C_8$ alkenyl, (hh) —$C_2$-$C_8$ alkynyl, (ii) —($C_1$-$C_8$ alkyl)-(3-14 membered saturated, unsaturated, or aromatic heterocycle containing one or more heteroatoms selected from the group consisting of nitrogen, oxygen, and sulfur), (jj) —($C_1$-$C_8$ alkyl)-(3-14 membered saturated, unsaturated, or aromatic carbocycle), (kk) -haloalkyl, (ll) -3-14 membered saturated, unsaturated, or aromatic heterocycle containing one or more heteroatoms selected from the group consisting of nitrogen, oxygen, and sulfur, (mm) -3-14 membered saturated, unsaturated, or aromatic carbocycle, and (nn) —$CHR^{11}$—NH-(3-14 membered saturated, unsaturated, or aromatic heterocycle containing one of more heteroatoms selected from the group consisting of nitrogen, oxygen, and sulfur);

wherein each (ff) through (nn) is optionally substituted with one or more $R^{12}$;

alternatively, wherein two substituents selected from $R^6$, $R^7$, and $R^8$ are taken together with the carbon atom to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur; wherein each (a) through (b) is optionally substituted with one or more $R^{12}$;

each $R^{11}$ is independently selected from (a) hydrogen, (b) halogen, (c) —OH, (d) —SH, (e) —($C_1$-$C_8$ alkyl)OH, (f) —$OCF_3$, (g) —$OCF_2H$, (h) —$OCFH_2$, (i) —$OCH_3$, (j) —$OR^{12}$, (k) —$COR^{12}$, (l) —CN, (m) —$NO_2$, (n) —$CONH_2$, (o) —$CONR^{12}R^{12}$, (p) —$COCH_3$, (q) —$S(O)_pCH_3$, (r) —$S(O)_pNR^{12}R^{12}$, (s) —$SR^{12}$, (t) —C(O)OH, (u) —C(O)OR^{12}$, (v) —$N_3$, (w) —$NH_2$, (x) —$NR^{12}C(O)R^{12}$, (y) —NH($C_1$-$C_8$ alkyl), (z) —N($C_1$-$C_8$ alkyl)$_2$, (aa) —$C_1$-$C_8$ alkyl, (bb) —$C_2$-$C_8$ alkenyl, (cc) —$C_2$-$C_8$ alkynyl, (dd) -haloalkyl, (ee) —($C_1$-$C_8$ alkyl)-(3-14 membered saturated, unsaturated, or aromatic heterocycle containing one or more heteroatoms selected from the group consisting of nitrogen, oxygen, and sulfur), (ff) —($C_1$-$C_8$ alkyl)-(3-14 membered saturated, unsaturated, or aromatic carbocycle), (gg) -3-14 membered saturated, unsaturated, or aromatic heterocycle containing one or more heteroatoms selected from the group consisting of nitrogen, oxygen, and sulfur, (hh) -3-14 membered saturated, unsaturated, or aromatic carbocycle, and (ii) —(C=NH)$NR^{12}R^{12}$;

wherein each (y) through (hh) is optionally substituted with one or more $R^{12}$;

alternatively two $R^{11}$ substituents are taken together to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur, wherein each (a) through (b) is optionally substituted with one or more $R^{12}$;

$R^3$ is selected from:

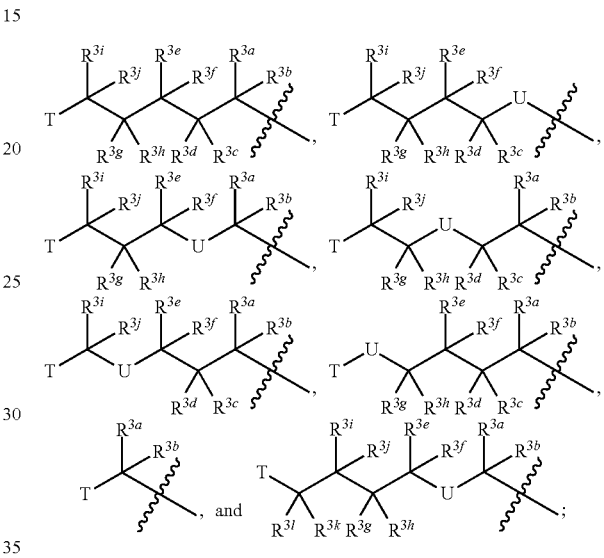

wherein $R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ are each independently selected from (a) hydrogen, (b) halogen, (c) —CN, (d) —$N_3$, (e) —$NO_2$, (f) —$OCF_3$, (g) —$OCF_2H$, (h) —$OCFH_2$, (i) —$OCH_3$, (j) —$OR^{11}$, (k) —$C(O)R^{11}$, (l) —$C(O)NR^{11}R^{11}$, (m) —$NH_2$, (n) —$NR^{11}R^{11}$, (o) —$NR^{11}C(O)R^{11}$, (p) —$S(O)_pR^{11}$, (q) —C(O)OH, (r) —C(O)OR^{11}$, (s) —$C_1$-$C_8$ alkyl, (t) —$C_2$-$C_8$ alkenyl, (u) —$C_2$-$C_8$ alkynyl, (v) haloalkyl, (w) -3-14 membered saturated, unsaturated, or aromatic heterocycle containing one or more heteroatoms selected from the group consisting of nitrogen, oxygen, and sulfur, and (x) -3-14 membered saturated, unsaturated, or aromatic carbocycle;

wherein each (s) through (x) is optionally substituted with one or more $R^{12}$;

alternatively, one or more pairs of substituents selected from $R^{3a}$ and $R^{3b}$, $R^{3c}$ and $R^{3d}$, $R^{3e}$ and $R^{3f}$, $R^{3g}$ and $R^{3h}$, $R^{3i}$ and $R^{3j}$, and $R^{3k}$ and $R^{3l}$ are taken together with the carbon atom to which they are attached to form (a) -3-7 membered saturated or unsaturated carbocyclic, (b) -3-7 membered saturated or unsaturated heterocyclic ring containing one or more heteroatoms selected from the group consisting of nitrogen, oxygen, and sulfur, (c) an exo carbon-carbon double bond, (d) carbonyl group, or (e) thiocarbonyl group;

wherein each (a) through (b) is optionally substituted with one or more $R^{12}$;

alternatively, wherein two substituents selected from $R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ on different carbon atoms are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

alternatively, wherein two substituents selected from $R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ on two adjacent carbon atoms are taken together with the bond between said adjacent carbon atoms form a substituted or unsubstituted carbon-carbon double bond, or wherein four substituents selected from $R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ on two adjacent carbon atoms are taken together with the bond between said adjacent carbon atoms form a carbon-carbon triple bond;

U is selected from —O—, —S(O)$_p$—, —NR$^{11}$—, —(C=O)—, —NR$^{11}$(C=O)—, —(C=O)NR$^{11}$—, S(O)$_p$NR$^{11}$—, —NR$^{11}$S(O)$_p$—, —NR$^{11}$S(O)$_p$NR$^{11}$—, and —NR$^{11}$C(O)NR$^{11}$—;

T is selected from —NR$^{11}$R$^{11}$, —NR$^{11}$(C=O)OR$^{11}$, —NR$^{11}$(C=NR$^{11}$)NR$^{11}$R$^{11}$, and OR$^{11}$;

alternatively, one $R^{11}$ and one substituent selected from $R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

$R^9$ is selected from:

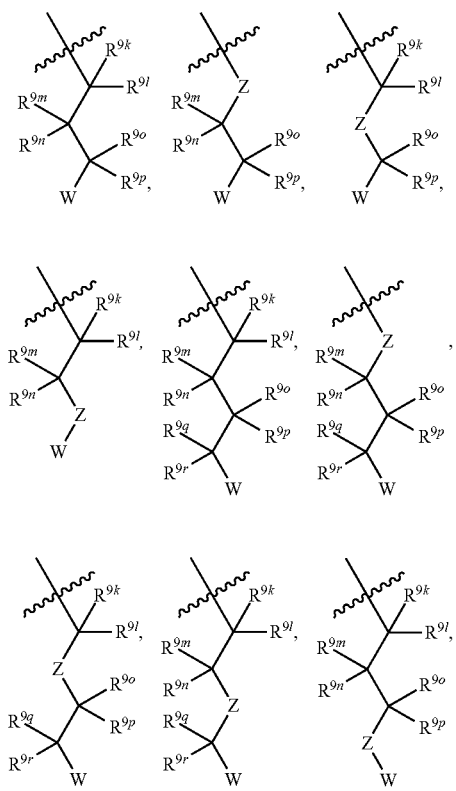

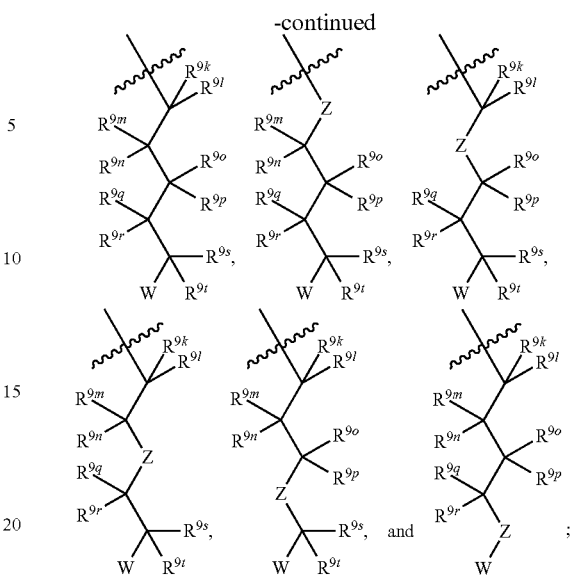

wherein $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are each independently selected from (a) hydrogen, (b) halogen, (c) —CN, (d) —N$_3$, (e) —NO$_2$, (f) —OCF$_3$, (g) —OCH$_3$, (h) —OCF$_2$H, (i) —OCFH$_2$, (j) —OR$^{11}$, (k) —NH$_2$, (l) —NR$^{11}$R$^{11}$, (m) —C(O)R$^{11}$, (n) —C(O)OR$^{11}$, (o) —C(O)NR$^{11}$R$^{11}$, (p) —NR$^{11}$C(O)R$^{11}$, (q) —S(O)$_p$R$^{11}$, (r) —C$_1$-C$_8$ alkyl, (s) —C$_2$-C$_8$ alkenyl, (t) —C$_1$-C$_8$ alkynyl, (u) haloalkyl, (v) -3-14 membered saturated, unsaturated, or aromatic heterocycle containing one or more heteroatoms selected from the group consisting of nitrogen, oxygen, and sulfur, and (w) -3-14 membered saturated, unsaturated, or aromatic carbocycle;

wherein each (r) through (w) is optionally substituted with one or more $R^{12}$;

alternatively, one or more pairs of substituents selected from $R^{9k}$ and $R^{9l}$, $R^{9m}$ and $R^{9n}$, $R^{9o}$ and $R^{9p}$, $R^{9q}$ and $R^{9r}$, and $R^{9s}$ and $R^{9t}$ are taken together with the carbon atom to which they are attached to form (a) 3-7 membered saturated or unsaturated carbocyclic, (b) 3-7 membered saturated or unsaturated heterocyclic ring containing one or more heteroatoms selected from the group consisting of nitrogen, oxygen, and sulfur, (c) an exo carbon-carbon double bond, (d) carbonyl group, or (e) thiocarbonyl group;

wherein each (a) through (c) is optionally substituted with one or more $R^{12}$;

alternatively, two substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on different carbon atoms are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

alternatively, two substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on two adjacent carbon atoms are taken together with the bond between said adjacent carbon atoms form a substituted or unsubstituted carbon-carbon double bond, or four substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on two adjacent carbon atoms are taken together with the bond between said adjacent carbon atoms form a carbon-carbon triple bond;

Z is selected from —O—, —S(O)$_p$—, —NR$^{11}$—, —(C=O)—, —NR$^{11}$(C=O)—, —(C=O)NR$^{11}$—, —S(O)$_p$NR$^{11}$—, —NR$^{11}$S(O)$_p$—, —NR$^{11}$S(O)$_p$NR$^{11}$—, and —NR$^{11}$C(O)NR$^{11}$—;

W is selected from —NR$^{11}$R$^{11}$, —NR$^{11}$(CO)OR$^{11}$, —NR$^{11}$(C=NR$^{11}$)NR$^{11}$R$^{11}$, and —OR$^{11}$;

alternatively, one R$^{11}$ and one substituent selected from R$^{9k}$, R$^{9l}$, R$^{9m}$, R$^{9n}$, R$^{9o}$, R$^{9p}$, R$^{9q}$, R$^{9r}$, R$^{9s}$, and R$^{9t}$ are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more R$^{12}$;

R$^{12}$ is independently selected from (a) hydrogen, (b) halogen, (c) —OH, (d) —SH, (e) —(C$_1$-C$_8$ alkyl)OH, (f) —OCF$_3$, (g) —OCH$_3$, (h) —OCF$_2$H, (i) —OCFH$_2$, (j) —O(C$_1$-C$_8$ alkyl), (k) —CN, (l) —NO$_2$, (m) —CONH$_2$, (n) C(O)NH(C$_1$-C$_8$ alkyl), (o) C(O)N(C$_1$-C$_8$ alkyl)$_2$, (p) —COH, (q) —COCH$_3$, (r) —S(O)$_p$CH$_3$, (s) —S(O)$_p$N(C$_1$-C$_8$ alkyl)$_2$, (t) —S(C$_1$-C$_8$ alkyl), (u) —C(O)OH, (v) —C(O)O(C$_1$-C$_8$ alkyl), (w) —N$_3$, (x) —NHC(O)(C$_1$-C$_8$ alkyl), (y) —N(C$_1$-C$_8$ alkyl)C(O)(C$_1$-C$_8$ alkyl), (z) —NH$_2$, (aa) —NH(C$_1$-C$_8$ alkyl), (bb) —N(C$_1$-C$_8$ alkyl)$_2$, (cc) —C$_1$-C$_8$ alkyl, (dd) —C$_2$-C$_8$ alkenyl, (ee) —C$_2$-C$_8$ alkynyl, (ff) -haloalkyl, (gg) —(C$_1$-C$_8$ alkyl)-(3-14 membered saturated, unsaturated, or aromatic heterocycle containing one or more heteroatoms selected from the group consisting of nitrogen, oxygen, and sulfur), (hh) —(C$_1$-C$_8$ alkyl)-(3-14 membered saturated, unsaturated, or aromatic carbocycle), (ii) -3-14 membered saturated, unsaturated, or aromatic heterocycle containing one or more heteroatoms selected from the group consisting of nitrogen, oxygen, and sulfur, (jj) -3-14 membered saturated, unsaturated, or aromatic carbocycle, (kk) —(C=NH)NH$_2$, (ll) —C(=NH)NH$_2$, (mm) —C(O)R$^{13}$, (nn) =O, and (oo) =NR$^{13}$;

wherein each (aa) through (jj) is optionally substituted with one or more R$^{13}$;

R$^{13}$ is independently selected from (a) hydrogen, (b) halogen, (c) —C$_1$-C$_8$ alkyl, (d) —C$_2$-C$_8$ alkenyl, (e) —C$_2$-C$_8$ alkynyl, (f) -haloalkyl, (g) —OH, (h) —OC$_1$-C$_8$ alkyl, (i) —OC$_2$-C$_8$ alkenyl, (j) —OC$_2$-C$_8$ alkynyl, (k) —OCF$_3$, (l) —OCH$_3$, (m) —OCF$_2$H, (n) —OCFH$_2$, (o) —NH$_2$, (p) —CN, (q) —N$_3$, (r) —S(O)$_p$C$_1$-C$_8$ alkyl, (s) -3-14 membered saturated, unsaturated, or aromatic heterocycle containing one or more heteroatoms selected from the group consisting of nitrogen, oxygen, and sulfur, and (t) -3-14 membered saturated, unsaturated, or aromatic carbocycle;

p is 0, 1, or 2; and t is 0, 1, or 2.

In some embodiments, the present invention relates to a compound or a tautomer thereof, or a pharmaceutically acceptable salt, ester, or prodrug of said compound or tautomer, having the formula:

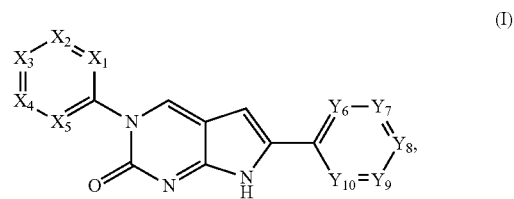

(I)

or a tautomer thereof, or a pharmaceutically acceptable salt, ester, or prodrug of said compound or tautomer, wherein $X_1$ is CR$^1$ or N; $X_2$ is CR$^2$ or N; $X_3$ is CR$^3$ or N; $X_4$ is CR$^4$ or N; $X_5$ is CR$^5$ or N; with the proviso that $X_1$, $X_2$, $X_3$, $X_4$, and $X_5$ are not all N;

$Y_6$ is CR$^6$ or N; $Y_7$ is CR$^7$ or N; $Y_8$ is CR$^8$ or N; $Y_9$ is CR$^9$ or N; $Y_{10}$ is CR$^{10}$ or N; with the proviso that $Y_6$, $Y_7$, $Y_8$, $Y_9$, and $Y_{10}$ are not all N; wherein R$^1$, R$^2$, R$^4$, R$^5$, R$^6$, R$^7$, R$^8$ and R$^{10}$ are each independently selected from (a) hydrogen, (b) F, (c) Cl, (d) Br, (e) I, (f) —CF$_3$, (g) —CF$_2$H, (h) —CFH$_2$, (i) —OCF$_3$, (j) —OCF$_2$H, (k) —OCFH$_2$, (l) —OCH$_3$, (m) —CN, (n) —N$_3$, (o) —NO$_2$, (p) —NR$^{11}$R$^{11}$, (q) —NR$^{11}$(CO)R$^{11}$, (r) —(CO)NR$^{11}$R$^{11}$, (s) —OR$^{11}$, (t) —COH, (u) —CO(C$_1$-C$_8$ alkyl), (v) —COR$^{11}$, (w) —NR$^{11}$(CNR$^{11}$)NR$^{11}$R$^{11}$, (x) —S(O)$_p$R$^{11}$, (y) —NR$^{11}$S(O)$_p$R$^{11}$, (z) —SR$^{11}$, (aa) —SCF$_3$, (bb) —C(CF$_3$)H—NH—CHR$^{11}$R$^{11}$, (cc) —COOR$^{11}$, (dd) —(OCH$_2$CH$_2$)$_t$R$^{11}$, (ee) —(OCH$_2$CH$_2$)$_t$OR$^{11}$, (ff) —C$_1$-C$_8$ alkyl, (gg) —C$_2$-C$_8$ alkenyl, (hh) —C$_2$-C$_8$ alkynyl, (ii) —(C$_1$-C$_8$ alkyl)-(3-14 membered saturated, unsaturated, or aromatic heterocycle containing one or more heteroatoms selected from the group consisting of nitrogen, oxygen, and sulfur), (jj) —(C$_1$-C$_8$ alkyl)-(3-14 membered saturated, unsaturated, or aromatic carbocycle), (kk) -haloalkyl, (ll) -3-14 membered saturated, unsaturated, or aromatic heterocycle containing one or more heteroatoms selected from the group consisting of nitrogen, oxygen, and sulfur, (mm) -3-14 membered saturated, unsaturated, or aromatic carbocycle, and (nn) —CHR$^{11}$—NH-(3-14 membered saturated, unsaturated, or aromatic heterocycle containing one of more heteroatoms selected from the group consisting of nitrogen, oxygen, and sulfur);

wherein each (ff) through (nn) is optionally substituted with one or more R$^{12}$;

each R$^{11}$ is independently selected from (a) hydrogen, (b) halogen, (c) —CF$_3$, (d) —CF$_2$H, (e) —CFH$_2$, (f) —OH, (g) —SH, (h) —(C$_1$-C$_8$ alkyl)OH, (i) —OCF$_3$, (j) —OCF$_2$H, (k) —OCFH$_2$, (l) —OCH$_3$, (m) —OR$^{12}$, (n) —COR$^{12}$, (o) —CN, (p) —NO$_2$, (q) —CONH$_2$, (r) —CONR$^{12}$R$^{12}$, (s) —C(O)CH$_3$, (t) —S(O)$_p$CH$_3$, (u) —S(O)$_p$NR$^{12}$R$^{12}$, (v) —SR$^{12}$, (w) —C(O)OH, (x) —C(O)OR$^{12}$, (y) —N$_3$, (z) —NH$_2$, (aa) —NR$^{12}$C(O)R$^{12}$, (bb) —NH(C$_1$-C$_8$ alkyl), (cc) —N(C$_1$-C$_8$ alkyl)$_2$, (dd) —C$_1$-C$_8$ alkyl, (ee) —C$_2$-C$_8$ alkenyl, (ff) —C$_2$-C$_8$ alkynyl, (gg) -haloalkyl, (hh) —(C$_1$-C$_8$ alkyl)-(3-14 membered saturated, unsaturated, or aromatic heterocycle containing one or more heteroatoms selected from the group consisting of nitrogen, oxygen, and sulfur), (ii) —(C$_1$-C$_8$ alkyl)-(3-14 membered saturated, unsaturated, or aromatic carbocycle), (jj) -3-14 membered saturated, unsaturated, or aromatic heterocycle containing one or more heteroatoms selected from the group consisting of nitrogen, oxygen, and sulfur, (kk) -3-14 membered saturated, unsaturated, or aromatic carbocycle, and (ll) —(C=NH)NR$^{12}$R$^{12}$;

wherein each (bb) through (kk) is optionally substituted with one or more R$^{12}$;

alternatively two R$^{11}$ substituents are taken together to form (a) 3-7 membered saturated or unsaturated carbocyclic or (b) 3-7 membered saturated or unsaturated heterocyclic ring containing one or more heteroatoms selected from the group consisting of nitrogen, oxygen, and sulfur, wherein each (a) through (b) is optionally substituted with one or more $R^{12}$;

$R^3$ is selected from:

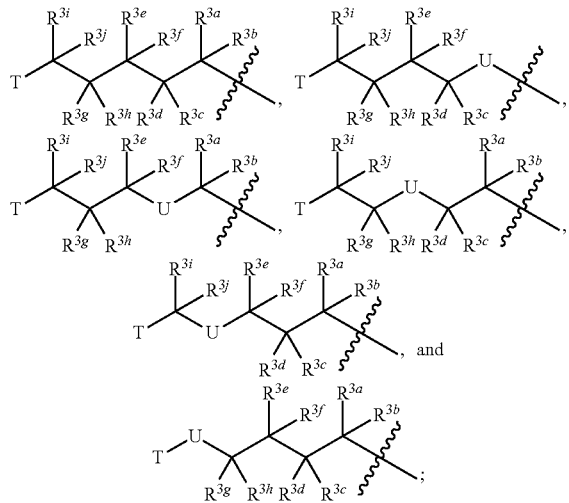

wherein $R^{3a}$, $R^{3b}$, $R^{3c}$, $R^{3d}$, $R^{3e}$, $R^{3f}$, $R^{3g}$, $R^{3h}$, $R^{3i}$, and $R^{3j}$ are each independently selected from (a) hydrogen, (b) halogen, (c) —$CH_3$, (d) —$CF_3$, (e) —$CF_2H$, (f) —$CFH_2$, (g) —$OCF_3$, (h) —$OCF_2H$, (i) —$OCFH_2$, (j) —$OCH_3$, (k) —$OR^{11}$, (l) —$C_1$-$C_8$ alkyl, (m) haloalkyl, (n) —3-14 membered saturated, unsaturated, or aromatic heterocycle containing one or more heteroatoms selected from the group consisting of nitrogen, oxygen, and sulfur, and (o) -3-14 membered saturated, unsaturated, or aromatic carbocycle;

wherein each (l) through (o) is optionally substituted with one or more $R^{12}$;

alternatively, one or more pairs of substituents selected from $R^{3a}$ and $R^{3b}$, $R^{3c}$ and $R^{3d}$, $R^{3e}$ and $R^{3f}$, $R^{3g}$ and $R^{3h}$, and $R^{3i}$ and $R^{3j}$ are taken together with the carbon atom to which they are attached to form (a) -3-7 membered saturated or unsaturated carbocyclic, (b) -3-7 membered saturated or unsaturated heterocyclic ring containing one or more heteroatoms selected from the group consisting of nitrogen, oxygen, and sulfur, (c) an exo carbon-carbon double bond, (d) carbonyl group, or (e) thiocarbonyl group;

wherein each (a) through (b) is optionally substituted with one or more $R^{12}$;

alternatively, wherein two substituents selected from $R^{3a}$, $R^{3b}$, $R^{3c}$, $R^{3d}$, $R^{3e}$, $R^{3f}$, $R^{3g}$, $R^{3h}$, $R^{3i}$, and $R^{3j}$ on different carbon atoms are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

alternatively, wherein two substituents selected from $R^{3a}$, $R^{3b}$, $R^{3c}$, $R^{3d}$, $R^{3e}$, $R^{3f}$, $R^{3g}$, $R^{3h}$, $R^{3i}$, and $R^{3j}$ on two adjacent carbon atoms are taken together with the bond between said adjacent carbon atoms form a substituted or unsubstituted carbon-carbon double bond, or wherein four substituents selected from $R^{3a}$, $R^{3b}$, $R^{3c}$, $R^{3d}$, $R^{3e}$, $R^{3f}$, $R^{3g}$, $R^{3h}$, $R^{3i}$, and $R^{3j}$ on two adjacent carbon atoms are taken together with the bond between said adjacent carbon atoms form a carbon-carbon triple bond;

U is selected from —O—, —$S(O)_p$—, —$NR^{11}$—, —(C=O)—, —$NR^{11}$(C=O)—, —(C=O)$NR^{11}$—, —$S(O)_p$ $NR^{11}$—, —$NR^{11}S(O)_p$— and —$NR^{11}S(O)_p$ $NR^{11}$—;

T is selected from —$NR^{11}R^{11}$, —$NR^{11}$(C=O)$OR^{11}$, —$NR^{11}$(C=$NR^{11}$)$NR^{11}R^{11}$, and $OR^{11}$;

alternatively, one $R^{11}$ and one substituent selected from $R^{3a}$, $R^{3b}$, $R^{3c}$, $R^{3d}$, $R^{3e}$, $R^{3f}$, $R^{3g}$, $R^{3h}$, $R^{3i}$, and $R^{3j}$ are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

$R^9$ is selected from:

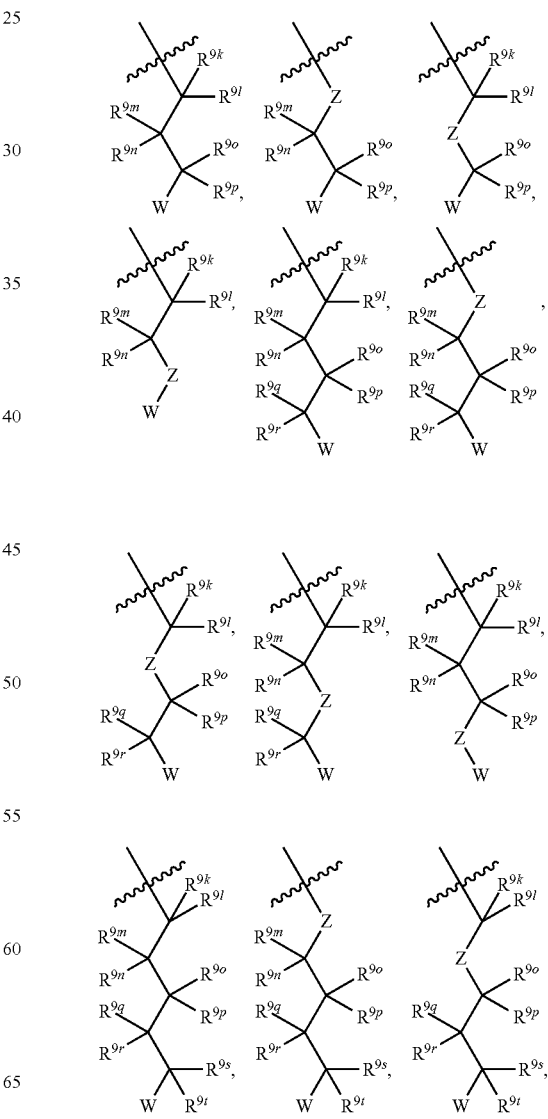

-continued

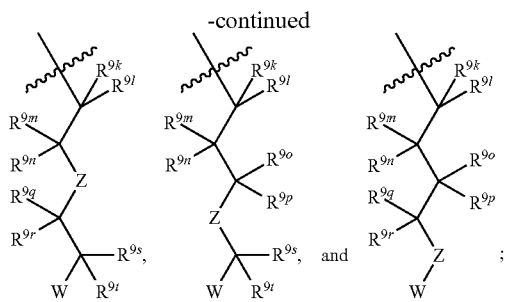

wherein $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are each independently selected from (a) hydrogen, (b) halogen, (c) —CH$_3$, (d) —CF$_3$, (e) —CF$_2$H, (f) —CFH$_2$, (g) —OCF$_3$, (h) —OCH$_3$, (i) —OCF$_2$H, (j) —OCFH$_2$, (k) —OR$^{11}$, (l) —C$_1$-C$_8$ alkyl, (m) haloalkyl, (n) -3-14 membered saturated, unsaturated, or aromatic heterocycle containing one or more heteroatoms selected from the group consisting of nitrogen, oxygen, and sulfur, and (o) -3-14 membered saturated, unsaturated, or aromatic carbocycle;

wherein each (l) through (o) is optionally substituted with one or more $R^{12}$;

alternatively, one or more pairs of substituents selected from $R^{9k}$ and $R^{9l}$, $R^{9m}$ and $R^{9n}$, $R^{9o}$ and $R^{9p}$, $R^{9q}$ and $R^{9r}$, and $R^{9s}$ and $R^{9t}$ are taken together with the carbon atom to which they are attached to form (a) -3-7 membered saturated or unsaturated carbocyclic, (b) -3-7 membered saturated or unsaturated heterocyclic ring containing one or more heteroatoms selected from the group consisting of nitrogen, oxygen, and sulfur, (c) an exo carbon-carbon double bond, (d) carbonyl group, and (e) thiocarbonyl group;

wherein each (a) through (c) is optionally substituted with one or more $R^{12}$;

alternatively, two substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on different carbon atoms are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

alternatively, two substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on two adjacent carbon atoms are taken together with the bond between said adjacent carbon atoms form a substituted or unsubstituted carbon-carbon double bond, or four substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on two adjacent carbon atoms are taken together with the bond between said adjacent carbon atoms form a carbon-carbon triple bond;

Z is selected from —O—, —S(O)$_p$—, —NR$^{11}$—, —NR$^{11}$(C═O)—, —(C═O)NR$^{11}$—, —S(O)$_p$NR$^{11}$—, —NR$^{11}$S(O)$_p$— and —NR$^{11}$S(O)$_p$NR$^{11}$—;

W is selected from —NR$^{11}$R$^{11}$, —NR$^{11}$(CO)OR$^{11}$, —NR$^{11}$(C═NR$^{11}$)NR$^{11}$R$^{11}$, and —OR$^{11}$;

alternatively, one R$^{11}$ and one substituent selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

$R^{12}$ is independently selected from (a) hydrogen, (b) halogen, (c) —CF$_3$, (d) —CF$_2$H, (e) —CFH$_2$, (O—OH, (g) —SH, (h) —(C$_1$-C$_8$ alkyl)OH, (i) —OCF$_3$, (j) —OCH$_3$, (k) —OCF$_2$H, (l) —OCFH$_2$, (m) —O(C$_1$-C$_8$ alkyl), (n) —CN, (o) —NO$_2$, (p) —CONH$_2$, (q) —C(O)H, (r) —C(O)CH$_3$, (s) —S(O)$_p$CH$_3$, (t) —S(O)$_p$N(C$_1$-C$_8$ alkyl)$_2$, (u) —S(C$_1$-C$_8$ alkyl), (v) —C(O)OH, (w) —C(O)O(C$_1$-C$_8$ alkyl), (x) —N$_3$, (y) —NHC(O)(C$_1$-C$_8$ alkyl), (z) —N(C$_1$-C$_8$ alkyl)C(O)(C$_1$-C$_8$ alkyl), (aa) (bb) —NH(C$_1$-C$_8$ alkyl), (cc) —N(C$_1$-C$_8$ alkyl)$_2$, (dd) —C$_1$-C$_8$ alkyl, (ee) —C$_2$-C$_8$ alkenyl, (ff) —C$_2$-C$_8$ alkynyl, (gg) -haloalkyl, (hh) —(C$_1$-C$_8$ alkyl)-(3-14 membered saturated, unsaturated, or aromatic heterocycle containing one or more heteroatoms selected from the group consisting of nitrogen, oxygen, and sulfur), (ii) —(C$_1$-C$_8$ alkyl)-(3-14 membered saturated, unsaturated, or aromatic carbocycle), (jj) -3-14 membered saturated, unsaturated, or aromatic heterocycle containing one or more heteroatoms selected from the group consisting of nitrogen, oxygen, and sulfur, (kk) -3-14 membered saturated, unsaturated, or aromatic carbocycle, (ll) —(C═NH)NH$_2$, (mm) —C(O)NH(C$_1$-C$_8$ alkyl), (nn) —C(O)N(C$_1$-C$_8$ alkyl)$_2$, and (oo) —C(═NH)NH$_2$;

p is 0, 1, or 2; and t is 0, 1, or 2.

In some embodiments, the present invention relates to a compound having the formula:

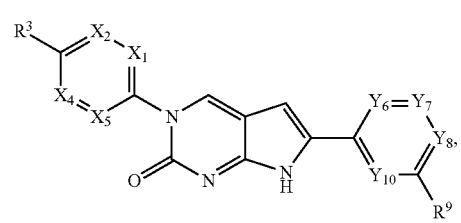

(II)

or a tautomer thereof, or a pharmaceutically acceptable salt, ester, or prodrug of said compound or tautomer, wherein $X_1$, $X_2$, $X_4$, $X_5$, $Y_6$, $Y_7$, $Y_8$, $Y_{10}$, $R^3$ and $R^9$ are as defined herein.

In some embodiments, the present invention relates to a compound having the formula:

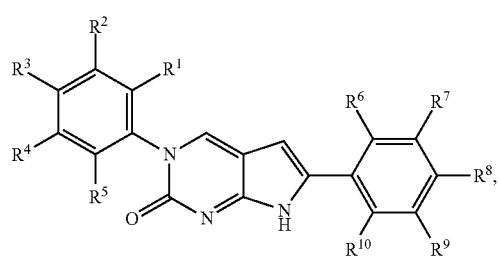

(III)

or a tautomer thereof, or a pharmaceutically acceptable salt, ester, or prodrug of said compound or tautomer, wherein $R^1$, $R^2$, $R^3$, $R^4$, $R^5$, $R^6$, $R^7$, $R^8$, $R^9$, and $R^{10}$ are as defined herein.

In some embodiments, the present invention relates to a compound having the formula:

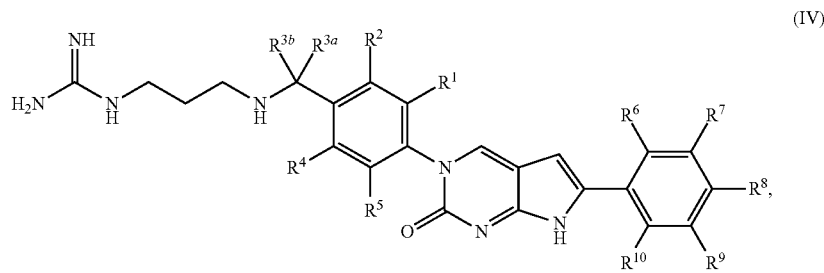

(IV)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^7$, $R^8$, $R^9$, and $R^{10}$ are as defined herein.

In some embodiments, the present invention relates to a compound having formula:

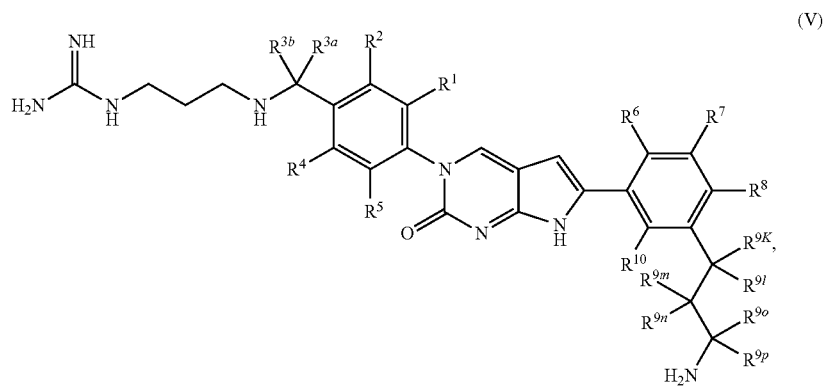

(V)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^7$, $R^8$, $R^{9k}$, $R^{9l}$, $R^{9m}$, $R^{9n}$, $R^{9o}$, $R^{9p}$, and $R^{10}$ are as defined herein.

In some embodiments, the present invention relates to a compound having formula:

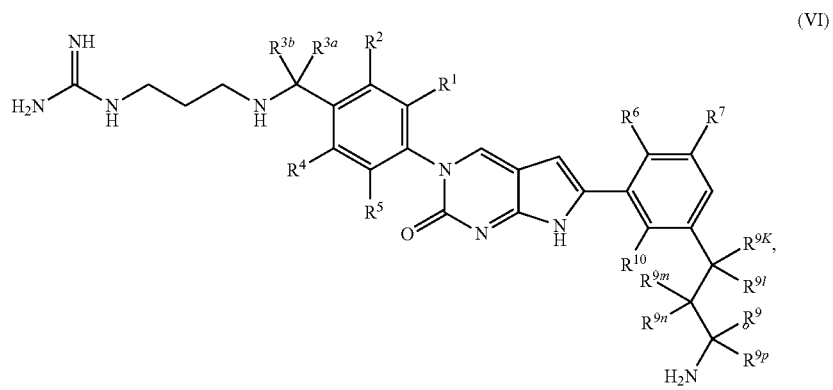

(VI)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^7$, $R^{9k}$, $R^{9l}$, $R^{9m}$, $R^{9n}$, $R^{9o}$, $R^{9p}$, and $R^{10}$ are as defined herein.

In some embodiments, the present invention relates to a compound having formula:

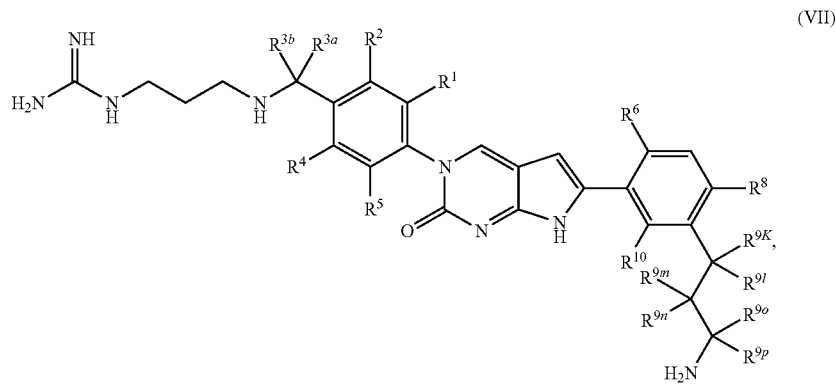

(VII)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^8$, $R^{9k}$, $R^{9l}$, $R^{9m}$, $R^{9n}$, $R^{9o}$, $R^{9p}$, and $R^{10}$ are as defined herein.

In some embodiments, the present invention relates to a compound having formula:

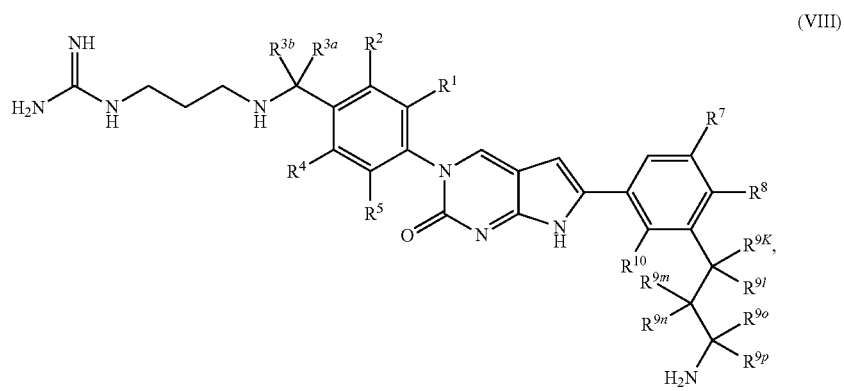

(VIII)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^7$, $R^8$, $R^{9k}$, $R^{9l}$, $R^{9m}$, $R^{9n}$, $R^{9o}$, $R^{9p}$, and $R^{10}$ are as defined herein.

In some embodiments, the present invention relates to a compound having formula:

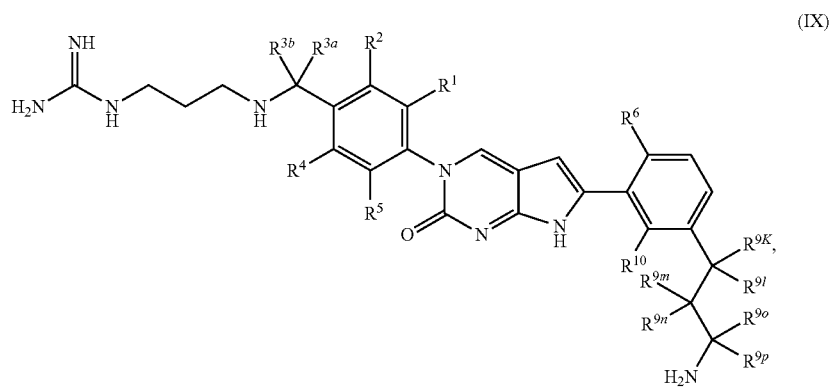

(IX)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^{9k}$, $R^{9l}$, $R^{9m}$, $R^{9n}$, $R^{9o}$, $R^{9p}$, and $R^{10}$ are as defined herein.

In some embodiments, the present invention relates to a compound having formula:

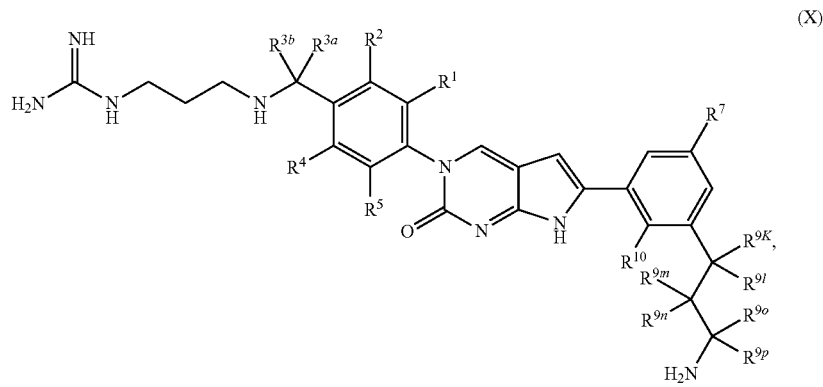

(X)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^7$, $R^{9k}$, $R^{9l}$, $R^{9m}$, $R^{9n}$, $R^{9o}$, $R^{9p}$, and $R^{10}$ are as defined herein.

In some embodiments, the present invention relates to a compound having formula:

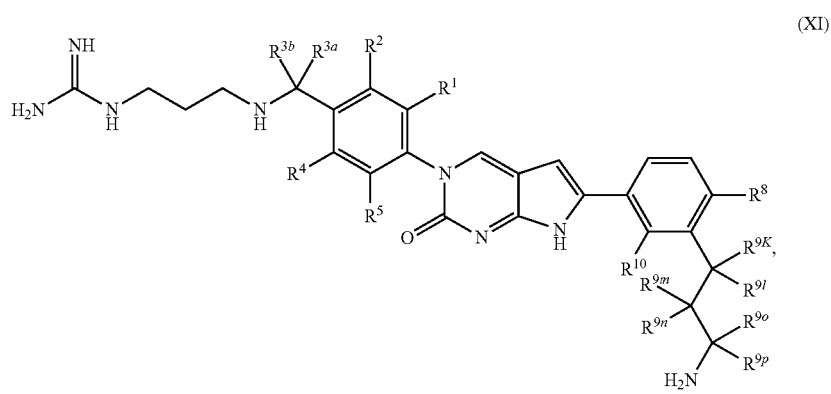

(XI)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^8$, $R^{9k}$, $R^{9l}$, $R^{9m}$, $R^{9n}$, $R^{9o}$, $R^{9p}$, and $R^{10}$ are as defined herein.

In some embodiments, the present invention relates to a compound having formula:

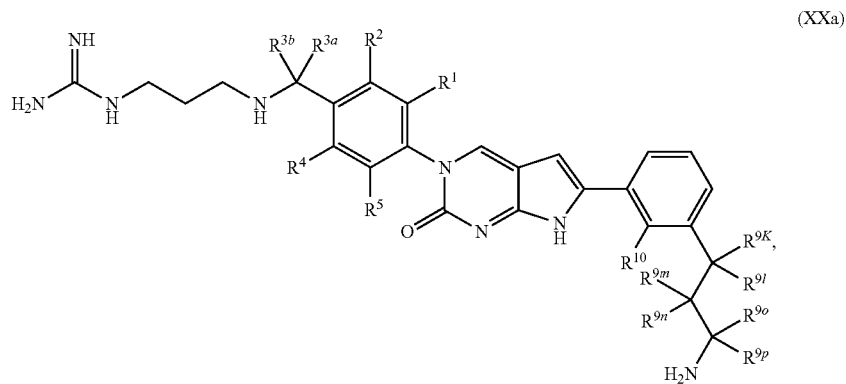

(XXa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^{9k}$, $R^{9l}$, $R^{9m}$, $R^{9n}$, $R^{9o}$, $R^{9p}$, and $R^{10}$ are as defined herein.

In some embodiments, the present invention relates to a compound having formula:

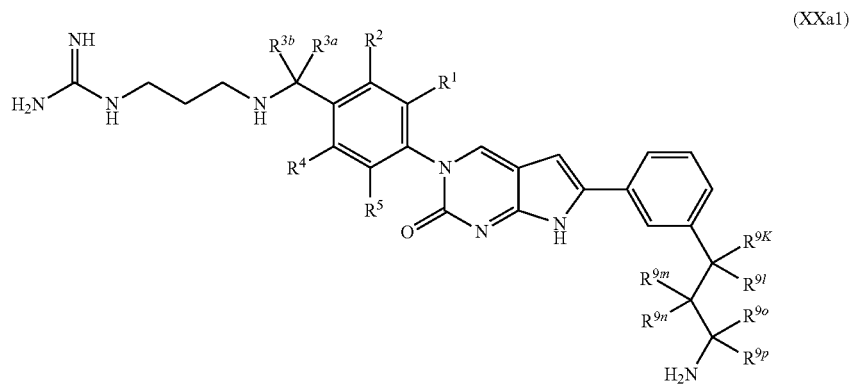

(XXa1)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^{9k}$, $R^{9l}$, $R^{9m}$, $R^{9n}$, $R^{9o}$, and $R^9$ are as defined herein.

In some embodiments, the present invention relates to a compound having formula:

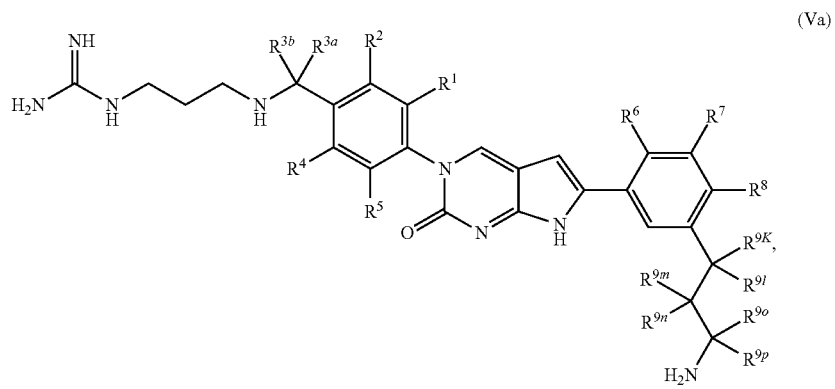

(Va)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^7$, $R^8$, $R^{9k}$, $R^{9l}$, $R^{9m}$, $R^{9n}$, $R^{9o}$, and $R^{9p}$ are as defined herein.

In some embodiments, the present invention relates to a compound having formula:

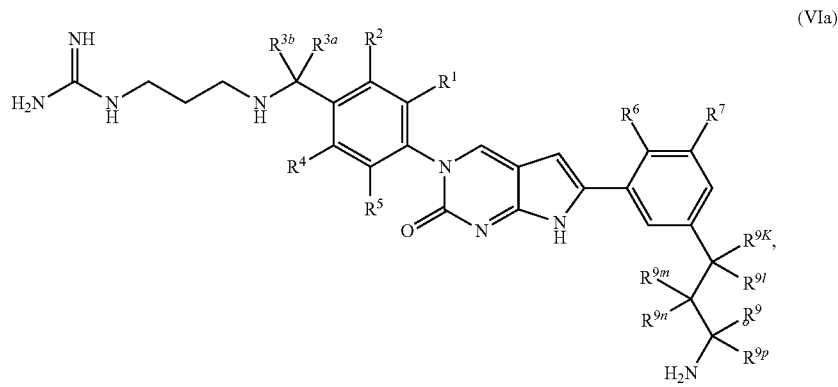

(VIa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^7$, $R^{9k}$, $R^{9l}$, $R^{9m}$, $R^{9n}$, $R^{9o}$, and $R^{9p}$ are as defined herein.

In some embodiments, the present invention relates to a compound having formula:

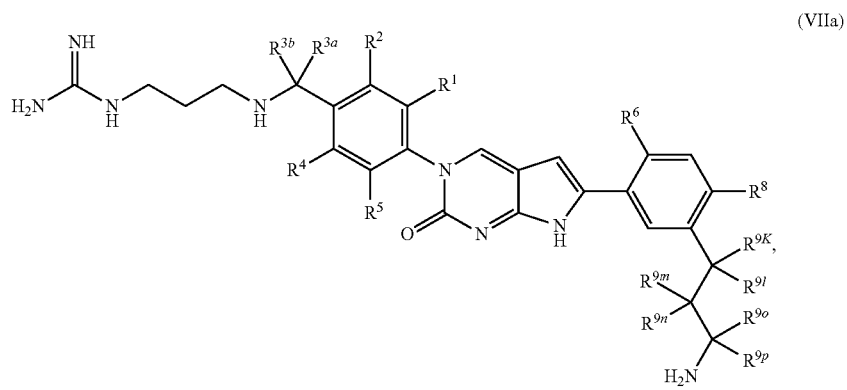

(VIIa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^8$, $R^{9k}$, $R^{9l}$, $R^{9m}$, $R^{9n}$, $R^{9o}$, and $R^{9p}$ are as defined herein.

In some embodiments, the present invention relates to a compound having formula:

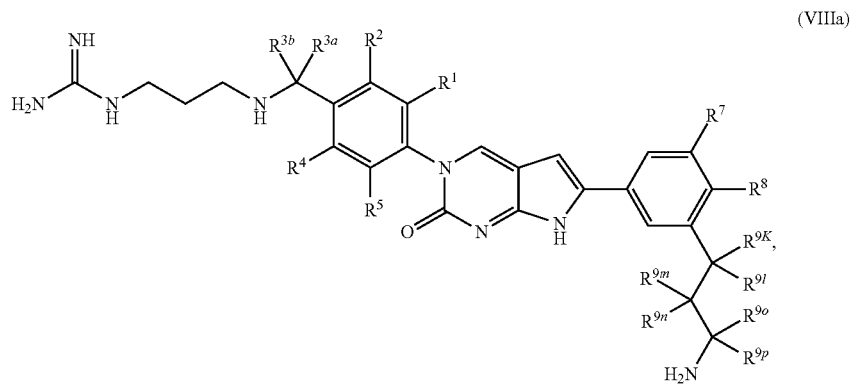

(VIIIa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^7$, $R^8$, $R^{9k}$, $R^{9l}$, $R^{9m}$, $R^{9n}$, $R^{9o}$, and $R^{9p}$ are as defined herein.

In some embodiments, the present invention relates to a compound having formula:

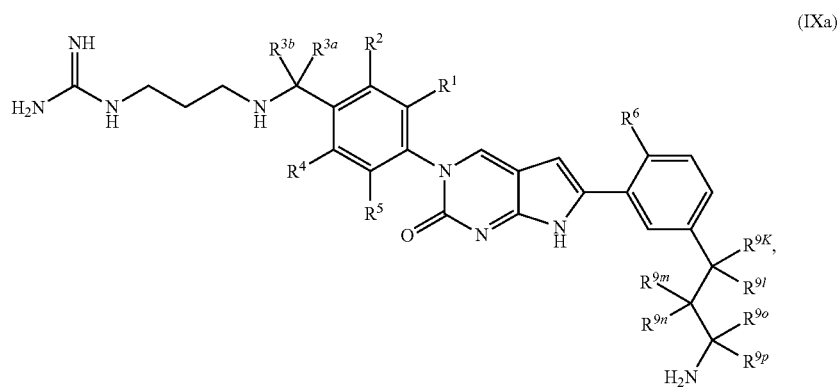

(IXa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^{9k}$, $R^{9l}$, $R^{9m}$, $R^{9n}$, $R^{9o}$, and $R^{9p}$ are as defined herein.

In some embodiments, the present invention relates to a compound having formula:

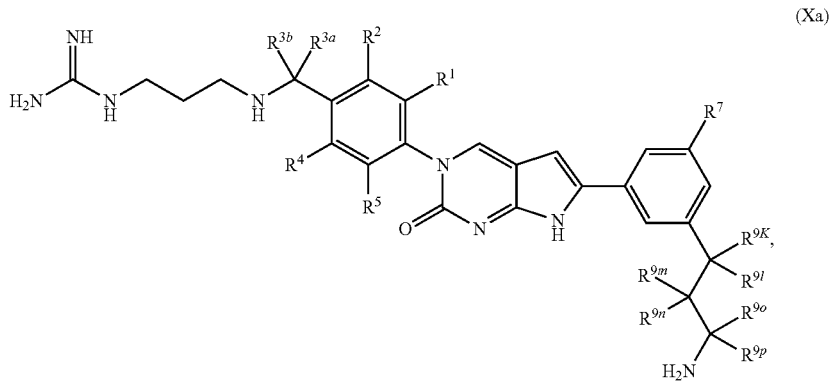

(Xa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^7$, $R^{9k}$, $R^{9l}$, $R^{9m}$, $R^{9n}$, $R^{9o}$, and $R^{9p}$ are as defined herein.

In some embodiments, the present invention relates to a compound having formula:

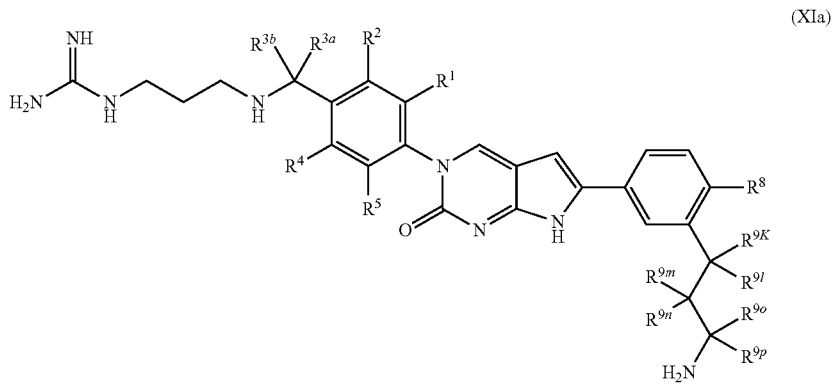

(XIa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^8$, $R^{9k}$, $R^{9l}$, $R^{9m}$, $R^{9n}$, $R^{9o}$, and $R^{9p}$ are as defined herein.

In some embodiments, the present invention relates to a compound having formula:

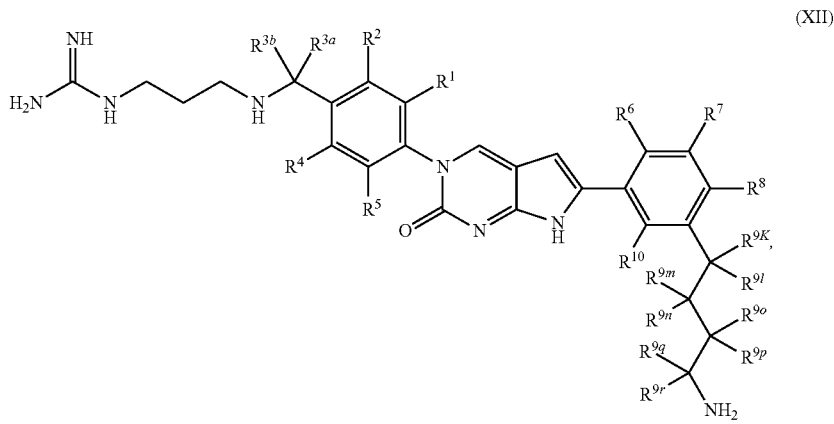

(XII)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^7$, $R^8$, $R^{9k}$, $R^{9l}$, $R^{9m}$, $R^{9n}$, $R^{9o}$, $R^{9p}$, $R^{9q}$, $R^{9r}$, and $R^{10}$ are as defined herein.

In some embodiments, the present invention relates to a compound having formula:

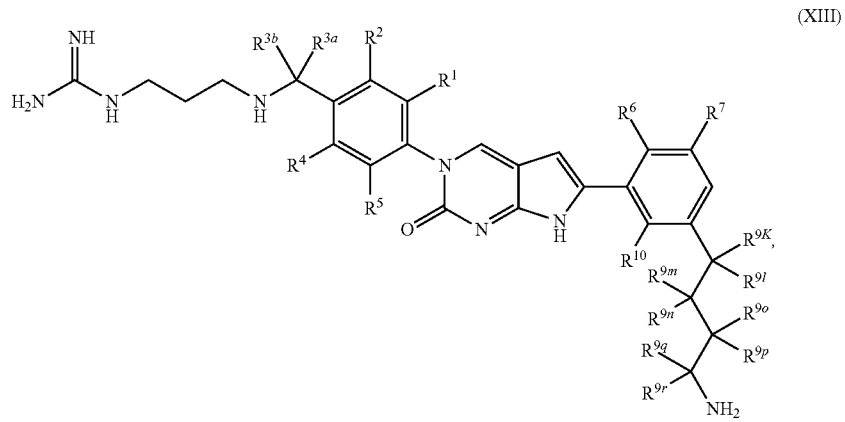

(XIII)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^7$, $R^{9k}$, $R^{9l}$, $R^{9m}$, $R^{9n}$, $R^{9o}$, $R^{9p}$, $R^{9q}$, $R^{9r}$, and $R^{10}$ are as defined herein.

In some embodiments, the present invention relates to a compound having formula:

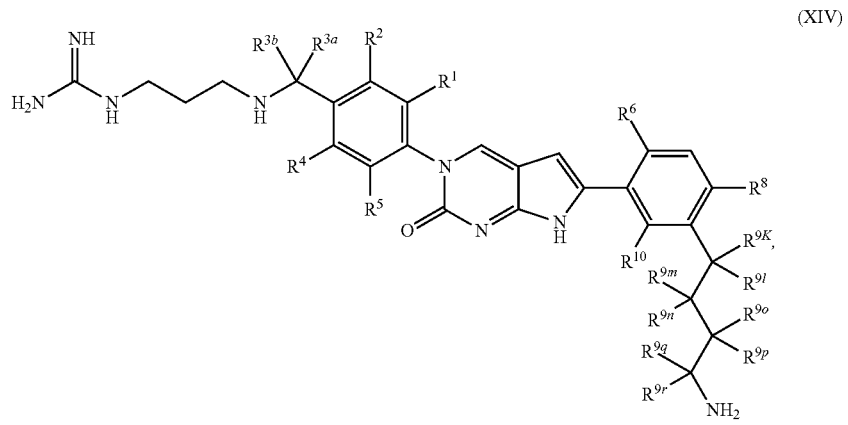

(XIV)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^8$, $R^{9k}$, $R^{9l}$, $R^{9m}$, $R^{9n}$, $R^{9o}$, $R^{9p}$, $R^{9q}$, $R^{9r}$, and $R^{10}$ are as defined herein.

In some embodiments, the present invention relates to a compound having formula:

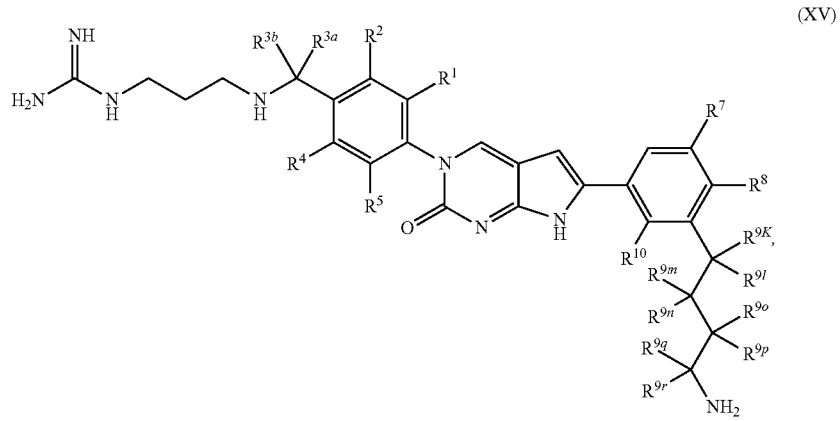

(XV)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^7$, $R^8$, $R^{9k}$, $R^{9l}$, $R^{9m}$, $R^{9n}$, $R^{9o}$, $R^{9p}$, $R^{9q}$, $R^{9r}$, and $R^{10}$ are as defined herein.

In some embodiments, the present invention relates to a compound having formula:

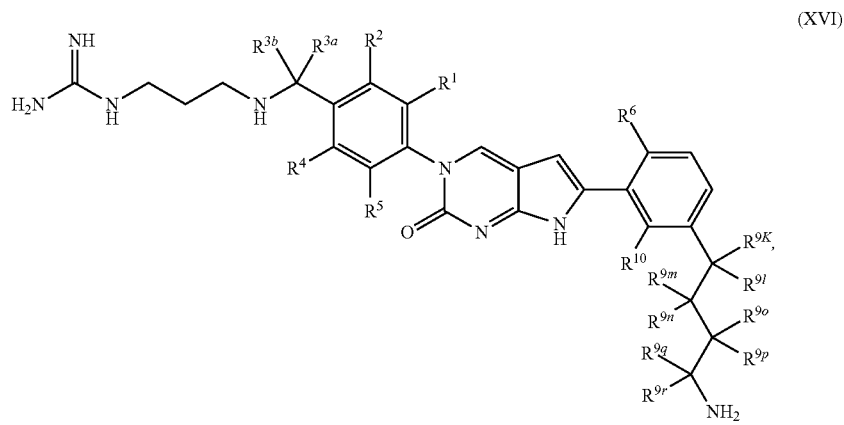

(XVI)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^{9k}$, $R^{9l}$, $R^{9m}$, $R^{9n}$, $R^{9o}$, $R^{9p}$, $R^{9q}$, $R^{9r}$, and $R^{10}$ are as defined herein.

In some embodiments, the present invention relates to a compound having formula:

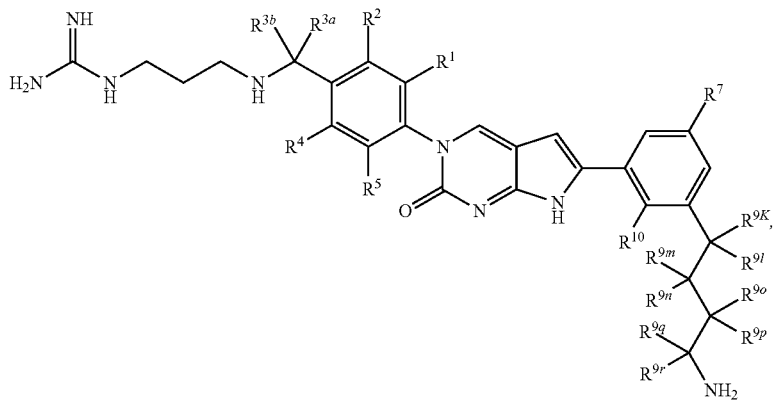

(XVII)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^7$, $R^{9k}$, $R^{9l}$, $R^{9m}$, $R^{9n}$, $R^{9o}$, $R^{9p}$, $R^{9q}$, $R^{9r}$, and $R^{10}$ are as defined herein.

In some embodiments, the present invention relates to a compound having formula:

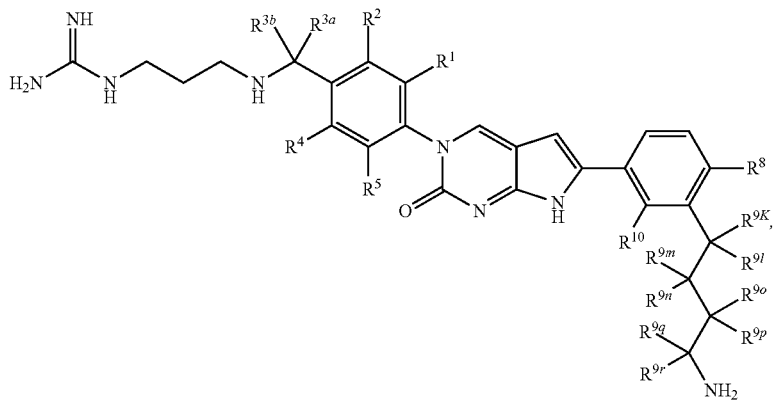

(XVIII)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^8$, $R^{9k}$, $R^{9l}$, $R^{9m}$, $R^{9n}$, $R^{9o}$, $R^{9p}$, $R^{9q}$, $R^{9r}$, and $R^{10}$ are as defined herein.

In some embodiments, the present invention relates to a compound having formula:

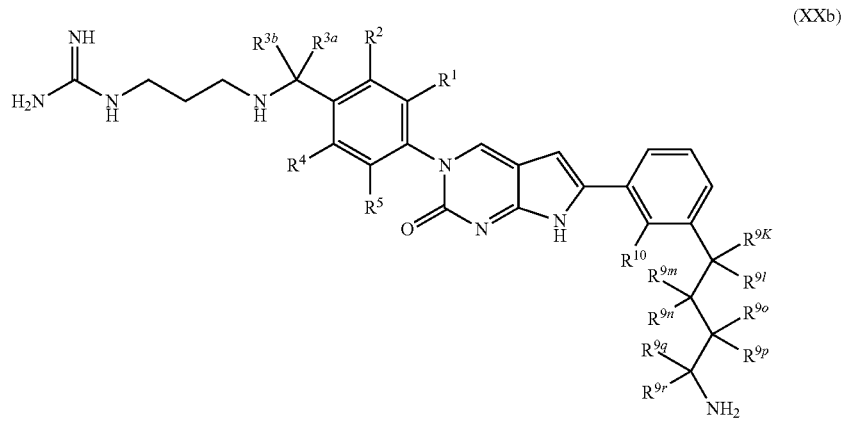

(XXb)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^{9k}$, $R^{9l}$, $R^{9m}$, $R^{9n}$, $R^{9o}$, $R^{9p}$, $R^{9q}$, $R^{9r}$, and $R^{10}$ are as defined herein.

In some embodiments, the present invention relates to a compound having formula:

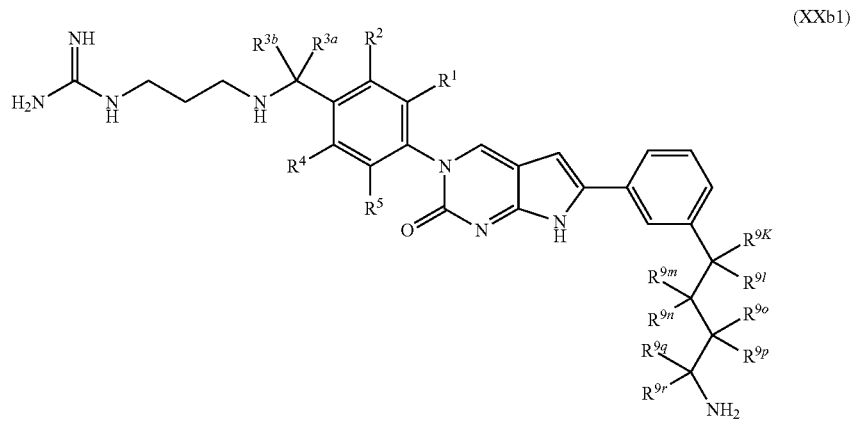

(XXb1)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^{9k}$, $R^{9l}$, $R^{9m}$, $R^{9n}$, $R^{9o}$, $R^{9p}$, $R^{9q}$, and $R^{9r}$ are as defined herein.

In some embodiments, the present invention relates to a compound having formula:

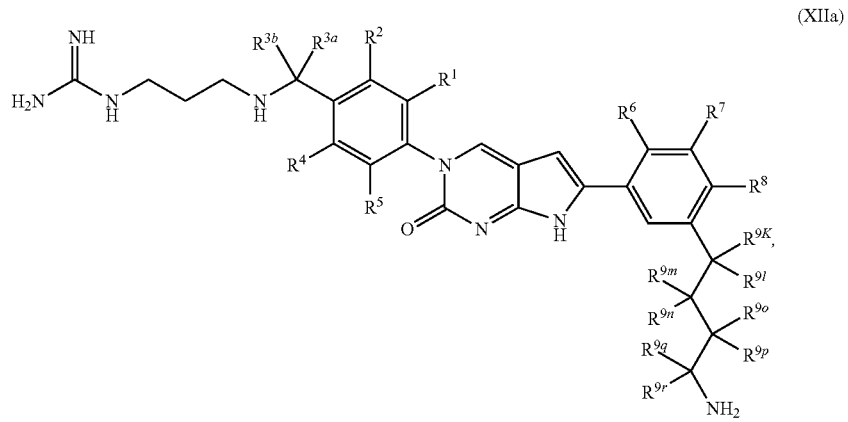

(XIIa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^7$, $R^8$, $R^{9k}$, $R^{9l}$, $R^{9m}$, $R^{9n}$, $R^{9o}$, $R^{9p}$, $R^{9q}$, and $R^{9r}$ are as defined herein.

In some embodiments, the present invention relates to a compound having formula:

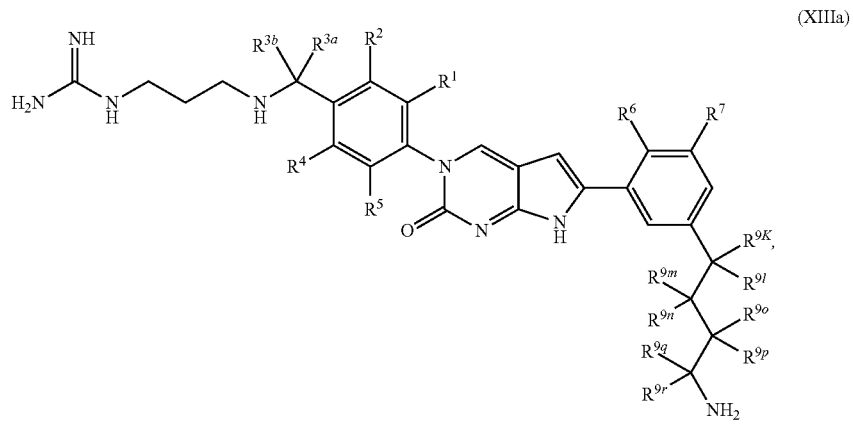

(XIIIa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^7$, $R^{9k}$, $R^{9l}$, $R^{9m}$, $R^{9n}$, $R^{9o}$, $R^{9p}$, $R^{9q}$, and $R^{9r}$ are as defined herein.

In some embodiments, the present invention relates to a compound having formula:

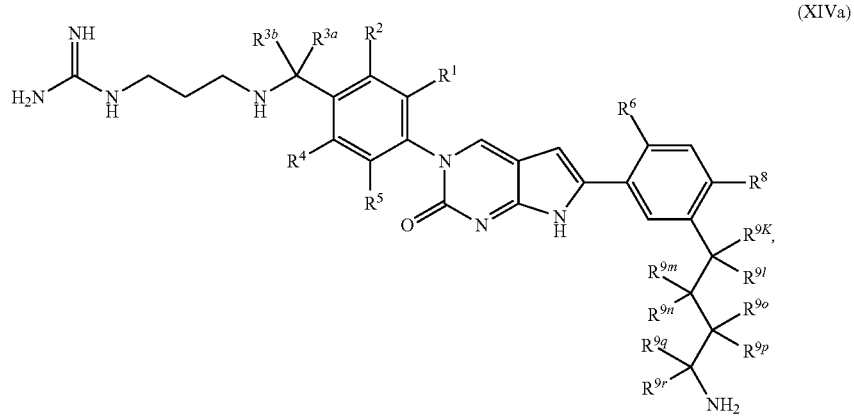

(XIVa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^8$, $R^{9k}$, $R^{9l}$, $R^{9m}$, $R^{9n}$, $R^{9o}$, $R^{9p}$, $R^{9q}$, and $R^{9r}$ are as defined herein.

In some embodiments, the present invention relates to a compound having formula:

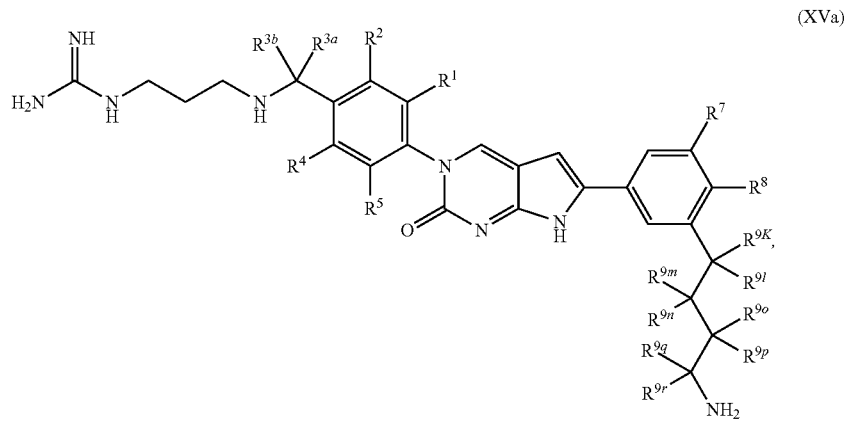

(XVa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^7$, $R^8$, $R^{9k}$, $R^{9l}$, $R^{9m}$, $R^{9n}$, $R^{9o}$, $R^{9p}$, $R^{9q}$, and $R^{9r}$ are as defined herein.

In some embodiments, the present invention relates to a compound having formula:

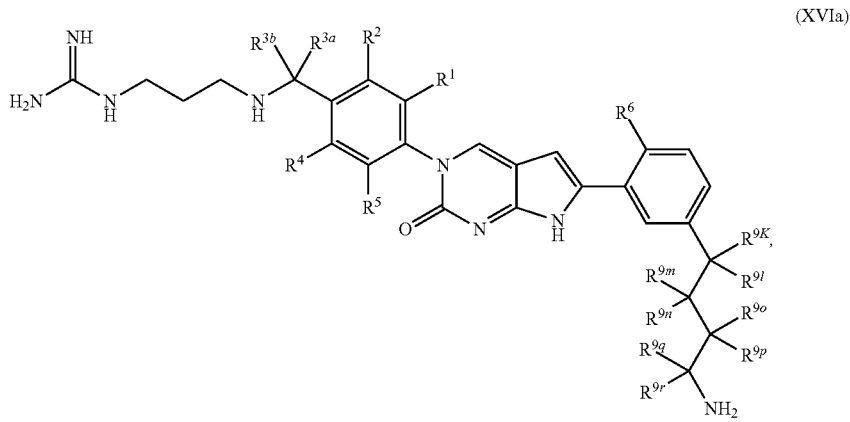

(XVIa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^6$, $R^{9k}$, $R^{9l}$, $R^{9m}$, $R^{9n}$, $R^{9o}$, $R^{9p}$, $R^{9q}$, and $R^{9r}$ are as defined herein.

In some embodiments, the present invention relates to a compound having formula:

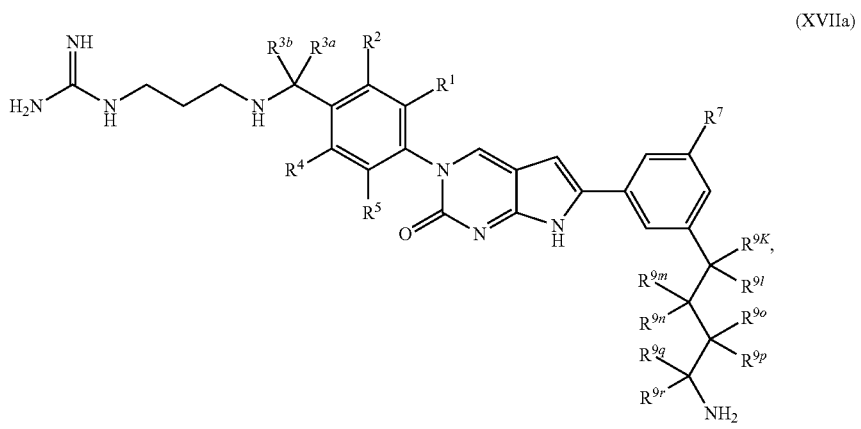

(XVIIa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^7$, $R^{9k}$, $R^{9l}$, $R^{9m}$, $R^{9n}$, $R^{9o}$, $R^{9p}$, $R^{9q}$, and $R^{9r}$ are as defined herein.

In some embodiments, the present invention relates to a compound having formula:

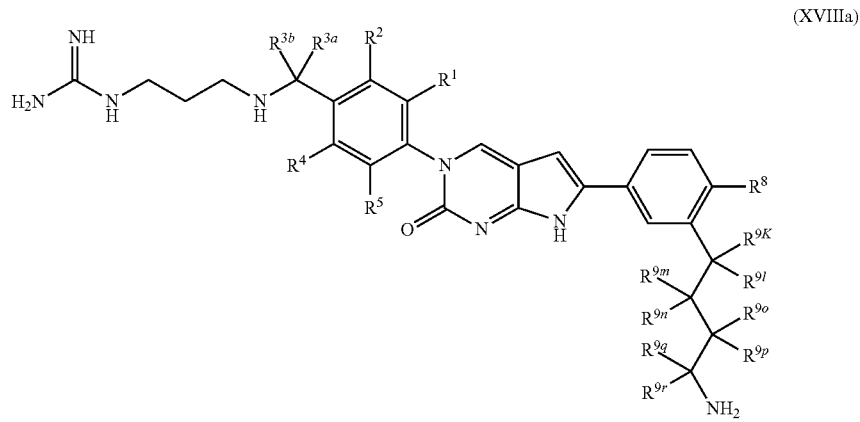

(XVIIIa)

or a tautomer thereof, or a pharmaceutically acceptable salt, ester, or prodrug of said compound or tautomer, wherein $R^1$, $R^2$, $R^{3a}$, $R^{3b}$, $R^4$, $R^5$, $R^8$, $R^{9k}$, $R^{9l}$, $R^{9m}$, $R^{9n}$, $R^{9o}$, $R^{9p}$, $R^{9q}$, and $R^{9r}$ are as defined herein.

In some embodiments, the present invention relates to a compound or a tautomer thereof, or a pharmaceutically acceptable salt, ester, or prodrug of said compound or tautomer, according to any formulae of the invention, wherein at least one substituent selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ is not hydrogen.

In some embodiments, the present invention relates to a compound or a tautomer thereof, or a pharmaceutically acceptable salt, ester, or prodrug of said compound or tautomer, according to any formulae of the invention, wherein at least two substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are not hydrogen.

In some embodiments, the present invention relates to a compound or a tautomer thereof, or a pharmaceutically acceptable salt, ester, or prodrug of said compound or tautomer, according to any formulae of the invention, wherein $R^1$, $R^2$, $R^4$ and $R^5$ are each independently selected from hydrogen and F. In some embodiments, $R^1$, $R^2$, $R^4$, and $R^5$ are each hydrogen.

In some embodiments, the present invention relates to a compound or a tautomer thereof, or a pharmaceutically acceptable salt, ester, or prodrug of said compound or tautomer, according to any formulae of the invention, wherein $R^{3a}$ and $R^{3b}$ are each independently selected from (a) hydrogen, (b) F, (c) Cl, (d) —CH$_3$, (e) —CF$_3$, (f) —CF$_2$H, (g) —CFH$_2$, (h) —OCF$_3$, (i) —OCF$_2$H, (j) —OCFH$_2$, (k) —OCH$_3$, and (l) —OH. In some embodiments, $R^{3a}$ and $R^{3b}$ are each hydrogen. In some embodiments, $R^{3a}$ and $R^{3b}$ are each hydrogen. In some embodiments, the stereochemistry of $R^{3a}$ and $R^{3b}$ is

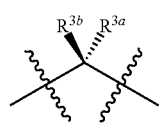

and $R^{3a}$ is methyl and $R^{3b}$ is hydrogen. In some embodiments, the stereochemistry of $R^{3a}$ and $R^{3b}$ is

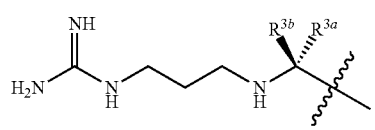

and $R^{3a}$ is methyl and $R^{3b}$ is hydrogen. In some embodiments, the stereochemistry of $R^{3a}$ and $R^{3b}$ is

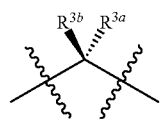

and $R^{3a}$ is hydrogen and $R^{3b}$ is methyl. In some embodiments, the stereochemistry of $R^{3a}$ and $R^{3b}$ is

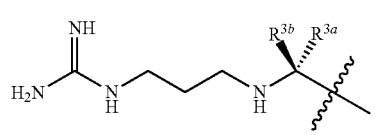

and $R^{3a}$ is hydrogen and $R^{3b}$ is methyl.

In some embodiments, the present invention relates to a compound having formula:

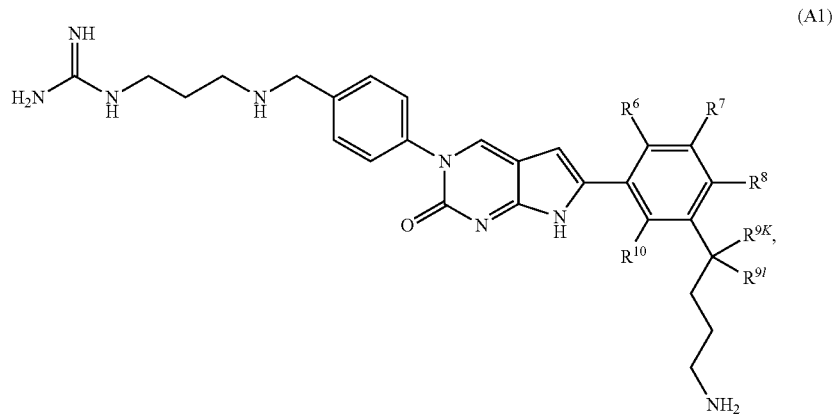

(A1)

or a tautomer thereof, or a pharmaceutically acceptable salt, ester, or prodrug of said compound or tautomer, wherein $R^6$, $R^7$, $R^8$, $R^{9k}$, $R^{9l}$, and $R^{10}$ are as defined herein.

In some embodiments, the present invention relates to a compound having formula:

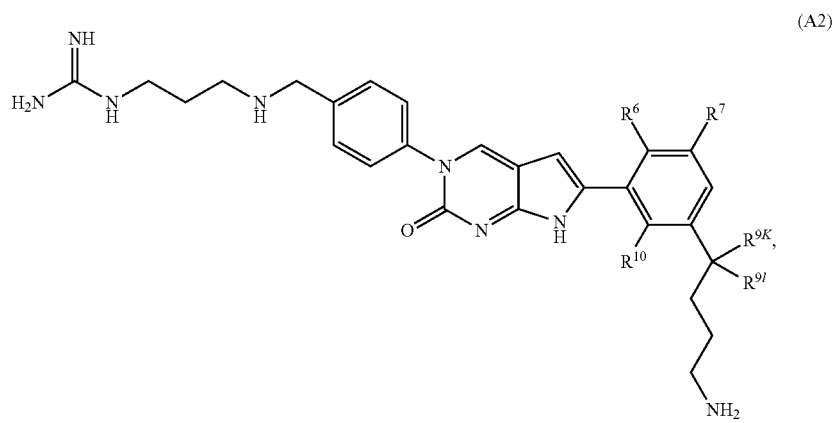

(A2)

or a tautomer thereof, or a pharmaceutically acceptable salt, ester, or prodrug of said compound or tautomer, wherein $R^6$, $R^7$, $R^{9k}$, $R^{9l}$, and $R^{10}$ are as defined herein.

In some embodiments, the present invention relates to a compound having formula:

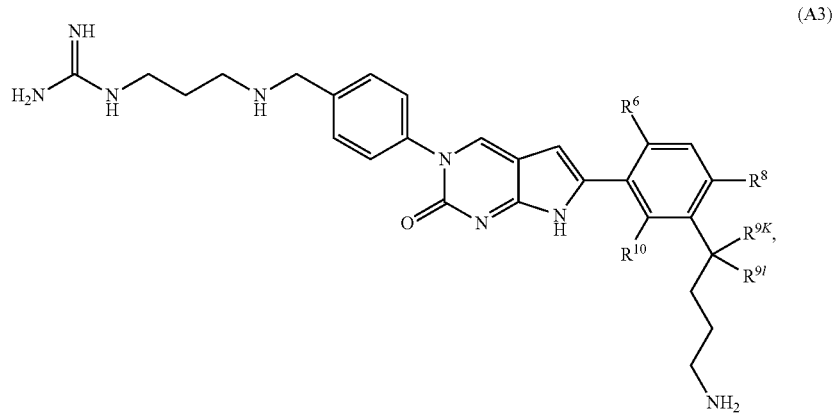

(A3)

or a tautomer thereof, or a pharmaceutically acceptable salt, ester, or prodrug of said compound or tautomer, wherein $R^6$, $R^8$, $R^{9k}$, $R^{9l}$, and $R^{10}$ are as defined herein.

In some embodiments, the present invention relates to a compound having formula:

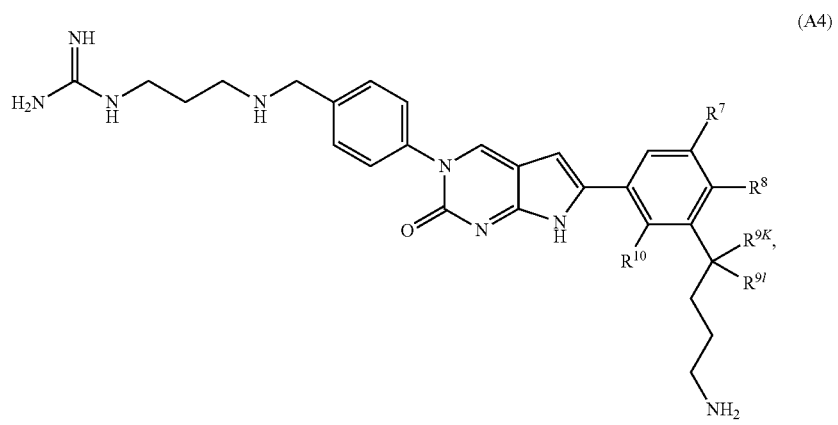

(A4)

or a tautomer thereof, or a pharmaceutically acceptable salt, ester, or prodrug of said compound or tautomer, wherein $R^7$, $R^8$, $R^{9k}$, $R^{9l}$, and $R^{10}$ are as defined herein.

In some embodiments, the present invention relates to a compound having formula:

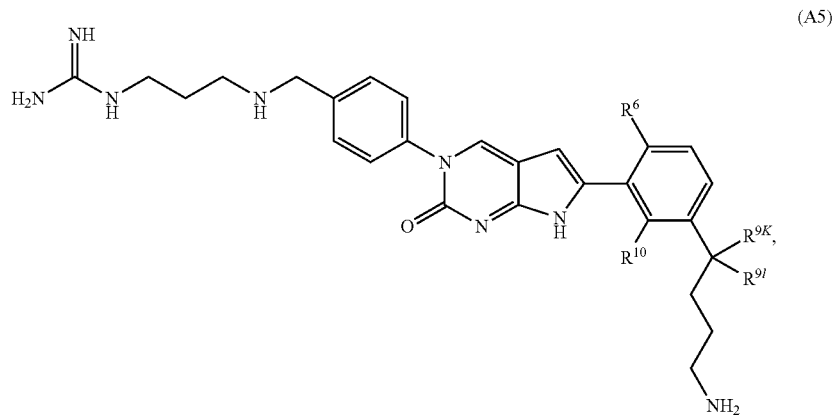

(A5)

or a tautomer thereof, or a pharmaceutically acceptable salt, ester, or prodrug of said compound or tautomer, wherein $R^6$, $R^{9k}$, $R^{9l}$, and $R^{10}$ are as defined herein.

In some embodiments, the present invention relates to a compound having formula:

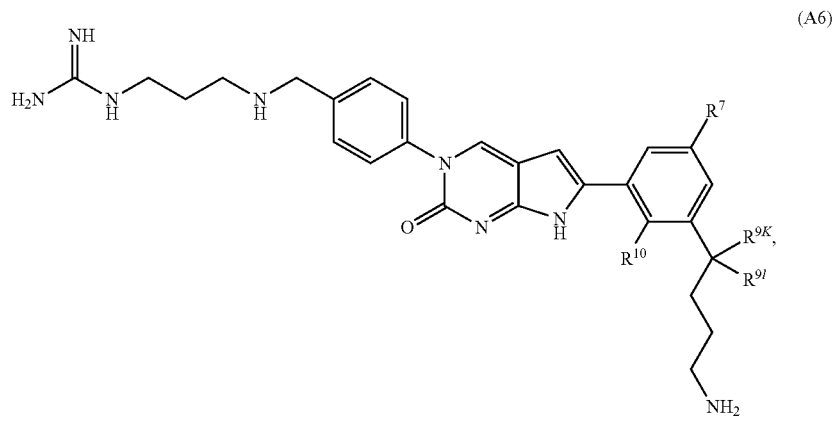

(A6)

or a tautomer thereof, or a pharmaceutically acceptable salt, ester, or prodrug of said compound or tautomer, wherein $R^7$, $R^{9k}$, $R^{9l}$, and $R^{10}$ are as defined herein.

In some embodiments, the present invention relates to a compound having formula:

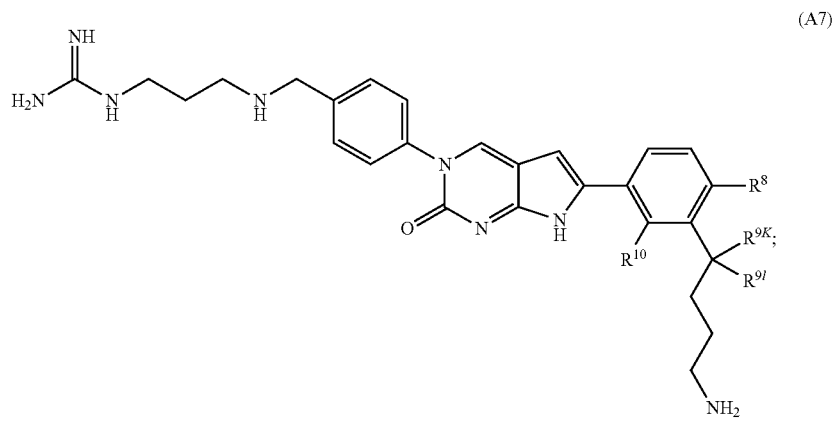

(A7)

or a tautomer thereof, or a pharmaceutically acceptable salt, ester, or prodrug of said compound or tautomer, wherein $R^8$, $R^{9k}$, $R^{9l}$, and $R^{10}$ are as defined herein.

In some embodiments, the present invention relates to a compound having formula:

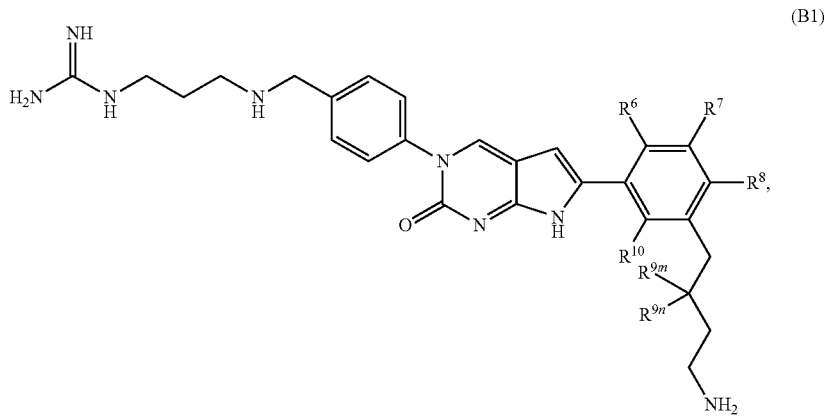

(B1)

or a tautomer thereof, or a pharmaceutically acceptable salt, ester, or prodrug of said compound or tautomer, wherein $R^6$, $R^7$, $R^8$, $R^{9m}$, $R^{9n}$, and $R^{10}$ are as defined herein.

In some embodiments, the present invention relates to a compound having formula:

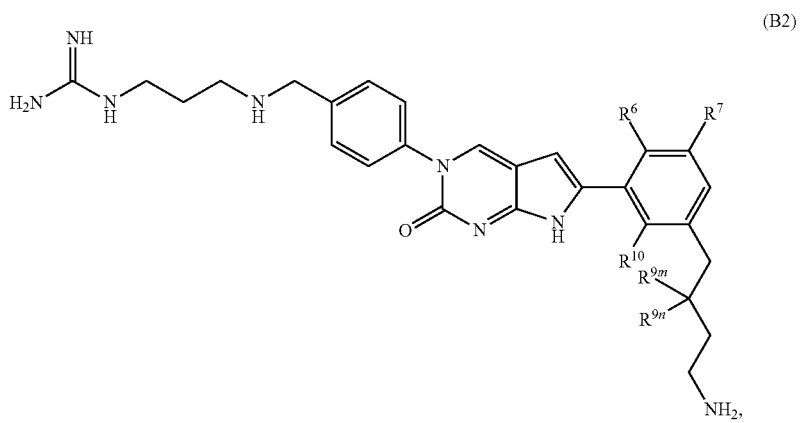

(B2)

or a tautomer thereof, or a pharmaceutically acceptable salt, ester, or prodrug of said compound or tautomer, wherein $R^6$, $R^7$, $R^{9m}$, $R^{9n}$, and $R^{10}$ are as defined herein.

In some embodiments, the present invention relates to a compound having formula:

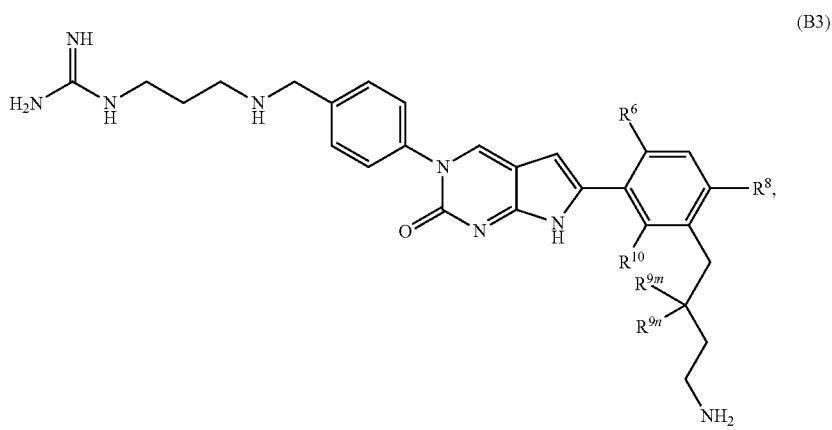

(B3)

or a tautomer thereof, or a pharmaceutically acceptable salt, ester, or prodrug of said compound or tautomer, wherein $R^6$, $R^8$, $R^{9m}$, $R^{9n}$, and $R^{10}$ are as defined herein.

In some embodiments, the present invention relates to a compound having formula:

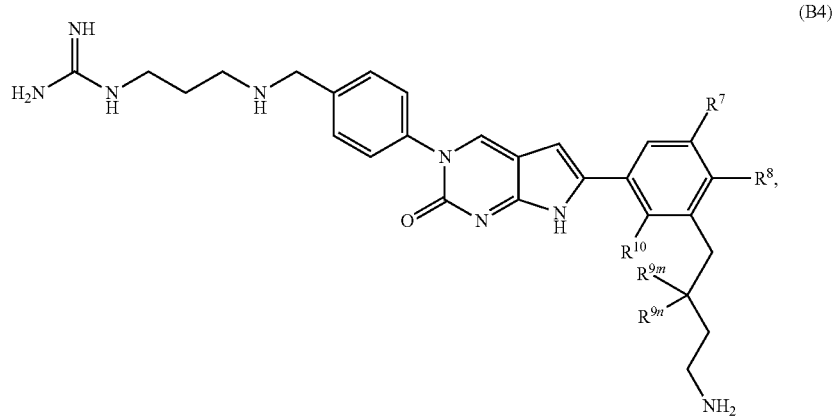

(B4)

or a tautomer thereof, or a pharmaceutically acceptable salt, ester, or prodrug of said compound or tautomer, wherein $R^7$, $R^8$, $R^{9m}$, $R^{9n}$, and $R^{10}$ are as defined herein.

In some embodiments, the present invention relates to a compound having formula:

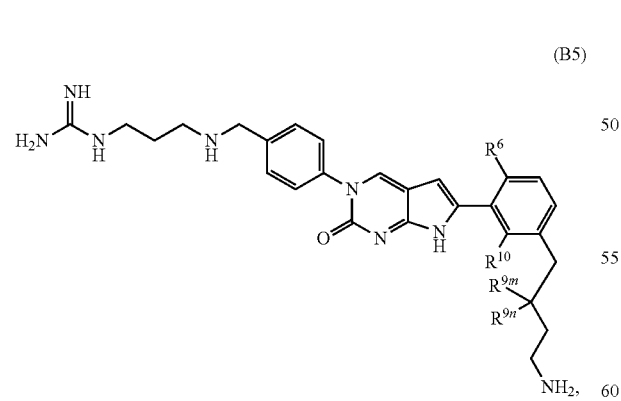

(B5)

or a tautomer thereof, or a pharmaceutically acceptable salt, ester, or prodrug of said compound or tautomer, wherein $R^6$, $R^{9m}$, $R^{9n}$, and $R^{10}$ are as defined herein.

In some embodiments, the present invention relates to a compound having formula:

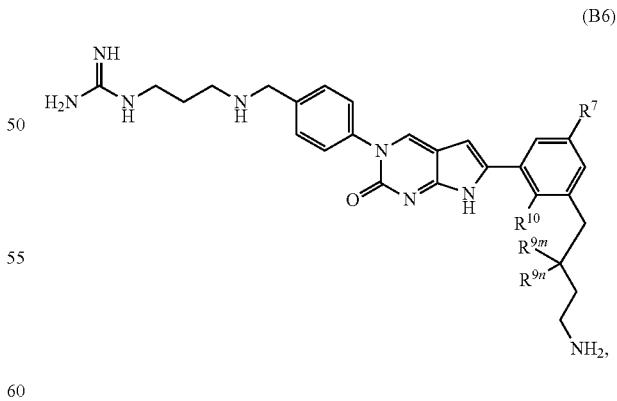

(B6)

or a tautomer thereof, or a pharmaceutically acceptable salt, ester, or prodrug of said compound or tautomer, wherein $R^7$, $R^{9m}$, $R^{9n}$, and $R^{10}$ are as defined herein.

In some embodiments, the present invention relates to a compound having formula:

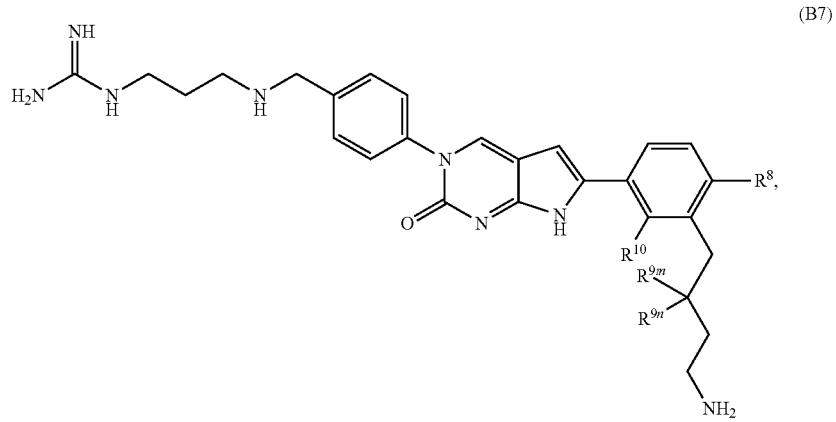

(B7)

or a tautomer thereof, or a pharmaceutically acceptable salt, ester, or prodrug of said compound or tautomer, wherein $R^8$, $R^{9m}$, $R^{9n}$, and $R^{10}$ are as defined herein.

In some embodiments, the present invention relates to a compound having formula:

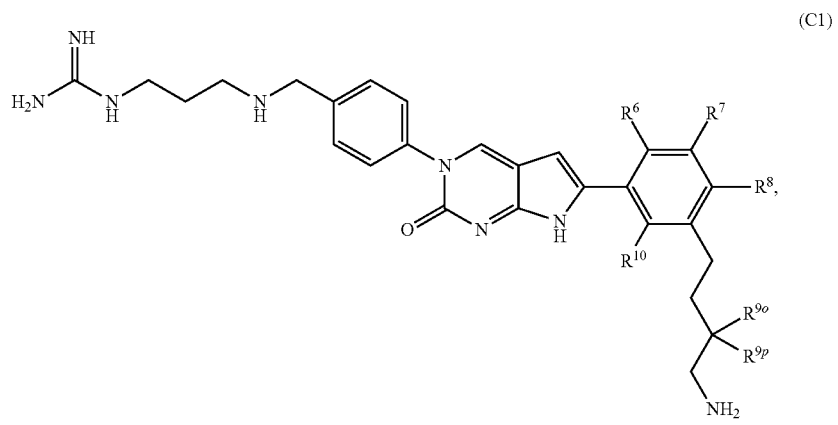

(C1)

or a tautomer thereof, or a pharmaceutically acceptable salt, ester, or prodrug of said compound or tautomer, wherein $R^6$, $R^7$, $R^8$, $R^{9o}$, $R^{9p}$, and $R^{10}$ are as defined herein.

In some embodiments, the present invention relates to a compound having formula:

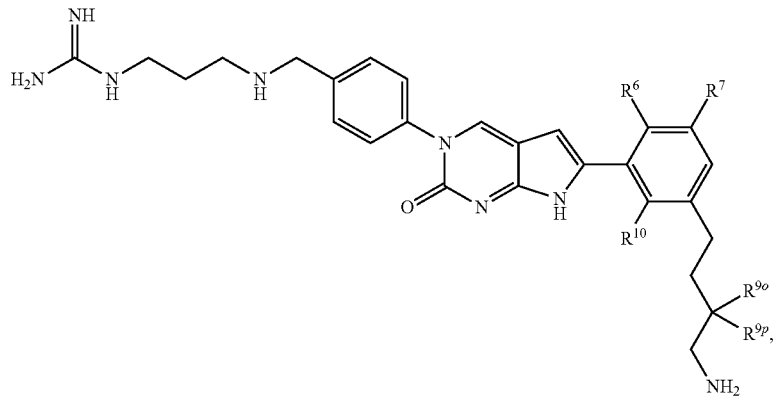

(C2)

or a tautomer thereof, or a pharmaceutically acceptable salt, ester, or prodrug of said compound or tautomer, wherein $R^6$, $R^7$, $R^{9o}$, $R^{9p}$, and $R^{10}$ are as defined herein.

In some embodiments, the present invention relates to a compound having formula:

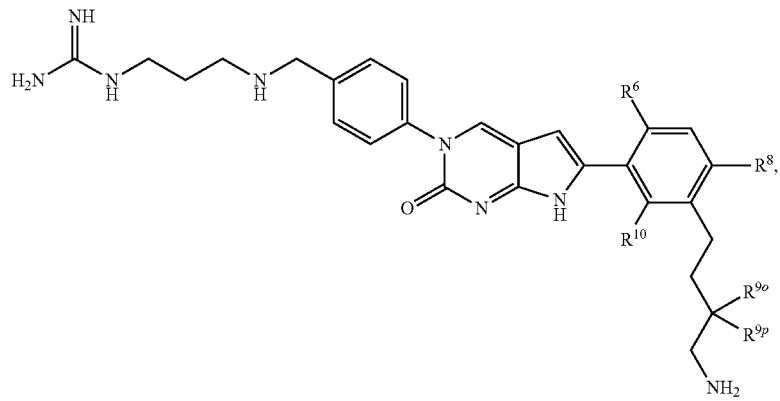

(C3)

or a tautomer thereof, or a pharmaceutically acceptable salt, ester, or prodrug of said compound or tautomer, wherein $R^6$, $R^8$, $R^{9o}$, $R^{9p}$, and $R^{10}$ are as defined herein.

In some embodiments, the present invention relates to a compound having formula:

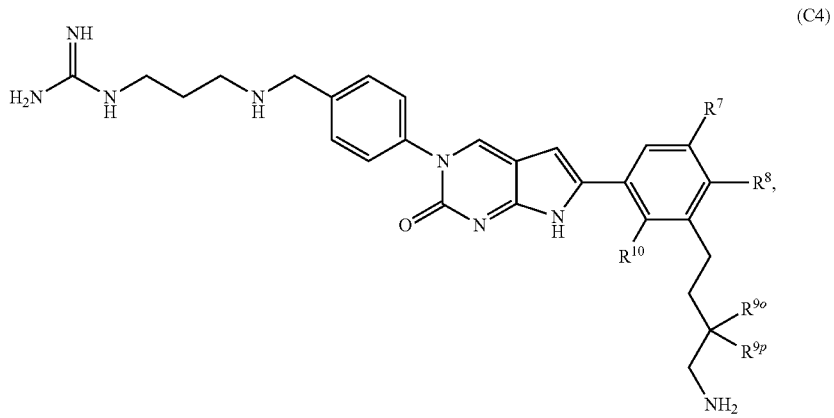

(C4)

or a tautomer thereof, or a pharmaceutically acceptable salt, ester, or prodrug of said compound or tautomer, wherein $R^7$, $R^8$, $R^{9o}$, $R^{9p}$, and $R^{10}$ are as defined herein.

In some embodiments, the present invention relates to a compound having formula:

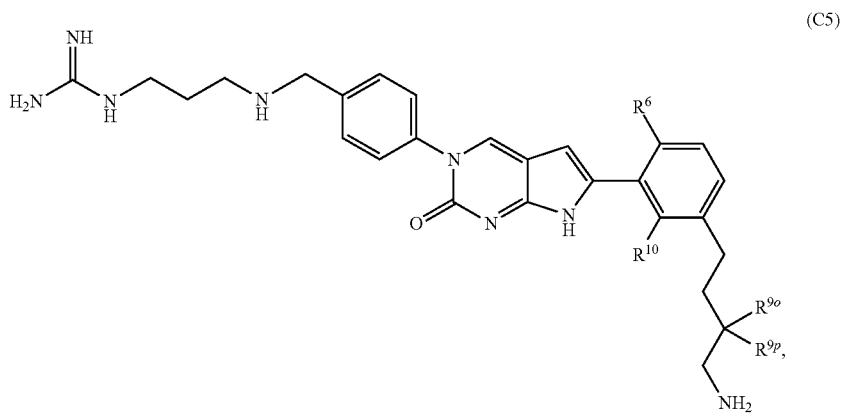

(C5)

or a tautomer thereof, or a pharmaceutically acceptable salt, ester, or prodrug of said compound or tautomer, wherein $R^6$, $R^{9o}$, $R^{9p}$, and $R^{10}$ are as defined herein.

In some embodiments, the present invention relates to a compound having formula:

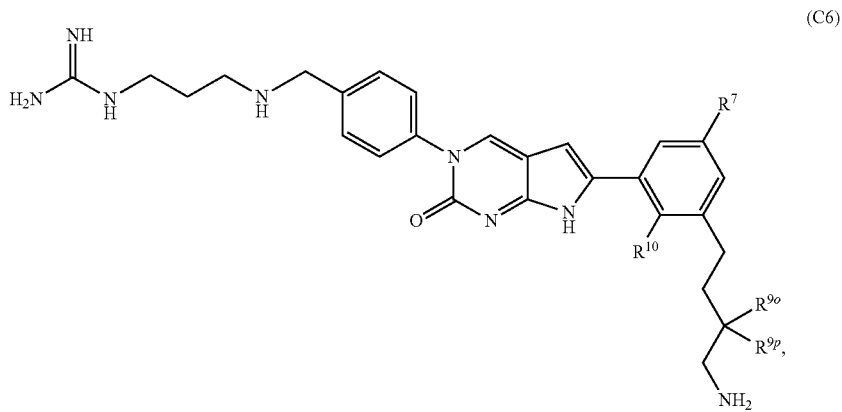

(C6)

or a tautomer thereof, or a pharmaceutically acceptable salt, ester, or prodrug of said compound or tautomer, wherein $R^7$, $R^{9o}$, $R^{9p}$, and $R^{10}$ are as defined herein.

In some embodiments, the present invention relates to a compound having formula:

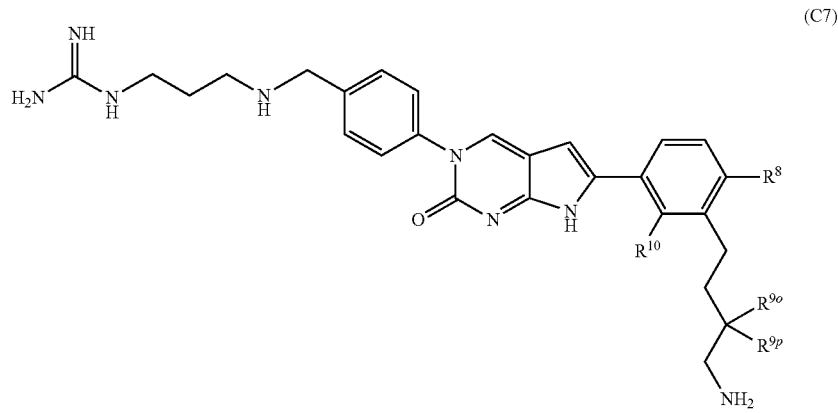

(C7)

or a tautomer thereof, or a pharmaceutically acceptable salt, ester, or prodrug of said compound or tautomer, wherein $R^8$, $R^{9o}$, $R^{9p}$, and $R^{10}$ are as defined herein.

In some embodiments, the present invention relates to a compound having formula:

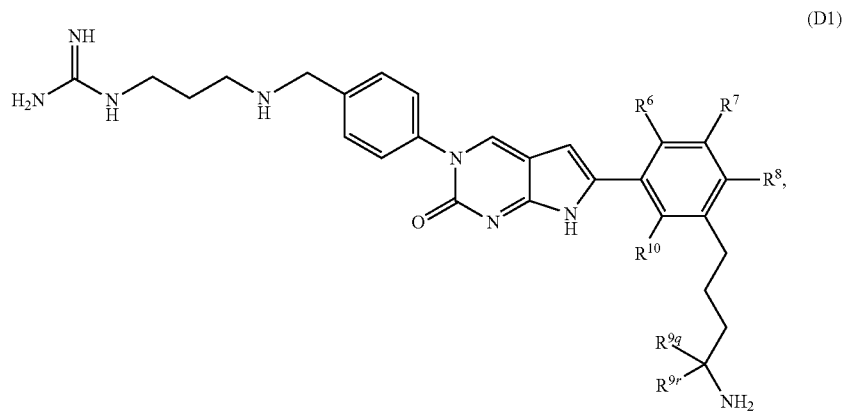

(D1)

or a tautomer thereof, or a pharmaceutically acceptable salt, ester, or prodrug of said compound or tautomer, wherein $R^6$, $R^7$, $R^8$, $R^{9q}$, $R^{9r}$, and $R^{10}$ are as defined herein.

In some embodiments, the present invention relates to a compound having formula:

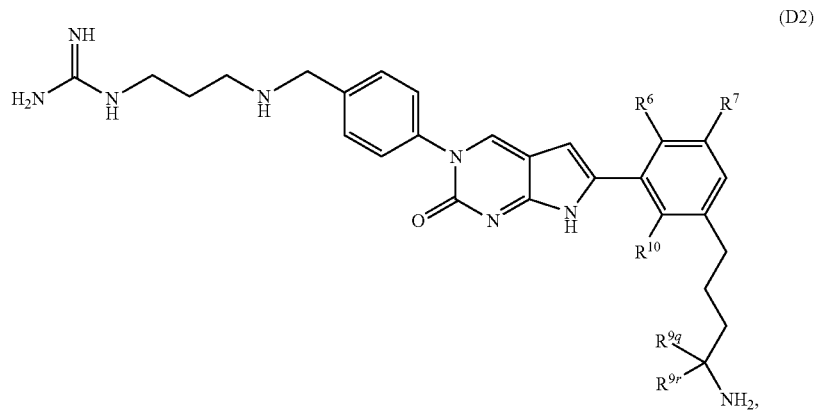

(D2)

or a tautomer thereof, or a pharmaceutically acceptable salt, ester, or prodrug of said compound or tautomer, wherein $R^6$, $R^7$, $R^{9q}$, $R^{9r}$, and $R^{10}$ are as defined herein.

In some embodiments, the present invention relates to a compound having formula:

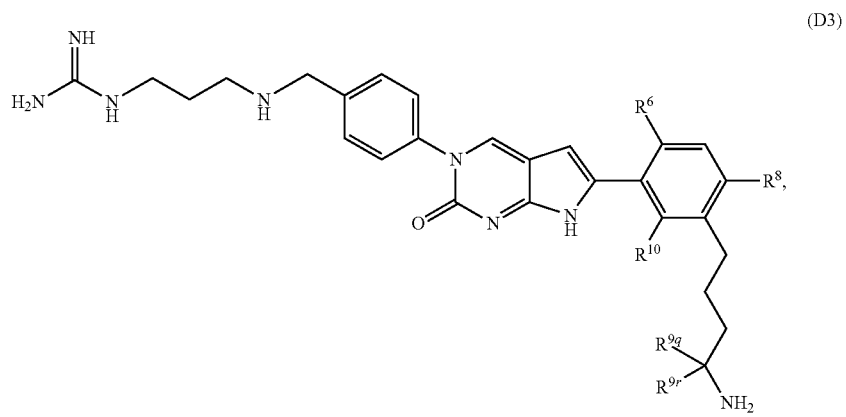

(D3)

or a tautomer thereof, or a pharmaceutically acceptable salt, ester, or prodrug of said compound or tautomer, wherein $R^6$, $R^8$, $R^{9q}$, $R^{9r}$, and $R^{10}$ are as defined herein.

In some embodiments, the present invention relates to a compound having formula:

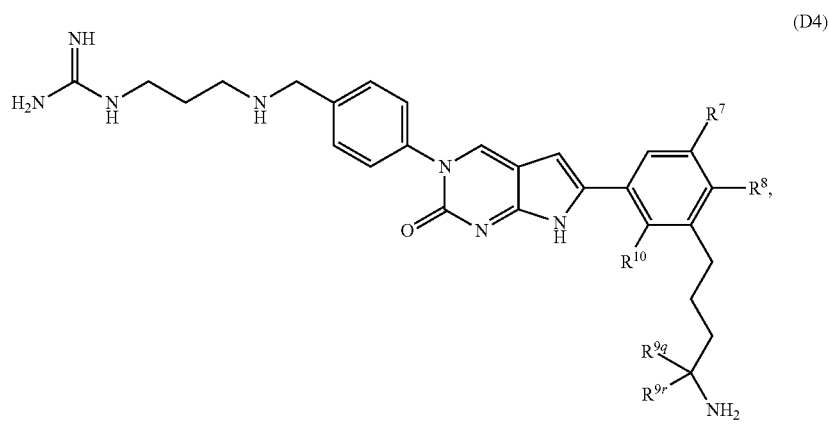

(D4)

or a tautomer thereof, or a pharmaceutically acceptable salt, ester, or prodrug of said compound or tautomer, wherein $R^7$, $R^8$, $R^{9q}$, $R^{9r}$, and $R^{10}$ are as defined herein.

In some embodiments, the present invention relates to a compound having formula:

(D5)

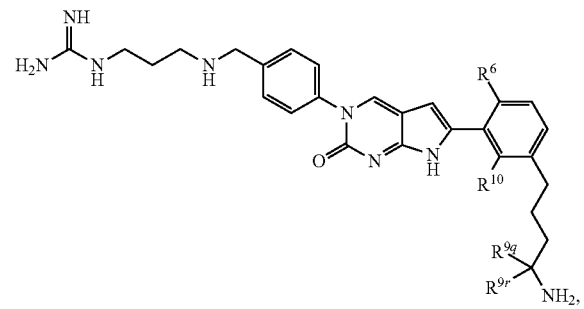

or a tautomer thereof, or a pharmaceutically acceptable salt, ester, or prodrug of said compound or tautomer, wherein $R^6$, $R^{9q}$, $R^{9r}$, and $R^{10}$ are as defined herein.

In some embodiments, the present invention relates to a compound having formula:

(D6)

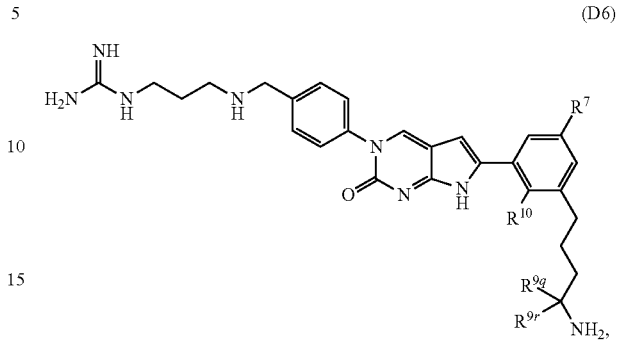

or a tautomer thereof, or a pharmaceutically acceptable salt, ester, or prodrug of said compound or tautomer, wherein $R^7$, $R^{9q}$, $R^{9r}$, and $R^{10}$ are as defined herein.

In some embodiments, the present invention relates to a compound having formula:

(D7)

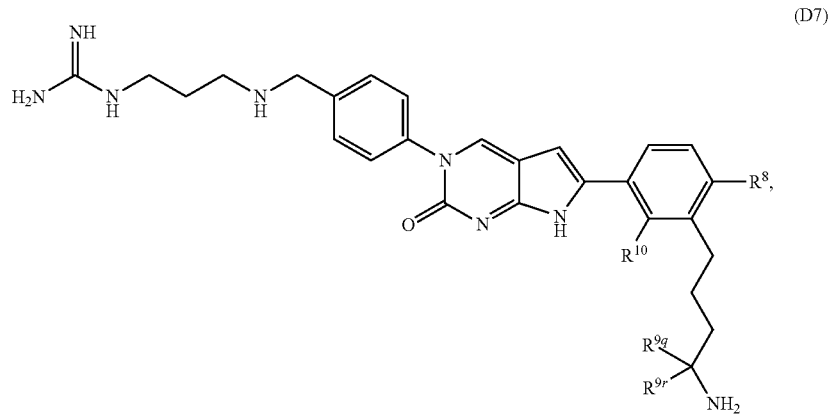

or a tautomer thereof, or a pharmaceutically acceptable salt, ester, or prodrug of said compound or tautomer, wherein $R^8$, $R^{9q}$, $R^{9r}$, and $R^{10}$ are as defined herein.

In some embodiments, the present invention relates to a compound having formula:

(E1)

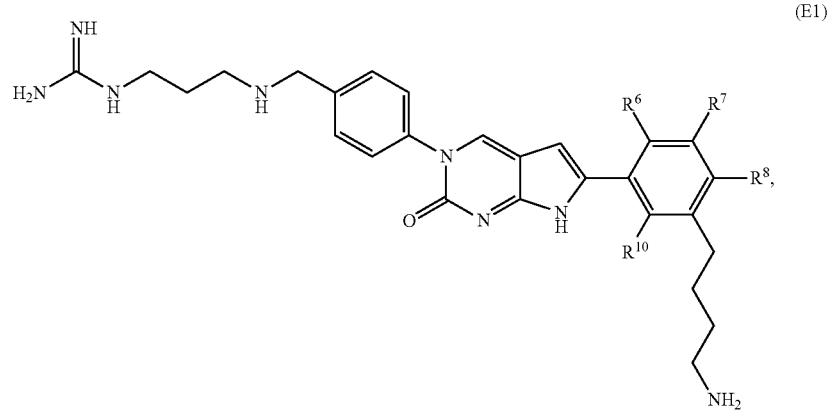

or a tautomer thereof, or a pharmaceutically acceptable salt, ester, or prodrug of said compound or tautomer, wherein $R^6$, $R^7$, $R^8$, and $R^{10}$ are as defined herein.

In some embodiments, the present invention relates to a compound having formula:

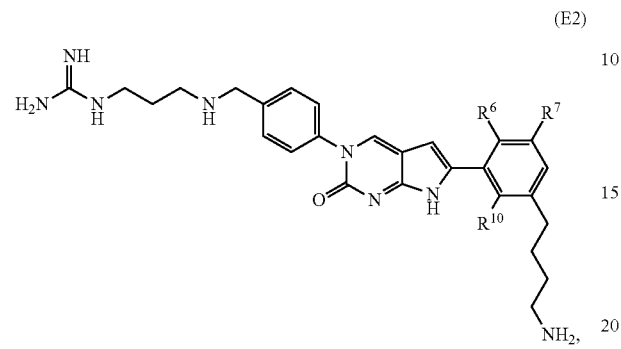

(E2)

or a tautomer thereof, or a pharmaceutically acceptable salt, ester, or prodrug of said compound or tautomer, wherein $R^6$, $R^7$, and $R^{10}$ are as defined herein.

In some embodiments, the present invention relates to a compound having formula:

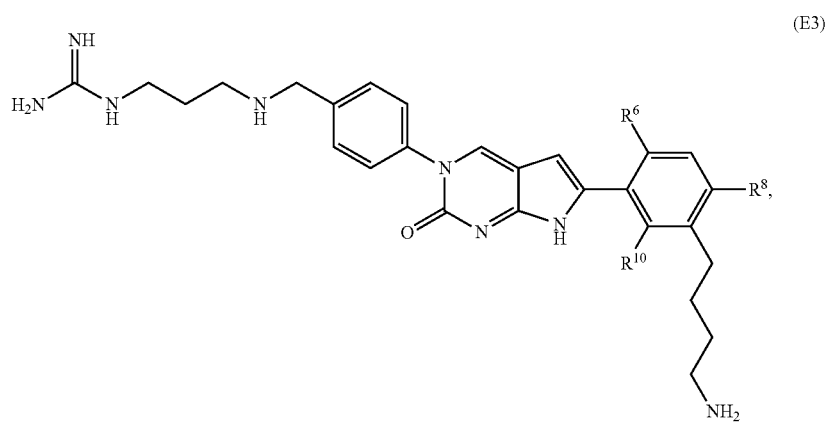

(E3)

or a tautomer thereof, or a pharmaceutically acceptable salt, ester, or prodrug of said compound or tautomer, wherein $R^6$, $R^8$, and $R^{10}$ are as defined herein.

In some embodiments, the present invention relates to a compound having formula:

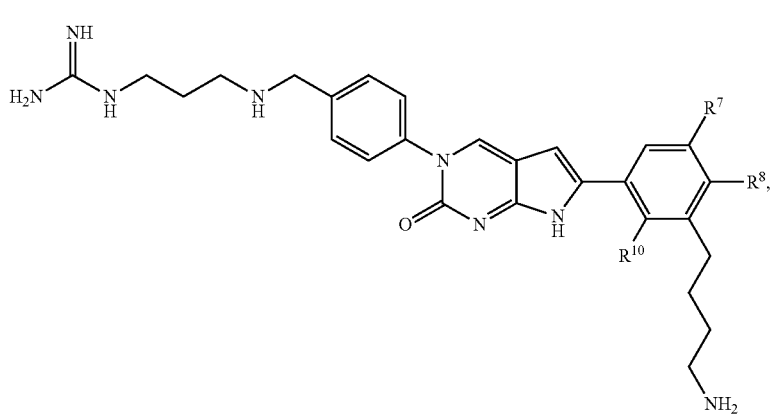

(E4)

or a tautomer thereof, or a pharmaceutically acceptable salt, ester, or prodrug of said compound or tautomer, wherein $R^7$, $R^8$, and $R^{10}$ are as defined herein.

In some embodiments, the present invention relates to a compound having formula:

(E5)

In some embodiments, the present invention relates to a compound having formula:

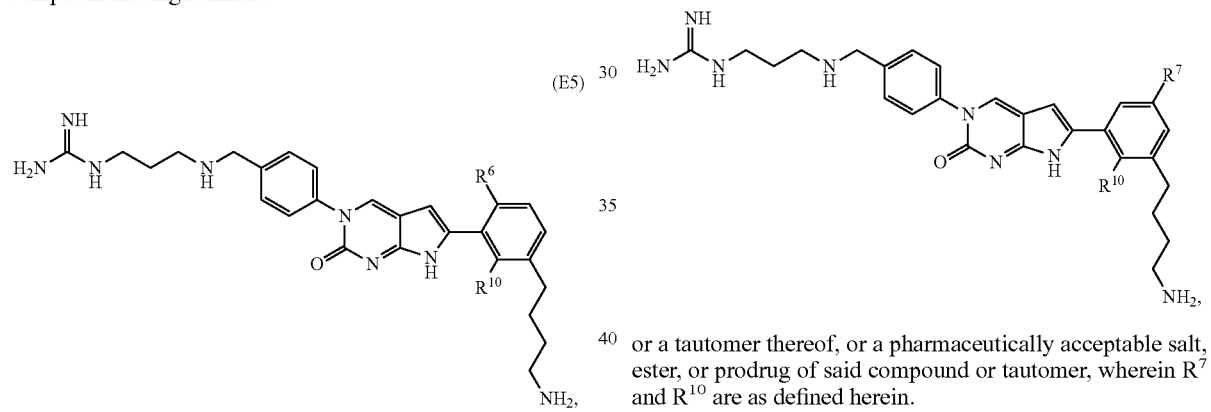

(E6)

or a tautomer thereof, or a pharmaceutically acceptable salt, ester, or prodrug of said compound or tautomer, wherein $R^7$ and $R^{10}$ are as defined herein.

In some embodiments, the present invention relates to a compound having formula:

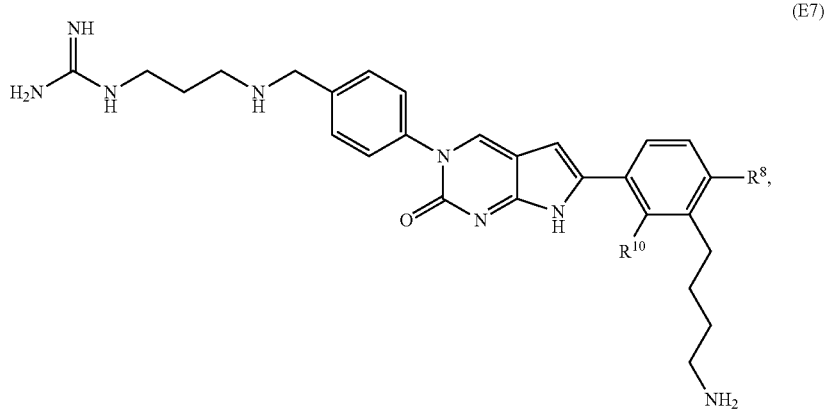

(E7)

or a tautomer thereof, or a pharmaceutically acceptable salt, ester, or prodrug of said compound or tautomer, wherein $R^6$ and $R^{10}$ are as defined herein.

or a tautomer thereof, or a pharmaceutically acceptable salt, ester, or prodrug of said compound or tautomer, wherein $R^8$ and $R^{10}$ are as defined herein.

In some embodiments, the present invention relates to a compound having formula:

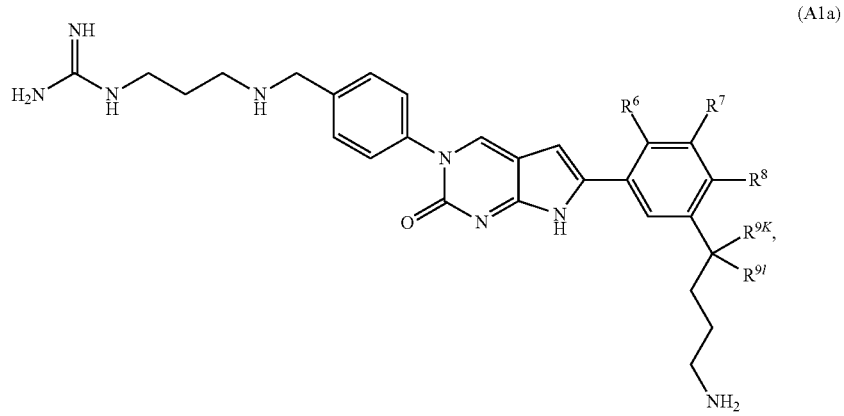

(A1a)

or a tautomer thereof, or a pharmaceutically acceptable salt, ester, or prodrug of said compound or tautomer, wherein $R^6$, $R^7$, $R^8$, $R^{9k}$ and $R^{9l}$ are as defined herein.

In some embodiments, the present invention relates to a compound having formula:

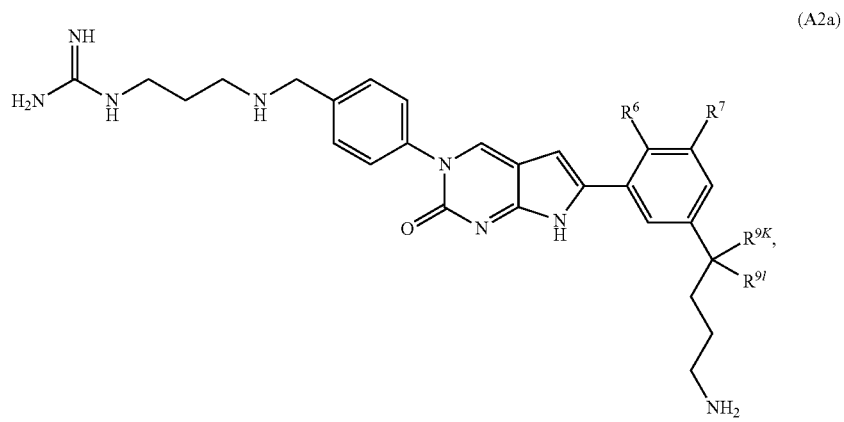

(A2a)

or a tautomer thereof, or a pharmaceutically acceptable salt, ester, or prodrug of said compound or tautomer, wherein $R^6$, $R^7$, $R^{9k}$ and $R^{9l}$ are as defined herein.

In some embodiments, the present invention relates to a compound having formula:

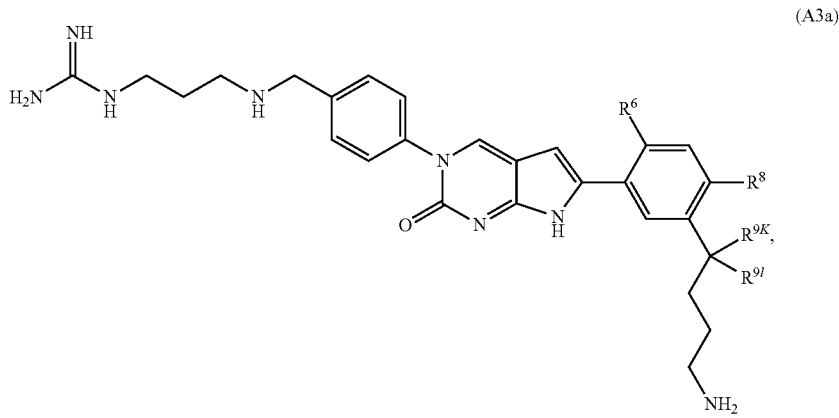

(A3a)

or a tautomer thereof, or a pharmaceutically acceptable salt, ester, or prodrug of said compound or tautomer, wherein $R^6$, $R^8$, $R^{9k}$ and $R^{9l}$ are as defined herein.

In some embodiments, the present invention relates to a compound having formula:

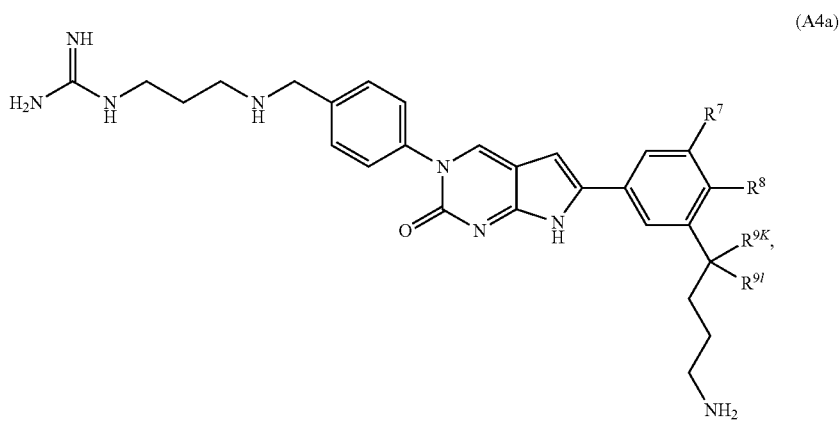

(A4a)

or a tautomer thereof, or a pharmaceutically acceptable salt, ester, or prodrug of said compound or tautomer, wherein $R^7$, $R^8$, $R^{9k}$ and $R^{9l}$ are as defined herein.

In some embodiments, the present invention relates to a compound having formula:

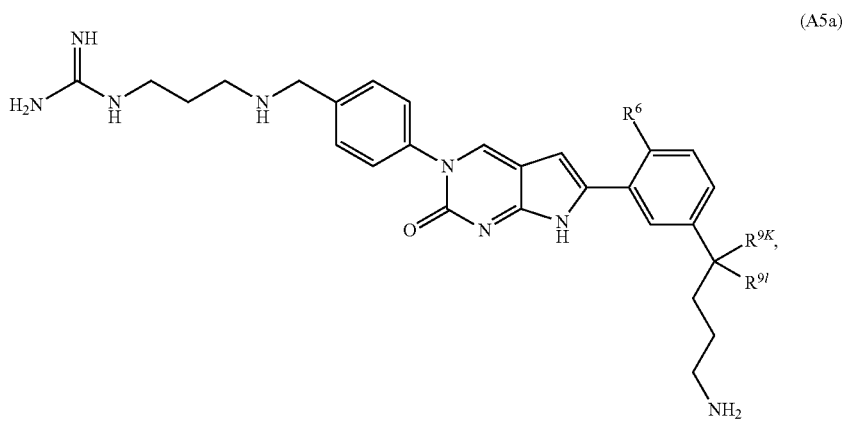

(A5a)

or a tautomer thereof, or a pharmaceutically acceptable salt, ester, or prodrug of said compound or tautomer, wherein $R^6$, $R^{9k}$ and $R^{9l}$ are as defined herein.

In some embodiments, the present invention relates to a compound having formula:

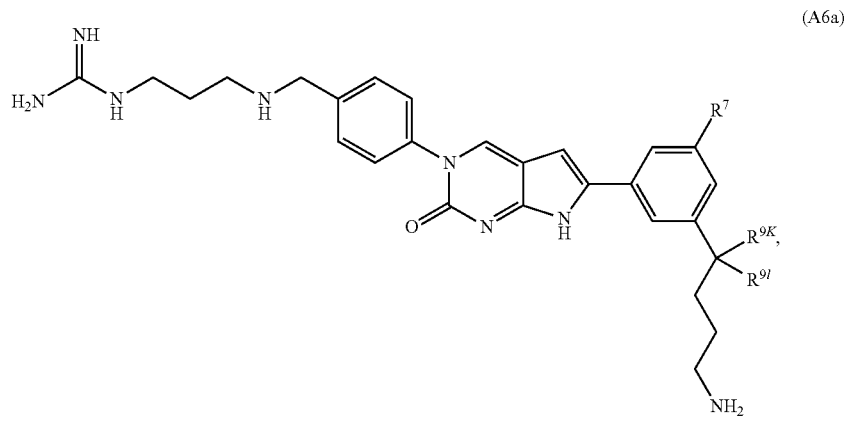

(A6a)

or a tautomer thereof, or a pharmaceutically acceptable salt, ester, or prodrug of said compound or tautomer, wherein $R^7$, $R^{9k}$ and $R^{9l}$ are as defined herein.

In some embodiments, the present invention relates to a compound having formula:

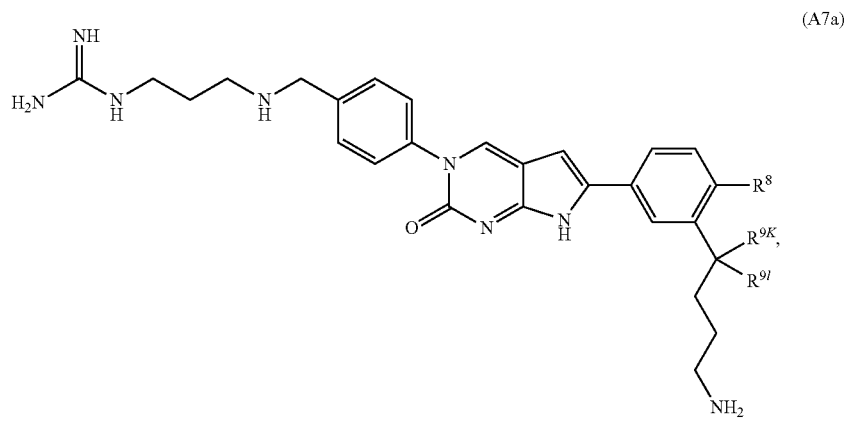

(A7a)

or a tautomer thereof, or a pharmaceutically acceptable salt, ester, or prodrug of said compound or tautomer, wherein $R^8$, $R^{9k}$ and $R^{9l}$ are as defined herein.

In some embodiments, the present invention relates to a compound having formula:

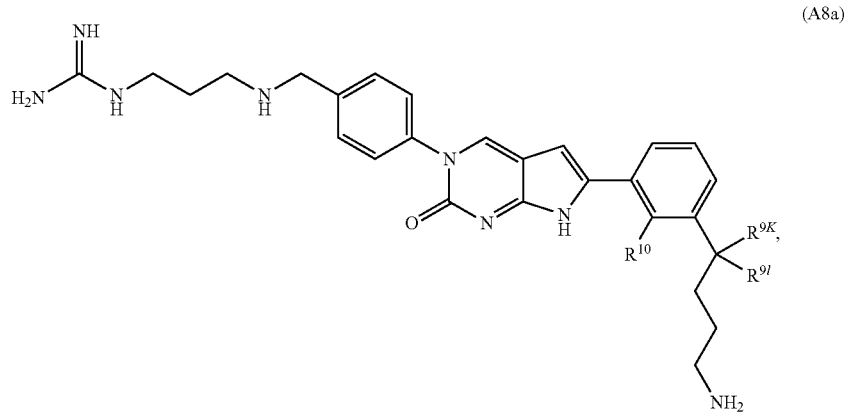

(A8a)

or a tautomer thereof, or a pharmaceutically acceptable salt, ester, or prodrug of said compound or tautomer, wherein $R^{9k}$, $R^{9l}$ and $R^{10}$ are as defined herein.

In some embodiments, the present invention relates to a compound having formula:

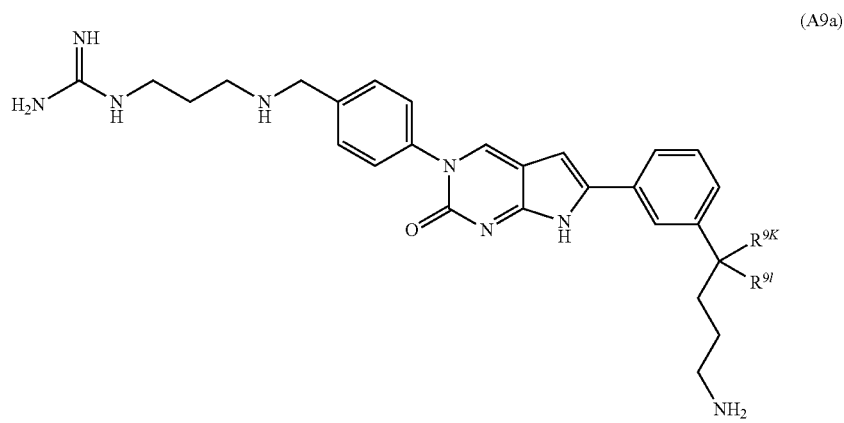

(A9a)

or a tautomer thereof, or a pharmaceutically acceptable salt, ester, or prodrug of said compound or tautomer, wherein $R^{9k}$ and $R^{9l}$ are as defined herein.

In some embodiments, the present invention relates to a compound having formula:

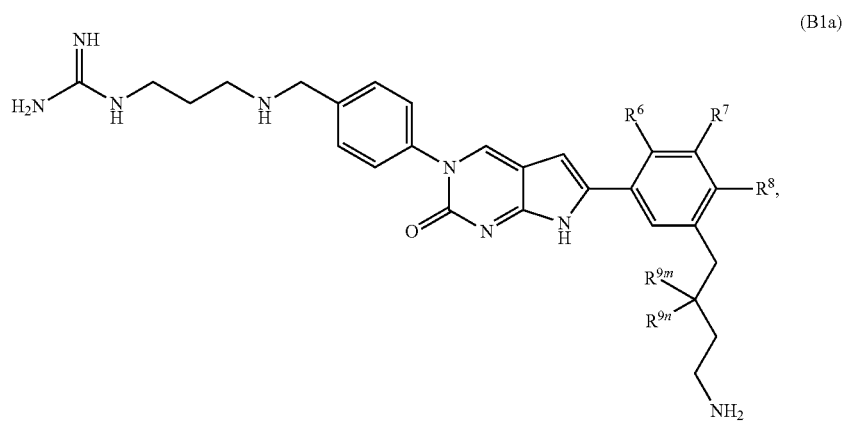

(B1a)

or a tautomer thereof, or a pharmaceutically acceptable salt, ester, or prodrug of said compound or tautomer, wherein $R^6$, $R^7$, $R^8$, $R^{9m}$ and $R^{9n}$ are as defined herein.

In some embodiments, the present invention relates to a compound having formula:

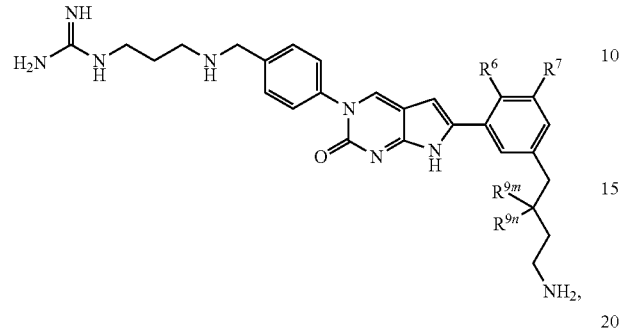

(B2a)

or a tautomer thereof, or a pharmaceutically acceptable salt, ester, or prodrug of said compound or tautomer, wherein $R^6$, $R^7$, $R^{9m}$ and $R^{9n}$ are as defined herein.

In some embodiments, the present invention relates to a compound having formula:

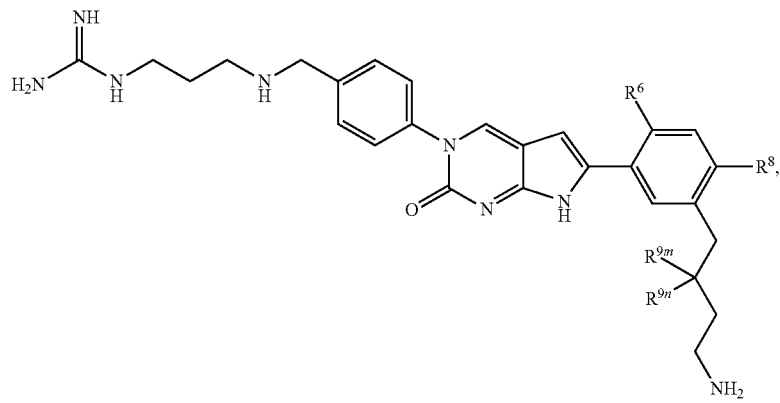

(B3a)

or a tautomer thereof, or a pharmaceutically acceptable salt, ester, or prodrug of said compound or tautomer, wherein $R^6$, $R^8$, $R^{9m}$ and $R^{9n}$ are as defined herein.

In some embodiments, the present invention relates to a compound having formula:

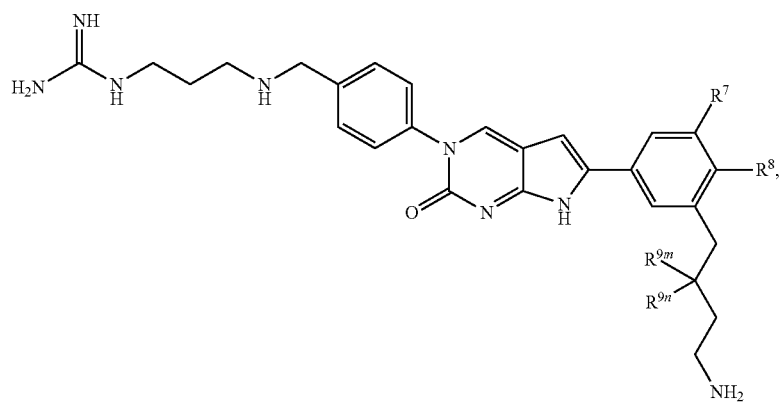

(B4a)

or a tautomer thereof, or a pharmaceutically acceptable salt, ester, or prodrug of said compound or tautomer, wherein $R^7$, $R^8$, $R^{9m}$ and $R^{9n}$ are as defined herein.

In some embodiments, the present invention relates to a compound having formula:

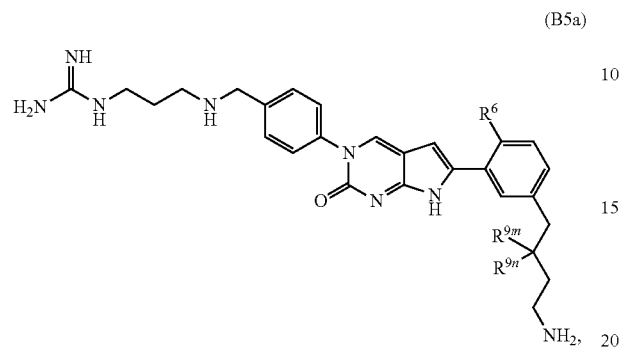

(B5a)

or a tautomer thereof, or a pharmaceutically acceptable salt, ester, or prodrug of said compound or tautomer, wherein $R^6$, $R^{9m}$ and $R^{9n}$ are as defined herein.

In some embodiments, the present invention relates to a compound having formula:

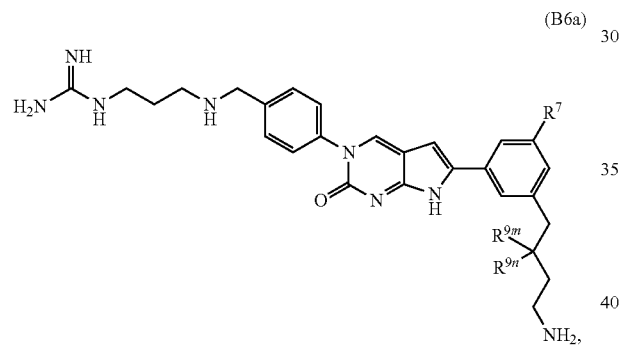

(B6a)

or a tautomer thereof, or a pharmaceutically acceptable salt, ester, or prodrug of said compound or tautomer, wherein $R^7$, $R^{9m}$ and $R^{9n}$ are as defined herein.

In some embodiments, the present invention relates to a compound having formula:

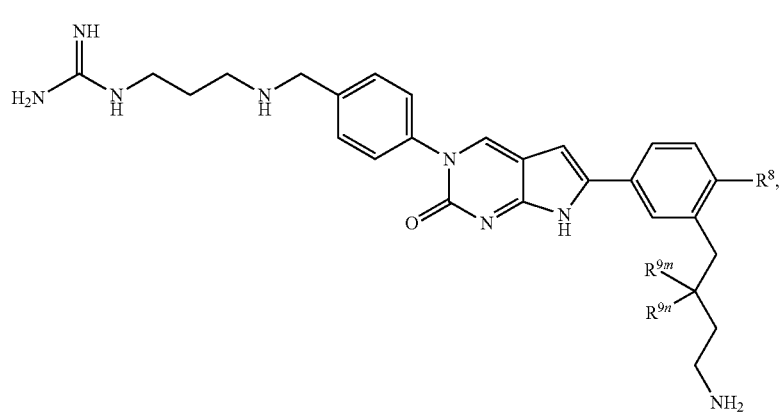

(B7a)

or a tautomer thereof, or a pharmaceutically acceptable salt, ester, or prodrug of said compound or tautomer, wherein $R^8$, $R^{9m}$ and $R^{9n}$ are as defined herein.

In some embodiments, the present invention relates to a compound having formula:

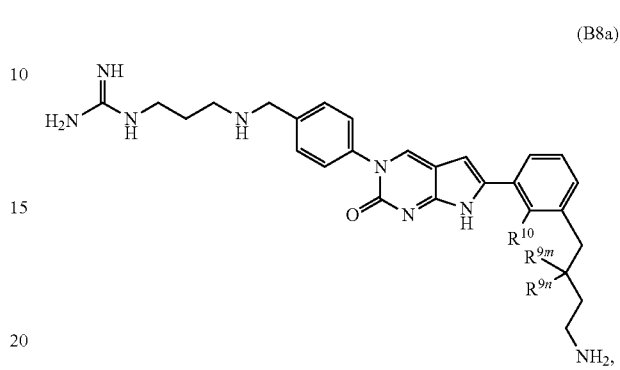

(B8a)

or a tautomer thereof, or a pharmaceutically acceptable salt, ester, or prodrug of said compound or tautomer, wherein $R^{9m}$, $R^{9n}$ and $R^{10}$ are as defined herein.

In some embodiments, the present invention relates to a compound having formula:

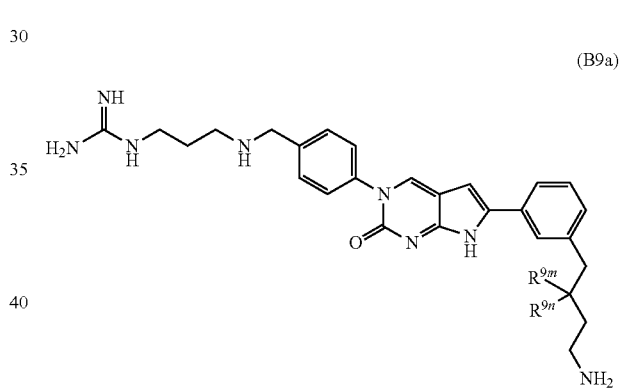

(B9a)

or a tautomer thereof, or a pharmaceutically acceptable salt, ester, or prodrug of said compound or tautomer, wherein $R^{9m}$ and $R^{9n}$ are as defined herein.

In some embodiments, the present invention relates to a compound having formula:

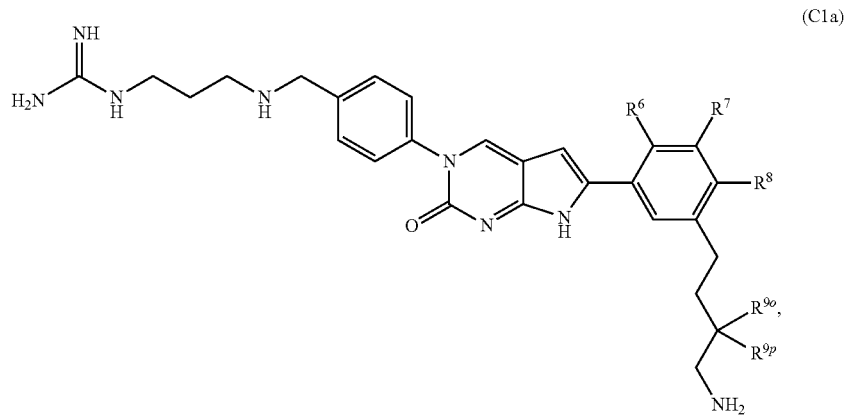

(C1a)

or a tautomer thereof, or a pharmaceutically acceptable salt, ester, or prodrug of said compound or tautomer, wherein $R^6$, $R^7$, $R^8$, $R^{9o}$ and $R^{9p}$ are as defined herein.

In some embodiments, the present invention relates to a compound having formula:

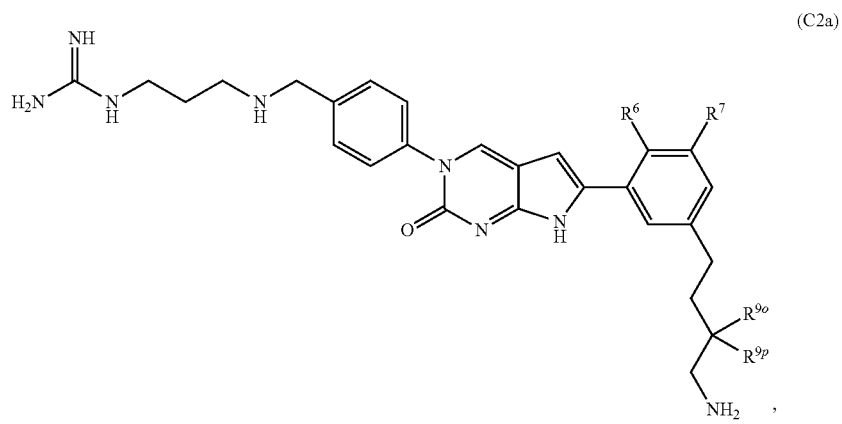

(C2a)

or a tautomer thereof, or a pharmaceutically acceptable salt, ester, or prodrug of said compound or tautomer, wherein $R^6$, $R^7$, $R^{9o}$ and $R^{9p}$ are as defined herein.

In some embodiments, the present invention relates to a compound having formula:

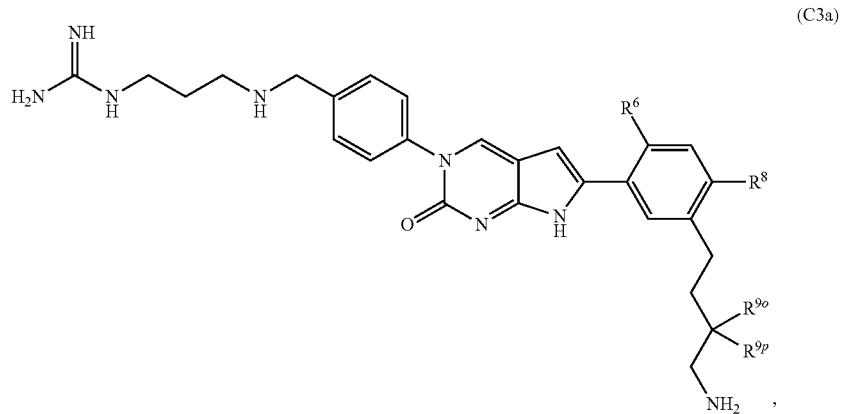

(C3a)

or a tautomer thereof, or a pharmaceutically acceptable salt, ester, or prodrug of said compound or tautomer, wherein $R^6$, $R^8$, $R^{9o}$ and $R^{9p}$ are as defined herein.

In some embodiments, the present invention relates to a compound having formula:

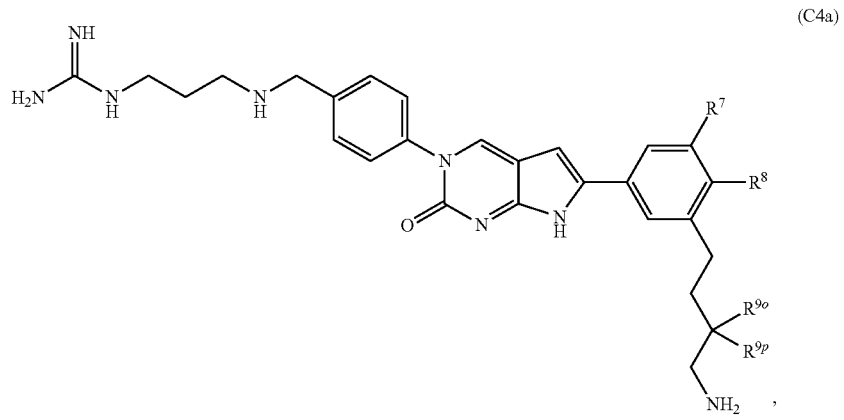

(C4a)

or a tautomer thereof, or a pharmaceutically acceptable salt, ester, or prodrug of said compound or tautomer, wherein $R^7$, $R^8$, $R^{9o}$ and $R^{9p}$ are as defined herein.

In some embodiments, the present invention relates to a compound having formula:

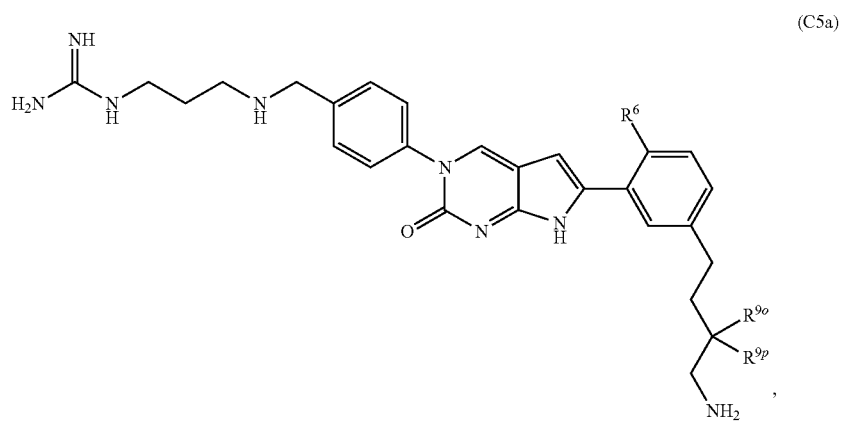

(C5a)

or a tautomer thereof, or a pharmaceutically acceptable salt, ester, or prodrug of said compound or tautomer, wherein $R^6$, $R^{9o}$ and $R^{9p}$ are as defined herein.

In some embodiments, the present invention relates to a compound having formula:

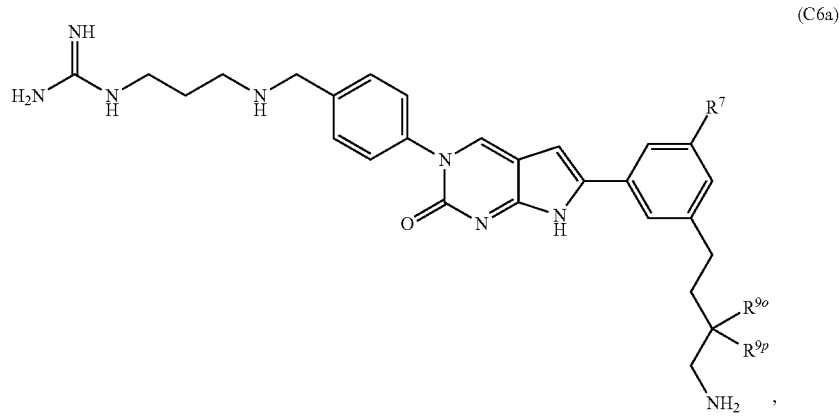
(C6a)

or a tautomer thereof, or a pharmaceutically acceptable salt, ester, or prodrug of said compound or tautomer, wherein $R^7$, $R^{9o}$ and $R^{9p}$ are as defined herein.

In some embodiments, the present invention relates to a compound having formula:

(C7a)

or a tautomer thereof, or a pharmaceutically acceptable salt, ester, or prodrug of said compound or tautomer, wherein $R^8$, $R^{9o}$ and $R^{9p}$ are as defined herein.

In some embodiments, the present invention relates to a compound having formula:

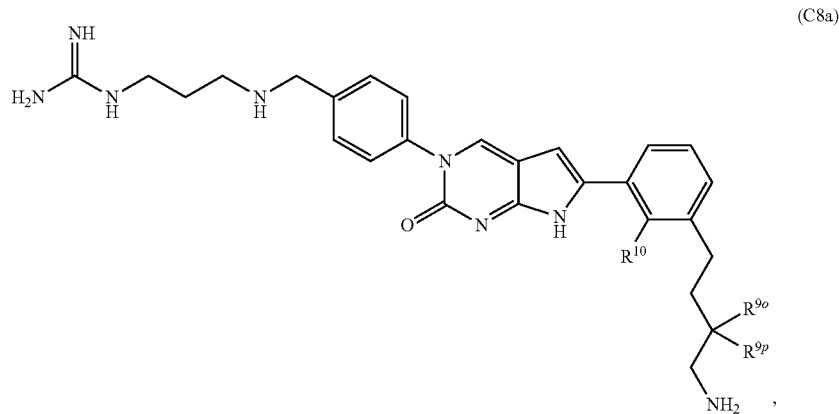
(C8a)

or a tautomer thereof, or a pharmaceutically acceptable salt, ester, or prodrug of said compound or tautomer, wherein $R^{9o}$, $R^{9p}$ and $R^{10}$ are as defined herein.

In some embodiments, the present invention relates to a compound having formula:

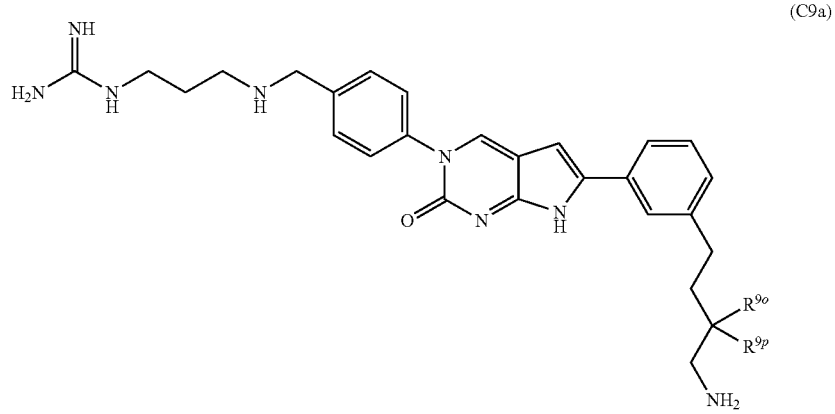

(C9a)

or a tautomer thereof, or a pharmaceutically acceptable salt, ester, or prodrug of said compound or tautomer, wherein $R^{9o}$ and $R^{9p}$ are as defined herein.

In some embodiments, the present invention relates to a compound having formula:

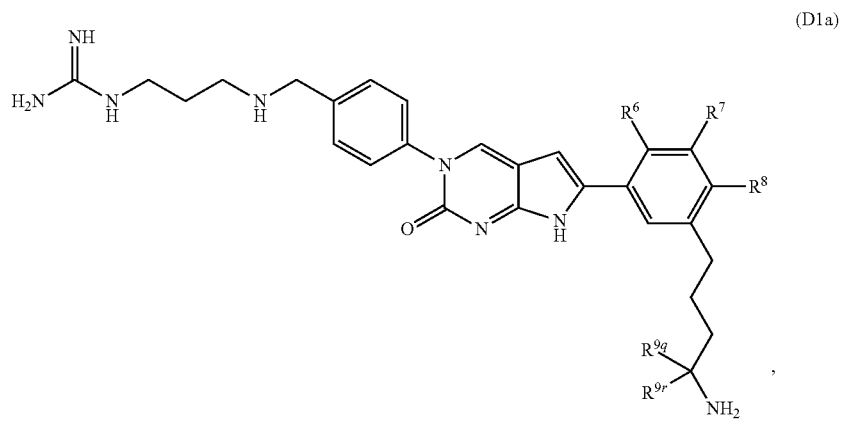

(D1a)

or a tautomer thereof, or a pharmaceutically acceptable salt, ester, or prodrug of said compound or tautomer, wherein $R^6$, $R^7$, $R^8$, $R^{9q}$, and $R^{9r}$ are as defined herein.

In some embodiments, the present invention relates to a compound having formula:

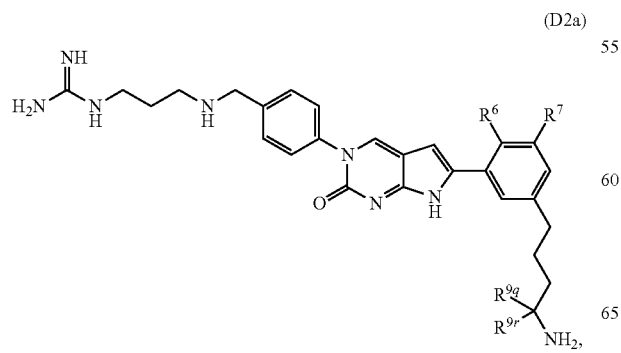

(D2a)

or a tautomer thereof, or a pharmaceutically acceptable salt, ester, or prodrug of said compound or tautomer, wherein $R^6$, $R^7$, $R^{9q}$, and $R^{9r}$ are as defined herein.

In some embodiments, the present invention relates to a compound having formula:

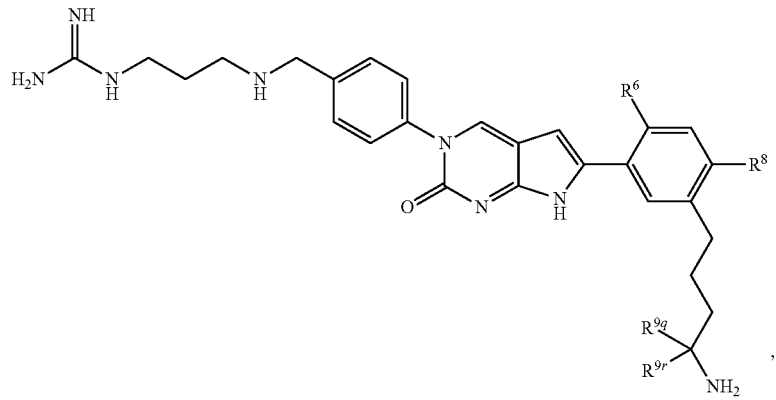

(D3a)

or a tautomer thereof, or a pharmaceutically acceptable salt, ester, or prodrug of said compound or tautomer, wherein $R^6$, $R^8$, $R^{9q}$, and $R^{9r}$ are as defined herein.

In some embodiments, the present invention relates to a compound having formula:

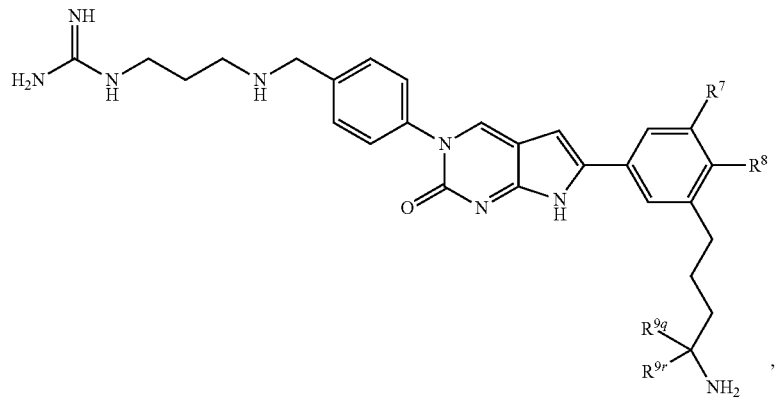

(D4a)

or a tautomer thereof, or a pharmaceutically acceptable salt, ester, or prodrug of said compound or tautomer, wherein $R^7$, $R^8$, $R^{9q}$, and $R^{9r}$ are as defined herein.

In some embodiments, the present invention relates to a compound having formula:

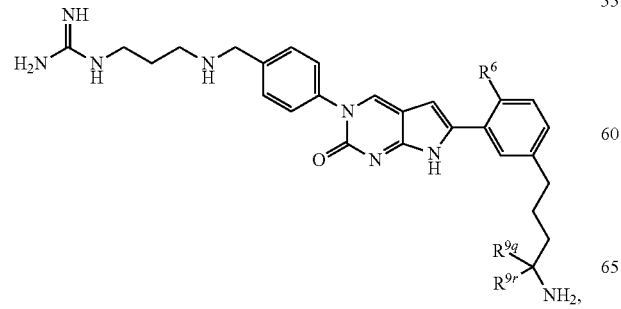

(D5a)

or a tautomer thereof, or a pharmaceutically acceptable salt, ester, or prodrug of said compound or tautomer, wherein $R^6$, $R^{9q}$, and $R^{9r}$ are as defined herein.

In some embodiments, the present invention relates to a compound having formula:

(D6a)

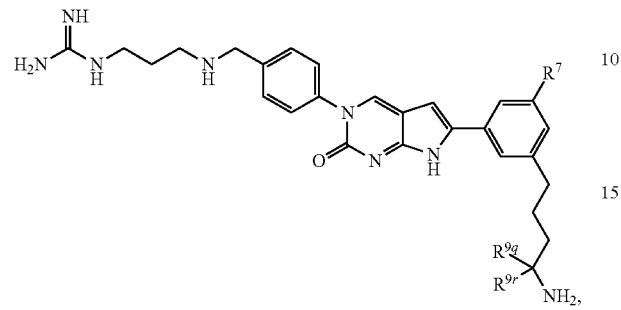

or a tautomer thereof, or a pharmaceutically acceptable salt, ester, or prodrug of said compound or tautomer, wherein $R^7$, $R^{9q}$, and $R^{9r}$ are as defined herein.

In some embodiments, the present invention relates to a compound having formula:

(D7a)

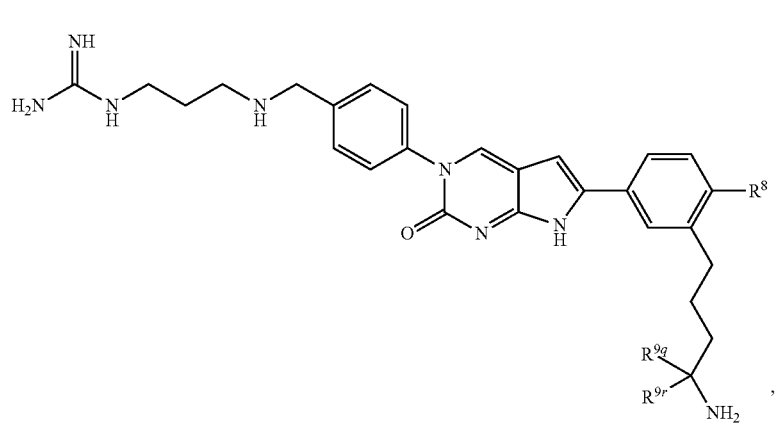

or a tautomer thereof, or a pharmaceutically acceptable salt, ester, or prodrug of said compound or tautomer, wherein $R^8$, $R^{9q}$, and $R^{9r}$ are as defined herein.

In some embodiments, the present invention relates to a compound having formula:

(D8a)

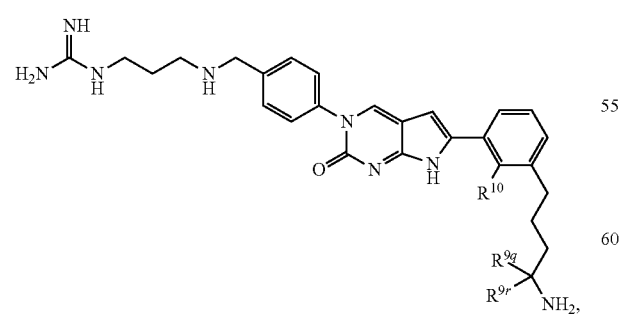

or a tautomer thereof, or a pharmaceutically acceptable salt, ester, or prodrug of said compound or tautomer, wherein $R^{9q}$, $R^{9r}$, and $R^{10}$ are as defined herein.

In some embodiments, the present invention relates to a compound having formula:

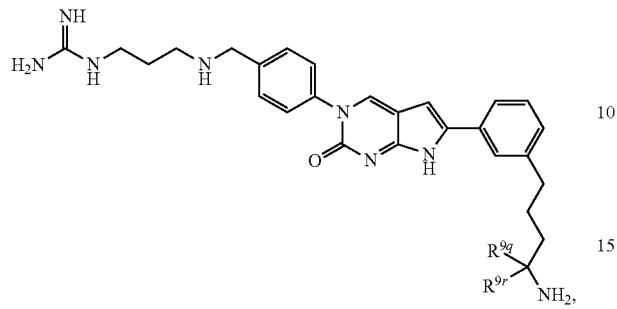

(D9a)

or a tautomer thereof, or a pharmaceutically acceptable salt, ester, or prodrug of said compound or tautomer, wherein $R^{9q}$ and $R^{9r}$ are as defined herein.

In some embodiments, the present invention relates to a compound having formula:

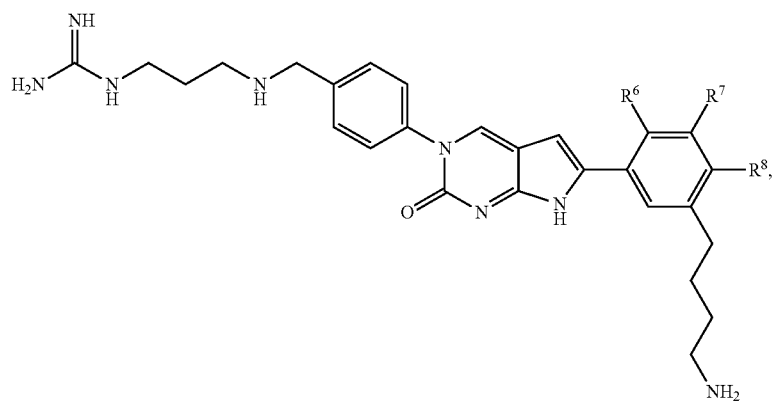

(E1a)

or a tautomer thereof, or a pharmaceutically acceptable salt, ester, or prodrug of said compound or tautomer, wherein $R^6$, $R^7$, and $R^8$ are as defined herein.

In some embodiments, the present invention relates to a compound having formula:

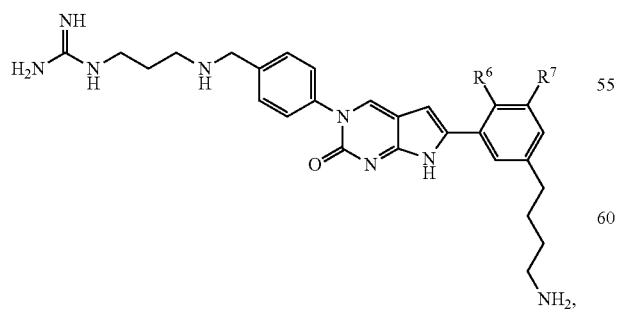

(E2a)

or a tautomer thereof, or a pharmaceutically acceptable salt, ester, or prodrug of said compound or tautomer, wherein $R^6$ and $R^7$ are as defined herein.

In some embodiments, the present invention relates to a compound having formula:

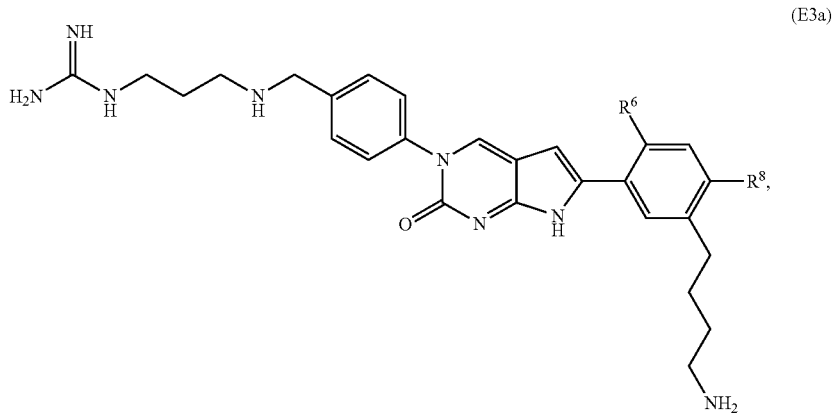

(E3a)

or a tautomer thereof, or a pharmaceutically acceptable salt, ester, or prodrug of said compound or tautomer, wherein $R^6$ and $R^8$ are as defined herein.

In some embodiments, the present invention relates to a compound having formula:

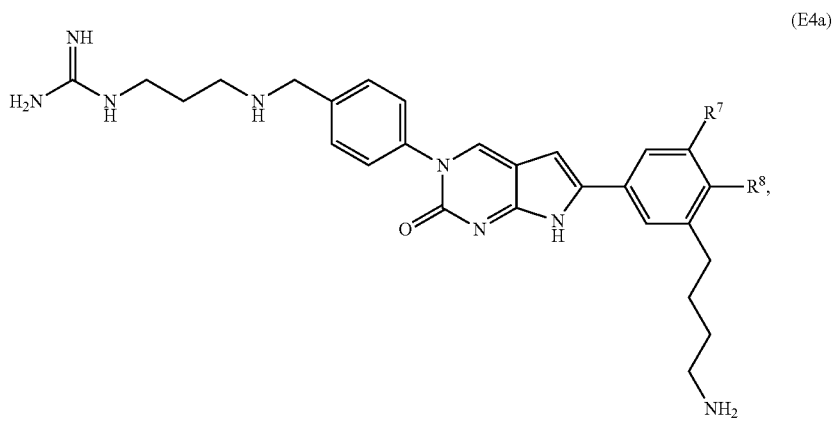

(E4a)

or a tautomer thereof, or a pharmaceutically acceptable salt, ester, or prodrug of said compound or tautomer, wherein $R^7$ and $R^8$ are as defined herein.

In some embodiments, the present invention relates to a compound having formula:

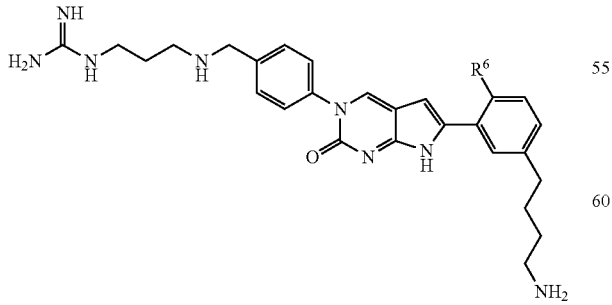

(E5a)

or a tautomer thereof, or a pharmaceutically acceptable salt, ester, or prodrug of said compound or tautomer, wherein $R^6$ is as defined herein.

In some embodiments, the present invention relates to a compound having formula:

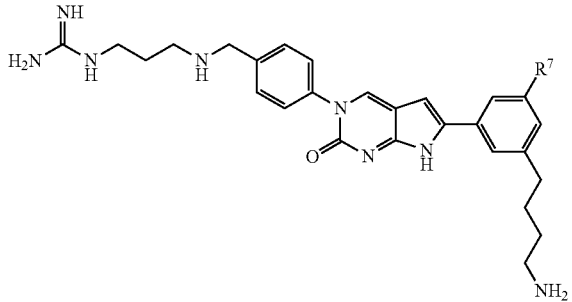

(E6a)

or a tautomer thereof, or a pharmaceutically acceptable salt, ester, or prodrug of said compound or tautomer, wherein $R^7$ is as defined herein.

In some embodiments, the present invention relates to a compound having formula:

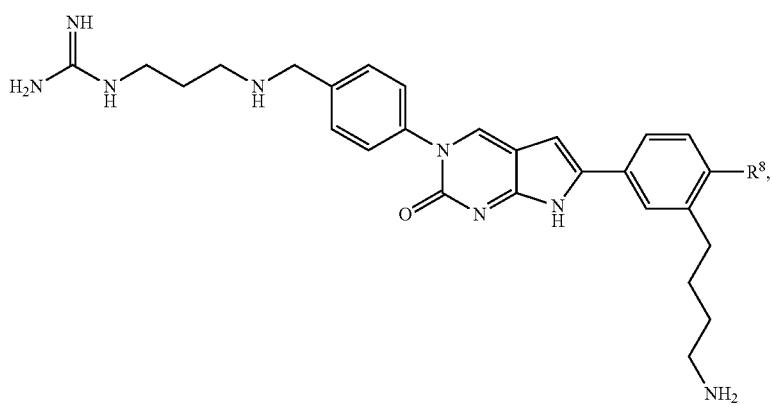

(E7a)

or a tautomer thereof, or a pharmaceutically acceptable salt, ester, or prodrug of said compound or tautomer, wherein $R^8$ is as defined herein.

In some embodiments, the present invention relates to a compound having formula:

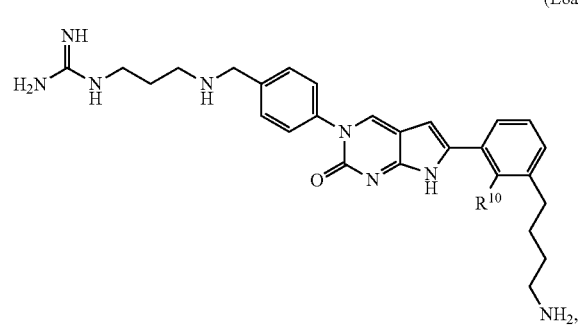

(E8a)

or a tautomer thereof, or a pharmaceutically acceptable salt, ester, or prodrug of said compound or tautomer, wherein $R^{10}$ is as defined herein.

In some embodiments, the present invention relates to a compound or a tautomer thereof, or a pharmaceutically acceptable salt, ester, or prodrug of said compound or tautomer, wherein $R^{10}$ is selected from hydrogen, F and Cl.

In some embodiments, the present invention relates to a compound or a tautomer thereof, or a pharmaceutically acceptable salt, ester, or prodrug of said compound or tautomer, wherein $R^6$, $R^7$, and $R^8$ are each independently selected from (a) F, (b) Cl, (c) —$CF_3$, (d) —$CF_2H$, (e) —$CFH_2$, (f) —$OCF_3$, (g) —$OCF_2H$, (h) —$OCFH_2$, (i) —$OCH_3$, (j) —CN, (k) —$OR^{11}$, (l) —$S(O)_pR^{11}$, (m) —$SCF_3$, (n) —$C_1$-$C_8$ alkyl, (o) -3-14 membered saturated, unsaturated, or aromatic heterocycle containing one or more heteroatoms selected from the group consisting of nitrogen, oxygen, and sulfur, (p) -3-14 membered saturated, unsaturated, or aromatic carbocycle, (q) —CHCHCN and (r) —CHCH—C(O)NH-t-butyl.

In some embodiments, the present invention relates to a compound or a tautomer thereof, or a pharmaceutically acceptable salt, ester, or prodrug of said compound or tautomer, wherein $R^6$, $R^7$, and $R^8$ are each independently selected from (a) F, (b) Cl, (c) —$CF_3$, (d) —$CF_2H$, (e) —$CFH_2$, (f) —$OCF_3$, (g) —$OCF_2H$, (h) —$OCFH_2$, (i) —$OCH_3$, (j) —CN, (k) —$OR^{11}$, (l) —$S(O)_pR^{11}$, (m) —$SCF_3$, (n) —$C_1$-$C_8$ alkyl, (o) -3-14 membered saturated, unsaturated, or aromatic heterocycle containing one or more heteroatoms selected from the group consisting of nitrogen, oxygen, and sulfur, and (p) -3-14 membered saturated, unsaturated, or aromatic carbocycle.

In some embodiments, the present invention relates to a compound or a tautomer thereof, or a pharmaceutically acceptable salt, ester, or prodrug of said compound or tautomer, wherein $R^6$, $R^7$, and $R^8$ are each independently selected from are each independently selected from (a) F; (b) Cl; (c) —$CF_3$; (d) —$CF_2H$; (e) —$CFH_2$; (f) —$OCF_3$; (g) —$OCF_2H$; (h) —$OCFH_2$; (i) —$OCH_3$; (j) —$O(C_1$-$C_4$ alkyl); (k) —$S(O)CH_3$; (l) —$S(O)CF_3$; (m) —$S(O)_2CH_3$; (n) —$S(O)_2$ $CF_3$; (o) —$SCF_3$;

(p) —C1-C4 alkyl selected from methyl, ethyl, isopropyl, and t-butyl;

(q) -3-7 membered saturated, unsaturated, or aromatic heterocycle selected from oxetanyl, azepanyl, pyridyl, dihydropyridyl, furanyl, tetrahydrofuranyl, tetrahydropyridyl, azetidinyl, pyrrolidinyl, piperidinyl, and piperidenyl; and (r) -3-7 membered saturated, unsaturated, or aromatic carbocycle selected from cyclopropyl, cyclobutyl, cyclopentyl, cyclohexyl, cycloheptyl, phenyl, cyclohexenyl, and cyclohexadienyl.

In some embodiments, the present invention relates to a compound or a tautomer thereof, or a pharmaceutically acceptable salt, ester, or prodrug of said compound or tautomer, wherein $R^6$, $R^7$, and $R^8$ are each independently selected from are each independently selected from (a) F, (b) Cl, (c) —$CF_3$, (d) —$OCF_3$, (e) —$OCH_3$, (f) methyl, (g) ethyl, (h) isopropyl, (i) t-butyl, (j) azepanyl, (k) cyclopropyl, (l) cyclobutyl, (m) cyclohexyl, (n) phenyl, (o) pyridyl, (p) azetidinyl, (q) pyrrolidinyl, (r) piperidinyl, and (s) piperidenyl.

In some embodiments, the present invention relates to a compound or a tautomer thereof, or a pharmaceutically acceptable salt, ester, or prodrug of said compound or tautomer, wherein $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are each independently selected from (a) hydrogen, (b) halogen, (c) —$CF_3$, (d) —$CF_2H$, (e) —$CFH_2$, (f) —$OCF_3$, (g) —$OCH_3$, (h) —$OCF_2H$, (i) —$OCFH_2$, (j) —$OR^{11}$, (k) —$C_1$-$C_8$ alkyl, (l) haloalkyl, (m) -3-14 membered saturated, unsaturated, or aromatic heterocycle containing one or more heteroatoms selected from the group consisting of nitrogen, oxygen, and sulfur, and (n) -3-14 membered saturated, unsaturated, or aromatic carbocycle;

alternatively, one or more of pairs of substituents selected from $R^{9k}$ and $R^{9l}$, $R^{9m}$ and $R^{9n}$, $R^{9o}$ and $R^{9p}$, $R^{9q}$ and $R^{9r}$, and $R^{9s}$ and $R^{9t}$ are taken together with the carbon atom to which they are attached to form (a) 3-7 membered saturated or unsaturated carbocyclic or (b) 3-7 membered saturated or unsaturated heterocyclic ring containing one or more heteroatoms selected from the group consisting of nitrogen, oxygen, and sulfur; and at least one substituent selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ is not hydrogen.

In some embodiments, the present invention relates to a compound or a tautomer thereof, or a pharmaceutically acceptable salt, ester, or prodrug of said compound or tautomer, wherein $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are each independently selected from (a) hydrogen; (b) halogen; (c) —$CF_3$; (d) —$CF_2H$; (e) —$CFH_2$; (f) —$OCF_3$; (g) —$OCH_3$; (h) —$OCF_2H$; (i) —$OCFH_2$; (j) —OH; (k) —$O(C_1$-$C_4$ alkyl);

(l) —$C_1$-$C_4$ alkyl selected from methyl, ethyl, isopropyl, and t-butyl;

(m) -3-7 membered saturated, unsaturated, or aromatic heterocycle selected from oxetanyl, azepanyl, pyridyl, dihydropyridyl, furanyl, tetrahydrofuranyl, tetrahydropyridyl, azetidinyl, pyrrolidinyl, piperidinyl, and piperidenyl; and
(n) -3-7 membered saturated, unsaturated, or aromatic carbocycle selected from cyclopropyl, cyclobutyl, cyclopentyl, cyclohexyl, cycloheptyl, phenyl, cyclohexenyl, and cyclohexadienyl;

alternatively, one or more of pairs of substituents are selected from $R^{9k}$ and $R^{9l}$, $R^{9m}$ and $R^{9n}$, $R^{9o}$ and $R^{9p}$, $R^{9q}$ and $R^{9r}$, and $R^{9s}$ and $R^{9t}$ are taken together with the carbon atom to which they are attached form cyclopropyl, cyclobutyl, or oxetanyl; and at least one substituent selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ is not hydrogen;

In some embodiments, the present invention relates to a compound or a tautomer thereof, or a pharmaceutically acceptable salt, ester, or prodrug of said compound or tautomer, wherein $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are each independently selected from (a) hydrogen, (b) halogen, (d) —$CF_3$, (e) —$CF_2H$, (f) —$CFH_2$, (g) —$OCF_3$, (h) —$OCH_3$, (i) —$OCF_2H$, (j) —$OCFH_2$, (k) —OH, (l) —$OCH_3$, (l) methyl, (m) ethyl, (n) isopropyl, and (o) t-butyl; and at least one substituent selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ is not hydrogen.

In some embodiments, the present invention relates to a compound or a tautomer thereof, or a pharmaceutically acceptable salt, ester, or prodrug of said compound or tautomer, wherein

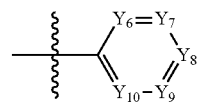

is selected from:

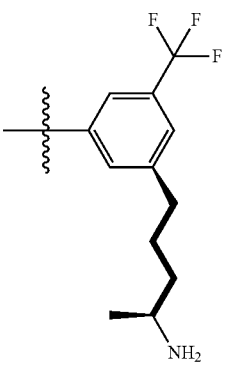
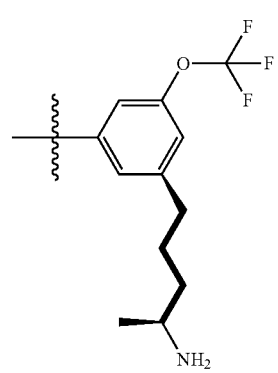

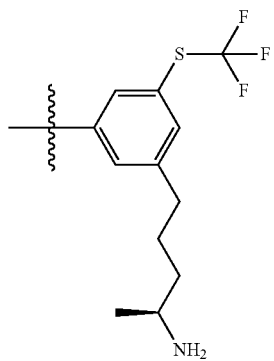
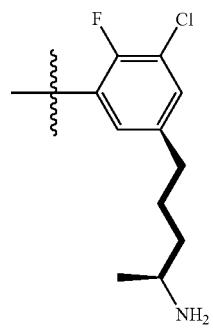

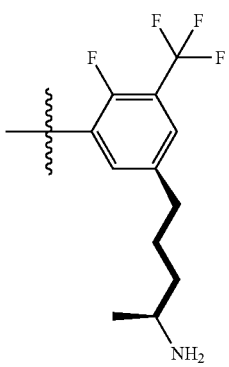
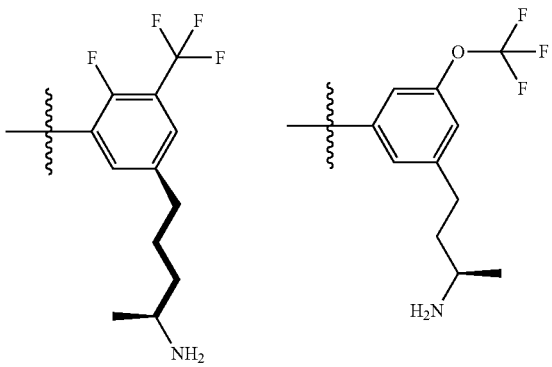

-continued
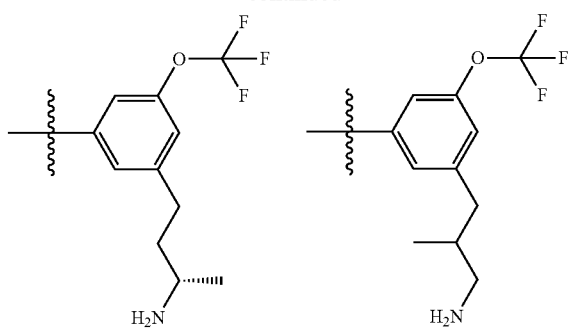
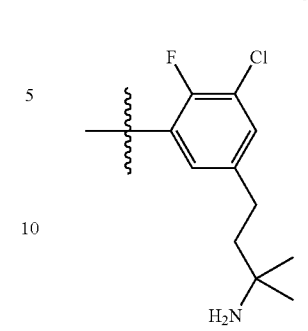
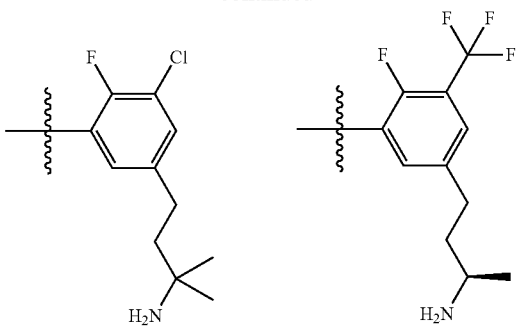
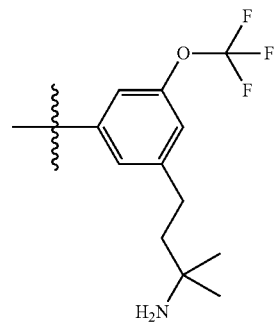
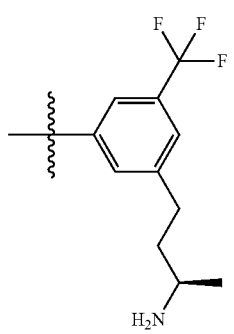
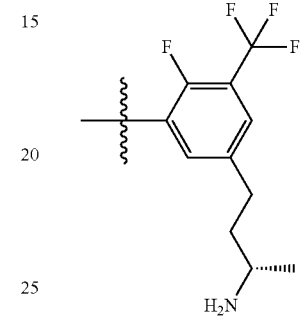
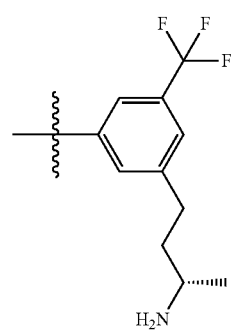
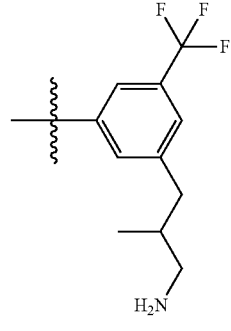
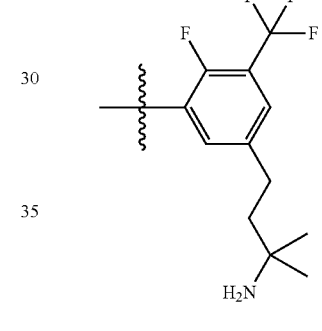
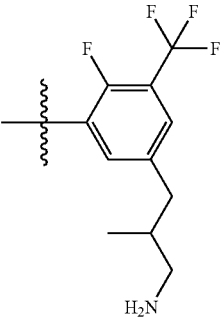
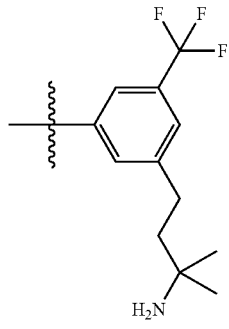
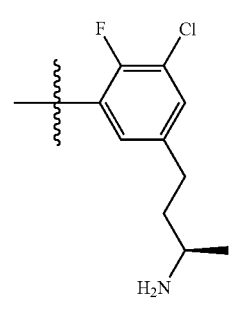
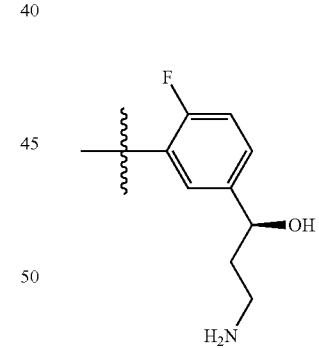
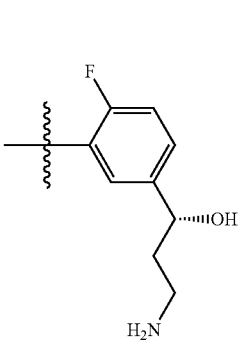
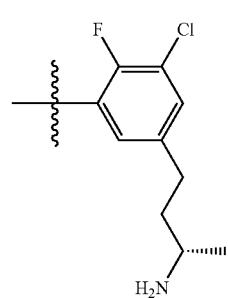
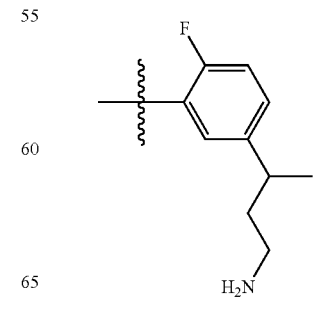

123
-continued
124
-continued
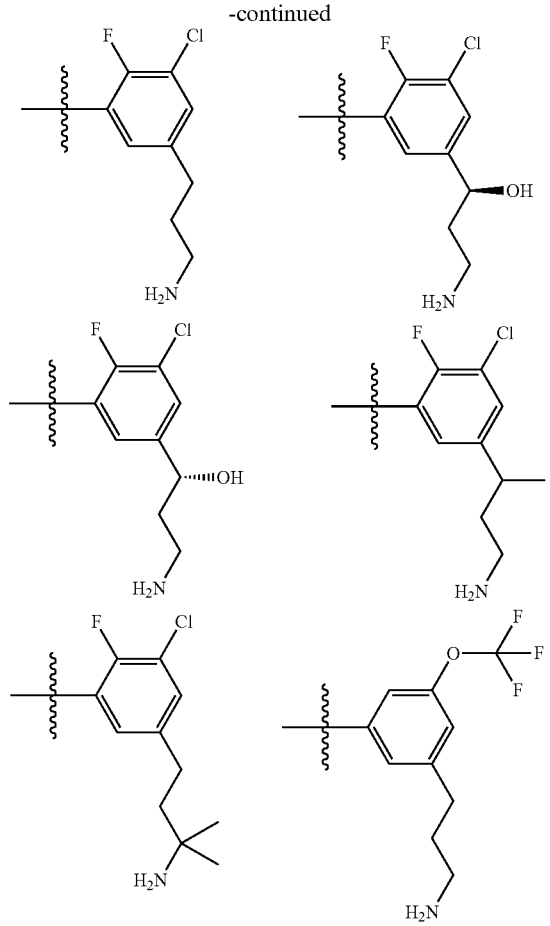
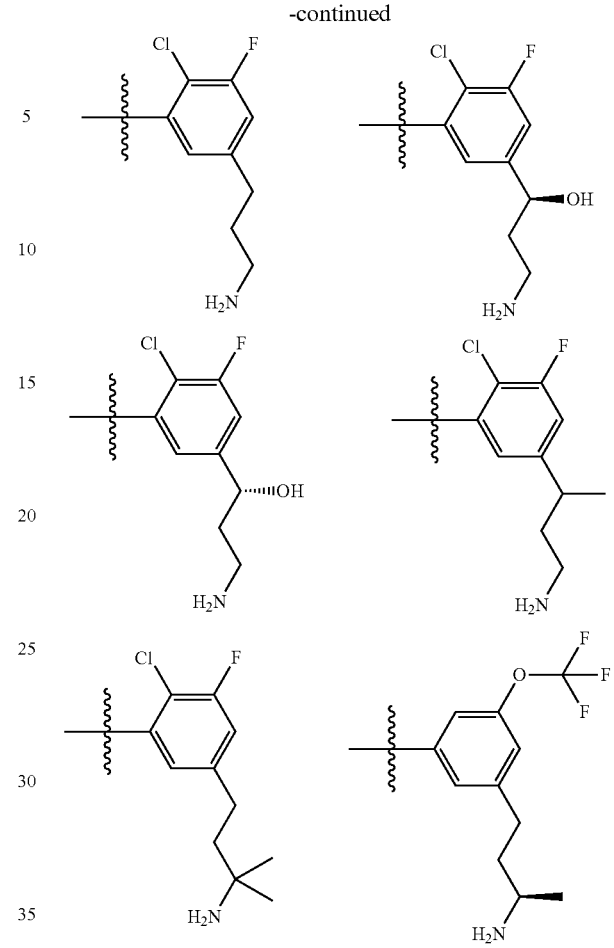
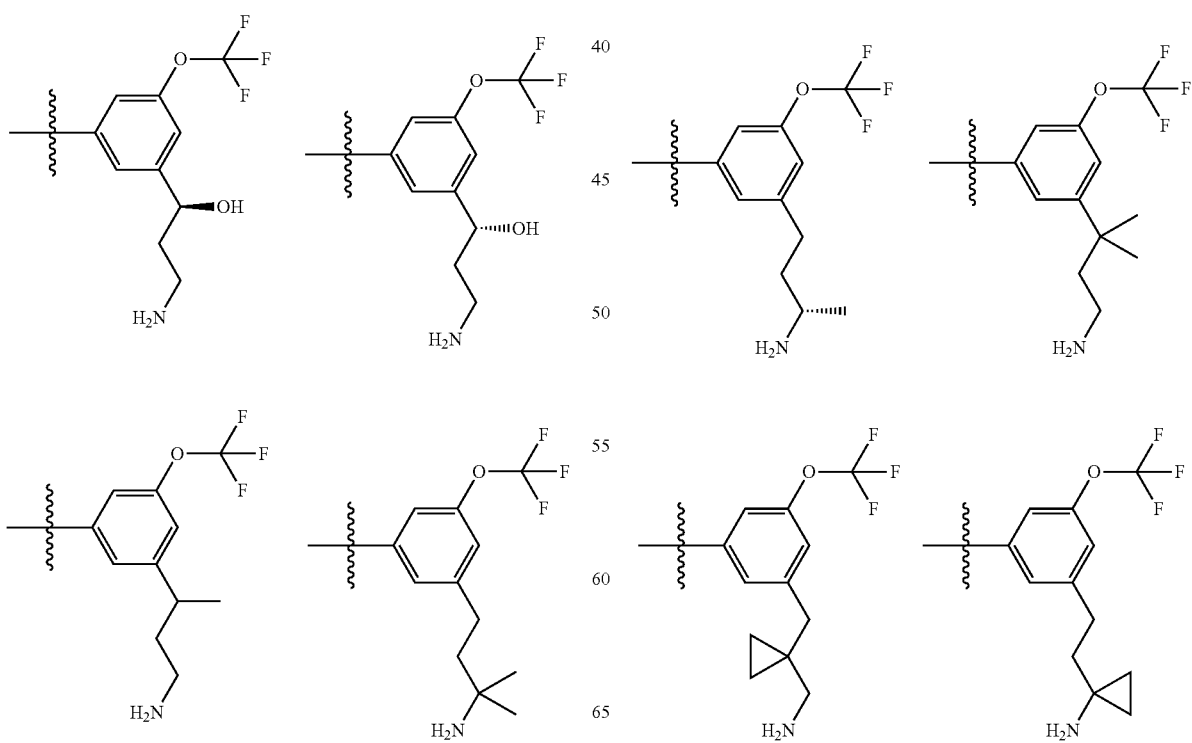

125
-continued
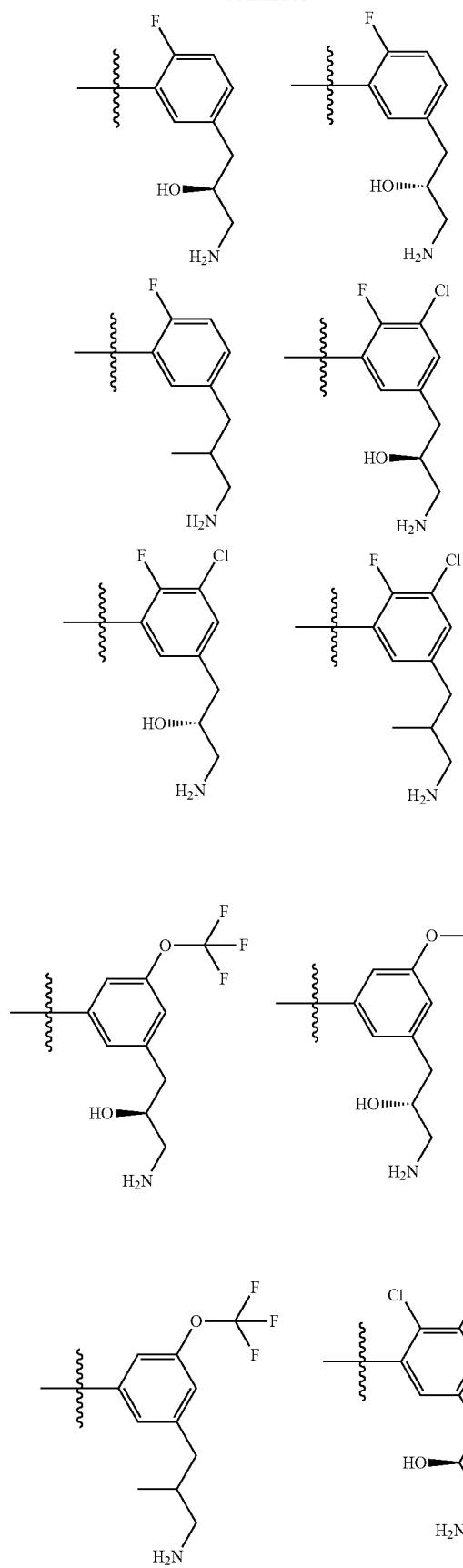
126
-continued
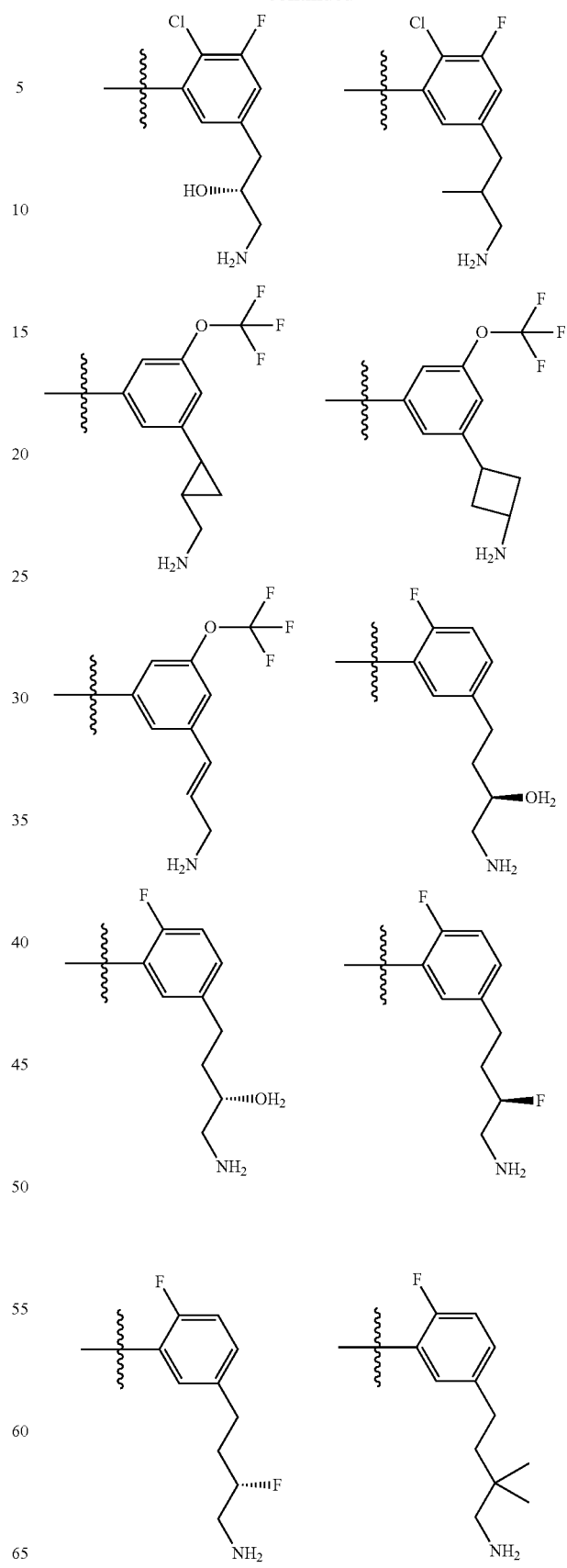

127
-continued
128
-continued
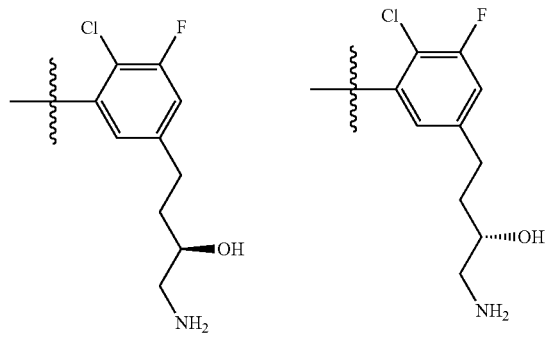
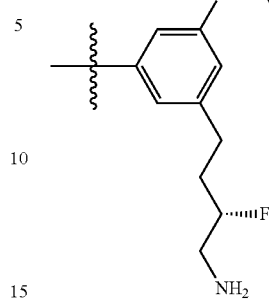
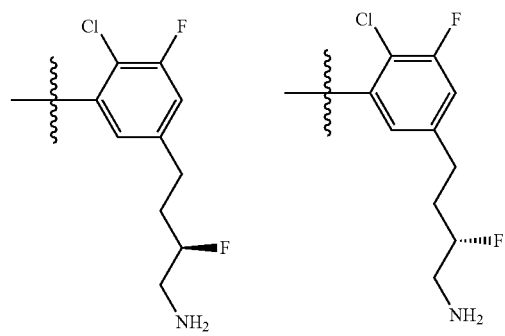
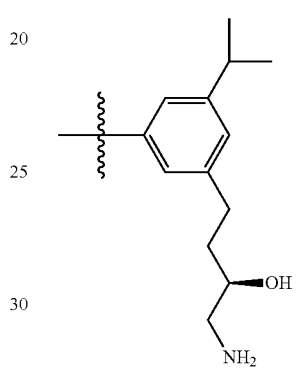
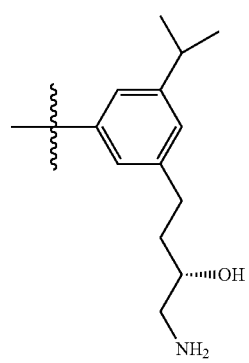
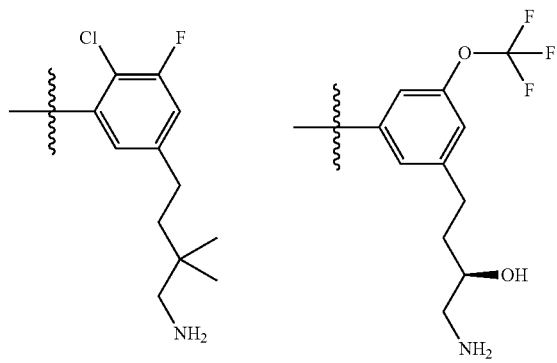
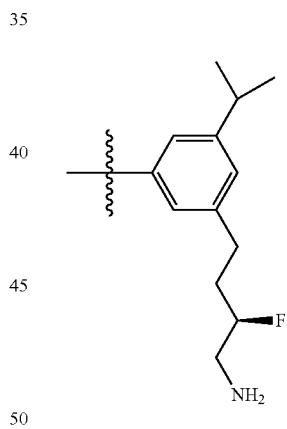
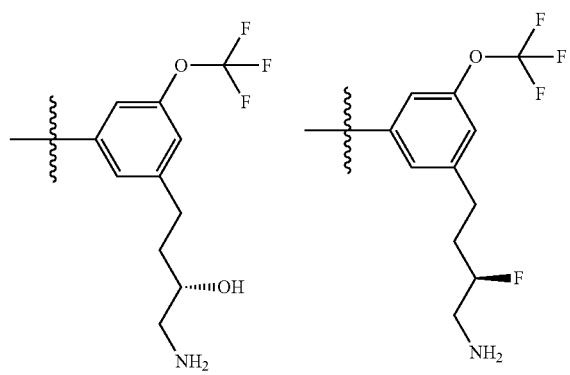
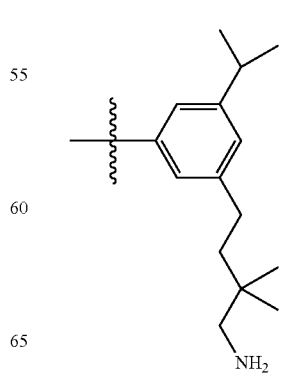

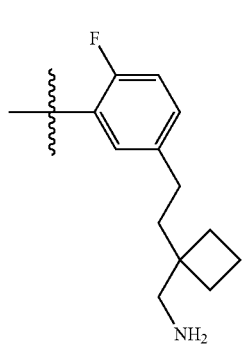
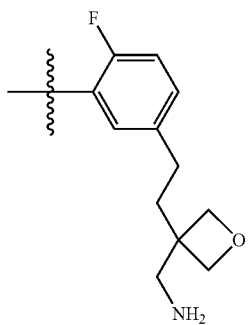
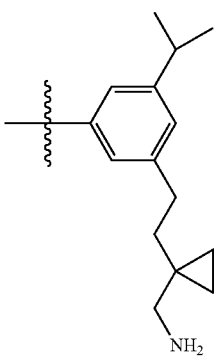
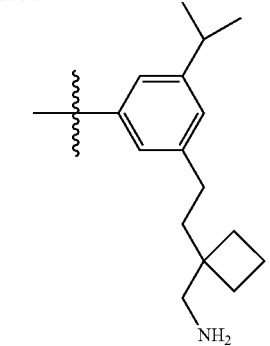
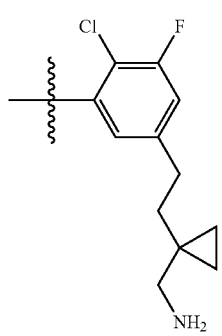
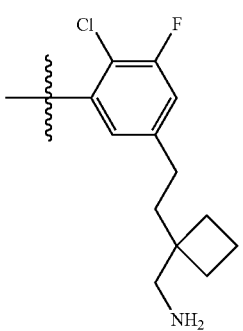
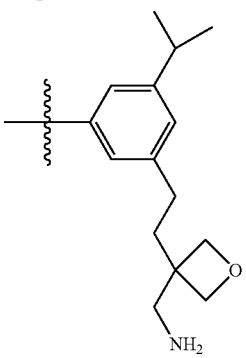 [SMILES: *c1cc(CCC2(CN)COC2)cc(C(C)C)c1]
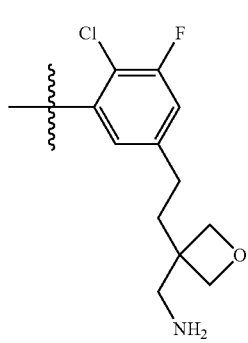
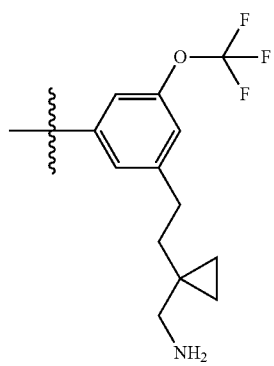
or a tautomer thereof, or a pharmaceutically acceptable salt, ester, or prodrug of said compound or tautomer.
In some embodiments,
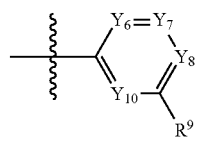
is selected from
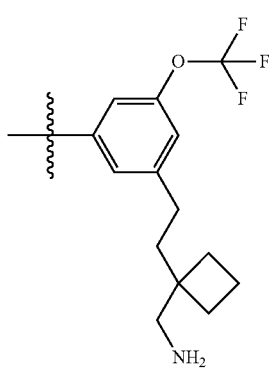
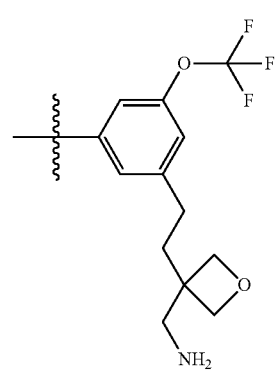
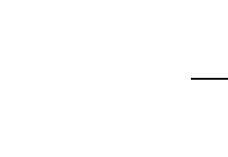
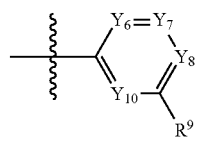
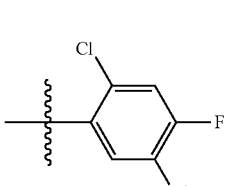
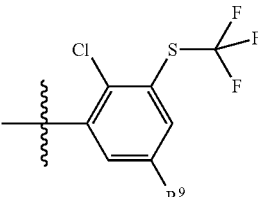
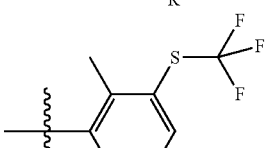
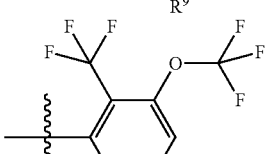
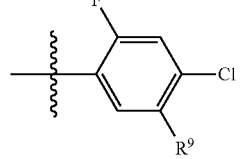
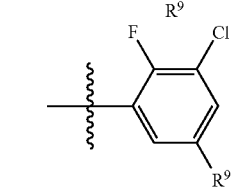

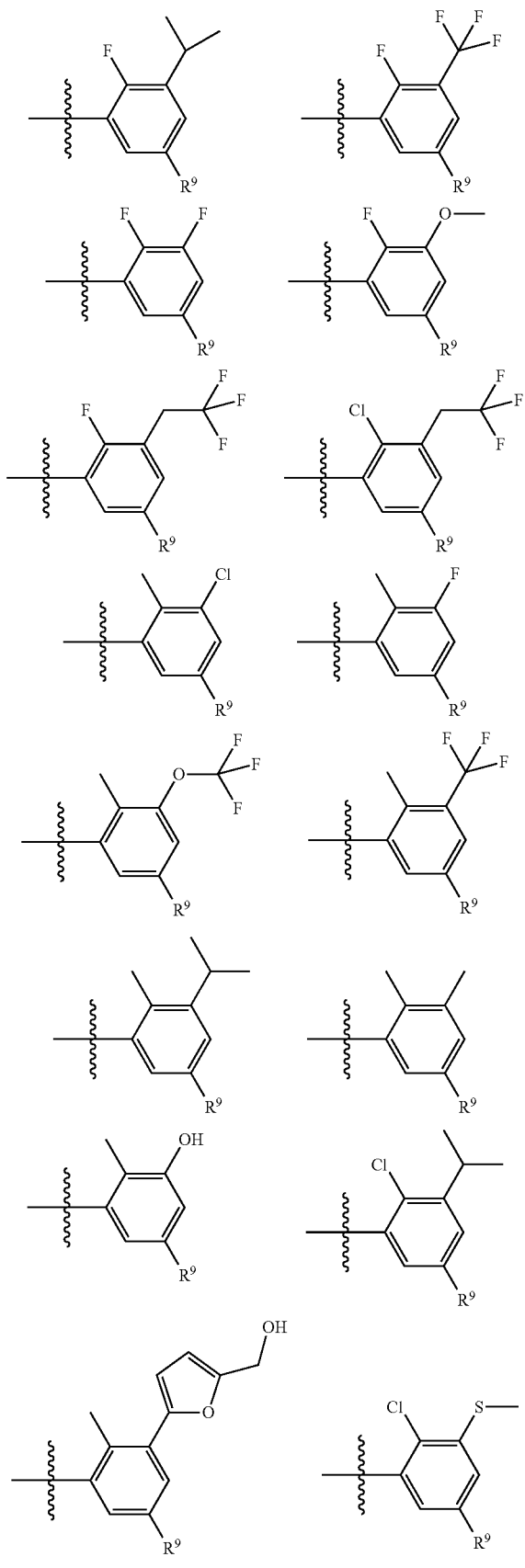
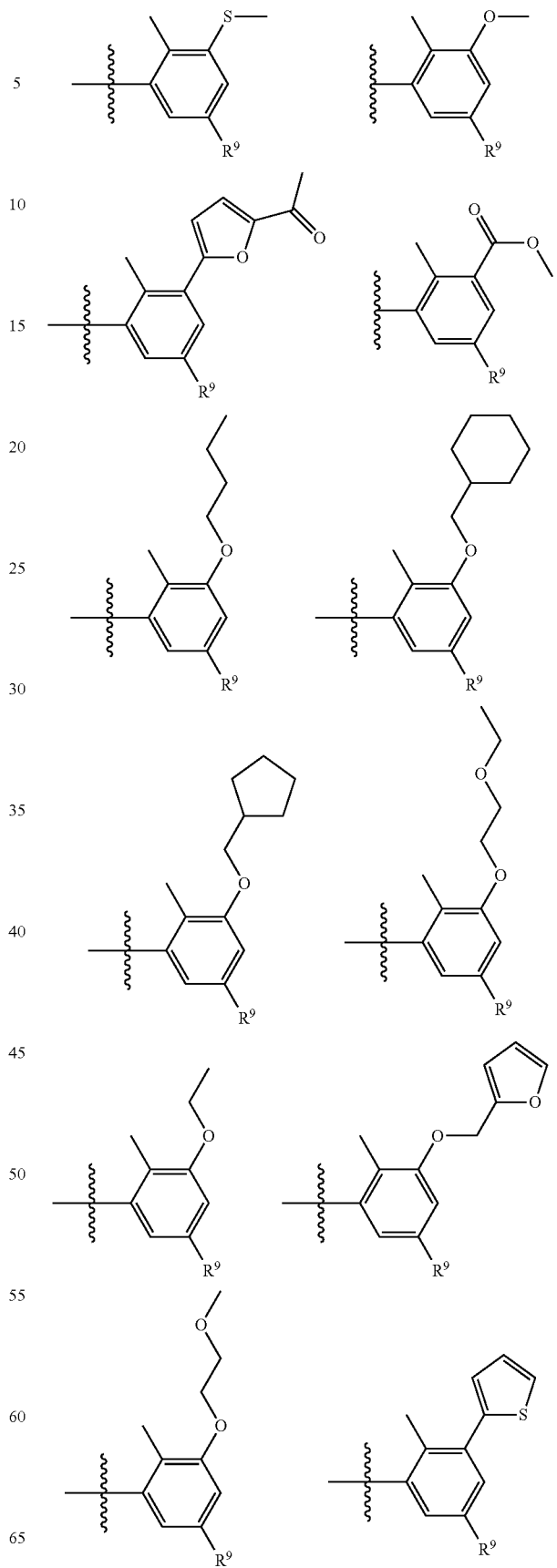

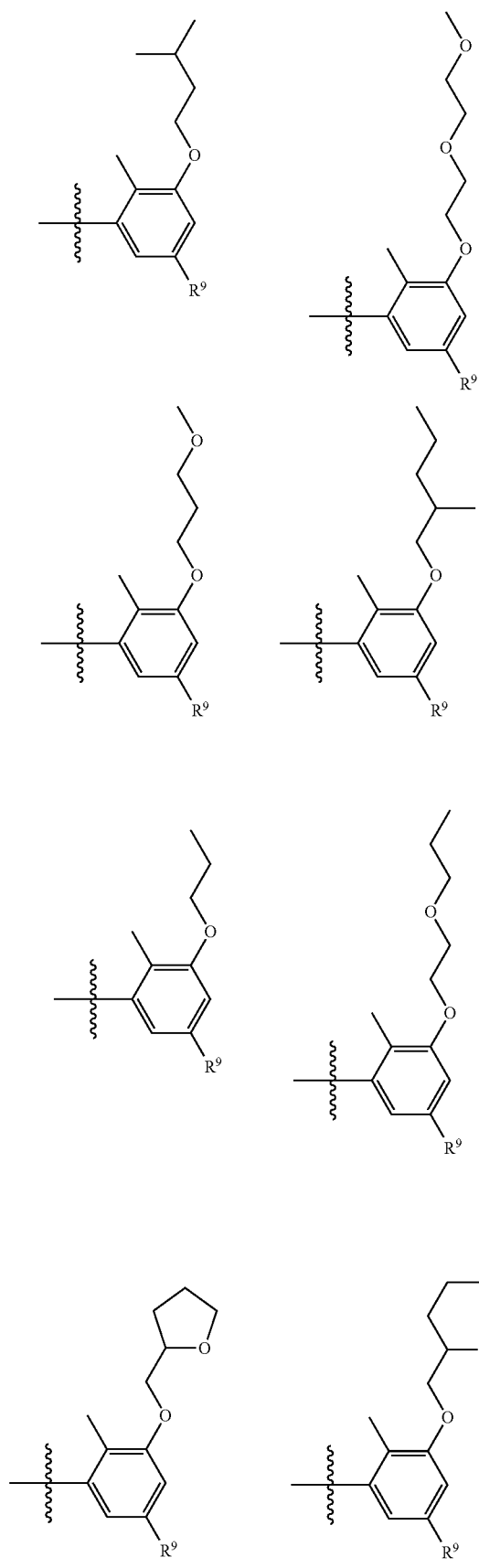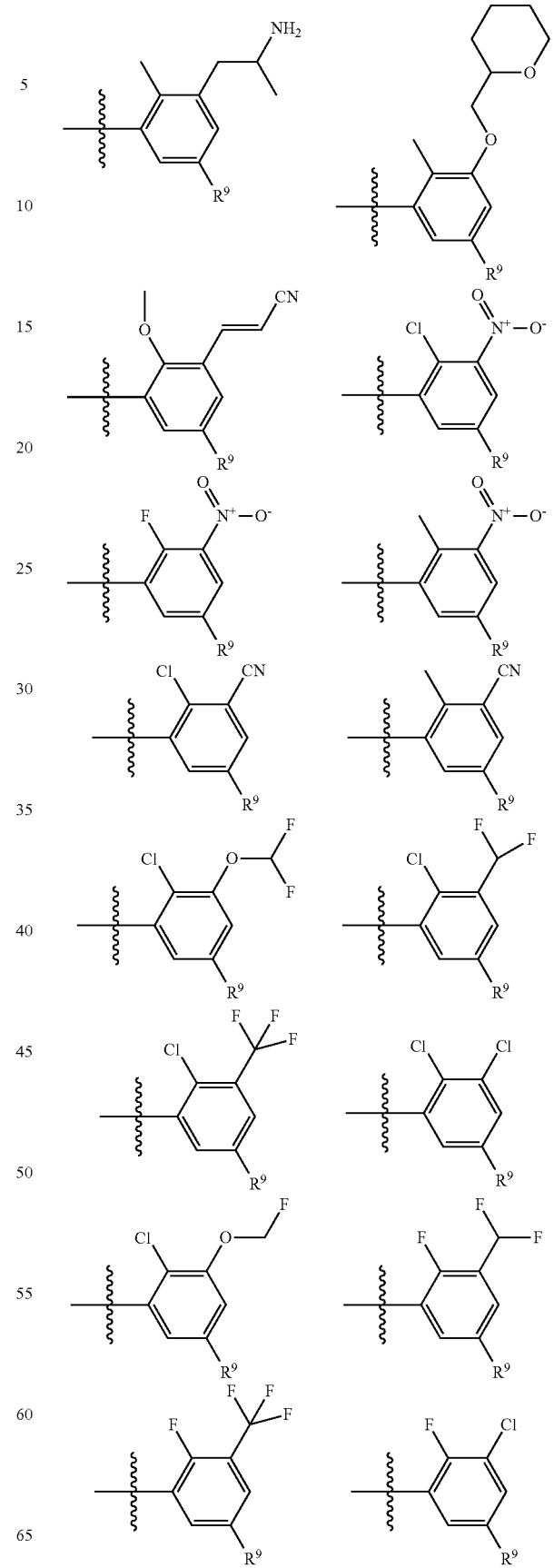

-continued
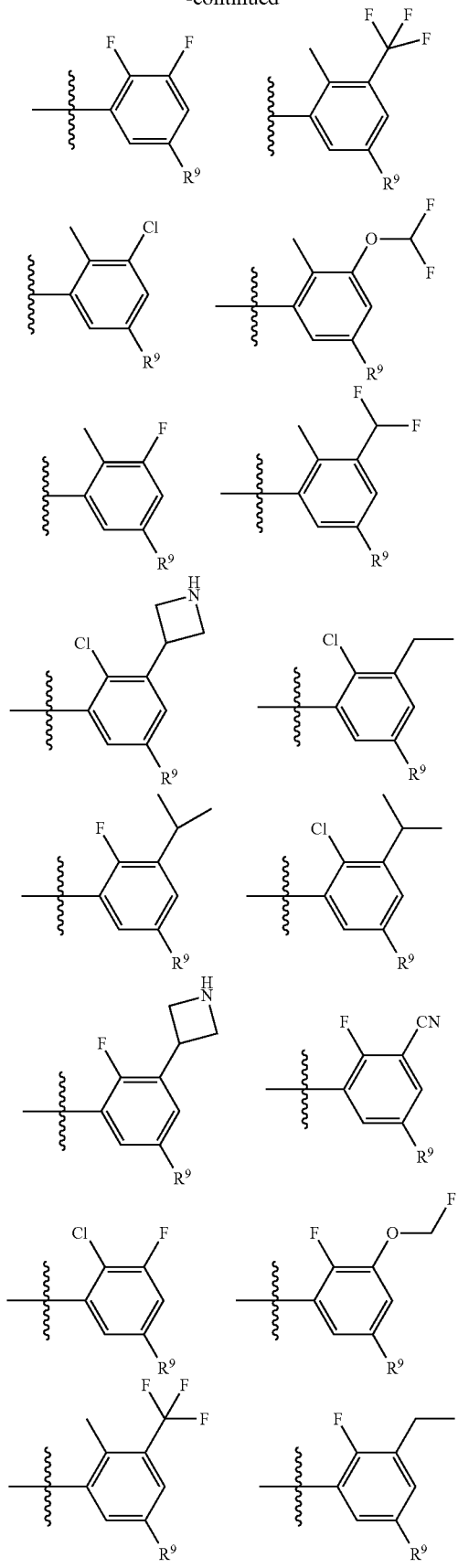
In some embodiments, the present invention relates to a compound or a tautomer thereof, or a pharmaceutically acceptable salt, ester, or prodrug of said compound or tautomer, wherein $R^3$ is selected from:
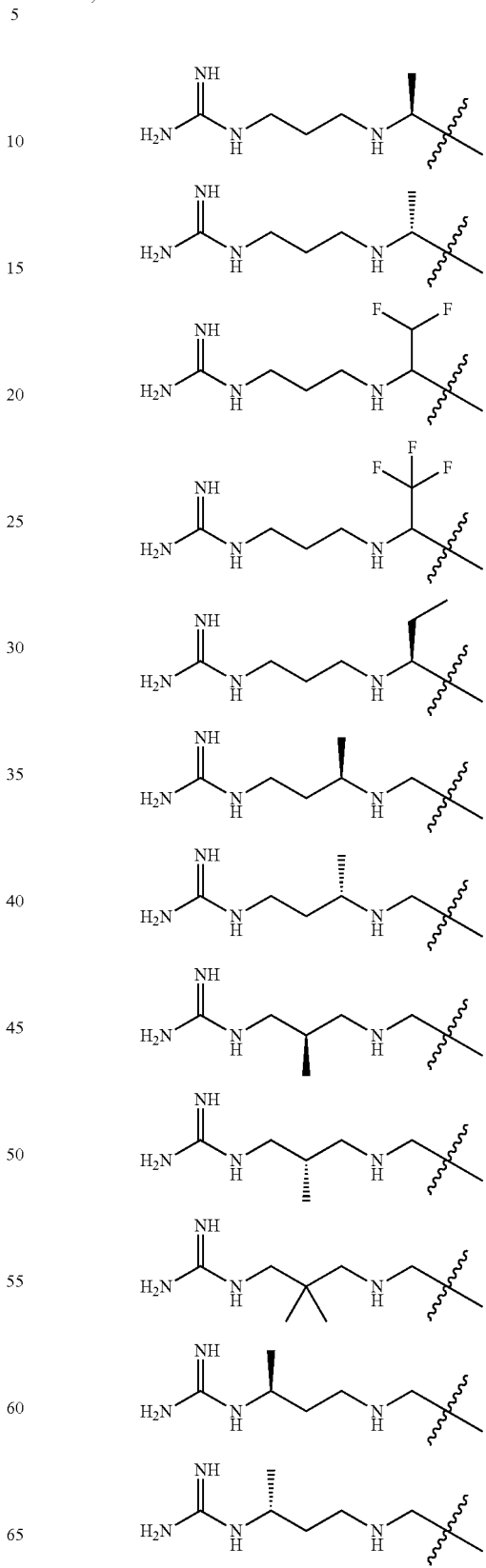

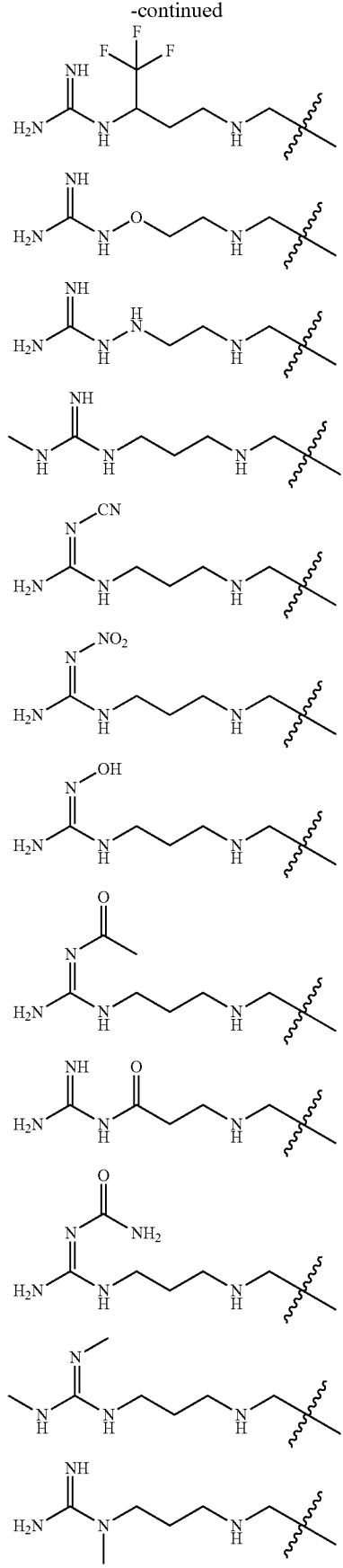
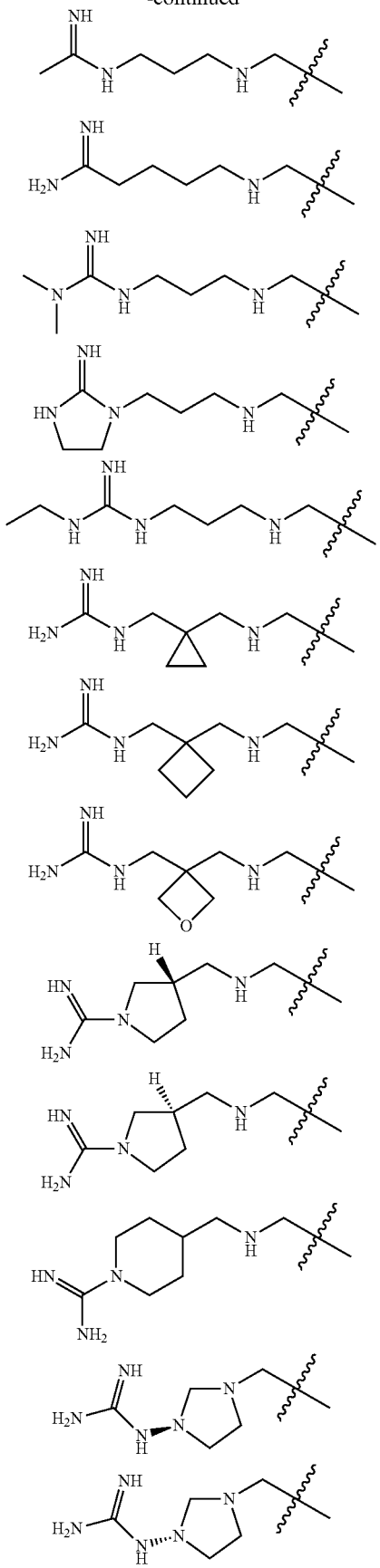

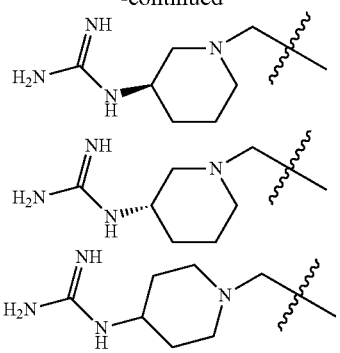

In some embodiments, the present invention relates to a compound having the formula:

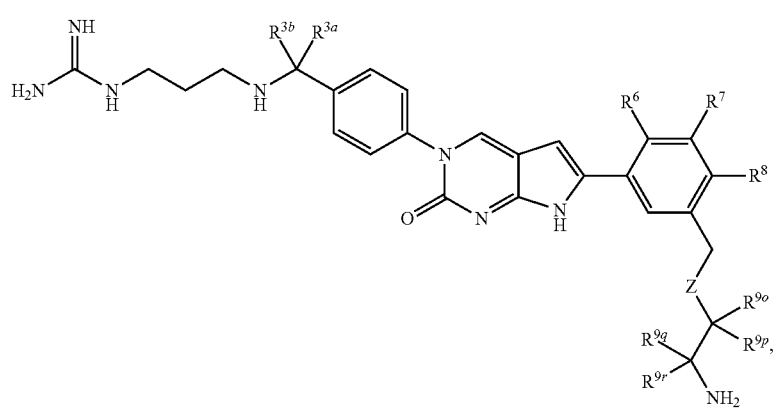

(F1)

or a tautomer thereof, or a pharmaceutically acceptable salt, ester, or prodrug of said compound or tautomer, wherein $R^{3a}$, $R^{3b}$, $R^6$, $R^7$, $R^8$, Z, $R^{9o}$, $R^{9p}$, $R^{9q}$, and $R^{9r}$ are as defined herein.

In some embodiments, the present invention relates to a compound having the formula:

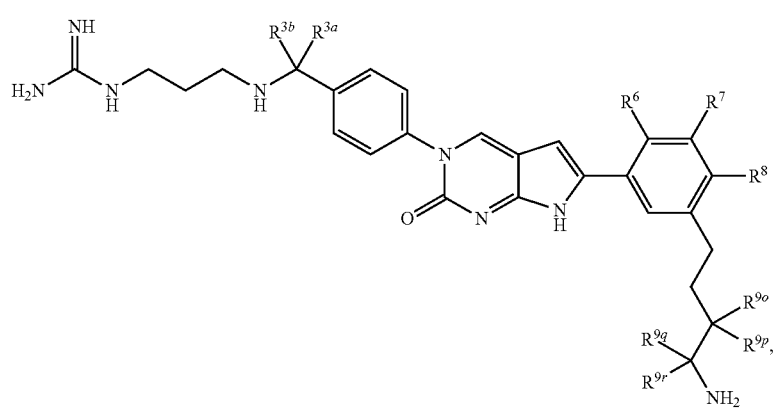

(F2)

or a tautomer thereof, or a pharmaceutically acceptable salt, ester, or prodrug of said compound or tautomer, wherein $R^{3a}$, $R^{3b}$, $R^6$, $R^7$, $R^8$, $R^{9o}$, $R^{9p}$, $R^{9q}$, and $R^{9r}$ are as defined herein.

In some embodiments, the present invention relates to a compound of formula F1 or F2, or a tautomer thereof, or a pharmaceutically acceptable salt, ester, or prodrug of said compound or tautomer, wherein Z is selected from —O—, —S(O)$_p$—, —NR$^{11}$, —(C=O)—, —NR$^{11}$(C=O)—, —(C=O)NR$^{11}$—, —S(O)$_p$ NR$^{11}$—, —NR$^{11}$S(O)$_p$—, and —NR$^{11}$S(O)$_p$ NR$^{11}$—;

$R^{3a}$ is selected from halogen and —C$_1$-C$_6$ alkyl;

$R^{3b}$ is selected from hydrogen, halogen, —OCF$_3$, —OCF$_2$H, —OCFH$_2$, —OCH$_3$, —OR$^{11}$, —C$_1$-C$_6$ alkyl, and haloalkyl;

$R^6$, $R^7$, and $R^8$ are each independently selected from (a) hydrogen, (b) F, (c) Cl, (d) Br, (e) I, (f) —CF$_3$, (g) —CF$_2$H, (h) —CFH$_2$, (i) —OCF$_3$, (j) —OCF$_2$H, (k) —OCFH$_2$, (l) —OCH$_3$, (m) —CN, (n) —N$_3$, (o) —NO$_2$, (p) —NR$^{11}$R$^{11}$, (q) —NR$^{11}$(CO)R$^{11}$, (r) —(CO)NR$^{11}$R$^{11}$, (s) —OR$^{11}$, (t) —COH, (u) —CO(C$_1$-C$_8$ alkyl), (v) —COR$^{11}$, (w) —NR$^{11}$(CNR$^{11}$)NR$^{11}$R$^{11}$, (x) —S(O)$_p$R$^{11}$, (y) —NR$^{11}$S(O)$_p$R$^{11}$, (z) —SR$^{11}$, (aa) —SCF$_3$, (bb) —C(CF$_3$)H—NH—CHR$^{11}$R$^{11}$, (cc) —COOR$^{11}$, (dd) —(OCH$_2$CH$_2$)$_r$R$^{11}$, (ee) —(OCH$_2$CH$_2$)$_r$OR$^{11}$, (ff) —C$_1$-C$_8$ alkyl, (gg) —C$_2$-C$_8$ alkenyl, and (hh) —C$_2$-C$_8$ alkynyl;

$R^{9o}$, $R^{9p}$, $R^{9q}$, and $R^{9r}$ are each independently selected from (a) hydrogen, (b) halogen, (c) —OCF$_3$, (d) —OCH$_3$, (e) —OCF$_2$H, (f) —OCFH$_2$, (g) —OR$^{11}$, (h) —C$_1$-C$_8$ alkyl, and (i) haloalkyl;

$R^{11}$ is selected from hydrogen, —$C_1$-$C_6$ alkyl, —$C_2$-$C_6$ alkenyl, —$C_2$-$C_6$ alkynyl, and haloalkyl;

p is 0, 1, or 2; and t is 0, 1, or 2.

In some embodiments, the present invention relates to a compound of formula F1, or a tautomer thereof, or a pharmaceutically acceptable salt, ester, or prodrug of said compound or tautomer, wherein Z is O;

$R^{9o}$, $R^{9p}$, $R^{9q}$, and $R^{9r}$ are each independently selected from $C_1$-$C_6$ alkyl and hydrogen;

$R^6$ and $R^8$ are each independently selected from hydrogen, F, Cl, Br, I, —$C_1$-$C_6$ alkyl, —$CH_2F$, —$CHF_2$, and —$CF_3$;

$R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p C_1$-$C_6$ alkyl, —$OCH_2F$, —$OCHF_2$, —$OCF_3$, —$S(O)_p$—$CH_3$, —$S(O)_p$—$CH_2F$, and —$S(O)_p$—$CF_3$; and $R^{3a}$ is selected from halogen and —$C_1$-$C_6$ alkyl;

$R^{3b}$ is selected from hydrogen, halogen, —$CF_3$, —$CF_2H$, —$CFH_2$, —$C_1$-$C_6$ alkyl, and haloalkyl; and p is 0, 1, or 2.

In some embodiments, the present invention relates to a compound of formula F2, or a tautomer thereof, or a pharmaceutically acceptable salt, ester, or prodrug of said compound or tautomer, wherein $R^{9o}$, $R^{9p}$, $R^{9q}$, and $R^{9r}$ are each independently selected from —$C_1$-$C_6$ alkyl and hydrogen;

$R^6$ and $R^8$ are each independently selected from hydrogen, F, Cl, Br, I, —$C_1$-$C_6$ alkyl, —$CH_2F$, —$CHF_2$, and —$CF_3$;

$R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p$—$C_1$-$C_6$ alkyl, —$OCH_2F$, —$OCHF_2$, —$OCF_3$, —$S(O)_p$—$CH_3$, —$S(O)_p$—$CH_2F$, and —$S(O)_p$—$CF_3$; and $R^{3a}$ is selected from halogen and —$C_1$-$C_6$ alkyl;

$R^{3b}$ is selected from hydrogen, halogen, —$CF_3$, —$CF_2H$, —$CFH_2$, —$C_1$-$C_6$ alkyl, and haloalkyl; and p is 0, 1, or 2.

In some embodiments, the present invention relates to a compound having the formula:

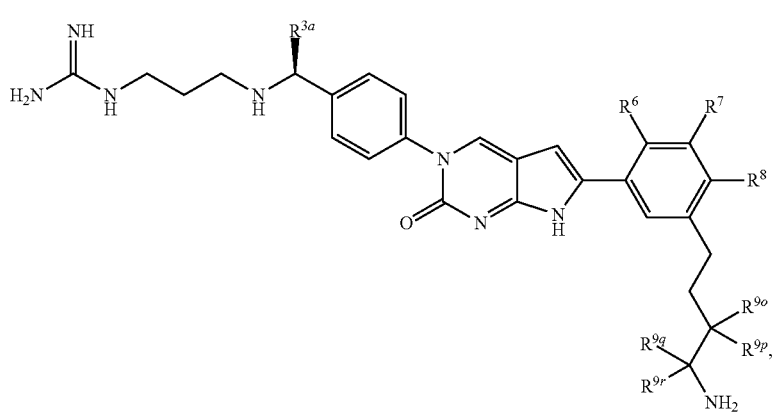

(G1)

or a tautomer thereof, or a pharmaceutically acceptable salt, ester, or prodrug of said compound or tautomer, wherein $R^{3a}$, $R^6$, $R^7$, $R^8$, $R^{9o}$, $R^{9p}$, $R^{9q}$, and $R^{9r}$ are as defined herein.

In some embodiments, the present invention relates to a compound having the formula:

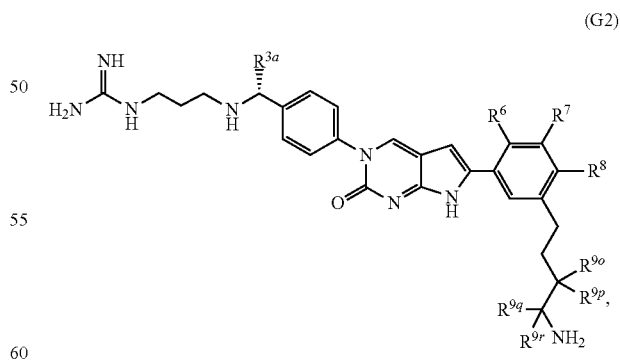

(G2)

or a tautomer thereof, or a pharmaceutically acceptable salt, ester, or prodrug of said compound or tautomer, wherein $R^{3a}$, $R^6$, $R^7$, $R^8$, $R^{9o}$, $R^{9p}$, $R^{9q}$, and $R^{9r}$ are as defined herein.

In some embodiments, the present invention relates to a compound having the formula:

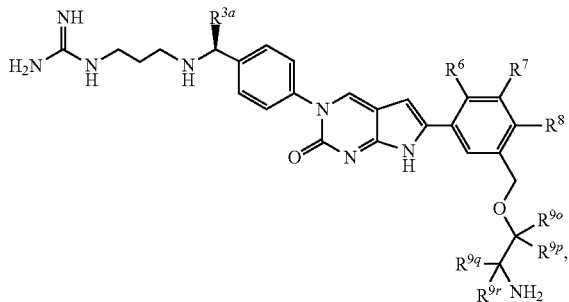

(G3)

or a tautomer thereof, or a pharmaceutically acceptable salt, ester, or prodrug of said compound or tautomer, wherein $R^{3a}$, $R^6$, $R^7$, $R^8$, $R^{9o}$, $R^{9p}$, $R^{9q}$, and $R^{9r}$ are as defined herein.

In some embodiments, the present invention relates to a compound having the formula:

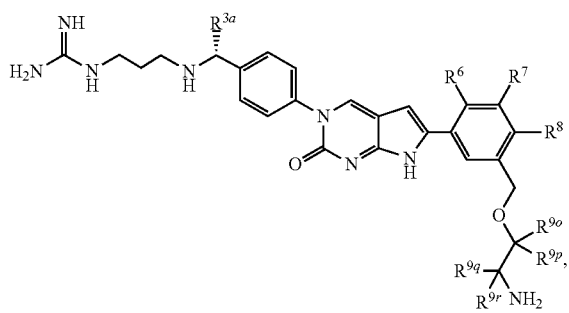

(G4)

or a tautomer thereof, or a pharmaceutically acceptable salt, ester, or prodrug of said compound or tautomer, wherein $R^{3a}$, $R^6$, $R^7$, $R^8$, $R^{9o}$, $R^{9p}$, $R^{9q}$, and $R^{9r}$ are as defined herein.

In some embodiments, the present invention relates to a compound of formulae G1, G2, G3, or G4, or a tautomer thereof, or a pharmaceutically acceptable salt, ester, or prodrug of said compound or tautomer, wherein $R^{9o}$, $R^{9p}$, $R^{9q}$, and $R^{9r}$ are each independently selected from —$C_1$-$C_6$ alkyl and hydrogen;
$R^6$ and $R^8$ are each independently selected from hydrogen, F, Cl, Br, I, —$C_1$-$C_6$ alkyl, —$CH_2F$, —$CHF_2$, and —$CF_3$;
$R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p$—$C_1$-$C_6$ alkyl, —$OCH_2F$, —$OCHF_2$, —$OCF_3$, —$S(O)_p$—$CH_3$, —$S(O)_p$—$CH_2F$, and —$S(O)_p$—$CF_3$; and
$R^{3a}$ is selected from halogen and —$C_1$-$C_6$ alkyl; and
p is 0, 1, or 2.

In some embodiments, the present invention relates to a compound of formulae G1, G2, G3, or G4, or a tautomer thereof, or a pharmaceutically acceptable salt, ester, or prodrug of said compound or tautomer, wherein $R^{9o}$, $R^{9p}$, $R^{9q}$, and $R^{9r}$ are each independently selected from —$C_1$-$C_6$ alkyl and hydrogen;
$R^6$ is selected from hydrogen, F, Cl, Br, I, —$C_1$-$C_6$ alkyl, —$CH_2F$, —$CHF_2$, and —$CF_3$;
$R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p$$C_1$-$C_6$ alkyl, —$OCH_2F$, —$OCHF_2$, —$OCF_3$, —$S(O)_p$—$CH_3$, —$S(O)_p$—$CH_2F$, and —$S(O)_p$—$CF_3$;
$R^8$ is hydrogen;
$R^{3a}$ is selected from halogen and —$C_1$-$C_6$ alkyl; and
p is 0, 1, or 2.

In some embodiments, the present invention relates to a compound having the formula:

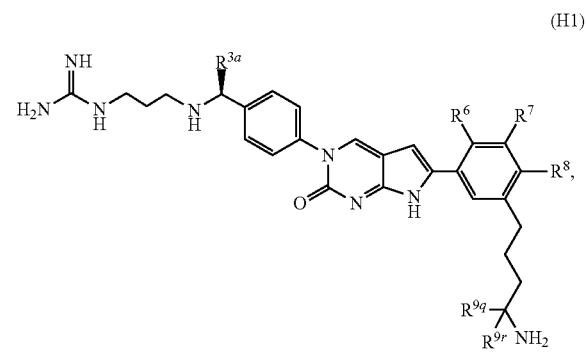

(H1)

or a tautomer thereof, or a pharmaceutically acceptable salt, ester, or prodrug of said compound or tautomer, wherein $R^{3a}$, $R^6$, $R^7$, $R^8$, $R^{9q}$, and $R^{9r}$ are as defined herein.

In some embodiments, the present invention relates to a compound having the formula:

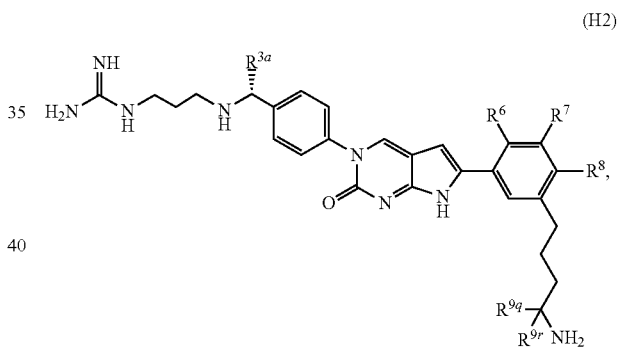

(H2)

or a tautomer thereof, or a pharmaceutically acceptable salt, ester, or prodrug of said compound or tautomer, wherein $R^{3a}$, $R^6$, $R^7$, $R^8$, $R^{9q}$, and $R^{9r}$ are as defined herein.

In some embodiments, the present invention relates to a compound having the formula:

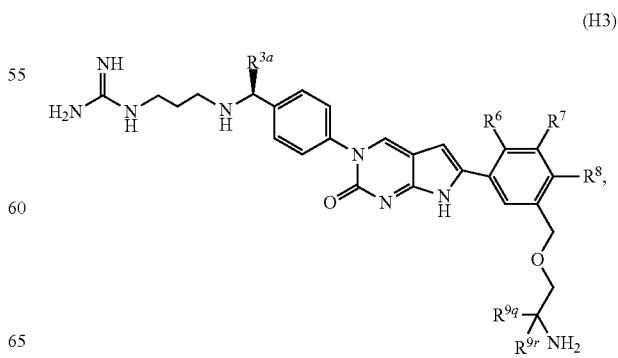

(H3)

or a tautomer thereof, or a pharmaceutically acceptable salt, ester, or prodrug of said compound or tautomer, wherein $R^{3a}$, $R^6$, $R^7$, $R^8$, $R^{9q}$, and $R^{9r}$ are as defined herein.

In some embodiments, the present invention relates to a compound having the formula:

(H4)

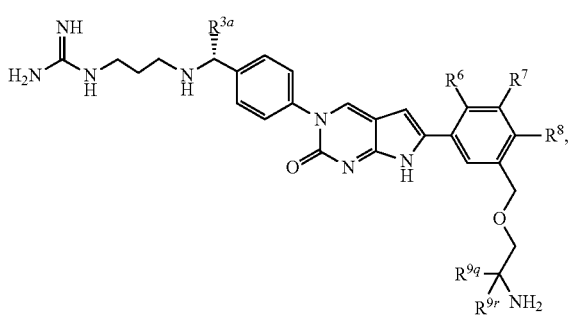

or a tautomer thereof, or a pharmaceutically acceptable salt, ester, or prodrug of said compound or tautomer, wherein $R^{3a}$, $R^6$, $R^7$, $R^8$, $R^{9q}$, and $R^{9r}$ are as defined herein.

In some embodiments, the present invention relates to a compound having the formula:

(H5)

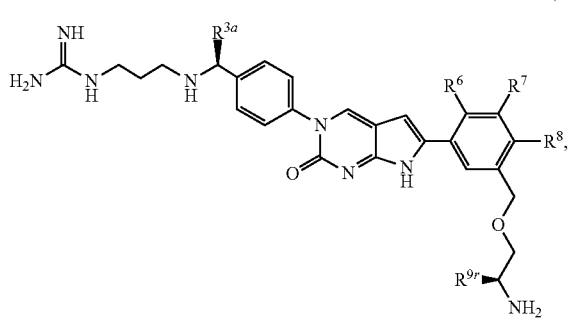

or a tautomer thereof, or a pharmaceutically acceptable salt, ester, or prodrug of said compound or tautomer, wherein $R^{3a}$, $R^6$, $R^7$, $R^8$, and $R^{9r}$ are as defined herein.

In some embodiments, the present invention relates to a compound having the formula:

(H6)

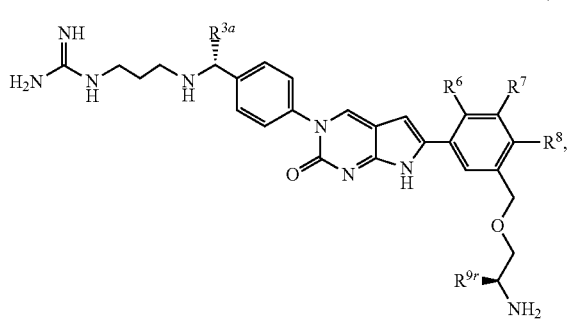

or a tautomer thereof, or a pharmaceutically acceptable salt, ester, or prodrug of said compound or tautomer, wherein $R^{3a}$, $R^6$, $R^7$, $R^8$, and $R^{9r}$ are as defined herein.

In some embodiments, the present invention relates to a compound having the formula:

(H7)

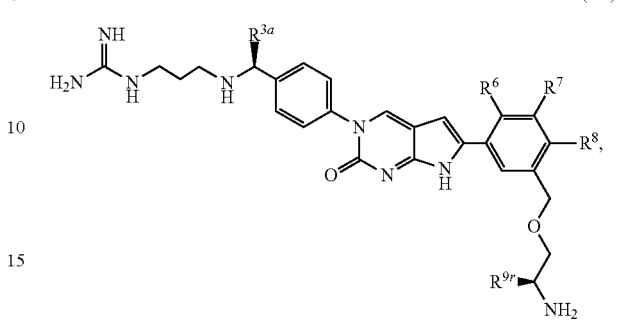

or a tautomer thereof, or a pharmaceutically acceptable salt, ester, or prodrug of said compound or tautomer, wherein $R^{3a}$, $R^6$, $R^7$, $R^8$, and $R^{9r}$ are as defined herein.

In some embodiments, the present invention relates to a compound having the formula:

(H8)

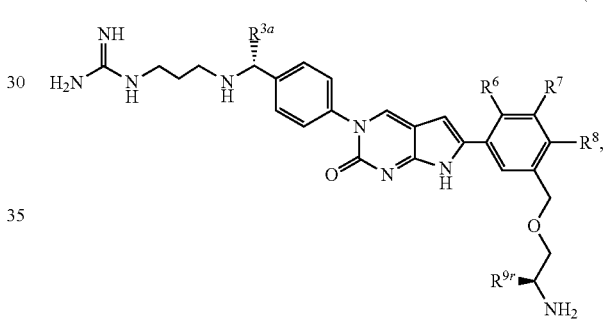

or a tautomer thereof, or a pharmaceutically acceptable salt, ester, or prodrug of said compound or tautomer, wherein $R^{3a}$, $R^6$, $R^7$, $R^8$, and $R^{9r}$ are as defined herein.

In some embodiments, the present invention relates to a compound having the formula:

(H9)

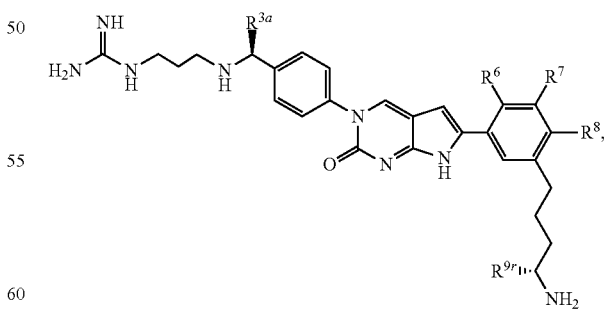

or a tautomer thereof, or a pharmaceutically acceptable salt, ester, or prodrug of said compound or tautomer, wherein $R^{3a}$, $R^6$, $R^7$, $R^8$, and $R^{9r}$ are as defined herein.

In some embodiments, the present invention relates to a compound having the formula:

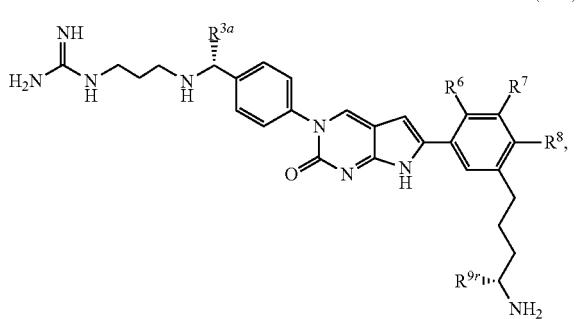

(H10)

wherein $R^{3a}$, $R^6$, $R^7$, $R^8$, and $R^{9r}$ are as defined herein,
or a tautomer thereof, or a pharmaceutically acceptable salt, ester, or prodrug of said compound or tautomer.

In some embodiments, the present invention relates to a compound having the formula:

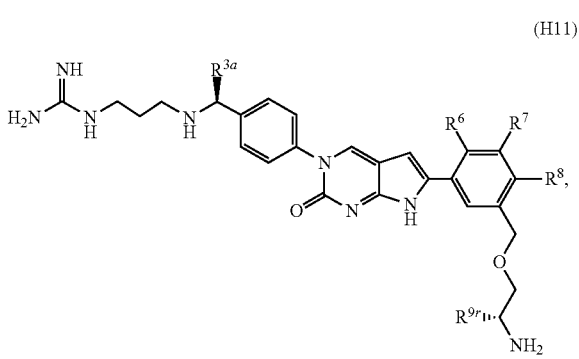

(H11)

or a tautomer thereof, or a pharmaceutically acceptable salt, ester, or prodrug of said compound or tautomer, wherein $R^{3a}$, $R^6$, $R^7$, $R^8$, and $R^{9r}$ are as defined herein.

In some embodiments, the present invention relates to a compound having the formula:

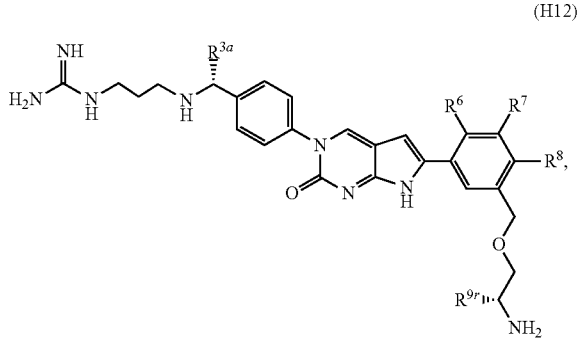

(H12)

or a tautomer thereof, or a pharmaceutically acceptable salt, ester, or prodrug of said compound or tautomer, wherein $R^{3a}$, $R^6$, $R^7$, $R^8$, and $R^{9r}$ are as defined herein.

In some embodiments, the present invention relates to a compound of formulae H1, H2, H3, or H4, or a tautomer thereof, or a pharmaceutically acceptable salt, ester, or prodrug of said compound or tautomer, wherein $R^{9q}$ and $R^{9r}$ are each independently selected from —$C_1$-$C_6$ alkyl and hydrogen;

$R^6$ and $R^8$ are each independently selected from hydrogen, F, Cl, Br, I, —$C_1$-$C_6$ alkyl, —$CH_2F$, —$CHF_2$, and —$CF_3$;

$R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p$—$C_1$-$C_6$ alkyl, —$OCH_2F$, —$OCHF_2$, —$OCF_3$, —$S(O)_p$—$CH_3$, —$S(O)_p$—$CH_2F$, and —$S(O)_p$—$CF_3$; and $R^{3a}$ is selected from halogen and —$C_1$-$C_6$ alkyl; and p is 0, 1, or 2.

In some embodiments, the present invention relates to a compound of formulae H1, H2, H3, or H4, or a tautomer thereof, or a pharmaceutically acceptable salt, ester, or prodrug of said compound or tautomer, wherein $R^{9q}$ and $R^{9r}$ are each independently selected from —$C_1$-$C_6$ alkyl and hydrogen;

$R^6$ is selected from hydrogen, F, Cl, Br, I, —$C_1$-$C_6$ alkyl, —$CH_2F$, —$CHF_2$, and —$CF_3$;

$R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p$—$C_1$-$C_6$ alkyl, —$OCH_2F$, —$OCHF_2$, —$OCF_3$, —$S(O)_p$—$CH_3$, —$S(O)_p$—$CH_2F$, and —$S(O)_p$—$CF_3$;

$R^8$ is hydrogen;

$R^{3a}$ is selected from halogen and —$C_1$-$C_6$ alkyl; and p is 0, 1, or 2.

In some embodiments, the present invention relates to a compound of formulae H5, H6, H7, H8, H9, H10, H11, or H12, or a tautomer thereof, or a pharmaceutically acceptable salt, ester, or prodrug of said compound or tautomer, wherein $R^{9r}$ is —$C_1$-$C_6$ alkyl;

$R^6$ is selected from hydrogen, F, Cl, Br, I, —$C_1$-$C_6$ alkyl, —$CH_2F$, —$CHF_2$, and —$CF_3$;

$R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p$—$C_1$-$C_6$ alkyl, —$OCH_2F$, —$OCHF_2$, —$OCF_3$, —$S(O)_p$—$CH_3$, —$S(O)_p$—$CH_2F$, and —$S(O)_p$—$CF_3$;

$R^8$ is hydrogen;

$R^{3a}$ is selected from halogen and —$C_1$-$C_6$ alkyl; and p is 0, 1, or 2.

In some embodiments, the present invention relates to a compound of formulae H5, H6, H7, H8, H9, H10, H11, or H12, or a tautomer thereof, or a pharmaceutically acceptable salt, ester, or prodrug of said compound or tautomer, wherein $R^{9r}$ is —$CH_3$;

$R^6$ is selected from hydrogen, F, Cl, Br, I, —$C_1$-$C_6$ alkyl, —$CH_2F$, —$CHF_2$, and —$CF_3$;

$R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p$—$C_1$-$C_6$ alkyl, —$OCH_2F$, —$OCHF_2$, —$OCF_3$, —$S(O)_p$—$CH_3$, —$S(O)_p$—$CH_2F$, and —$S(O)_p$—$CF_3$;

$R^8$ is hydrogen;

$R^{3a}$ is —$CH_3$; and p is 0, 1, or 2.

In some embodiments, the present invention relates to a compound having the formula:

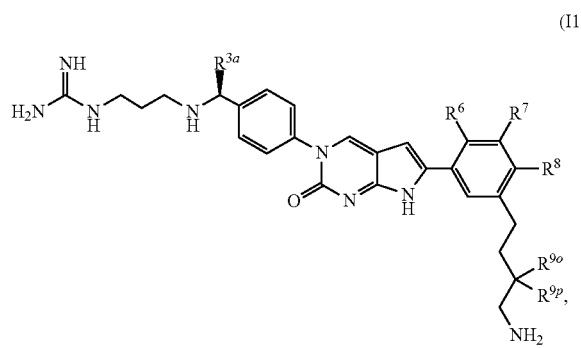

(I1)

or a tautomer thereof, or a pharmaceutically acceptable salt, ester, or prodrug of said compound or tautomer, wherein $R^{3a}$, $R^6$, $R^7$, $R^8$, $R^{9o}$, and $R^{9p}$ are as defined herein.

In some embodiments, the present invention relates to a compound having the formula:

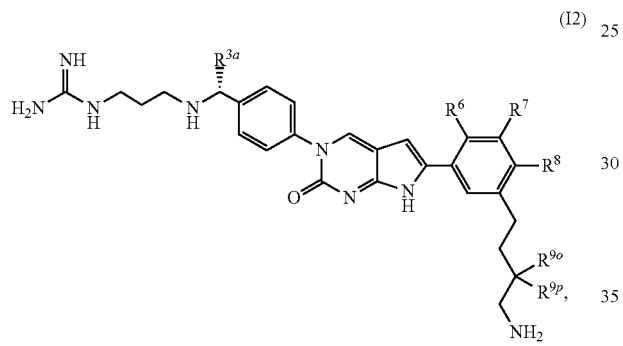

(I2)

or a tautomer thereof, or a pharmaceutically acceptable salt, ester, or prodrug of said compound or tautomer, wherein $R^{3a}$, $R^6$, $R^7$, $R^8$, $R^{9o}$, and $R^{9p}$ are as defined herein.

In some embodiments, the present invention relates to a compound having the formula:

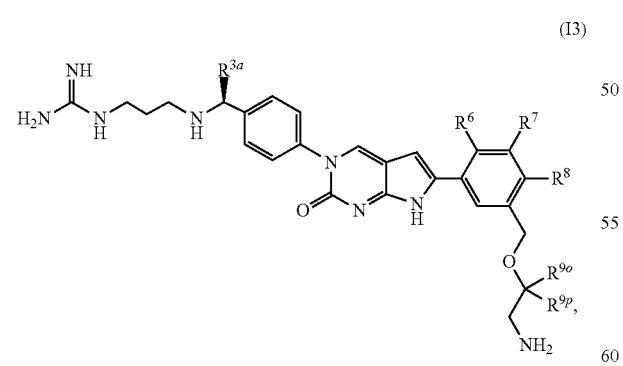

(I3)

or a tautomer thereof, or a pharmaceutically acceptable salt, ester, or prodrug of said compound or tautomer, wherein $R^{3a}$, $R^6$, $R^7$, $R^8$, $R^{9o}$, and $R^{9p}$ are as defined herein.

In some embodiments, the present invention relates to a compound having the formula:

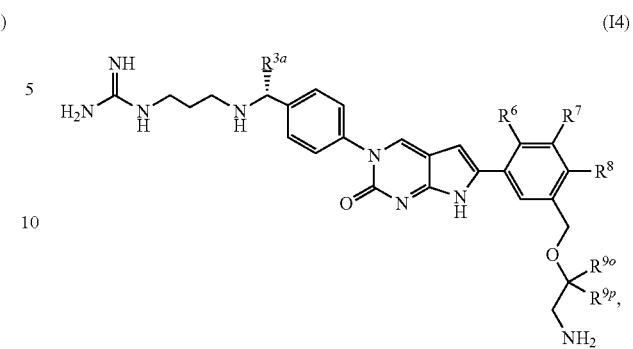

(I4)

or a tautomer thereof, or a pharmaceutically acceptable salt, ester, or prodrug of said compound or tautomer, wherein $R^{3a}$, $R^6$, $R^7$, $R^8$, $R^{9o}$, and $R^{9p}$ are as defined herein.

In some embodiments, the present invention relates to a compound having the formula:

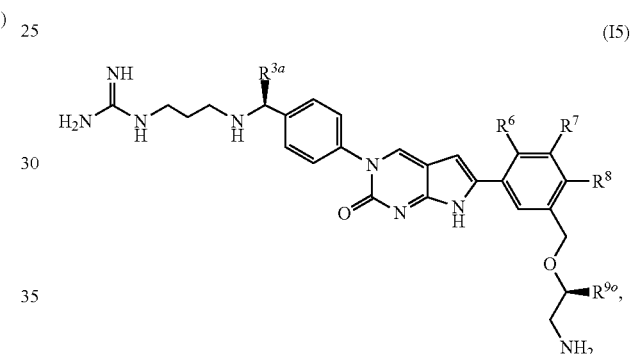

(I5)

or a tautomer thereof, or a pharmaceutically acceptable salt, ester, or prodrug of said compound or tautomer, wherein $R^{3a}$, $R^6$, $R^7$, $R^8$, and $R^{9o}$ are as defined herein.

In some embodiments, the present invention relates to a compound having the formula:

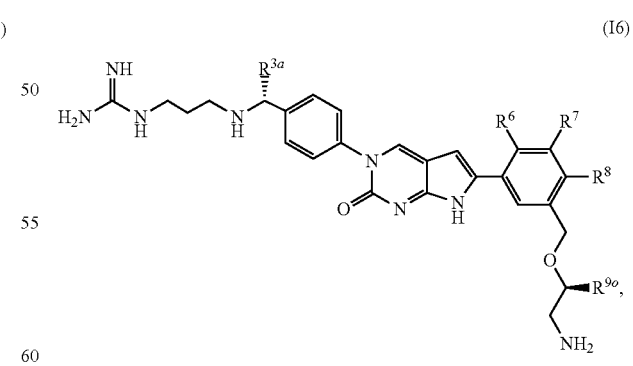

(I6)

or a tautomer thereof, or a pharmaceutically acceptable salt, ester, or prodrug of said compound or tautomer, wherein $R^{3a}$, $R^6$, $R^7$, $R^8$, and $R^{9o}$ are as defined herein.

In some embodiments, the present invention relates to a compound having the formula:

(I7)

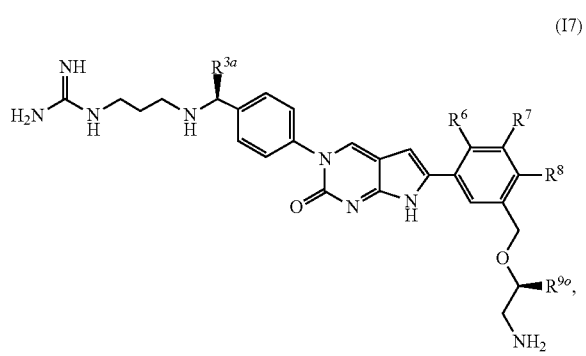

or a tautomer thereof, or a pharmaceutically acceptable salt, ester, or prodrug of said compound or tautomer, wherein $R^{3a}$, $R^6$, $R^7$, $R^8$, and $R^{9o}$ are as defined herein.

In some embodiments, the present invention relates to a compound having the formula:

(I8)

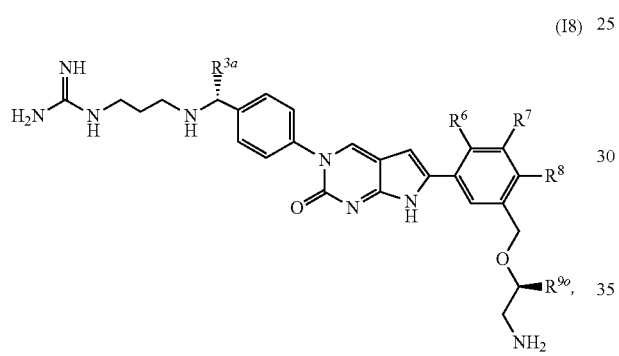

or a tautomer thereof, or a pharmaceutically acceptable salt, ester, or prodrug of said compound or tautomer, wherein $R^{3a}$, $R^6$, $R^7$, $R^8$, and $R^{9o}$ are as defined herein.

In some embodiments, the present invention relates to a compound having the formula:

(I9)

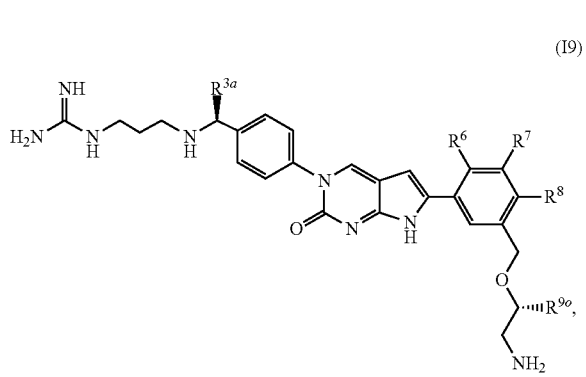

or a tautomer thereof, or a pharmaceutically acceptable salt, ester, or prodrug of said compound or tautomer, wherein $R^{3a}$, $R^6$, $R^7$, $R^8$, and $R^{9o}$ are as defined herein.

In some embodiments, the present invention relates to a compound having the formula:

(I10)

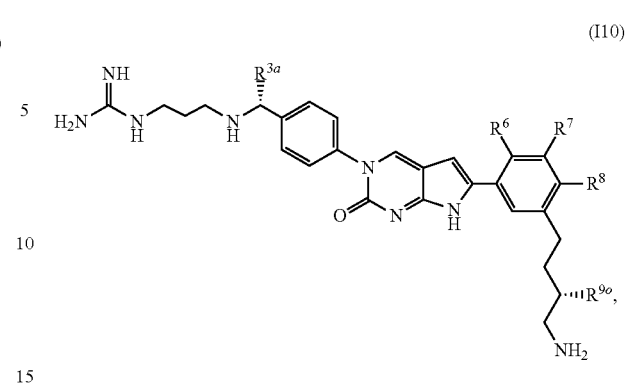

or a tautomer thereof, or a pharmaceutically acceptable salt, ester, or prodrug of said compound or tautomer, wherein $R^{3a}$, $R^6$, $R^7$, $R^8$, and $R^{9o}$ are as defined herein.

In some embodiments, the present invention relates to a compound having the formula:

(I11)

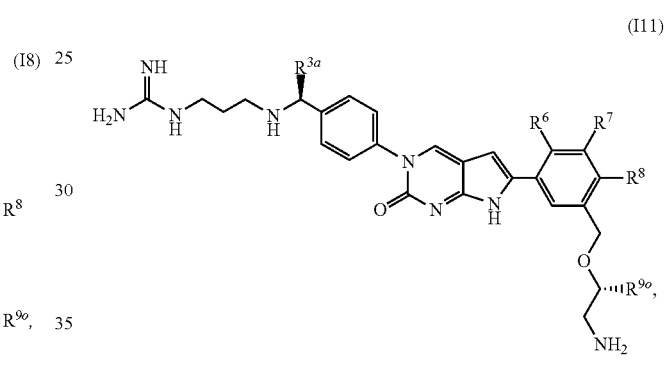

or a tautomer thereof, or a pharmaceutically acceptable salt, ester, or prodrug of said compound or tautomer, wherein $R^{3a}$, $R^6$, $R^7$, $R^8$, and $R^{9o}$ are as defined herein.

In some embodiments, the present invention relates to a compound having the formula:

(I12)

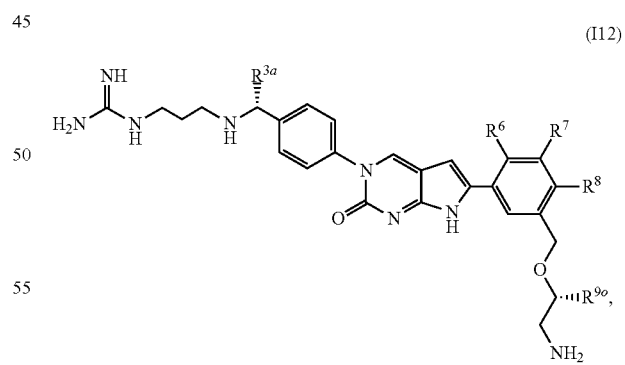

or a tautomer thereof, or a pharmaceutically acceptable salt, ester, or prodrug of said compound or tautomer, wherein $R^{3a}$, $R^6$, $R^7$, $R^8$, and $R^{9o}$ are as defined herein.

In some embodiments, the present invention relates to a compound of formulae I1, I2, I3, or I4, or a tautomer thereof, or a pharmaceutically acceptable salt, ester, or prodrug of said compound or tautomer, wherein $R^{9o}$ and $R^{9p}$ are each independently selected from —$C_1$-$C_6$ alkyl and hydrogen;

$R^6$ and $R^8$ are each independently selected from hydrogen, F, Cl, Br, I, —$C_1$-$C_6$ alkyl, —$CH_2F$, —$CHF_2$, and —$CF_3$;

$R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p$—$C_1$-$C_6$ alkyl, —$OCH_2F$, $OCHF_2$, —$OCF_3$, $S(O)_p$—$CH_3$, —$S(O)_p$—$CH_2F$, and —$S(O)_p$—$CF_3$; and $R^{3a}$ is selected from halogen and —$C_1$-$C_6$ alkyl; and p is 0, 1, or 2.

In some embodiments, the present invention relates to a compound of formulae I1, I2, I3, or I4, or a tautomer thereof, or a pharmaceutically acceptable salt, ester, or prodrug of said compound or tautomer, wherein $R^{9o}$ and $R^{9p}$ are each independently selected from —$C_1$-$C_6$ alkyl and hydrogen;

$R^6$ is selected from hydrogen, F, Cl, Br, I, $C_1$-$C_6$ alkyl, —$CH_2F$, —$CHF_2$, and —$CF_3$;

$R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p$—$C_1$-$C_6$ alkyl, —$OCH_2F$, —$OCHF_2$, —$OCF_3$, —$S(O)_p$—$CH_3$, —$S(O)_p$—$CH_2F$, and —$S(O)_p$—$CF_3$;

$R^8$ is hydrogen;

$R^{3a}$ is selected from halogen and —$C_1$-$C_6$ alkyl; and p is 0, 1, or 2.

In some embodiments, the present invention relates to a compound of formulae I5, I6, I7, I8, I9, I10, I11, or I12, or a tautomer thereof, or a pharmaceutically acceptable salt, ester, or prodrug of said compound or tautomer, wherein $R^{9o}$ is —$C_1$-$C_6$ alkyl;

$R^6$ is selected from hydrogen, F, Cl, Br, I, —$C_1$-$C_6$ alkyl, —$CH_2F$, —$CHF_2$, and —$CF_3$;

$R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p$—$C_1$-$C_6$ alkyl, —$OCH_2F$, —$OCHF_2$, —$OCF_3$, —$S(O)_p CH_3$, —$S(O)_p$—$CH_2F$, and —$S(O)_p$—$CF_3$;

$R^8$ is hydrogen;

$R^{3a}$ is selected from halogen and —$C_1$-$C_6$ alkyl; and p is 0, 1, or 2.

In some embodiments, the present invention relates to a compound of formulae I5, I6, I7, I8, I9, I10, I11, or I12, or a tautomer thereof, or a pharmaceutically acceptable salt, ester, or prodrug of said compound or tautomer, wherein $R^{9o}$ is —$CH_3$;

$R^6$ is selected from hydrogen, F, Cl, Br, I, —$C_1$-$C_6$ alkyl, —$CH_2F$, —$CHF_2$, and —$CF_3$;

$R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p$—$C_1$-$C_6$ alkyl, —$OCH_2F$, —$OCHF_2$, —$OCF_3$, —$S(O)_p CH_3$, —$S(O)_p$—$CH_2F$, and —$S(O)_p$—$CF_3$;

$R^8$ is hydrogen;

$R^{3a}$ is —$CH_3$; and p is 0, 1, or 2.

In some embodiments, the present invention relates to a compound of formulae IV, V, VI, VII, VIII, IX, X, XI, XXa, XXa1, Va, VIIa, VIIa, VIIIa, IXa, Xa, XIa, XII, XIII, XIV, XV, XVI, XVII, XVIII, XXb, XXb1, XIIa, XIIIa, XIVa, XVa, XVIa, XVIIa, XVIIIa, F1, or F2, or a tautomer thereof, or a pharmaceutically acceptable salt, ester, or prodrug of said compound or tautomer, wherein the moiety

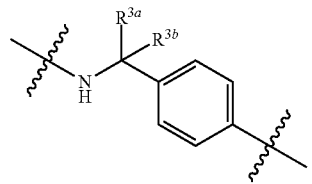

and $R^{3b}$ is H, is selected from:

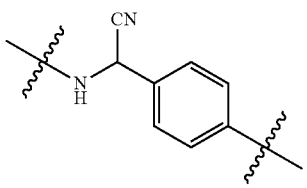

,

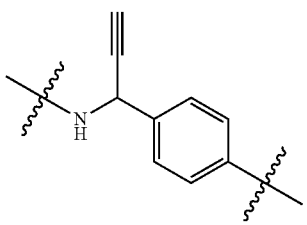

,

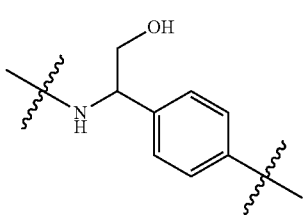

,

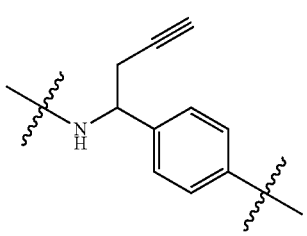

,

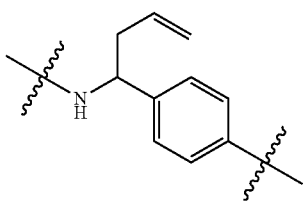

,

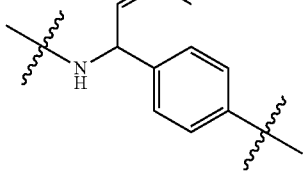

,

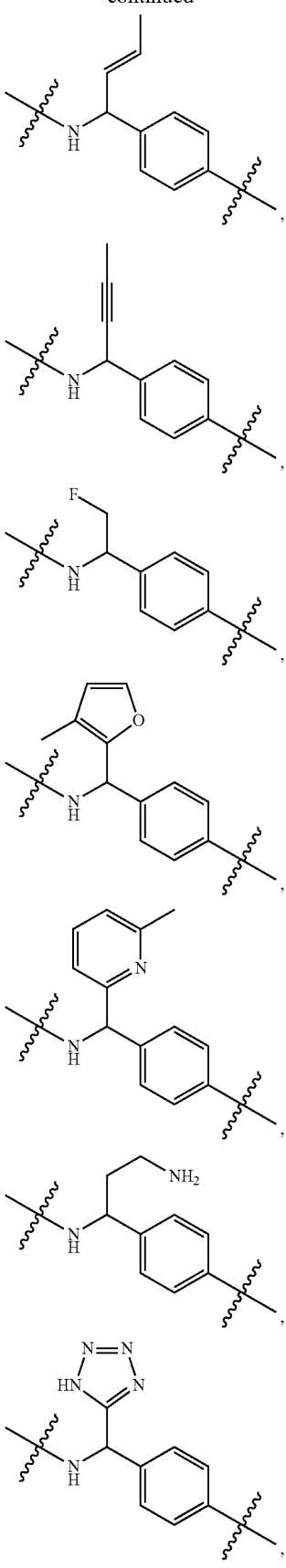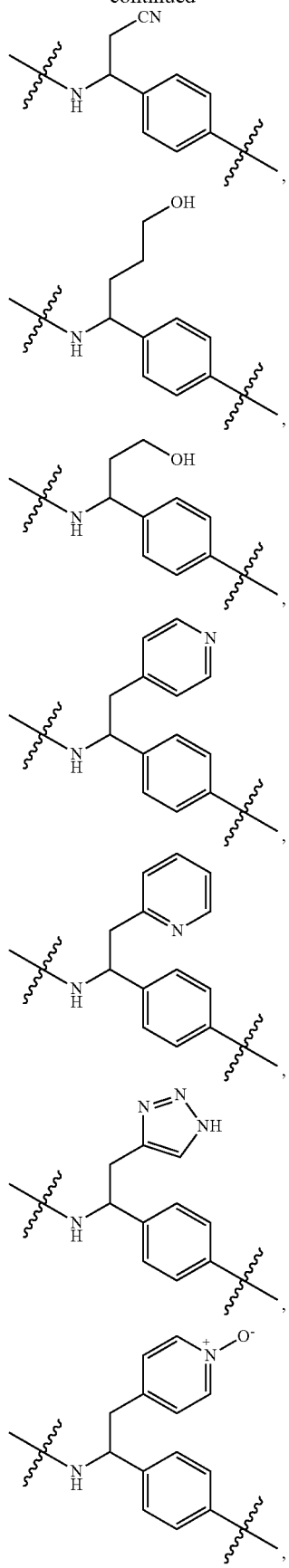

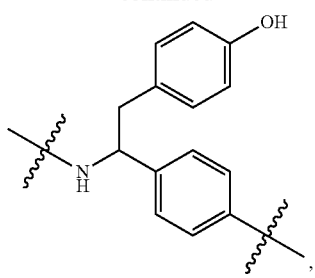,
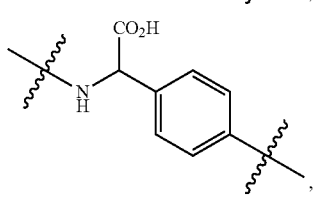,
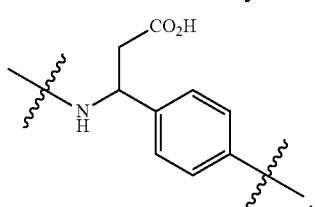,
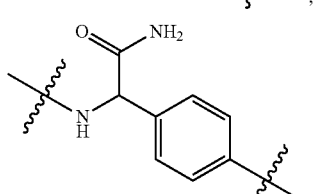,
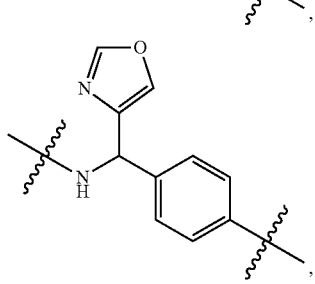,
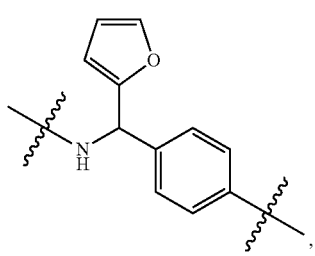,
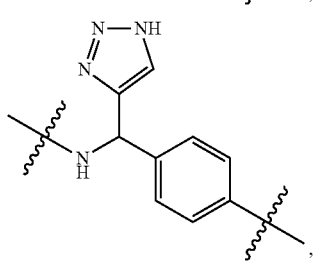,
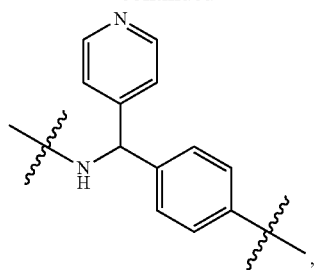,
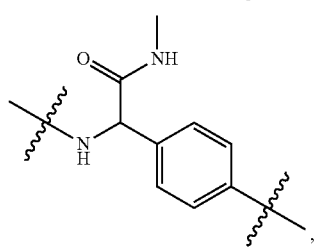,
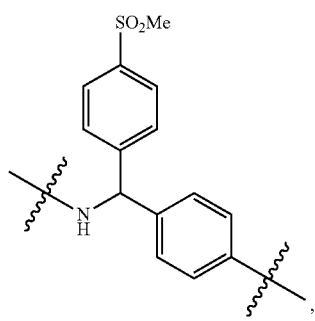,
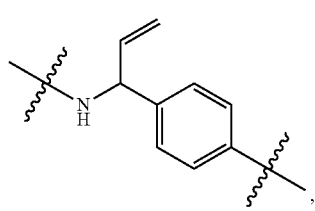,
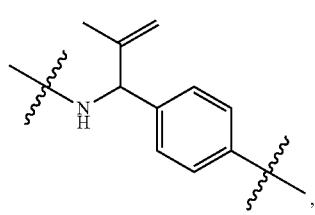,
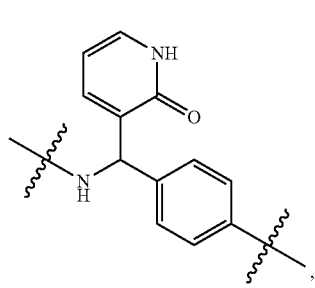,

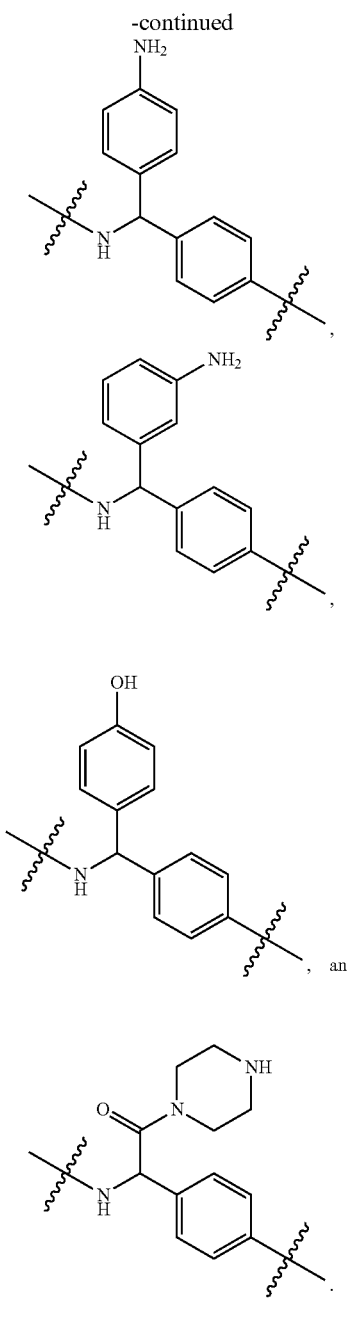
, and
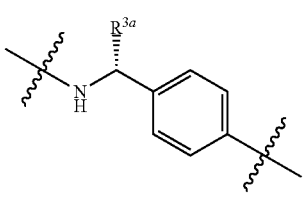
In some embodiments, the present invention relates to a compound of formulae F1 ($R^{3b}$ is H), F2 ($R^{3b}$ is H), G2, G4, H2, H4, H6, H8, H10, H12, I2, I4, I6, I8, I10, or I12, or a tautomer thereof, or a pharmaceutically acceptable salt, ester, or prodrug of said compound or tautomer, wherein the moiety
is selected from:
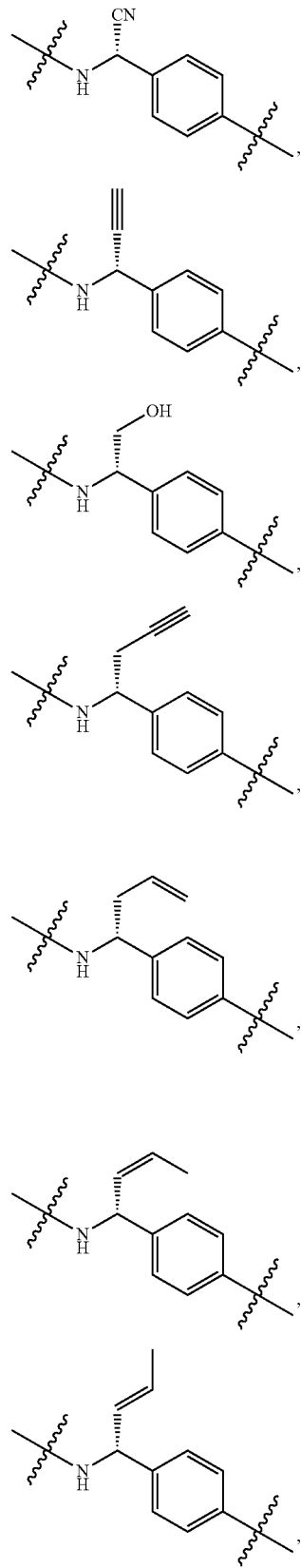

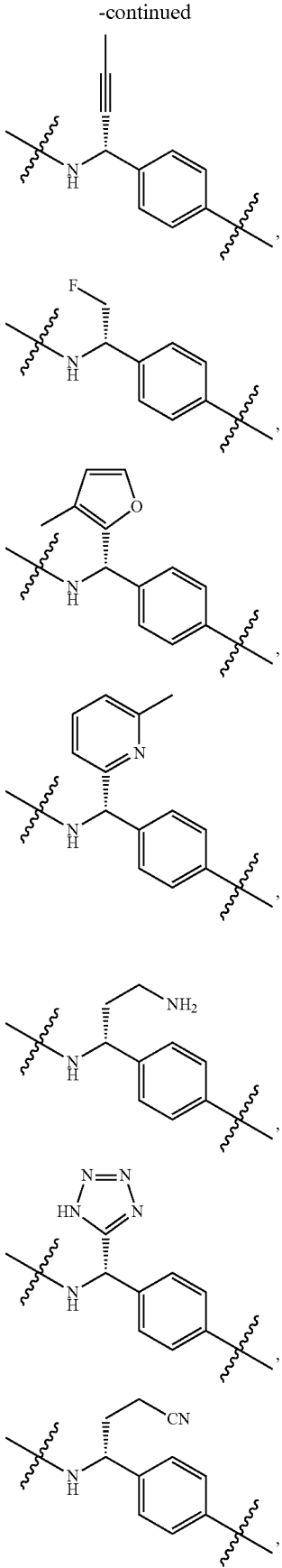
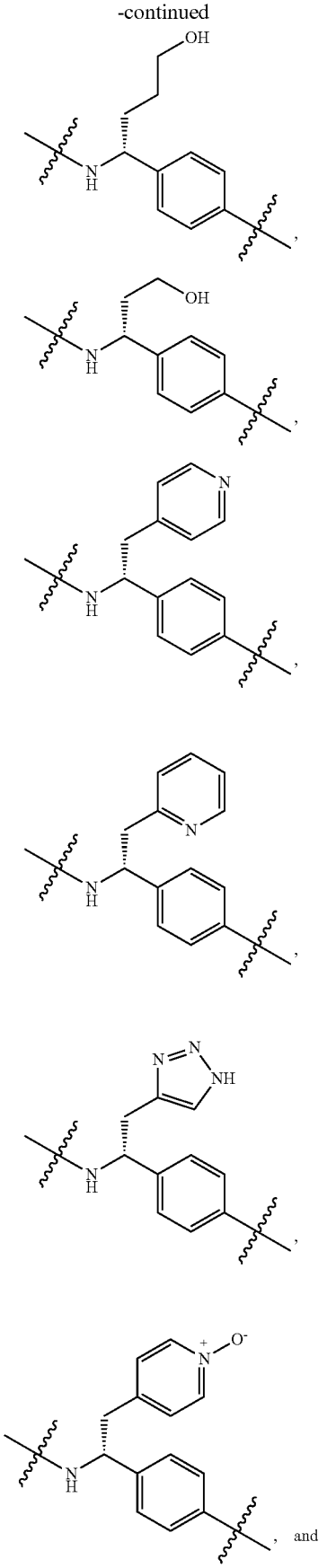

-continued
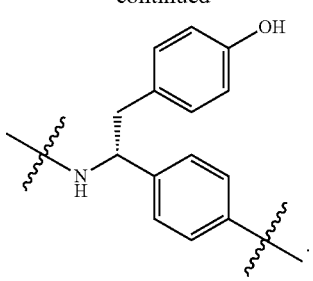
In some embodiments, the present invention relates to a compound of formulae F1 ($R^{3b}$ is H), F2 ($R^{3b}$ is H), G1, G3, H1, H3, H5, H7, H9, H11, I1, I3, I5, I7, I9, or I11, or a tautomer thereof, or a pharmaceutically acceptable salt, ester, or prodrug of said compound or tautomer, wherein the moiety
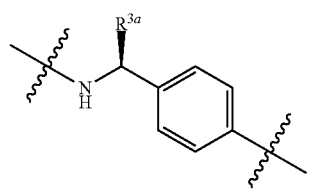
is selected from:
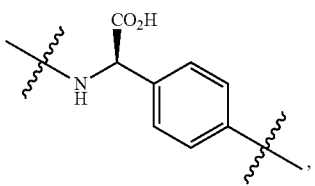
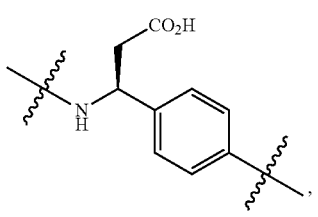
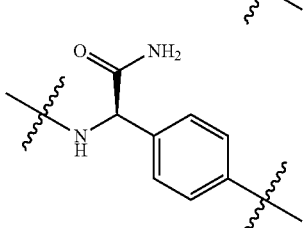
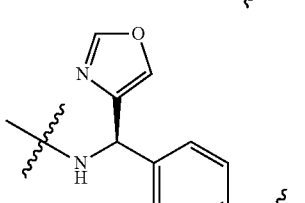
-continued
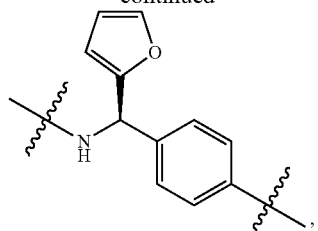
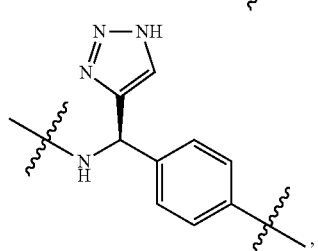
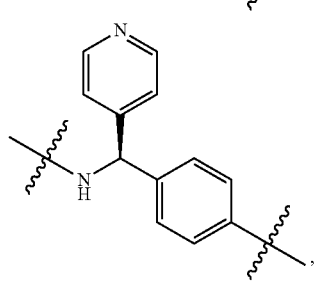
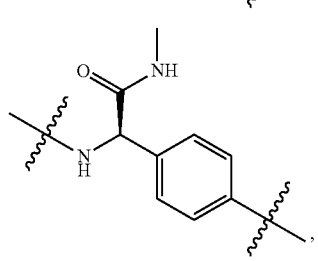
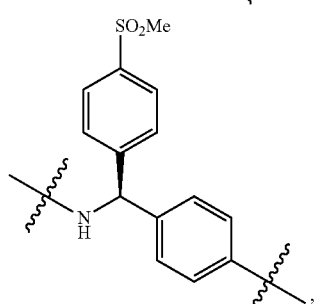
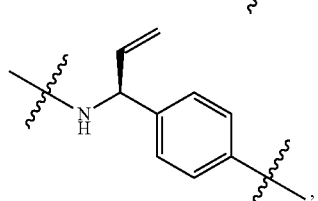
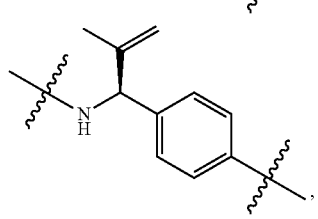

-continued

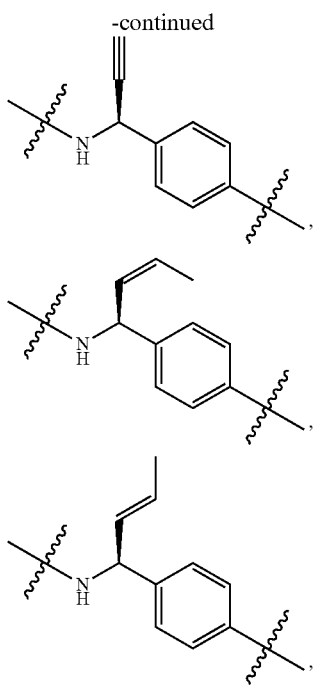

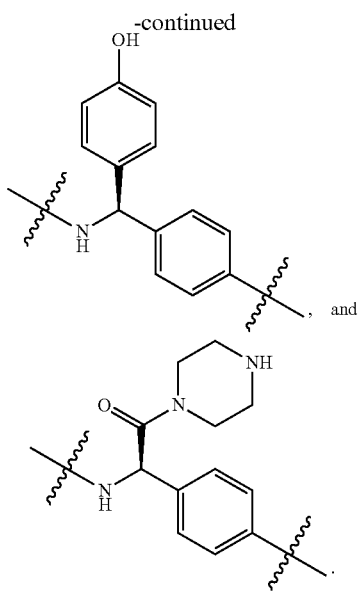

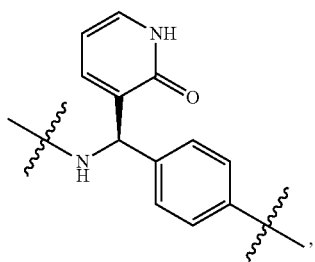

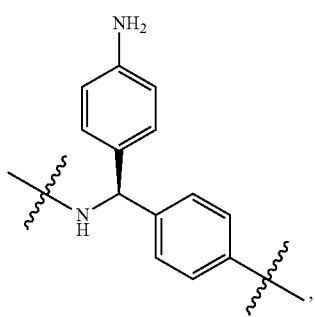

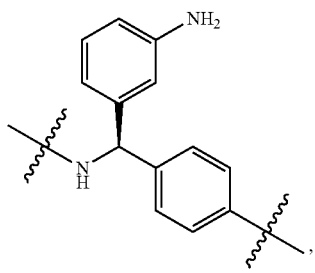

In some embodiments, the present invention relates to a compound or a tautomer thereof, or a pharmaceutically acceptable salt, ester, or prodrug of said compound or tautomer, according to any one the compounds in Table 1, Table 2, Table 2a, and Table 2aa.

In some embodiments, the present invention relates to a compound or a tautomer thereof, or a pharmaceutically acceptable salt, ester, or prodrug of said compound or tautomer that binds the ribosome. In some embodiments, the ribosome is a bacterial ribosome.

In some embodiments, the present invention relates to a pharmaceutical composition comprising a compound of the invention, or a tautomer thereof, or a pharmaceutically acceptable salt, ester, or prodrug of said compound or tautomer, and a pharmaceutically acceptable carrier. In some embodiments, the present invention relates to a compound or a tautomer thereof, or a pharmaceutically acceptable salt, ester, or prodrug of said compound or tautomer of the invention and a means for delivery.

In some embodiments, the present invention relates to a method of treating, preventing, or reducing the risk of a disease state in a human or animal comprising administering to the human or animal in need thereof an effective amount of a compound of the invention, or a tautomer thereof, or a pharmaceutically acceptable salt, ester, or prodrug of said compound or tautomer.

In some embodiments, the present invention relates to a method of treating, preventing, or reducing a microbial infection in a human or animal comprising administering to the human or animal an effective amount of a compound of the invention, or a tautomer thereof, or a pharmaceutically acceptable salt, ester, or prodrug of said compound or tautomer.

In some embodiments, the present invention relates to use of a compound of the invention, or a tautomer thereof, or a pharmaceutically acceptable salt, ester, or prodrug of said compound or tautomer, in the manufacture of a medicament for treating, preventing, or reducing a microbial infection in a human or animal.

In some embodiments, the present invention relates to a compound of the invention, or a tautomer thereof, or a pharmaceutically acceptable salt, ester, or prodrug of said compound or tautomer, for use in treating, preventing, or reducing a microbial infection in a human or animal.

In some embodiments, the present invention relates to a method of treating, preventing, or reducing the risk of a microbial infection in a human or animal comprising administering to the human or animal an effective amount of a compound or a tautomer thereof, or a pharmaceutically acceptable salt, ester, or prodrug of said compound or tautomer, wherein said microbial infection is caused by one or more of the following microorganisms: *Acinetobacter* spp. (*Acinetobacter baumanni*), *Bacteroides distasonis*, *Bacteroides fragilis*, *Bacteroides ovatus*, *Bacteroides thetaiotaomicron*, *Bacteroides uniformis*, *Bacteroides vulgatus*, *Citrobacter freundii*, *Citrobacter koser*, *Clostridium clostridioforme*, *Clostridium perfringens*, *Enterobacter aerogenes*, *Enterobacter cloacae*, *Enterococcus faecalis*, *Enterococcus* spp. (vancomycin susceptible and resistant isolates), *Escherichia coli* (including ESBL and KPC producing isolates), *Eubacterium lentum*, *Fusobacterium* spp., *Haemophilus influenzae* (including beta-lactamase positive isolates), *Haemophilus parainfluenzae*, *Klebsiella pneumoniae* (including ESBL and KPC producing isolates), *Klebsiella oxytoca* (including ESBL and KPC producing isolates), *Legionella pneumophilia Moraxella catarrhalis*, *Morganella morganii*, *Mycoplasma* spp., *Peptostreptococcus* spp., *Porphyromonas asaccharolytica*, *Prevotella bivia*, *Proteus mirabilis*, *Proteus vulgaris*, *Providencia rettgeri*, *Providencia stuartii*, *Pseudomonas aeruginosa*, *Serratia marcescens*, *Streptococcus anginosus*, *Staphylococcus aureus* (methicillin susceptible and resistant isolates), *Staphylococcus epidermidis* (methicillin susceptible and resistant isolates), *Stenotrophomonas maltophilia*, *Streptococcus agalactiae*, *Streptococcus constellatus*, *Streptococcus pneumoniae* (penicillin susceptible and resistant isolates), *Streptococcus pyogenes*, or *Streptococcus pyogenes*.

In some embodiments, the present invention relates to a method of treating, preventing, or reducing the risk of a microbial infection in a human or animal comprising administering to the human or animal an effective amount of a compound or a tautomer thereof, or a pharmaceutically acceptable salt, ester, or prodrug of said compound or tautomer, wherein said infection is caused by or involves one or more microorganisms selected from: *Acinetobacter* spp. (*Acinetobacter baumanni*), *Bacteroides distasonis*, *Bacteroides fragilis*, *Bacteroides ovatus*, *Bacteroides thetaiotaomicron*, *Bacteroides uniformis*, *Bacteroides vulgatus*, *Citrobacter freundii*, *Citrobacter koser*, *Clostridium clostridioforme*, *Clostridium perfringens*, *Enterobacter aerogenes*, *Enterobacter cloacae*, *Enterococcus faecalis*, *Enterococcus* spp., *Escherichia coli*, *Eubacterium lentum*, *Fusobacterium* spp., *Haemophilus influenzae*, *Haemophilus parainfluenzae*, *Klebsiella pneumoniae*, *Klebsiella oxytoca*, *Legionella pneumophilia*, *Moraxella catarrhalis*, *Morganella morganii*, *Mycoplasma* spp., *Peptostreptococcus* spp., *Porphyromonas asaccharolytica*, *Prevotella bivia*, *Proteus mirabilis*, *Proteus vulgaris*, *Providencia rettgeri*, *Providencia stuartii*, *Pseudomonas aeruginosa*, *Serratia marcescens*, *Streptococcus anginosus*, *Staphylococcus aureus*, *Staphylococcus epidermidis*, *Stenotrophomonas maltophilia*, *Streptococcus agalactiae*, *Streptococcus constellatus*, *Streptococcus pneumoniae*, *Streptococcus pyogenes*, and *Streptococcus pyogenes*.

In some embodiments, the present invention relates to a method wherein said infection is caused by or involves one or more of aerobic and facultative gram-positive microorganism selected from: *Staphylococcus aureus*, *Streptococcus pneumoniae*, *Enterococcus* spp., *Streptococcus agalactiae*, *Streptococcus pyogenes*, and *Staphylococcus epidermidis*.

In some embodiments, the present invention relates to a method wherein said infection is caused by or involves one or more of aerobic and facultative gram-negative microorganism selected from: *Escherichia coli*, *Haemophilus influenzae*, *Klebsiella pneumoniae*, *Citrobacter freundii*, *Enterobacter aerogenes*, *Enterobacter cloacae*, *Morganella morganii*, *Serratia marcescens*, *Pseudomonas aeruginosa*, *Acinetobacter baumanni*, *Moraxella catarrhalis*, *Proteus mirabilis*, *Citrobacter koseri*, *Haemophilus parainfluenzae*, *Klebsiella oxytoca*, *Proteus vulgaris*, *Providencia rettgeri*, and *Providencia stuartii*.

In some embodiments, the present invention relates to a method wherein, said infection is caused by or involves one or more of anaerobic microorganism: *Bacteroides fragilis*, *Bacteroides distasonis*, *Bacteroides ovatus*, *Bacteroides thetaiotaomicron*, *Bacteroides uniformis*, *Clostridium clostridioforme*, *Eubacterium lentum*, *Peptostreptococcus* spp., *Porphyromonas asaccharolytica*, *Prevotella bivia*, *Bacteroides vulgatus*, *Clostridium perfringens*, and *Fusobacterium* spp.

In some embodiments, the present invention relates to a method, wherein the microorganism *Enterococcus* spp. is selected from vancomycin susceptible isolate and vancomycin resistant isolate.

In some embodiments, the present invention relates to a method wherein, the microorganism *Escherichia coli* is selected from extended spectrum beta-lactamase (ESBL) producing isolate and *Klebsiella pneumoniae* carbapenemase (KPC) producing isolate.

In some embodiments, the present invention relates to a method wherein, the microorganism *Haemophilus influenzae* is a beta-lactamase positive isolate.

In some embodiments, the present invention relates to a method wherein, the microorganism *Klebsiella pneumoniae* is selected from extended spectrum beta-lactamase (ESBL) producing isolate and *Klebsiella pneumoniae* carbapenemase (KPC) producing isolate.

In some embodiments, the present invention relates to a method wherein, the microorganism *Klebsiella oxytoca* selected from extended spectrum beta-lactamase (ESBL) producing isolate and *Klebsiella pneumoniae* carbapenemase (KPC) producing isolate.

In some embodiments, the present invention relates to a method wherein, the microorganism *Staphylococcus aureus* is selected from methicillin susceptible isolate and methicillin resistant isolate.

In some embodiments, the present invention relates to a method wherein, the microorganism *Staphylococcus epidermidis* is selected from methicillin susceptible isolate and methicillin resistant isolate.

In some embodiments, the present invention relates to a method wherein, the microorganism *Streptococcus pneumoniae* is selected from penicillin susceptible isolate and penicillin resistant isolate.

In some embodiments, the present invention relates to a method of treating, preventing or reducing the risk of a microbial infection in a human or animal comprising administering to the human or animal an effective amount of a compound of the invention, or a tautomer thereof, or a pharmaceutically acceptable salt, ester, or prodrug of said compound or tautomer, or use of a compound of the invention, or a tautomer thereof, or a pharmaceutically acceptable salt, ester, or prodrug of said compound or tautomer, in the manufacture of a medicament for treating, preventing, or reducing the risk of a microbial infection in a human or animal, wherein the microbial infection is selected from the group consisting of a skin infection, a Gram positive infection, a Gram negative infection, nosocomial pneumonia, community acquired pneumonia, post-viral pneumonia, hospital acquired pneumonia/ventilator associated pneumonia, a respiratory tract infection such as chronic respiratory tract infection (CRTI), acute pelvic infection, a complicated skin and skin structure infection, a skin and soft tissue infection (SSTI) including uncomplicated skin and soft tissue infections (uSSTI)s and complicated skin and soft tissue infections, an abdominal infection, a complicated intra-abdominal infection, a urinary tract infection, bacteremia, septicemia, endocarditis, an atrio-ventricular shunt infection, a vascular access infection, meningitis, surgical prophylaxis, a peritoneal infection, a bone infection, a joint infection, a methicillin-resistant *Staphylococcus aureus* infection, a vancomycin-resistant *Enterococci* infection, a linezolid-resistant organism infection, a *Bacillus anthracis* infection, a *Francisella tularensis* infection, a *Yersinia pestis* infection, and tuberculosis.

The compounds of the present invention can be used, for example for the treatment of patients with moderate to severe infections, which may be caused by susceptible isolates of the indicated microorganisms:

In some embodiments, the present invention relates to a method of treating, preventing or reducing the risk of a complicated intra-abdominal infection in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing or reducing the risk of a complicated intra-abdominal infection in a human or animal, In some embodiments, the complicated intra-abdominal infection is selected from polymicrobial infections such as abscess due to *Escherichia coli, Clostridium clostridioforme, Eubacterium lentum, Peptostreptococcus* spp., *Bacteroides fragilis, Bacteroides distasonis, Bacteroides ovatus, Bacteroides thetaiotaomicron, Bacteroides uniformis, Streptococcus anginosus, Streptococcus constellatus, Enterococcus faecalis, Proteus mirabilis,* or *Clostridium perfringens.*

In some embodiments, the present invention relates to a method of treating, preventing or reducing the risk of a complicated skin and skin structure infection (cSSSI, also known as acute bacterial skin and skin structure infections or ABSSSI) in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing or reducing the risk of a complicated skin and skin structure infection, In some embodiments, the complicated skin and skin structure infection is selected from diabetic foot infections without osteomyelitis due to *Staphylococcus aureus* (methicillin susceptible and resistant isolates), *Streptococcus agalactiae, Streptococcus pyogenes, Escherichia coli, Klebsiella pneumoniae, Proteus mirabilis, Bacteroides fragilis, Peptostreptococcus species, Porphyromonas asaccharolytica,* or *Prevotella bivia.*

In some embodiments, the present invention relates to a method of treating, preventing, or reducing the risk of a community acquired pneumonia (CAP) in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing or reducing the risk of community acquired pneumonia, In some embodiment, the community acquired pneumonia is due to *Streptococcus pneumoniae* (penicillin susceptible and resistant isolates) including cases with concurrent bacteremia, *Haemophilus influenzae* (including beta-lactamase positive isolates), *Moraxella catarrhalis,* or atypical bacteria like *Mycoplasma* spp.

In some embodiments, the present invention relates to a method of treating, preventing, or reducing the risk of a complicated urinary tract infection (cUTI) in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing or reducing the risk of a complicated urinary tract infection, In some embodiment, the complicated urinary tract infection is selected from pyelonephritis due to *Escherichia coli,* concurrent bacteremia, or *Klebsiella pneumoniae.*

In some embodiments, the present invention relates to a method of treating, preventing, or reducing the risk of an acute pelvic infection in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing or reducing the risk of an cute pelvic infection, In some embodiments, the acute pelvic infection is selected from postpartum endomyometritis, septic abortion and post surgical gynecologic infections and the infection is due to a microorganism selected from *Streptococcus agalactiae, Escherichia coli, Bacteroides fragilis, Porphyromonas asaccharolytica, Peptostreptococcus* spp., and *Prevotella bivia.*

In some embodiments, the present invention relates to a method of treating, preventing, or reducing the risk of a hospital acquired pneumonia (HAP)/ventilator associated pneumonia (VAP) in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing or reducing the risk of hospital acquired pneumonia/ventilator associated pneumonia, In some embodiments, the hospital acquired pneumonia/ventilator associated pneumonia is due to a microorganism selected from *Streptococcus pneumoniae* (penicillin susceptible and resistant isolates), *Staphylococcus aureus* (methicillin susceptible and resistant isolates), *Klebsiella pneumoniae, Pseudomonas aeruginosa, Acinetobacter* spp., *Stenotrophomonas maltophilia, Haemophilus influenzae* (including beta-lactamase positive isolates), and *Legionella pneumophilia*.

The compounds or tautomers or pharmaceutically acceptable salts, esters or prodrugs of said compounds or tautomers of the present invention may also be useful for the prevention, prophylaxis, or reduction of surgical site infections. In some embodiments, the compounds or tautomers or pharmaceutically acceptable salts, esters or prodrugs of said compounds or tautomers of the present invention are useful following elective colorectal surgery.

Appropriate specimens for bacteriological examination should be obtained in order to isolate and identify the causative organisms and to determine their susceptibility to the compounds of the present invention. Therapy with the compounds or tautomers or pharmaceutically acceptable salts, esters or prodrugs of said compounds or tautomers of the present invention may be initiated empirically before results of these tests are known; once results become available, antimicrobial therapy should be adjusted accordingly.

To reduce the development of drug-resistant bacteria and maintain the effectiveness of the compounds or tautomers or pharmaceutically acceptable salts, esters or prodrugs of said compounds or tautomers of the present invention and other antibacterial drugs, the compounds or tautomers or pharmaceutically acceptable salts, esters or prodrugs of said compounds or tautomers should be used only to treat or prevent infections that are proven or strongly suspected to be caused by susceptible bacteria. When culture and susceptibility information are available, they should be considered in selecting or modifying antibacterial therapy. In the absence of such data, local epidemiology and susceptibility patterns may contribute to the empiric selection of therapy.

In some embodiments, the present invention relates to a method of treating, preventing, or reducing the risk of a microbial infection due to an aerobic or facultative gram-positive microorganism in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing or reducing the risk of a microbial infection due to an aerobic or facultative gram-positive microorganism.

In some embodiments, the aerobic or facultative gram-positive microorganism is selected from:
*Staphylococcus aureus* (methicillin susceptible and resistant isolates), *Streptococcus pneumoniae* (penicillin susceptible and resistant isolates), *Enterococcus* spp. (vancomycin susceptible and resistant isolates), *Streptococcus agalactiae, Streptococcus pyogenes*, and *Staphylococcus epidermidis* (methicillin susceptible and resistant isolates).

In some embodiments, the present invention relates to a method of treating, preventing, or reducing the risk of a microbial infection due to an aerobic and facultative gram-negative microorganism in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing or reducing the risk of a microbial infection due to an aerobic or facultative gram-positive microorganism.

In some embodiments, the aerobic and facultative gram-negative microorganism is selected from: *Escherichia coli* [including extended spectrum beta-lactamase (ESBL) and *Klebsiella pneumonia* (KPC) producing isolates), *Haemophilus influenzae* (including Beta-lactamase positive isolates), *Klebsiella pneumoniae* (including ESBL and KPC producing isolates), *Citrobacter freundii, Enterobacter aerogenes, Enterobacter cloacae, Morganella morganii, Serratia marcescens, Pseudomonas aeruginosa, Acinetobacter baumanni, Moraxella catarrhalis, Proteus mirabilis, Citrobacter koseri, Haemophilus parainfluenzae, Klebsiella oxytoca* (including ESBL and KPC producing isolates), *Proteus vulgaris, Providencia rettgeri*, and *Providencia stuartii*.

In some embodiments, the present invention relates to a method of treating, preventing, or reducing the risk of a microbial infection due to an anaerobic microorganism in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing or reducing the risk of a microbial infection due to an anaerobic microorganism.

In some embodiments, the anaerobic microorganism is selected from: *Bacteroides fragilis, Bacteroides distasonis, Bacteroides ovatus, Bacteroides thetaiotaomicron, Bacteroides uniformis, Clostridium clostridioforme, Eubacterium lentum, Peptostreptococcus* species, *Porphyromonas asaccharolytica, Prevotella bivia, Bacteroides vulgates, Clostridium perfringens*, and *Fusobacterium* spp.

In some embodiments, the present invention relates to a method of treating or reducing the risk of a microbial infection in a human or animal comprising administering to the human or animal an effective amount of a compound of the invention, or a tautomer thereof, or a pharmaceutically acceptable salt, ester, or prodrug of said compound or tautomer, or to the use of a compound of the invention, or a tautomer thereof, or a pharmaceutically acceptable salt, ester, or prodrug of said compound or tautomer, in the manufacture of a medicament for treating, preventing or reducing the risk of a microbial infection.

In some embodiments, the microorganism is *Legionella pneumophilia*.

In some embodiments, the microorganism *Enterococcus* spp. is selected from vancomycin susceptible isolate and vancomycin resistant isolate. In some embodiments, the microorganism *Escherichia coli* is selected from extended spectrum beta-lactamase (ESBL) producing isolate and *Klebsiella pneumoniae* carbapenemase (KPC) producing isolate. In some embodiments, the microorganism *Haemophilus influenzae* is a beta-lactamase positive isolate. In some embodiments, the microorganism *Klebsiella pneumoniae* is selected from extended spectrum beta-lactamase (ESBL) producing isolate and *Klebsiella pneumoniae* carbapenemase (KPC) producing isolate. In some embodiments, the microorganism *Klebsiella oxytoca* selected from extended spectrum beta-lactamase (ESBL) producing isolate and *Klebsiella pneumoniae* carbapenemase (KPC) producing isolate. In some embodiments, the microorganism *Staphylococcus aureus* is selected from methicillin susceptible isolate and methicillin resistant isolate. In some embodiments, the microorganism *Staphylococcus epidermidis* is selected from methicillin susceptible isolate and methicillin resistant isolate. In some embodiments, the microorganism *Streptococcus pneumoniae* is selected from penicillin susceptible isolate and penicillin resistant isolate.

In some embodiments, the present invention relates to a method, use, or compound of the invention, wherein the amount of compound or a tautomer thereof, or a pharmaceutically acceptable salt, ester, or prodrug of said compound or tautomer comprises from 0.1 mg to 1500 mg.

In some embodiments, the present invention relates to a method, use, or compound of the invention wherein the amount of compound or a tautomer thereof, or a pharmaceutically acceptable salt, ester, or prodrug of said compound or tautomer comprises about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325, or about 350 mg, or about 375 mg, or about 400 mg, or about 425 mg, or about 450 mg, or about 475 mg, or about 500 mg, or about 525 mg, or about 550 mg, or about 575 mg, or about 600 mg, or about 625 mg, or about 650 mg, or about 675 mg, or about 700 mg, or about 725 mg, or about 750 mg, or about 775 mg, or about 800 mg, or about 825 mg, or about 850 mg, or about 875 mg, or about 900 mg, or about 925 mg, or about 950 mg, or about 975 mg, or about 1000 mg, or about 1025 mg, or about 1050, mg, or about 1075 mg, or about 1100 mg, or about 1125 mg, or about 1150 mg, or about 1175 mg, or about 1200 mg, or about 1225 mg, or about 1250 mg, or about 1275 mg, or about 1300 mg, or about 1325 mg, or about 1350 mg, or about 1375 mg, or about 1400 mg, or about 1425 mg, or about 1450 mg, or about 1475 mg, or about 1500 mg.

In some embodiments, the present invention relates to a method, use, or compound of the invention wherein the compound, or a tautomer thereof, or a pharmaceutically acceptable salt, ester, or prodrug of said compound or tautomer, is administered otically, ophthalmically, nasally, orally, parenterally, topically, or intravenously.

In some embodiments, the present invention relates to a method of synthesizing a compound of the invention, or a tautomer thereof, or a pharmaceutically acceptable salt, ester, or prodrug of said compound or tautomer.

In some embodiments, the present invention relates to a medical device containing a compound of the invention or a tautomer thereof, or a pharmaceutically acceptable salt, ester, or prodrug of said compound or tautomer. In some embodiments, the device is a stent.

3. SYNTHESIS OF THE COMPOUNDS OF THE INVENTION

Compounds of the invention can be prepared according to methods known in the art. More specifically, compounds of the invention can be prepared according to the procedures and examples described herein. In one aspect, a compound of the invention can be synthesized by coupling two fragments A and B:

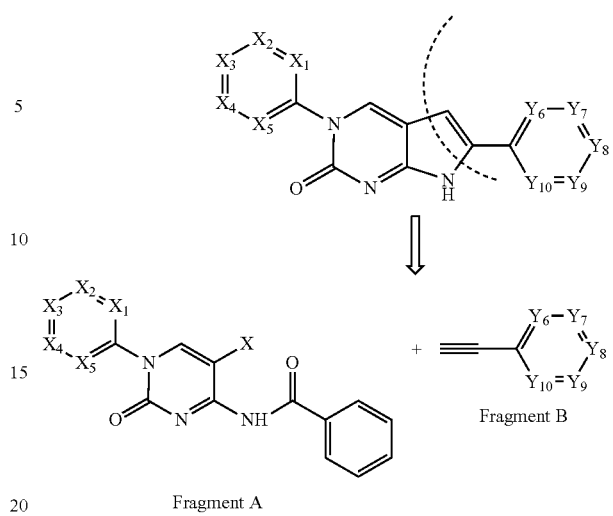

In one aspect, a compound of the invention can be synthesized as outlined Scheme 1.

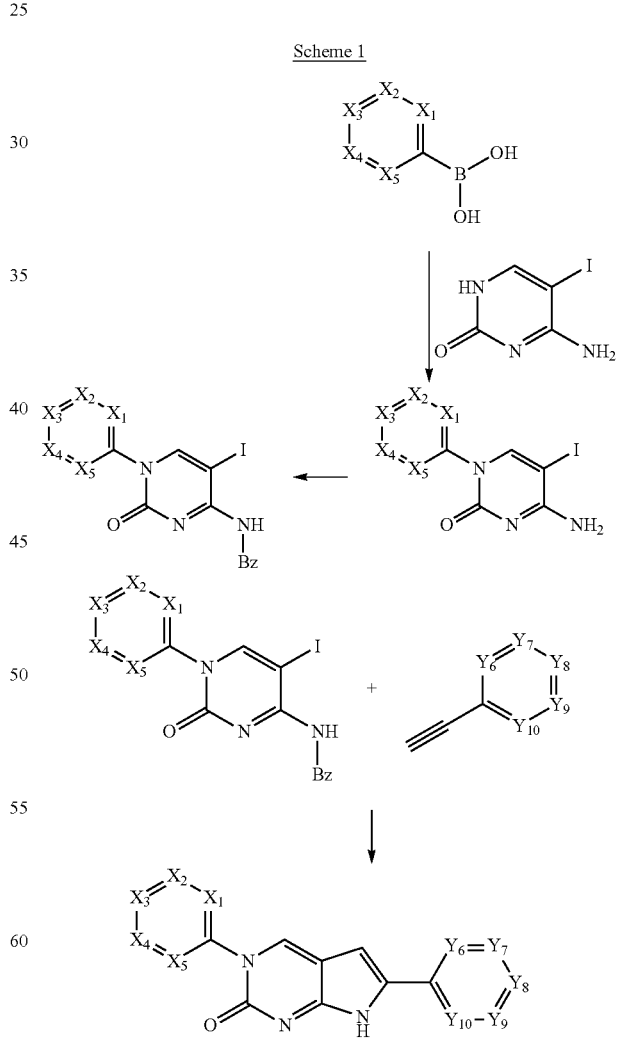

In one aspect, a compound of the invention can be synthesized as outlined in Scheme 2. The scheme depicts the preparation of a compound of formula I having certain values where $X_3$ is $CR^3$ and $Y^9$ is $CR^9$. It is understood that one skilled in the art would be able to readily apply this scheme for the synthesis of compounds having other $R^3$ and $R^9$ groups as described herein.

and Wojciechowski, F., Hudson, R. H. E. "Fluorescence and Hybridization Properties of Peptide Nucleic Acid Containing a Substituted Phenylpyrrolocytosine Designed to Engage Guanine with an Additional H-Bond" J. Am. Chem. Soc., 2008, 130(38), 12574-12575. In one aspect, X in Fragment A Scheme 2

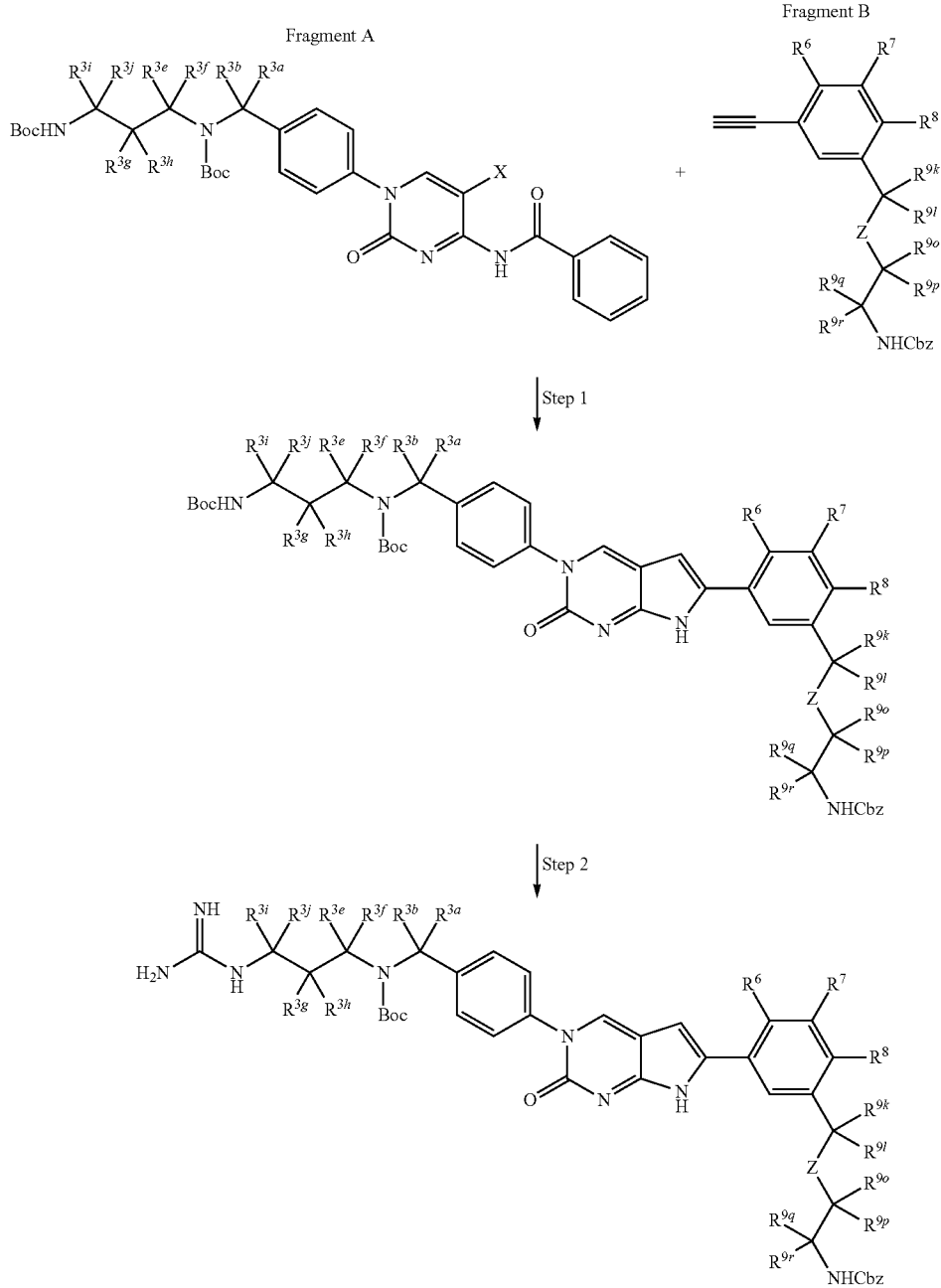

In one aspect, the transformation of step 1 of the synthesis described above is based on a coupling reaction of Fragments A and B to form the core pyrrolocytosine ring. See e.g., Wojciechowski, F., Hudson, R. H. E. "Peptide Nucleic Acid Containing a Meta-Substituted Phenylpyrrolocytosine Exhibits a Fluorescence Response and Increased Binding Affinity toward RNA." Org. Lett. 2009, 11(21), 4878-4881 is I or Br and $R^{3a}$, $R^{3b}$, $R^{3e}$, $R^{3f}$, $R^{3g}$, $R^{3h}$, $R^{3i}$, $R^{3j}$, $R^6$, $R^7$, $R^8$, $R^{9k}$, $R^{9l}$, $R^{9o}$, $R^{9p}$, $R^{9q}$, $R^{9p}$, $R^{9q}$, $R^{9r}$, and Z are as described herein.

Fragments A and B can be coupled using a variety of methods known in the art. Step 2 of the synthesis involves the installation of a guanidine functional group using methods known in the art. In one aspect, the protected terminal amine on the left-hand side of the molecule can be deprotected to afford the primary amine. Guanidine can then be installed by selective addition to the primary amine on the basis of steric factors and the diminished reactivity of the benzylic nitrogen. Global deprotection then produces the final compound in the form of a polyamine salt.

In one aspect, a compound of the invention can be synthesized as shown in the Scheme 3. The scheme depicts the preparation of a compound having certain values defined, however one skilled in the art would understand that the methodology outlined below could be readily applied for the preparation of other compounds of the invention described herein.

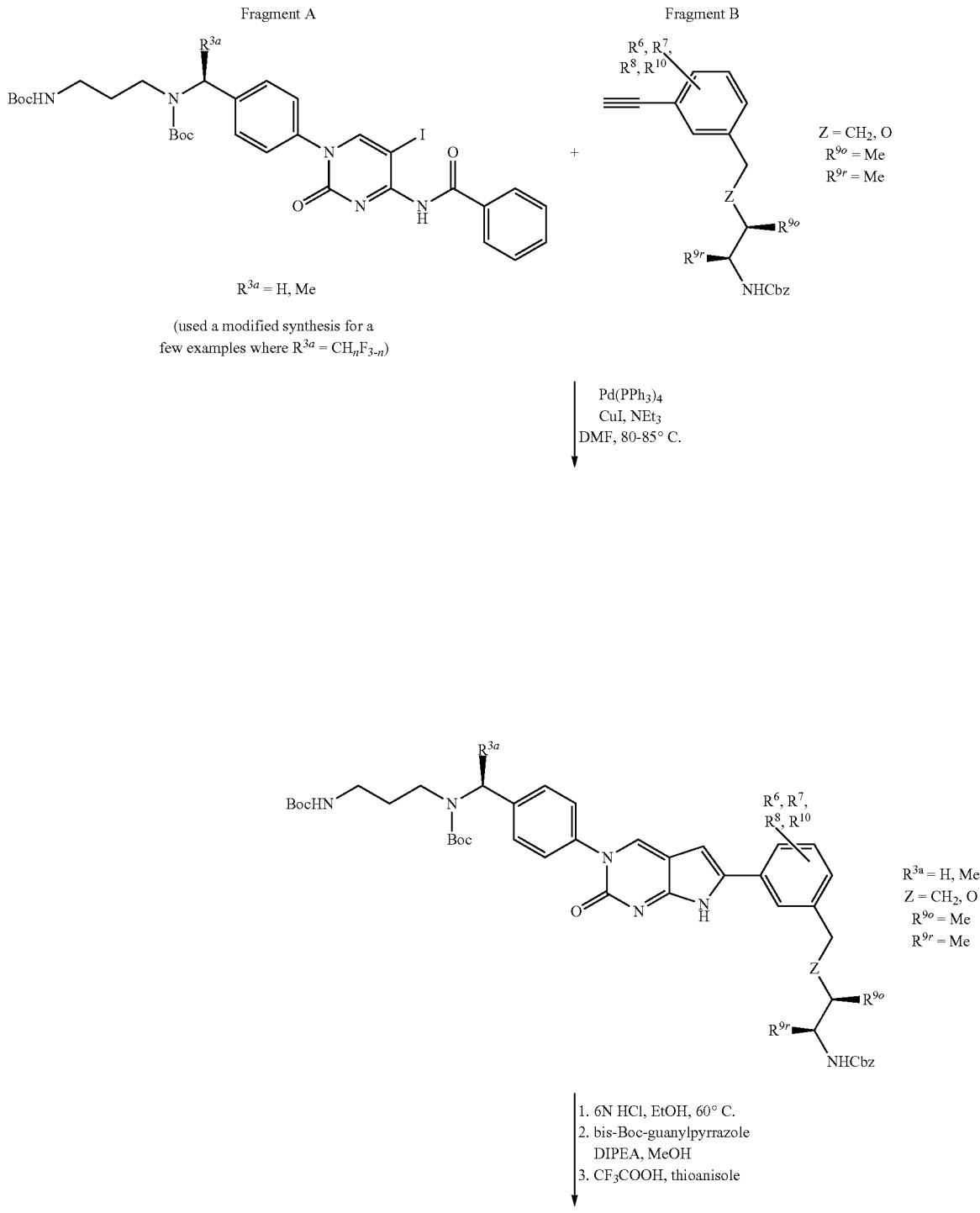

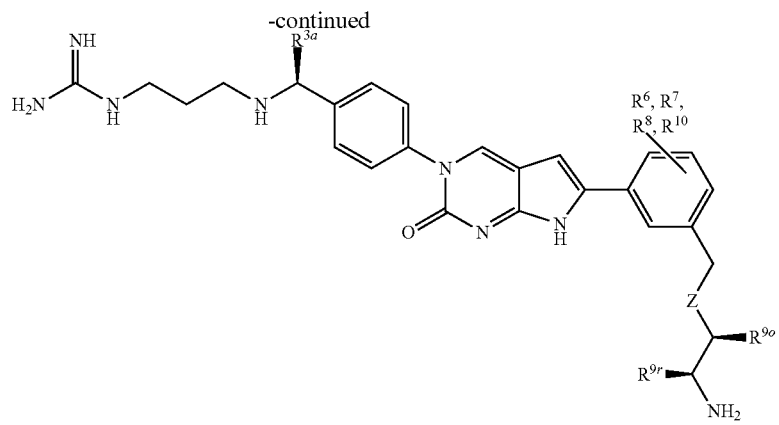

Although Scheme 3 shown above is depicted with certain values for $R^{3a}$, $R^{9o}$, $R^{9r}$, and Z, it is understood that one skilled in the art would be able to readily apply this scheme for the synthesis of compounds having other $R^{3a}$, $R^{9o}$, $R^{9r}$, and Z groups. Furthermore, it is understood that Scheme 3 above is applicable for the variety of aryl groups described herein e.g.,

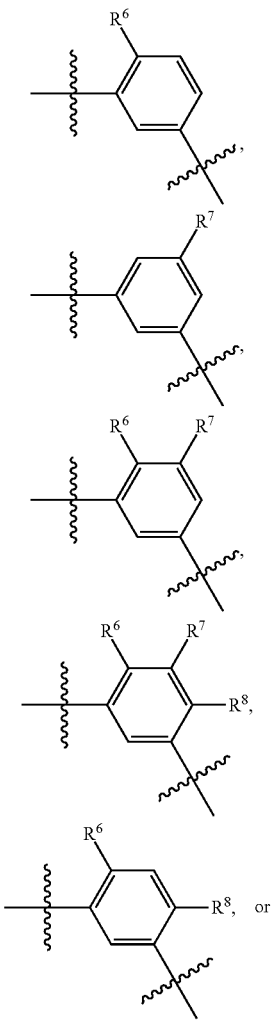

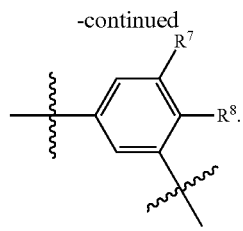

Preparation of Fragment A

Fragment A intermediates can be prepared according to methods known in the art. The schemes below outline strategies that can be applied for the synthesis of Fragment A intermediates and used to prepare compounds of the invention. Procedures for the preparation of Fragment A intermediates are also found in the examples provided herein. In one aspect, Fragment A can be synthesized using a 4 step process as outlined below.

Step 1 uses a reductive amination strategy to form a benzyl amine intermediate. The amine and aldehyde groups can be on either one of the compounds involved in the reductive amination reaction. Reductive amination is a well known procedure in the chemical arts and thus, the skilled person would be able to optimize Step 1 for the preparation of a compound of the invention.

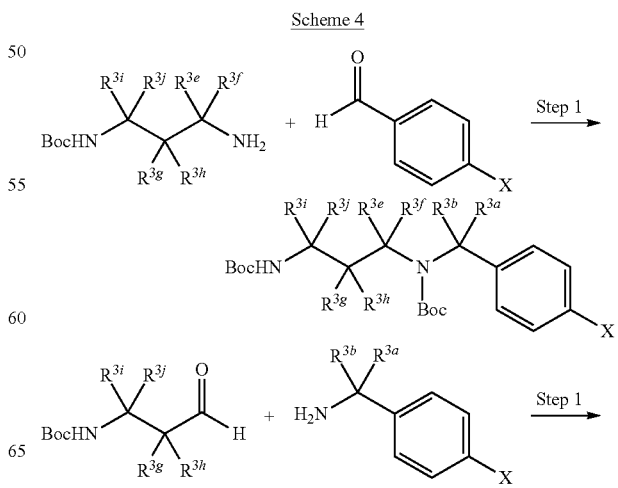

-continued

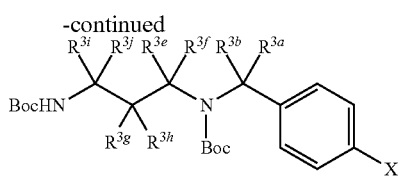

Following formation of the benzyl amine intermediate, Step 2 is a coupling reaction to form a pinacol borane compound, which is then coupled in Step 3 with an iodocytosine moiety. Step 4 involves acylation of the amine group of the pyrimidinone to form a Fragment A intermediate.

the resulting benzyl amine intermediate has at least one substituent ($R^{3a}$ is not H) in the benzylic position. It is understood that the second procedure can be used to prepare a variety of different benzyl amine intermediates e.g., intermediates with $R^{3a}$ selected from ethyl, propyl, alkenyl, cyclopropyl, $CO_2H$, $CO_2Me$, alkyl substituted with $CO_2Me$, $CO_2H$, etc.

Scheme 6

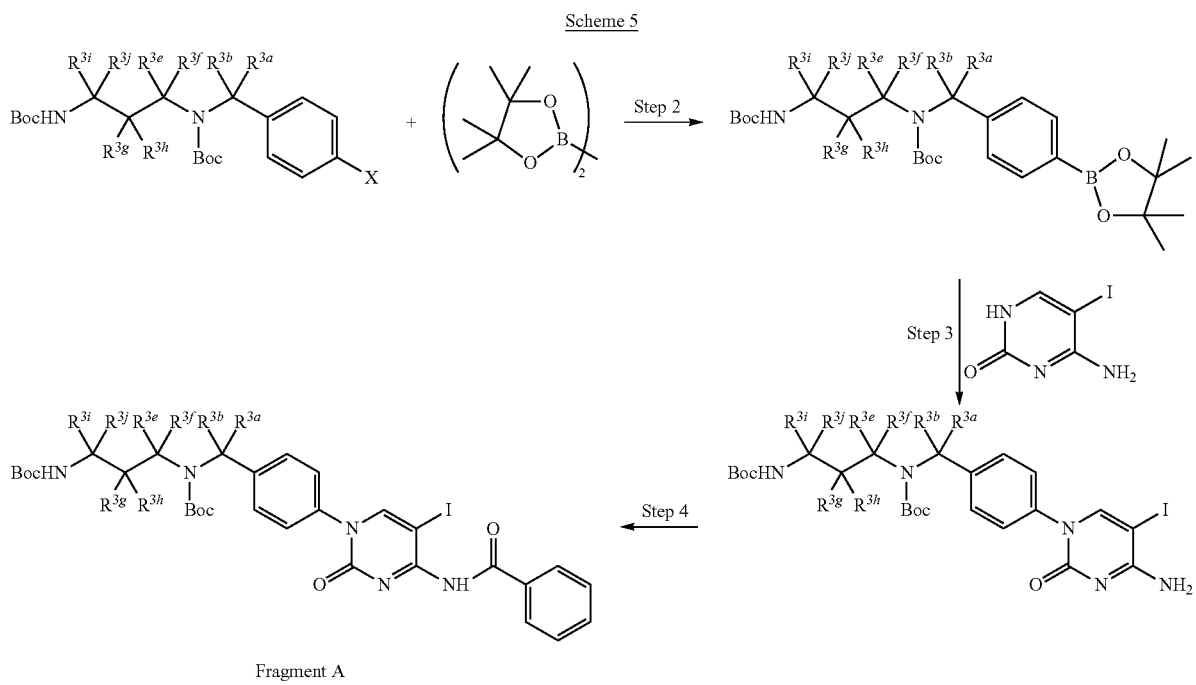

Fragment A

Scheme 6 and Scheme 7 below show a 4-step for the synthesis of the Fragment A intermediate:

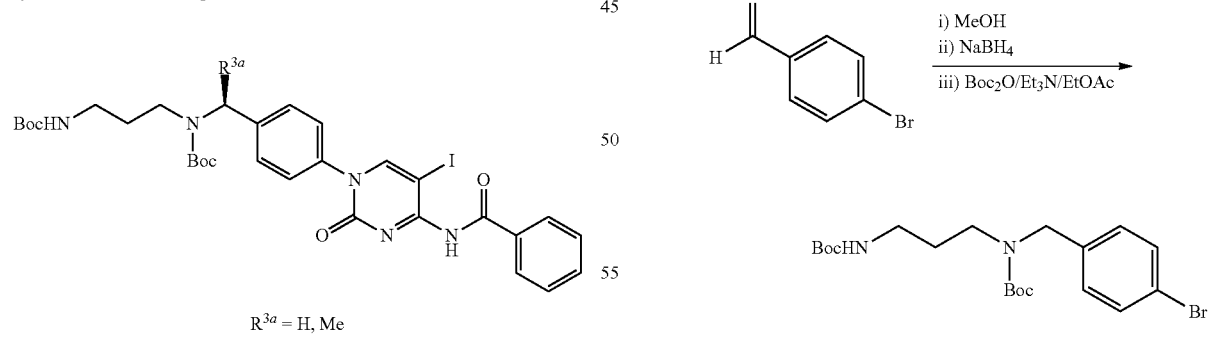

$R^{3a}$ = H, Me

Although the schemes depict the preparation of compounds having certain values defined, one skilled in the art would understand that the methodology outlined below could be readily applied for the preparation of other compounds of the invention described herein. The scheme below shows two alternative procedures for Step 1 in the synthesis of the Fragment A intermediate above. In the first procedure, the resulting benzyl amine intermediate does not have a substituent at the benzylic position (i.e., $R^{3a}$=H). In the second procedure, -continued

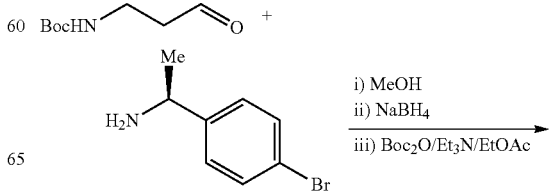

-continued

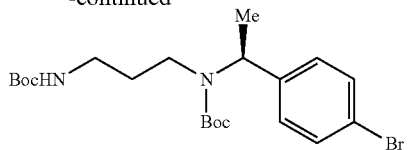

Steps 2-4 are shown below for the preparation of Fragment A. The steps are the same for compounds having $R^{3a}$ as H or $CH_3$. Although the steps are depicted with compounds having $R^{3a}$ defined as H or $CH_3$, one skilled in the art could readily apply the procedures described herein and in the examples for the preparation of a different Fragment A e.g., a Fragment A with $R^{3a}$ selected from ethyl, propyl, alkenyl, cyclopropyl, $CO_2H$, $CO_2Me$, alkyl substituted with $CO_2Me$, $CO_2H$, etc.

Scheme 7

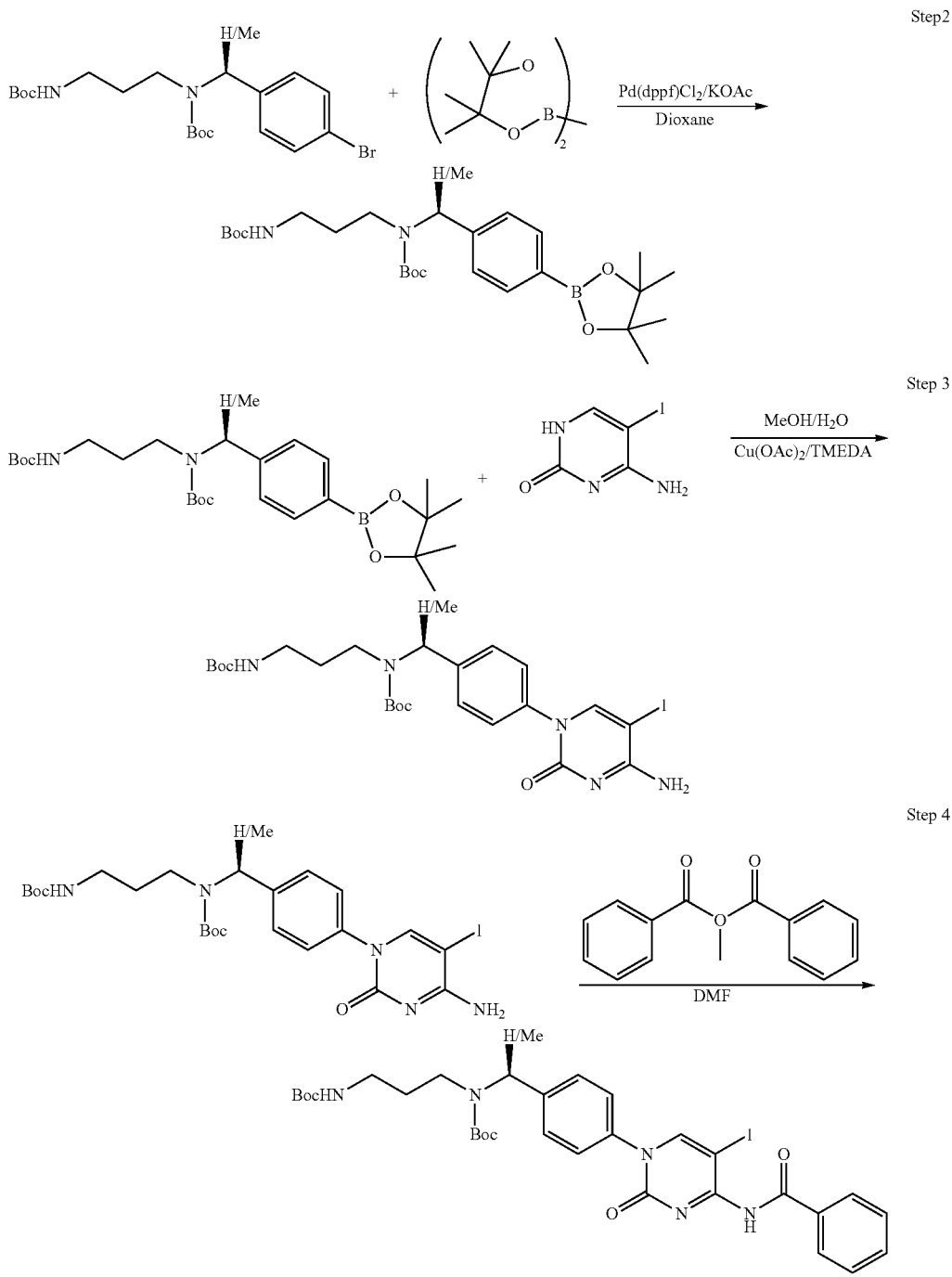

Preparation of Fragment B

Fragment B intermediates can be prepared according to methods known in the art. The schemes below outline strategies that can be applied for the synthesis of Fragment B intermediates and used to prepare compounds of the invention. Procedures for the preparation of Fragment B intermediates are also found in the examples provided herein. Scheme 8 below is a retro-synthetic analysis which shows the strategy for attaching a $R^9$ group to the aryl moiety. The strategy involves the coupling of an aryl halide with an aminoalkene moiety. This strategy is applicable for the synthesis of Fragment B intermediates where the $R^9$ group is an all carbon chain (i.e., Z is $CH_2$). Although the Scheme 8 illustrates a transformation to form a Fragment B intermediate with a certain $R^9$ group, it is understood that the strategy can be applied to prepare different Fragment B intermediates with a different $R^9$ group as described herein, where Z is $CH_2$.

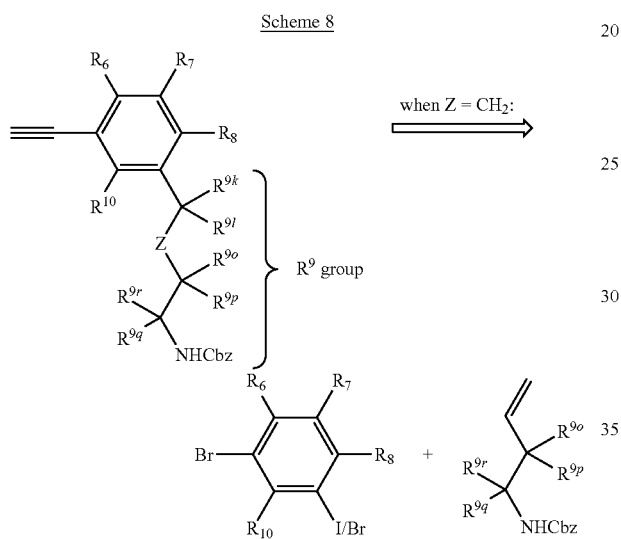

An example of the preparation of the aminoalkene compound is shown below. Further details regarding the preparation of this aminoalkene compound are found in the examples herein.

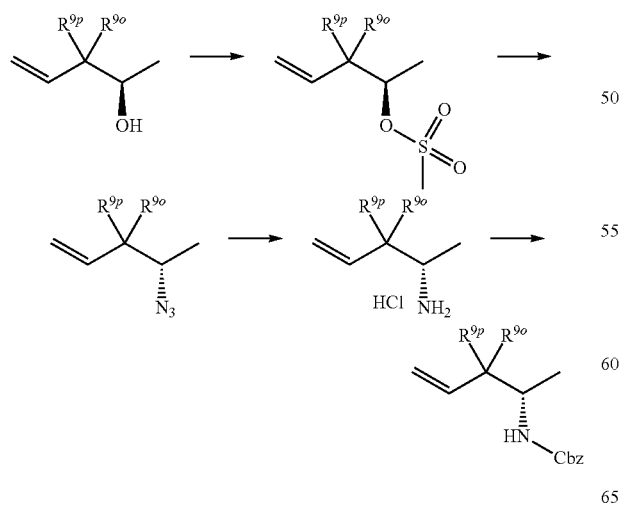

Alternatively, Scheme 9 below depicts a retro-synthetic strategy for the synthesis of Fragment B intermediates that have an oxygen atom in the $R^9$ chain. In one aspect, the synthesis of the Fragment B intermediate begins with a dibromide or dihalide (Br and I) aryl compound (labeled A and B below). The synthesis involves conversion of an aryl bromide or iodide to an aldehyde group, reduction of the aldehyde to a primary alcohol, which is next converted to a leaving group (LG). The $R^9$ chain is then elaborated by the displacement of the OLG group with a primary alcohol. The primary alcohol has functionality that can be unmasked and elaborated to a nitrogen group using chemistry known in the art.

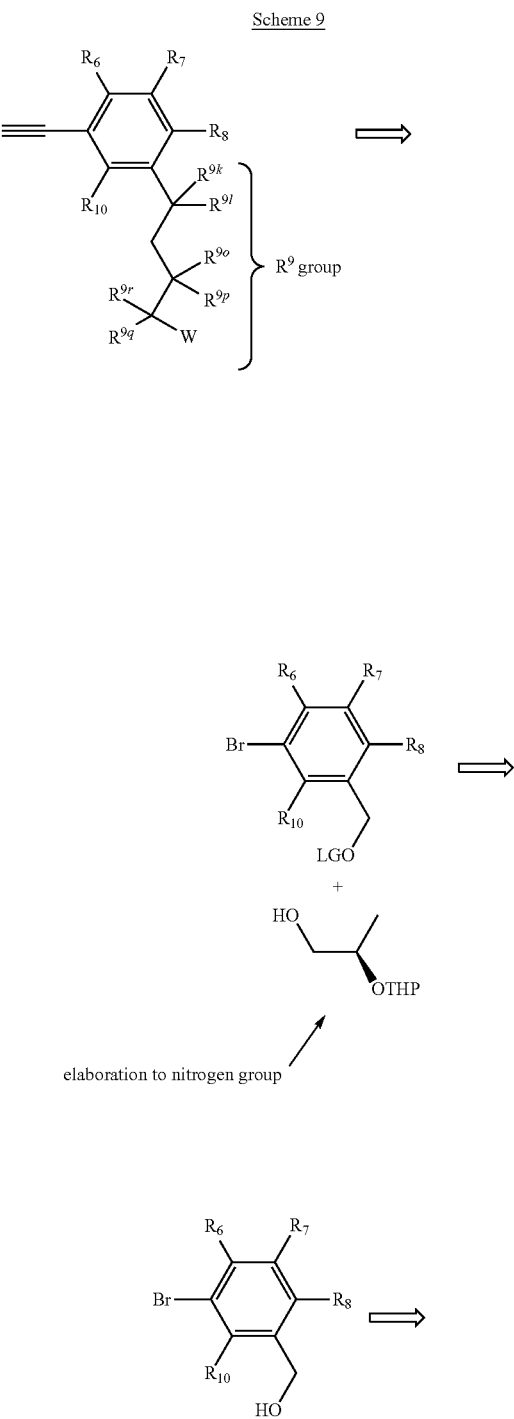

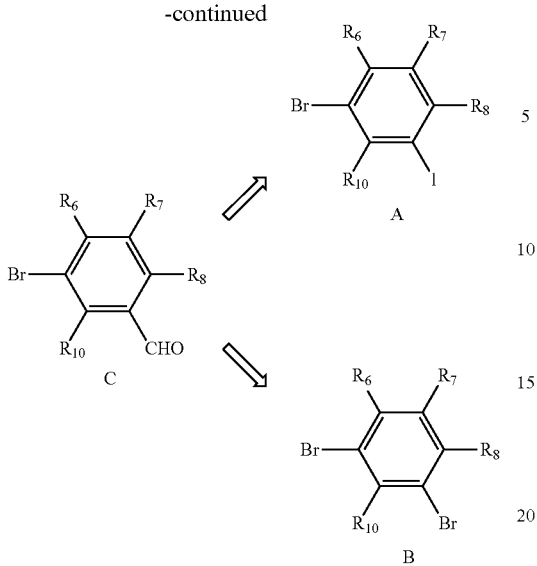

Alternatively, the R⁹ chain can be installed to produce a Fragment B intermediate starting with an aldehyde aryl compound (labeled C in Scheme 9). The synthesis can involve a Wittig olefination reaction to install the R⁹ chain as shown in Scheme 10, which depicts the retro-synthesis of fragment B.

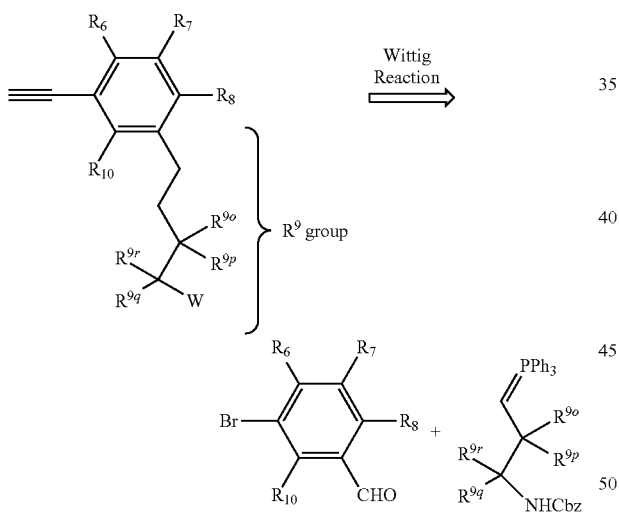

It is understood that the synthetic procedures described above and in the examples can be used to prepare compounds of the invention having a variety of aryl groups. Some representative aryl groups include e.g.,

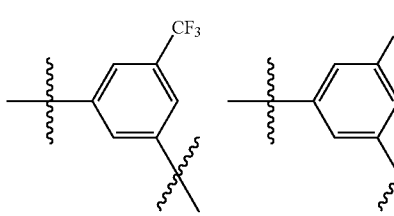

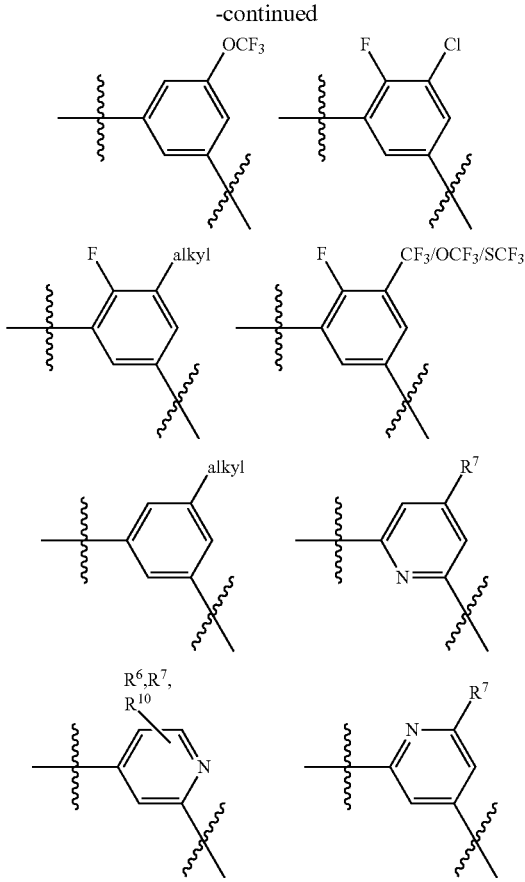

It is understood that the synthetic procedures described above and in the examples can be used to prepare compounds of the invention having a variety of different R⁹ chains. Some representative R⁹ chains include e.g.,

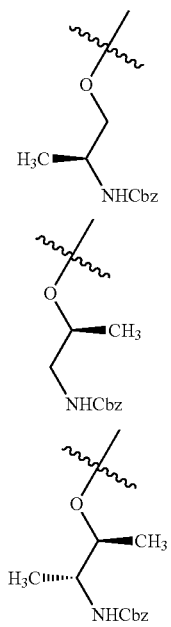

189

-continued

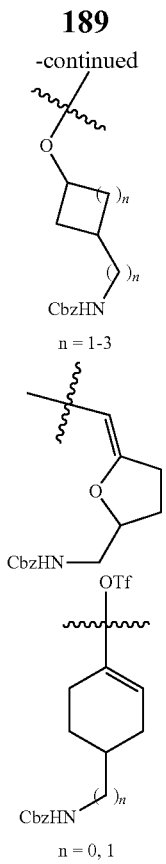

n = 1-3 n = 0, 1

In the last R⁹ chain, there is no CH₂ group between the aryl group and cyclic group.

Precursors for the preparation of the R⁹ chain include e.g.,

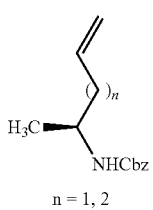

n = 1, 2

190

-continued

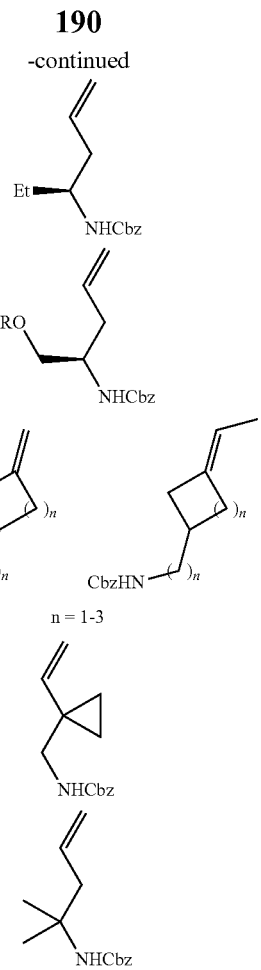

n = 1-3

The three schemes (Schemes 11-13) below illustrate several general strategies for preparing Fragment B intermediates. Scheme 11 illustrates how the dihalide aryl compound (labelled compound 8) is a key intermediate which can be coupled with a variety of different R⁹ chains to synthesize a Fragment B intermediate and used to prepare many of the compounds of the invention. Synthetic procedures for the preparation of dihalide aryl intermediates used to prepare compounds of the invention are found in the examples herein.

Scheme 11

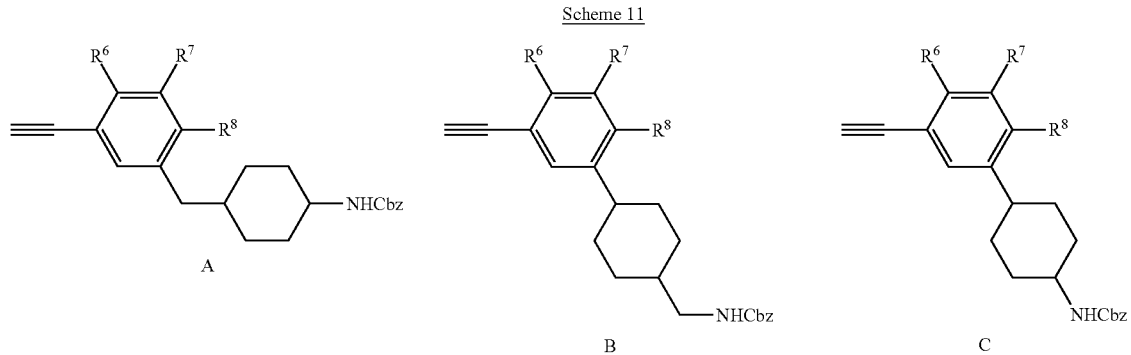

A    B    C 191 192
-continued
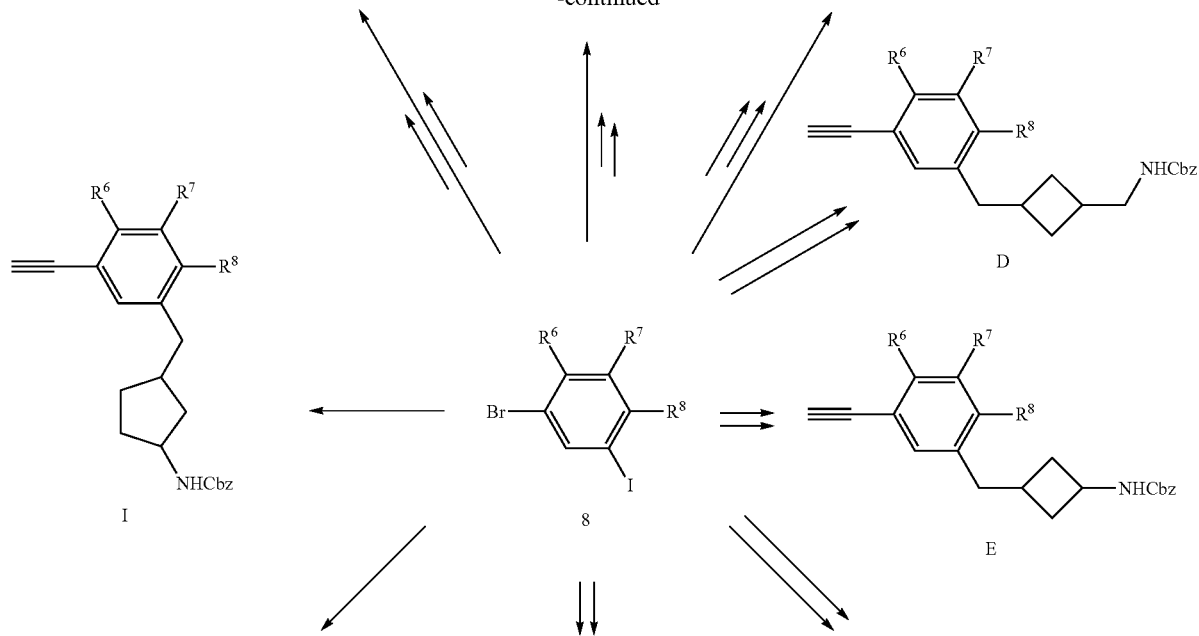
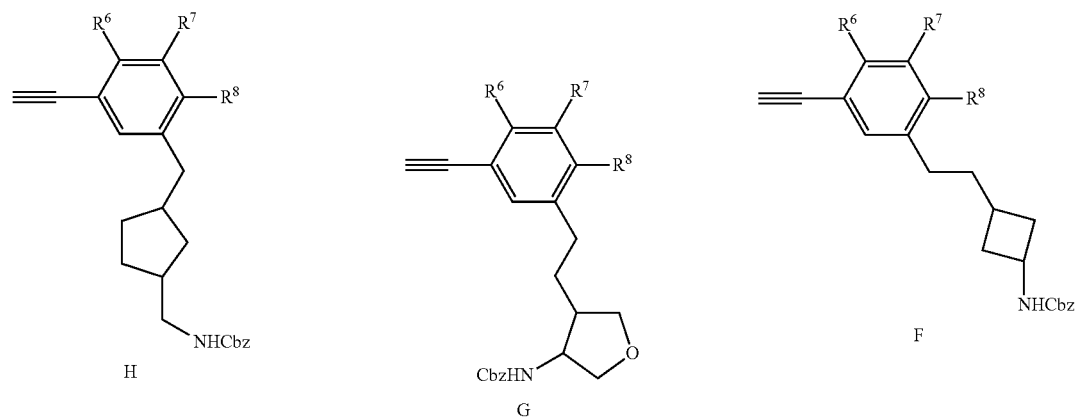
Scheme 12 shows a key transformation of the dihalide aryl intermediate compound 8 to compound 21, which can be elaborated to many different Fragment B intermediates.

Scheme 12
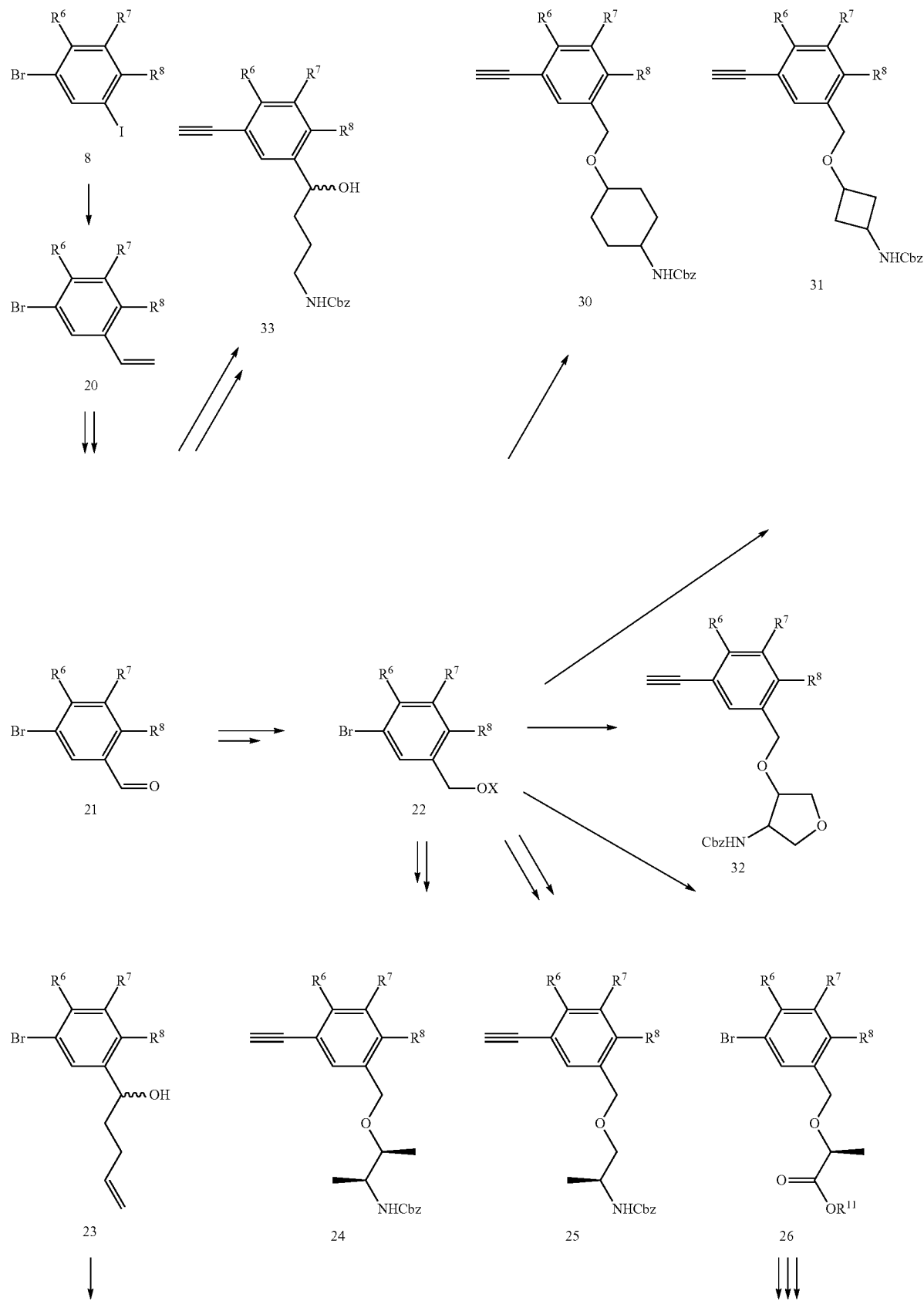

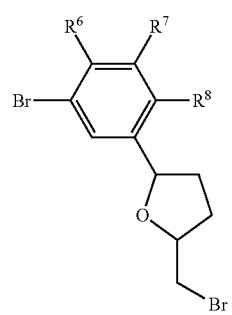 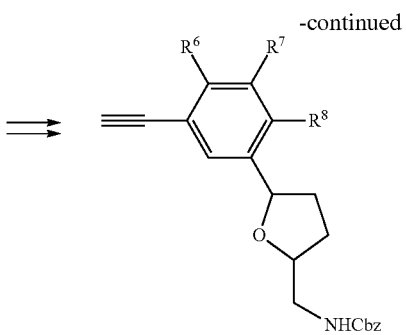 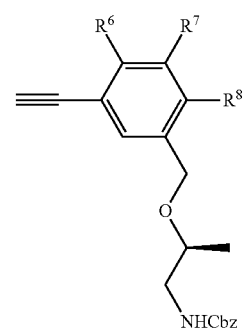
Scheme 13 emphasizes the utility of the aniline moiety for the regioselective installation of either iodide or bromide either in a stepwise manner (eg. 2→6→7) or in one pot (2→3). The diversity of aniline compounds, either commercially available or prepared from other starting materials (eg. 1→2), allows access to a variety of substitution patterns.
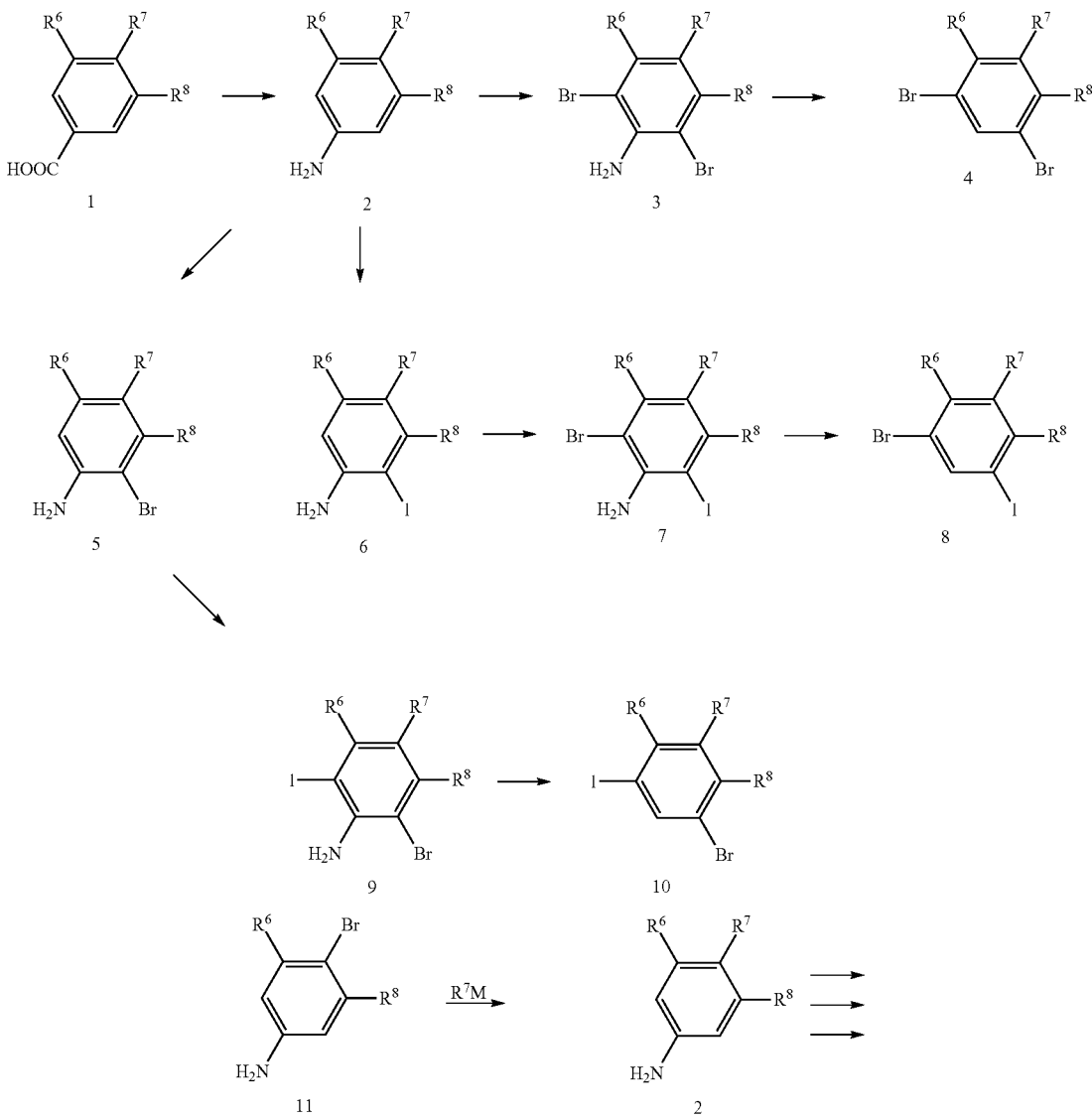

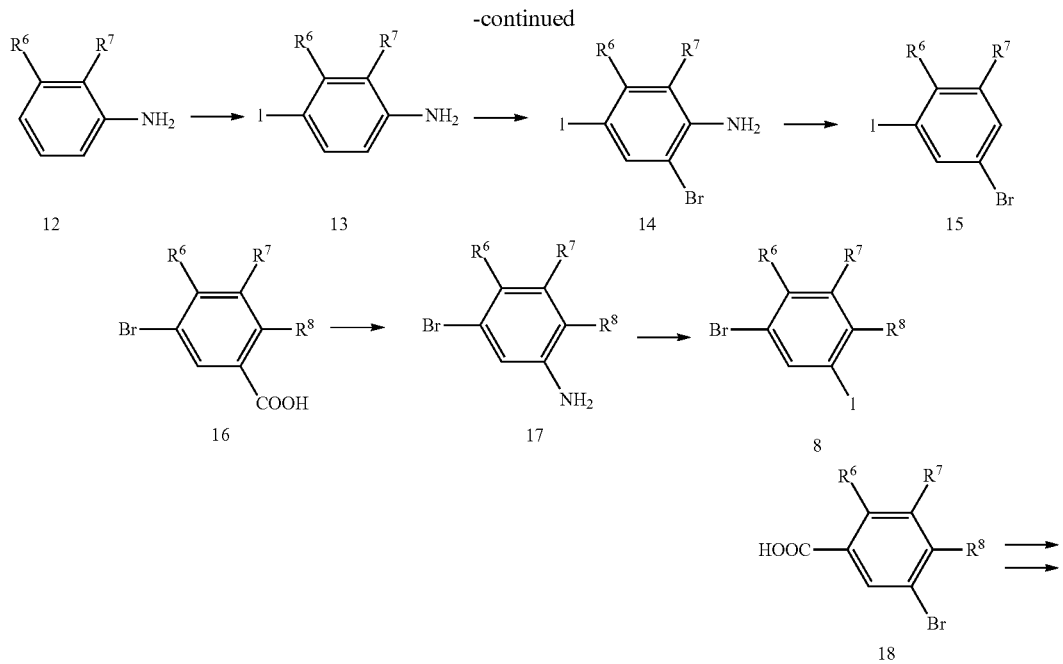

Scheme 14 below shows the preparation of a Fragment B intermediate having a ring in the $R^9$ chain. In one aspect, the process of attaching the $R^9$ group to the aryl moiety includes coupling of a dihalide aryl intermediate compound 8 with an aminoalkene moiety having a ring structure e.g.,

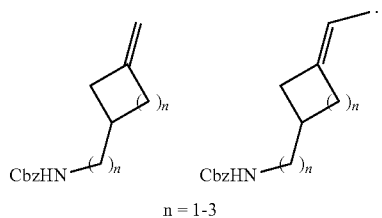

n = 1-3

Scheme 14 illustrates a strategy for preparing $R^9$ chains having any size ring incorporated into the chain e.g., a 3-, 4-, 5-, 6-, etc. membered ring. In one aspect, the amino group can be installed via either a Curtius rearrangement (2→3) or a nitrile reduction (1→7). In one aspect, the aminoalkene moiety can be attached to the aryl moiety via the Suzuki-coupling reaction. For example, the aminoalkene can first be converted to a alkylborane by treatment with 9-BBN and then reacted with compound 8, replacing the more reactive iodide first. The terminal alkyne can be installed by a variety of methods know in the art. Reagents such as trimethylsilyl acetylene can be employed to generate fragment B.

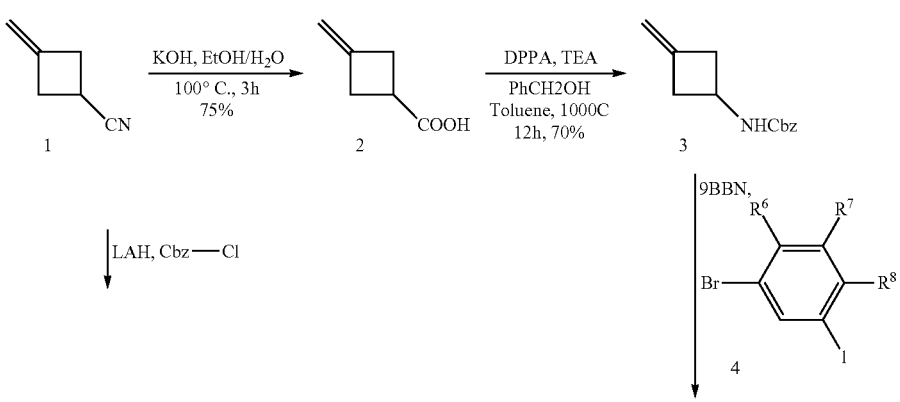

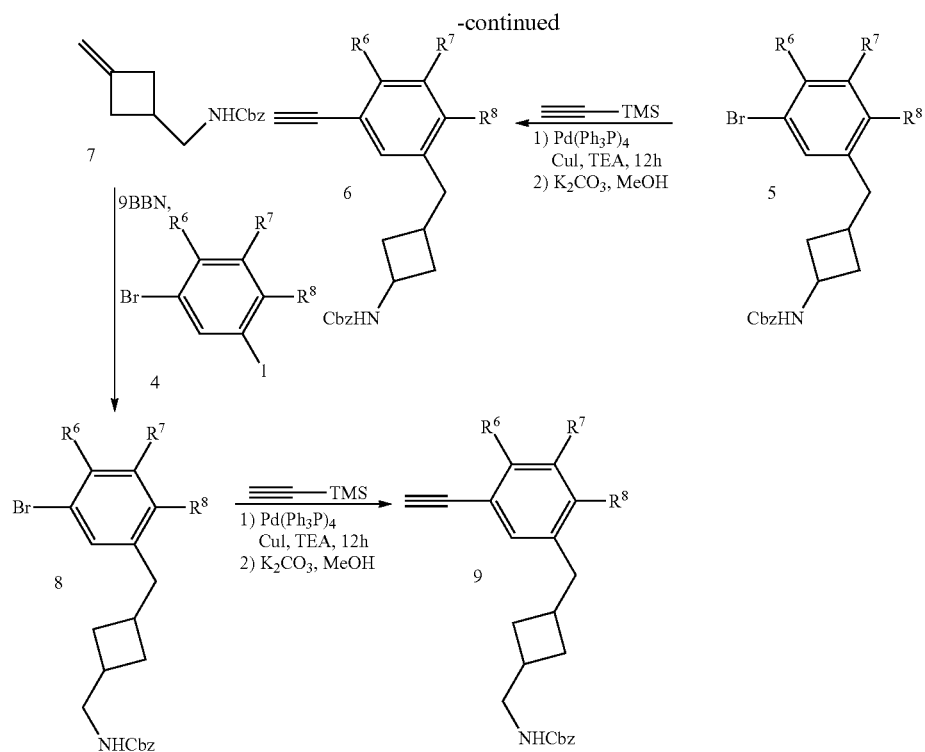

4. CHARACTERIZATION OF COMPOUNDS OF THE INVENTION

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, for example, as anti-cancer, anti-bacterial, anti-fungal, anti-parasitic or anti-viral agents. Also, it can be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

(1) Surface Binding Studies.

A variety of binding assays can be useful in screening new molecules for their binding activity. One approach includes surface plasmon resonance (SPR) that can be used to evaluate the binding properties of molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor® from Pharmacia Biosensor, Piscataway, N.J.) provides a focused beam of polychromatic light to the interface between a gold film (provided as a disposable biosensor "chip") and a buffer compartment that can be regulated by the user. A 100 nm thick "hydrogel" composed of carboxylated dextran that provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies that are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization.

Fluorescence polarization (FP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis.

It is contemplated that, in addition to characterization by the foregoing biochemical assays, the compound of interest can also be characterized as a modulator (for example, an inhibitor of protein synthesis) of the functional activity of the ribosome or ribosomal subunit.

Furthermore, more specific protein synthesis inhibition assays can be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3H$ leucine or $^{35}S$ methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is a inhibitor of protein synthesis.

(4) Antimicrobial Assays and Other Evaluation.

Furthermore, the compounds can be assayed for anti-proliferative or anti-infective properties on a cellular level. For example, where the target organism is a microorganism, the activity of compounds of interest can be assayed by growing the microorganisms of interest in media either containing or lacking the compound. Growth inhibition can be indicative that the molecule can be acting as a protein synthesis inhibitor. More specifically, the activity of the compounds of interest against bacterial pathogens can be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms.

The in vitro activity of the compounds of the present invention can be determined. Antimicrobial testing is typically performed to determine the minimum inhibitory concentration (MIC). Minimum inhibitory concentrations (MICs) are determined by the microdilution method in a final volume of 100 µl according to protocols outlined by The Clinical and Laboratory Standards Institute (CLSI). Performance standards for reference strains are assessed within the same experimental design to maintain quality control. See, for example, Clinical Laboratory Standards Institute: Methods for dilution antimicrobial susceptibility tests for bacteria that grow aerobically M7-A8. Approved Standard-Eighth Edition. Wayne, Pa.: CLSI; December 2008; and Clinical Laboratory Standards Institute: Performance Standards for Antimicrobial Susceptibility Testing M100-S20; Approved Standard-Twentieth Edition. Wayne, Pa.: CLSI; June 2010.

The antimicrobial and other drug properties of the compounds can further be evaluated in various in vivo mammalian assays, such as a mouse or rat peritonitis infectious models, skin and soft tissue models (often referred to as the thigh model), or a mouse pneumonia model. There are septicemia or organ infection models known to those skilled in the art. These efficacy models can be used as part of the evaluation process and can be used as a guide of potential efficacy in humans. Endpoints can vary from reduction in bacterial burden to lethality. For the latter endpoint, results are often expressed as a $PD_{50}$ value, or the dose of drug that protects 50% of the animals from mortality.

To further assess a compound's drug-like properties, measurements of inhibition of cytochrome P450 enzymes and phase II metabolizing enzyme activity can also be measured either using recombinant human enzyme systems or more complex systems like human liver microsomes. Further, compounds can be assessed as substrates of these metabolic enzyme activities as well. These activities are useful in determining the potential of a compound to cause drug-drug interactions or generate metabolites that retain or have no useful antimicrobial activity.

To get an estimate of the potential of the compound to be orally bioavailable, one can also perform solubility and Caco-2 assays. The latter is a cell line from human epithelium that allows measurement of drug uptake and passage through a Caco-2 cell monolayer often growing within wells of a 24-well microtiter plate equipped with a 1 micron membrane. Free drug concentrations can be measured on the basolateral side of the monolayer, assessing the amount of drug that can pass through the intestinal monolayer. Appropriate controls to ensure monolayer integrity and tightness of gap junctions are needed. Using this same system one can get an estimate of P-glycoprotein mediated efflux. P-glycoprotein is a pump that localizes to the apical membrane of cells, forming polarized monolayers. This pump can abrogate the active or passive uptake across the Caco-2 cell membrane, resulting in less drug passing through the intestinal epithelial layer. These results are often done in conjunction with solubility measurements and both of these factors are known to contribute to oral bioavailability in mammals. Measurements of oral bioavailability in animals and ultimately in man using traditional pharmacokinetic experiments will determine the absolute oral bioavailability.

Experimental results can also be used to build models that help predict physical-chemical parameters that contribute to drug-like properties. When such a model is verified, experimental methodology can be reduced, with increased reliance on the model predictability.

(5) Animal Pharmacology and Toxicology.

The compounds of the present invention can be evaluated for efficacy in well-known animal models. The following table provides representative animal models for various infection indications.

| Target Infection Indication | Animal Model of Efficacy |
|---|---|
| HAP/VAP | Efficacy in mouse and/or rat *pneumoniae* model vs. respiratory tract infection pathogens of interest (*Streptococcus pneumoniae*, including multi-drug resistant *Streptococcus pneumoniae*, *H. influenzae*, methicillin resistant *Staphylococcus aureus* (MRSA), and *Pseudomonas. aeruginosa*) |

| Target Infection Indication | Animal Model of Efficacy |
|---|---|
| cSSSI | Efficacy in mouse model against pathogens of interest (MRSA, *K. pneumoniae*) |
| Sepsis | Efficacy in mouse peritonitis model vs. pathogens of interest (*E. coli, K. pneumoniae, E. faecalis*, MRSA) |
| cUTI | Efficacy in mouse model against *E. coli, K. pneumoniae* and/or MRSA) |
| Febrile neutropenia | Efficacy in mouse peritonitis model against *S. aureus, S. epidermidis, S. pneumoniae, S. pyogenes, P. aeruginosa* |

Animal Model for Complicated Skin and Skin Structure Infections (cSSSI): Murine Skin and Soft Tissue Infection Model of *Klebsiella pneumoniae* 1705966 in Thighs of Neutropenic Female CD-1 Mice This model is useful to assess the efficacy of compounds of the present invention in a *Klebsiella pneumoniae* 1705966 neutropenic mouse thigh infection model using female ICR (CD-1) mice.

Study Design:

Species: Female ICR (CD-1) Mice, 8 to 9 weeks old, weighting 25-29 g.

Inoculum: *Klebsiella pneumoniae* 17059663 was streaked from frozen stock onto Blood agar (Tryptic Soy Agar+5% Sheep Blood), BD, #221261) and incubated overnight at 35° C. After overnight incubation, enough bacteria (approx. 1 full loop) to measure $OD_{625}$=0.990 was transferred from plate and diluted into 10 ml pre-warmed Mueller-Hinton broth. This culture was further diluted 1:1000 into pre-warmed MH broth and grown for approximately 2 hrs at 35° C. with shaking. Each mouse was given 0.1 mL of 1:1000 dilution culture injected into both caudal thigh muscles under isoflurane inhalation anesthesia.

| Dilution | Initial O.D. | Final O.D. (after ~2 hr. incubation) |
|---|---|---|
| 1:10 | 0.135 | 0.424 |
| 1:100 | 0.014 | 0.215 |
| 1:1000 | 0.001 | 0.035 |

Neutropenia is induced by intraperitoneal (I.P.) administration of Cyclophosphamide monohydrateon Day −4 (150 mg/kg) and Day −1 (100 mg/kg).

Vehicle: 0.9% sodium chloride

Dosing: Each mouse in the treated groups was given the appropriate dose of the compound to be tested in a volume of 0.2 ml, 2 and 8 hrs. post bacterial inoculation.

Time points:

Controls: 0, 2, 6, and 24 hrs.

Treated: 24 hrs.

Sampling: 2 or 3 mice/time point were euthanized via $CO_2$, and their caudal thigh muscles excised and homogenized. The thigh muscles were placed in 5 ml sterile PBS in Stomacher Filter bag and homogenized with MicroBiomaster80 (Brinkmann) for 60 seconds, normal setting and 1:10 dilutions were made per standard protocol in a 96-well plate. Aliquots of 25 ul for each dilution, as well as the homogenate, were plated on blood agar plates and incubated at 35° C. to determine the CFU/mL over the time course. After overnight incubation, colonies were counted.

Animal Model for Sespsis:

Murine Peritonitis Model (*E. Coli, K. Pneumoniae, E. Faecalis*, MRSA)

This model is used to evaluate the effect of subcutaneous (SC) treatment with compounds of the present invention on growth of *Escherichia coli* ATCC 25922 in a mouse peritonitis model using female Swiss Webster mice.

Controls:

Negative: Inoculum only

Inoculum Vehicle Intraperitoneal

Positive: Ciprofloxacin

Study Design:

Species: Female Swiss Webster Mice

Inoculation: *Escherichia coli* ATCC 25922 is made by adding 1 ml (Apr. 6, 2007) stock to 9 ml 0.25% Brewer's Yeast to make (1:10), then 1 ml of the (1:10) will be added to 9 ml 0.25% Brewer's Yeast to make (1:100), then 1 ml of the (1:100) will be added to 9 ml 0.25% Brewer's Yeast to make (1:1000), then 2.5 ml of the (1:1000) will be added to 122.5 ml 0.25% Brewer's Yeast to make (1:50,000), 1 ml/mouse will by inoculated intraperitoneally (IP).

Route of Administration: SC

Dosing: Vehicle for compounds of the present invention: Saline or 50 mM Sodium phosphate buffer in 10% Captisol in water, pH=7.2.

Dose Administration: Q3H×3 beginning at 30 min post bacterial inoculation

Study Duration: 24 hrs. 0.25% Brewer's Yeast Extract (BYE): Dilute 2% prepared on Nov. 12, 2009 (Lot. 2158K, MP Biomedicals) 25 ml 2%+175 ml 1×PBS.

Outcome Measures: Colony Forming Unit's from peritoneal wash and spleen homogenate and drug levels from wash, spleen homogenate, and plasma.

Blood is collected via cardiac puncture while mouse is under $CO_2$ narcosis. The whole blood sample is placed in heparinized eppendorf tubes and kept on wet ice until centrifuged (4 min@14,000 rpm). Plasma is transferred to 96 deep-well block on dry ice and stored at −20° C. Immediately following blood collection, 2 ml of sterile PBS (phosphate buffered saline) was injected into the peritoneal cavity with a 25G needle. The abdomen was gently massaged, and a small incision was made to allow access to the peritoneal cavity. The peritoneal wash fluid was collected using sterile technique, serially diluted 1:10, plated on blood agar plates, and incubated overnight at 35° C.

Spleens were harvested and placed in 1 ml sterile PBS in Stomacher bag and homogenized with MicroBiomaster80 (Brinkmann) for 60 seconds, normal setting and 1:10 dilutions were made. 25 ul of each dilution, as well as the homogenate, was plated on blood agar plates and incubated at 35° C. to determine the CFU/mL over the time course. After overnight incubation, colonies were counted.

Other Animal Models

Similarly, other animal infection models can be used for hospital acquired pneumonia (HAP)/ventilator acquired pneumonia (VAP), complicated urinary tract infections (cUTI), and febrile neutropenia.

5. FORMULATION AND ADMINISTRATION

The compositions and methods of the present invention can be practiced by delivering the compounds of the present invention using a means for delivery e.g., any suitable carrier. The dose of active compound, mode of administration and use of suitable carrier will depend upon the intended patient or subject and the targeted microorganism, e.g., the target bacterial organism. The formulations, both for human medical use and veterinary use, of compounds according to the present invention typically include such compounds in association with a pharmaceutically acceptable carrier.

The carrier(s) should be "acceptable" in the sense of being compatible with compounds of the present invention and not deleterious to the recipient. Pharmaceutically acceptable carriers, in this regard, are intended to include any and all solvents, dispersion media, coatings, absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations can conveniently be presented in dosage unit form and can be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

A pharmaceutical composition of the invention should be formulated to be compatible with its intended route of administration. Solutions or suspensions can include the following components: a sterile diluent such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

A wide variety of formulations and administration methods, including, e.g., intravenous formulations and administration methods can be found in S. K. Niazi, ed., Handbook of Pharmaceutical Formulations, Vols. 1-6 [Vol. 1 Compressed Solid Products, Vol. 2 Uncompressed Drug Products, Vol. 3 Liquid Products, Vol. 4 Semi-Solid Products, Vol. 5 Over the Counter Products, and Vol. 6 Sterile Products], CRC Press, Apr. 27, 2004.

Useful solutions for oral or parenteral administration can be prepared by any of the methods well known in the pharmaceutical art, described, for example, in *Remington's Pharmaceutical Sciences,* 18th ed. (Mack Publishing Company, 1990). Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in effective amounts, e.g., amounts that provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations described herein and/or known in the art. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

In conjunction with the methods of the present invention, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

Generally, an effective amount of dosage of active compound will be in the range of from about 0.1 to about 100 mg/kg of body weight/day, more preferably from about 1.0 to about 50 mg/kg of body weight/day. The amount administered will also likely depend on such variables as the type of surgery or invasive medical procedure, the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

Nonlimiting doses of active compound comprise from about 0.1 to about 1500 mg per dose. Nonlimiting examples of doses, which can be formulated as a unit dose for convenient administration to a patient include: about 25 mg, about 50 mg, about 75 mg, about 100 mg, about 125 mg, about 150 mg, about 175 mg, about 200 mg, about 225 mg, about 250 mg, about 275 mg, about 300 mg, about 325, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050, mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, and about 1500 mg. The foregoing doses are useful for administering the compounds of the present invention according to the methods of the present invention.

As is understood by one of ordinary skill in the art, generally, when dosages are described for a pharmaceutical active, the dosage is given on the basis of the parent or active moiety. Therefore, if a salt, hydrate, or another form of the parent or active moiety is used, a corresponding adjustment in the weight of the compound is made, although the dose is still referred to on the basis of the parent or active moiety delivered. As a nonlimiting example, if the parent or active moiety of interest is a monocarboxylic acid having a molecular weight of 250, and if the monosodium salt of the acid is desired to be delivered to be delivered at the same dosage, then an adjustment is made recognizing that the monosodium salt would have a molecular weight of approximately 272 (i.e. minus 1H or 1.008 atomic mass units and plus 1 Na or 22.99 atomic mass units). Therefore, a 250 mg dosage of the parent or active compound would correspond to about 272 mg of the monosodium salt, which would also deliver 250 mg of the parent or active compound. Said another way, about 272 mg of the monosodium salt would be equivalent to a 250 mg dosage of the parent or active compound.

Formulation Examples

I. Formulation for Intravenous Administration

| Ingredients | Amount |
| --- | --- |
| Antimicrobial Compound of the present invention | 0.1-1500 total mg |
| Dextrose, USP | 50 mg/ml |
| Sodium citrate, USP | 1.60-1.75 mg/ml |
| Citric Acid, USP | 0.80-0.90 mg/ml |
| Water, USP | q.s |

This formulation for intravenous administration is formulated by heating water for injection to about 60° C. Next the sodium citrate, citric acid and dextrose are added and stirred until dissolved. A solution or aqueous slurry of the antimicrobial compound is added to the previous mixture and stirred until dissolved. The mixture is cooled to 25° C. with stirring. The pH is measured and adjusted if necessary. Lastly the mixture is brought to the desired volume, if necessary, with water for injection. The mixture is filtered, filled into the desired container (vial, syringe, infusion container, etc.), over wrapped and terminally moist heat sterilized.
This formulation is useful for intravenous administration, either bolus or infusion, to a patient for treating, preventing, or reducing the risk of infection.

II. Lyophilisate for Reconstitution

Alternatively, the antimicrobial compound can be provided as a lyophilisate which can be reconstituted before intravenous or intramuscular administration.

| Ingredient | mg per injection vial |
| --- | --- |
| Antimicrobial Compound of the present invention | 0.1-1500 |
| Cyclodextin | 1500 |

Reconstitution solution for a volume to be administered of 50 ml (infusion): 5% aqueous glucose solution.
Reconstitution solution for a volume to be administered of 15 ml (bolus): 3.3% aqueous glucose solution.
The foregoing lyophilisate is useful for reconstitution and intravenous administration, either bolus or infusion, to a patient for treating, preventing, or reducing the risk of infection.

III. Lyophilisate for Reconstitution

| Ingredient | mg per injection vial |
| --- | --- |
| Antimicrobial Compound of the present invention | 0.1 -1500 |
| soya lecithin | 2250 |
| Sodium cholate | 1500 |

Reconstitution solution for a volume to be administered of 50 ml (infusion): 4% aqueous glucose solution.
Reconstitution solution for a volume to be administered of 15 ml (bolus): 2% aqueous glucose solution
The foregoing lyophilisate is useful for reconstitution and intravenous administration, either bolus or infusion, to a patient for treating, preventing, or reducing the risk of infection.

IV. Lyophilisate for Reconstitution

| Ingredient | mg per injection vial |
| --- | --- |
| Antimicrobial Compound of the present invetnion | 0.1-1500 |
| soya lecithin | 900 |
| Sodium glycocholate | 540 |

Reconstitution solution for a volume to be administered of 15 ml (bolus): 3.3% aqueous glucose solution.
The foregoing lyophilisate is useful for reconstitution and intravenous administration, either bolus or infusion, to a patient for treating, preventing, or reducing the risk of infection.

V. Tablet for Oral Administration

| Ingredients | Per Tablet | Per 4000 Tablets |
| --- | --- | --- |
| Antimicrobial Compound of the present invention | 0.1-1500 mg | 0.4-6000 g |
| Anhydrous Lactose, NF | 110.45 mg | 441.8 g |

| Ingredients | Per Tablet | Per 4000 Tablets |
|---|---|---|
| Microcrystalline Cellulose NF | 80.0 mg | 320.0 g |
| Magnesium Stearate Impalpable Powder NF | 1.00 mg | 4.0 g |
| Croscarmellose Sodium NF Type A | 2.00 mg | 8.0 g |

The antimicrobial compound (any of the compounds equivalent to the desired delivery strength, e.g., 50 to 1500 mg per tablet) is premixed with ⅓ of the microcrystalline cellulose NF and ½ of the anhydrous lactose NF in a ribbon blender for 5 minutes at 20 RPM. To the premix is added the remaining ⅔ of the microcrystalline cellulose NF and the remaining ½ of the anhydrous lactose NF. This is blended for 10 minutes at 20 RPM. Crosscarmellose sodium is added to the blended powders and mixed for 5 minutes at 20 RPM. Finally the magnesium stearate is added to the mixture by passing through a 90 mesh screen and blended for an additional 5 minutes at 20 RPM. The lubricated mixture is compressed to provide tablets of 500 mg active ingredient.

These tablets are useful for oral administration to a patient for treating, prevention, or reducing the risk of infection.

6. EXAMPLES

Nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

The compounds or tautomers thereof, or pharmaceutically acceptable salts, esters or prodrugs of said compounds or tautomers of the present invention can be prepared using known chemical transformations adapted to the particular situation at hand.

Some of the abbreviations used in the following experimental details of the synthesis of the examples are defined below: h or hr=hour(s); min=minute(s); mol=mole(s); mmol=millimole(s); M=molar; µM=micromolar; g=gram(s); µg=microgram(s); rt=room temperature; L=liter(s); mL=milliliter(s); $Et_2O$=diethyl ether; THF=tetrahydrofuran; DMSO=dimethyl sulfoxide; EtOAc=ethyl acetate; $Et_3N$=triethylamine; i-$Pr_2NEt$ or DIPEA=diisopropylethylamine; $CH_2Cl_2$=methylene chloride; $CHCl_3$=chloroform; $CDCl_3$=deuterated chloroform; $CCl_4$=carbon tetrachloride; MeOH=methanol; $CD_3OD$=deuterated methanol; EtOH=ethanol; DMF=dimethylformamide; BOC=t-butoxycarbonyl; CBZ=benzyloxycarbonyl; TBS=t-butyldimethylsilyl; TBSCl=t-butyldimethylsilyl chloride; TFA=trifluoroacetic acid; DBU=diazabicycloundecene; TBDPSCl=t-butyldiphenylchlorosilane; Hunig's Base=N,N-diisopropylethylamine; DMAP=4-dimethylaminopyridine; CuI=copper (I) iodide; MsCl=methanesulfonyl chloride; $NaN_3$=sodium azide; $Na_2SO_4$=sodium sulfate; $NaHCO_3$=sodium bicarbonate; NaOH=sodium hydroxide; $MgSO_4$=magnesium sulfate; $K_2CO_3$=potassium carbonate; KOH=potassium hydroxide; $NH_4OH$=ammonium hydroxide; $NH_4Cl$=ammonium chloride; $SiO_2$=silica; Pd—C=palladium on carbon; Pd(dppf)$Cl_2$=dichloro[1,1'-bis(diphenylphosphino)ferrocene] palladium (II).

Exemplary compounds synthesized in accordance with the invention are listed in Table 1, Table 2, Table 2a and Table 2aa. A bolded or dashed bond is shown to indicate a particular stereochemistry at a chiral center, whereas a wavy bond indicates that the substituent can be in either orientation or that the compound is a mixture thereof. It should also be known that in the interest of conserving space, the chemical structures of some compounds have been split into two parts with the two points of connection each being indicated by a bond crossed by a wavy line. See, e.g. compound 1, which was drawn in two parts as:

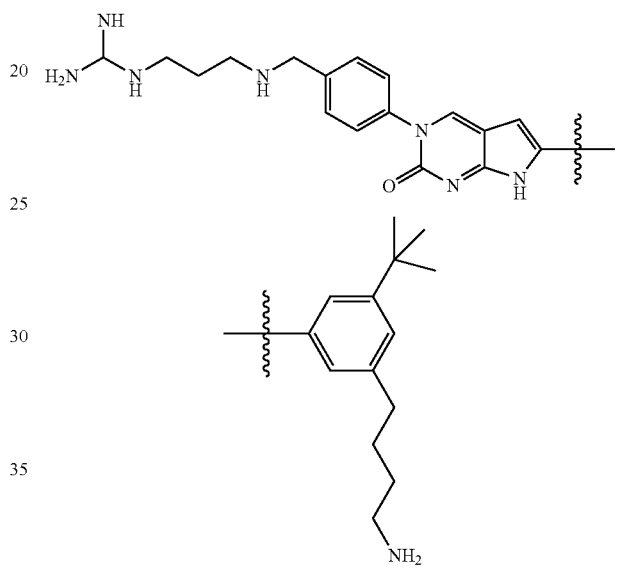

but corresponds to the complete chemical structure:

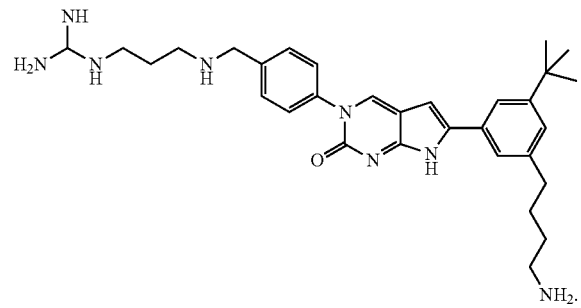 [SMILES: CC(C)(C)c1cc(CCCCN)cc(-c2cc3cn(-c4ccc(CNCCCNC(N)N)cc4)c(=O)nc3[nH]2)c1]

The compounds of the present invention can be prepared, formulated, and delivered as salts, esters, and prodrugs. For convenience, the compounds are generally shown without indicating a particular salt, ester, or prodrug form.

Compounds of the present invention are shown in Table 1, Table 2, Table 2a, and Table 2aa. LCMS (liquid chromatography mass spectral) data are provided, where available. When data is not available this is indicated by "NA". The LCMS data are provided using the convention for m/z in the format, [M+H]+, except where otherwise indicated.

TABLE 1
| Comp. No. | Structure | LCMS |
|---|---|---|
| 1 | 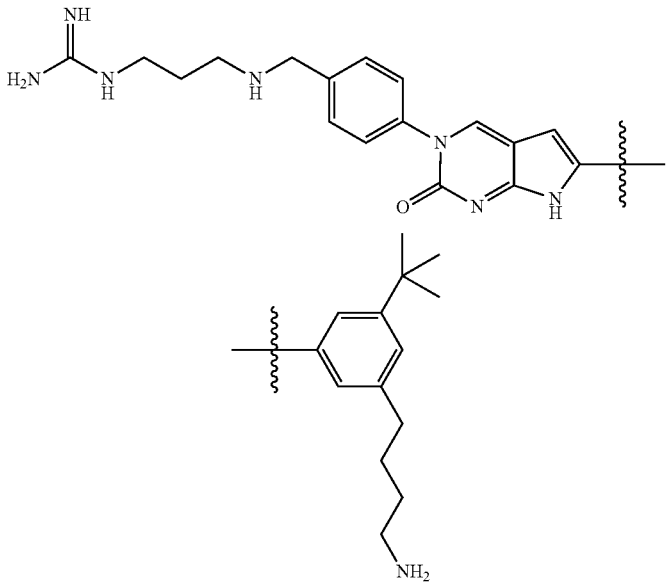 | 543.1 |
| 2 | 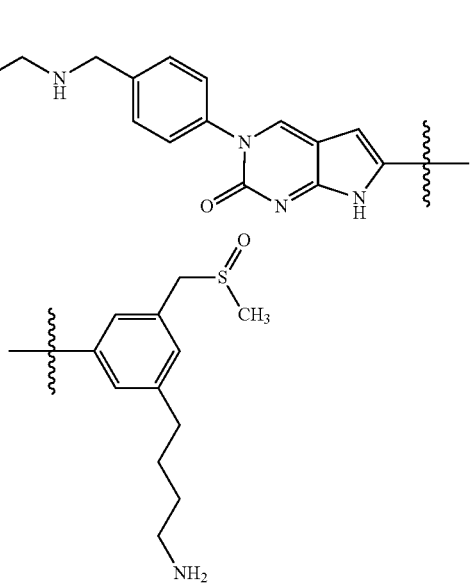 | 563.1 |

TABLE 1-continued
| Comp. No. | Structure | LCMS |
|---|---|---|
| 3 | 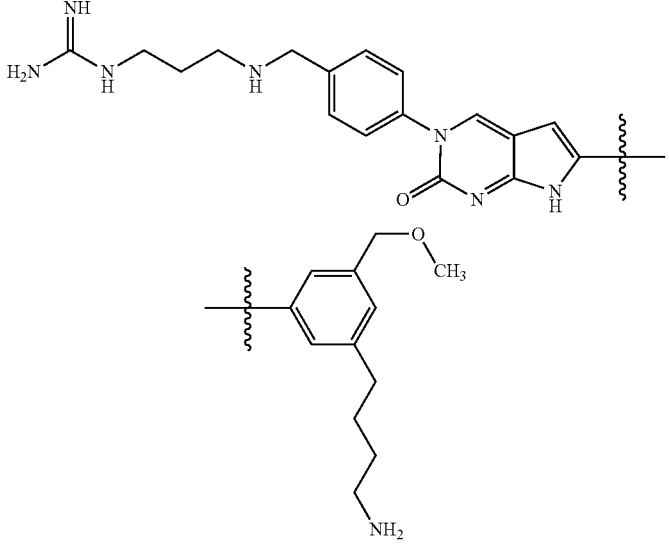 | 531.1 |
| 4 | 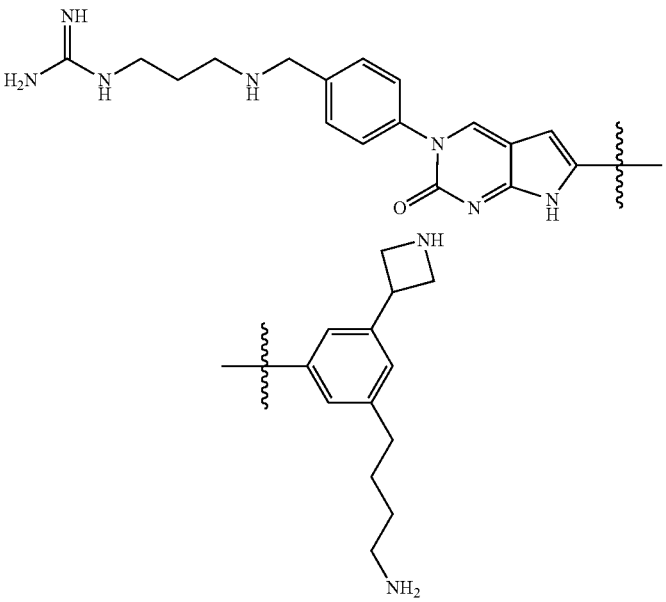 | 542.1 |

TABLE 1-continued
| Comp. No. | Structure | LCMS |
|---|---|---|
| 5 | 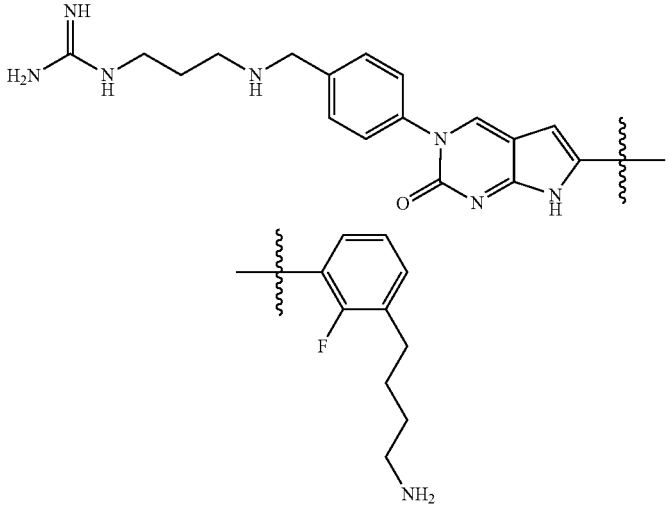 | 505.2 |
| 6 | 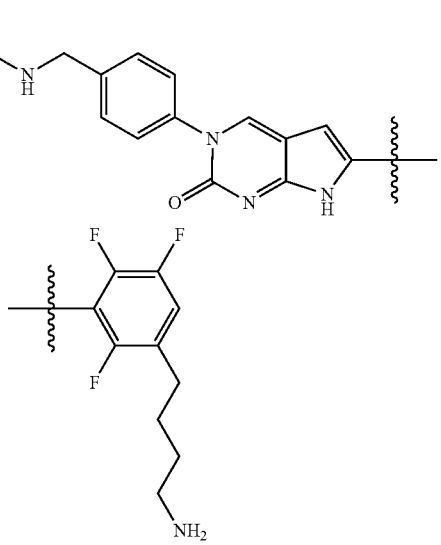 | 541.1 |
| 7 | 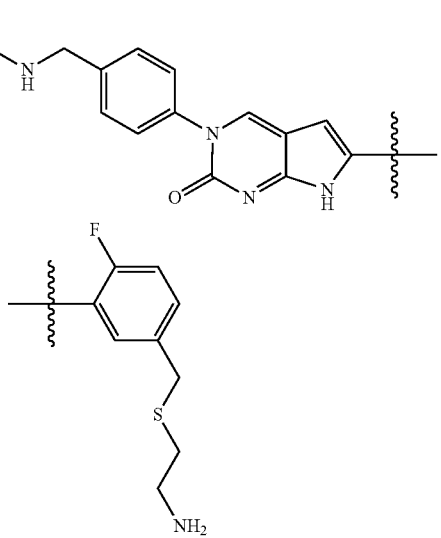 | 523.1 |

TABLE 1-continued
| Comp. No. | Structure | LCMS |
|---|---|---|
| 8 | 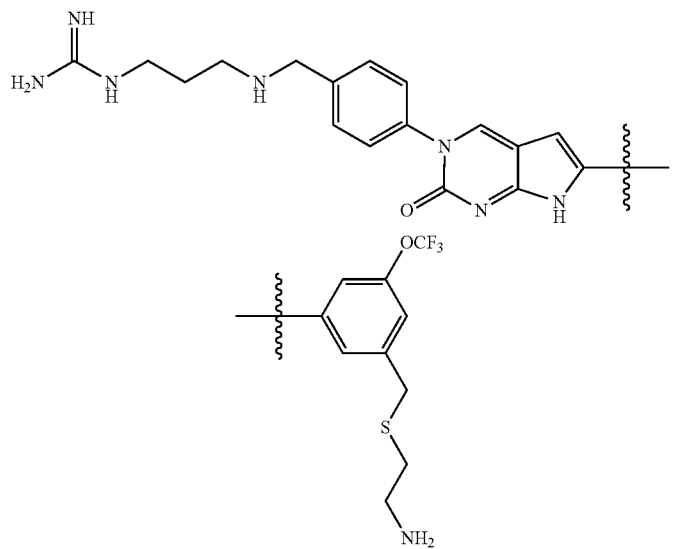 | 589.1 |
| 9 | 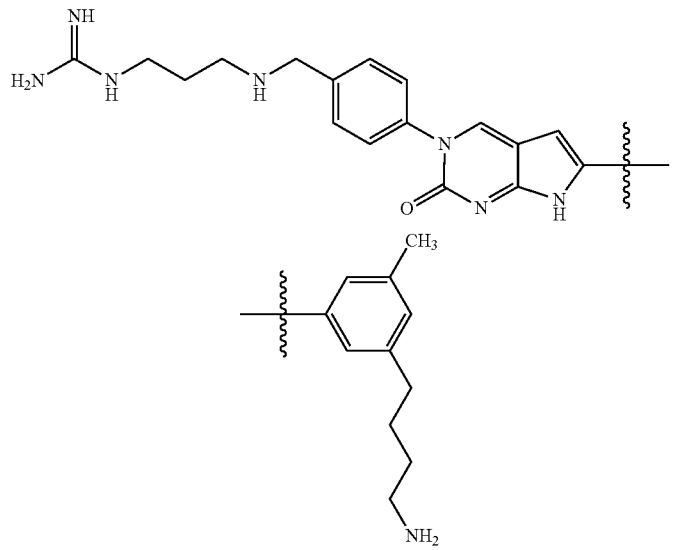 | 501.1 |

TABLE 1-continued
| Comp. No. | Structure | LCMS |
|---|---|---|
| 10 | 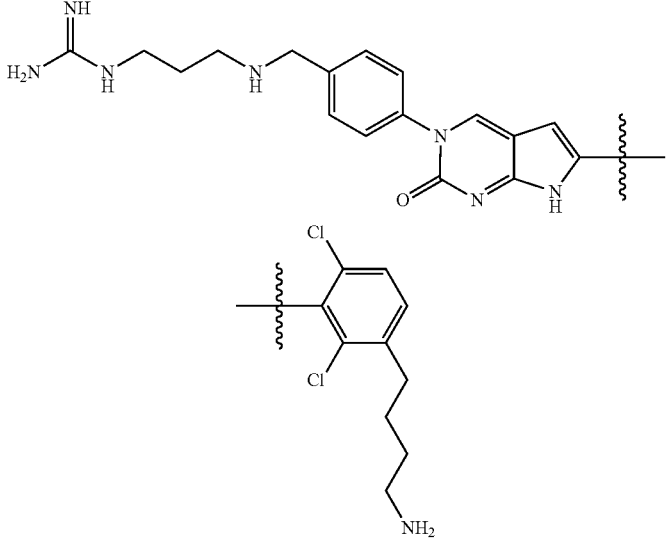 [SMILES: *c1cc2cn(-c3ccc(CNCCCNC(=N)N)cc3)c(=O)nc2[nH]1 ; *c1c(Cl)ccc(CCCCN)c1Cl] | 555.1 |
| 11 | 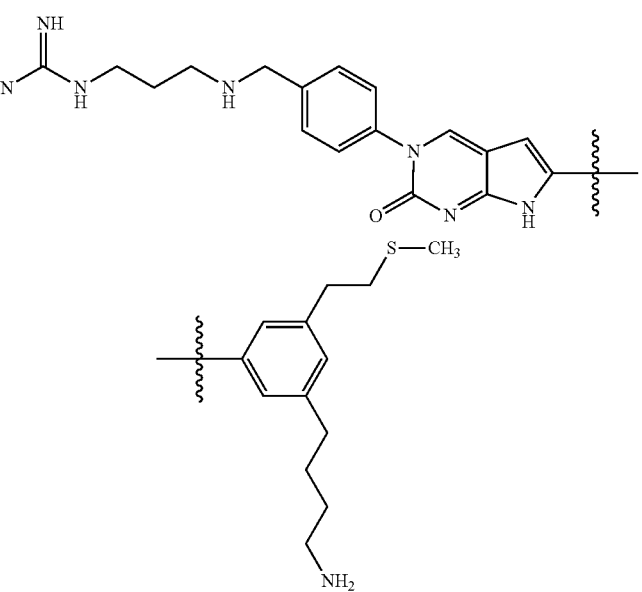 | 561.1 |

TABLE 1-continued
| Comp. No. | Structure | LCMS |
|---|---|---|
| 12 | 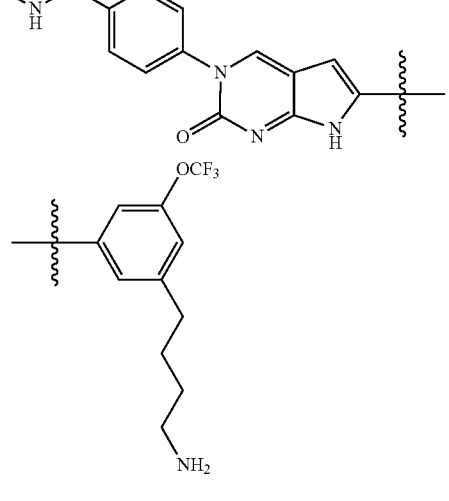 | 589.1 |
| 13 | 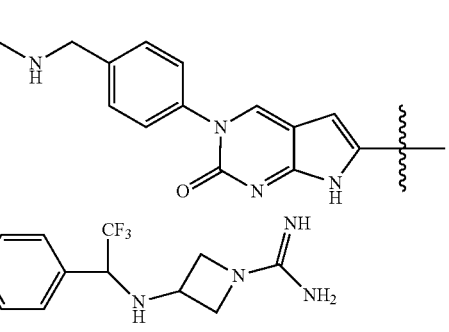 | 628.2 |
| 14 | 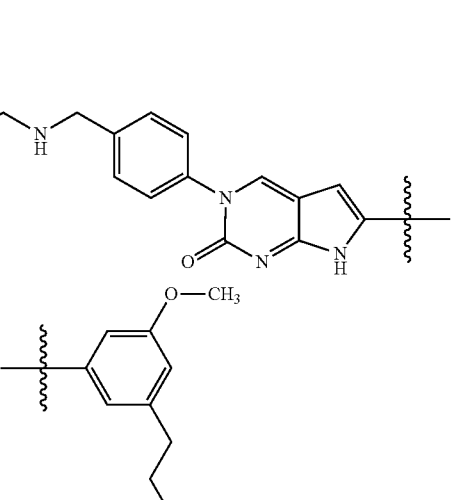 | 517.1 |

TABLE 1-continued
| Comp. No. | Structure | LCMS |
|---|---|---|
| 15 | 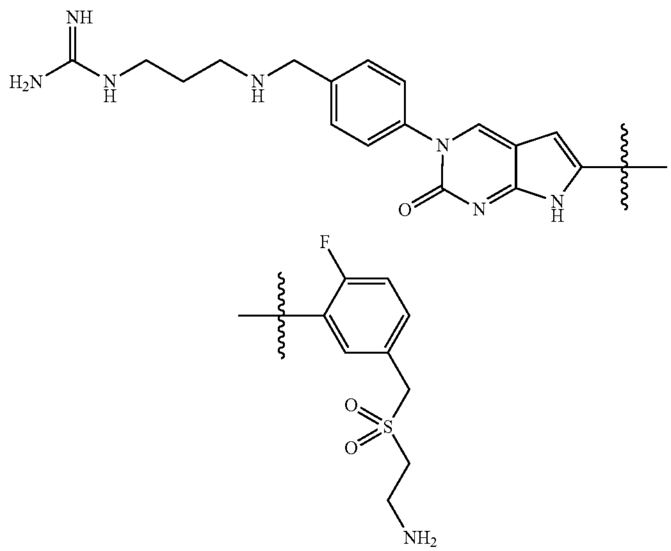 [SMILES: *c1cc2cn(-c3ccc(CNCCCNC(=N)N)cc3)c(=O)nc2[nH]1 ; *c1cc(CS(=O)(=O)CCN)ccc1F] | 555.1 |
| 16 | 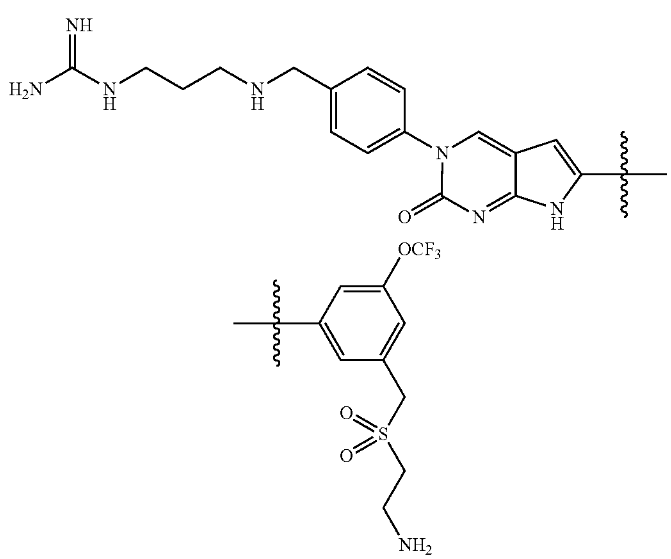 | 621.1 |

TABLE 1-continued
| Comp. No. | Structure | LCMS |
|---|---|---|
| 17 | 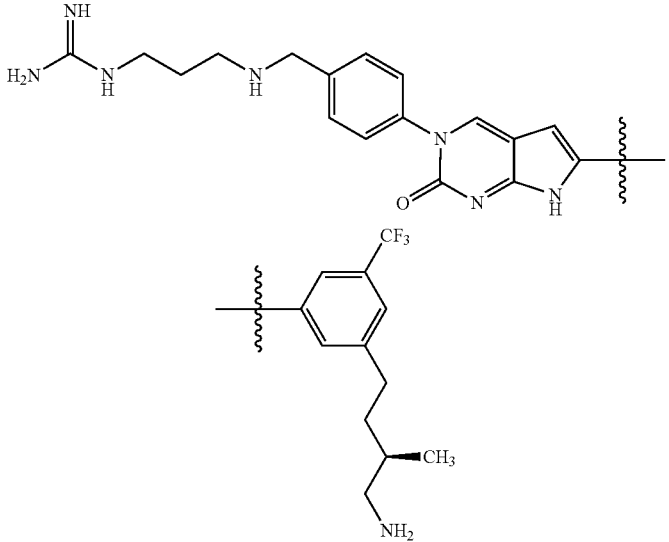 | 569.1 |
| 18 | 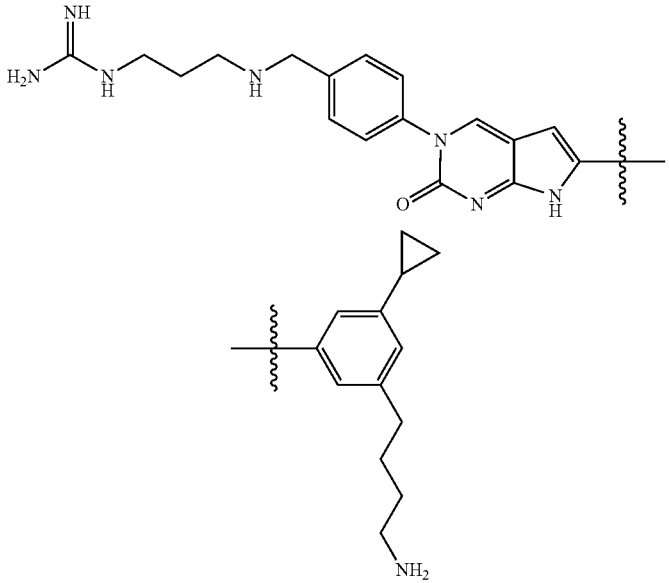 | 527.2 |

TABLE 1-continued
| Comp. No. | Structure | LCMS |
|---|---|---|
| 19 | 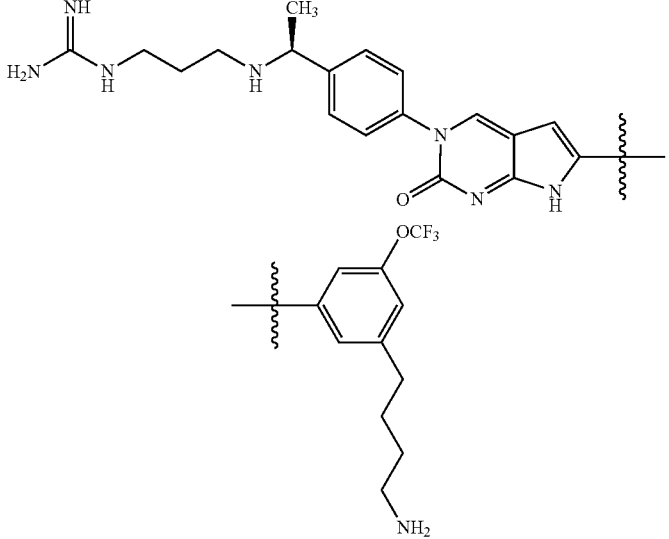 | 585.1 |
| 20 | 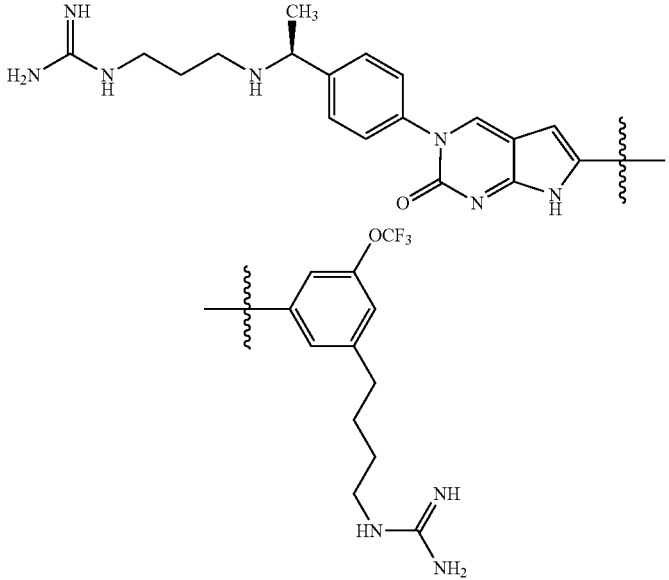 | 627.2 |
| 21 | 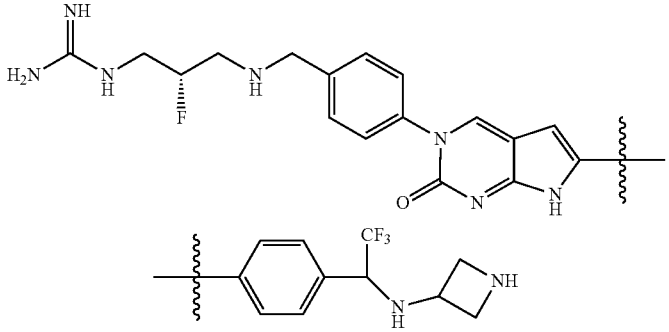 | 586.1 |

TABLE 1-continued
| Comp. No. | Structure | LCMS |
|---|---|---|
| 22 | 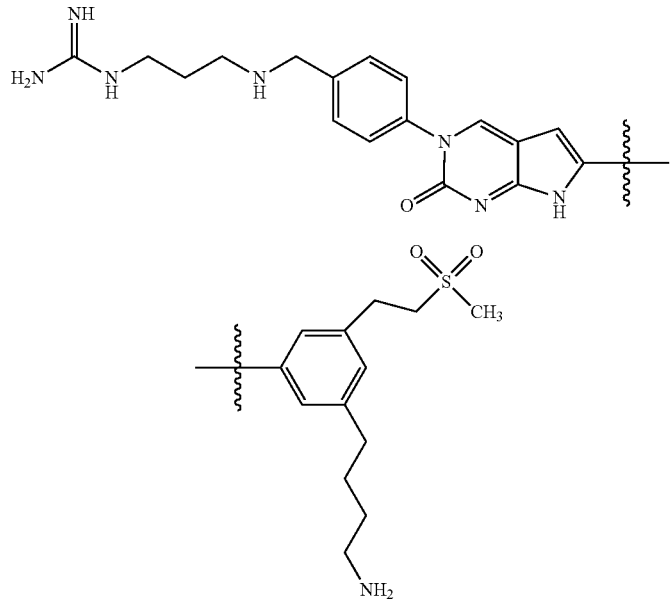 | 593.1 |
| 23 | 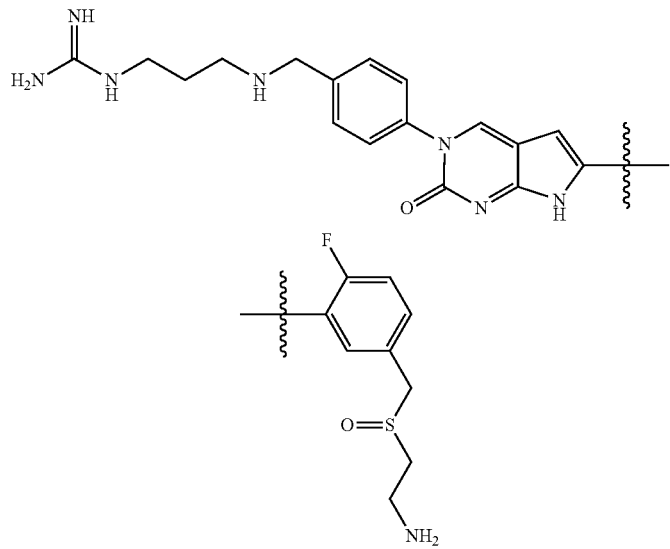 [SMILES: *c1cc2cn(-c3ccc(CNCCCNC(=N)N)cc3)c(=O)nc2[nH]1 ; *c1cc(CS(=O)CCN)ccc1F] | 539.1 |

TABLE 1-continued
| Comp. No. | Structure | LCMS |
|---|---|---|
| 24 | 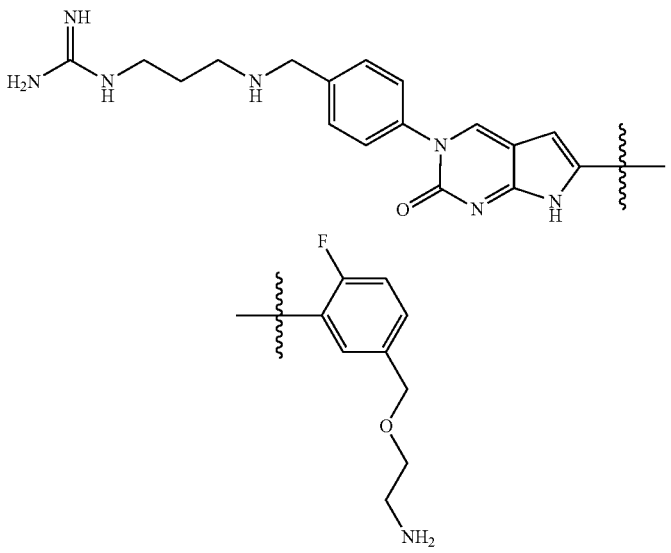 [SMILES: *c1cc2cn(-c3ccc(CNCCCNC(=N)N)cc3)c(=O)nc2[nH]1 ; *c1cc(COCCN)ccc1F] | 507.1 |
| 25 | 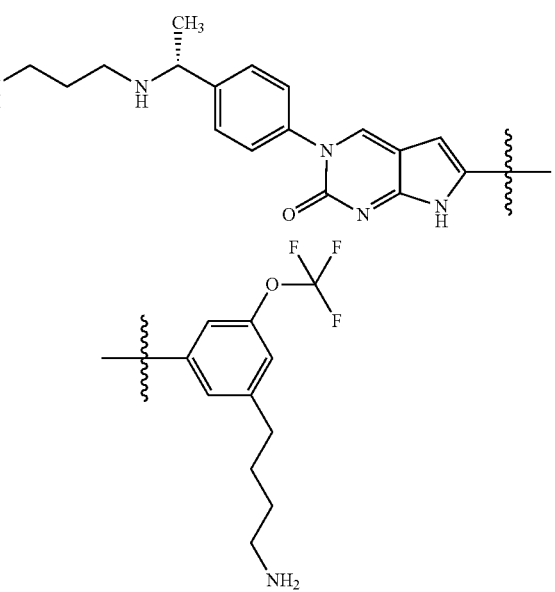 | 585.1 |

TABLE 1-continued

| Comp. No. | Structure | LCMS |
|---|---|---|
| 26 | 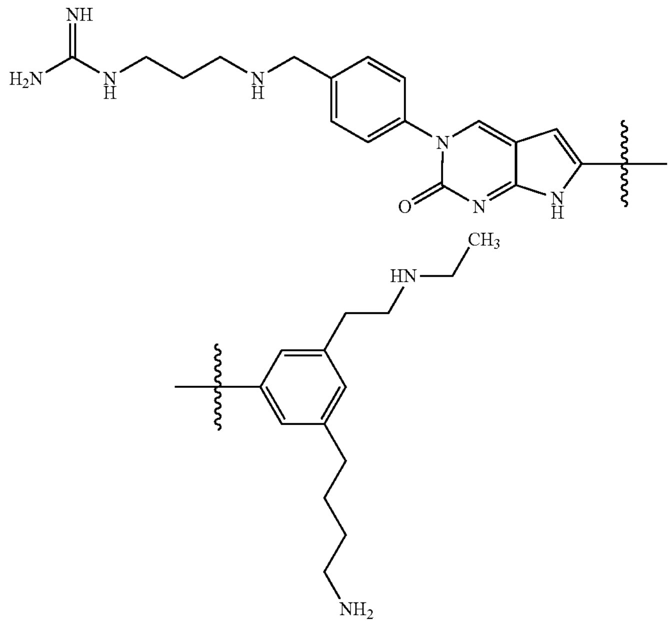 | 558.3 |
| 27 | 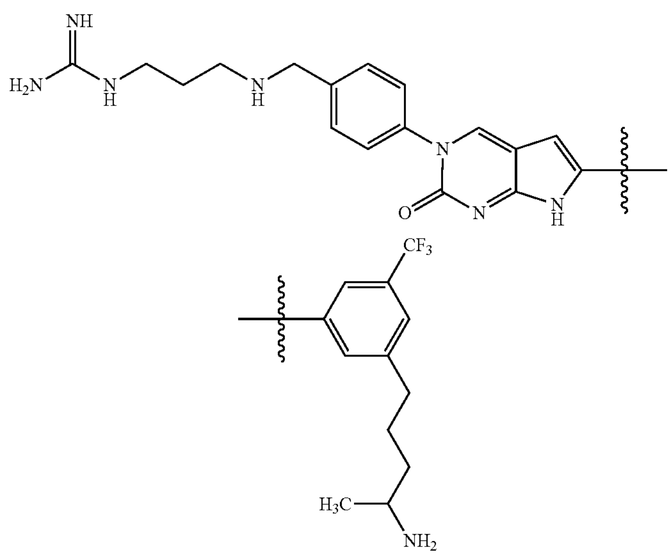 | 569.2 |
| 28 | 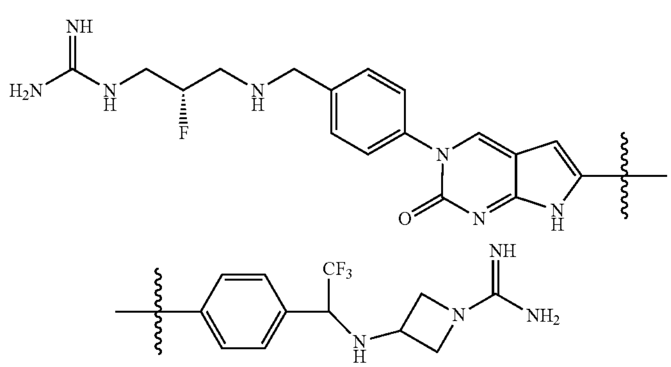 | 628.1 |

TABLE 1-continued

| Comp. No. | Structure | LCMS |
|---|---|---|
| 29 | 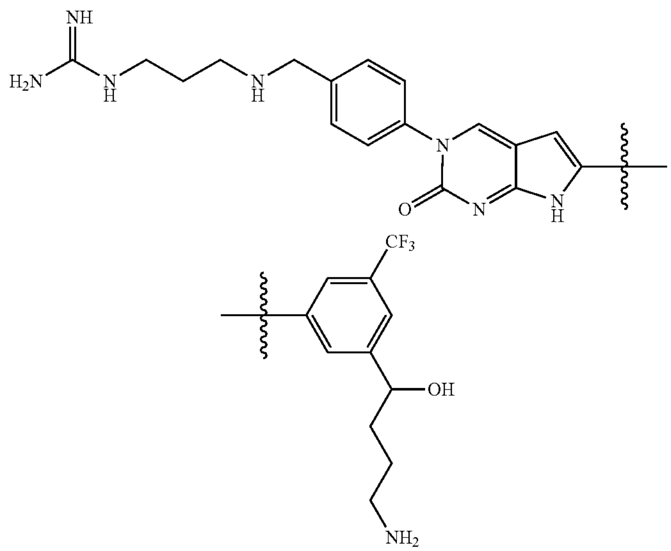 | 571.2 |
| 30 | 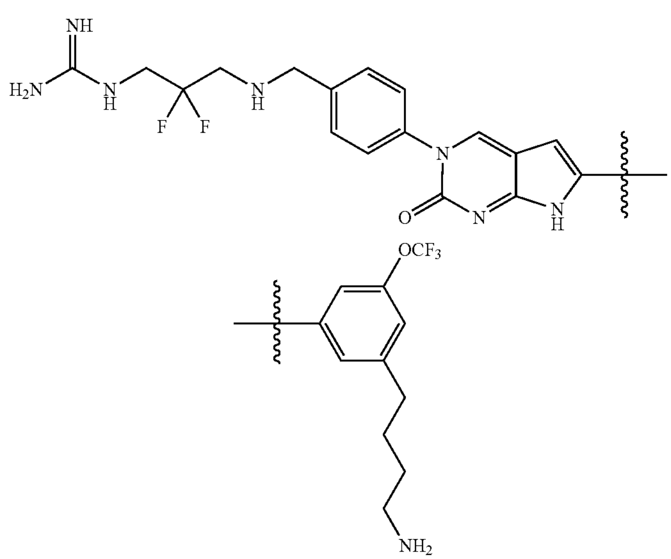 | 607.1 |

TABLE 1-continued
| Comp. No. | Structure | LCMS |
|---|---|---|
| 31 | 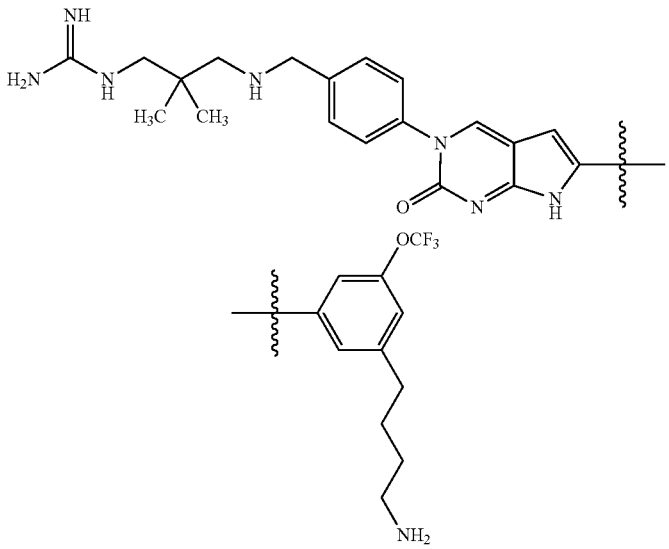 | 599.1 |
| 32 | 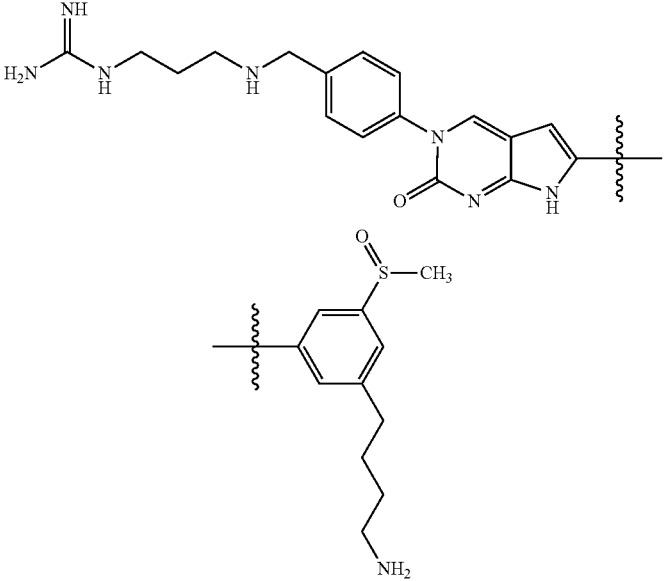 | 549.1 |

TABLE 1-continued
| Comp. No. | Structure | LCMS |
|---|---|---|
| 33 | 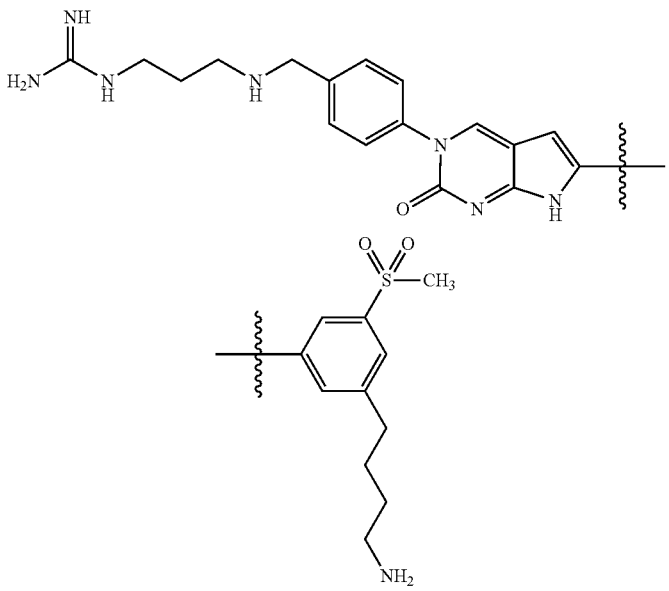 | 565.1 |
| 34 | 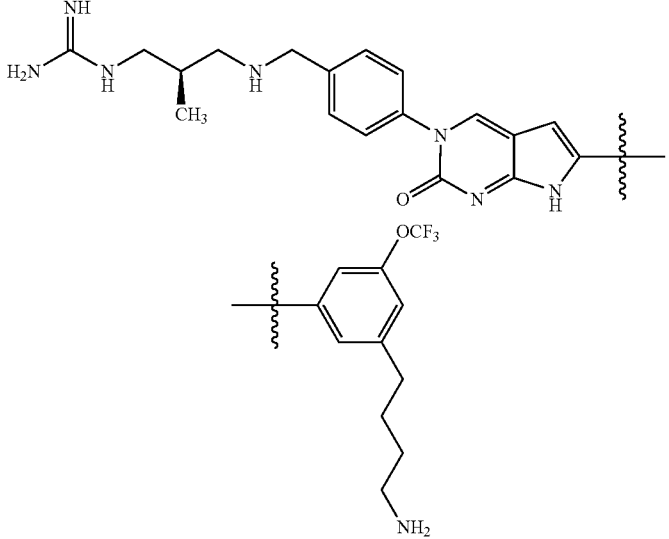 | 585.1 |

TABLE 1-continued

| Comp. No. | Structure | LCMS |
|---|---|---|
| 35 | 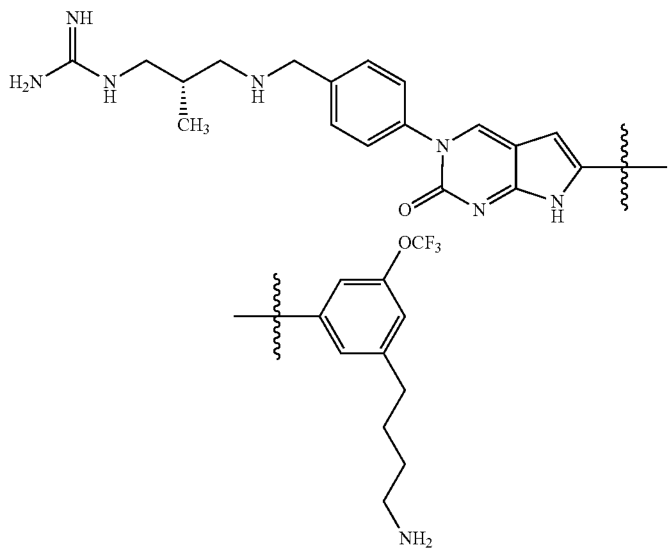 | 585.1 |
| 36 | 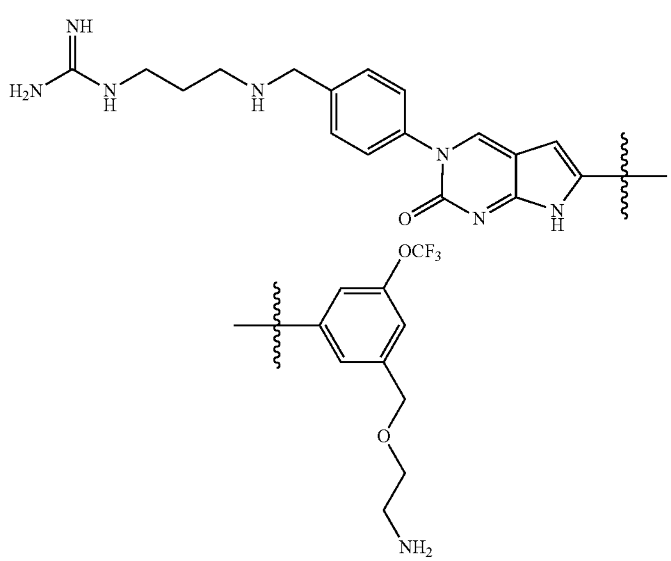 | 573.0 |

TABLE 1-continued
| Comp. No. | Structure | LCMS |
|---|---|---|
| 37 | 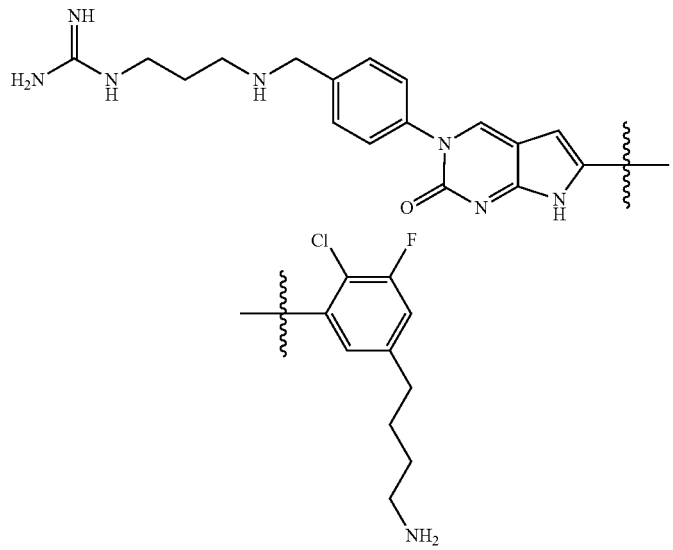 | 539.0 |
| 38 | 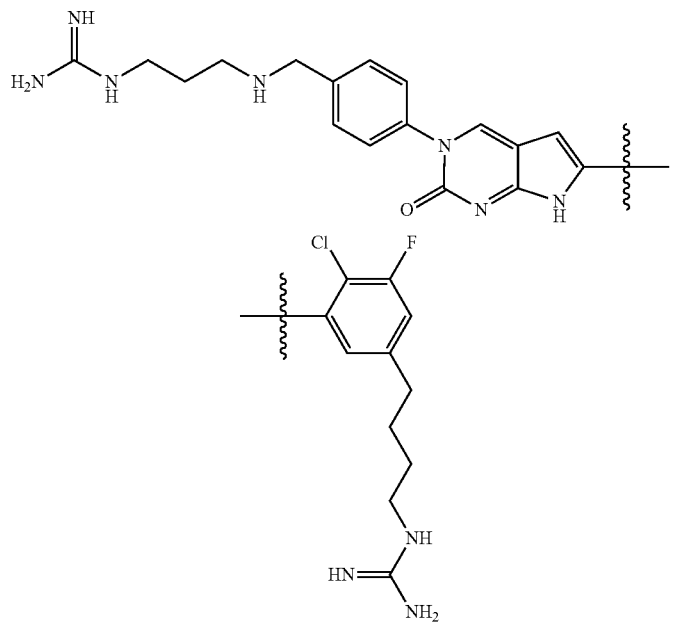 | 581.1 |

TABLE 1-continued
| Comp. No. | Structure | LCMS |
|---|---|---|
| 39 | 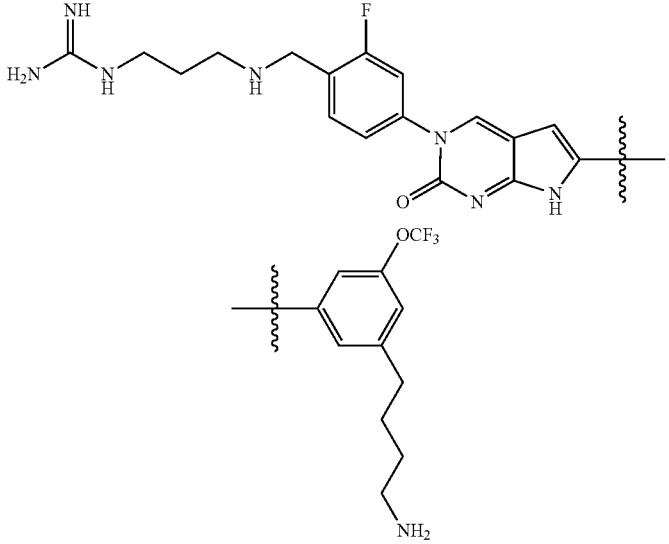 | 589.0 |
| 40 | 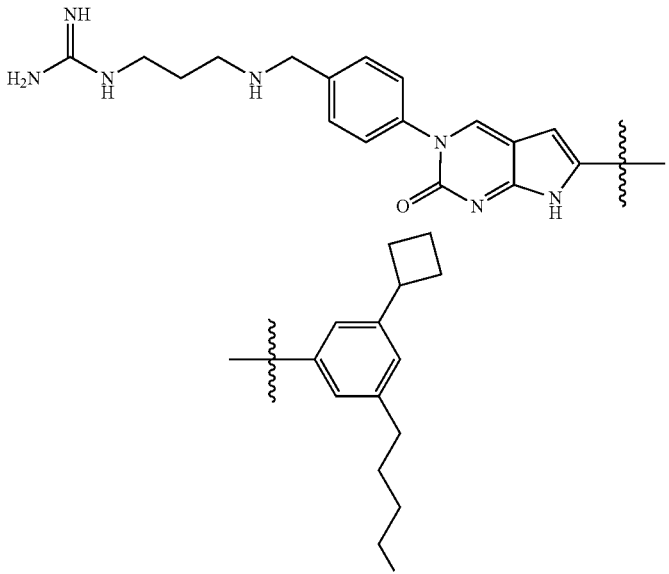 | 541.1 |

TABLE 1-continued

| Comp. No. | Structure | LCMS |
|---|---|---|
| 41 | (structure) | 544.4 |
| 42 | (structure) | 587.1 |
| 43 | (structure) | 666.9 |

TABLE 1-continued
| Comp. No. | Structure | LCMS |
|---|---|---|
| 44 | 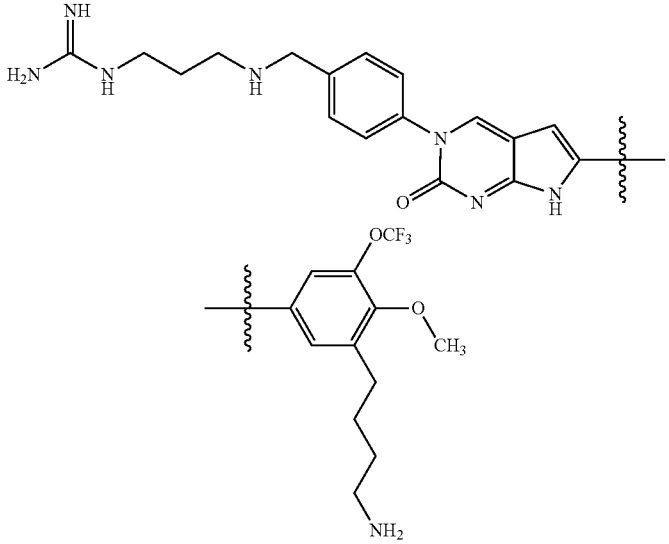 | 601.1 |
| 45 | 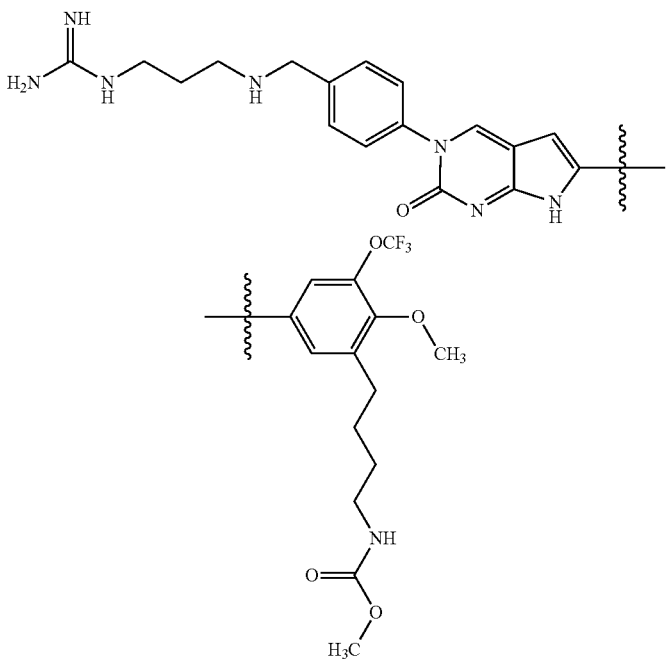 | 659.0 |

TABLE 1-continued
| Comp. No. | Structure | LCMS |
|---|---|---|
| 46 | 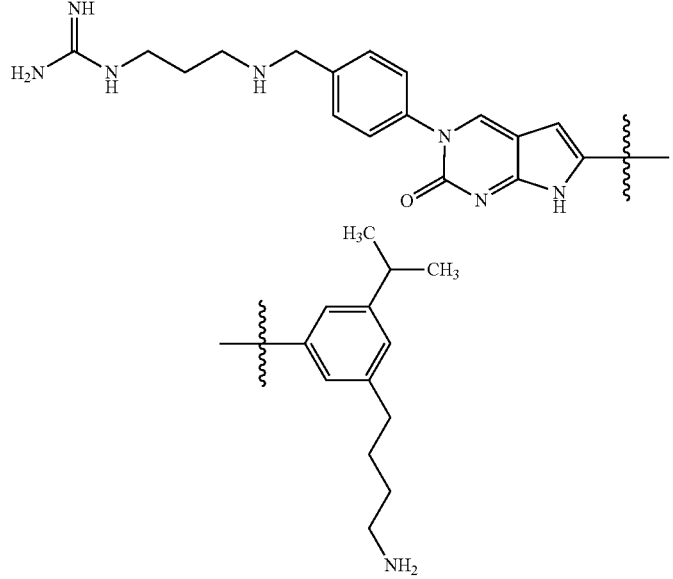 | 529.1 |
| 47 | 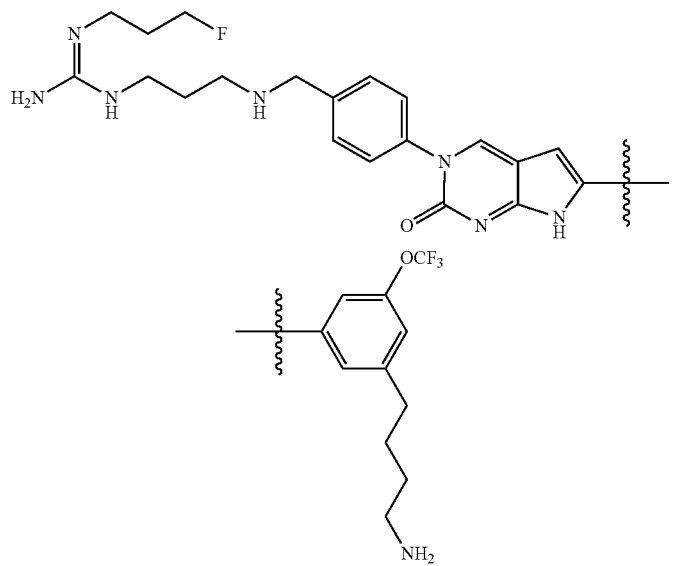 | 631.1 |

TABLE 1-continued
| Comp. No. | Structure | LCMS |
|---|---|---|
| 48 | 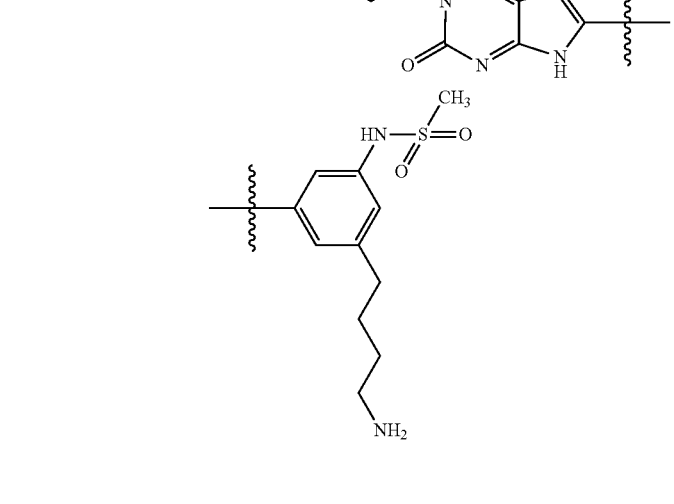 | 580.0 |
| 49 | 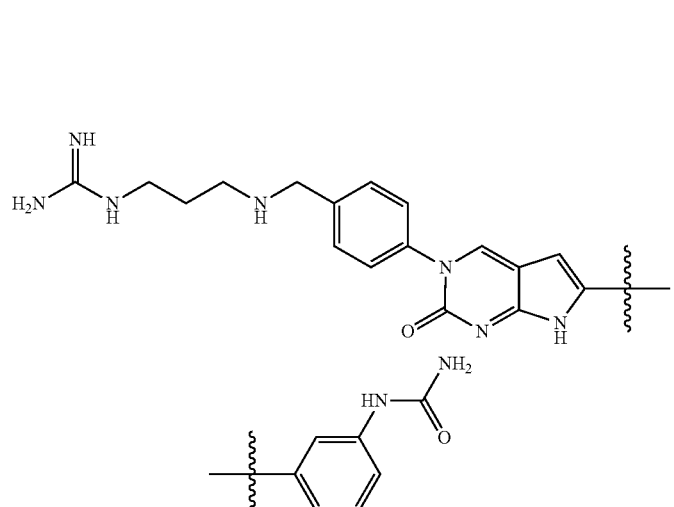 | 545.0 |

TABLE 1-continued
| Comp. No. | Structure | LCMS |
|---|---|---|
| 50 | 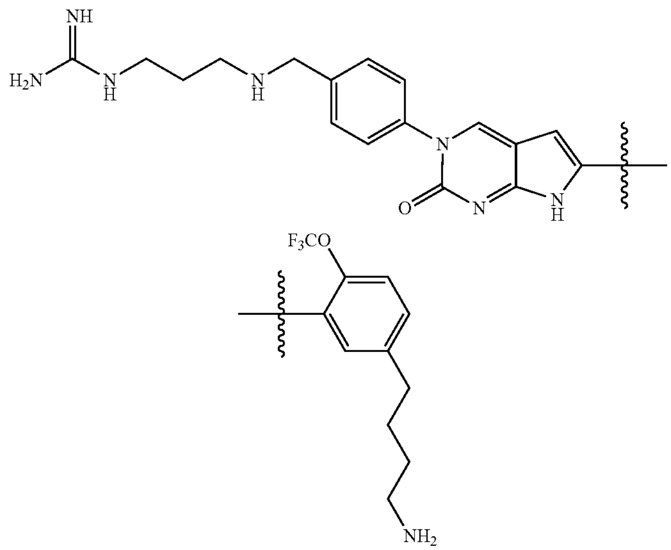 [SMILES: *c1cc2cn(-c3ccc(CNCCCNC(=N)N)cc3)c(=O)nc2[nH]1 ; *c1cc(CCCCN)ccc1OC(F)(F)F] | 571.1 |
| 51 | 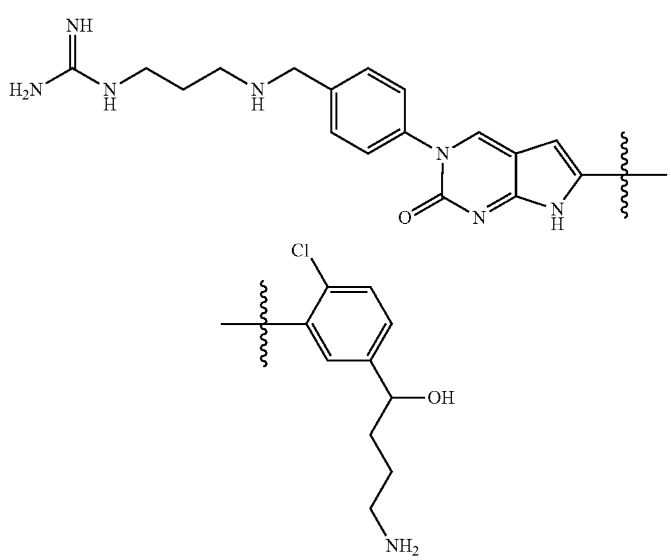 [SMILES: *c1cc2cn(-c3ccc(CNCCCNC(=N)N)cc3)c(=O)nc2[nH]1 ; *c1cc(C(O)CCCN)ccc1Cl] | 537.0 |

TABLE 1-continued

| Comp. No. | Structure | LCMS |
|---|---|---|
| 52 | 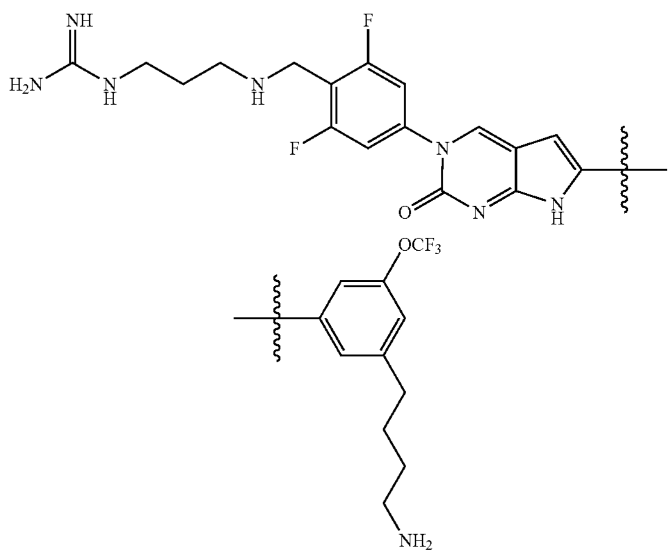 | 607.1 |
| 53 | 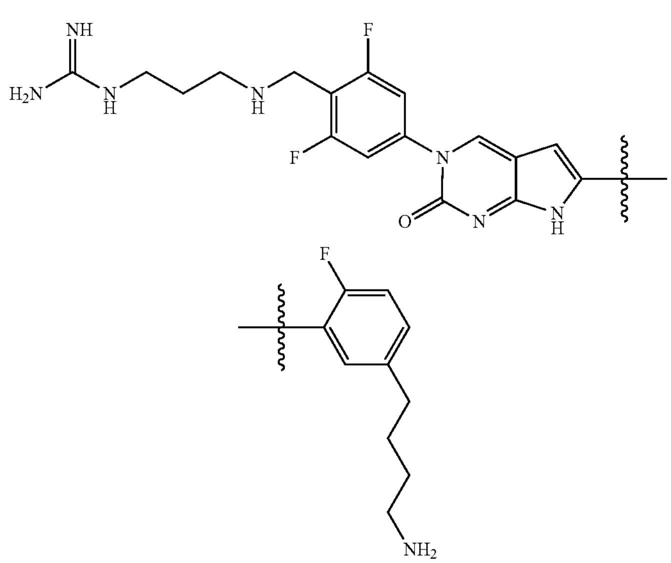 [SMILES: *c1cc2cn(-c3cc(F)c(CNCCCNC(=N)N)c(F)c3)c(=O)nc2[nH]1 ; *c1cc(CCCCN)ccc1F] | 541.1 |

TABLE 1-continued
| Comp. No. | Structure | LCMS |
|---|---|---|
| 54 | 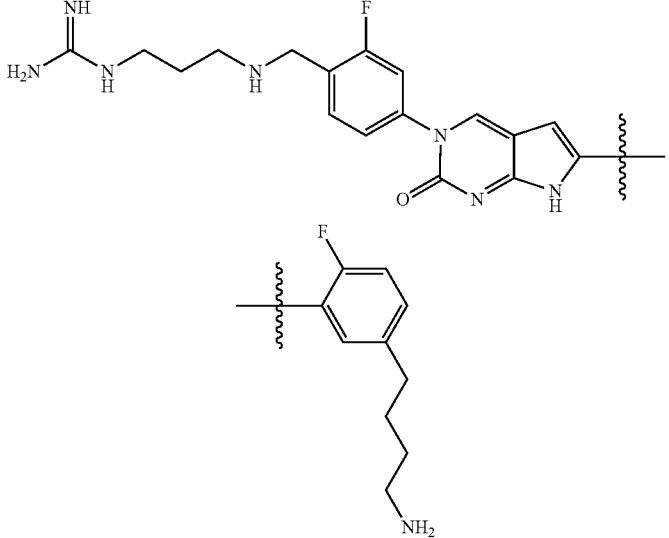 [SMILES: *c1cc2cn(-c3ccc(CNCCCNC(=N)N)c(F)c3)c(=O)nc2[nH]1 ; *c1cc(CCCCN)ccc1F] | 523.1 |
| 55 | 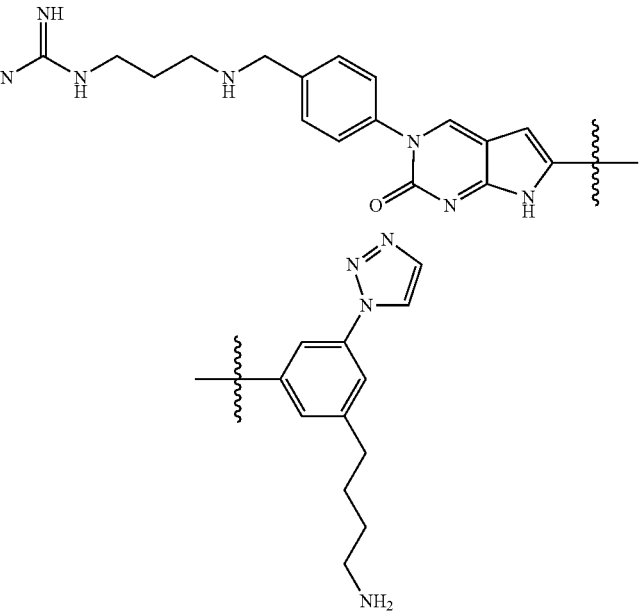 | 554.1 |

TABLE 1-continued
| Comp. No. | Structure | LCMS |
|---|---|---|
| 56 | 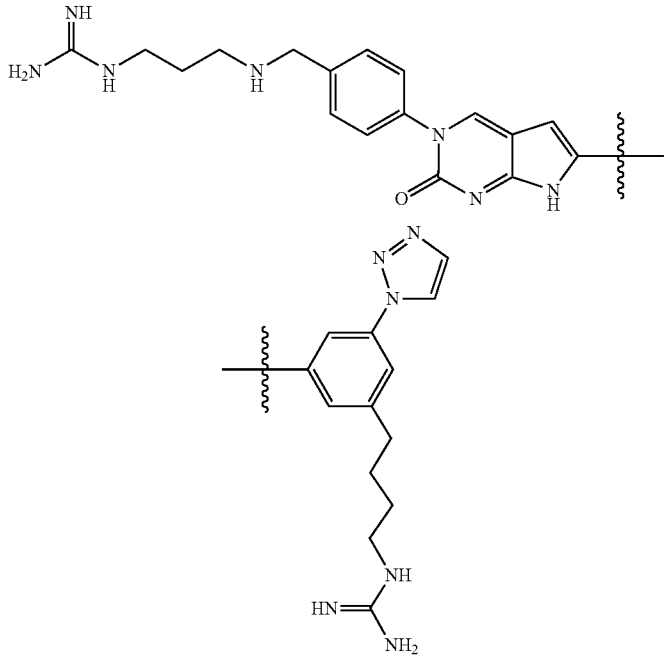 | 596.1 |
| 57 | 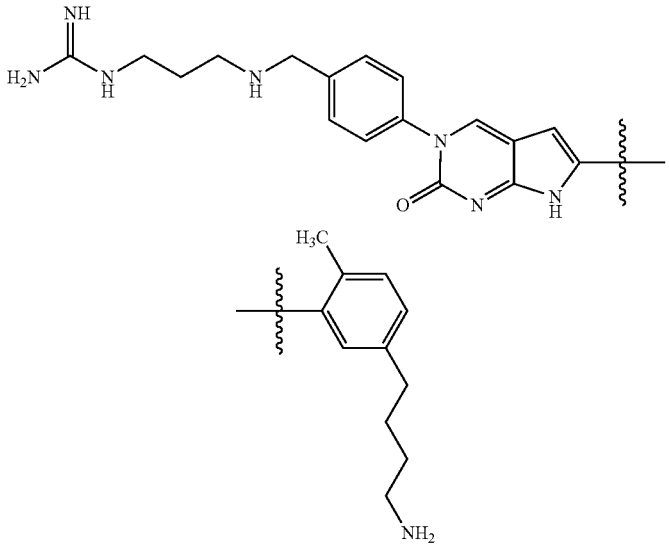 [SMILES: *c1cc2cn(-c3ccc(CNCCCNC(=N)N)cc3)c(=O)nc2[nH]1 ; *c1cc(CCCCN)ccc1C] | |

TABLE 1-continued
| Comp. No. | Structure | LCMS |
|---|---|---|
| 58 | 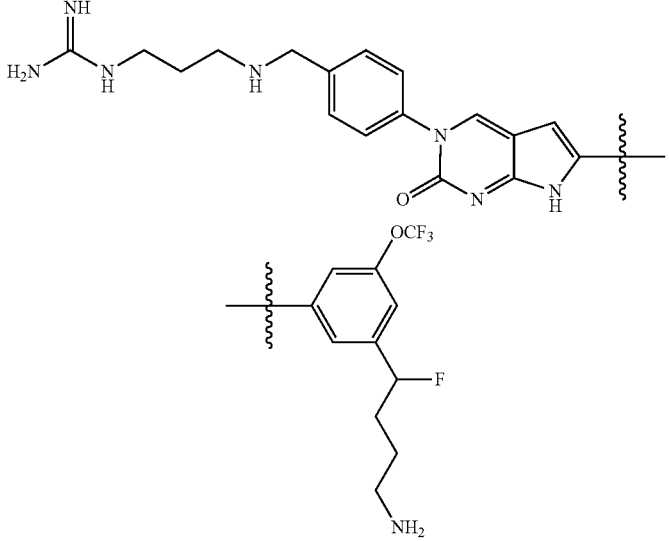 | 589.0 |
| 59 | 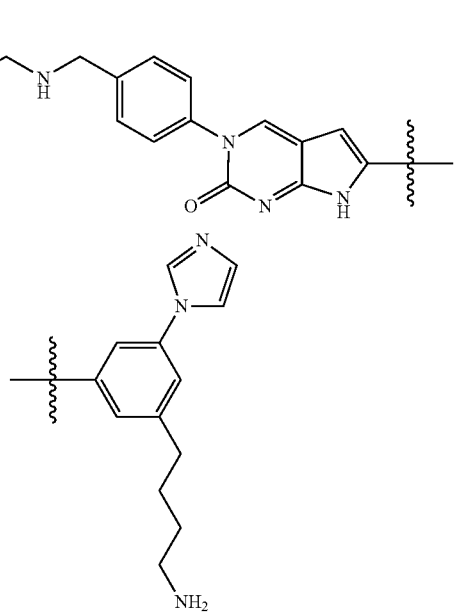 | 553.0 |

TABLE 1-continued
| Comp. No. | Structure | LCMS |
|---|---|---|
| 60 | 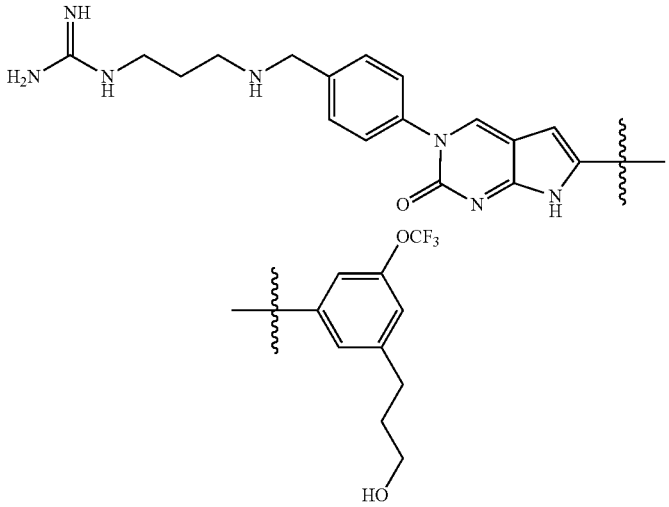 | 558.1 |
| 61 | 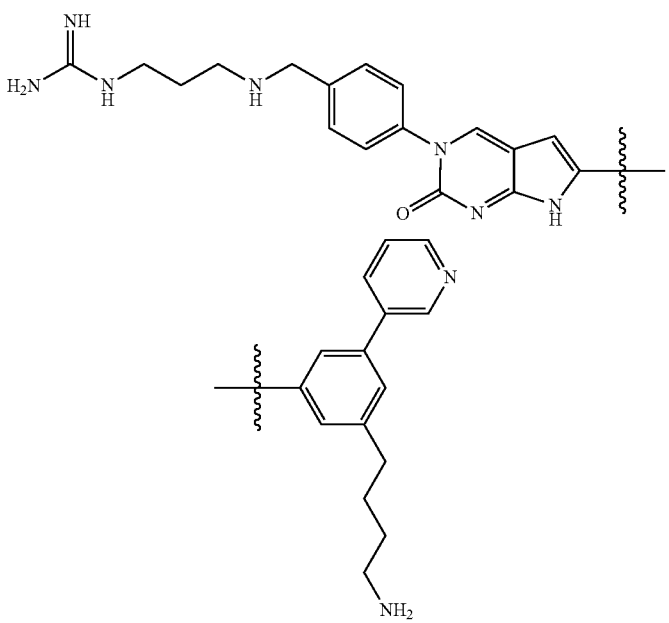 | 564.3 |

TABLE 1-continued
| Comp. No. | Structure | LCMS |
|---|---|---|
| 62 | 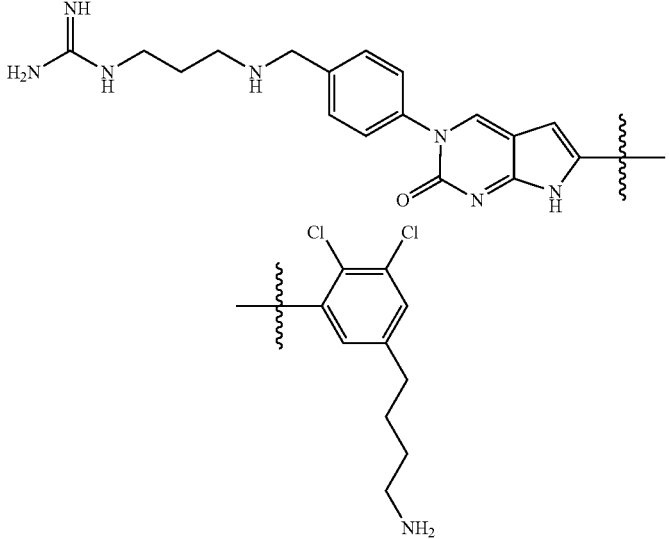 | 555.1 |
| 63 | 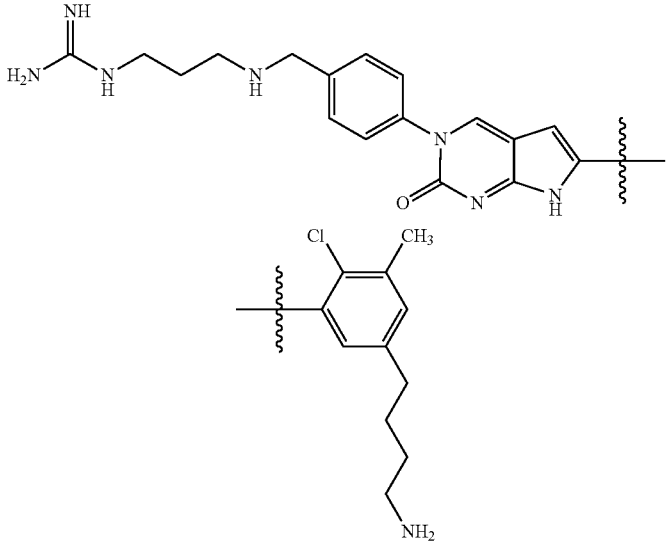 | 535.0 |

TABLE 1-continued
| Comp. No. | Structure | LCMS |
|---|---|---|
| 64 | 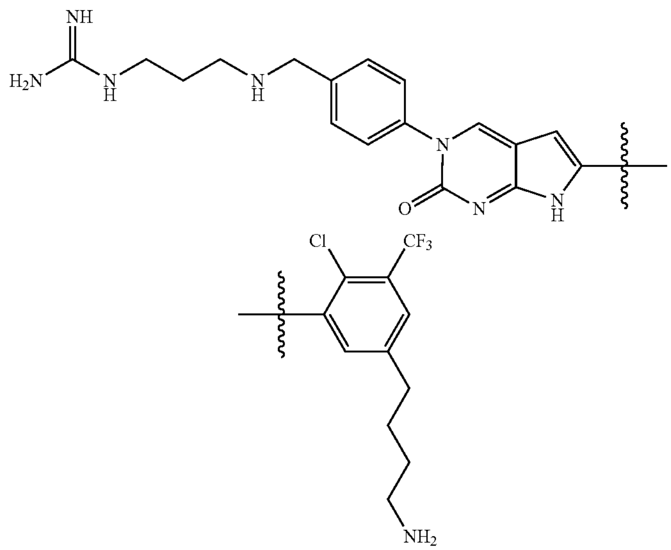 | 589.0 |
| 65 | 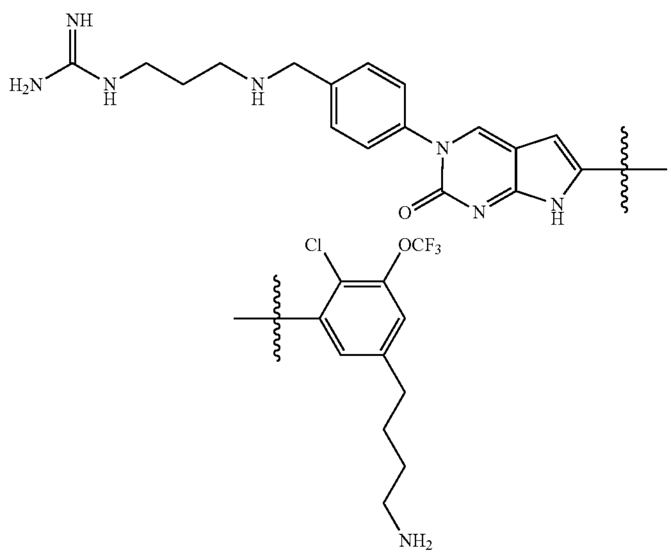 | 605.0 |
| 66 | 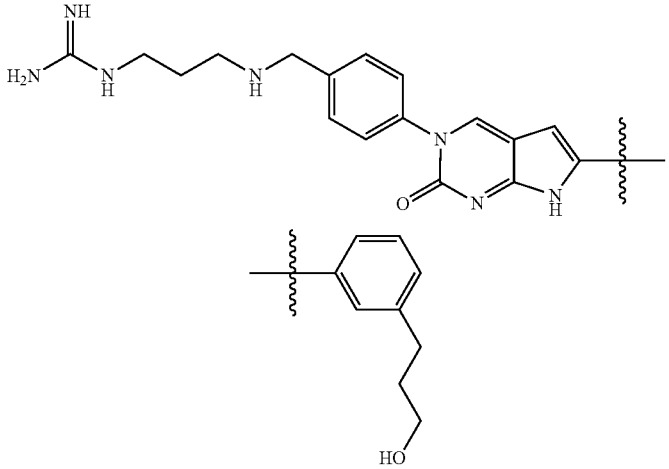 | 474.1 |

TABLE 1-continued
| Comp. No. | Structure | LCMS |
|---|---|---|
| 67 | 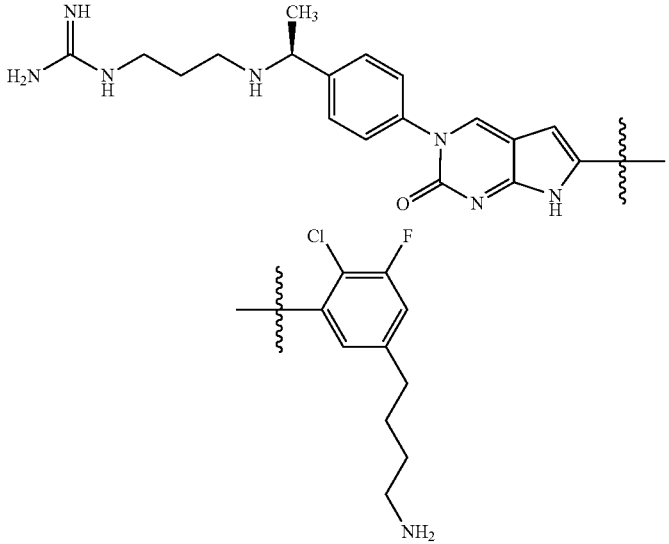 | 553.1 |
| 68 | 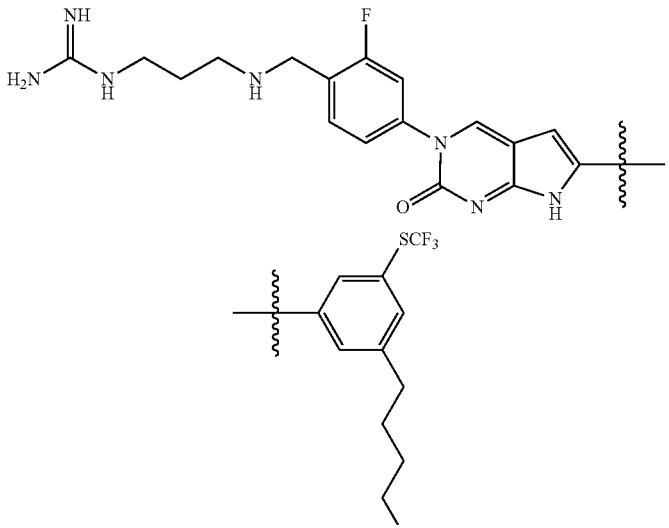 | 605.3 |

TABLE 1-continued
| Comp. No. | Structure | LCMS |
|---|---|---|
| 69 | 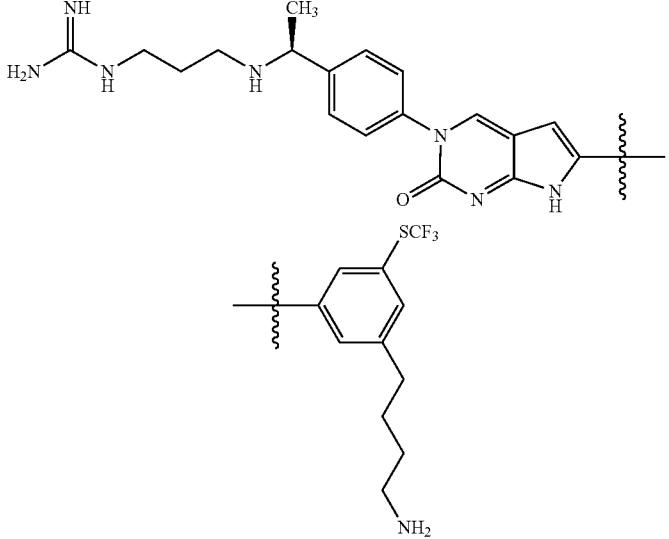 | 601.0 |
| 70 | 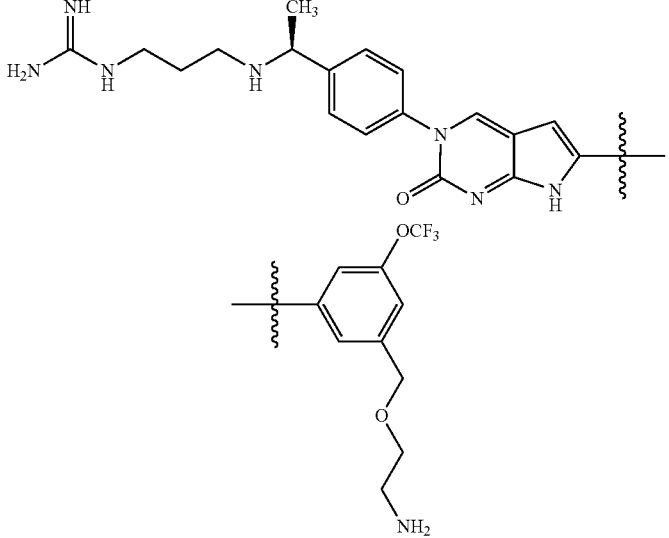 | 587.1 |

TABLE 1-continued
| Comp. No. | Structure | LCMS |
|---|---|---|
| 71 | 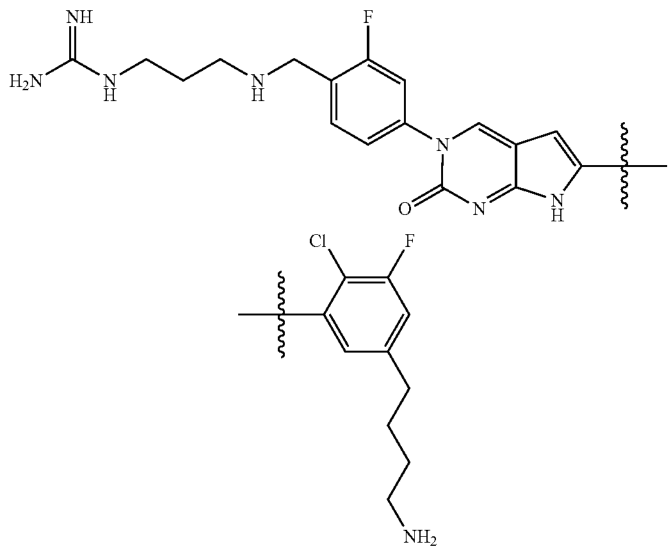 | 557.0 |
| 72 | 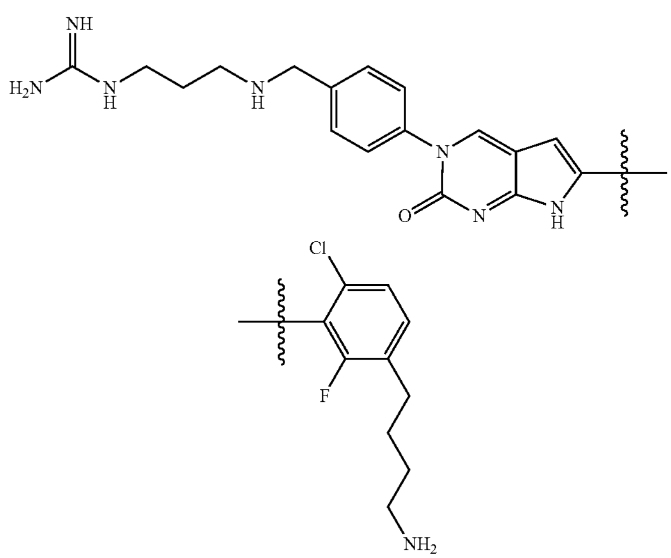 [SMILES: *c1cc2cn(-c3ccc(CNCCCNC(=N)N)cc3)c(=O)nc2[nH]1 ; *c1c(Cl)ccc(CCCCN)c1F] | |

TABLE 1-continued
| Comp. No. | Structure | LCMS |
|---|---|---|
| 73 | 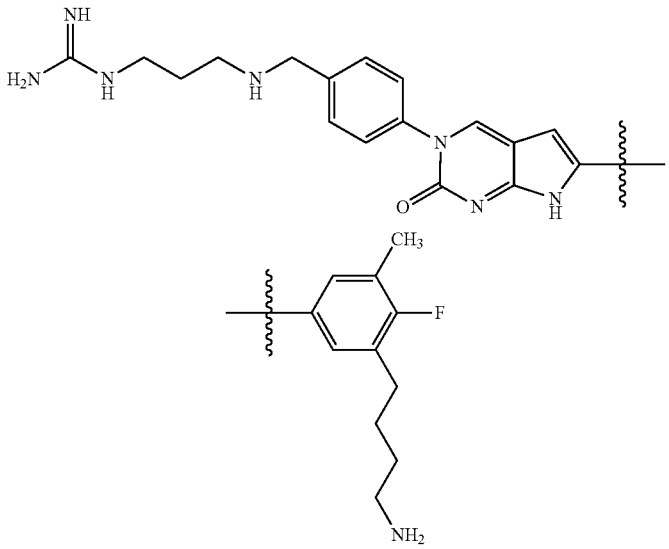 | 519.1 |
| 74 | 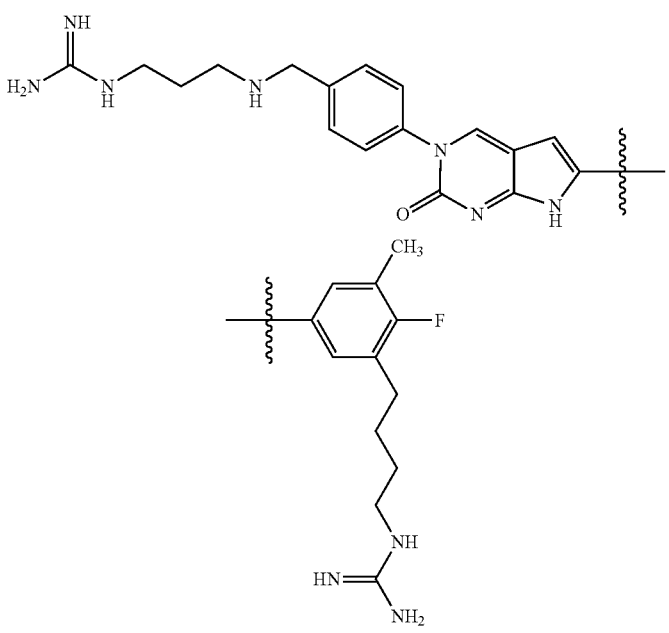 | 561.1 |

TABLE 1-continued
| Comp. No. | Structure | LCMS |
|---|---|---|
| 75 | 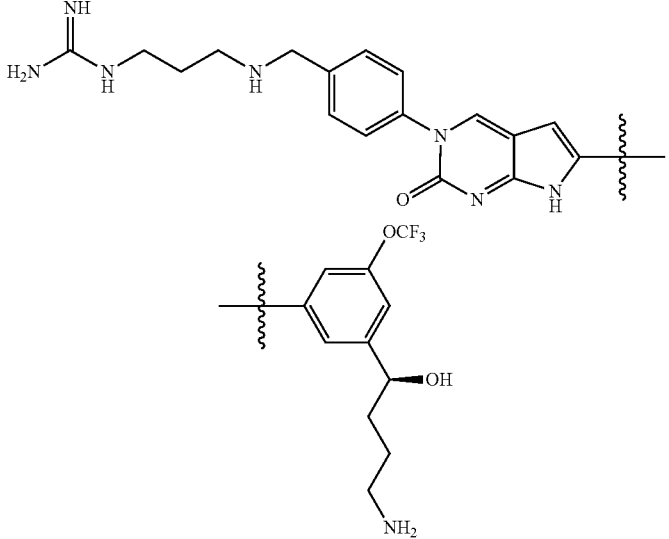 | 587.0 |
| 76 | 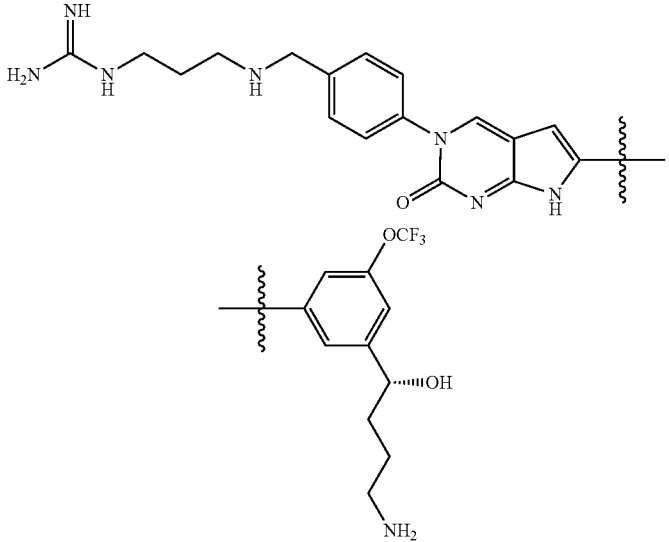 | 587 |

TABLE 1-continued
| Comp. No. | Structure | LCMS |
|---|---|---|
| 77 | 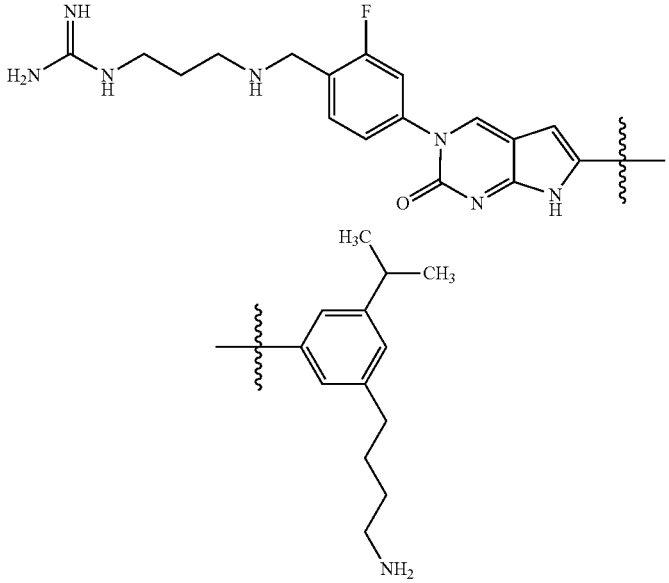 | 547.1 |
| 78 | 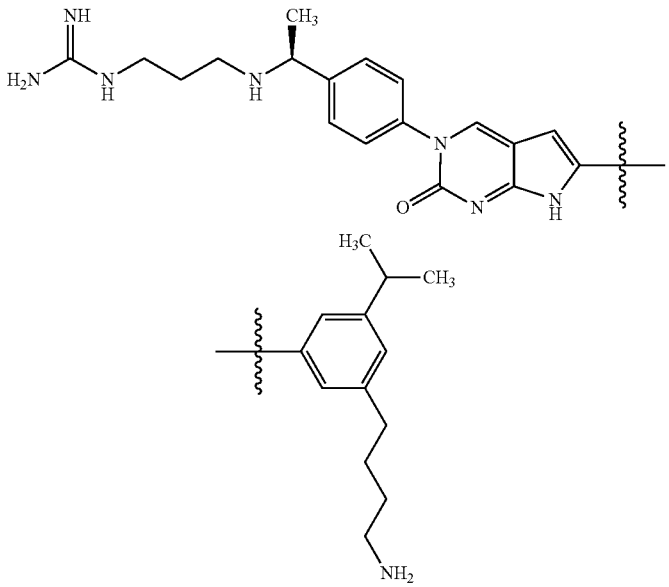 | 543.1 |

TABLE 1-continued
| Comp. No. | Structure | LCMS |
|---|---|---|
| 79 | 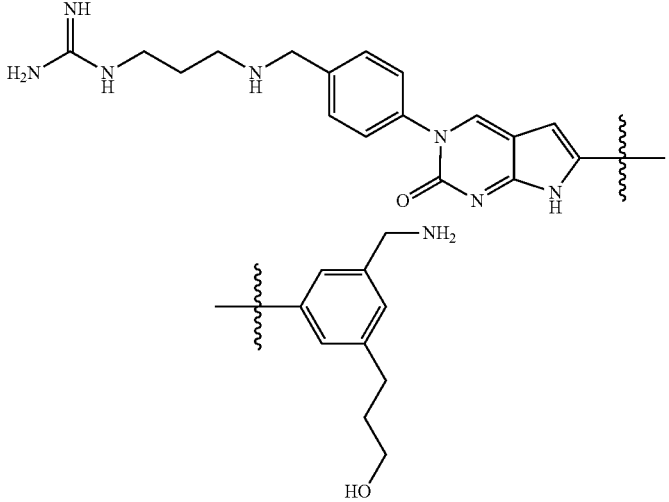 | 503.2 |
| 80 | 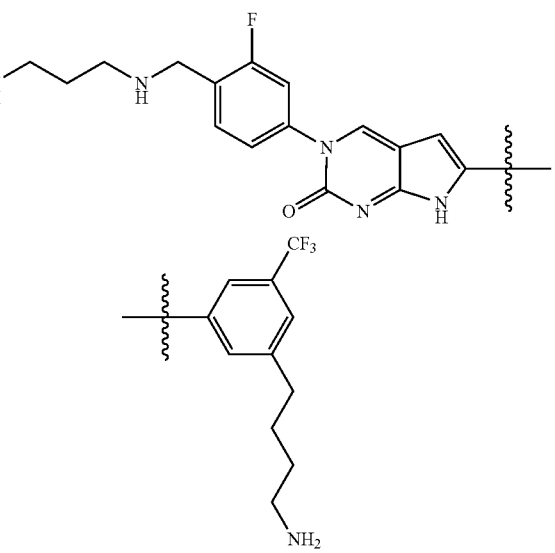 | 573.1 |
| 81 | 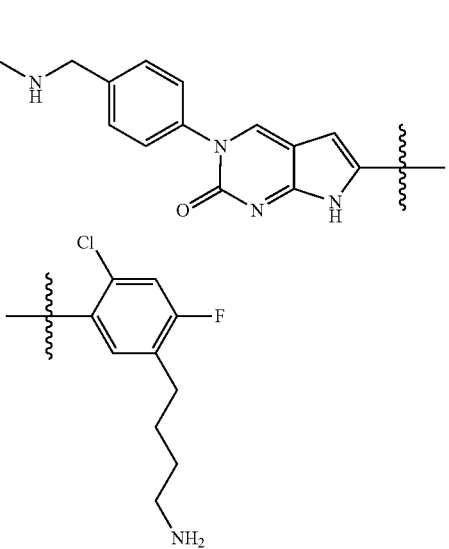 | 539.0 |

TABLE 1-continued
| Comp. No. | Structure | LCMS |
|---|---|---|
| 82 | 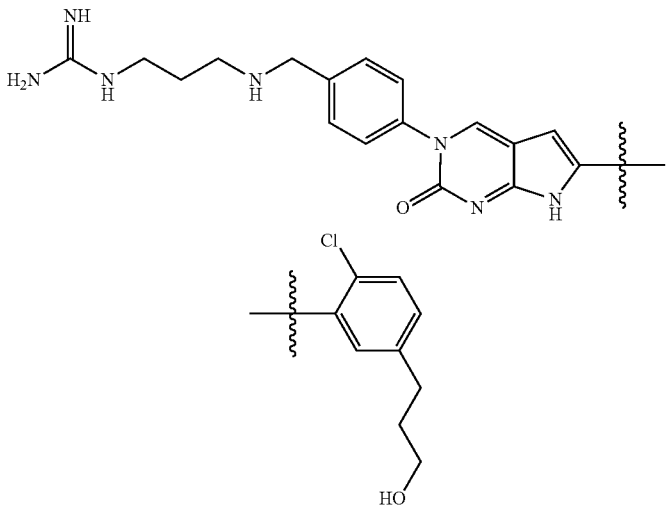 [SMILES: *c1cc2cn(-c3ccc(CNCCCNC(=N)N)cc3)c(=O)nc2[nH]1 ; *c1cc(CCCO)ccc1Cl] | 508.0 |
| 83 | 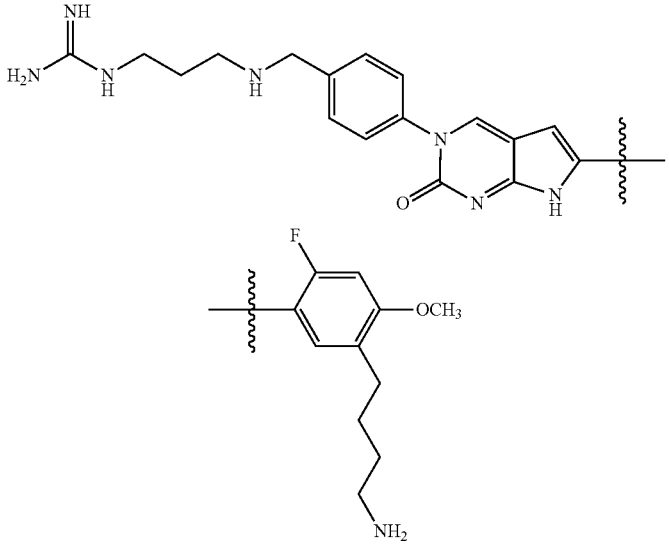 [SMILES: *c1cc2cn(-c3ccc(CNCCCNC(=N)N)cc3)c(=O)nc2[nH]1 ; *c1cc(CCCCN)c(OC)cc1F] | 535.1 |
| 84 | 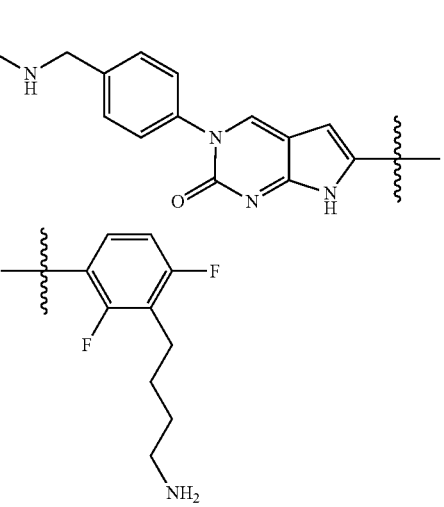 | 523.0 |

TABLE 1-continued

| Comp. No. | Structure | LCMS |
|---|---|---|
| 85 | 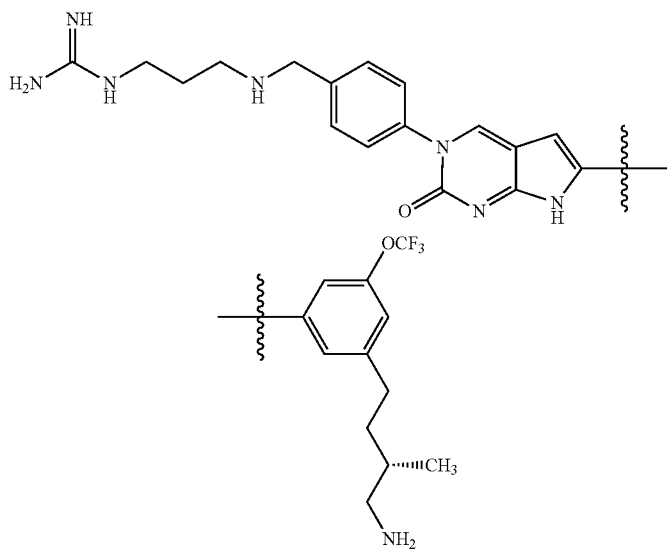 | 585.1 |
| 86 | 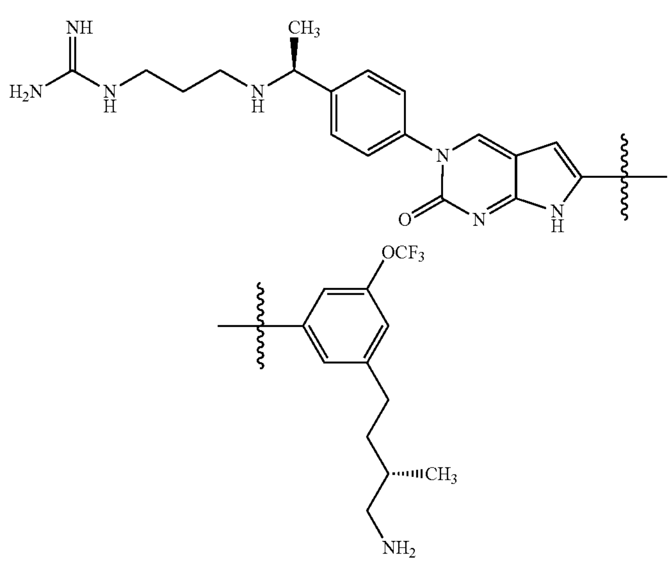 | 599.1 |

TABLE 1-continued
| Comp. No. | Structure | LCMS |
|---|---|---|
| 87 | 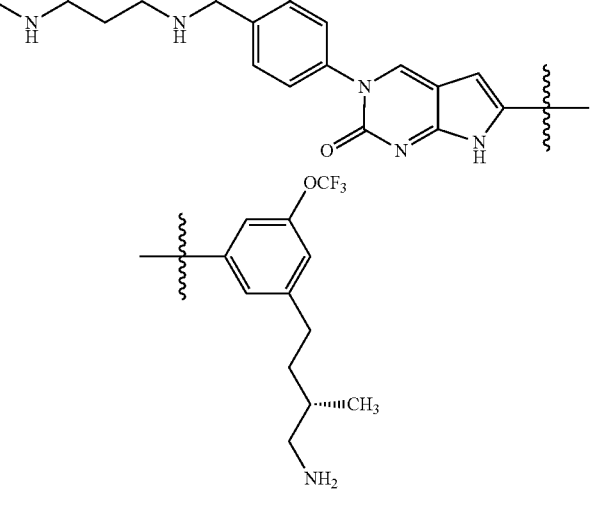 | 603.3 |
| 88 | 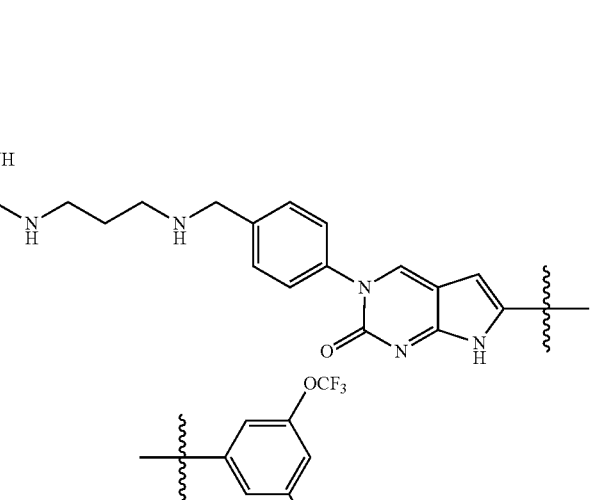 | 587.0 |

TABLE 1-continued
| Comp. No. | Structure | LCMS |
|---|---|---|
| 89 | 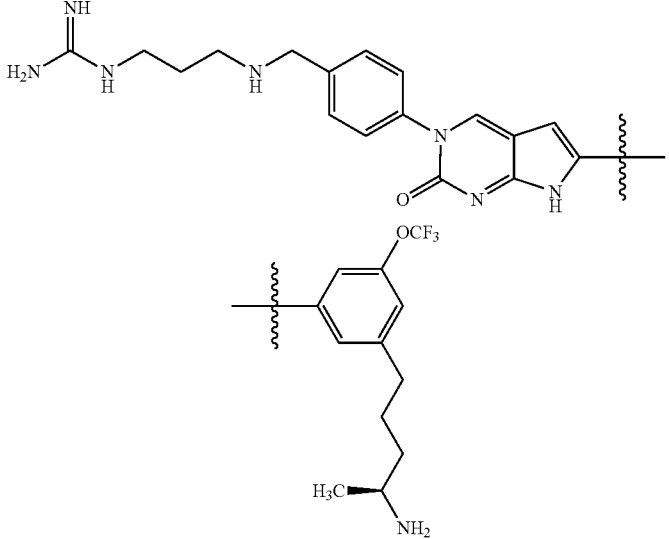 | 585.0 |
| 90 | 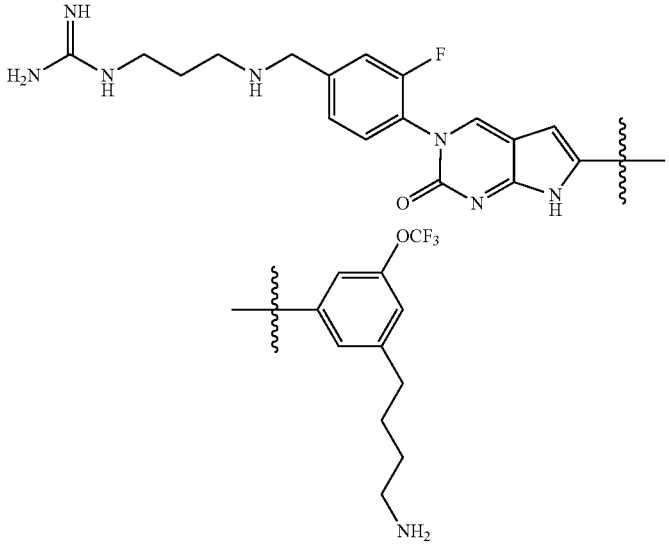 | 589.1 |

TABLE 1-continued
| Comp. No. | Structure | LCMS |
|---|---|---|
| 91 | 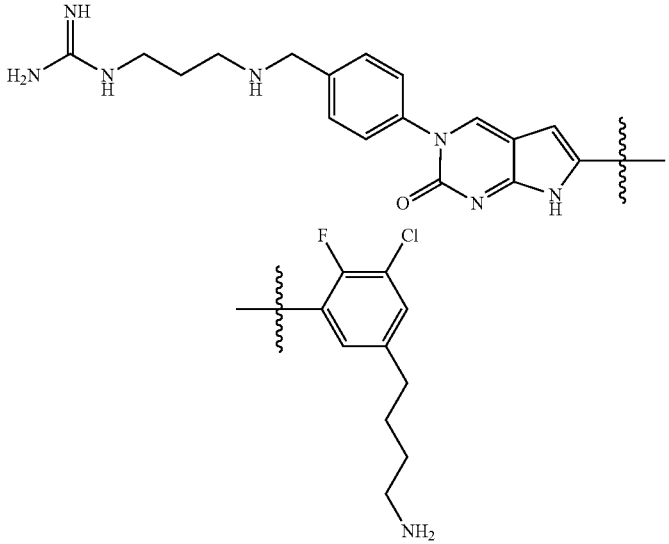 | 539.0 |
| 92 | 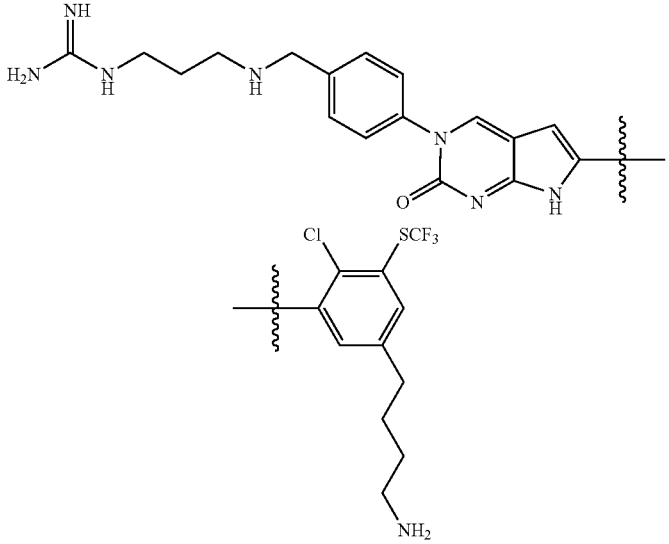 | 621.0 |

TABLE 1-continued
| Comp. No. | Structure | LCMS |
|---|---|---|
| 93 | 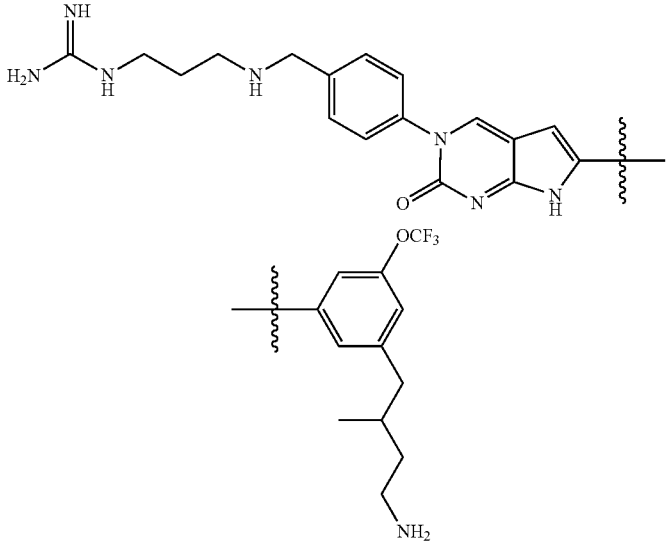 | 585.1 |
| 94 | 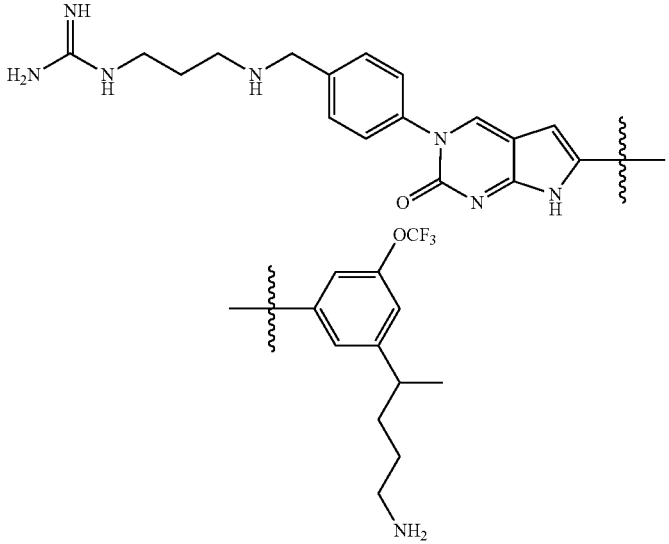 | 585.5 |

TABLE 1-continued
| Comp. No. | Structure | LCMS |
|---|---|---|
| 95 | 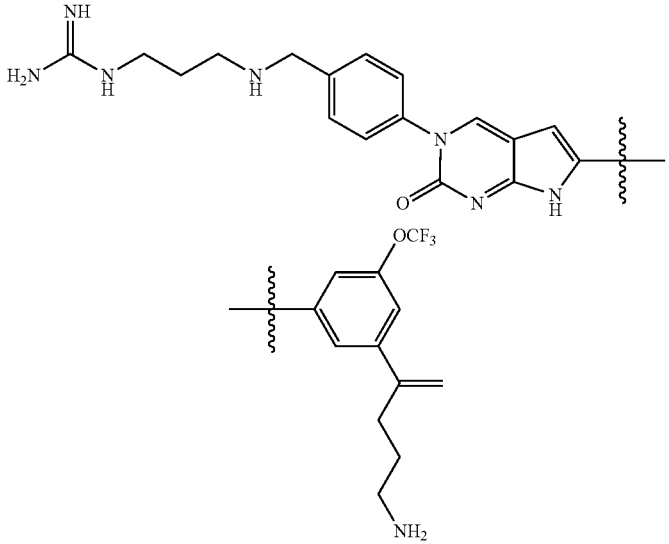 | 583.5 |
| 96 | 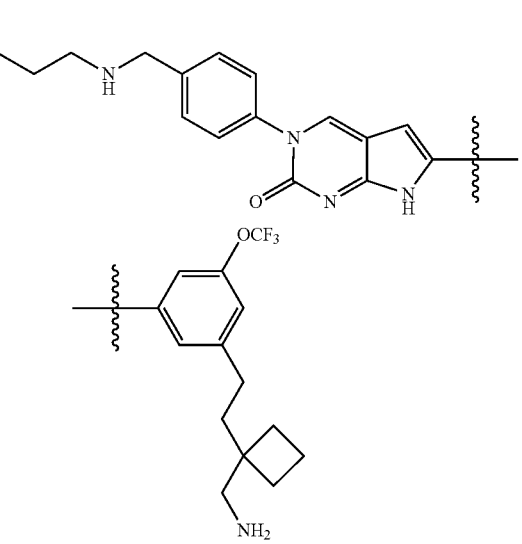 | 611.0 |

TABLE 1-continued
| Comp. No. | Structure | LCMS |
|---|---|---|
| 97 | 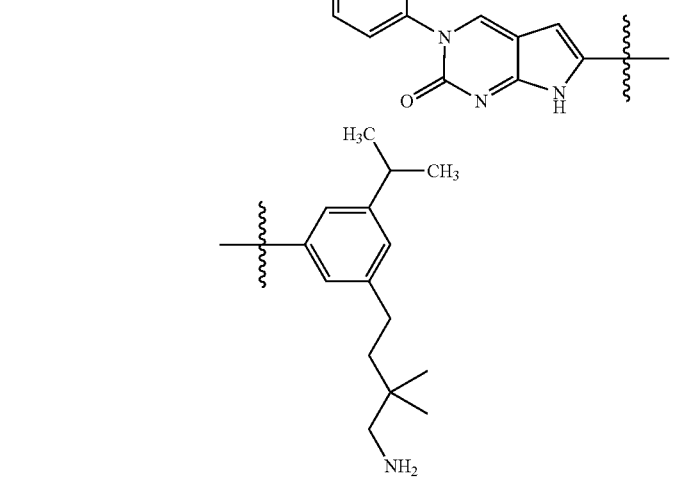 | 557.0 |
| 98 | 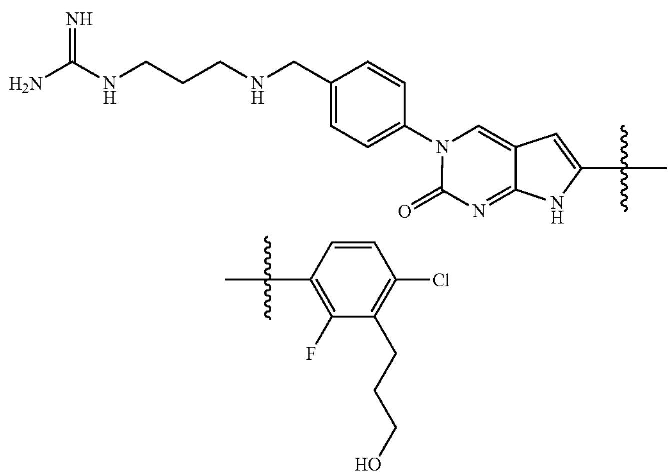 | 539.0 |
| 99 | 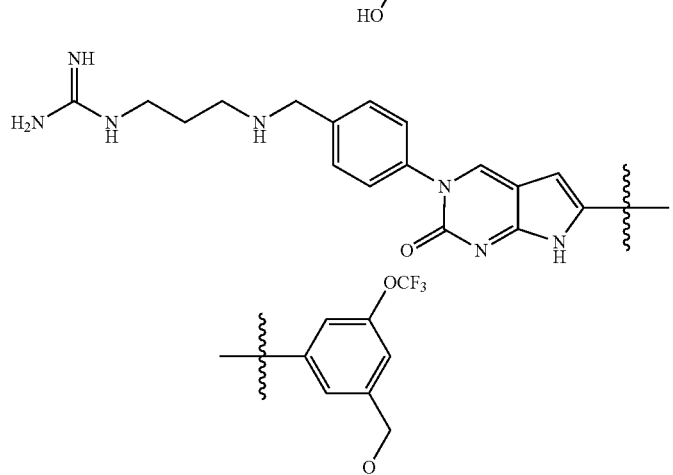 | 587.1 |

TABLE 1-continued
| Comp. No. | Structure | LCMS |
|---|---|---|
| 100 | 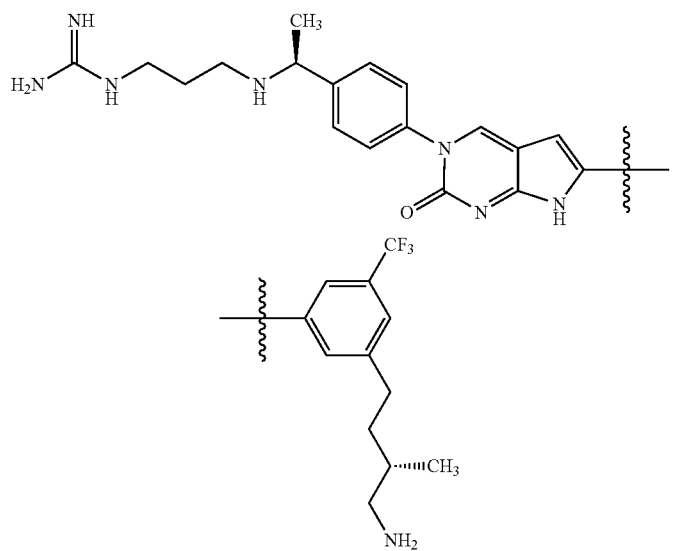 | 583.1 |
| 101 | 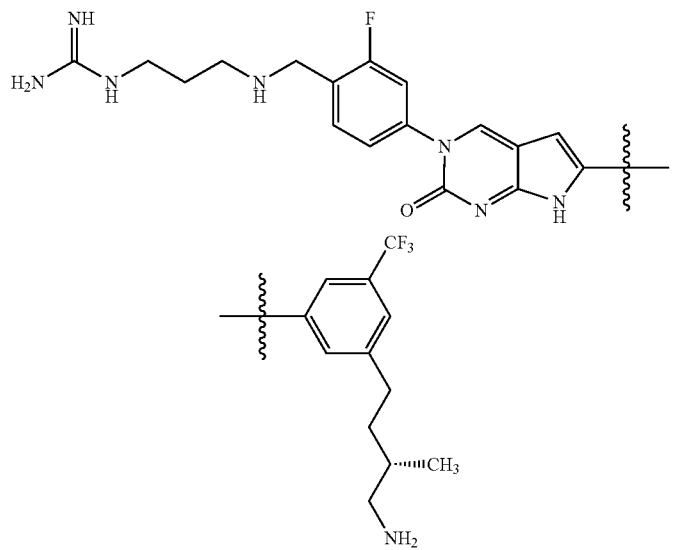 | 587.1 |

TABLE 1-continued
| Comp. No. | Structure | LCMS |
|---|---|---|
| 102 | 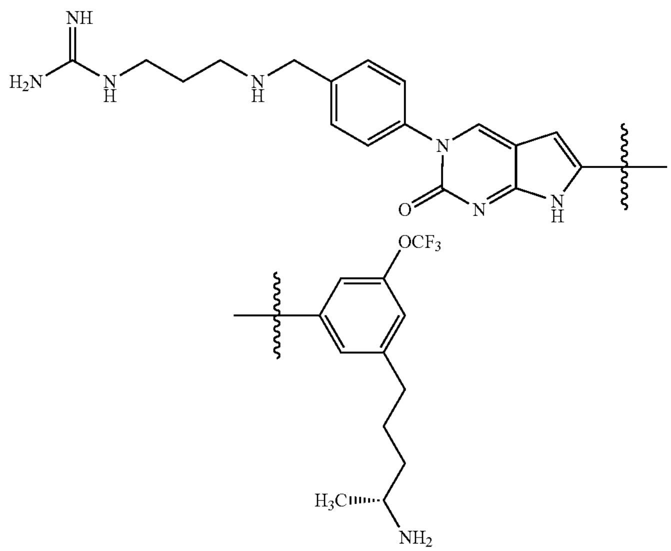 | 585.0 |
| 103 | 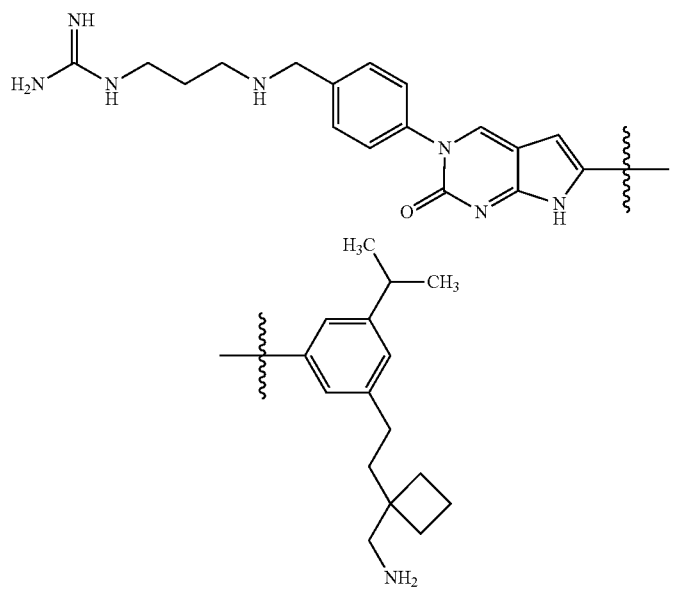 | 569.0 |

TABLE 1-continued
| Comp. No. | Structure | LCMS |
|---|---|---|
| 104 | 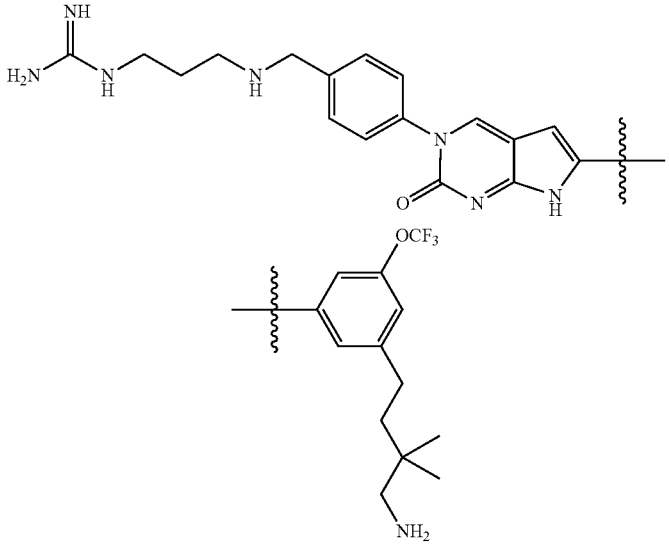 | 599.0 |
| 105 | 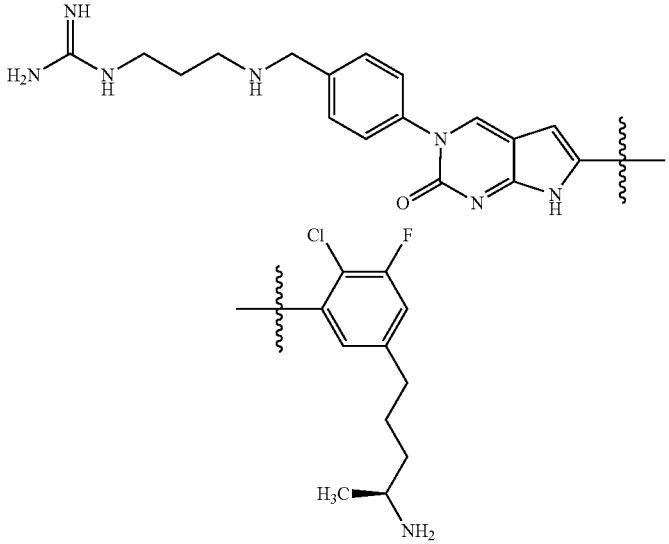 | 553.1 |

TABLE 1-continued
| Comp. No. | Structure | LCMS |
|---|---|---|
| 106 | 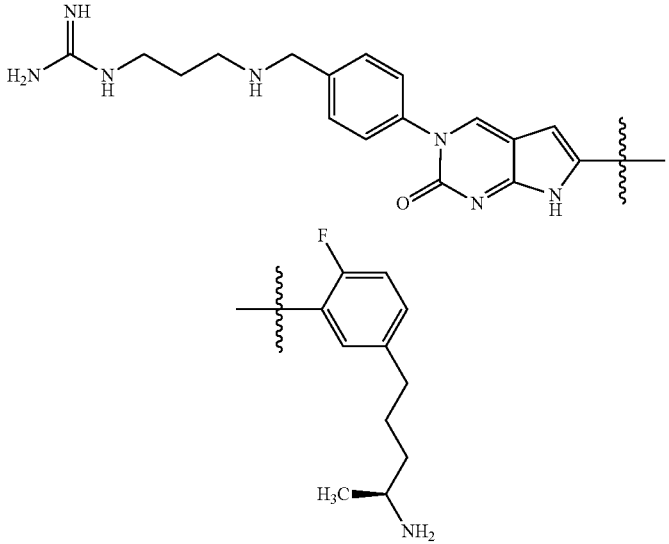 [SMILES: *c1cc2cn(-c3ccc(CNCCCNC(=N)N)cc3)c(=O)nc2[nH]1 ; *c1cc(CCC[C@H](C)N)ccc1F] | 519.1 |
| 107 | 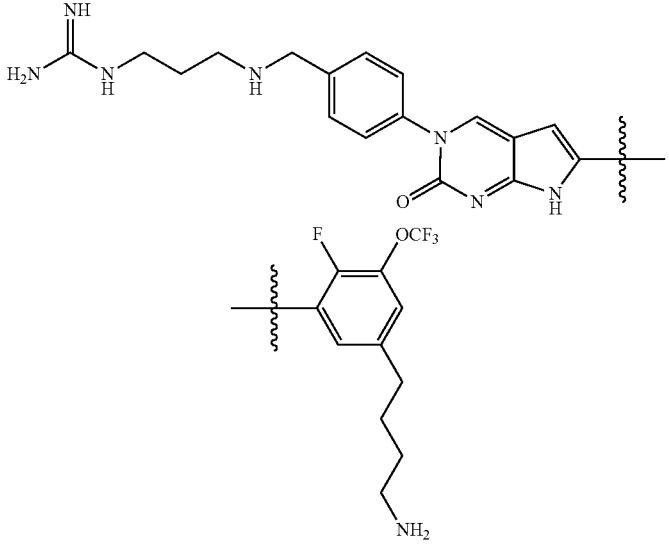 | 589.0 |

TABLE 1-continued
| Comp. No. | Structure | LCMS |
|---|---|---|
| 108 | 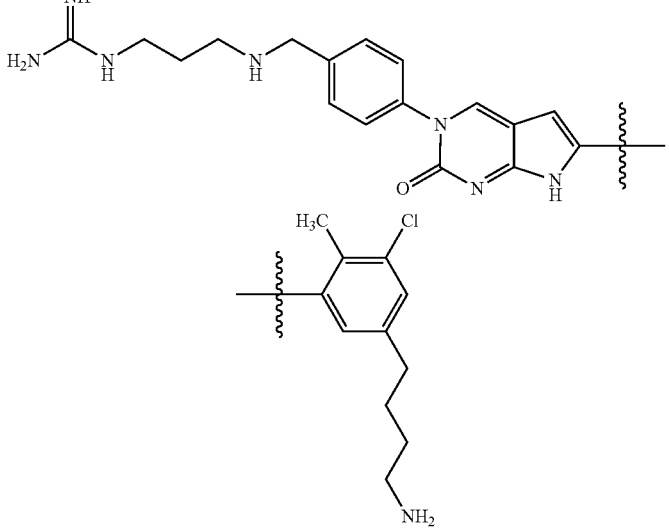 | 535.1 |
| 109 | 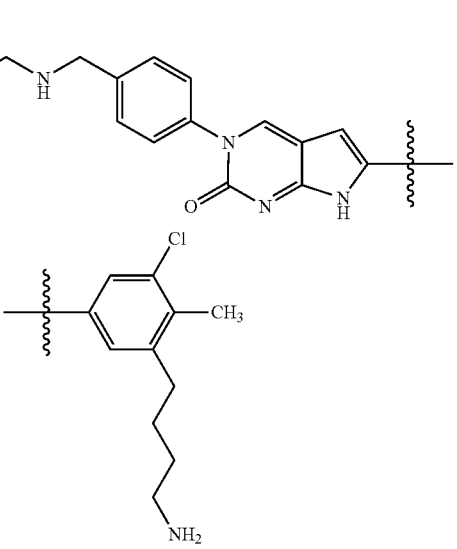 | 535.1 |
| 110 | 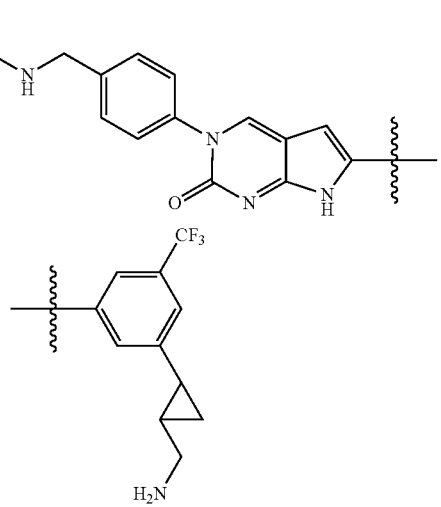 | 553.1 |

TABLE 1-continued
| Comp. No. | Structure | LCMS |
|---|---|---|
| 111 | 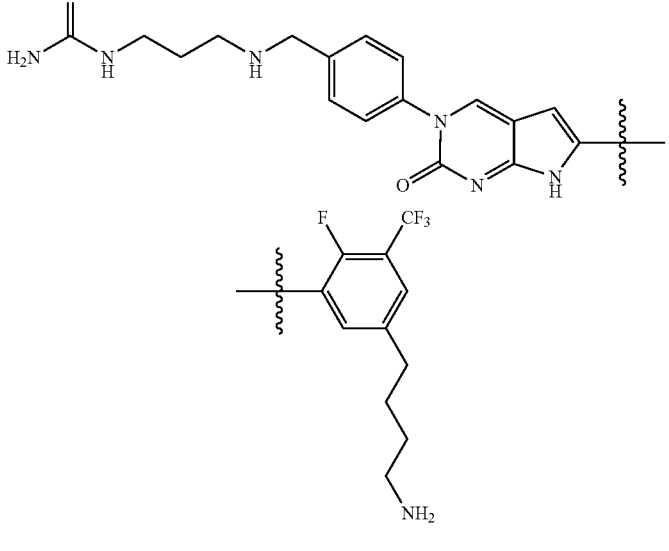 | 573.1 |
| 112 | 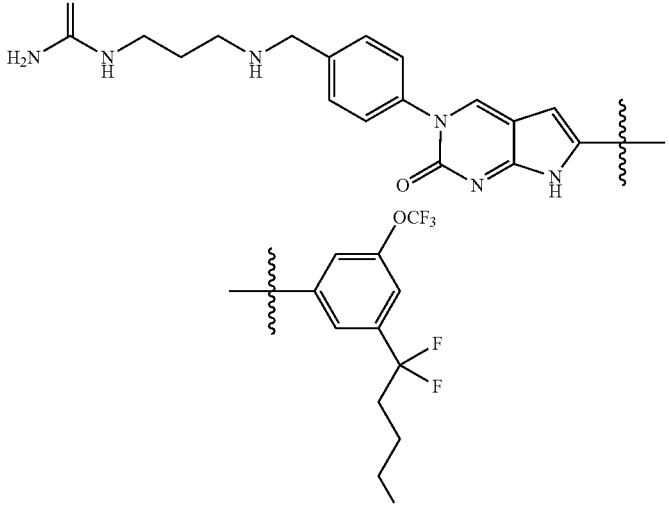 | 607.1 |

TABLE 1-continued
| Comp. No. | Structure | LCMS |
|---|---|---|
| 113 | 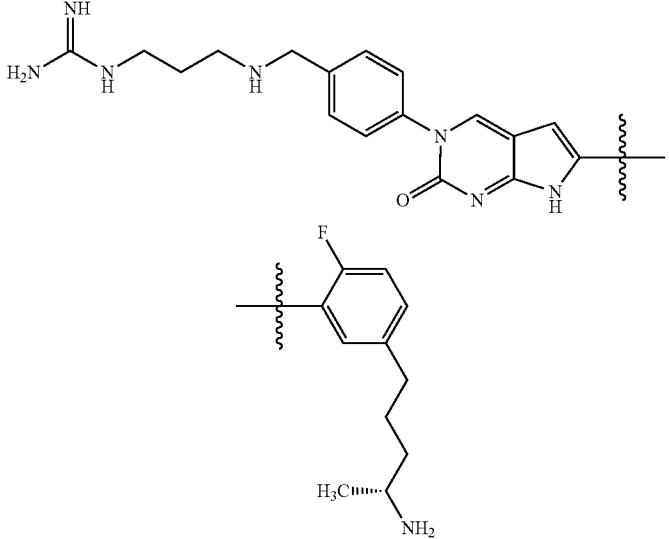 [SMILES: *c1cc2cn(-c3ccc(CNCCCNC(=N)N)cc3)c(=O)nc2[nH]1 ; *c1cc(CCC[C@@H](C)N)ccc1F] | 519.1 |
| 114 | 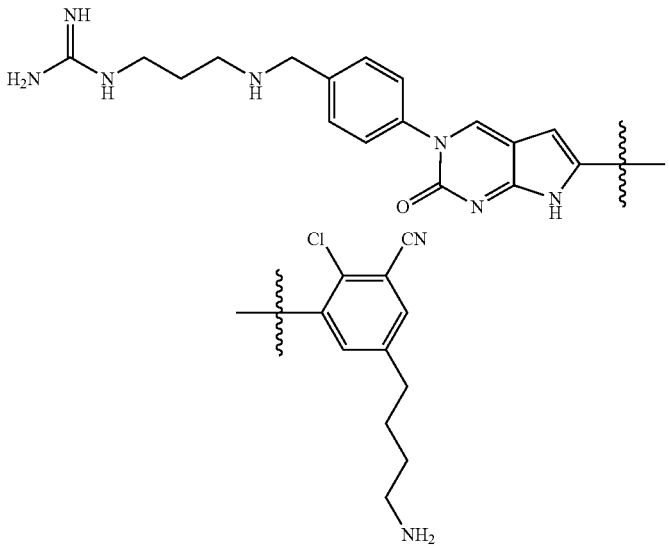 | 546.0 |

TABLE 1-continued
| Comp. No. | Structure | LCMS |
|---|---|---|
| 115 | 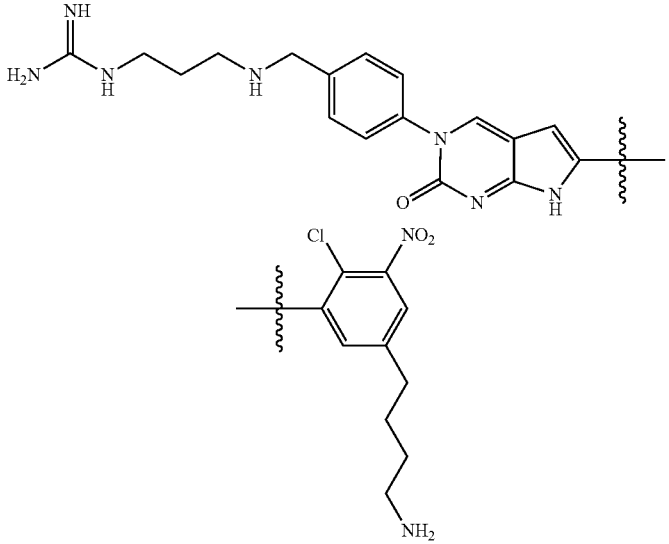 | 566.1 |
| 116 | 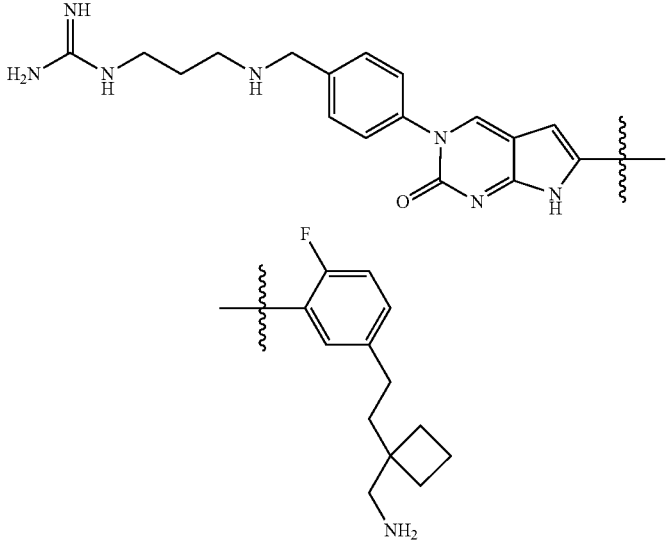 [SMILES: *c1cc2cn(-c3ccc(CNCCCNC(=N)N)cc3)c(=O)nc2[nH]1 ; *c1cc(CCC2(CN)CCC2)ccc1F] | 545.0 |

TABLE 1-continued
| Comp. No. | Structure | LCMS |
|---|---|---|
| 117 | 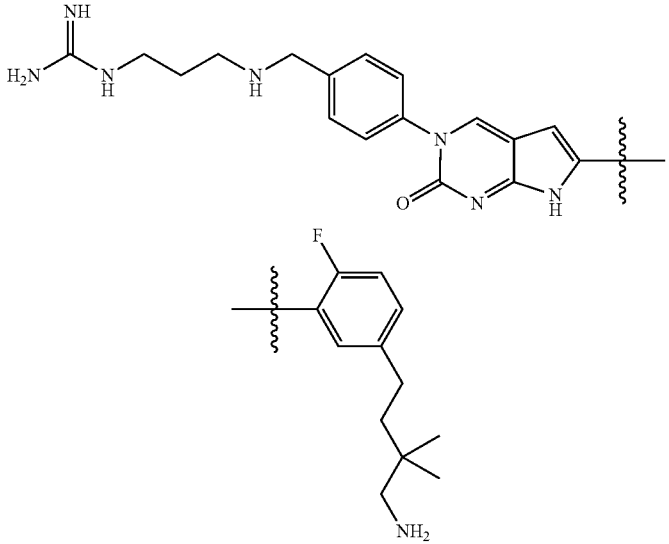 [SMILES: *c1cc2cn(-c3ccc(CNCCCNC(=N)N)cc3)c(=O)nc2[nH]1 ; *c1cc(CCC(C)(C)CN)ccc1F] | 533.0 |
| 118 | 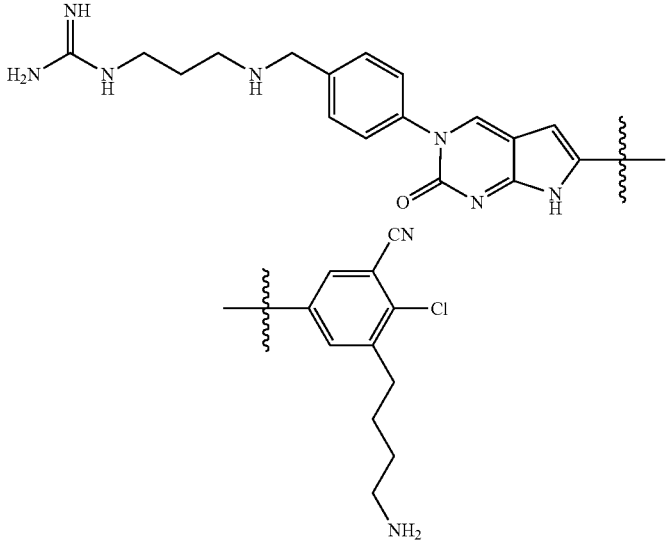 | 546.0 |

TABLE 1-continued
| Comp. No. | Structure | LCMS |
|---|---|---|
| 119 | 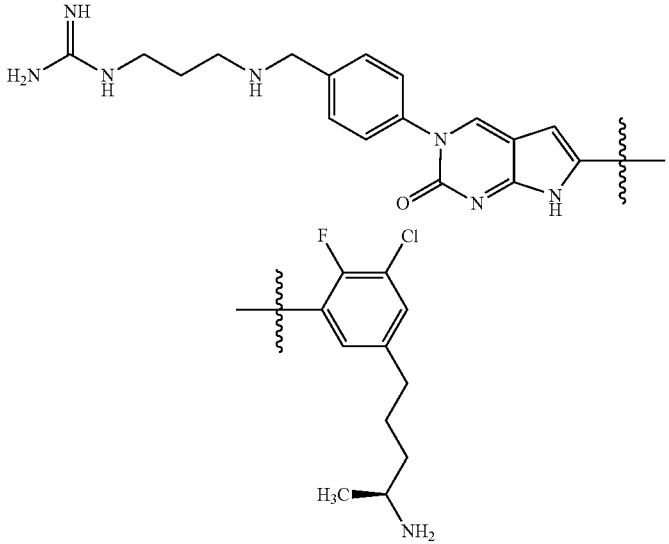 | 553.1 |
| 120 | 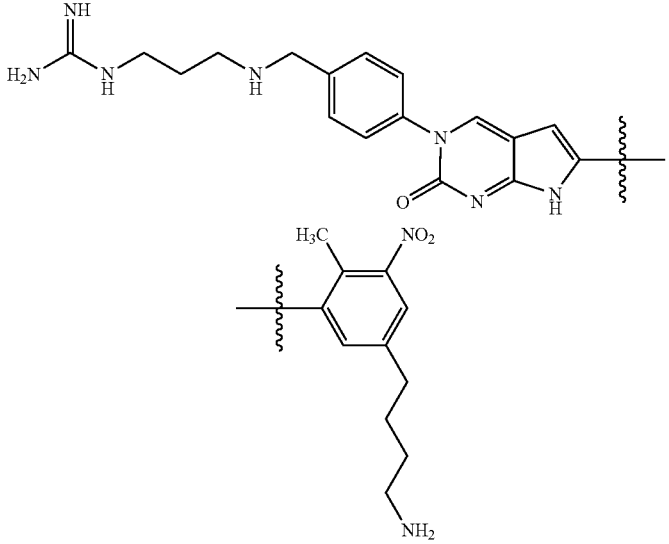 | 546.1 |

TABLE 1-continued
| Comp. No. | Structure | LCMS |
|---|---|---|
| 121 | 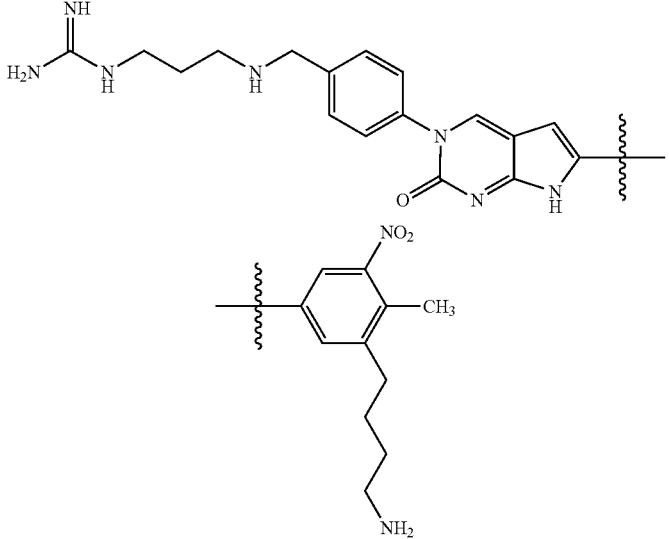 | 546.0 |
| 122 | 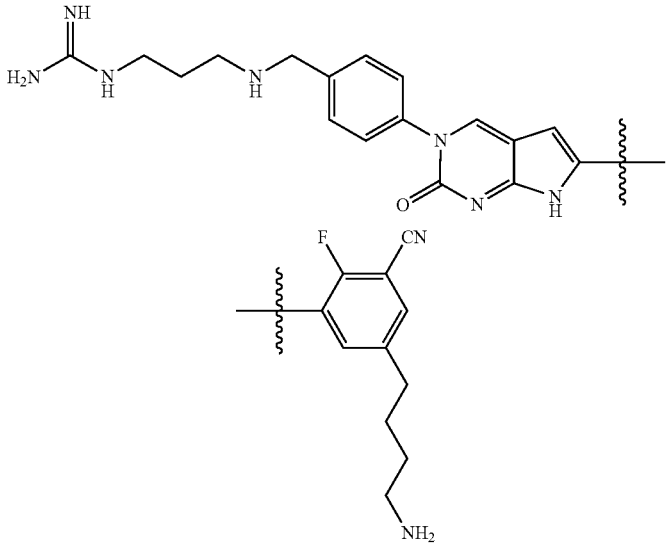 | 530.1 |

TABLE 1-continued
| Comp. No. | Structure | LCMS |
|---|---|---|
| 123 | 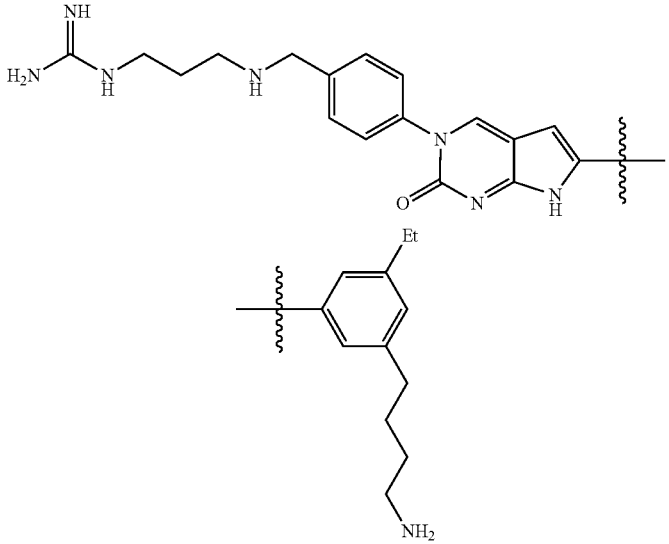 | 515.1 |
| 124 | 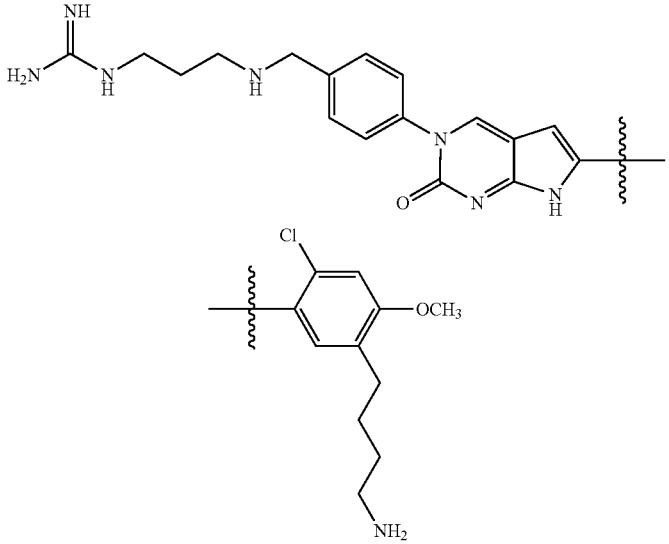 | |

TABLE 1-continued
| Comp. No. | Structure | LCMS |
|---|---|---|
| 125 | 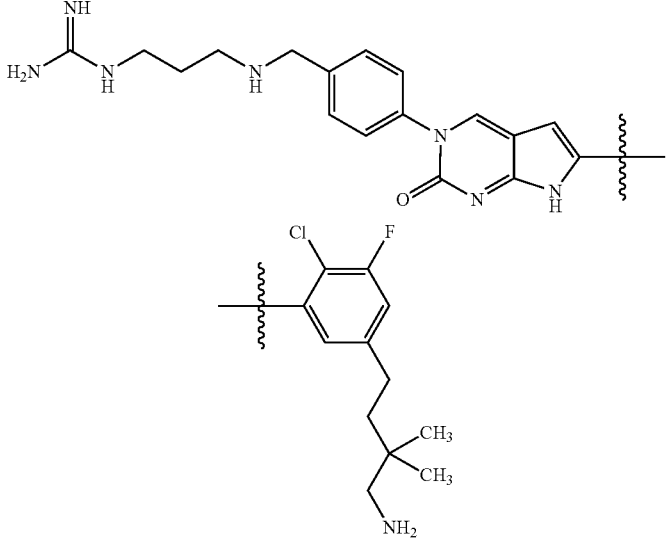 | 567.0 |
| 126 | 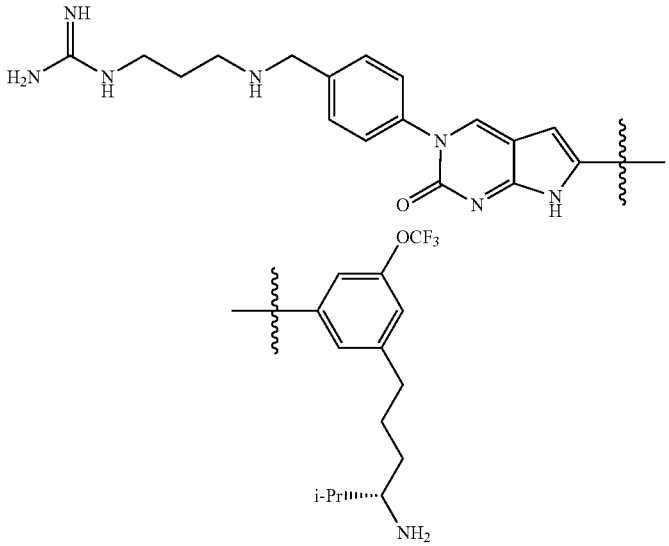 | 613.1 |

TABLE 1-continued
| Comp. No. | Structure | LCMS |
|---|---|---|
| 127 | 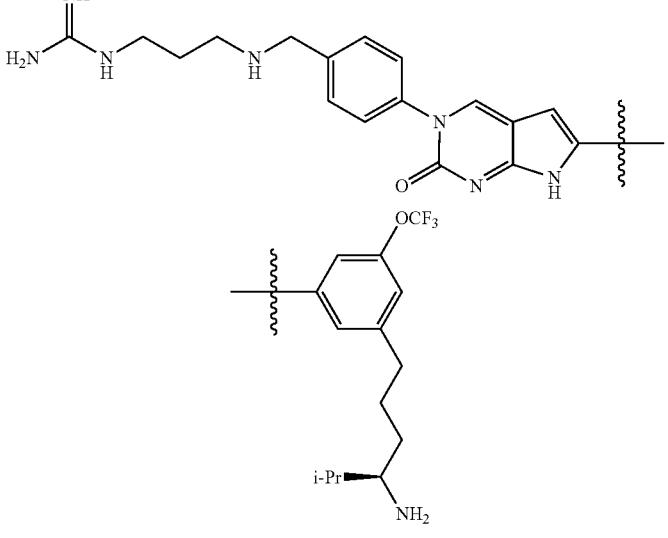 | 613.1 |
| 128 | 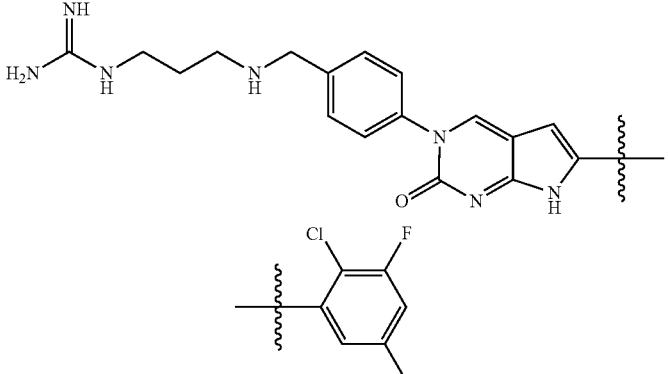 | 553.1 |

TABLE 1-continued
| Comp. No. | Structure | LCMS |
|---|---|---|
| 129 | 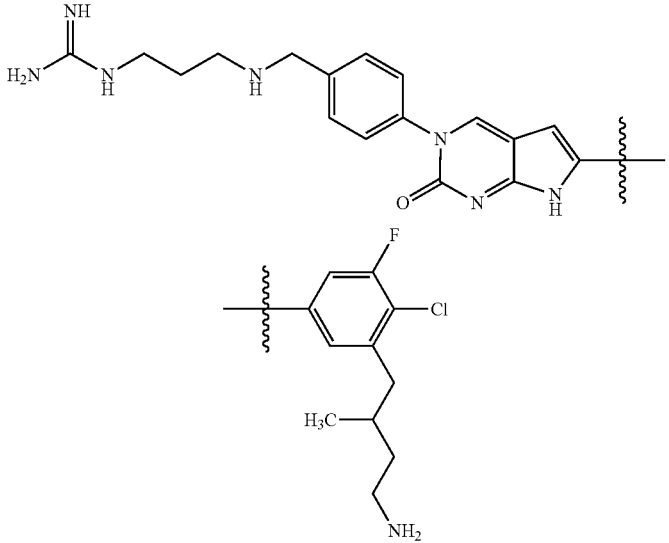 | 552.9 |
| 130 | 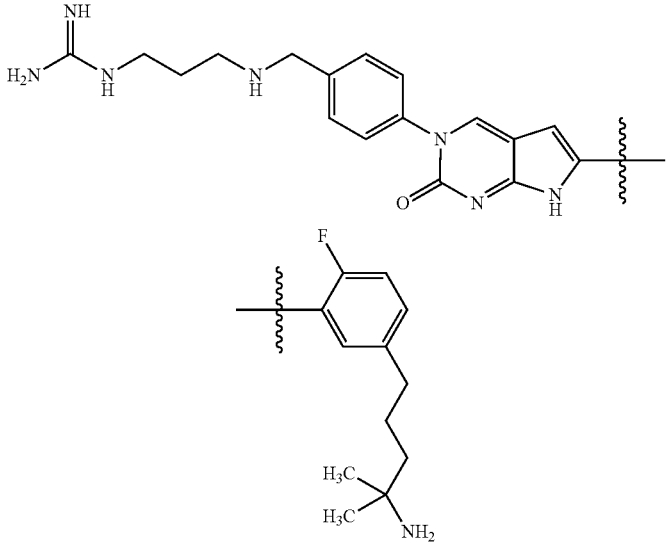 [SMILES: *c1cc2cn(-c3ccc(CNCCCNC(=N)N)cc3)c(=O)nc2[nH]1 ; *c1cc(CCCC(C)(C)N)ccc1F] | 533.1 |

TABLE 1-continued

| Comp. No. | Structure | LCMS |
|---|---|---|
| 131 | 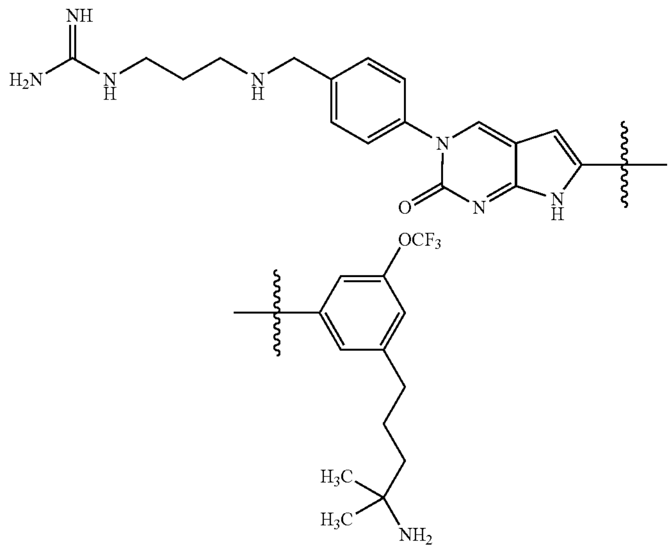 | 599.0 |
| 132 | 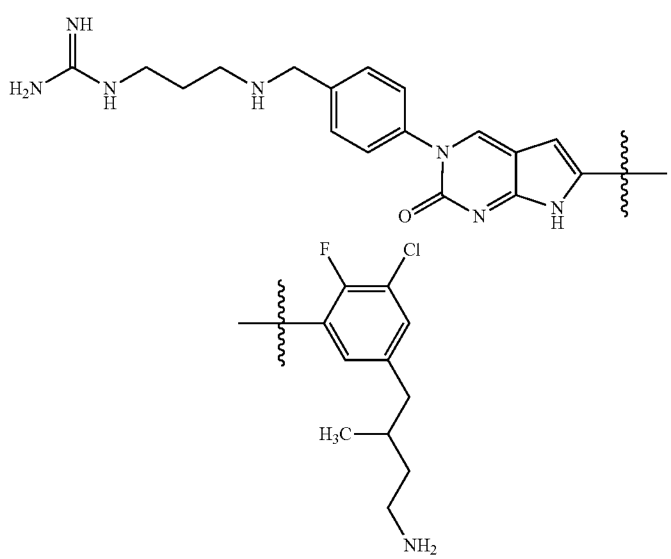 | 553.0 |

TABLE 1-continued

| Comp. No. | Structure | LCMS |
|---|---|---|
| 133 | 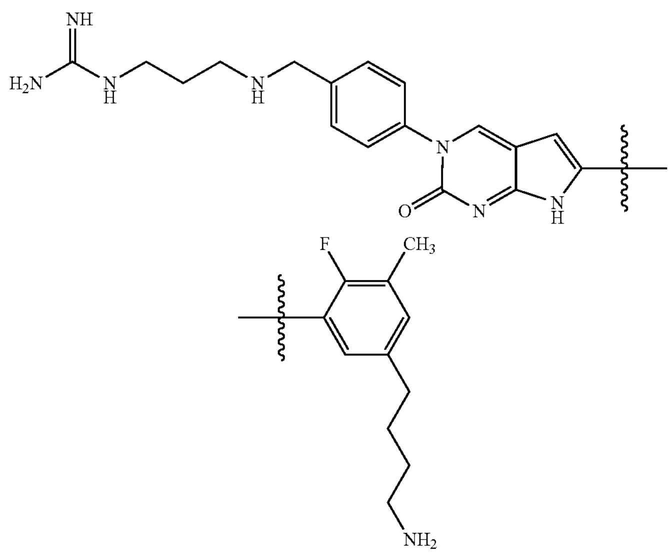 | 519.0 |
| 134 | 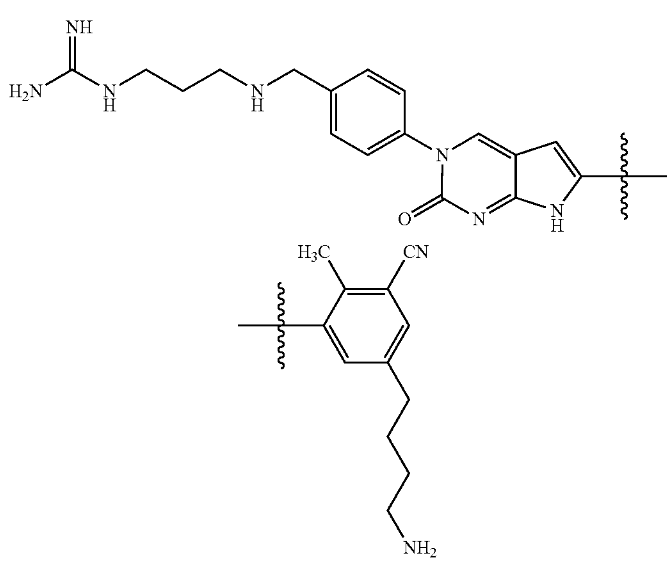 | 526.1 |

TABLE 1-continued
| Comp. No. | Structure | LCMS |
|---|---|---|
| 135 | 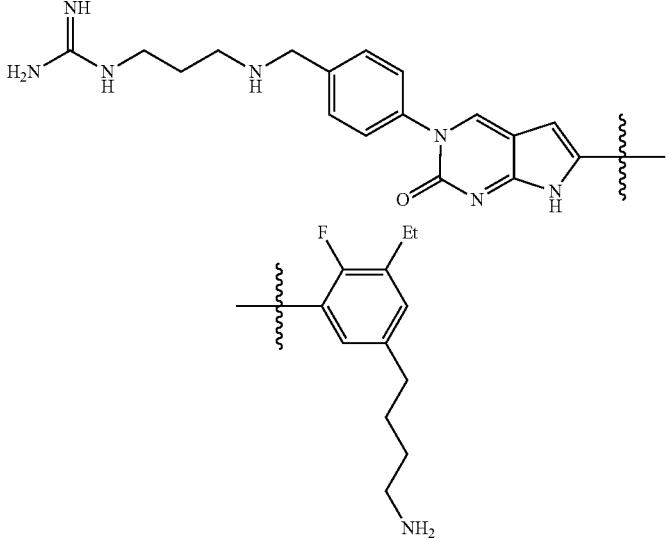 | 533.1 |
| 136 | 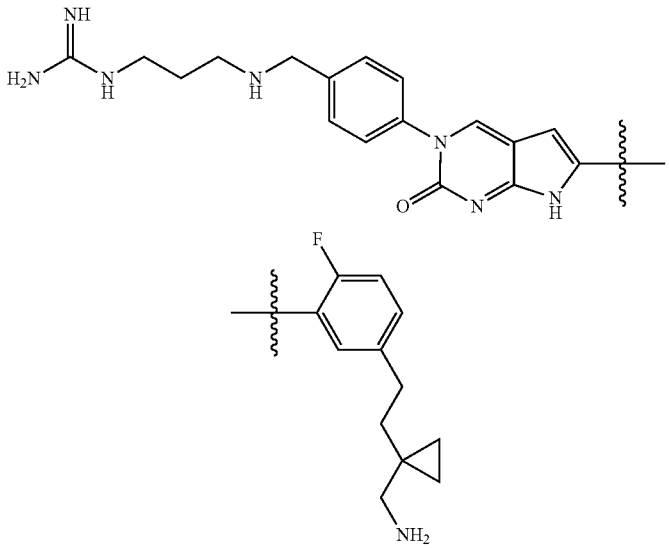 [SMILES: *c1cc2cn(-c3ccc(CNCCCNC(=N)N)cc3)c(=O)nc2[nH]1 ; *c1cc(CCC2(CN)CC2)ccc1F] | 531.0 |

TABLE 1-continued
| Comp. No. | Structure | LCMS |
|---|---|---|
| 137 | 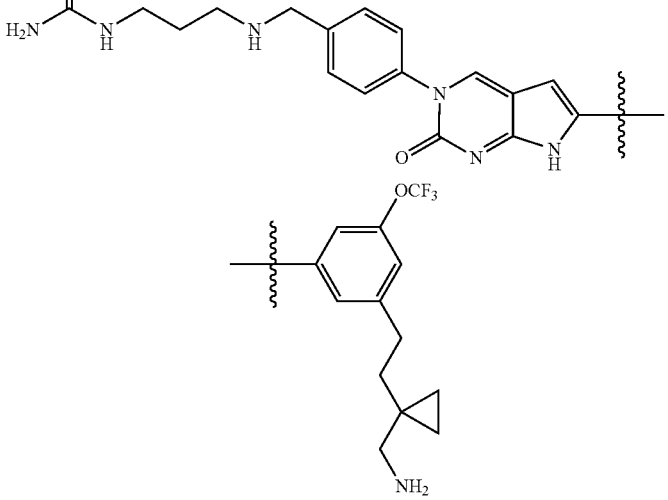 | 597.0 |
| 138 | 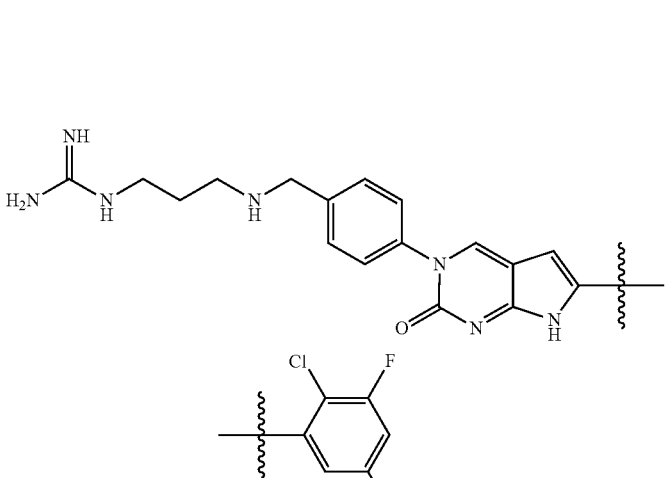 | 579.0 |

TABLE 1-continued
| Comp. No. | Structure | LCMS |
|---|---|---|
| 139 | 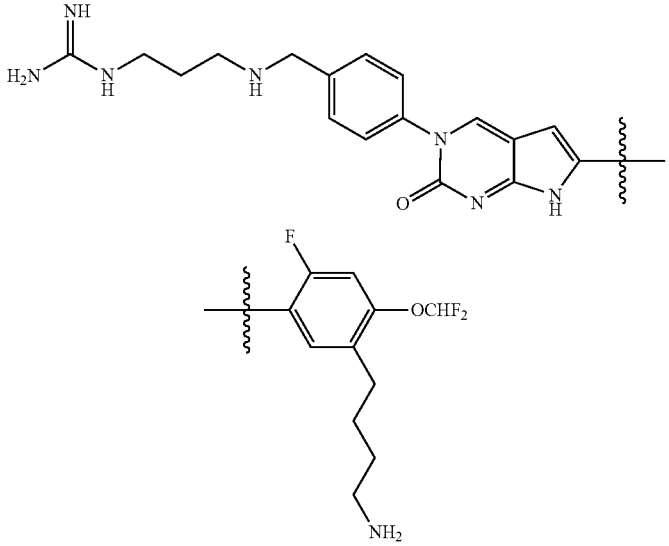 [SMILES: *c1cc2cn(-c3ccc(CNCCCNC(=N)N)cc3)c(=O)nc2[nH]1 ; *c1cc(CCCCN)c(OC(F)F)cc1F] | 571.0 |
| 140 | 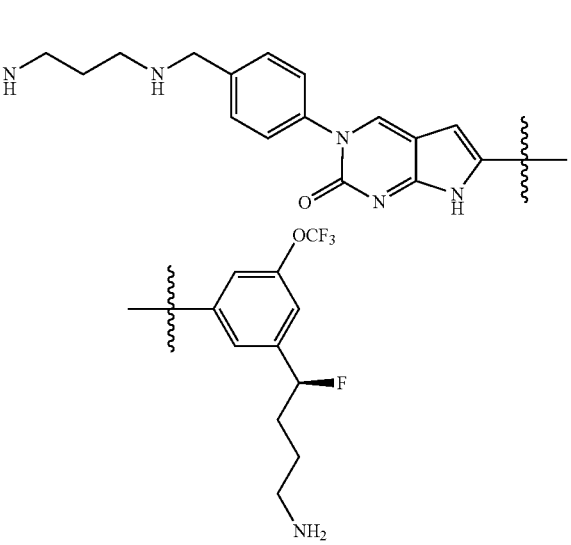 | 589.0 |
| 141 | 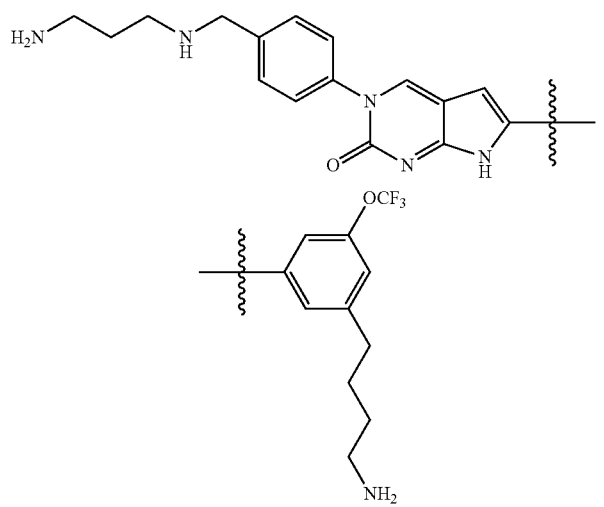 | 529.0 |

TABLE 1-continued
| Comp. No. | Structure | LCMS |
|---|---|---|
| 142 | 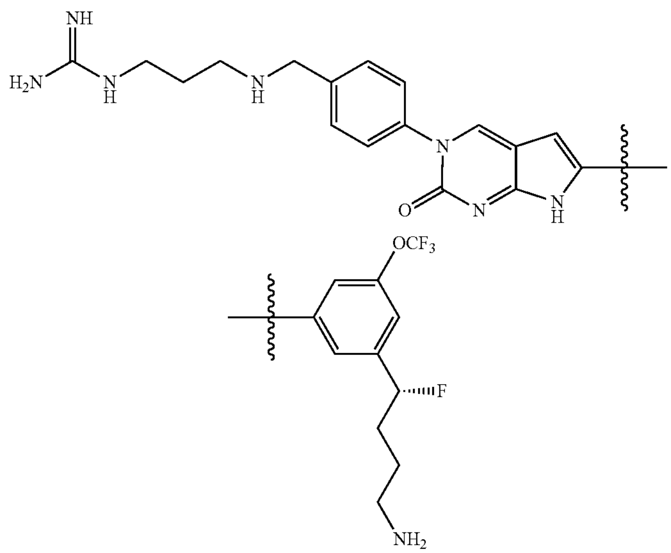 | 589.0 |
| 143 | 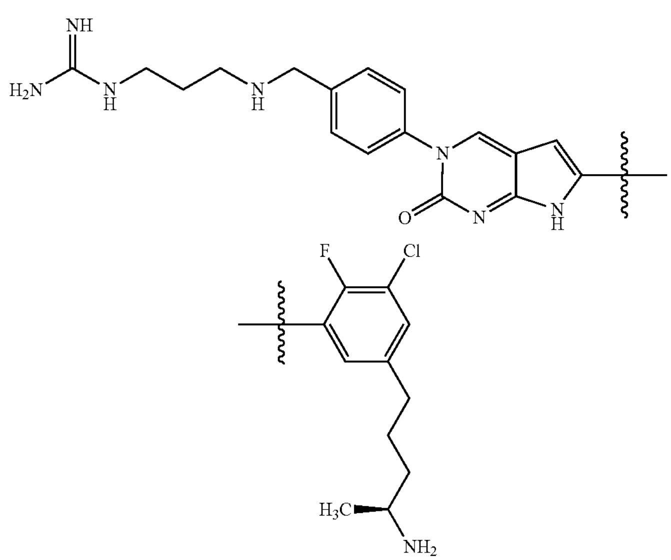 | 511.0 |

TABLE 1-continued
| Comp. No. | Structure | LCMS |
|---|---|---|
| 144 | 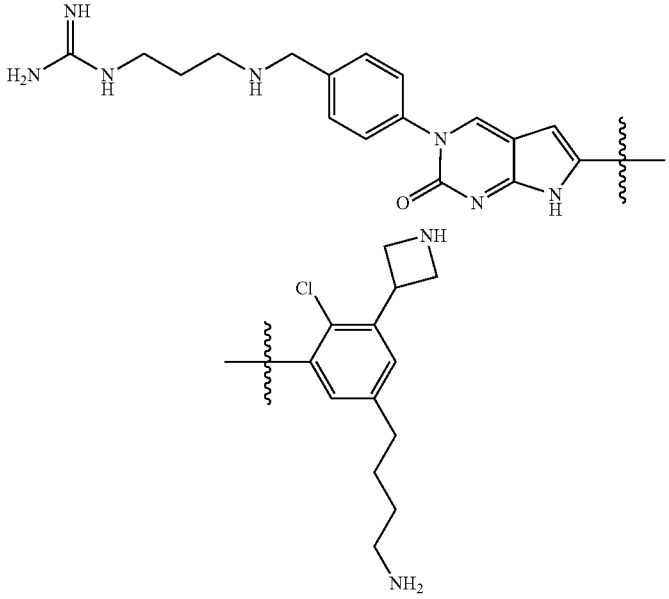 | 576.1 |
| 145 | 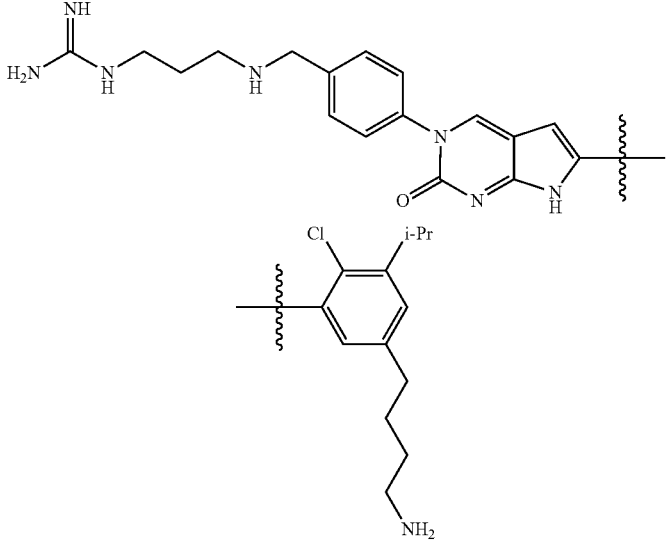 | |

TABLE 1-continued

| Comp. No. | Structure | LCMS |
|---|---|---|
| 146 | (guanidine-propyl-NH-CH2-phenyl attached to pyrrolopyrimidinone N; other substituent: 3-OCF3-5-(4-amino-4-cyclopropylbutyl)phenyl) | 611.1 |
| 147 | (guanidine-propyl-NH-CH2-phenyl attached to pyrrolopyrimidinone N; other substituent: 3-methyl-4-fluoro-5-(4-aminobutyl)phenyl) wait — 3-F, 4-CH3, 5-(aminobutyl)phenyl | 519.1 |
| 148 | (guanidine-propyl-NH-CH2-phenyl attached to pyrrolopyrimidinone N; other substituent: 3-Cl-4-F-5-(3-aminopropyl)phenyl) | 525.0 |

TABLE 1-continued
| Comp. No. | Structure | LCMS |
|---|---|---|
| 149 | 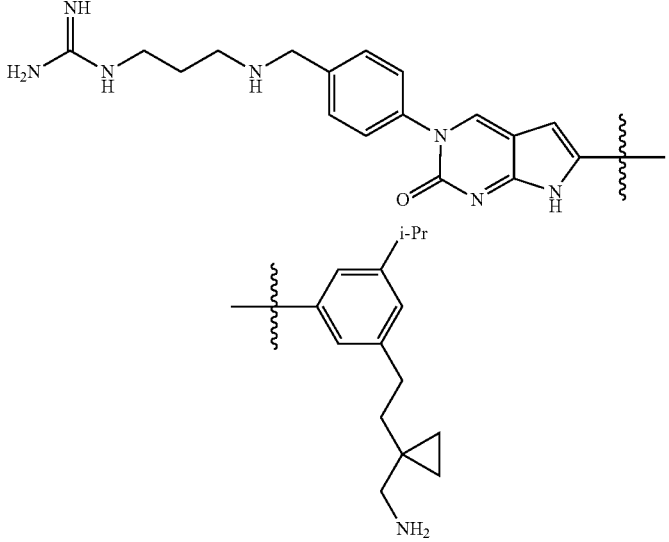 | 555.0 |
| 192 | 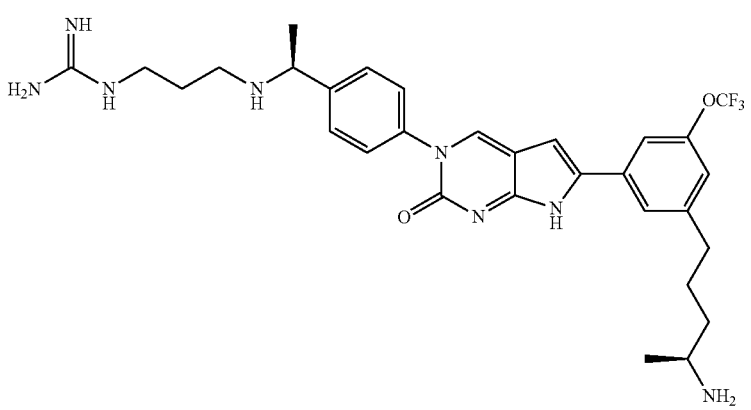 [SMILES: C[C@H](N)CCCc1cc(OC(F)(F)F)cc(-c2cc3cn(-c4ccc([C@H](C)NCCCNC(=N)N)cc4)c(=O)nc3[nH]2)c1] | |
| 194 | 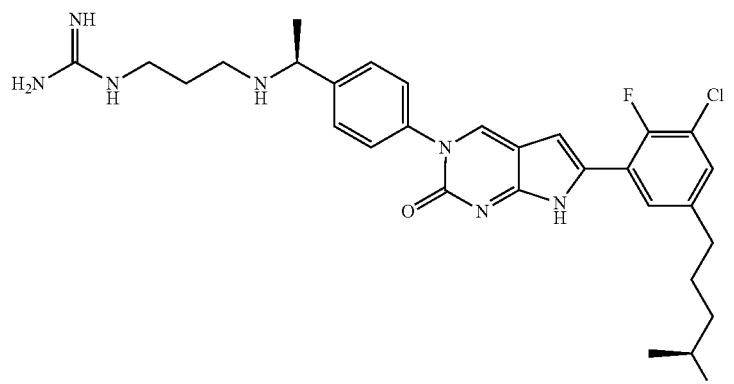 | |

TABLE 1-continued

| Comp. No. | Structure | LCMS |
|---|---|---|
| 195 | 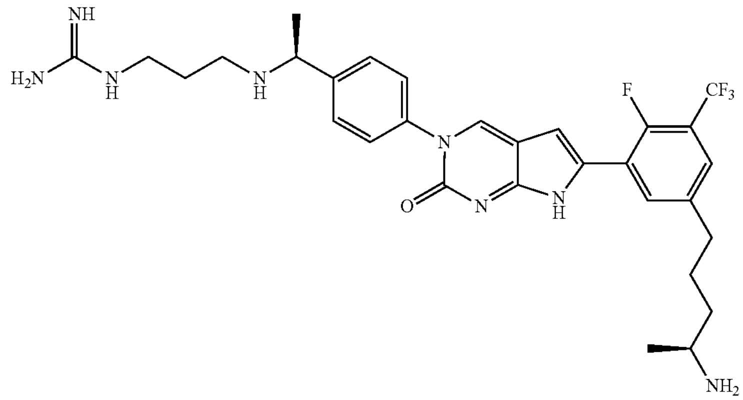 | |
| 196 | 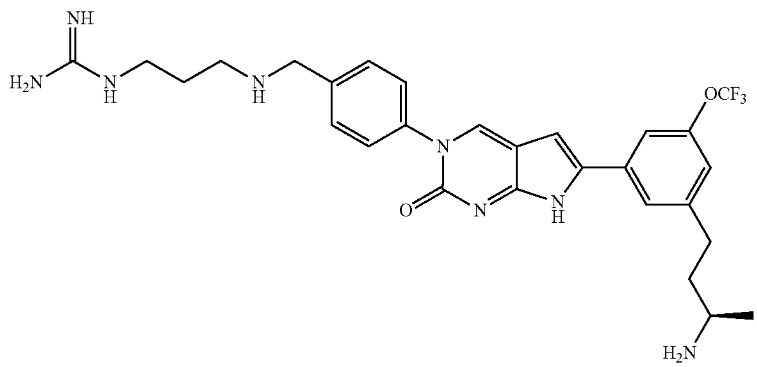 [SMILES: C[C@@H](N)CCc1cc(OC(F)(F)F)cc(-c2cc3cn(-c4ccc(CNCCCNC(=N)N)cc4)c(=O)nc3[nH]2)c1] | |
| 197 | 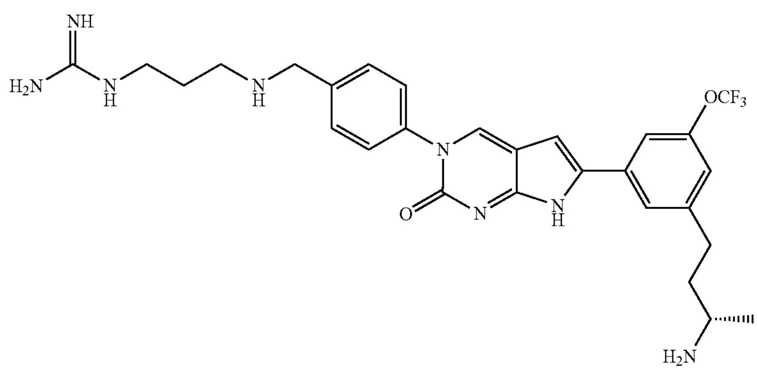 [SMILES: C[C@H](N)CCc1cc(OC(F)(F)F)cc(-c2cc3cn(-c4ccc(CNCCCNC(=N)N)cc4)c(=O)nc3[nH]2)c1] | |
| 198 | 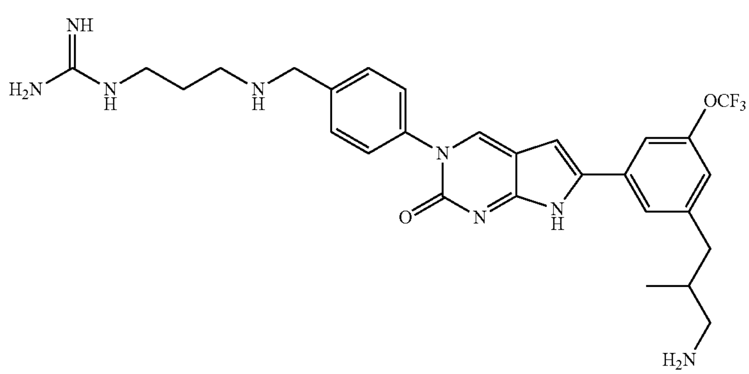 [SMILES: CC(CN)Cc1cc(OC(F)(F)F)cc(-c2cc3cn(-c4ccc(CNCCCNC(=N)N)cc4)c(=O)nc3[nH]2)c1] | |

TABLE 1-continued

| Comp. No. | Structure | LCMS |
|---|---|---|
| 199 | 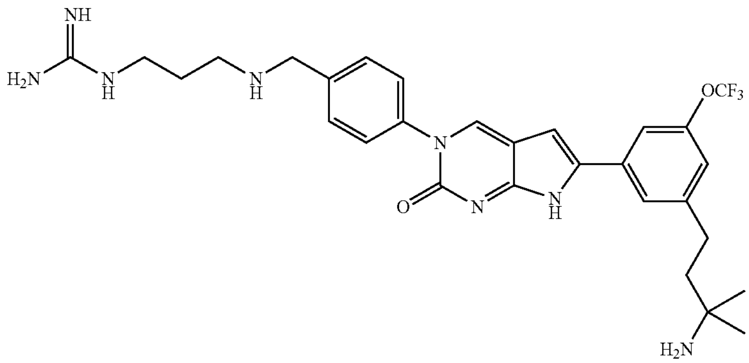 | |
| 200 | 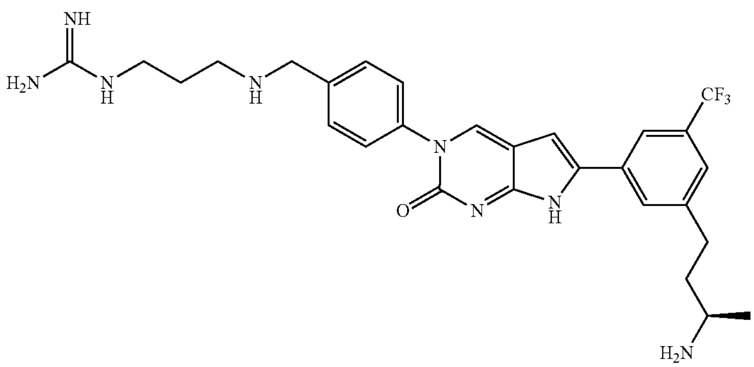 [SMILES: C[C@@H](N)CCc1cc(-c2cc3cn(-c4ccc(CNCCCNC(=N)N)cc4)c(=O)nc3[nH]2)cc(C(F)(F)F)c1] | |
| 201 | 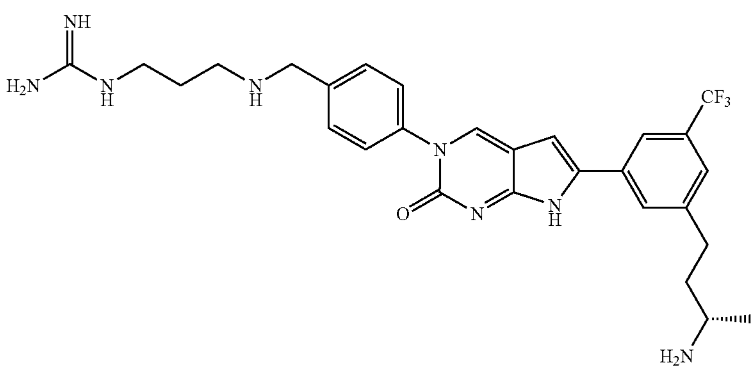 [SMILES: C[C@H](N)CCc1cc(-c2cc3cn(-c4ccc(CNCCCNC(=N)N)cc4)c(=O)nc3[nH]2)cc(C(F)(F)F)c1] | |
| 202 | 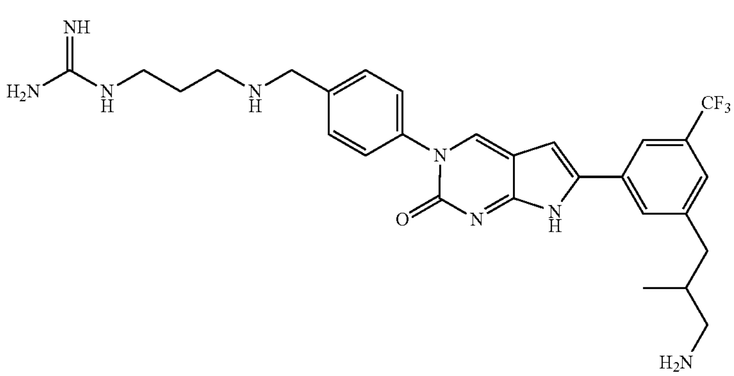 [SMILES: CC(CN)Cc1cc(-c2cc3cn(-c4ccc(CNCCCNC(=N)N)cc4)c(=O)nc3[nH]2)cc(C(F)(F)F)c1] | |

TABLE 1-continued
| Comp. No. | Structure | LCMS |
|---|---|---|
| 203 | 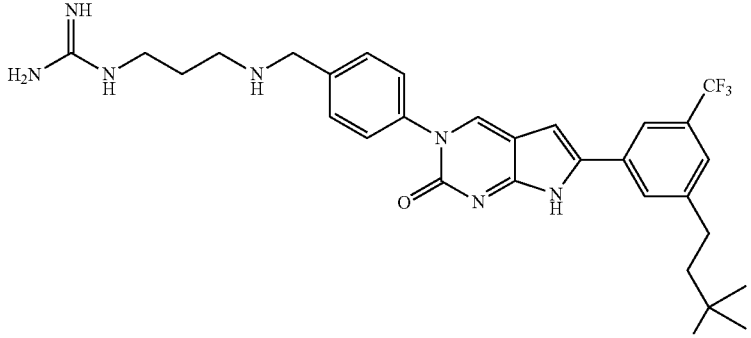 | |
| 204 | 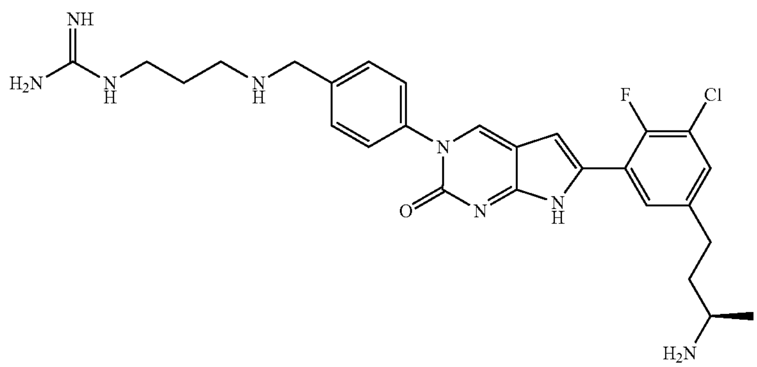 [SMILES: C[C@@H](N)CCc1cc(Cl)c(F)c(-c2cc3cn(-c4ccc(CNCCCNC(=N)N)cc4)c(=O)nc3[nH]2)c1] | |
| 205 | 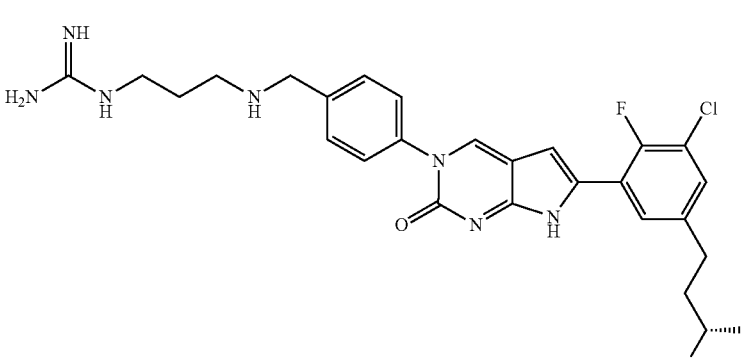 | |
| 206 | 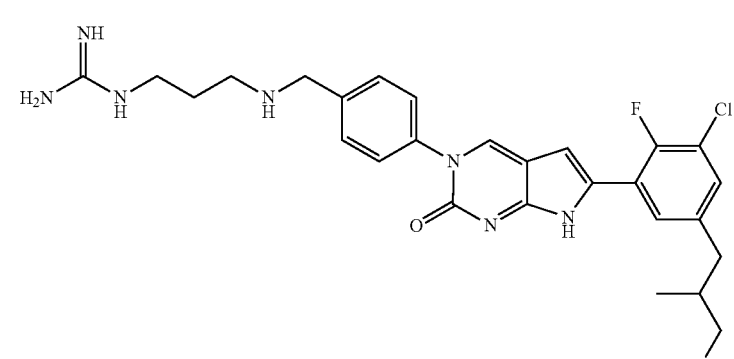 | |

TABLE 1-continued

| Comp. No. | Structure | LCMS |
|---|---|---|
| 207 | 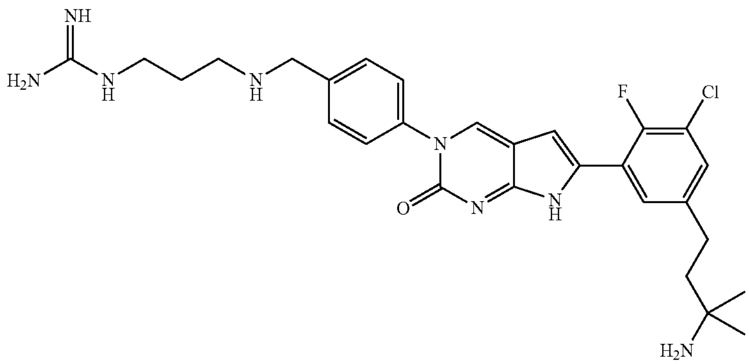 [SMILES: CC(C)(N)CCc1cc(Cl)c(F)c(-c2cc3cn(-c4ccc(CNCCCNC(=N)N)cc4)c(=O)nc3[nH]2)c1] | |
| 208 | 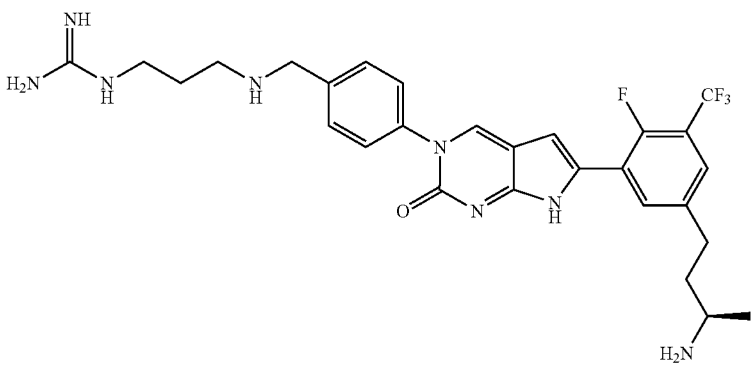 [SMILES: C[C@@H](N)CCc1cc(-c2cc3cn(-c4ccc(CNCCCNC(=N)N)cc4)c(=O)nc3[nH]2)c(F)c(C(F)(F)F)c1] | |
| 209 | 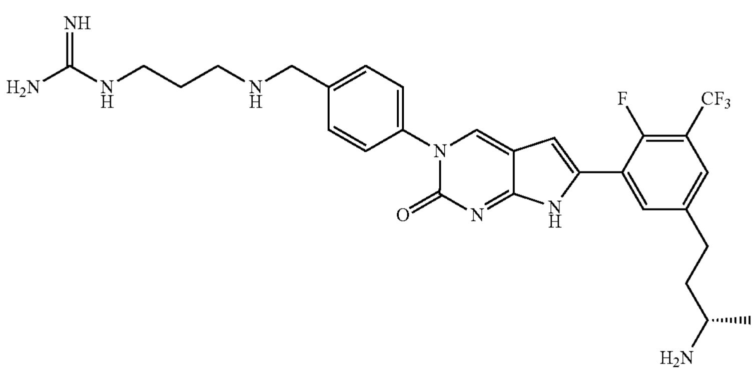 [SMILES: C[C@H](N)CCc1cc(-c2cc3cn(-c4ccc(CNCCCNC(=N)N)cc4)c(=O)nc3[nH]2)c(F)c(C(F)(F)F)c1] | |
| 210 | 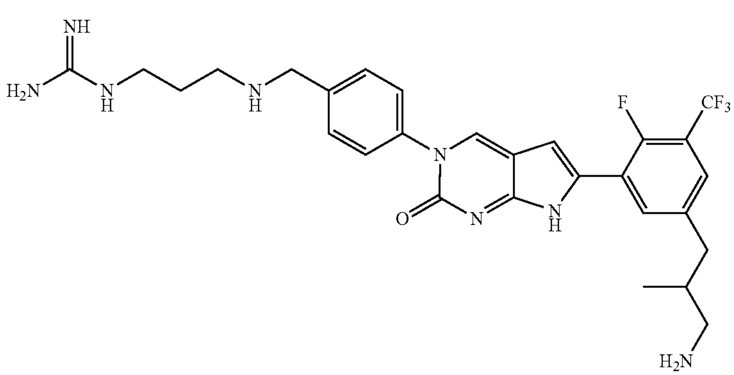 [SMILES: CC(CN)Cc1cc(-c2cc3cn(-c4ccc(CNCCCNC(=N)N)cc4)c(=O)nc3[nH]2)c(F)c(C(F)(F)F)c1] | |

TABLE 1-continued

| Comp. No. | Structure | LCMS |
|---|---|---|
| 211 | 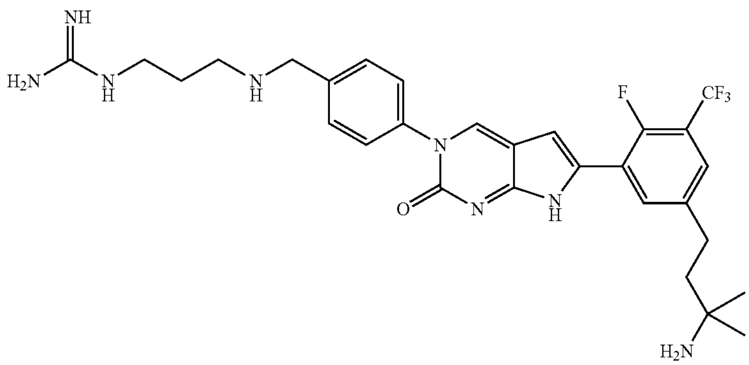 | |
| 212 | 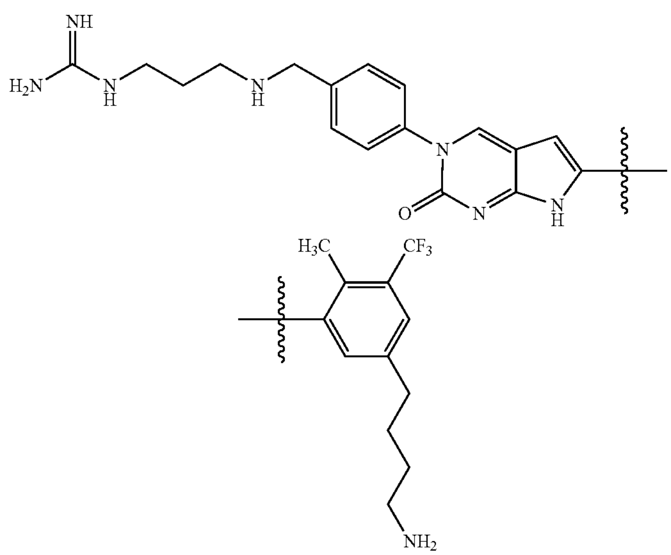 | 569.0 |
| 213 | 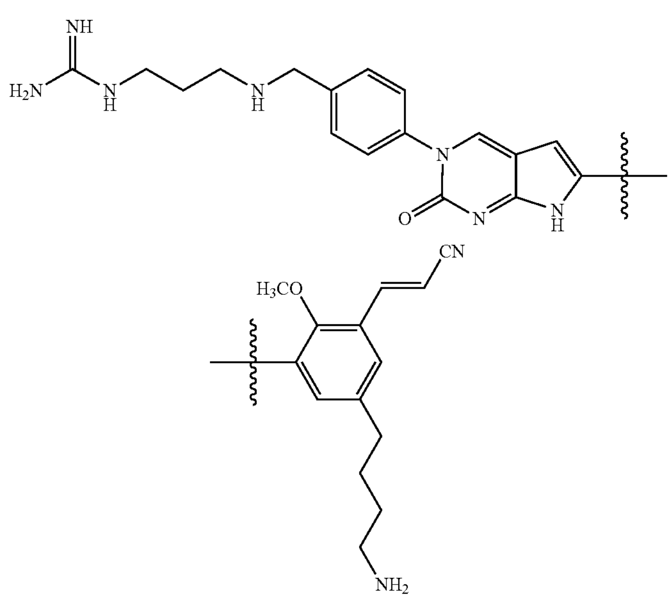 | 568.1 |

TABLE 1-continued

| Comp. No. | Structure | LCMS |
|---|---|---|
| 214 | 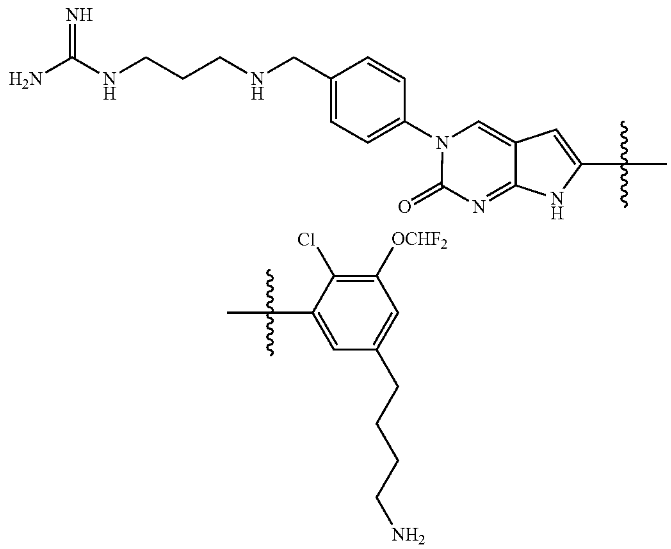 | 587.1 |
| 215 | 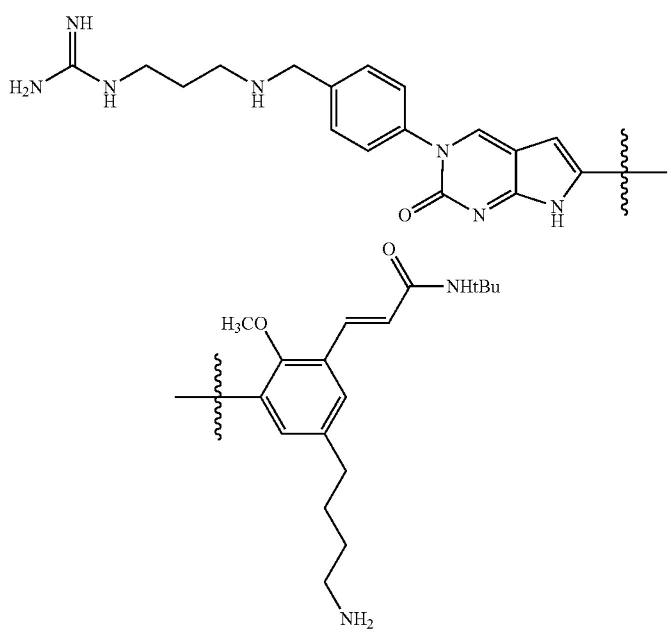 | 642.3 |

TABLE 1-continued
| Comp. No. | Structure | LCMS |
|---|---|---|
| 216 | 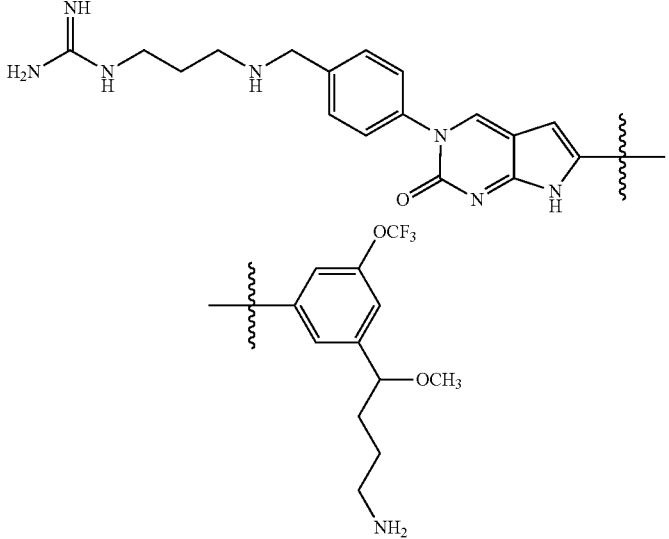 | 601.0 |
| 217 | 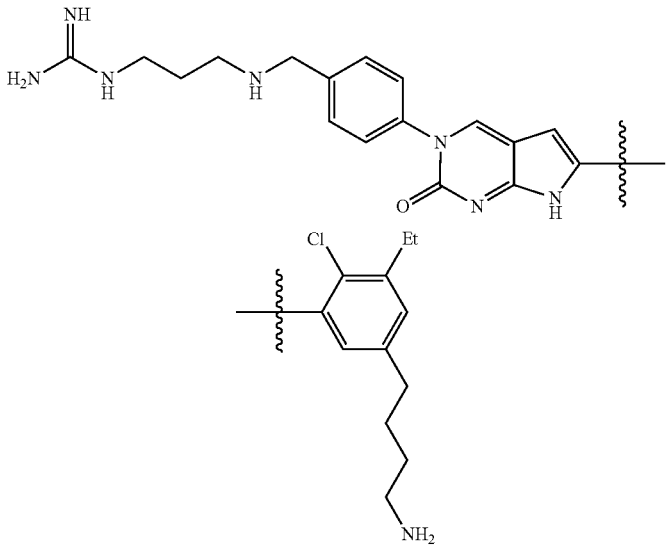 | 549.1 |

TABLE 1-continued

| Comp. No. | Structure | LCMS |
|---|---|---|
| 218 | 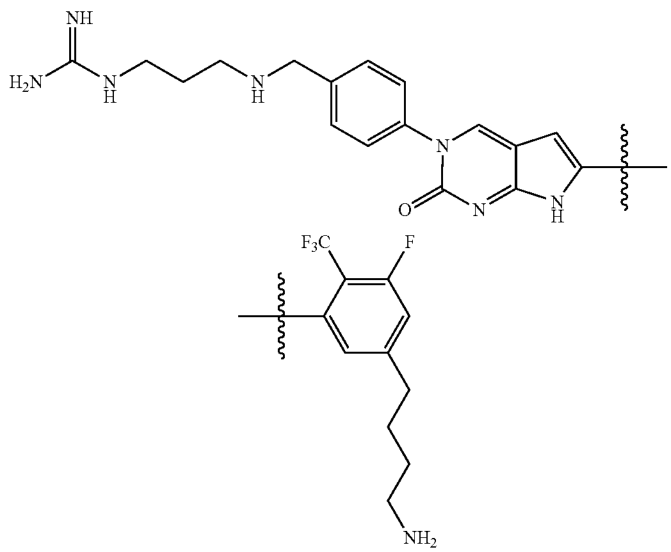 | 573.0 |
| 219 | 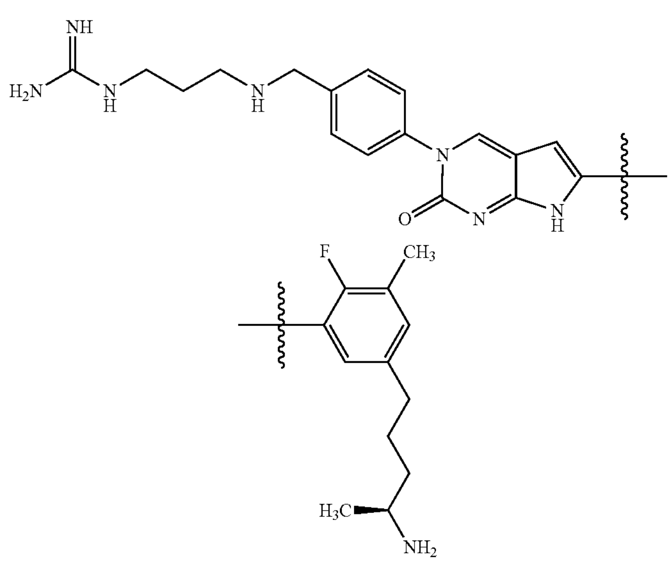 | 533.1 |

TABLE 1-continued
| Comp. No. | Structure | LCMS |
|---|---|---|
| 220 | 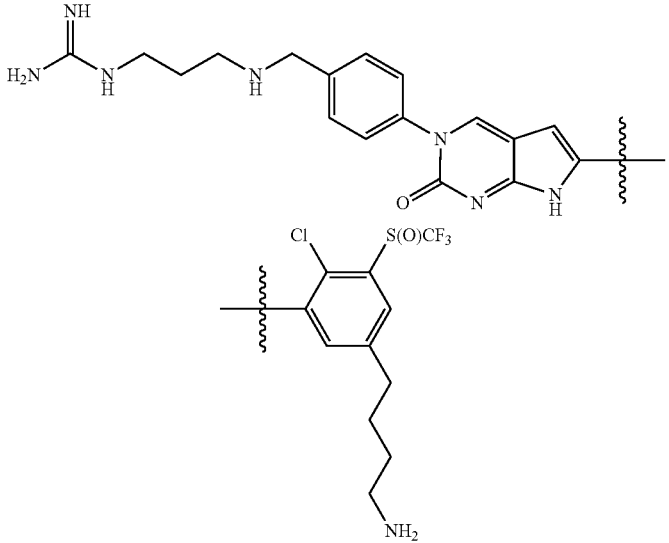 | 637.0 |
| 221 | 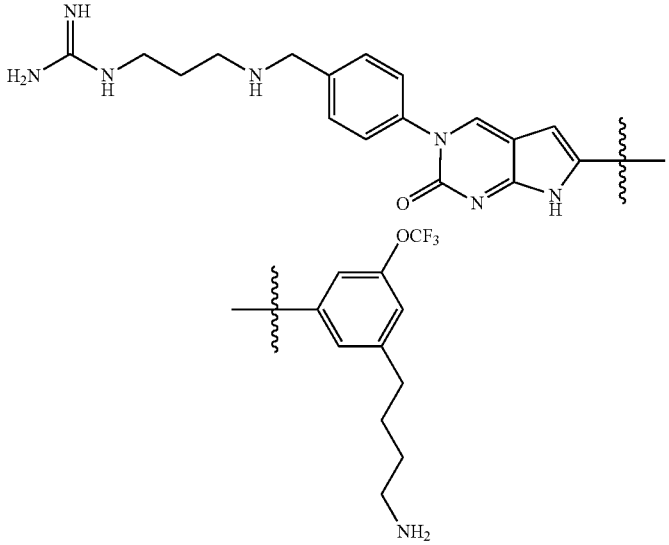 | 570.1 |

TABLE 1-continued
| Comp. No. | Structure | LCMS |
|---|---|---|
| 222 | 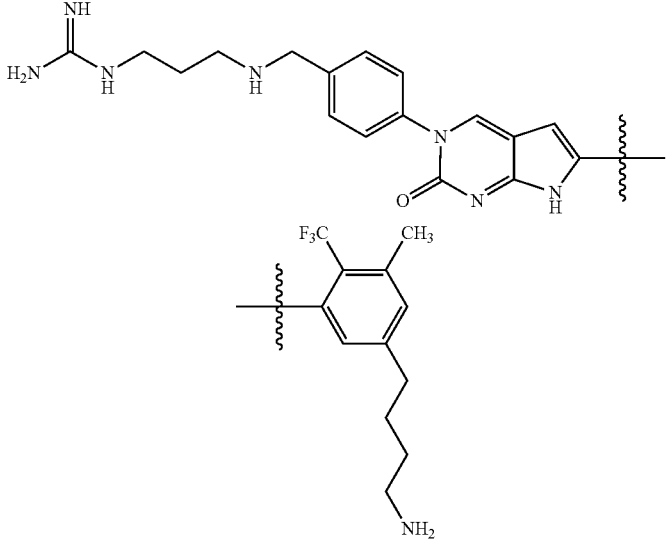 | 569.0 |
| 223 | 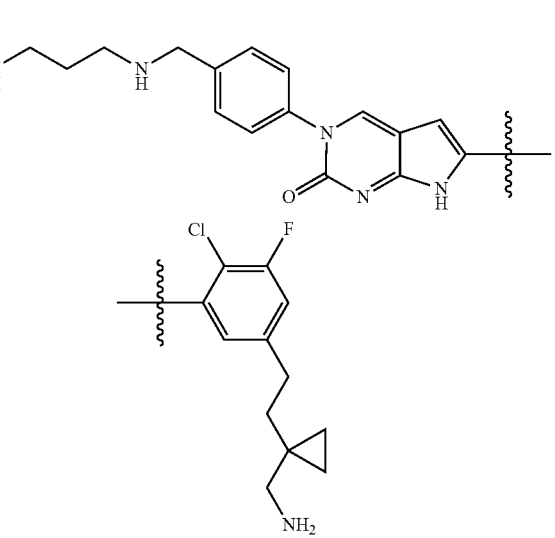 | 565.0 |
| 224 | 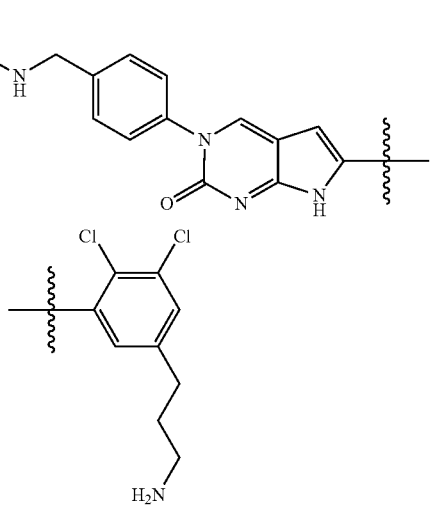 | 541.0 |

TABLE 1-continued
| Comp. No. | Structure | LCMS |
|---|---|---|
| 225 | 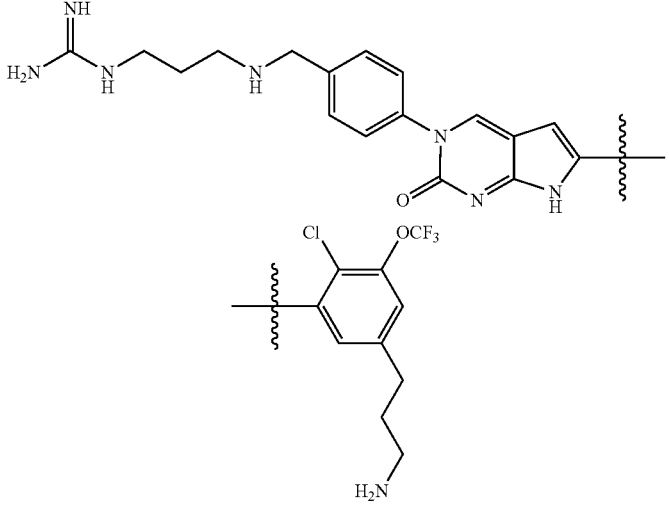 | 591.0 |
| 226 | 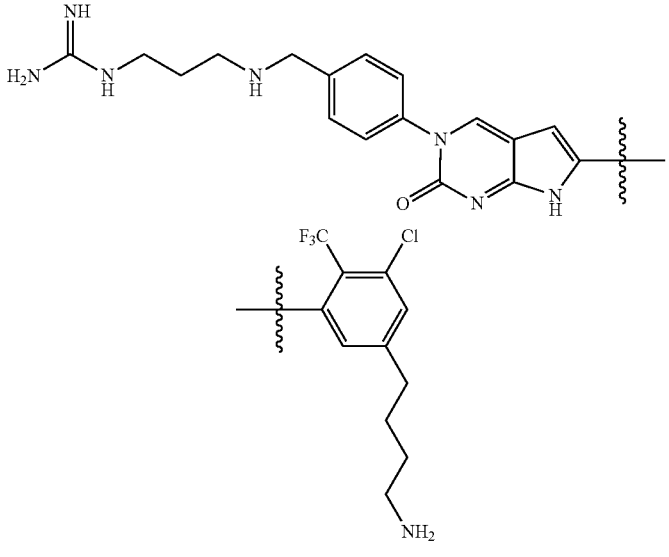 | 589.0 [M] |
| 227 | 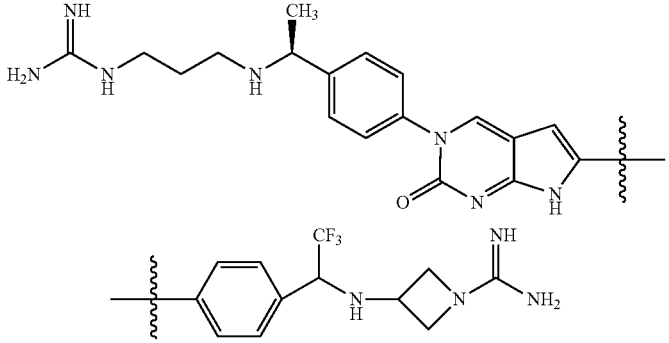 | 624.1 |

TABLE 1-continued
| Comp. No. | Structure | LCMS |
|---|---|---|
| 228 | 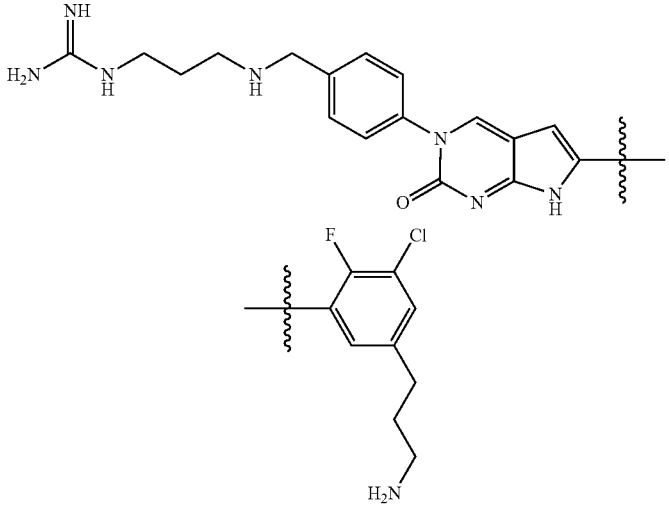 | 525.0 |
| 229 | 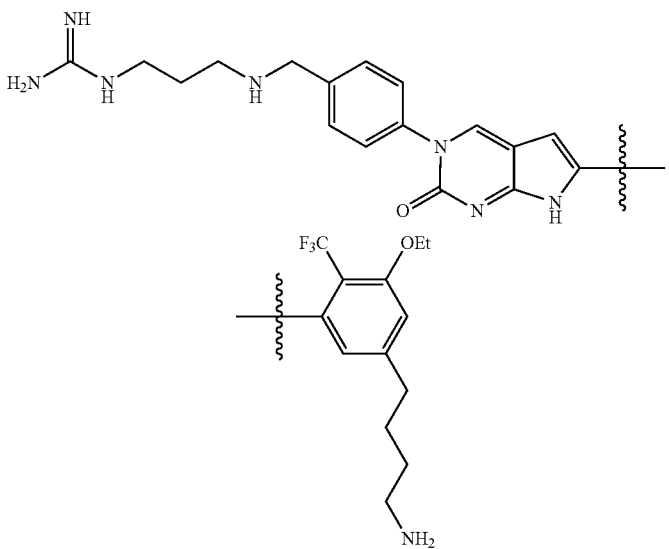 | 599.1 |
| 230 | 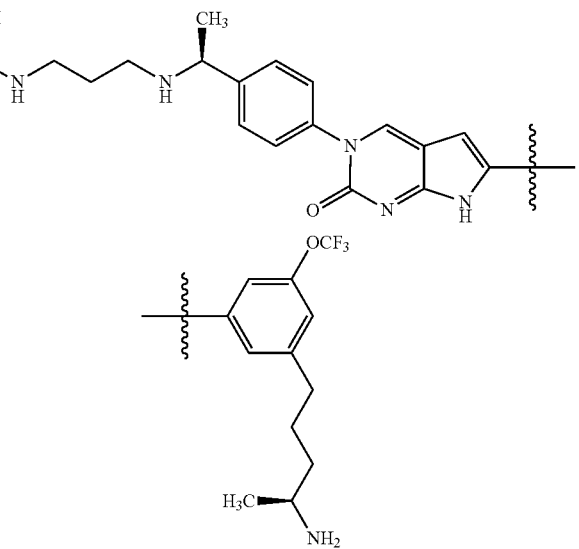 | 599.0 |

TABLE 1-continued
| Comp. No. | Structure | LCMS |
|---|---|---|
| 231 | 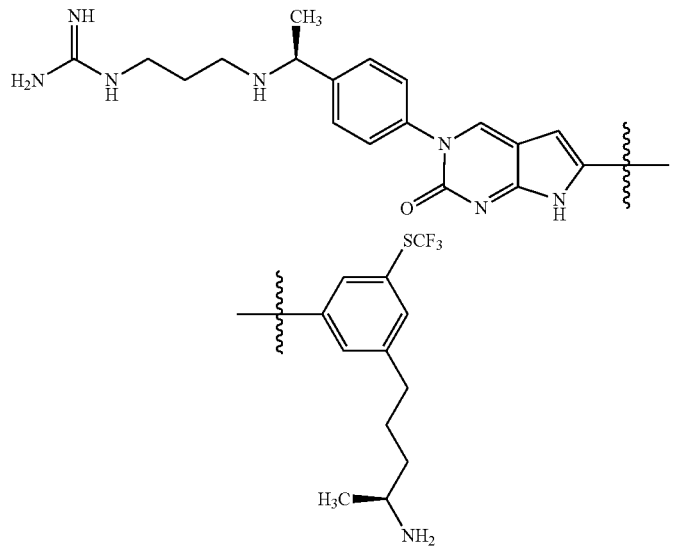 | |
| 232 | 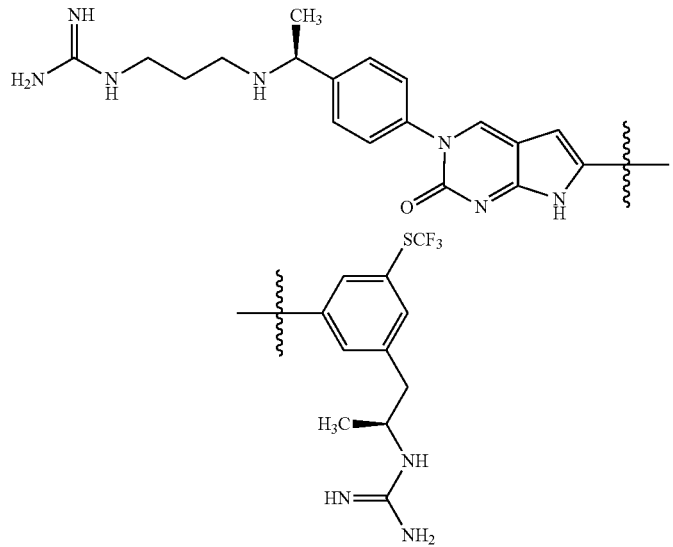 | 657.0 |

TABLE 1-continued

| Comp. No. | Structure | LCMS |
|---|---|---|
| 233 | 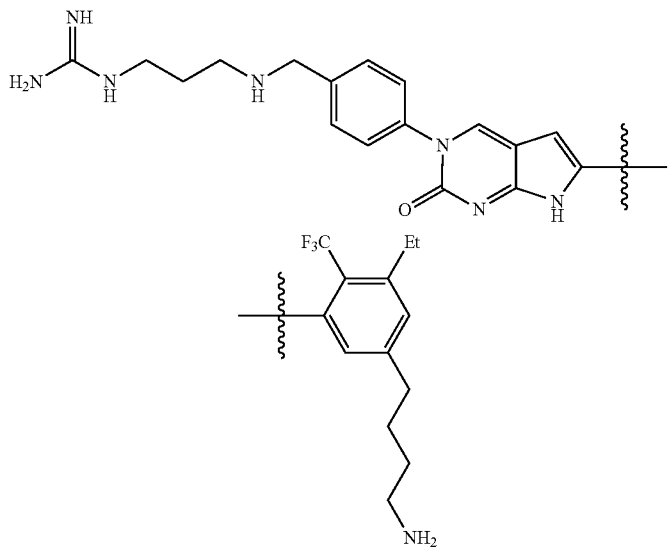 | 583.1 |
| 234 | 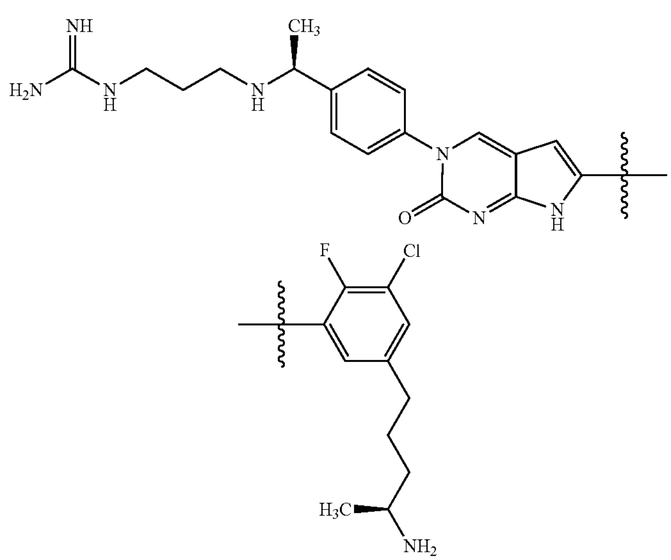 | 567.2 |

TABLE 1-continued
| Comp. No. | Structure | LCMS |
|---|---|---|
| 235 | 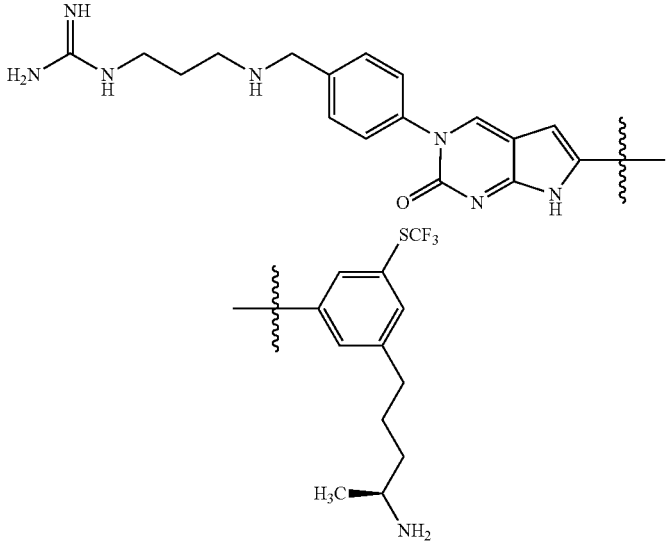 | 601.0 |
| 236 | 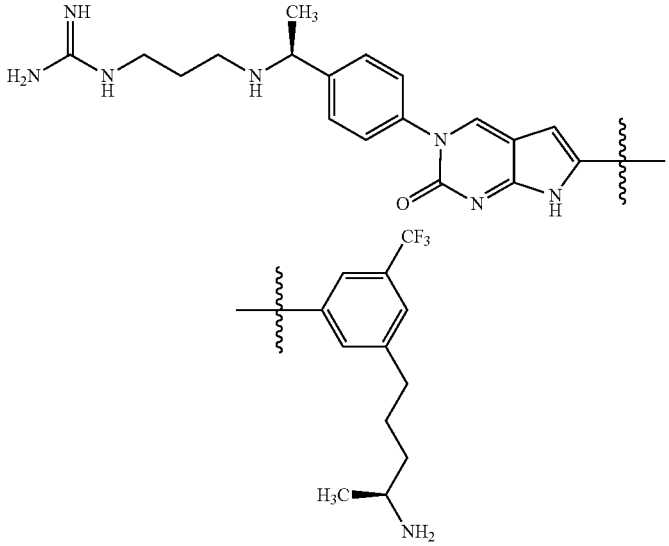 | 583.0 |

TABLE 1-continued
| Comp. No. | Structure | LCMS |
|---|---|---|
| 237 | 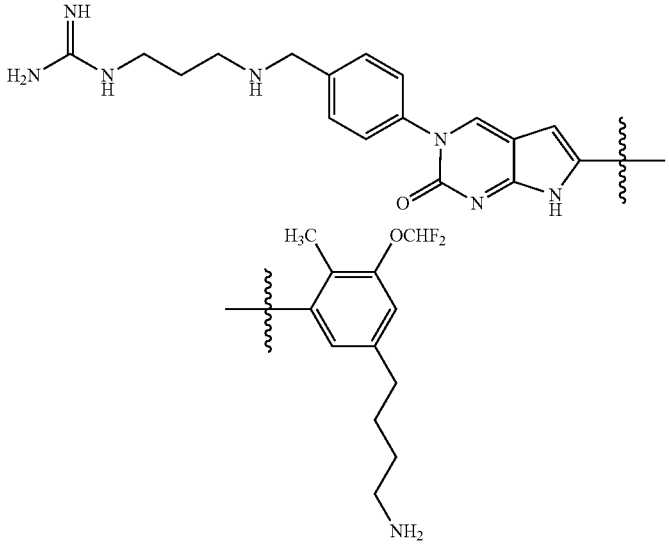 | 567.1 |
| 238 | 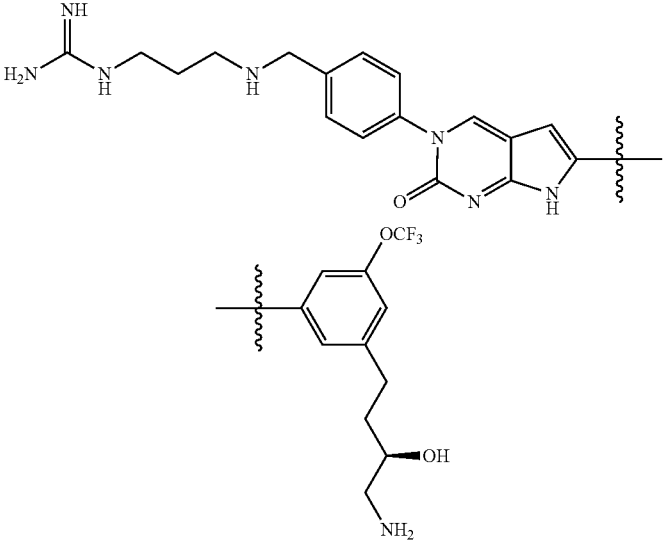 | 587.0 |

TABLE 1-continued
| Comp. No. | Structure | LCMS |
|---|---|---|
| 239 | 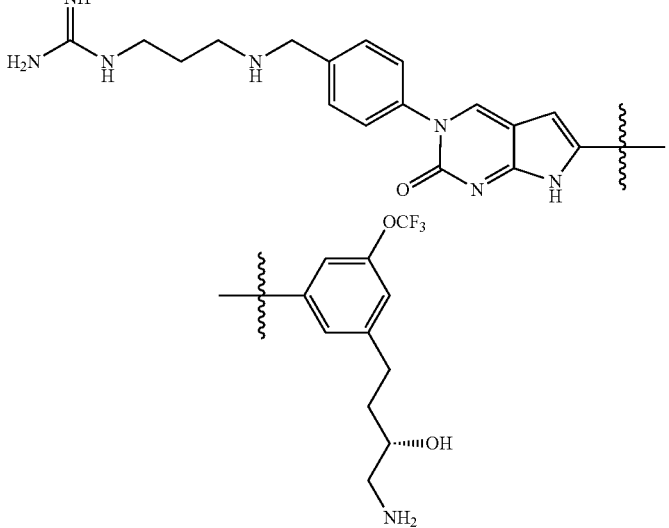 | 587.0 |
| 240 | 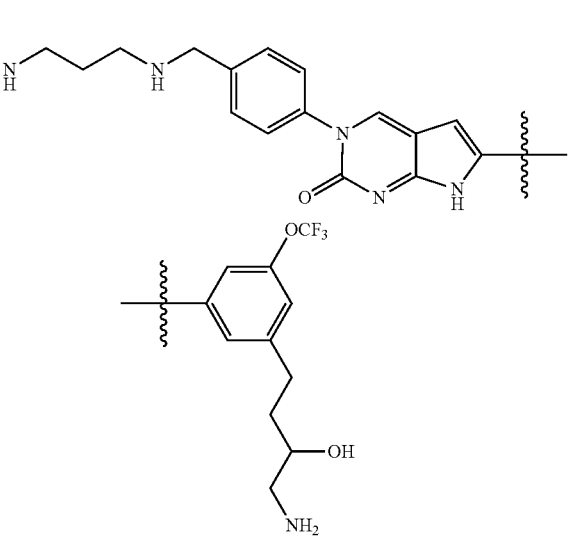 | 587.0 |
| 241 | 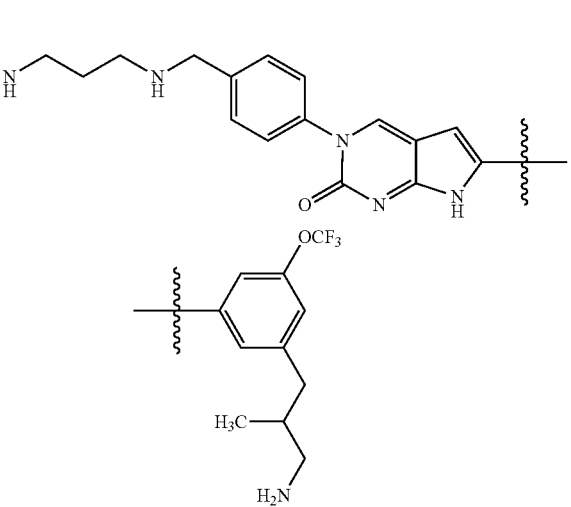 | 571.0 |

TABLE 1-continued
| Comp. No. | Structure | LCMS |
|---|---|---|
| 242 | 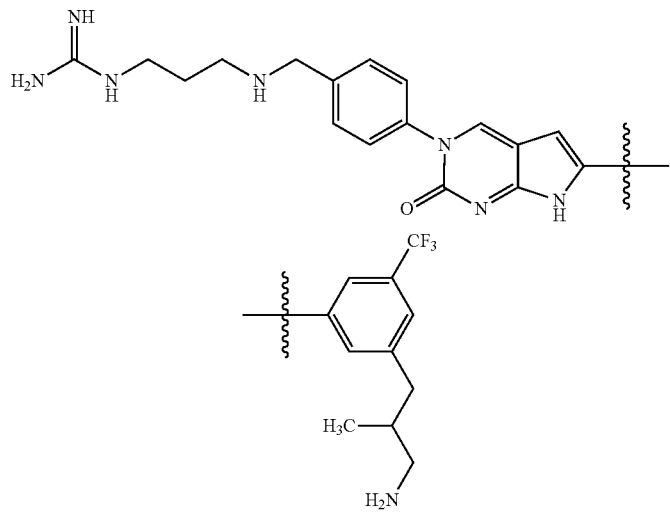 | 555.0 |
| 243 | 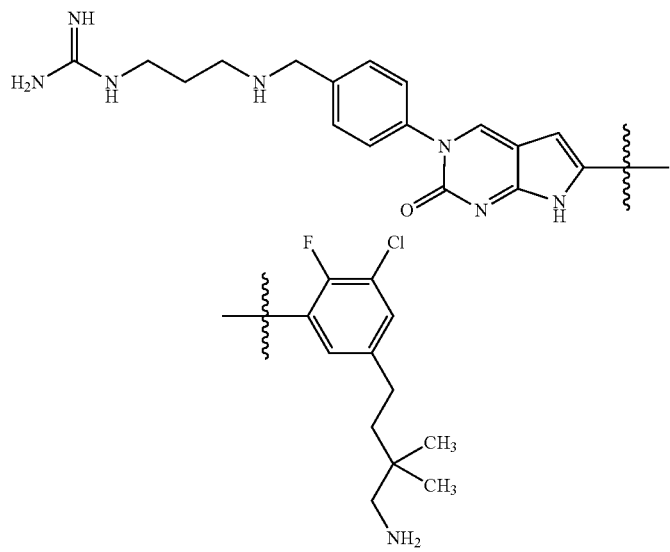 | 567.0 |

TABLE 1-continued
| Comp. No. | Structure | LCMS |
|---|---|---|
| 244 | 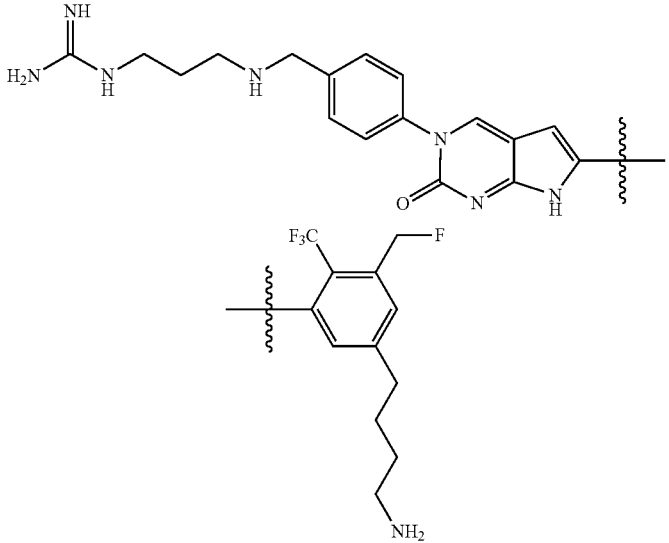 | 587.1 |
| 245 | 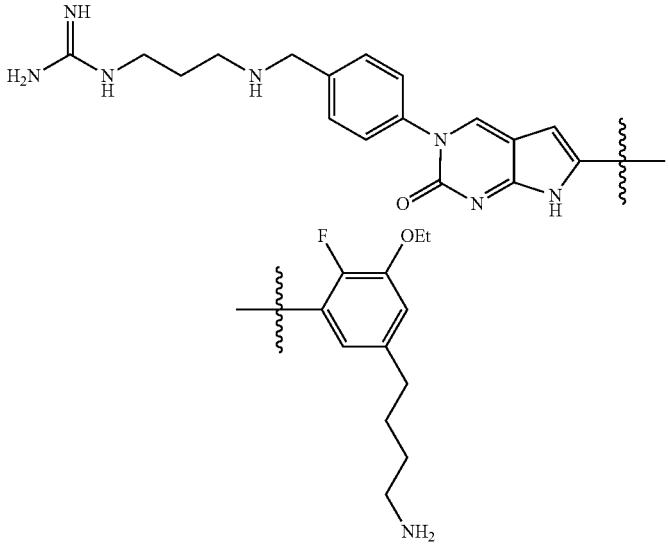 | 549.1 |

TABLE 1-continued
| Comp. No. | Structure | LCMS |
|---|---|---|
| 246 | 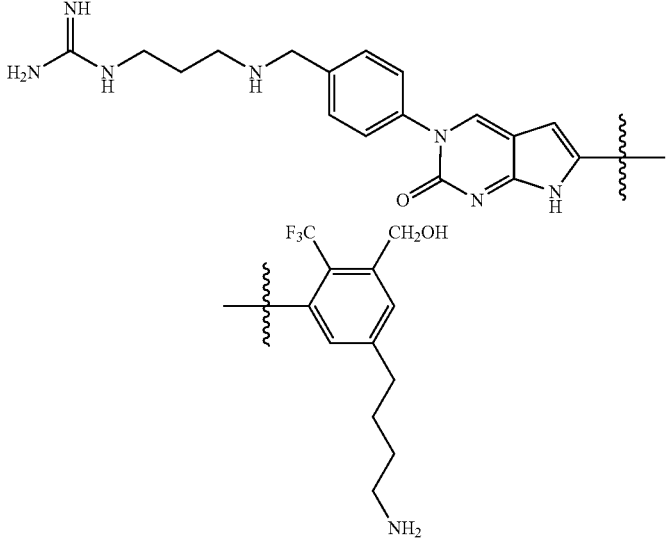 | 585.1 |
| 247 | 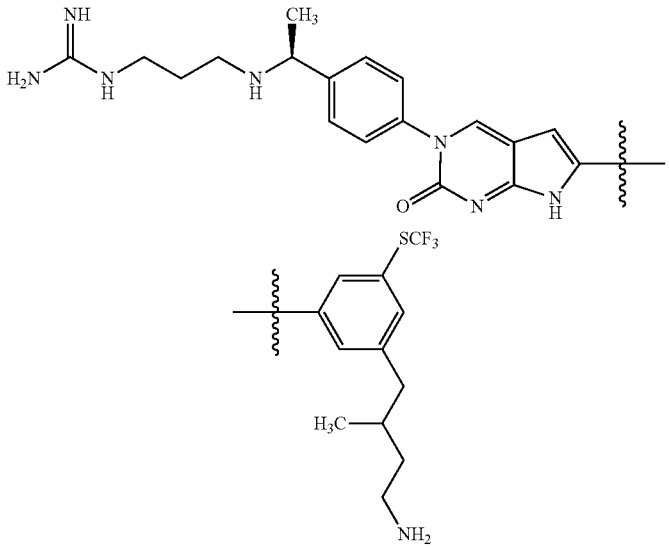 | 615.1 |

TABLE 1-continued
| Comp. No. | Structure | LCMS |
|---|---|---|
| 248 | 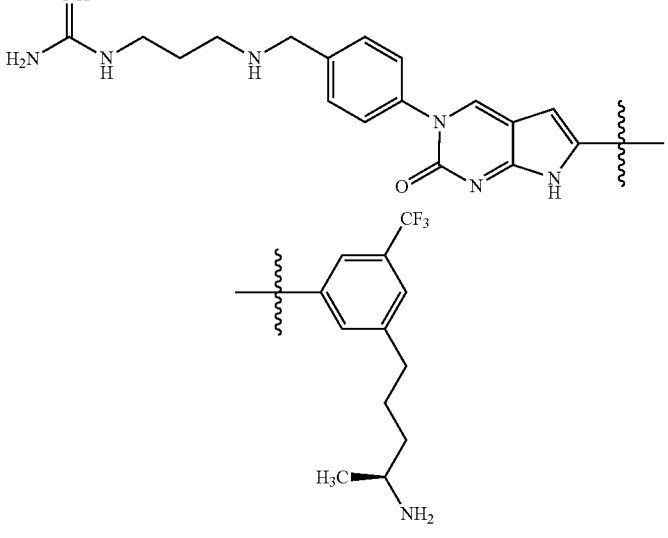 | 569.1 |
| 249 | 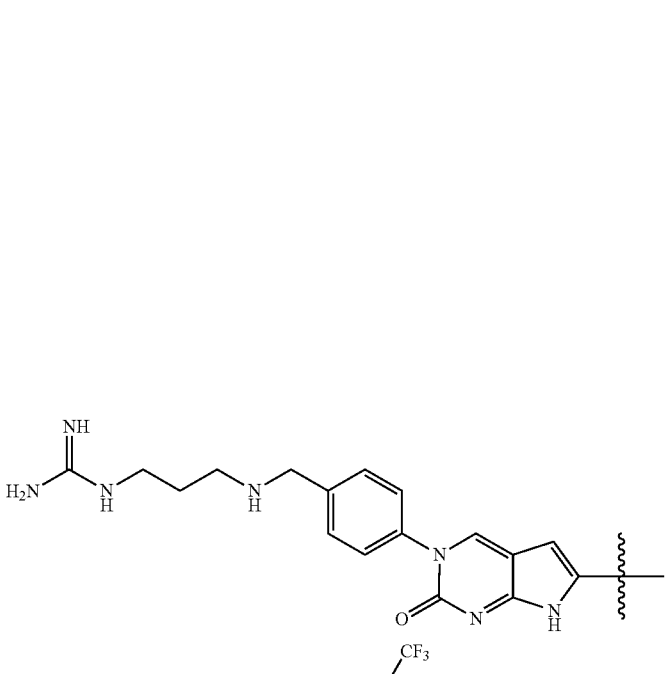 | 569.1 |

TABLE 1-continued

| Comp. No. | Structure | LCMS |
|---|---|---|
| 250 | 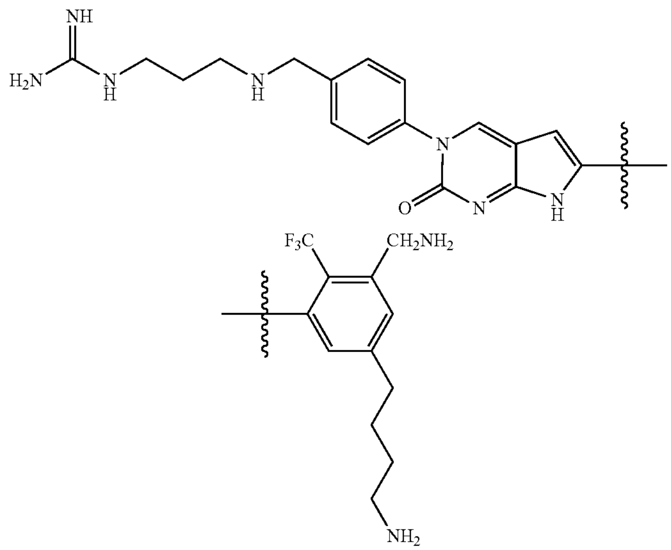 | 584.3 |
| 251 | 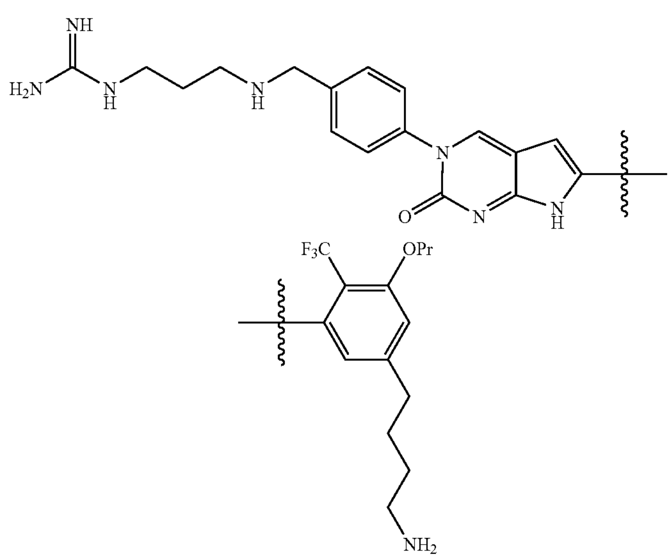 | 613.1 |

TABLE 1-continued
| Comp. No. | Structure | LCMS |
|---|---|---|
| 252 | 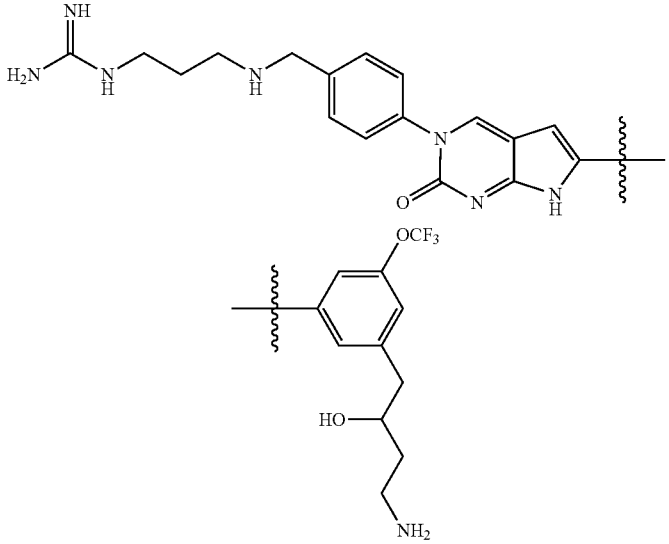 | 587.0 |
| 253 | 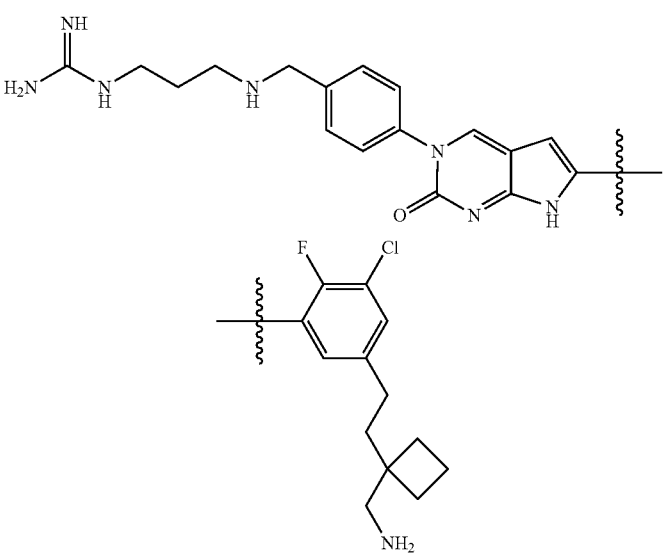 | |

TABLE 1-continued
| Comp. No. | Structure | LCMS |
|---|---|---|
| 254 | 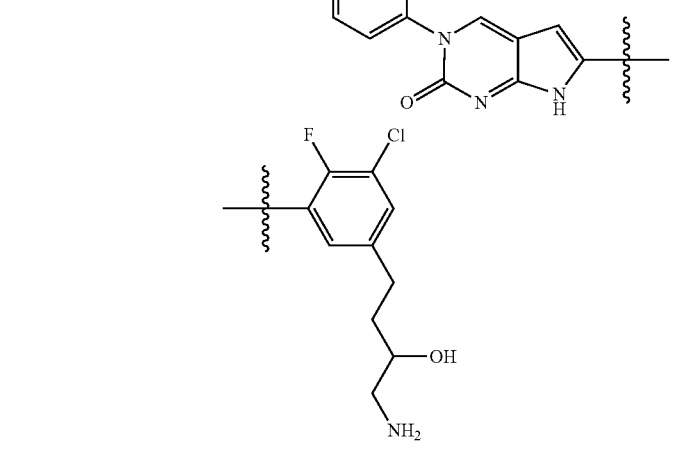 | |
| 255 | 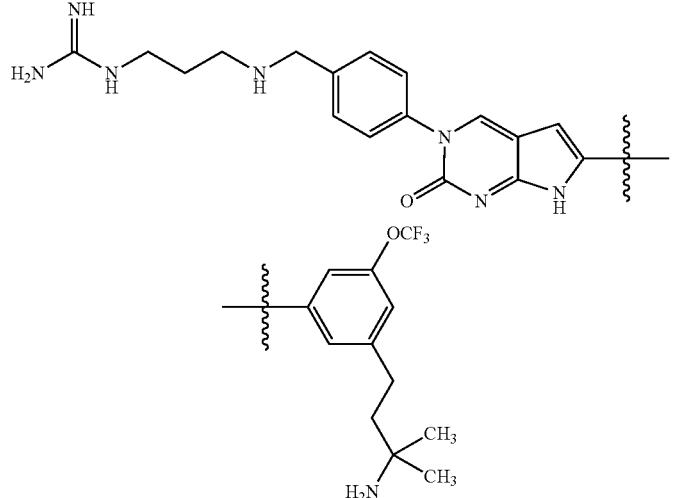 | |
| 256 | 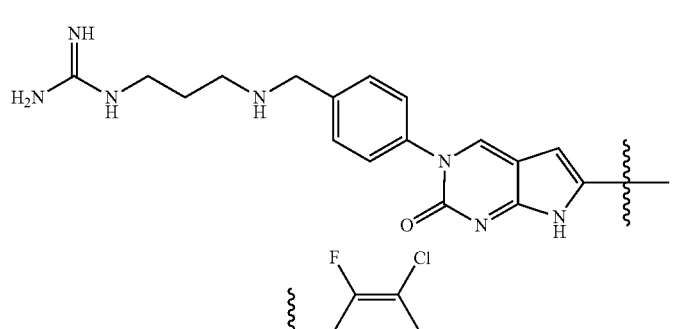 | |

US 9,221,827 B2
TABLE 1-continued
| Comp. No. | Structure | LCMS |
|---|---|---|
| 257 | 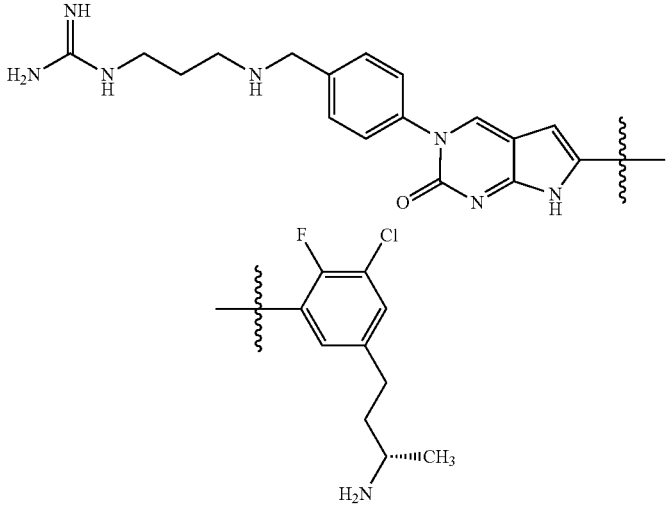 | |
| 258 | 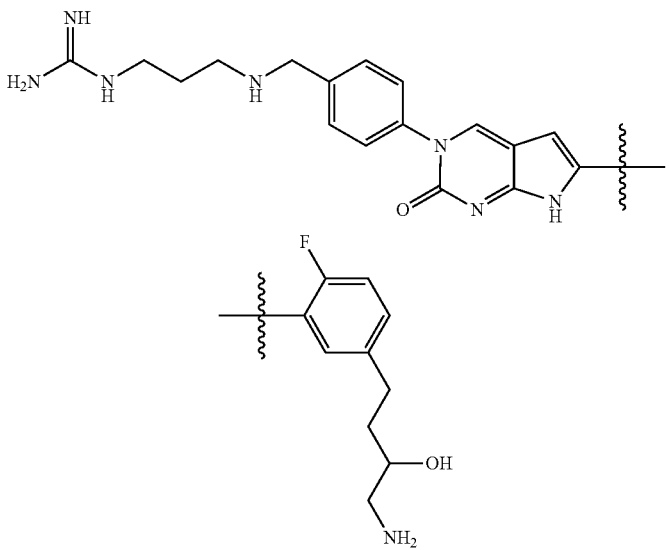 [SMILES: *c1cc2cn(-c3ccc(CNCCCNC(=N)N)cc3)c(=O)nc2[nH]1 ; *c1cc(CCC(O)CN)ccc1F] | |
| 259 | 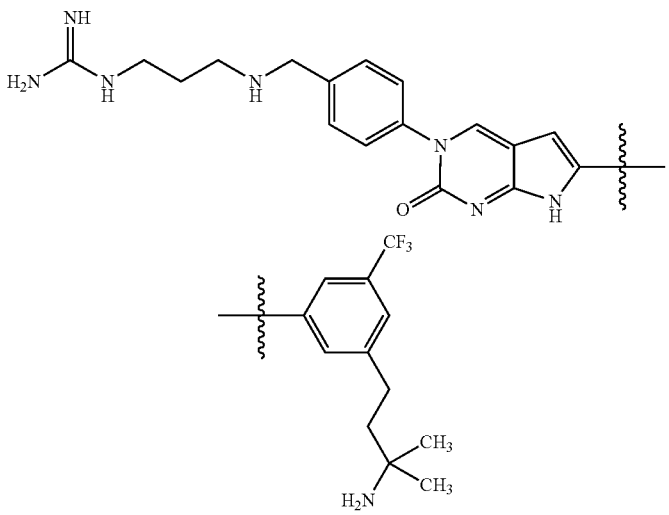 | |

TABLE 1-continued
| Comp. No. | Structure | LCMS |
|---|---|---|
| 260 | 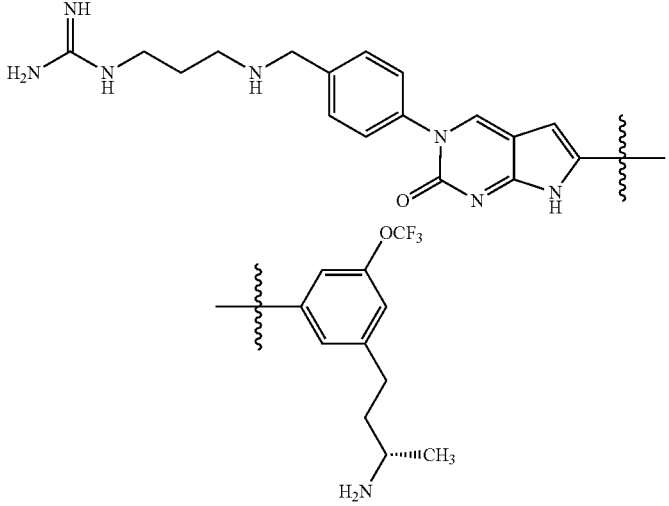 | |
| 261 | 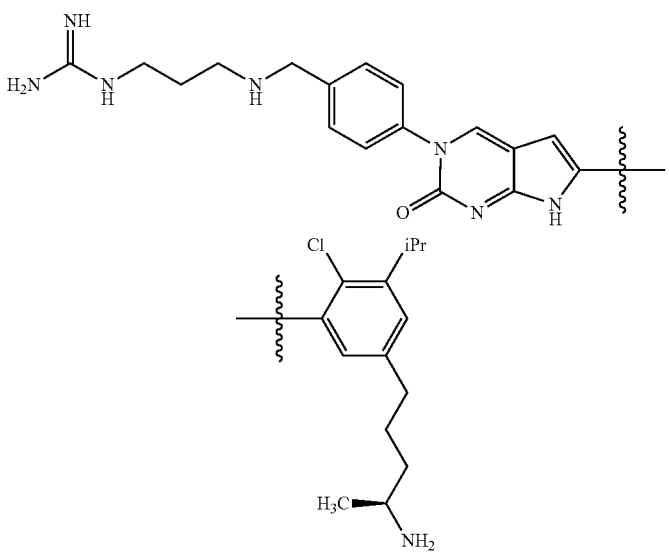 | 577.1 |
| 262 | 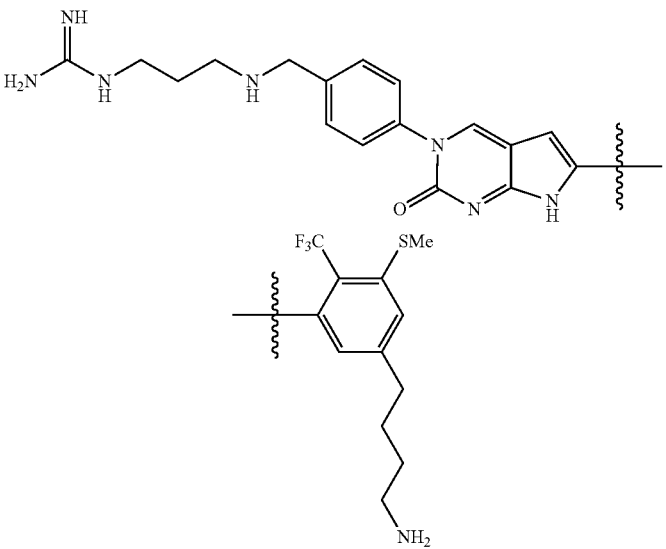 | 601.1 |

TABLE 1-continued
| Comp. No. | Structure | LCMS |
|---|---|---|
| 263 | 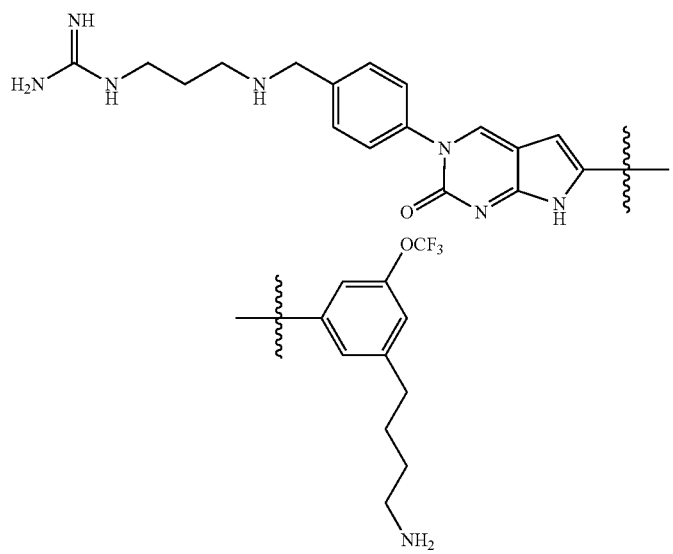 | 556.1 |
| 264 | 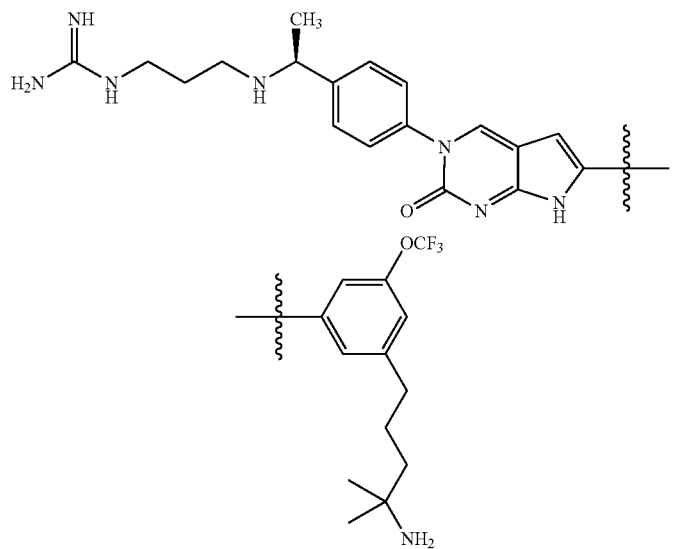 | 613.2 |

TABLE 1-continued
| Comp. No. | Structure | LCMS |
|---|---|---|
| 265 | 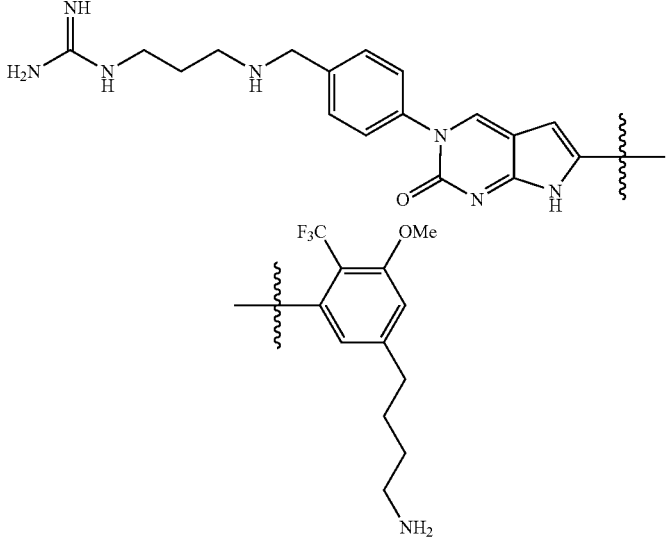 | 585.1 |
| 266 | 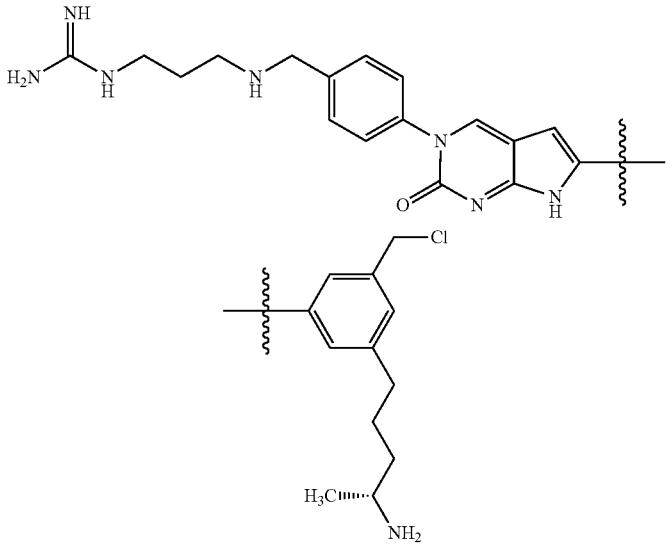 | 549.1 |

TABLE 1-continued
| Comp. No. | Structure | LCMS |
|---|---|---|
| 267 | 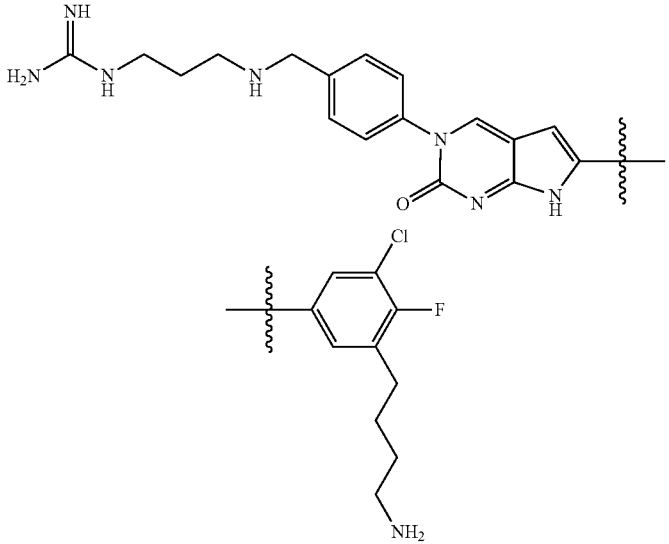 | 539.1 |
| 268 | 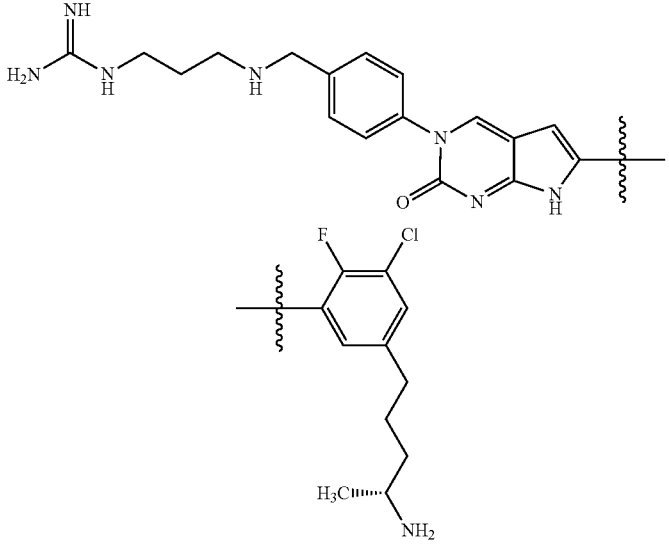 | 553.3 |

TABLE 1-continued
| Comp. No. | Structure | LCMS |
|---|---|---|
| 269 | 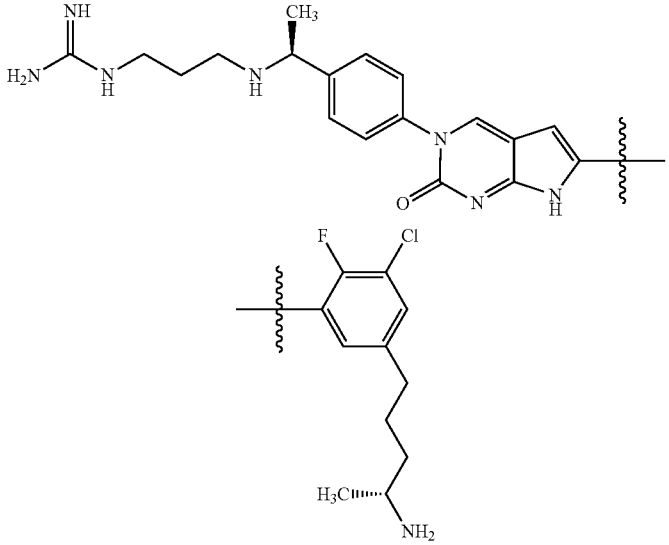 | 567.3 |
| 270 | 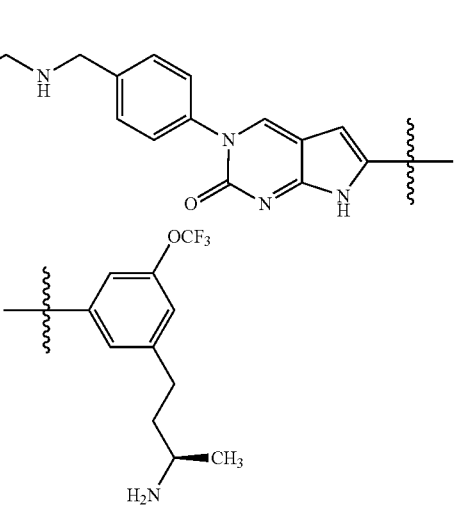 | |
| 271 | 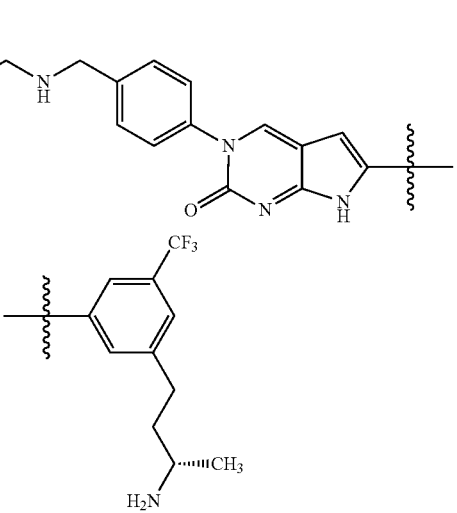 | |

TABLE 1-continued
| Comp. No. | Structure | LCMS |
|---|---|---|
| 272 | 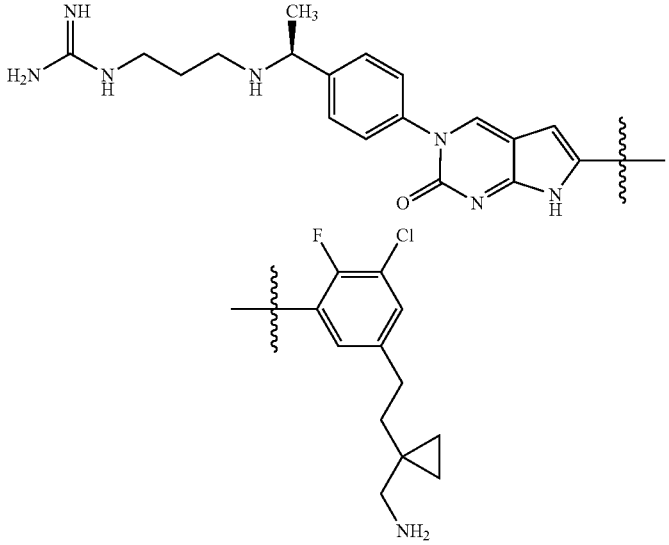 | |
| 273 | 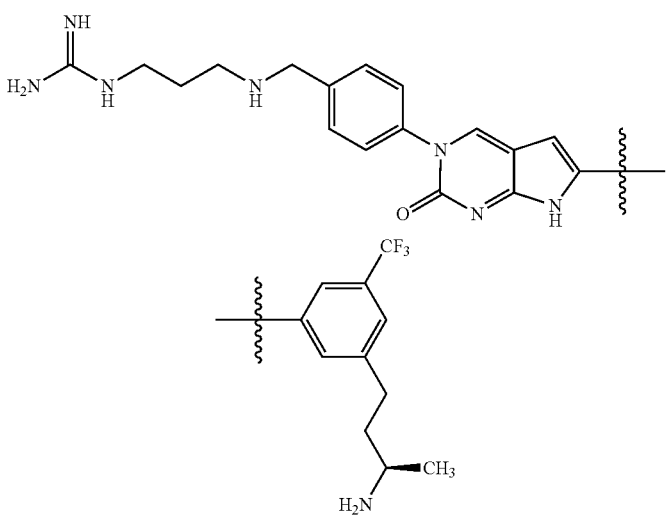 | |
| 274 | 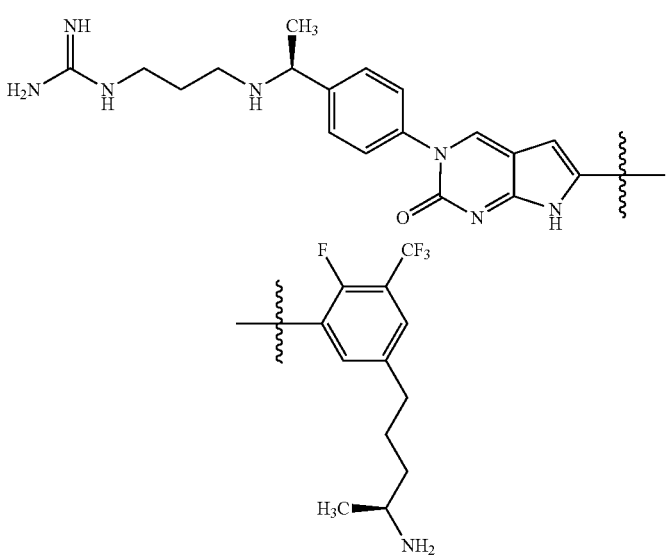 | 602.2 |

TABLE 1-continued
| Comp. No. | Structure | LCMS |
|---|---|---|
| 275 | 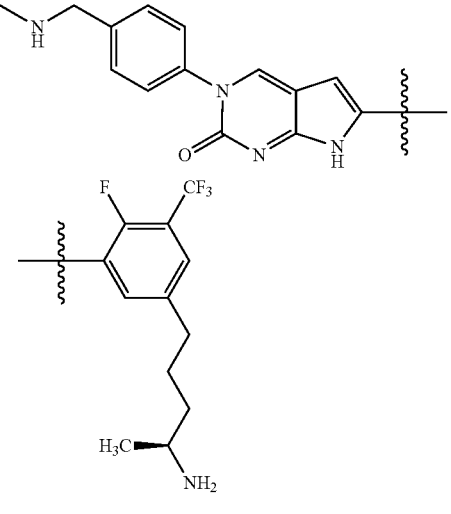 | 588.2 |
| 276 | 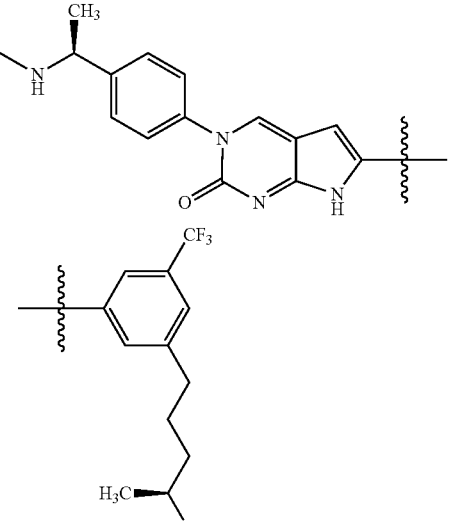 | 625.0 [M/2] + 1 |
| 277 | 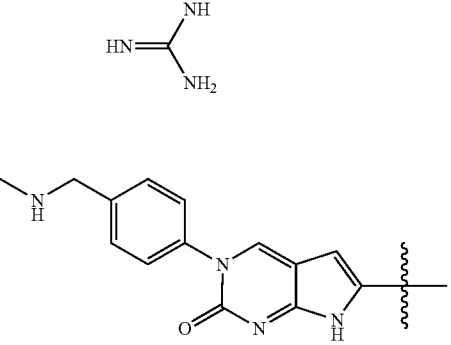 | 314.4 [M + 1]/2 |

TABLE 1-continued
| Comp. No. | Structure | LCMS |
|---|---|---|
| 278 | 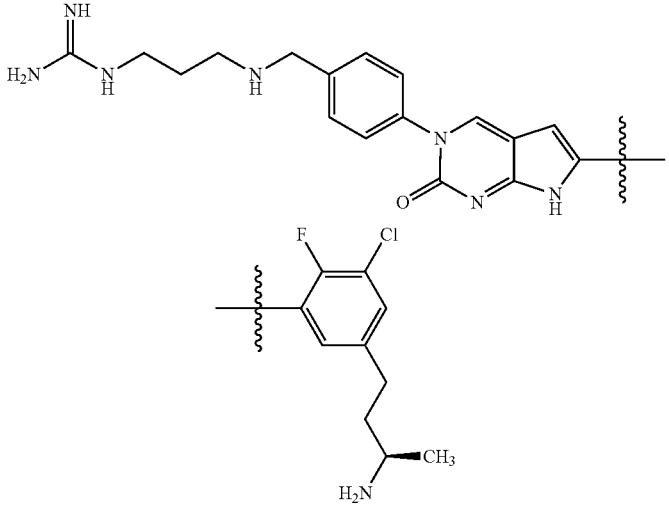 | |
| 279 | 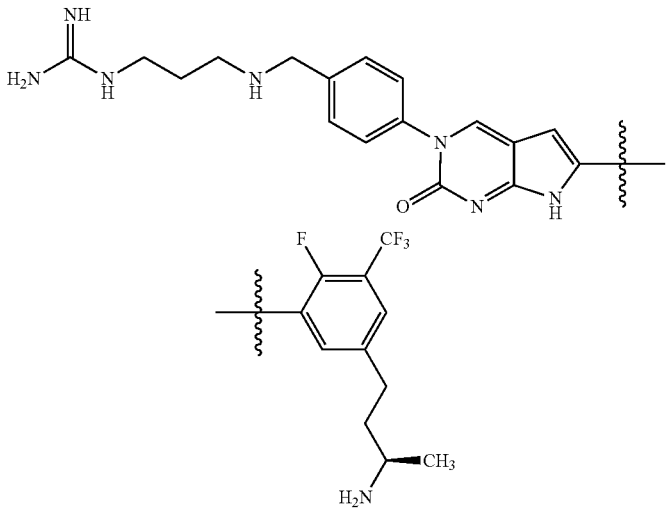 | |
| 280 | 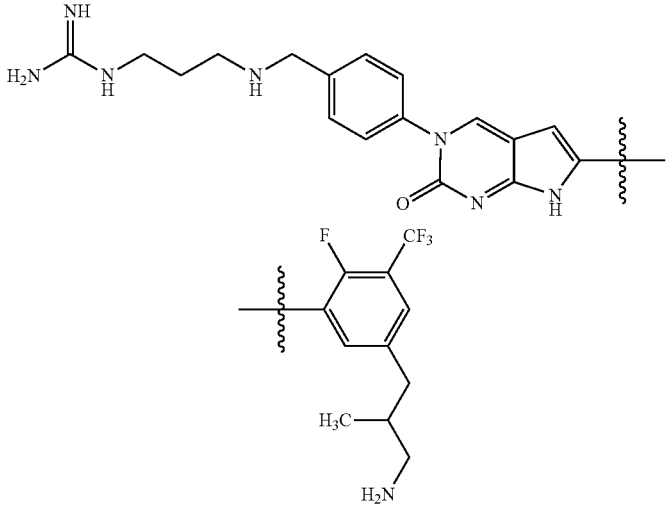 | |

TABLE 1-continued
| Comp. No. | Structure | LCMS |
|---|---|---|
| 281 | 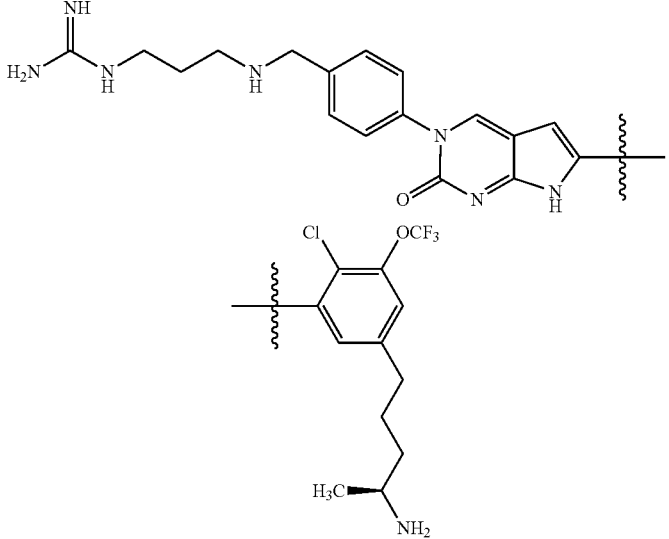 | 310.3 [M + 2H]/2 |
| 282 | 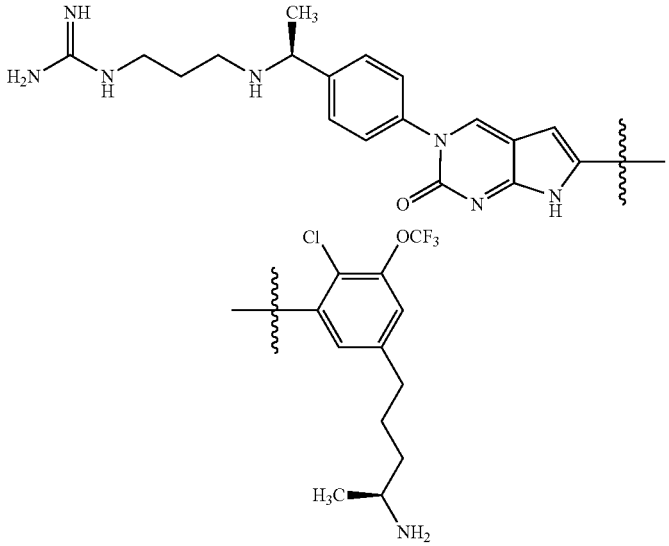 | 317.2 [M + 2H]/2 |

TABLE 1-continued
| Comp. No. | Structure | LCMS |
|---|---|---|
| 283 | 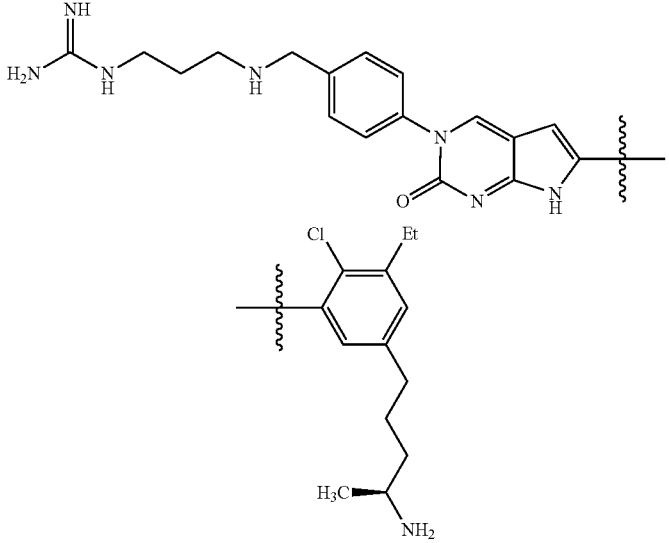 | 563.1 |
| 284 | 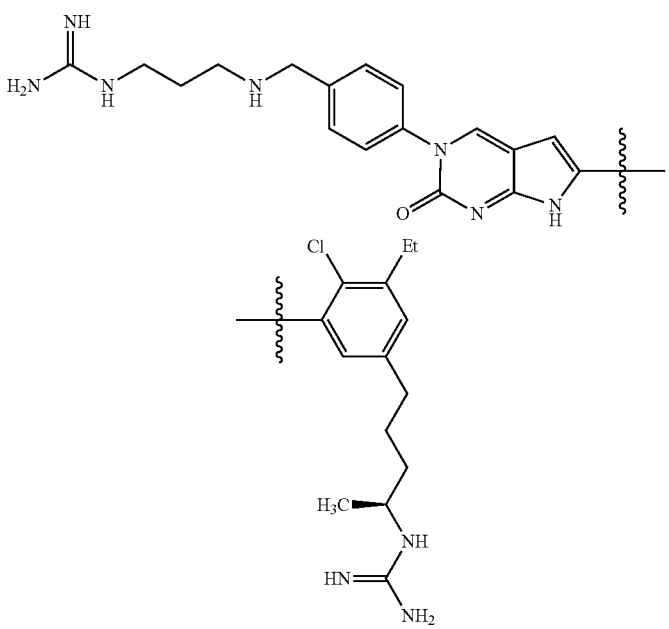 | 605.1 |

TABLE 1-continued

| Comp. No. | Structure | LCMS |
|---|---|---|
| 285 | 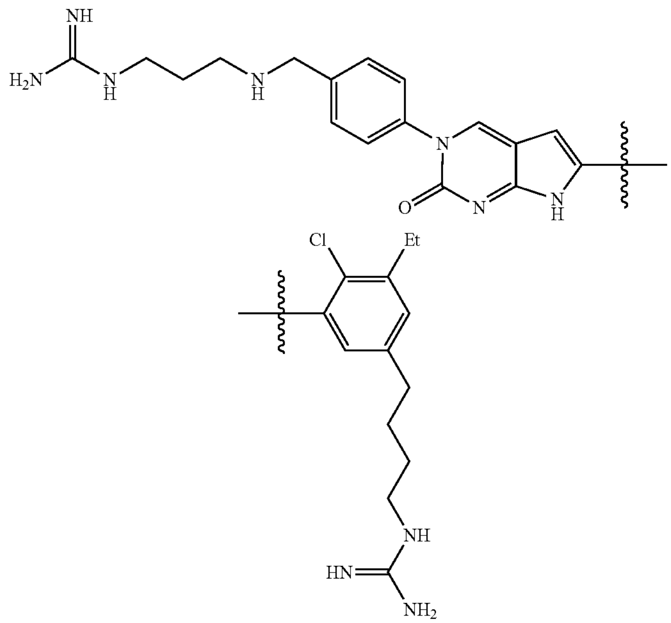 | 591.1 |
| 286 | 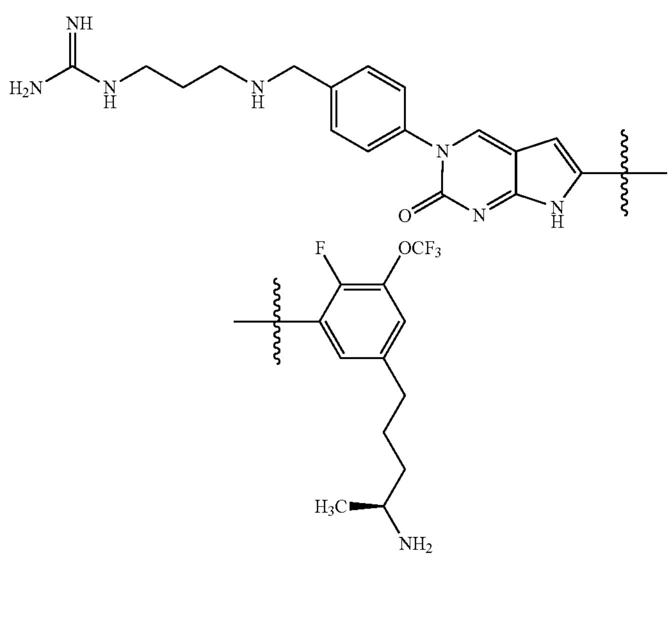 | 603.0 |

TABLE 1-continued
| Comp. No. | Structure | LCMS |
|---|---|---|
| 287 | 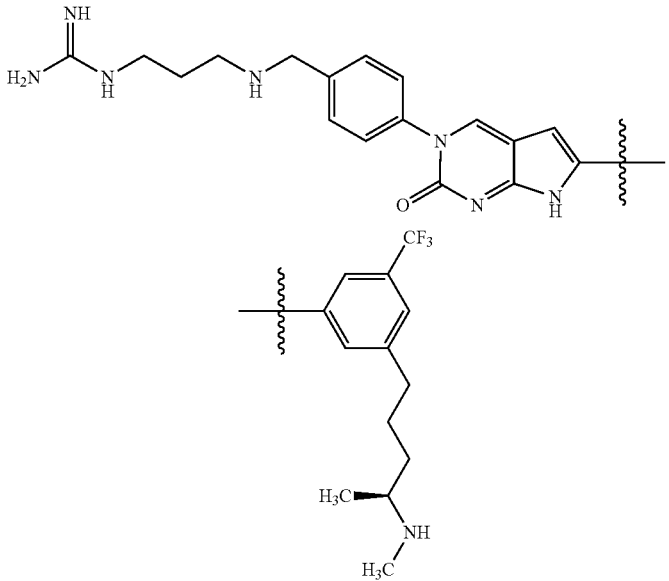 | 583.0 |
| 288 | 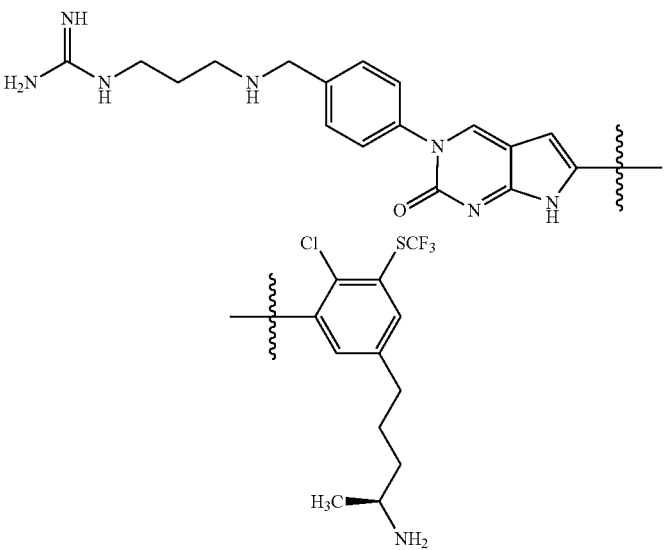 | 635.2 |

TABLE 1-continued

| Comp. No. | Structure | LCMS |
|---|---|---|
| 289 | 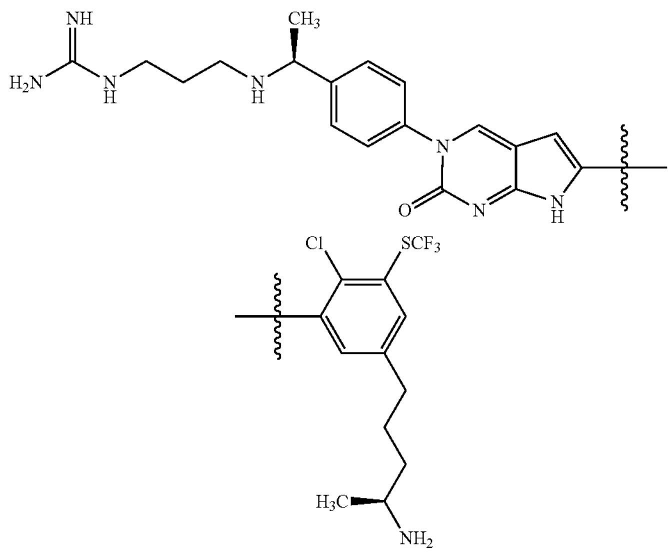 | 649.1 |
| 290 | 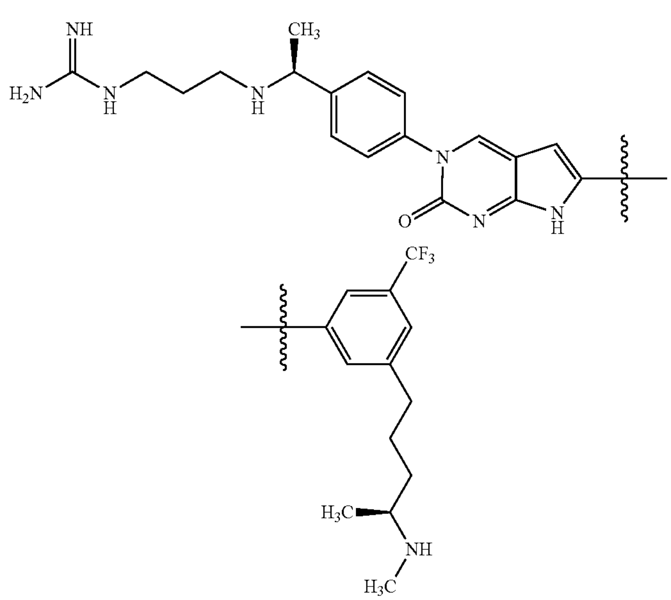 | 597.0 |

TABLE 1-continued

| Comp. No. | Structure | LCMS |
|---|---|---|
| 291 | 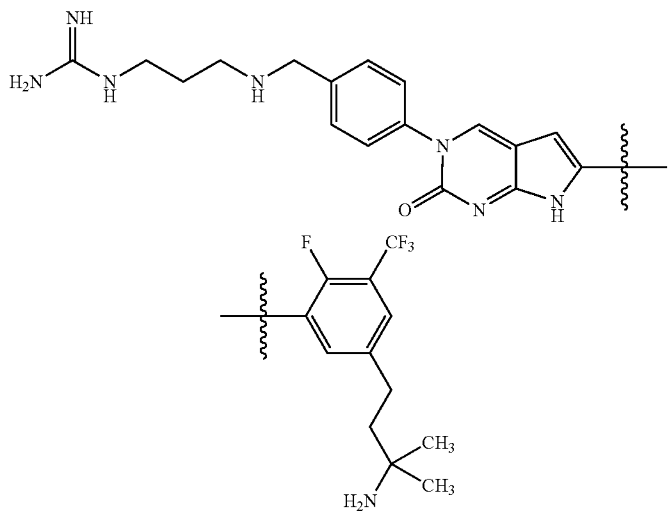 | 553.1 |
| 292 | 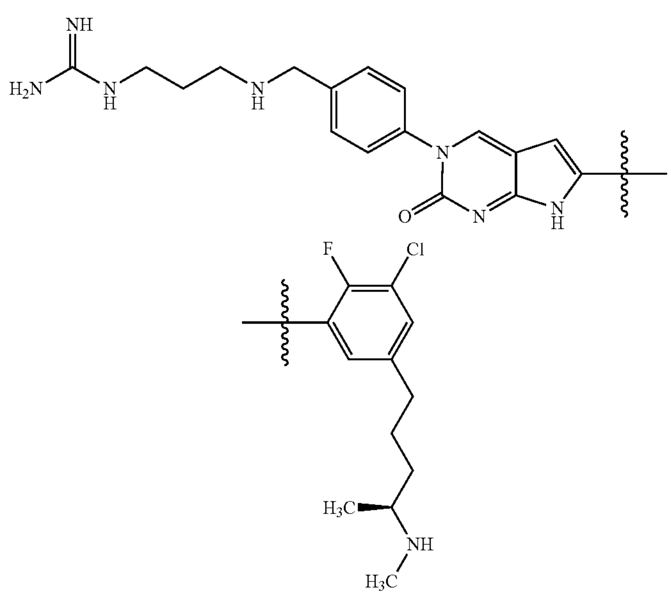 | 567.2 |

TABLE 1-continued
| Comp. No. | Structure | LCMS |
|---|---|---|
| 293 | 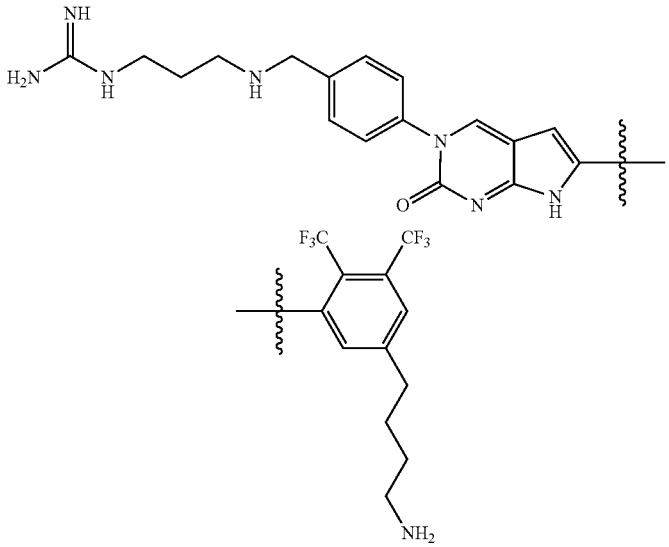 | 623.2 |
| 294 | 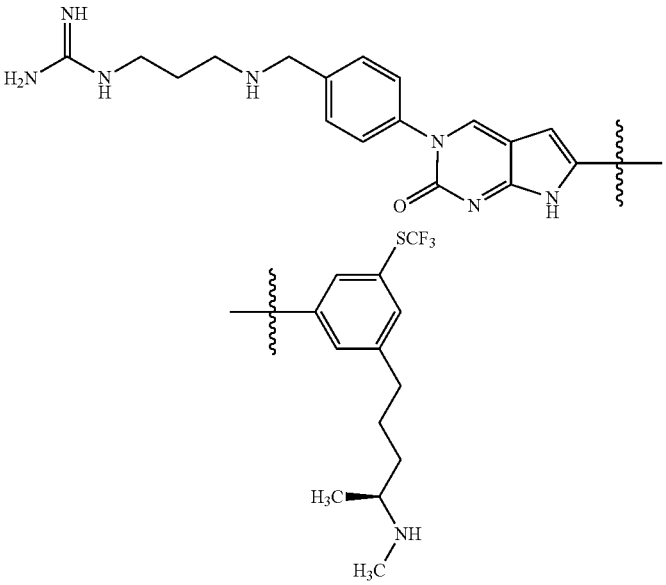 | 615.1 |

TABLE 1-continued

| Comp. No. | Structure | LCMS |
|---|---|---|
| 295 | 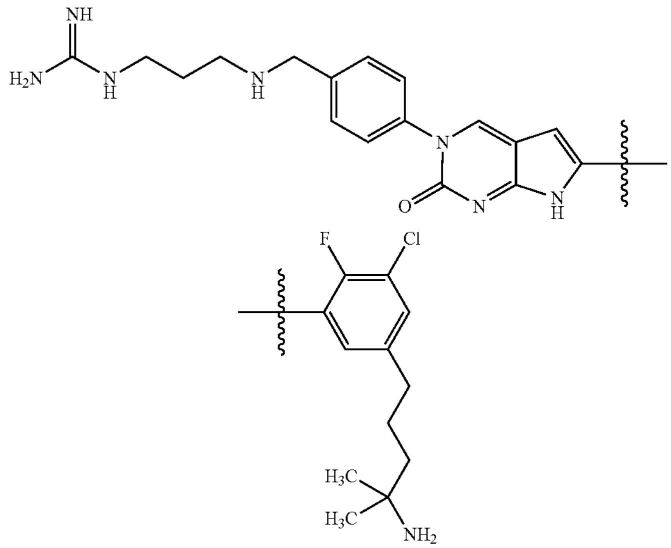 | 567.1 |
| 296 | 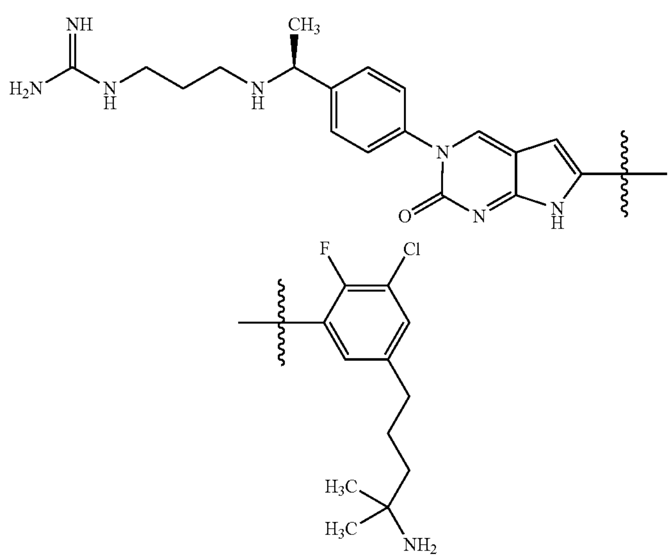 | 581.1 |

TABLE 1-continued
| Comp. No. | Structure | LCMS |
|---|---|---|
| 297 | 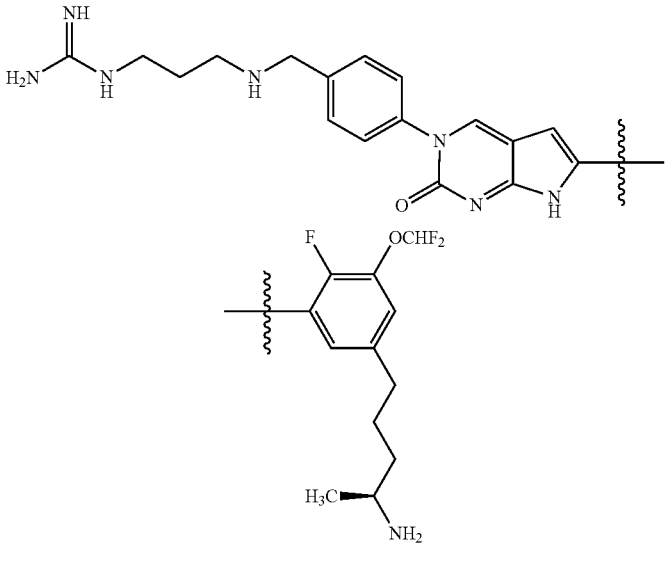 | 585.1 |
| 298 | 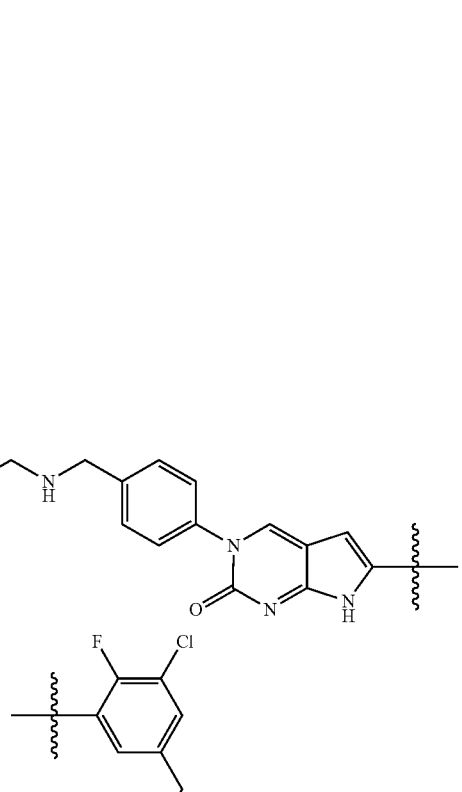 | 581.1 |

TABLE 1-continued

| Comp. No. | Structure | LCMS |
|---|---|---|
| 299 | 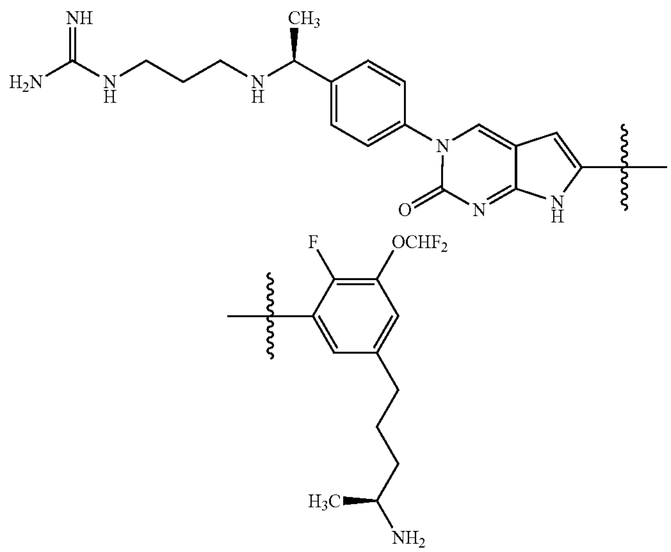 | 599.1 |
| 300 | 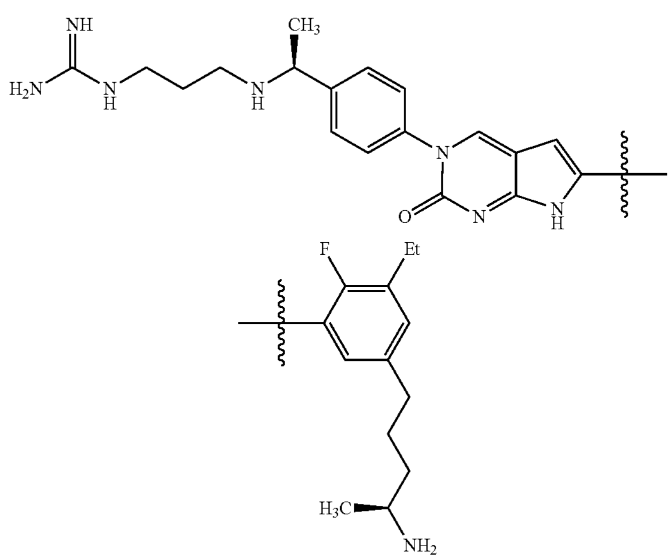 | 561.4 |

TABLE 1-continued
| Comp. No. | Structure | LCMS |
|---|---|---|
| 301 | 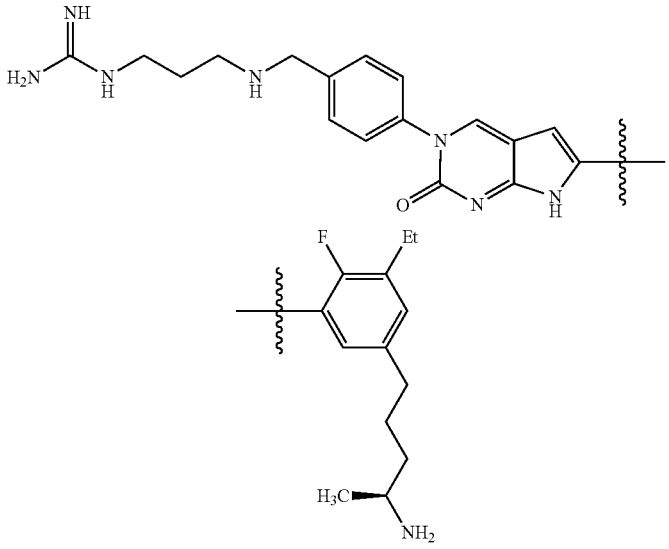 | 547.1 |
| 302 | 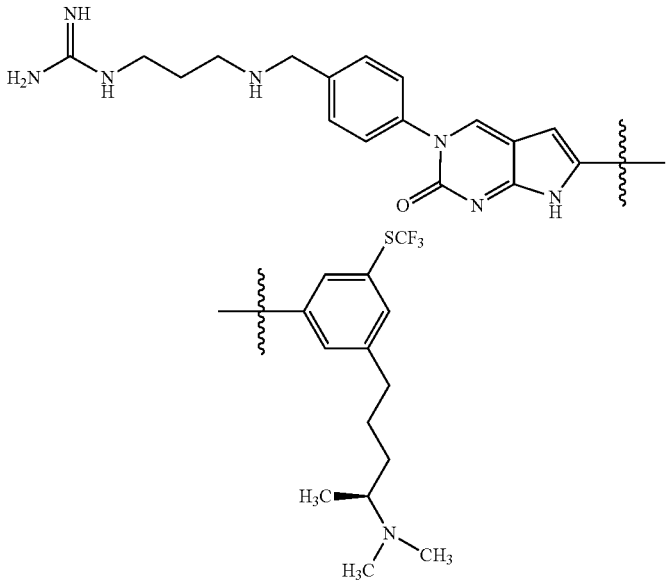 | 629.1 |

TABLE 1-continued
| Comp. No. | Structure | LCMS |
|---|---|---|
| 303 | 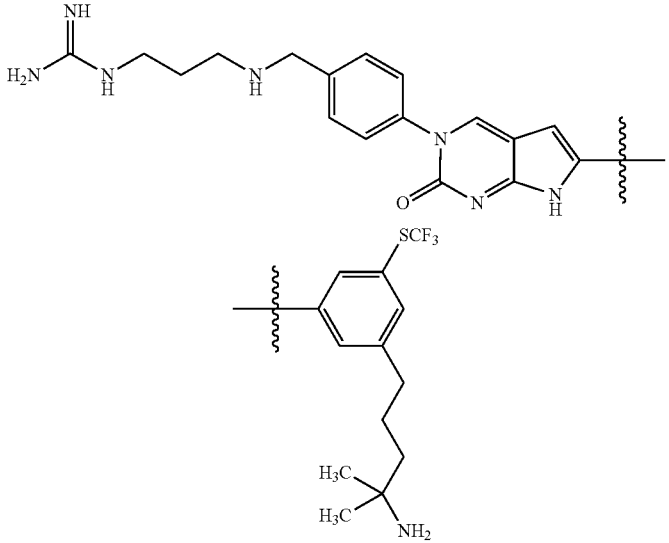 | 615.1 |
| 304 | 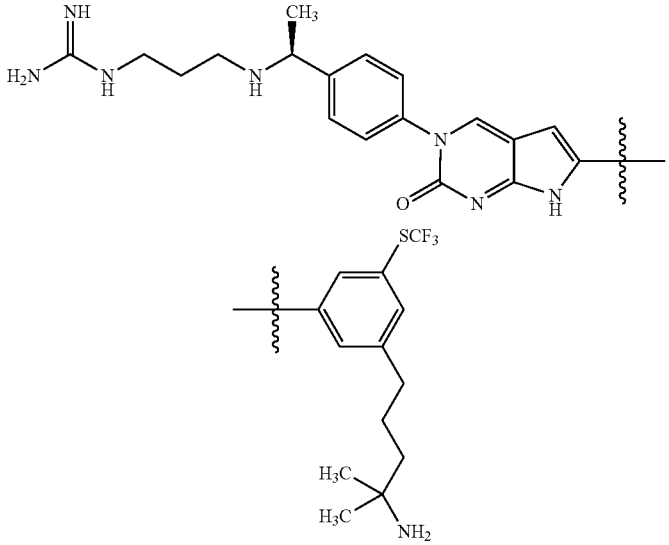 | 629.1 |

TABLE 1-continued

| Comp. No. | Structure | LCMS |
|---|---|---|
| 305 | 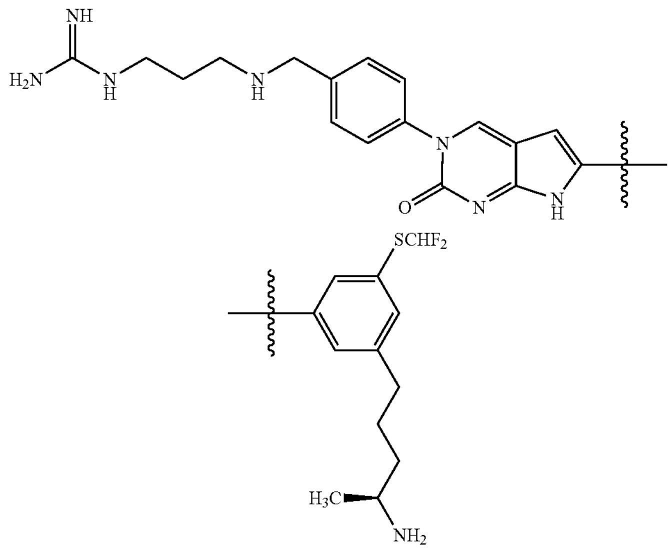 | 583.0 |
| 306 | 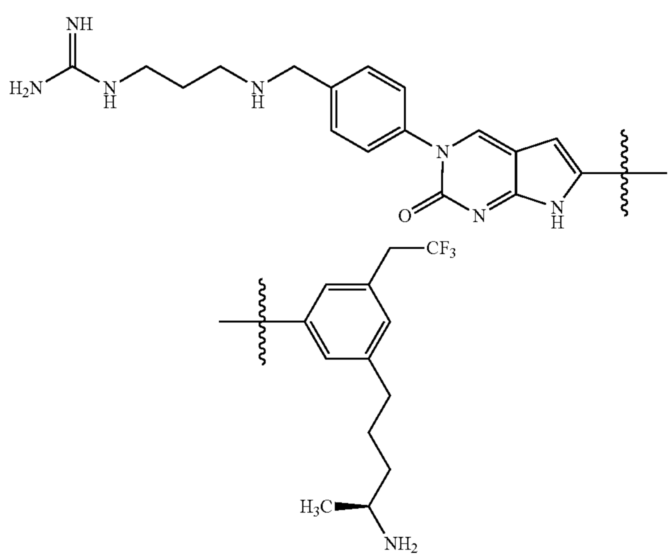 | 583.1 |

TABLE 1-continued
| Comp. No. | Structure | LCMS |
|---|---|---|
| 307 | 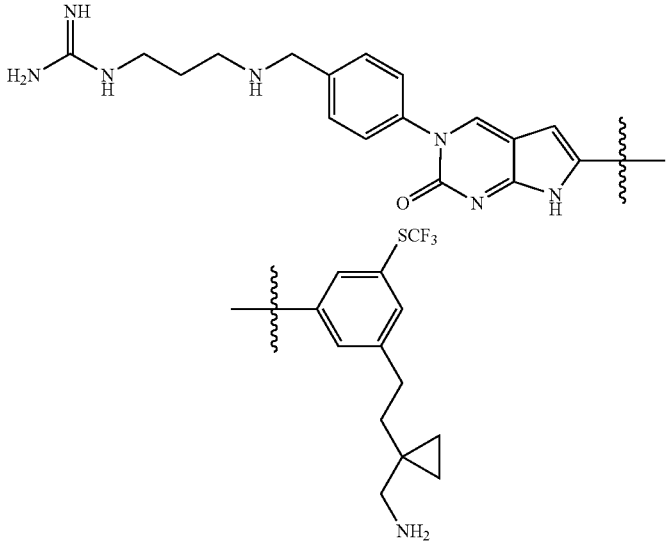 | 613.1 (m/e) |
| 308 | 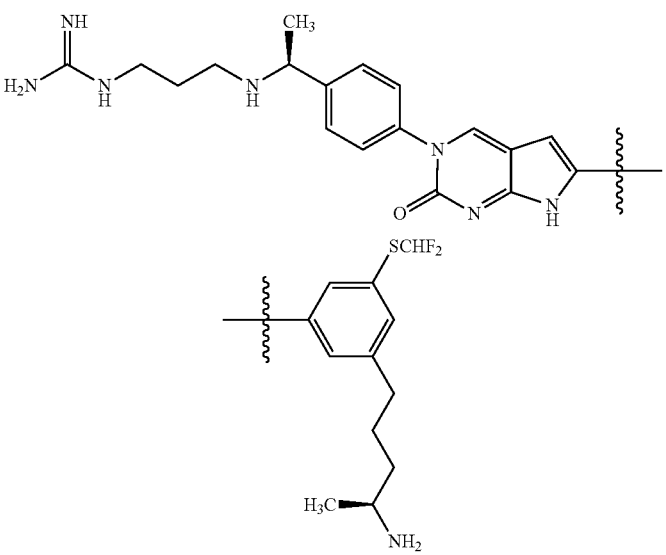 | 597.0 |

TABLE 1-continued

| Comp. No. | Structure | LCMS |
|---|---|---|
| 309 | 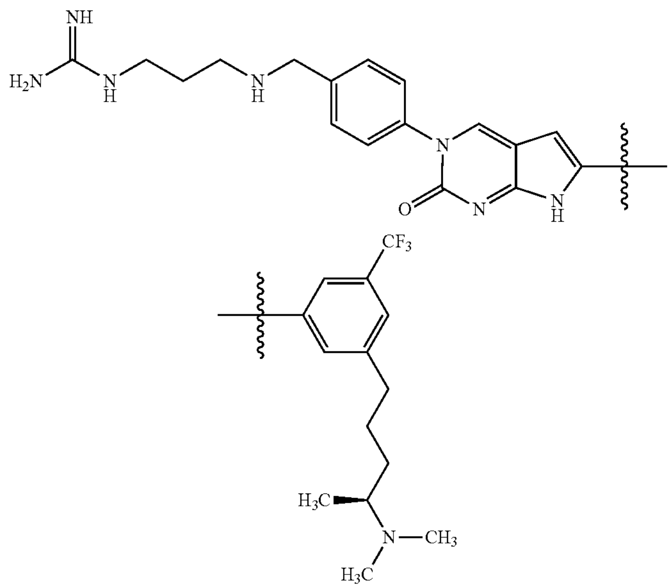 | 597.0 |
| 310 | 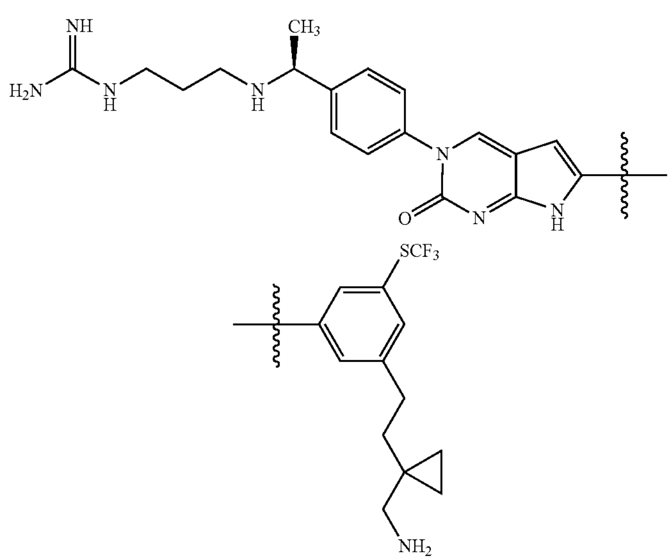 | 627.4 (m/e) |

TABLE 1-continued
| Comp. No. | Structure | LCMS |
|---|---|---|
| 311 | 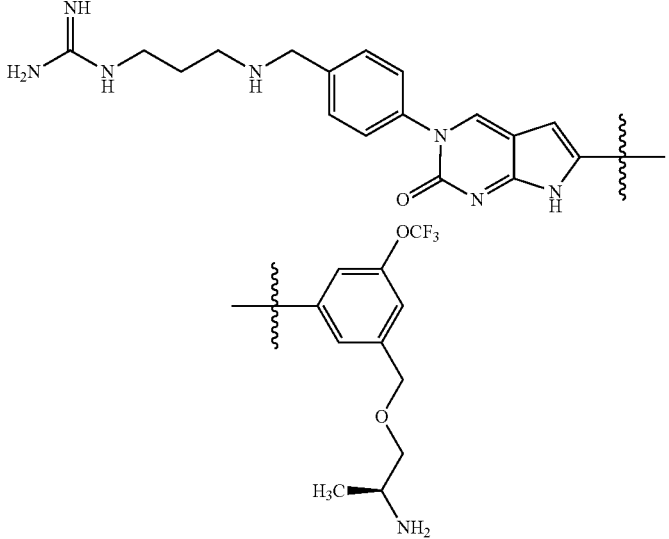 | 587.3 (m/e) |
| 312 | 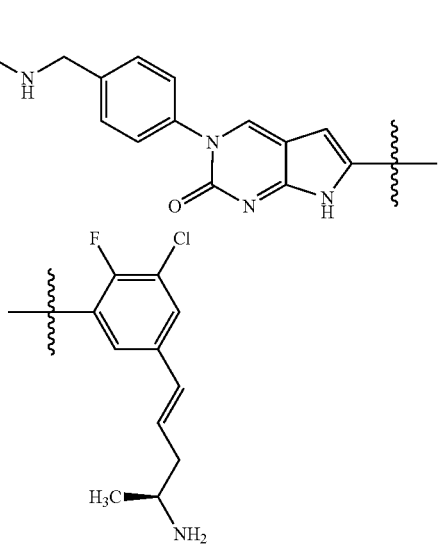 | 551.1 (m/e) |

TABLE 1-continued
| Comp. No. | Structure | LCMS |
|---|---|---|
| 313 | 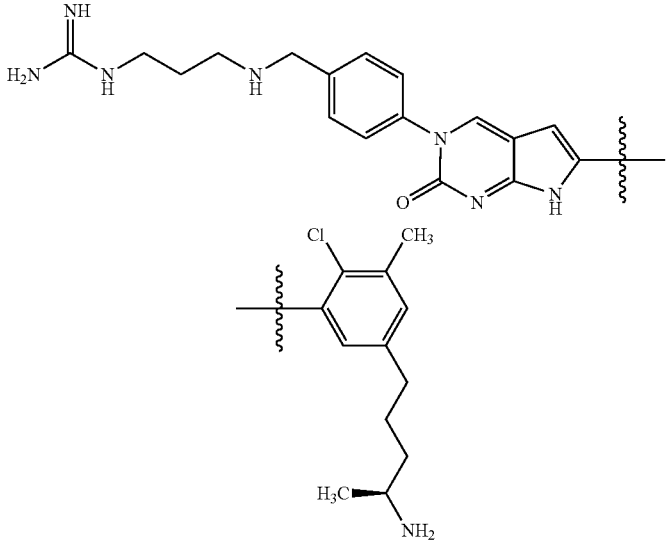 | 549.1 |
| 314 | 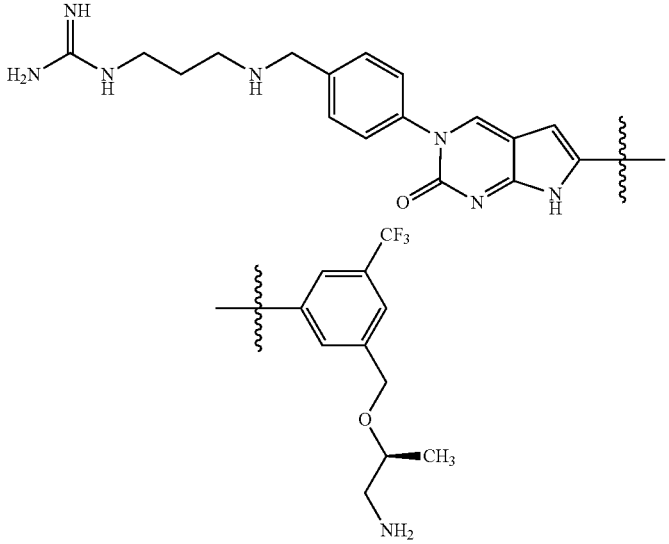 | 571.2 |

TABLE 1-continued

| Comp. No. | Structure | LCMS |
|---|---|---|
| 315 | 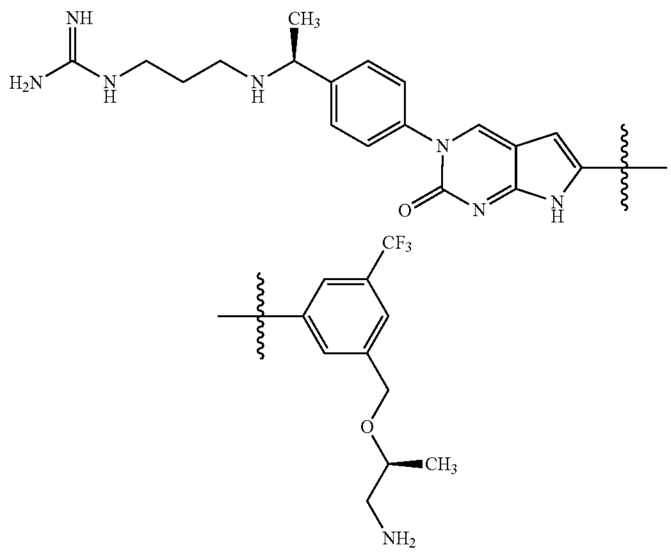 | 585.1 |
| 316 | 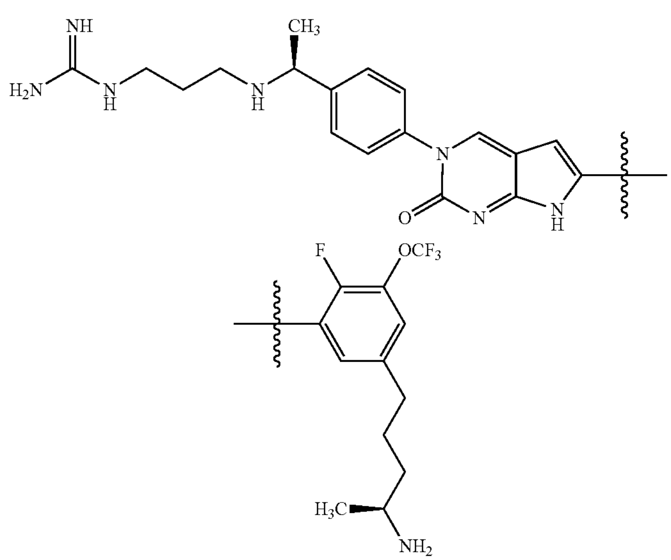 | 617.0 |

TABLE 1-continued
| Comp. No. | Structure | LCMS |
|---|---|---|
| 317 | 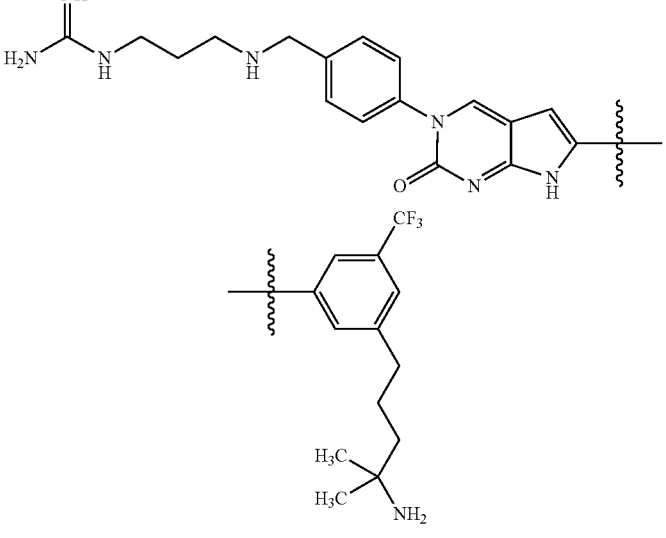 | 583.1 |
| 318 | 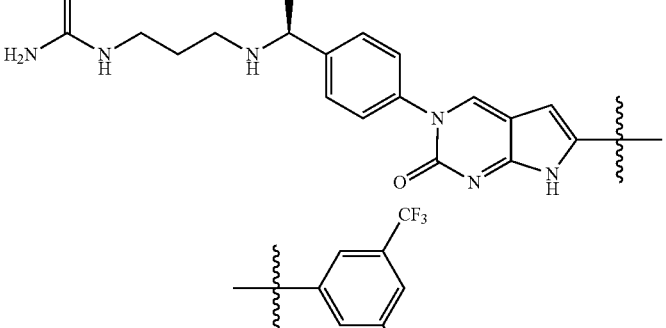 | 597.2 |

TABLE 1-continued

| Comp. No. | Structure | LCMS |
|---|---|---|
| 319 | 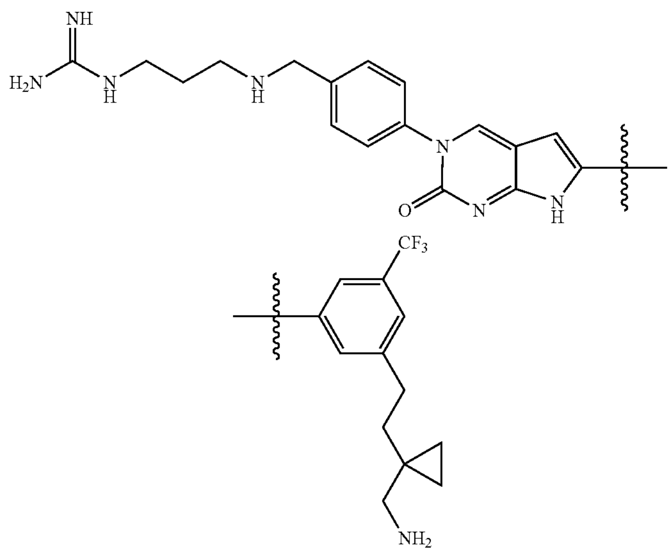 | 581.1 |
| 320 | 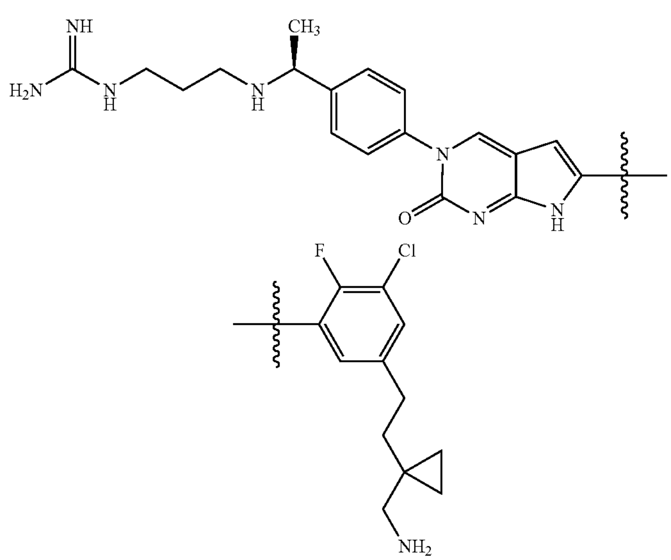 | 579.3 |

TABLE 1-continued
| Comp. No. | Structure | LCMS |
|---|---|---|
| 321 | 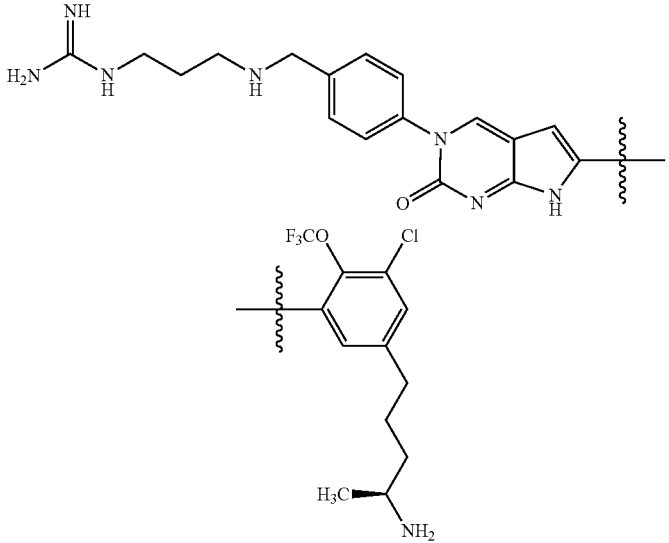 | 619.8 |
| 322 | 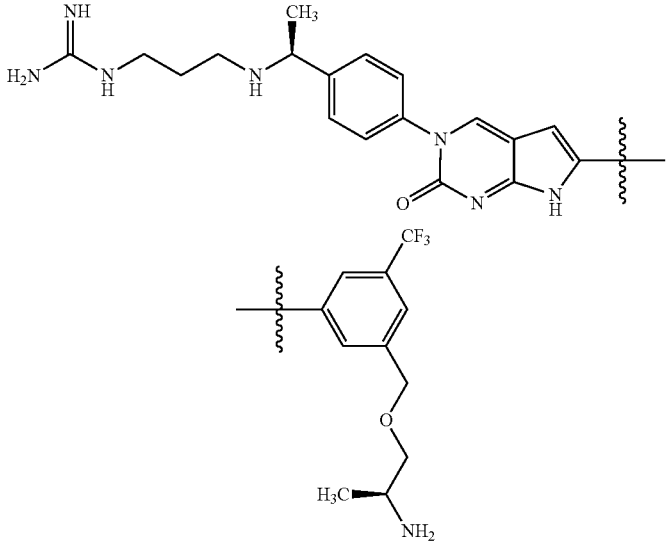 | 585.3 |

TABLE 1-continued
| Comp. No. | Structure | LCMS |
|---|---|---|
| 323 | 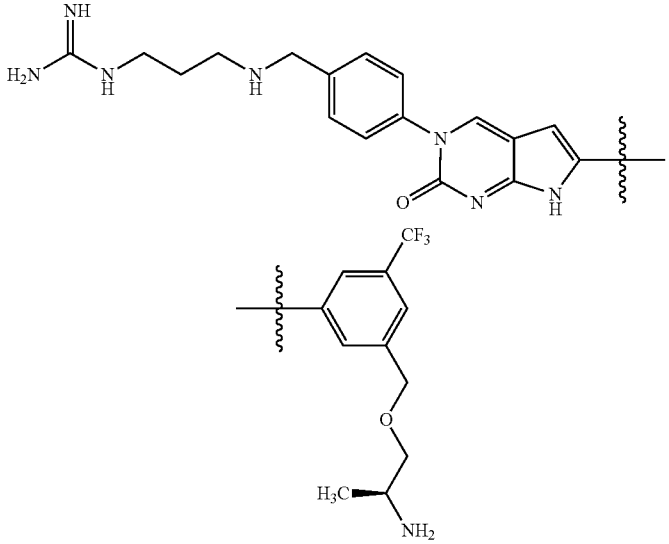 | 571.3 |
| 324 | 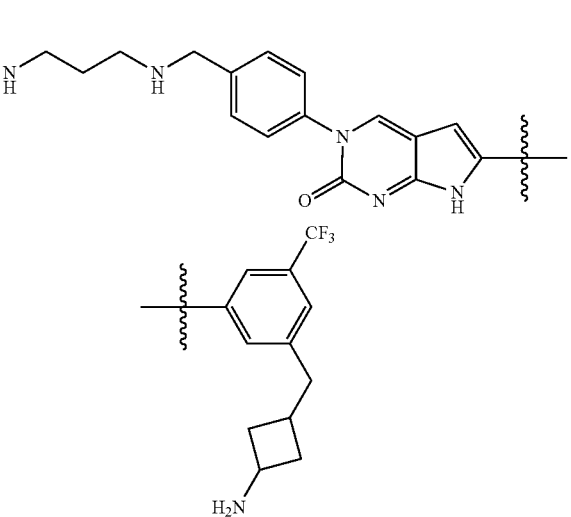 | 567.0 |
| 325 | 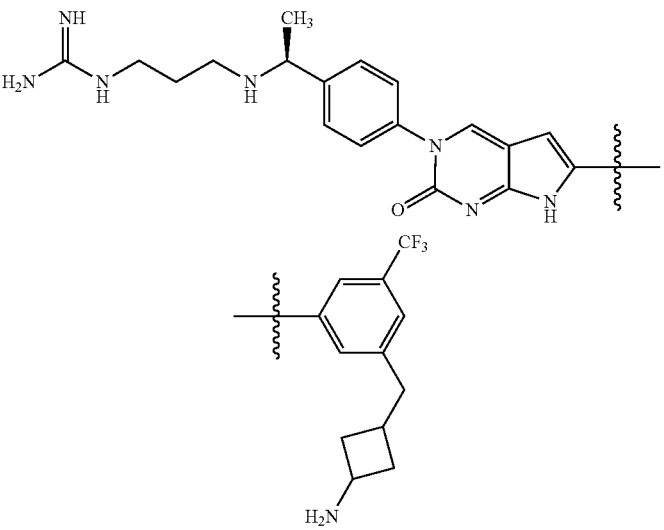 | 581.0 |

TABLE 1-continued
| Comp. No. | Structure | LCMS |
|---|---|---|
| 326 | 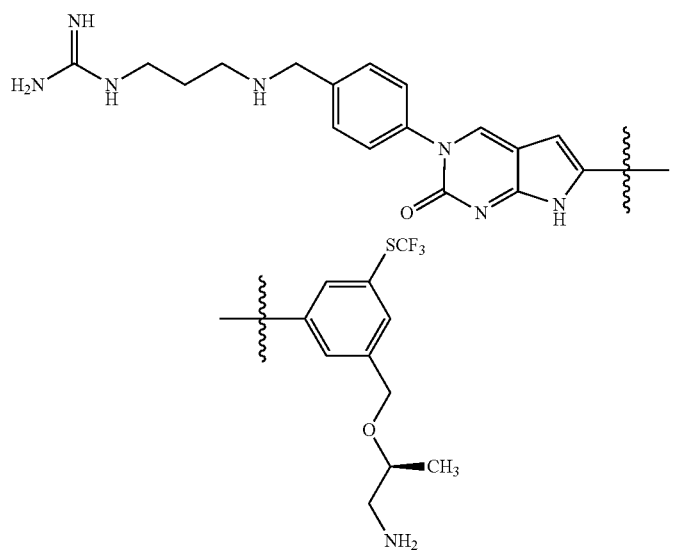 | 603.3 |
| 327 | 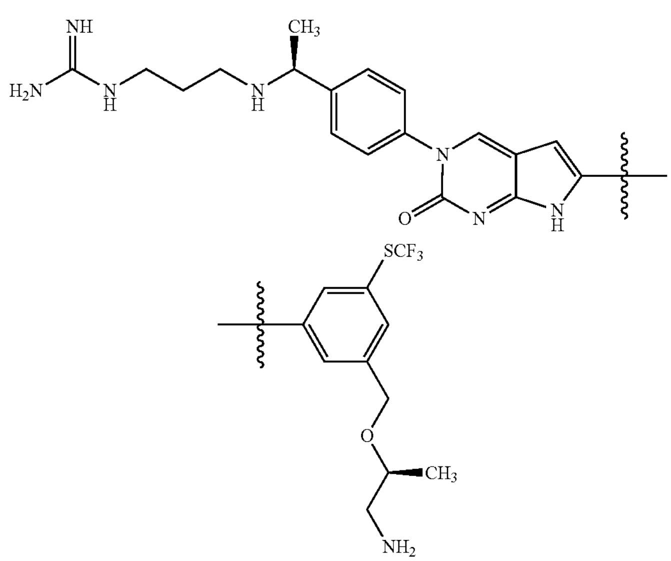 | 617.3 |

TABLE 1-continued

| Comp. No. | Structure | LCMS |
|---|---|---|
| 328 | 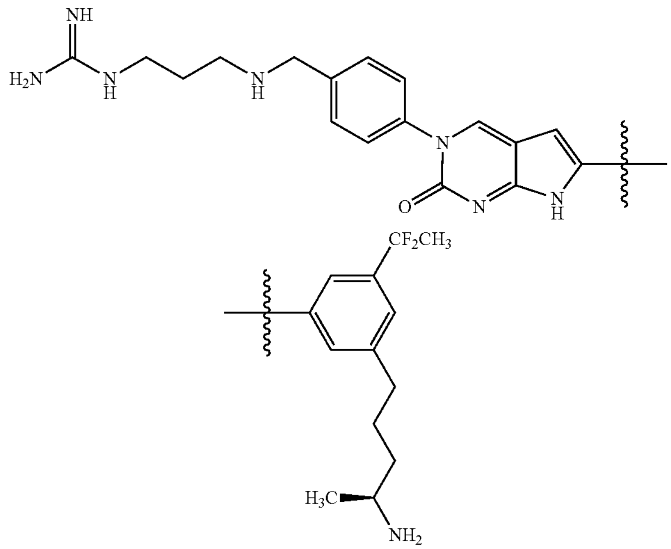 | 565.5 |
| 329 | 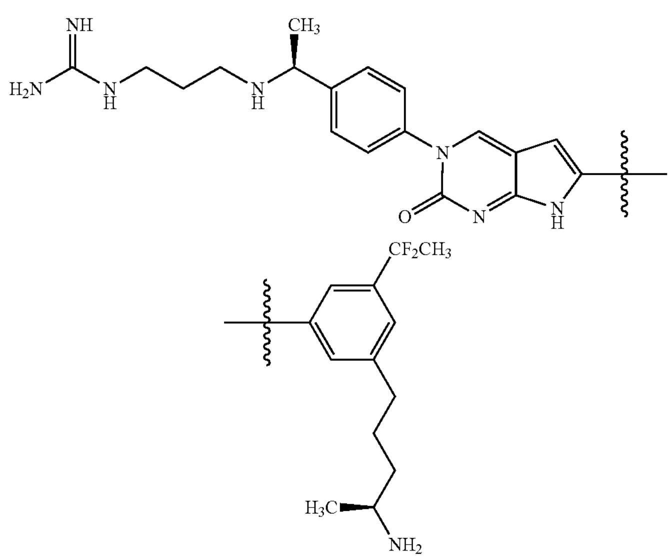 | 579.1 |

TABLE 1-continued
| Comp. No. | Structure | LCMS |
|---|---|---|
| 330 | 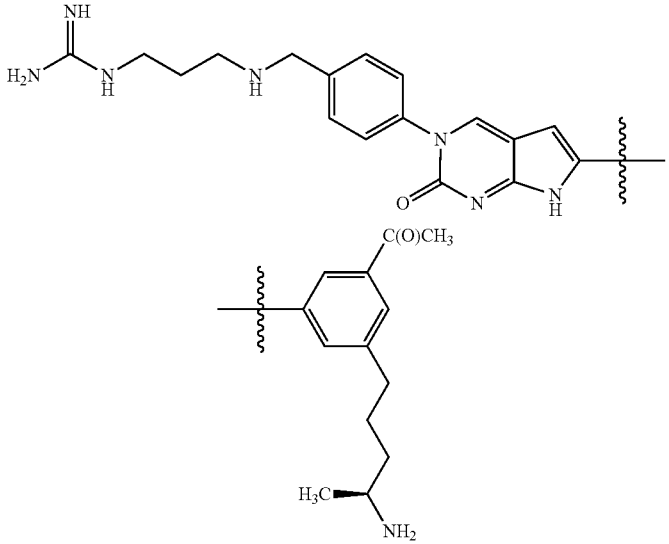 | 543.3 |
| 331 | 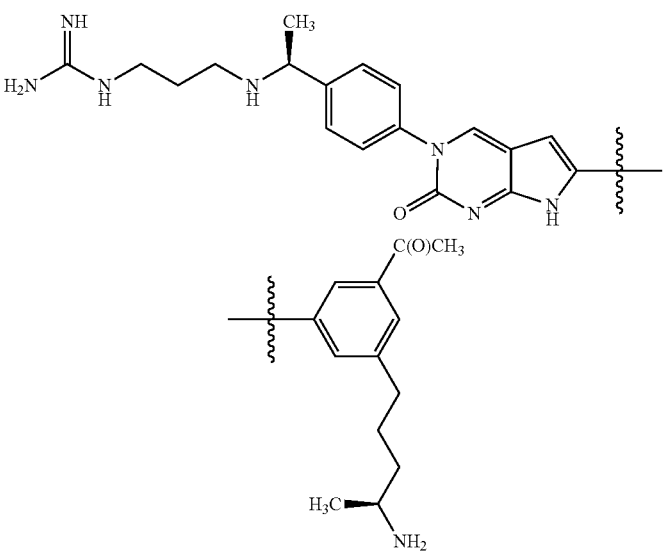 | 557.7 |

TABLE 2
| Comp. No. | Structure | LCMS |
|---|---|---|
| 150 | 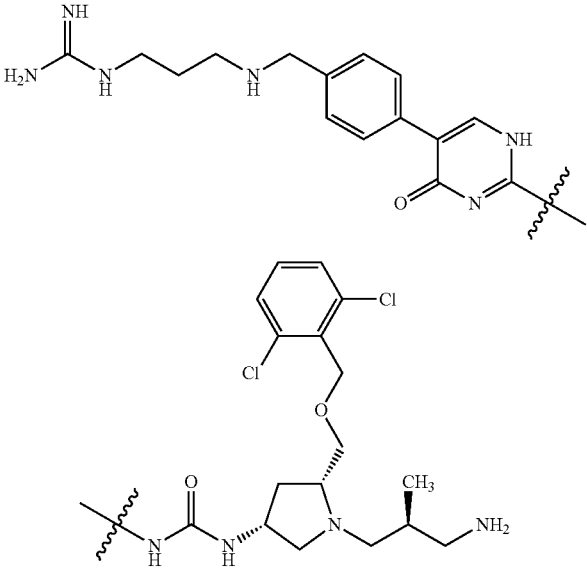 [SMILES: *c1nc(=O)c(-c2ccc(CNCCCNC(=N)N)cc2)c[nH]1 ; *NC(=O)N[C@@H]1C[C@H](COCc2c(Cl)cccc2Cl)N(C[C@@H](C)CN)C1] | 689.0 |
| 151 | 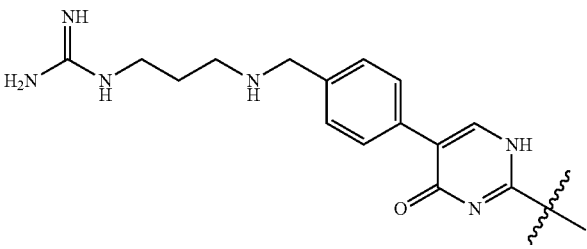 | 543.0 |

TABLE 2-continued
| Comp. No. | Structure | LCMS |
|---|---|---|
| 152 | 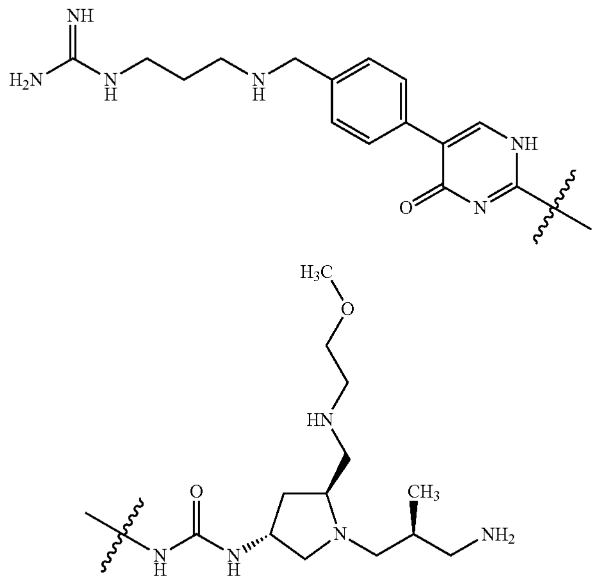 [SMILES: *c1nc(=O)c(-c2ccc(CNCCCNC(=N)N)cc2)c[nH]1 ; *NC(=O)N[C@@H]1C[C@@H](CNCCOC)N(C[C@@H](C)CN)C1] | 587.0 |
| 153 | 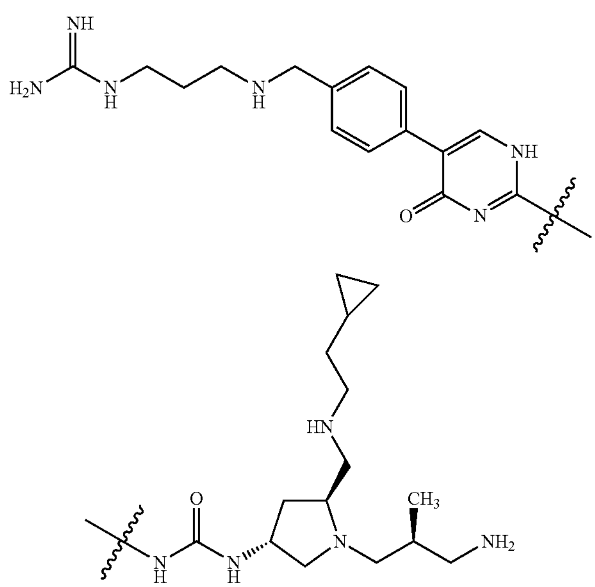 [SMILES: *c1nc(=O)c(-c2ccc(CNCCCNC(=N)N)cc2)c[nH]1 ; *NC(=O)N[C@@H]1C[C@@H](CNCCC2CC2)N(C[C@@H](C)CN)C1] | 597.0 |

TABLE 2-continued
| Comp. No. | Structure | LCMS |
|---|---|---|
| 154 | 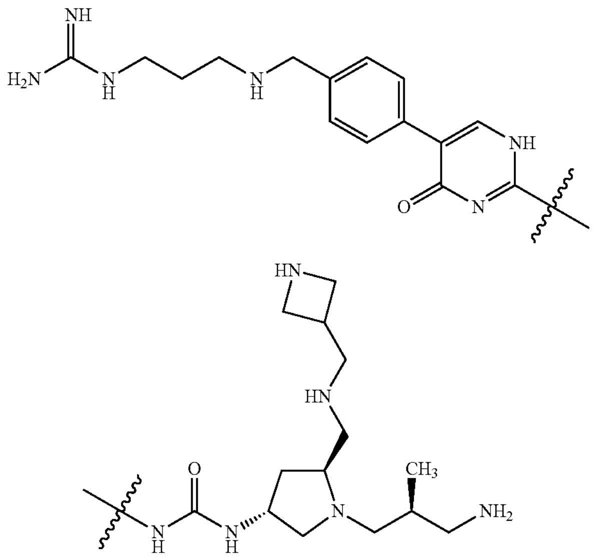 [SMILES: *c1nc(=O)c(-c2ccc(CNCCCNC(=N)N)cc2)c[nH]1 ; *NC(=O)N[C@@H]1C[C@@H](CNCC2CNC2)N(C[C@@H](C)CN)C1] | 598.0 |
| 155 | 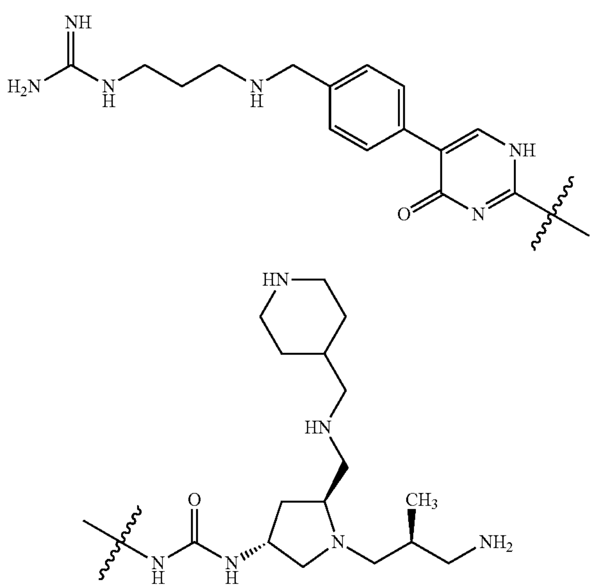 [SMILES: *c1nc(=O)c(-c2ccc(CNCCCNC(=N)N)cc2)c[nH]1 ; *NC(=O)N[C@@H]1C[C@@H](CNCC2CCNCC2)N(C[C@@H](C)CN)C1] | 626.0 |

TABLE 2-continued
| Comp. No. | Structure | LCMS |
|---|---|---|
| 156 | 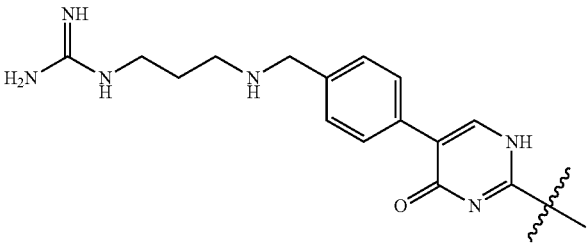 | 601.0 |
| 157 | 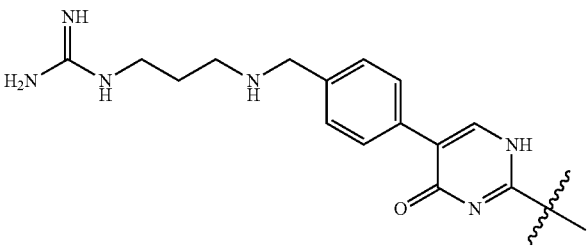 | 693.0 |

TABLE 2-continued
| Comp. No. | Structure | LCMS |
|---|---|---|
| 158 | 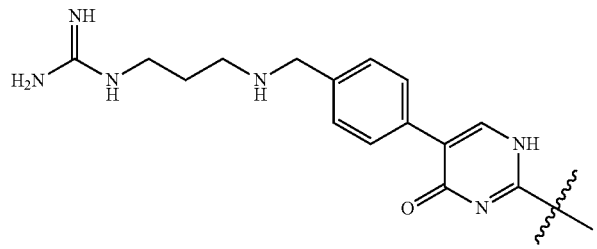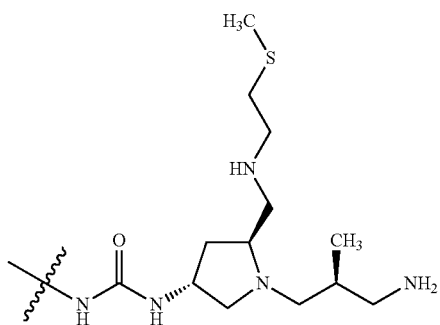 | 603.0 |
| 159 | 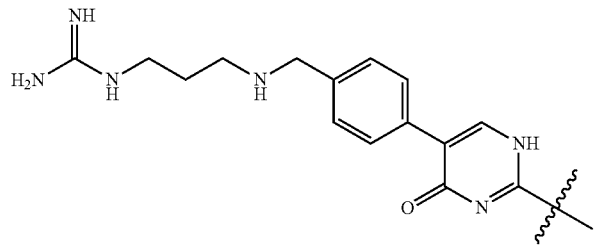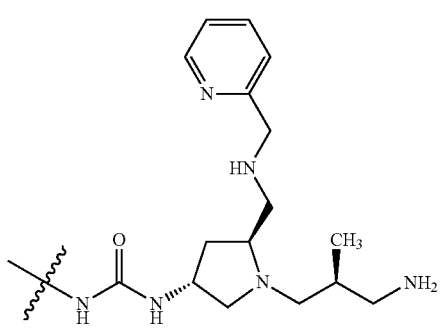 | 619.0 |

TABLE 2-continued
| Comp. No. | Structure | LCMS |
|---|---|---|
| 160 | 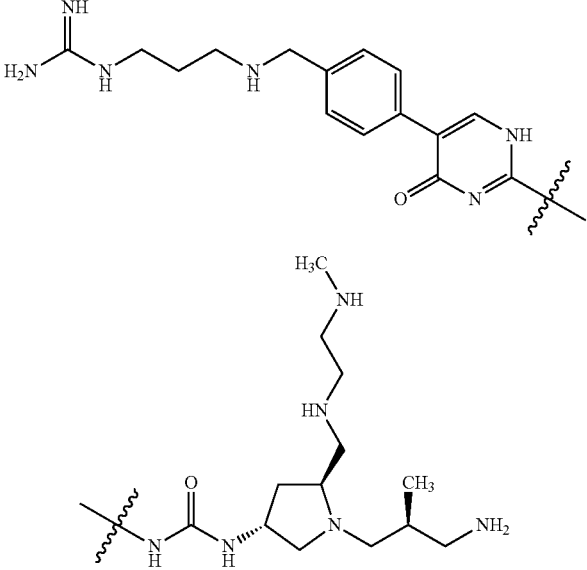 [SMILES: *c1nc(=O)c(-c2ccc(CNCCCNC(=N)N)cc2)c[nH]1 ; *NC(=O)N[C@@H]1C[C@@H](CNCCNC)N(C[C@@H](C)CN)C1] | 585.0 |
| 161 | 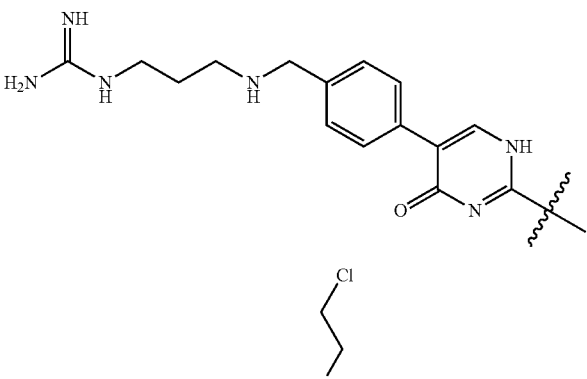 | 590.0 |

TABLE 2-continued
| Comp. No. | Structure | LCMS |
|---|---|---|
| 162 | 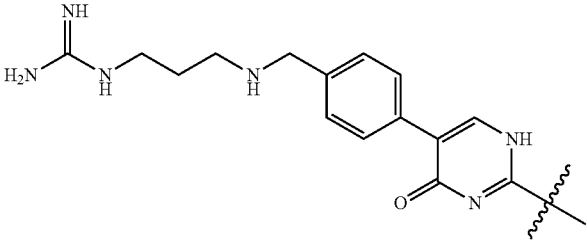 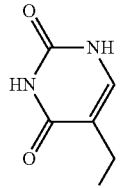 | 652.0 |
| 163 | 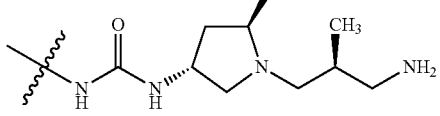 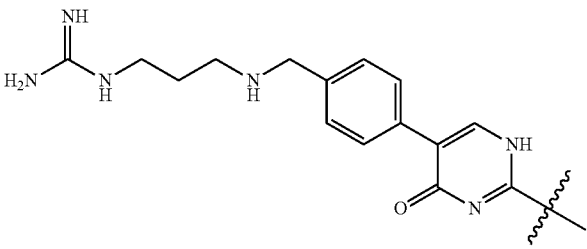 | 522.0 |

TABLE 2-continued
| Comp. No. | Structure | LCMS |
|---|---|---|
| 164 | 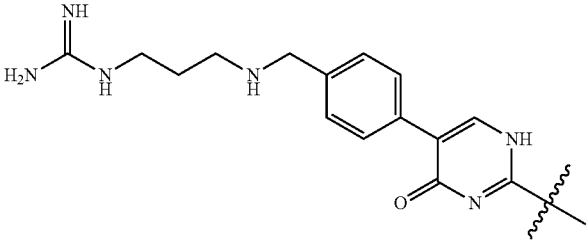 | 613.0 |
| 165 | 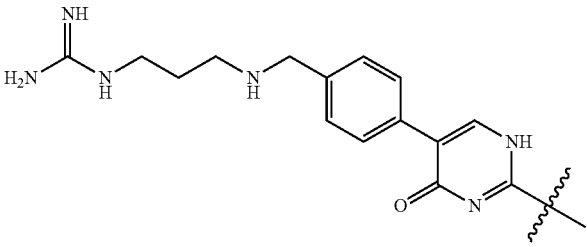 | 522.0 |

TABLE 2-continued
| Comp. No. | Structure | LCMS |
|---|---|---|
| 166 | 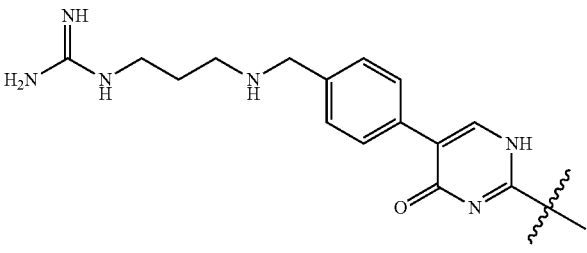 | 522.0 |
|  | 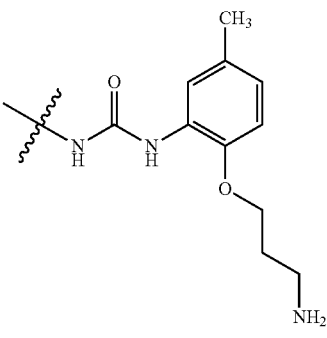 |  |
| 167 | 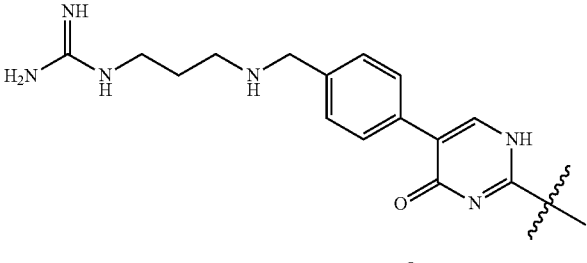 | 538.0 |
|  | 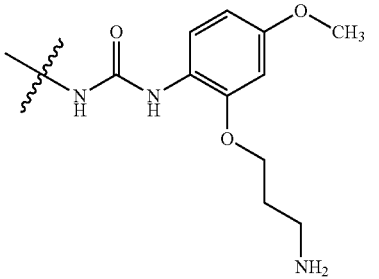 |  |
| 168 | 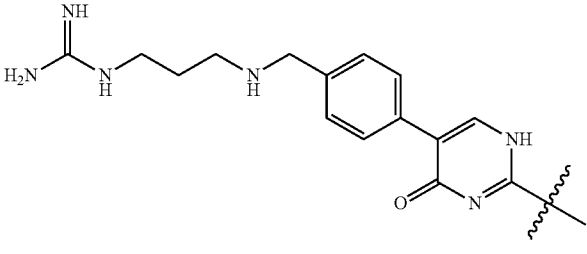 | 633.0 |
|  | 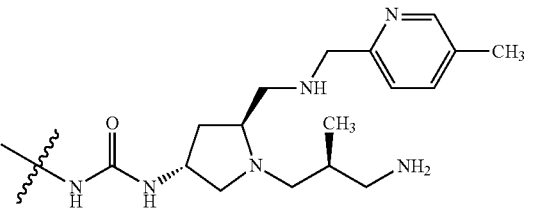 |  |

TABLE 2-continued

| Comp. No. | Structure | LCMS |
|---|---|---|
| 169 | guanidine-propyl-NH-CH2-(phenyl)-pyrimidinone linker; second fragment: urea-pyrrolidine with CH2OCH2CF3 and CH2-CHF-CH2NH2 substituents | 615.0 |
| 170 | guanidine-propyl-NH-CH2-(phenyl)-pyrimidinone linker; second fragment: urea-(4-fluoro-2-(3-aminopropoxy)phenyl) | 526.0 |
| 171 | guanidine-propyl-NH-CH2-(phenyl)-pyrimidinone linker; second fragment: urea-(5-fluoro-2-(3-aminopropoxy)phenyl) | 526.0 |

TABLE 2-continued
| Comp. No. | Structure | LCMS |
|---|---|---|
| 172 | 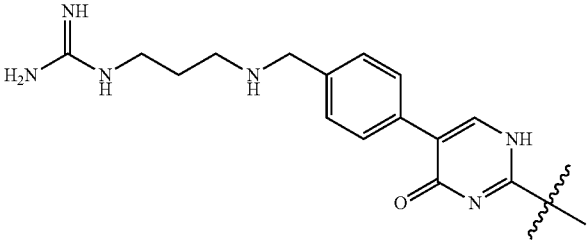 | 542.0 |
| 173 | 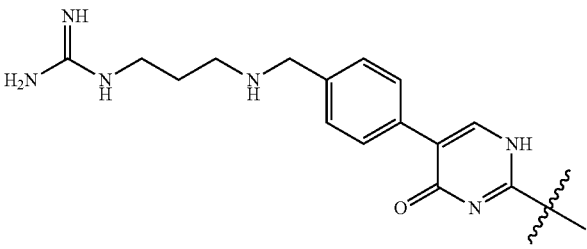 | 526.0 |

TABLE 2-continued

| Comp. No. | Structure | LCMS |
|---|---|---|
| 174 | 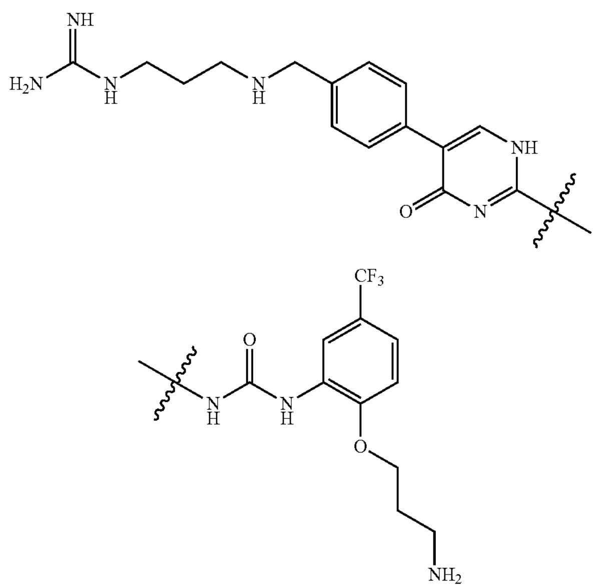 | 576.0 |
| 175 | 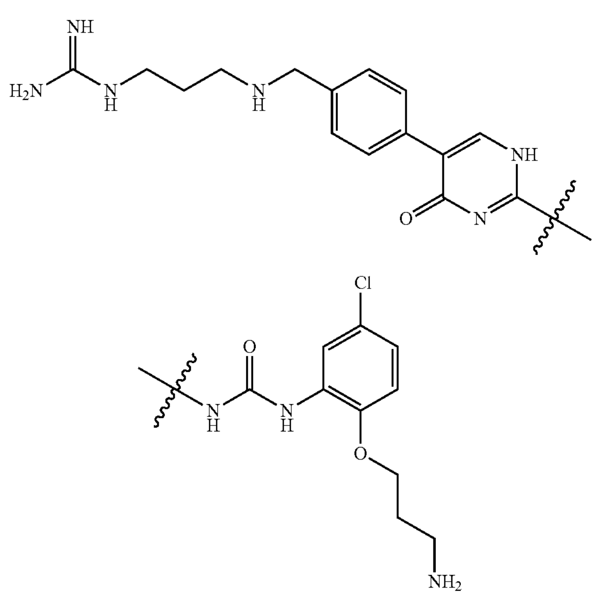 [SMILES: *c1nc(=O)c(-c2ccc(CNCCCNC(=N)N)cc2)c[nH]1 ; *NC(=O)Nc1cc(Cl)ccc1OCCCN] | 542.0 |

TABLE 2-continued
| Comp. No. | Structure | LCMS |
|---|---|---|
| 176 | 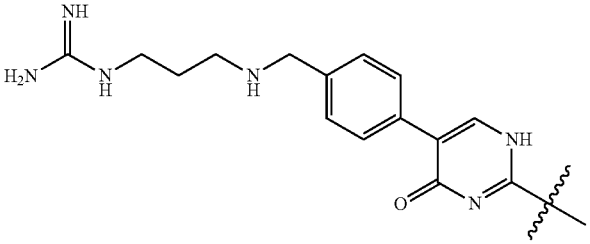 | 550.0 |
| 177 | 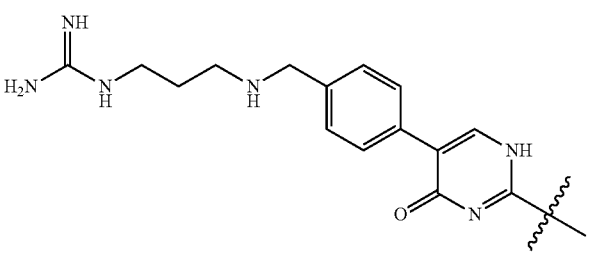 | 576.0 |

TABLE 2-continued
| Comp. No. | Structure | LCMS |
|---|---|---|
| 178 | 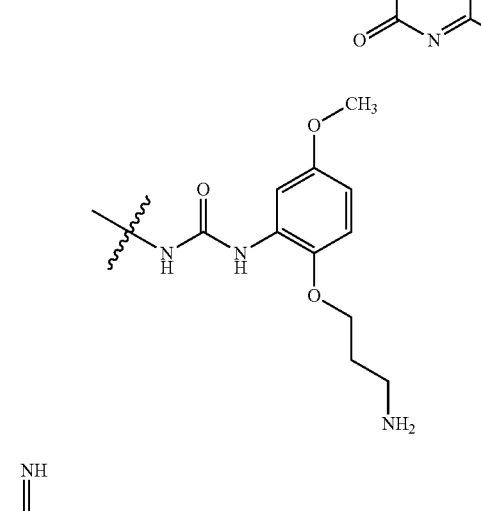 | 538.0 |
| 179 | 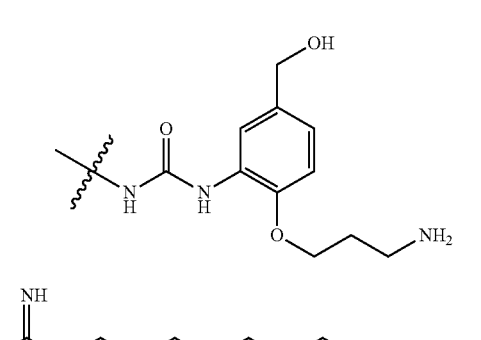 | 538.0 |
| 180 | 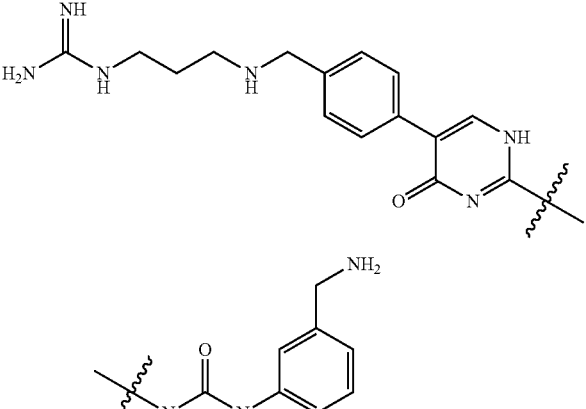 | 537.0 |

TABLE 2-continued
| Comp. No. | Structure | LCMS |
|---|---|---|
| 181 | 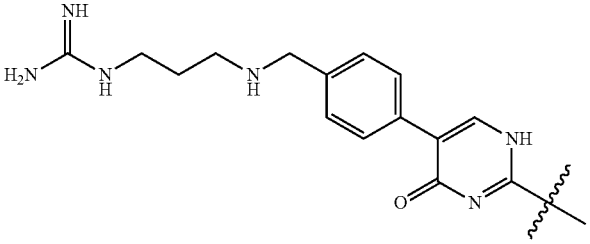 | 548.0 |
| 182 | 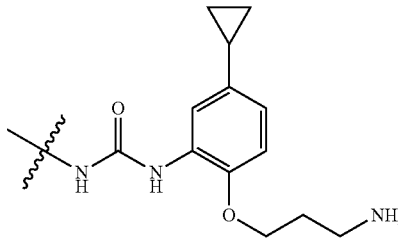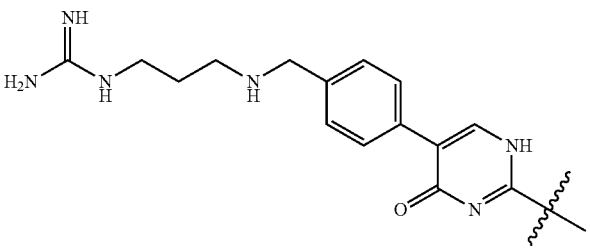 | 550.0 |
| 183 | 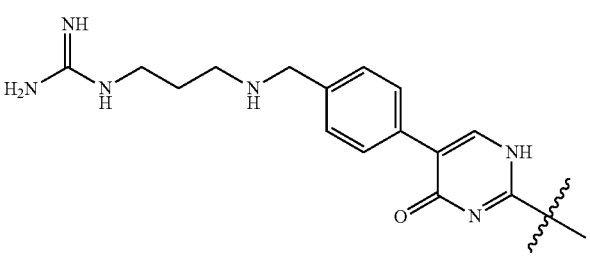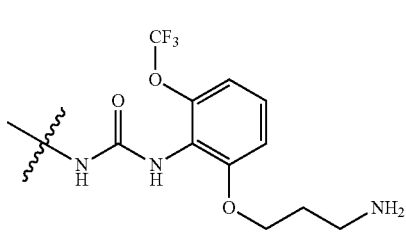 | 592.0 |

TABLE 2-continued
| Comp. No. | Structure | LCMS |
|---|---|---|
| 184 | 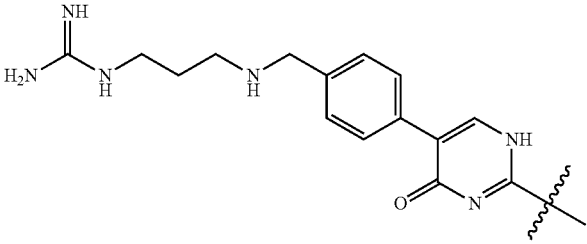 | 548.0 |
| 185 | 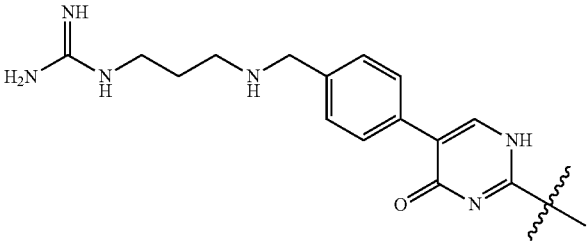 | 538.0 |

US 9,221,827 B2
499                                                                                              500
TABLE 2-continued
| Comp. No. | Structure | LCMS |
|---|---|---|
| 186 | 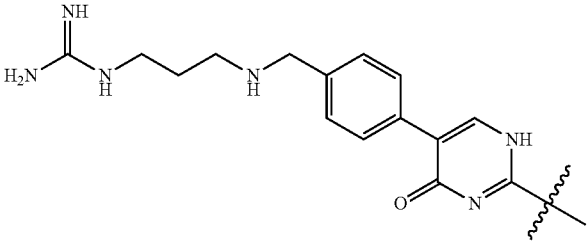 | 550.0 |
| 187 | 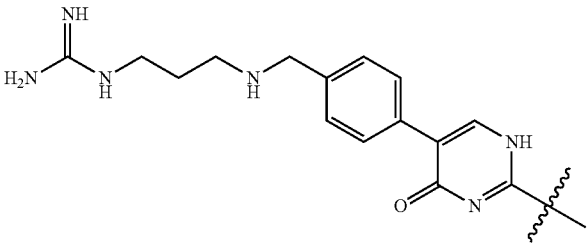 | 542.0 |

TABLE 2-continued
| Comp. No. | Structure | LCMS |
|---|---|---|
| 188 | 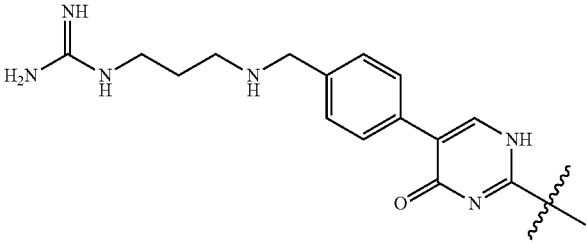 | 558.0 |
| 189 | 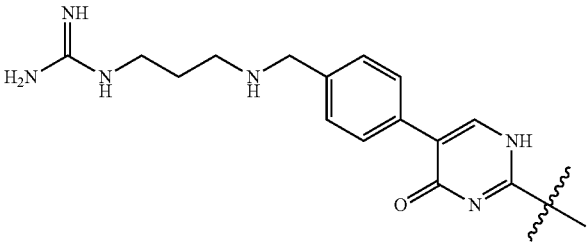 | 548.0 |

TABLE 2-continued
| Comp. No. | Structure | LCMS |
|---|---|---|
| 190 | 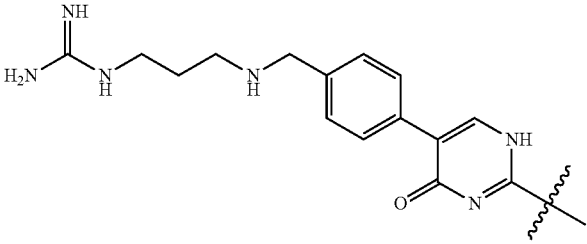 | 538.0 |
|  | 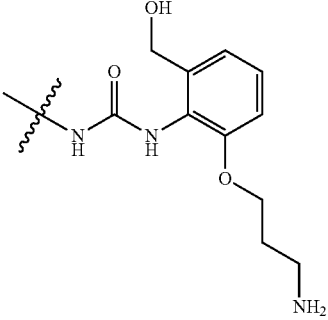 |  |
| 332 | 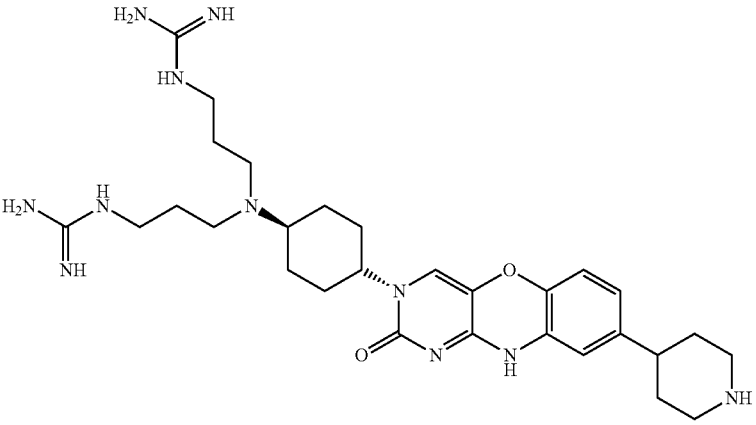 | 580.3 |

TABLE 2a

| Comp. No. | Structure | LCMS |
|---|---|---|
| 333 | 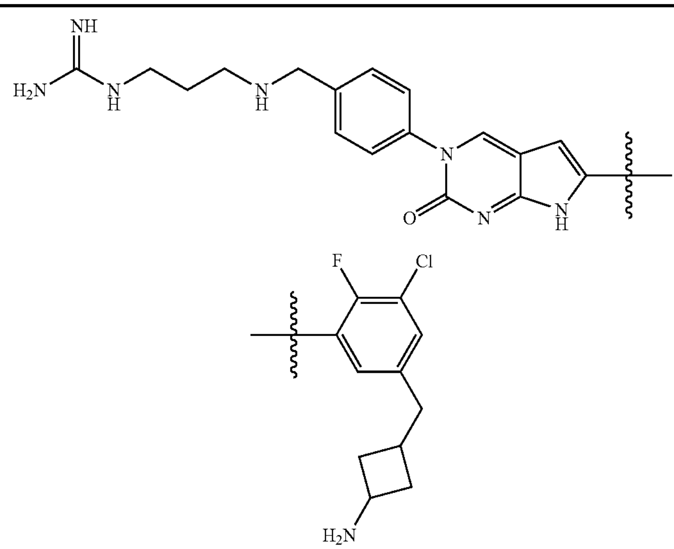 | 552.0 |
| 334 | 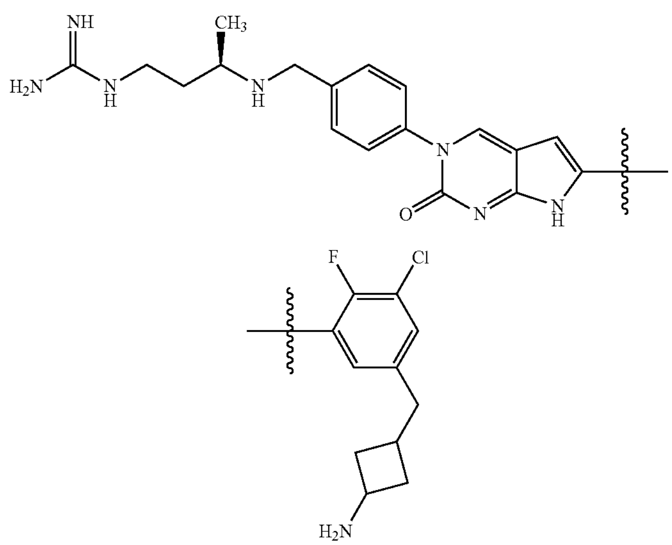 | 566.0 |
| 335 | 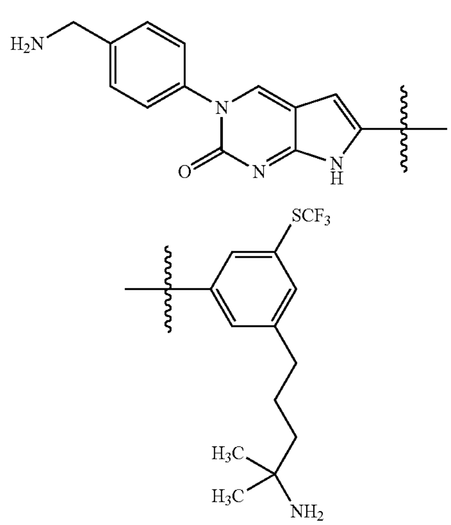 | 516.0 |

TABLE 2a-continued
| Comp. No. | Structure | LCMS |
|---|---|---|
| 336 | 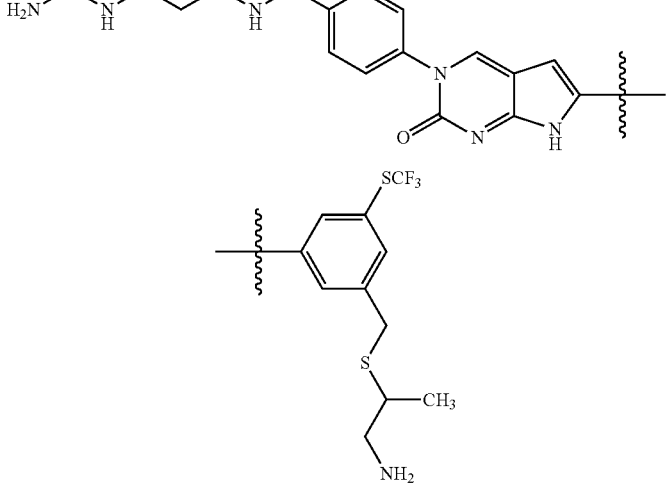 | 619.1 |
| 337 | 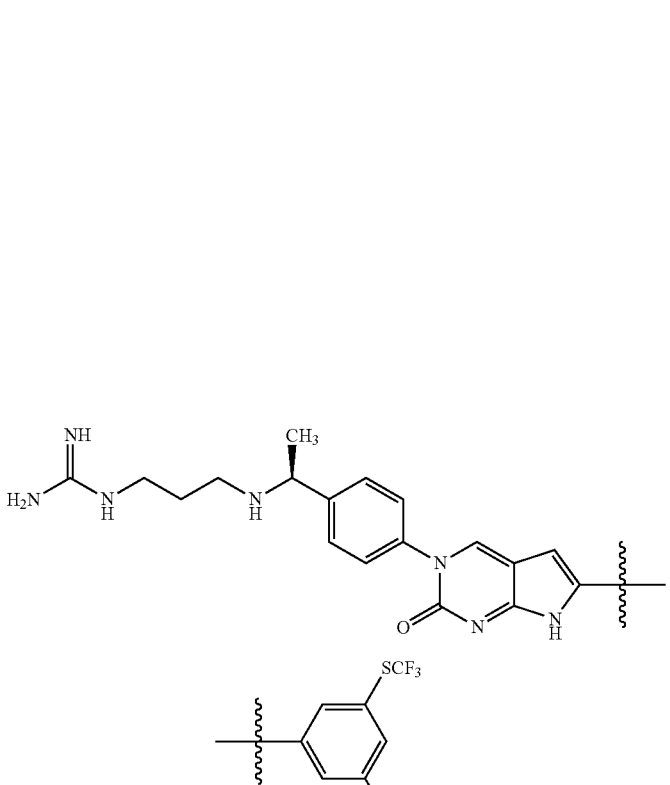 | 632.9 |

TABLE 2a-continued
| Comp. No. | Structure | LCMS |
|---|---|---|
| 338 | 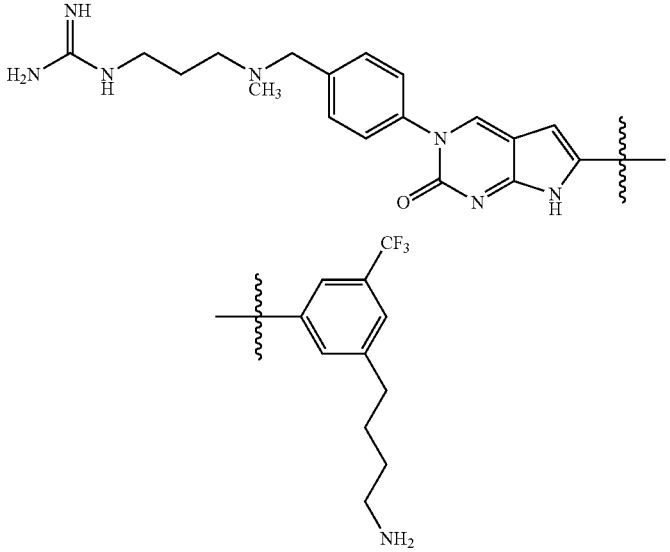 | 569.3 |
| 339 | 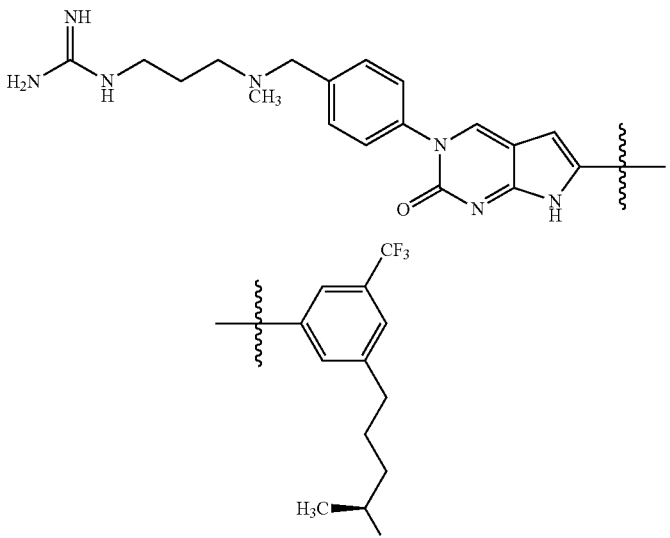 | 583.4 |

TABLE 2a-continued
| Comp. No. | Structure | LCMS |
|---|---|---|
| 340 | 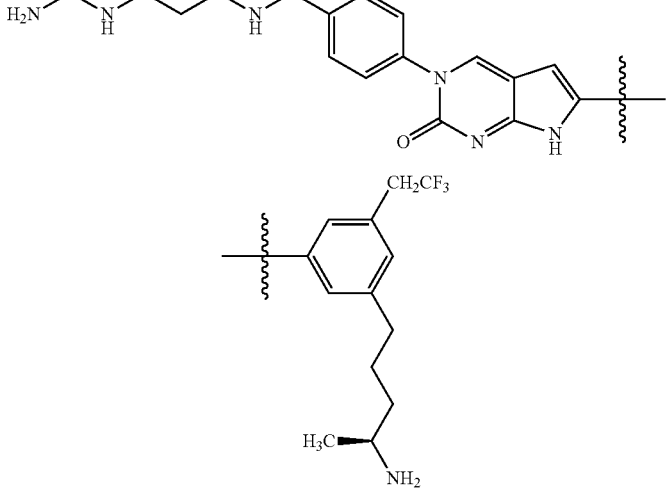 | 597.1 |
| 341 | 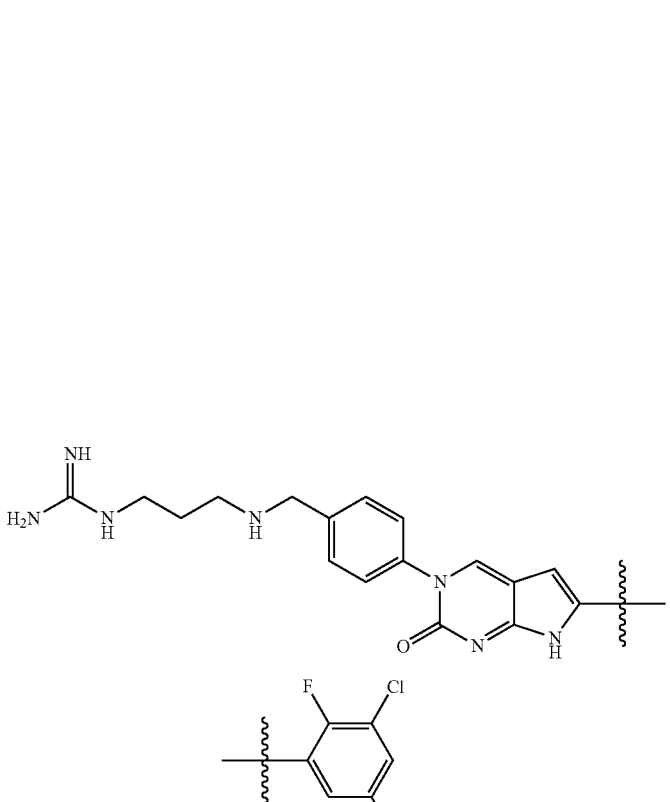 | 567.2 |

TABLE 2a-continued
| Comp. No. | Structure | LCMS |
|---|---|---|
| 342 | 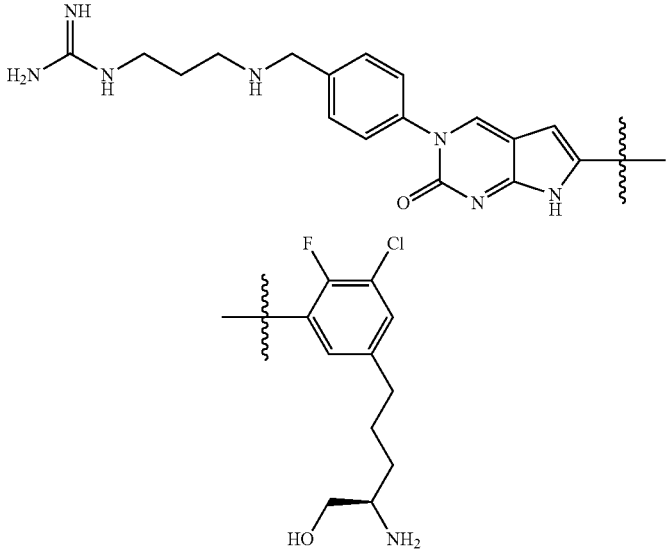 | 569.2 |
| 343 | 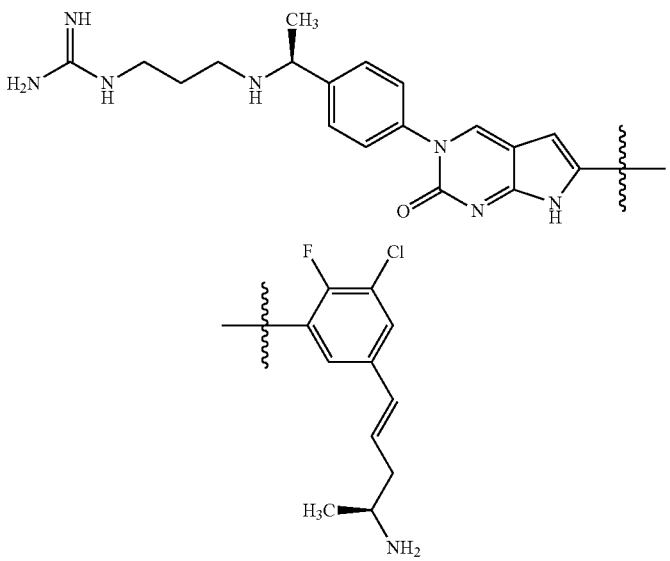 | 566.9 |

TABLE 2a-continued
| Comp. No. | Structure | LCMS |
|---|---|---|
| 344 | 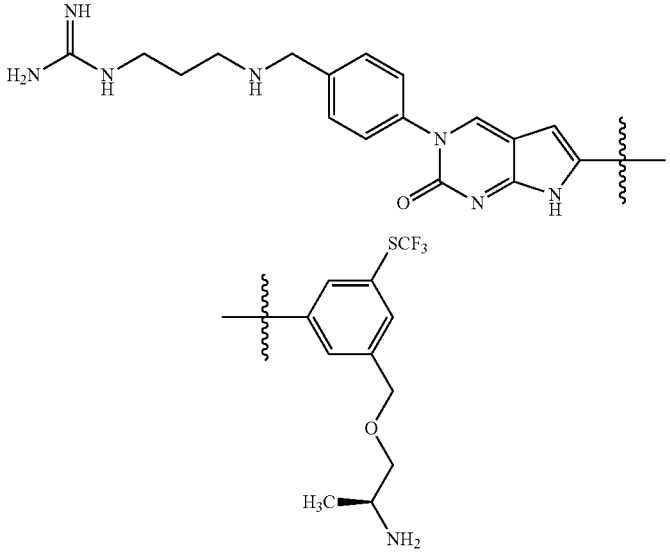 | 603.1 |
| 345 | 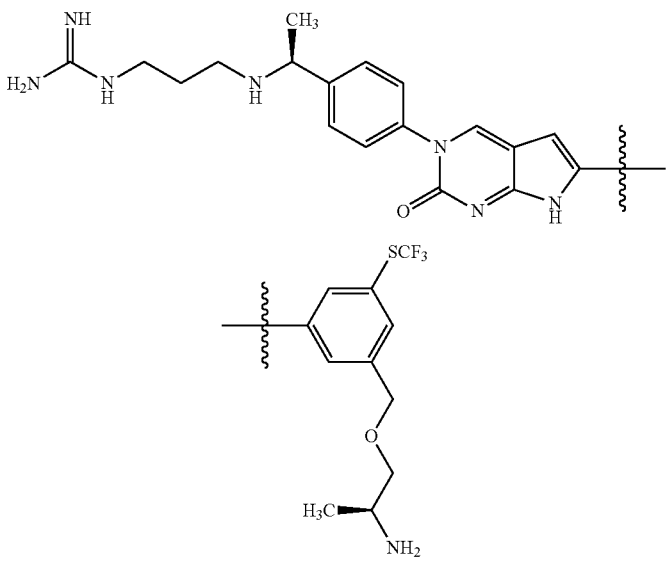 | 617.1 |

TABLE 2a-continued
| Comp. No. | Structure | LCMS |
|---|---|---|
| 346 | 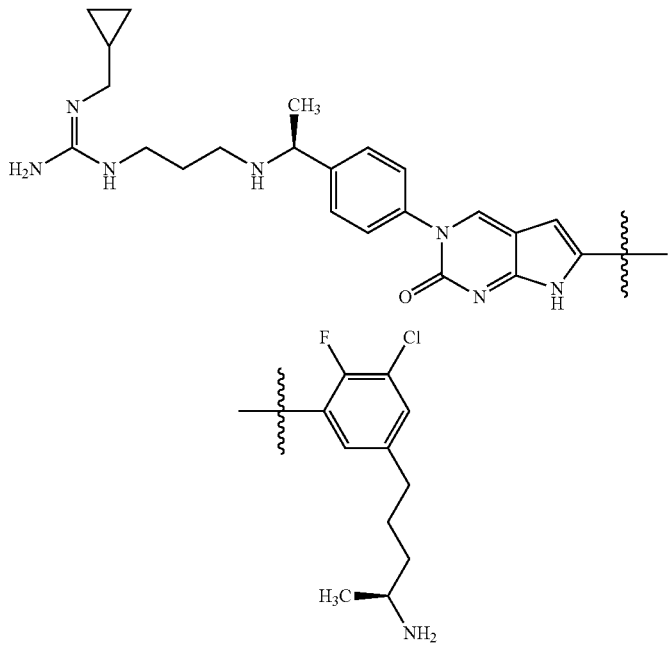 | 621.4 |
| 347 | 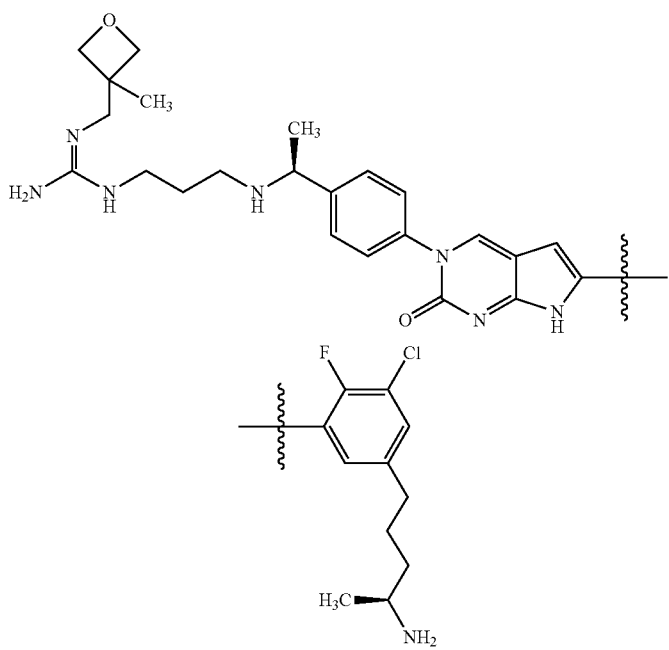 | 695.5 |

TABLE 2a-continued
| Comp. No. | Structure | LCMS |
|---|---|---|
| 348 | 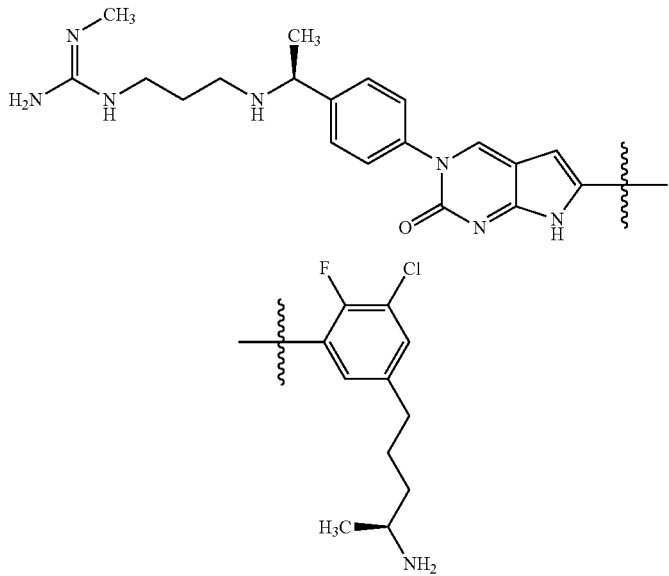 | 581.0 |
| 349 | 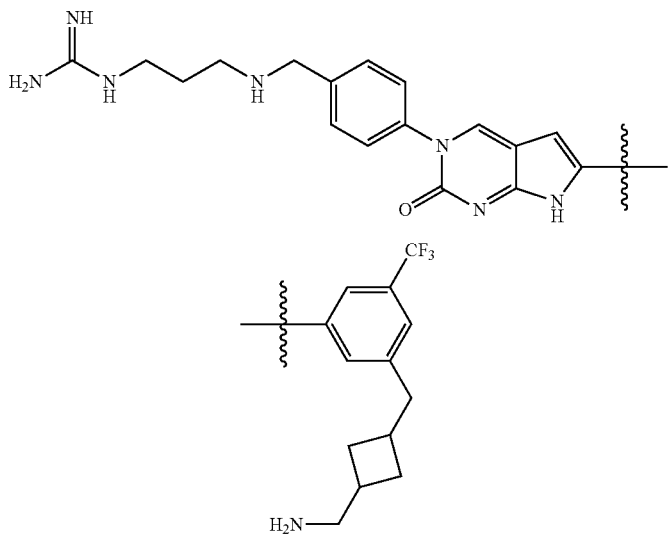 | 581.0 |

TABLE 2a-continued

| Comp. No. | Structure | LCMS |
|---|---|---|
| 350 | 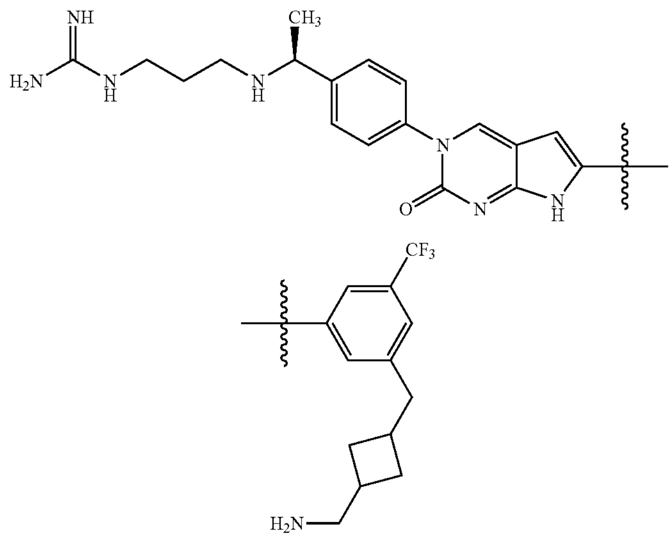 | 595.0 |
| 351 | 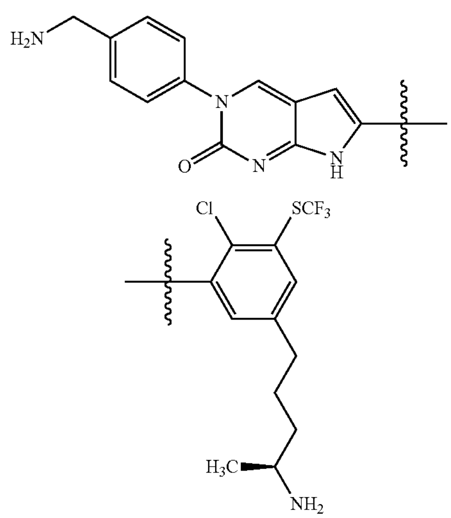 | 536.1 |
| 352 | 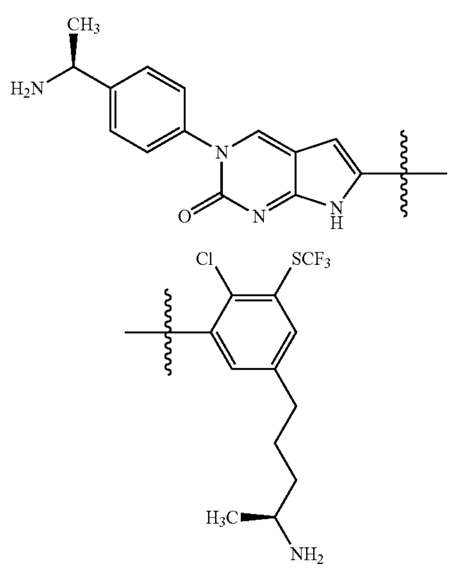 | 550.1 |

TABLE 2a-continued

| Comp. No. | Structure | LCMS |
|---|---|---|
| 353 | 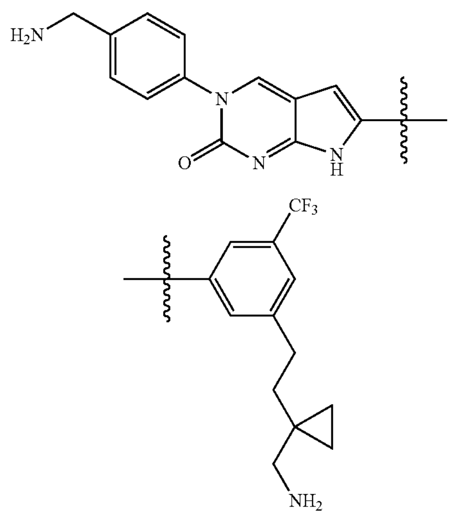 | 428.0 |
| 354 | 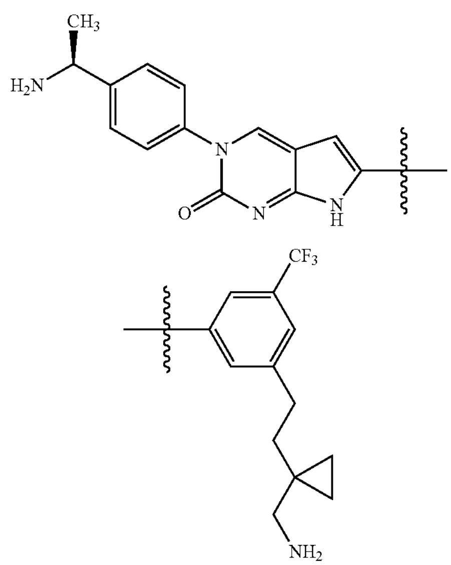 | 496.3 |
| 355 | 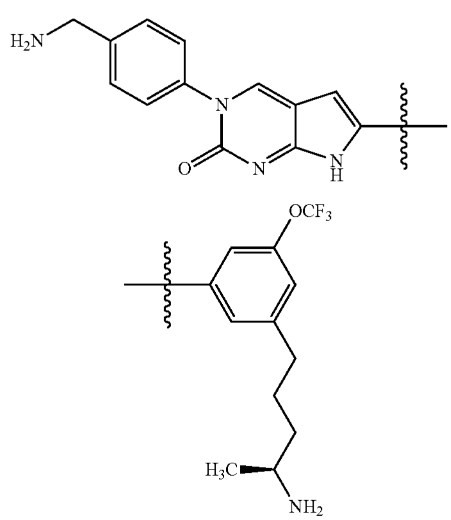 | 486.3 |

TABLE 2a-continued
| Comp. No. | Structure | LCMS |
|---|---|---|
| 356 | 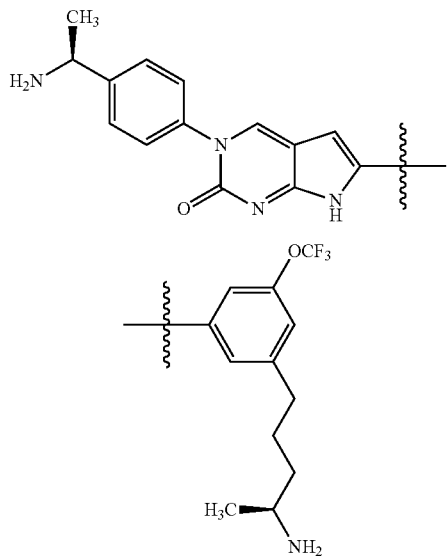 | 500.2 |
| 357 | 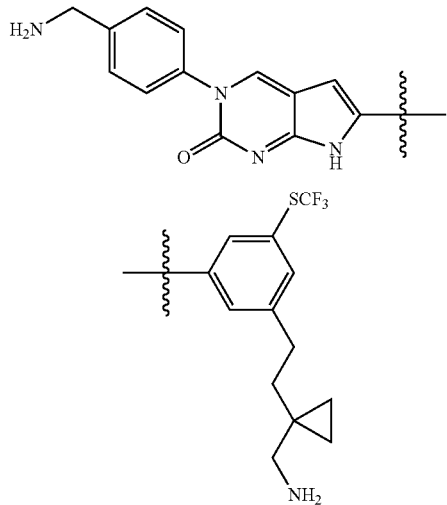 | 514.1 |

TABLE 2a-continued
| Comp. No. | Structure | LCMS |
|---|---|---|
| 358 | 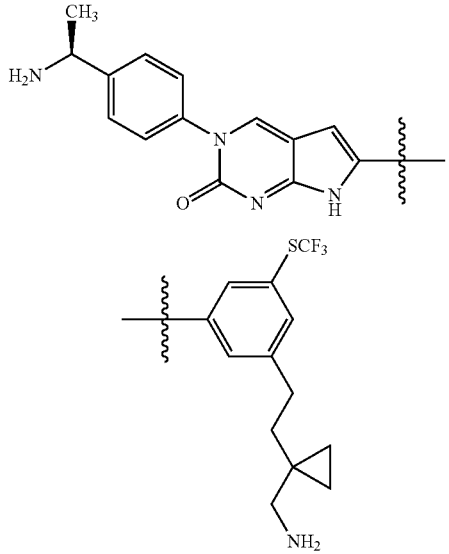 | 528.1 |
| 359 | 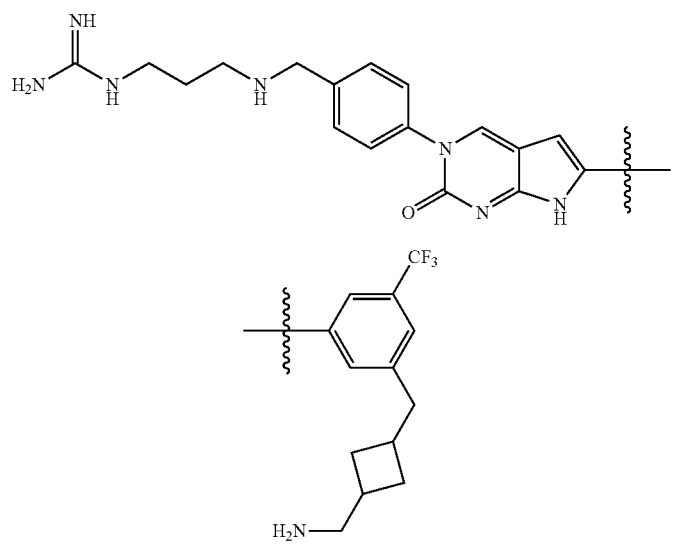 | 565.0 |

TABLE 2a-continued
| Comp. No. | Structure | LCMS |
|---|---|---|
| 360 | 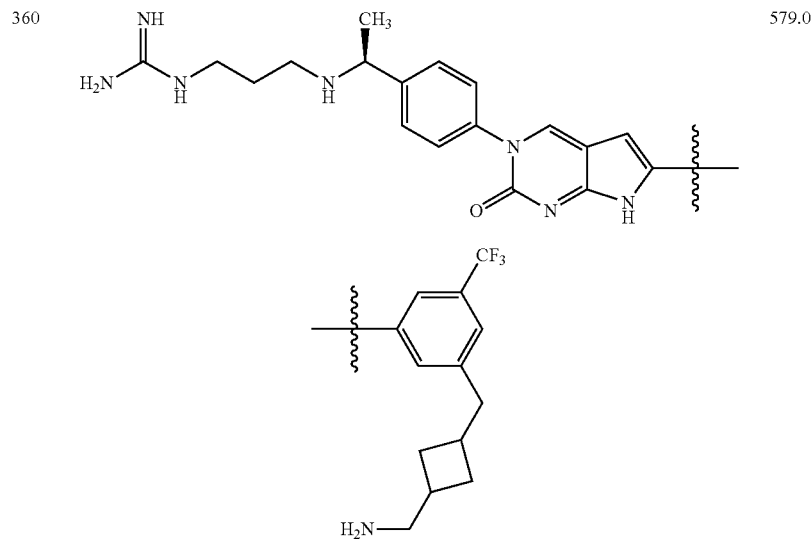 | 579.0 |
| 361 | 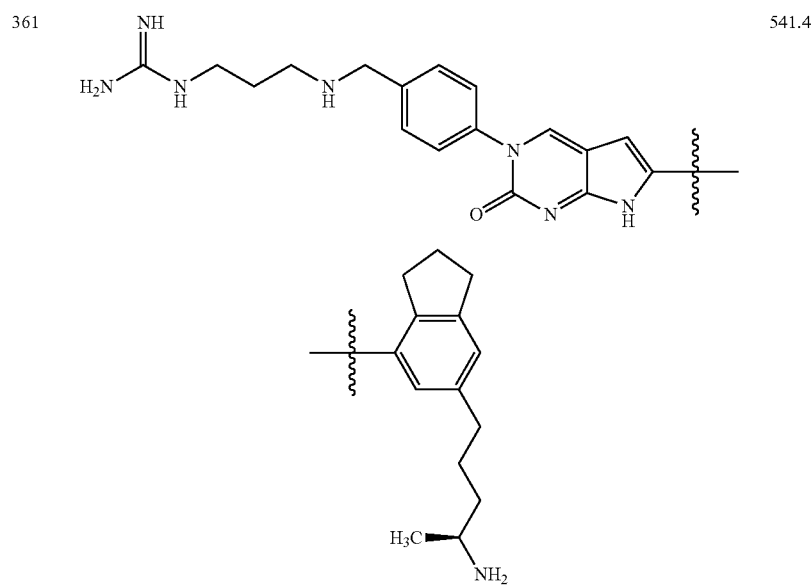 | 541.4 |

TABLE 2a-continued
| Comp. No. | Structure | LCMS |
|---|---|---|
| 362 | 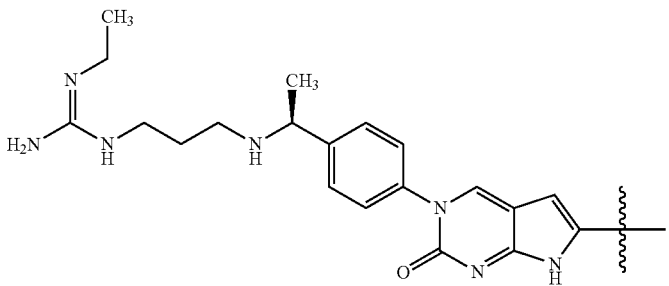<br>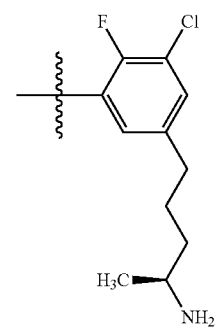 | 595.4 |
| 363 | 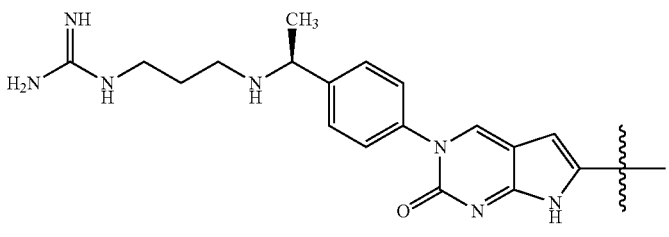<br>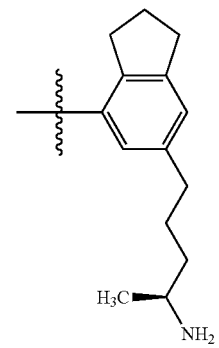 | 555.2 |

TABLE 2a-continued
| Comp. No. | Structure | LCMS |
|---|---|---|
| 364 | 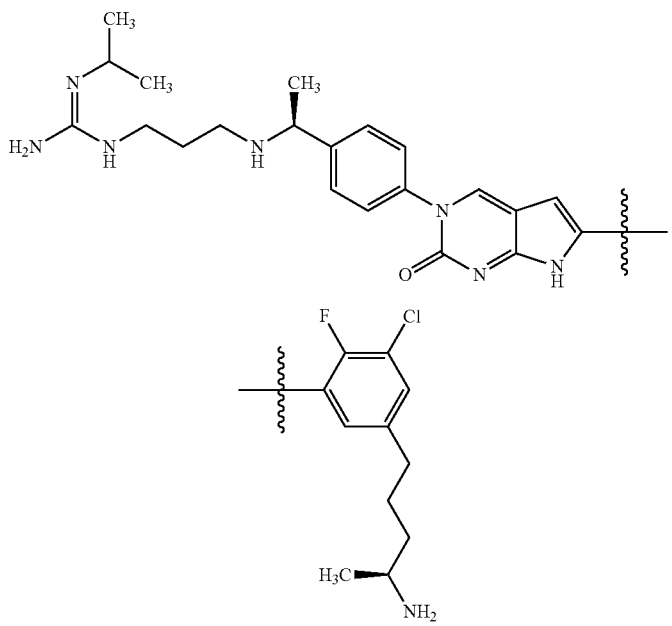 | 609.1 |
| 365 | 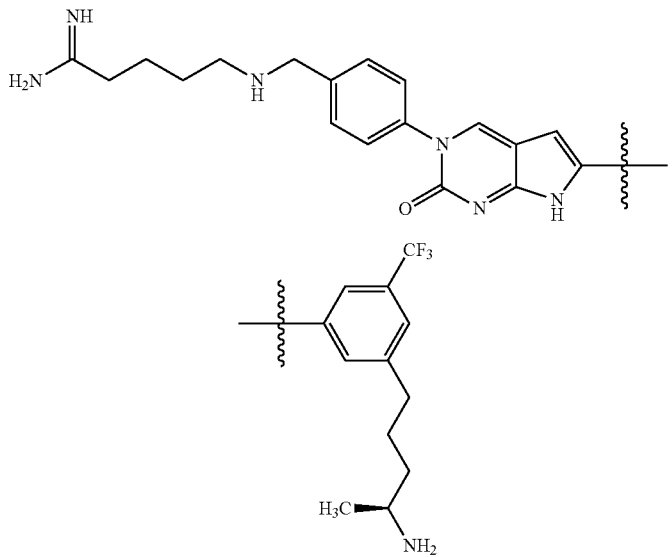 | 569.0 |

TABLE 2a-continued
| Comp. No. | Structure | LCMS |
|---|---|---|
| 366 | 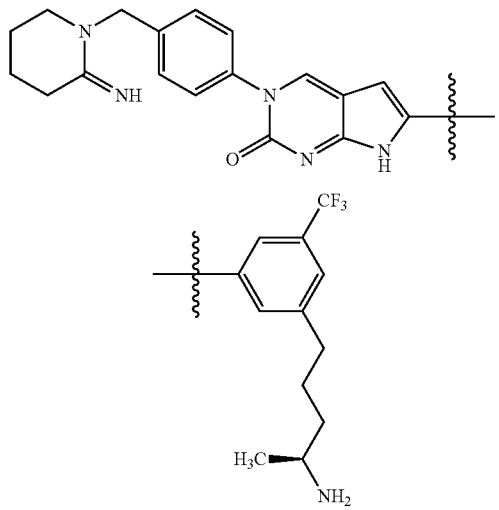 | 552.0 |
| 367 | 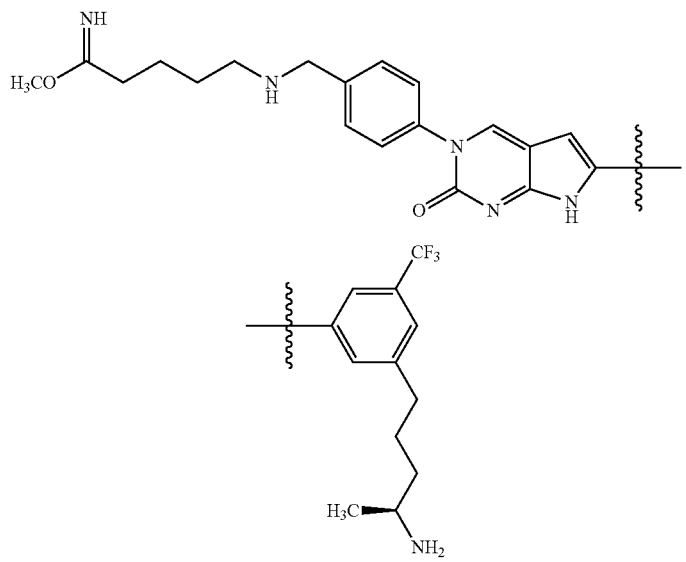 | 584.0 |

TABLE 2a-continued
| Comp. No. | Structure | LCMS |
|---|---|---|
| 368 | 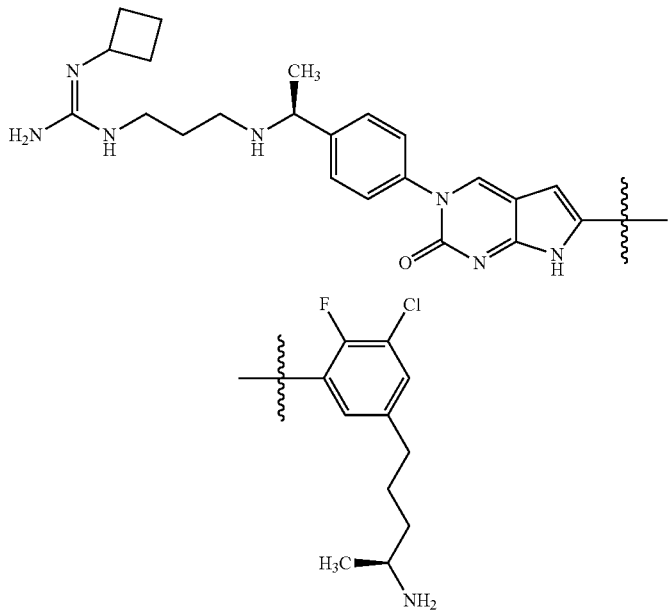 | 621.2 |
| 369 | 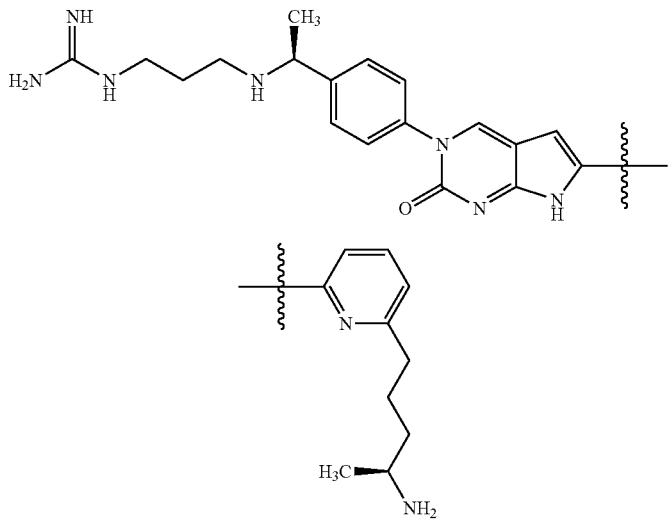 | 516.1 |

TABLE 2a-continued
| Comp. No. | Structure | LCMS |
|---|---|---|
| 370 | 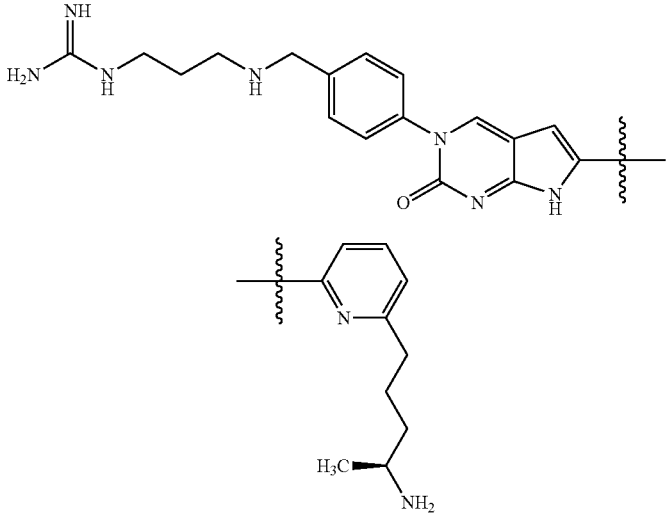 | 502.1 |
| 371 | 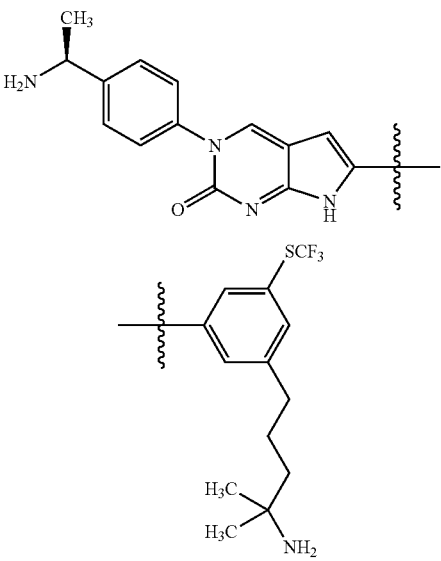 | 530.2 |
| 372 | 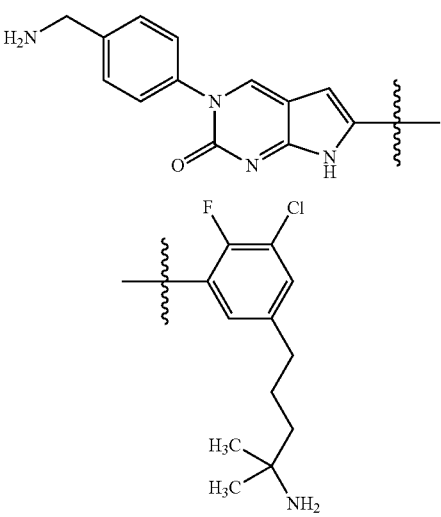 | 468.2 |

TABLE 2a-continued
| Comp. No. | Structure | LCMS |
|---|---|---|
| 373 | 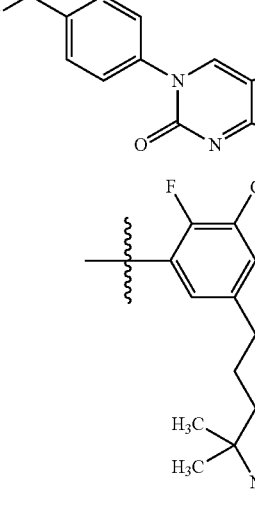 | 482.2 |
| 374 | 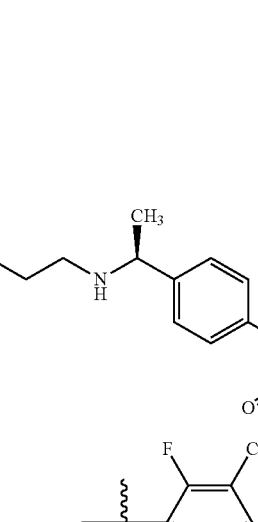 | 581.2 |

TABLE 2a-continued
| Comp. No. | Structure | LCMS |
|---|---|---|
| 375 | 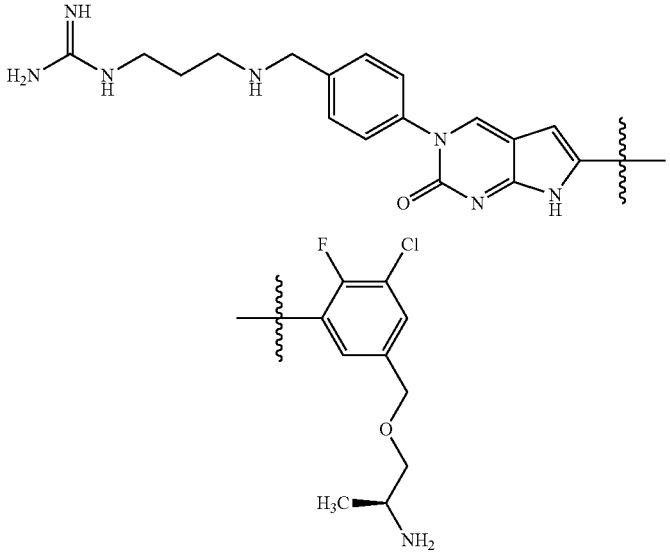 | 555.0 |
| 376 | 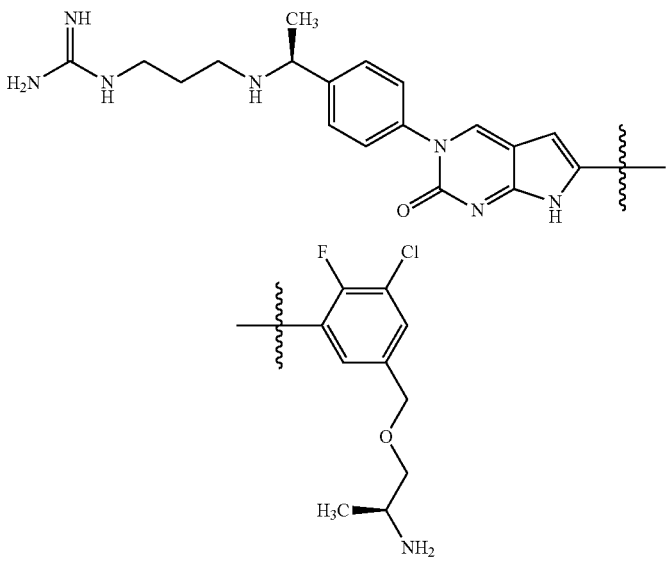 | 569.0 |

TABLE 2a-continued
| Comp. No. | Structure | LCMS |
|---|---|---|
| 377 | 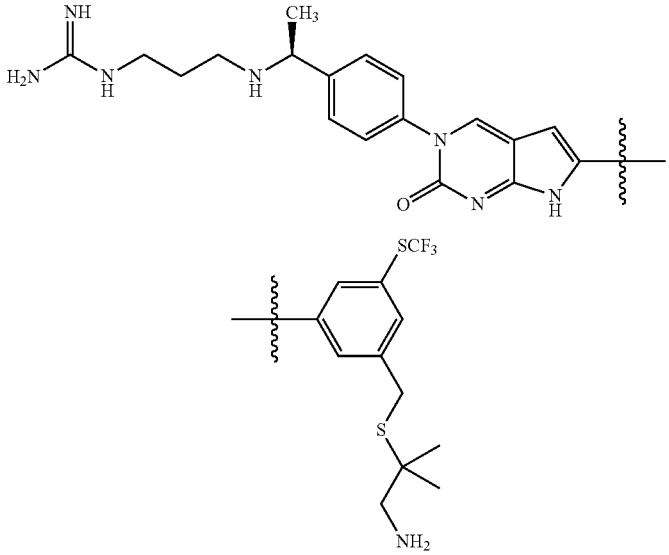 | 647.5 |
| 378 | 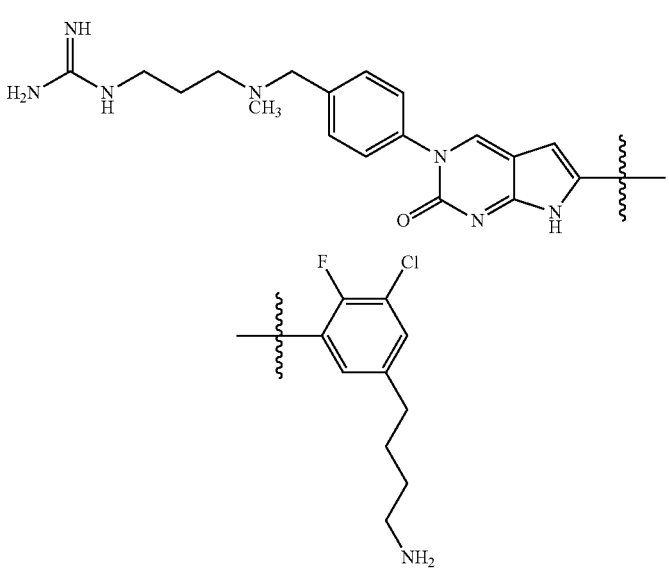 | 554.6 |

TABLE 2a-continued
| Comp. No. | Structure | LCMS |
|---|---|---|
| 379 | 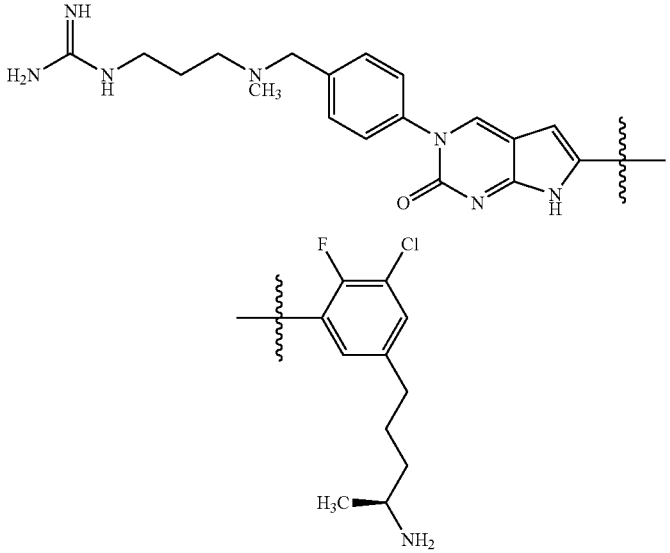 | 568.1 |
| 380 | 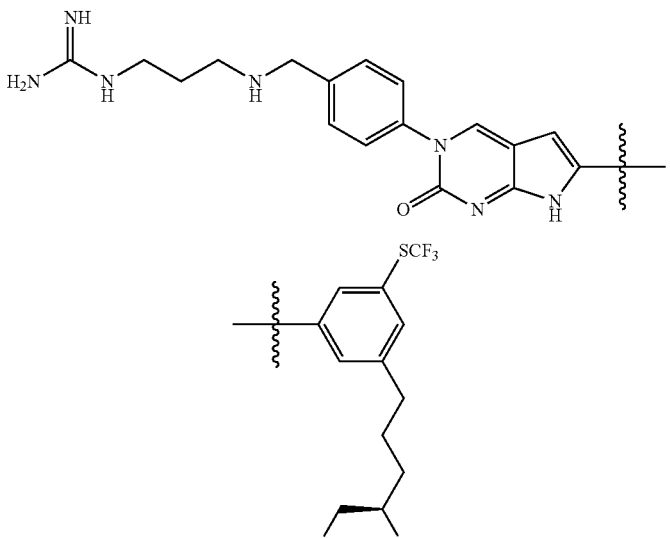 | 615.1 |

TABLE 2a-continued
| Comp. No. | Structure | LCMS |
|---|---|---|
| 381 | 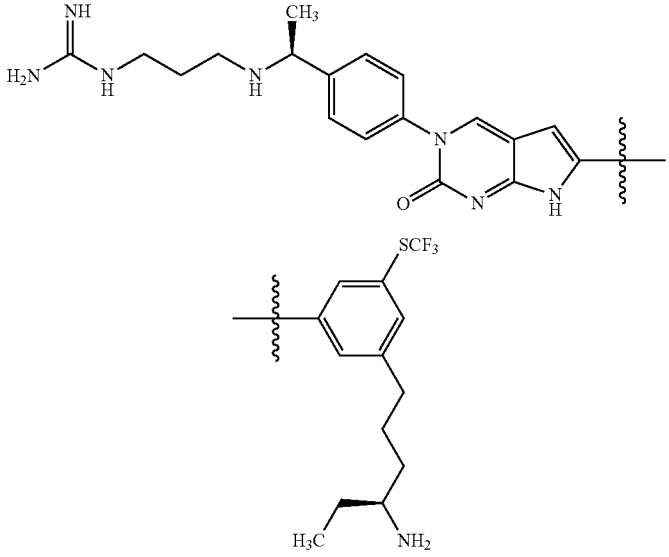 | 629.5 |
| 382 | 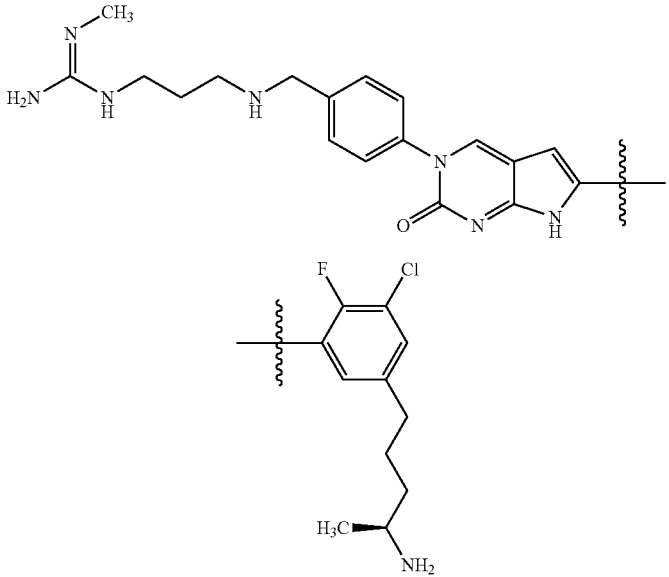 | 567.1 |

TABLE 2a-continued
| Comp. No. | Structure | LCMS |
|---|---|---|
| 383 | 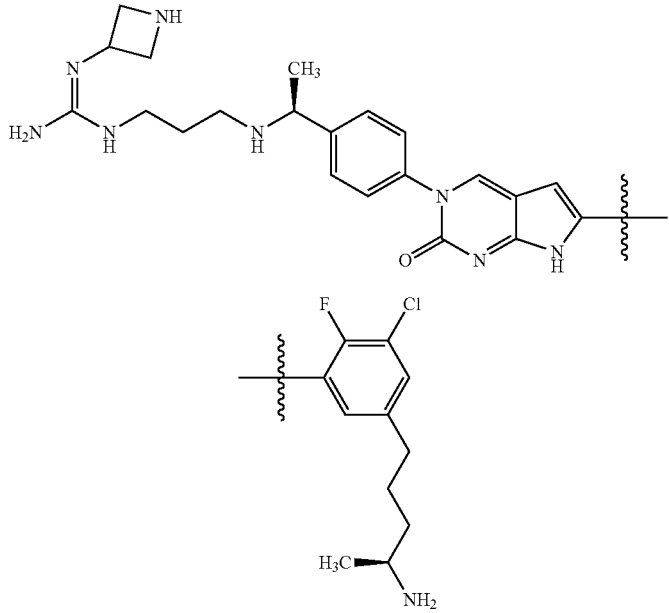 | 622.3 |
| 384 | 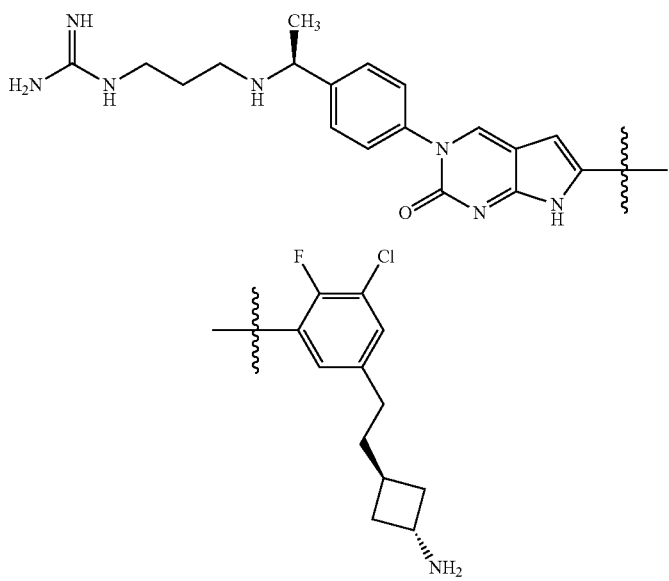 | 579.1 |

TABLE 2a-continued
| Comp. No. | Structure | LCMS |
|---|---|---|
| 385 | 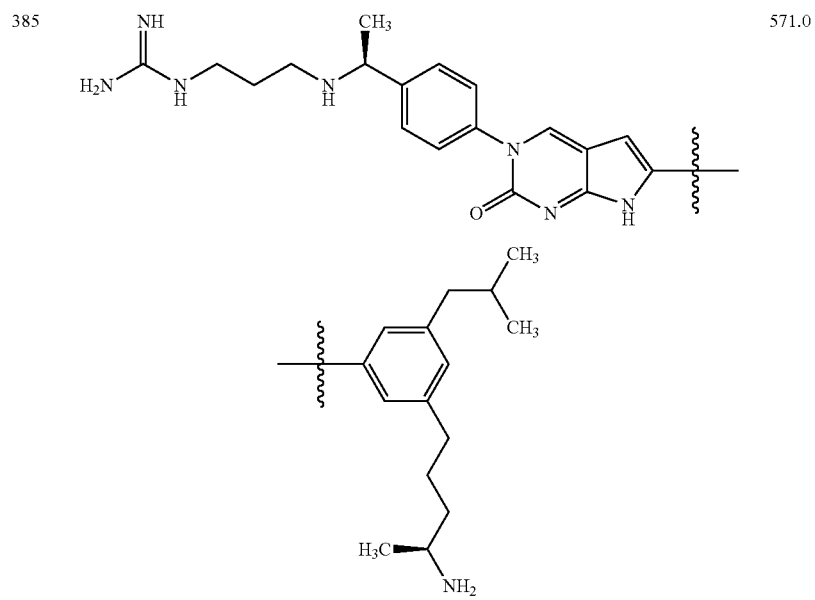 | 571.0 |
| 386 | 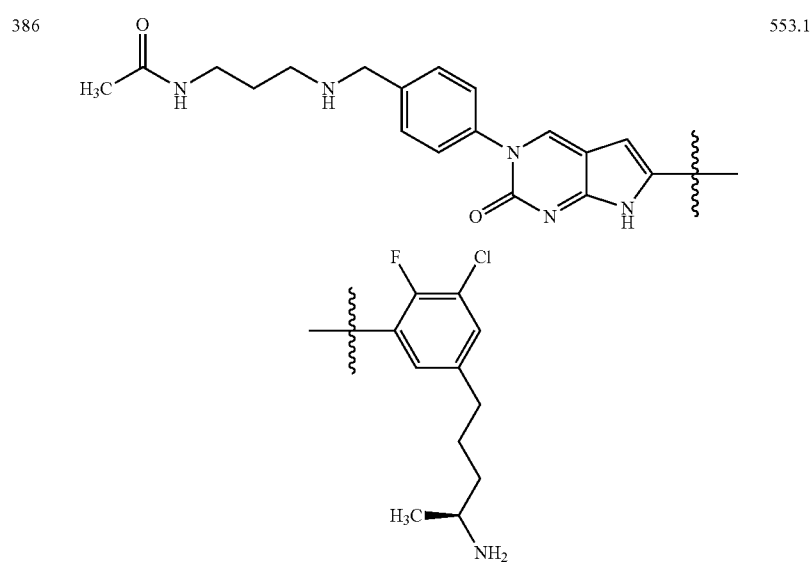 | 553.1 |

TABLE 2a-continued
| Comp. No. | Structure | LCMS |
|---|---|---|
| 387 | 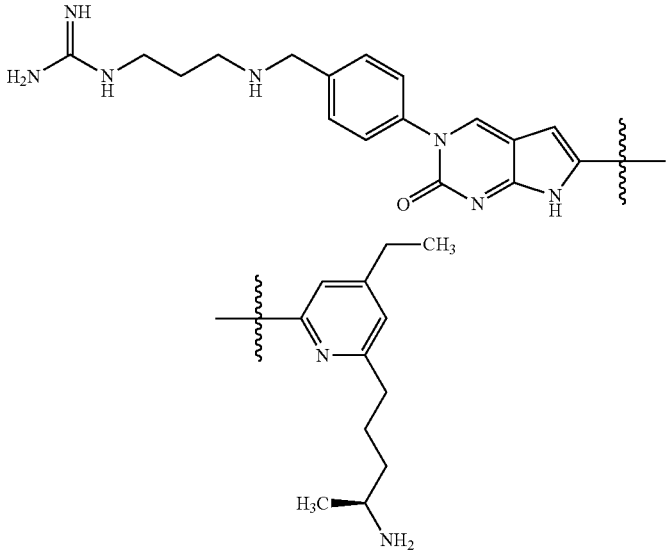 | 530.2 |
| 388 | 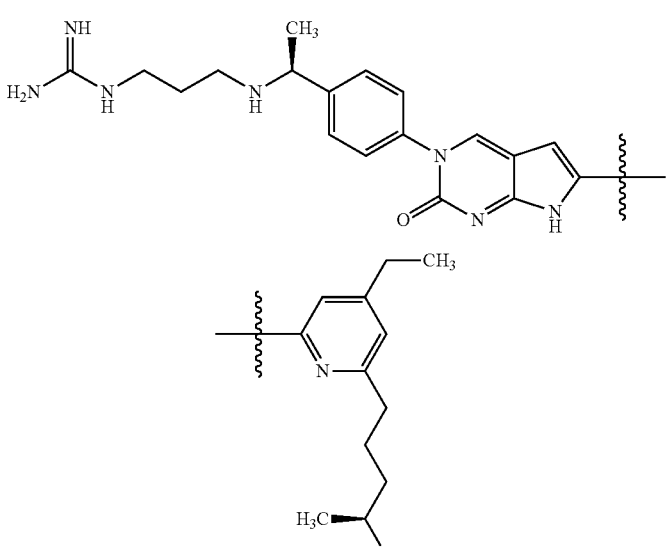 | 544.1 |

TABLE 2a-continued
| Comp. No. | Structure | LCMS |
|---|---|---|
| 389 | 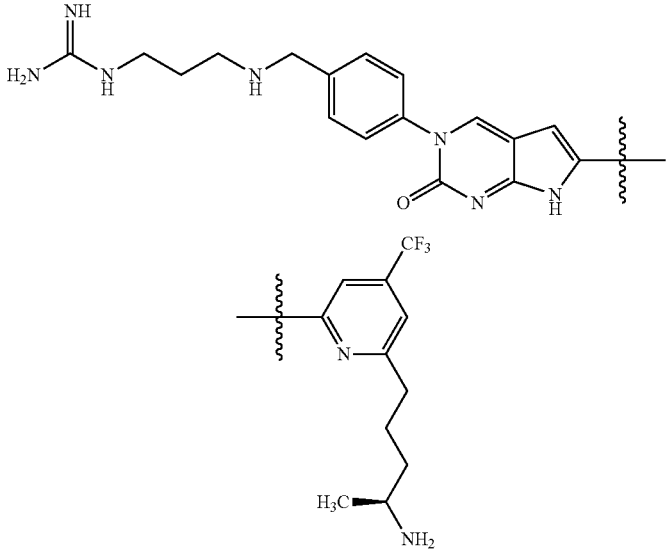 | 570.1 |
| 390 | 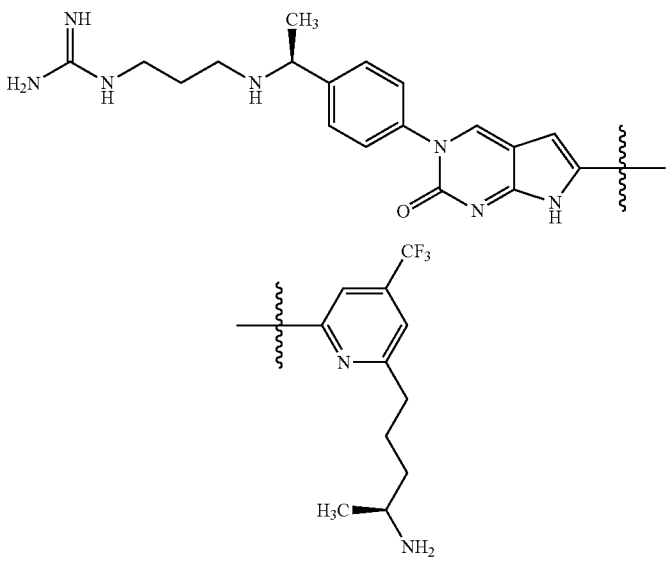 | 584.1 |

TABLE 2a-continued
| Comp. No. | Structure | LCMS |
|---|---|---|
| 391 | 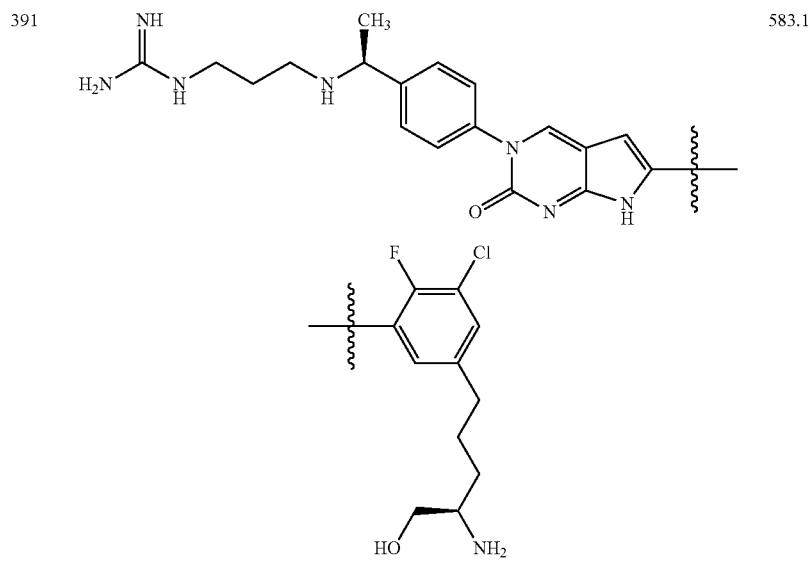 | 583.1 |
| 392 | 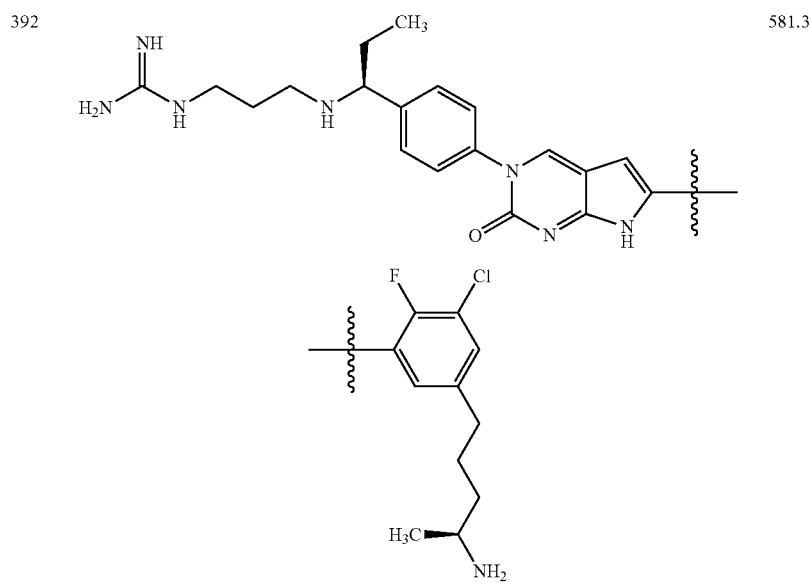 | 581.3 |

TABLE 2a-continued
| Comp. No. | Structure | LCMS |
|---|---|---|
| 393 | 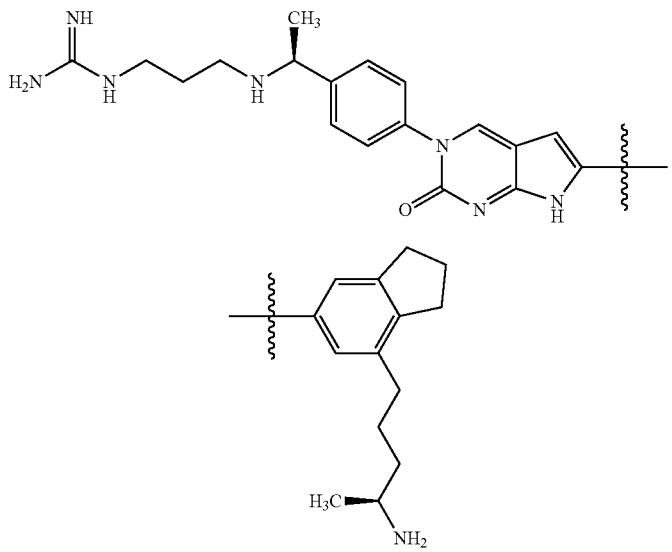 | 555.2 |
| 394 | 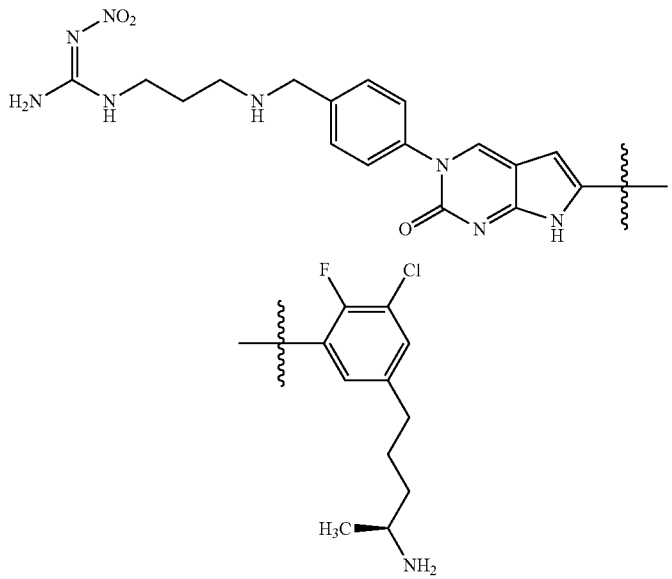 | 598.1 |

TABLE 2a-continued
| Comp. No. | Structure | LCMS |
|---|---|---|
| 395 | 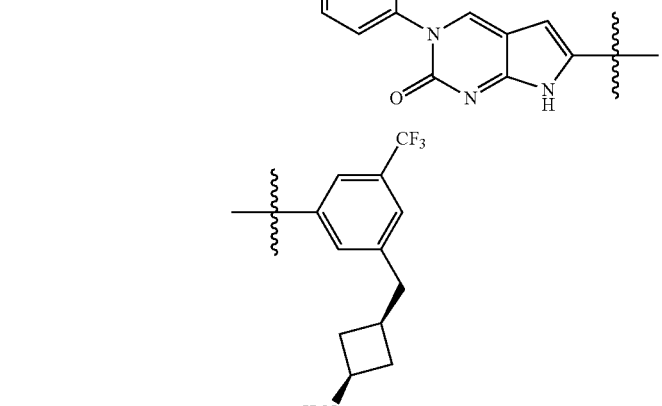 | 581.0 |
| 396 | 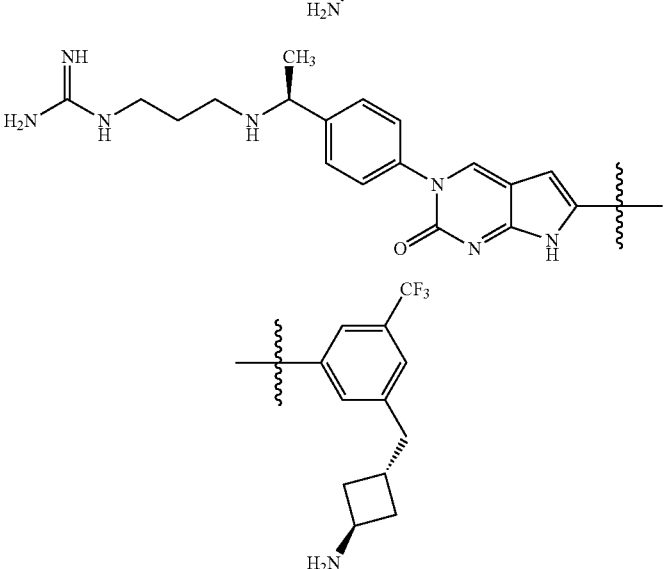 | 581.1 |
| 397 | 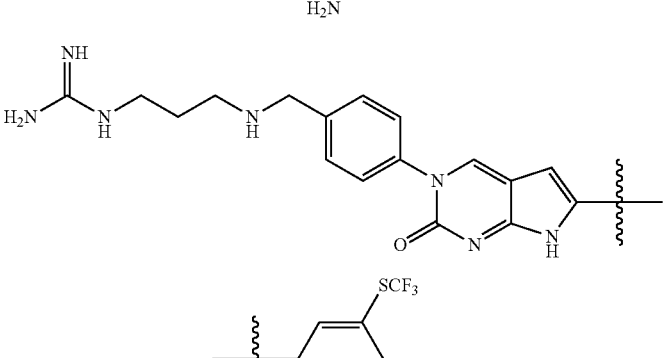 | 587.6 |

TABLE 2a-continued
| Comp. No. | Structure | LCMS |
|---|---|---|
| 398 | 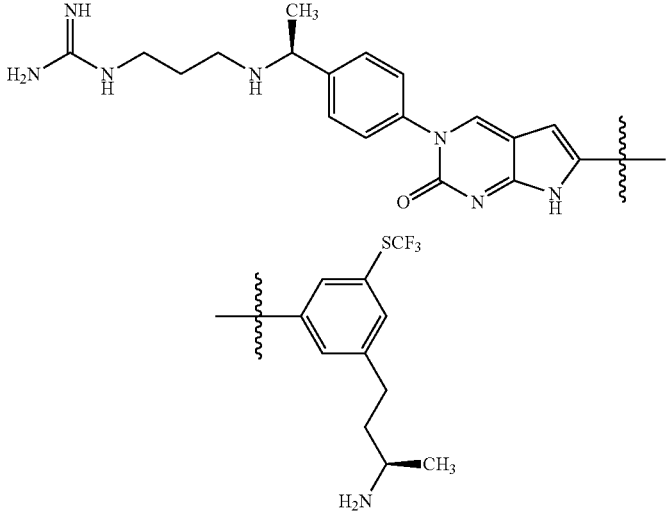 | 601.7 |
| 399 | 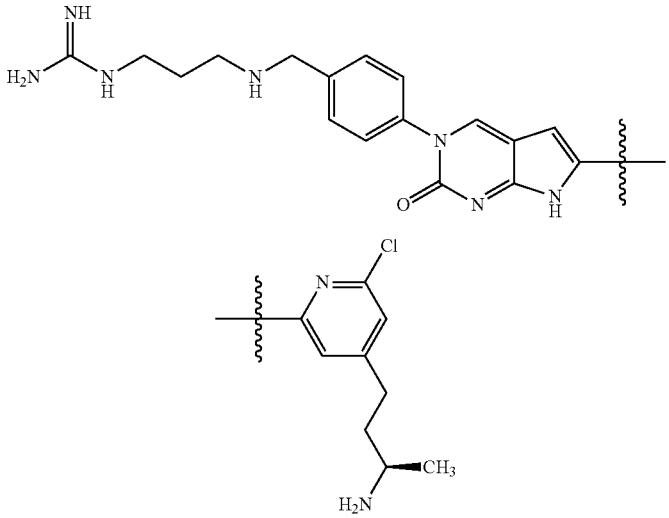 | 550.1 |
| 400 | 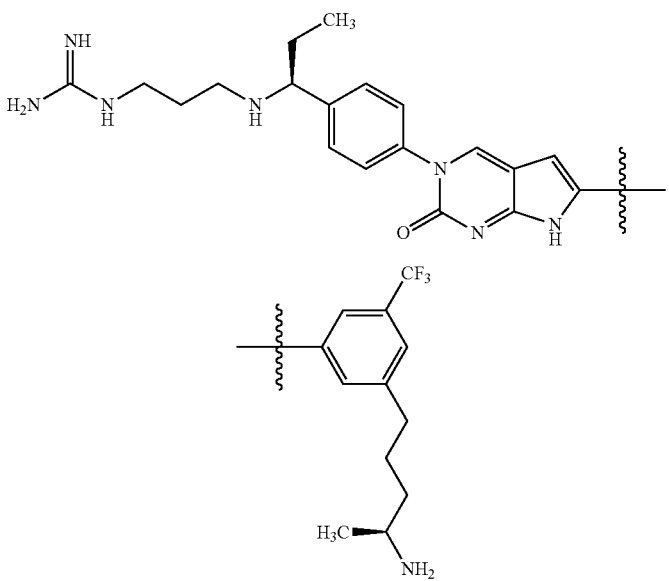 | 597.2 |

TABLE 2a-continued
| Comp. No. | Structure | LCMS |
|---|---|---|
| 401 | 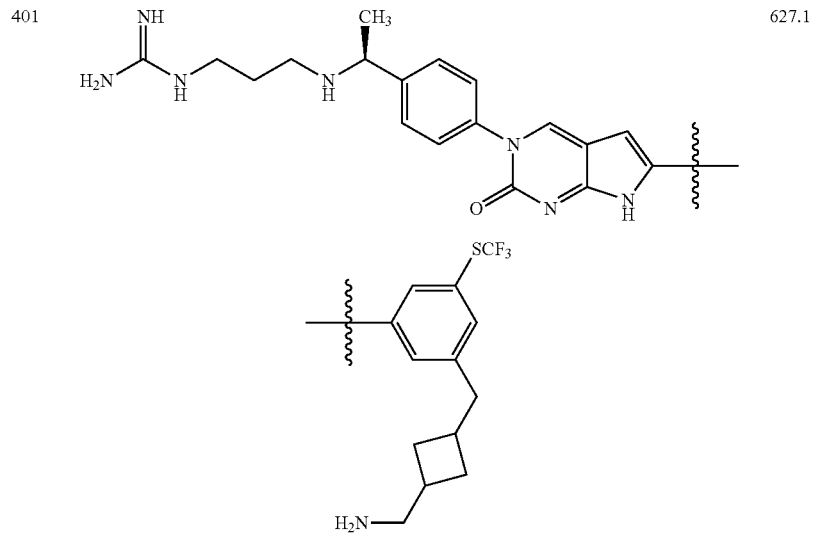 | 627.1 |
| 402 | 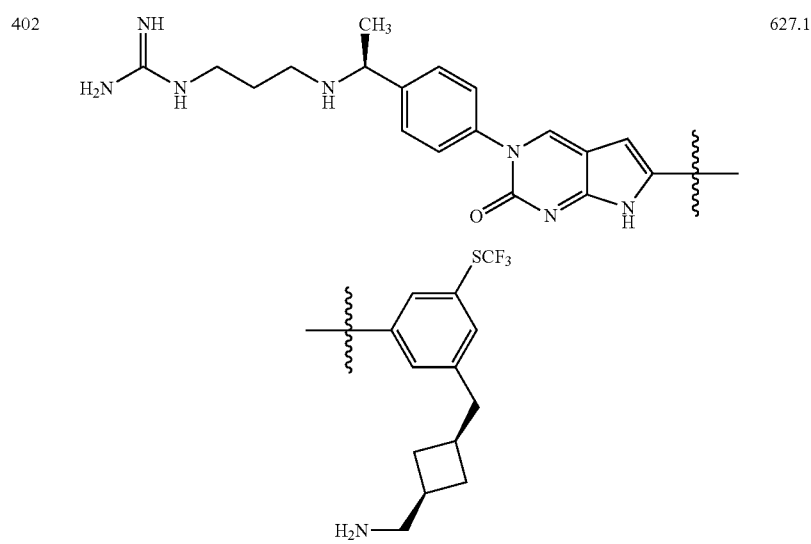 | 627.1 |

TABLE 2a-continued
| Comp. No. | Structure | LCMS |
|---|---|---|
| 403 | 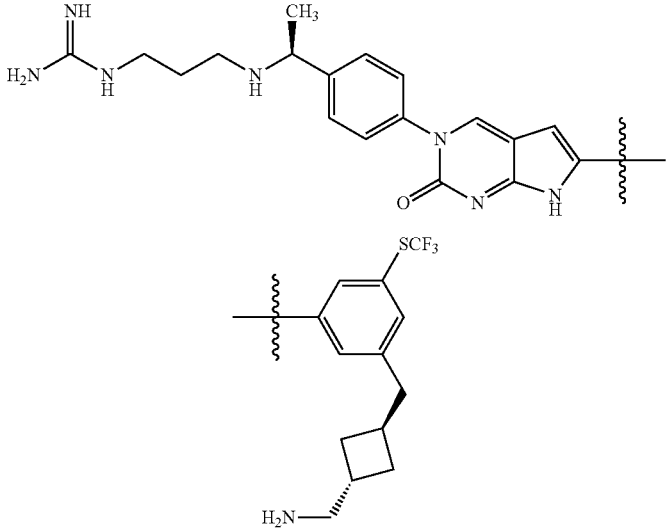 | 627.1 |
| 404 | 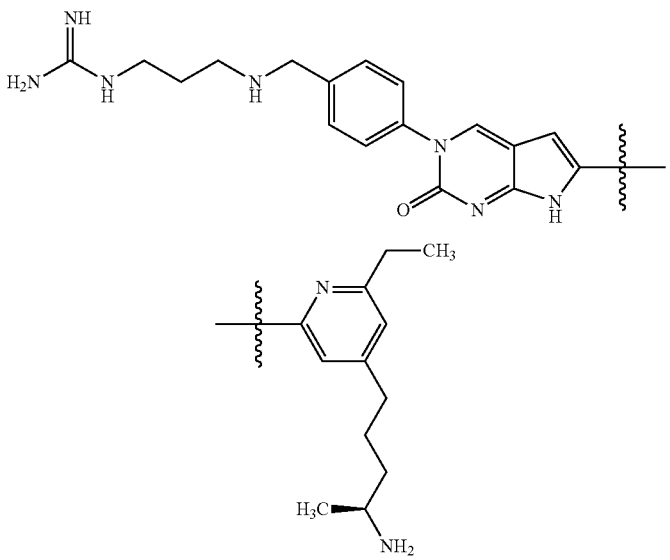 | 544.4 |

TABLE 2a-continued
| Comp. No. | Structure | LCMS |
|---|---|---|
| 405 | 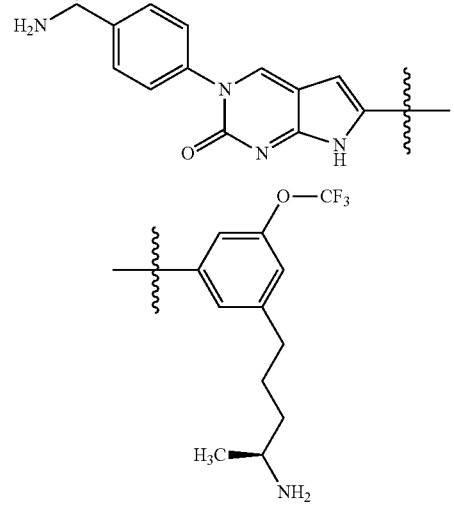 | 500.1 |
| 406 | 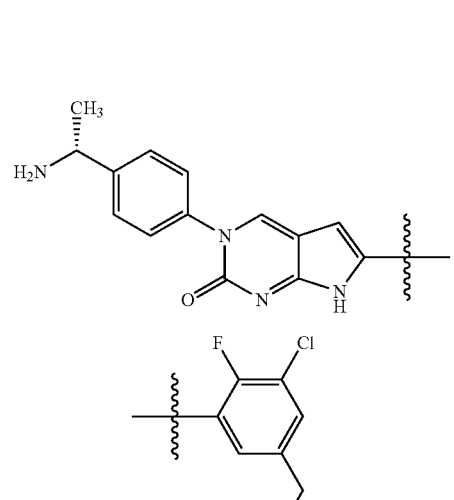 | 468.1 |

TABLE 2a-continued
| Comp. No. | Structure | LCMS |
|---|---|---|
| 407 | 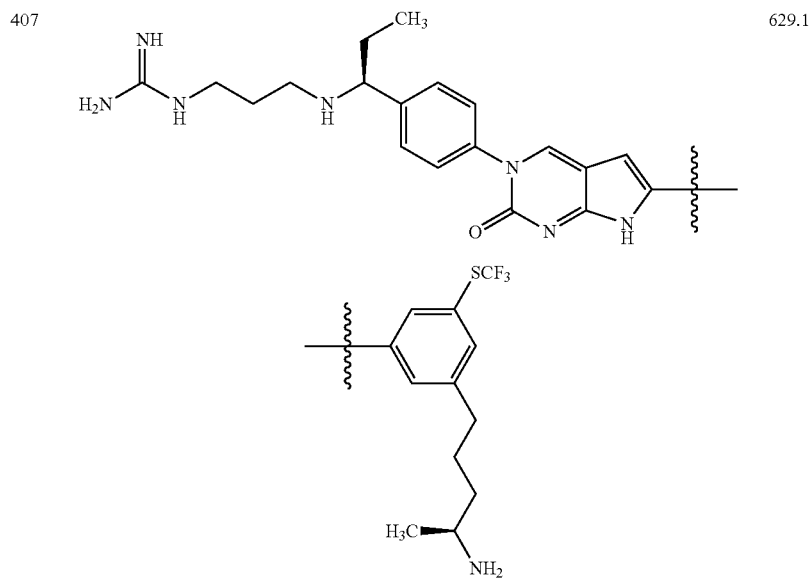 | 629.1 |
| 408 | 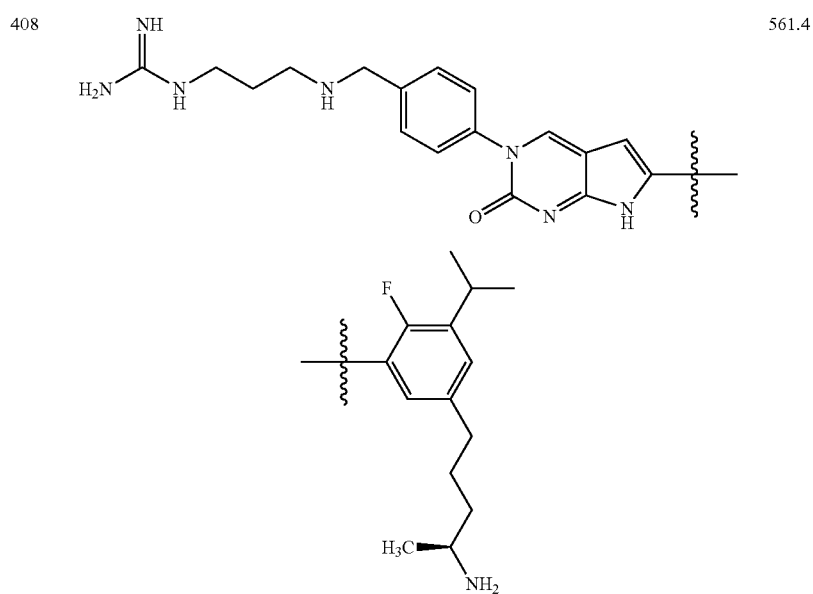 | 561.4 |

TABLE 2a-continued

| Comp. No. | Structure | LCMS |
|---|---|---|
| 409 | 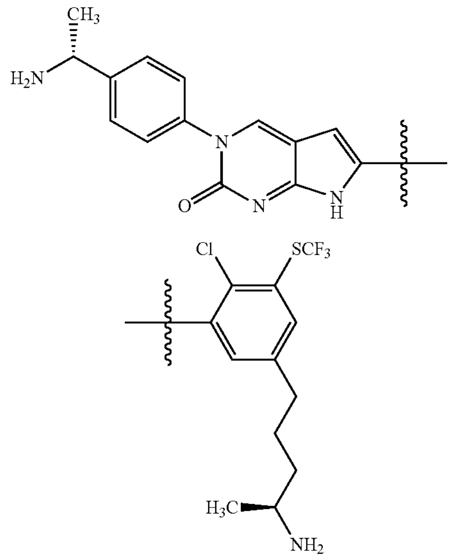 | 550.0 |
| 410 | 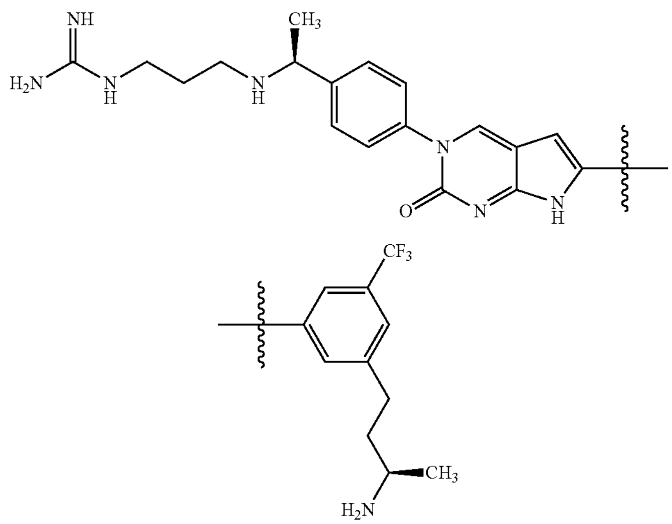 | 569.1 |
| 411 | 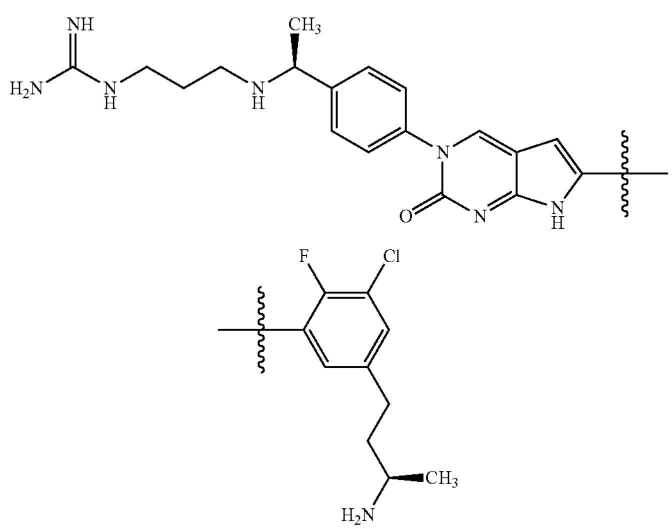 | 553.1 |

TABLE 2a-continued
| Comp. No. | Structure | LCMS |
|---|---|---|
| 412 | 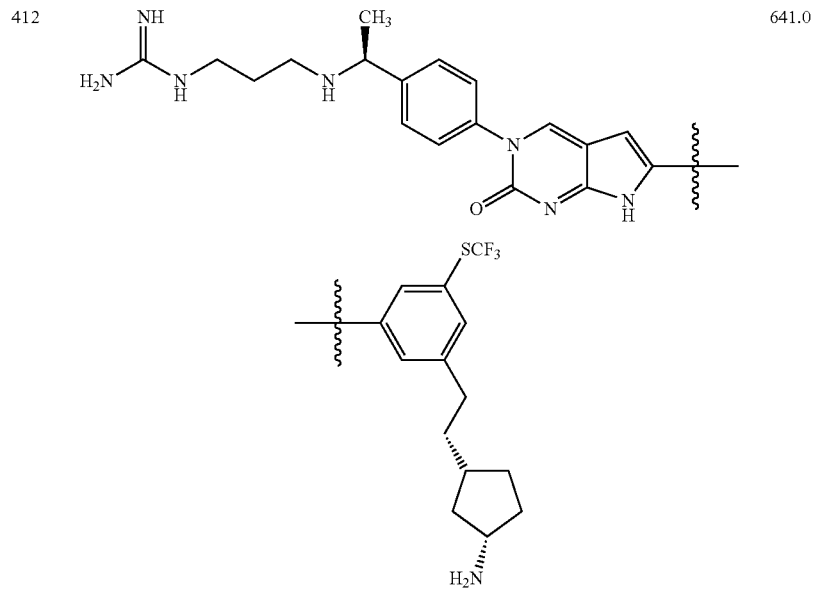 | 641.0 |
| 413 | 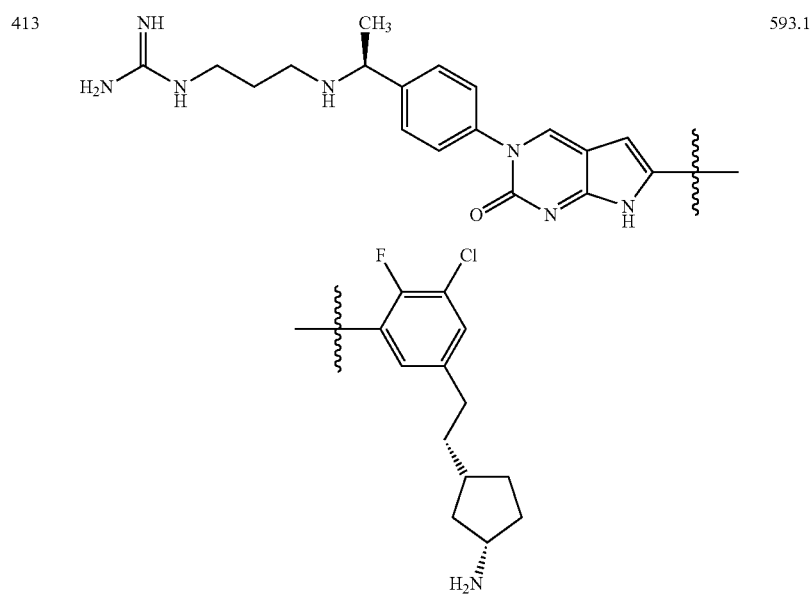 | 593.1 |

TABLE 2a-continued
| Comp. No. | Structure | LCMS |
|---|---|---|
| 414 | 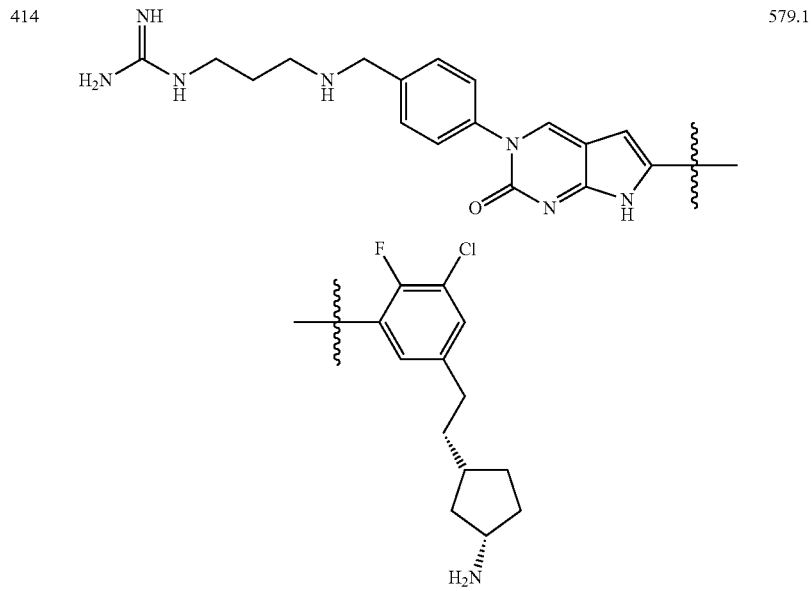 | 579.1 |
| 415 | 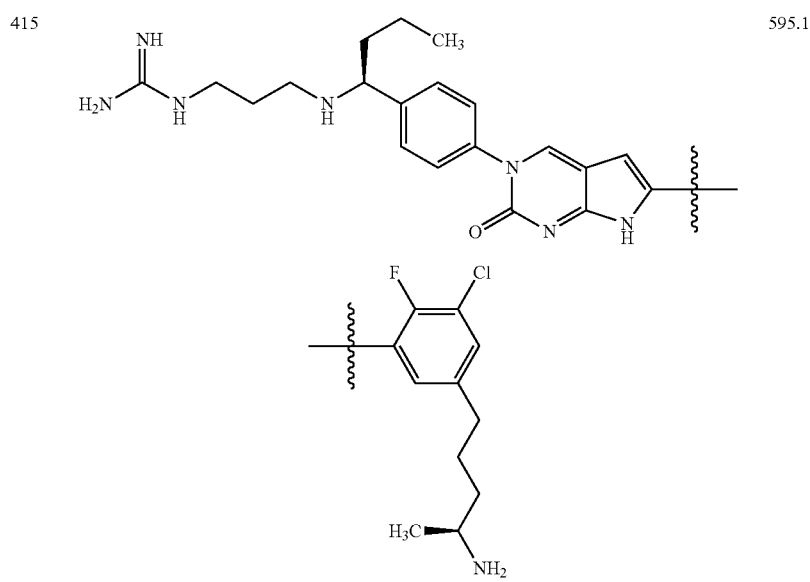 | 595.1 |

TABLE 2a-continued

| Comp. No. | Structure | LCMS |
|---|---|---|
| 416 | 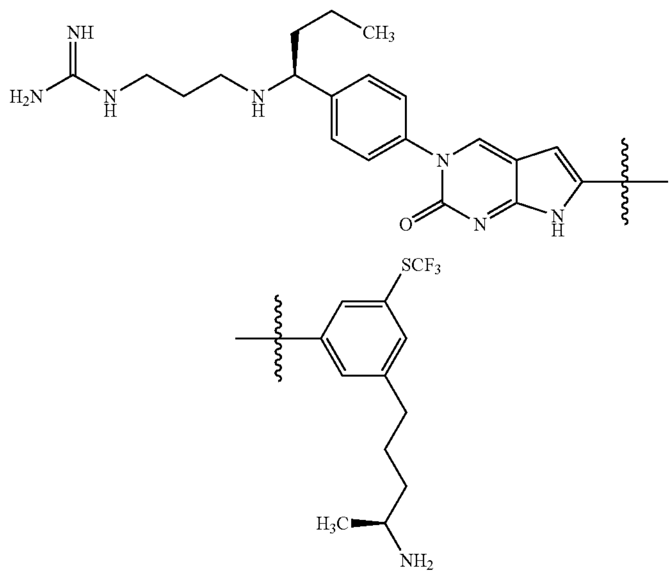 | 643.3 |
| 417 | 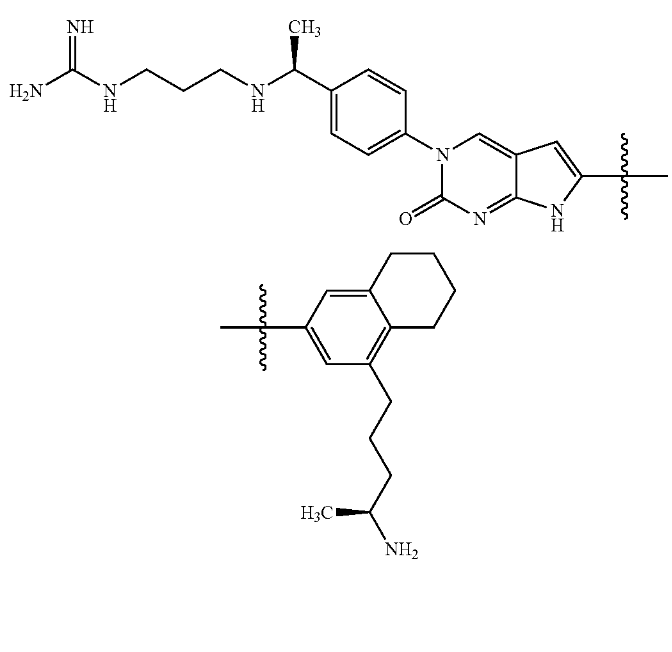 | 569.2 |

TABLE 2a-continued

| Comp. No. | Structure | LCMS |
|---|---|---|
| 418 | 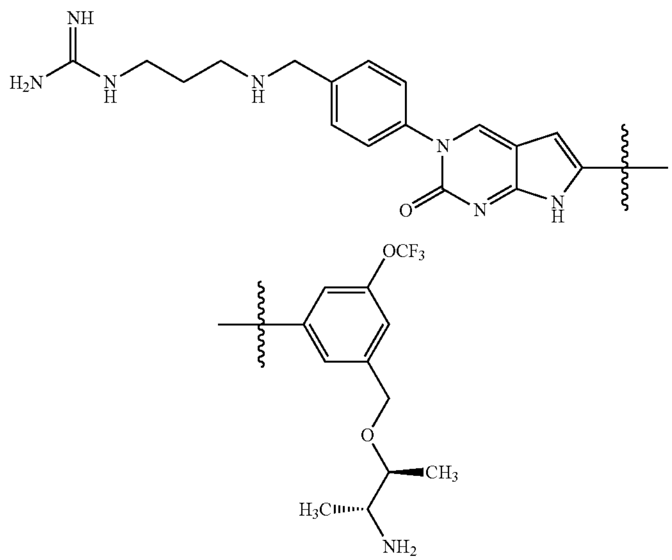 | 601.0 |
| 419 | 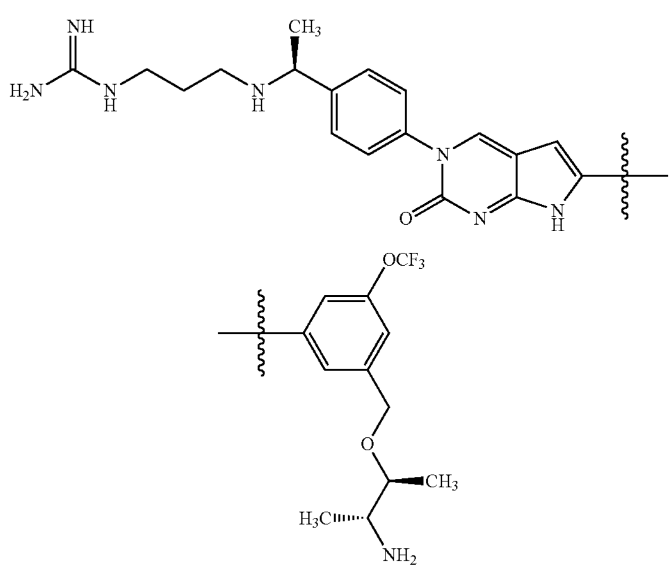 | 615.1 |

TABLE 2a-continued
| Comp. No. | Structure | LCMS |
|---|---|---|
| 420 | 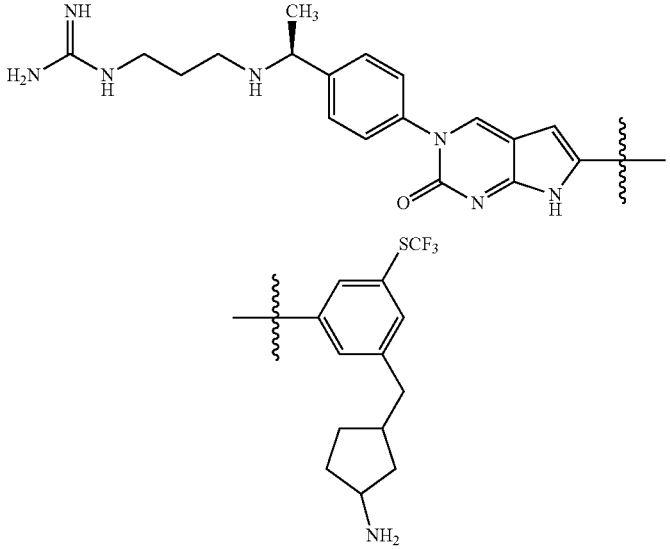 | 627.3 |
| 421 | 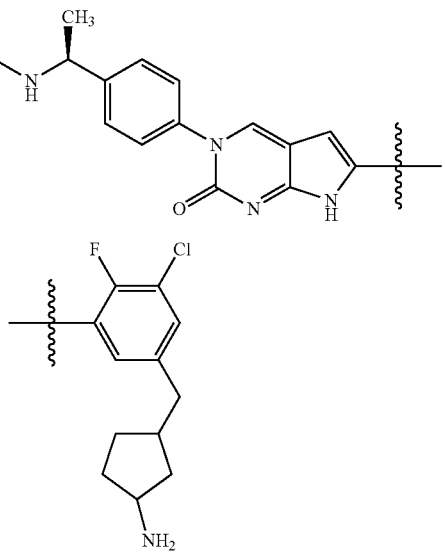 | 579.2 |

TABLE 2a-continued
| Comp. No. | Structure | LCMS |
|---|---|---|
| 422 | 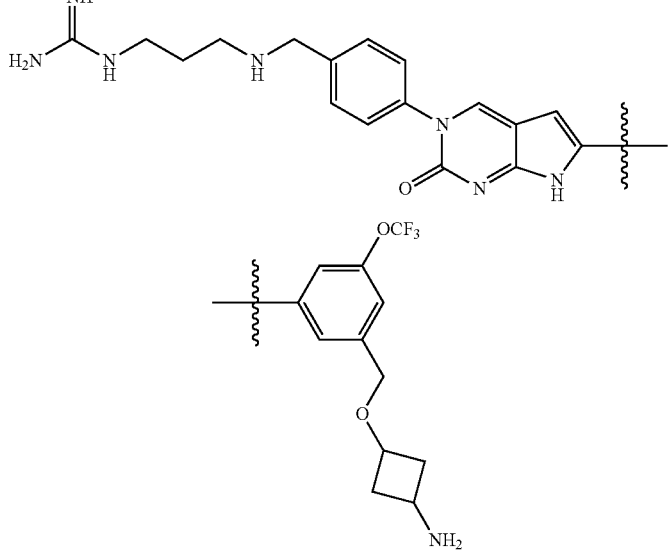 | 599.0 |
| 423 | 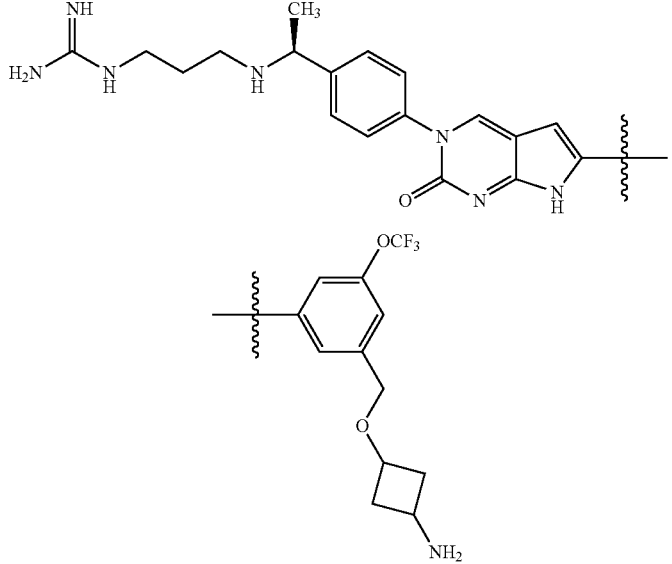 | 613.0 |

TABLE 2a-continued
| Comp. No. | Structure | LCMS |
|---|---|---|
| 424 | 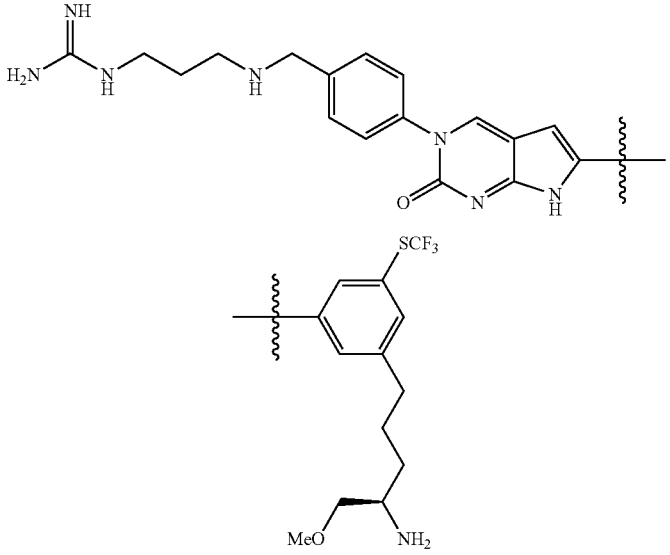 | 631.2 |
| 425 | 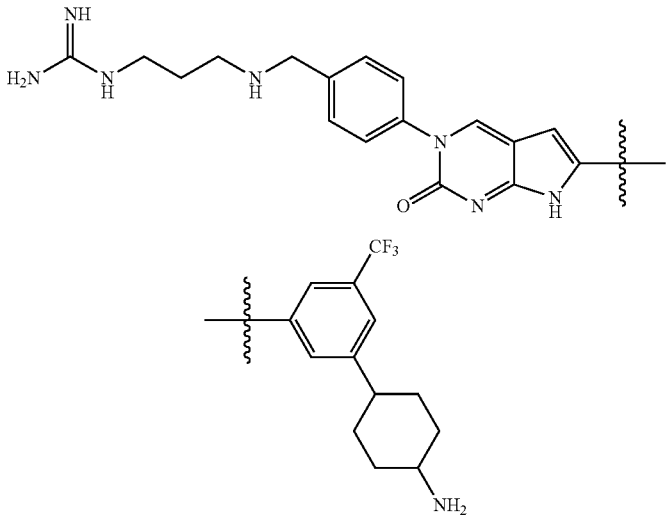 | 581.1 |
| 426 | 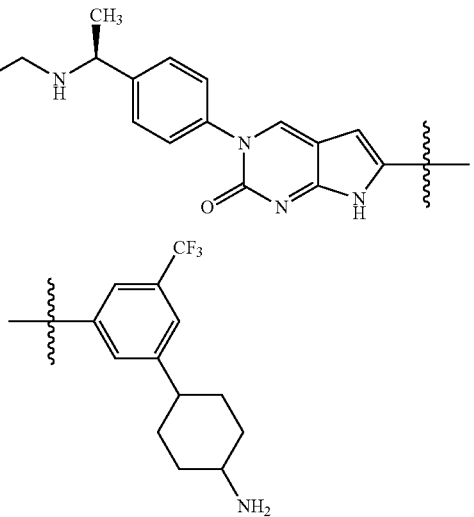 | 595.1 |

TABLE 2a-continued
| Comp. No. | Structure | LCMS |
|---|---|---|
| 427 | 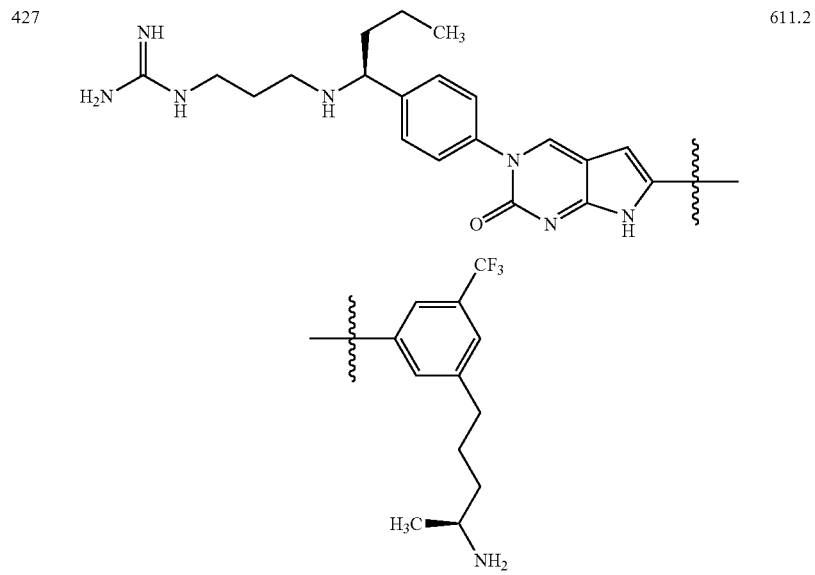 | 611.2 |
| 428 | 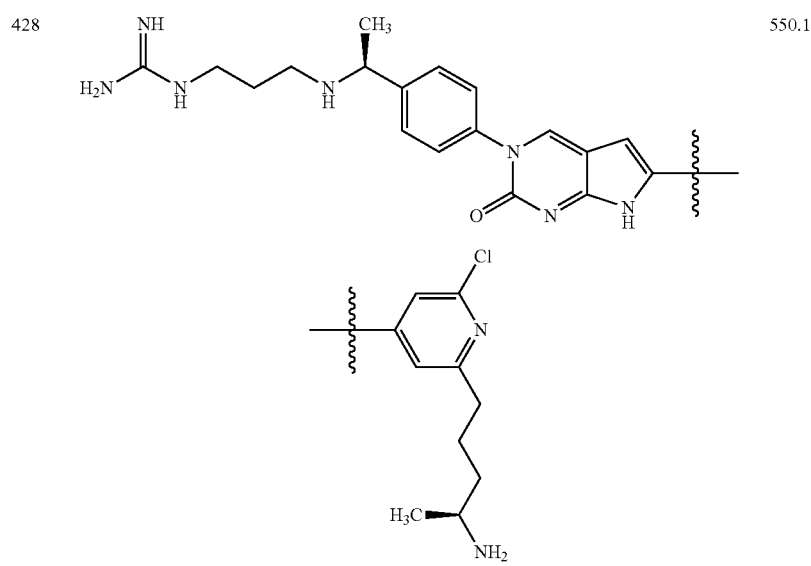 | 550.1 |

TABLE 2a-continued

| Comp. No. | Structure | LCMS |
|---|---|---|
| 429 | (structure) | 595.1 |
| 430 | (structure) | 609.1 |

TABLE 2a-continued
| Comp. No. | Structure | LCMS |
|---|---|---|
| 431 | 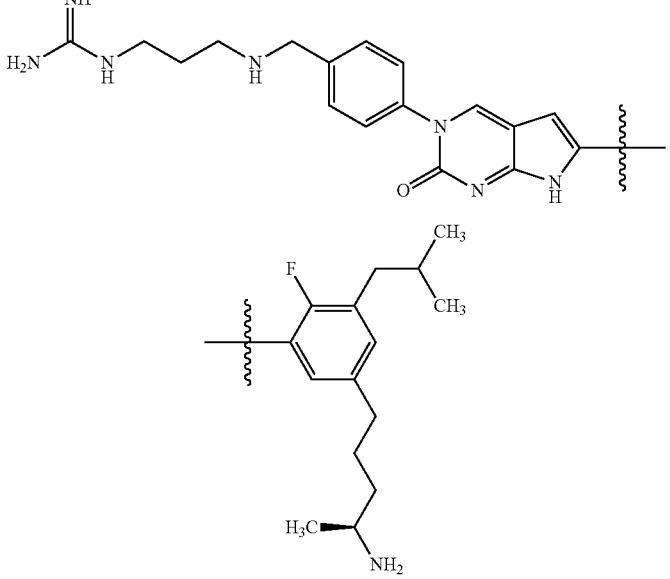 | 575.0 |
| 432 | 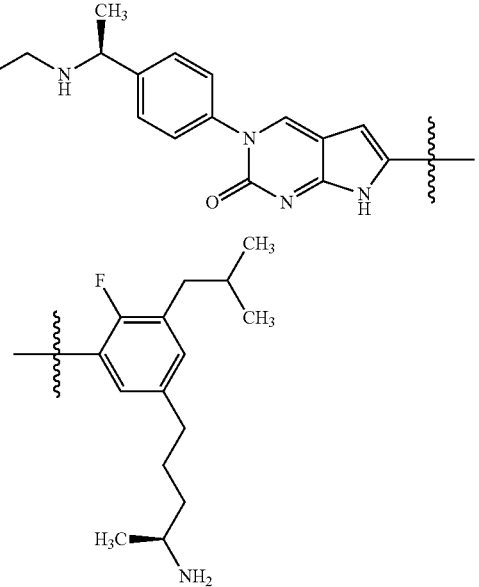 | 589.0 |

TABLE 2a-continued
| Comp. No. | Structure | LCMS |
|---|---|---|
| 433 | 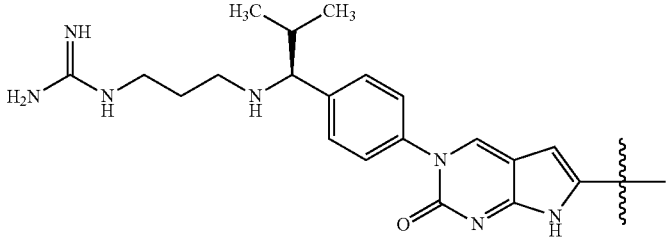 | 595.2 |
| 434 | 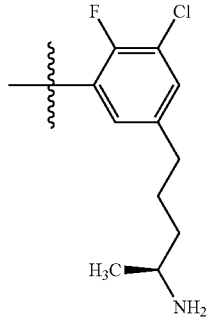 | 571.2 |

TABLE 2a-continued

| Comp. No. | Structure | LCMS |
|---|---|---|
| 435 | 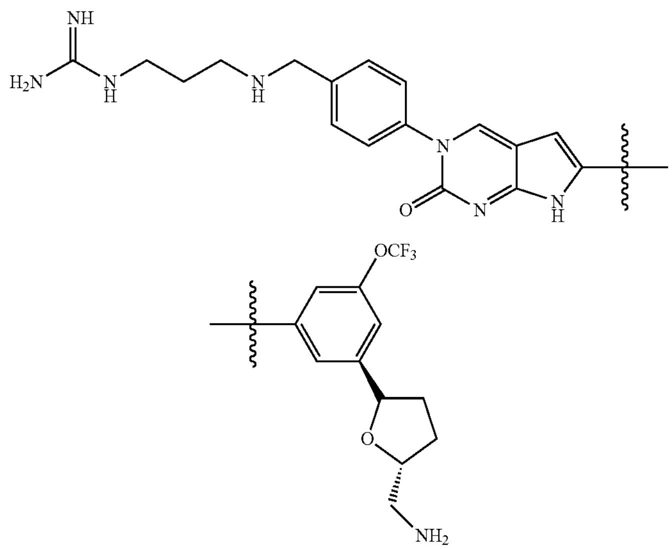 | 599.0 |
| 436 | 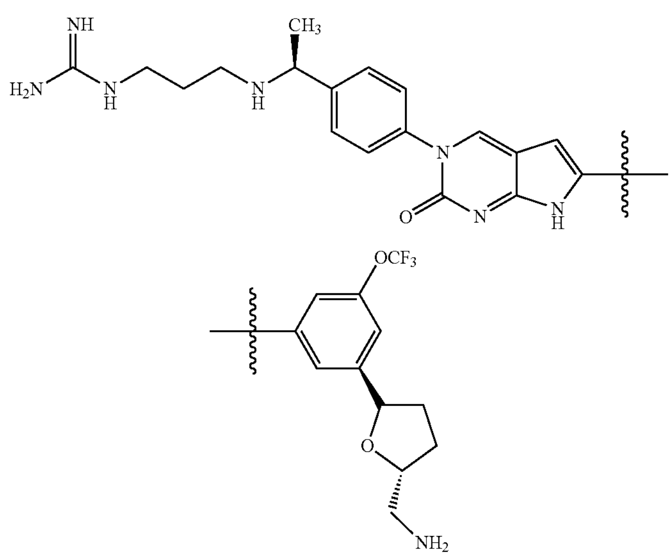 | 613.1 |

TABLE 2a-continued

| Comp. No. | Structure | LCMS |
|---|---|---|
| 437 | 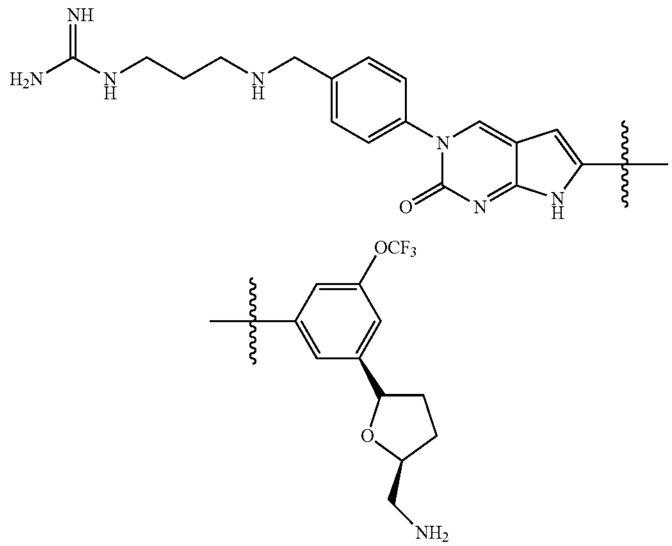 | 599.1 |
| 438 | 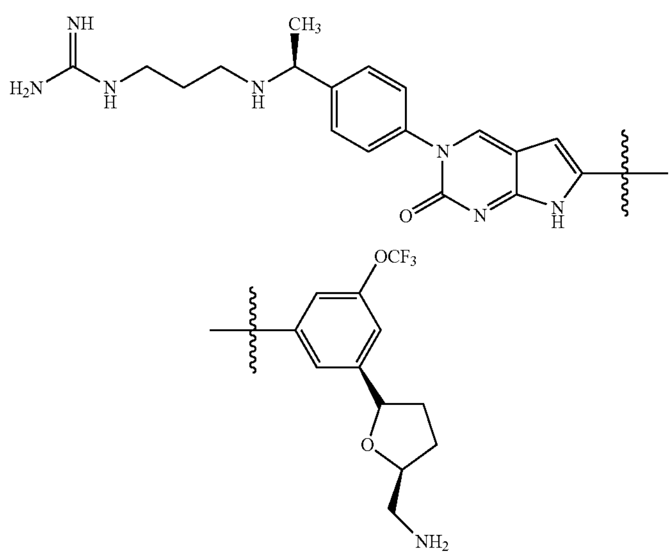 | 613.1 |

TABLE 2a-continued
| Comp. No. | Structure | LCMS |
|---|---|---|
| 439 | 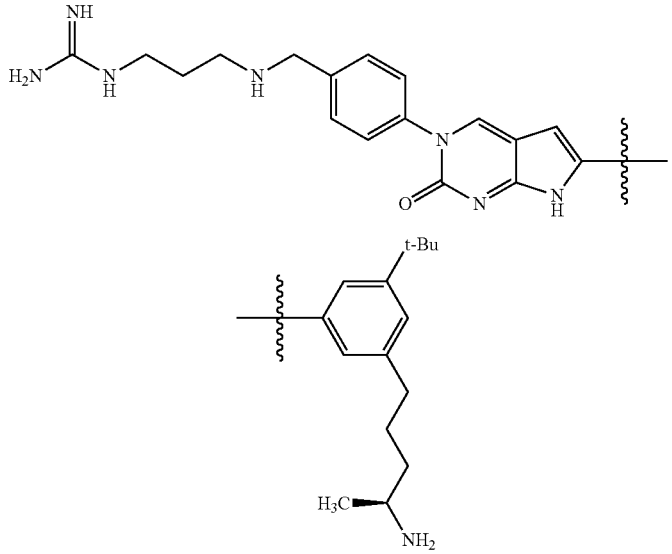 | 557.1 |
| 440 | 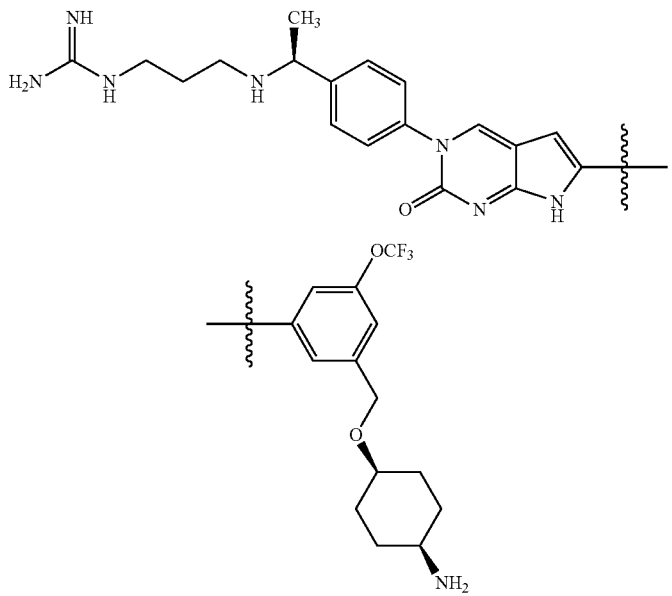 | 641.0 |

TABLE 2a-continued
| Comp. No. | Structure | LCMS |
|---|---|---|
| 441 | 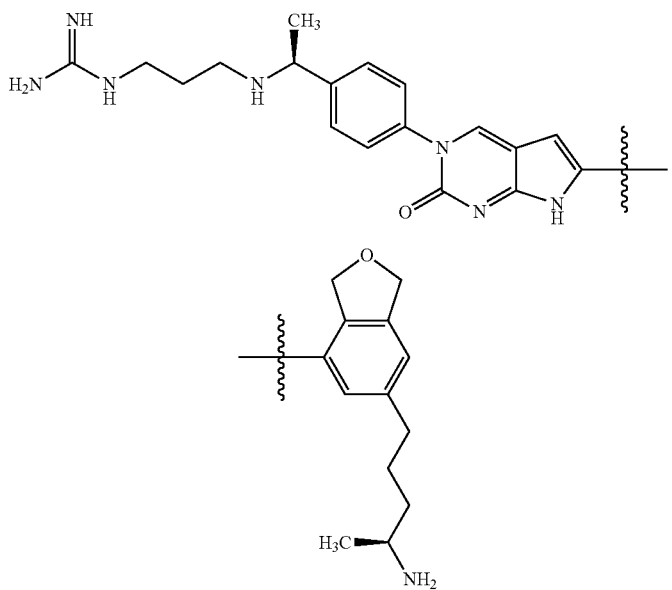 | 557.0 |
| 442 | 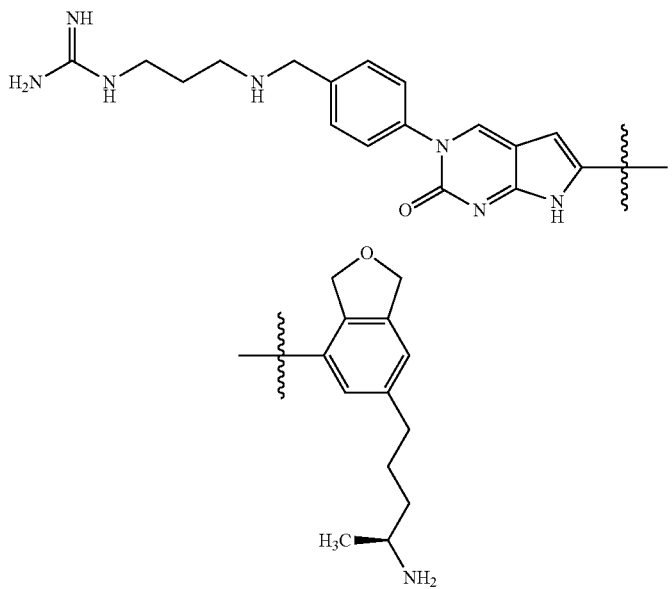 | 543.1 |

TABLE 2a-continued
| Comp. No. | Structure | LCMS |
|---|---|---|
| 443 | 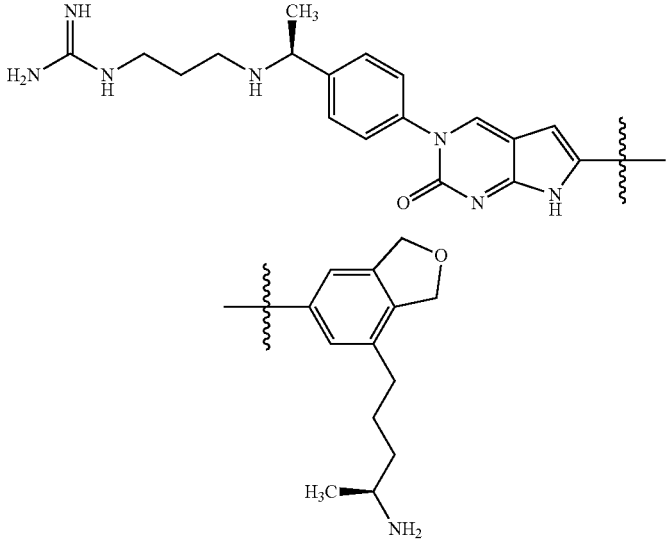 | 557.1 |
| 444 | 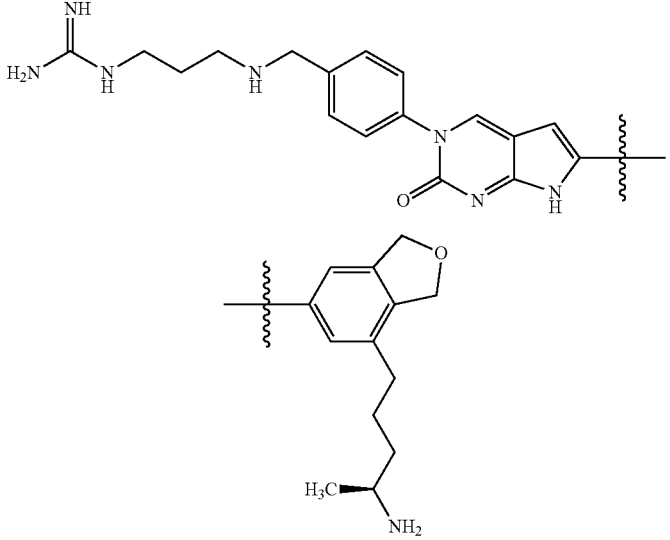 | 543.1 |

TABLE 2a-continued

| Comp. No. | Structure | LCMS |
|---|---|---|
| 445 | 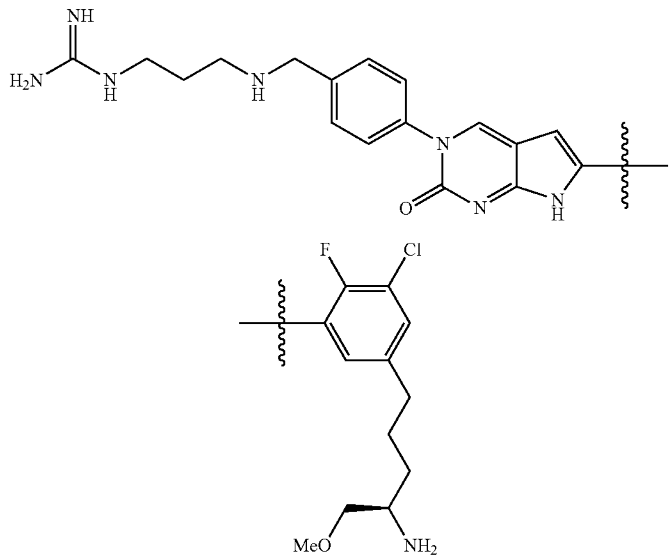 | 583.1 |
| 446 | 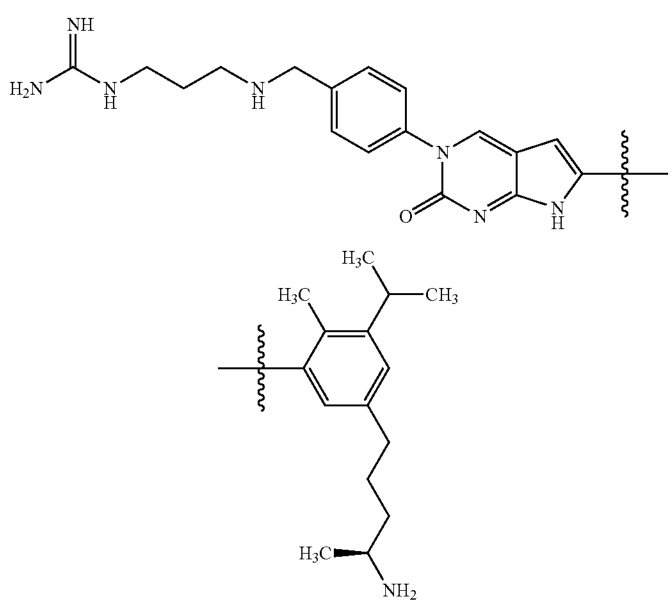 | 557.1 |

TABLE 2a-continued
| Comp. No. | Structure | LCMS |
|---|---|---|
| 447 | 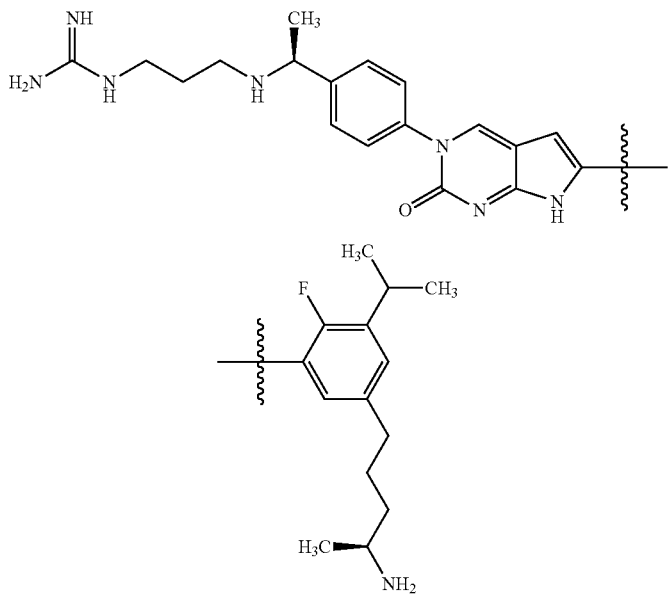 | 575.1 |
| 448 | 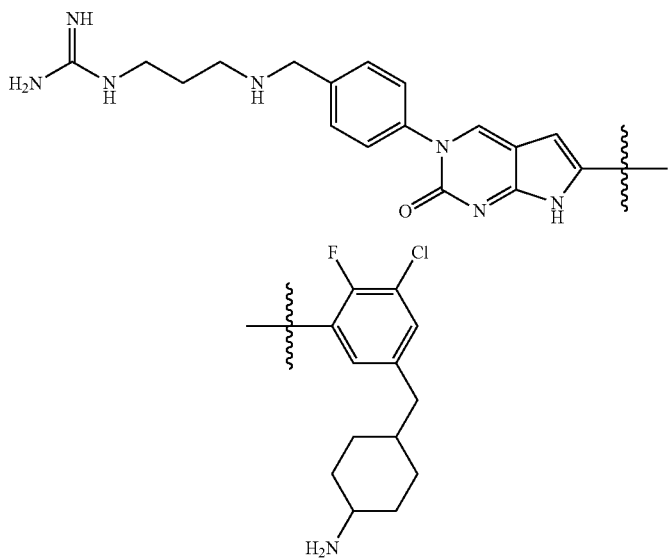 | 579.2 |

TABLE 2a-continued
| Comp. No. | Structure | LCMS |
|---|---|---|
| 449 | 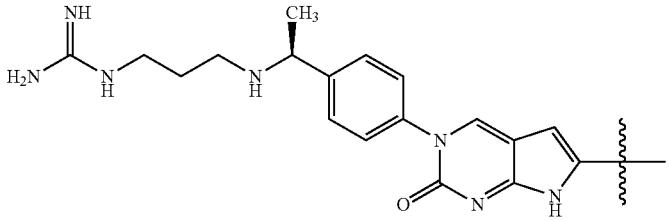 | 593.0 |
| 450 | 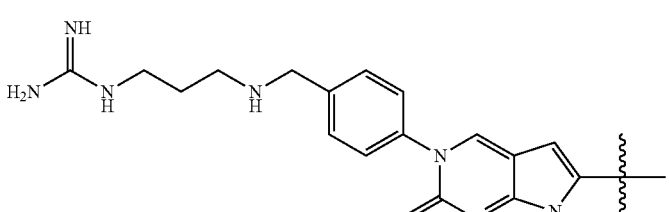 | 579.0 |

TABLE 2a-continued
| Comp. No. | Structure | LCMS |
|---|---|---|
| 451 | 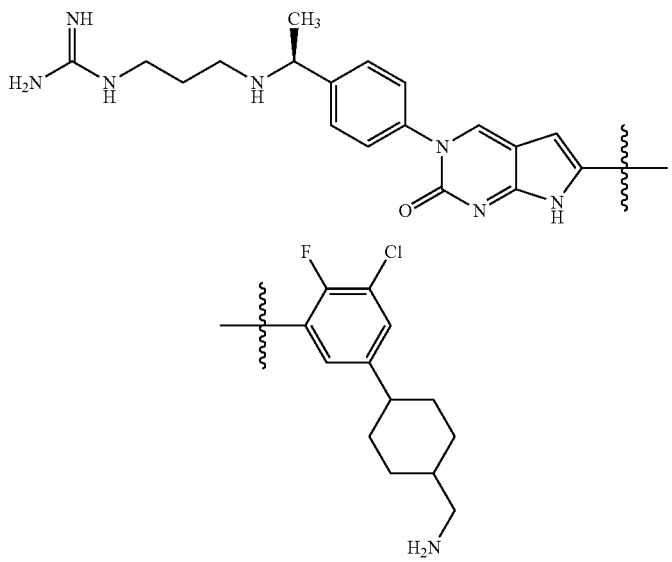 | 593.0 |
| 452 | 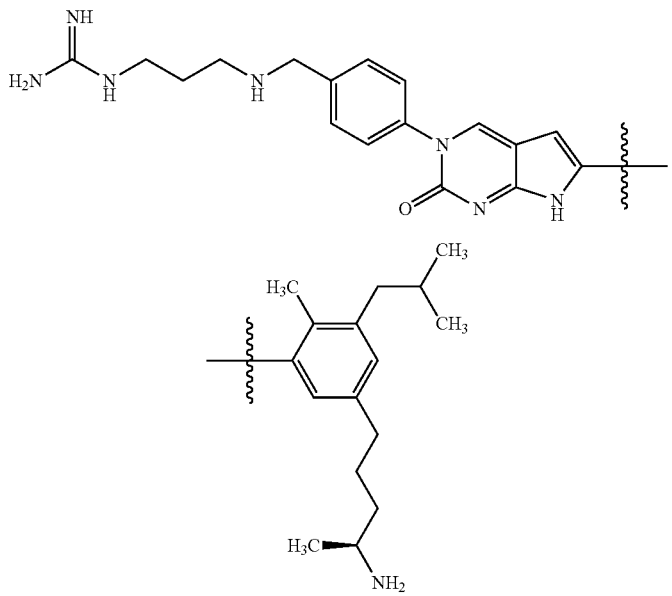 | 571.0 |

TABLE 2a-continued
| Comp. No. | Structure | LCMS |
|---|---|---|
| 453 | 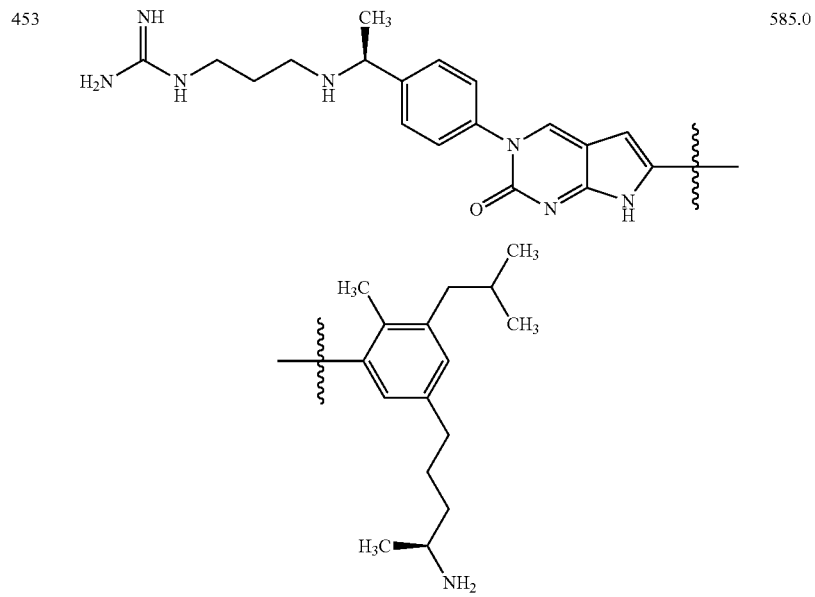 | 585.0 |
| 454 | 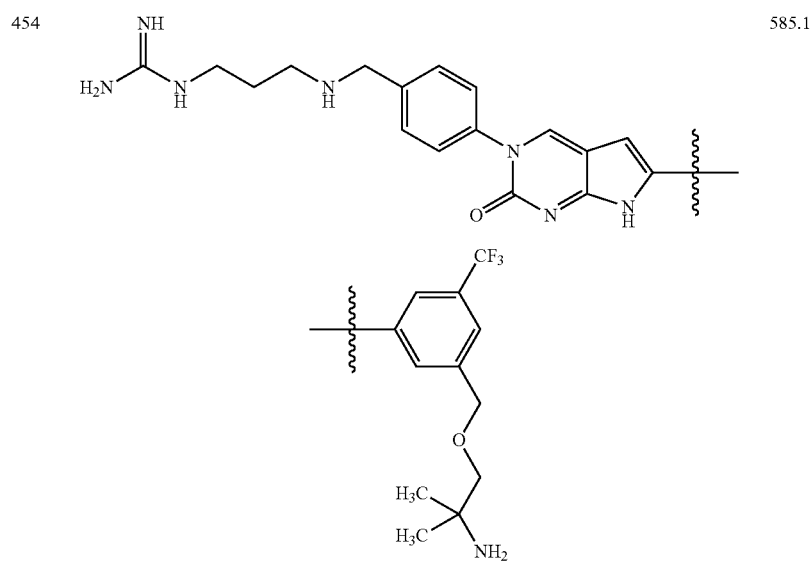 | 585.1 |

TABLE 2a-continued
| Comp. No. | Structure | LCMS |
|---|---|---|
| 455 | 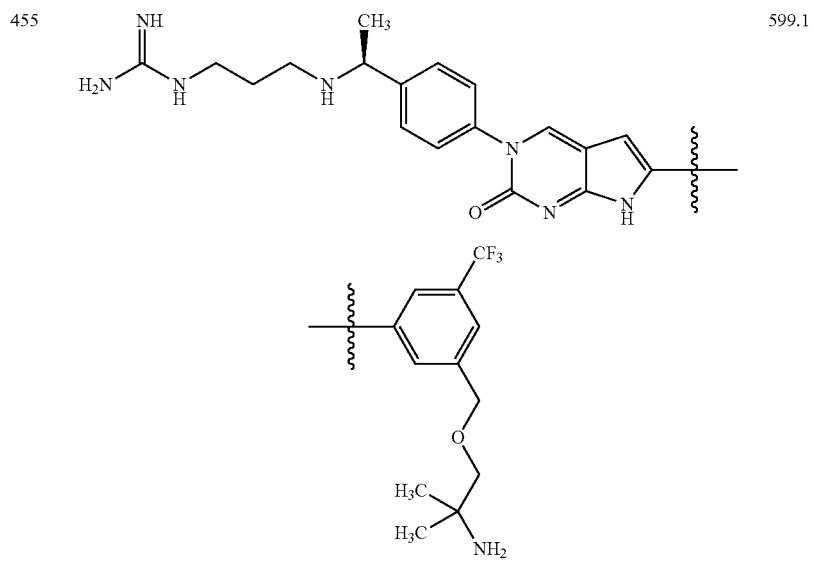 | 599.1 |
| 456 | 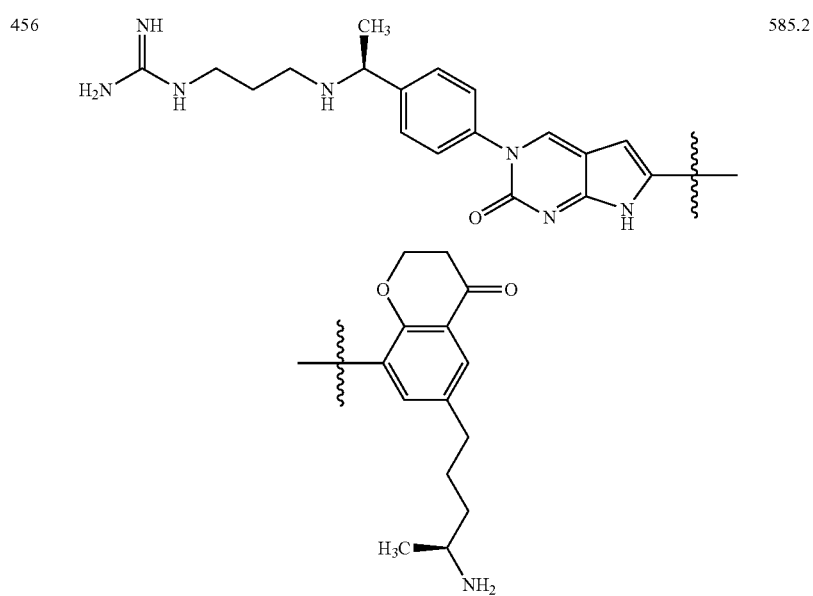 | 585.2 |

TABLE 2a-continued
| Comp. No. | Structure | LCMS |
|---|---|---|
| 457 | 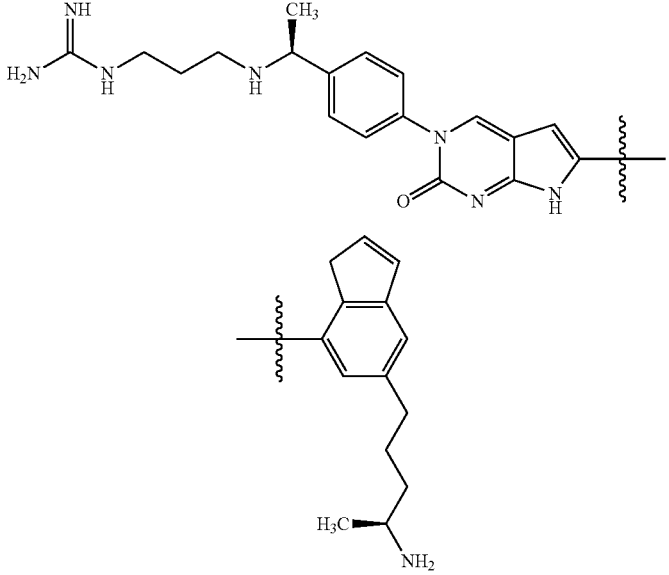 | 553.1 |
| 458 | 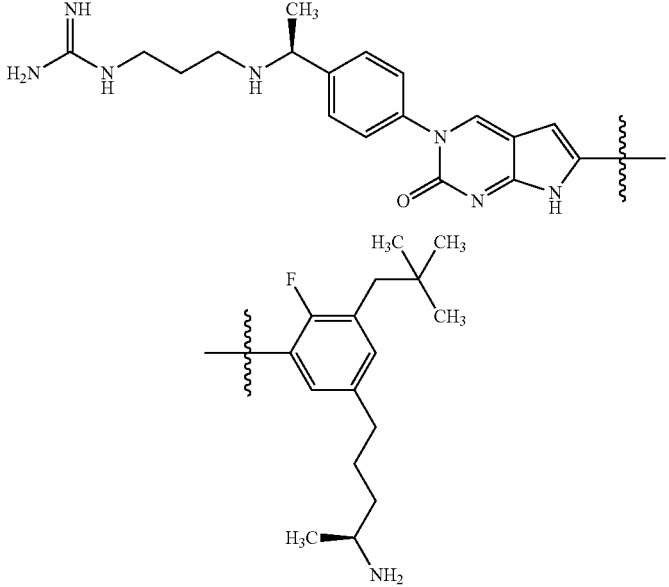 | 603.0 |

TABLE 2a-continued

| Comp. No. | Structure | LCMS |
|---|---|---|
| 459 | 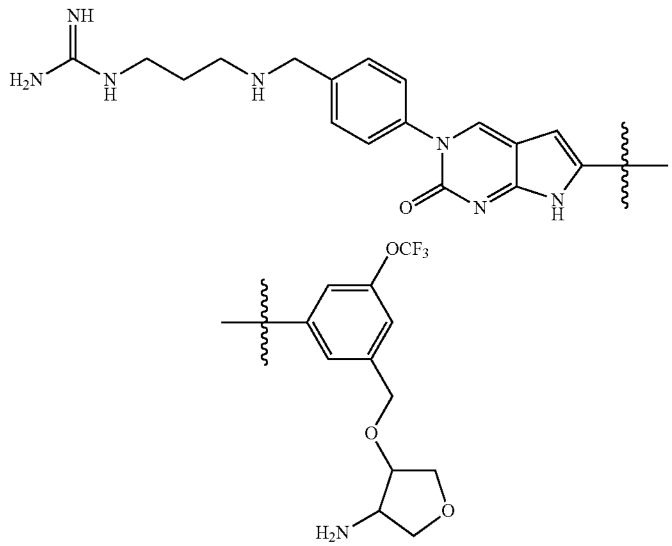 | 615.0 |
| 460 | 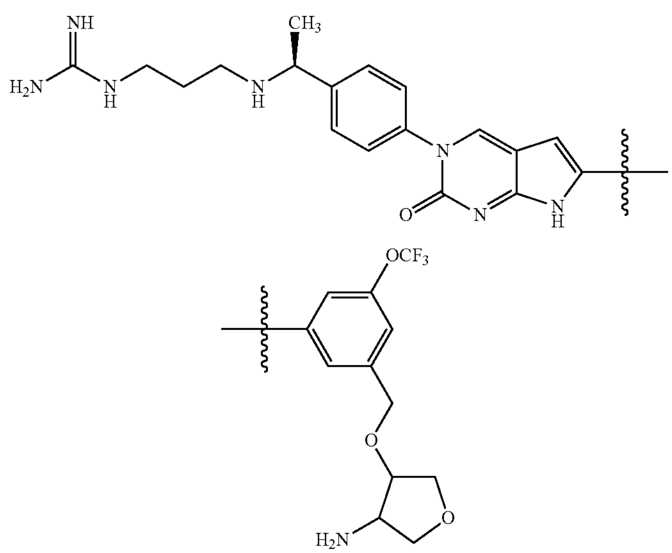 | 629.0 |

TABLE 2a-continued
| Comp. No. | Structure | LCMS |
|---|---|---|
| 461 | 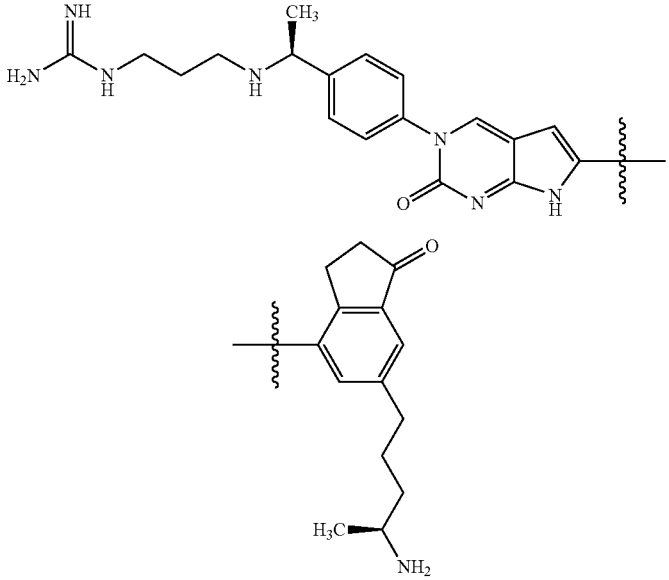 | 569.1 |
| 462 | 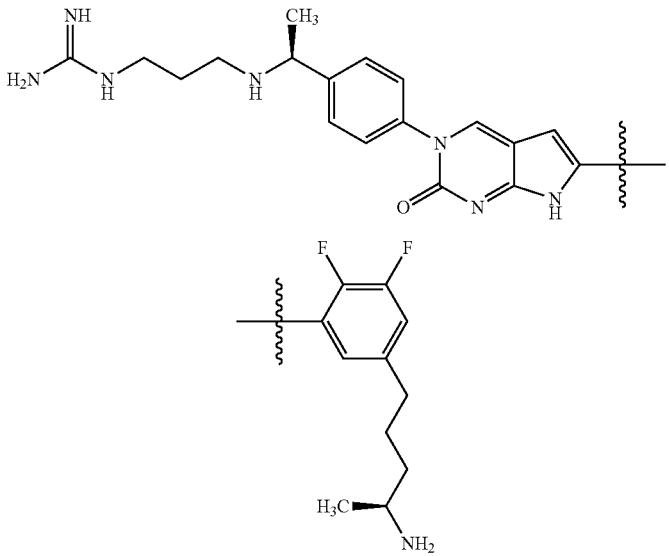 | 551.1 |

TABLE 2a-continued
| Comp. No. | Structure | LCMS |
|---|---|---|
| 463 | 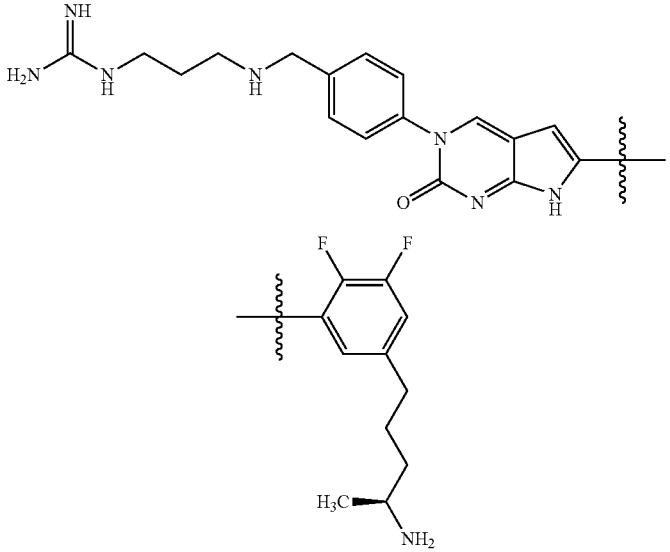 | 537.0 |
| 464 | 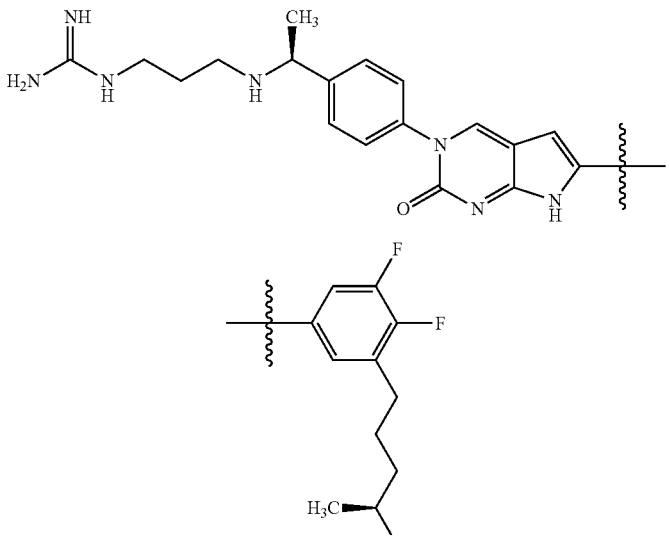 | 551.1 |

TABLE 2a-continued
| Comp. No. | Structure | LCMS |
|---|---|---|
| 465 | 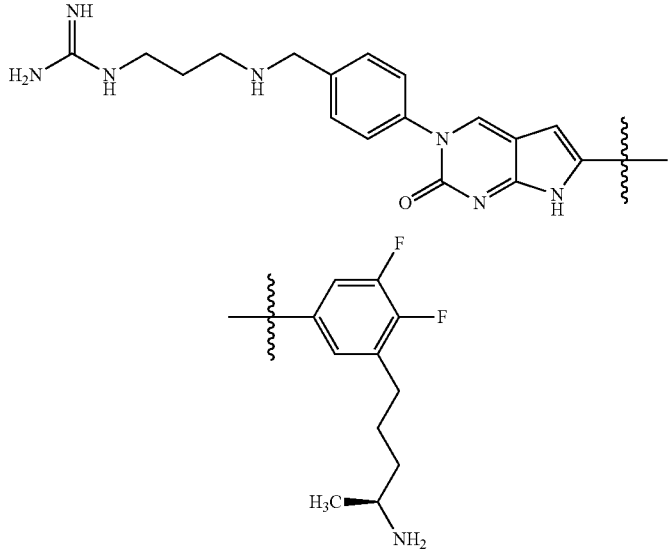 | 537.1 |
| 466 | 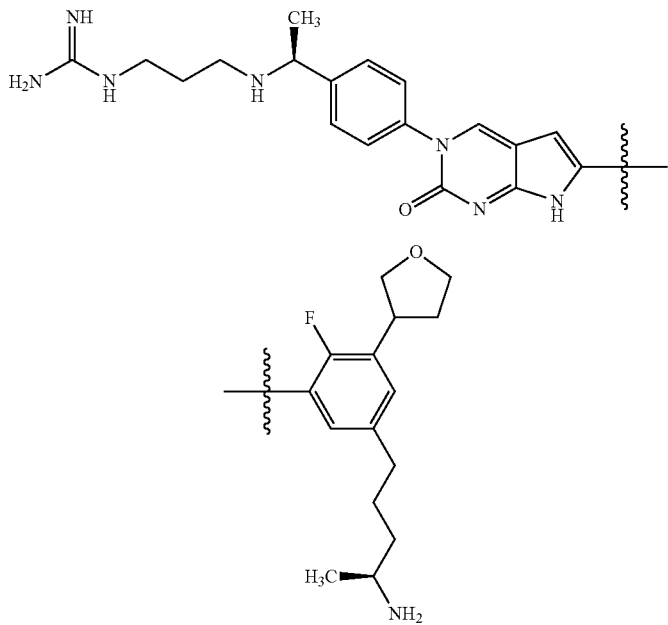 | 603.1 |

TABLE 2a-continued
| Comp. No. | Structure | LCMS |
|---|---|---|
| 467 | 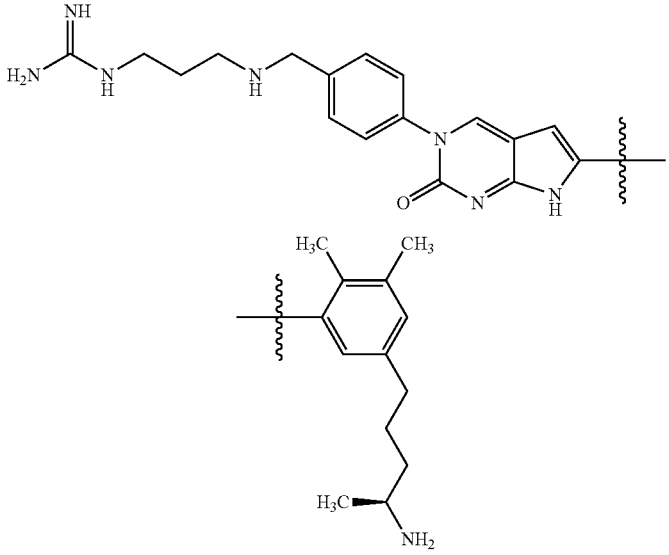 | 529.1 |
| 468 | 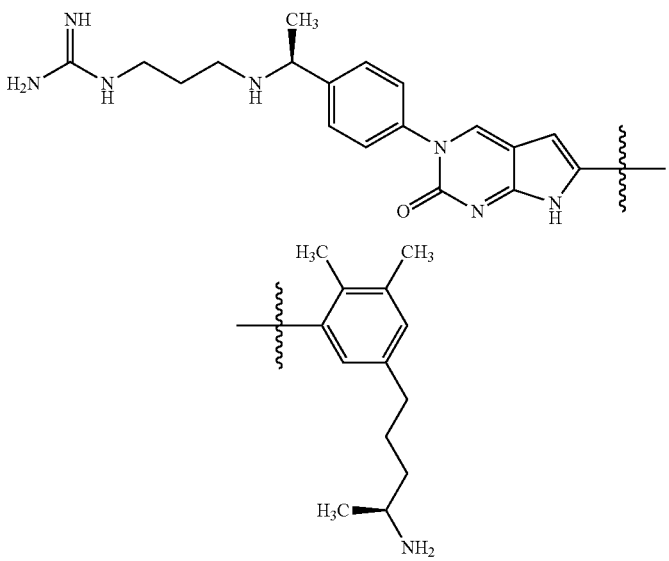 | 543.1 |

TABLE 2aa
| Comp. No. | Structure | LCMS |
|---|---|---|
| 469 | 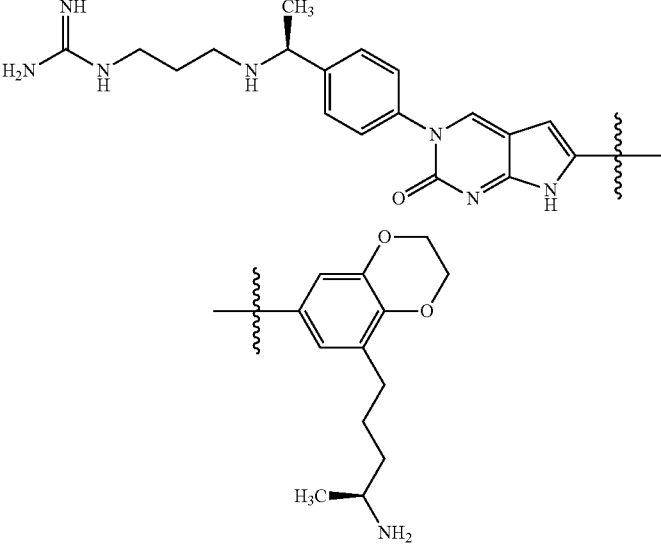 | 573.1 |
| 470 | 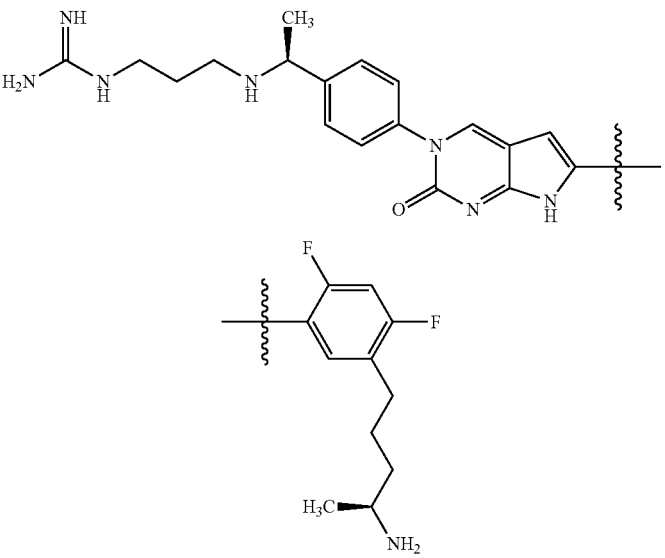 [SMILES: *c1cc2cn(-c3ccc([C@H](C)NCCCNC(=N)N)cc3)c(=O)nc2[nH]1 ; *c1cc(CCC[C@H](C)N)c(F)cc1F] | 551.1 |

TABLE 2aa-continued
| Comp. No. | Structure | LCMS |
|---|---|---|
| 471 | 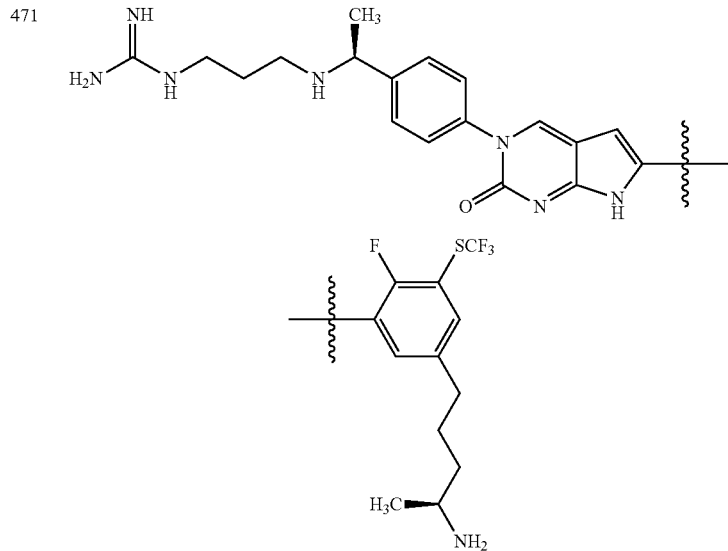 | 633.1 |
| 472 | 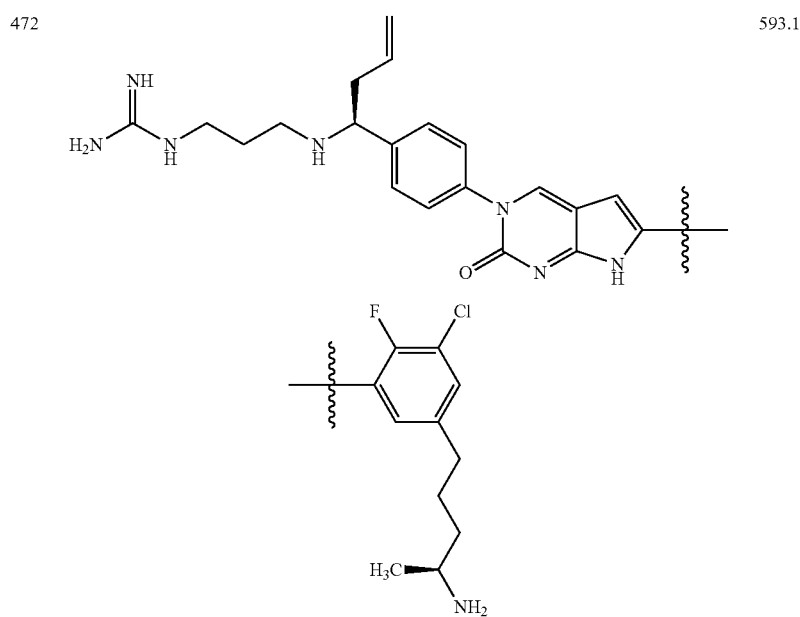 | 593.1 |

TABLE 2aa-continued
| Comp. No. | Structure | LCMS |
|---|---|---|
| 473 | 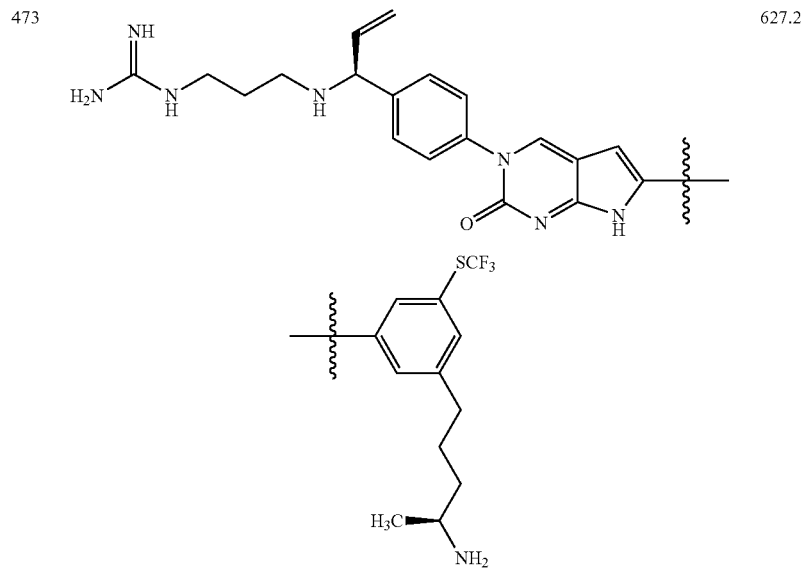 | 627.2 |
| 474 | 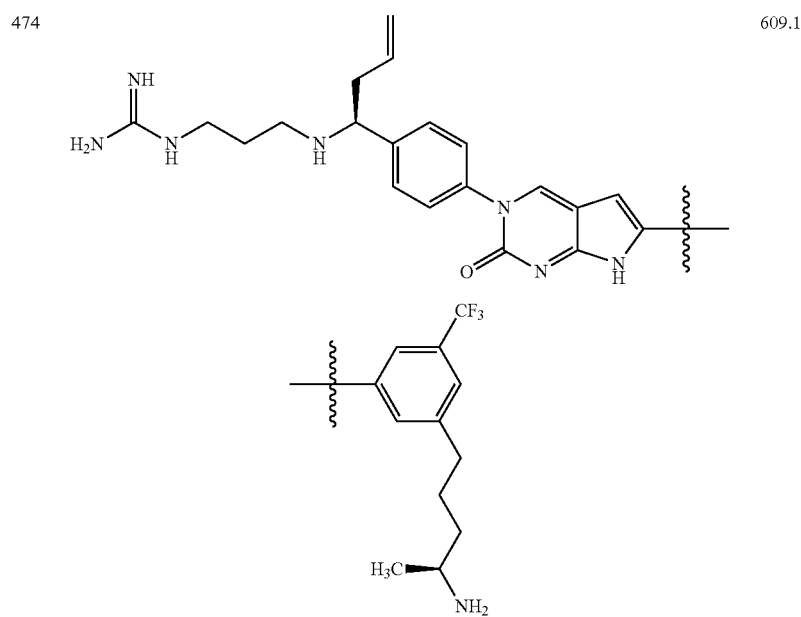 | 609.1 |

TABLE 2aa-continued

| Comp. No. | Structure | LCMS |
|---|---|---|
| 475 | 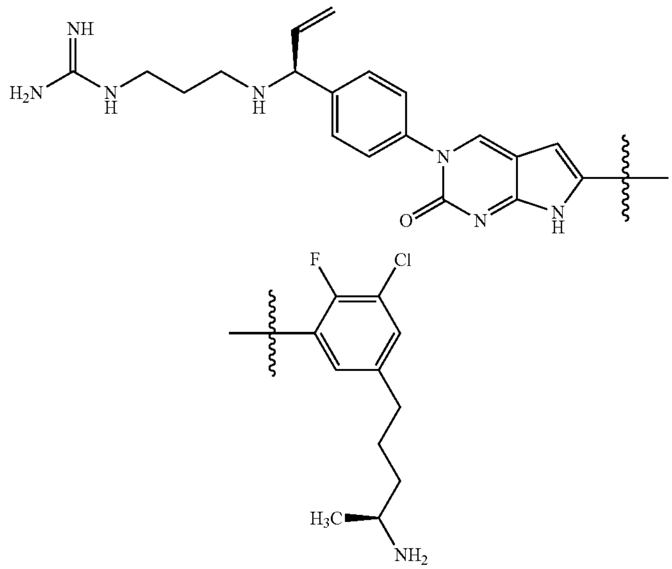 | 579.1 |
| 476 | 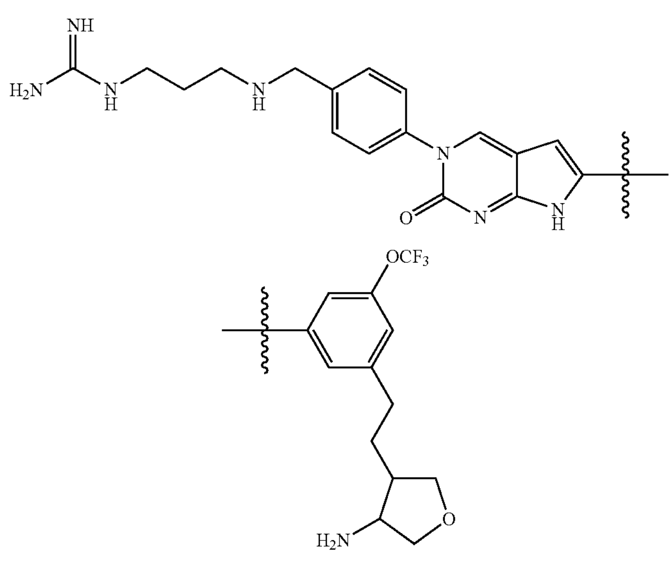 | 613.1 |

TABLE 2aa-continued

| Comp. No. | Structure | LCMS |
|---|---|---|
| 477 | 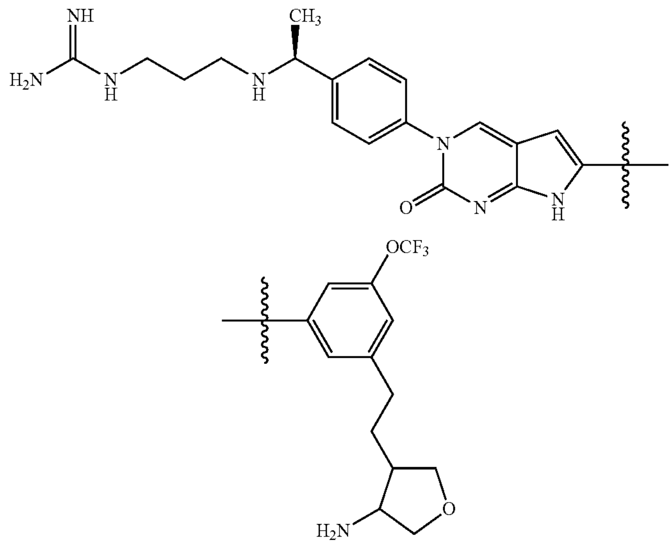 | 627.2 |
| 478 | 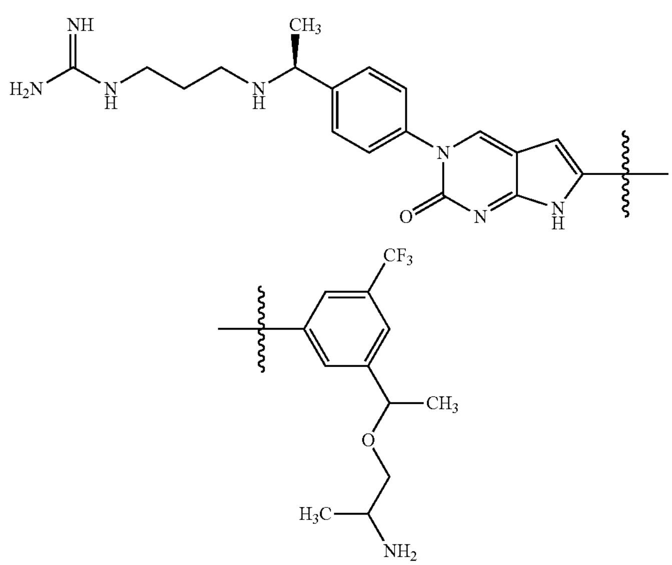 | 599.2 |

TABLE 2aa-continued
| Comp. No. | Structure | LCMS |
|---|---|---|
| 479 | 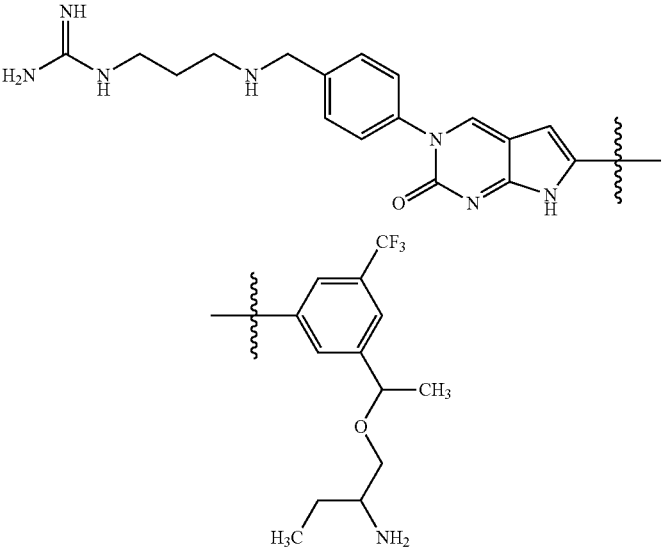 | 599.1 |
| 480 | 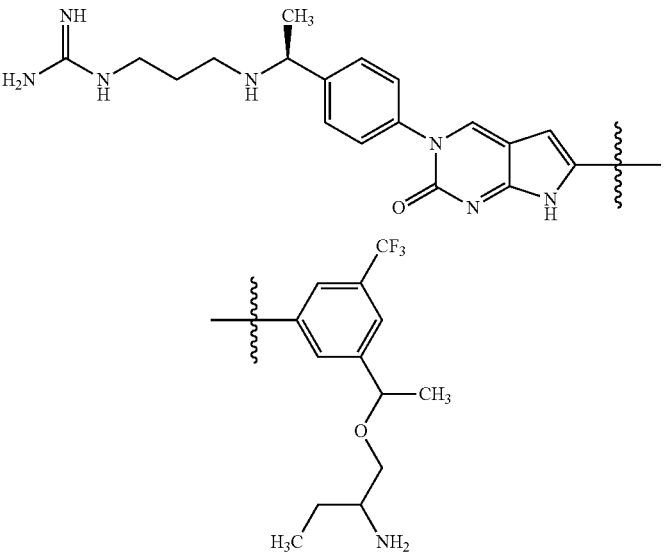 | 613.1 |

TABLE 2aa-continued

| Comp. No. | Structure | LCMS |
|---|---|---|
| 481 | 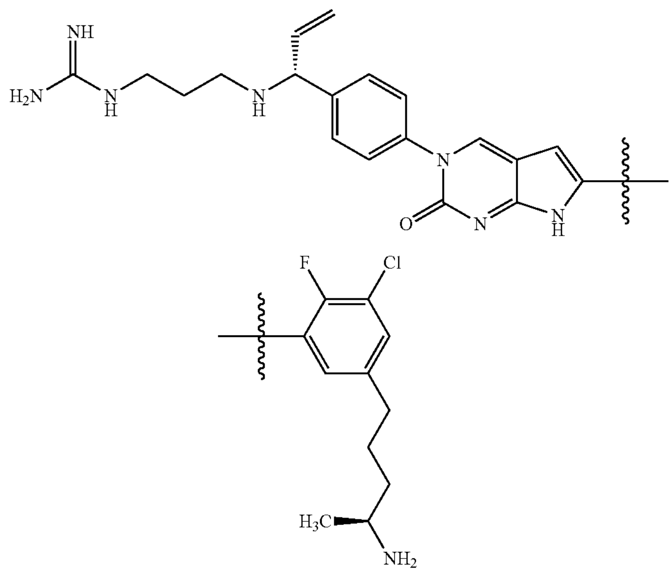 | 579.1 |
| 482 | 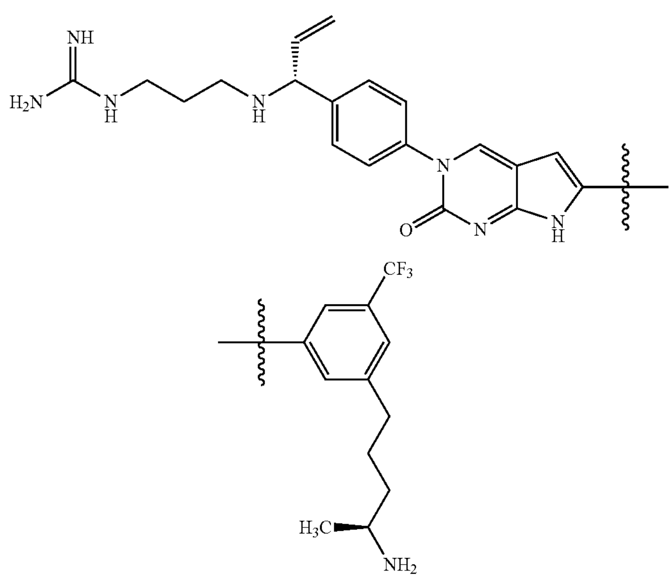 | 595.1 |

TABLE 2aa-continued
| Comp. No. | Structure | LCMS |
|---|---|---|
| 483 | 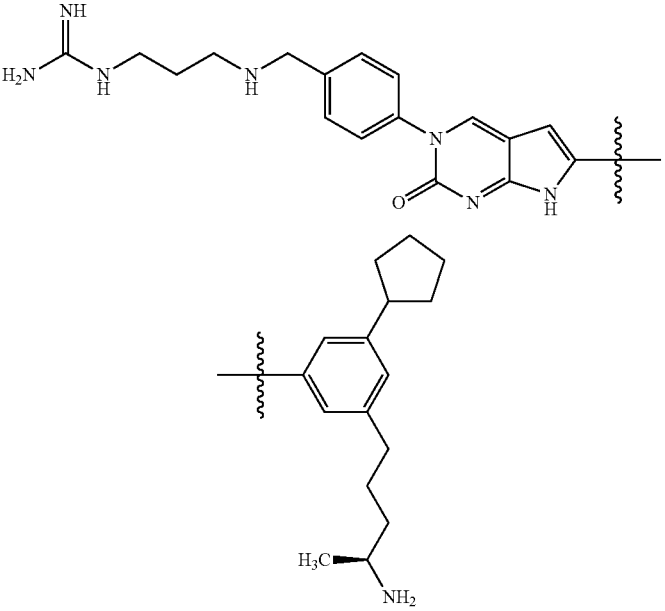 | 569.3 |
| 484 | 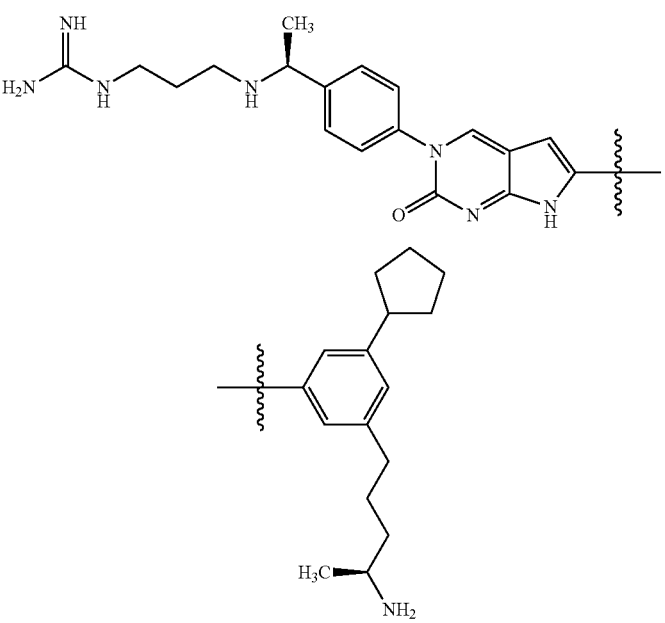 | 583.1 |

TABLE 2aa-continued
| Comp. No. | Structure | LCMS |
|---|---|---|
| 485 | 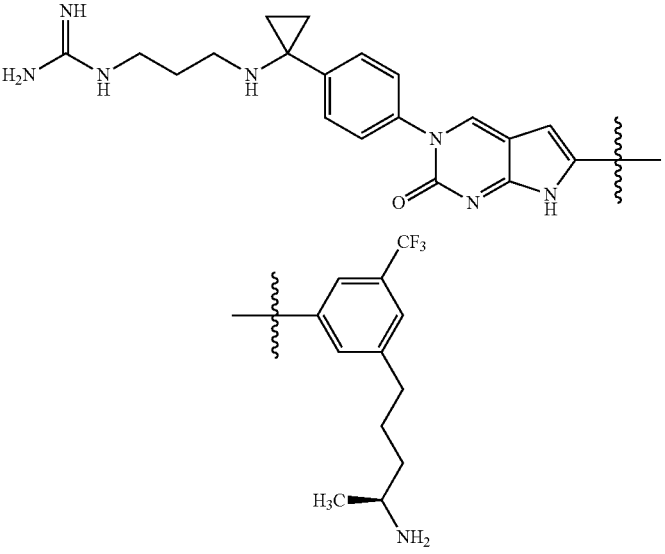 | 595.1 |
| 486 | 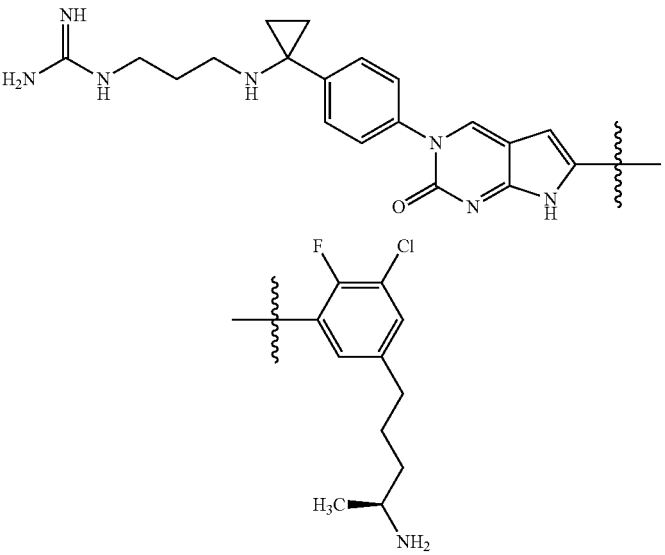 | 579.1 |

TABLE 2aa-continued
| Comp. No. | Structure | LCMS |
|---|---|---|
| 487 | 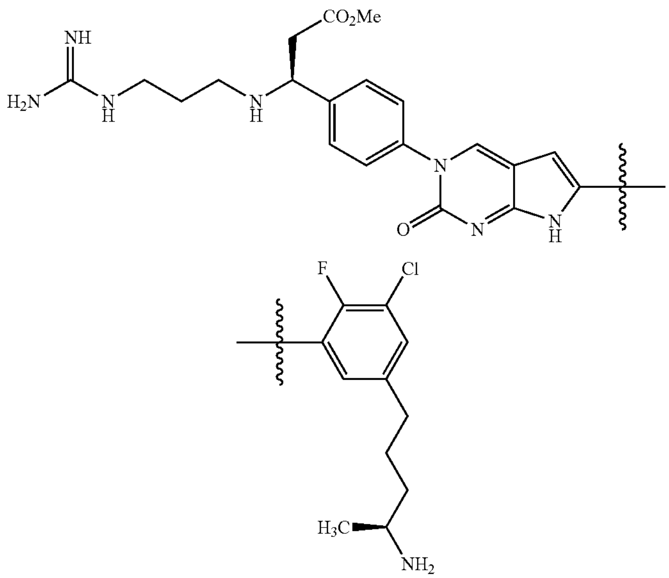 | 625.1 |
| 488 | 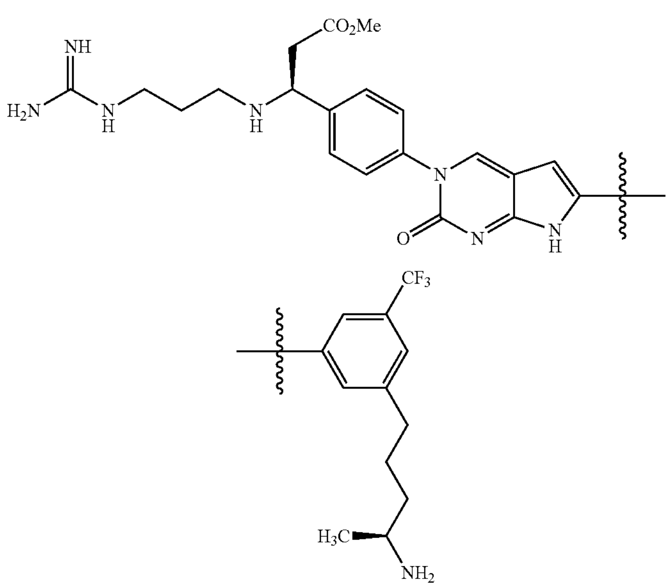 | 641.0 |

TABLE 2aa-continued
| Comp. No. | Structure | LCMS |
|---|---|---|
| 489 | 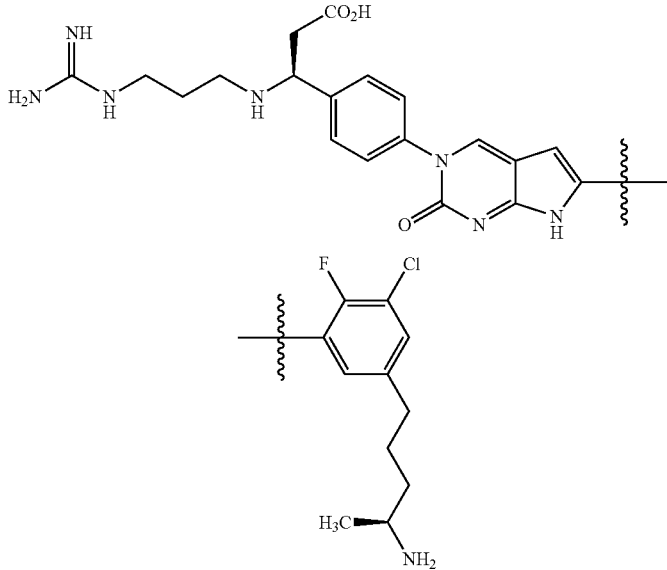 | 611.1 |
| 490 | 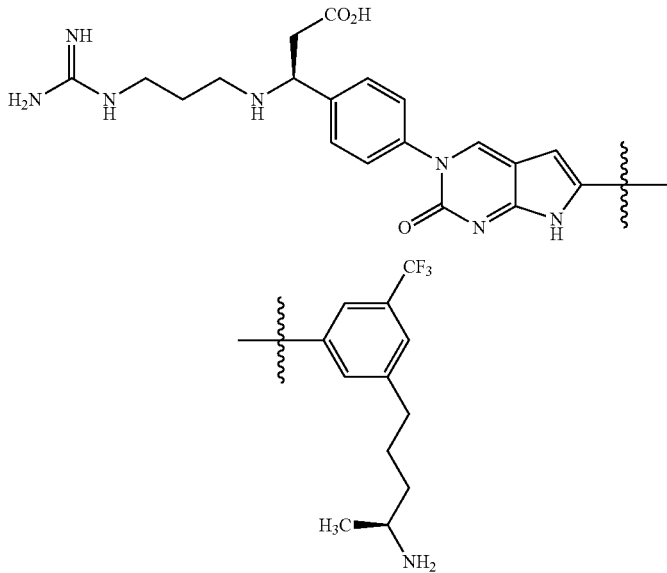 | 627.1 |

TABLE 2aa-continued
| Comp. No. | Structure | LCMS |
|---|---|---|
| 491 | 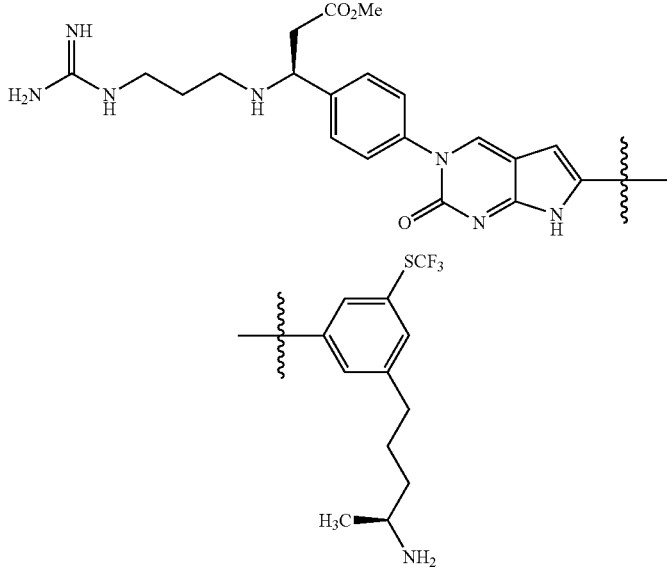 | 673.2 |
| 492 | 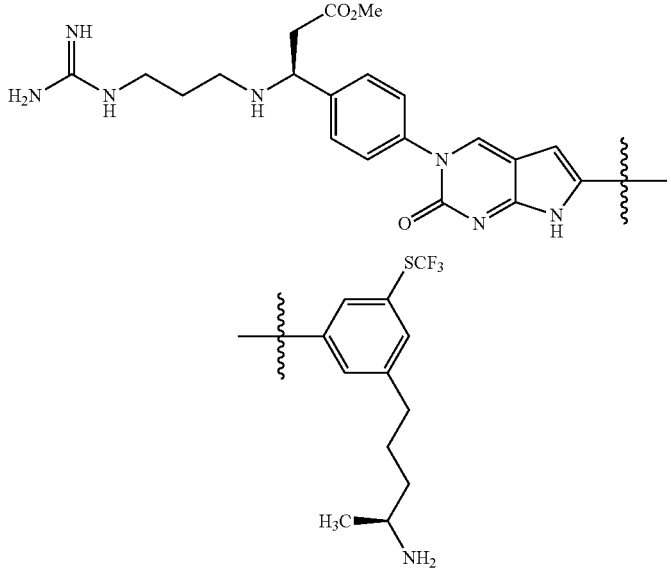 | 659.1 |

TABLE 2aa-continued
| Comp. No. | Structure | LCMS |
|---|---|---|
| 493 | 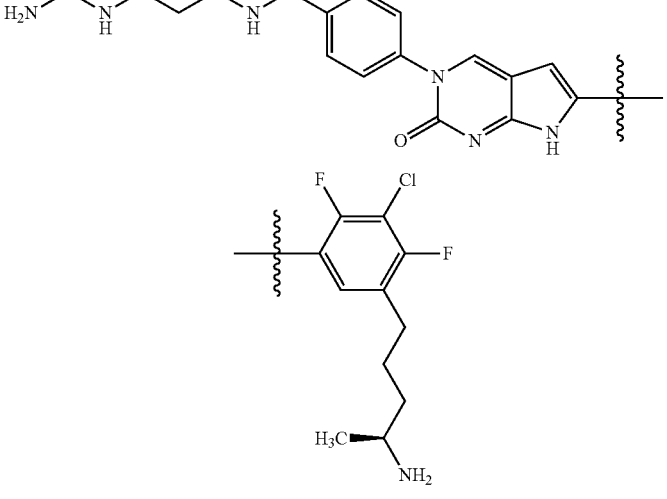 | 585.1 |
| 494 | 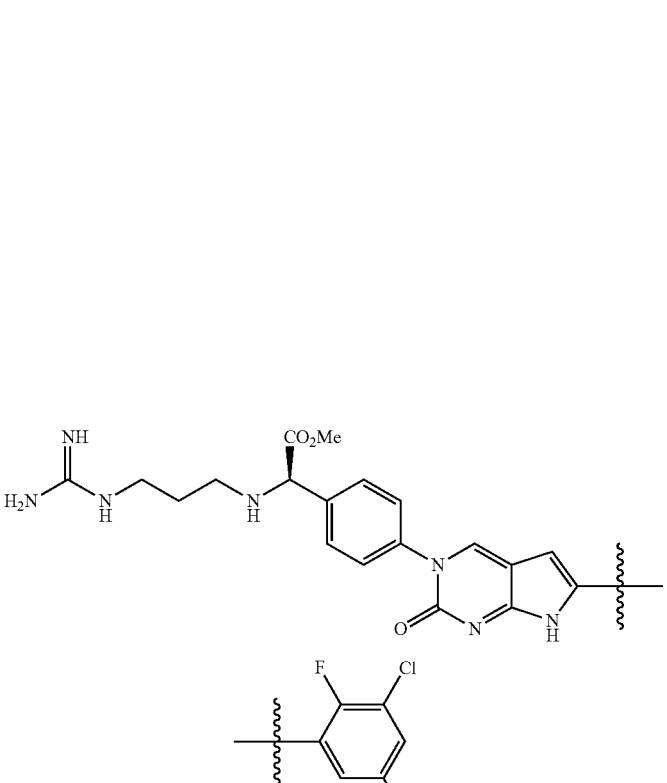 | 611.1 |

TABLE 2aa-continued
| Comp. No. | Structure | LCMS |
|---|---|---|
| 495 | 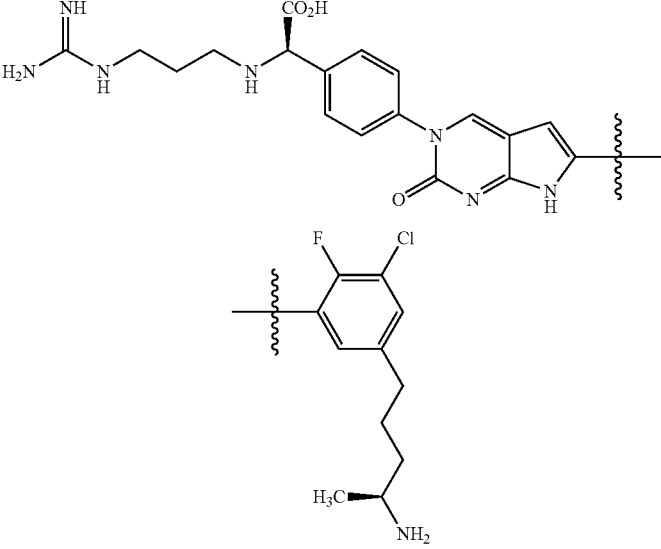 | 597.0 |
| 496 | 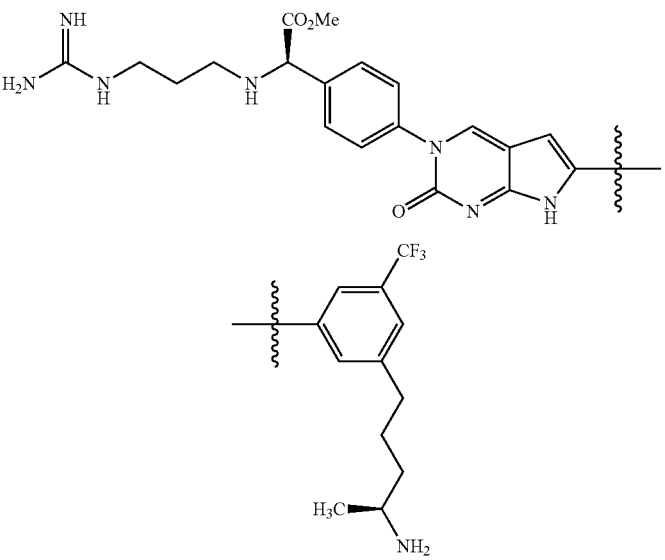 | 627.1 |

TABLE 2aa-continued
| Comp. No. | Structure | LCMS |
|---|---|---|
| 497 | 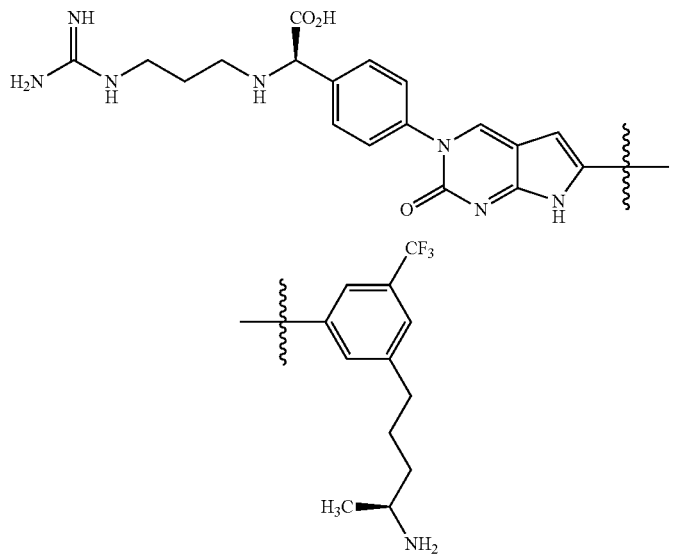 | 613.0 |
| 498 | 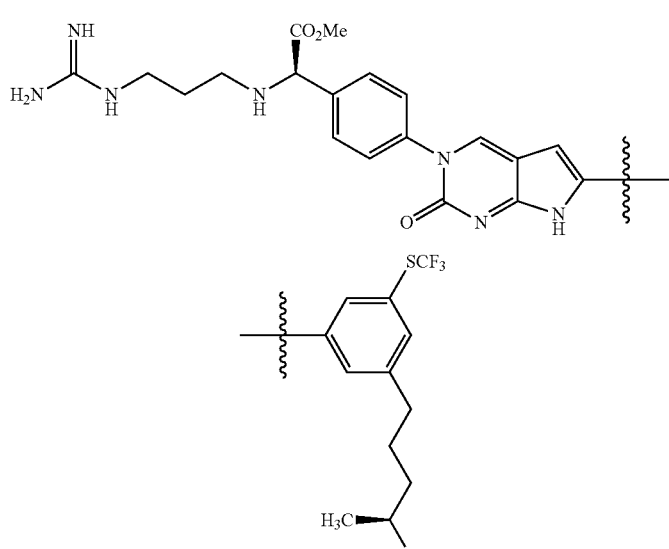 | 659.2 |

TABLE 2aa-continued
| Comp. No. | Structure | LCMS |
|---|---|---|
| 499 | 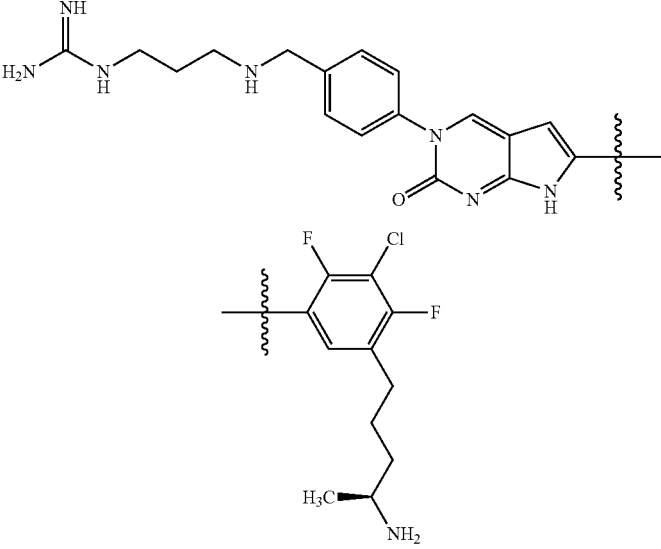 | 571.0 |
| 500 | 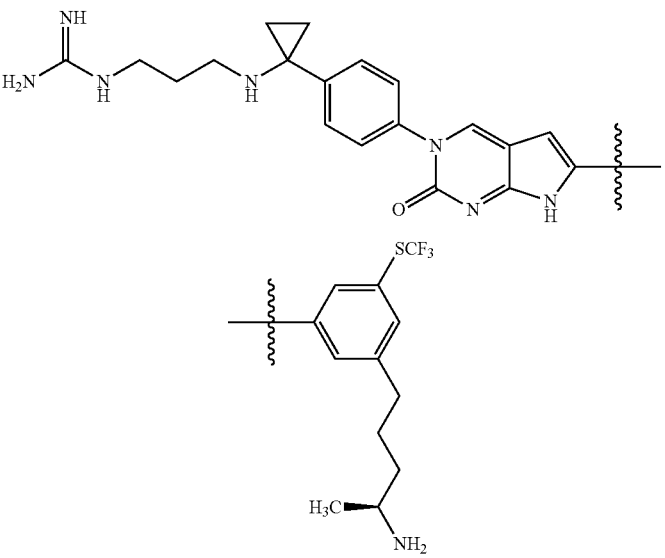 | 627.0 |

TABLE 2aa-continued
| Comp. No. | Structure | LCMS |
|---|---|---|
| 501 | 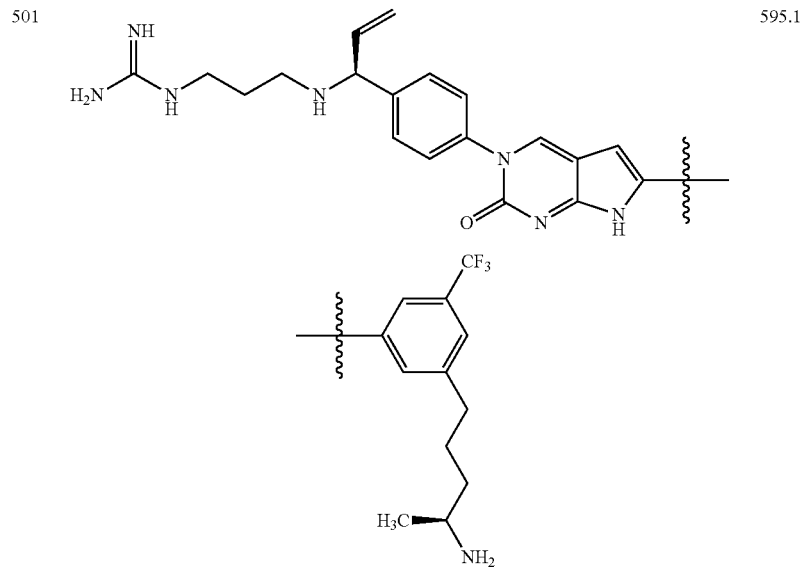 | 595.1 |
| 502 | 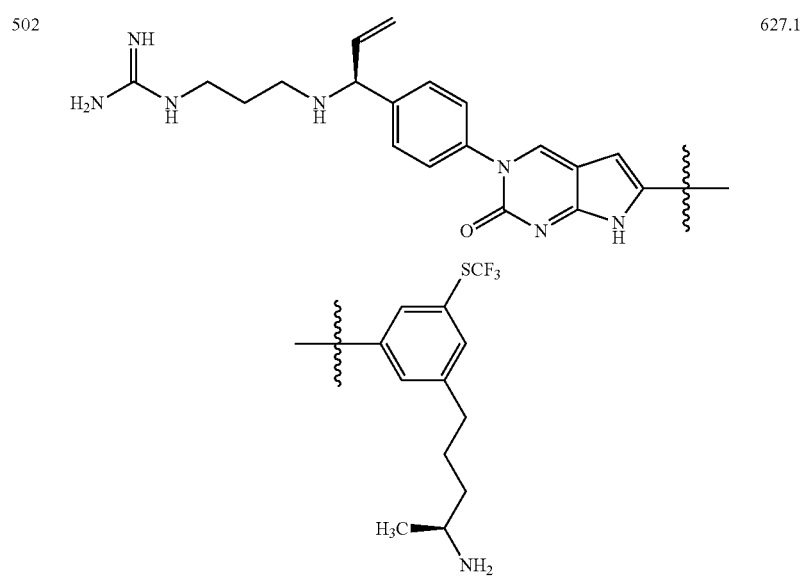 | 627.1 |

TABLE 2aa-continued
| Comp. No. | Structure | LCMS |
|---|---|---|
| 503 | 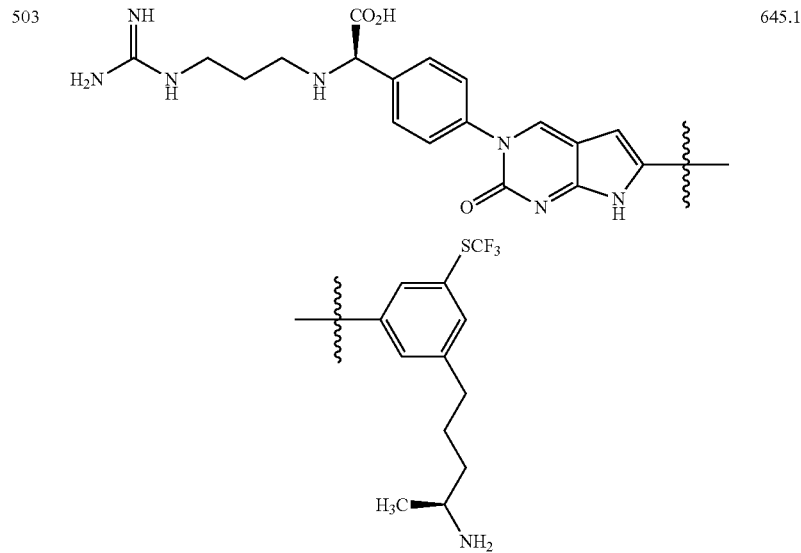 | 645.1 |
| 504 | 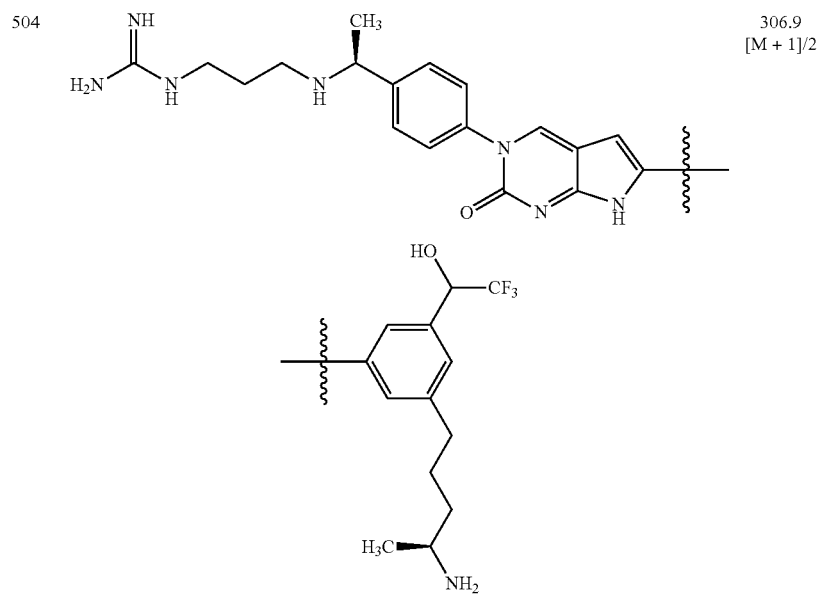 | 306.9 [M + 1]/2 |

TABLE 2aa-continued
| Comp. No. | Structure | LCMS |
|---|---|---|
| 505 | 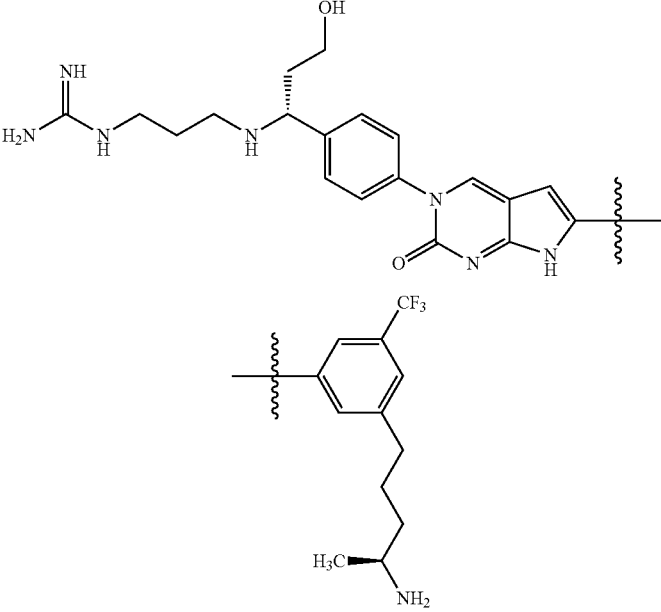 | 613.1 |
| 506 | 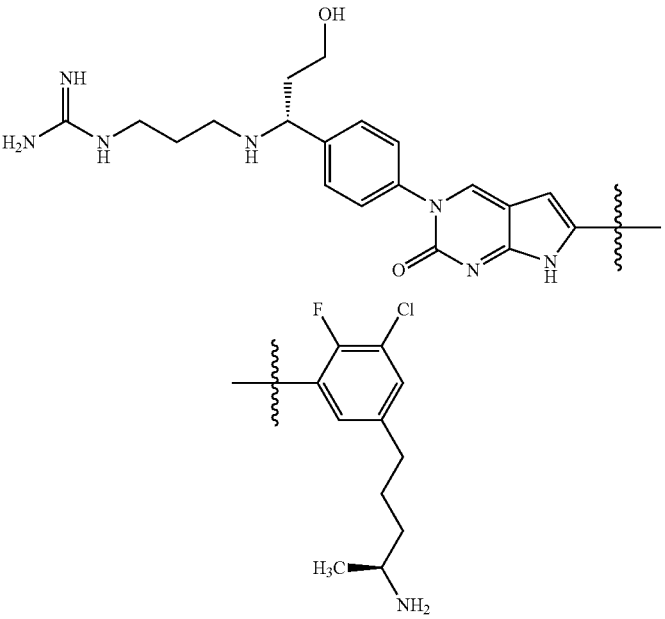 | 597.1 |

TABLE 2aa-continued
| Comp. No. | Structure | LCMS |
|---|---|---|
| 507 | 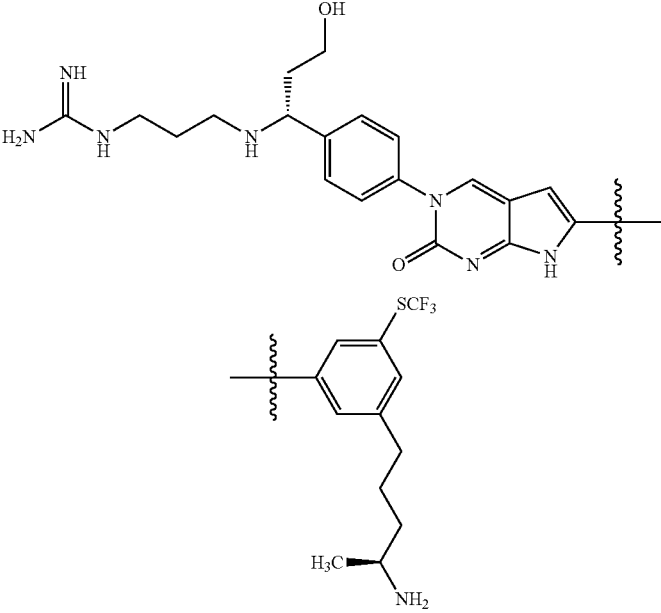 | 645.3 |
| 508 | 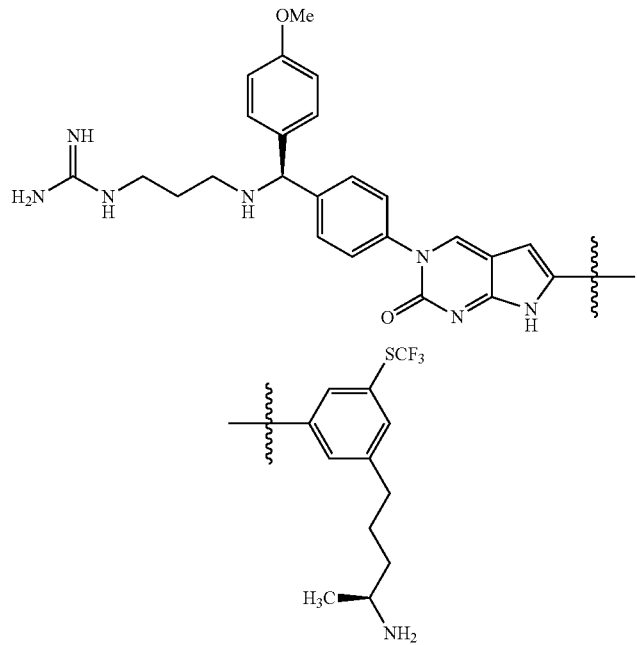 | 707.1 |

In one embodiment, the invention is not the compound selected from:
TABLE AA
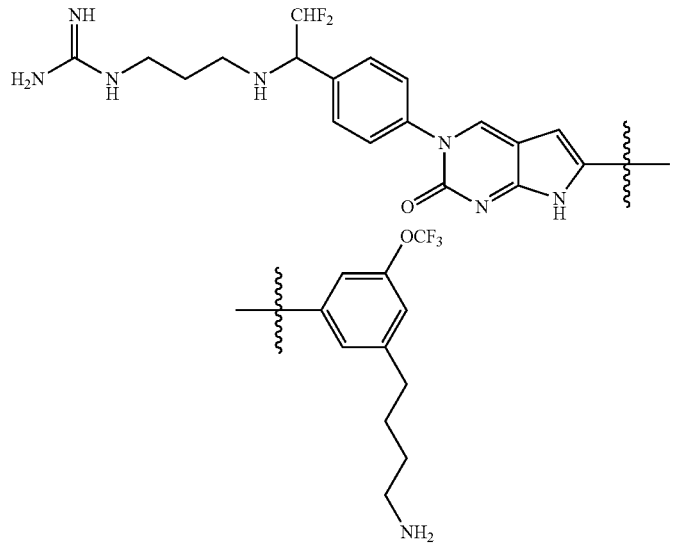
Z1
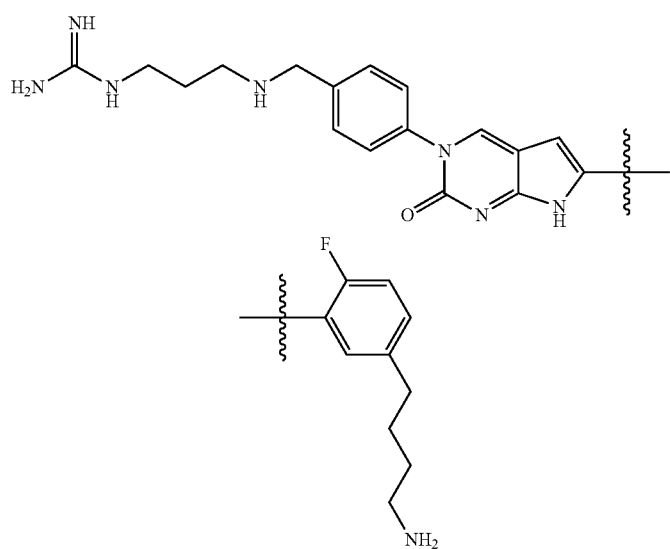
Z2

TABLE AA-continued
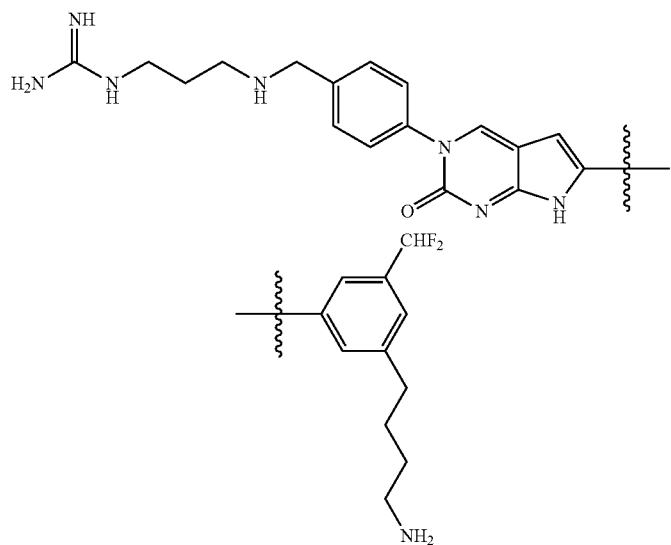
Z3
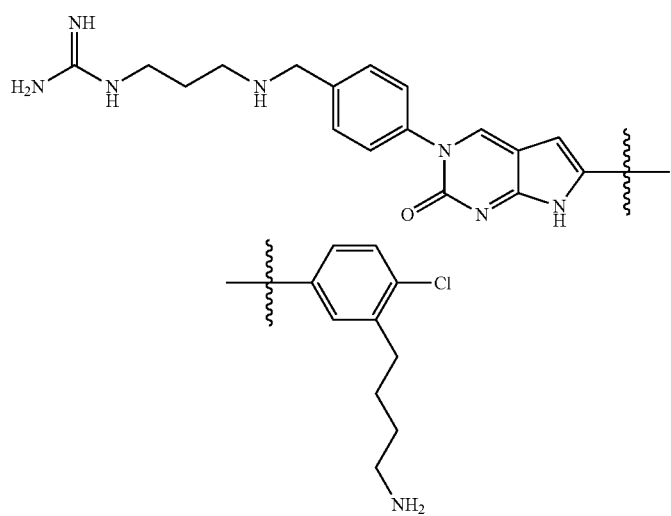
Z4
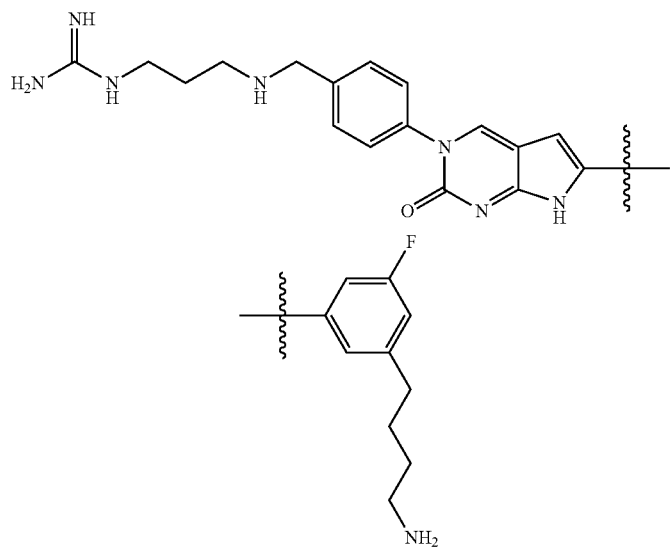
Z5

TABLE AA-continued
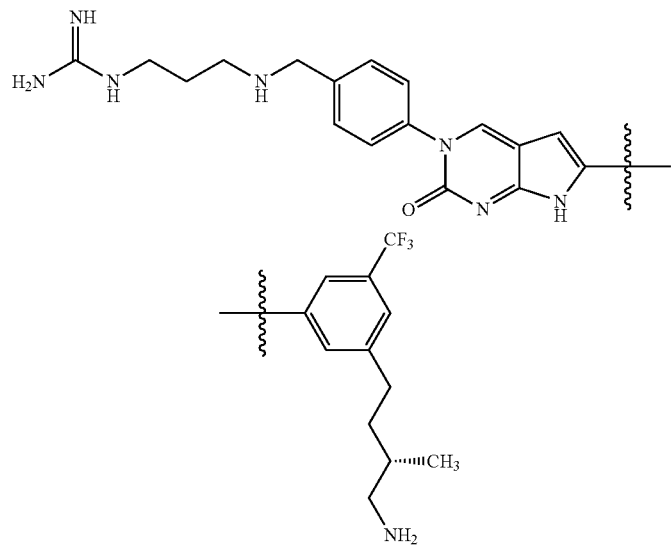
Z6
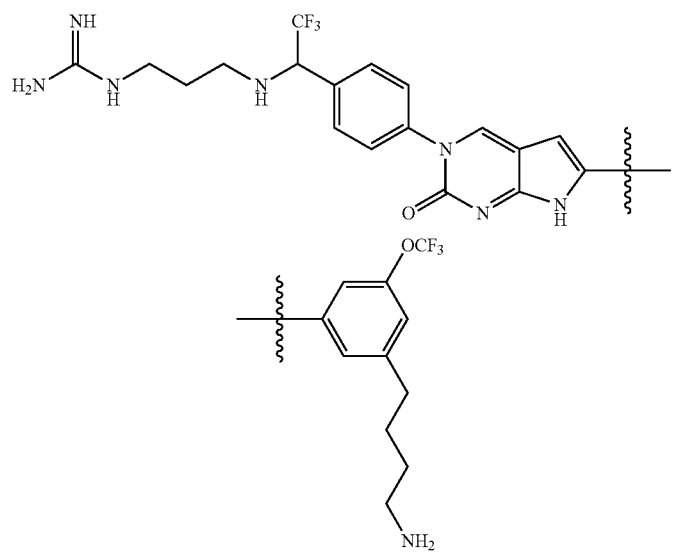
Z7
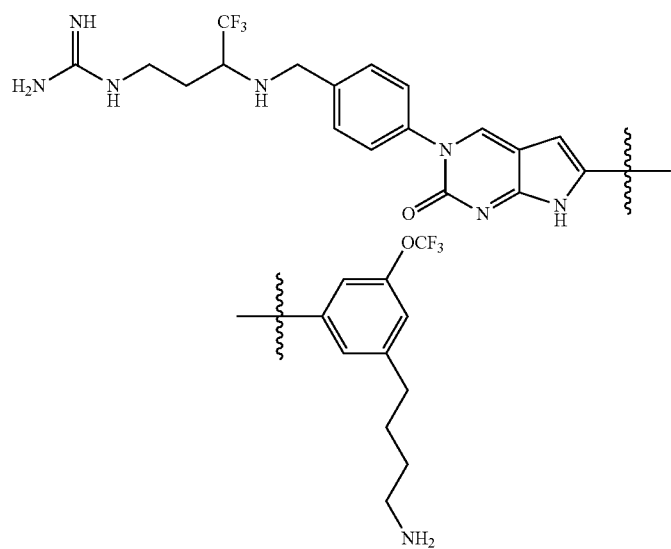
Z8

TABLE AA-continued
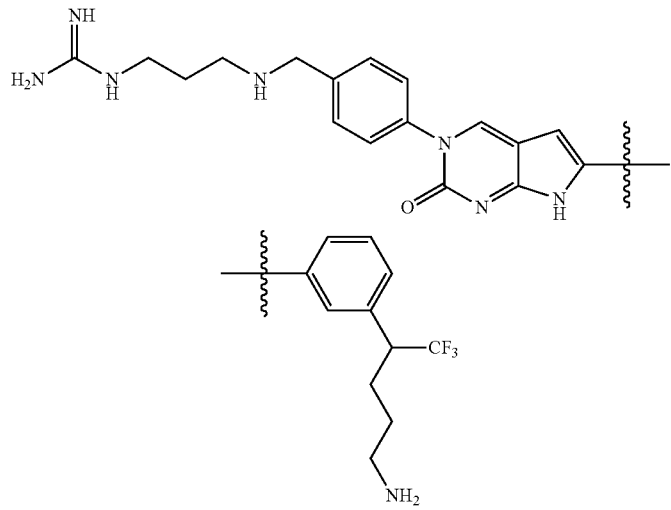
Z9
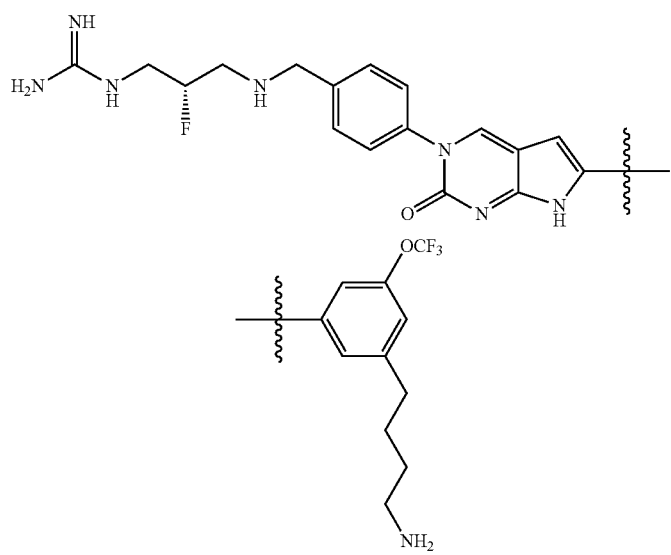
Z10
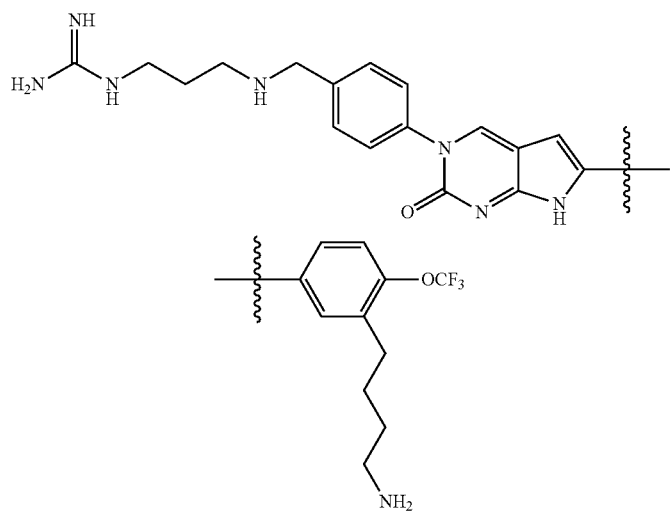
Z11

TABLE AA-continued
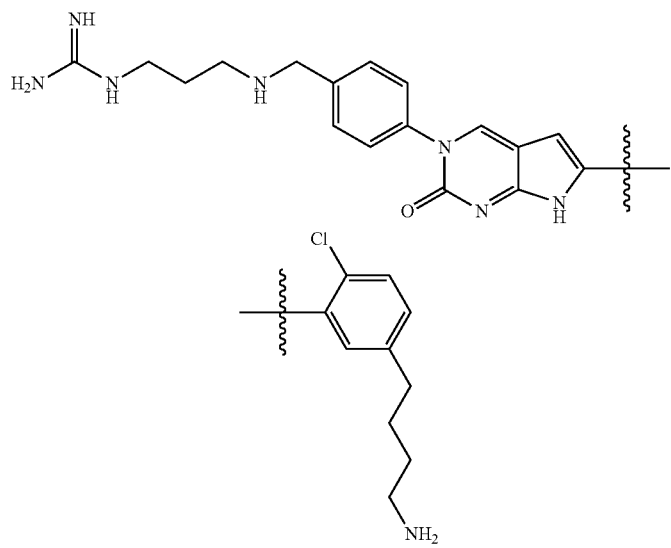
Z12
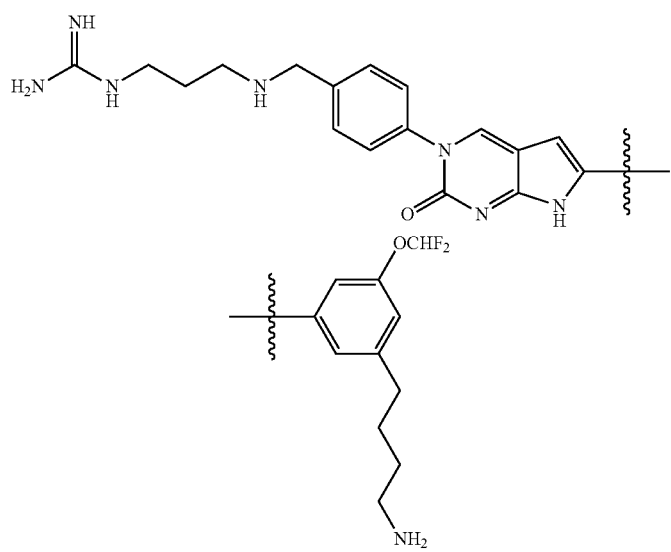
Z13
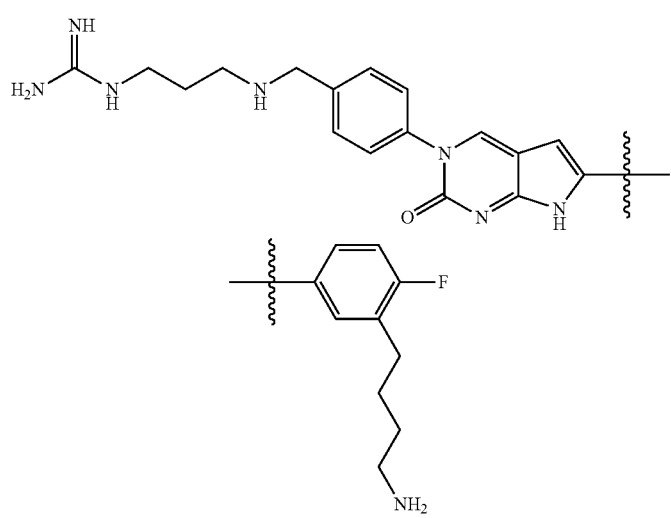
Z14

TABLE AA-continued
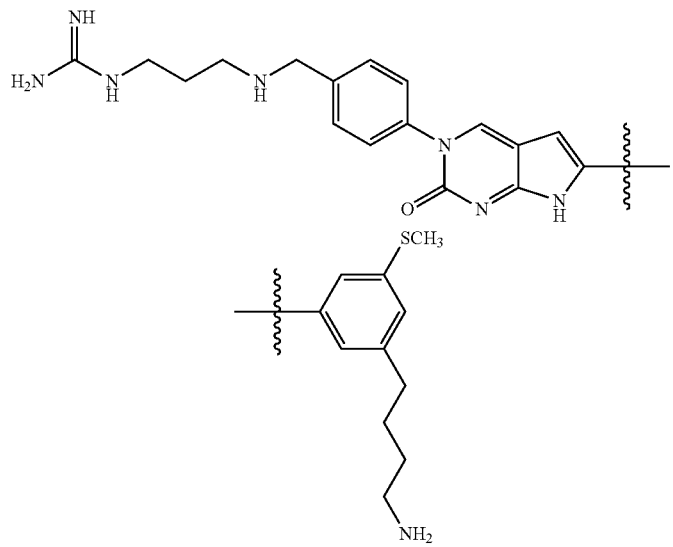
Z15
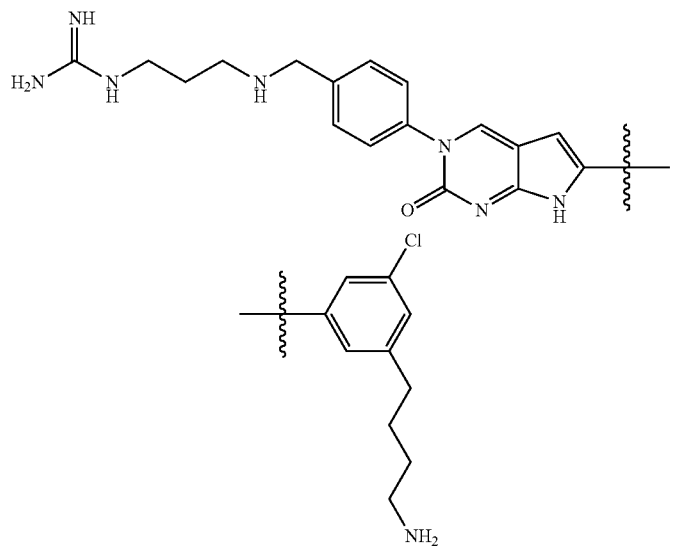
Z16
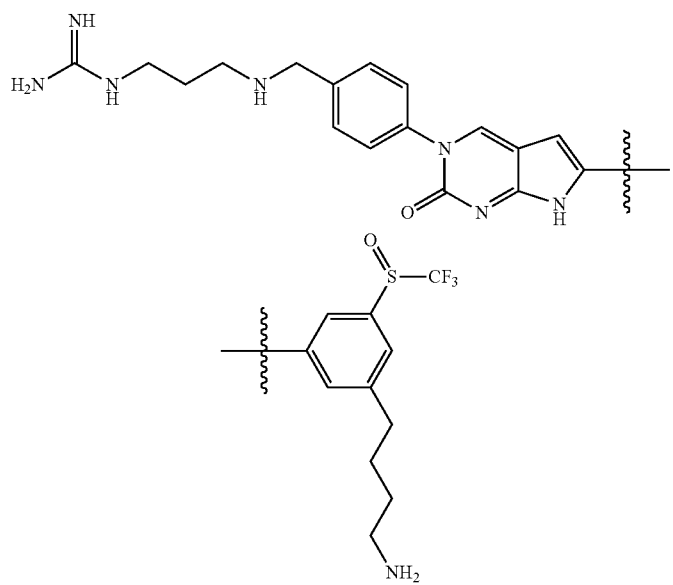
Z17

TABLE AA-continued
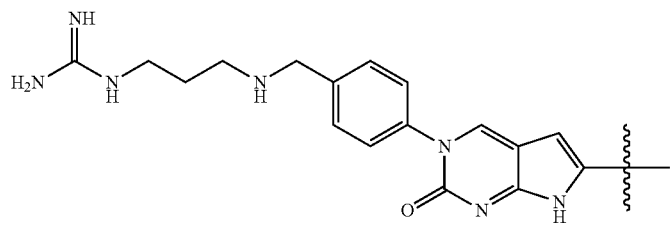 [SMILES: *c1cc2cn(-c3ccc(CNCCCNC(=N)N)cc3)c(=O)nc2[nH]1]
Z18
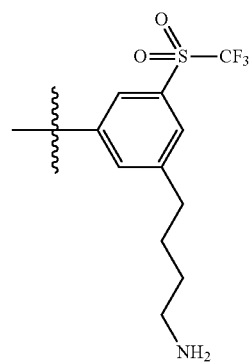
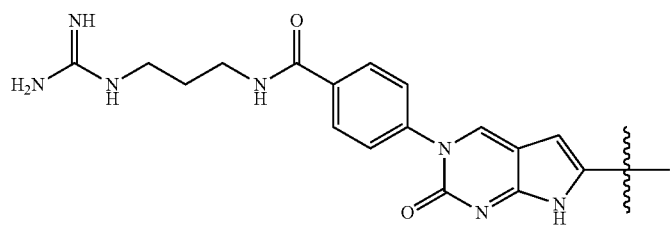
Z19
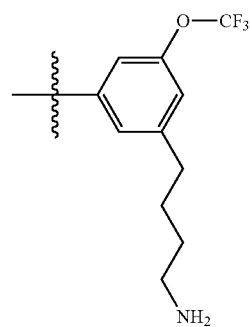

TABLE AA-continued
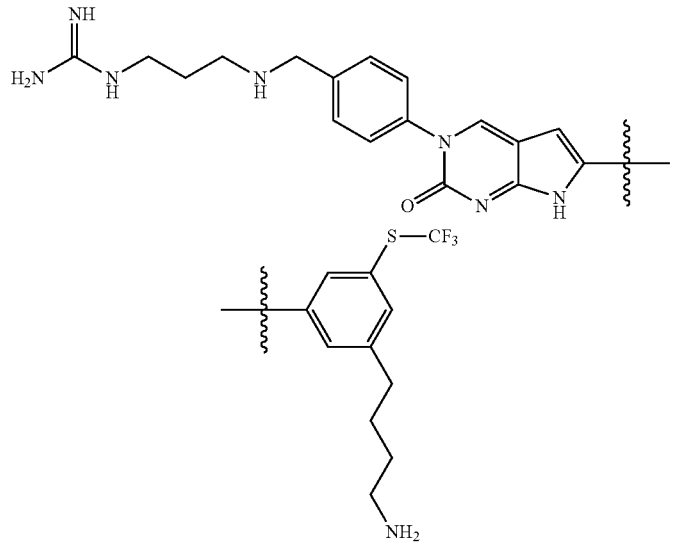
Z20
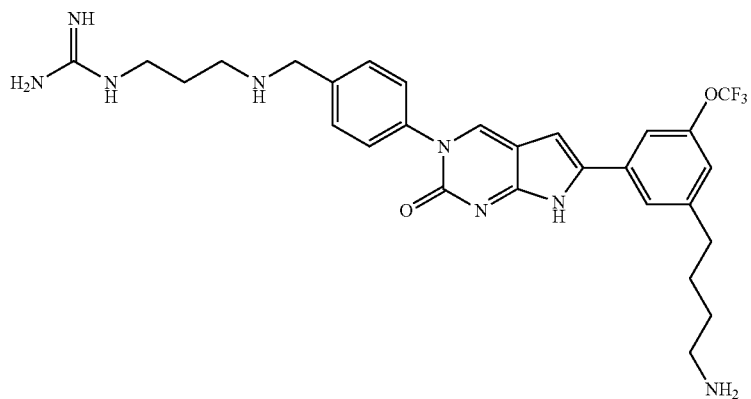
Z21
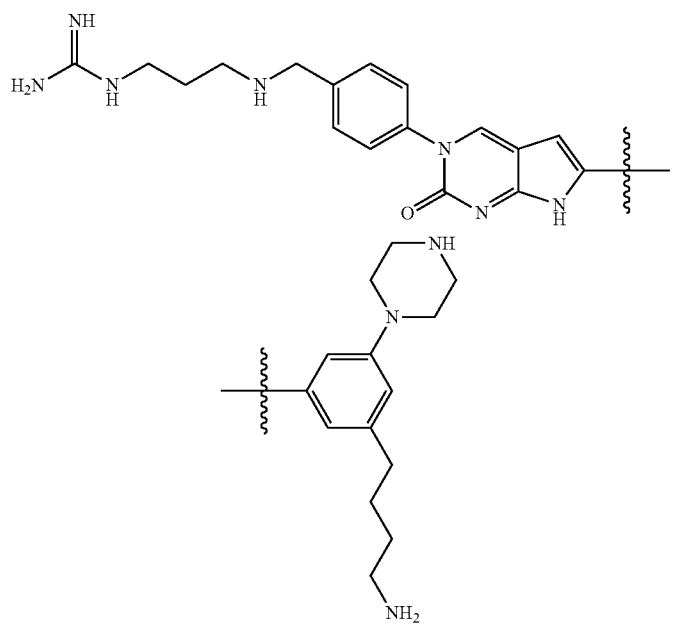
Z22

TABLE AA-continued
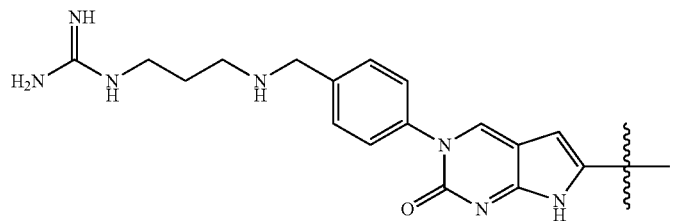 [SMILES: *c1cc2cn(-c3ccc(CNCCCNC(=N)N)cc3)c(=O)nc2[nH]1]
Z23
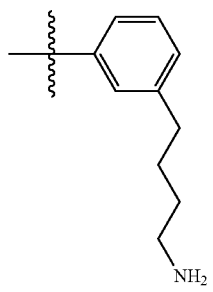
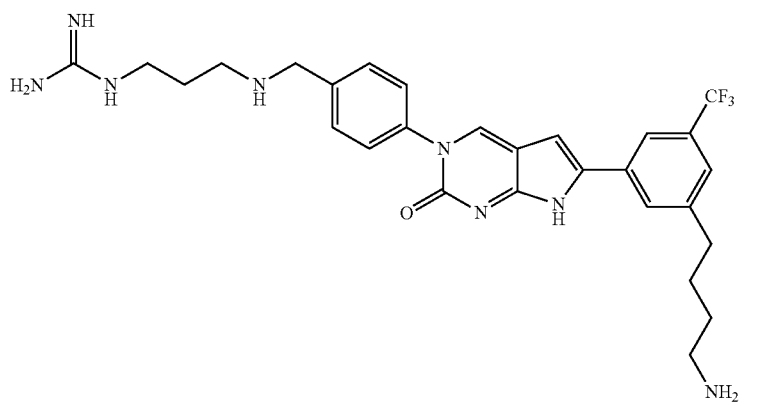
Z24
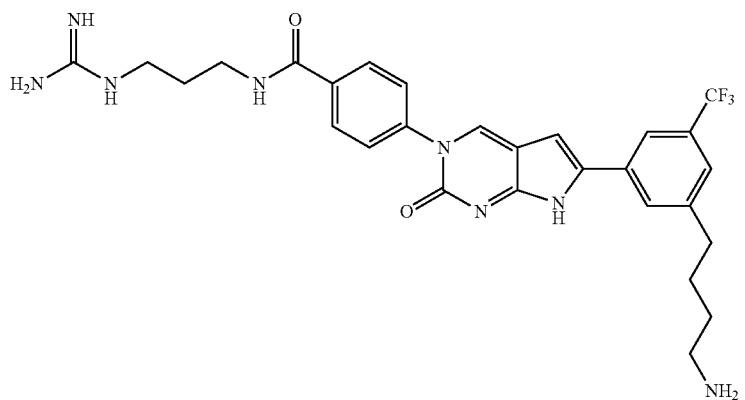
Z25

TABLE AA-continued
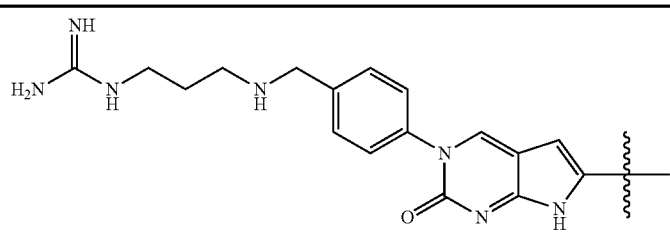
Z26
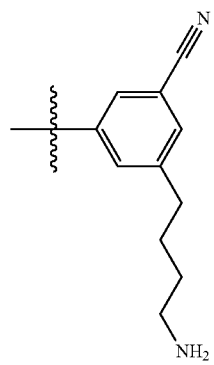
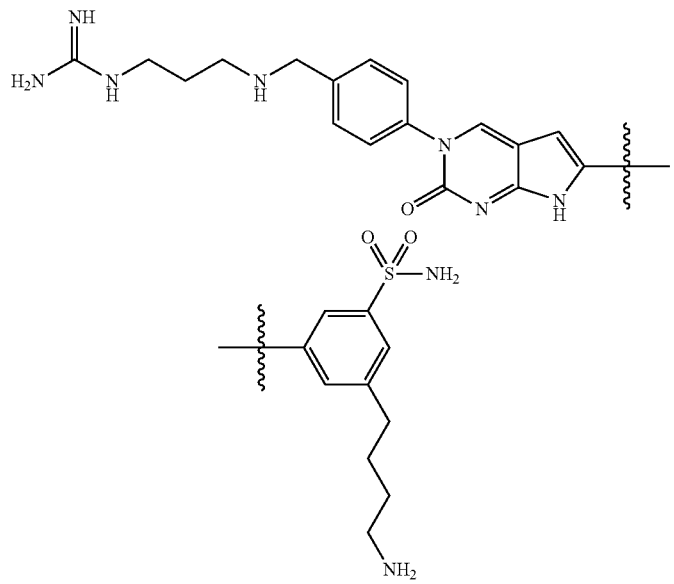
Z27
The compounds of the present invention can be made using synthetic chemical techniques well known to those of skill in the art.
EXAMPLES
Example 1
Synthesis of Alkyne Intermediate
The alkyne intermediate can generally be synthesized according to the scheme:
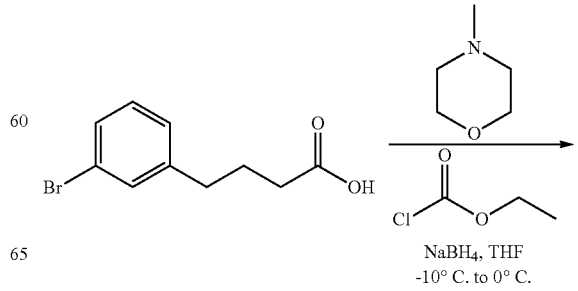
NaBH₄, THF
-10° C. to 0° C.

-continued

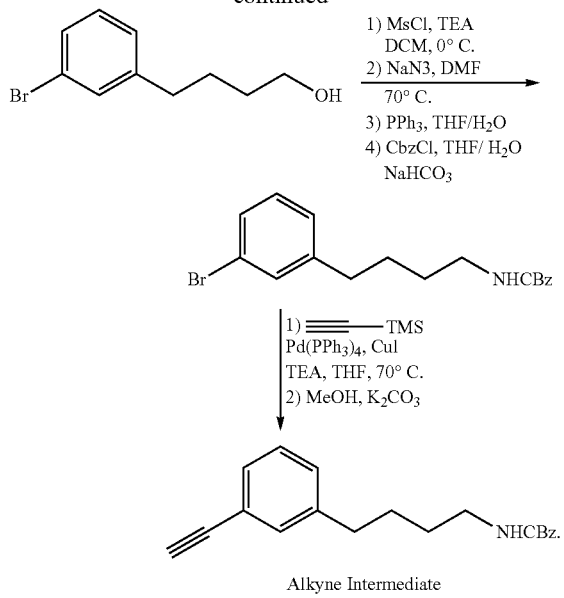

Alkyne Intermediate

Example 2

Synthesis of Pyrrolocytosines Compound 37 ($R^1$=Cl, $R^2$=F) and Compound 91 ($R^1$=F, $R^2$=Cl)

Compounds 37 and 91 can be synthesized according to the scheme. Compound 37 can be synthesized according to the procedures detailed below. Similar procedures can be used to synthesize compound 91. Variables $R^1$ and $R^2$ in the scheme are not the same as in the claims, and they are used in this scheme for purposes of this particular example.

Synthesis of Compound 31 from 1,5-dibromo-2-chloro-3-fluoro-benzene (2a)

A solution of 2,6-dibromo-3-chloro-4-fluoro-phenylamine (1a, 4.85 g, 16 mmol, 1 eq.) in DMF (20 mL) was added to a solution of isoamylnitrite (3.46 mL, 25.6 mmol, 1.6 eq.) in DMF (12 mL) at 70° C. The mixture was heated at 70° C. for 3 h before it was cooled to room temperature, quenched with 1 N NaOH aqueous solution (150 mL), and extracted with EtOAc (200 mL). The EtOAc extract was washed with brine (100 mL×2), dried over $MgSO_4$, filtered and concentrated. The residue was purified by flash chromatography (heptane) to give desired product 2a as colorless oil (3.70 g, 80%).

Synthesis of [4-(3-bromo-4-chloro-5-fluoro-phenyl)-butyl]-carbamic acid benzyl ester (3a)

A solution of but-3-enyl-carbamic acid benzyl ester (5.00 g, 24.36 mmol, 1 eq) in anhydrous toluene (60 mL) was cooled under argon to 0-5° C. 9-BBN (0.50 M, solution in THF; 54.6 mL, 26.80 mmol, 1.1 eq.) was added dropwise, and the mixture was allowed to reach room temperature. After 24 h, the resulting solution was added dropwise at room temperature to a mixture of 2a (7.03 g, 24.36 mmol, 1 eq.), 1N $NaOH/H_2O$ (40 mL, 40 mmol, 1.6 eq.), and toluene (20 mL). The mixture was then degassed with argon and $Pd(PPh_3)_4$ (1.13 g, 0.98 mmol, 0.04 eq.) was added. The mixture was rapidly stirred under argon at 60° C. for 24 h, before cooling to room temperature. The mixture was partitioned between EtOAc (150 mL) and brine (150 mL). The organic phase was washed with brine (200 mL), dried over $Na_2SO_4$, filtered and concentrated. The crude product was purified by flash chro-

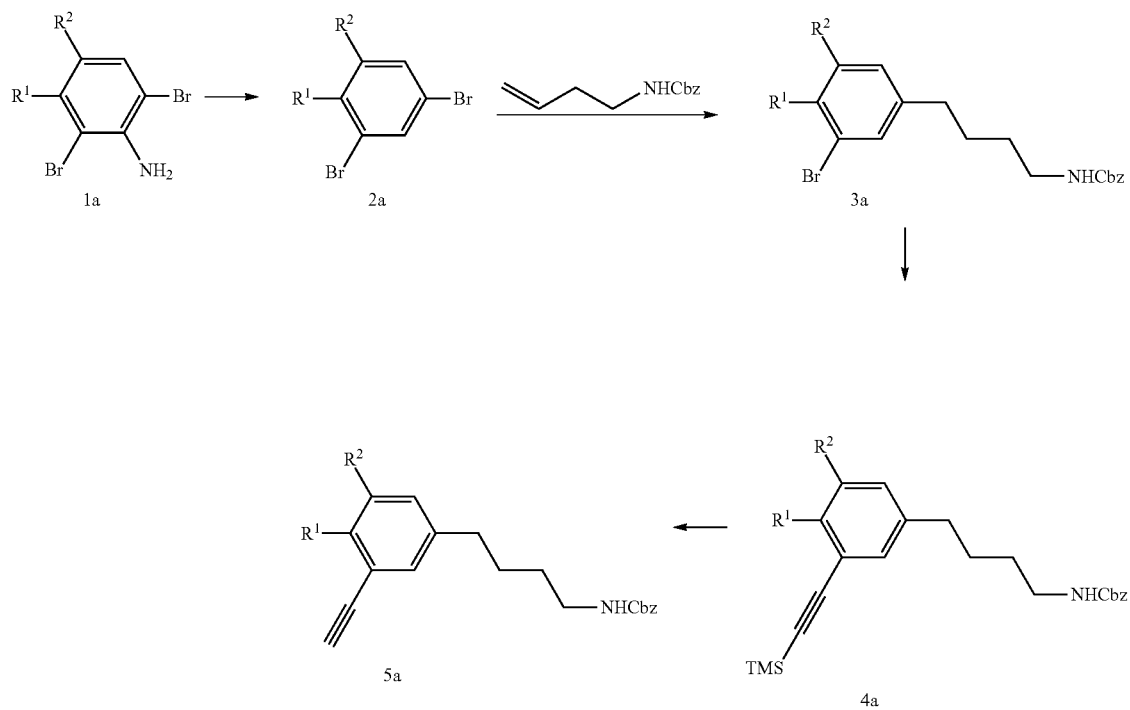

matography on silica gel (0-50% EtOAc in Heptane) to afford 3a as a colorless oil (3.54 g, 35%).

Synthesis of [4-(4-chloro-3-fluoro-5-trimethylsilanylethynyl-phenyl)-butyl]-carbamic acid benzyl ester (4a)

A mixture of 3a (4.78 g, 11.51 mmol, 1 eq.), CuI (175 mg, 0.92 mmol, 0.08 eq.), Pd(PPh₃)₂Cl₂ (323 mg, 0.46 mmol, 0.04 eq.) and DMF (30 mL) was degassed. Trimethsilylacetylene (4.23 mL, 21.02 mmol, 2 eq.) was added under argon, followed by Et₃N (4.81 mL, 34.53 mmol, 3 eq.). The resulting mixture was heated at 70° C. for 24 h. After cooling to room temperature, the reaction mixture was diluted with EtOAc (250 mL) was washed with brine (150 mL×2 containing 15 mL 28% NH₄OH). The EtOAc solution was dried over MgSO₄, filtered and concentrated. The crude product was purified by flash chromatography (0-50%, EtOAc in heptane) to afford 4a (4.50 g, 90%).

Synthesis of [4-(4-Chloro-3-ethynyl-5-fluoro-phenyl)-butyl]-carbamic acid benzyl ester (5a)

K₂CO₃ (2.76 g, 20 mmol, 2 eq.) was added to a solution of 4a (4.50 g, 10.36 mmol, 1 eq.) in degassed MeOH (200 mL). The suspension was stirred at room temperature for 30 min. before concentration. The residue was partitioned between EtOAc (200 mL) and brine (200 mL). The EtOAc layer was separated and washed further with brine (100 mL), dried over MgSO₄, filtered and concentrated. The crude product was purified by flash chromatography (0-50%, EtOAc in heptane) to afford 5a as a colorless oil (3.60 g, 96%).

Synthesis of 6a

Intermediate 6a can generally be synthesized according to the scheme:

Synthesis of Compound 3b

Compound 2b (65.0 g, 373 mmol) was dissolved in ethanol (150 mL). The flask was purged with argon. Compound 1b (55.93 g, 373 mmol) was then added and the mixture was stirred at room temperature for 2 h. The reaction solution was then added via addition funnel, over 20 minutes, to a suspension of NaBH₄ (14.18 g, 373 mmol) in toluene (150 mL), at 0° C. The ice bath was removed, and the resulting mixture was stirred at room temperature for 3 h. 1N HCl (750 mL) was added to the solution, and the mixture was stirred at room temperature for 30 min. K₂CO₃ (205.9 g, 1.49 mol), Boc₂O (81.41 g, 373 mmol), and THF (200 mL) were added to the solution, and stirred at room temperature for 23 h. Reaction solution was partitioned between EtOAc and 1:1 brine/H₂O. The aqueous layer was washed with EtOAc (2×300 mL). The combined organic layers were washed with brine (500 mL); dried over Na₂SO₄; filtered, and concentrated. The crude product was purified by Combi Flash chromatography, in 3 portions, affording the product as a white solid (119.43 g, 78%); ¹H-NMR (300 MHz, CDCl₃) δ 1.43 (bs, 18H), 1.63 (m, 2H), 2.95-3.30 (m, 4H), 4.45 (m, 2H), 5.93 (bs, 1H), 7.22 (bs, 1H), 7.34 (bs, 1H), 7.78 (d: 8 Hz, 1H), 8.19 (d: 8 Hz, 1H).

Synthesis of Compound 5b

To a mixture of compound 3b (42.28 g, 103.5 mmol) and compound 4b (24.54 g, 103.5 mmol) were added MeOH (3 L) and H₂O (750 mL). The mixture was stirred vigorously open to air, at room temperature, for 30 min. Cu(OAc)₂.H₂O (20.67 g, 103.5 mmol) was then added followed by TMEDA (18.63 mL, 124.3 mmol). The solution was stirred open to air, at room temperature, for 5 h. Once the reaction was complete, the solution was concentrated to 0.7 L, and then partitioned between CH₂Cl₂ (700 mL) and 20% NH₄OH/H₂O saturated with NH₄Cl (500 mL). The aqueous layer was washed with

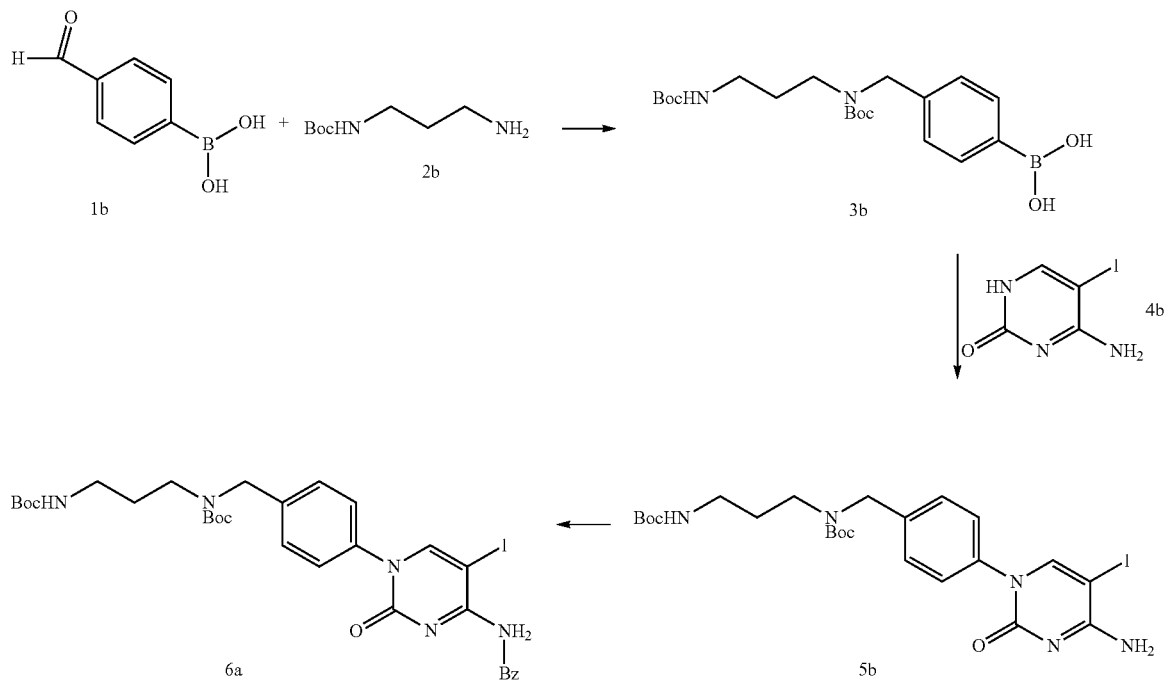

CH$_2$Cl$_2$ (500 mL, 200 mL). The combined organic layers were dried over MgSO$_4$, filtered, and concentrated. The crude product was purified by Combi Flash chromatography: A: CH$_2$Cl$_2$ B: 15:1 CH$_2$Cl$_2$/2N NH$_3$/MeOH, 0-100% B over 85 min. (two 330 g columns). This gave the product as a white solid (35.52 g, 58%); LCMS (ESI): m/e 600 (M+H)$^+$.

Synthesis of Compound 6a

Compound 5b (10.0 g, 16.68 mmol) was dissolved in THF (40 mL). The flask was purged with argon. Pyridine (40 mL) was then added followed by BzCl (3.10 mL, 26.69 mmol). The solution was stirred at room temperature under argon atmosphere for 3 h. MeOH (4 mL) was added, the mixture was stirred at room temperature for 10 min, and then it was partitioned between EtOAc (200 mL), heptane (100 mL), and 5% KHCO$_3$/H$_2$O (200 mL). The aqueous layer was washed with EtOAc (100 mL, 50 mL). The combined organic layers were washed with 5% KHCO$_3$/H$_2$O (300 mL); dried over Na$_2$SO$_4$; filtered, and concentrated. The crude product was purified by Combi Flash chromatography: 0-100% EtOAc/heptane, over 55 min. (330 g column). The product was obtained as an off-white powder (9.81 g, 84%); LCMS (ESI): m/e 704 (M+H)$^+$.

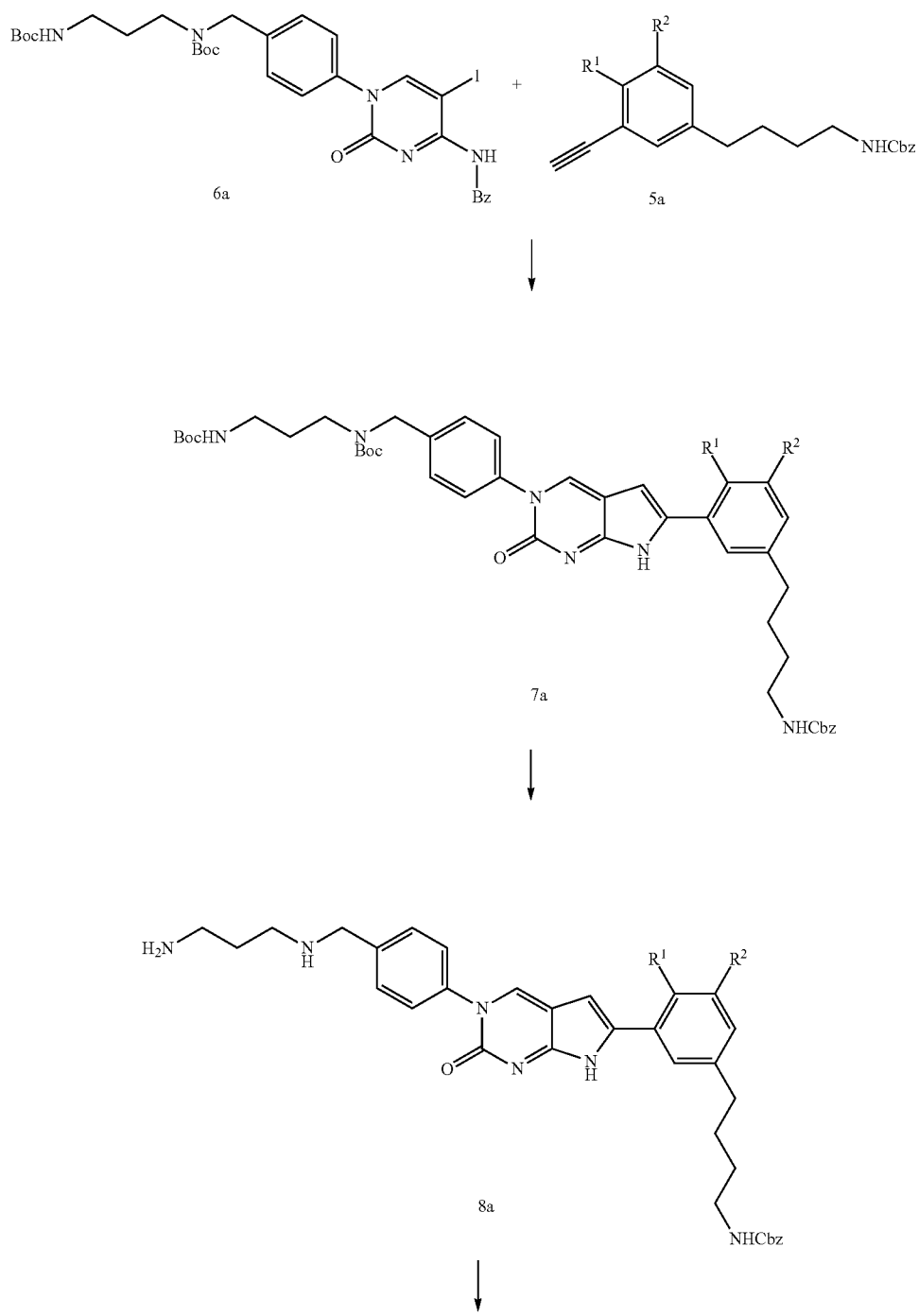

-continued

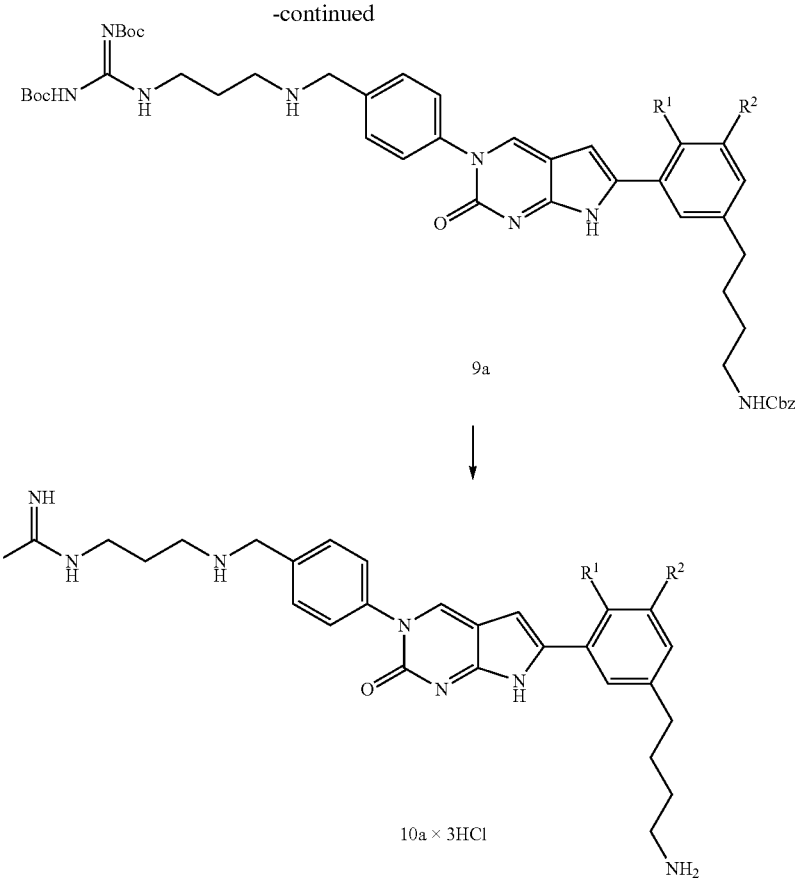

Synthesis of 7a

Pyrrolocytosine 7a was prepared from the coupling of common intermediate 6a and alkyne 5a according to the procedure describing this type of reaction. For example: compound 6a (1 eq) and compound 5a (1 eq) were placed in a pressure vessel, and anhydrous DMF was added. The solution was purged with argon, and then CuI (0.1 eq), Pd(PPh$_3$)$_4$ (0.05 eq), and Et$_3$N (6 eq) were added, the vessel was sealed, and the mixture was stirred at 22° C., for 15 min. Subsequently, the temperature was increased to 80-85° C., and the mixture was stirred for 14 h. It was cooled to ambient temperature, MeOH was added, the vessel was sealed, and the mixture was stirred at 90° C. for 3 h. After cooling to ambient temperature, the mixture was partitioned between sat. KH$_2$PO$_4$/H$_2$O and EtOAc, the organic phase was washed with brine, dried over Na$_2$SO$_4$, filtered and concentrated. The crude product was purified by flash chromatography on silica gel using 5% (2.5M NH$_3$/MeOH)/CH$_2$Cl$_2$. Starting from 360 mg of 5a, 600 mg of the desired compound 7a was obtained as an orange-brown solid (72%); LCMS (ESI) m/e 813.2 (M+1)$^+$.

Synthesis of 8a

Boc-deprotection of 7a (0.60 g, 0.72 mmol) was accomplished with 8 mL of 6N HCl in 25 mL EtOH at 60° C. (2 h). Following solvent evaporation, the crude residue was taken to the next step without further purification. LCMS (ESI) m/e 613.0 (M+1)$^+$.

Synthesis of 9a

Guanidine formation was carried out by dissolving 8a in a 5:1 DMF/MeOH (0.1 M) at rt. After treating with diisopropylethylamine (8 eq), N,N-bis-boc-guanylpyrrazole (1.3 eq) was added as a solid. The reaction mixture was stirred for 6 h, and upon completion the solvents were removed by rotary evaporation. Crude 9a was used without further purification.

Synthesis of 10a (Compound 31)

Under argon, fully protected guanidine 9a (0.60-0.80 mmol) was dissolved in 25 mL of trifluoroacetic acid. Thioanisole (0.5 mL) was added dropwise and the solution was stirred at rt for 4 h. Upon completion, solvent was evaporated affording an oil. Diethyl ether was added and the liquid layer containing most of the residual thioanisole was decanted. Crude 10a was then dissolved in [(20% MeOH-80% H$_2$O)+ 0.15% TFA] (10 mL). An aliquot (10 mL) was injected on a Dynamax 41.4 mm, C-18 prep HPLC Unit (guard+column), which was eluted with a gradient of solvents of 20%-80% (MeOH/H$_2$O+0.15% TFA), over 45 min. The pure fractions were combined and concentrated with EtOH to dryness. This sample was treated with 1N HCl/H$_2$O (5 mL) and EtOH (70 mL), and concentrated. This operation was repeated; the solid thus obtained was lyophilized from H$_2$O-MeCN (4:1), affording compound 10a as a yellow powder (250 mg); LCMS (ESI) m/e 539.0 (M+1)$^+$; $^1$H NMR (300 MHz, D$_2$O) δ 1.50-1.60 (m, 4H), 1.82-1.95 (m, 2H), 2.57 (t, J=6.9 Hz, 2H), 2.86 (t, J=6.9 Hz, 2H), 3.06 (t, J=6.9 Hz, 2H), 3.17 (t, J=6.9 Hz, 2H), 4.23

(s, 2H), 6.78 (s, 1H), 7.08 (d, J=8.5 Hz, 1H), 7.18 (s, 1H), 7.44 (d, J=8.7, 2H), 7.58 (d, J=8.7 Hz, 2H), 8.48 (s, 1H).

Example 3

Synthesis of a Benzylic Methylated Fragment A Intermediate

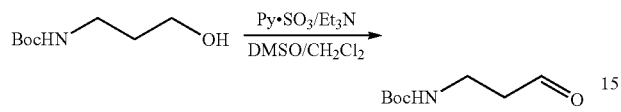

Pyridine sulfurtrioxide complex (20 g, 125 mmol, 2.5 eq.) was added to a mixture of (3-hydroxy-propyl)-carbamic acid tert-butyl ester (8.75 g, 50 mmol, 1 eq.), Et$_3$N (17.67 g, 175 mmol, 2.5 eq.), DMSO (25 mL) and CH$_2$Cl$_2$ (100 mL) at 0° C. The resulted mixture was stirred at 0° C. for 1 h and warmed up to room temperature and continuously stirred for 3 h. After concentration, the residue was diluted with EtOAc (200 mL) and washed with H$_2$O (200 mL), brine (100 mL), dried over MgSO$_4$, filtered and concentrated to give desired aldehyde as colorless oil (8.60 g, 99%).

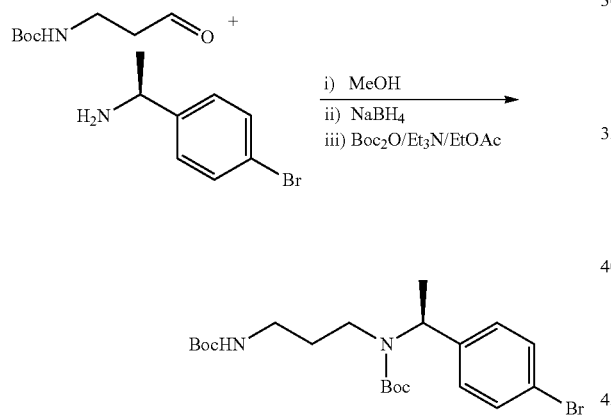

A mixture of (3-oxo-propyl)-carbamic acid tert-butyl ester (8.94 g, 51.7 mmol, 1 eq.), (S)-(−)-1-(4-bromo-phenyl)-ethylamine (10.33 g, 51.7 mmol, 1.0 eq.) and MeOH (50 mL) was stirred at RT for 18 h. NaBH$_4$ (1.98 mg, 52.1 mmol, 1.01 eq.) was added slowly to the above solution. The resulted mixture was stirred at RT for 1 h, additional (3-oxo-propyl)-carbamic acid tert-butyl ester (0.8 g, 4.6 mmol) was added and stirred for 2 h. additional NaBH$_4$ (0.21 g, 5.53 mmol) was added and stirred for 1 h. EtOAc (120 mL) was added and washed with 1N NaOH (40 mL×2), 1N HCl (60 mL) and water, dried over MgSO$_4$, filtered and concentrated. The crude product was dissolved in EtOAc (120 mL) and MeOH (20 mL), Et$_3$N (10.8 mL, 77.52 mmol, 1.5 eq.) was added, followed by Boc$_2$O (11.3 g, 51.8 mmol, 1.0 eq.). The resulted mixture was stirred at RT for 3 days (weekend), washed with H$_2$O, dried over MgSO$_4$, filtered and concentrated. The crude product was purified by flash chromatography (EtOAc:Heptane/1:5) to afford (3-{[1-(4-bromo-phenyl)-ethyl]-tert-butoxycarbonyl-amino}-propyl)-carbamic acid tert-butyl ester (17.5 g, 74%).

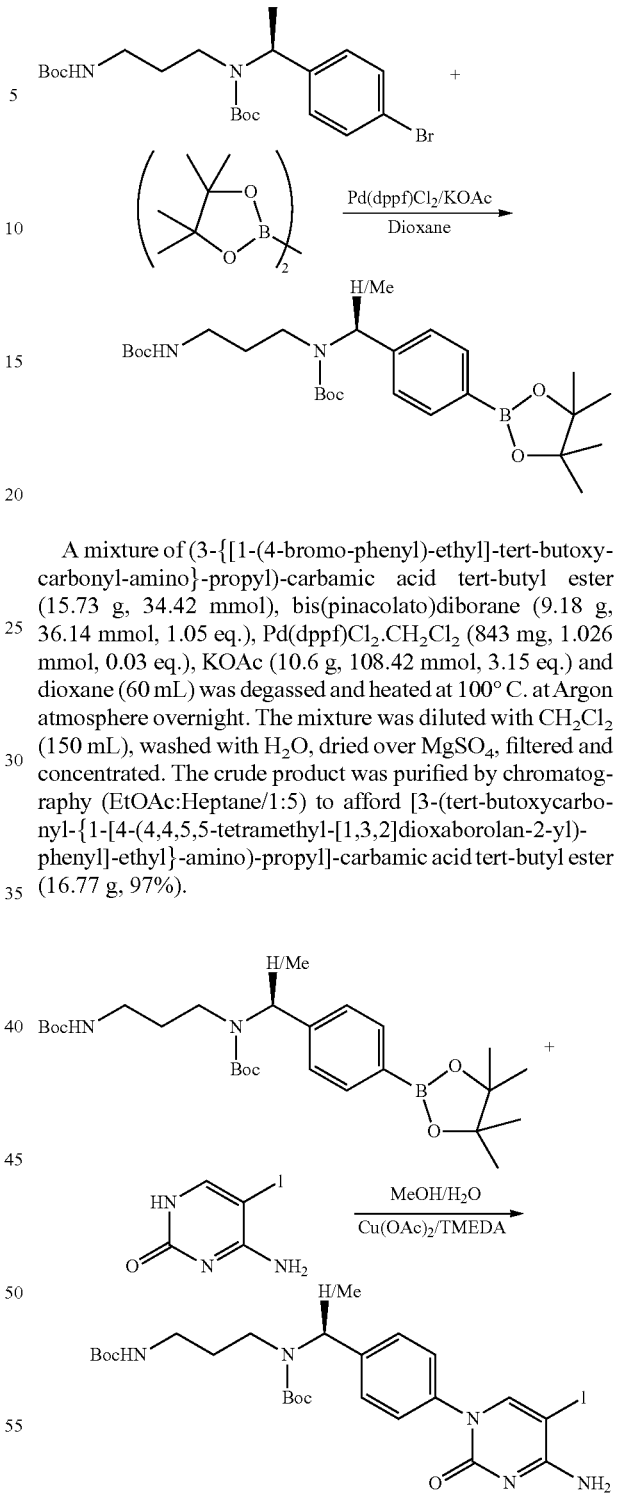

A mixture of (3-{[1-(4-bromo-phenyl)-ethyl]-tert-butoxycarbonyl-amino}-propyl)-carbamic acid tert-butyl ester (15.73 g, 34.42 mmol), bis(pinacolato)diborane (9.18 g, 36.14 mmol, 1.05 eq.), Pd(dppf)Cl$_2$.CH$_2$Cl$_2$ (843 mg, 1.026 mmol, 0.03 eq.), KOAc (10.6 g, 108.42 mmol, 3.15 eq.) and dioxane (60 mL) was degassed and heated at 100° C. at Argon atmosphere overnight. The mixture was diluted with CH$_2$Cl$_2$ (150 mL), washed with H$_2$O, dried over MgSO$_4$, filtered and concentrated. The crude product was purified by chromatography (EtOAc:Heptane/1:5) to afford [3-(tert-butoxycarbonyl-{1-[4-(4,4,5,5-tetramethyl-[1,3,2]dioxaborolan-2-yl)-phenyl]-ethyl}-amino)-propyl]-carbamic acid tert-butyl ester (16.77 g, 97%).

References for above rxn: Jacobsen, M. F.; Knudsen, M. M.; Gothelf, K. V. "Efficient N-Arylation and N-Alkenylation of the Five DNA/RNA Nucleobases" *J. Org. Chem.* 2006, 71, 9183-9190.

Dai, Q.; Ran, C.; Harvey, R. G. "Regioselective Arylation of 2'Deoxyribonucleosides on Amido or Imino Sites by Copper (II)-Mediated Direct Coupling with Arylboronic Acids" *Tetrahedron* 2006, 62, 1764-1771.

Cu(OAc)$_2$ (6.02 g, 33.13 mmol, 1.1 eq.) was added to a mixture of [3-(tert-butoxycarbonyl-{1-[4-(4,4,5,5-tetramethyl-[1,3,2]dioxaborolan-2-yl)-phenyl]-ethyl}-amino)-propyl]-carbamic acid tert-butyl ester (15.18 g, 30.12 mmol, 1 eq.), 4-amino-5-iodo-1H-pyrimidin-2-one (7.85 g, 33.13 mmol, 1.1 eq.), MeOH (400 mL) and H$_2$O (100 mL), followed by N,N,N',N'-tetramethyl-ethane-1,2-diamine (7.69 g, 66.26 mmol, 2.2 eq.). The Mixture was stirred at RT under air for 48 h (weekend) before concentrated to a volume ca. 130 mL. The residue was diluted with CH$_2$Cl$_2$ (200 mL). The CH$_2$Cl$_2$ extract was washed with brine and concentrated. The crude product was purified by flash chromatography (CH$_2$Cl$_2$:MeOH:NH$_4$OH/35:1:0.01) to afford [3-({1-[4-(4-amino-5-iodo-2-oxo-2H-pyrimidin-1-yl)-phenyl]-ethyl}-tert-butoxycarbonyl-amino)-propyl]-carbamic acid tert-butyl ester (16.06 g, 87%).

Benzoic anhydride (5.26 g, 23.25 mmol, 1.05 eq.) was added to a solution of [3-({1-[4-(4-amino-5-iodo-2-oxo-2H-pyrimidin-1-yl)-phenyl]-ethyl}-tert-butoxycarbonyl-amino)-propyl]-carbamic acid tert-butyl ester (13.58 g, 22.15 mmol) in DMF (60 mL). The mixture was heated at 70° C. for 2 h and at RT for 20 h. EtOAc (150 mL) was added to the mixture and washed with saturated sodium bicarbonate and brine, dried over MgSO$_4$, filtered and concentrated. The crude product was purified by chromatography (CH$_2$Cl$_2$:MeOH:NH$_4$OH/50:1:0.01) to afford benzoic acid 1-(4-{1-[tert-butoxycarbonyl-(3-tert-butoxycarbonylamino-propyl)-amino]-ethyl}-phenyl)-5-iodo-2-oxo-1,2-dihydro-pyrimidin-4-yl ester (15.5 g, 98%).

Example 4

Synthesis of the Fragment B Intermediates

The preparation of the Fragment B intermediates 5b and 5c was carried out as described below. The Wittig Olefination can be performed according to methods known in the art or according to Gerpe, A., Convenient Route to Primary (Z)-Allyl Amines and Homologs." *Synth. Commun.* 2009, 39, 29-47. In one aspect, the intermediates 5b and 5c were used to prepare compounds 27 and 100.

Synthesis of Phosphonium Bromide XXb

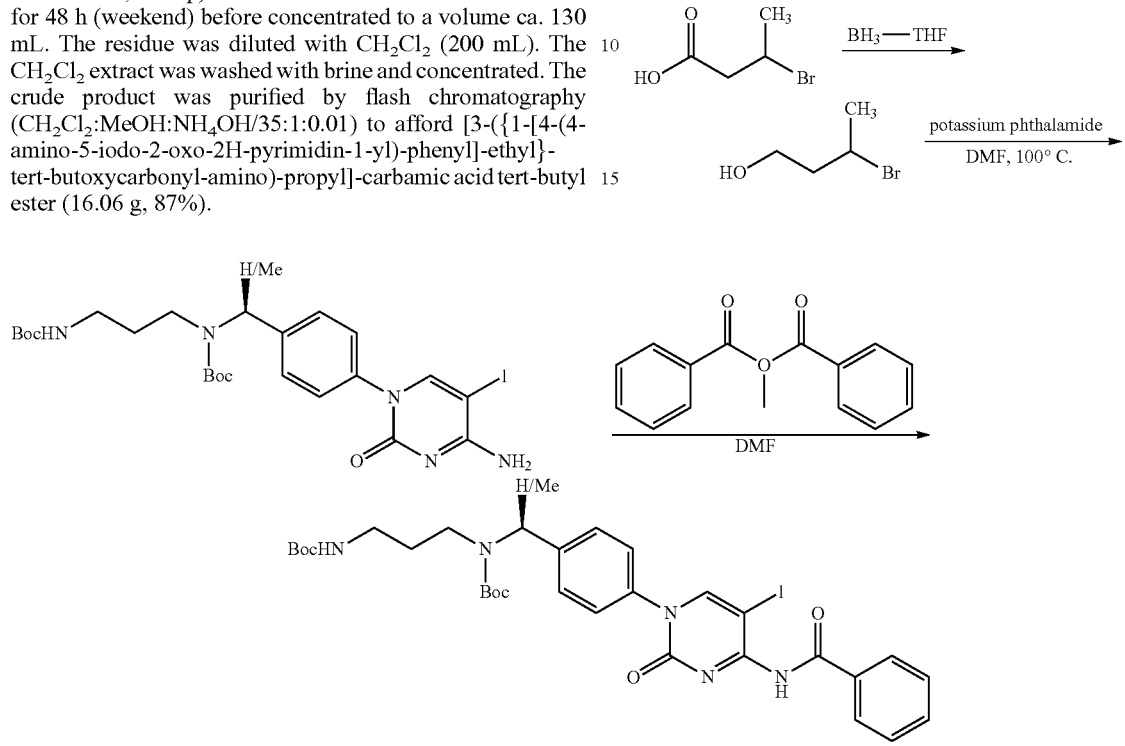

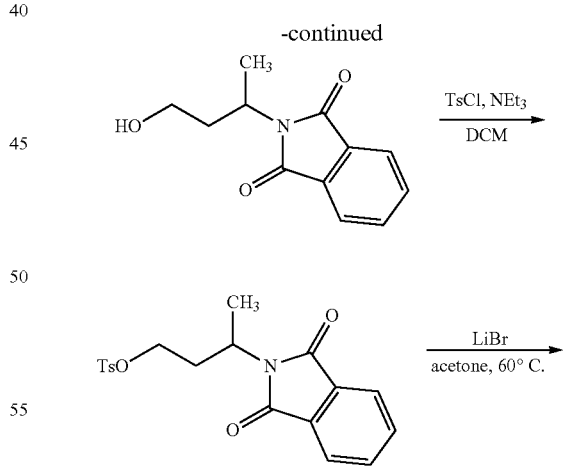

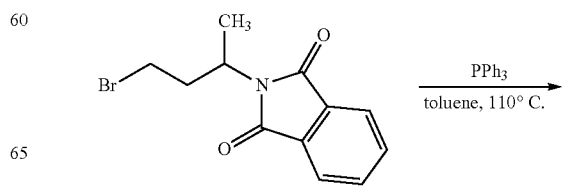

-continued
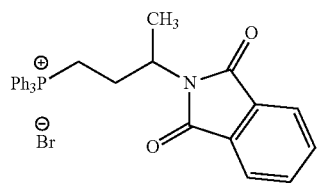
XXb
Synthesis of Phosphonium Bromide XXc
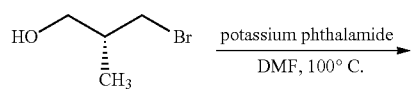
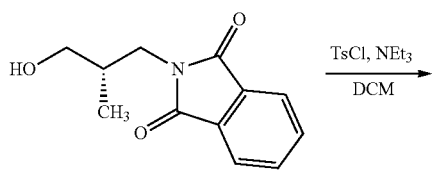
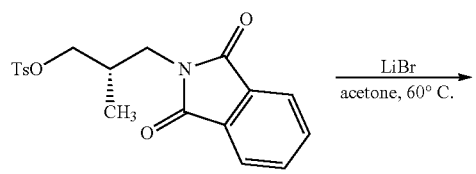
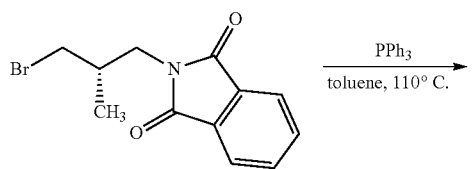
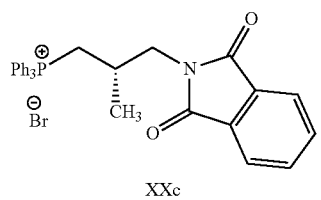
XXc
Synthesis of Fragment B Intermediates via Wittig Olefination
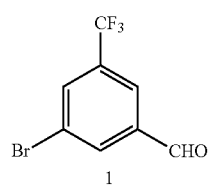
1
-continued
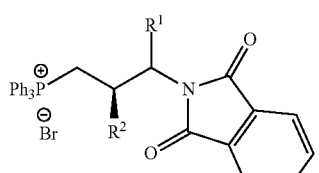
XXb R$^1$ = CH$_3$ R$^2$ = H
XXc R$^1$ = H R$^2$ = CH$_3$
K$_2$CO$_3$,
18-C-6
toluene
110° C.
2b-2c
H$_2$, Pd/C
EtOAc, rt
3b-3c
1. H$_2$NNH$_2$
   EtOH, 65° C.
2. CbzCl
   NEt$_3$, DCM
4b-4c
1. TMS—≡
   Pd(Ph$_3$)$_4$,
   CuI, NEt$_3$
   THF, 65° C.
2. K$_2$CO$_3$, MeOH
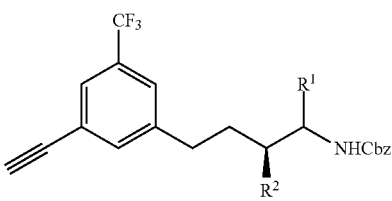
5b R$^1$ = CH$_3$ R$^2$ = H  compound 27
5c R$^1$ = H R$^2$ = CH$_3$  compound 100

Example 5

Synthesis of Compound 234

The preparation of compound 234 was carried out by coupling Fragment A (5) and Fragment B (H). The preparation of Fragment B involves the coupling of intermediates 1 and 2.

Synthesis of N-Cbz (S)-4-aminopentene 1 intermediate

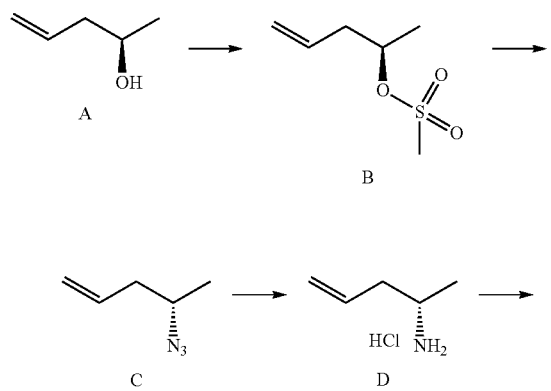

1
yield/4 steps = 93.2%
35.6 g; purity 99%
(heptane 1%)

(R)-4-Hydroxy-1-pentene A (15.00 g, 174.15 mmol) was dissolved in $CH_2Cl_2$ (180 mL). To the solution, stirred/Ar at 0° C. was added triethylamine (30.4 mL, 217.69 mmol), followed by dropwise addition of methanesulfonyl chloride (14.43 mL, 186.35 mmol), over 10 min. After 5 min, the cold bath was removed and the mixture was stirred for 75 min, concentrated to 50 mL, and partitioned between heptane (80 mL), EtOAc (200 mL), $H_2O$ (100 mL) and brine (100 mL). The phases were separated, the organic phase was washed with $H_2O$-brine (2:1; 150 mL), dried over $Na_2SO_4$, filtered and concentrated, affording intermediate B (28.6 g, yield=100%).

Compound B (28.6 g, 174.15 mmol) was dissolved in anhydrous DMF (250 mL) and $NaN_3$ (48.46 g; 745.4 mmol) was added. The mixture was stirred/Ar at RT for 5 min, and then at 70-75° C. for 90 min. Afterwards, the mixture was cooled to RT and partitioned between ice (150 g), water (500 mL) and $Et_2O$ (150 mL). The phases were separated, the aqueous phase was extracted with $Et_2O$ (3×100 mL) (Note: $Et_2O$ could be substituted by 2-Me-THF). The organic extracts were combined and washed with brine (2×150 mL), resulting in a solution of compound C, which was used directly in the next step.

To the solution of C (174.15 mmol) was added THF (100 mL), followed by $H_2O$ (35 mL). The mixture was stirred at RT/Ar, and triphenylphosphine 58.65 g, 223.6 mmol) was added in small portions, over 5 min. Afterwards, the flask was equipped with a reflux condenser and the mixture was stirred at 40-42° C., for 16 hrs. Water (60 mL) was added, followed by dropwise addition of 3N $HCl/H_2O$ (57 mL) to achieve pH=ca. 2.0. The phases were separated, and the organic phase was washed with a mixture of $H_2O$ (40 mL) and 3N $HCl/H_2O$ (3.5 mL). The aqueous phases were combined and washed with EtOAc (2×70 mL), resulting in a solution of salt D, which was used directly in the next step.

The aqueous solution of D (174 mmol) was stirred under argon, while the flask was cooled in a water bath at 20° C. $Na_2CO_3$ (18.44 g, 174 mmol) was added in small portions, followed by $KHCO_3$ (34.84 g, 348 mmol), and THF (150 mL). To this mixture, stirred rapidly, was dropwise added benzyl chloroformate (27.3 mL; 191.4 mmol), over 10 min. The mixture was stirred for 2 hrs. Next, water (150 mL) and EtOAc (200 mL) were added, and the mixture was stirred for 10 min. The phases were separated and the aqueous phase was extracted with EtOAc (2×70 mL). The organic layers were combined, washed with brine (100 mL), dried over $Na_2SO_4$, filtered and concentrated (50.5 g). This sample was purified by flash chromatography on Si-gel (230-400 mesh; 750 g), using 5% EtOAc/heptane (4 L) and then 10% EtOAc/heptane (5 L). This gave a colorless viscous oil of compound 1, which solidified upon standing (35.6 g; purity (NMR) 99%—contains 1% of heptane; yield=93.2% over 4 steps).

Synthesis of 1-bromo-3-chloro-2-fluoro-5-iodo-benzene 2 intermediate

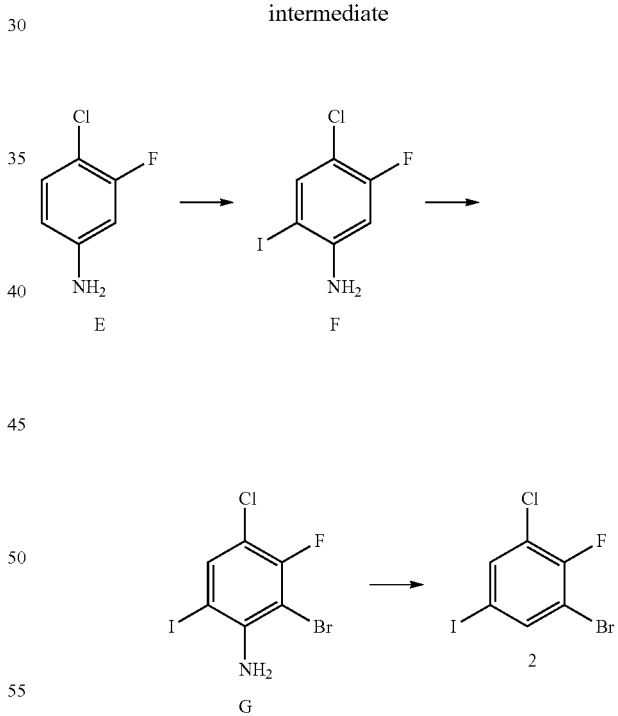

N-Iodosuccinimide (286.2 g, 1.272 mol) was slowly added under argon to rapidly stirred DMF (0.85 L) (Note: It is important to do it in this order because if DMF is added to NIS, a very insoluble solid forms), and then methanesulfonic acid (1.90 mL, 29.3 mmol) was added. The mixture was stirred for 5 min and filtered, which gave a clear solution. Separately, 4-chloro-3-fluoroaniline E (176.3 g, 1.211 mol) was dissolved/Ar in DMF (1.10 L), the solution was cooled to 0° C., and methanesulfonic acid (2.03 mL, 31.3 mmol) was added. The mixture was stirred at 0° C./Ar and the above described solution of NIS in DMF was added dropwise, at 0-5° C., over 1 h 20 min. Subsequently, the mixture was stirred at 0-3° C. for 2.5 h, and then a solution of monosodium ascorbate (24.0 g, 0.121 mol) in H₂O (70 mL) was added dropwise at 0-5° C., over 10 min. The mixture was stirred at 0-5° C. for 20 min, and then EtOAc (1.3 L) and heptane (0.2 L) are added, followed by 5% KHCO₃/H₂O (1.4 L). After 5 minutes of stirring, the phases are separated, and the aqueous phase is extracted with EtOAc (500 mL). The organic phases are combined, washed with water (1 L), dried/Na₂SO₄, filtered and concentrated (401 g). This material is purified by flash chromatography on Si-gel (230-400 mesh; 3.0 kg), using 7%-9% EtOAc/heptane. During the concentration of fractions, the product F precipitates; the solid was filtered and dried in vacuo to give aniline F as a crystalline solid (206.68 g, yield: 77.5%).

N-Bromosuccinimide (142.29 g, 799.43 mmol) was dissolved under argon in DMF-AcOH (5:1; 0.40 L), stirred for 5 min, which resulted in a clear solution.

Separately, compound F (206.68 g, 761.36 mmol) was dissolved under argon in DMF-AcOH (5:1; 1.40 L). The solution was cooled to 0-4° C. and the above described solution of NBS was added dropwise, at 0-4° C., over 20 min. The mixture was stirred at 0-4° C. for 30 min, and then at 12-14° C. (Note: it is important not to exceed the specified temperature range due to a sudden drop in selectivity at higher temperatures), for 5 h, with HPLC monitoring. Subsequently, the mixture was cooled to 0-5° C. and a solution of monosodium ascorbate (15.08 g, 76.14 mmol) in water (40 mL) is added at 0-10° C., over 10 min. The mixture is stirred at 5-10° C. for 10 min, and then EtOAc (1.6 L), heptane (0.2 L), H₂O (3.2 L), and brine (0.6 L) are added, the mixture is stirred for 5 min, and the phases are separated. The aqueous phase is extracted with EtOAc (0.40 L), the organic phases are combined and washed with 10% KHCO₃/H₂O (2×1.1 L), dried over Na₂SO₄, and concentrated (320 g). The crude material is dissolved in minimal amount of CH₂Cl₂, and purified by flash chromatography on Si-gel (3.0 kg) using 2% EtOAc in heptane. The fractions are concentrated to ca. 600 g, at which point a solid precipitates. The mixture is cooled at 10-15° C. and stirred for 1 hr, the product is filtered, and dried to give aniline G (124.15 g, yield: 46.5%).

A solution of isoamyl nitrite (94.9 mL, 708.7 mmol) in DMF (500 mL) was stirred and heated under argon, at 65° C. To this solution was added dropwise a solution of aniline G in DMF (200 mL), over 40 min, while maintaining the temperature at 65-75° C. The mixture was stirred at 65-70° C. for 30 min, and then cooled to 30-40° C. Heptane (0.80 L), EtOAc (0.40 L) and 0.5 N HCl/H₂O (1.6 L) were added, after extraction the phases were separated, and the aqueous phase was washed with a mixture of heptane (0.20 L) and EtOAc (0.30 L). The organic phases were combined, washed with 2N HCl/H₂O (0.70 L), and then with water (0.50 L), dried over Na₂SO₄, filtered, and concentrated (brown oil, 160 g). This sample was purified by flash chromatography on Si-gel (3.0 kg) using 100% heptane as the eluent. This gave a solidifying, thick oil (90.5 g), which was dissolved at 40° C. in heptane (100 mL), and then crystallized from the solution at 0° C. After filtration, the filtrate was recrystallized under similar conditions, and the crystals were combined. This gave compound 2 (67.0 g, yield: 56.4%; HPLC purity (PDA)>93%) as colorless crystals (Note: The major impurity (3-5%) is identified as 1,5-dibromo-3-chloro-2-fluoro-benzene, which is expected to show utility in the present synthesis, essentially similar to compound 2).

Synthesis of alkyne Fragment B intermediate 5

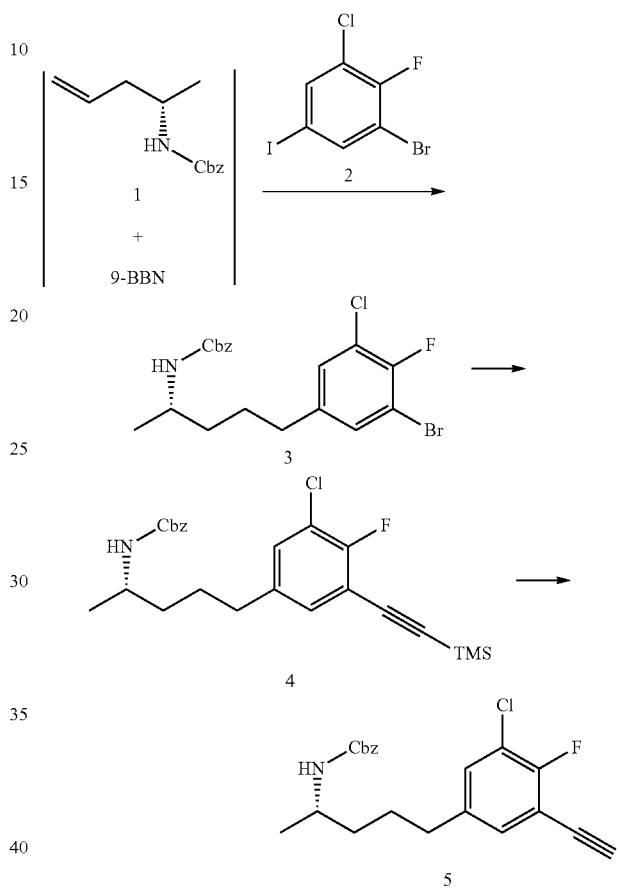

The Suzuki-coupling reaction is preformed according to methods known in the art e.g., Al-Hellani, R.; Schluter, A. D. "On the Synthesis and Selective Deprotection of Low-Generation Dendrons with Orthogonally Protected Peripheral Amine Groups and a Possible Impact of the Deprotection Conditions on the Stability of Dendronized Polymers' Skeletons."*Helv. Chim. Acta.* 2006, 89, 2745-2763.

A solution of olefin 1 (18.62 g, 84.06 mmol) in dry toluene (185 mL) was purged with argon, and then cooled to 0° C. under argon, at which point 9-BBN (11.08 g, 90.80 mmol) was added in a few portions. The mixture was stirred at 0-5° C. for 20 min, and then at RT for 21 h, which gave a solution of the trialkylborane.

To a solution of iodide 2 (28.19 g, 84.06 mmol) in toluene (65 mL) was added 1N NaOH/H₂O (142.9 mL, 142.9 mmol). The mixture was purged with argon, and the above described solution of trialkylborane was added under argon, followed by tetrakis(triphenylphosphine)Pd(0) (4.86 g, 4.20 mmol). The mixture was purged with argon, the flask was transferred to an oil bath (60-64° C.), and the mixture was stirred under argon for 9 h. After cooling to RT, EtOAc (150 mL) and brine (150 mL) were added, the phases were separated, the organic phase was washed with 1N NaOH/H₂O (100 mL), and with brine (100 mL). The organic layer was dried over Na₂SO₄, filtered, and concentrated (56.1 g). This sample was purified by flash chromatography on Si-gel (750 g) using 15% EtOAc in heptane as the eluent. The fractions were combined and concentrated to ca. 300 mL, at which point crystallization occurred. The solid was filtered and dried. This gave compound 3 as a white solid (27.9 g; yield: 77.4%).

The bromide 3 (27.85 g; 64.96 mmol) was dissolved in DMF (220 mL), the solution was purged with argon. Under a gentle stream of argon, trimethylsilyl acetylene (27.5 mL, 194.9 mmol) was added, followed by CuI (990 mg, 5.2 mmol), Pd (PPh$_3$)$_4$ (3.0 g, 2.6 mmol) and triethylamine (stored under argon; 72.5 mL, 519.7 mmol). The flask was equipped with a reflux condenser, and the mixture was stirred under argon, at 70° C. for 2.5 h. After cooling the mixture to RT, brine (300 mL), water (1.0 L) and EtOAc (0.75 L) were added, and after extraction the phases were separated. The organic layer was washed with H$_2$O (0.75 L), dried over Na$_2$SO$_4$, filtered and concentrated. The crude product was purified by flash chromatography on Si-gel (750 g) using 15% EtOAc in heptane. This purification was repeated under the same conditions (Note: due to the potential for ready dimer formation in the next step, it is essential to eliminate from 4 as much transition metal residues as possible). This gave compound 4 as a pale-yellow, thick oil (29.8 g).

This sample was dissolved in MeOH (previously purged with argon; 350 mL), K$_2$CO$_3$ (19 g, 137.47 mmol) was added, the mixture was stirred under a stream of argon for 5 min, and then it was stirred in darkness, under argon, at 45° C. After 35 min the mixture was cooled/Ar to RT, concentrated, and purified by flash chromatography on Si-gel (750 g) using 17% EtOAc in heptane (Note: these operations are performed quickly to avoid alkyne dimerization; after chromatographic purification the alkyne is stable). This afforded alkyne 5 as a white, crystalline solid (20.20 g, yield: 83.2%).

Synthesis of Compound 234

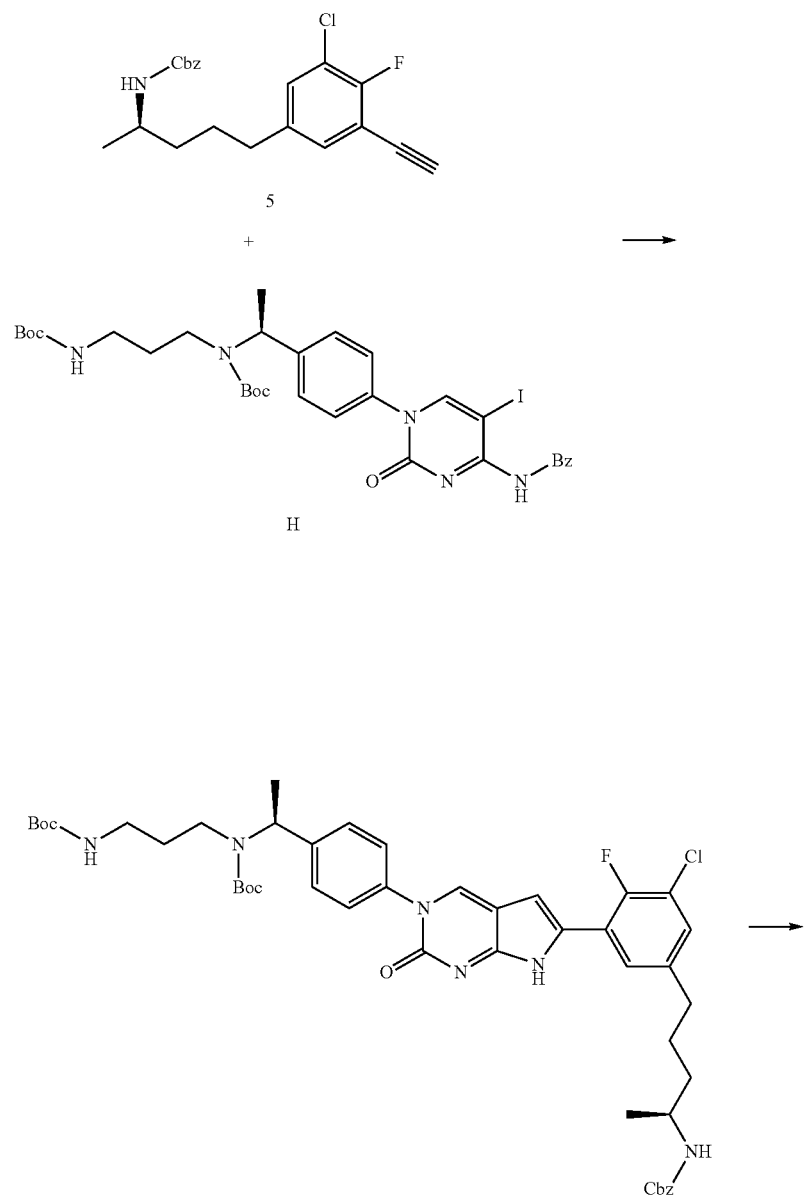

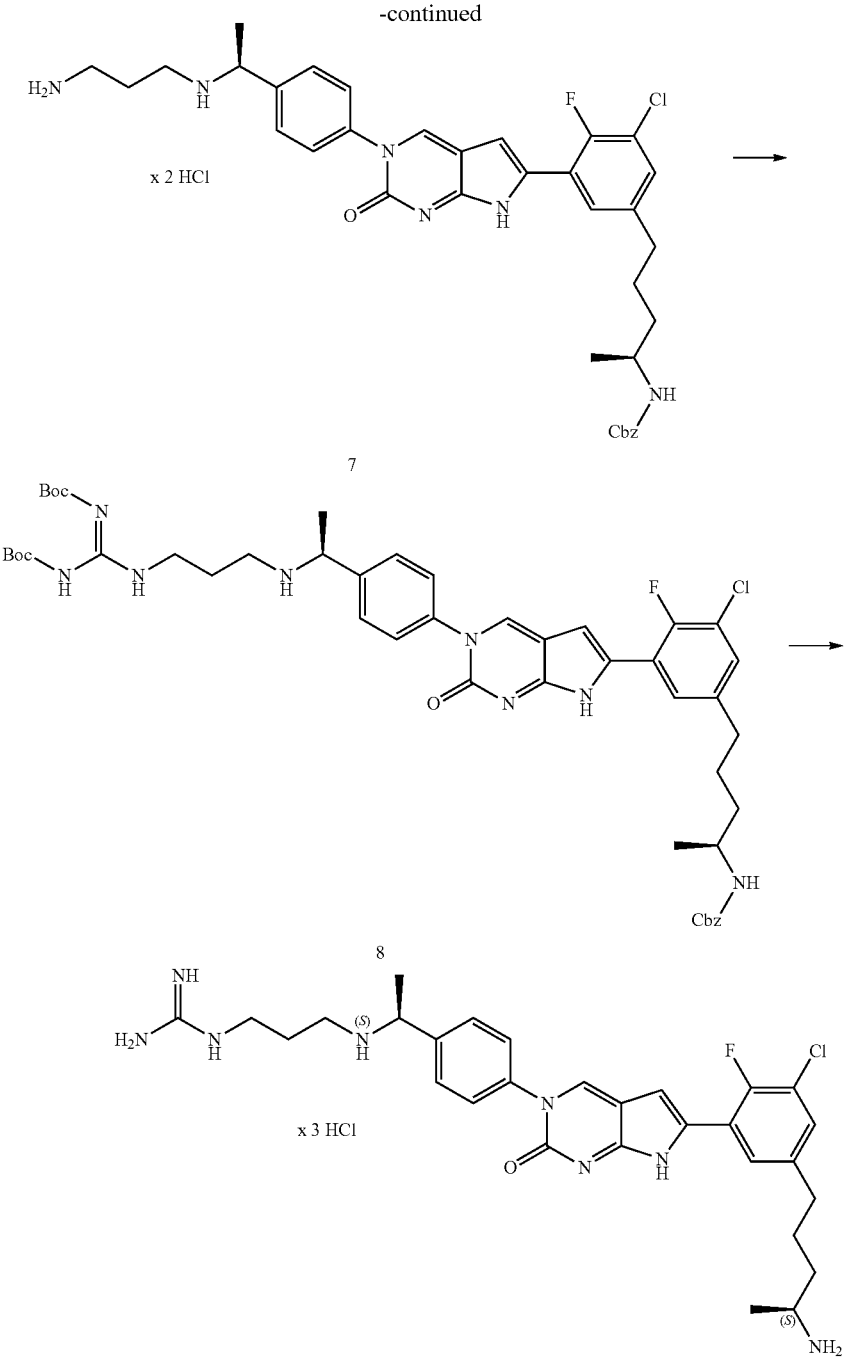

The Fragment A intermediate H was prepared according to methods described herein. H (38.77 g, 54.03 mmol) and alkyne 5 (20.20 g, 54.03 mmol) were dissolved in acetonitrile and the solution was stirred under gentle stream of argon. Copper(I) iodide (617 mg, 3.24 mmol) and Pd(PPh$_3$)$_4$ (1.87 g, 1.62 mmol) were added, followed by diisopropylethyl amine (26.8 mL, 162.1 mmol). The mixture was stirred under Ar, at RT, for 5 min, and then it was heated at 72-75° C. for 4.5 h. Afterwards, MeOH (100 mL) was added and the mixture was stirred/Ar, at 72-75° C., for 15 h. After cooling to RT, the mixture was concentrated, the gummy solid thus obtained was dissolved in EtOAc (300 mL), and the solution was washed with NH$_4$Cl/NH$_4$OH (3×200 mL). The organic phase was concentrated and purified by flash chromatography on Si-gel (750 g) using 5% (2.5M NH$_3$/MeOH) in CH$_2$Cl$_2$. The chromatography was repeated under similar conditions, thus affording a red-brown, gummy solid (41.5 g). To a solution of this sample in MeOH (300 mL), was added charcoal (Aldrich No. 242276; 45 g) and the mixture was stirred for 2 h at RT. Afterwards, the mixture was filtered through a silica gel plug prepared in MeOH, the solids were washed with MeOH (1.0 L), concentrated, and dried in vacuo to give compound 6 as a light-brown solid (32.5 g, 70%).

The pyrrolocytosine 6 (32.5 g, 37.82 mmol) was dissolved under argon in EtOH (200 proof; 200 mL), 6N HCl/H$_2$O 75.6 mL, 453.8 mmol) was added, and the mixture was stirred under argon, at 70-72° C., for 1 h 40 min. Afterwards, the mixture was cooled to 40-45° C., and IPA (200 mL) was added. After 3 min, abundant precipitation occurred—more IPA (350 mL) was added, the mixture was stirred for 10 min, and then filtered. The solid was washed with IPA (2×80 mL), and dried in vacuo overnight, affording salt 7 as a crystalline solid (20.7 g, yield: 75%).

Salt 7 (20.7 g, 28.3 mmol) was added under argon to rapidly stirred MeOH (350 mL), followed by addition of triethylamine (15.8 mL, 113.2 mmol). After the solid dissolved completely (pH ca. 9.5), N,N'-bis-Boc-1-guanylpyrazole (10.54 g, 33.96 mmol) was added and the mixture was stirred for 1 h, at which time more N,N'-bis-Boc-1-guanylpyrazole (0.88 g, 2.83 mmol) was added. The stirring was continued for 1 h; the mixture was concentrated, and the thus obtained semi-solid was purified by flash chromatography on Si-gel (750 g) using 3% MeOH-2% Et$_3$N-95% CH$_2$Cl$_2$. (Note: it is believed that during this chromatography most of palladium residues are removed in the form of a complex with the by-product pyrazole) This gave a partially purified product (29.0 g) which was additionally purified by flash chromatography on Si-gel (750 g) using 3% (2.5M NH$_3$/MeOH) in CH$_2$Cl$_2$. This gave compound 8 as a bright-yellow, solid foam (21.6 g, yield: 84.5%); ICP-OES Pd: 8 ppm, Cu<1 ppm.

Compound 8 (21.30 g) was placed under argon in a 1 L round-bottom flask. With stirring, a pre-formed mixture of thioanisole (8.32 mL, 70.9 mmol) and TFA (300 mL) was added. The reaction mixture was stirred/Ar, at 40-45° C., for 2 h 40 min, and then it was cooled to RT, concentrated, and dried in vacuo. The thus obtained glassy solid was treated with 6N HCl/H$_2$O (50 mL) and EtOH (200 proof, 200 mL), and the mixture was concentrated to a semi-solid. This material was again treated with 6N HCl/H$_2$O (50 mL) and EtOH (200 mL), and the mixture was concentrated, and dried to a solid. This solid was dissolved in 3N HCl/H$_2$O (45 mL), the solution was stirred/Ar, and THF (80 mL) was added dropwise to precipitate an oil. The mixture was rapidly stirred for 5 min, and then the phases were separated. The bottom phase (64.5 g) was placed under argon in a 500 mL flask, stirred at RT under argon, and then the product was precipitated by addition of EtOH (150 mL) and isopropanol (50 mL), and the mixture was stirred at RT for 1 h. The solid was filtered, washed with IPA (4×40 mL), dried with suction, and then dried in vacuo (1 mm Hg, RT) overnight. This gave the product (14.40 g), which contained 1 equivalent IPA (by $^1$H-NMR), in addition to some ethanol and THF. This sample (14.0 g) was dissolved in 1N HCl/H$_2$O (21 mL), and solvents (5 mL) were distilled-off. The sample remaining in the flask was diluted with EtOH (40 mL), and solvents (35 mL) were distilled-off. The residue was stirred/Ar at RT, EtOH (150 mL) was added dropwise, the resulting thick suspension was stirred for 1.5 h at RT, and then filtered. The canary-yellow solid was washed with EtOH (3×30 mL), dried in vacuo at RT for 2 h, and then dried in an oven at 70° C., for 40 h. This gave compound 234 as a yellow powder (11.94 g; Yield: 75% from 8; HPLC Purity (PDA): 98.9%; Solvents: EtOH 0.3%$_{wt}$).

Example 6

Synthesis of Compound 248

The preparation of compound 248 was carried out by coupling Fragment A (10) and Fragment B (9).

Synthesis of Fragment B Intermediate 9

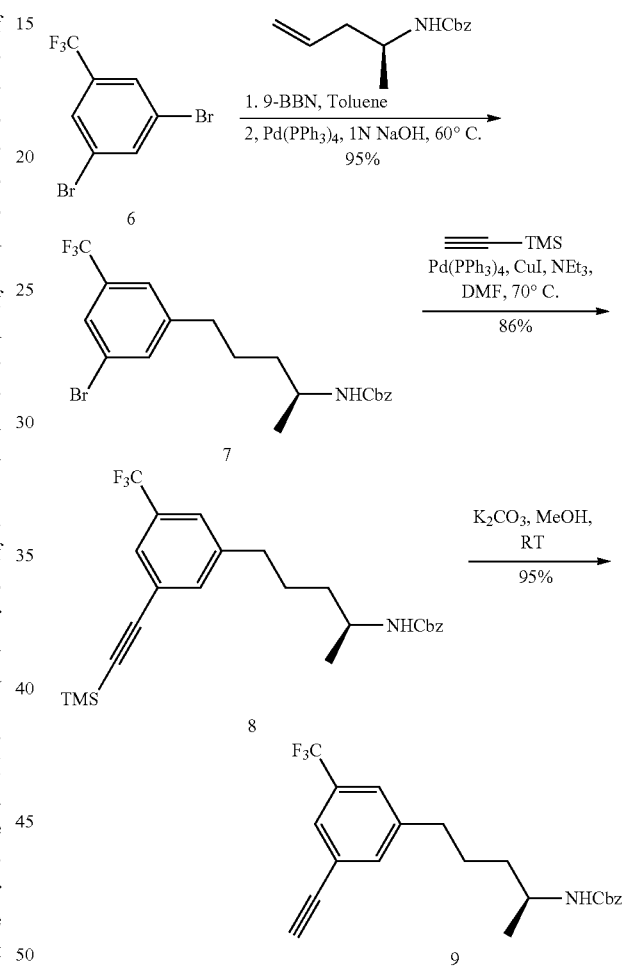

Synthesis of 7

A solution of (S)—N-Cbz-4-aminopentene (16.425 g, 75 mmol) and 9-BBN (dimer, 10.065 g, 41.25 mmol) in toluene was stirred at RT under argon for 16 hrs. 1N NaOH (120 mL), compound 6 (22.79 g, 75 mmol) in toluene (100 mL) and Pd(PPh$_3$)$_4$ (3.5 g, 3.0 mmol) was added. The mixture was stirred under argon at 60° C. for 18 hrs, The mixture was diluted with EtOAc (150 mL), washed with brine (150 mL), dried over MgSO$_4$, filtered and concentrated. The crude product was purified by chromatography on silica gel (0-20% EtOAc in Heptane) to afford 7 as a colorless oil (31.5 g, 95%). Note the procedure to prepare the starting material (S)—N-Cbz-4-aminopentene is described herein.

Synthesis of 8

A mixture of 7 (31.5 g, 70.96 mmol), CuI (674 mg, 3.55 mmol), $PdCl_2(PPh_3)_2$ (996 mg, 1.42 mmol) and DMF (110 mL) was degassed. $Et_3N$ (19.8 mL, 142.12 mmol) and trimethsilylacetylene (10.43 g, 106.42 mmol) was added under argon. The resulting mixture was heated at 70° C. for 24 h. After cooling to room temperature, the reaction mixture was diluted with EtOAc (250 mL), washed with 15% $NH_4OH$ and brine (100 mL×2). The EtOAc solution was dried over $MgSO_4$, filtered and concentrated. The crude product was purified by flash chromatography (0-10%, EtOAc in heptane) to afford 8 as a light yellow oil (28.10 g, 86%).

Synthesis of 9

The suspension of 8 (28.10 g, 60.96 mmol) and $K_2CO_3$ (4.4 g, 31.88 mmol) in MeOH (100 mL) was stirred at room temperature for 1 h. The reaction was diluted with $CH_2Cl_2$ (150 mL), washed with water, dried over $MgSO_4$, filtered and concentrated. The crude product was purified by flash chromatography (5-20%, EtOAc in heptane) to afford 9 as a light brown oil (22.60 g, 95%).

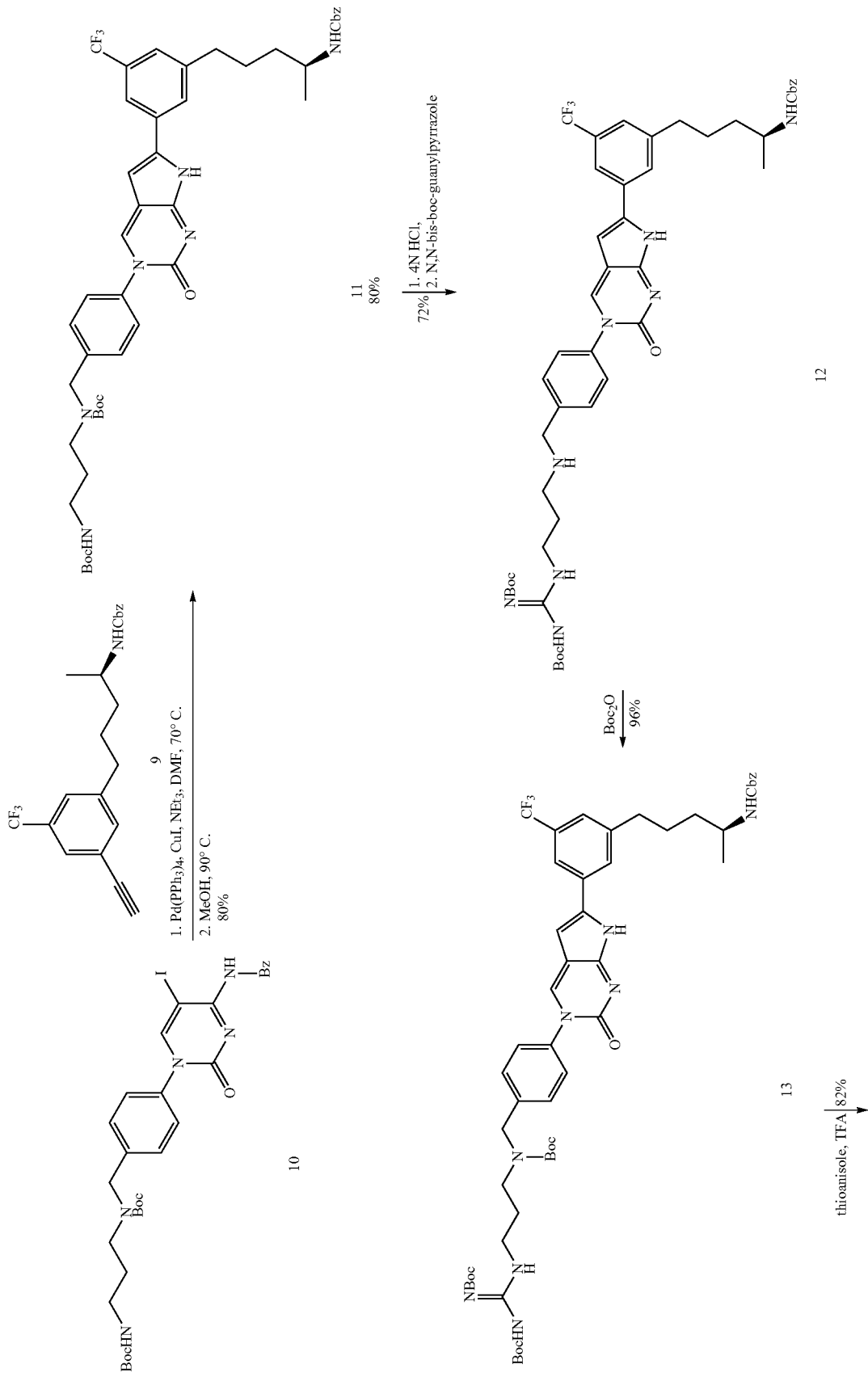

721 722
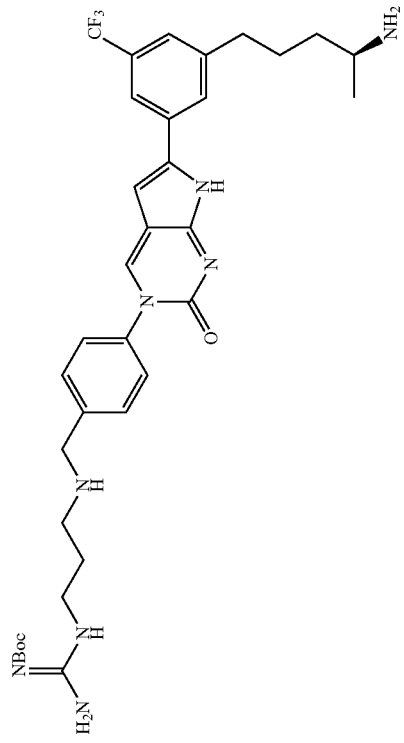
248

Synthesis of 11

Compound 9 (13.0 g, 33.38 mmol) and compound 10 (23.47 g, 33.38 mmol) were dissolved in anhydrous DMF (80 mL). The solution was purged with argon, and then CuI (381 mg, 2.0 mmol), Pd(PPh$_3$)$_4$ (1.157 g, 1.0 mmol), and Et$_3$N (13.95 mL, 100.15 mmol) were added. After stirring at 70° C. for 18 h, MeOH (30 mL) was added, and the mixture was stirred at 90° C. for 3 h. After cooling to ambient temperature, the mixture was diluted with EtOAc (200 mL), washed with 15% NH$_4$OH and brine (150 mL), dried over MgSO$_4$, filtered and concentrated. The crude product was purified by flash chromatography (1-4%, 2.5M NH$_3$/MeOH in CH$_2$Cl$_2$) to give product 11 (22.94 g, 80%).

Synthesis of 12

To a solution of 11 (20.94 g, 24.38 mmol) in MeOH (200 mL) and CH$_2$Cl$_2$ (200 mL) was added 4N HCl in dioxane (150 mL) at 0° C. The reaction was concentrated after stirring at RT for 16 h. The residue was dissolved in DMF (200 mL). Diisopropylethyl amine (21 mL) was added, followed by N,N-bis-boc-guanylpyrrazole (7.56 g, 24.38 mmol). After stirring at RT for 2 days, the reaction was diluted with EtOAc (250 mL), washed with brine (100 mL×2), The EtOAc solution was dried over MgSO$_4$, filtered and concentrated. The crude product was purified by flash chromatography (0-5%, 2.5M NH$_3$/MeOH in CH$_2$Cl$_2$) to give product 12 (15.76 g, 72%) as a yellow foam. 12 was further treated with charcoal (1.5 g) in EtOAc (200 mL) at RT for 4 hrs before next step use.

Synthesis of 13

To a solution of 12 (10.42 g, 11.55 mmol) in CH$_2$Cl$_2$ (70 mL) was added Boc$_2$O (3.07 g, 14.07 mmol). The reaction was concentrated after stirring at RT for 3 h. The residue was purified by flash chromatography (25-90%, EtOAc in Heptane) to give product 13 (11.08 g, 96%) as a yellow foam.

Synthesis of Compound 248

To a solution of 13 (10.42 g, 10.40 mmol) in TFA (20 mL) was added thioanisole (3.9 g, 31.45 mmol). The reaction was concentrated after stirring at 50° C. for 8 h. MeOH (20 mL) and 3N HCl/H$_2$O (40 mL) were added, the resulted solution was concentrated (this sequence was repeated once). The residue was dissolved in 1N HCl (120 mL), washed with diethyl ether (80 mL×3). The acidic aqueous solution was concentrated and recrystallized from MeOH/water/ethanol (2 mL/2 mL/20 mL) to afford the final product 248 (5.8 g, >99% purity, 82% yield).

Example 7

Synthesis of Compounds 387 and 388

Compounds 387 and 388 were prepared according to the procedure below.

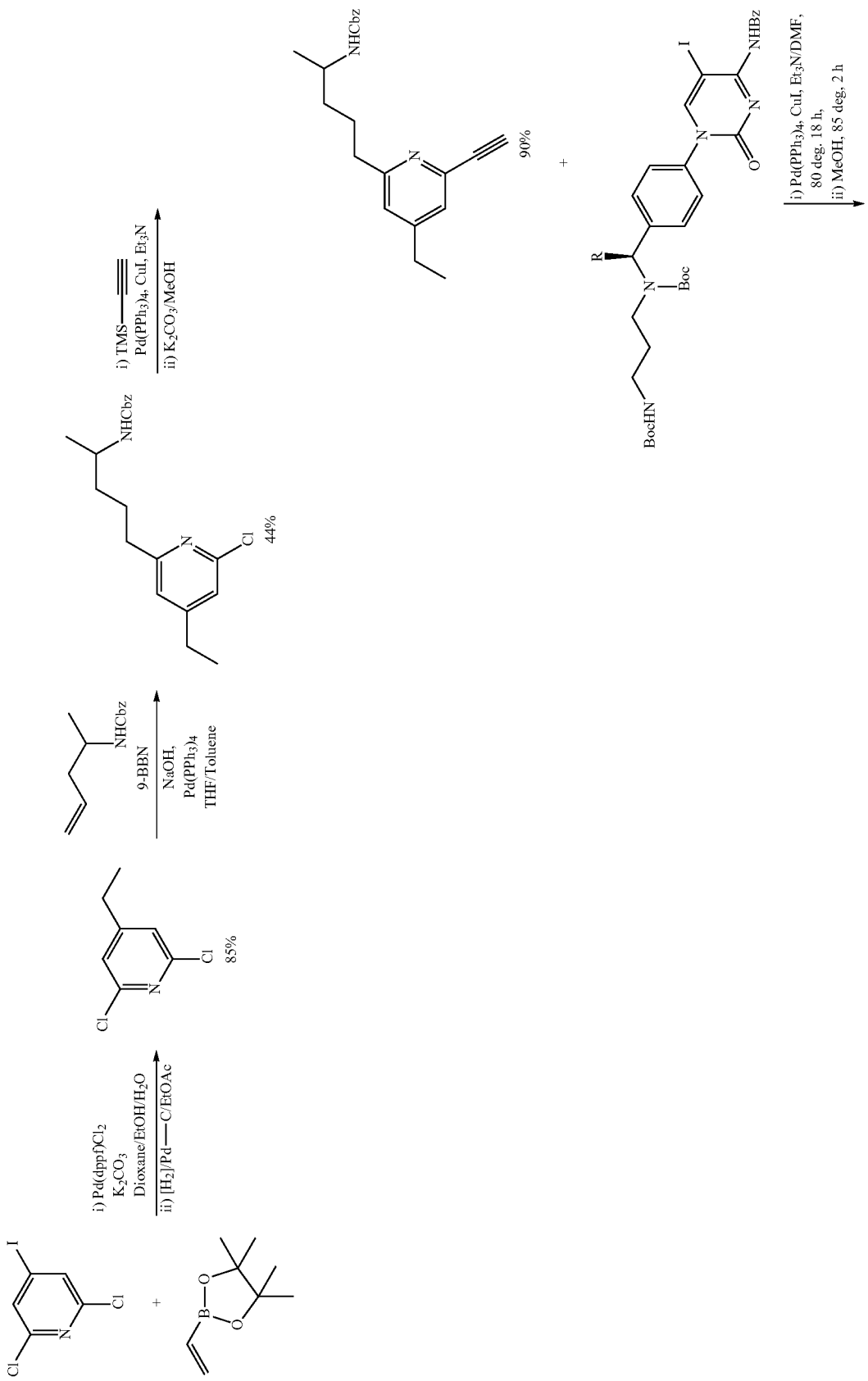

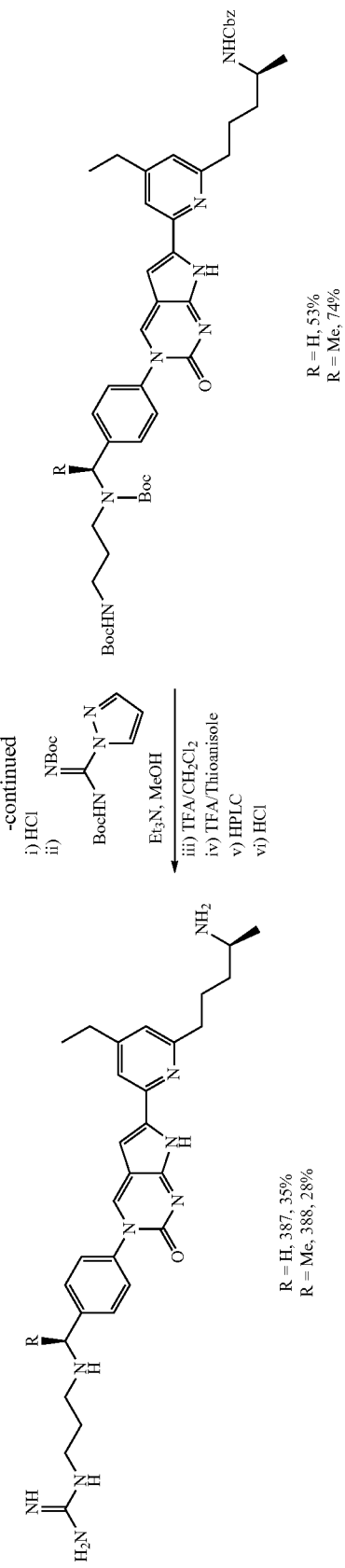

Example 8

Synthesis of Compounds 389 and 390

Compounds 389 and 390 were prepared according to the procedure below.

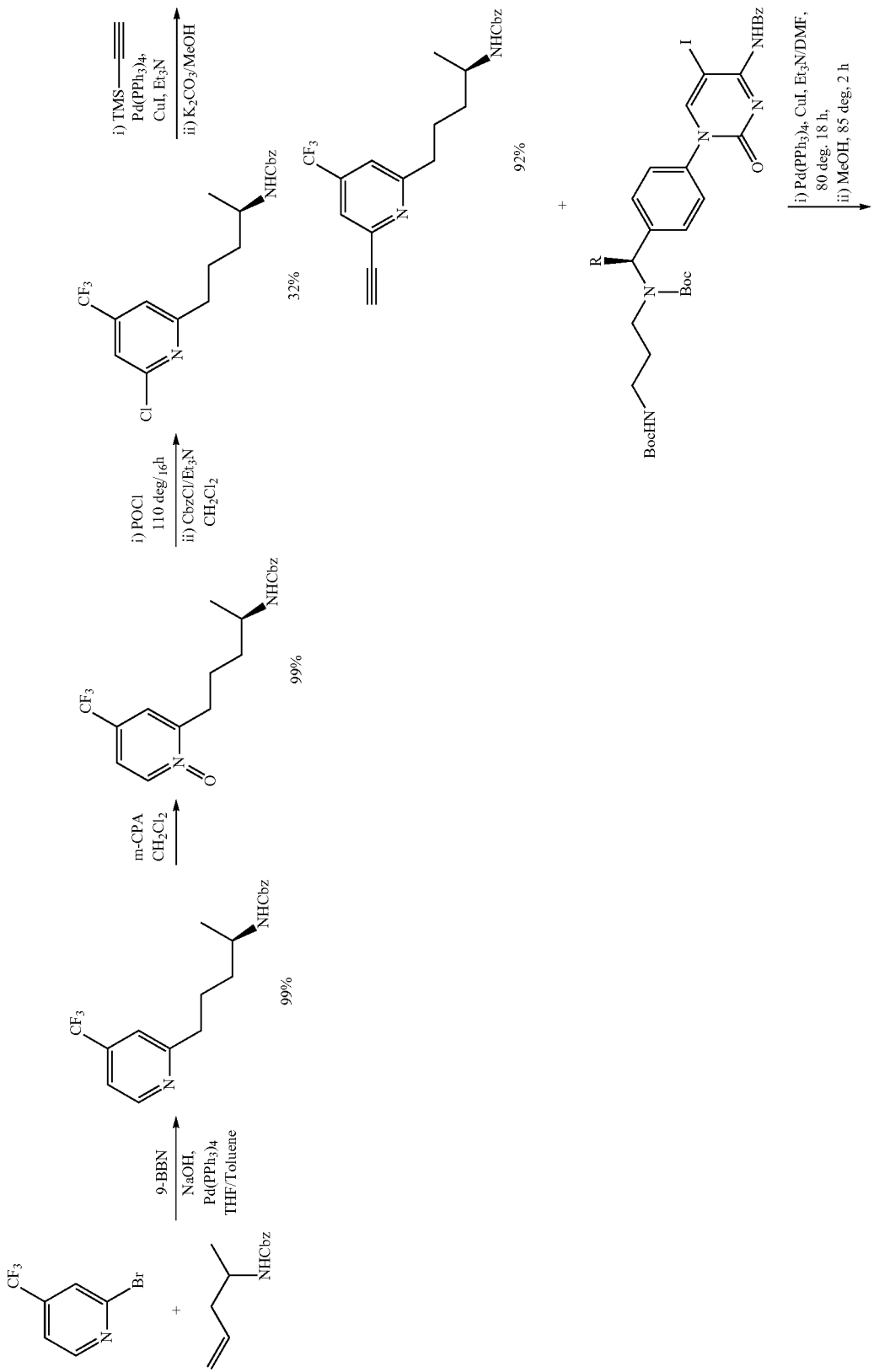

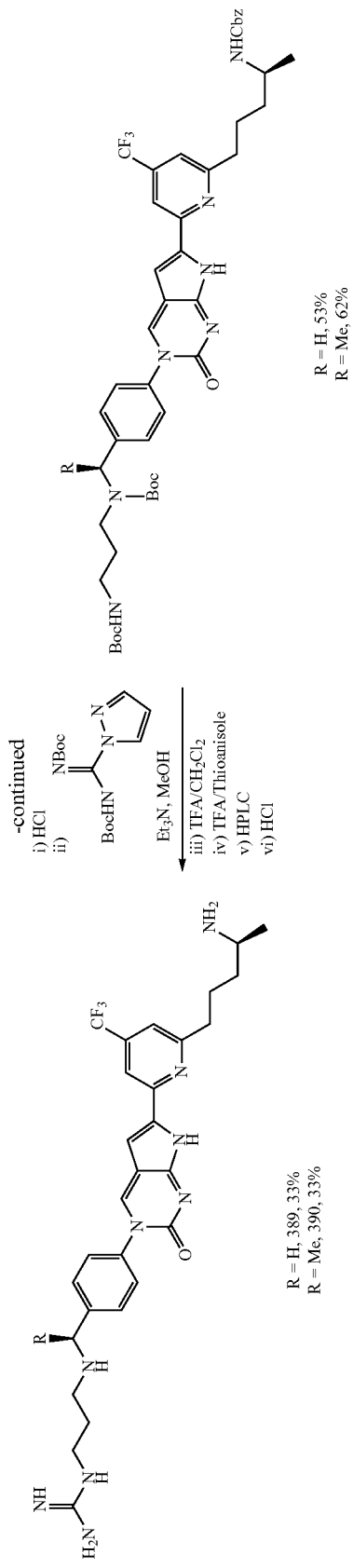

Example 9

Synthesis of Compound 399

Compound 399 was prepared according to the procedure below.

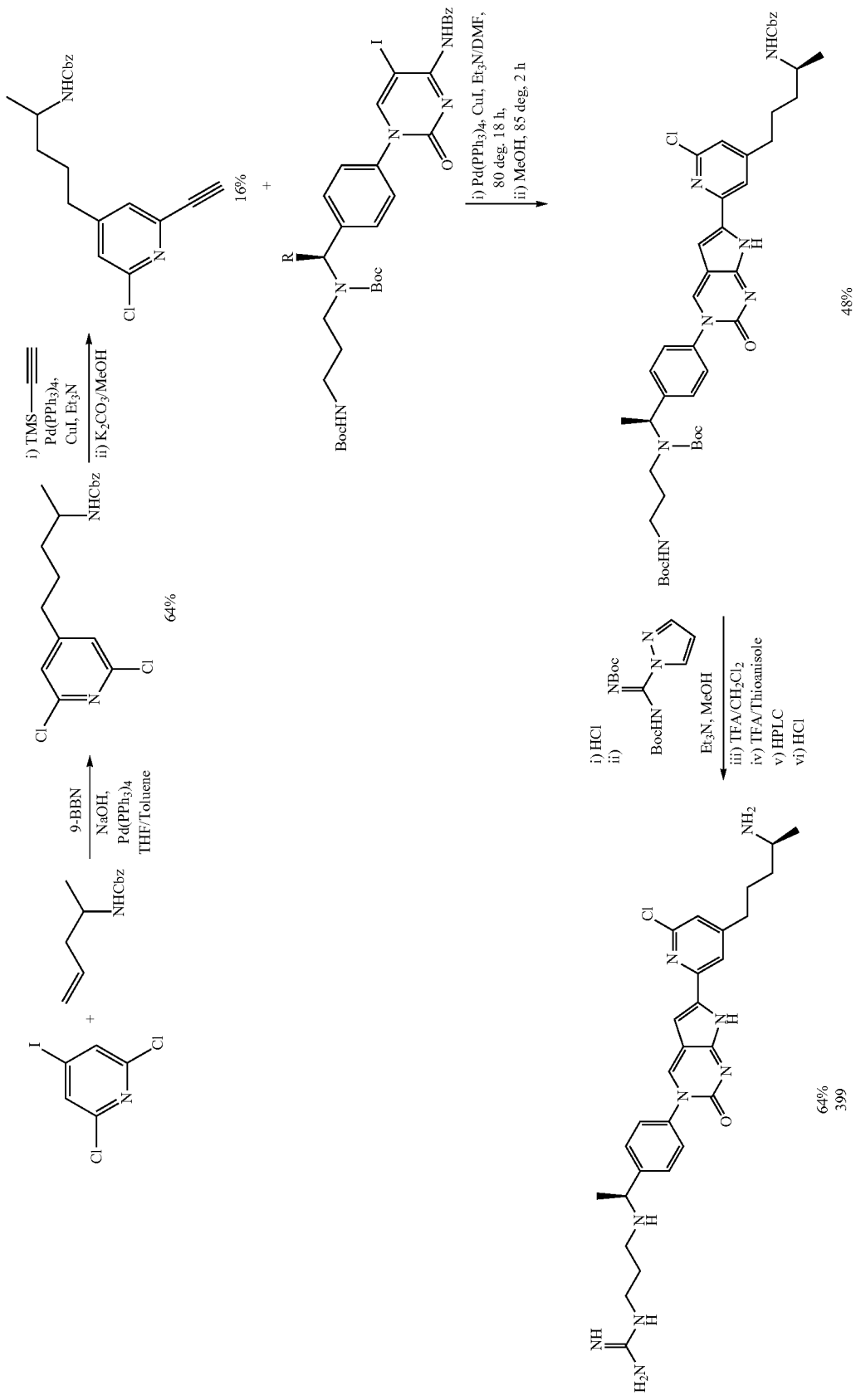

Example 10

Synthesis of Compound 404

Compound 404 was prepared according to the procedure below.

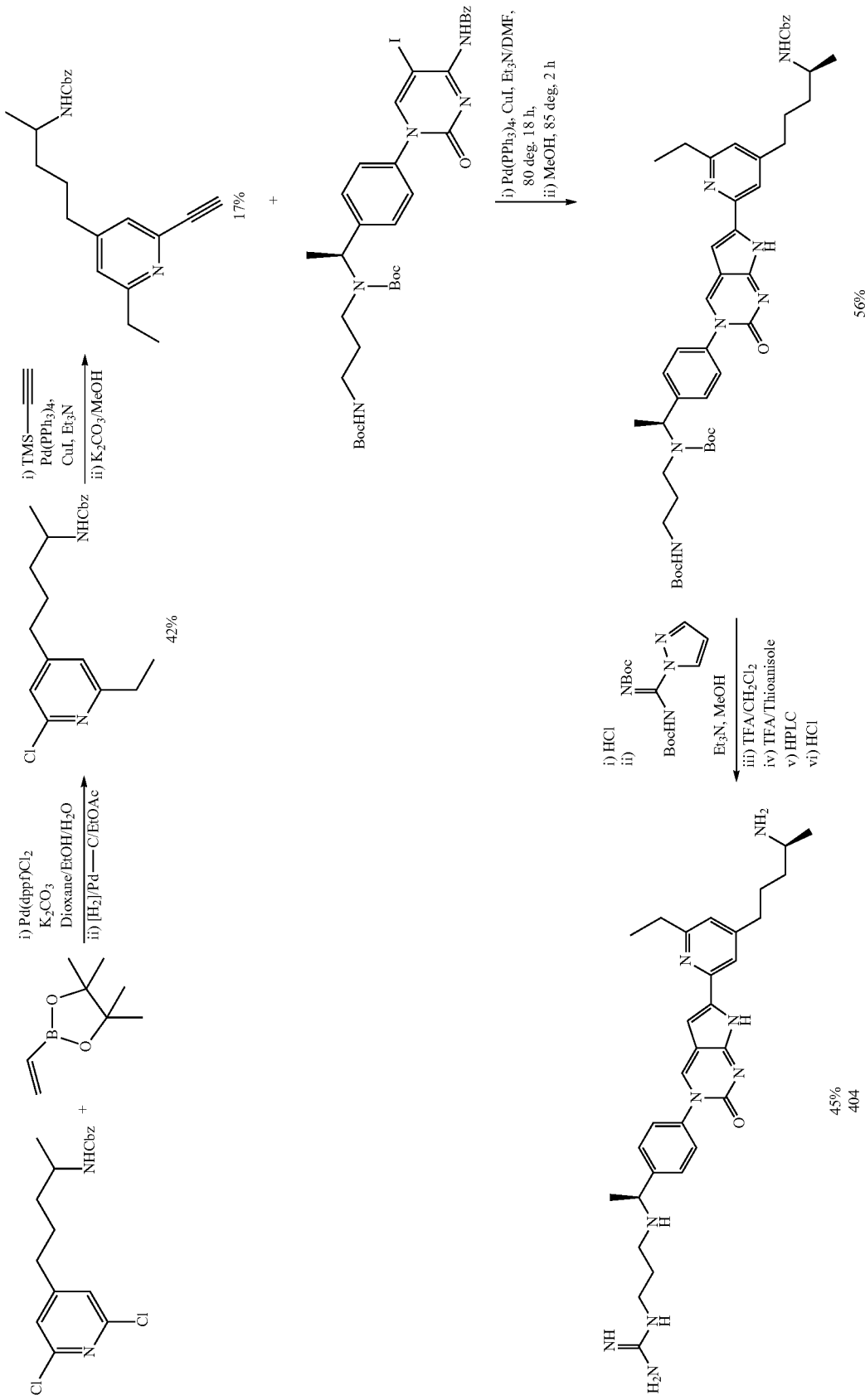

Example 11

Synthesis of Compound 390

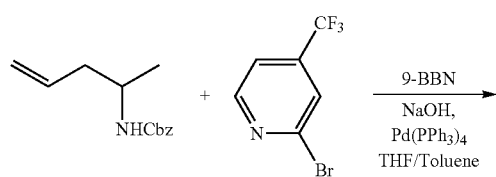

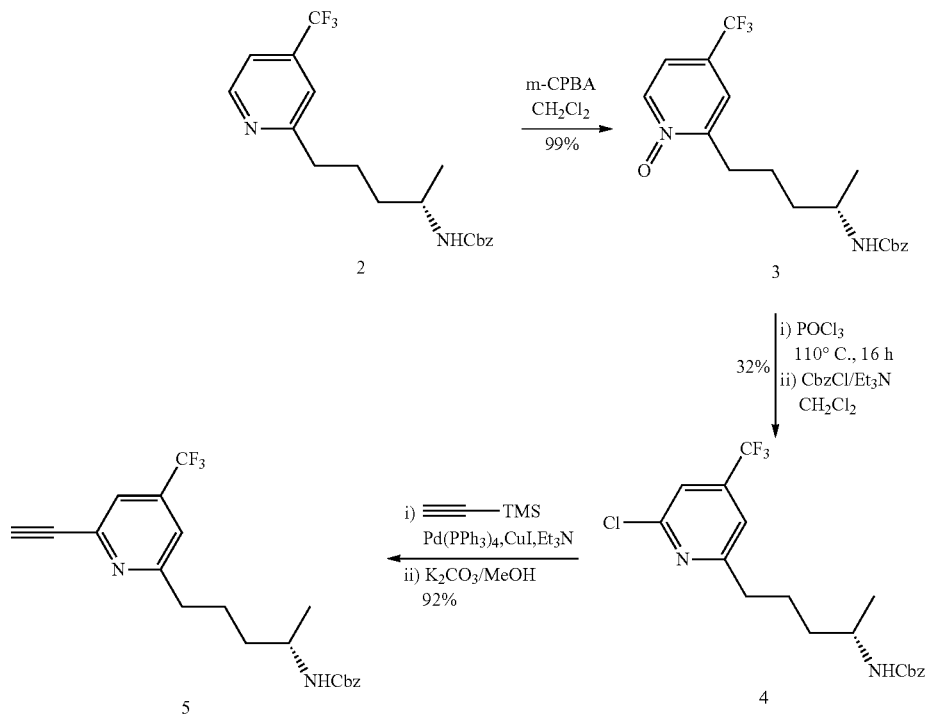

Synthesis of [1-Methyl-4-(4-trifluoromethyl-pyridin-2-yl)-butyl]-carbamic acid benzyl ester (2)

A solution of but-3-enyl-carbamic acid benzyl ester (3.06 g, 14.0 mmol, 1 eq) in anhydrous toluene (40 mL) was cooled under argon to 0-5° C. 9-BBN (0.50 M, solution in THF; 30.8 mL, 1504 mmol, 1.1 eq.) was added dropwise, the mixture was stirred and allowed to reach room temperature. After 24 h, 1N NaOH/H$_2$O (23.8 mL, 23.8 mmol, 1.7 eq.) was added, followed by 2-bromo-4-trifluoromethyl-pyridine (3.16 g, 14.0 mmol, 1 eq.) and toluene (25 mL). The resulting mixture was degassed and Pd(PPh$_3$)$_4$ (0.89 g, 0.70 mmol, 0.05 eq.) was added. The mixture was rapidly stirred under argon at 60° C. for 24 h, and then it was cooled to room temperature. Afterwards, the mixture was partitioned between EtOAc (100 mL) and brine (100 mL). The organic phase was washed with brine (100 mL), dried over Na$_2$SO$_4$, filtered and concentrated. The crude product was purified by flash chromatography on silica gel (0-50% EtOAc in Heptane) to afford 2 as colorless oil (5.1 g, 99%).

Synthesis of [1-methyl-4-(1-oxy-4-trifluoromethyl-pyridin-2-yl)-butyl]-carbamic acid benzyl ester (3)

To a solution of 2 (5.1 g, 13.94 mmol, 1 eq.) in CH$_2$Cl$_2$ (50 ml) was added m-chloroperoxybenzoic acid (2.88 g, 16.72 mmol, 1.2 eq.). The mixture was stirred at room temperature for 18 h before quenching with NaHCO$_3$ (sat. 50 ml). The organic solution was washed with brine (50 mL×2), dried over MgSO$_4$, filtered and concentrated. The crude product was purified by flash chromatography (0-10%, MeOH in CH$_2$Cl$_2$) to afford 3 (5.30 g, 99%).

Synthesis of [4-(6-Chloro-4-trifluoromethyl-pyridin-2-yl)-1-methyl-butyl]-carbamic acid benzyl ester (4)

A solution of 3 (1.52 g, 4.0 mmol) in POCl$_3$ (6 ml) was heated at 110° C. for 15 h before cooling to room temperature.

-continued

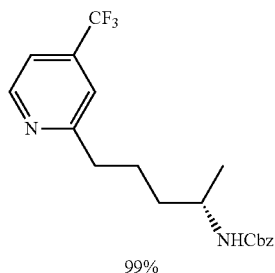

99%

The reaction mixture was quenched with ice, basified with NaOH to pH ca. 10, and extracted with EtOAc (50 mL×2). The EtOAc solution was washed with brine (50 mL×2), dried over MgSO$_4$, filtered and concentrated. The crude product was purified by flash chromatography (0-10%, MeOH in CH$_2$Cl$_2$) to afford the 2-chloropyridine derivative (360 mg). The resulting product was dissolved in CH$_2$Cl$_2$ (10 ml). Hunig's base (520 mg, 4.03 mmol) was added at 0° C. followed by CbzCl (343 mg, 2.02 mmol). The mixture was stirred for 3 h at 0° C., then concentrated and purified by flash chromatography (0-50%, EtOAc in heptane) to afford 4 (470 mg, 32%).

Synthesis of [4-(6-Ethynyl-4-trifluoromethyl-pyridin-2-yl)-1-methyl-butyl]-carbamic acid benzyl ester (5)

A mixture of 4 (470 mg, 1.17 mmol, 1 eq), CuI (23 mg, 0.117 mmol, 0.1 eq.), Pd(PPh$_3$)$_4$ (68 mg, 0.058 mmol, 0.05 eq.) and DMF (8 mL) was degassed. Trimethsilyacetylene (173 mg, 1.760 mmol, 1.5 eq.) was added under Argon, followed by Et$_3$N (356 mg, 4.81 mL, 3.52 mmol, 3 eq.). The mixture was heated at 70° C. for 24 h. After being cooled to room temperature, the reaction mixture was diluted with EtOAc (50 mL) and washed with brine (20 mL×2). The EtOAc solution was dried over MgSO$_4$, filtered and concentrated. The crude product was purified by flash chromatography (0-30%, EtOAc in heptane) to afford the desired trimethsilyacetylene derivative (500 mg, 92%). The product was dissolved in MeOH (20 mL), and K$_2$CO$_3$ (138 mg, 1 mmol) was added. The reaction mixture was stirred at room temperature for 30 min before concentration. The residue was partitioned between EtOAc (20 mL) and H$_2$O (20 mL). The EtOAc layer was washed with brine (10 mL), dried over MgSO$_4$, filtered and concentrated. The crude product was purified by flash chromatography (0-50%, EtOAc in heptane) to afford 5 as colorless oil (423 mg, 100%).

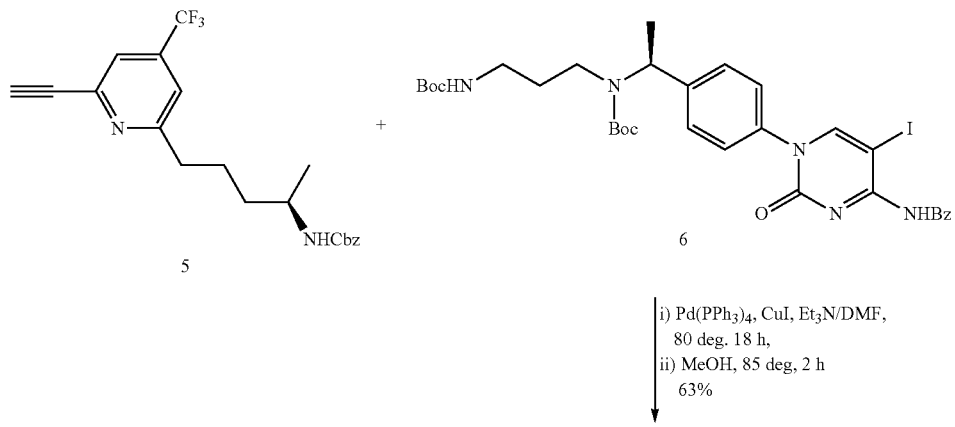

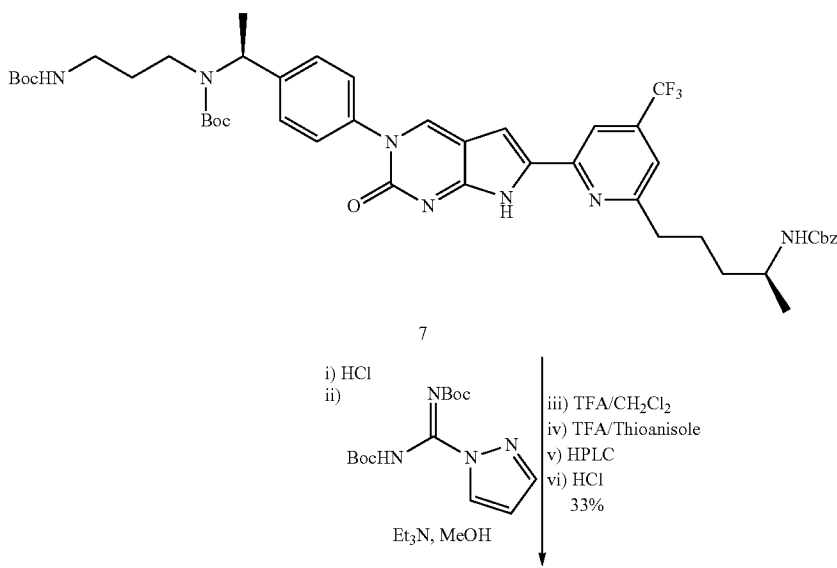

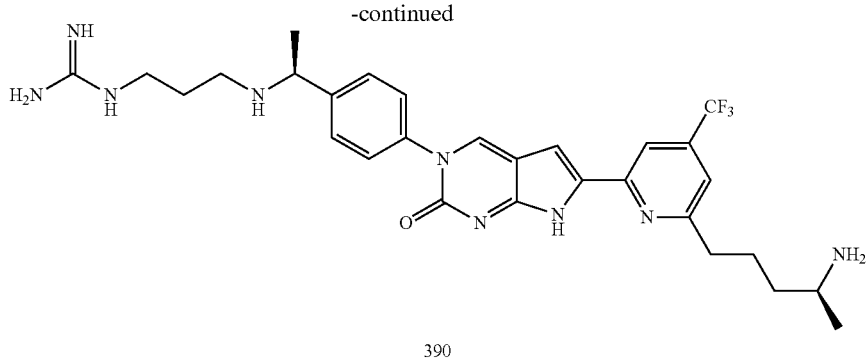

390

Synthesis of 7

Pyrrolocytosine 7 was prepared from the coupling of common intermediate 6 and alkyne 5 according to the procedure described previously. Starting from 230 mg of 5, 320 mg of the desired compound was obtained as an orange-brown solid (62%); LCMS (ESI) m/e 876.2 (M+1)$^+$.

Synthesis of Compound 390

Boc-deprotection of 7 (0.32 g) was accomplished with 2 mL of 4N HCl in dioxane and CH$_2$Cl$_2$ (10 mL) at room temperature (2 h). Following solvent evaporation, the crude residue was taken to the next step without further purification. LCMS (ESI) m/e 613.0 (M+1)$^+$. Guanidine formation was carried out according to the protocol used to prepare the other described compounds (bis-Boc-guanylpyrrazole, Et$_3$N, MeOH, RT). Deprotection was found to work best using a stepwise procedure to first remove the Boc-groups (trifluoroacetic acid in 10 mL of CH$_2$Cl$_2$). Following concentration, the Cbz group was removed by redissolving the yellow-brown solid in 5 mL of trifluoroacetic acid and adding thioanisole (0.1 mL) dropwise. The solution was stirred at rt overnight, and upon completion solvent was evaporated affording the final compound as a brown oil. Diethyl ether was added and the liquid layer containing most of the residual thioanisole was decanted. Crude product was then dissolved in [(20% MeOH-90% H$_2$O)+0.15% TFA] (10 mL). An aliquot (10 mL) was injected on a Dynamax 41.4 mm, C-18 prep HPLC Unit (guard+column), which was eluted with a gradient of solvents of 15%-70% (MeOH/H$_2$O+0.15% TFA), over 45 min. The pure fractions were combined and concentrated with EtOH to dryness. This sample was treated with 1N HCl/H$_2$O (5 mL) and EtOH (10 mL), and concentrated. This operation was repeated; the solid thus obtained was lyophilized from H$_2$O-MeCN (4:1), affording compound 390 as a yellow powder (86 mg); LCMS (ESI) m/e 584.1 (M+1)$^+$; $^1$H NMR (300 MHz, D$_2$O) δ 1.20 (d, J=6.6 Hz, 3H), 1.56 (m, 2H), 1.65 (d, J=6.8 Hz, 3H), 1.85 (m, 2H), 2.87 (m, 1H), 2.89 (t, J=6.9 Hz, 2H), 3.00 (m, 1H), 3.15 (t, J=6.9 Hz, 2H), 3.31 (q, J=6.8 Hz, 1H), 4.47 (q, J=6.6 Hz, 1H), 7.05 (s, 1H), 7.50 (d, J=8.1 Hz, 2H), 7.51 (s, 1H), 7.61 (d, J=8.1 Hz, 2H), 7.94 (s, 1H), 8.51 (s, 1H).

Example 12

Synthesis of Compound 322

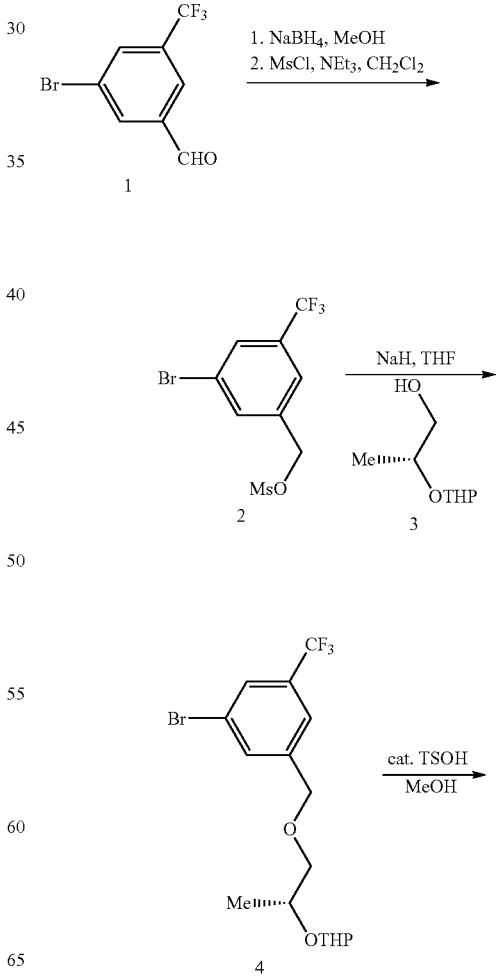

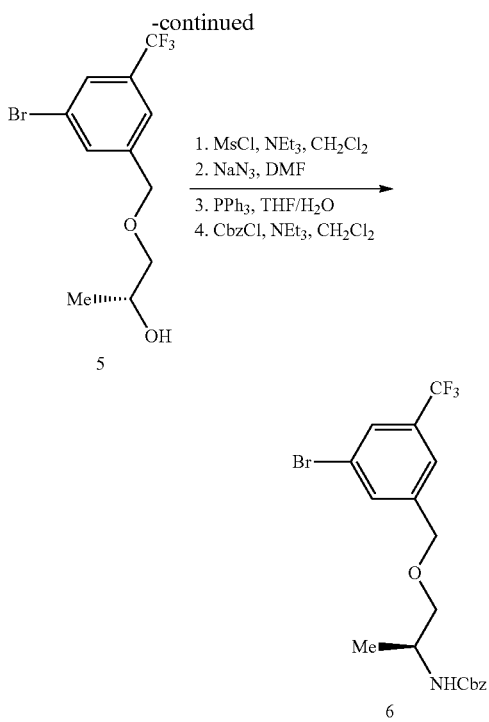

Synthesis of Mesylate 2 from Aldehyde 1

Aldehyde 1 (11.8 g, 46.6 mmol) was dissolved in MeOH (70 mL) and the solution was cooled to 0° C. NaBH$_4$ (2.13 g, 56 mmol) was added slowly as a solid in several portions. After 30 minutes, the mixture was warmed to RT, resulting in the formation of a clear solution. Stirring for an addition 1.5 h at RT led to complete consumption of starting material. MeOH was then evaporated and the residue was partitioned between EtOAc and H$_2$O. The organic layer was collected, dried over MgSO$_4$, and concentrated to a viscous, colorless oil (12.5 g, 99%). This oil was then redissolved in CH$_2$Cl$_2$ at 0° C., and Et$_3$N was added. The dropwise addition of MsCl produced a slightly yellow solution that was allowed to gradually warm to RT. Upon completion, the reaction was quenched with NaHCO$_3$. The organic layer was separated and the aqueous phase was extracted 2× with fresh CH$_2$Cl$_2$. The combined organics were dried over Na$_2$SO$_4$ and concentrated to give an oil (8.10 g, 53%) that was used directly in the next step.

Synthesis of Aryl THP Ether 4

To a flask containing NaH (4.2 g, 105.7 mmol, 60% dispersion in oil) in 20 mL of THF at 0° C. was added THP-protected ether 3 (16.9 g, 105.7 mmol) in 30 mL THF. An additional 20 mL of solvent was added to reduce foaming. After 5 min, the ice bath was removed and the mixture was brought to RT and stirring was continued for 1 h. Mesylate 2 (4.4 g, 13.21 mmol) in 50 mL of THF was then added dropwise at RT and the resulting solution was heated for 1.5 h at 45-50° C. Complete conversion was observed by LCMS, so the reaction was quenched with NH$_4$Cl. EtOAc was added and the phases were separated. The aqueous layer was extracted 2× with fresh EtOAc and the combined organics were dried over MgSO$_4$ and concentrated. The crude material was purified by column chromatography (5-30% EtOAc in heptanes) to provide 2.10 g of product (40%).

Synthesis of Aryl Alcohol 5

THP-protected aryl ether 4 (2.10 g, 5.28 mmol) was dissolved in 35 mL of MeOH and treated with cat. TsOH (0.1 eq). After 5 h at RT, the reaction was complete as indicated by LCMS and TLC. MeOH was removed and the mixture was partitioned between EtOAc and H$_2$O. The organic layer was separated, dried over MgSO$_4$, and concentrated to a slightly yellow-colored oil (1.54 g, 93%). This material was used without further purification.

Synthesis of Cbz-Protected Aryl Amine 6

The same procedure for mesylation was used that was part of the two step conversion starting from aldehyde 1. From 0.86 g (2.73 mmol) of alcohol 5, 1.29 g of crude mesylate was obtained and used directly for azide formation.

This residue (1.29 g) was dissolved in DMF (10 mL) and treated with a single portion of NaN$_3$ (0.6 g. 9.3 mmol). The resulting mixture was then allowed to stir overnight at RT. Upon completion, ether was added and the organic layer was separated. The aqueous phase was washed 3× with additional ether and the organics were combined, washed 4× with H$_2$O, dried over MgSO$_4$, and concentrated. The crude oil (~1 g) was used directly in the next step without purification.

For the reduction to amine, the azide material (~3 mmol) was then dissolved in 10 mL THF along with 1 mL of H$_2$O and triphenylphosphine (1.6 g, 6.0 mmol). The contents were heated from 55-60° C. overnight to obtain complete consumption of starting material. THF was then removed in vacuo.

Cbz-protection was then accomplished by placing the amine in 15 mL of CH$_2$Cl$_2$ and 15 mL of sat. NaHCO$_3$. The solution was cooled to 0° C. prior to the addition of CbzCl (0.64 mL, 4.5 mmol, 1.5 eq). After 4 h at RT, the organic layer was separated. The aqueous phase was washed 2× with fresh CH$_2$Cl$_2$ and the combined organics were dried over Na$_2$SO$_4$ and concentrated. The crude material was purified by column chromatography (3:1 heptanes/EtOAc) to produce 1.2 g of desired compound (97% yield from aryl alcohol 5).

Note: The remainder of the synthesis (i.e. alkyne formation, Sonogashira/cyclization, and guanidine installation) is according the procedures described above for compounds 234 and 248).

Example 13

Antimicrobial Activity

The compounds of the present invention were tested for antimicrobial activity. These data are presented in Table 3, Table 4, Table 5, and Table 6. The compounds were run against *Escherichia coli* strain ATCC25922 using a standard microdilution assay to determine minimum inhibitory concentrations (MICs). The data is presented whereby a "+" indicates that the compound has an MIC value of 16 micrograms/ml or less and a "−" indicates that the compound has an MIC value greater than 16 micrograms/ml. A "N/A" means that data is unavailable. It will be recognized by one skilled in the art that the compounds can be assessed against other bacterial organisms and that the presentation of data for activity against *Escherichia coli* is illustrative and in no way is intended to limit the scope of the present invention. The compounds of the present invention can be assayed against a range of other microorganisms depending upon the performance activity desired to be gathered. Furthermore, the "+", "−", and "N/A" representation and the selection of a cutoff value of 16 micrograms/ml is also illustrative and in no way is intended to limit the scope of the present invention. For example, a "−" is not meant to indicate that the compound necessarily lacks activity or utility, but rather that its MIC value against the indicated microorganism is greater than 16 micrograms/ml.

TABLE 3

| Compound no. | E. coli ATCC25922 MIC |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | − |
| 61 | + |
| 62 | + |
| 63 | + |

TABLE 3-continued

| Compound no. | E. coli ATCC25922 MIC |
|---|---|
| 64 | + |
| 65 | + |
| 66 | − |
| 67 | + |
| 68 | + |
| 69 | + |
| 70 | + |
| 71 | + |
| 72 | + |
| 73 | + |
| 74 | + |
| 75 | + |
| 76 | + |
| 77 | + |
| 78 | + |
| 79 | + |
| 80 | + |
| 81 | + |
| 82 | + |
| 83 | + |
| 84 | + |
| 85 | + |
| 86 | + |
| 87 | + |
| 88 | + |
| 89 | + |
| 90 | + |
| 91 | + |
| 92 | + |
| 93 | + |
| 94 | + |
| 95 | + |
| 96 | + |
| 97 | + |
| 98 | + |
| 99 | + |
| 100 | + |
| 101 | + |
| 102 | + |
| 103 | + |
| 104 | + |
| 105 | + |
| 106 | + |
| 107 | + |
| 108 | + |
| 109 | + |
| 110 | + |
| 111 | + |
| 112 | + |
| 113 | + |
| 114 | + |
| 115 | + |
| 116 | + |
| 117 | + |
| 118 | + |
| 119 | + |
| 120 | + |
| 121 | + |
| 122 | + |
| 123 | + |
| 124 | + |
| 125 | + |
| 126 | + |
| 127 | + |
| 128 | + |
| 129 | + |
| 130 | + |
| 131 | + |
| 132 | + |
| 133 | + |
| 134 | + |
| 135 | + |
| 136 | + |
| 137 | + |
| 138 | + |
| 139 | + |

TABLE 3-continued

| Compound no. | E. coli ATCC25922 MIC |
|---|---|
| 140 | + |
| 212 | + |
| 213 | + |
| 214 | + |
| 215 | + |
| 216 | + |
| 217 | + |
| 218 | + |
| 219 | + |
| 220 | + |
| 221 | + |
| 222 | + |
| 223 | + |
| 224 | + |
| 225 | + |
| 226 | + |
| 227 | + |
| 228 | + |
| 229 | + |
| 230 | + |
| 231 | + |
| 232 | + |
| 233 | + |
| 234 | + |
| 235 | + |
| 236 | + |
| 237 | + |
| 238 | + |
| 239 | + |
| 240 | + |
| 241 | + |
| 242 | + |
| 243 | + |
| 244 | + |
| 245 | + |
| 246 | + |
| 247 | + |
| 248 | + |
| 249 | + |
| 250 | + |
| 251 | + |
| 252 | + |
| 253 | + |
| 254 | + |
| 255 | + |
| 256 | + |
| 257 | + |
| 258 | + |
| 259 | + |
| 260 | + |
| 261 | + |
| 262 | + |
| 263 | + |
| 264 | + |
| 265 | + |
| 266 | + |
| 267 | + |
| 268 | + |
| 269 | + |
| 270 | + |
| 271 | + |
| 272 | + |
| 273 | + |
| 274 | + |
| 275 | + |
| 276 | + |
| 277 | + |
| 278 | + |
| 279 | + |
| 280 | + |
| 281 | + |
| 282 | + |
| 283 | + |
| 284 | + |
| 285 | + |
| 286 | + |
| 287 | + |
| 288 | + |
| 289 | + |
| 290 | + |
| 291 | + |
| 292 | + |
| 293 | + |
| 294 | + |
| 295 | + |
| 296 | + |
| 297 | + |
| 298 | + |
| 299 | + |
| 300 | + |
| 301 | + |
| 302 | + |
| 303 | + |
| 304 | + |
| 305 | + |
| 306 | + |
| 307 | + |
| 308 | + |
| 309 | + |
| 310 | + |
| 311 | + |
| 312 | + |
| 313 | + |
| 314 | + |
| 315 | + |
| 316 | + |
| 317 | + |
| 318 | + |
| 319 | + |
| 320 | + |
| 321 | + |
| 322 | + |
| 323 | + |
| 324 | + |
| 325 | + |
| 326 | + |
| 327 | + |

TABLE 4

| Compound no. | E. coli ATCC25922 MIC |
|---|---|
| 150 | − |
| 151 | + |
| 152 | + |
| 153 | + |
| 154 | + |
| 155 | + |
| 156 | + |
| 157 | + |
| 158 | + |
| 159 | + |
| 160 | + |
| 161 | + |
| 162 | + |
| 163 | + |
| 164 | + |
| 165 | − |
| 166 | + |
| 167 | + |
| 168 | + |
| 169 | + |
| 170 | + |
| 171 | + |
| 172 | + |
| 173 | + |
| 174 | + |

TABLE 4-continued

| Compound no. | E. coli ATCC25922 MIC |
|---|---|
| 175 | + |
| 176 | + |
| 177 | − |
| 178 | + |
| 179 | + |
| 180 | + |
| 181 | + |
| 182 | + |
| 183 | − |
| 184 | + |
| 185 | − |
| 186 | − |
| 187 | − |
| 188 | + |
| 189 | − |
| 190 | − |

TABLE 5

| Compound no. | E. coli ATCC25922 MIC |
|---|---|
| 333 | + |
| 334 | + |
| 335 | + |
| 336 | + |
| 337 | + |
| 338 | + |
| 339 | + |
| 340 | + |
| 341 | + |
| 342 | + |
| 343 | + |
| 344 | + |
| 345 | + |
| 346 | + |
| 347 | + |
| 348 | + |
| 349 | + |
| 350 | + |
| 351 | − |
| 352 | − |
| 353 | − |
| 354 | − |
| 355 | − |
| 356 | − |
| 357 | − |
| 358 | − |
| 359 | + |
| 360 | + |
| 361 | + |
| 362 | + |
| 363 | + |
| 364 | + |
| 365 | − |
| 366 | − |
| 367 | − |
| 368 | + |
| 369 | + |
| 370 | + |
| 371 | − |
| 372 | − |
| 373 | − |
| 374 | + |
| 375 | + |
| 376 | + |
| 377 | + |
| 378 | + |
| 379 | + |
| 380 | + |
| 381 | + |
| 382 | + |

TABLE 5-continued

| Compound no. | E. coli ATCC25922 MIC |
|---|---|
| 383 | + |
| 384 | + |
| 385 | + |
| 386 | − |
| 387 | + |
| 388 | + |
| 389 | + |
| 390 | + |
| 391 | + |
| 392 | + |
| 393 | + |
| 394 | + |
| 395 | + |
| 396 | + |
| 397 | + |
| 398 | + |
| 399 | + |
| 400 | + |
| 401 | + |
| 402 | + |
| 403 | + |
| 404 | + |
| 405 | − |
| 406 | − |
| 407 | + |
| 408 | + |
| 409 | − |
| 410 | + |
| 411 | + |
| 412 | + |
| 413 | + |
| 414 | + |
| 415 | + |
| 416 | + |
| 417 | + |
| 418 | + |
| 419 | + |
| 420 | + |
| 421 | + |
| 522 | + |
| 423 | + |
| 424 | + |
| 425 | + |
| 426 | + |
| 427 | + |
| 428 | + |
| 429 | + |
| 430 | + |
| 431 | + |
| 432 | + |
| 433 | + |
| 434 | + |
| 435 | + |
| 436 | + |
| 437 | + |
| 438 | + |
| 439 | + |
| 440 | + |
| 441 | + |
| 442 | + |
| 443 | + |
| 444 | + |
| 445 | + |
| 446 | + |
| 447 | + |
| 448 | + |
| 449 | + |
| 450 | + |
| 451 | + |
| 452 | + |
| 453 | + |
| 454 | + |
| 455 | + |
| 456 | + |
| 457 | + |
| 458 | + |

TABLE 5-continued

| Compound no. | E. coli ATCC25922 MIC |
|---|---|
| 459 | + |
| 460 | + |
| 461 | + |
| 462 | + |
| 463 | + |
| 464 | + |
| 465 | + |
| 466 | + |
| 467 | + |
| 468 | + |

TABLE 6

| Compound no. | E. coli ATCC25922 MIC |
|---|---|
| 469 | + |
| 470 | + |
| 471 | + |
| 472 | + |
| 473 | + |
| 474 | + |
| 475 | + |
| 476 | + |
| 477 | + |
| 478 | + |
| 479 | + |
| 480 | + |
| 481 | + |
| 482 | + |
| 483 | + |
| 484 | + |
| 485 | + |
| 486 | + |
| 487 | + |
| 488 | + |
| 489 | + |
| 490 | − |
| 491 | + |
| 492 | − |
| 493 | + |
| 494 | + |
| 495 | + |
| 496 | + |
| 497 | − |
| 498 | + |
| 499 | + |
| 500 | + |
| 501 | + |
| 502 | + |
| 503 | − |
| 504 | + |
| 505 | + |
| 506 | + |
| 507 | + |

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:
1. A compound having the formula:

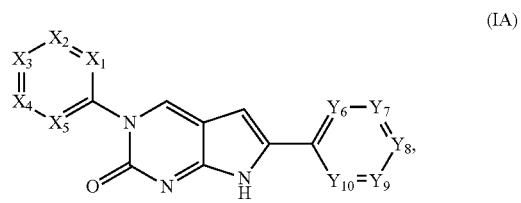

(IA)

or a tautomer thereof, or a pharmaceutically acceptable salt, ester, or prodrug of said compound or tautomer, wherein
$X_1$ is $CR^1$ or N; $X_2$ is $CR^2$ or N; $X_3$ is $CR^3$ or N; $X_4$ is $CR^4$ or N; $X_5$ is $CR^5$ or N; with the proviso that $X_1$, $X_2$, $X_3$, $X_4$, and $X_5$ are not all N;
$Y_6$ is $CR^6$ or N; $Y_7$ is $CR^7$ or N; $Y_8$ is $CR^8$ or N; $Y_9$ is $CR^9$ or N; $Y_{10}$ is $CR^{10}$ or N; with the proviso that $Y_6$, $Y_7$, $Y_8$, $Y_9$, and $Y_{10}$ are not all N; wherein
$R^1$, $R^2$, $R^4$, $R^5$, $R^6$, $R^7$, $R^8$ and $R^{10}$ are each independently selected from (a) hydrogen, (b) F, (c) Cl, (d) Br, (e) I, (f) —$CF_3$, (g) —$CF_2H$, (h) —$CFH_2$, (i) —$OCF_3$, (j) —$OCF_2H$, (k) —$OCFH_2$, (l) —$OCH_3$, (m) —CN, (n) —$N_3$, (o) —$NO_2$, (p) —$NR^{11}R^{11}$, (q) —$NR^{11}C(O)R^{11}$, (r) —$C(O)NR^{11}R^{11}$, (s) —$OR^{11}$, (t) —COH, (u) —CO($C_1$-$C_8$ alkyl), (v) —$COR^{11}$, (w) —$NR^{11}(CNR^{11})NR^{11}R^{11}$, (x) —$S(O)_pR^{11}$, (y) —$NR^{11}S(O)_pR^{11}$, (z) —$SR^{11}$, (aa) —$SCF_3$, (bb) —$C(CF_3)H$—NH—$CHR^{11}R^{11}$, (cc) —$COOR^{11}$, (dd) —$(OCH_2CH_2)_xR^{11}$, (ee) —$(OCH_2CH_2)_xOR^{11}$, (ff) —$C_1$-$C_8$ alkyl, (gg) —$C_2$-$C_8$ alkenyl, (hh) —$C_2$-$C_8$ alkynyl, (ii) —($C_1$-$C_8$ alkyl)-(3-14 membered saturated, unsaturated, or aromatic heterocycle containing one or more heteroatoms selected from the group consisting of nitrogen, oxygen, and sulfur), (jj) —($C_1$-$C_8$ alkyl)-(3-14 membered saturated, unsaturated, or aromatic carbocycle), (kk) -haloalkyl, (ll) -3-14 membered saturated, unsaturated, or aromatic heterocycle containing one or more heteroatoms selected from the group consisting of nitrogen, oxygen, and sulfur, (mm) -3-14 membered saturated, unsaturated, or aromatic carbocycle, and (nn) —$CHR^{11}$—NH-(3-14 membered saturated, unsaturated, or aromatic heterocycle containing one of more heteroatoms selected from the group consisting of nitrogen, oxygen, and sulfur);
wherein each (ff) through (nn) is optionally substituted with one or more $R^{12}$;
alternatively, wherein two substituents selected from $R^6$, $R^7$, and $R^8$ are taken together with the carbon atom to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur; wherein each (a) through (b) is optionally substituted with one or more $R^{12}$;
each $R^{11}$ is independently selected from (a) hydrogen, (b) halogen, (c) —OH, (d) —SH, (e) —($C_1$-$C_8$ alkyl)OH, (f) —$OCF_3$, (g) —$OCF_2H$, (h) —$OCFH_2$, (i) —$OCH_3$, (j) —$OR^{12}$, (k) —$COR^{12}$, (l) —CN, (m) —$NO_2$, (n) —$CONH_2$, (o) —$CONR^{12}R^{12}$, (p) —$COCH_3$, (q) —$S(O)_pCH_3$, (r) —$S(O)_pNR^{12}R^{12}$, (s) —$SR^{12}$, (t)

—C(O)OH, (u) —C(O)OR$^{12}$, (v) —N$_3$, (w) —NH$_2$, (x) —NR$^{12}$C(O)R$^{12}$, (y) —NH(C$_1$-C$_8$ alkyl), (z) —N(C$_1$-C$_8$ alkyl)$_2$, (aa) —C$_1$-C$_8$ alkyl, (bb) —C$_2$-C$_8$ alkenyl, (cc) —C$_2$-C$_8$ alkynyl, (dd) -haloalkyl, (ee) —(C$_1$-C$_8$ alkyl)-(3-14 membered saturated, unsaturated, or aromatic heterocycle containing one or more heteroatoms selected from the group consisting of nitrogen, oxygen, and sulfur), (ff) —(C$_1$-C$_8$ alkyl)-(3-14 membered saturated, unsaturated, or aromatic carbocycle), (gg) —3-14 membered saturated, unsaturated, or aromatic heterocycle containing one or more heteroatoms selected from the group consisting of nitrogen, oxygen, and sulfur, (hh) —3-14 membered saturated, unsaturated, or aromatic carbocycle, and (ii) —(C=NH)NR$^{12}$R$^{12}$;

wherein each (y) through (hh) is optionally substituted with one or more R$^{12}$;

alternatively two R$^{11}$ substituents are taken together to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur, wherein each (a) through (b) is optionally substituted with one or more R$^{12}$;

R$^3$ is selected from:

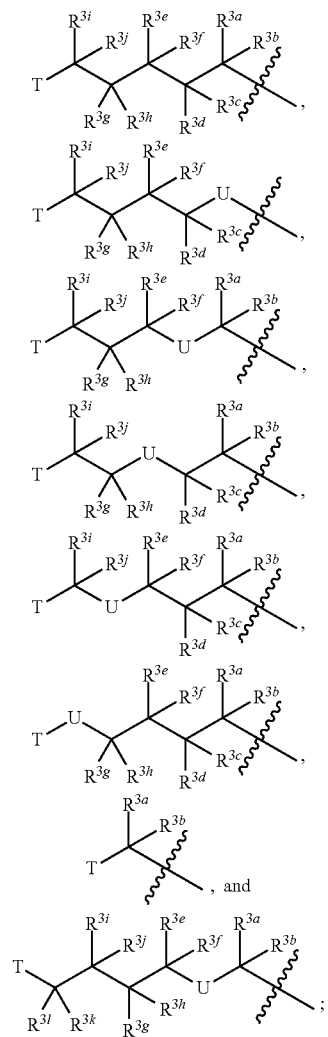

wherein R$^{3a}$, R$^{3b}$, R$^{3c}$, R$^{3d}$, R$^{3e}$, R$^{3f}$, R$^{3g}$, R$^{3h}$, R$^{3i}$, R$^{3j}$, R$^{3k}$, and R$^{3l}$ are each independently selected from (a) hydrogen, (b) halogen, (c) —CN, (d) —N$_3$, (e) —NO$_2$, (f) —OCF$_3$, (g) —OCF$_2$H, (h) —OCFH$_2$, (i) —OCH$_3$, (j) —OR$^{11}$, (k) —C(O)R$^{11}$, (l) —C(O)NR$^{11}$R$^{11}$, (m) —NH$_2$, (n) —NR$^{11}$R$^{11}$, (o) —NR$^{11}$C(O)R$^{11}$, (p) —S(O)$_p$R$^{11}$, (q) —C(O)OH, (r) —C(O)OR$^{11}$, (s) —C$_1$-C$_8$ alkyl, (t) —C$_2$-C$_8$ alkenyl, (u) —C$_2$-C$_8$ alkynyl, (v) haloalkyl, (w) -3-14 membered saturated, unsaturated, or aromatic heterocycle containing one or more heteroatoms selected from the group consisting of nitrogen, oxygen, and sulfur, and (x) -3-14 membered saturated, unsaturated, or aromatic carbocycle;

wherein each (s) through (x) is optionally substituted with one or more R$^{12}$;

alternatively, one or more pairs of substituents selected from R$^{3a}$ and R$^{3b}$, R$^{3c}$ and R$^{3d}$, R$^{3e}$ and R$^{3f}$, R$^{3g}$ and R$^{3h}$, R$^{3i}$ and R$^{3j}$, and R$^{3k}$ and R$^{3l}$ are taken together with the carbon atom to which they are attached to form (a) -3-7 membered saturated or unsaturated carbocyclic, (b) -3-7 membered saturated or unsaturated heterocyclic ring containing one or more heteroatoms selected from the group consisting of nitrogen, oxygen, and sulfur, (c) an exo carbon-carbon double bond, (d) carbonyl group, or (e) thiocarbonyl group;

wherein each (a) through (b) is optionally substituted with one or more R$^{12}$;

alternatively, wherein two substituents selected from R$^{3a}$, R$^{3b}$, R$^{3c}$, R$^{3d}$, R$^{3e}$, R$^{3f}$, R$^{3g}$, R$^{3h}$, R$^{3i}$, R$^{3j}$, R$^{3k}$, and R$^{3l}$ on different carbon atoms are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more R$^{12}$;

alternatively, wherein two substituents selected from R$^{3a}$, R$^{3b}$, R$^{3c}$, R$^{3d}$, R$^{3e}$, R$^{3f}$, R$^{3g}$, R$^{3h}$, R$^{3i}$, R$^{3j}$, R$^{3k}$, and R$^{3l}$ on two adjacent carbon atoms are taken together with the bond between said adjacent carbon atoms to form a substituted or unsubstituted carbon-carbon double bond, or wherein four substituents selected from R$^{3a}$, R$^{3b}$, R$^{3c}$, R$^{3d}$, R$^{3e}$, R$^{3f}$, R$^{3g}$, R$^{3h}$, R$^{3i}$, R$^{3j}$, R$^{3k}$, and R$^{3l}$ on two adjacent carbon atoms are taken together with the bond between said adjacent carbon atoms to form a carbon-carbon triple bond;

U is selected from —O—, —S(O)$_p$—, —NR$^{11}$—, —(C=O)—, —NR$^{11}$(C=O)—, —(C=O)NR$^{11}$—, —S(O)$_p$NR$^{11}$—, —NR$^{11}$S(O)$_p$—, —NR$^{11}$S(O)$_p$NR$^{11}$—, and —NR$^{11}$C(O)NR$^{11}$—;

T is selected from —NR$^{11}$R$^{11}$, —NR$^{11}$(C=O)OR$^{11}$, —NR$^{11}$(C=NR$^{11}$)NR$^{11}$R$^{11}$, and OR$^{11}$;

alternatively, one R$^{11}$ and one substituent selected from R$^{3a}$, R$^{3b}$, R$^{3c}$, R$^{3d}$, R$^{3e}$, R$^{3f}$, R$^{3g}$, R$^{3h}$, R$^{3i}$, R$^{3j}$, R$^{3k}$, and R$^{3l}$ are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more R$^{12}$;

$R^9$ is selected from:

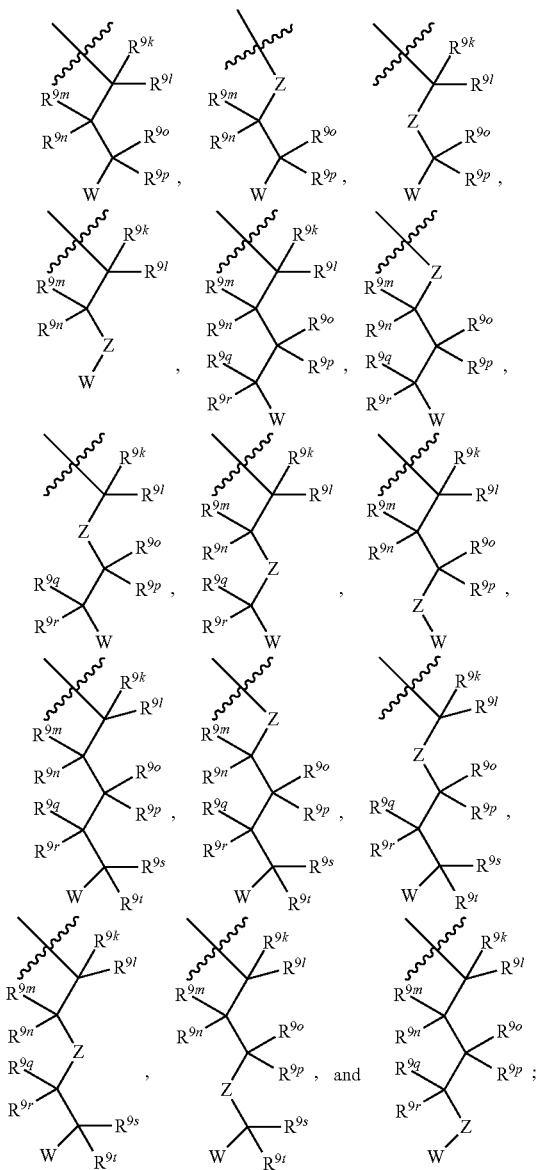

wherein $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are each independently selected from (a) hydrogen, (b) halogen, (c) —CN, (d) —$N_3$, (e) —$NO_2$, (f) —$OCF_3$, (g) —$OCH_3$, (h) —$OCF_2H$, (i) —$OCFH_2$, (j) —$OR^{11}$, (k) —$NH_2$, (l) —$NR^{11}R^{11}$, (m) —$C(O)R^{11}$, (n) —$C(O)OR^{11}$, (o) —$C(O)NR^{11}R^{11}$, (p) —$NR^{11}C(O)R^{11}$, (q) —$S(O)_pR^{11}$, (r) —$C_1$-$C_8$ alkyl, (s) —$C_2$-$C_8$ alkenyl, (t) —$C_1$-$C_8$ alkynyl, (u) haloalkyl, (v) -3-14 membered saturated, unsaturated, or aromatic heterocycle containing one or more heteroatoms selected from the group consisting of nitrogen, oxygen, and sulfur, and (w) -3-14 membered saturated, unsaturated, or aromatic carbocycle;

wherein each (r) through (w) is optionally substituted with one or more $R^{12}$;

alternatively, one or more pairs of substituents selected from $R^{9k}$ and $R^{9l}$, $R^{9m}$ and $R^{9n}$, $R^{9o}$ and $R^{9p}$, $R^{9q}$ and $R^{9r}$, and $R^{9s}$ and $R^{9t}$ are taken together with the carbon atom to which they are attached to form (a) 3-7 membered saturated or unsaturated carbocyclic, (b) 3-7 membered saturated or unsaturated heterocyclic ring containing one or more heteroatoms selected from the group consisting of nitrogen, oxygen, and sulfur, (c) an exo carbon-carbon double bond, (d) carbonyl group, or (e) thiocarbonyl group;

wherein each (a) through (c) is optionally substituted with one or more $R^{12}$;

alternatively, two substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on different carbon atoms are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

alternatively, two substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on two adjacent carbon atoms are taken together with the bond between said adjacent carbon atoms form a substituted or unsubstituted carbon-carbon double bond, or four substituents selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ on two adjacent carbon atoms are taken together with the bond between said adjacent carbon atoms form a carbon-carbon triple bond;

Z is selected from —O—, —$S(O)_p$—, —$NR^{11}$—, —(C=O)—, —$NR^{11}(C=O)$—, —(C=O)$NR^{11}$—, —$S(O)_pNR^{11}$—, —$NR^{11}S(O)_p$—, —$NR^{11}S(O)_pNR^{11}$—, and —$NR^{11}C(O)NR^{11}$—;

W is selected from —$NR^{11}R^{11}$, —$NR^{11}(CO)OR^{11}$, —$NR^{11}(C=NR^{11})NR^{11}R^{11}$, and —$OR^{11}$;

alternatively, one $R^{11}$ and one substituent selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are taken together with the intervening atoms to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur;

wherein each (a) through (b) is optionally substituted with one or more $R^{12}$;

$R^{12}$ is independently selected from (a) hydrogen, (b) halogen, (c) —OH, (d) —SH, (e) —($C_1$-$C_8$ alkyl)OH, (f) —$OCF_3$, (g) —$OCH_3$, (h) —$OCF_2H$, (i) —$OCFH_2$, (j) —$O(C_1$-$C_8$ alkyl), (k) —CN, (l) —$NO_2$, (m) —$CONH_2$, (n) $C(O)NH(C_1$-$C_8$ alkyl), (o) $C(O)N(C_1$-$C_8$ alkyl)$_2$, (p) —COH, (q) —$COCH_3$, (r) —$S(O)_pCH_3$, (s) —$S(O)_pN(C_1$-$C_8$ alkyl)$_2$, (t) —$S(C_1$-$C_8$ alkyl), (u) —C(O)OH, (v) —C(O)O($C_1$-$C_8$ alkyl), (w) —$N_3$, (x) —NHC(O)($C_1$-$C_8$ alkyl), (y) —N($C_1$-$C_8$ alkyl)C(O)($C_1$-$C_8$ alkyl), (z) —$NH_2$, (aa) —NH($C_1$-$C_8$ alkyl), (bb) —N($C_1$-$C_8$ alkyl)$_2$, (cc) —$C_1$-$C_8$ alkyl, (dd) —$C_2$-$C_8$ alkenyl, (ee) —$C_2$-$C_8$ alkynyl, (ff) -haloalkyl, (gg) —($C_1$-$C_8$ alkyl)-(3-14 membered saturated, unsaturated, or aromatic heterocycle containing one or more heteroatoms selected from the group consisting of nitrogen, oxygen, and sulfur), (hh) —($C_1$-$C_8$ alkyl)-(3-14 membered saturated, unsaturated, or aromatic carbocycle), (ii) -3-14 membered saturated, unsaturated, or aromatic heterocycle containing one or more heteroatoms selected from the group consisting of nitrogen, oxygen, and sulfur, (jj) -3-14 membered saturated, unsaturated, or aromatic carbocycle, (kk) —(C=NH)$NH_2$, (ll) —C(=NH)$NH_2$, (mm) —$C(O)R^{13}$, (nn) =O, and (oo) =$NR^{13}$;

wherein each (aa) through (jj) is optionally substituted with one or more R[13];

R[13] is independently selected from (a) hydrogen, (b) halogen, (c) —$C_1$-$C_8$ alkyl, (d) —$C_2$-$C_8$ alkenyl, (e) —$C_2$-$C_8$ alkynyl, (f) -haloalkyl, (g) —OH, (h) —$OC_1$-$C_8$ alkyl, (i) —$OC_2$-$C_8$ alkenyl, (j) —$OC_2$-$C_8$ alkynyl, (k) —$OCF_3$, (l) —$OCH_3$, (m) —$OCF_2H$, (n) —$OCFH_2$, (o) —$NH_2$, (p) —CN, (q) —$N_3$, (r) —$S(O)_pC_1$-$C_8$ alkyl, (s) -3-14 membered saturated, unsaturated, or aromatic heterocycle containing one or more heteroatoms selected from the group consisting of nitrogen, oxygen, and sulfur, and (t) -3-14 membered saturated, unsaturated, or aromatic carbocycle;

p is 0, 1, or 2; and t is 0, 1, or 2.

2. The compound according to claim 1 having the formula:

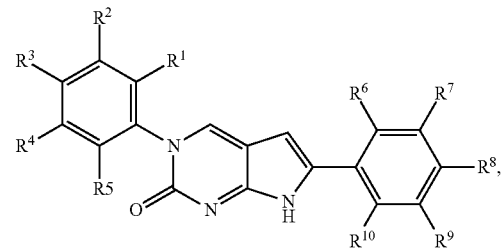

(III)

or a tautomer thereof, or a pharmaceutically acceptable salt, ester, or prodrug of said compound or tautomer.

3. The compound according to claim 2 having the formula:

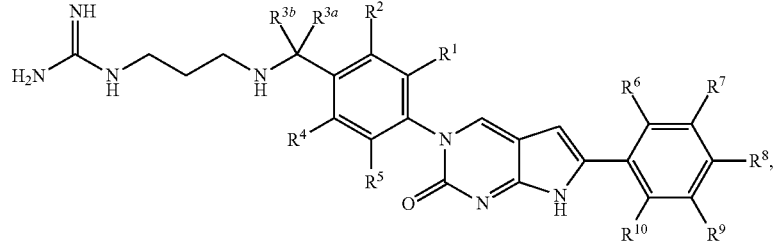

(IV)

or a tautomer thereof, or a pharmaceutically acceptable salt, ester, or prodrug of said compound or tautomer.

4. The compound according to claim 3 having a formula selected from:

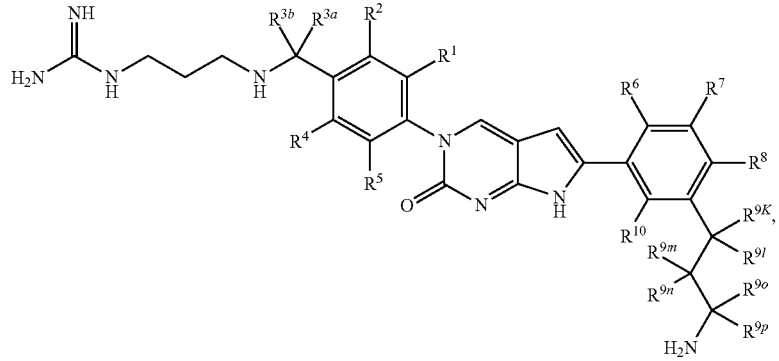

(V)

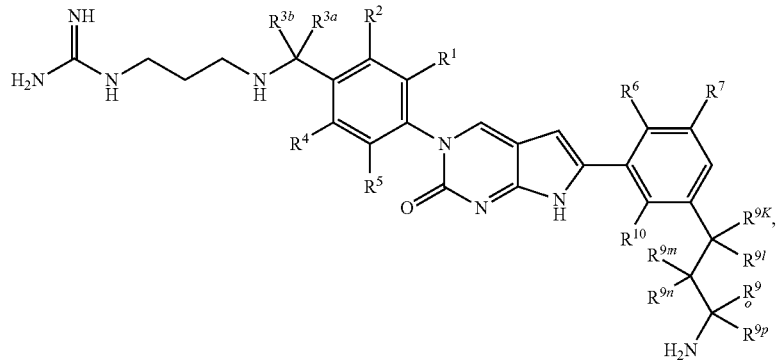

(VI)

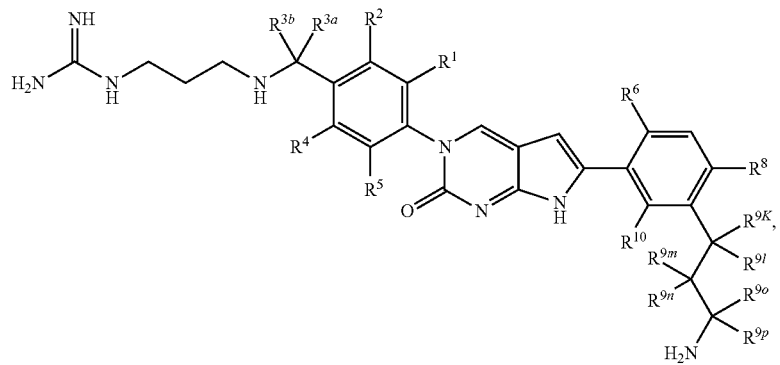
(VII)
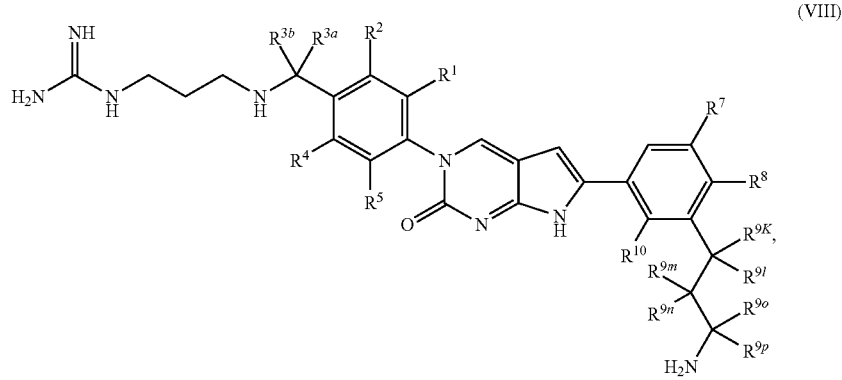
(VIII)
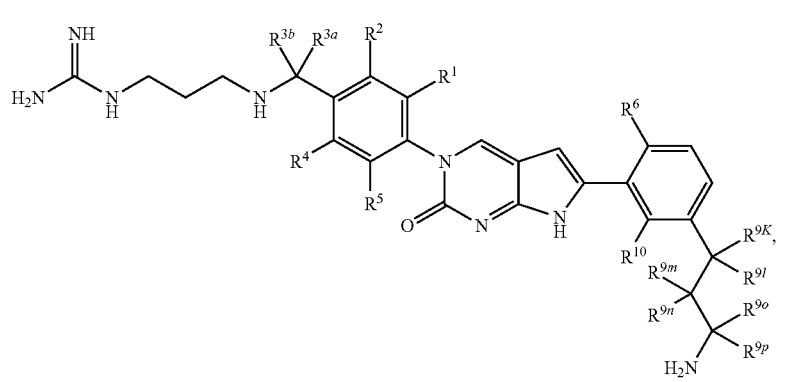
(IX)
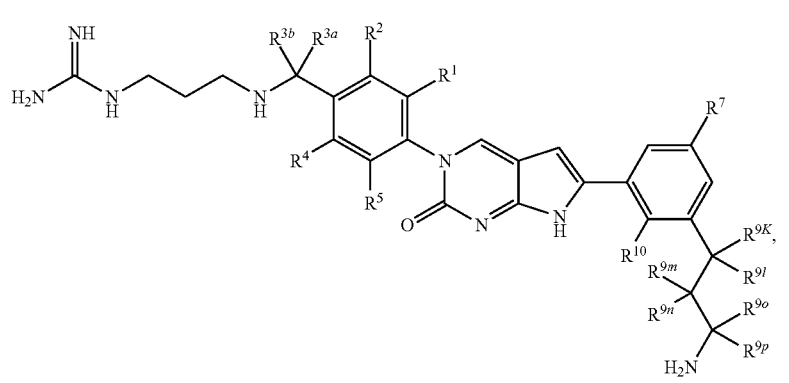
(X)

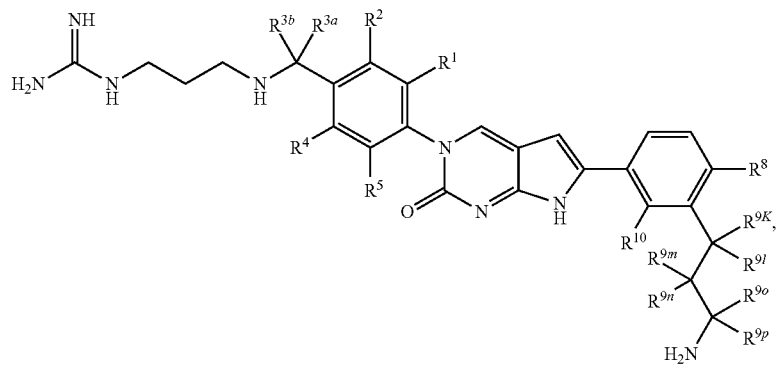
(XI)
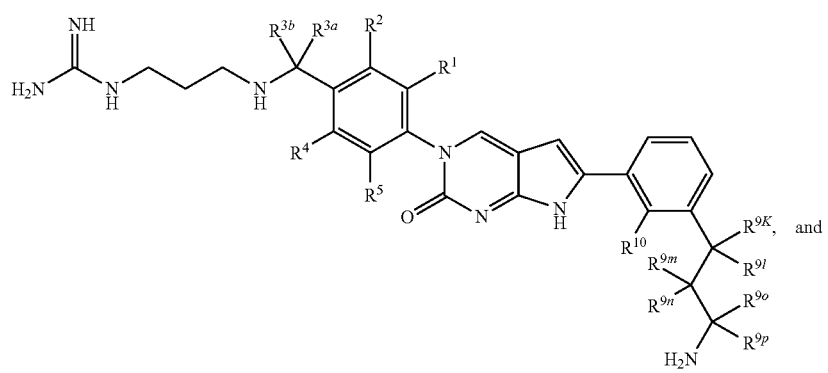
(XXa)
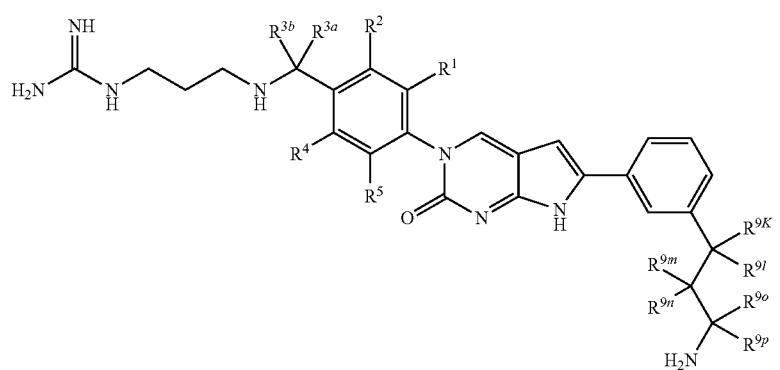
(XXa1)
or a tautomer thereof, or a pharmaceutically acceptable salt, ester, or prodrug of said compound or tautomer.

5. The compound according to claim 3 having a formula selected from:
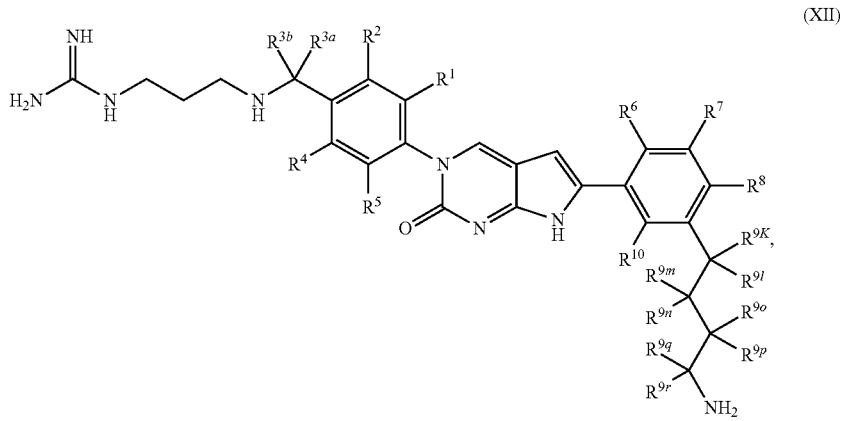
(XII)
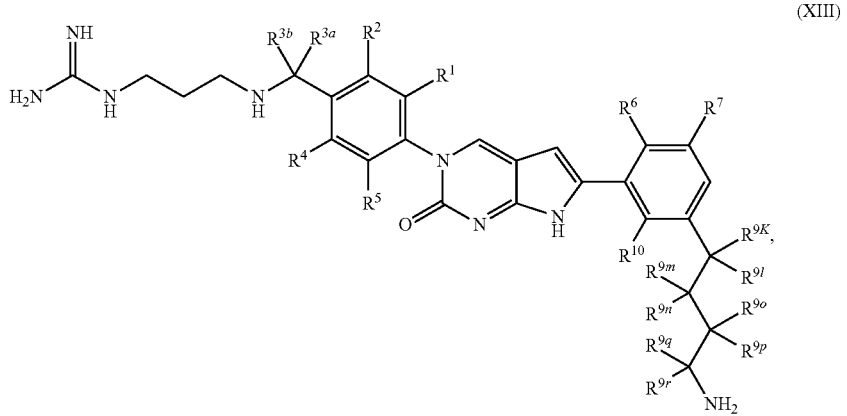
(XIII)
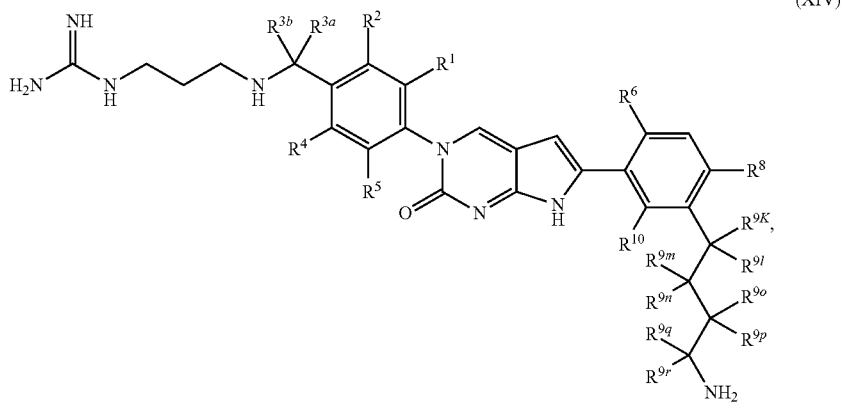
(XIV)
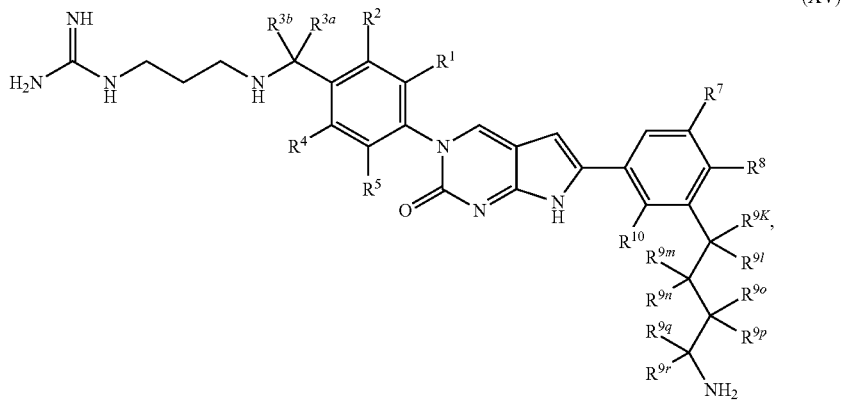
(XV)

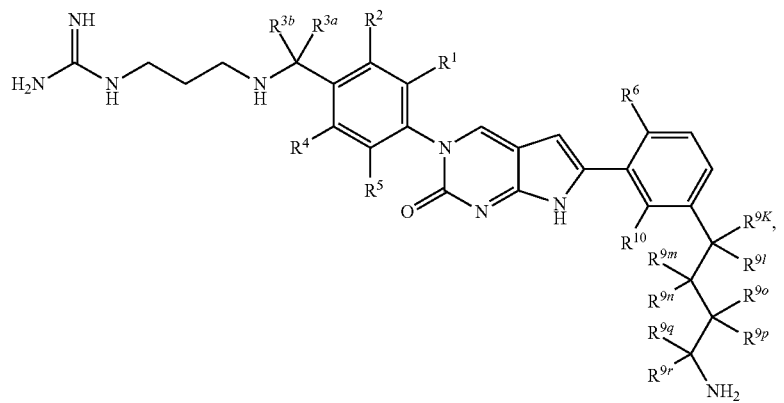
(XVI)
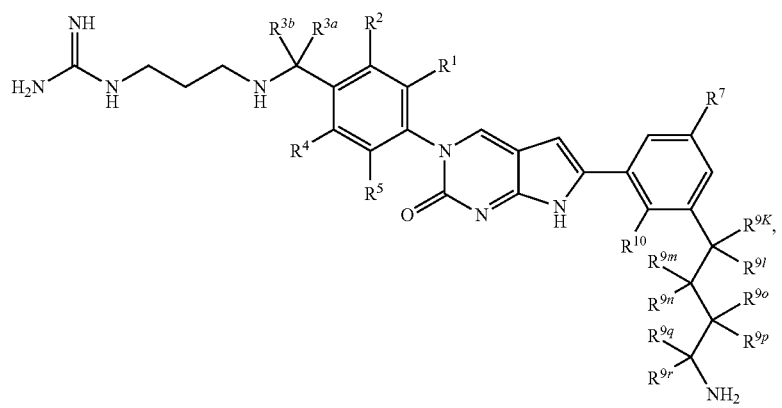
(XVII)
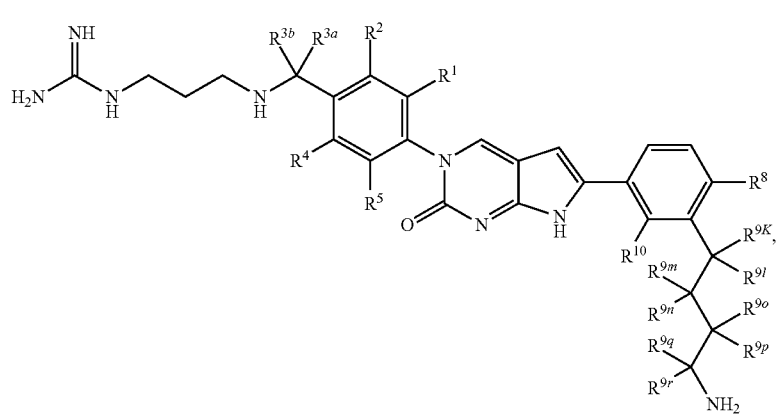
(XVIII)

(XXb)

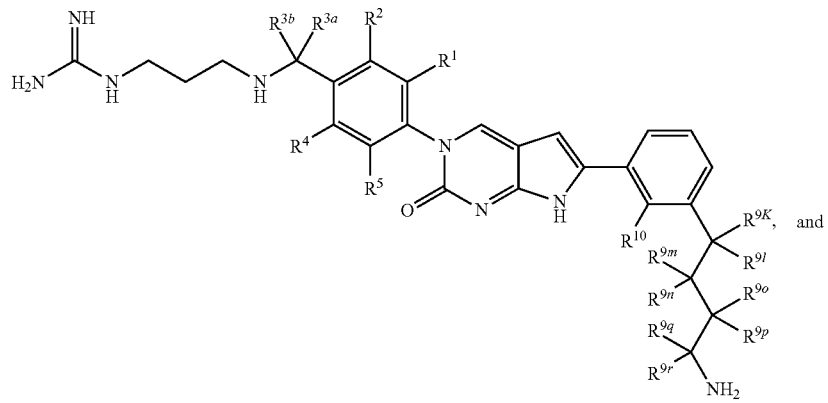

(XXb1)

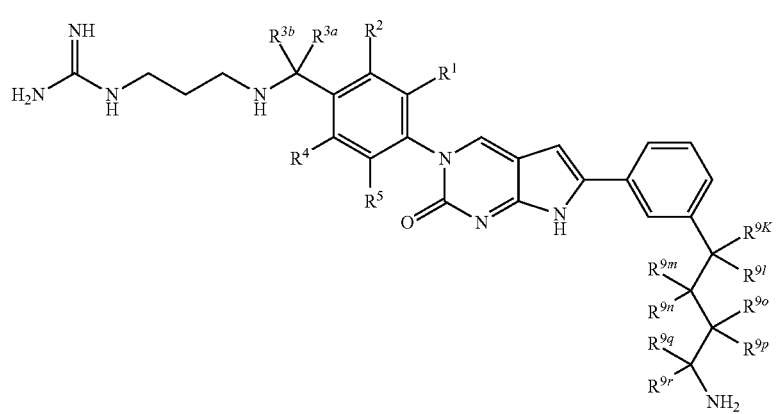

or a tautomer thereof, or a pharmaceutically acceptable salt, ester, or prodrug of said compound or tautomer.

6. The compound or a tautomer thereof, or a pharmaceutically acceptable salt, ester, or prodrug of said compound or tautomer, according to claim 1, wherein at least one substituent selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ is not hydrogen.

7. The compound or a tautomer thereof, or a pharmaceutically acceptable salt, ester, or prodrug of said compound or tautomer, according to claim 2 wherein $R^1$, $R^2$, $R^4$, and $R^5$ are each hydrogen.

8. The compound or a tautomer thereof, or a pharmaceutically acceptable salt, ester, or prodrug of said compound or tautomer, according to claim 3, wherein $R^{3a}$ and $R^{3b}$ are each independently selected from (a) hydrogen, (b) F, (c) Cl, (d) —CH$_3$, (e) —CF$_3$, (f) —CF$_2$H, (g) —CFH$_2$, (h) —OCF$_3$, (i) —OCF$_2$H, (j) —OCFH$_2$, (k) —OCH$_3$, and (l) —OH.

9. The compound or a tautomer thereof, or a pharmaceutically acceptable salt, ester, or prodrug of said compound or tautomer, according to claim 1, wherein $R^{10}$ is selected from hydrogen, F and Cl.

10. The compound or a tautomer thereof, or a pharmaceutically acceptable salt, ester, or prodrug of said compound or tautomer, according to claim 1, wherein $R^6$ and $R^7$ are each independently selected from (a) F, (b) Cl, (c) —CF$_3$, (d) —CF$_2$H, (e) —CFH$_2$, (f) —OCF$_3$, (g) —OCF$_2$H, (h) —OCFH$_2$, (i) —OCH$_3$, (j) —CN, (k) —OR$^{11}$, (l) —S(O)$_p$R$^{11}$, (m) —SCF$_3$, (n) —C$_1$-C$_8$ alkyl, (o) -3-14 membered saturated, unsaturated, or aromatic heterocycle containing one or more heteroatoms selected from the group consisting of nitrogen, oxygen, and sulfur, (p) -3-14 membered saturated, unsaturated, or aromatic carbocycle, (q) —CHCHCN and (r) —CHCH—C(O)NH-t-butyl.

11. The compound or a tautomer thereof, or a pharmaceutically acceptable salt, ester, or prodrug of said compound or tautomer, according to claim 1, wherein $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are each independently selected from (a) hydrogen, (b) halogen, (c) —CF$_3$, (d) —CF$_2$H, (e) —CFH$_2$, (f) —OCF$_3$, (g) —OCH$_3$, (h) —OCF$_2$H, (i) —OCFH$_2$, (j) —OR$^{11}$, (k) —C$_1$-C$_8$ alkyl, (l) haloalkyl, (m) -3-14 membered saturated, unsaturated, or aromatic heterocycle containing one or more heteroatoms selected from the group consisting of nitrogen, oxygen, and sulfur, and (n) -3-14 membered saturated, unsaturated, or aromatic carbocycle;

alternatively, one or more of pairs of substituents selected from $R^{9k}$ and $R^{9l}$, $R^{9m}$ and $R^{9n}$, $R^{9o}$ and $R^{9p}$, $R^{9q}$ and $R^{9r}$, and $R^{9s}$ and $R^{9t}$ are taken together with the carbon atom to which they are attached to form (a) -3-7 membered saturated or unsaturated carbocyclic or (b) -3-7 membered saturated or unsaturated heterocyclic ring containing one or more heteroatoms selected from the group consisting of nitrogen, oxygen, and sulfur; and at least one substituent selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ is not hydrogen.

12. The compound or a tautomer thereof, or a pharmaceutically acceptable salt, ester, or prodrug of said compound or tautomer, according to claim 11 wherein $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ are each independently selected from (a) hydrogen, (b) halogen, (d) —CF$_3$, (e) —CF$_2$H, (f) —CFH$_2$, (g) —OCF$_3$, (h) —OCH$_3$, (i) —OCF$_2$H, (j) —OCFH$_2$, (k) —OH, (c) —OCH$_3$, (l) methyl, (m) ethyl, (n) isopropyl, and (o) t-butyl; and at least one substituent selected from $R^{9k}$, $R^{9l}$, $R^{9m}$, $R^{9n}$, $R^{9o}$, $R^{9p}$, $R^{9q}$, $R^{9r}$, $R^{9s}$, and $R^{9t}$ is not hydrogen.
13. The compound according to claim 1 having a formula selected from:
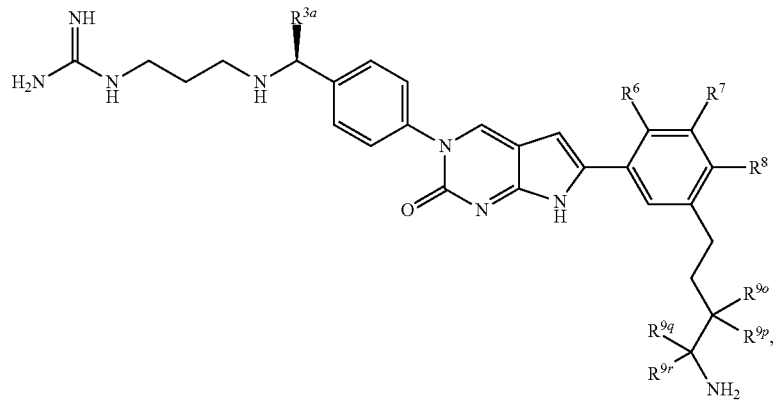
(G1)

(G2)
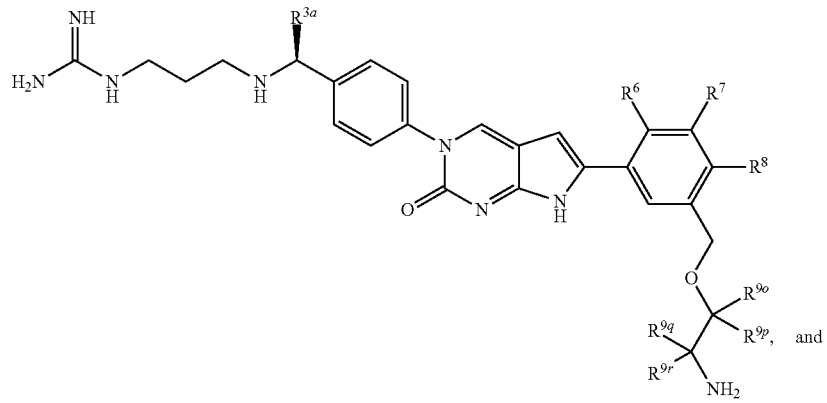
(G3)
and

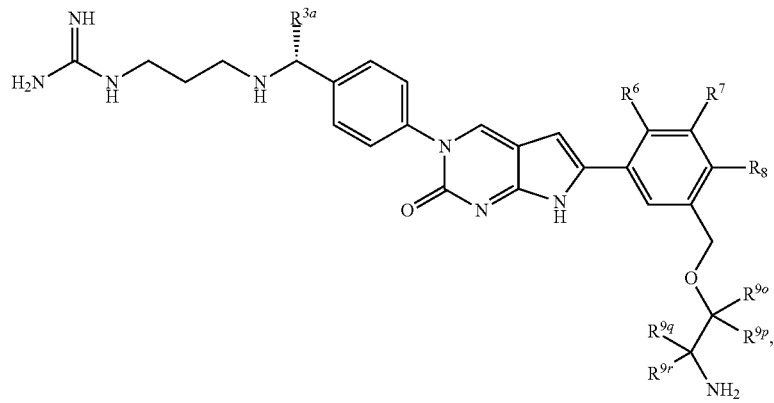

(G4)

or a tautomer thereof, or a pharmaceutically acceptable salt, ester, or prodrug of said compound or tautomer.

14. The compound or a tautomer thereof, or a pharmaceutically acceptable salt, ester, or prodrug of said compound or tautomer, according to claim 13, wherein $R^{9o}$, $R^{9p}$, $R^{9q}$, and $R^{9r}$ are each independently selected from —$C_1$-$C_6$ alkyl and hydrogen;
- $R^6$ and $R^8$ are each independently selected from hydrogen, F, Cl, Br, I, —$C_1$-$C_6$ alkyl, —$CH_2F$, —$CHF_2$, and —$CF_3$;
- $R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p$—$C_1$-$C_6$ alkyl, —$OCH_2F$, —$OCHF_2$, —$OCF_3$, —$S(O)_p$—$CH_3$, —$S(O)_p$—$CH_2F$, and —$S(O)_p$—$CF_3$; and
- $R^{3a}$ is selected from halogen and $C_1$-$C_6$ alkyl; and
- p is 0, 1, or 2.

15. The compound or a tautomer thereof, or a pharmaceutically acceptable salt, ester, or prodrug of said compound or tautomer, according to claim 13, wherein $R^{9o}$, $R^{9p}$, $R^{9q}$, and $R^{9r}$ are each independently selected from $C_1$-$C_6$ alkyl and hydrogen;
- $R^6$ is selected from hydrogen, F, Cl, Br, I, —$C_1$-$C_6$ alkyl, —$CH_2F$, —$CHF_2$, and —$CF_3$;
- $R^7$ is selected from hydrogen, F, Cl, Br, I, —$C_1$-$C_6$ alkyl, —$CH_2F$, —$CHF_2$, —$CF_3$, —$OC_1$-$C_6$ alkyl, —$S(O)_p$—$C_1$-$C_6$ alkyl, —$OCH_2F$, —$OCHF_2$, —$OCF_3$, —$S(O)_p$—$CH_3$, —$S(O)_p$—$CH_2F$, and —$S(O)_p$—$CF_3$;
- $R^8$ is hydrogen;
- $R^{3a}$ is selected from halogen and —$C_1$-$C_6$ alkyl; and
- p is 0, 1, or 2.

16. The compound of claim 1, or a tautomer thereof, or a pharmaceutically acceptable salt, ester, or prodrug of said compound or tautomer selected from:

1

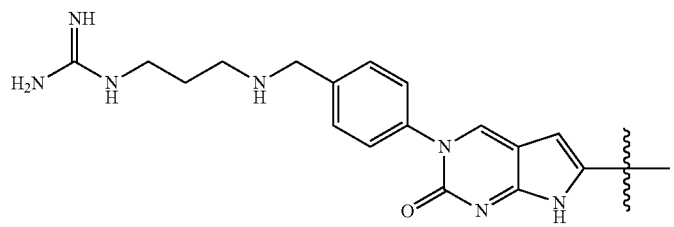 [SMILES: *c1cc2cn(-c3ccc(CNCCCNC(=N)N)cc3)c(=O)nc2[nH]1]

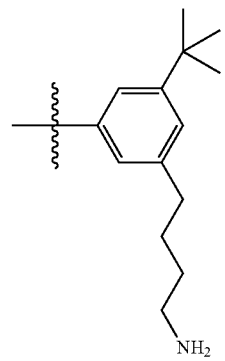

2 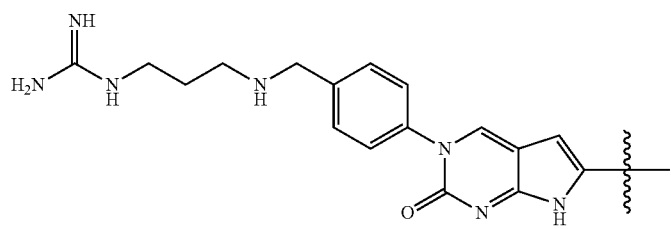 [SMILES: *c1cc2cn(-c3ccc(CNCCCNC(=N)N)cc3)c(=O)nc2[nH]1]
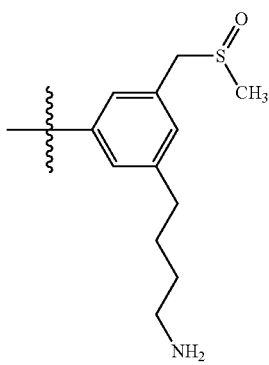
3 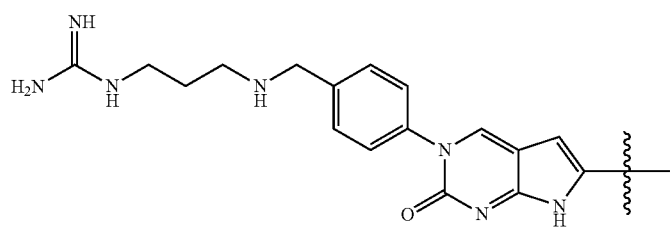 [SMILES: *c1cc2cn(-c3ccc(CNCCCNC(=N)N)cc3)c(=O)nc2[nH]1]
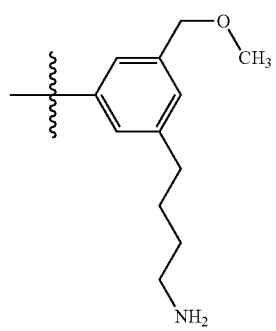

4 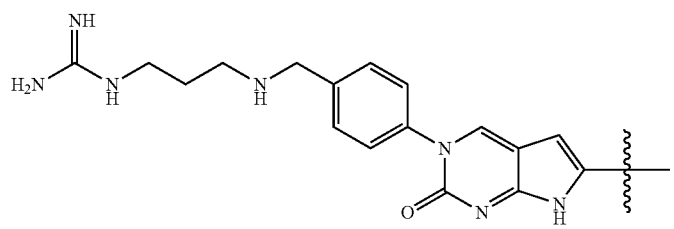 [SMILES: *c1cc2cn(-c3ccc(CNCCCNC(=N)N)cc3)c(=O)nc2[nH]1]
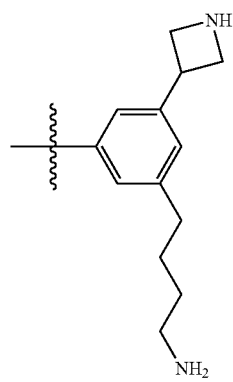
5 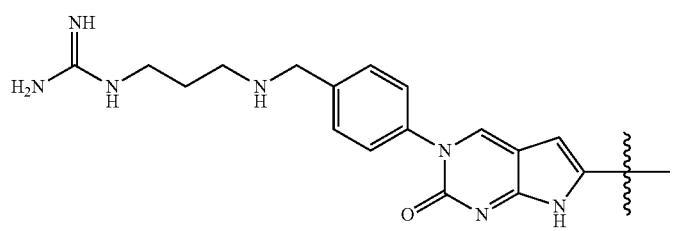 [SMILES: *c1cc2cn(-c3ccc(CNCCCNC(=N)N)cc3)c(=O)nc2[nH]1]
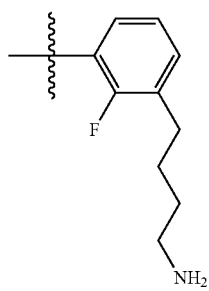

6 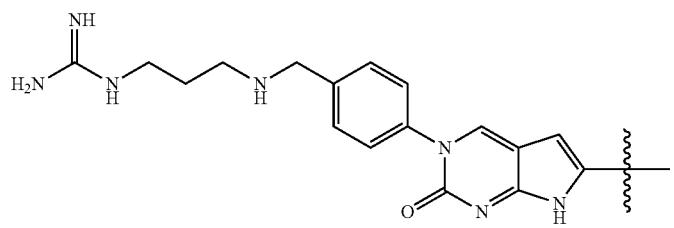 [SMILES: *c1cc2cn(-c3ccc(CNCCCNC(=N)N)cc3)c(=O)nc2[nH]1]
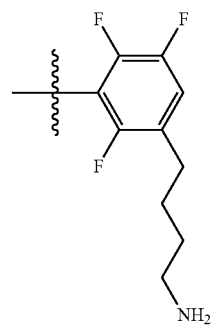
7 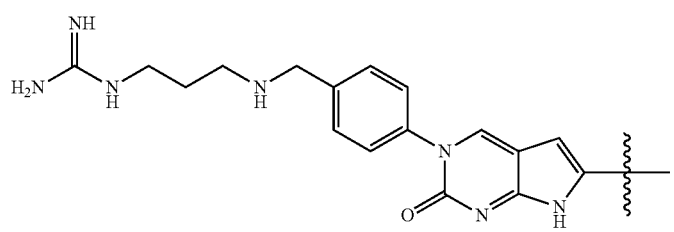 [SMILES: *c1cc2cn(-c3ccc(CNCCCNC(=N)N)cc3)c(=O)nc2[nH]1]
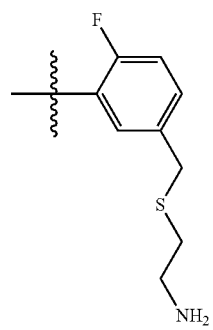

8 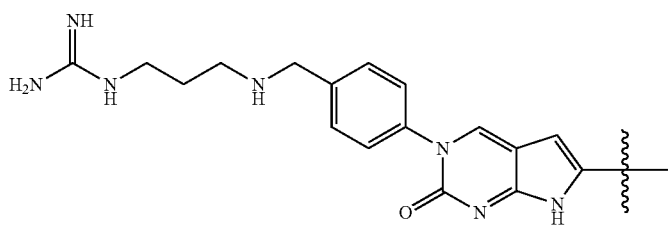 [SMILES: *c1cc2cn(-c3ccc(CNCCCNC(=N)N)cc3)c(=O)nc2[nH]1]
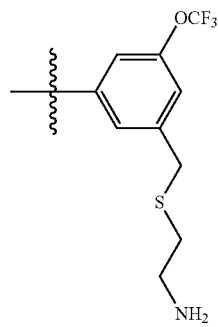
9 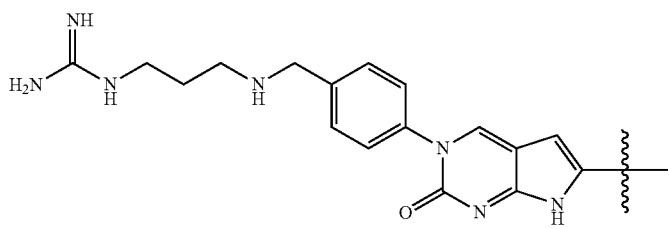 [SMILES: *c1cc2cn(-c3ccc(CNCCCNC(=N)N)cc3)c(=O)nc2[nH]1]
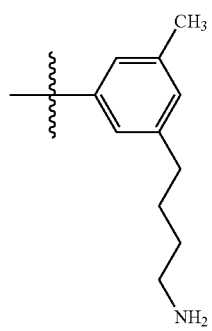 [SMILES: *c1cc(Cl)cc(CCCCN)c1]
10 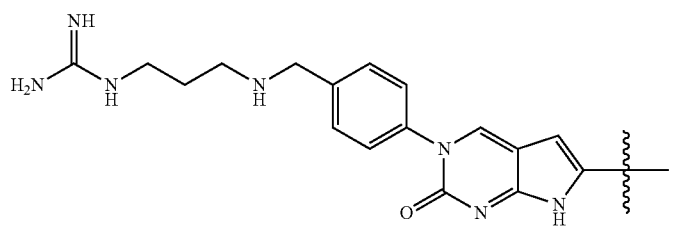 [SMILES: *c1cc2cn(-c3ccc(CNCCCNC(=N)N)cc3)c(=O)nc2[nH]1] 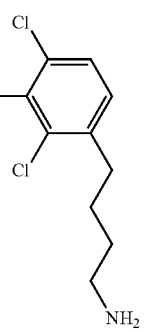

| | |
|---|---|
| 11 | 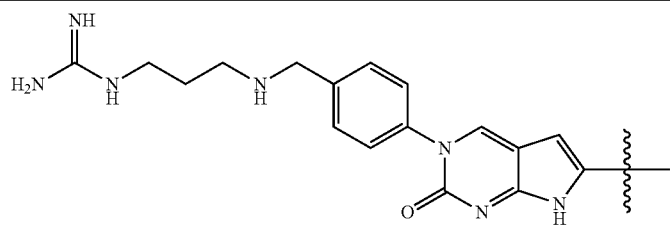 |
| | 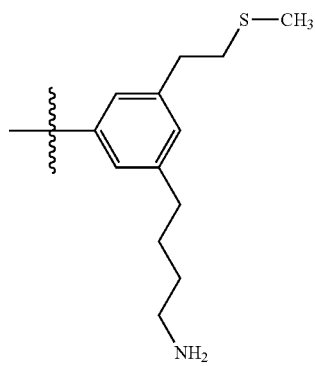 |
| 12 | 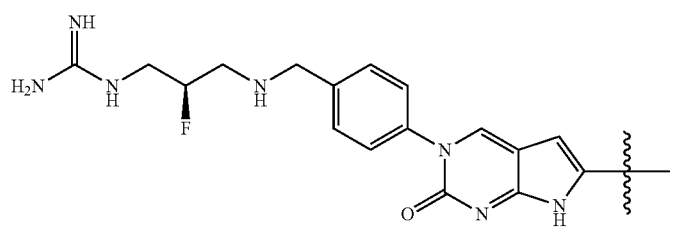 |
| | 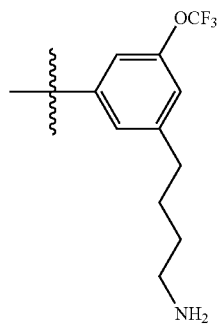 |
| 13 | 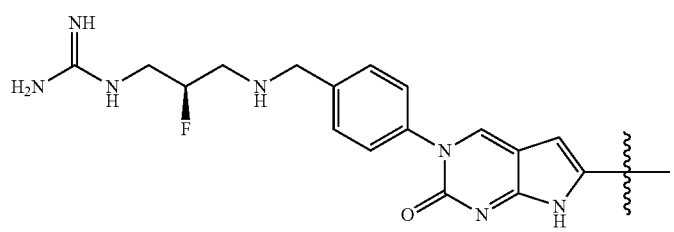 |
| | 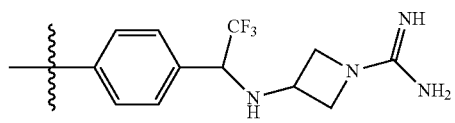 |

14 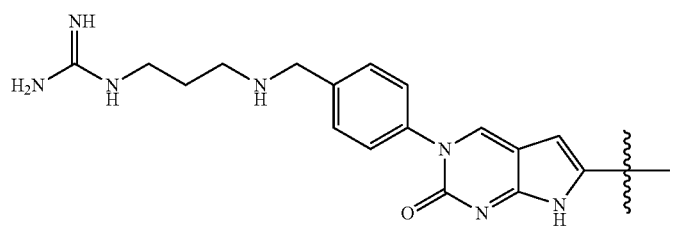 [SMILES: *c1cc2cn(-c3ccc(CNCCCNC(=N)N)cc3)c(=O)nc2[nH]1]
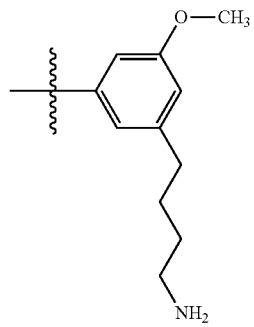
15 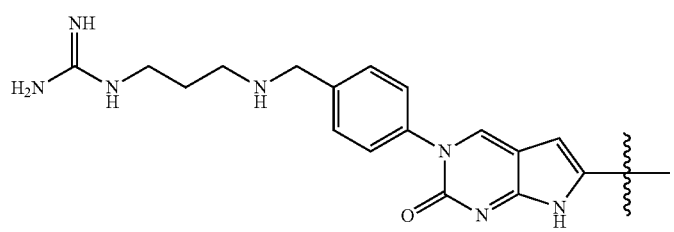 [SMILES: *c1cc2cn(-c3ccc(CNCCCNC(=N)N)cc3)c(=O)nc2[nH]1]
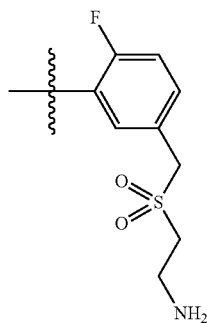

16 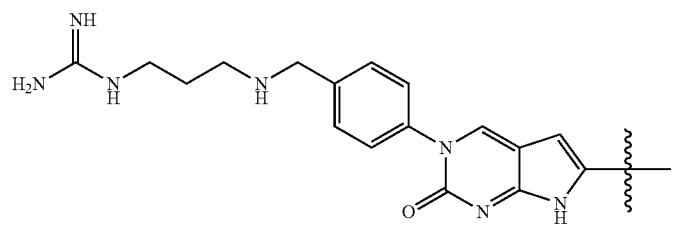 [SMILES: *c1cc2cn(-c3ccc(CNCCCNC(=N)N)cc3)c(=O)nc2[nH]1]
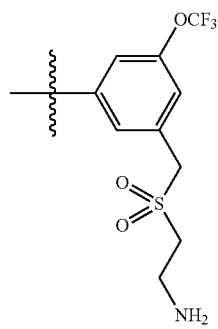
17 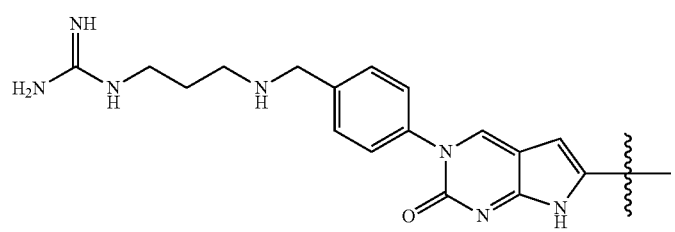 [SMILES: *c1cc2cn(-c3ccc(CNCCCNC(=N)N)cc3)c(=O)nc2[nH]1]
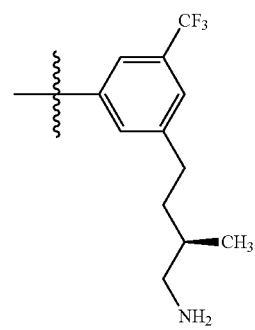

18 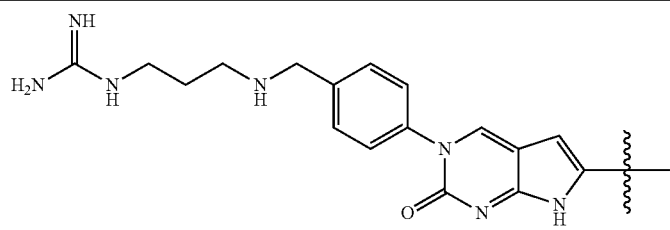
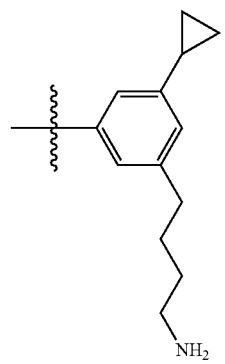
19 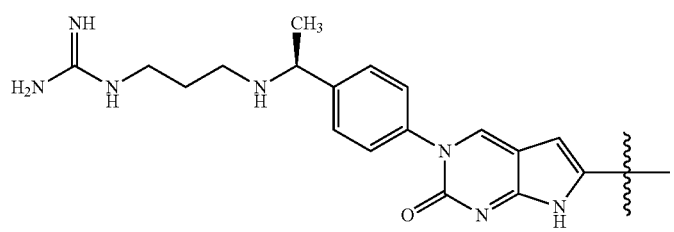
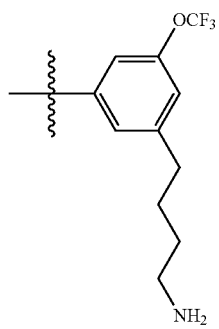

20
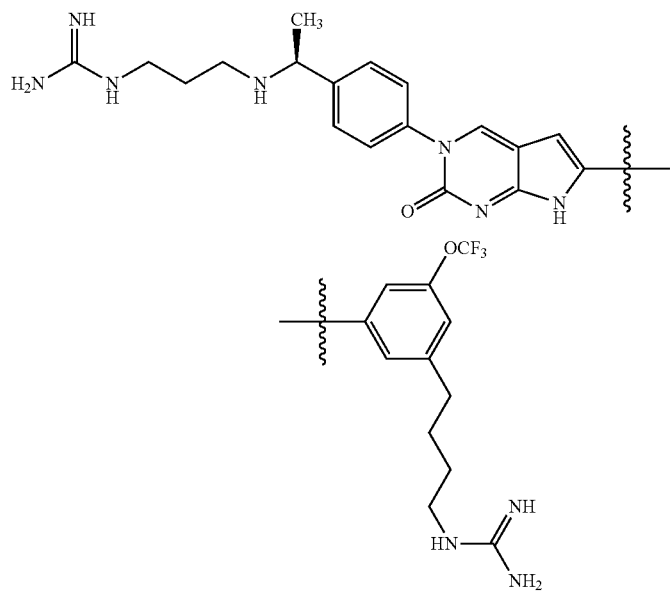
21
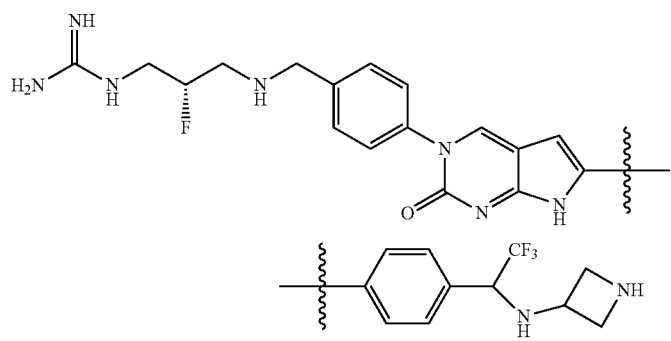
22
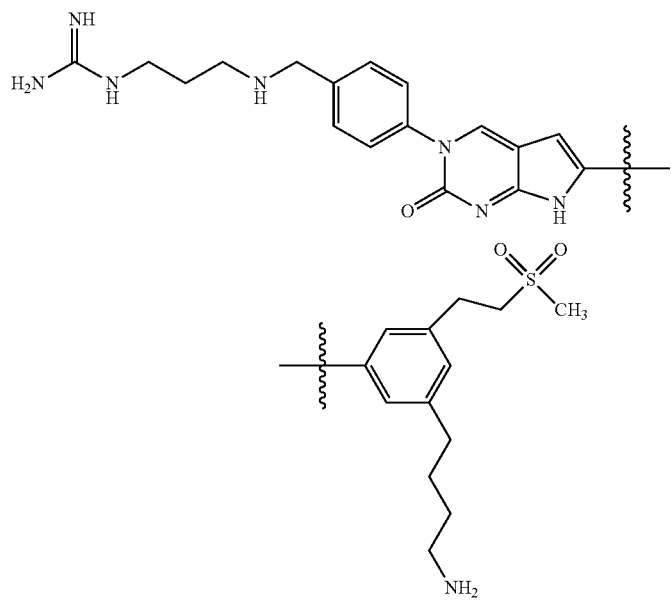

-continued
| 23 | 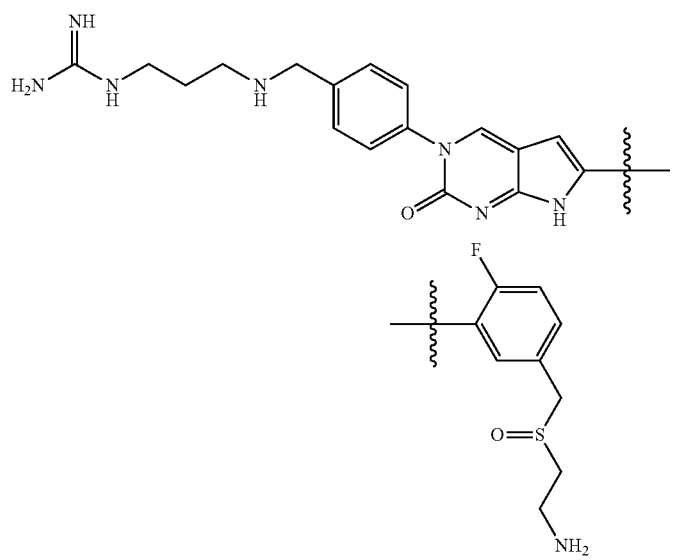 |
|---|---|
| 24 | 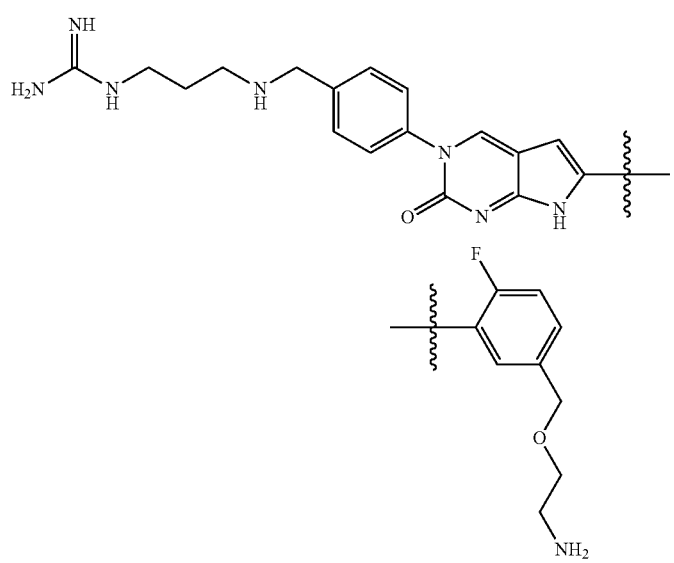 |

25 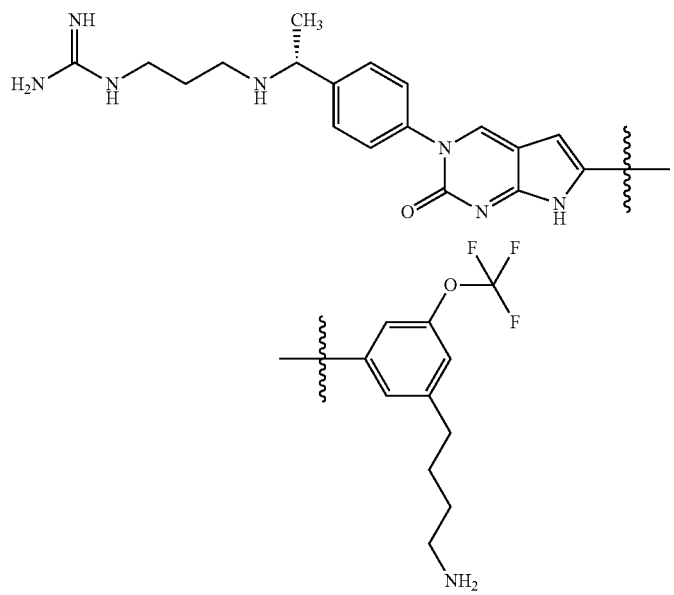
26 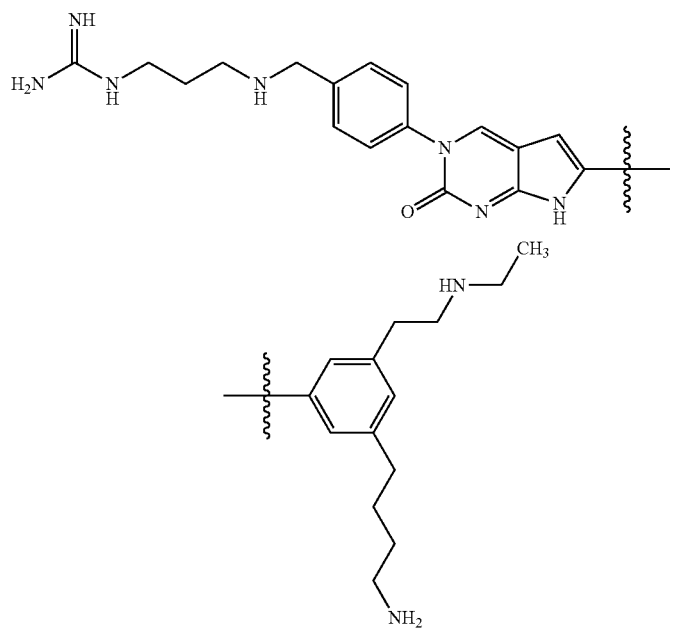

27 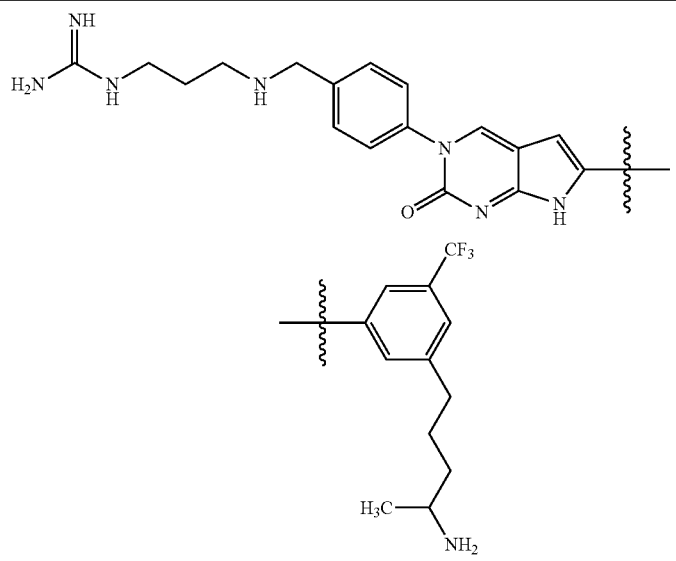
28 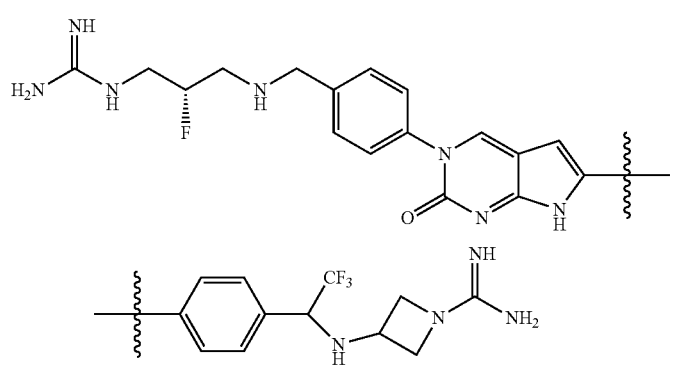
29 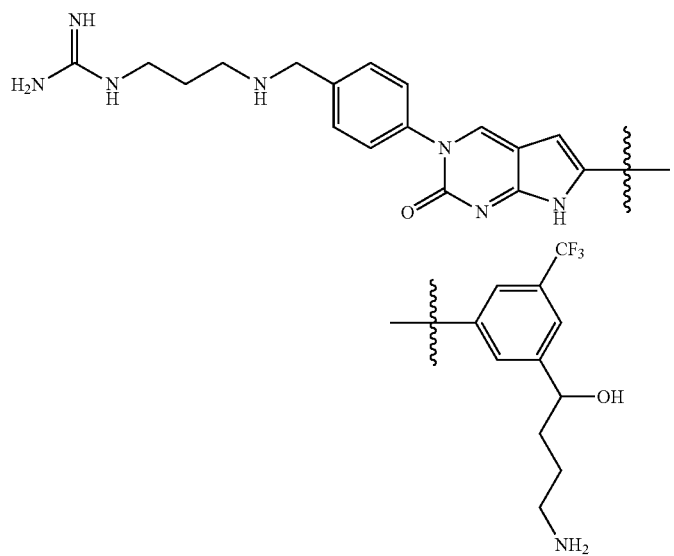

30 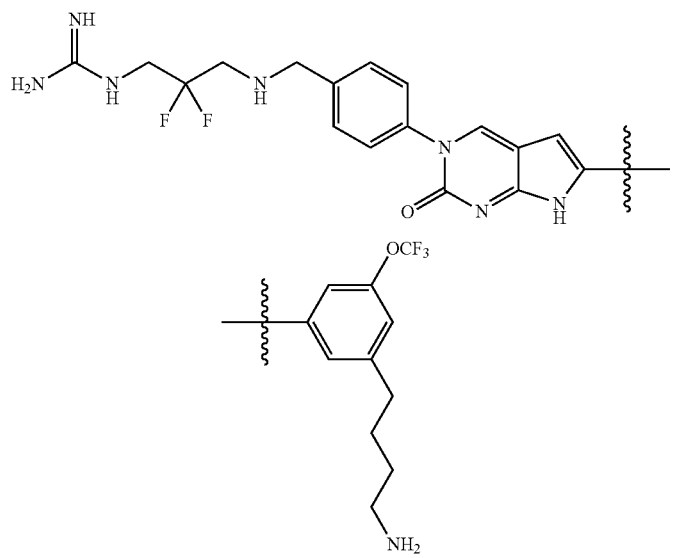
31 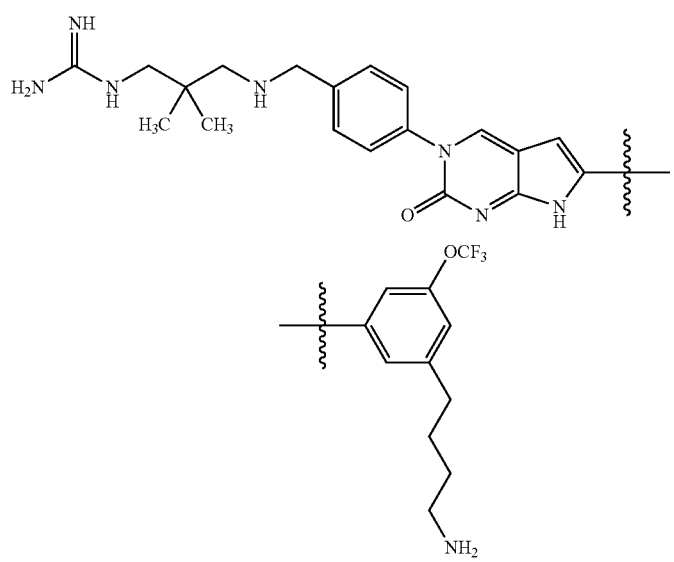

32 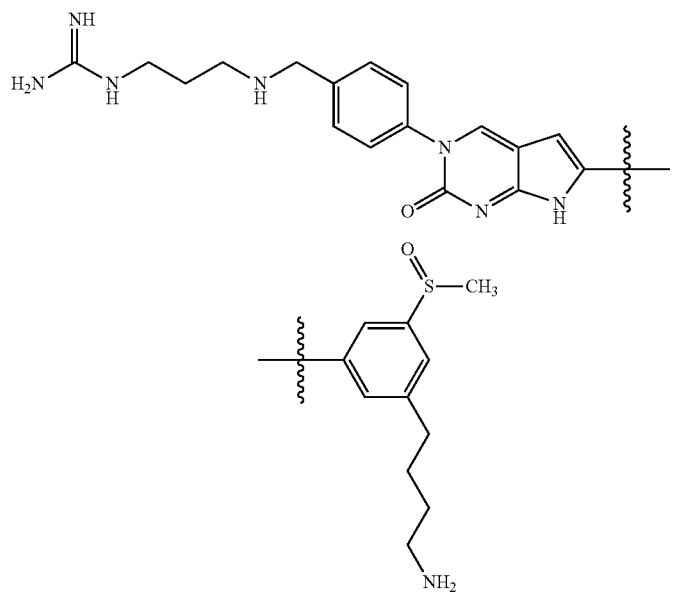
33 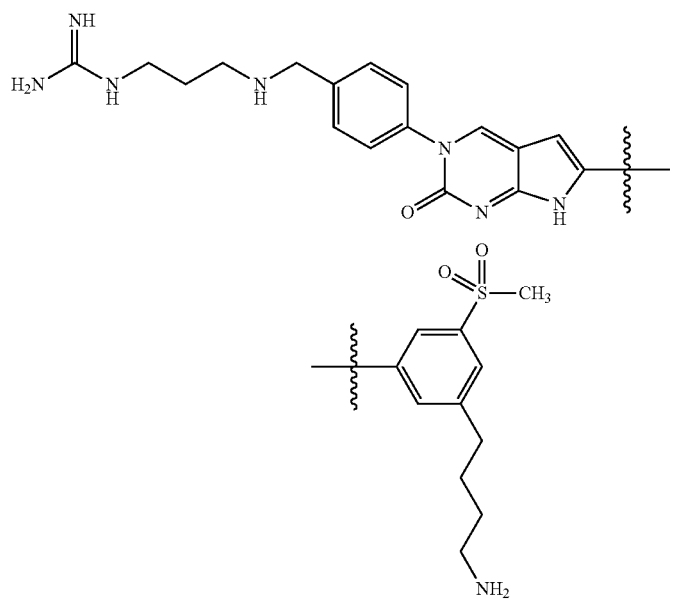

34 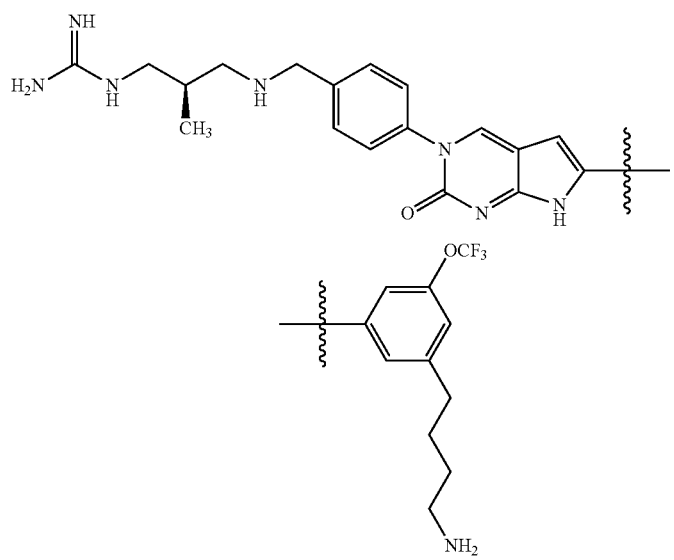
35 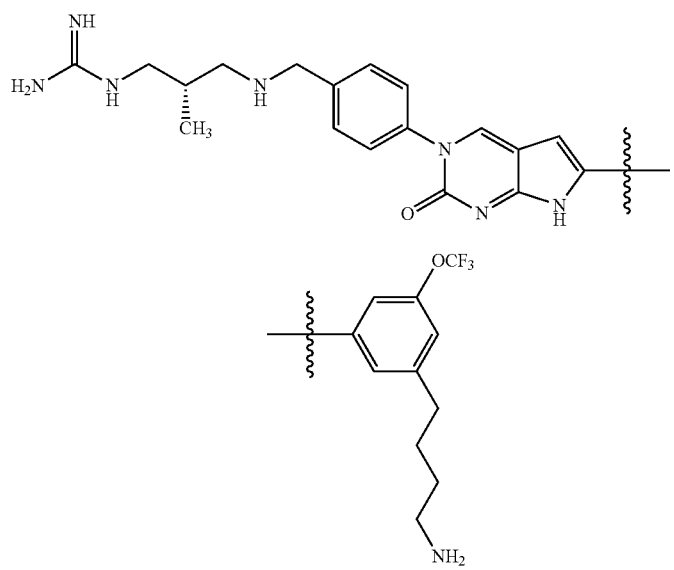

-continued
36 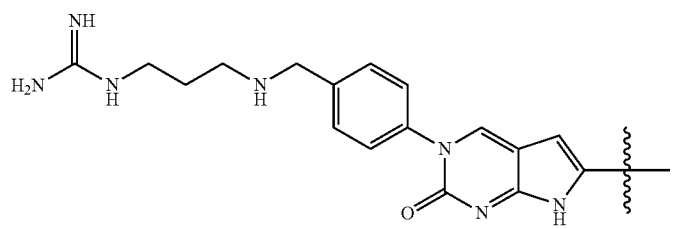
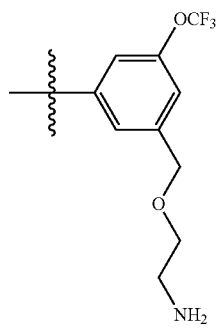
37 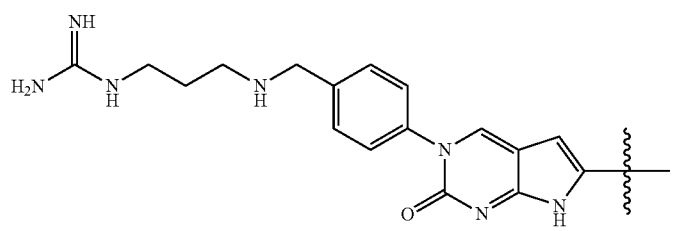
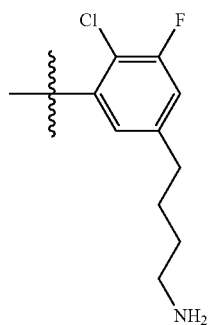

38 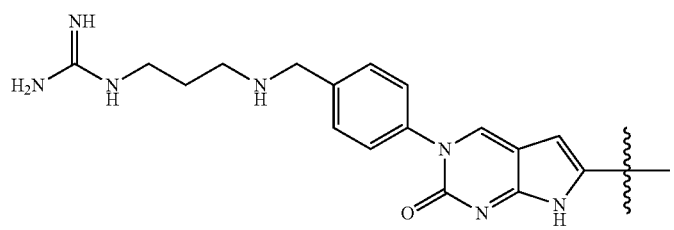
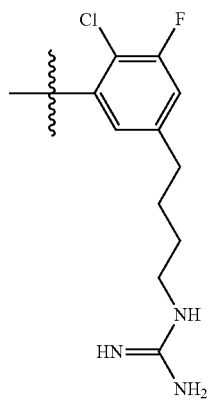
39 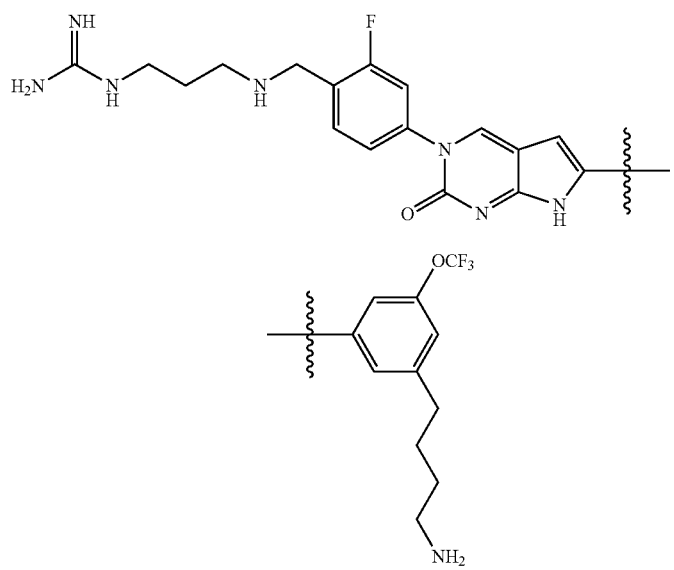

40
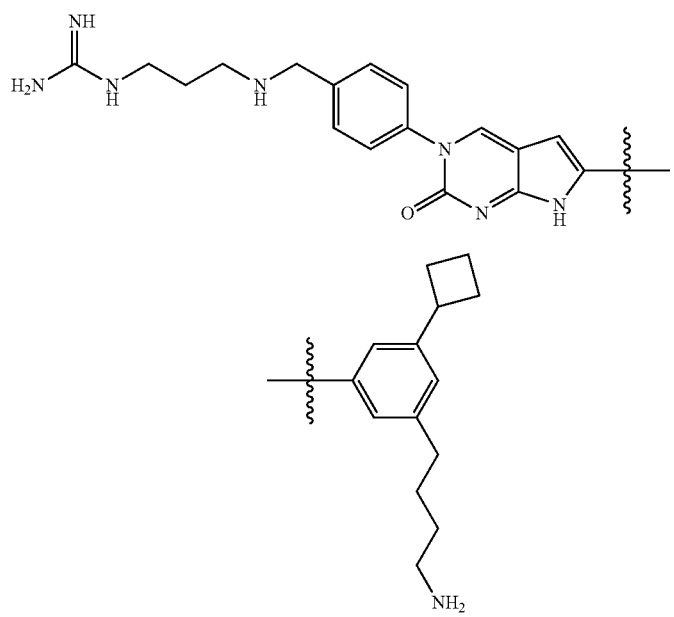
41
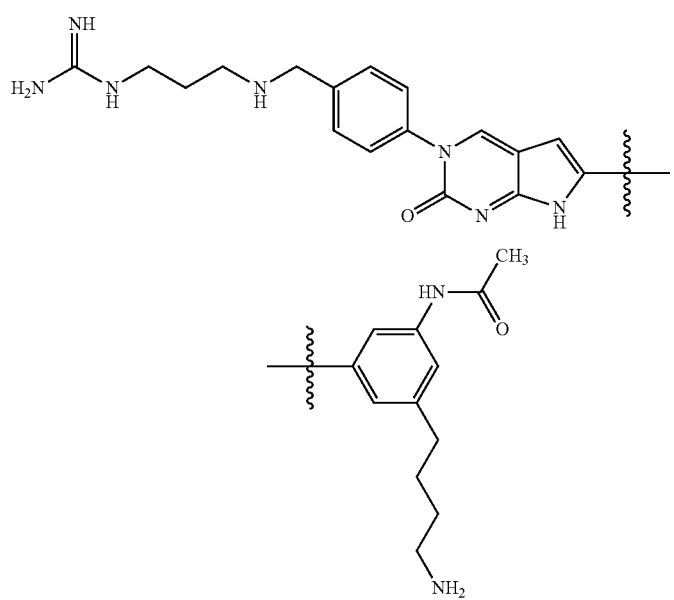

42 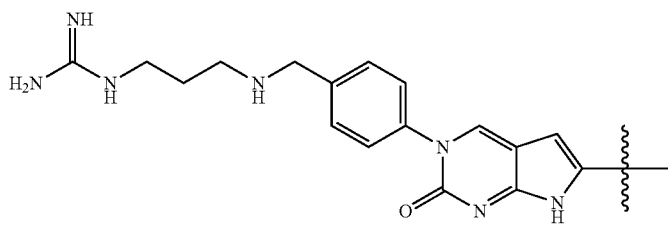
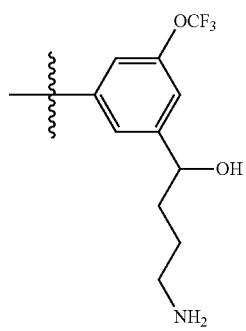
43 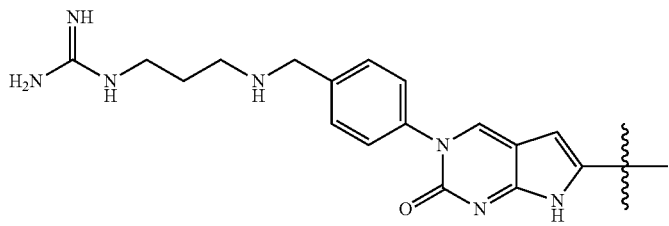
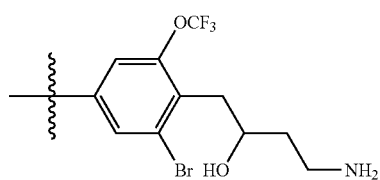
44 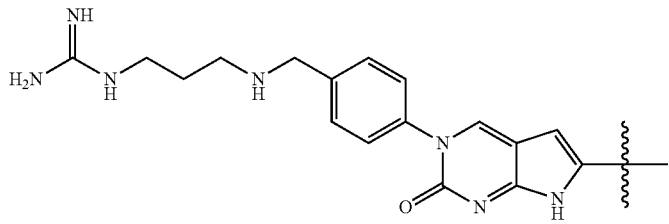
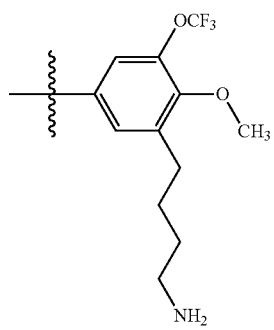

45 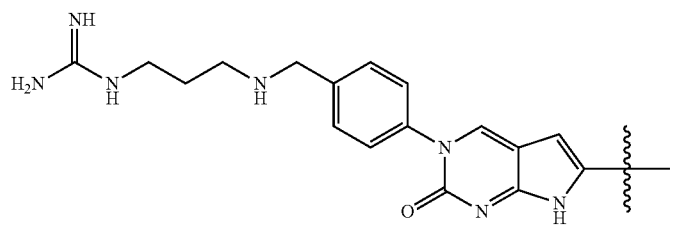
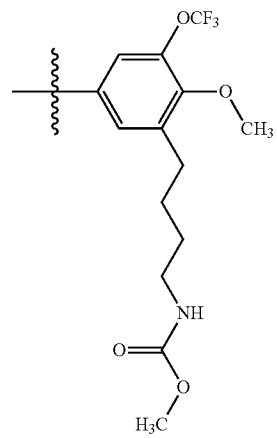
46 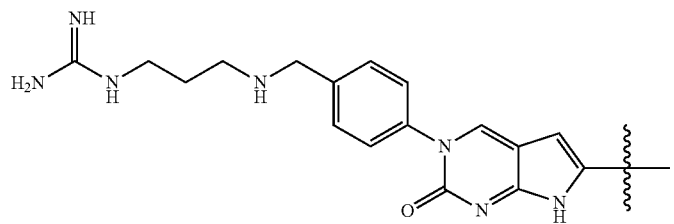
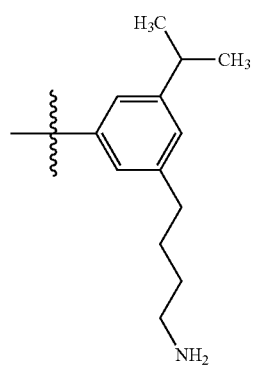

47 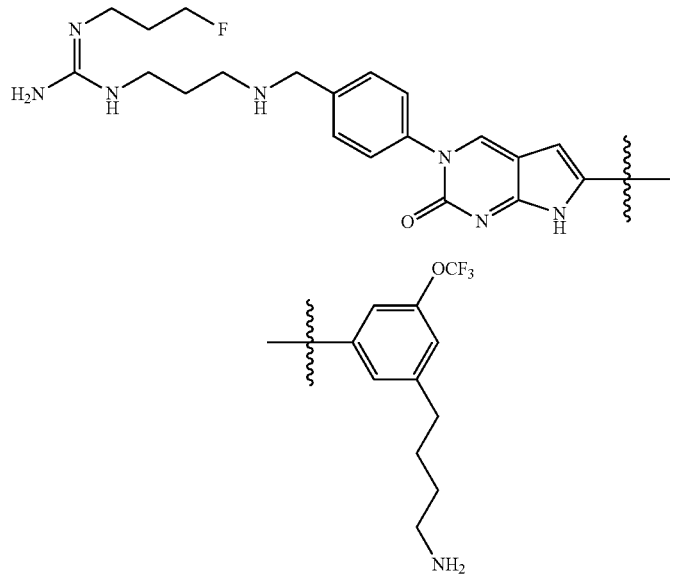
48 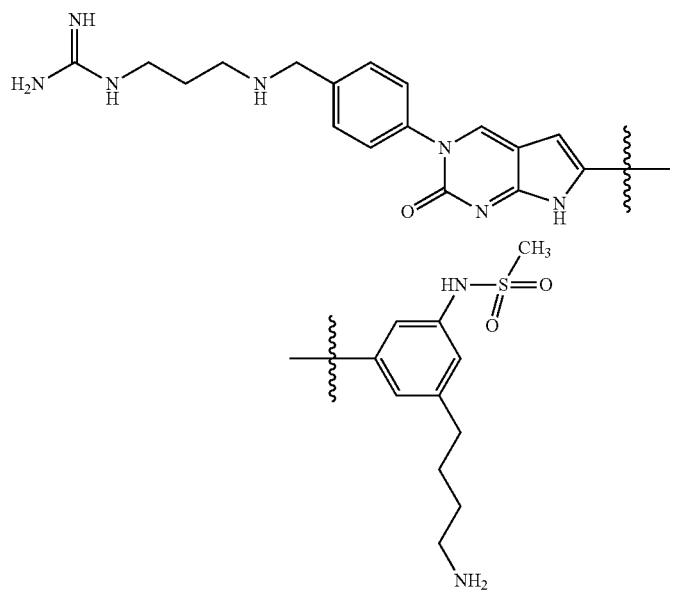

49
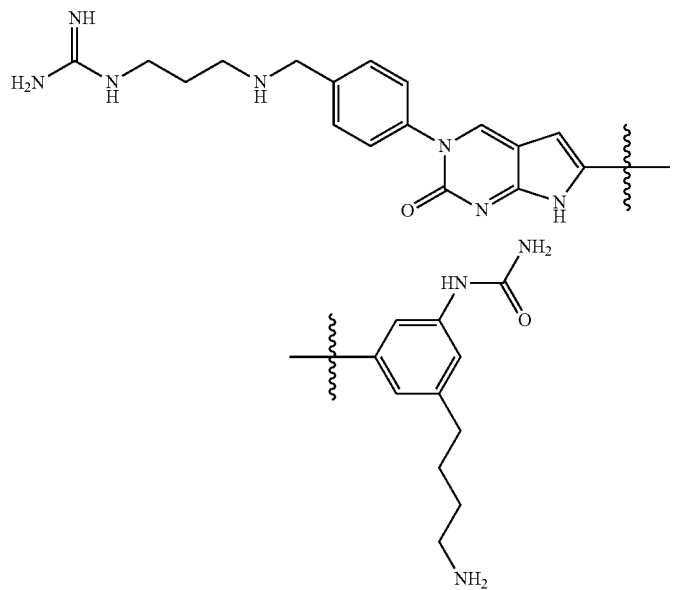
50
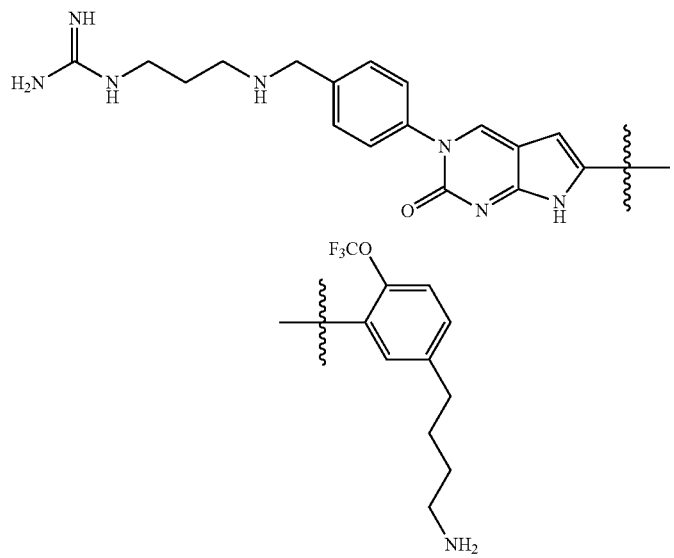

-continued
51 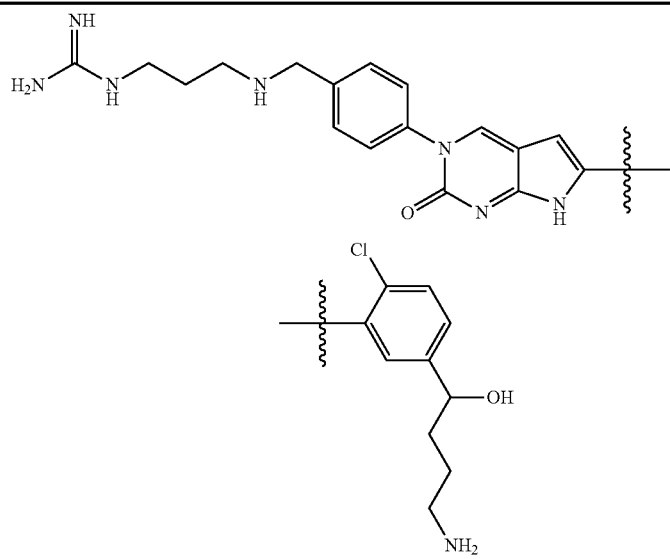
52 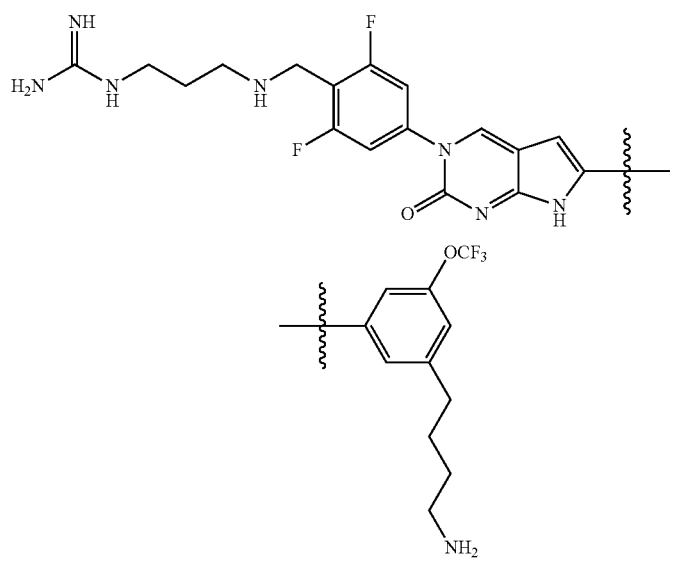
53 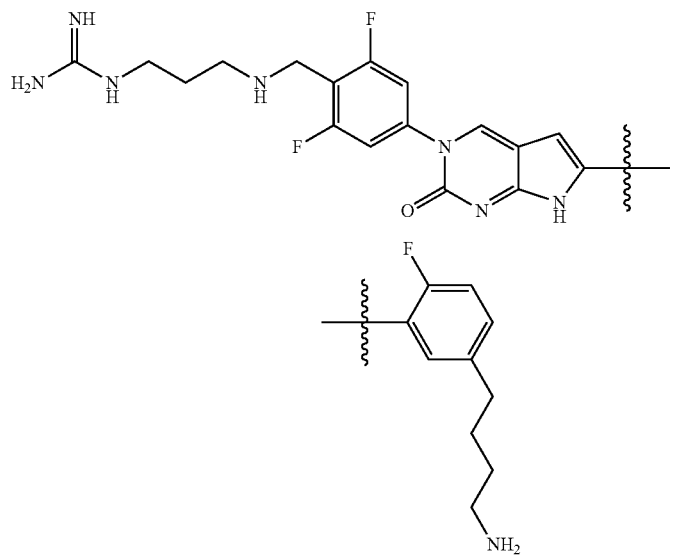

54
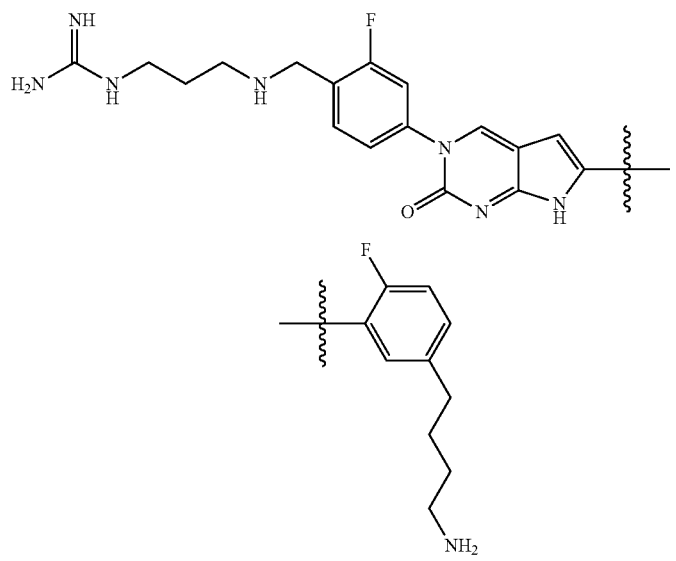
55
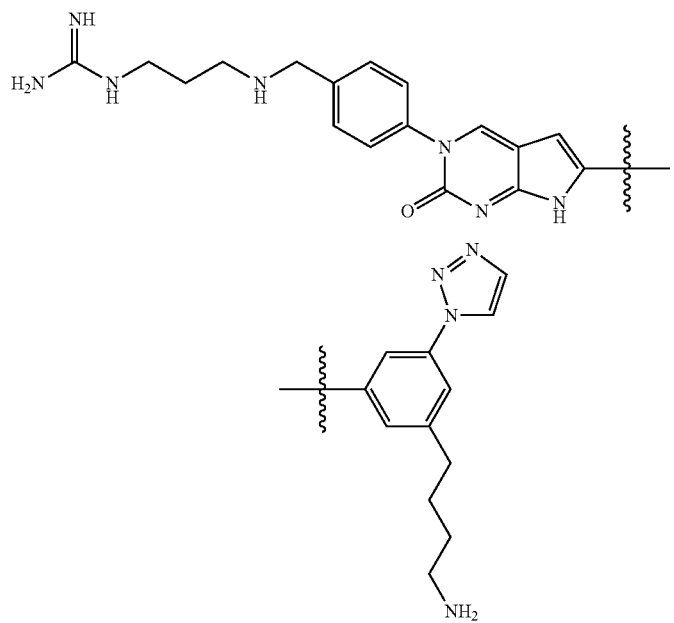

56 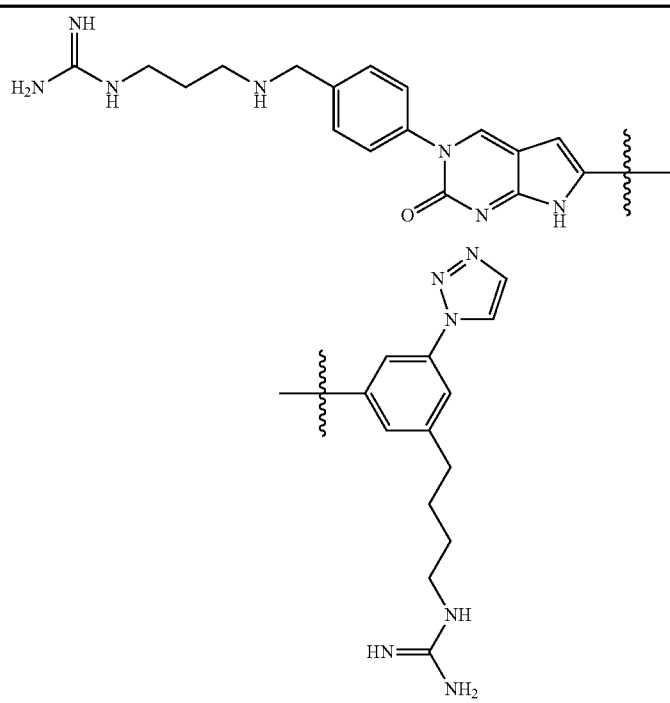
57 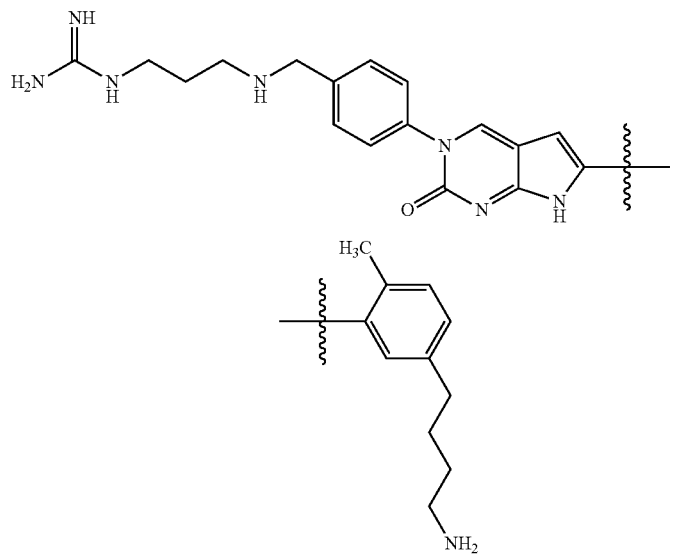

58 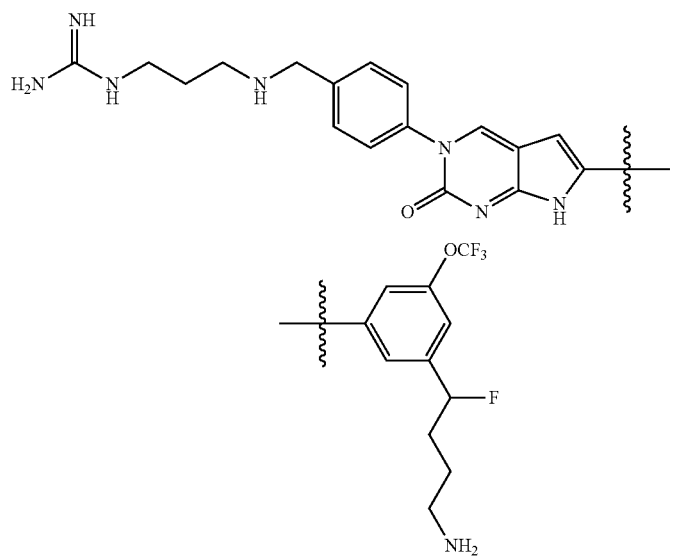
59 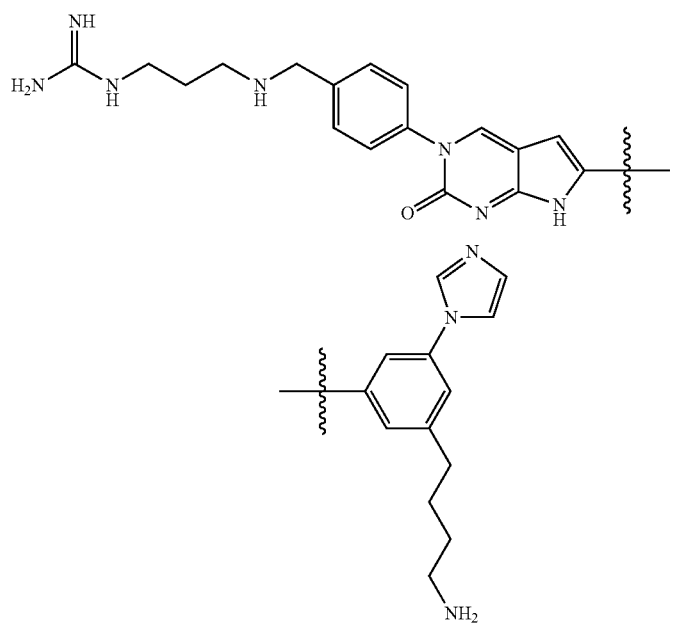

60 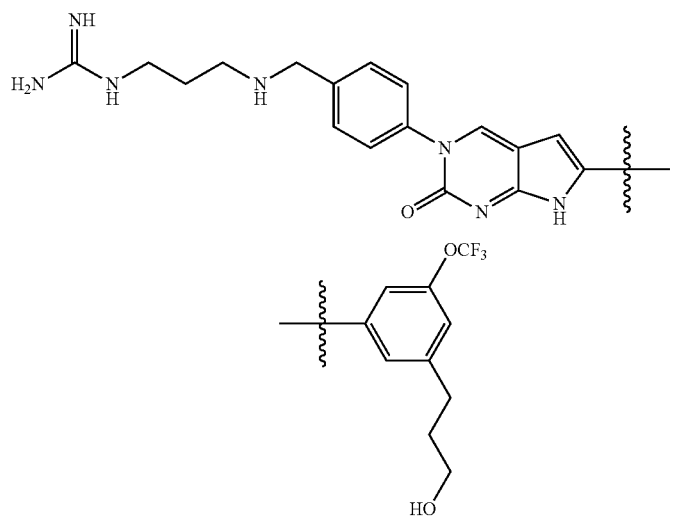
61 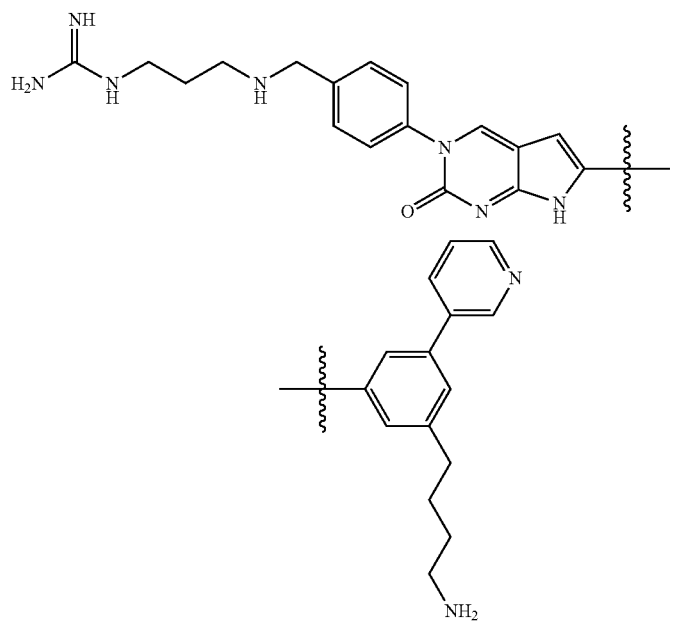

-continued
| 62 | 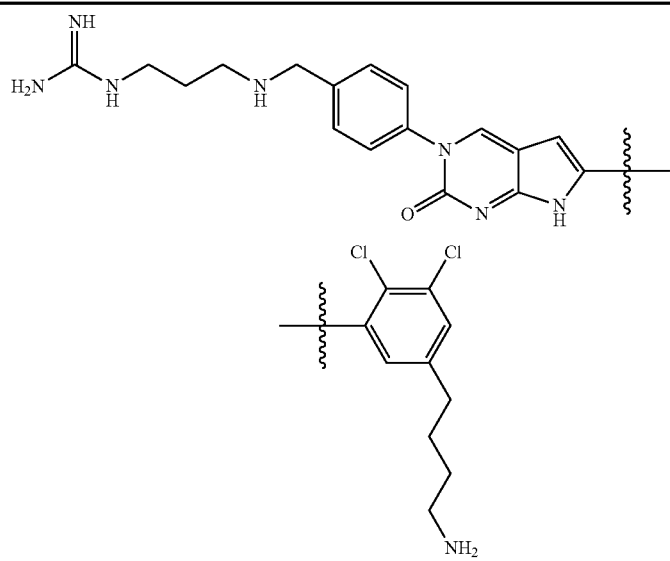 |
|---|---|
| 63 | 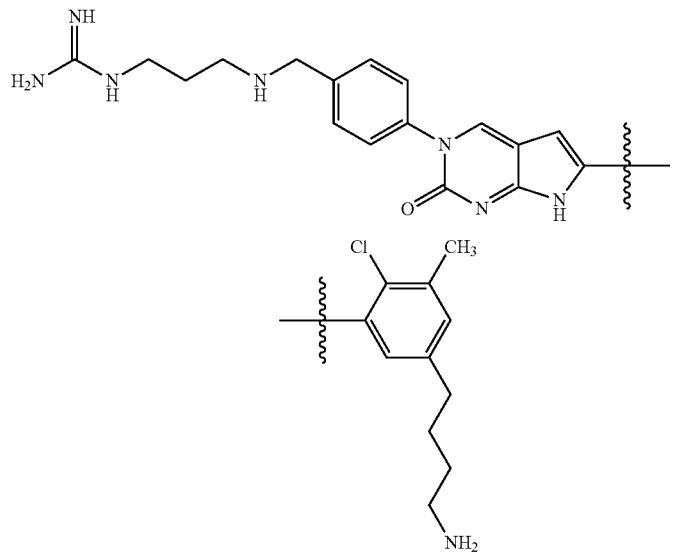 |
| 64 | 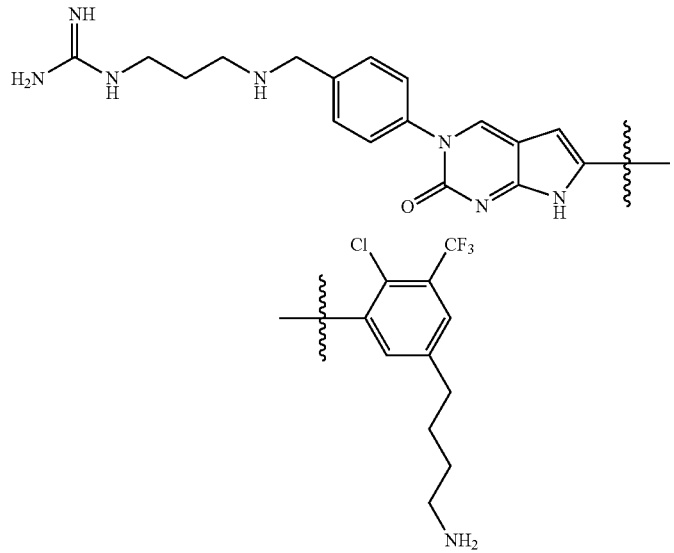 |

65 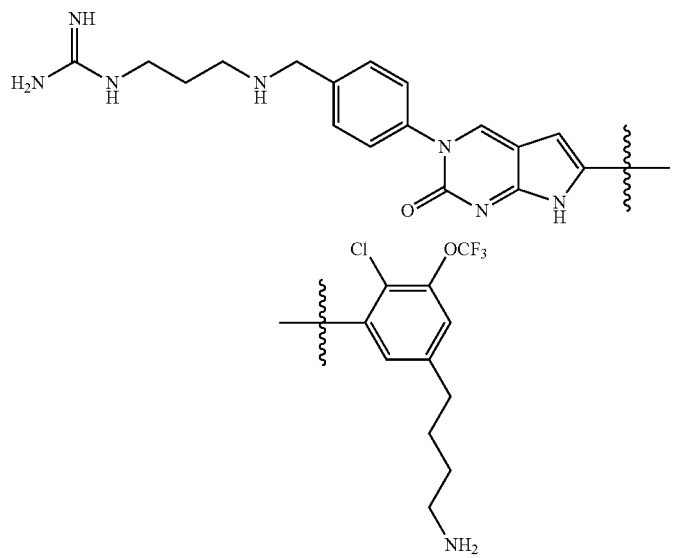
66 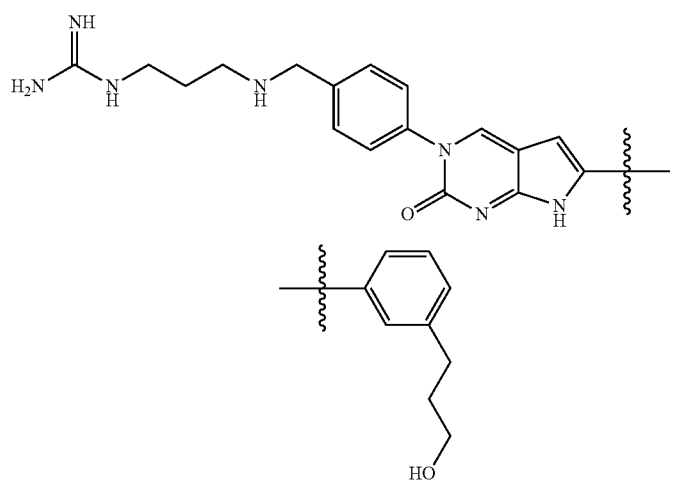
67 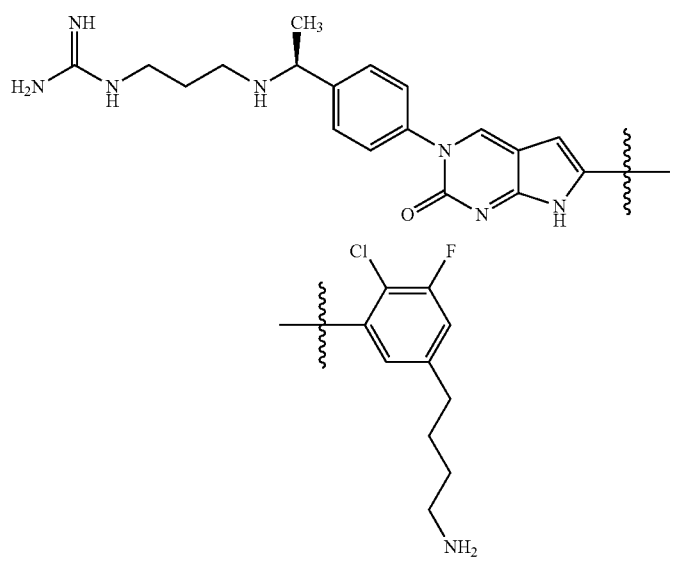

68 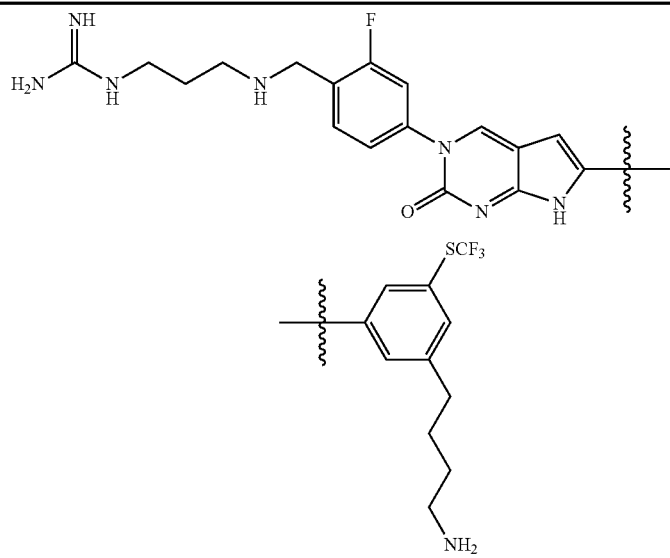
69 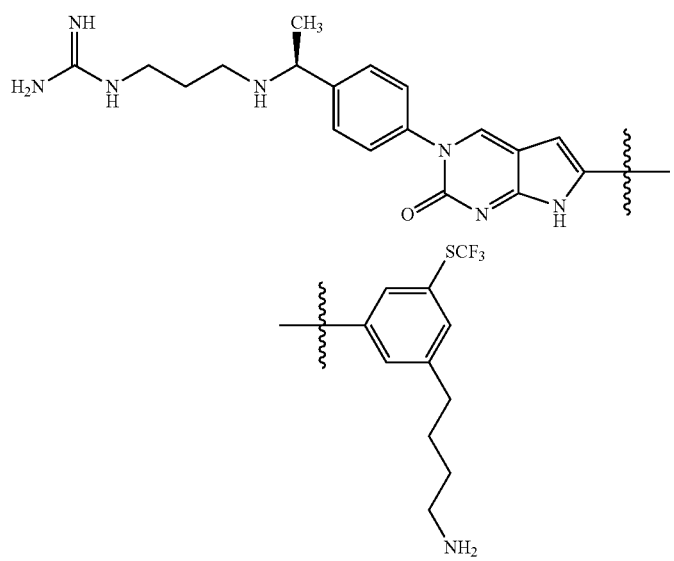
70 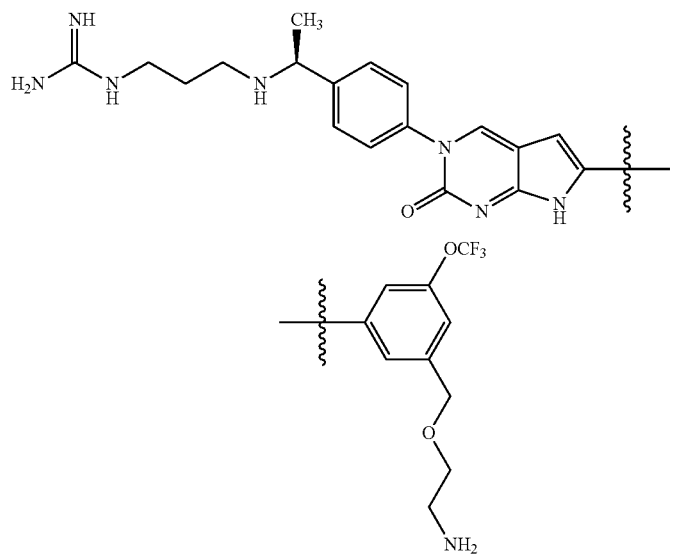

71 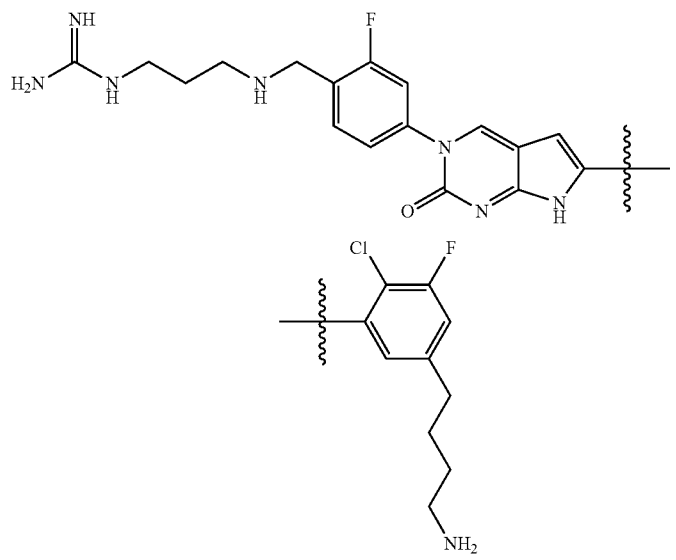
72 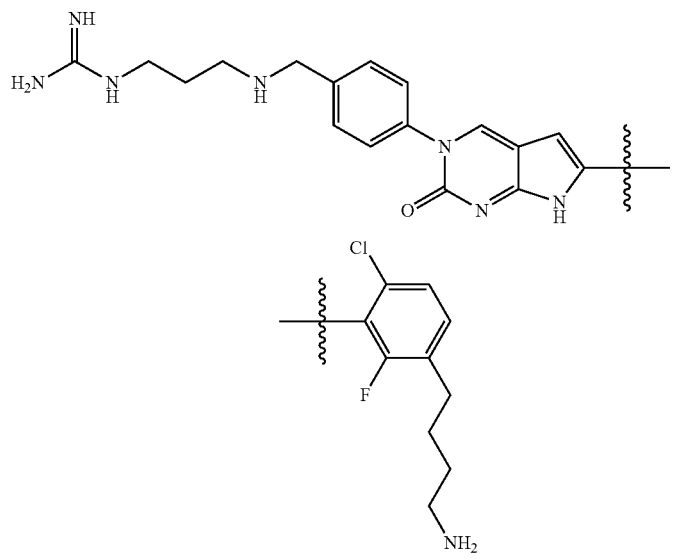

73 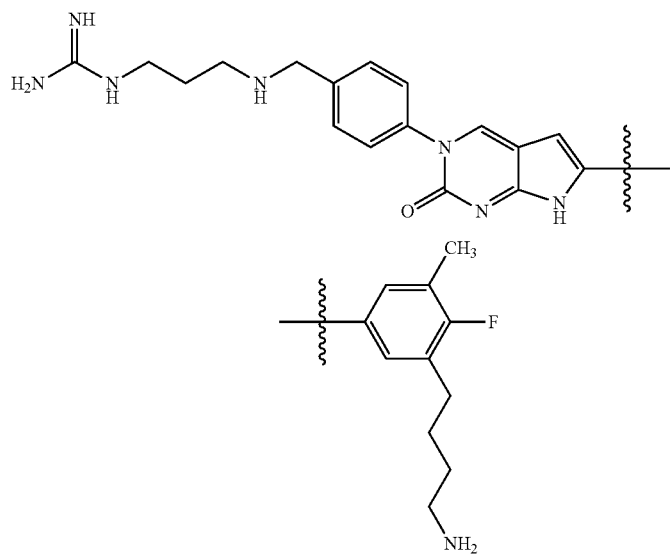
74 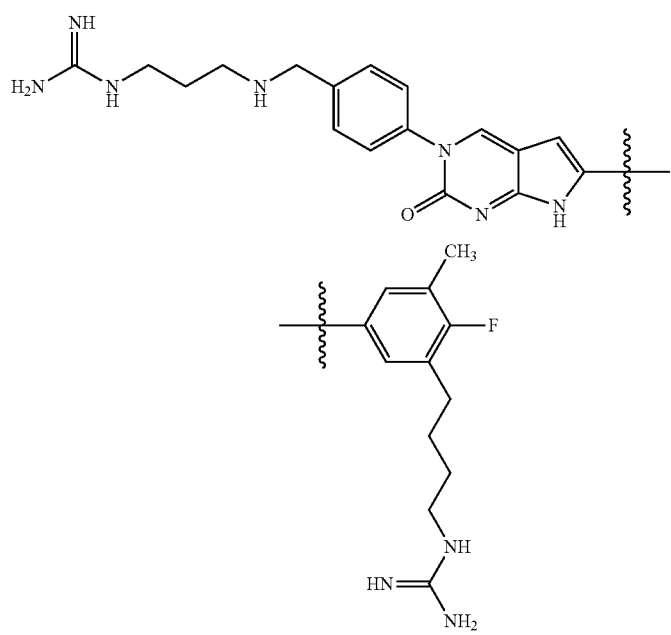

75
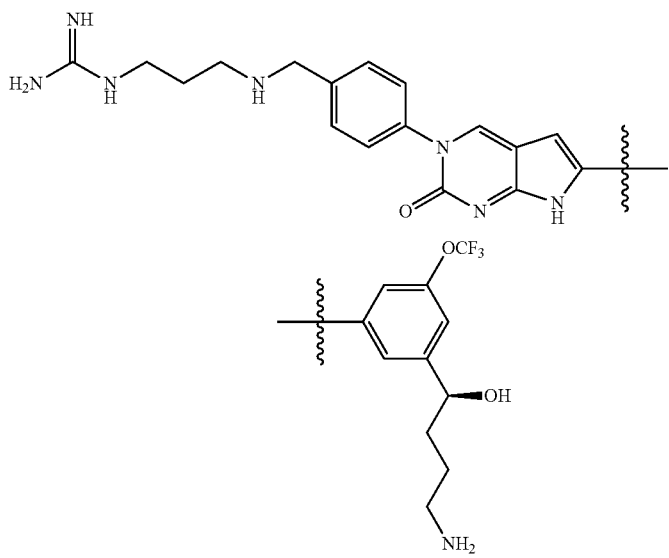
76
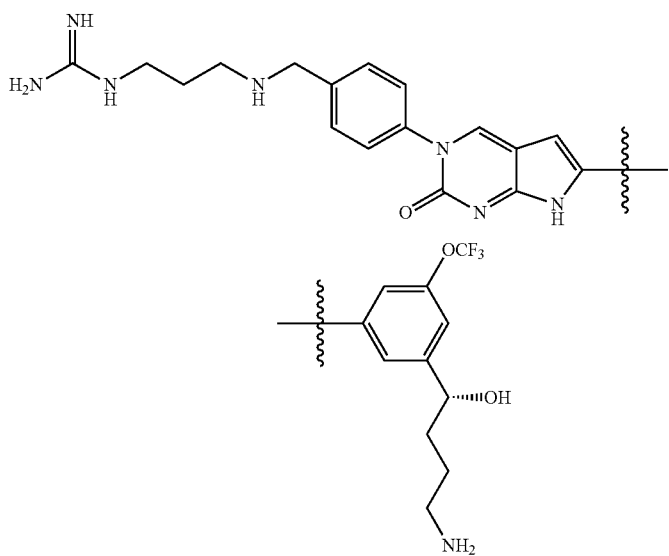

77 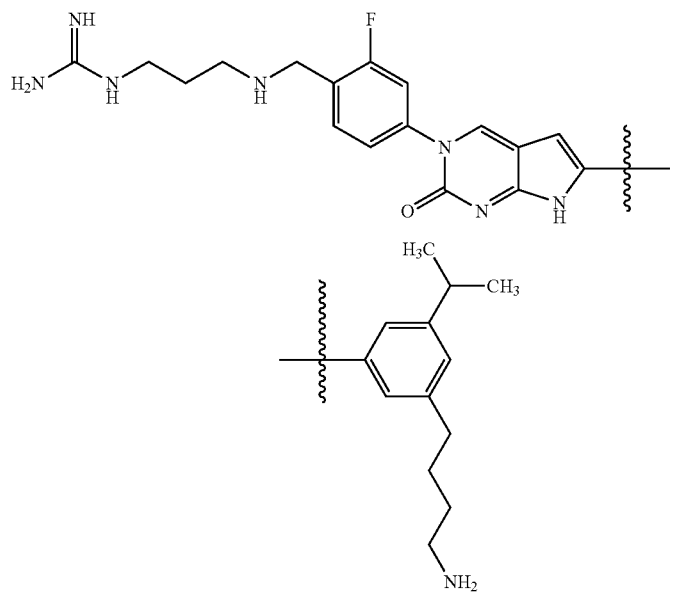
78 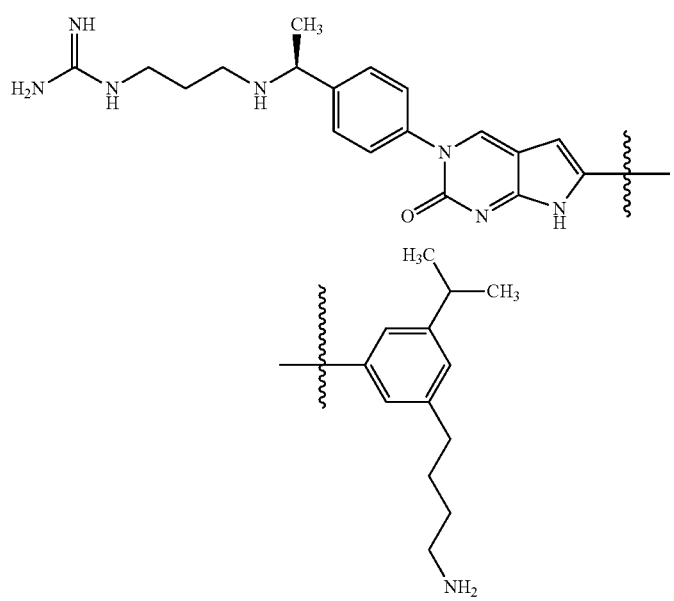

79 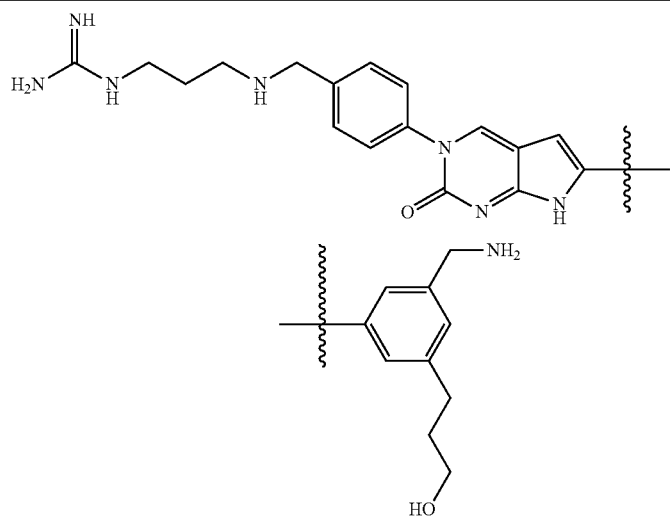
80 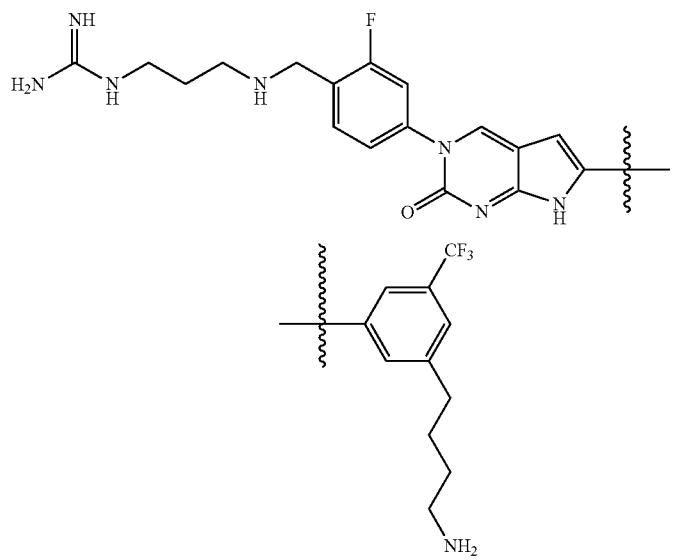
81 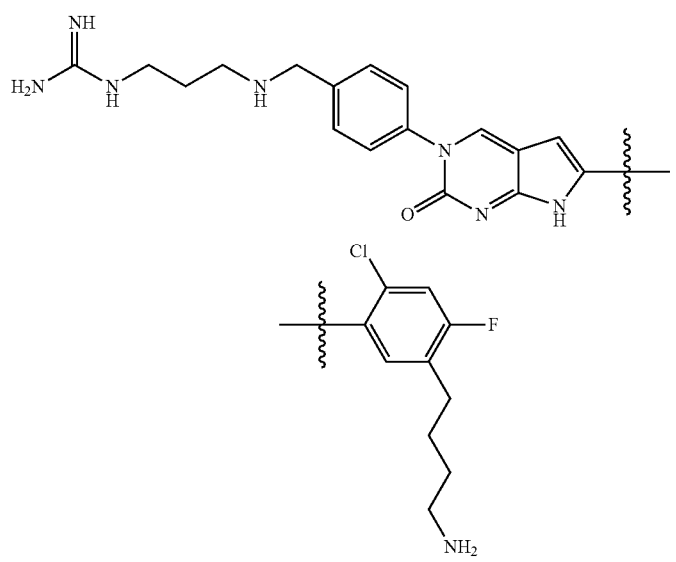

| | |
|---|---|
| 82 | 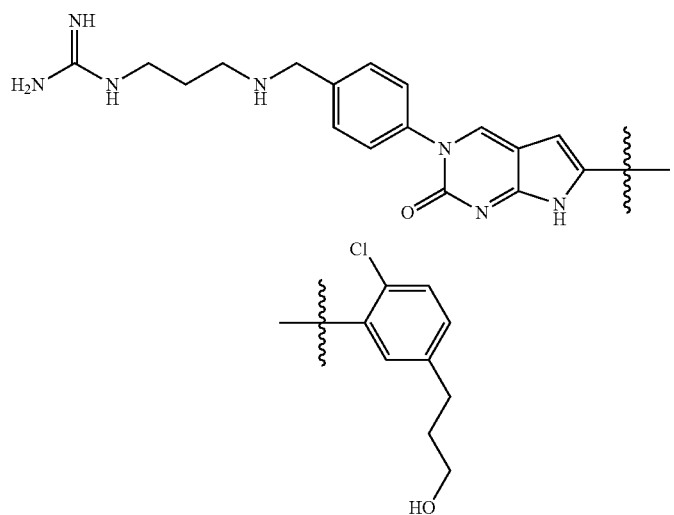 |
| 83 | 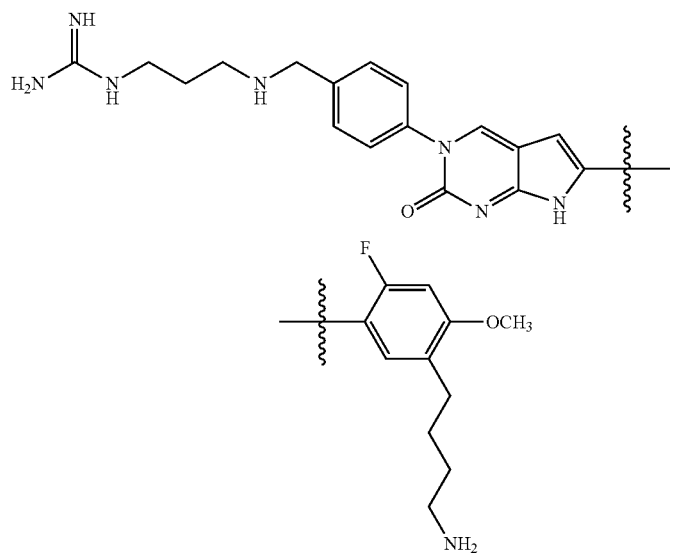 |
| 84 | 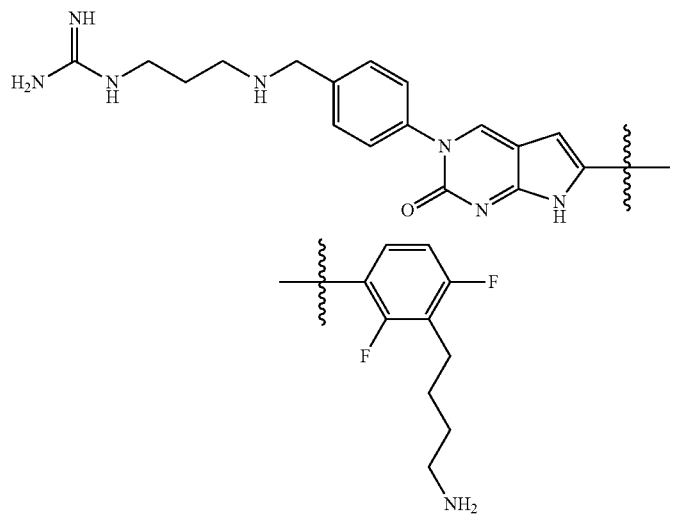 |

85 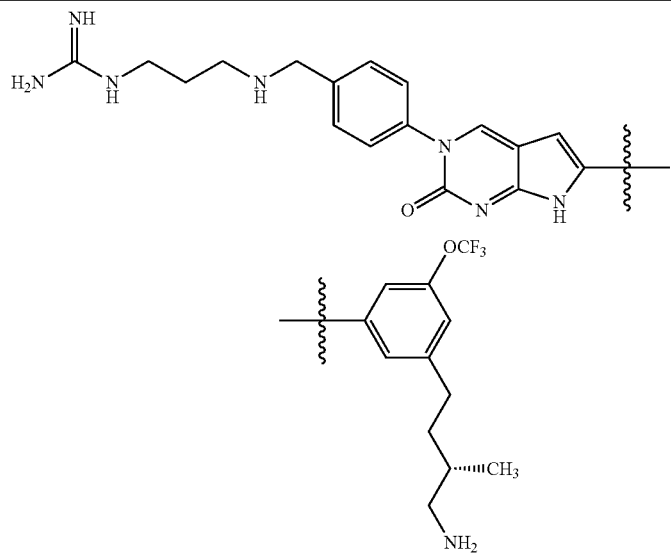
86 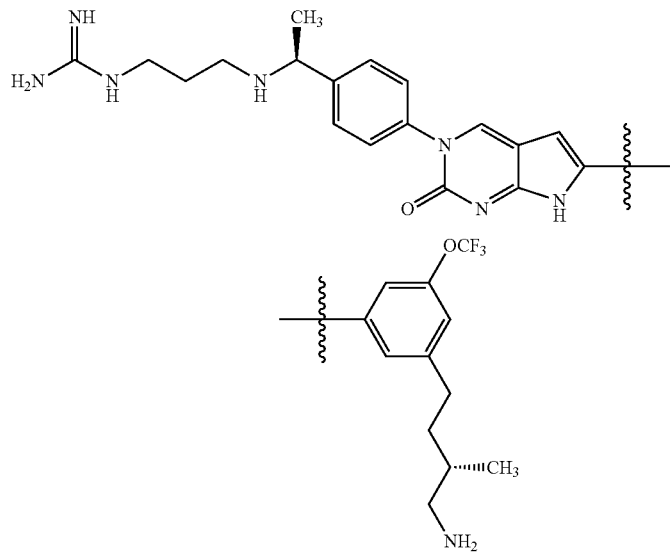
87 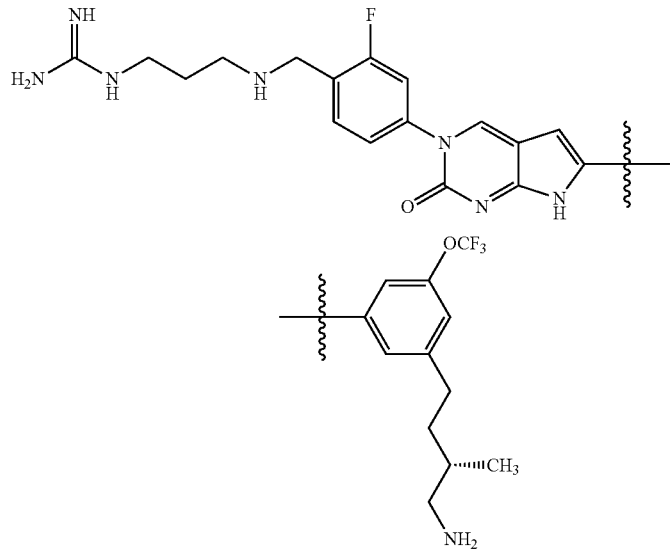

88 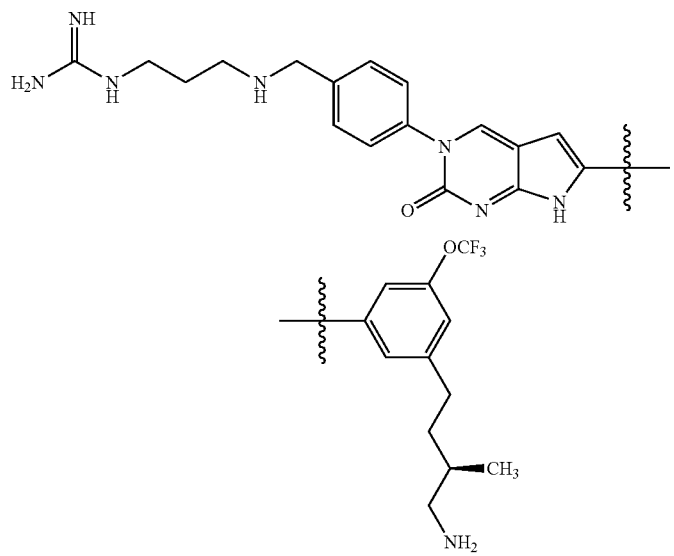
89 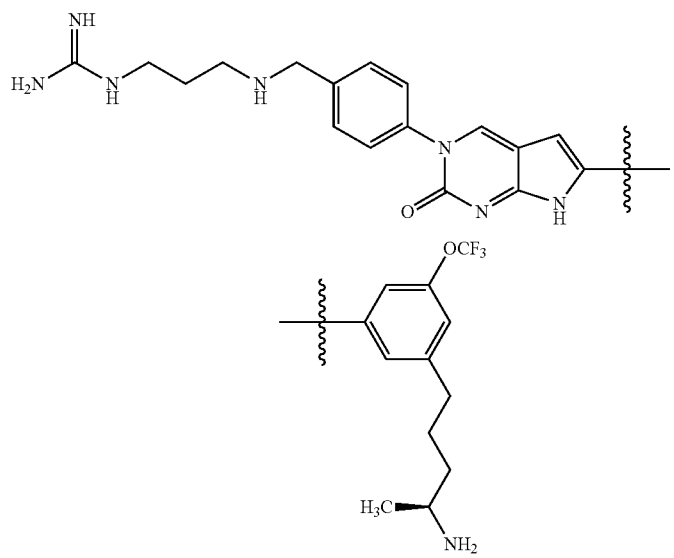

90 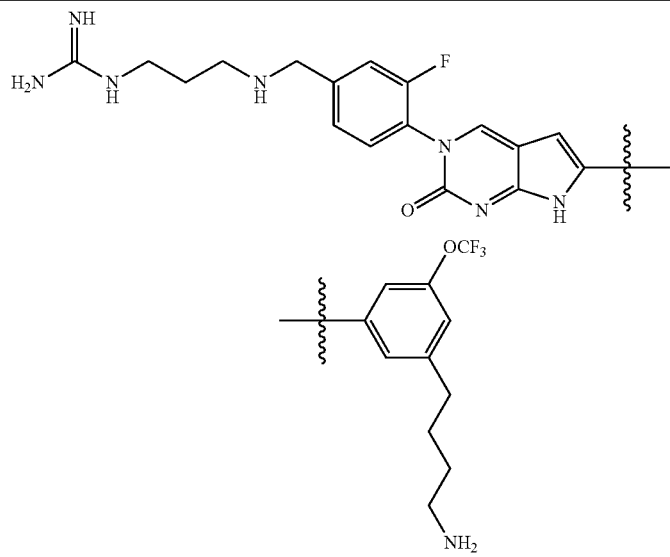
91 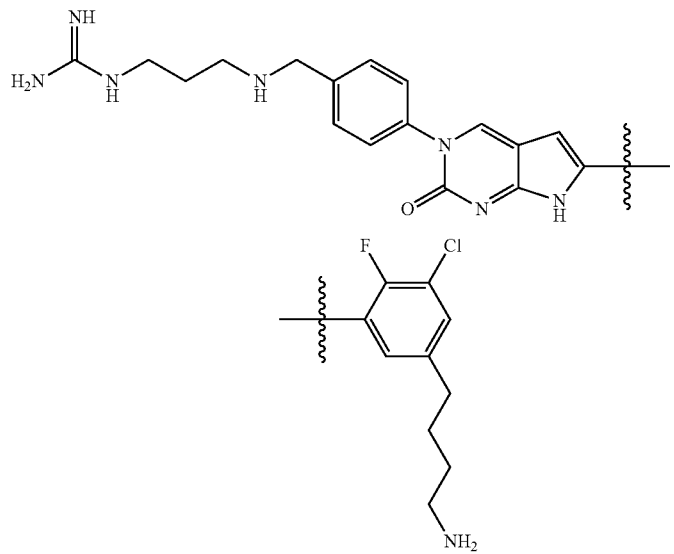
92 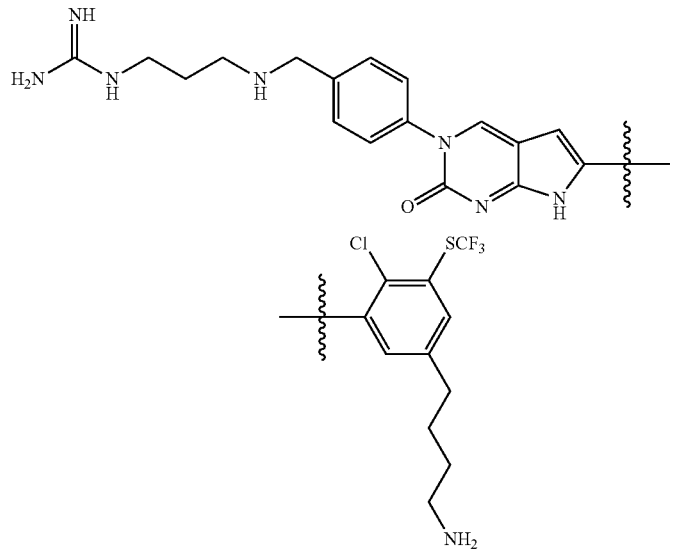

93
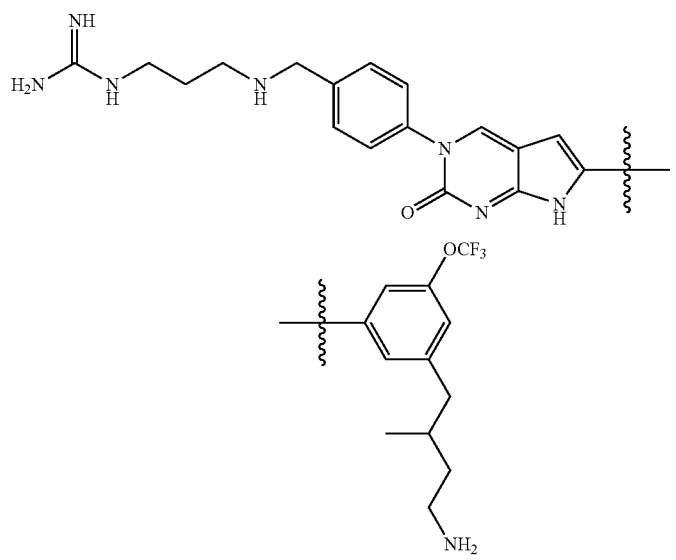
94
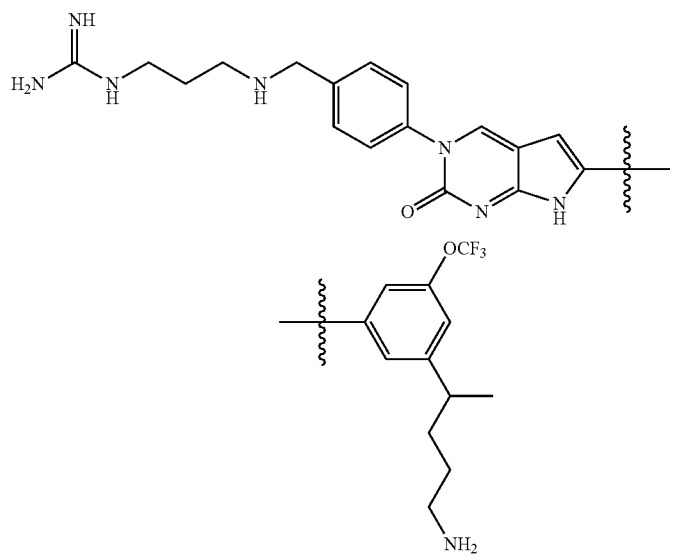

95 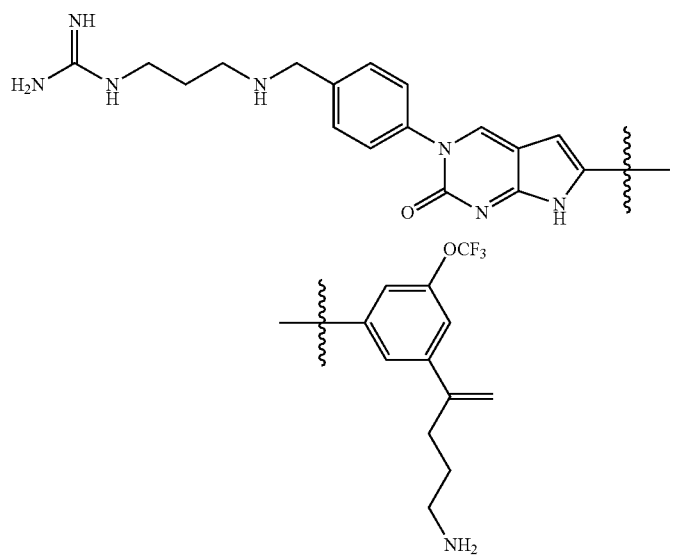
96 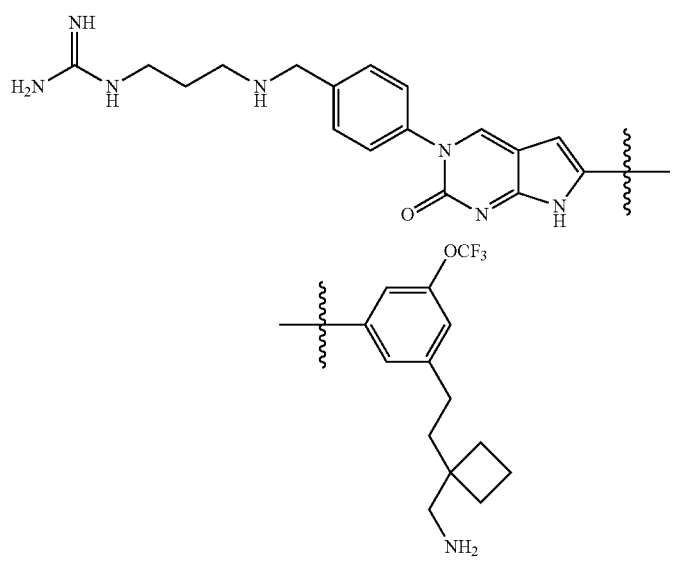

97 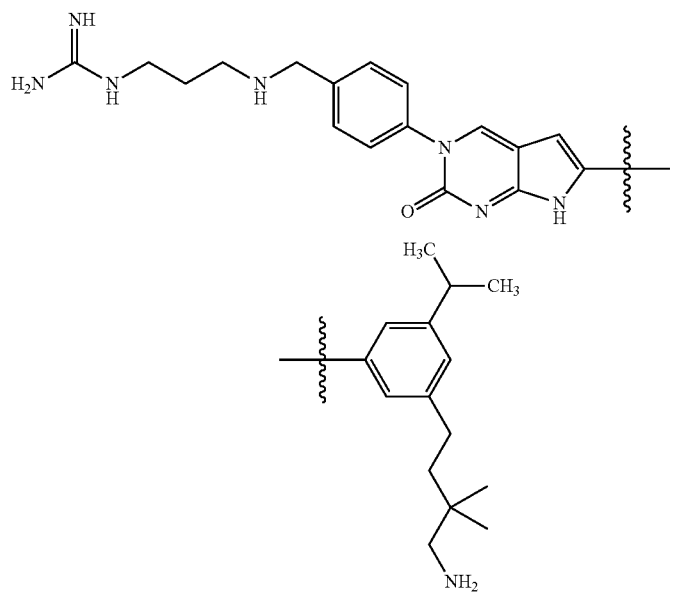
98 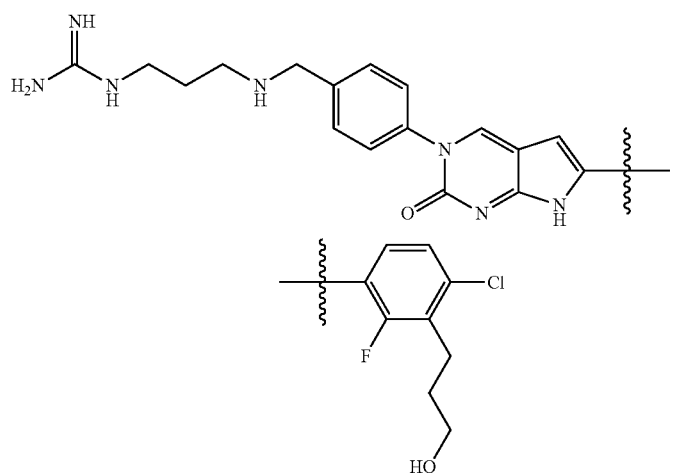
99 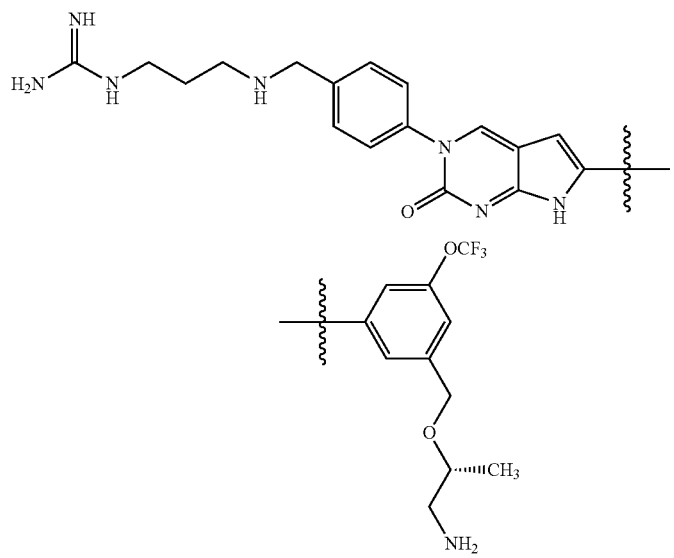

| | |
|---|---|
| 100 | 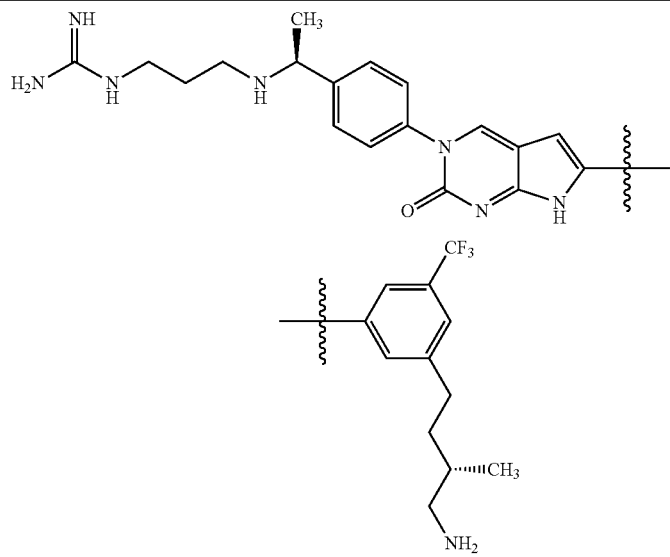 |
| 101 | 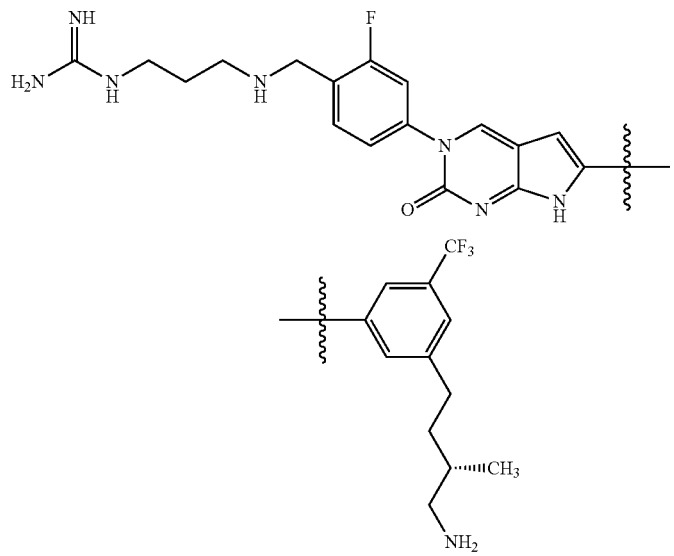 |
| 102 | 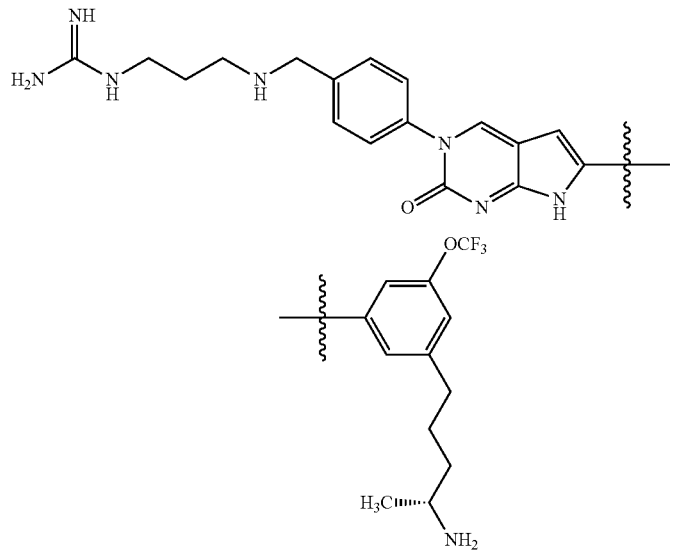 |

103 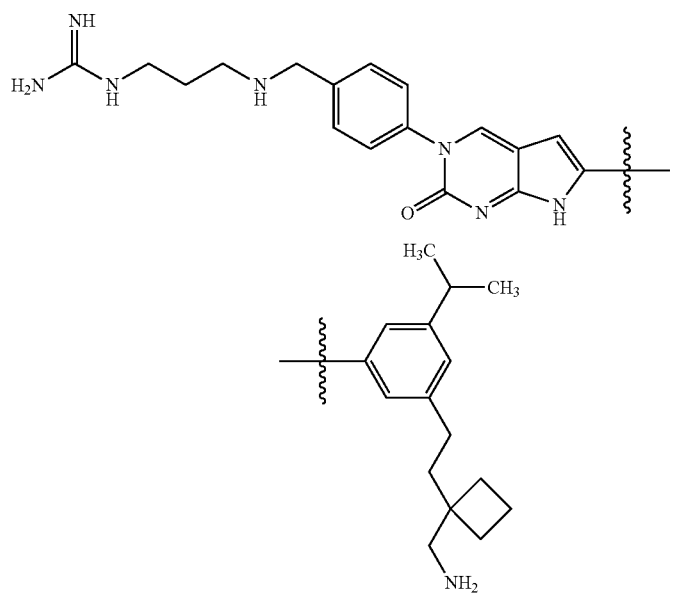
104 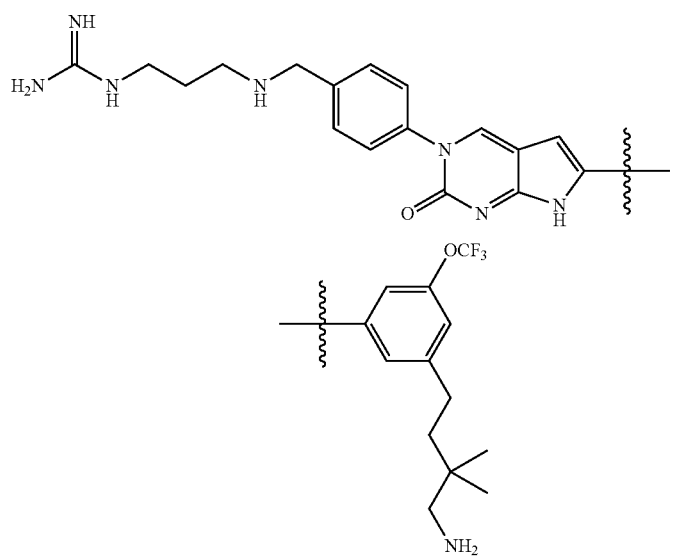

105 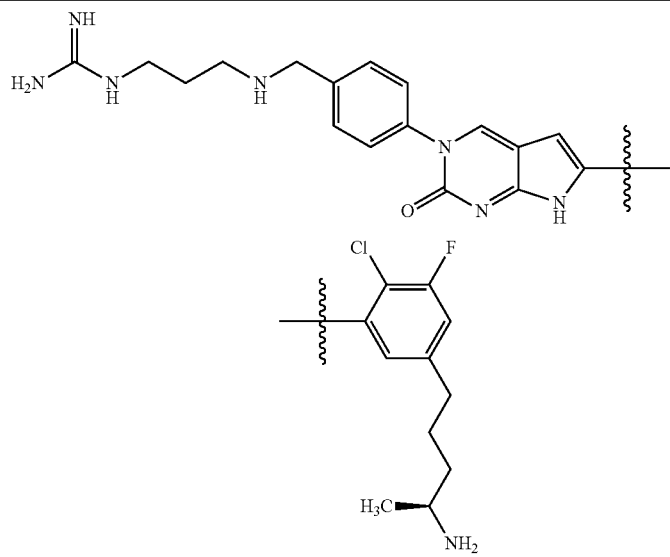
106 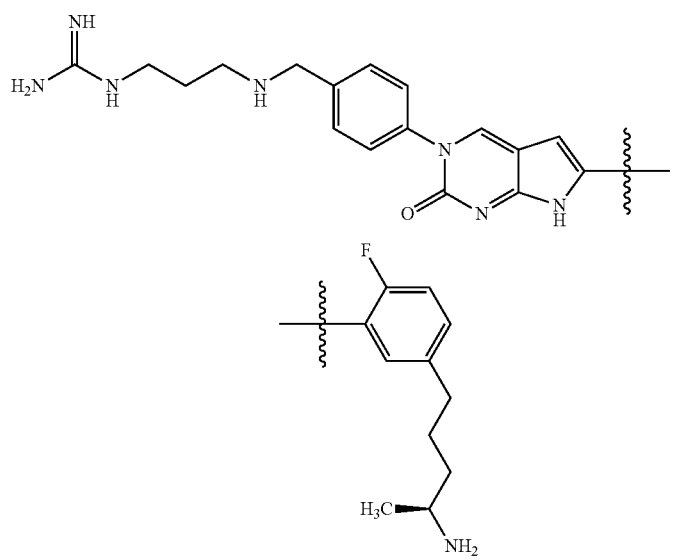
107 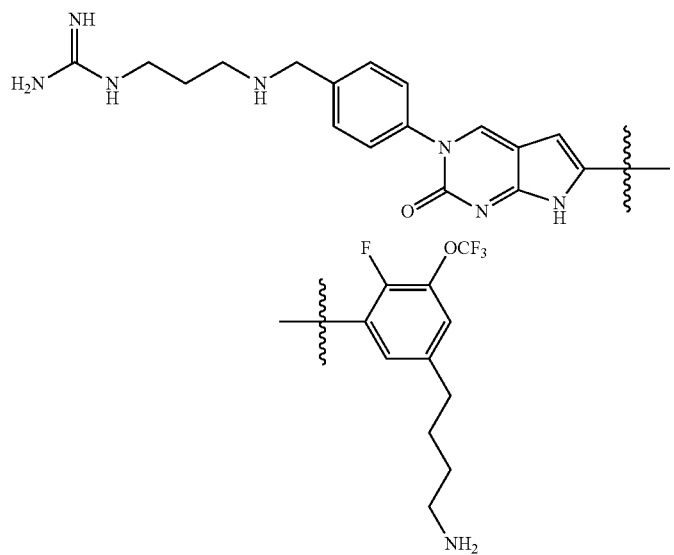

-continued
108
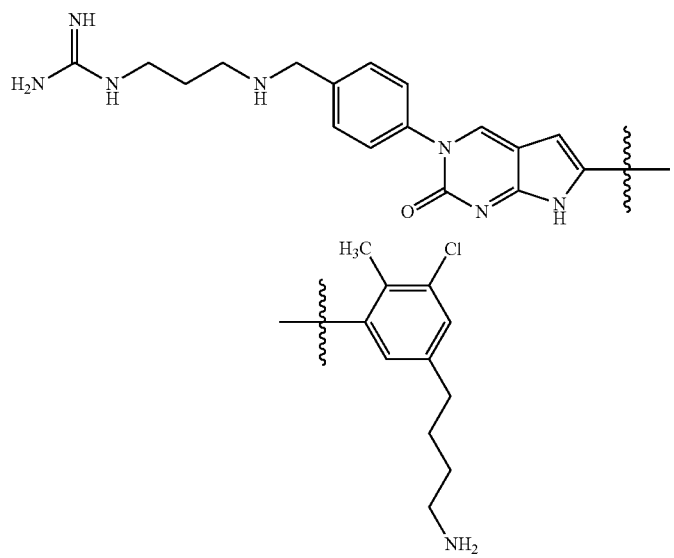
109
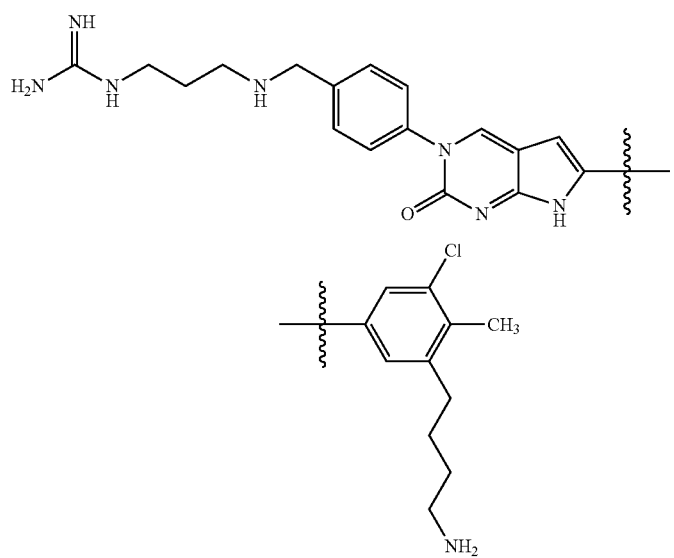
110
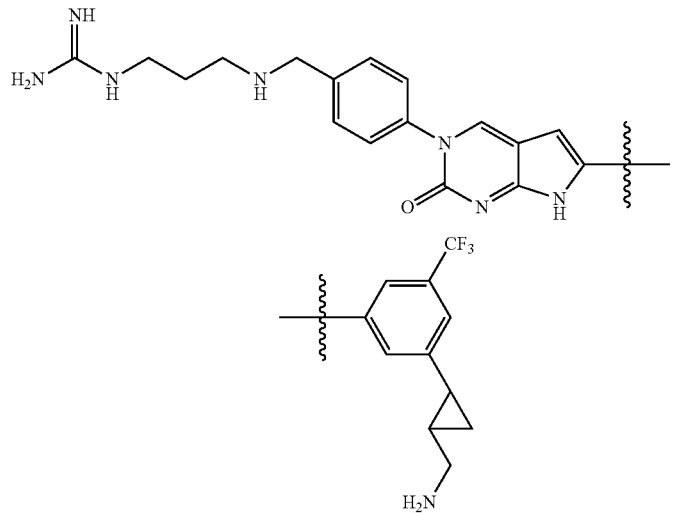

-continued
111
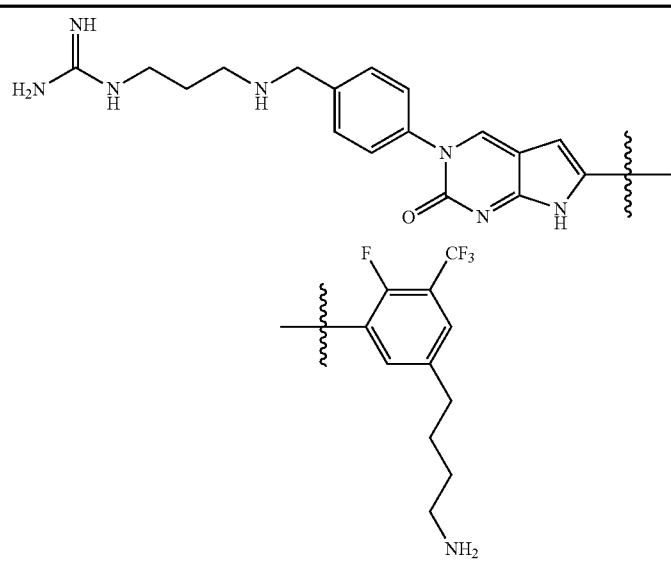
112
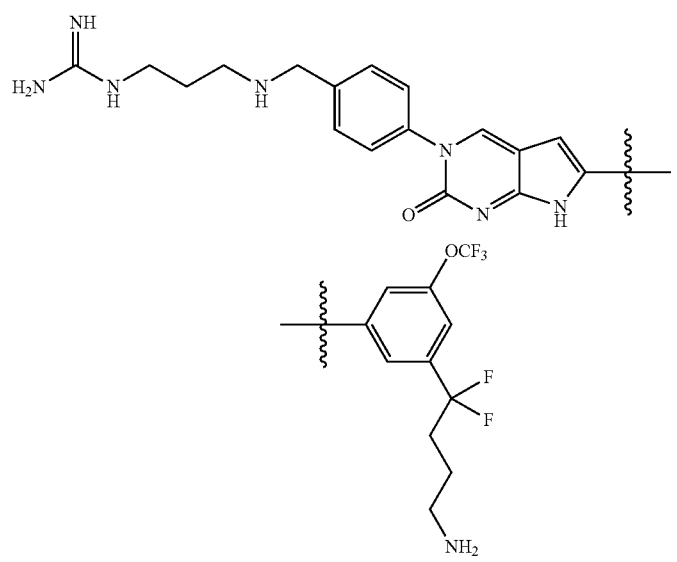
113
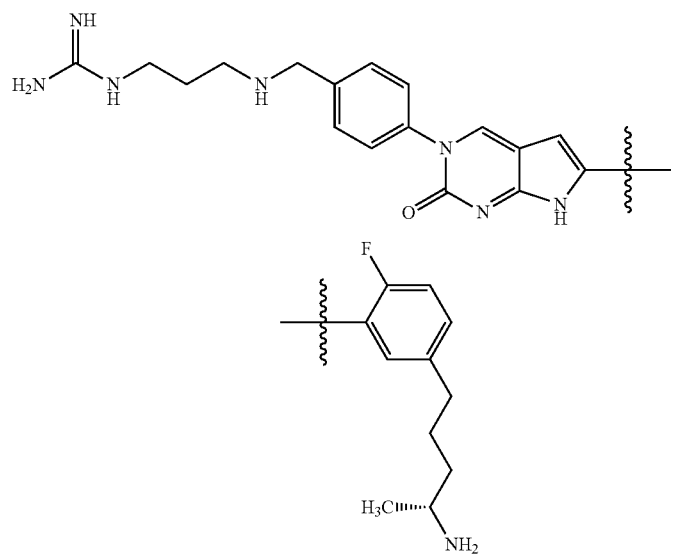

114 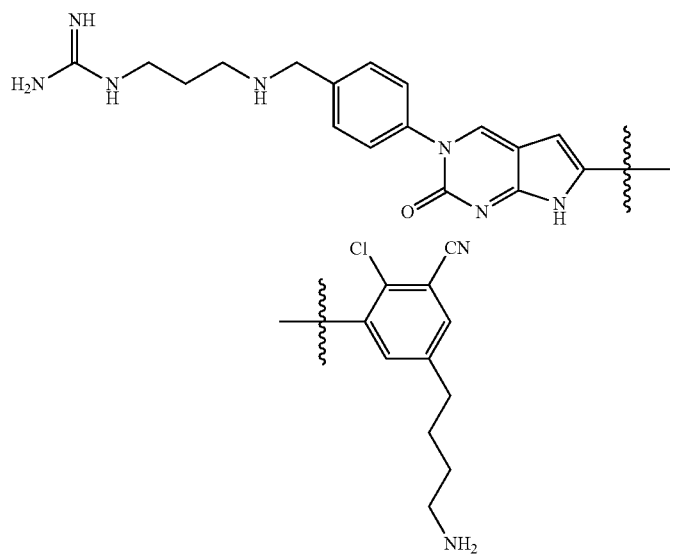
115 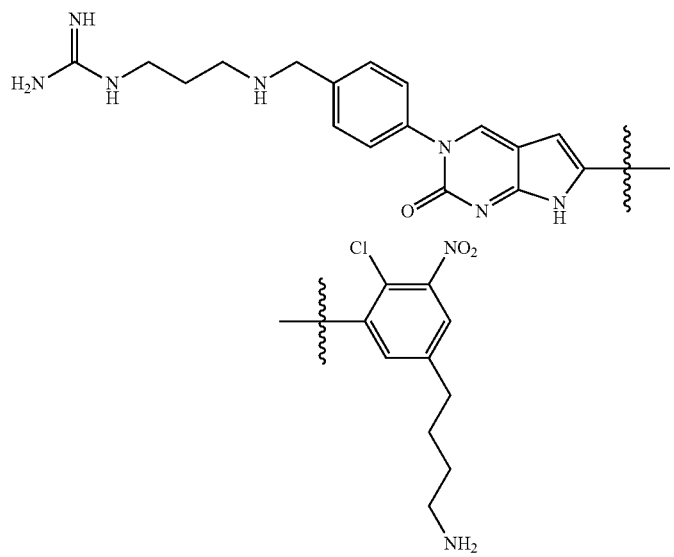

116 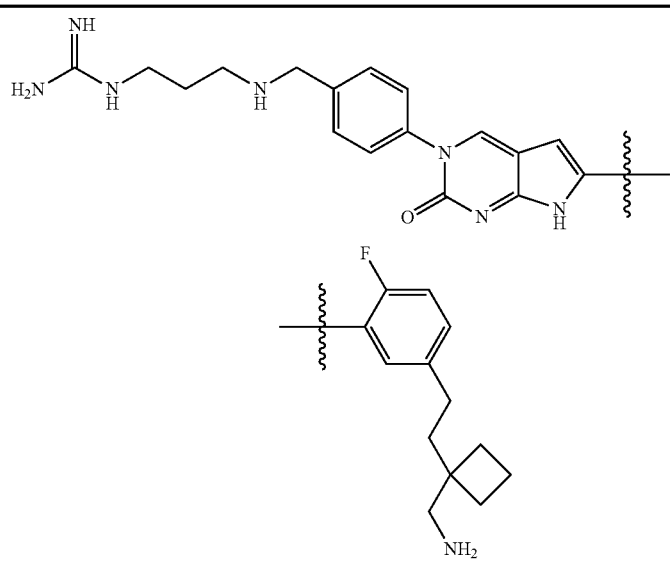
117 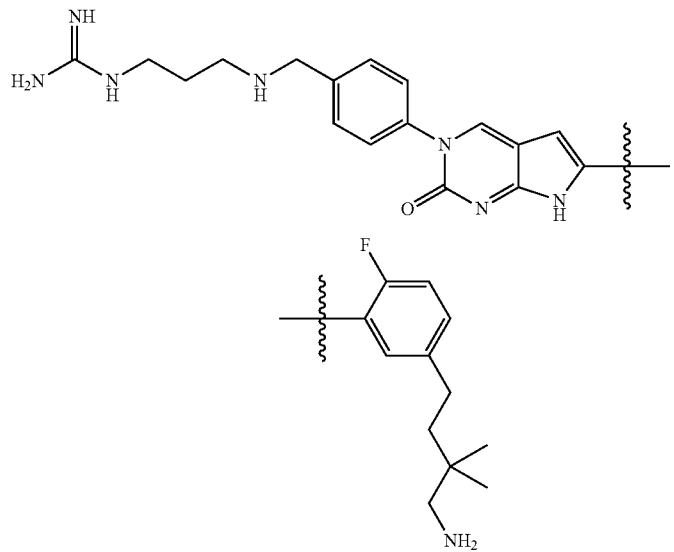
118 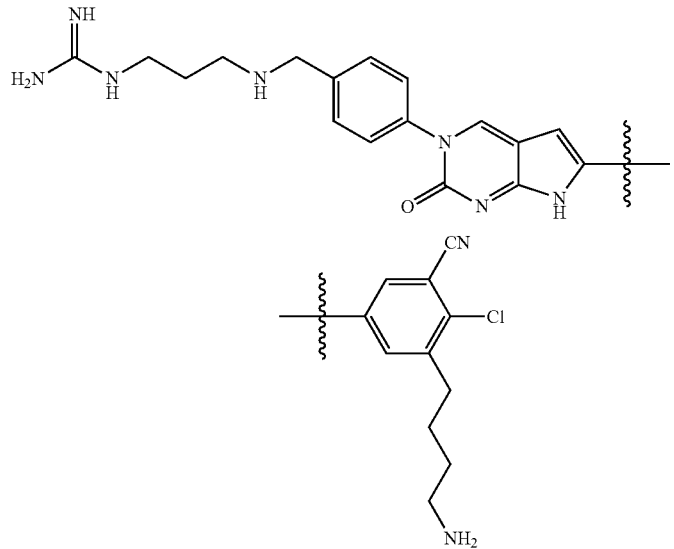

119 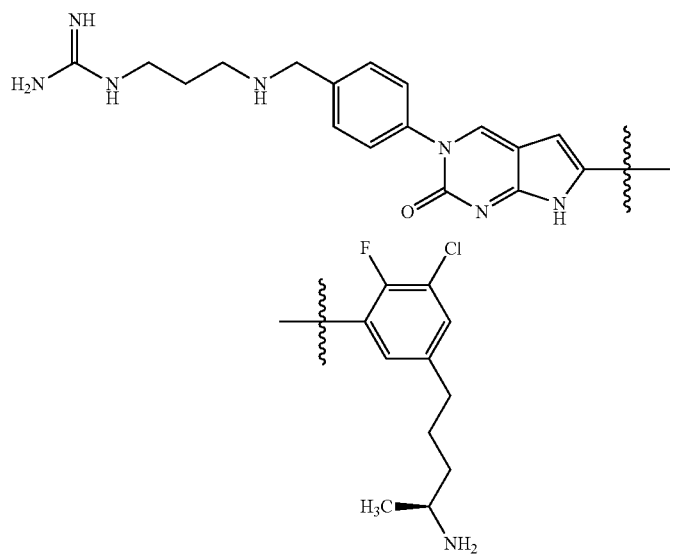
120 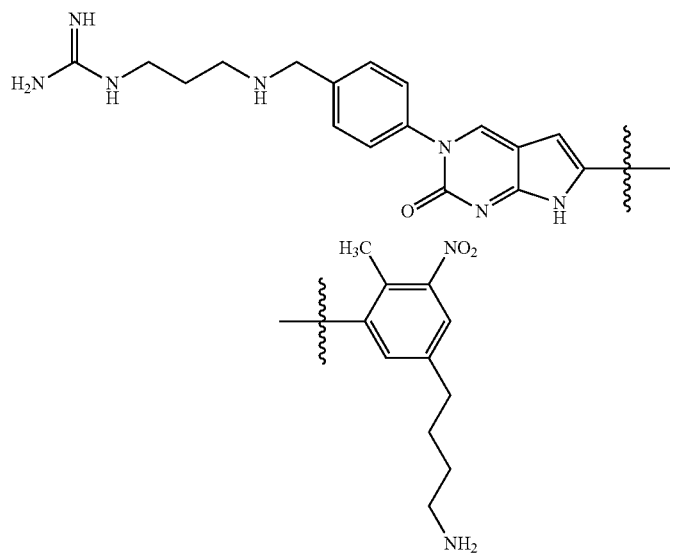

121 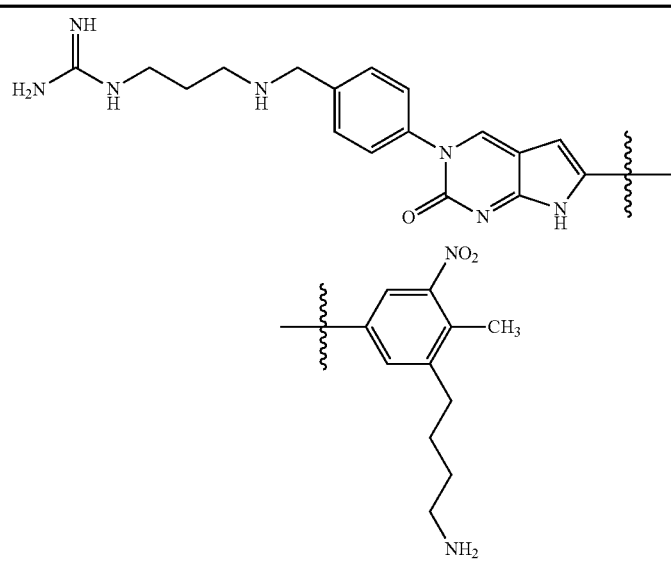
122 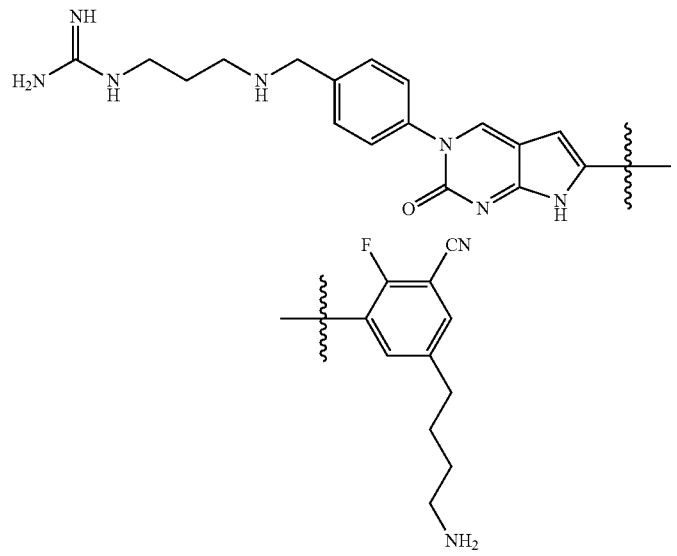
123 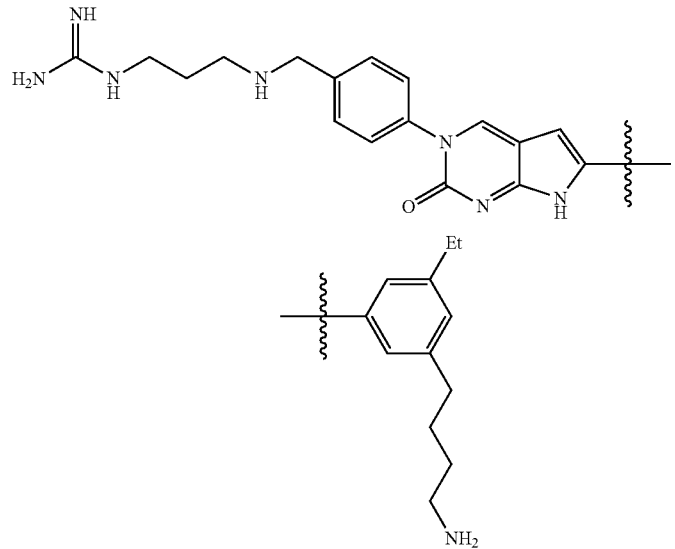

124 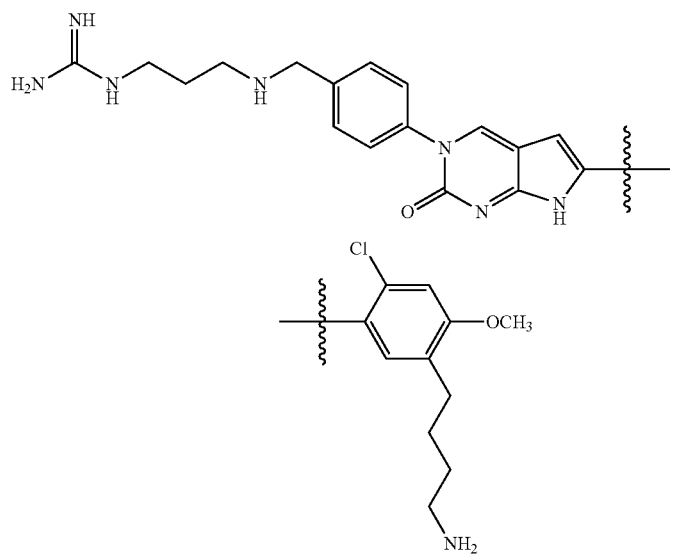
125 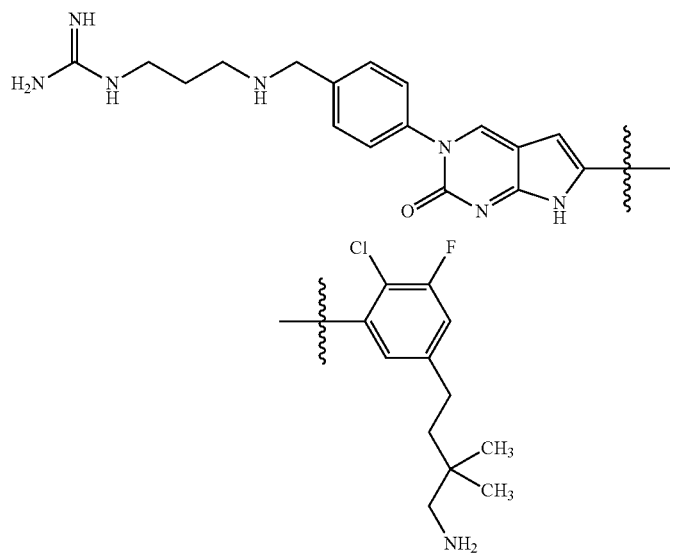

126 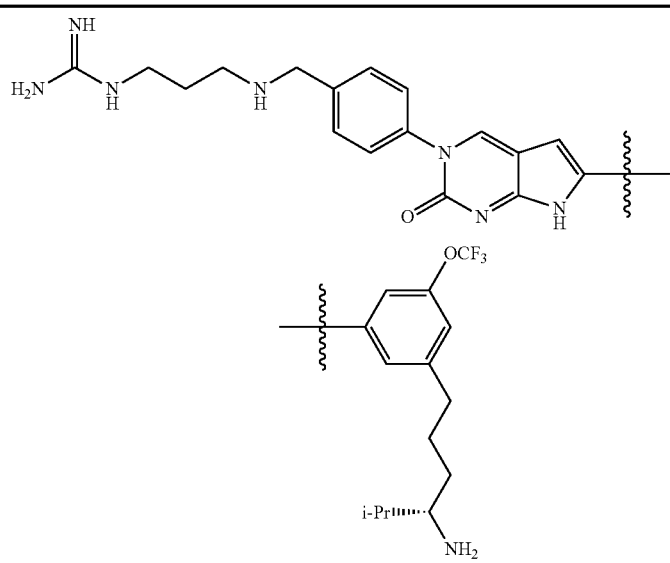
127 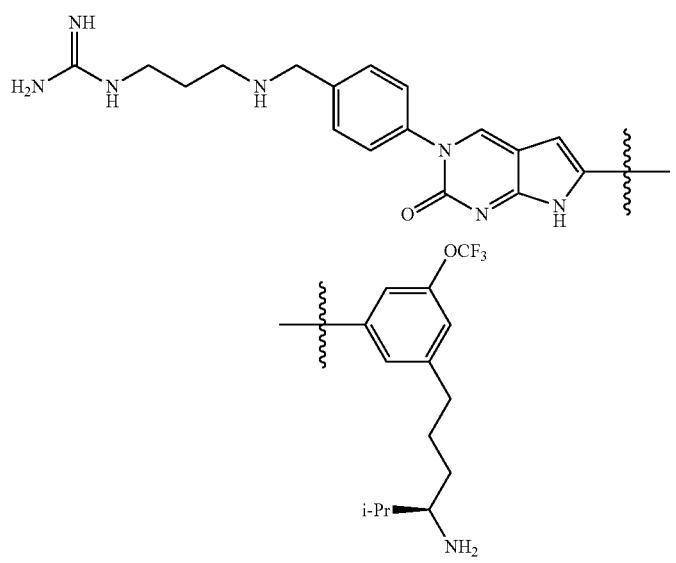
128 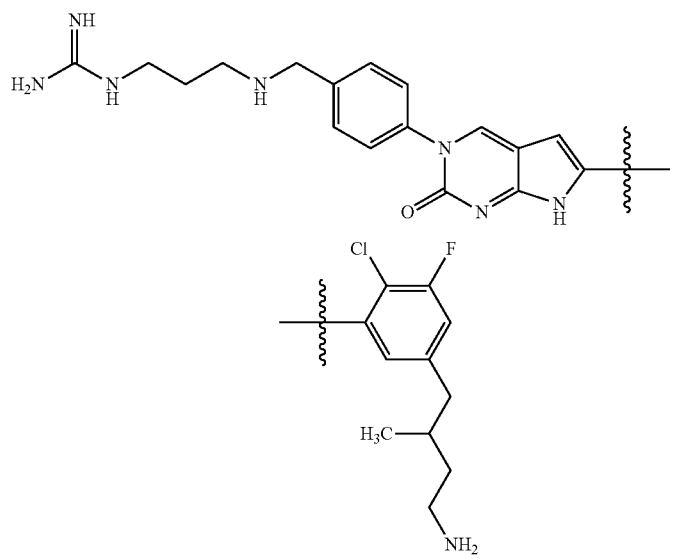

129 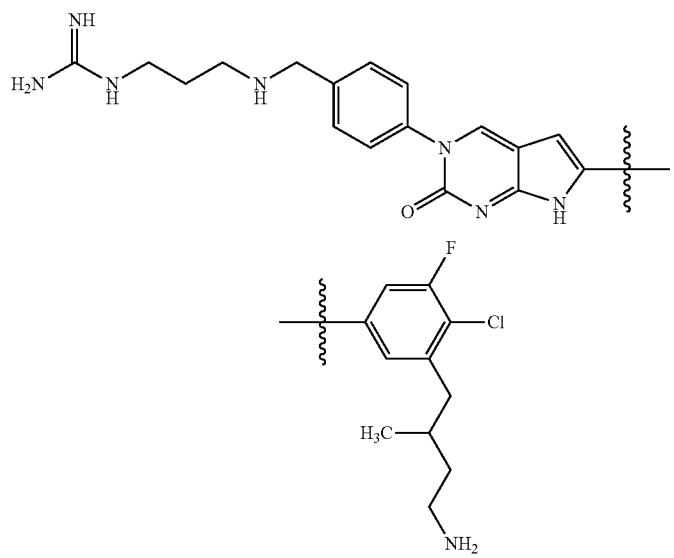
130 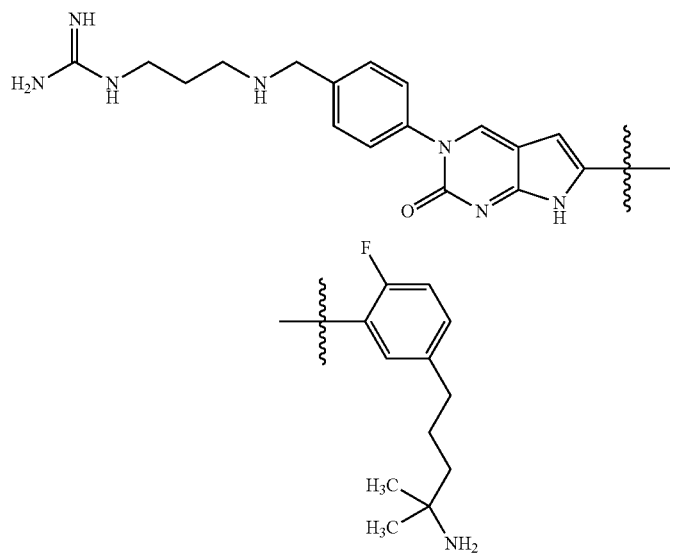

131 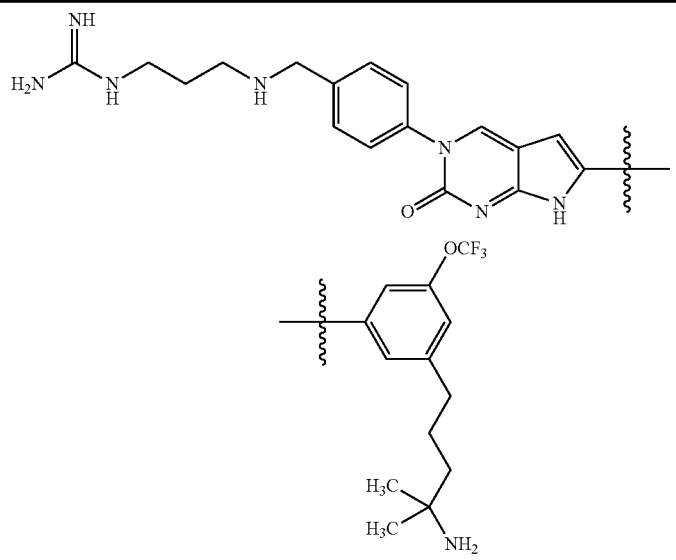
132 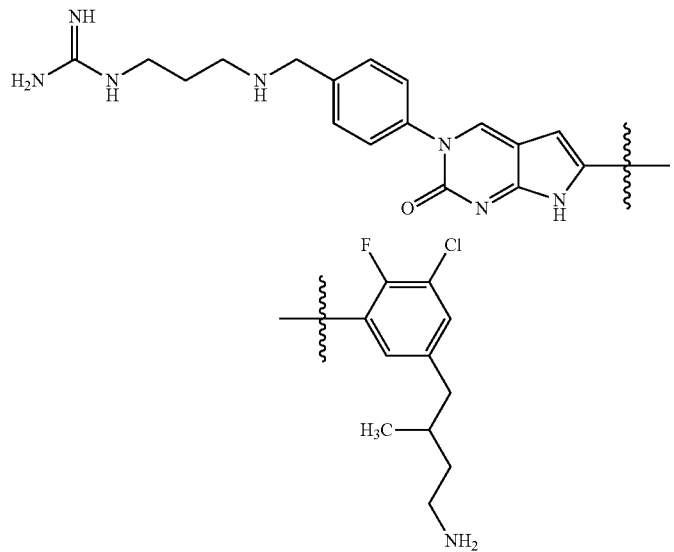
133 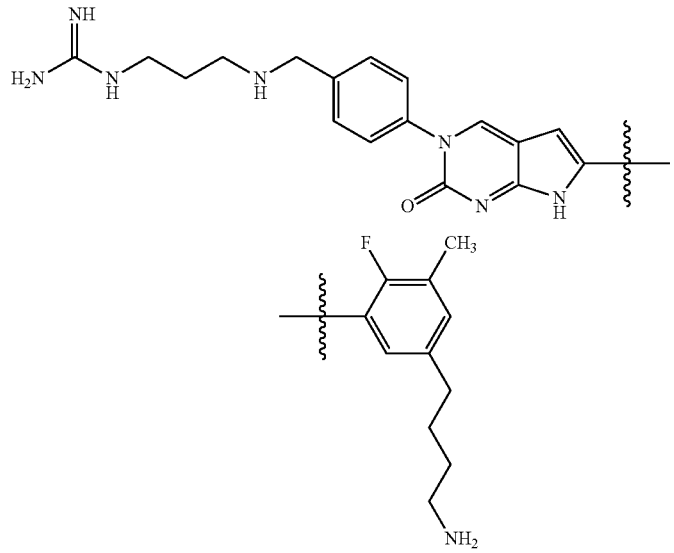

134 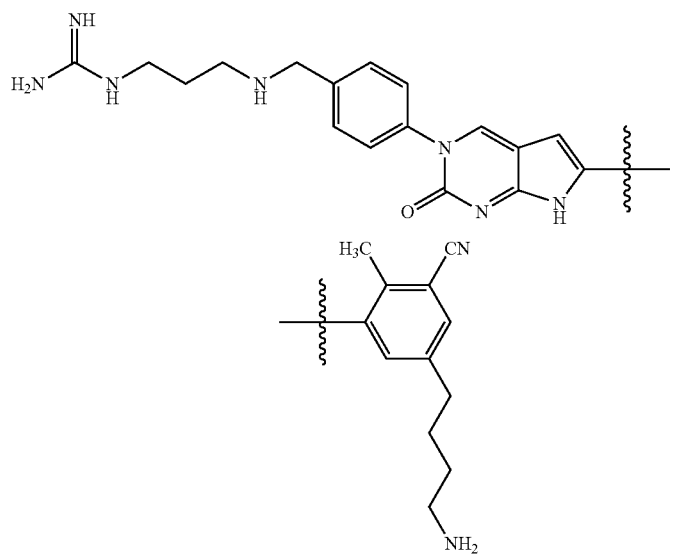
135 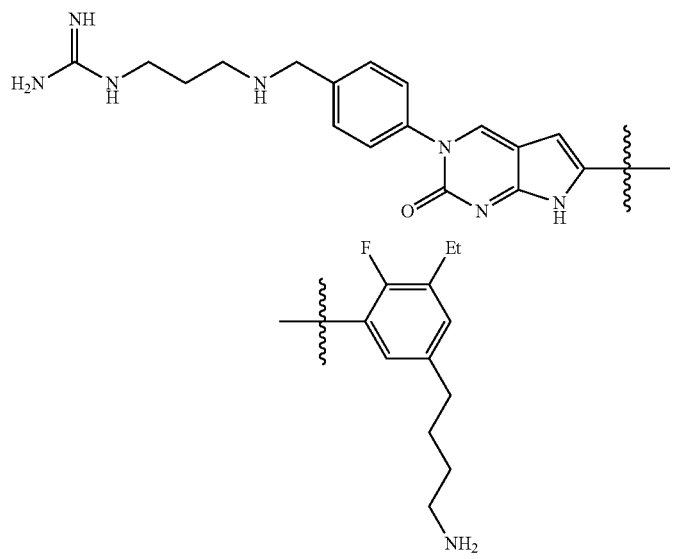

136 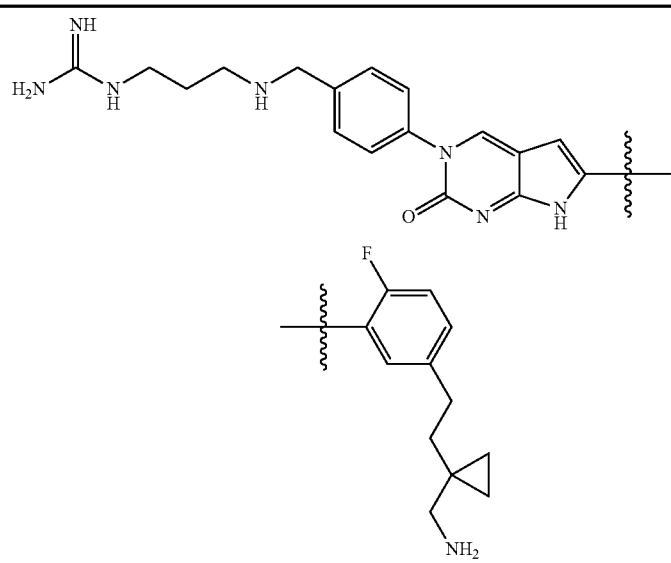
136 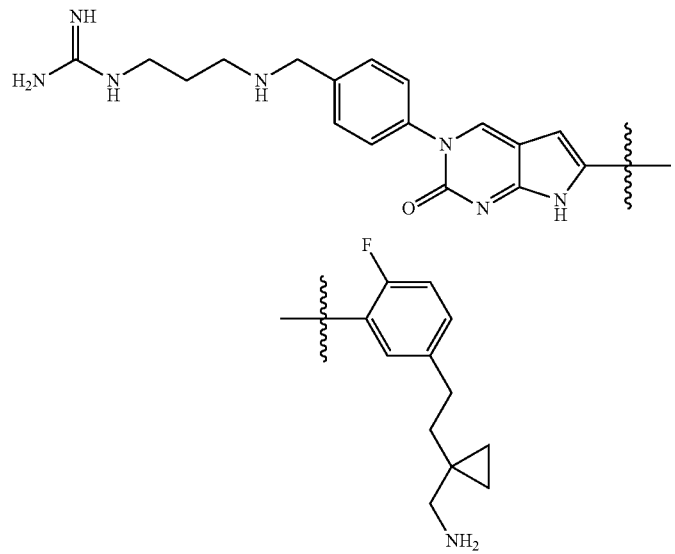
137 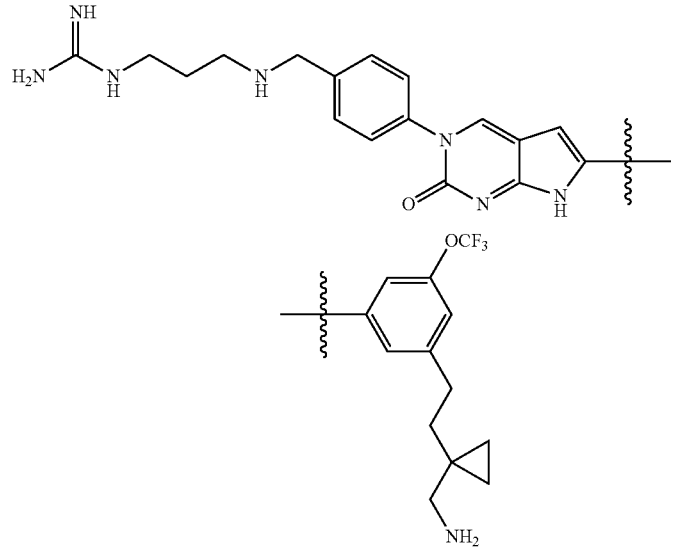

138 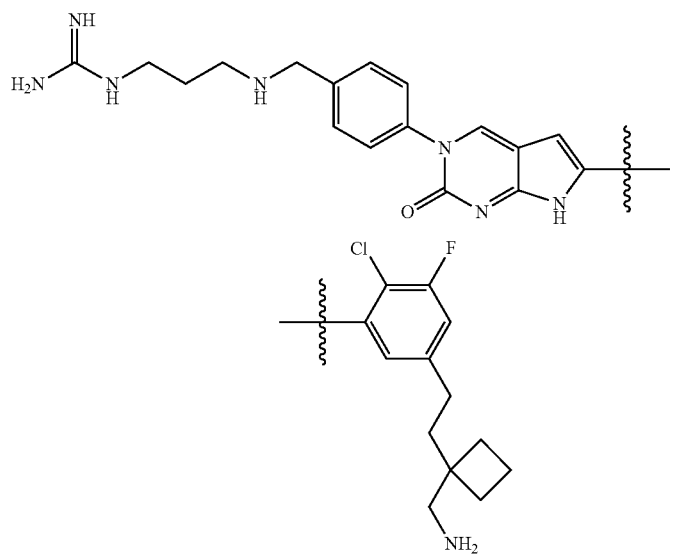
139 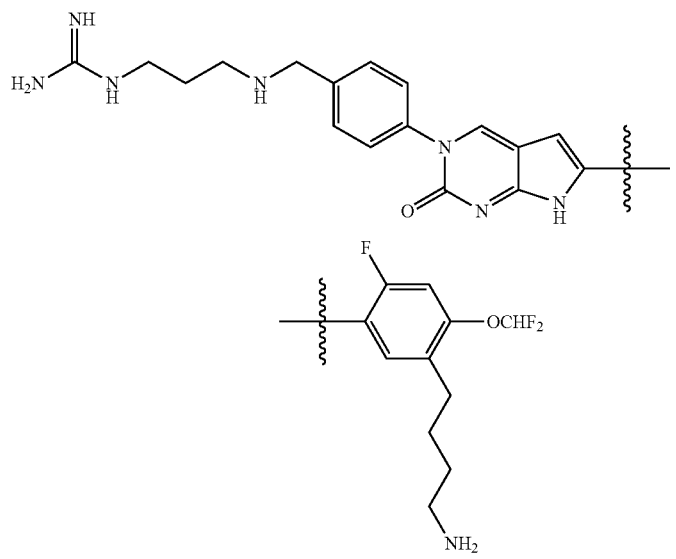

140
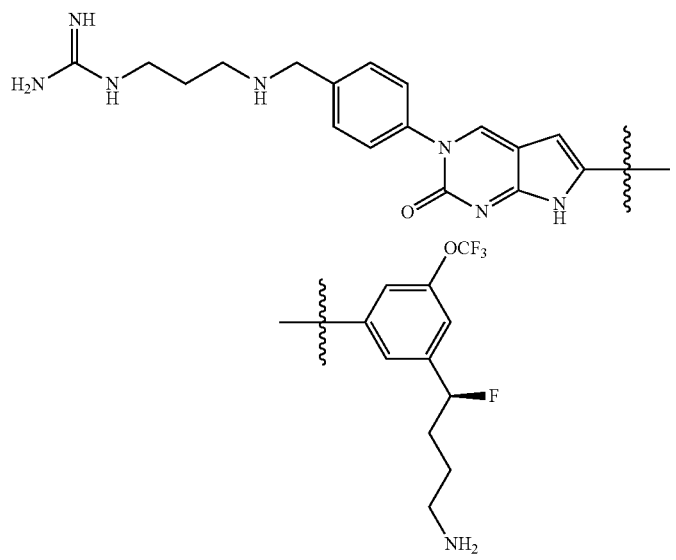
141
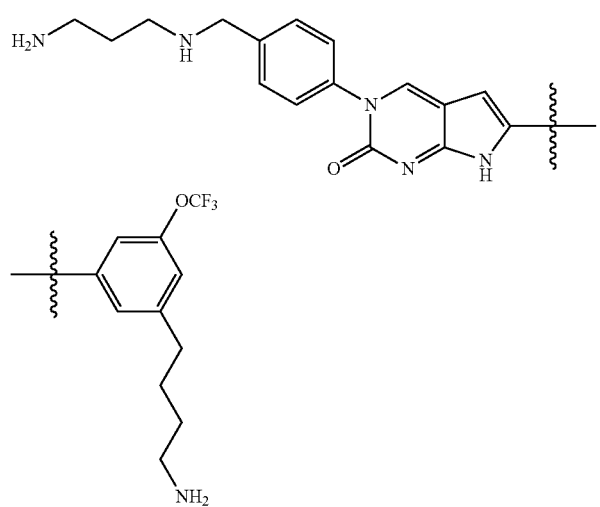
142
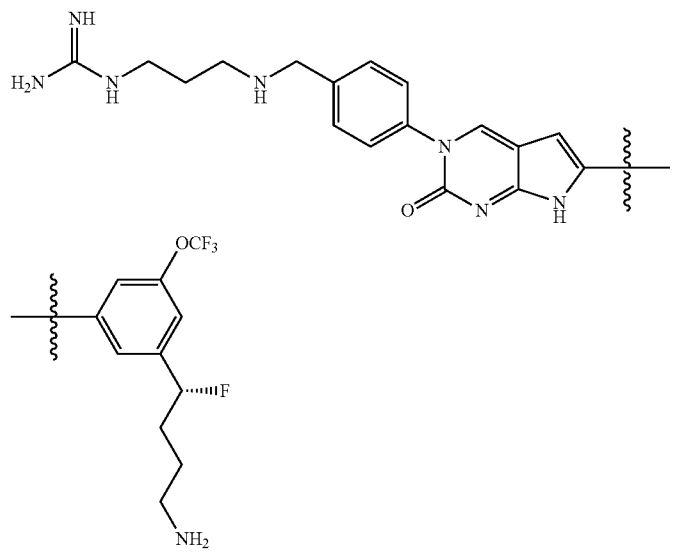

143 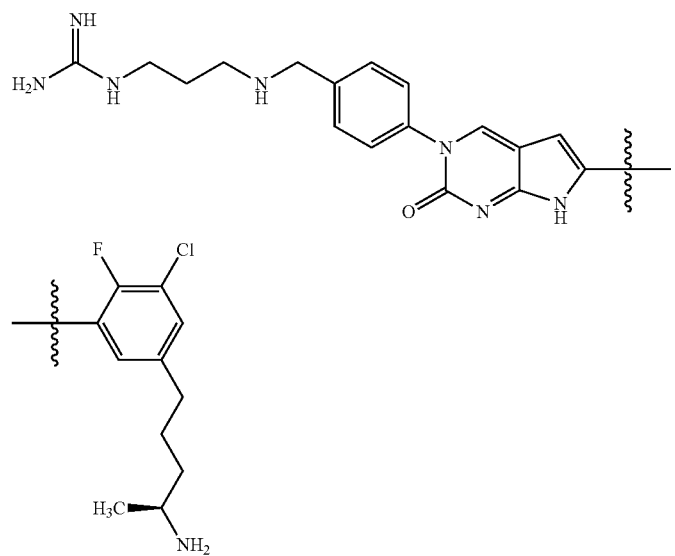
144 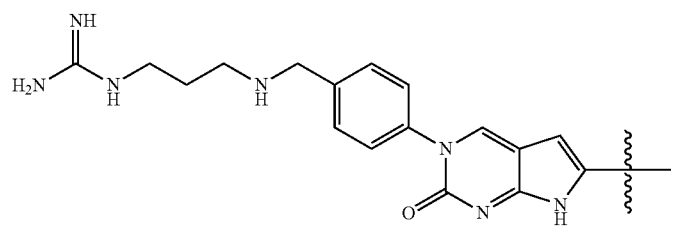
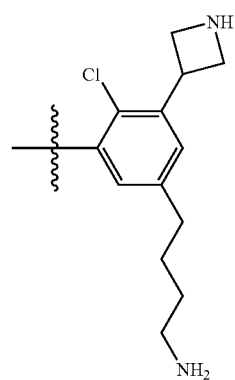
145 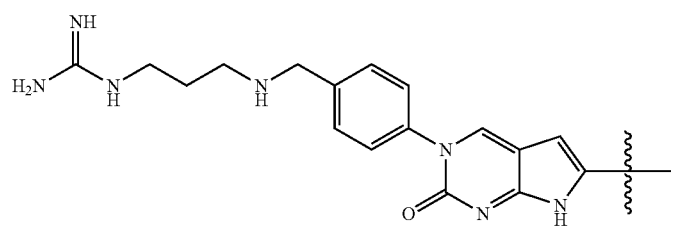

-continued
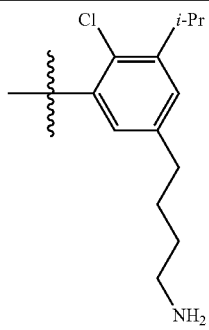
146 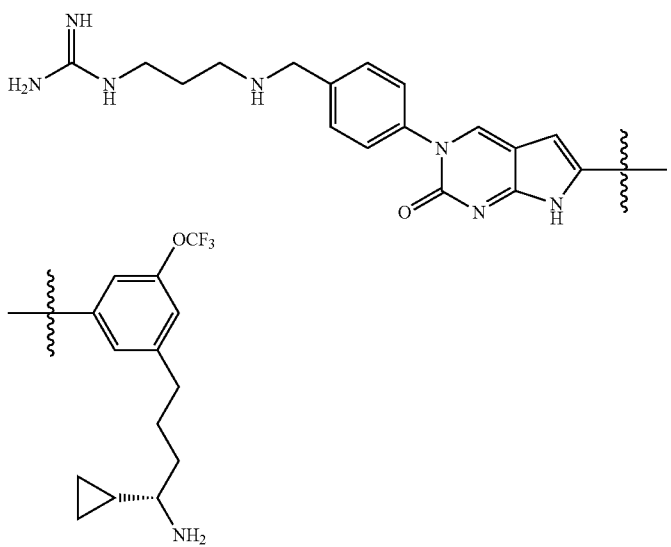
147 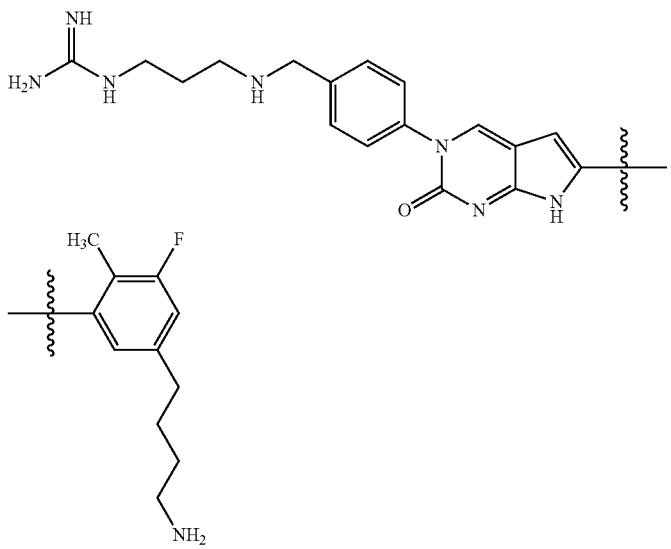
148 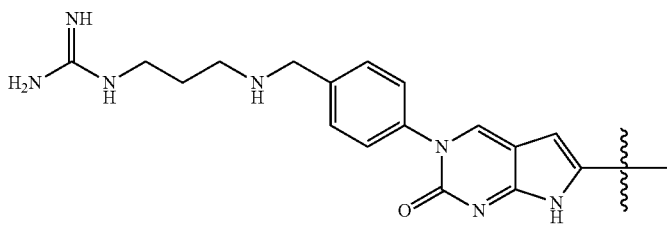

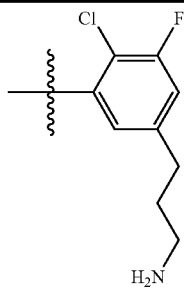
149 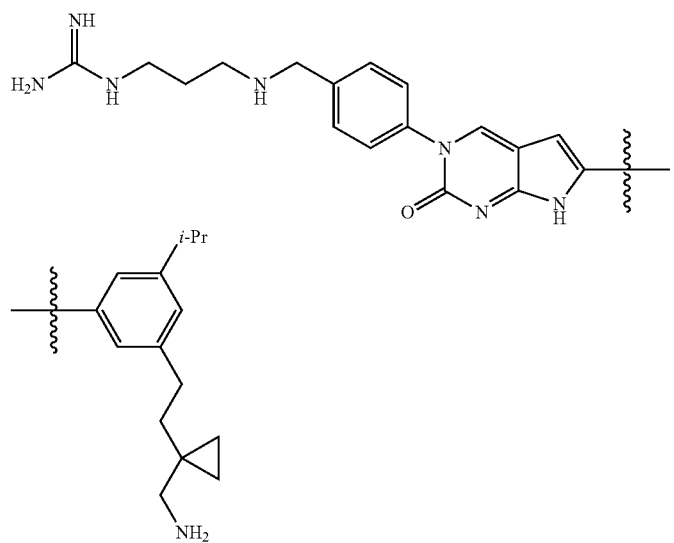
192 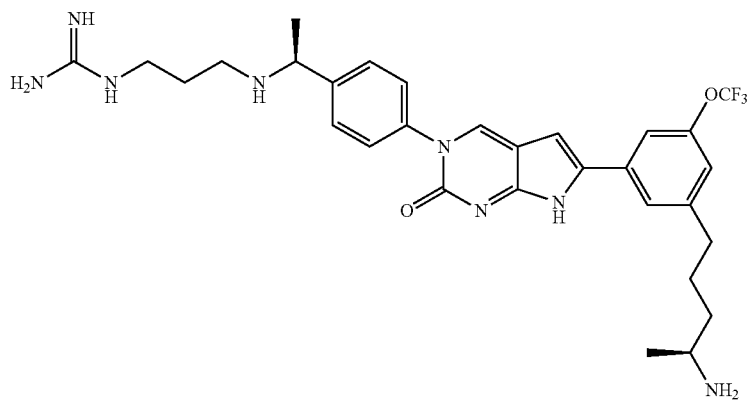 [SMILES: C[C@H](N)CCCc1cc(OC(F)(F)F)cc(-c2cc3cn(-c4ccc([C@H](C)NCCCNC(=N)N)cc4)c(=O)nc3[nH]2)c1]
194 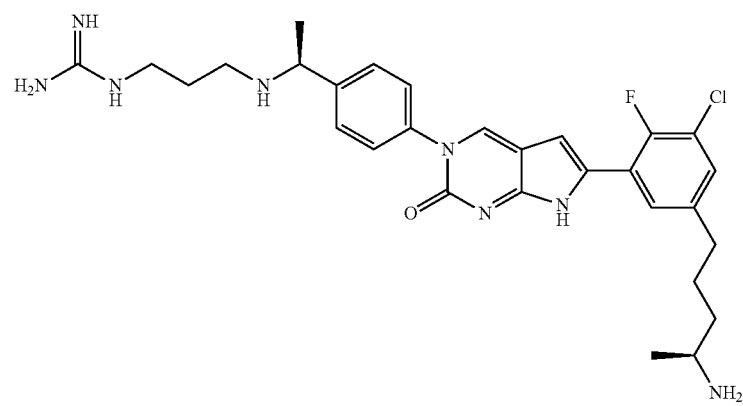 [SMILES: C[C@H](N)CCCc1cc(Cl)c(F)c(-c2cc3cn(-c4ccc([C@H](C)NCCCNC(=N)N)cc4)c(=O)nc3[nH]2)c1]

-continued
195 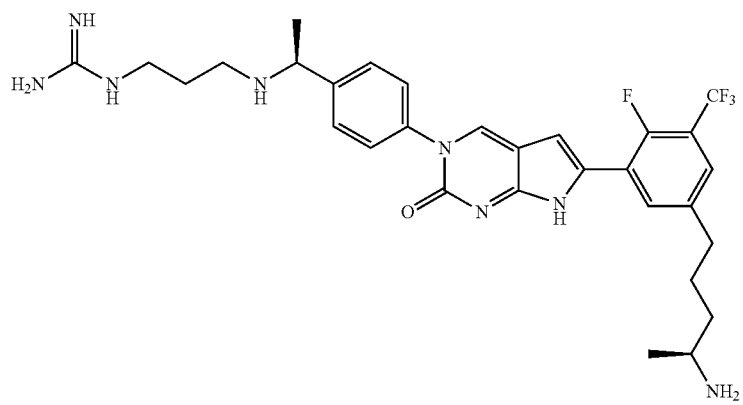
196 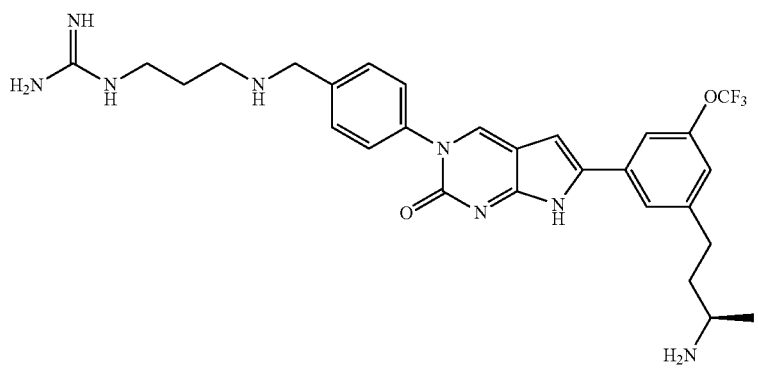
197 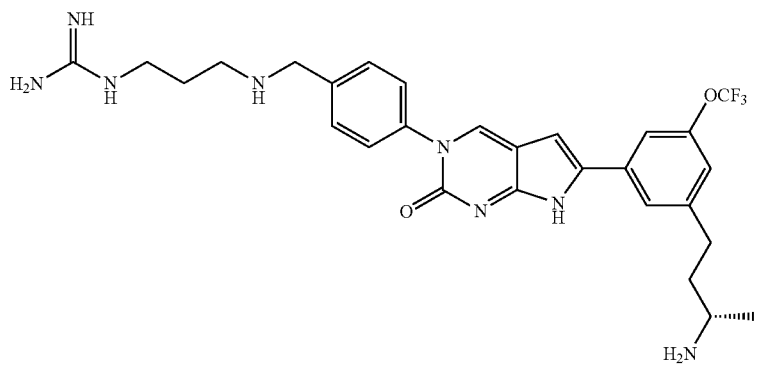
198 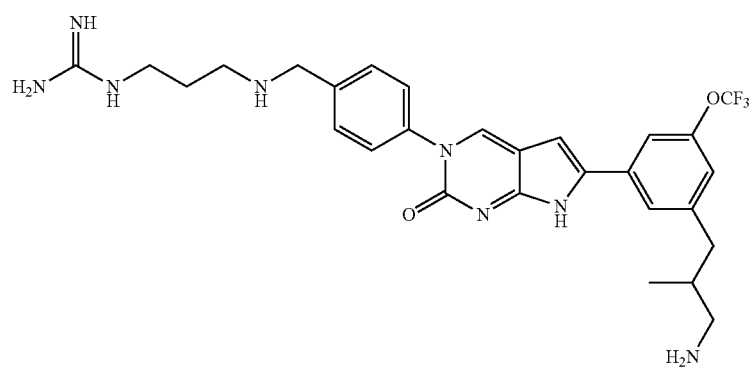 [SMILES: CC(CN)Cc1cc(OC(F)(F)F)cc(-c2cc3cn(-c4ccc(CNCCCNC(=N)N)cc4)c(=O)nc3[nH]2)c1]

199 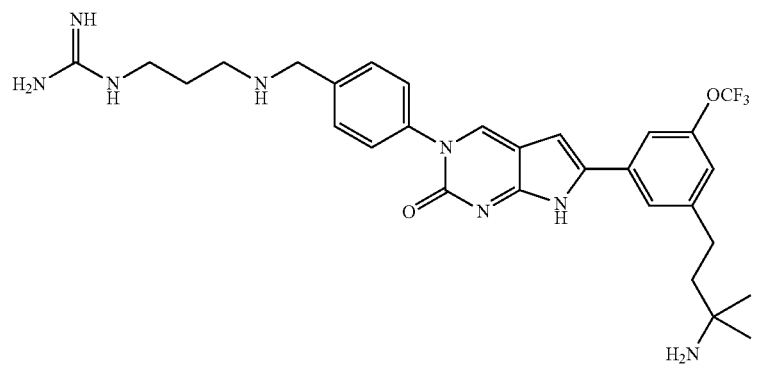 [SMILES: CC(C)(N)CCc1cc(OC(F)(F)F)cc(-c2cc3cn(-c4ccc(CNCCCNC(=N)N)cc4)c(=O)nc3[nH]2)c1]
200 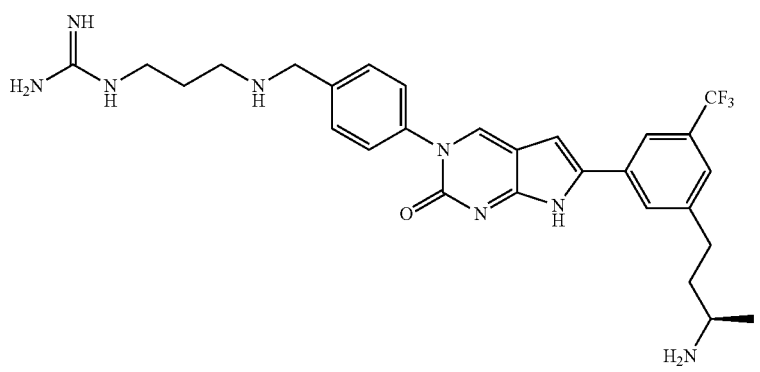
201 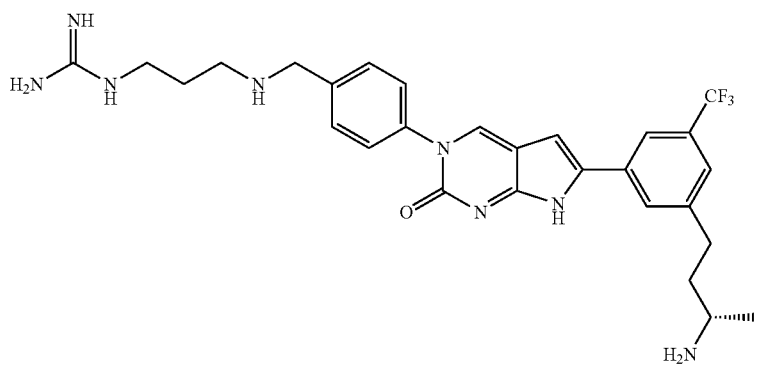 [SMILES: C[C@H](N)CCc1cc(-c2cc3cn(-c4ccc(CNCCCNC(=N)N)cc4)c(=O)nc3[nH]2)cc(C(F)(F)F)c1]
202 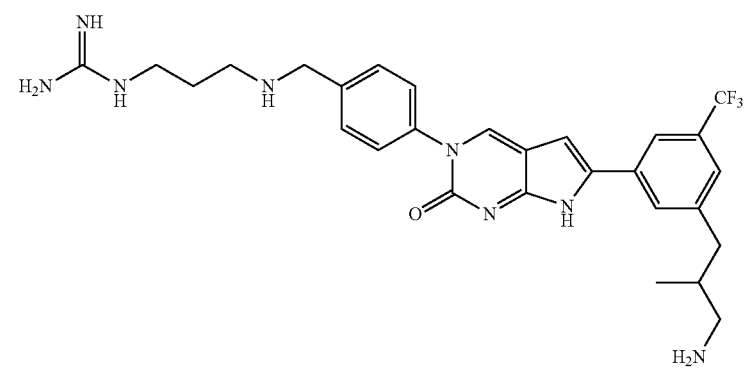 [SMILES: CC(CN)Cc1cc(-c2cc3cn(-c4ccc(CNCCCNC(=N)N)cc4)c(=O)nc3[nH]2)cc(C(F)(F)F)c1]

203 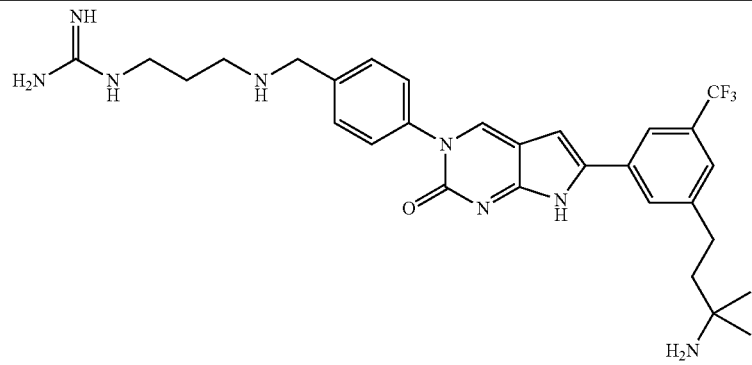
204 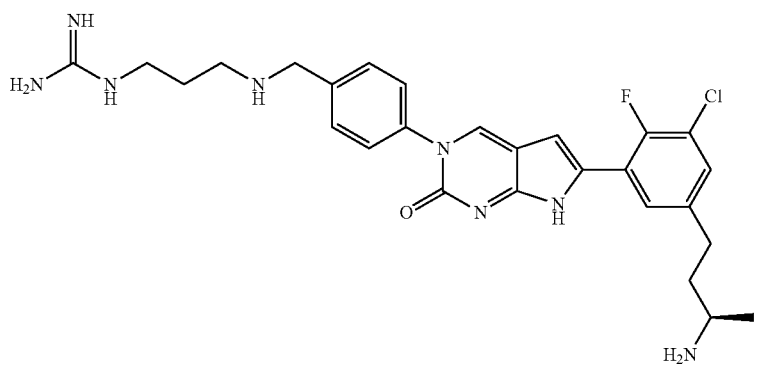
205 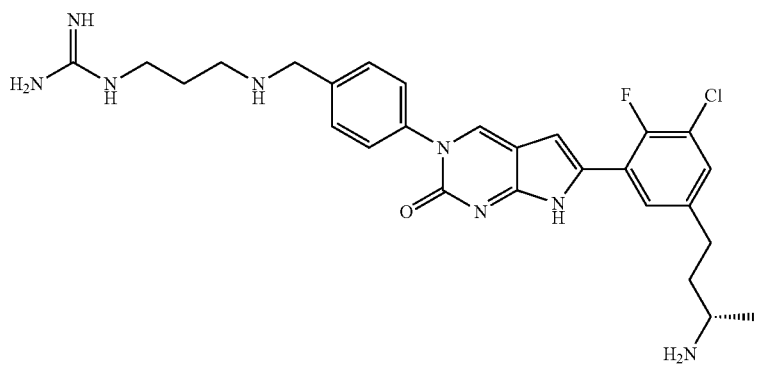
206 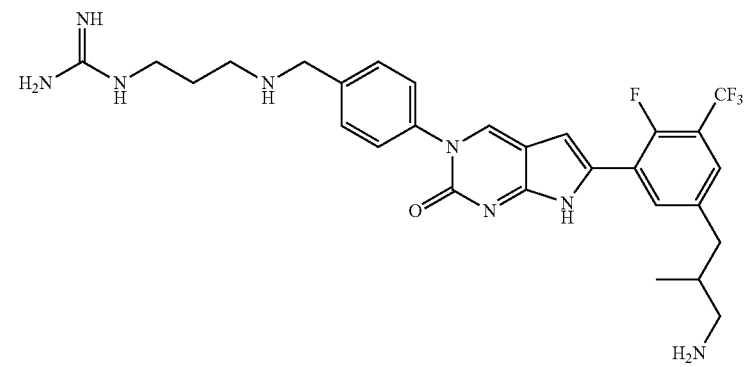

207 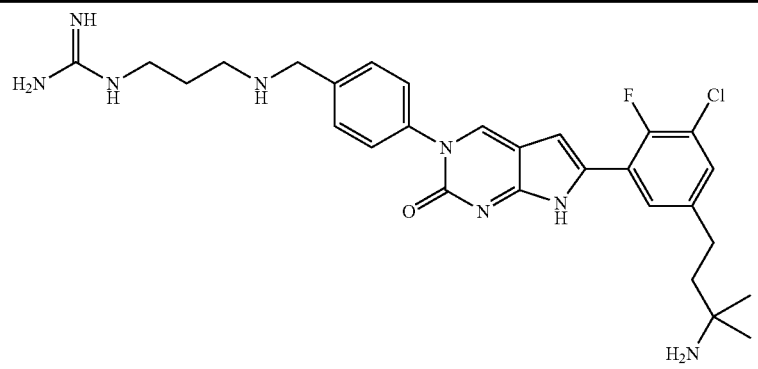
208 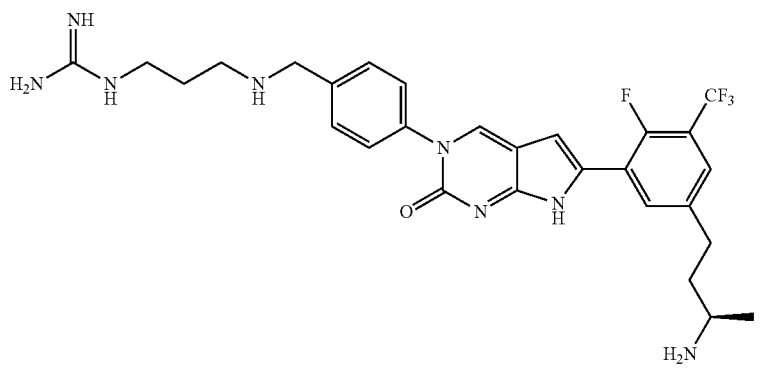
209 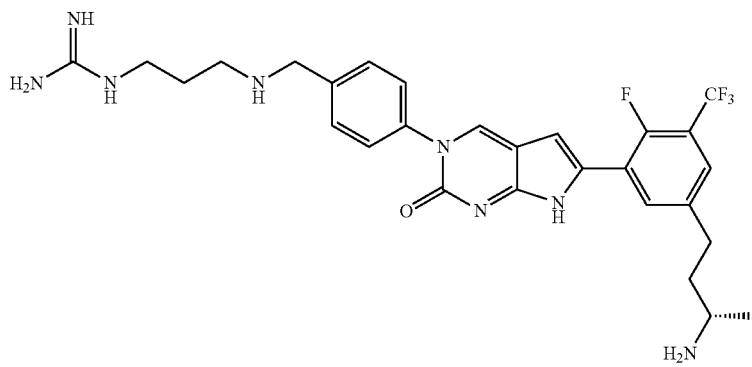
210 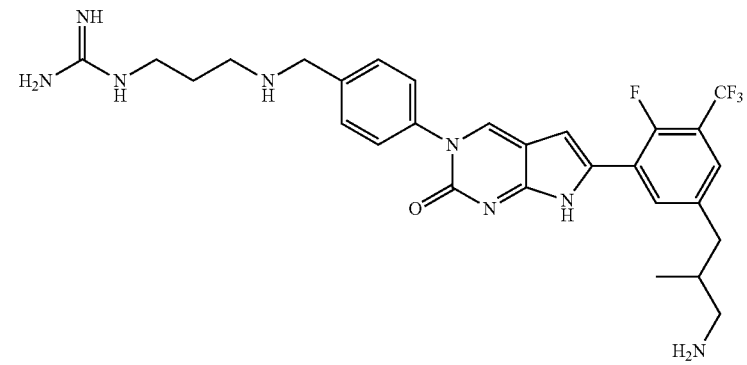

211 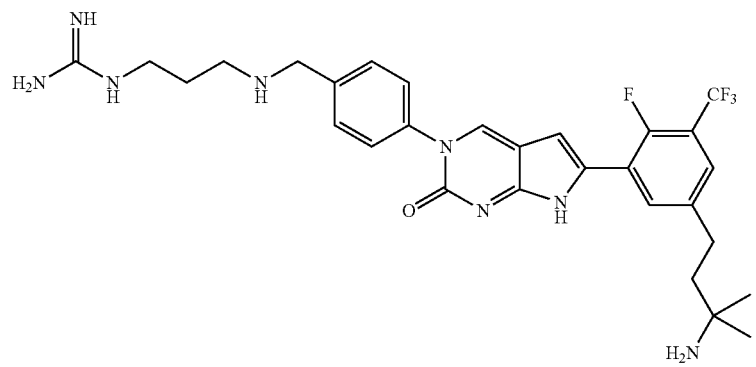 [SMILES: CC(C)(N)CCc1cc(Cl)c(F)c(-c2cc3cn(-c4ccc(CNCCCNC(=N)N)cc4)c(=O)nc3[nH]2)c1]
212 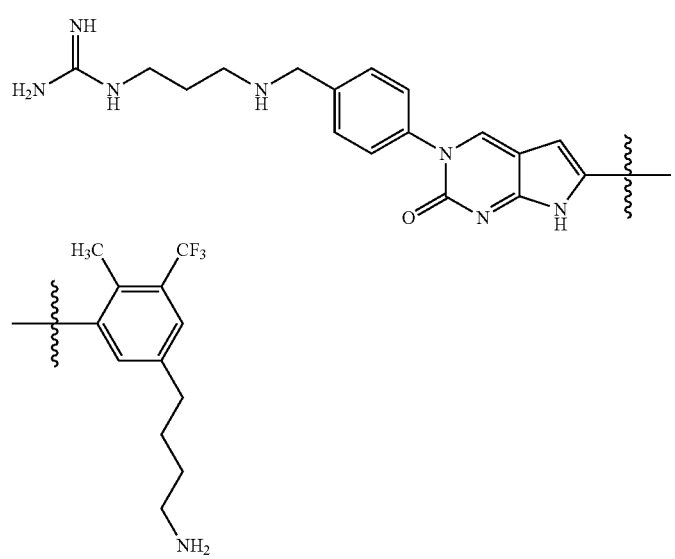
213 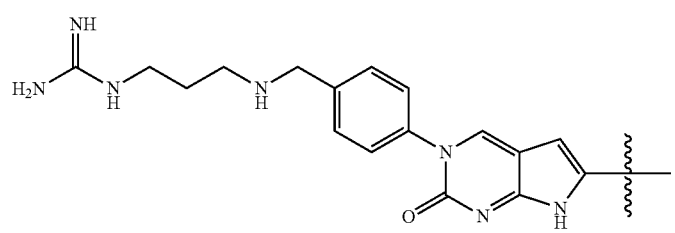
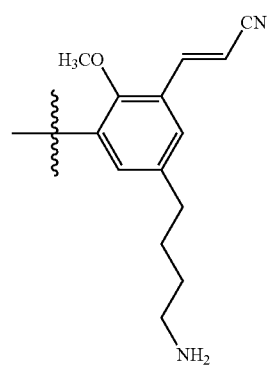

214 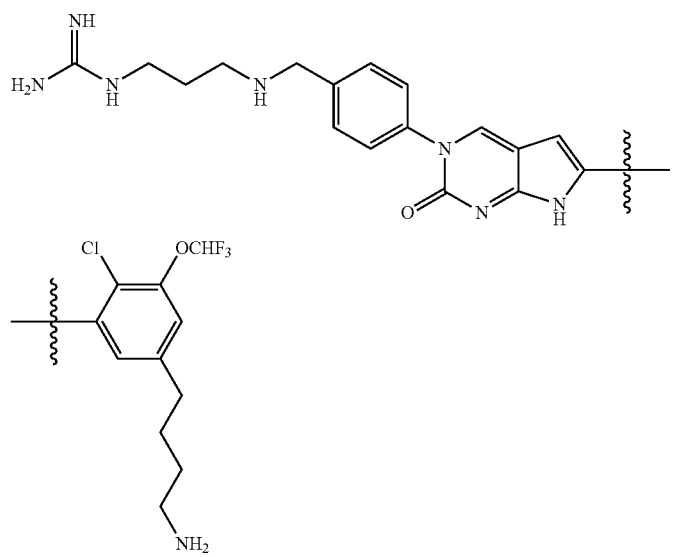
215 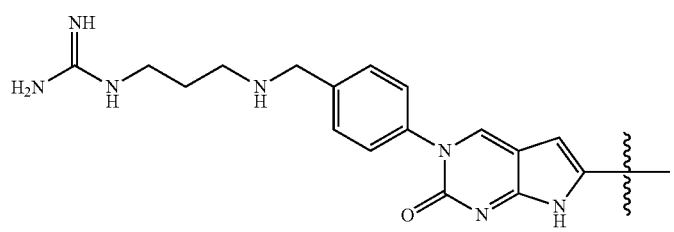
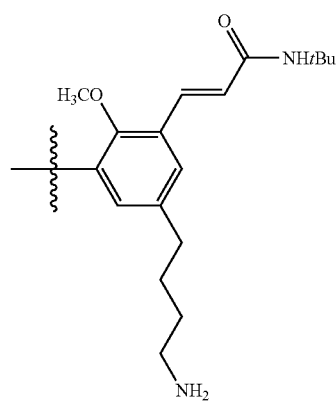
216 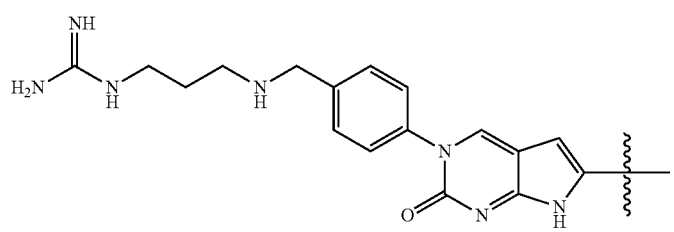

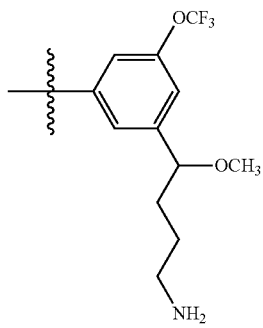
217 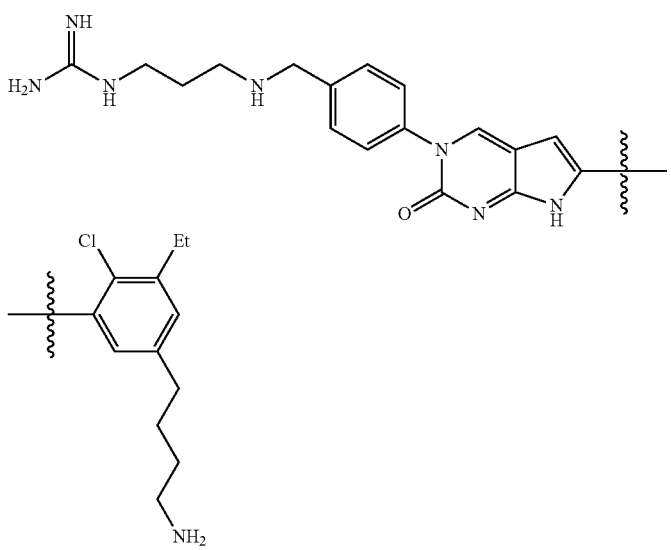
218 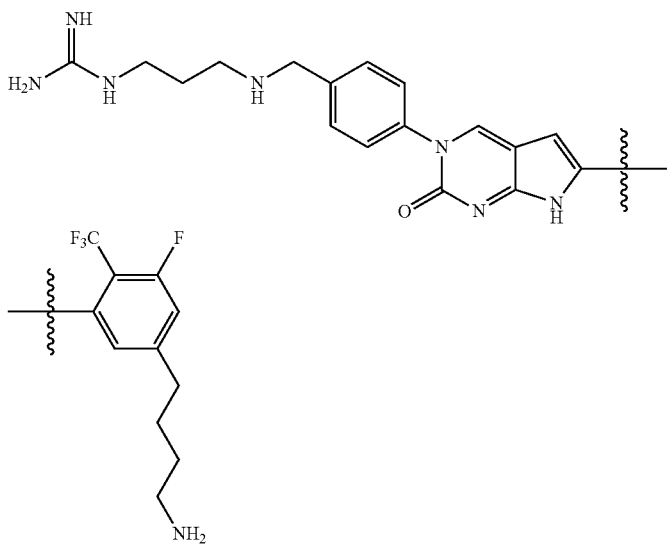
219 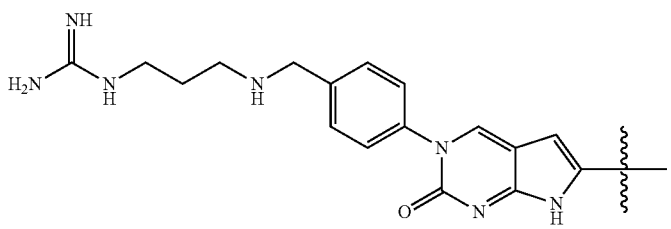

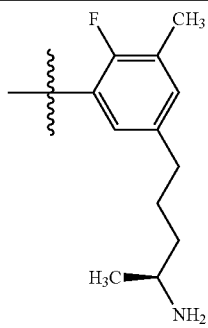
220 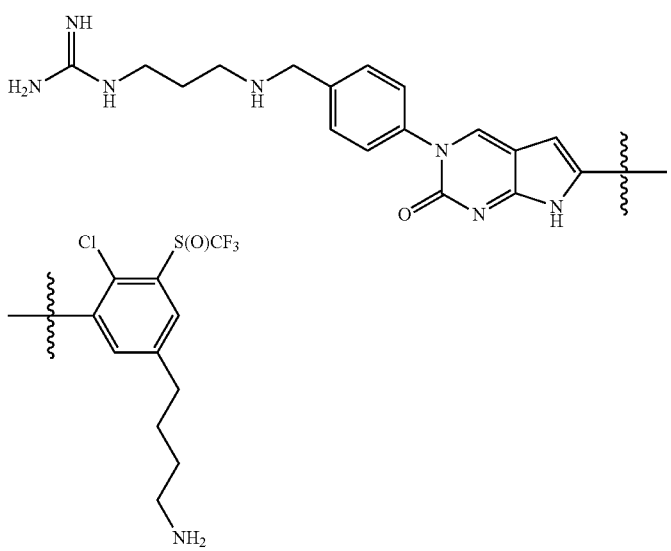
221 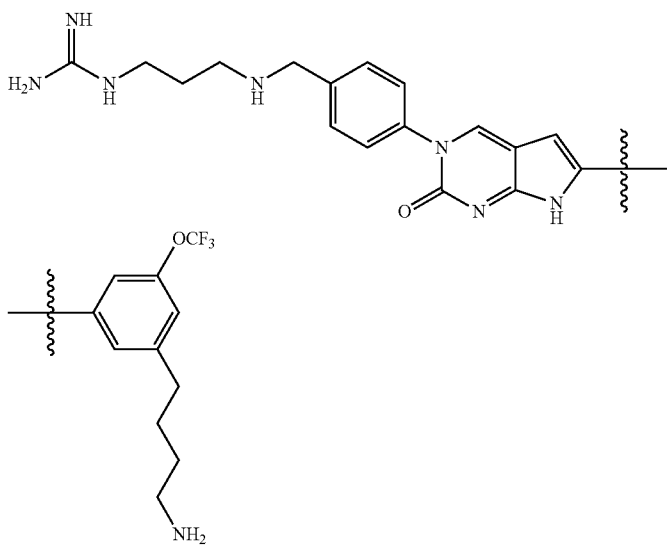
222 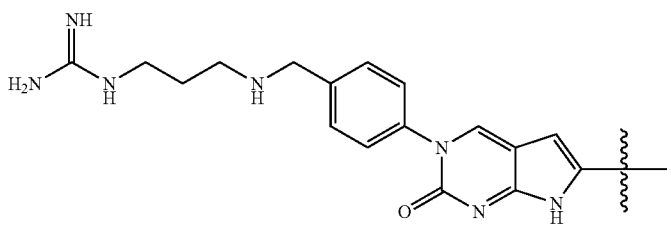

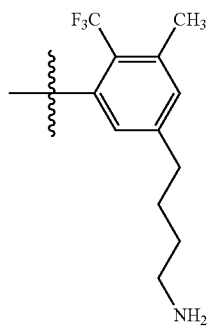
223 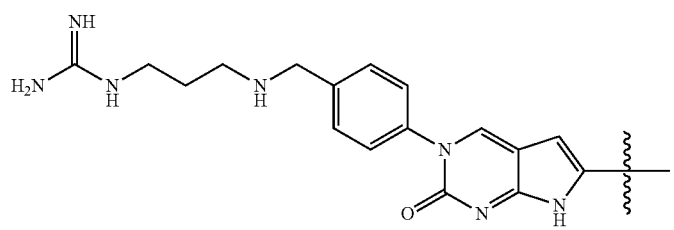
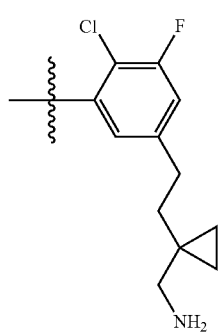
224 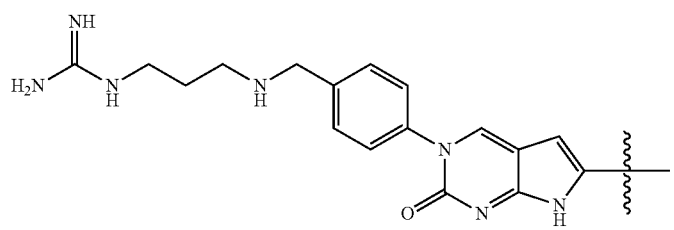
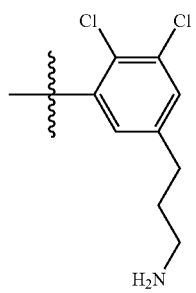
225 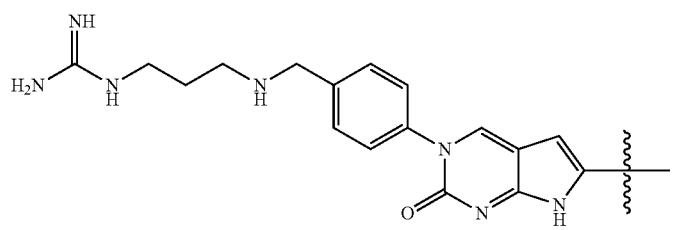

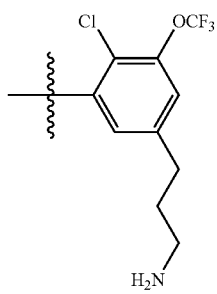
226
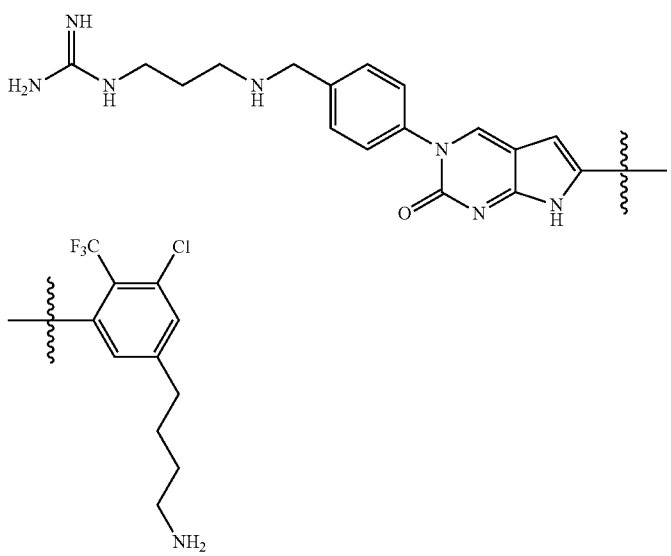
227
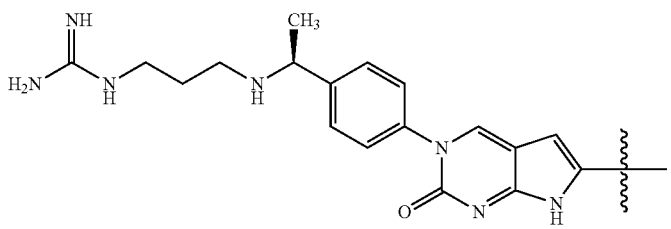
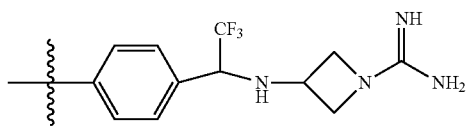
228
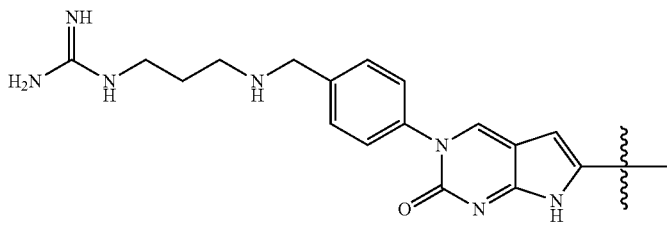

-continued
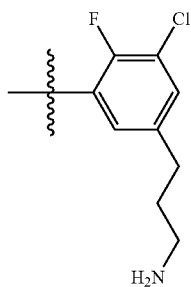
229 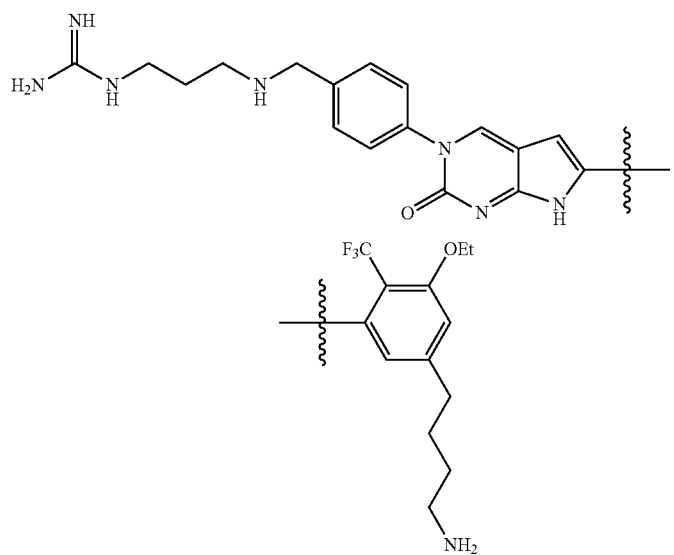
230 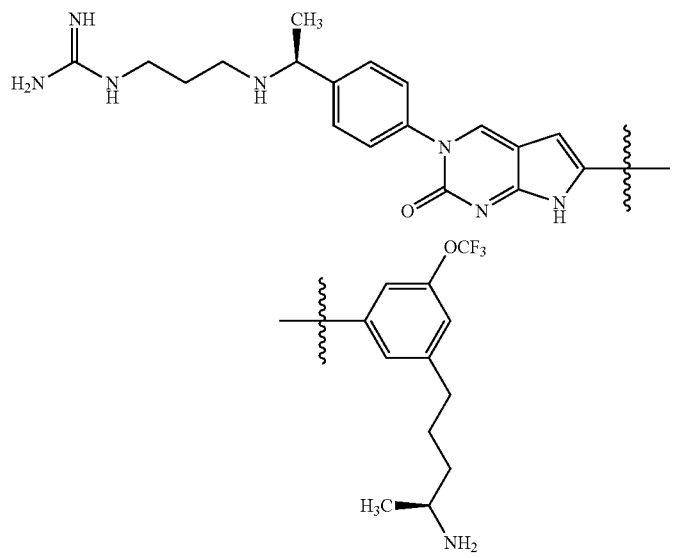

231
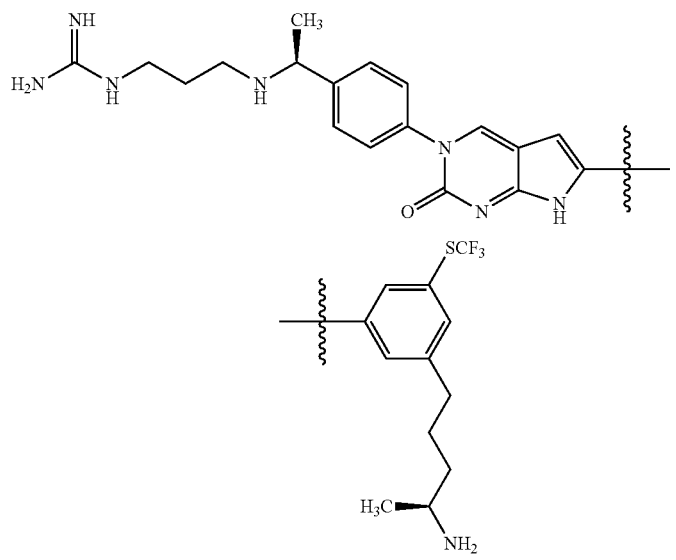
232
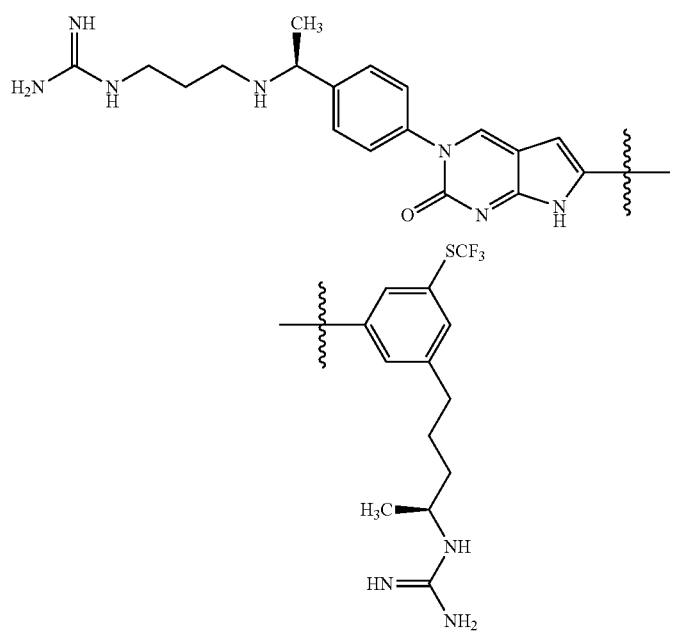

-continued
| | |
|---|---|
| 233 | 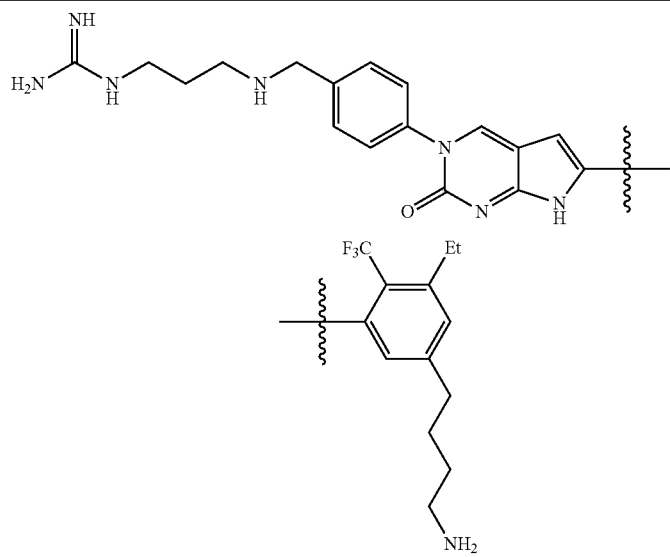 |
| 234 | 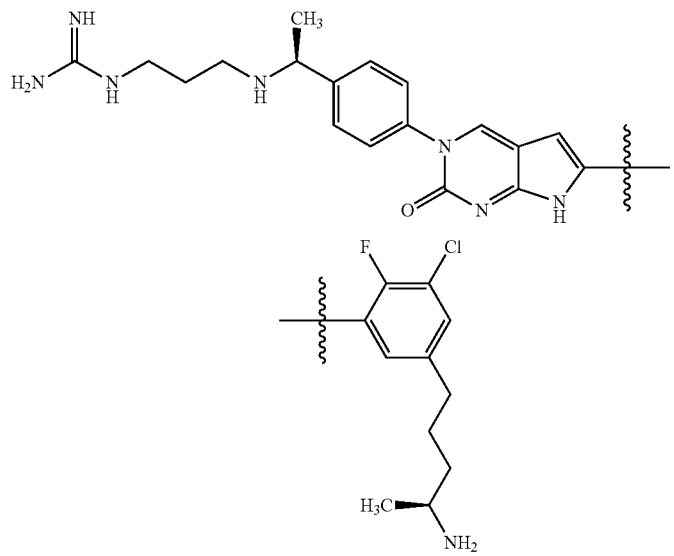 |
| 235 | 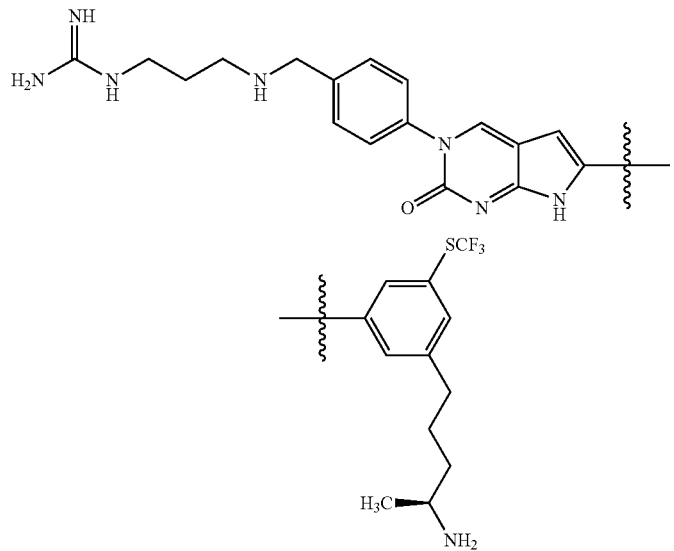 |

236 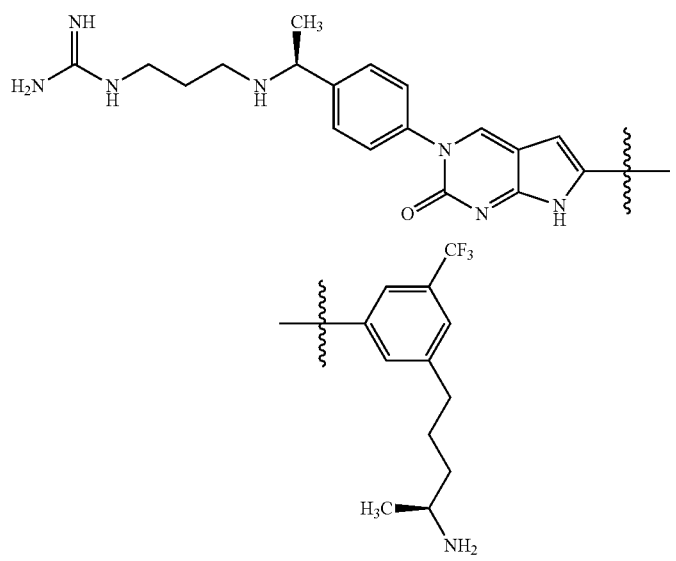
237 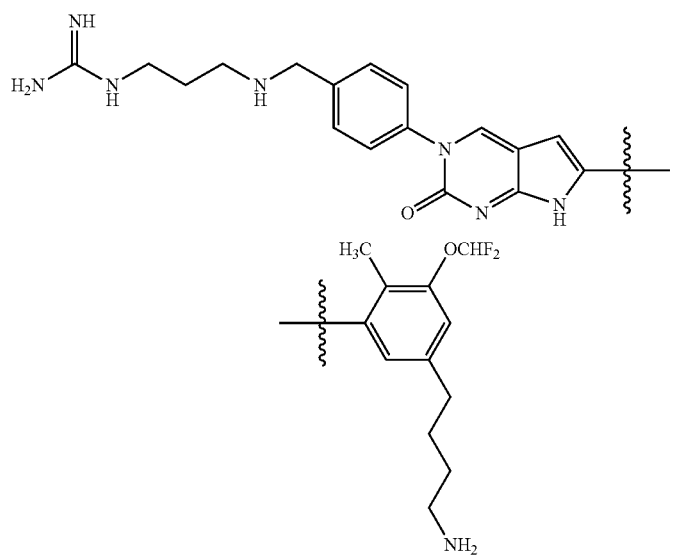

| | |
|---|---|
| 238 | 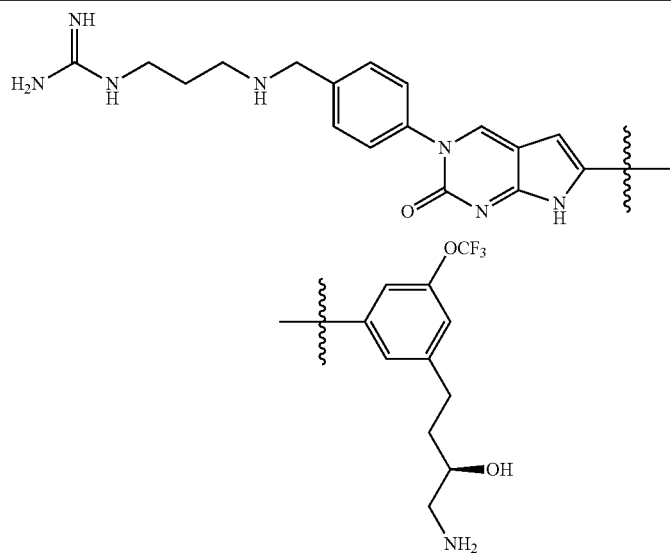 |
| 239 | 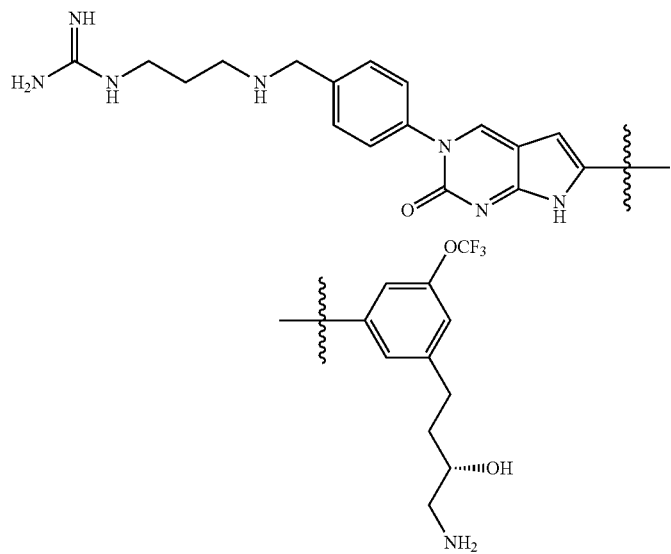 |
| 240 | 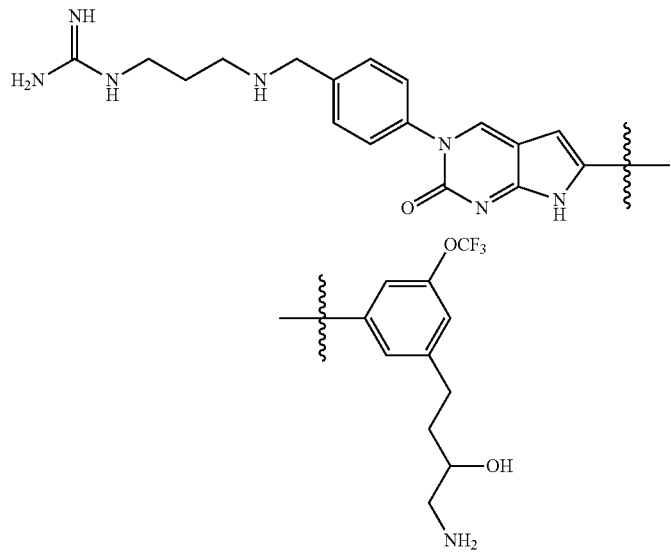 |

241 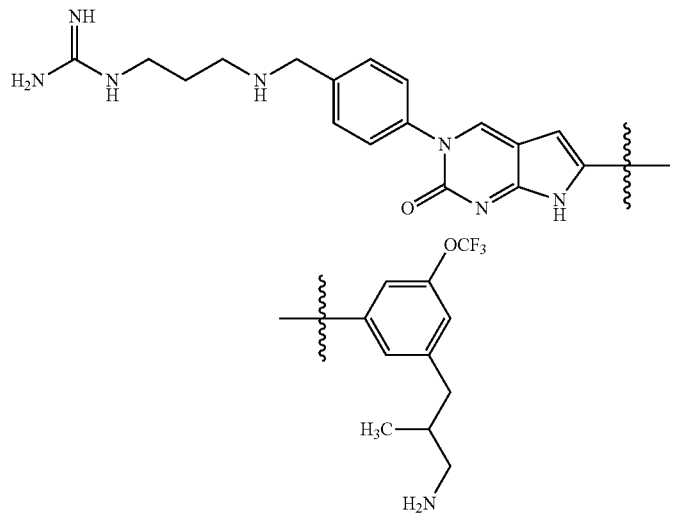
242 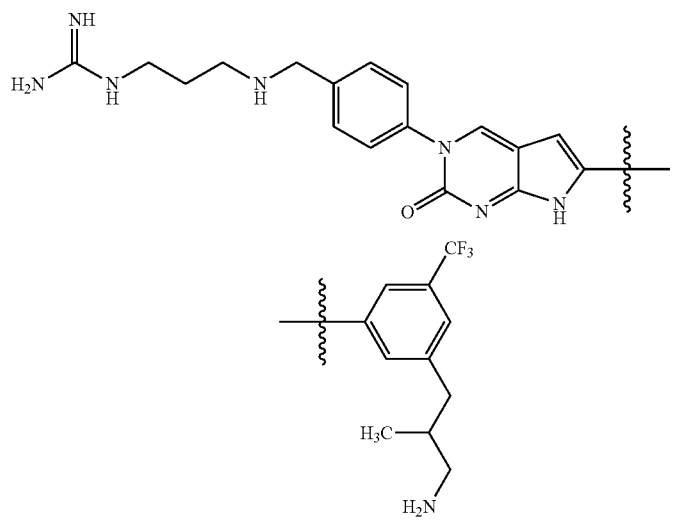
243 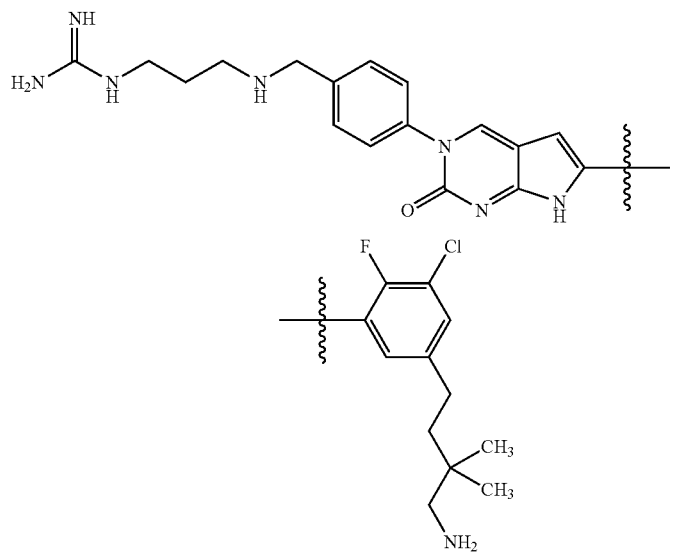

244 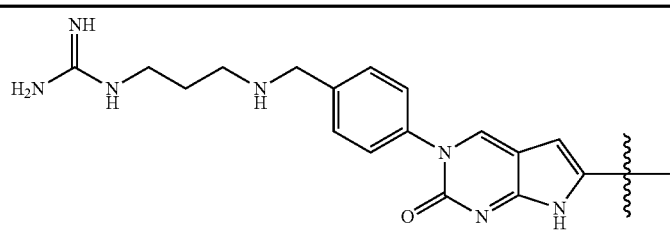
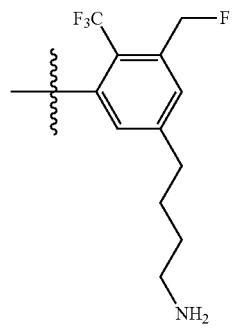
245 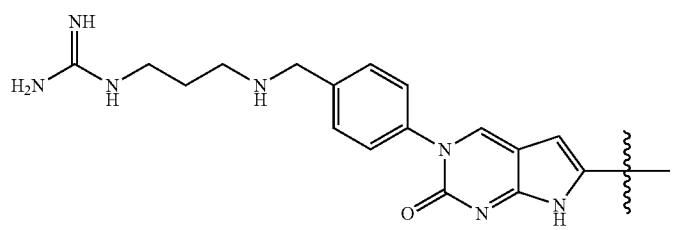
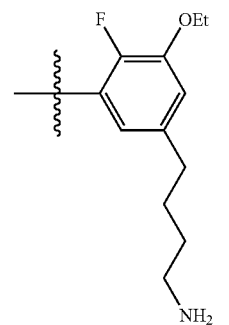

246 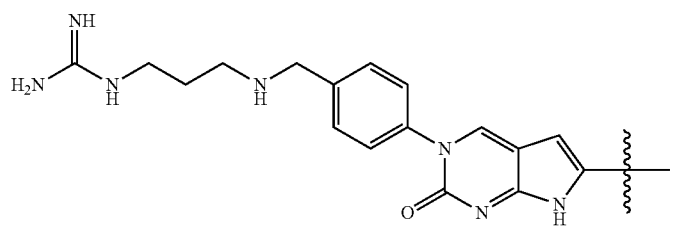
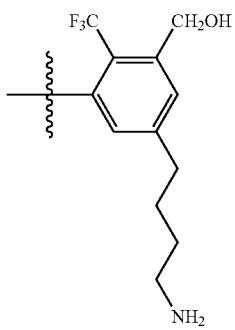
247 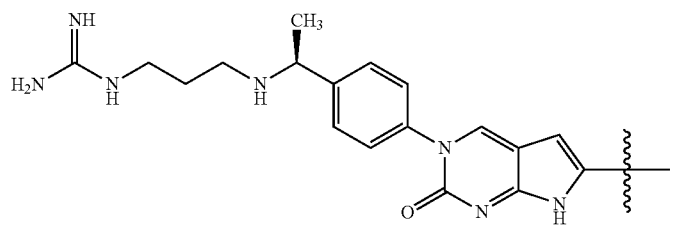
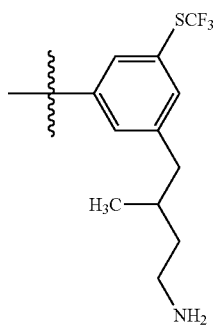

248
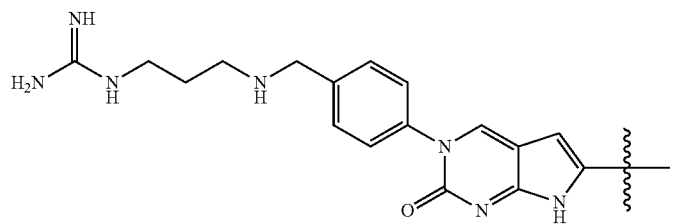
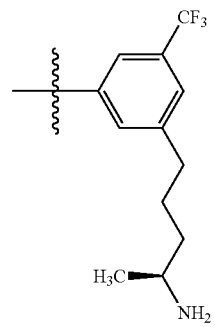
249
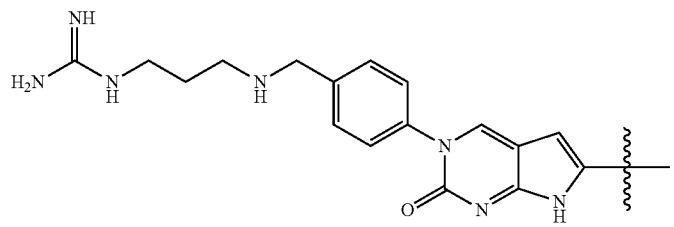
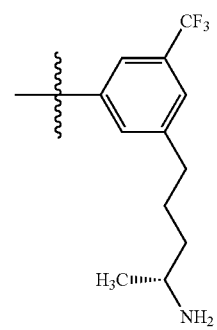

250 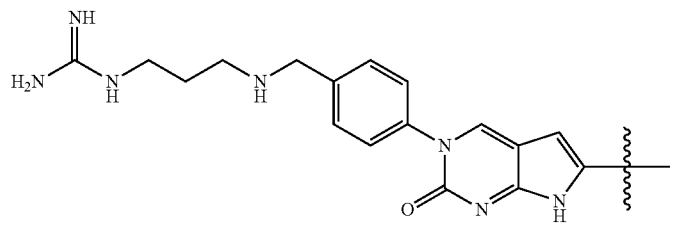
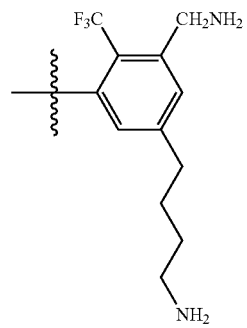
251 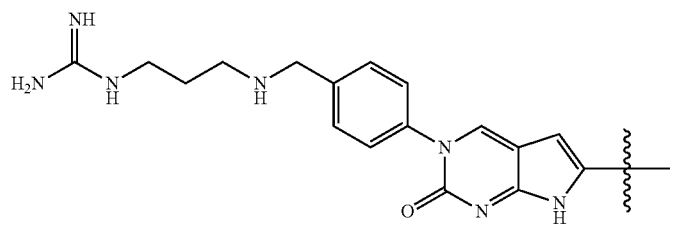
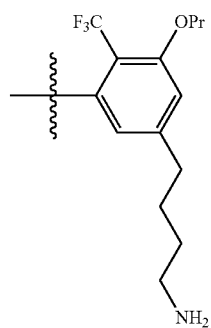

252 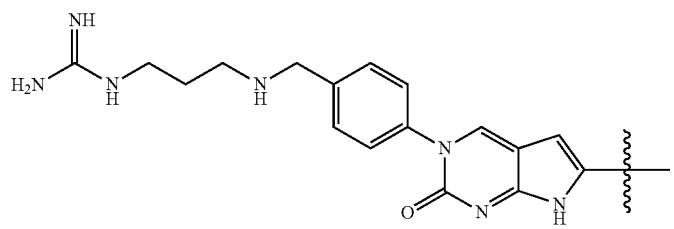
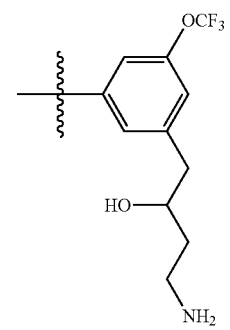
253 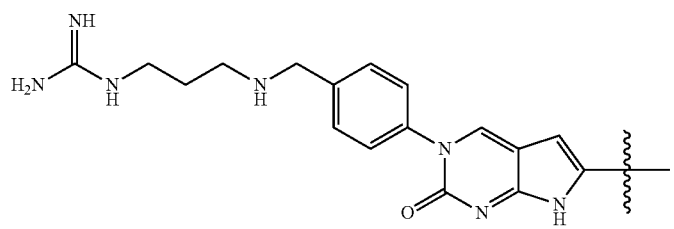
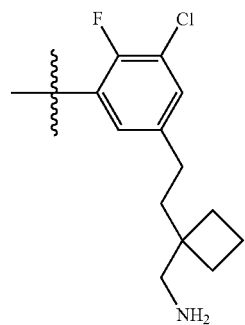

254 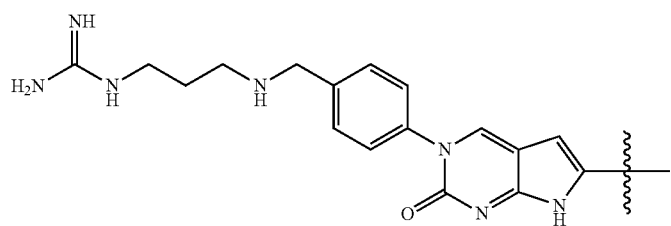
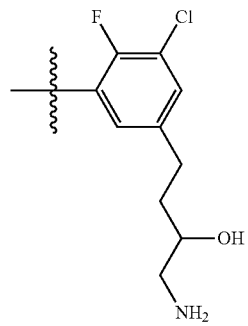
255 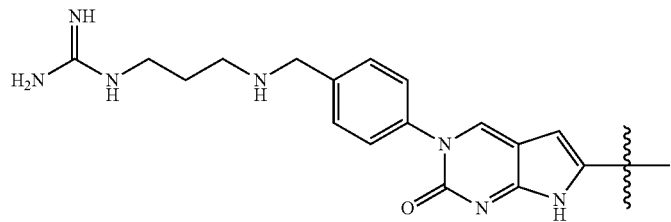
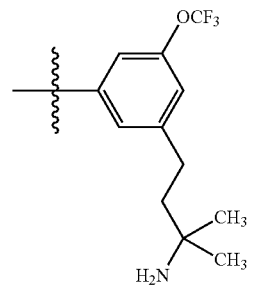

256
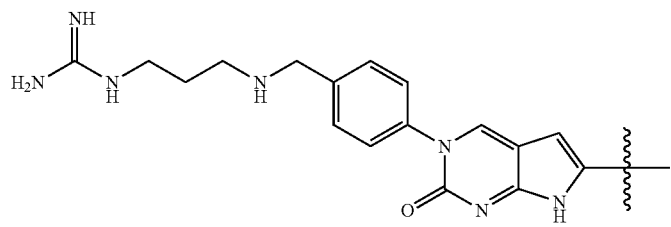
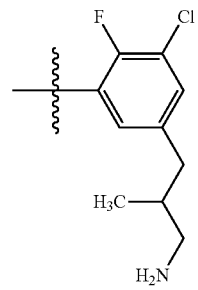
257
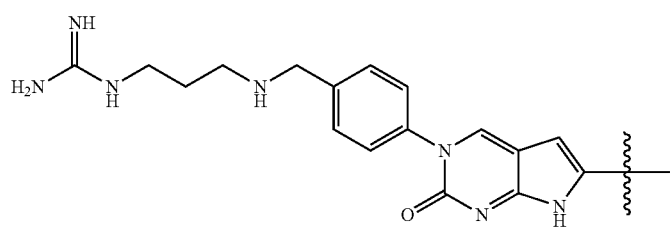
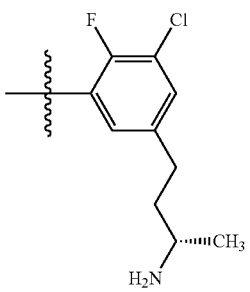

258 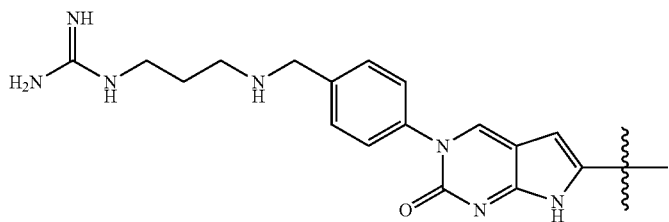
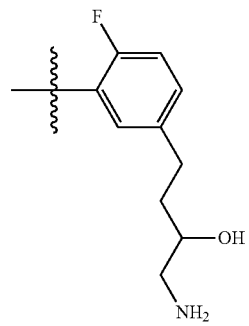
259 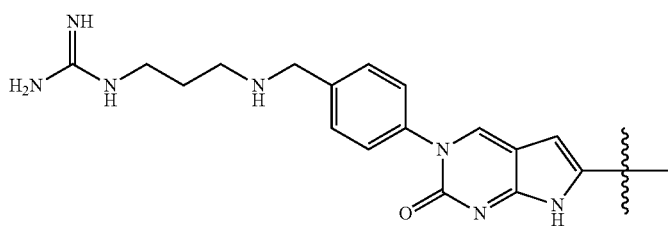
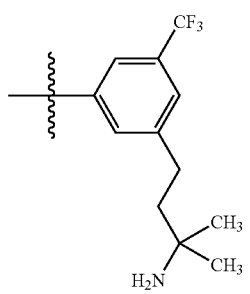
260 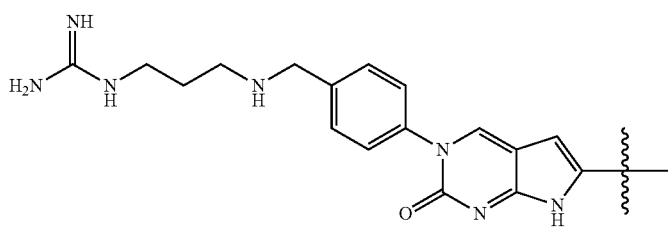
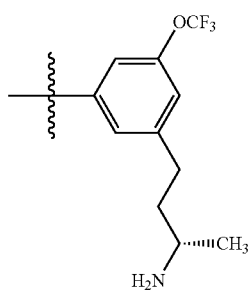

261 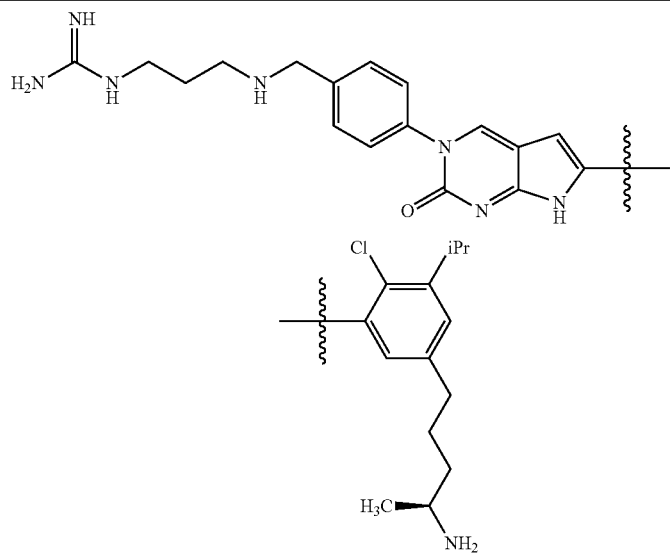
262 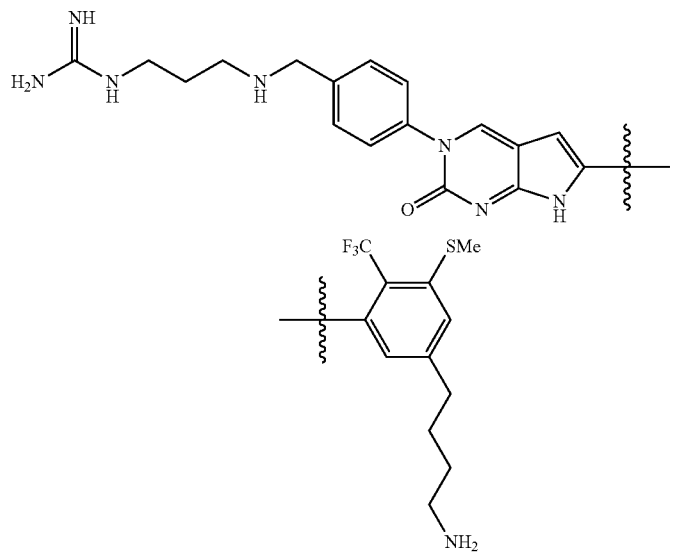
263 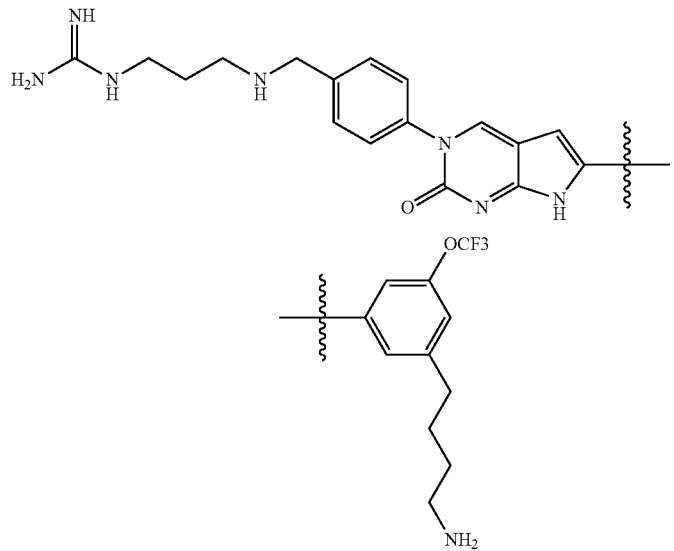

264
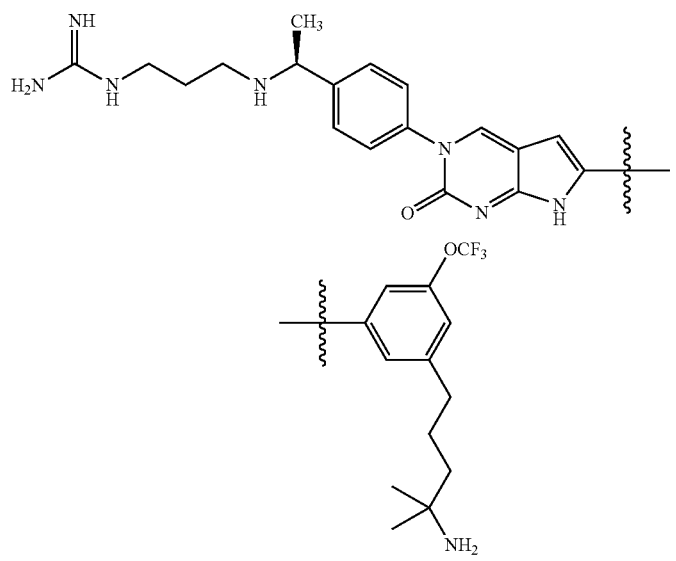
265
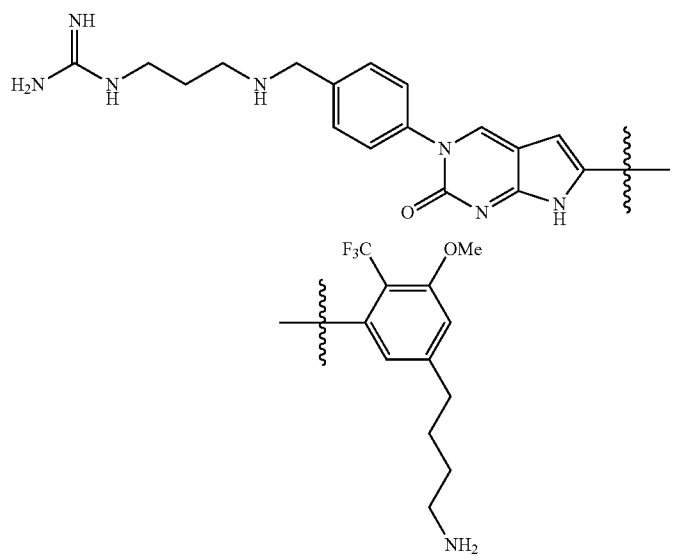

266 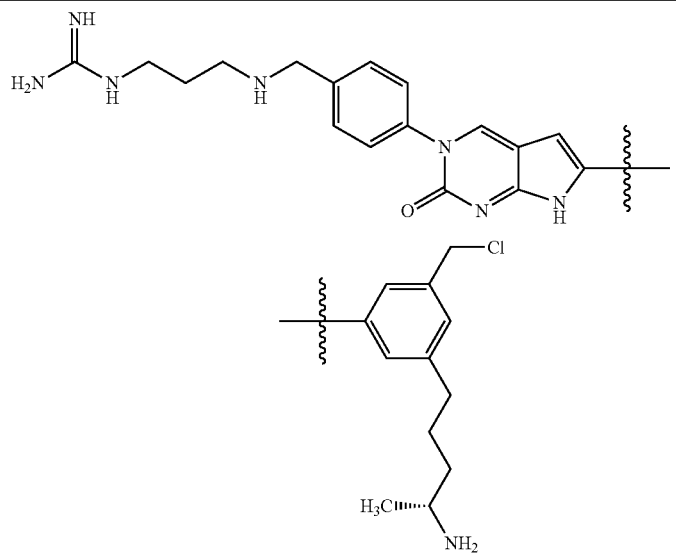
267 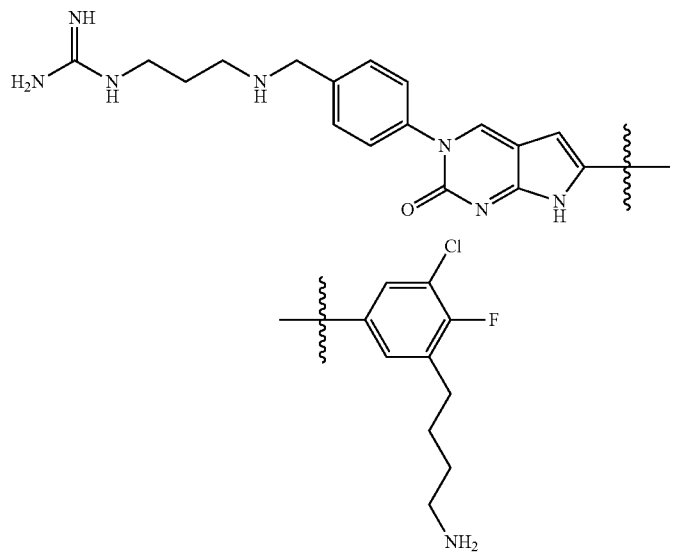
268 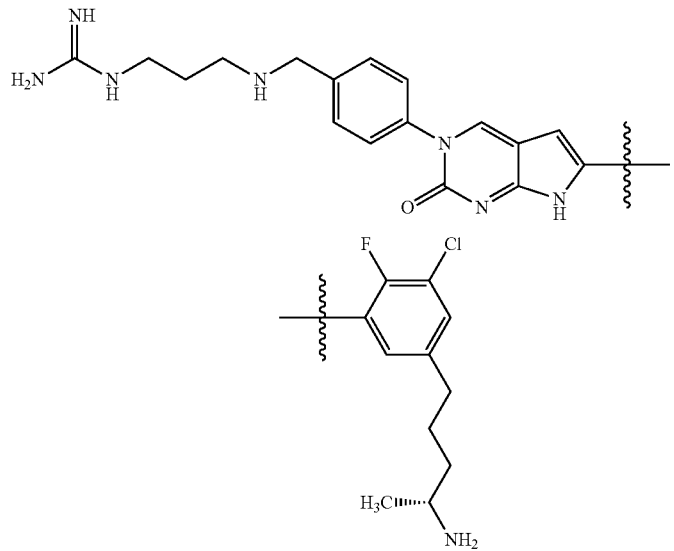

269 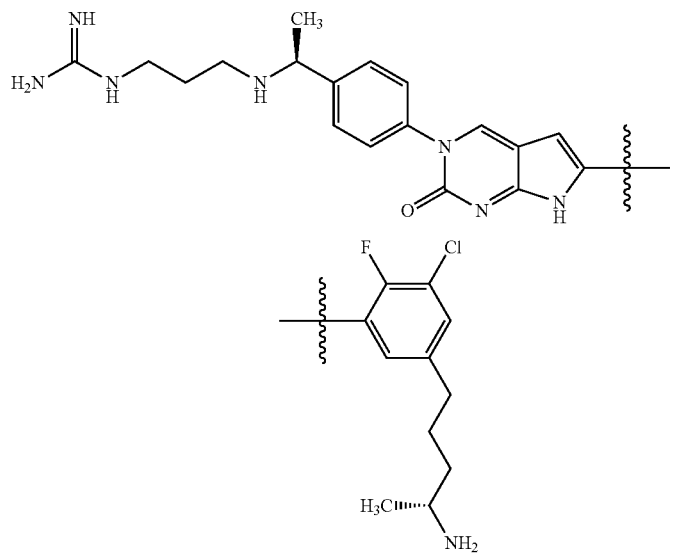
270 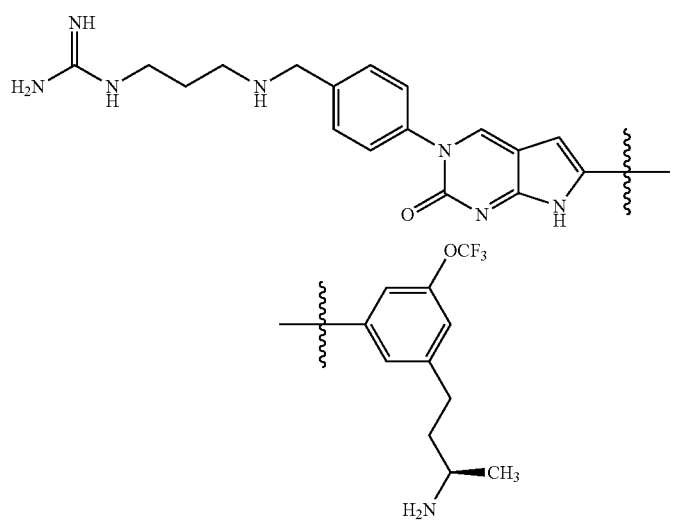
271 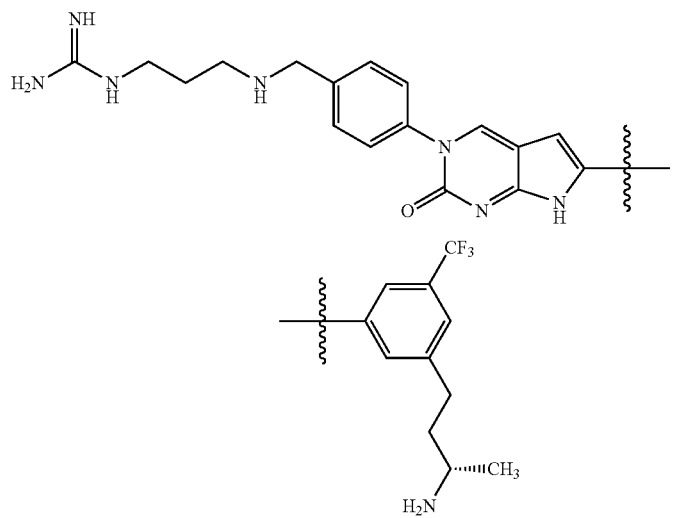

272 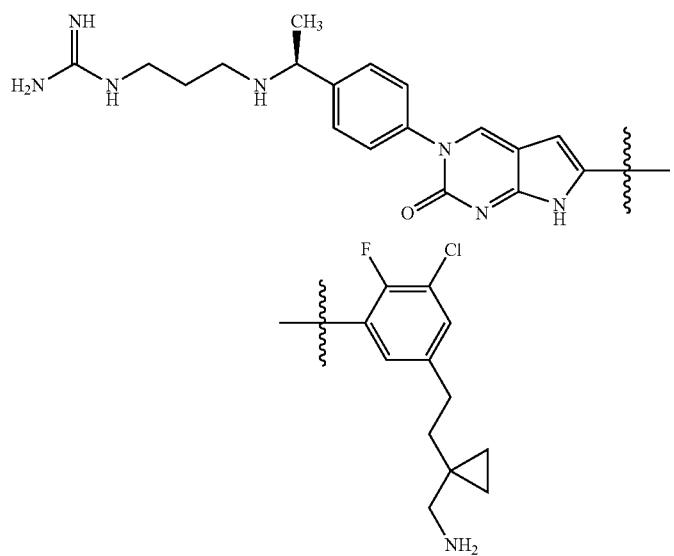
273 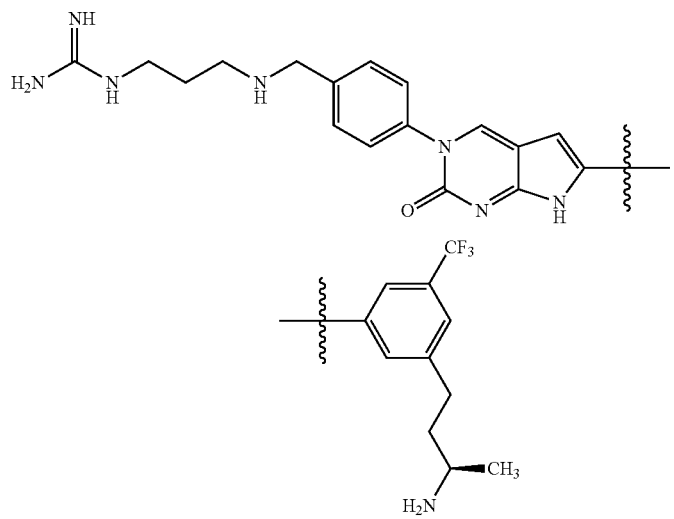

274 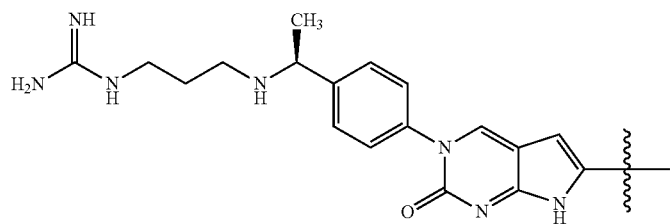
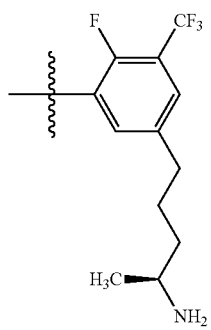
275 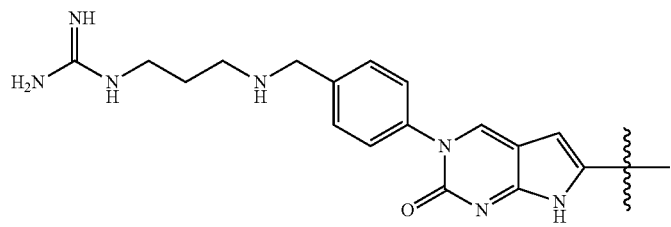
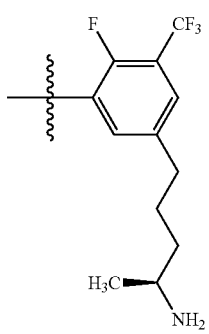

| | |
|---|---|
| 276 | 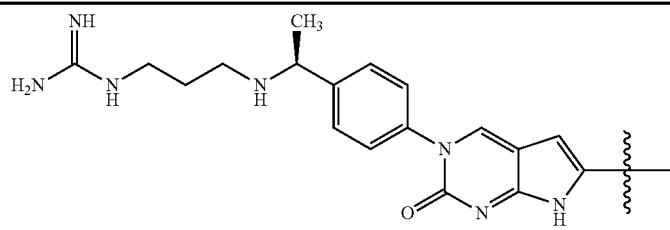 |
| | 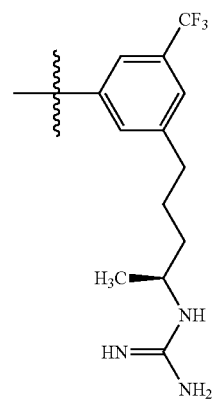 |
| 277 | 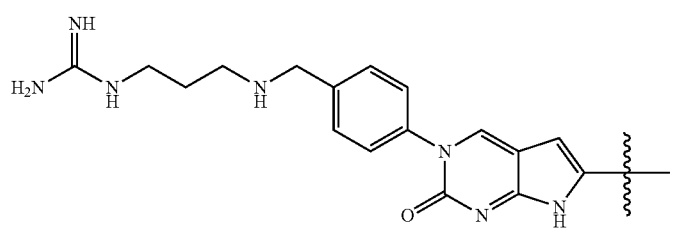 |
| | 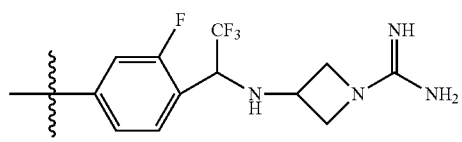 |
| 278 | 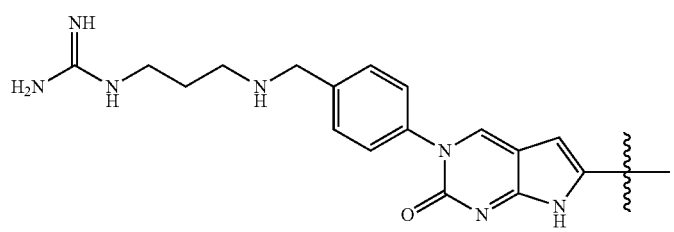 |
| | 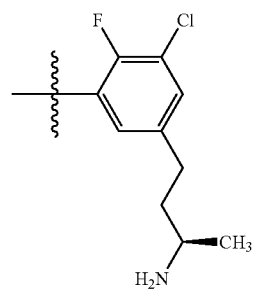 |

279 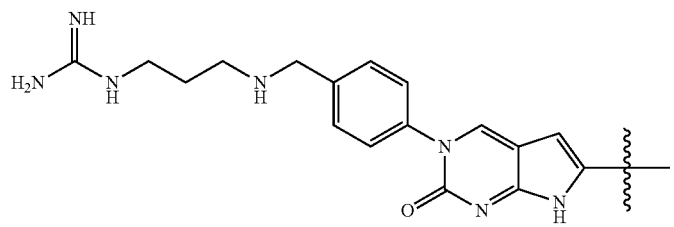
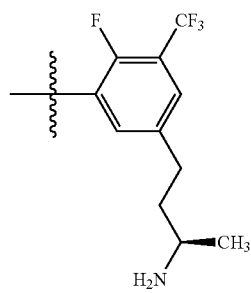
280 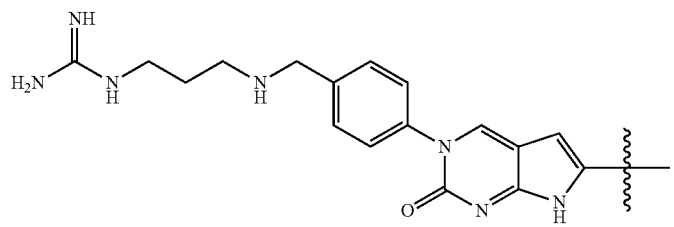
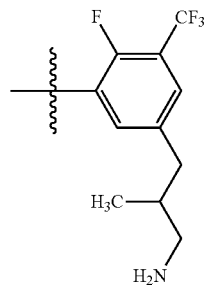

281 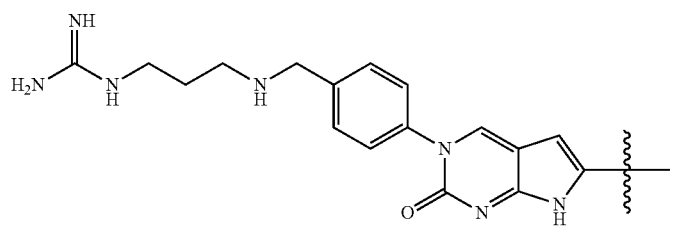
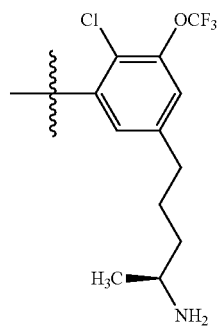
282 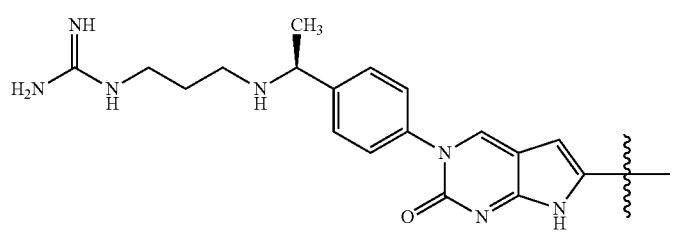
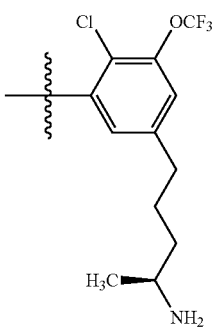

283 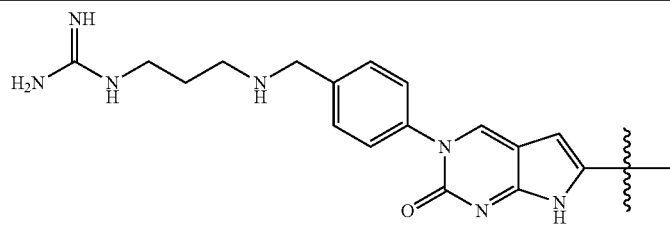
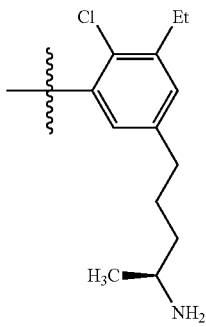
284 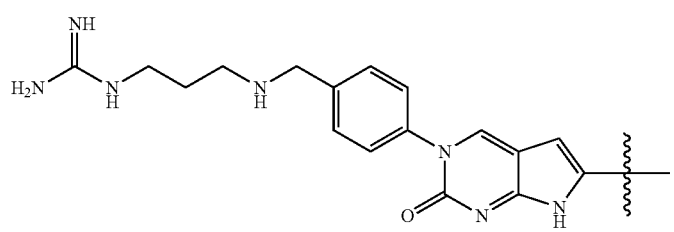
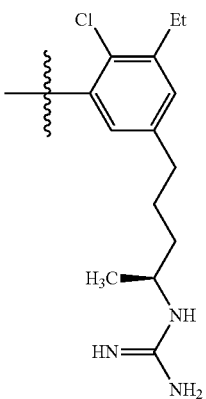

285 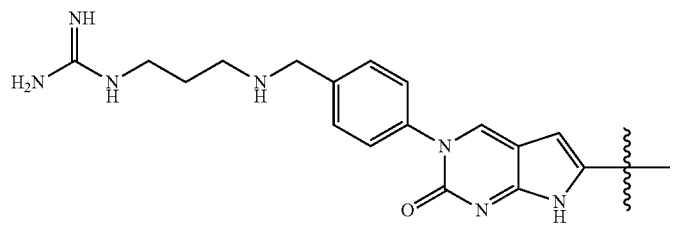
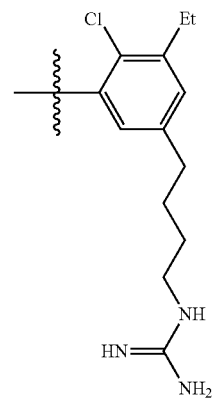
286 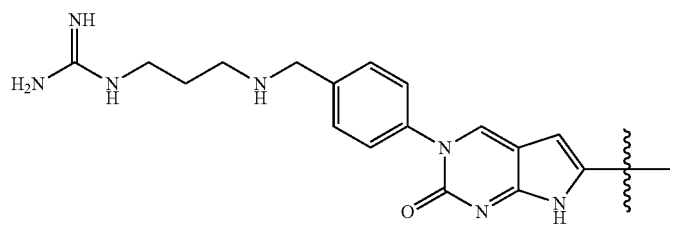
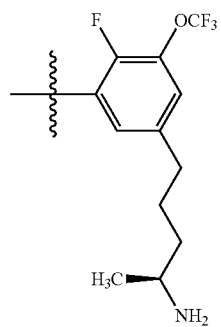

287 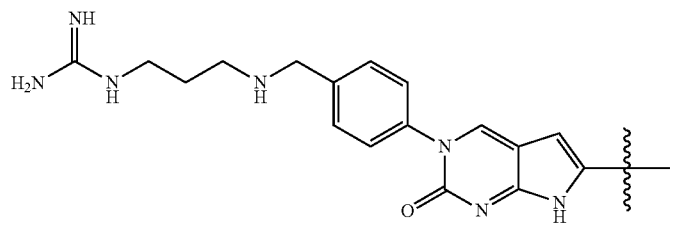
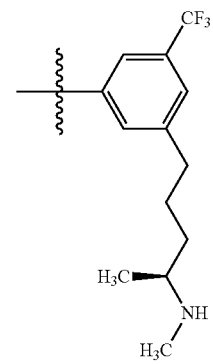
288 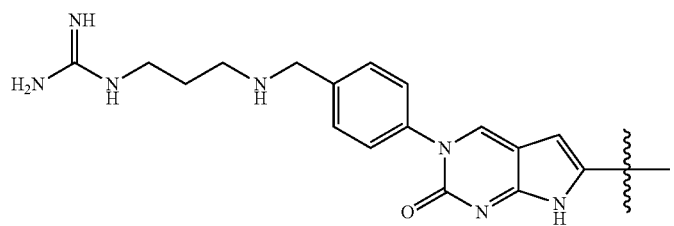
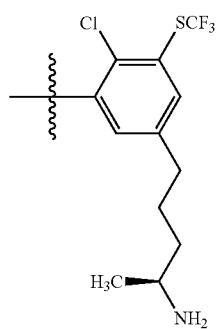

289 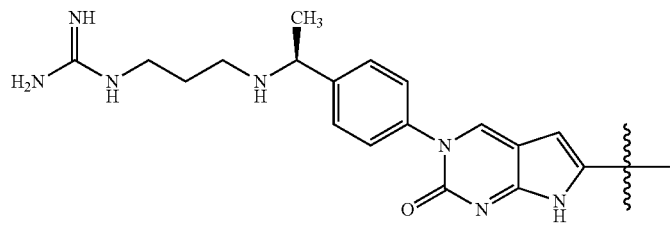
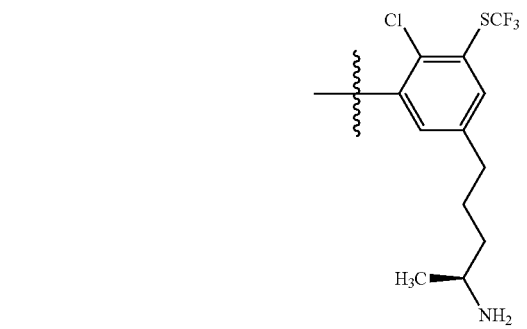
290 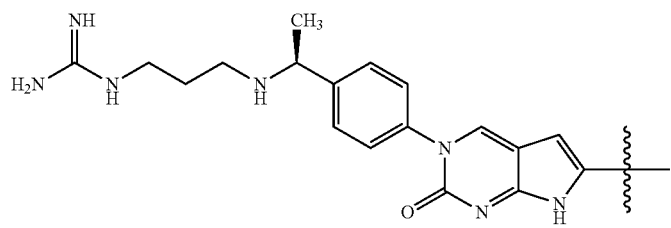
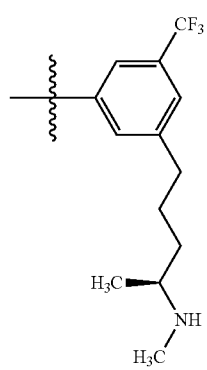

291 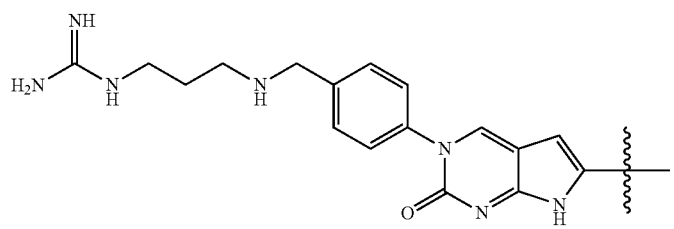
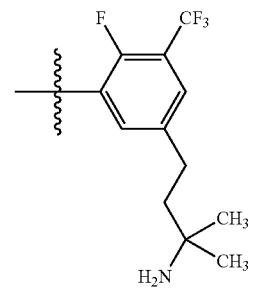
292 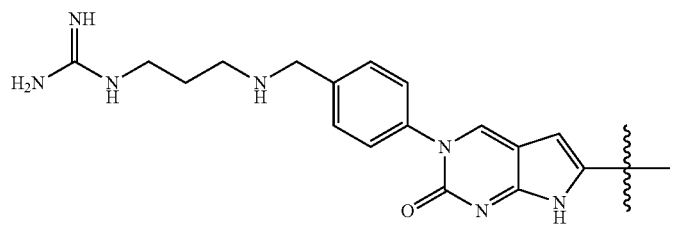
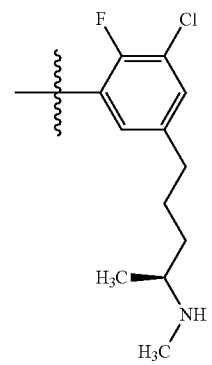

293 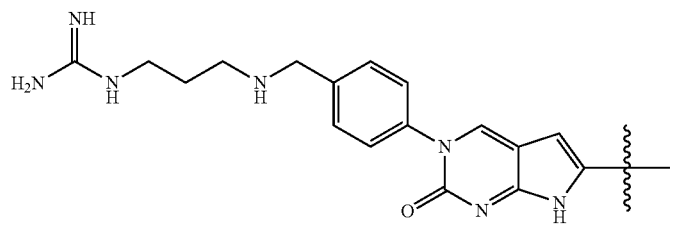
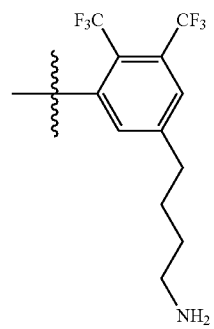
294 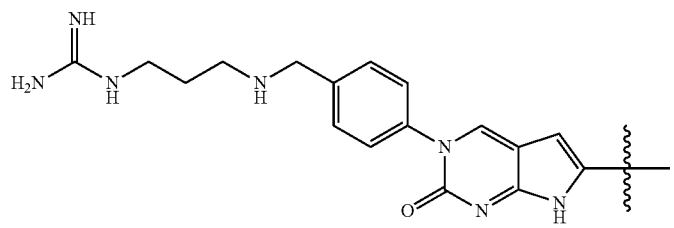
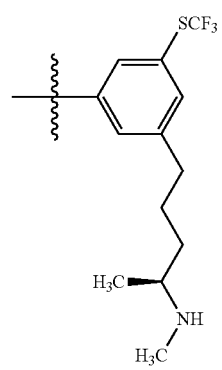

295 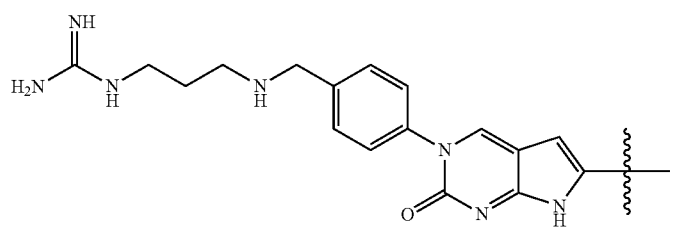
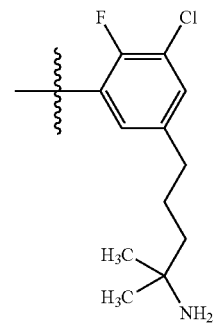
296 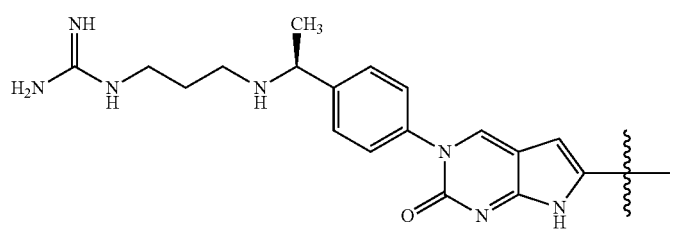
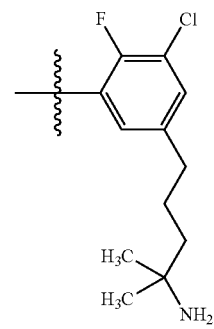

297 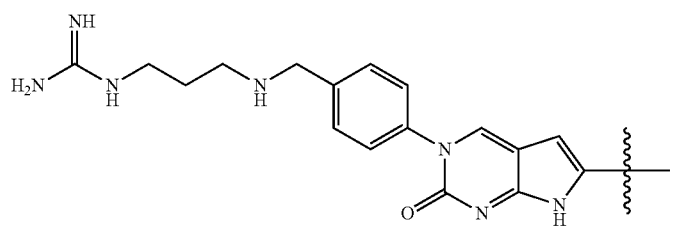
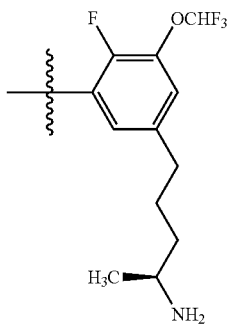
298 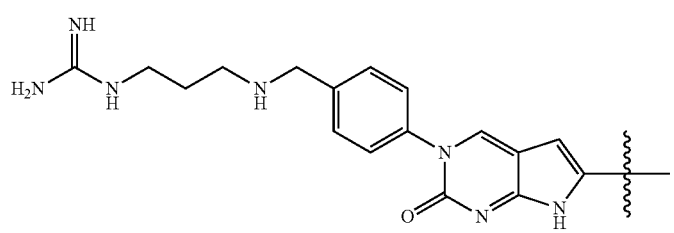
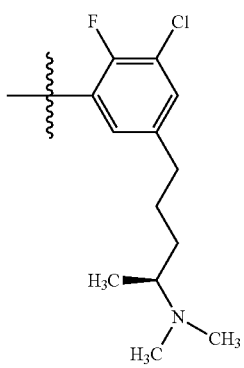

299
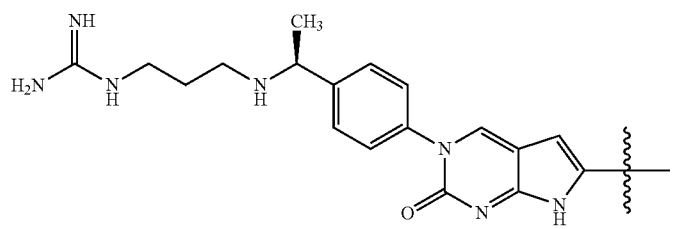
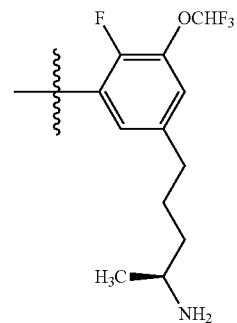
300
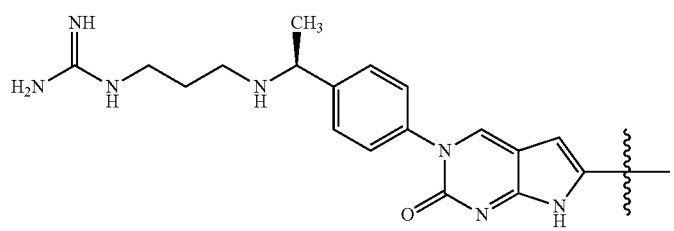
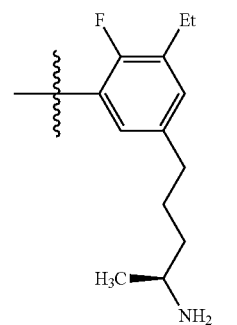

301 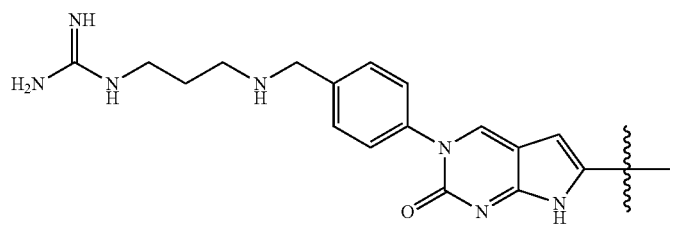
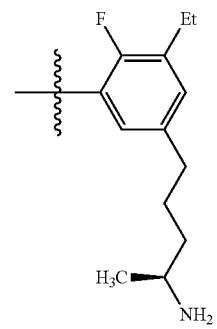
302 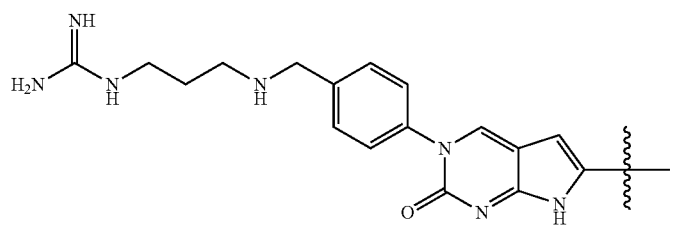
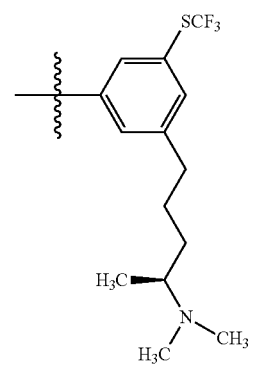

303 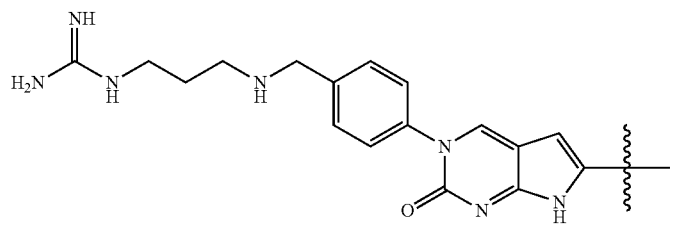
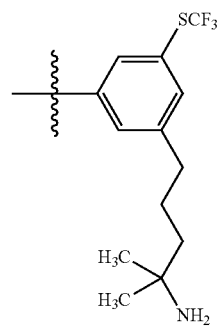
304 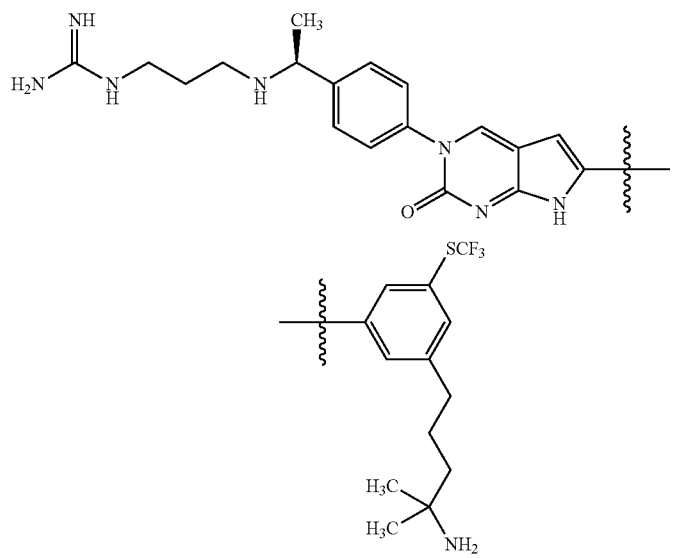

305 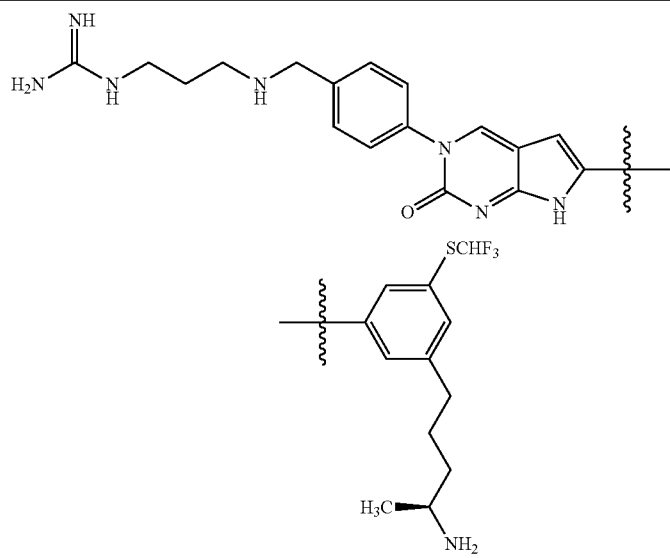
306 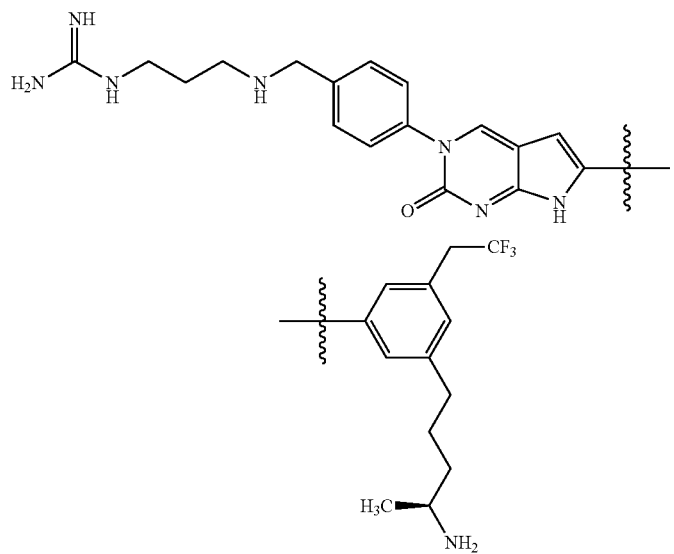
307 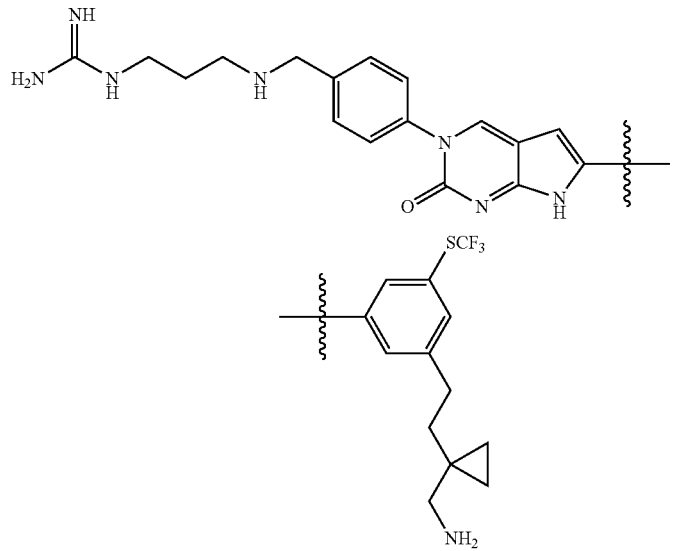

308 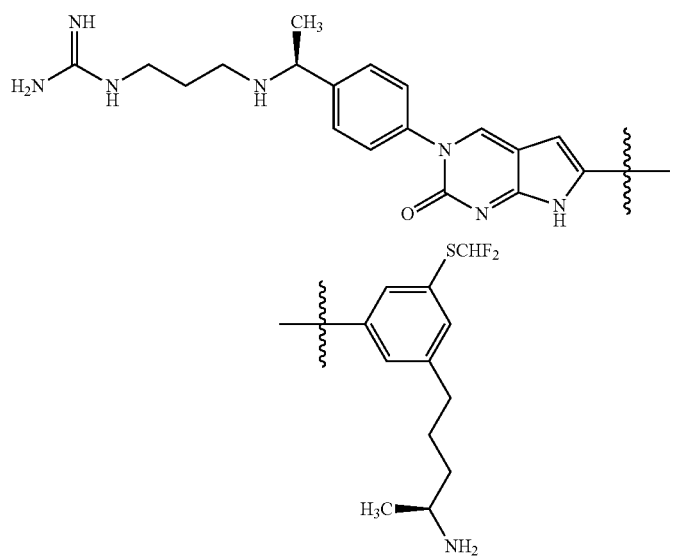
309 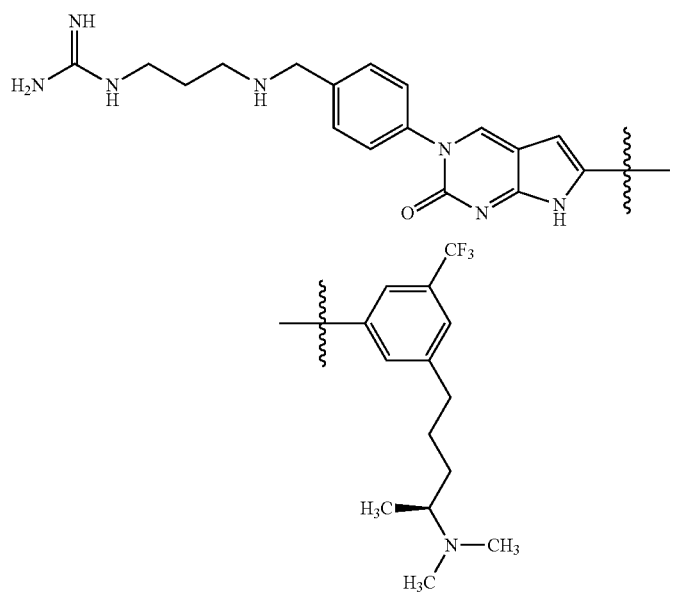

310
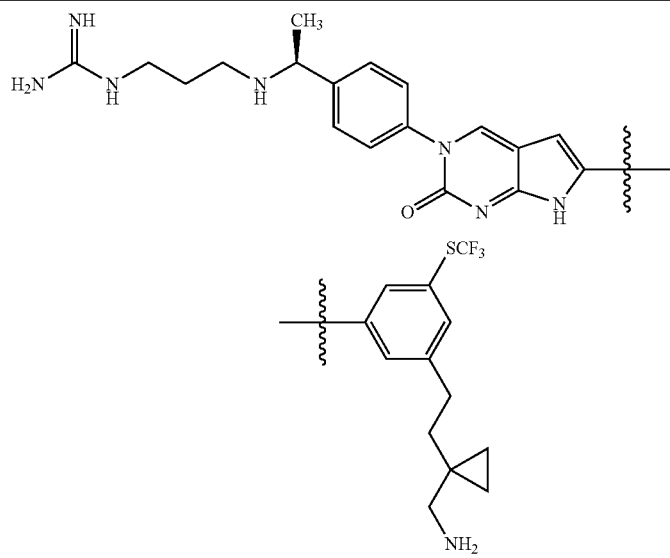
311
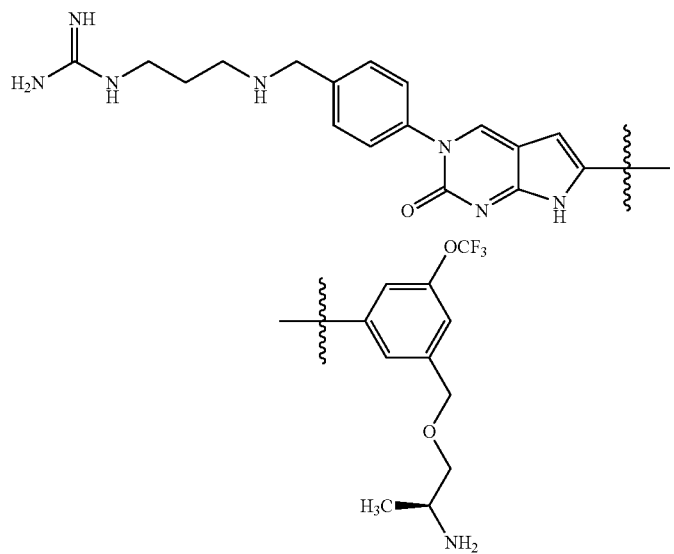
312
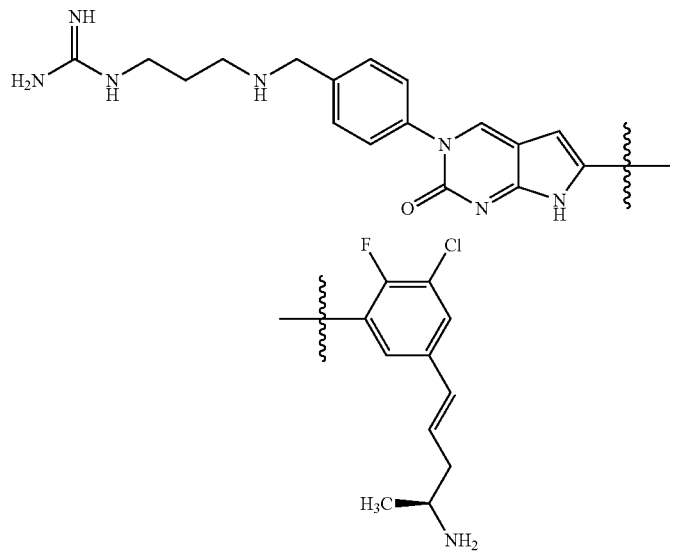

313 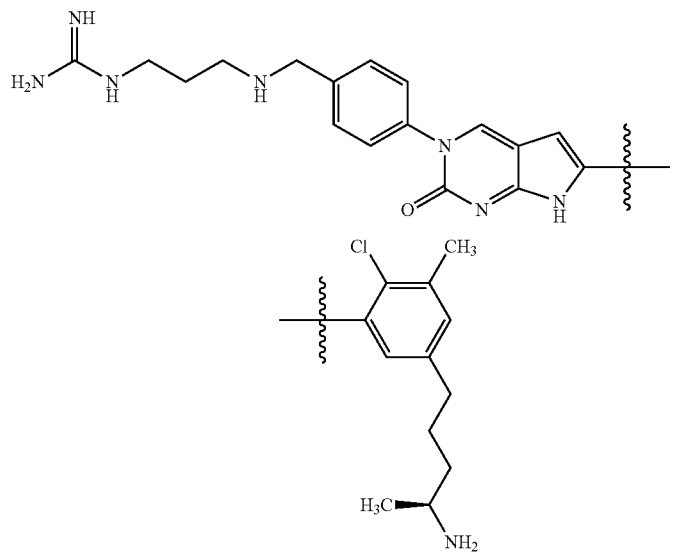
314 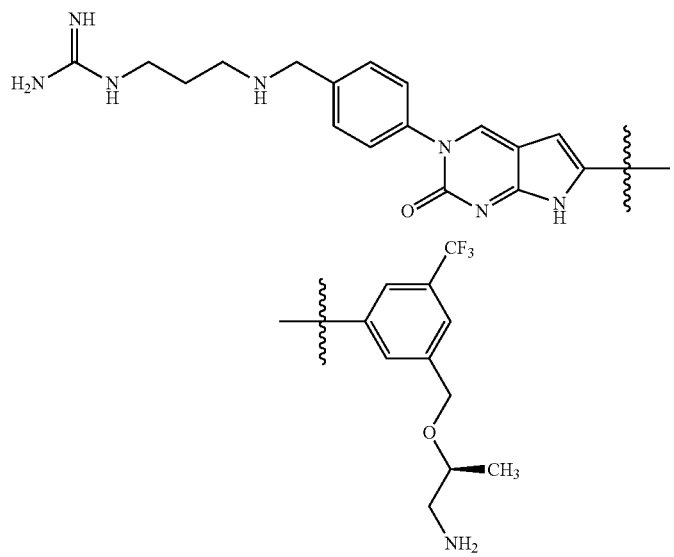

315 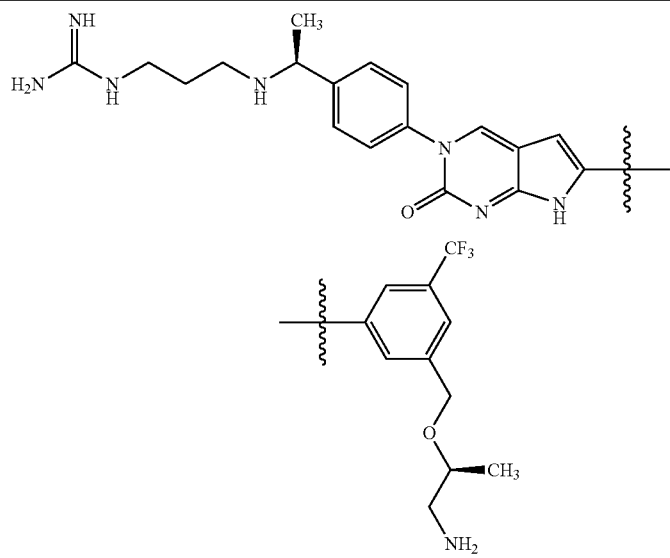
316 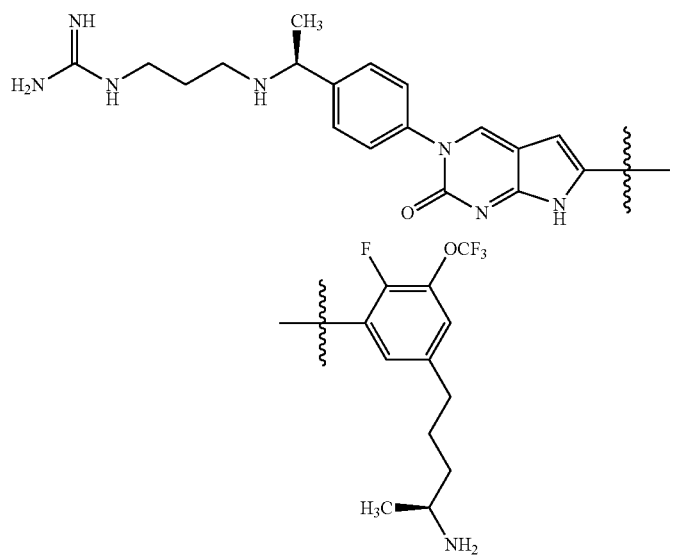
317 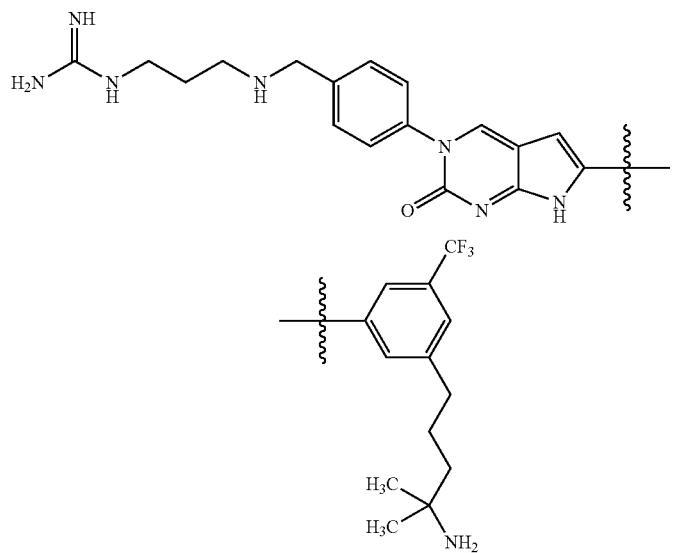

318 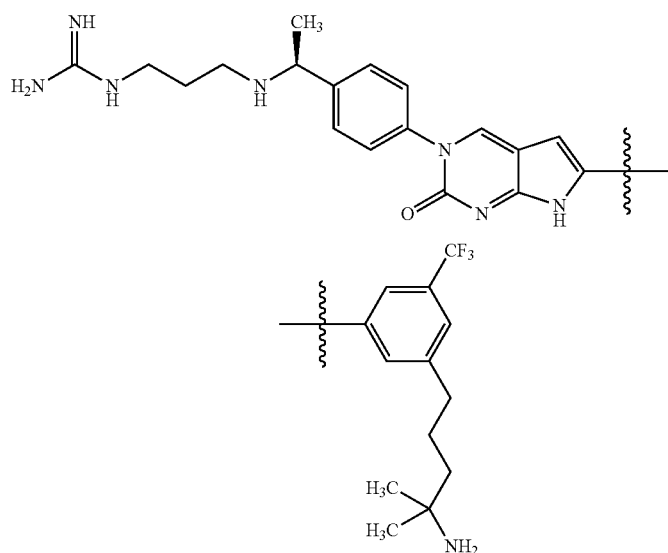
319 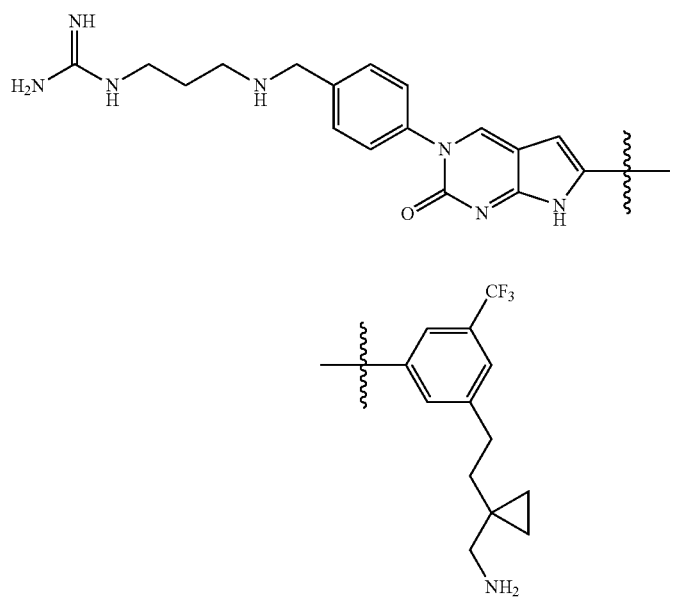 [SMILES: *c1cc2cn(-c3ccc(CNCCCNC(=N)N)cc3)c(=O)nc2[nH]1 ; *c1cc(CCC2(CN)CC2)cc(C(F)(F)F)c1]

| | |
|---|---|
| 320 | 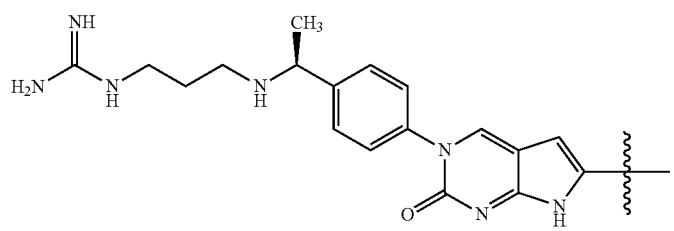 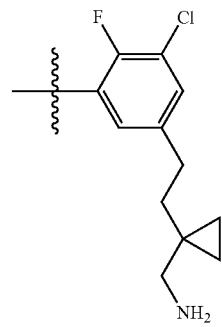 |
| 321 | 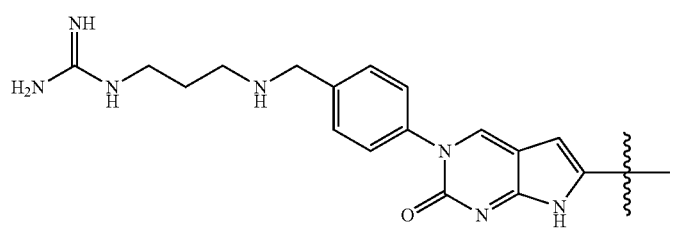 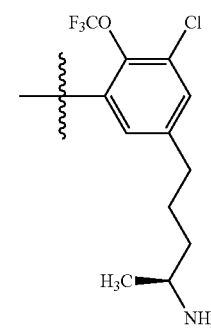 |

| 322 | 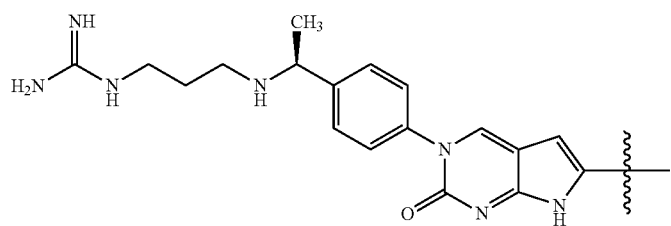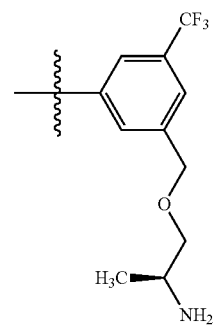 |
|---|---|
| 323 | 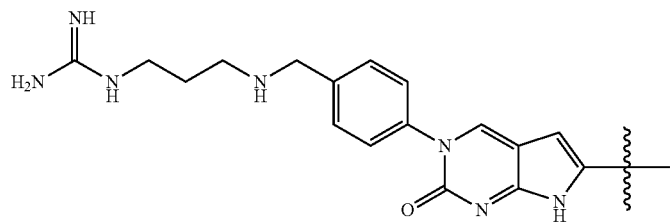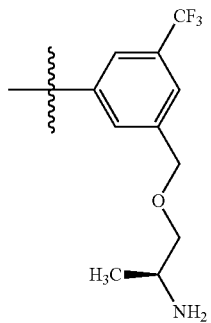 |

| | |
|---|---|
| 324 | 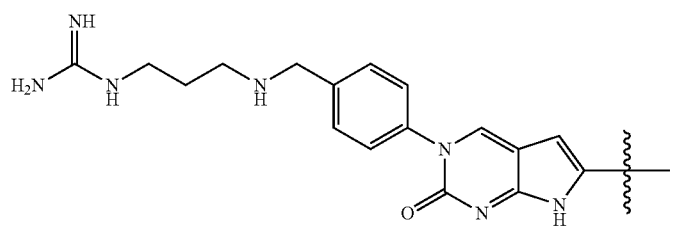<br>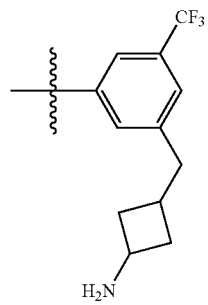 |
| 325 | 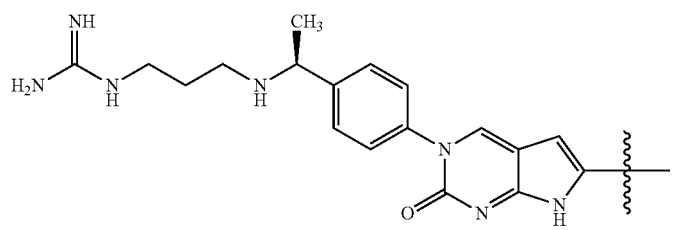<br>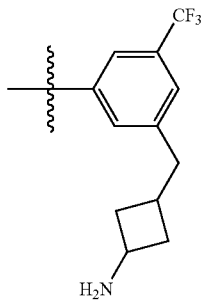 |

326 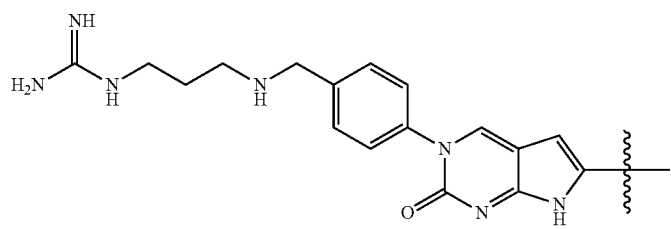
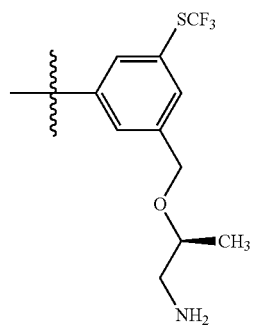
327 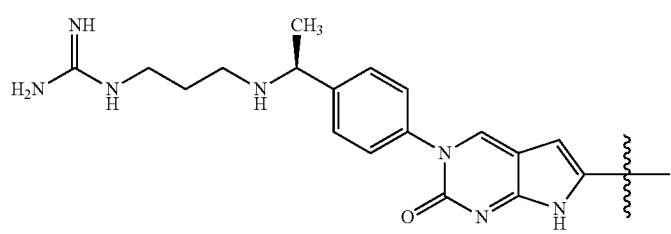
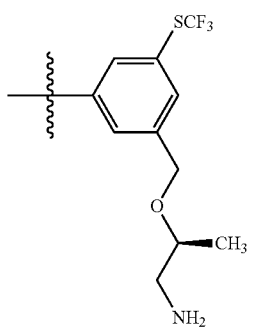

| | |
|---|---|
| 328 | 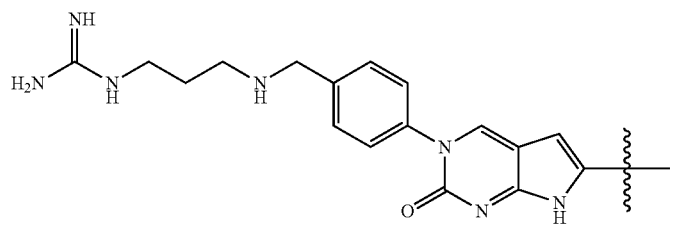 |
| | 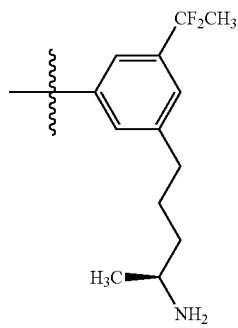 |
| 329 | 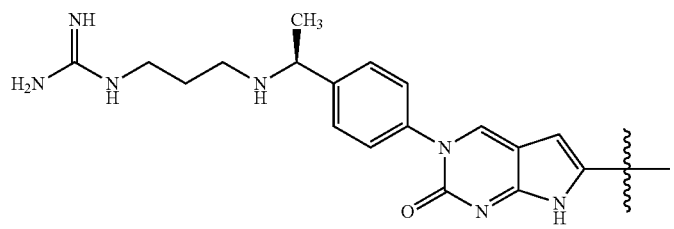 |
| | 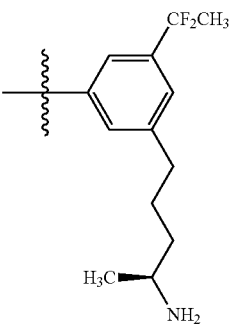 |

330
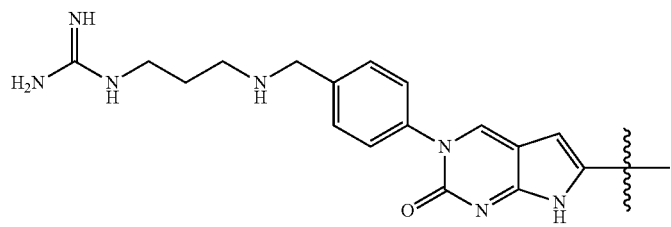
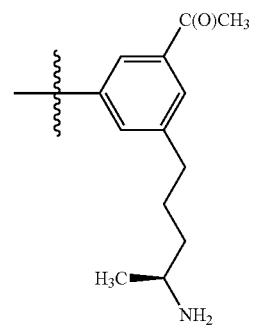
331
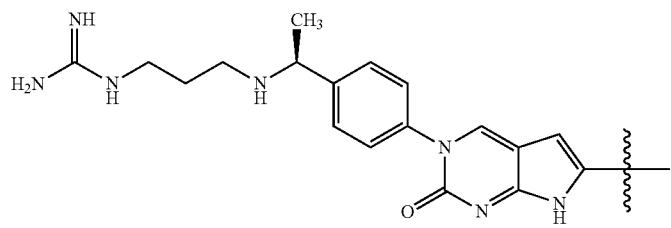
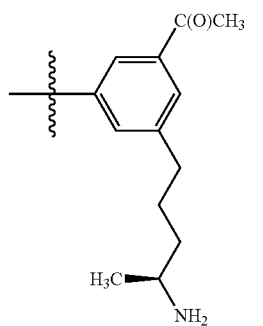

333 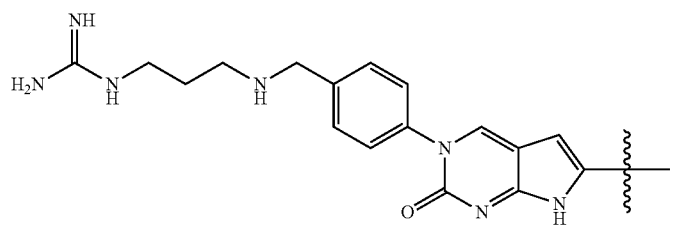
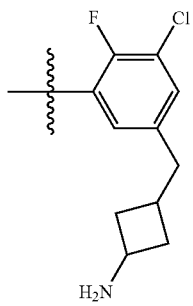
334 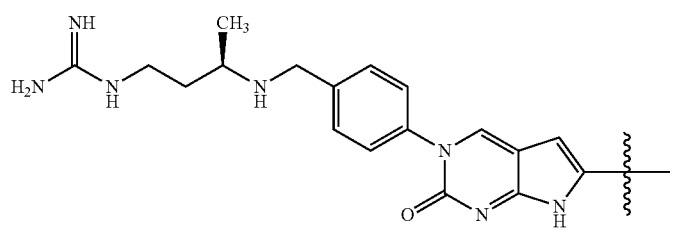
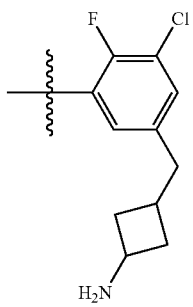
335 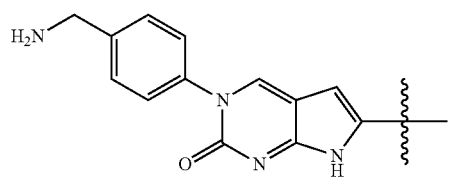
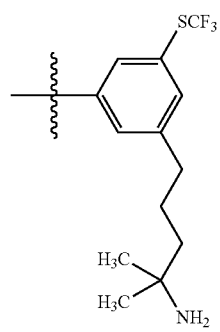

-continued
336
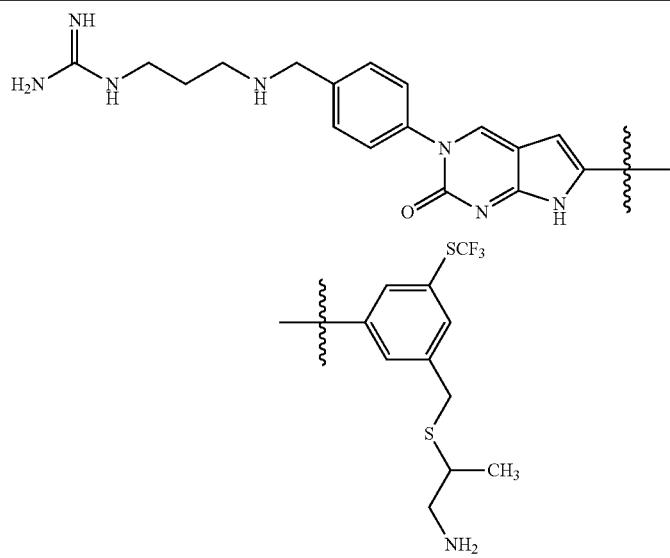
337
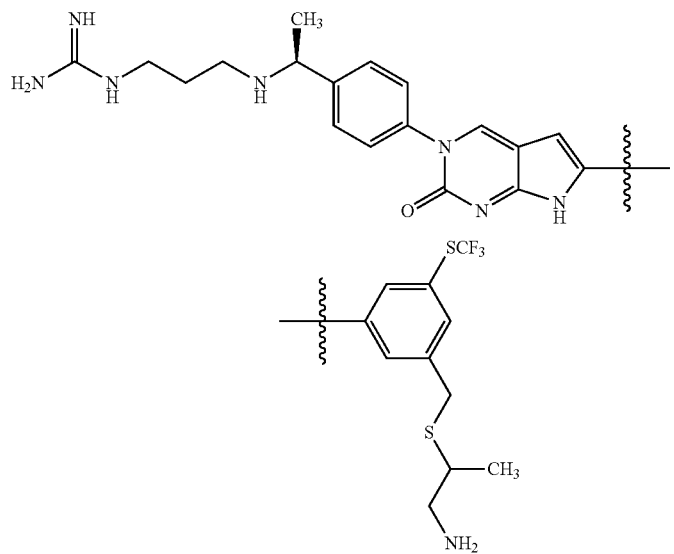
338
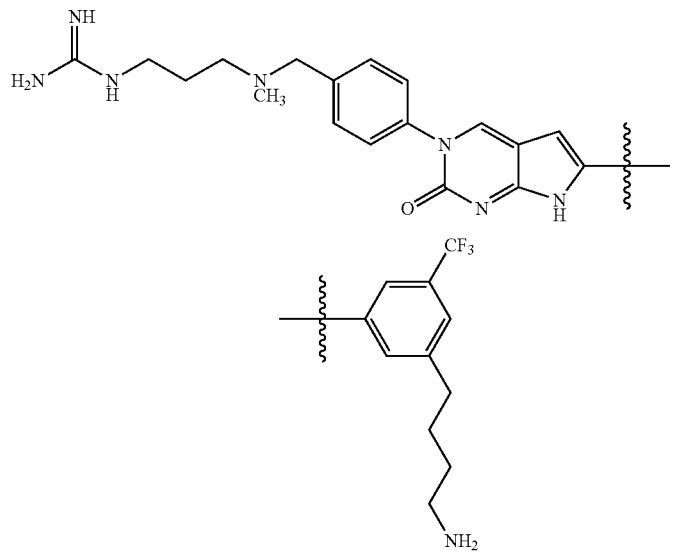

339 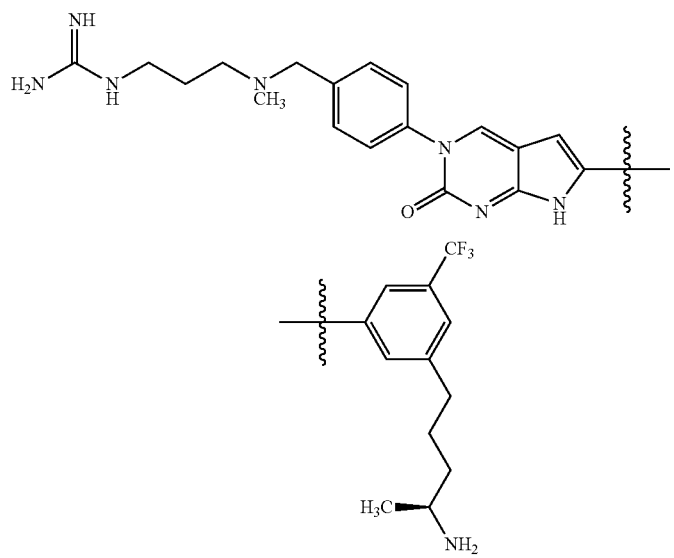
340 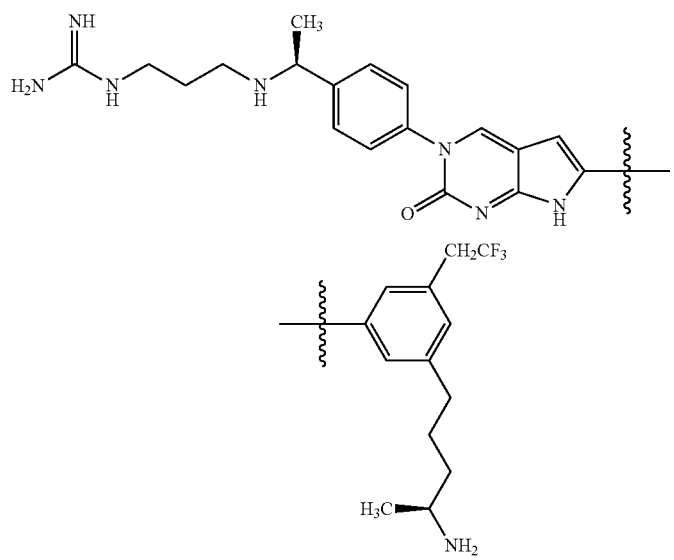

341 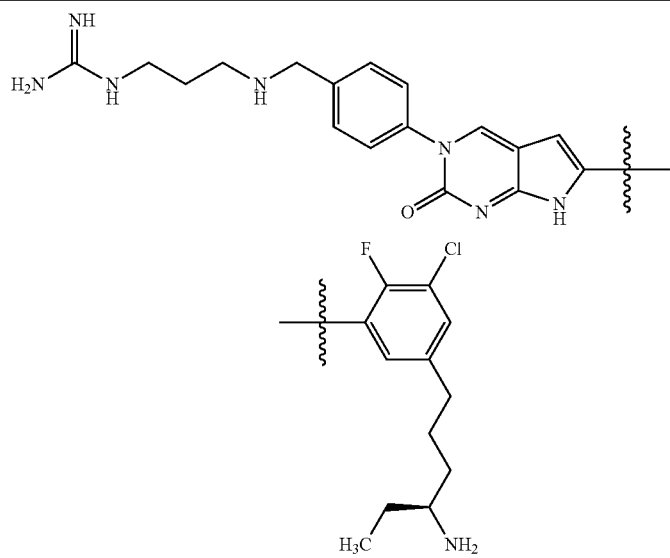
342 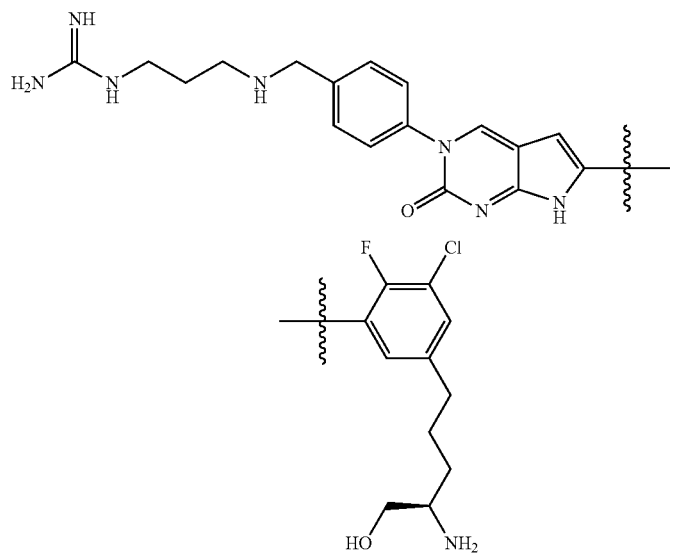
343 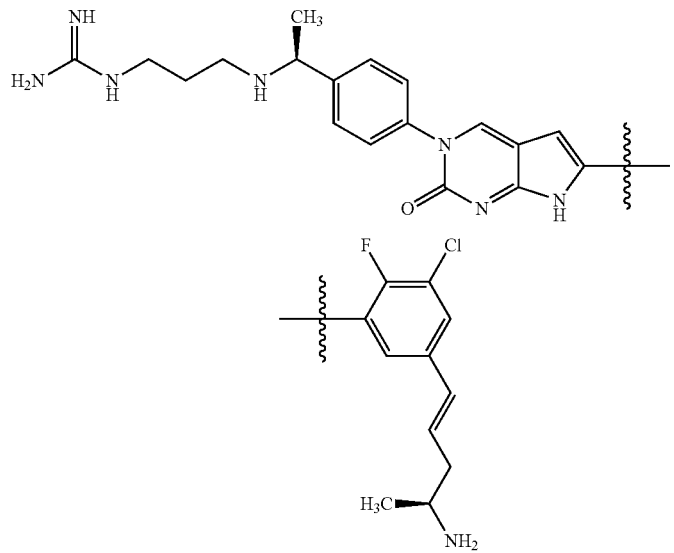

344
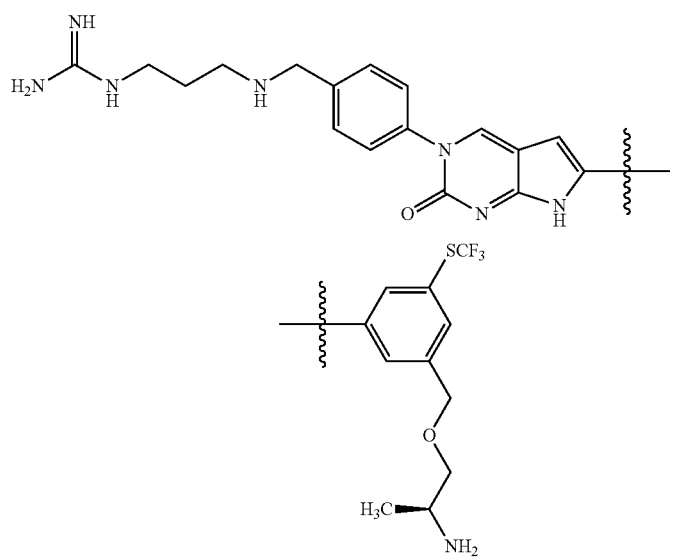
345
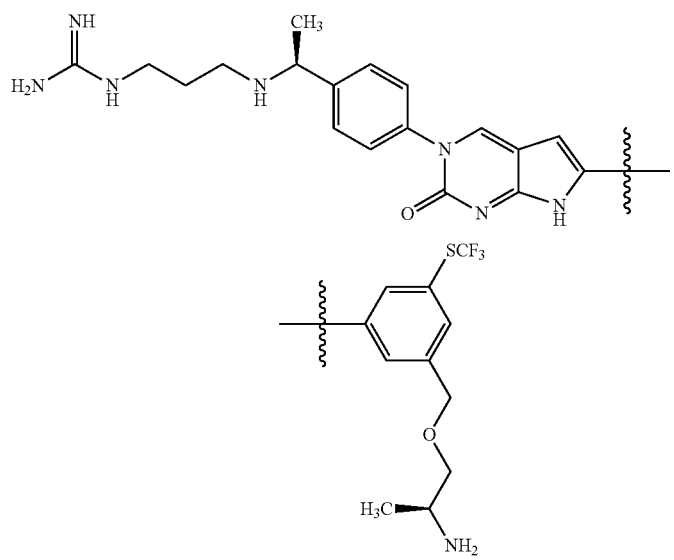

346 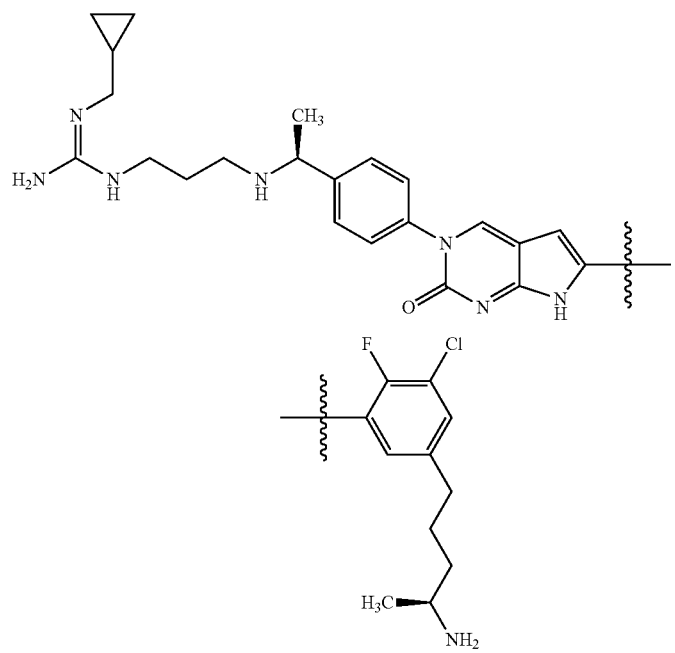
347 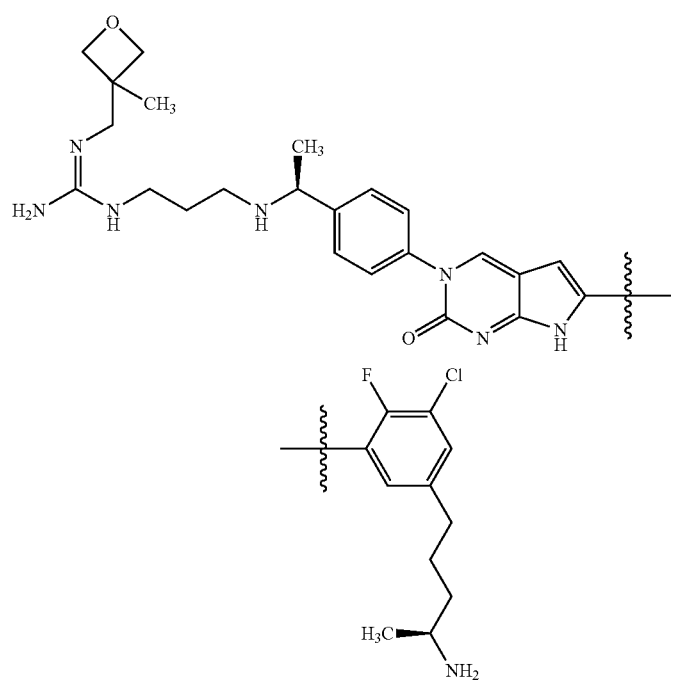

348 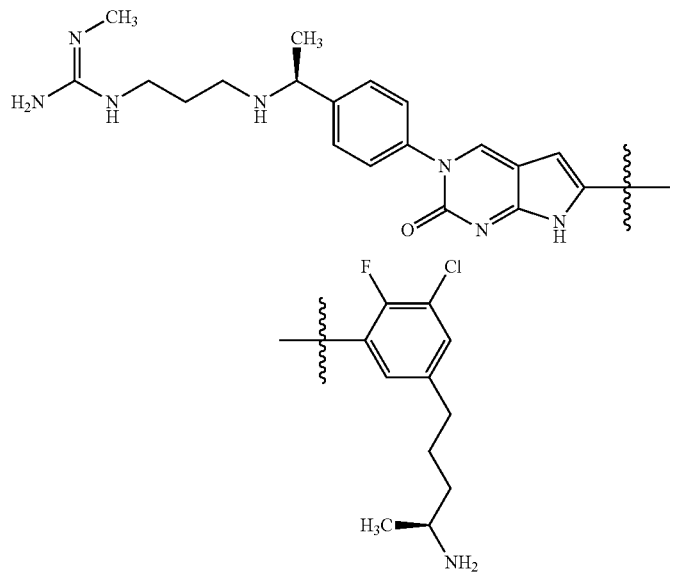
349 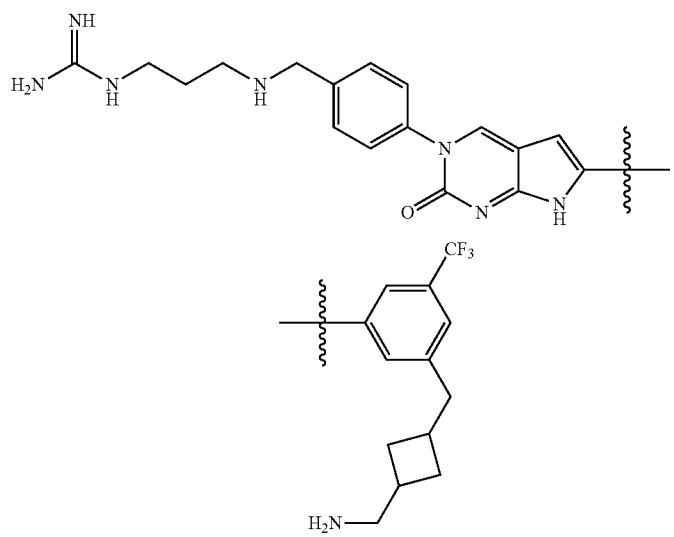
350 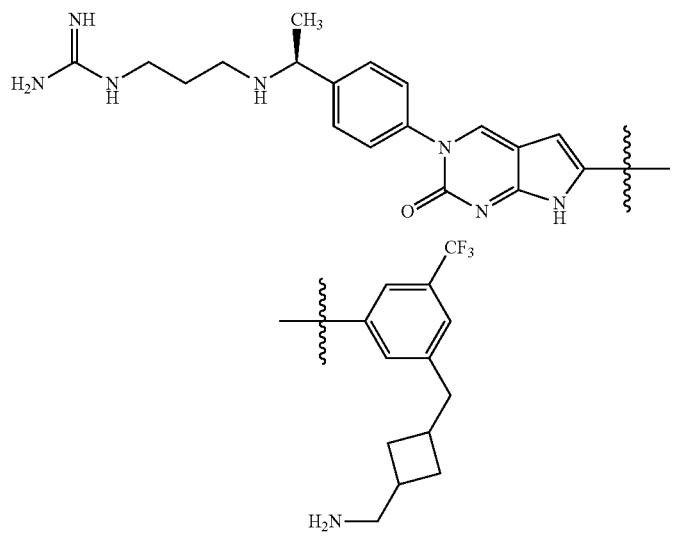

351 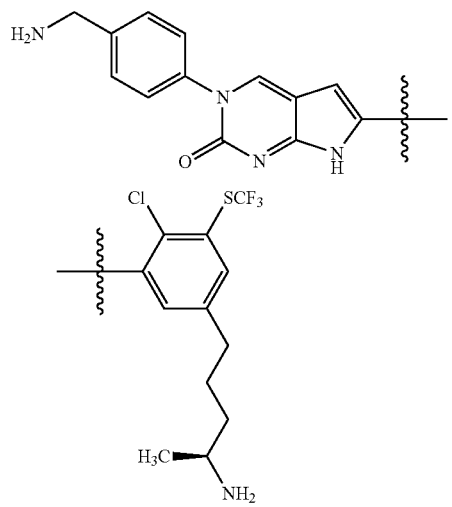
352 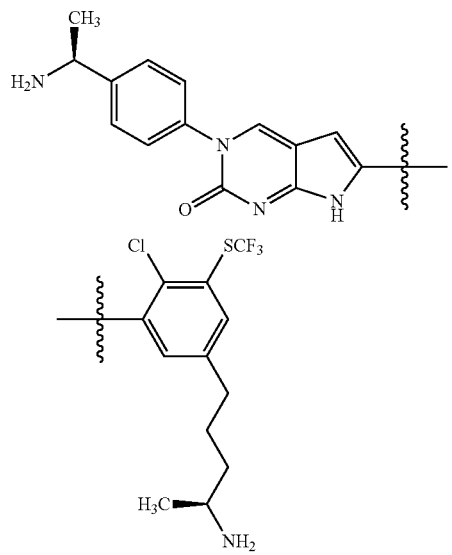
353 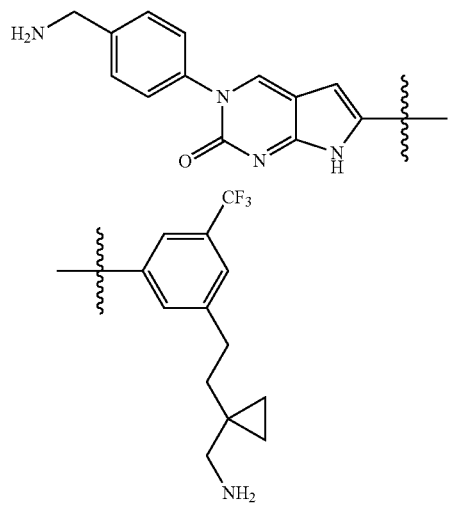

354 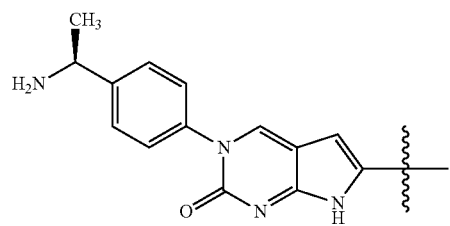
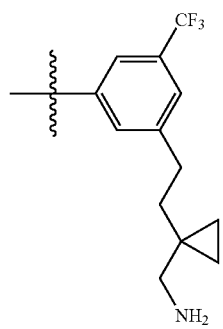
355 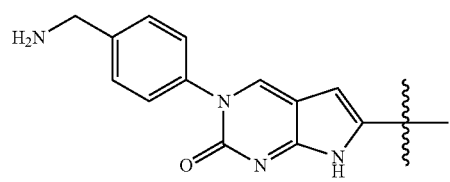
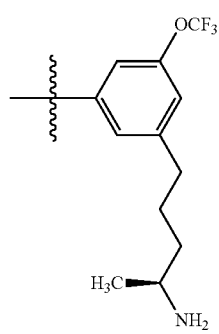
356 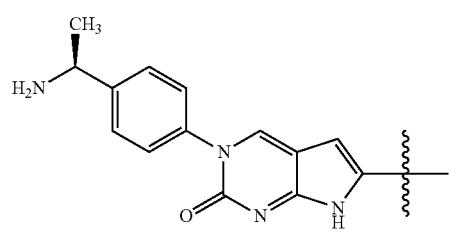
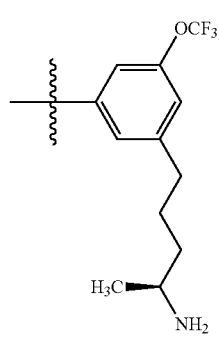

| | |
|---|---|
| 357 | 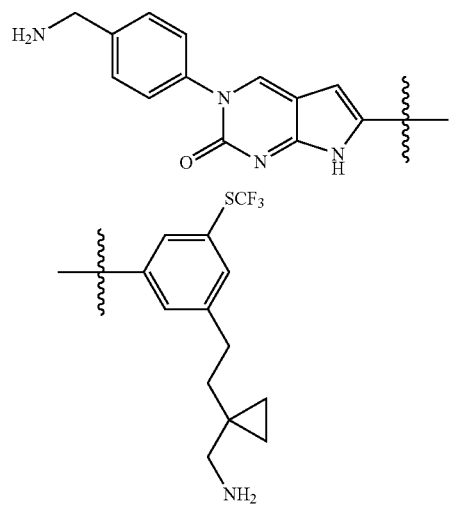 |
| 358 | 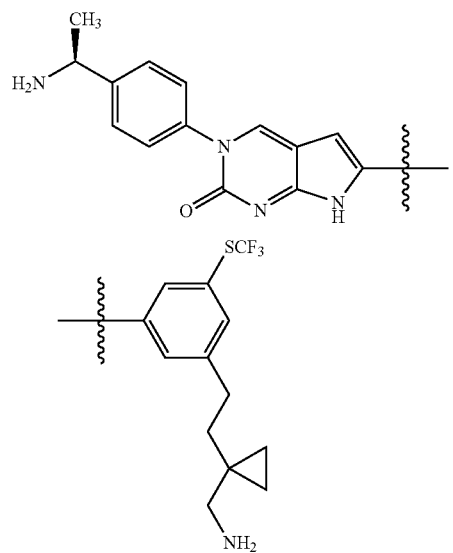 |
| 359 | 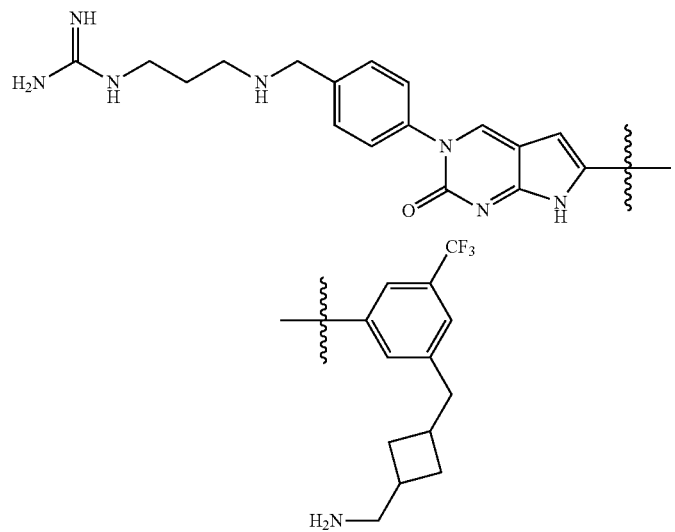 |

360
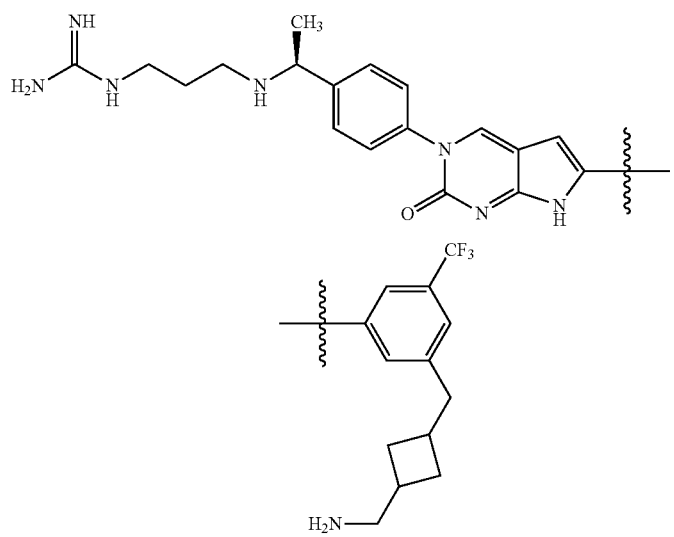
361
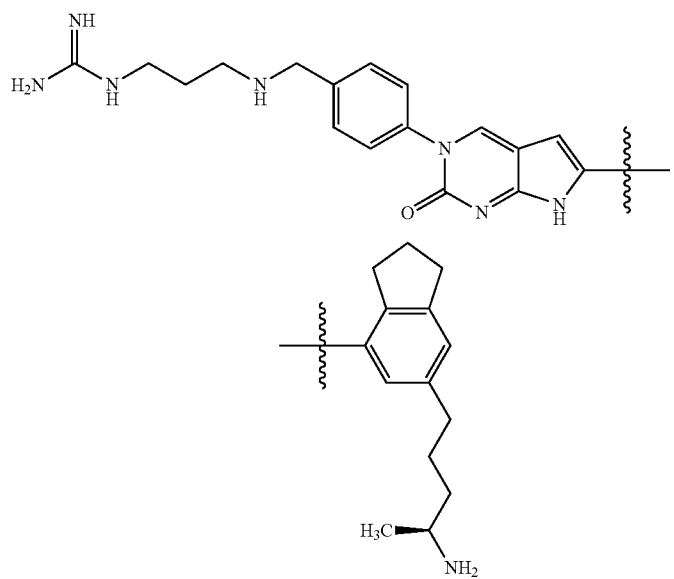

-continued
362 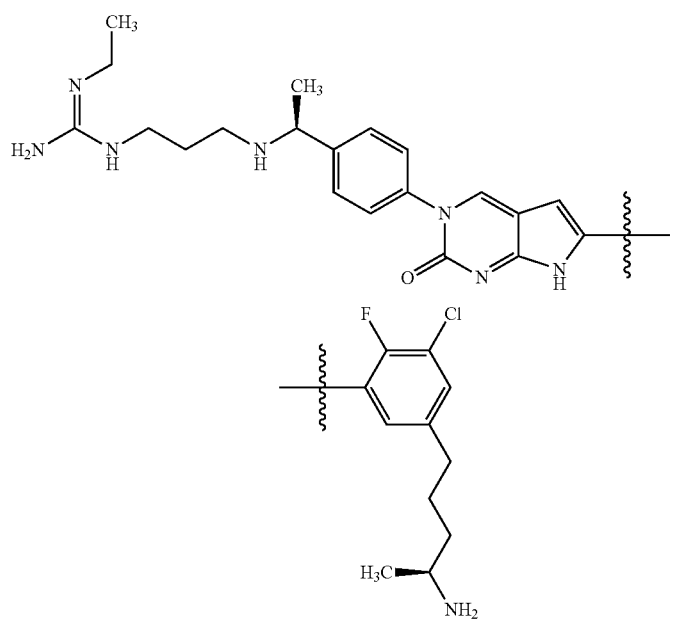
363 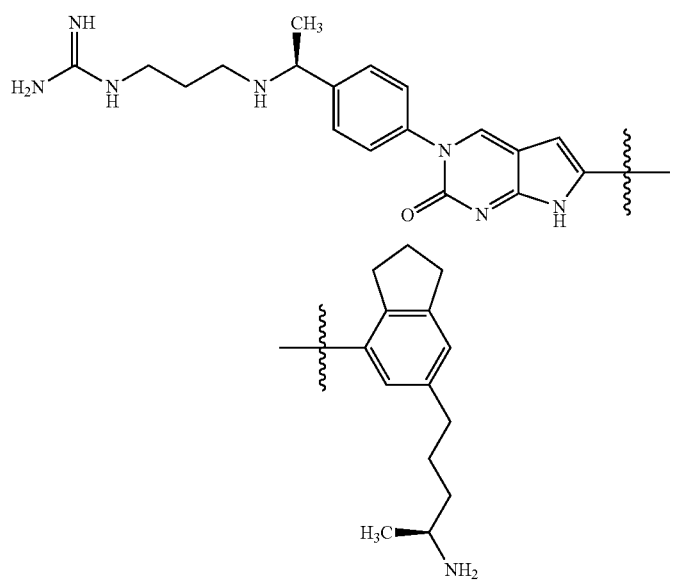

364
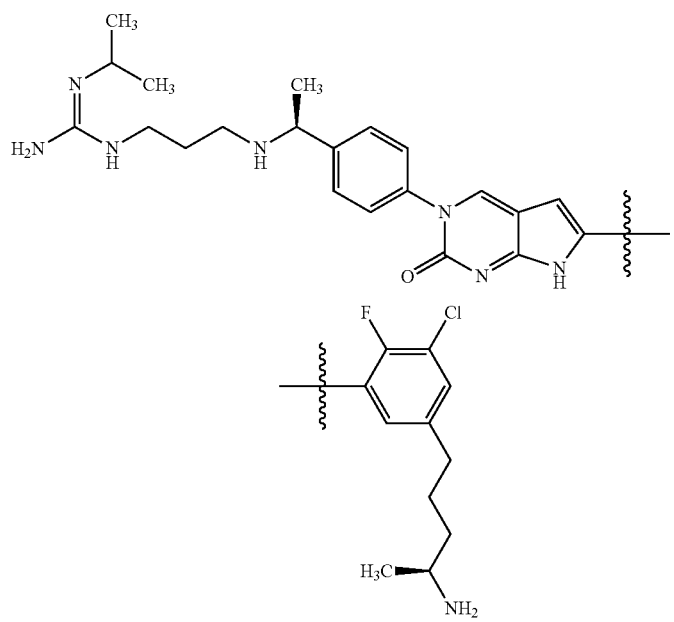
365
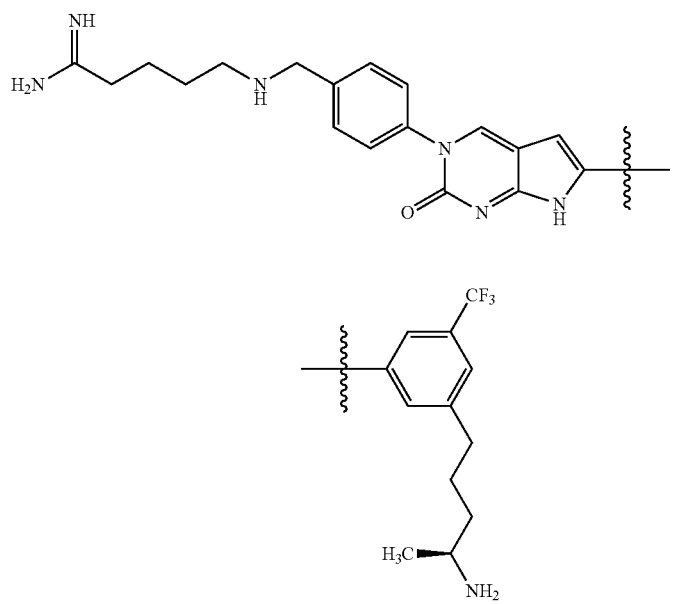 [SMILES: *c1cc2cn(-c3ccc(CNCCCCC(=N)N)cc3)c(=O)nc2[nH]1 ; *c1cc(CCC[C@H](C)N)cc(C(F)(F)F)c1]

366 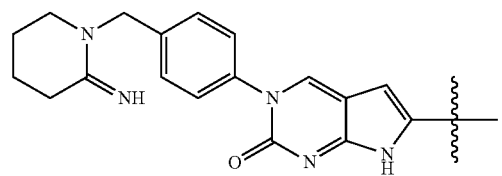
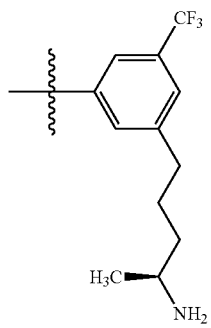
367 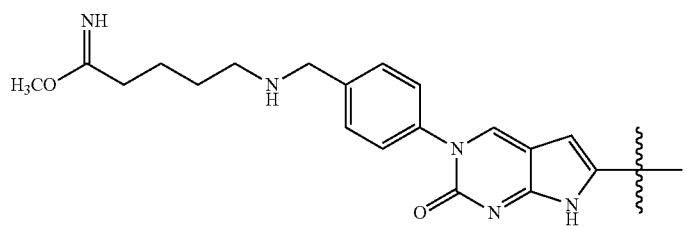
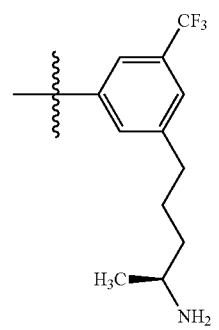

368 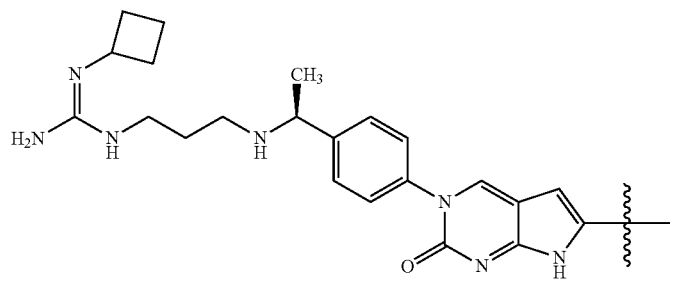
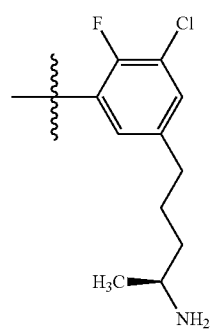
371 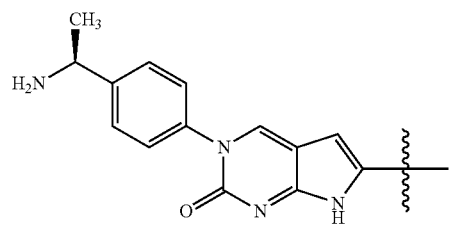
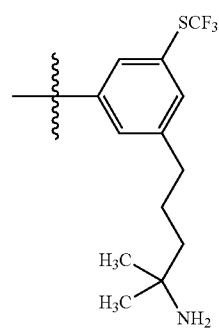

372 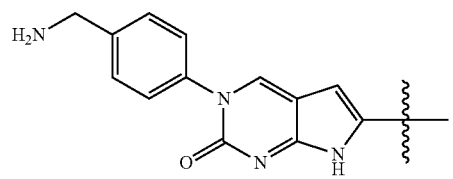
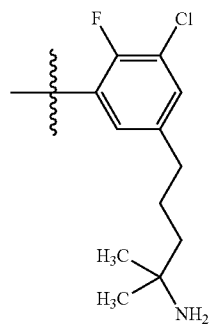
373 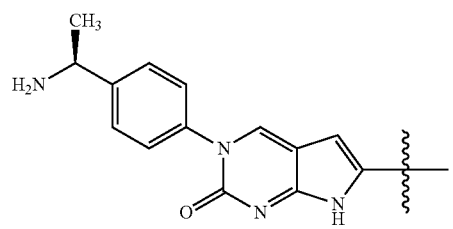
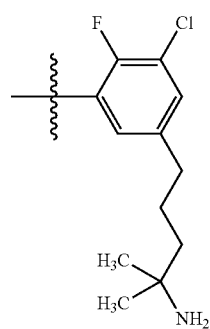

374 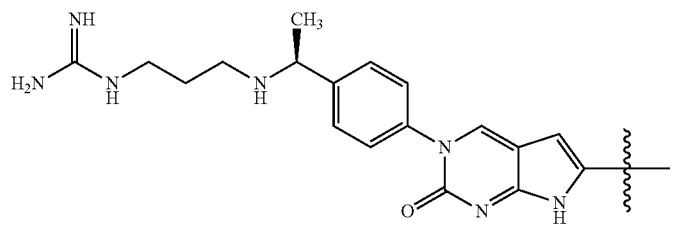
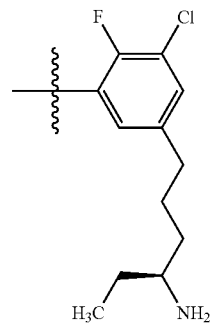
375 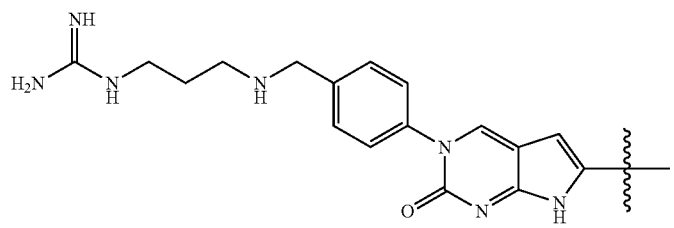
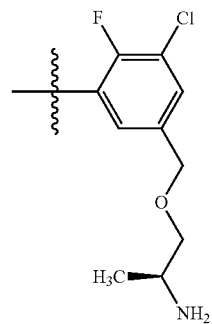

| | |
|---|---|
| 376 | 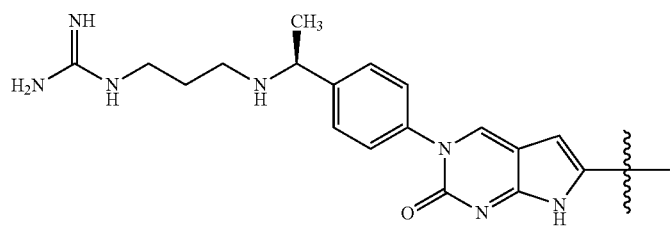 |
| | 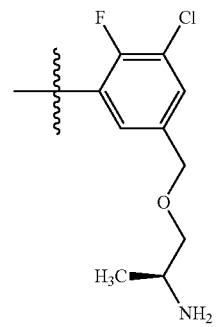 |
| 377 | 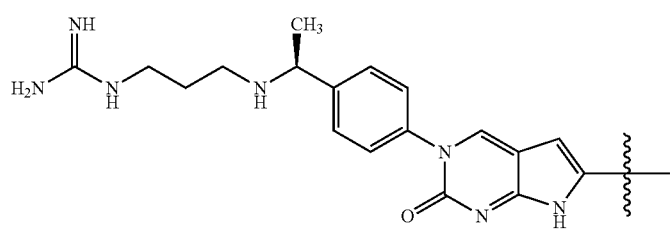 |
| | 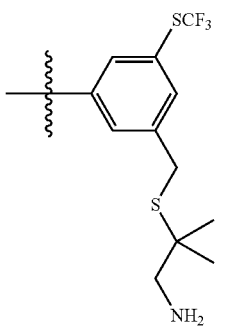 |

378 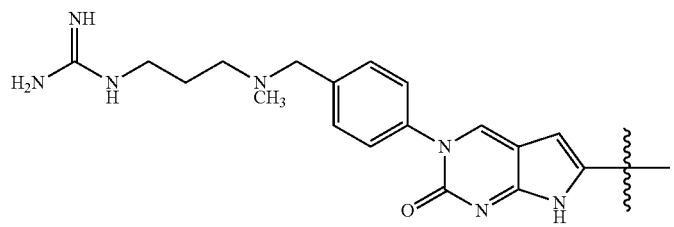
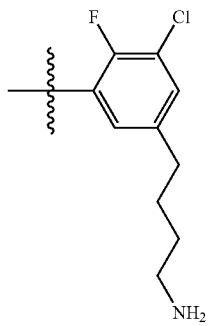
379 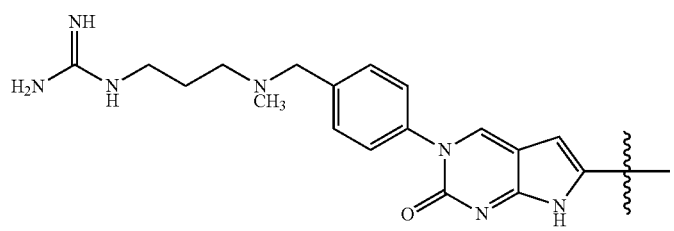
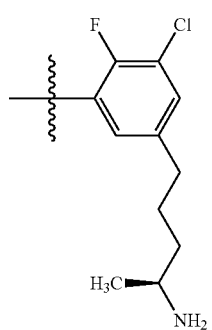

380
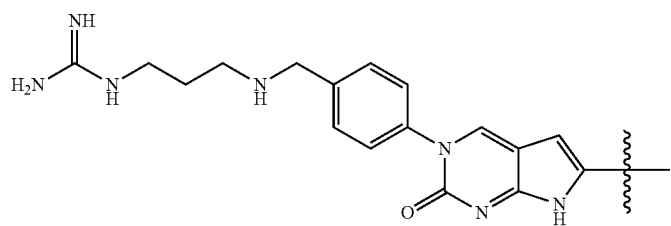
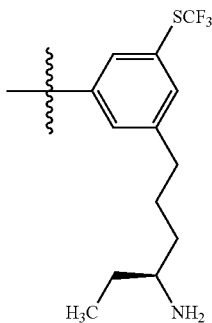
381
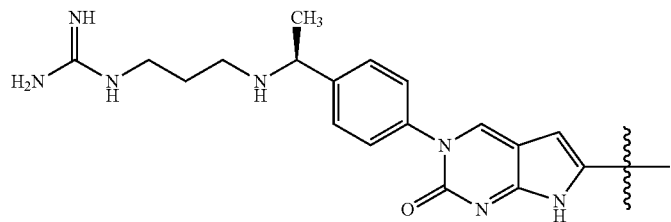
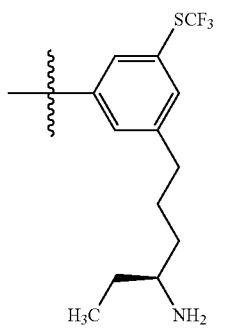

382 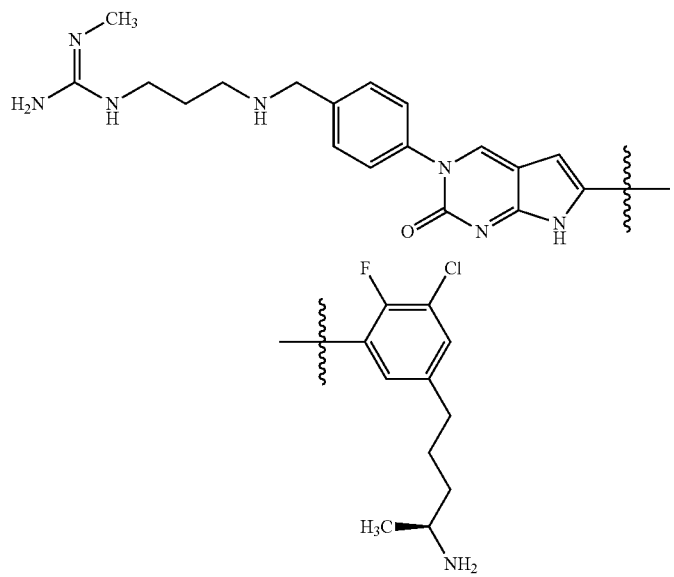
383 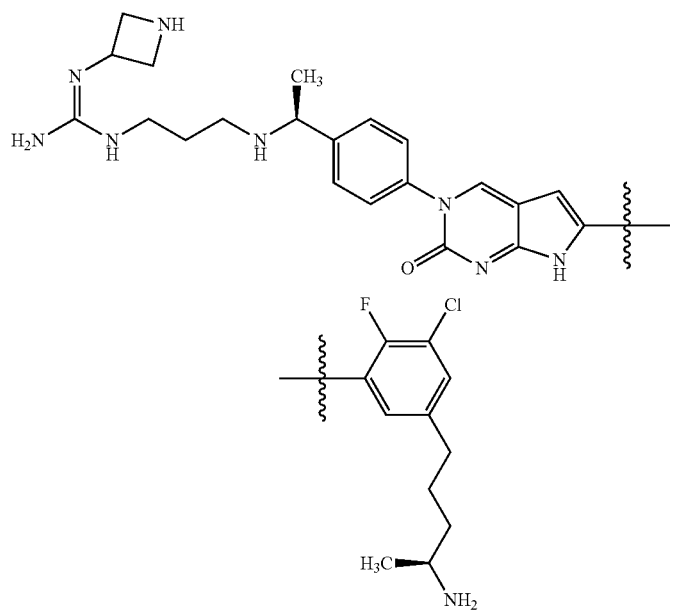

384 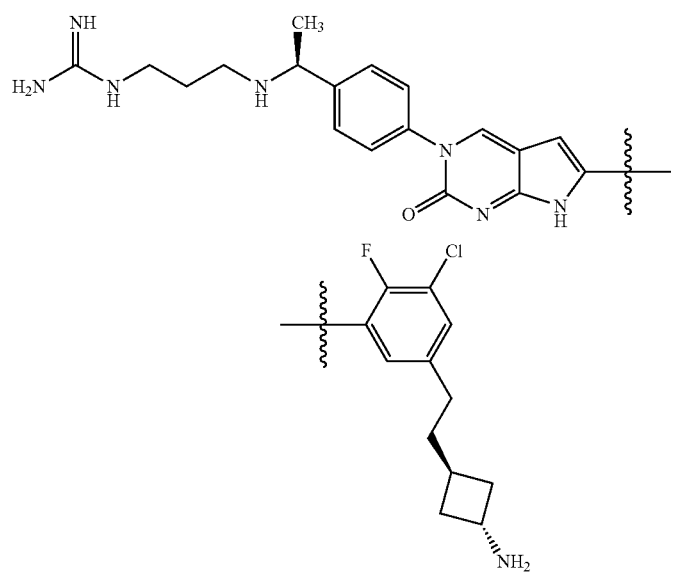
385 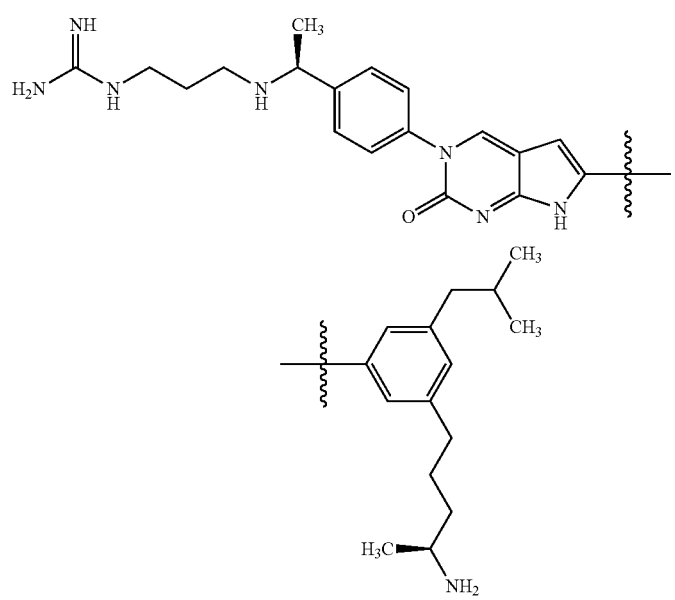

386 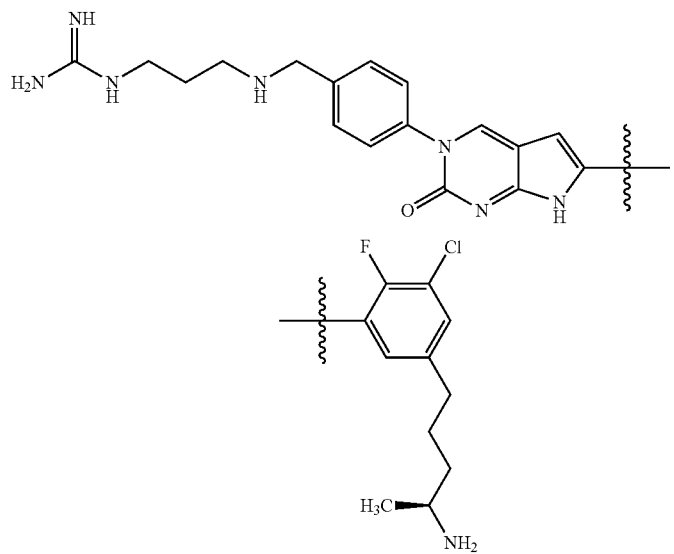
391 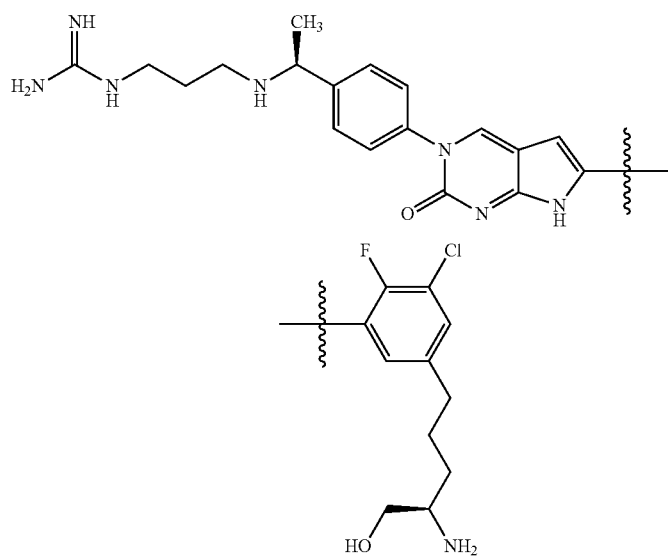

392 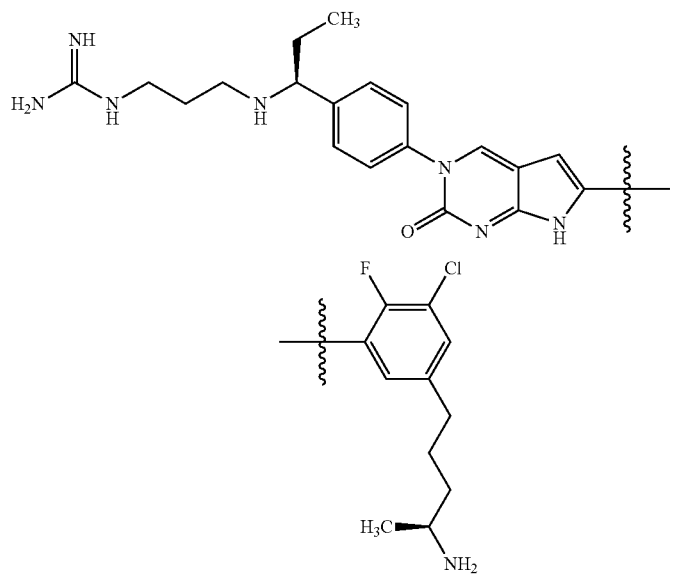
393 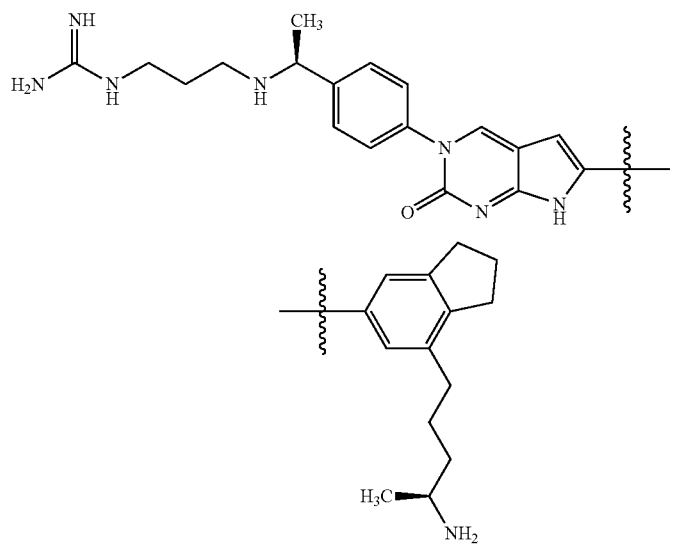

394 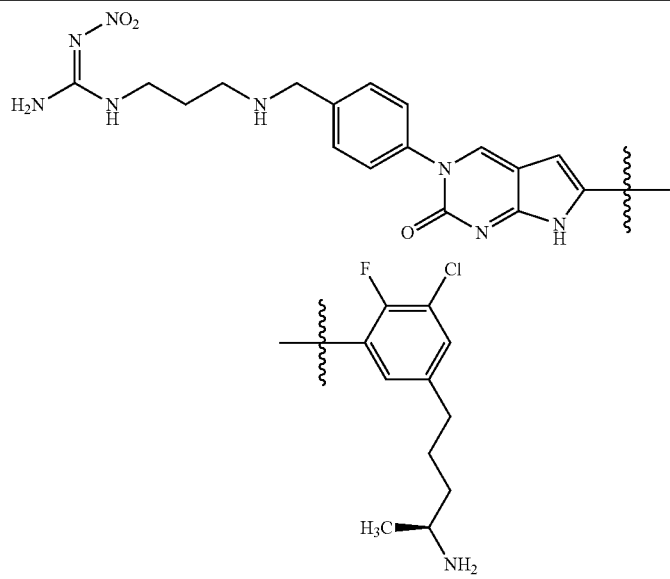
395 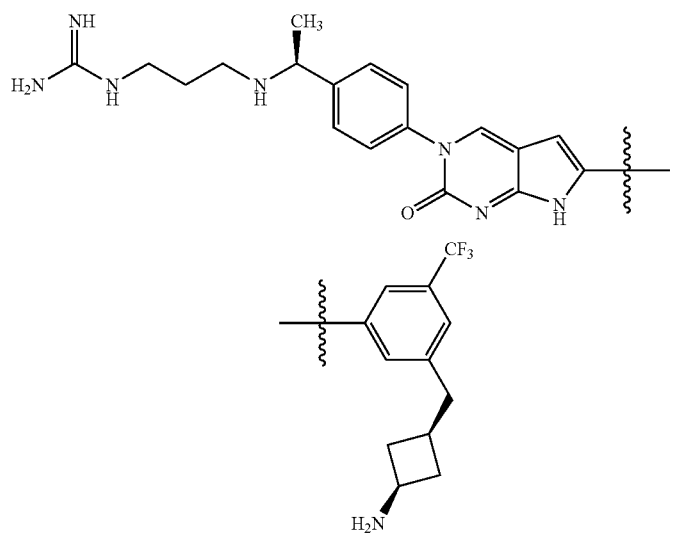
396 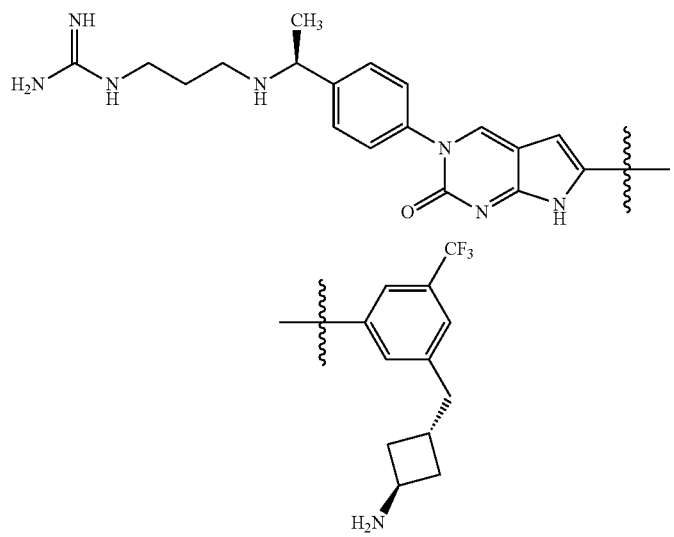

397 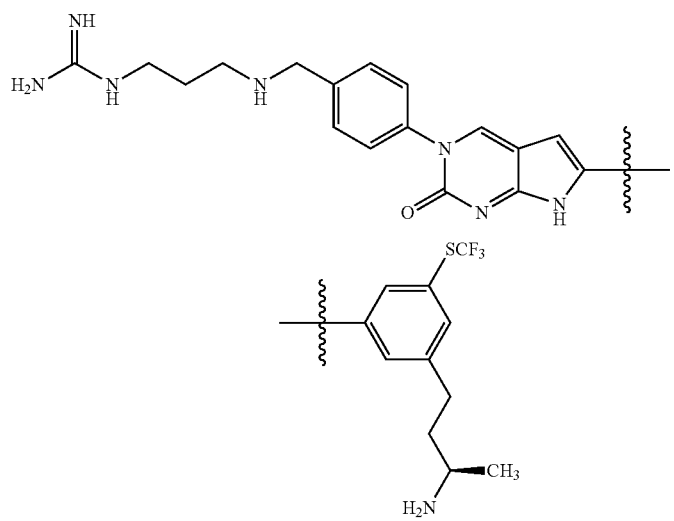
398 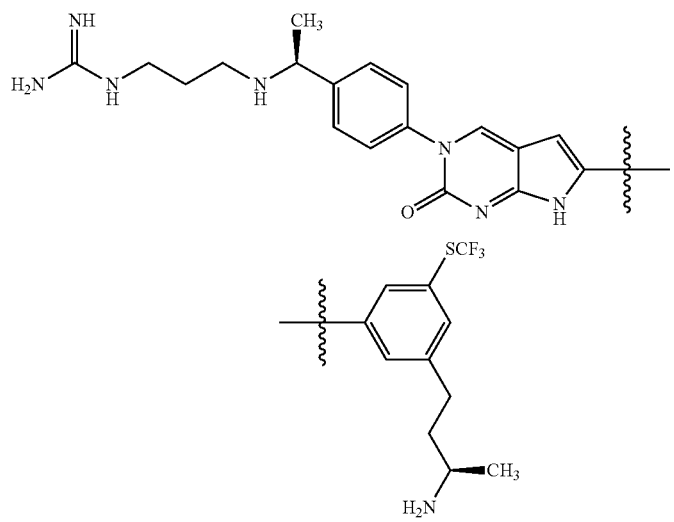
400 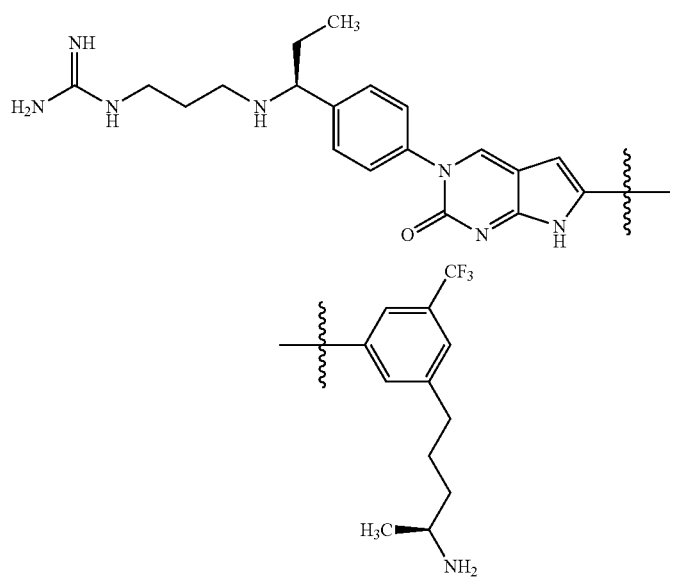

401 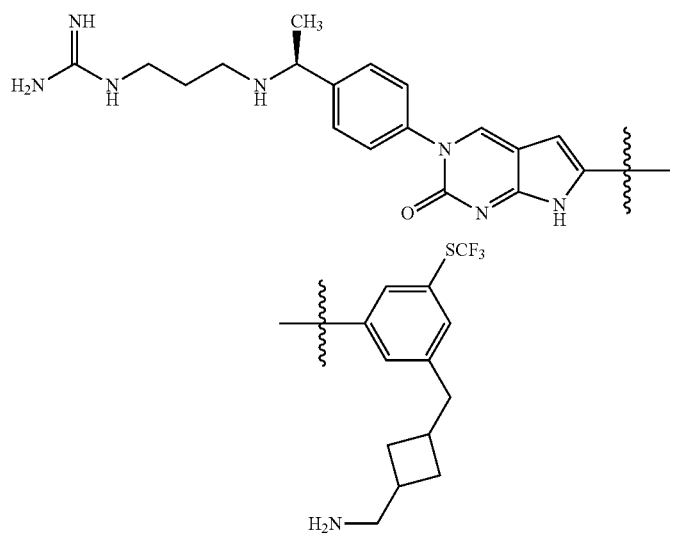
402 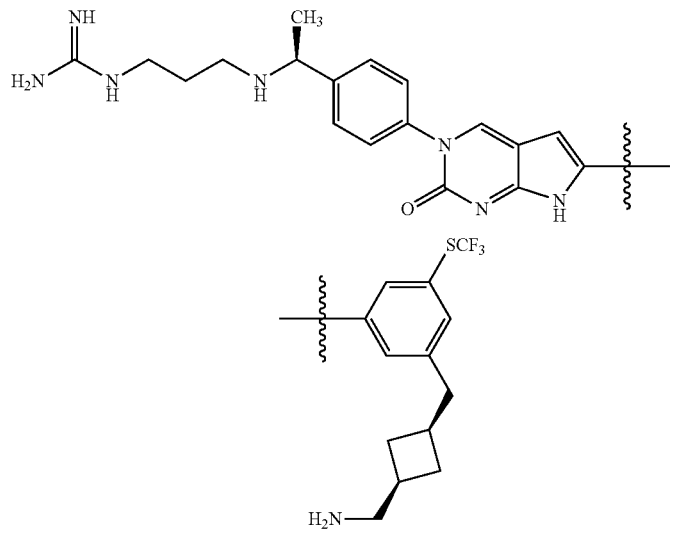
403 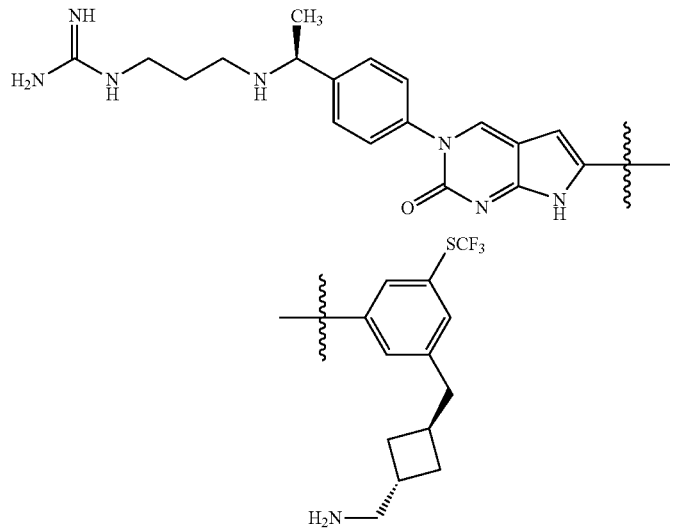

405 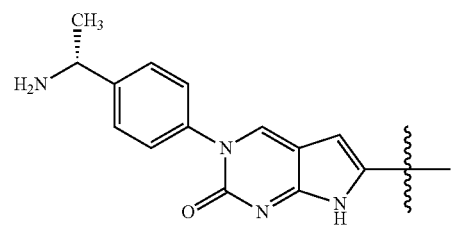 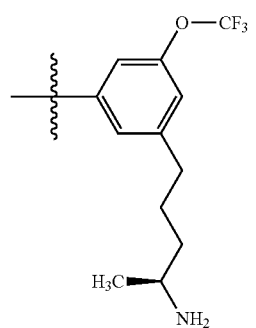
406 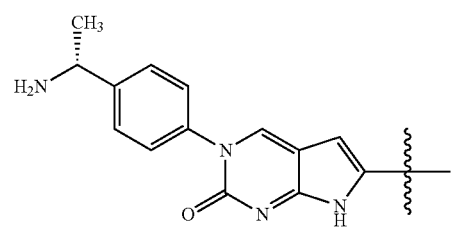 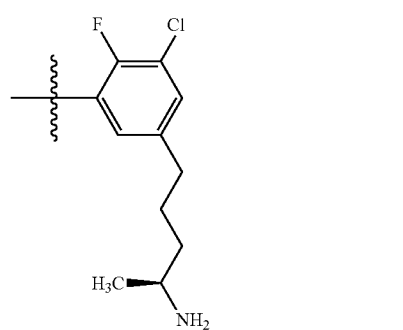

407
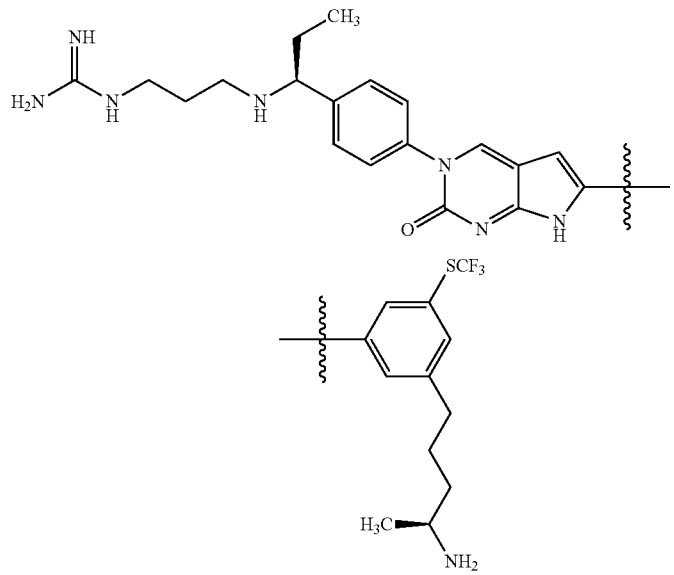
408
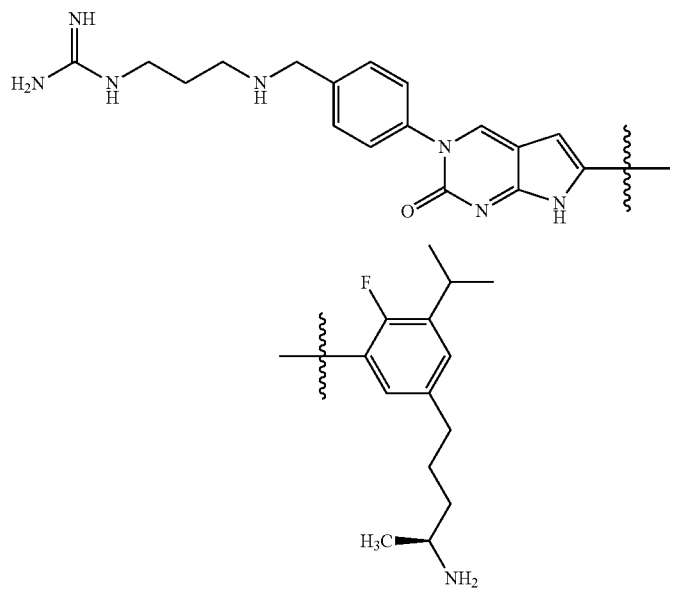

409 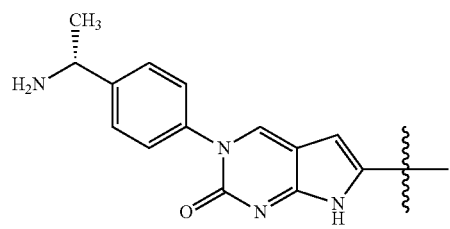
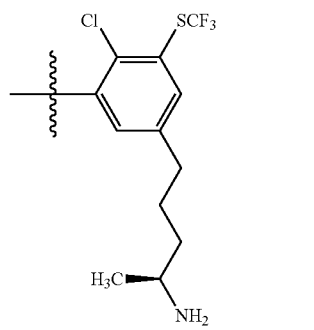
410 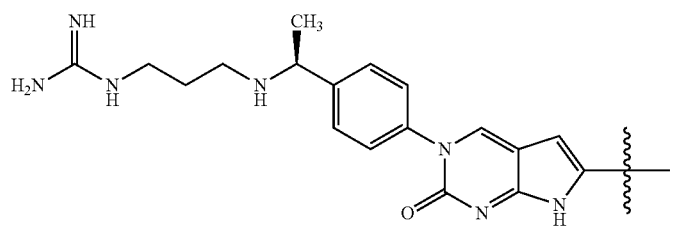
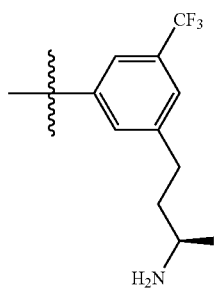
411 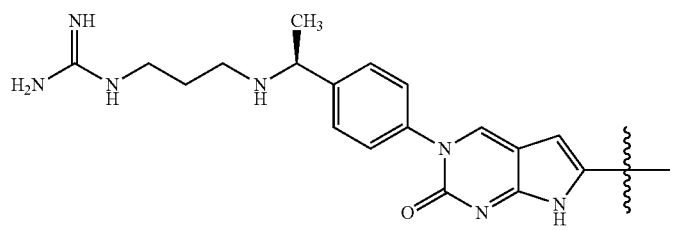
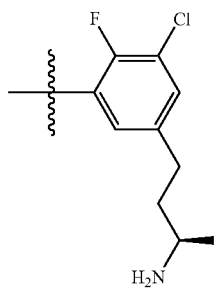

412 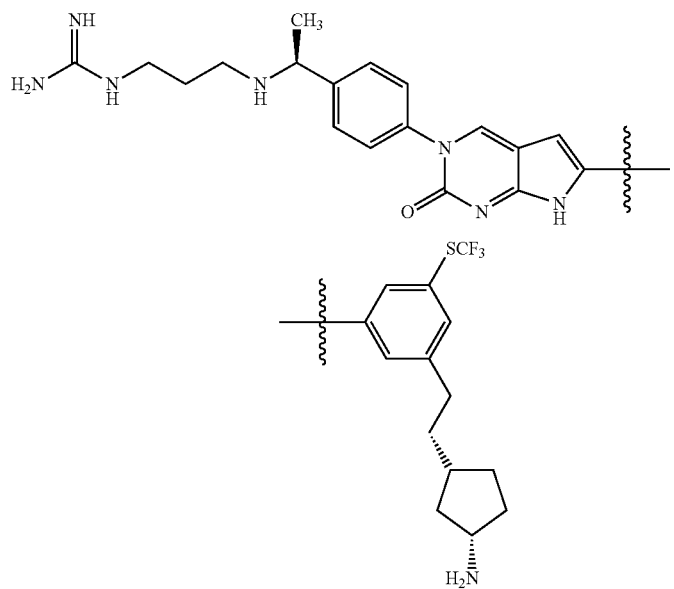
413 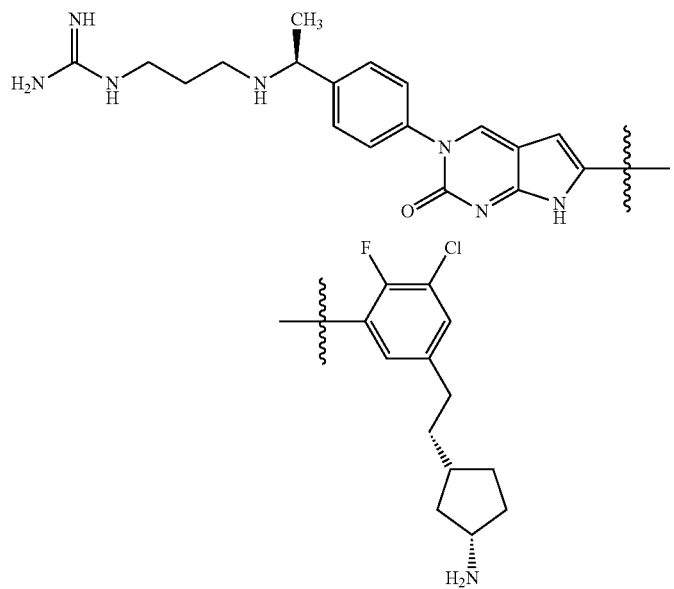

414
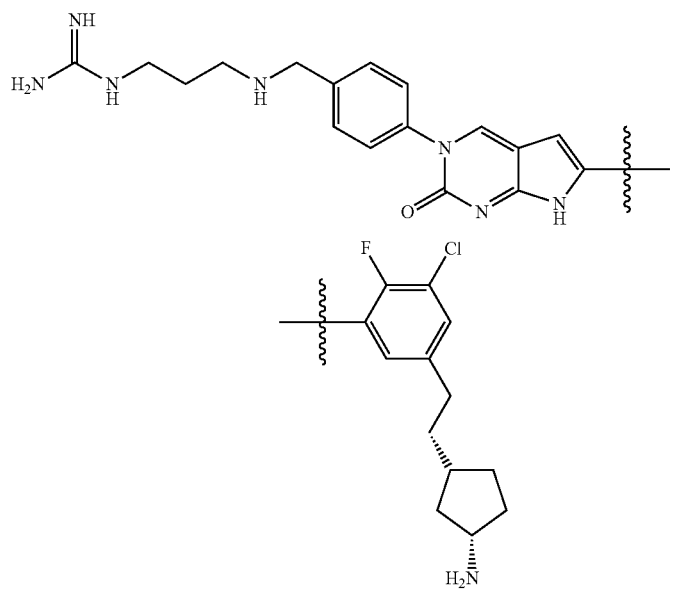
415
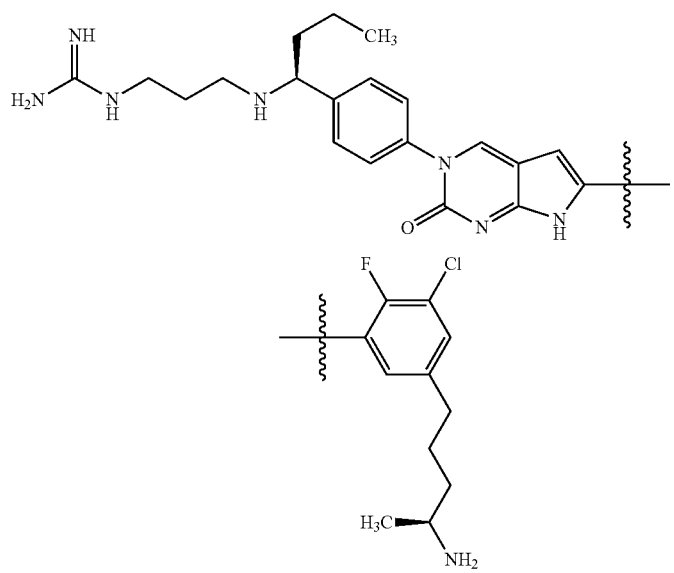

416 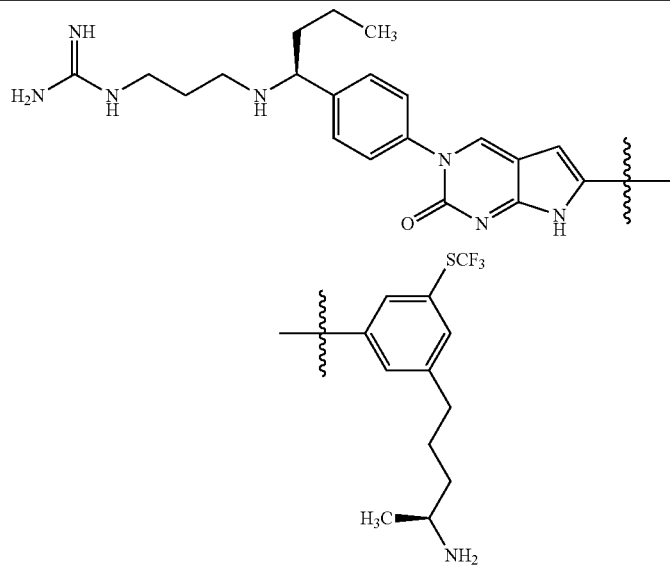
417 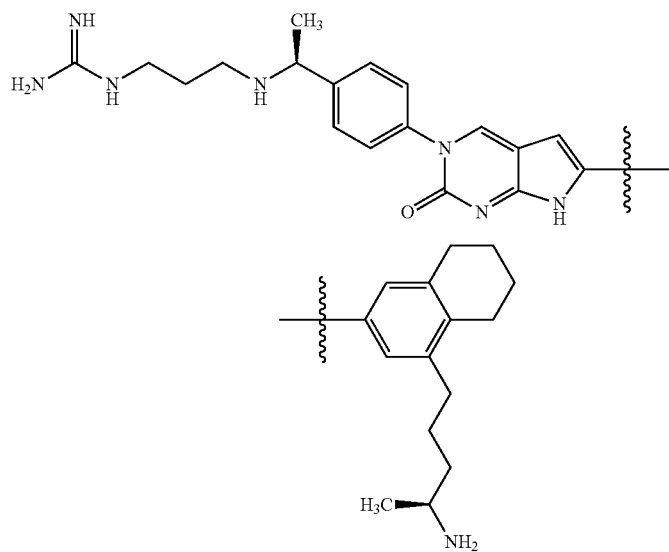
418 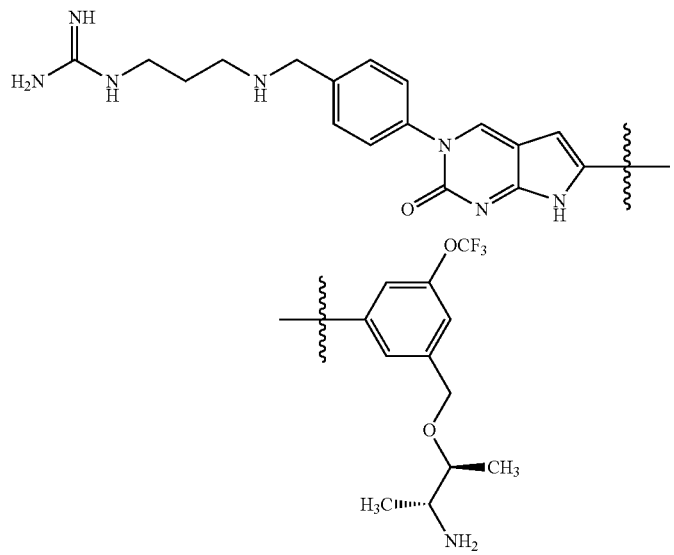

419 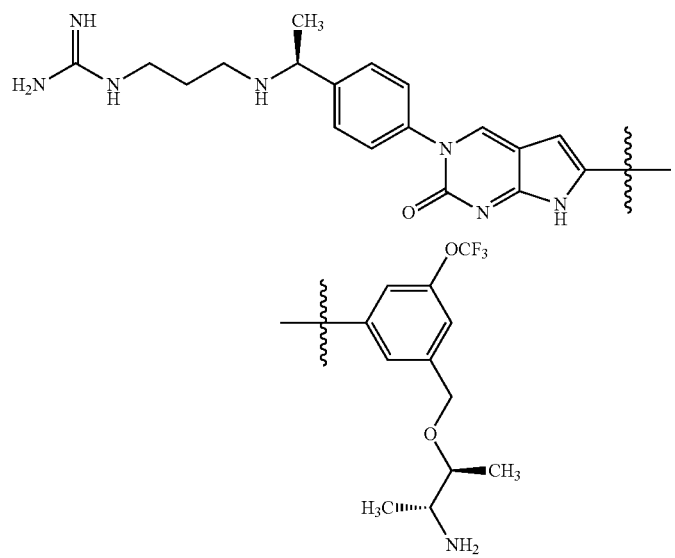
420 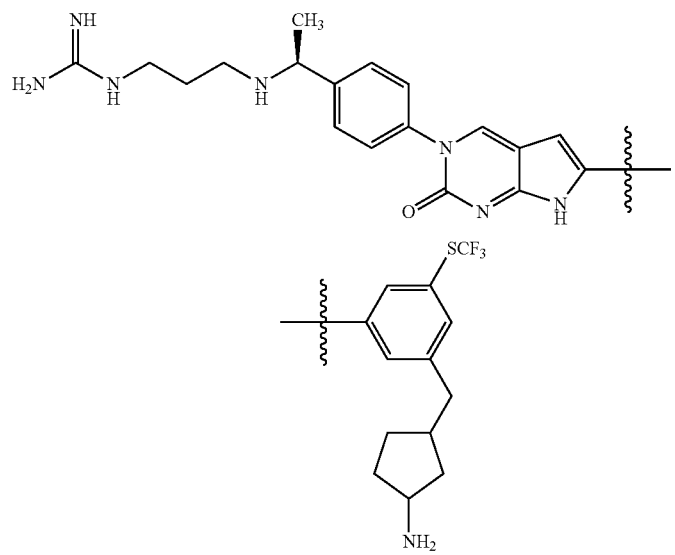

421 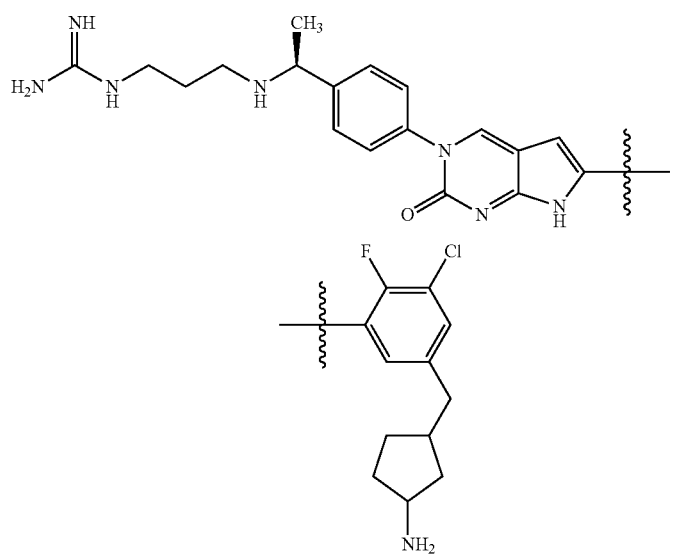
422 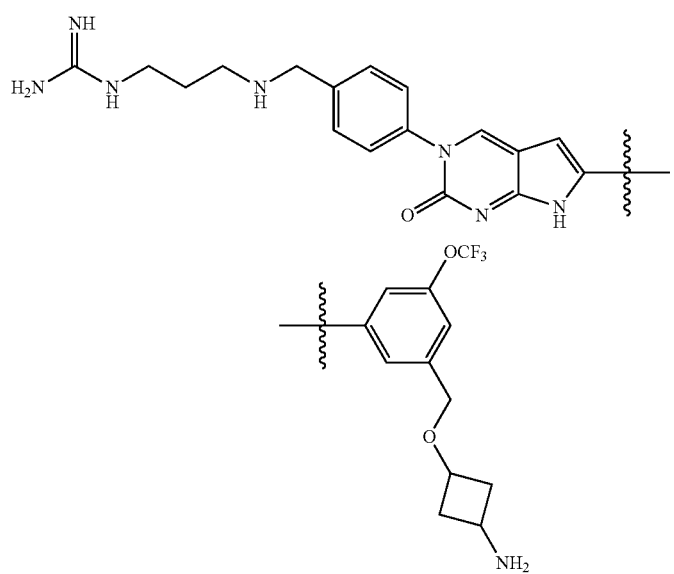

-continued
| | |
|---|---|
| 423 | 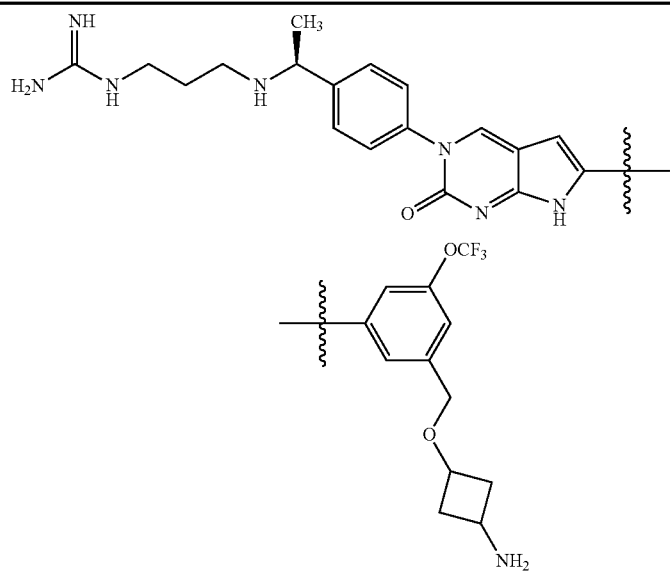 |
| 424 | 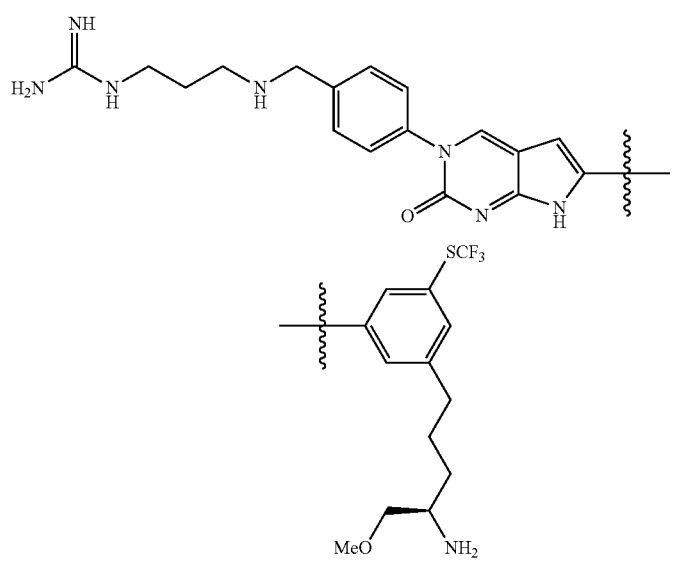 |
| 425 | 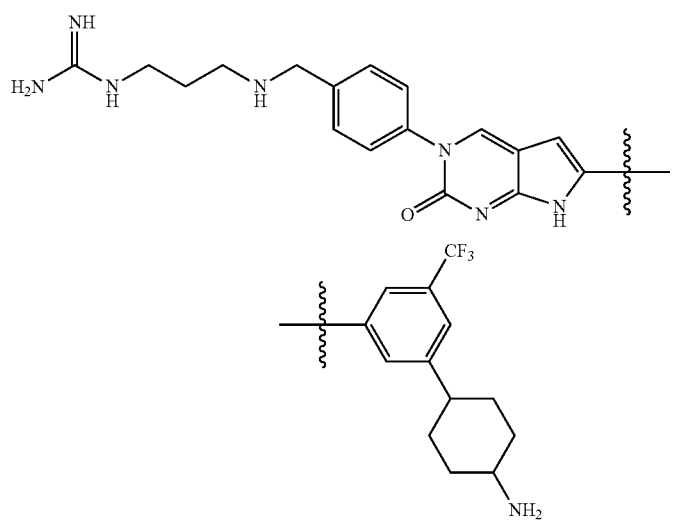 |

426 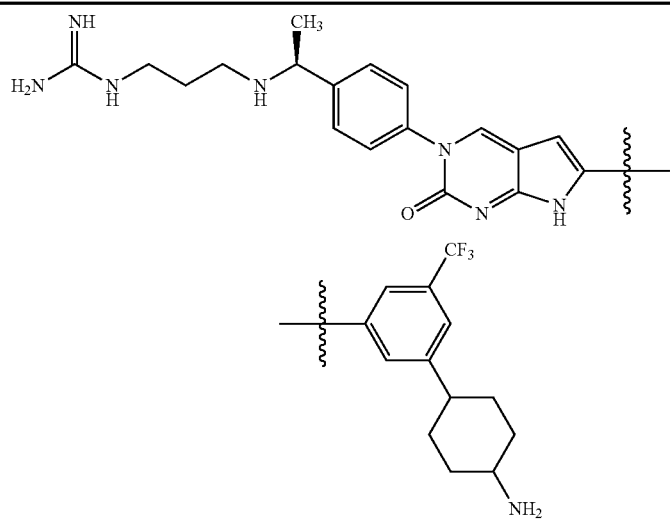
427 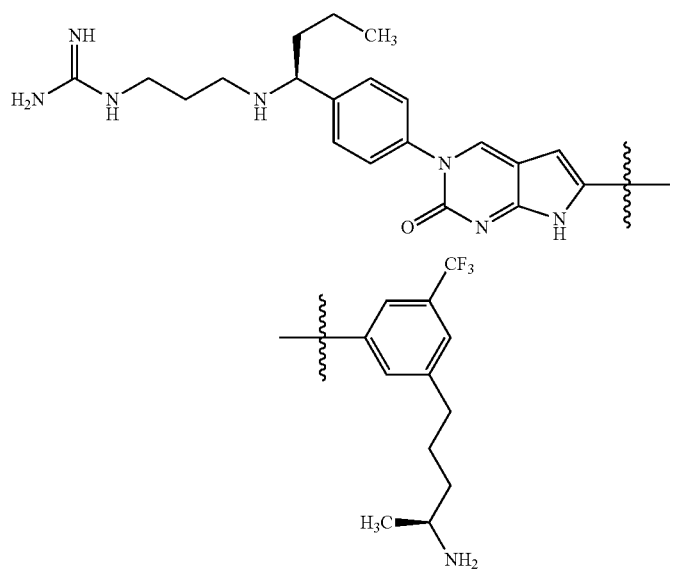
429 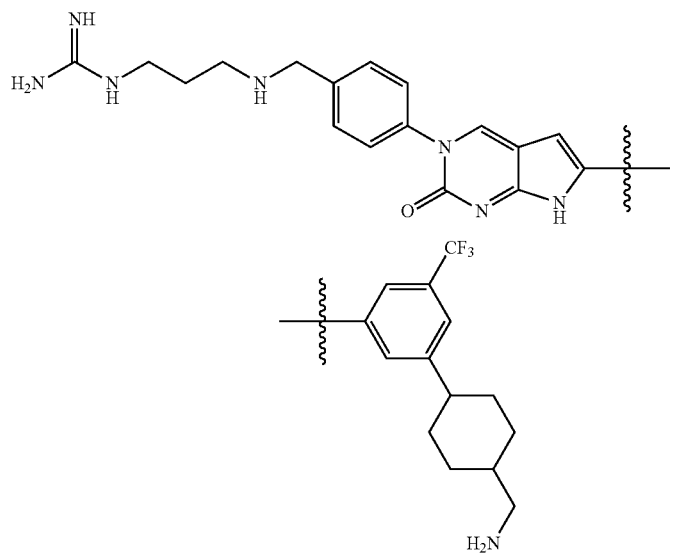

| | |
|---|---|
| 430 | 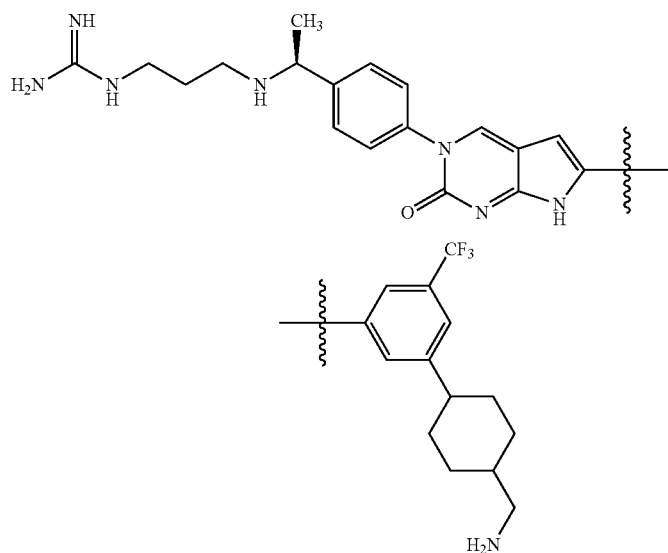 |
| 431 | 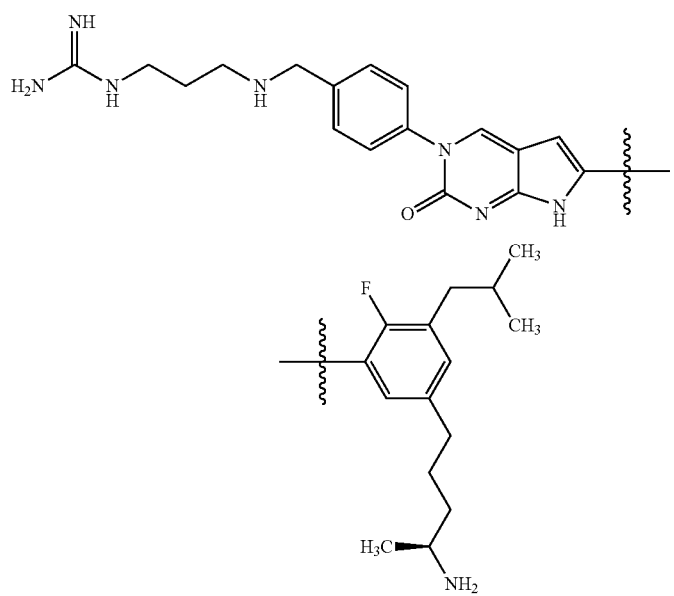 |

432 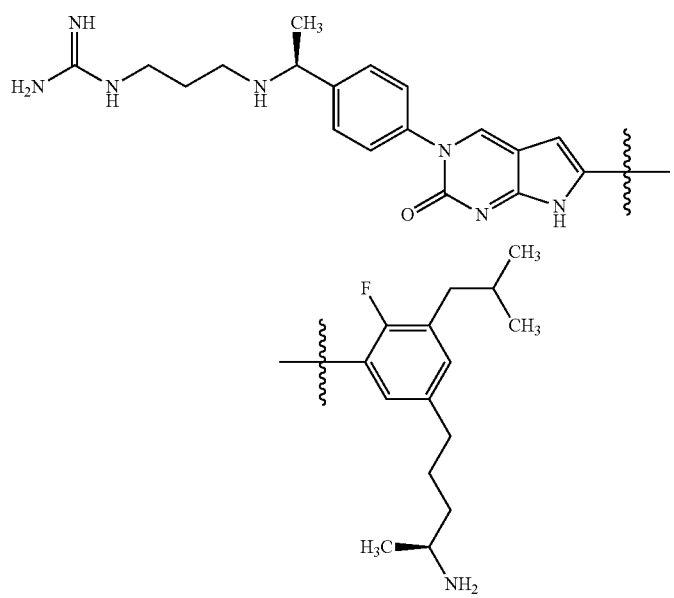
433 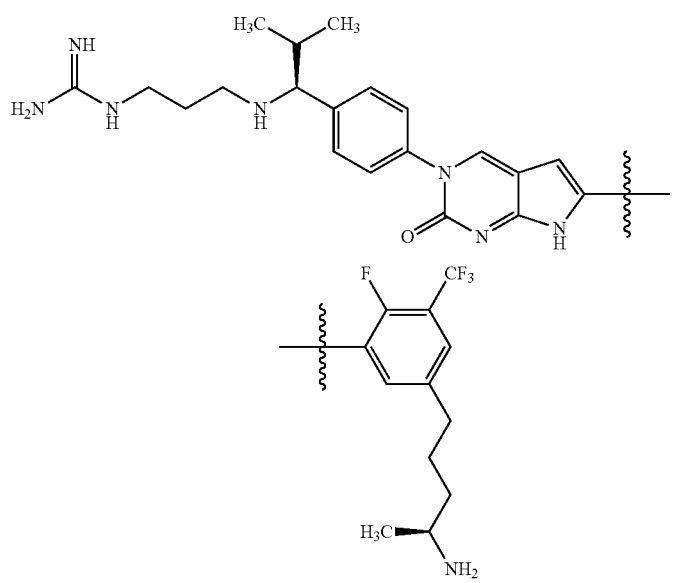

| 434 | 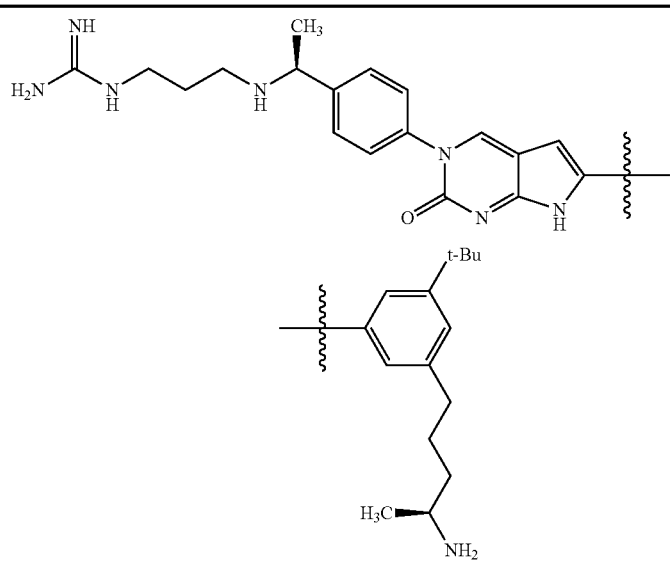 |
| 435 | 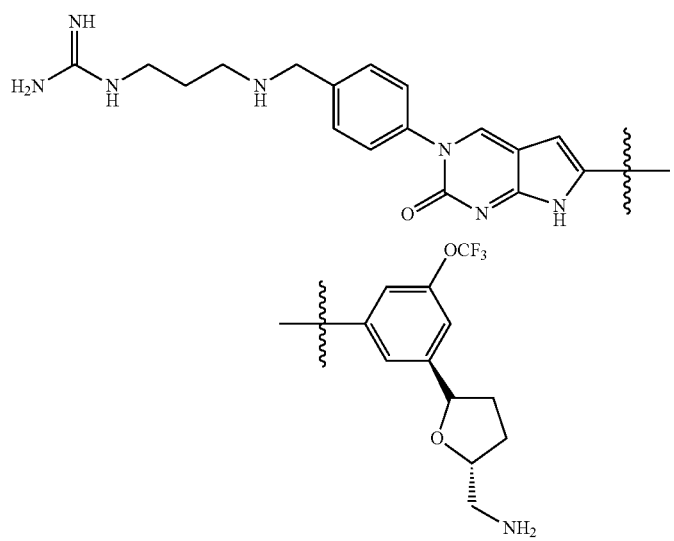 |
| 436 | 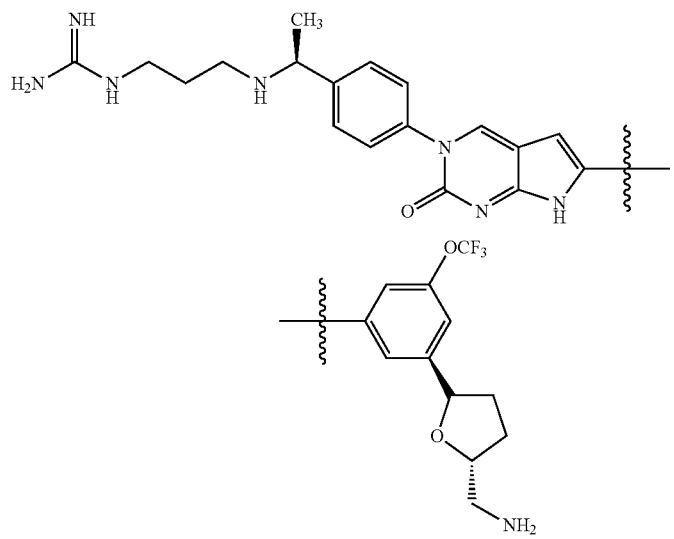 |

437 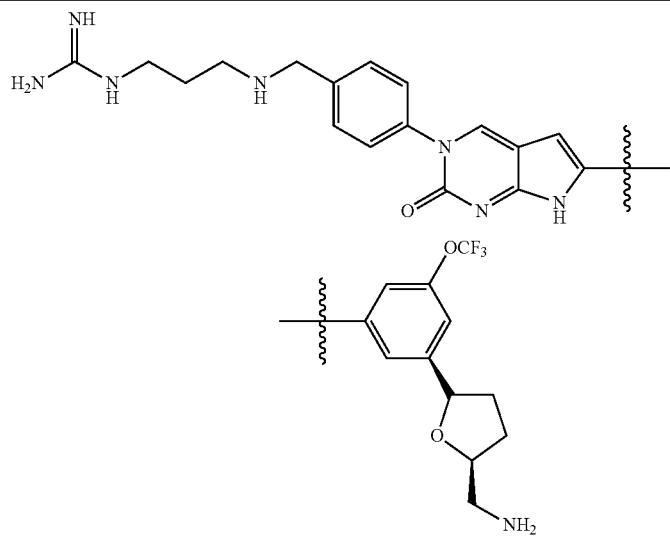
438 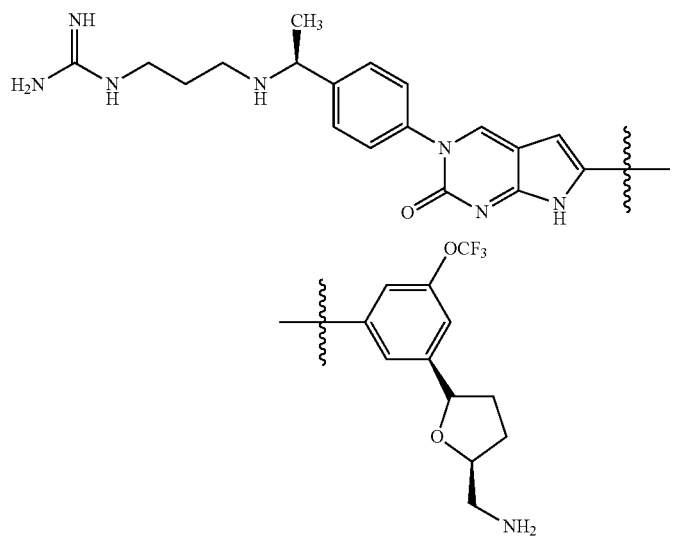
439 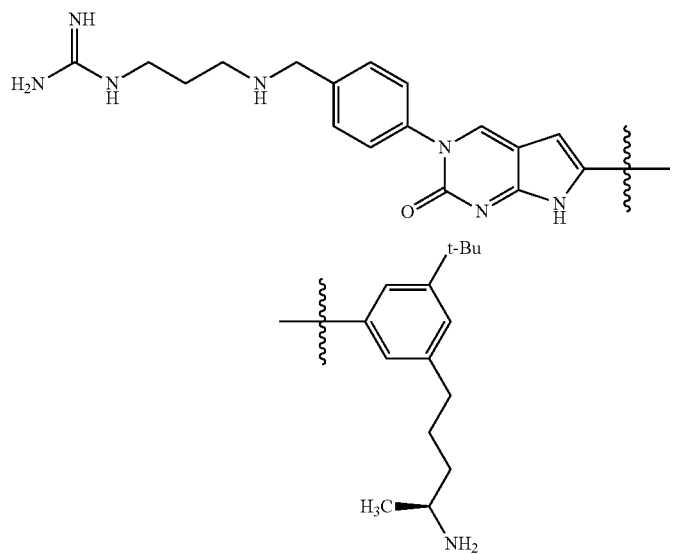

440 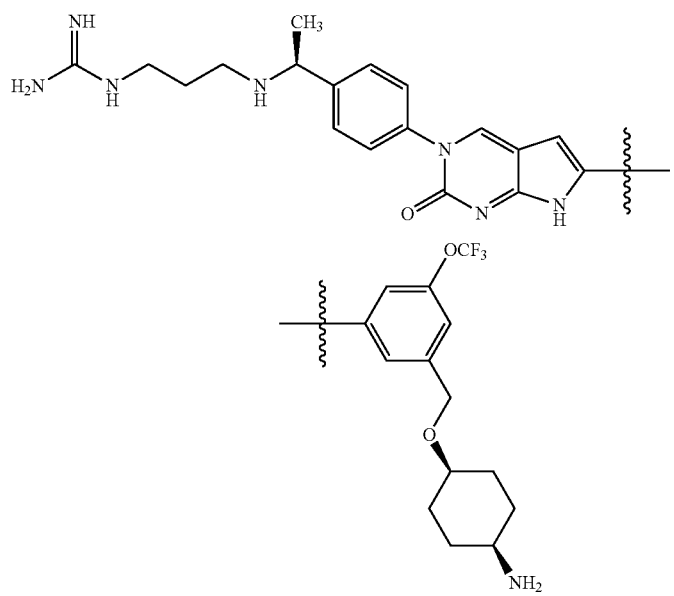
441 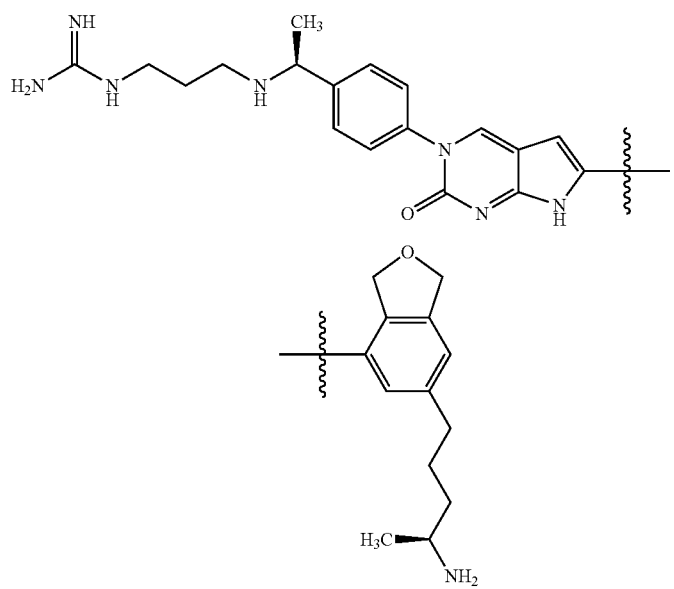

| | |
|---|---|
| 442 | 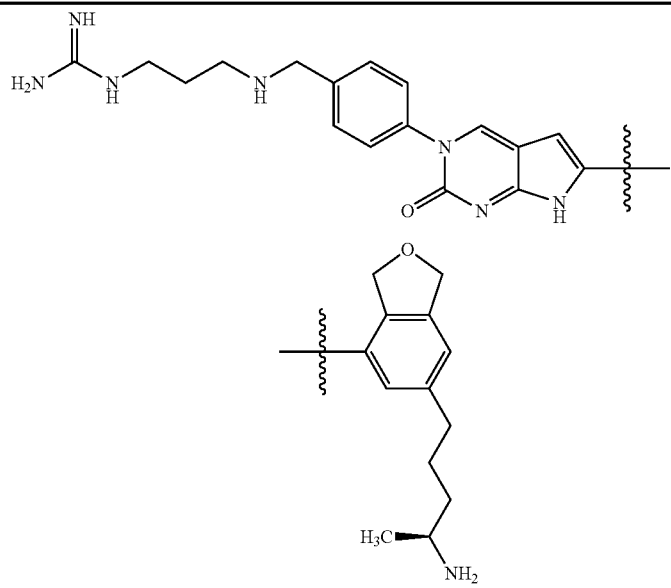 |
| 443 | 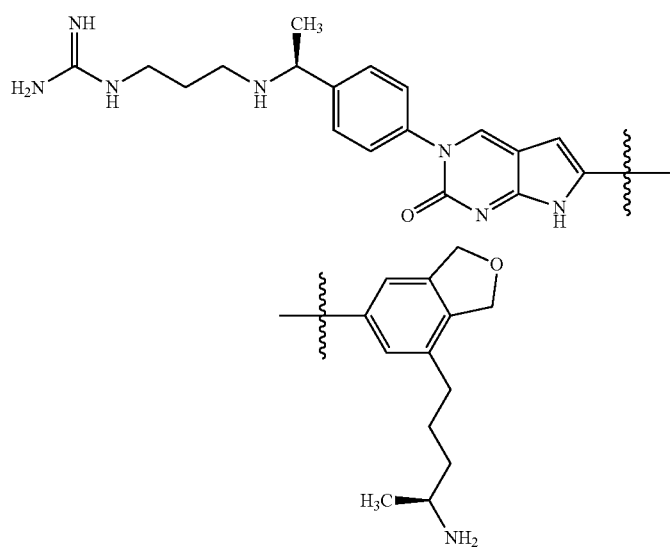 |
| 444 | 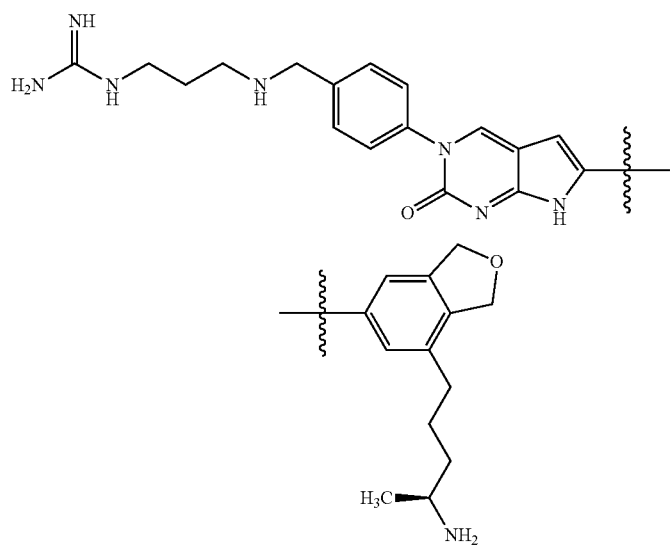 |

445
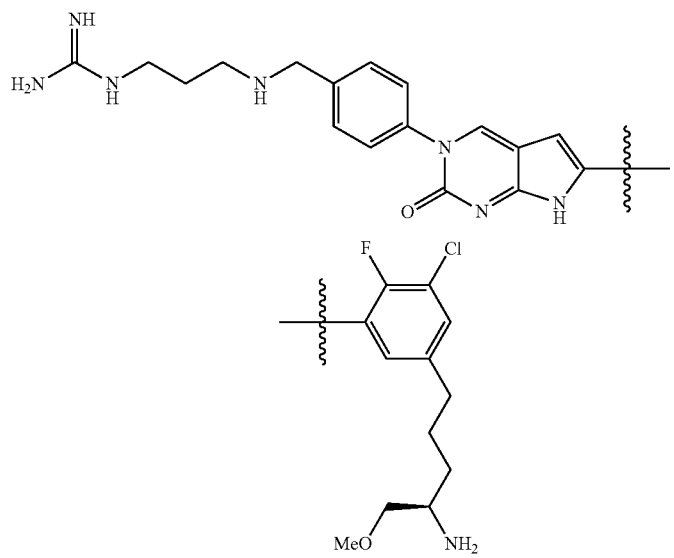
446
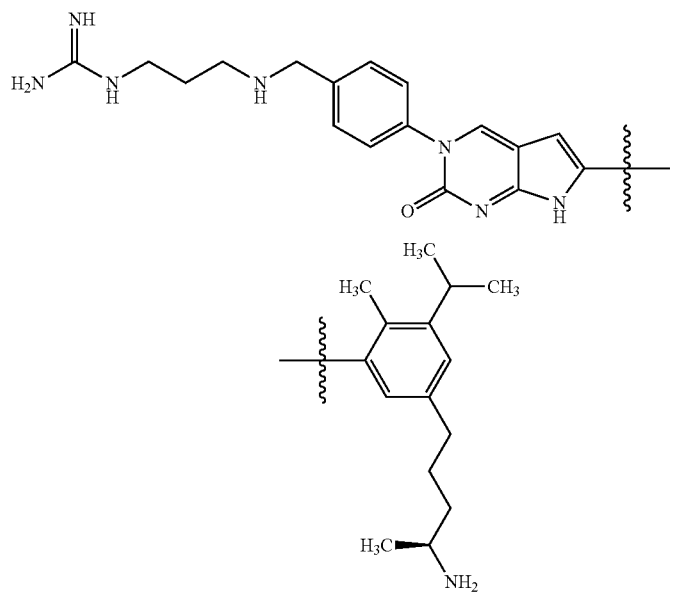

| | |
|---|---|
| 447 | 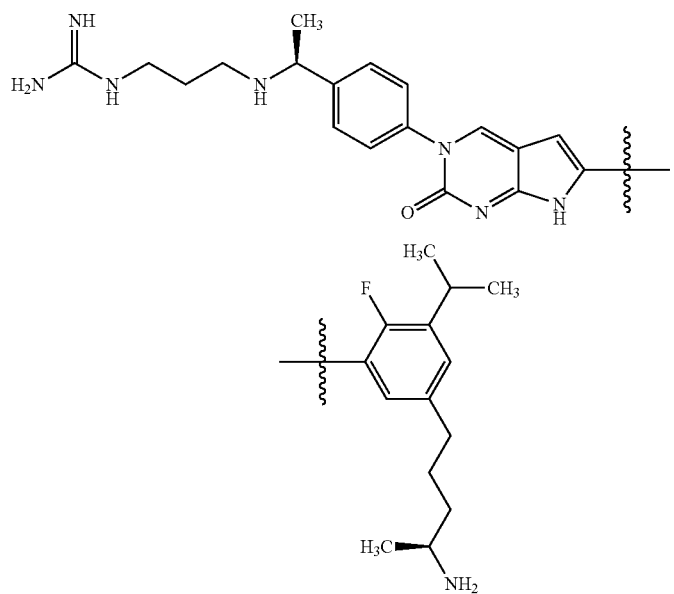 |
| 448 | 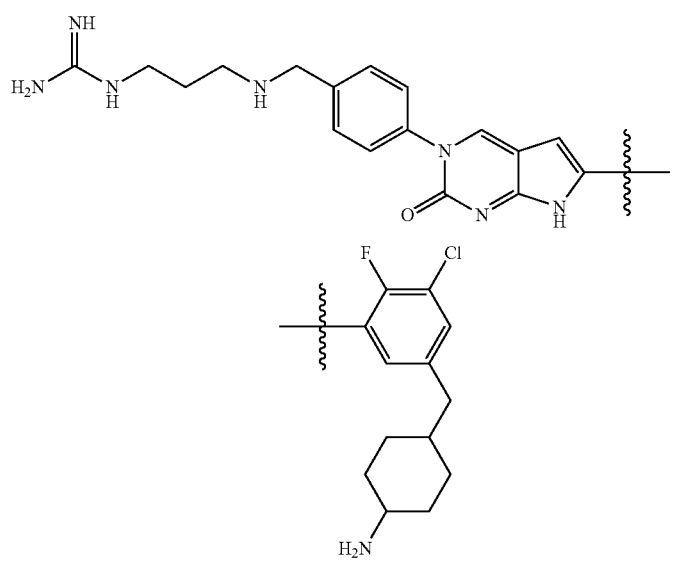 |

449 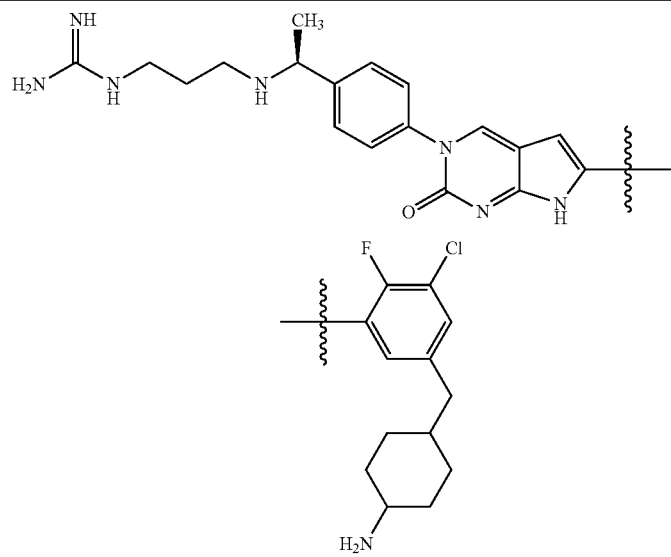
450 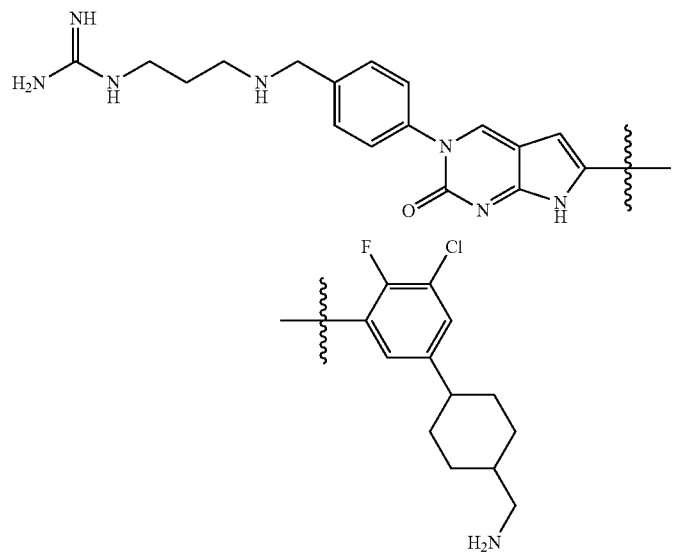
451 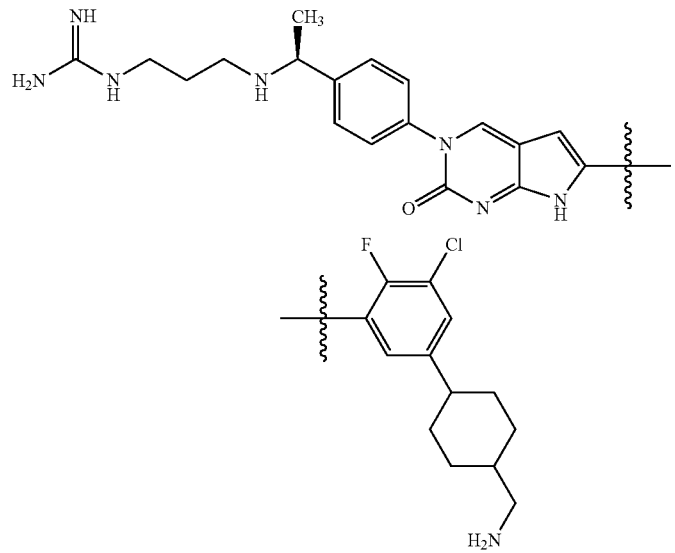

452
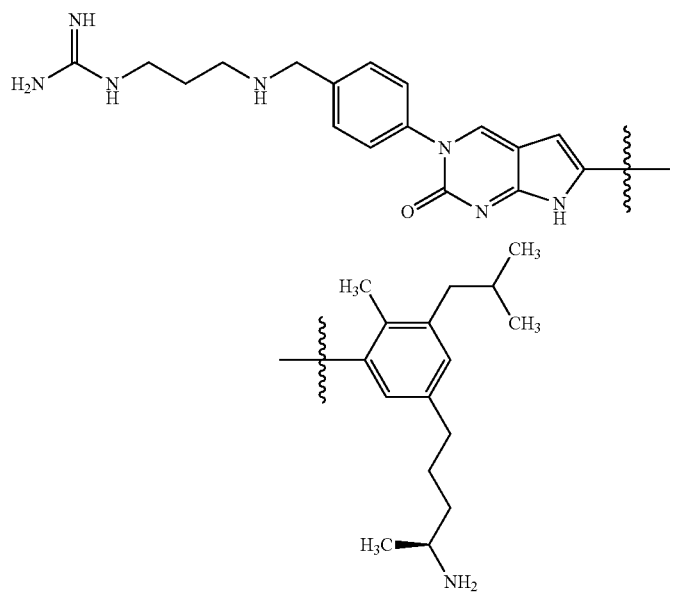
453
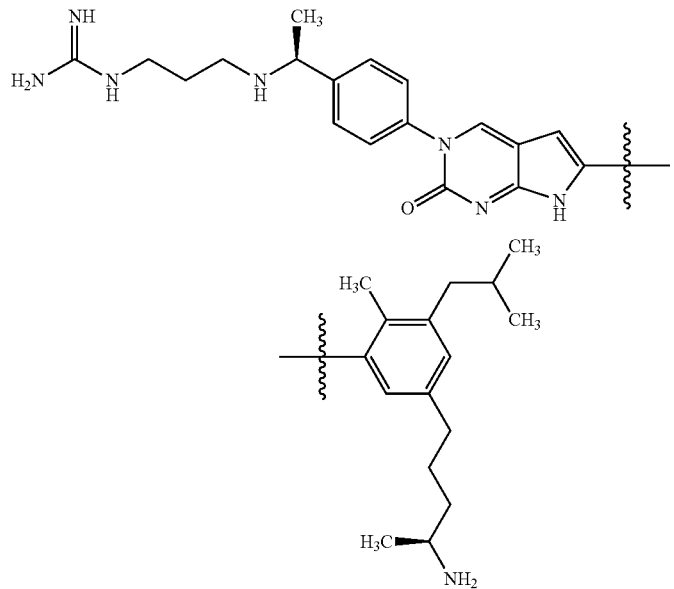

454
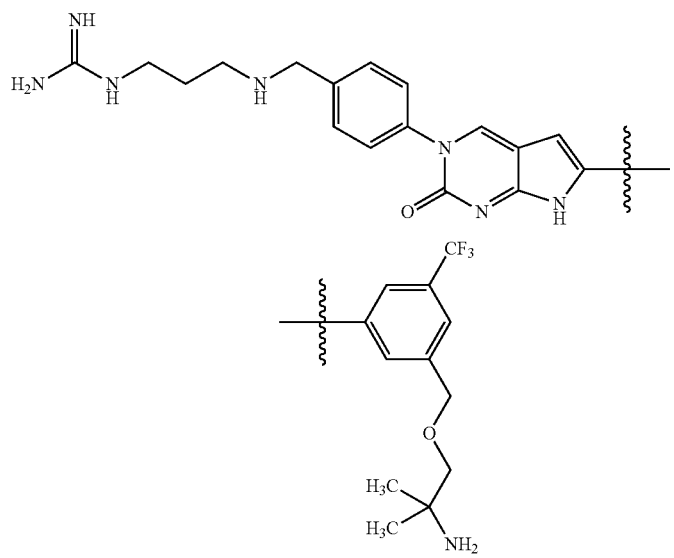
455
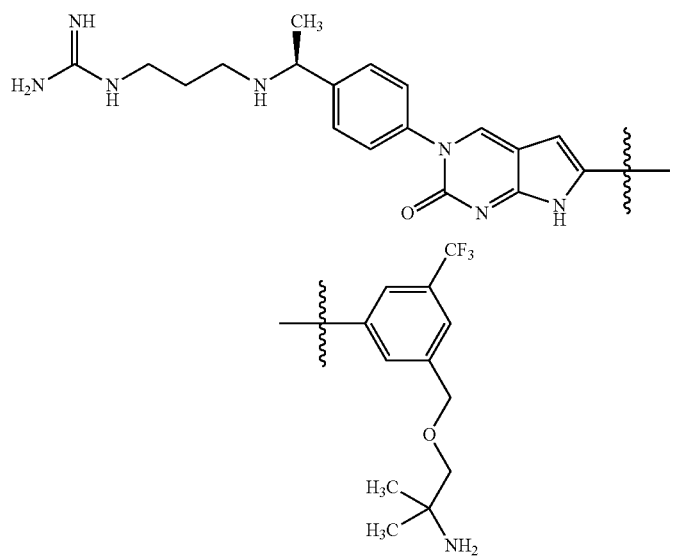

456 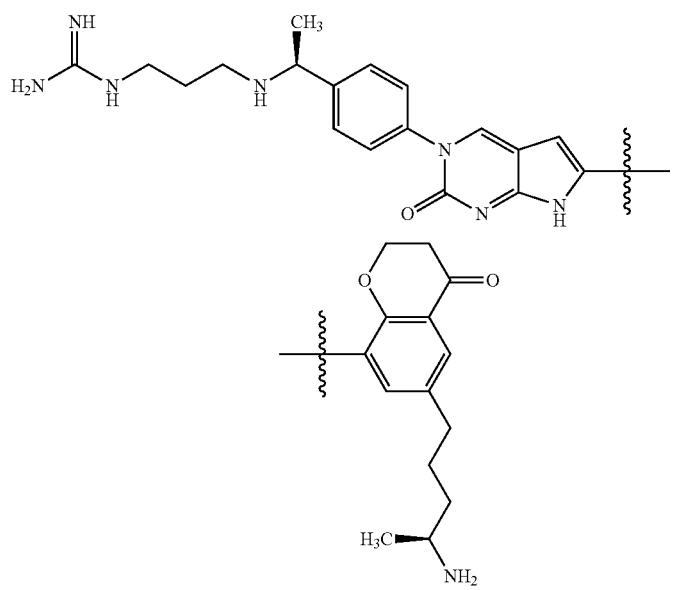
457 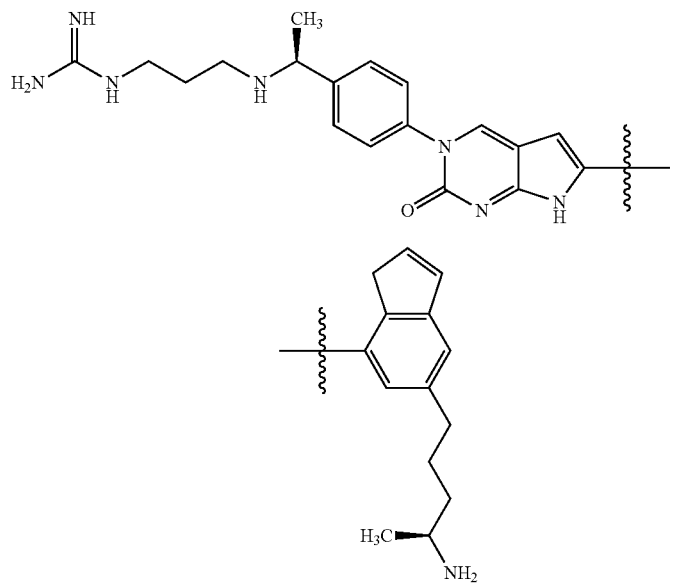

-continued
458 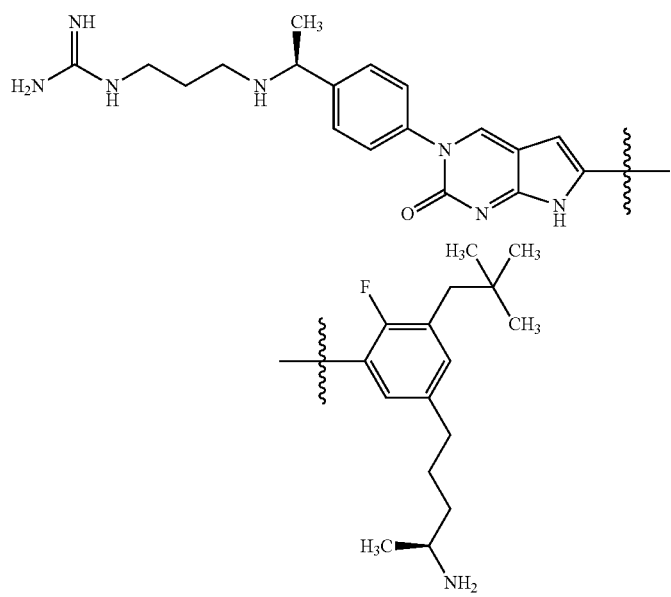
459 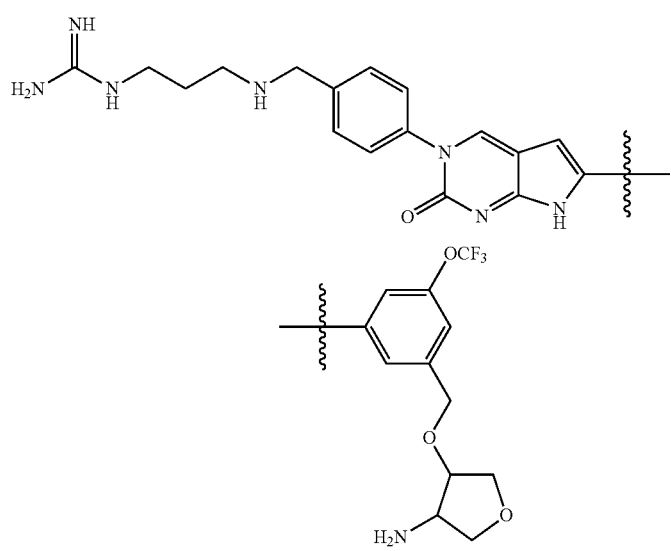

460 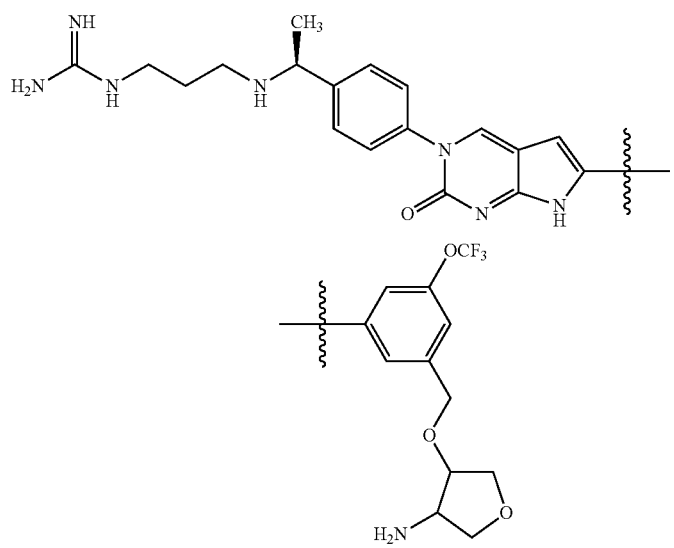
461 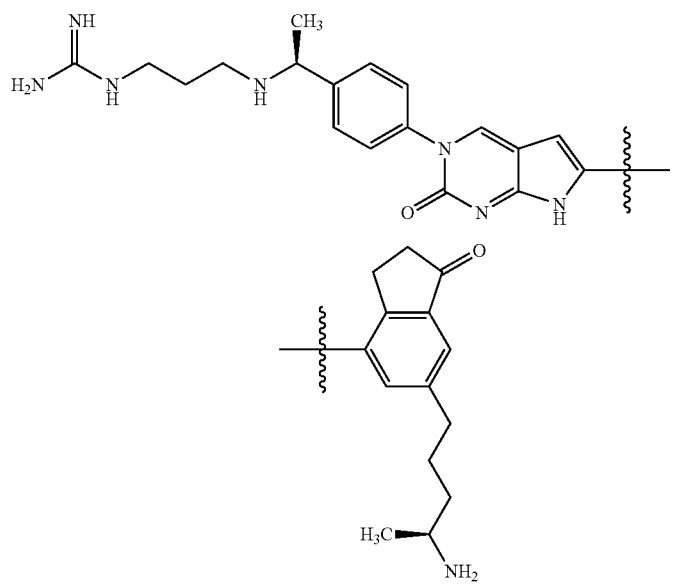

-continued
| | |
|---|---|
| 462 | 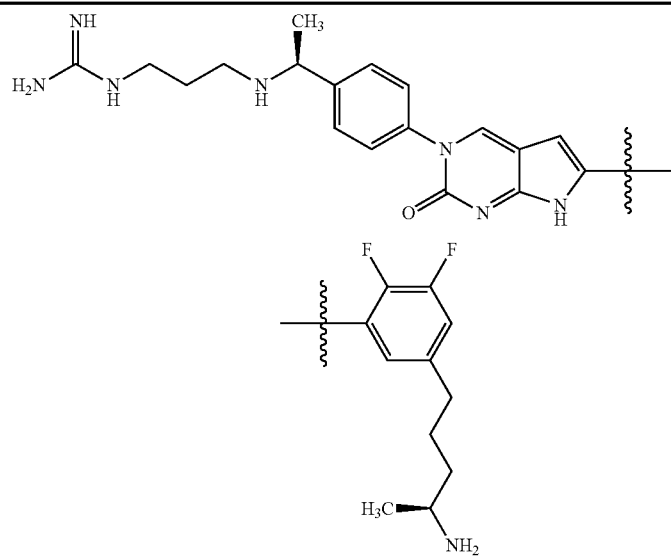 |
| 463 | 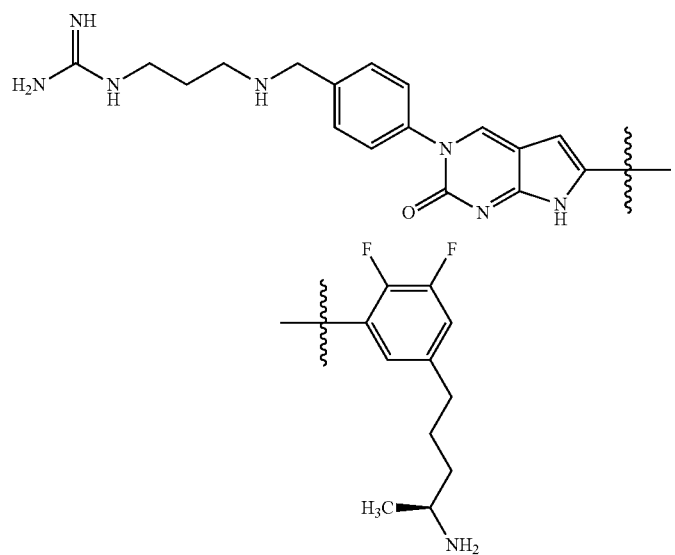 |
| 464 | 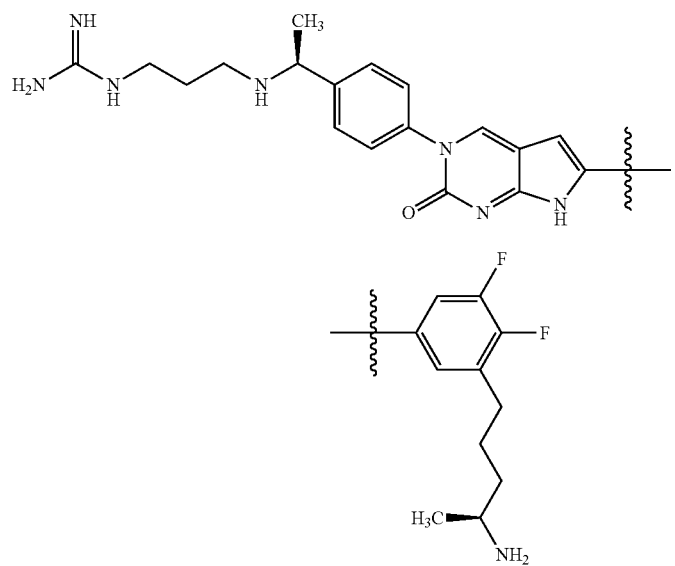 |

465 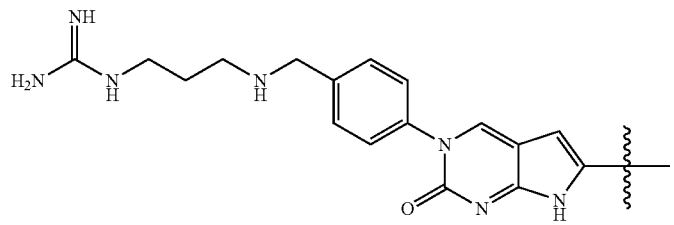
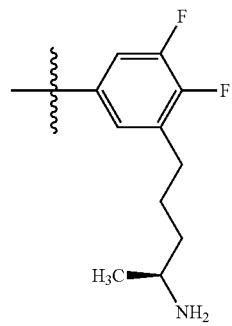
466 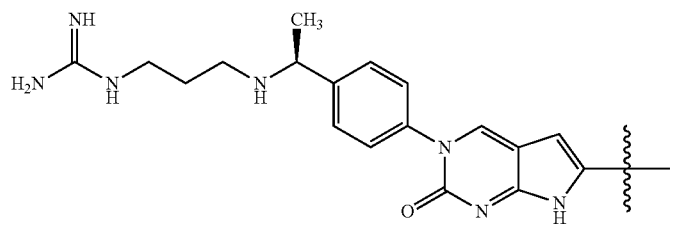
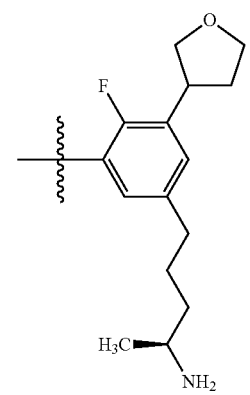

467 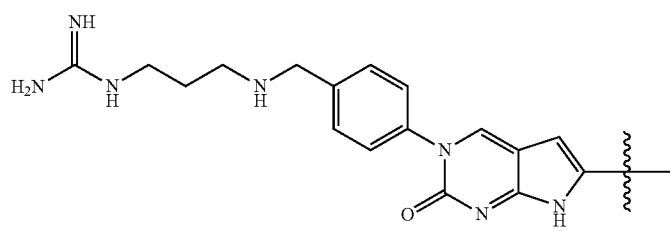
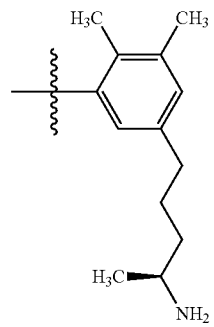
468 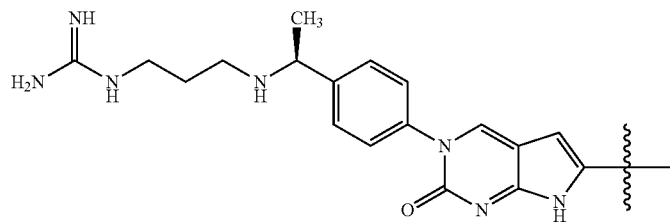
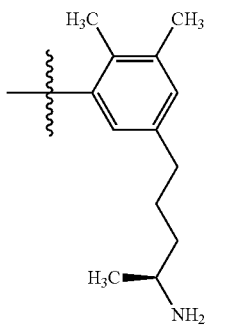

| | |
|---|---|
| 469 | 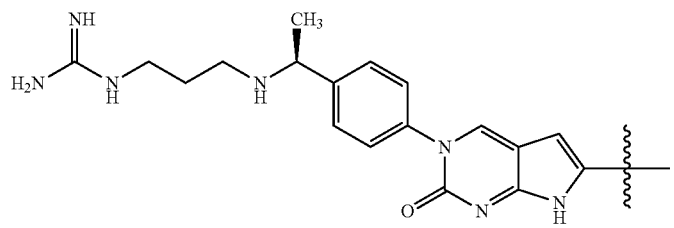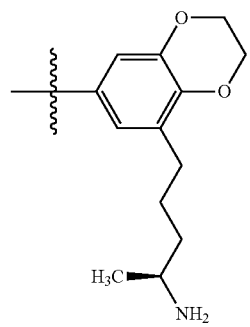 |
| 470 | 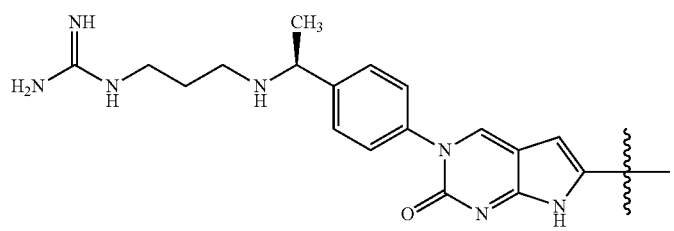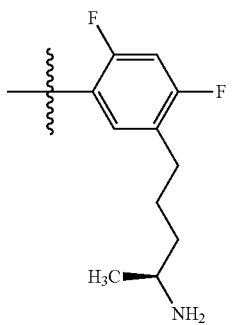 |

471 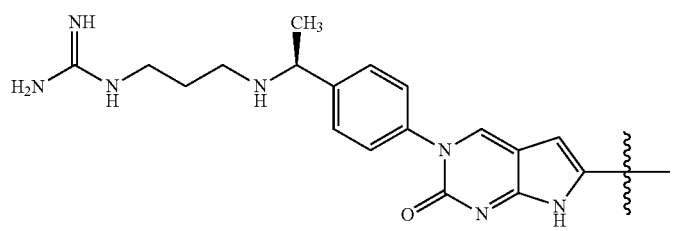
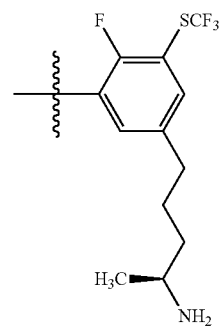
472 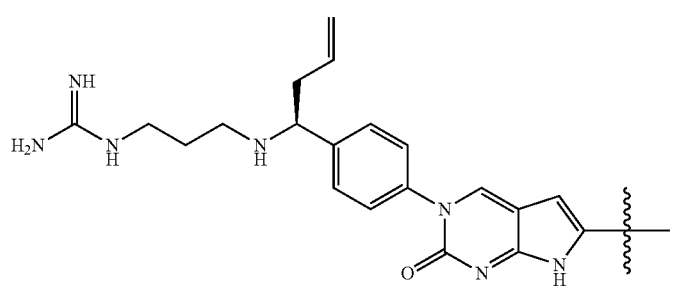
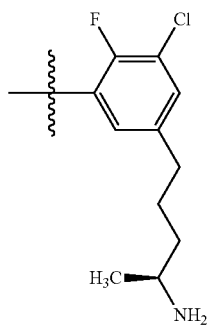

473 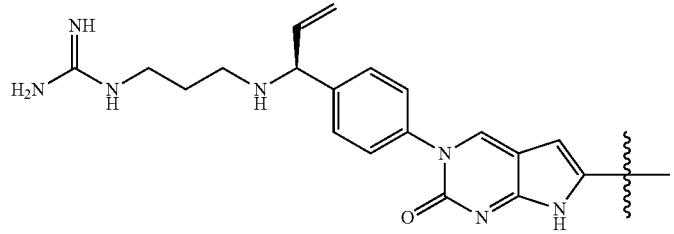
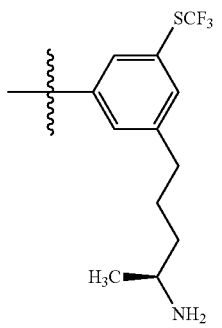
474 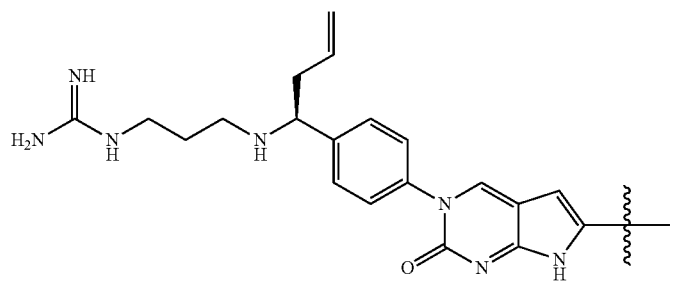
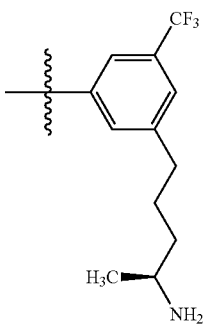

| | |
|---|---|
| 475 | 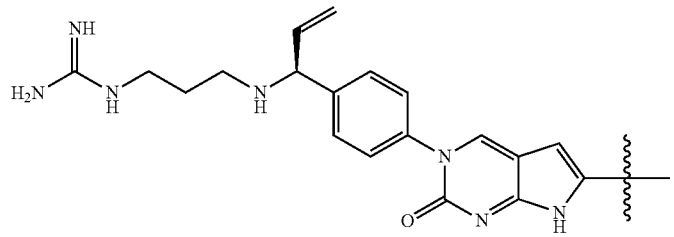 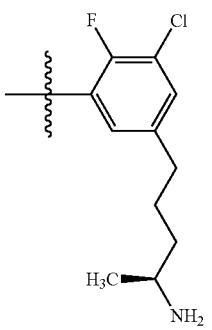 |
| 476 | 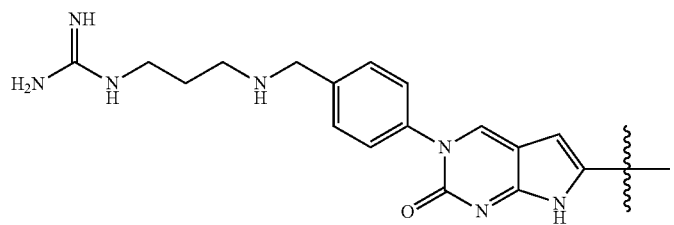 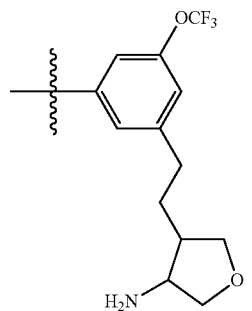 |

| | |
|---|---|
| 477 | 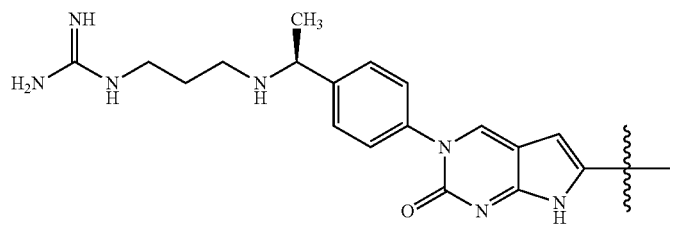<br>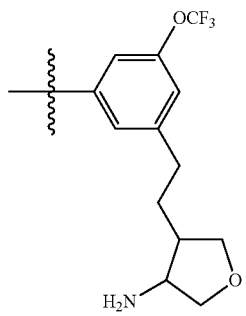 |
| 478 | 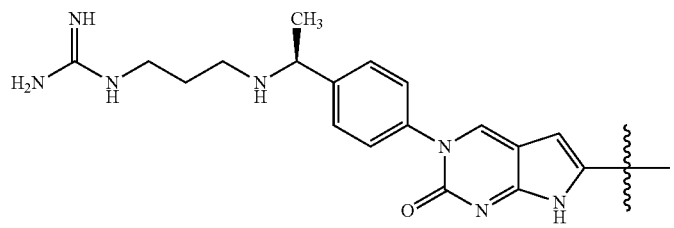<br>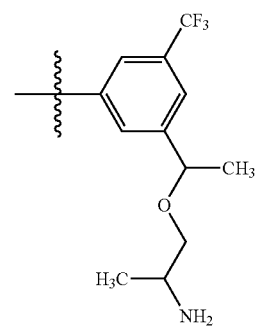 |

| 479 | 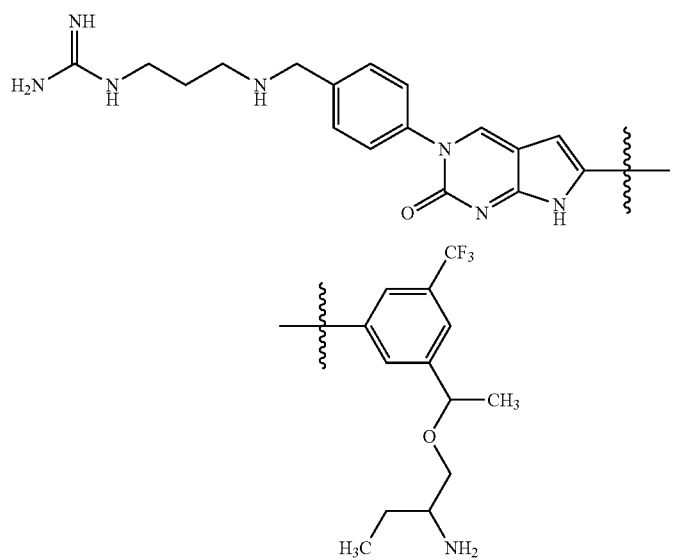 |
|---|---|
| 480 | 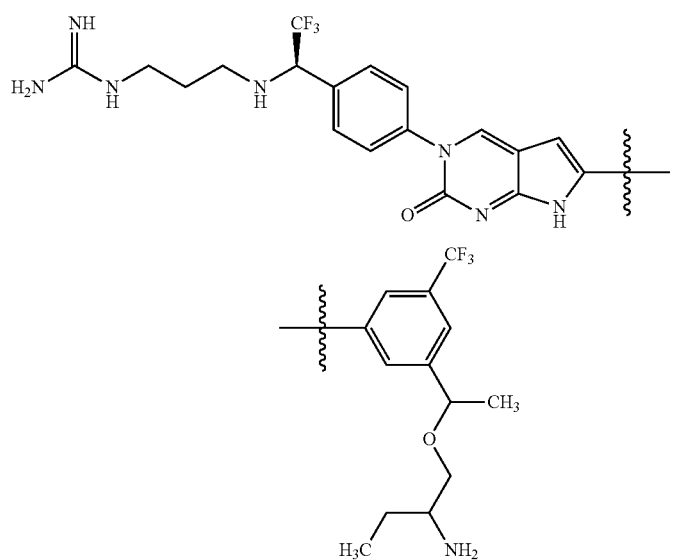 |

481
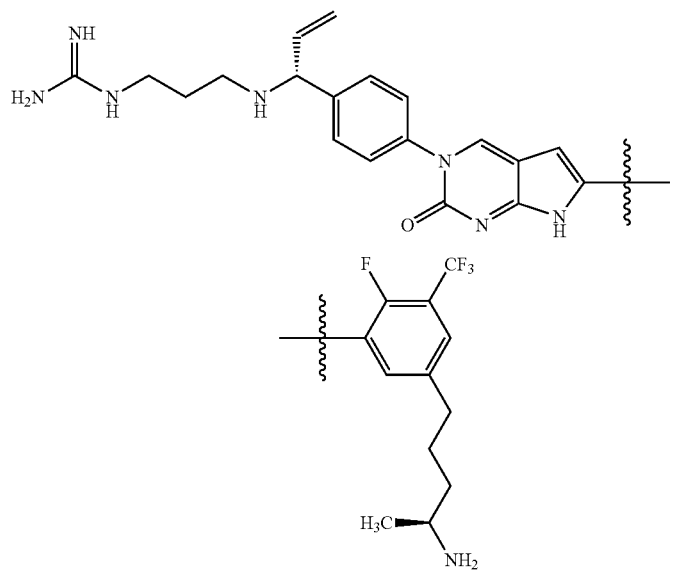
482
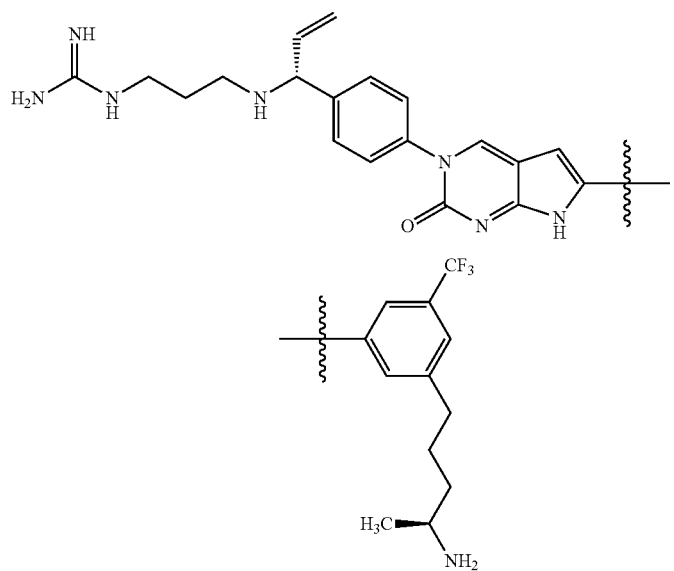

483 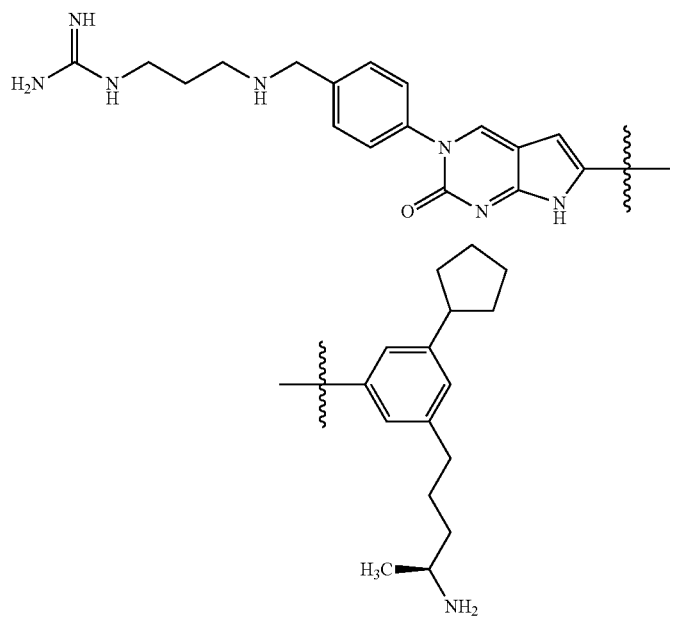
484 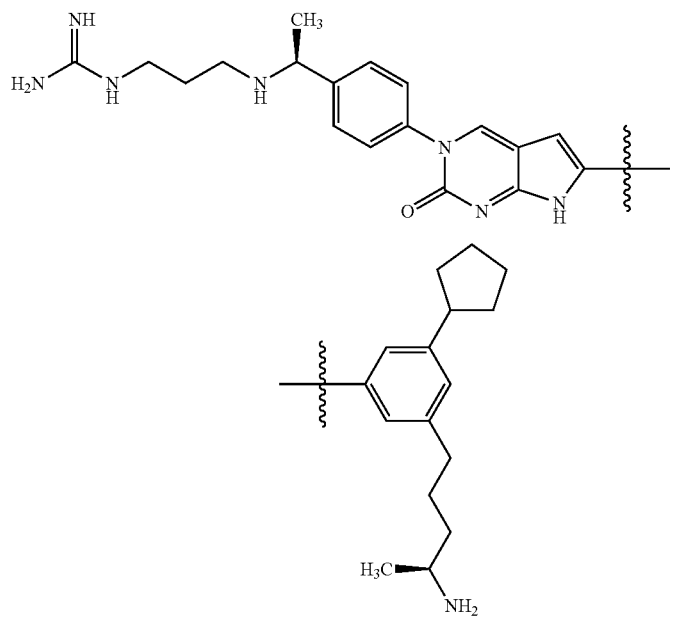

485 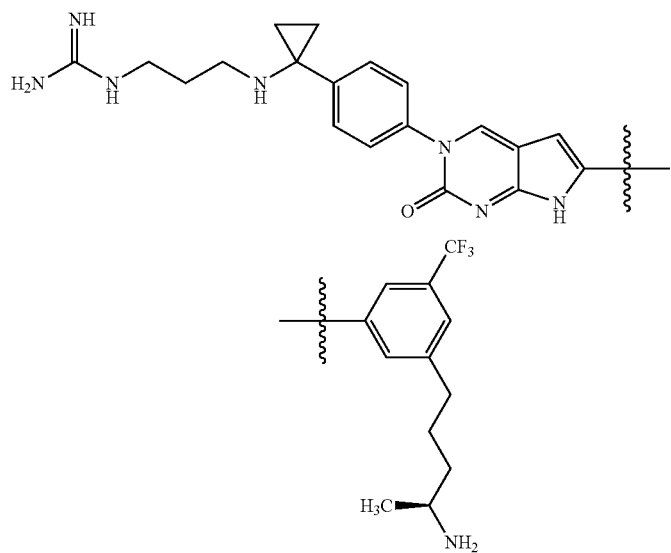
486 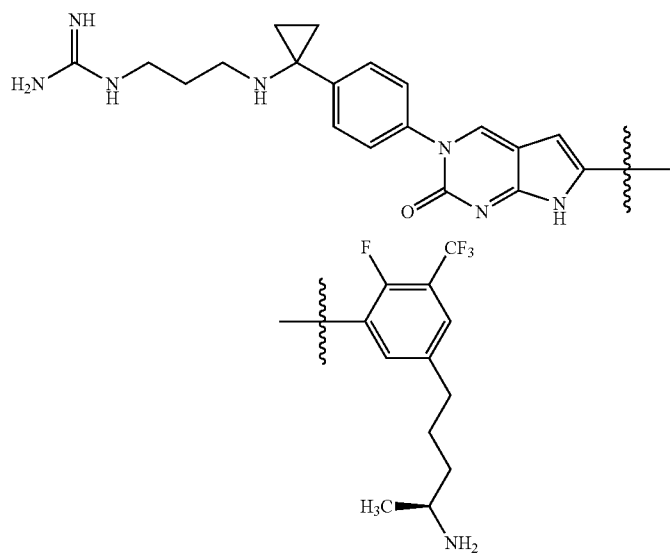

487 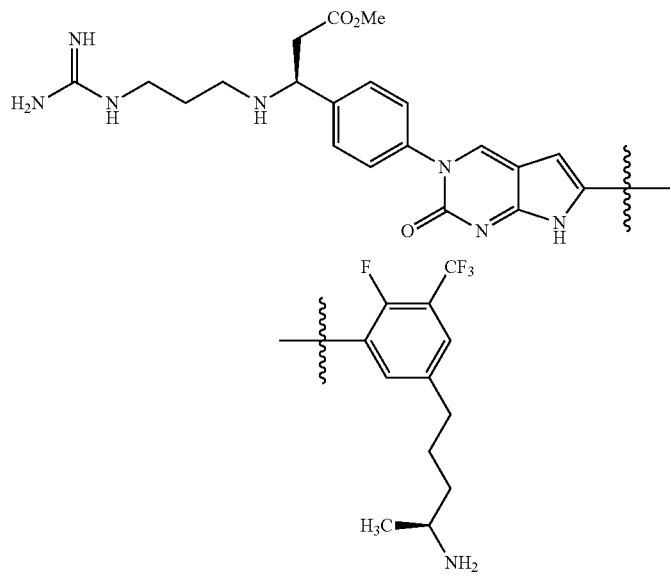
488 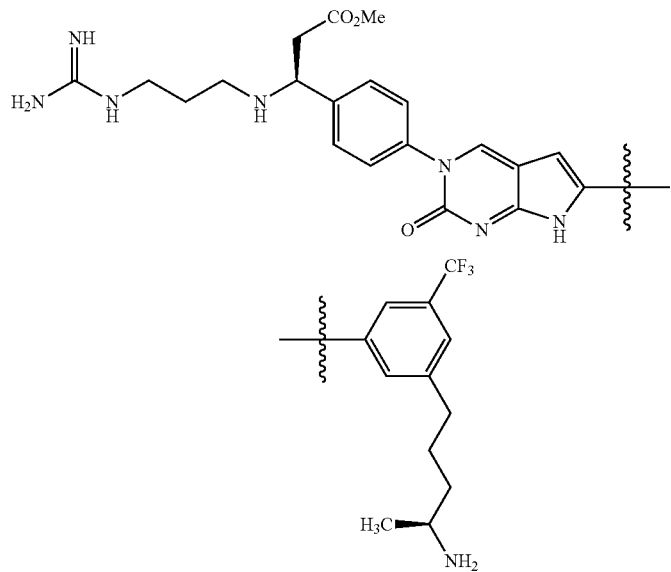

489 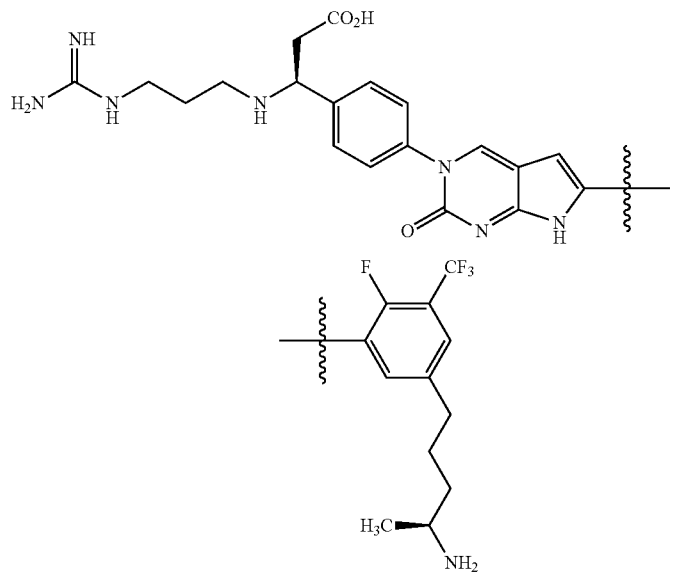
490 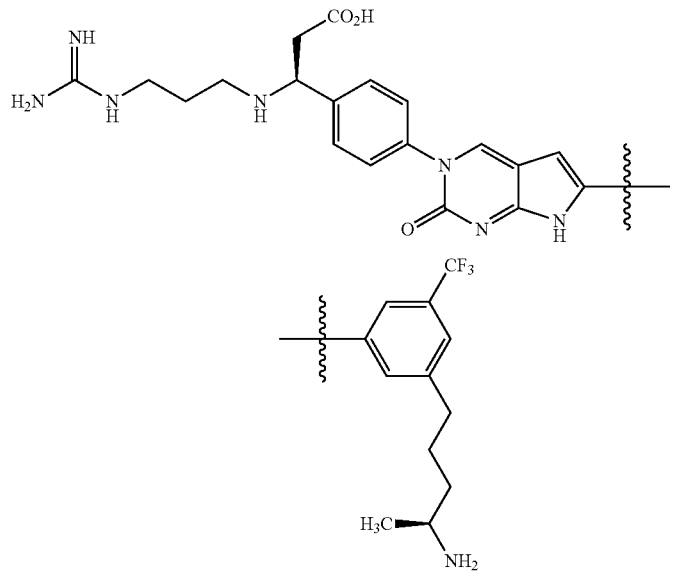

491 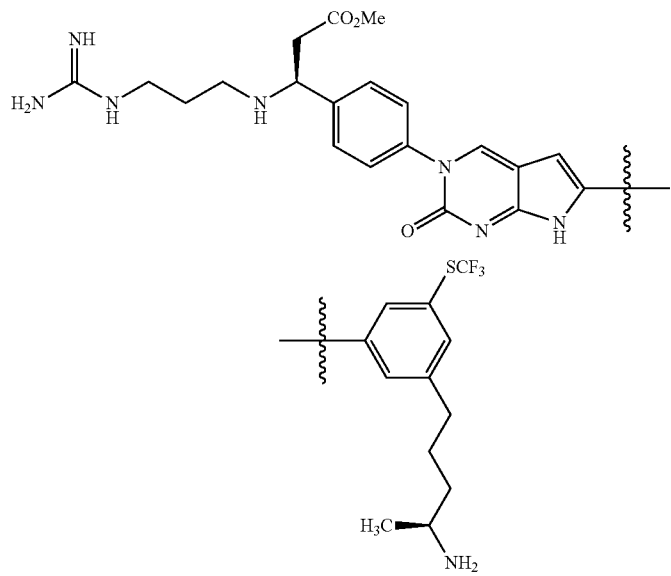
492 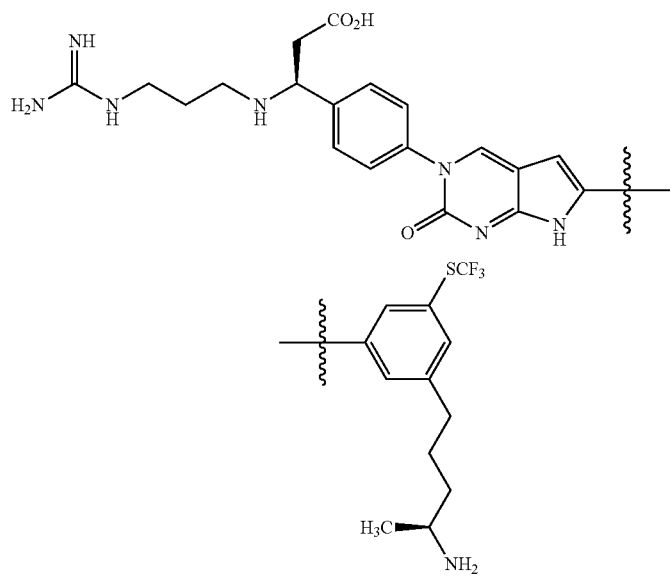

| | |
|---|---|
| 493 | 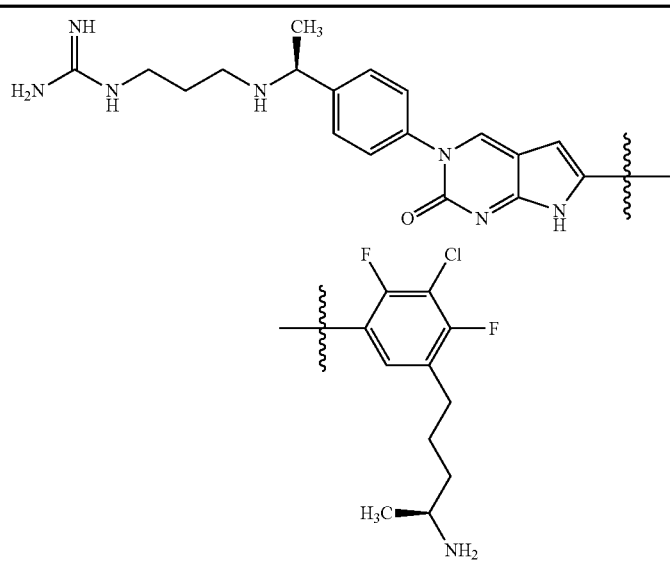 |
| 494 | 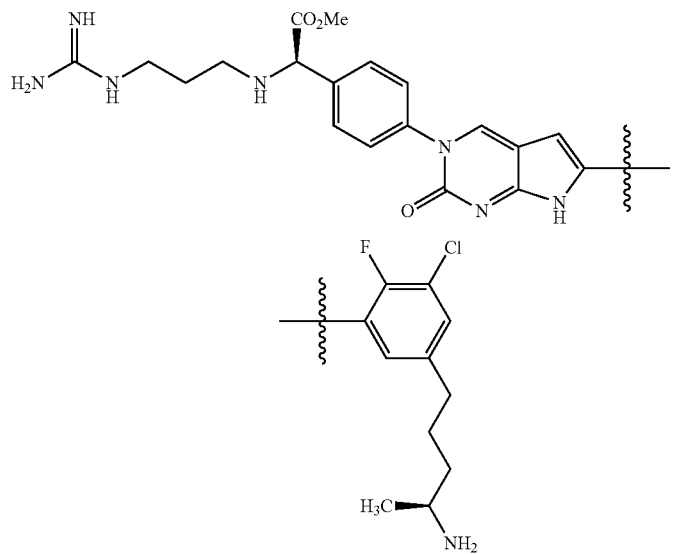 |
| 495 | 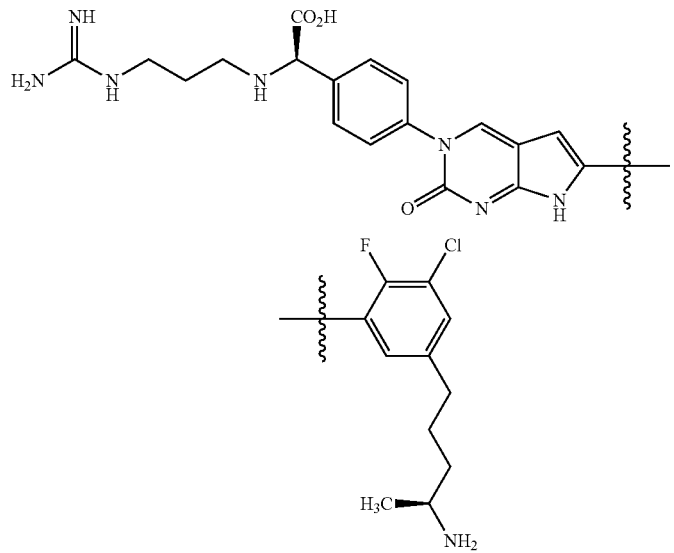 |

496 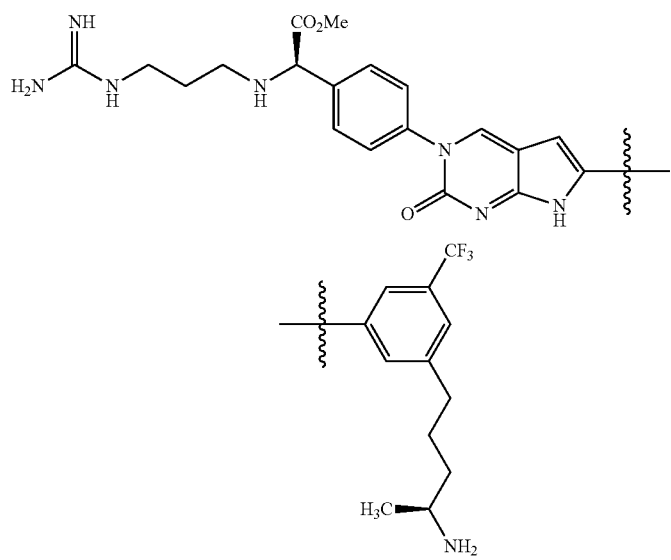
497 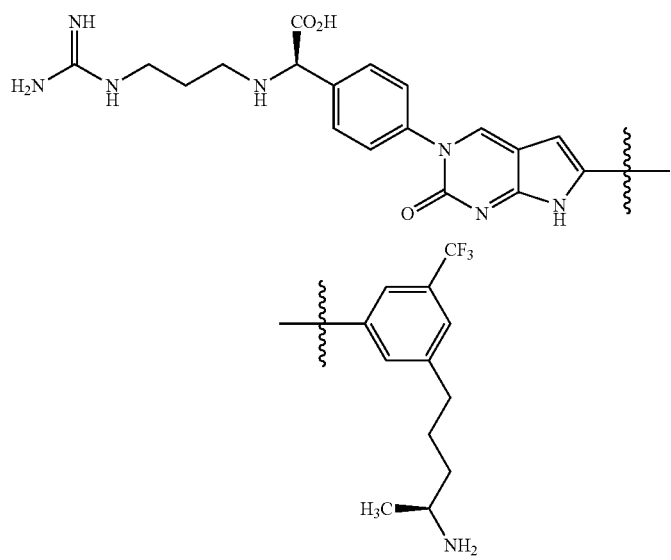

-continued
| | |
|---|---|
| 498 | 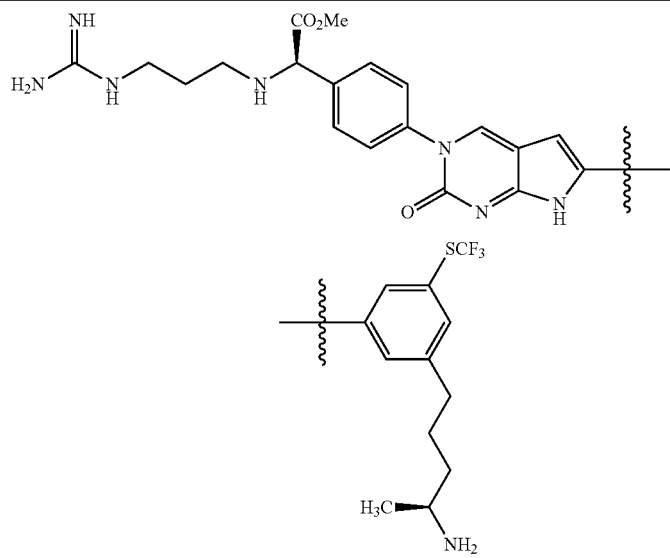 |
| 499 | 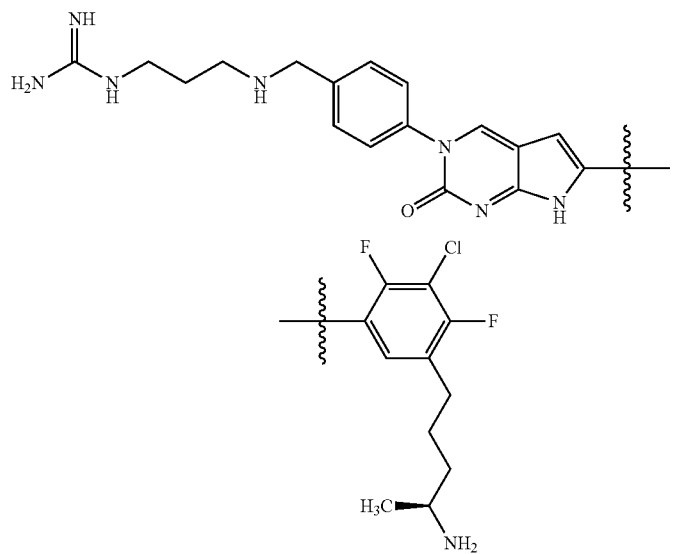 |
| 500 | 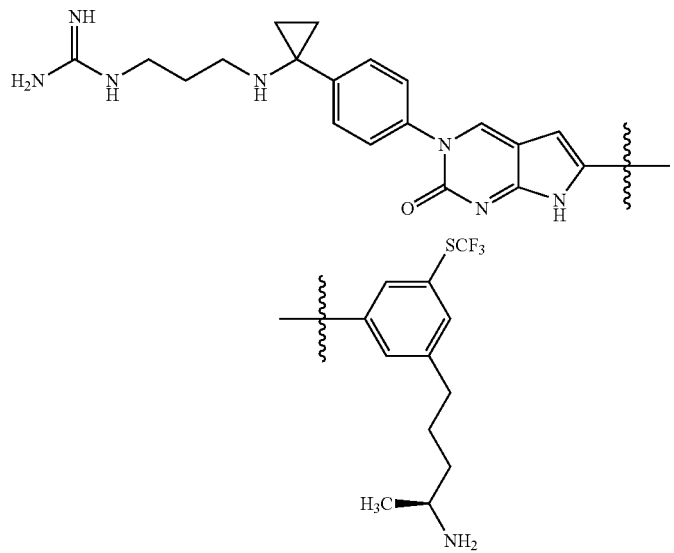 |

501 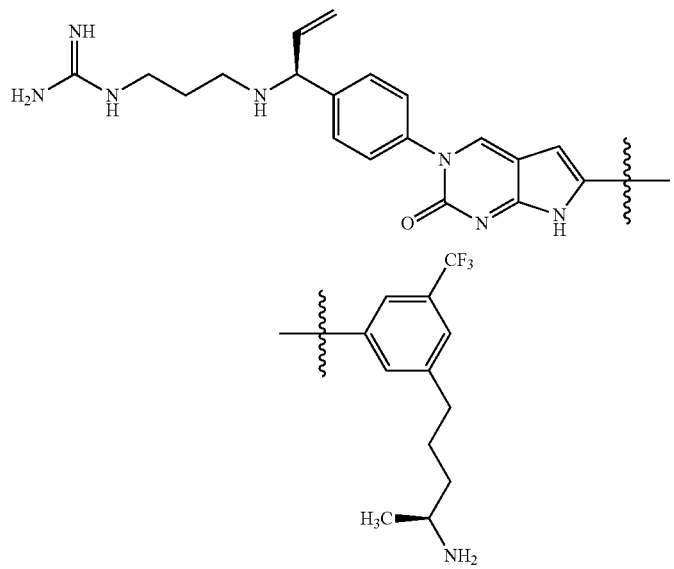
502 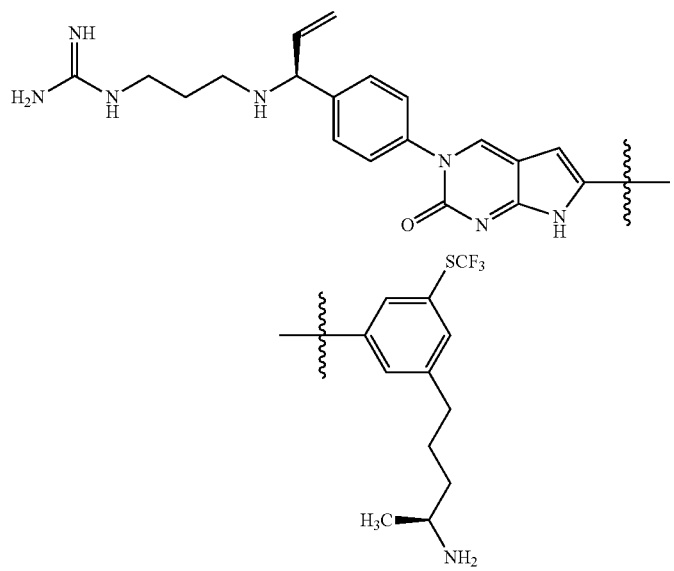

503
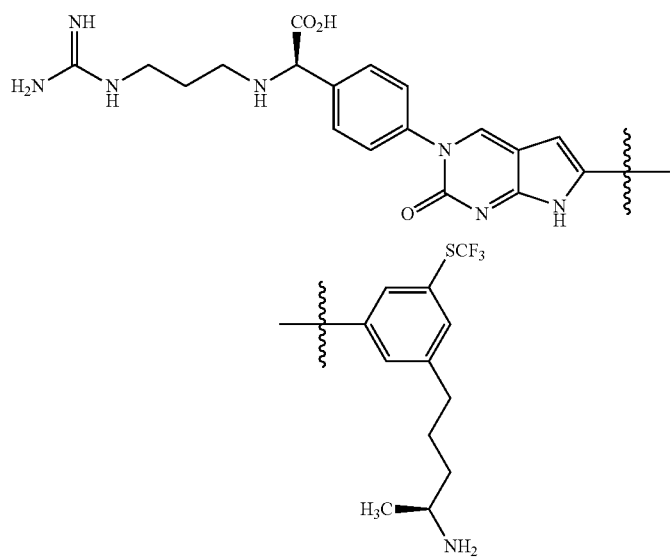
504
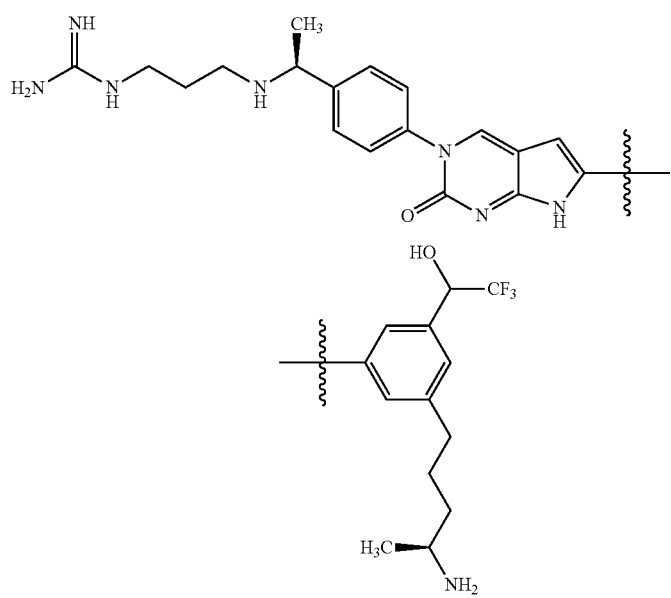

505 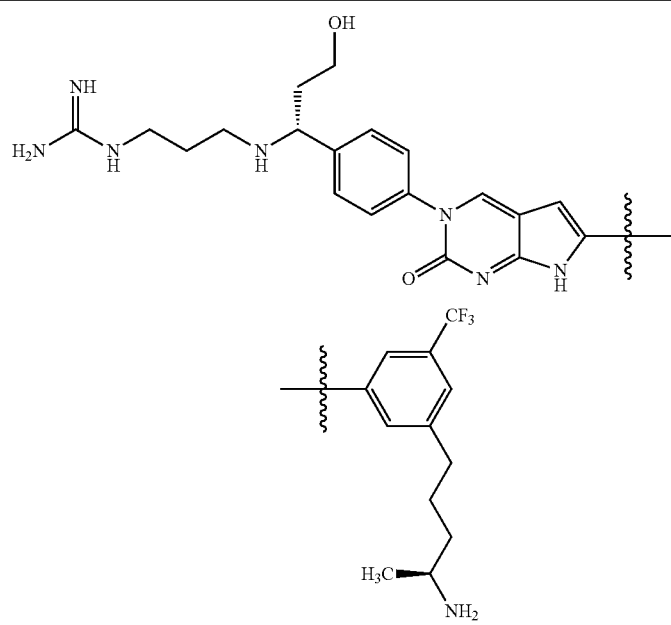
506 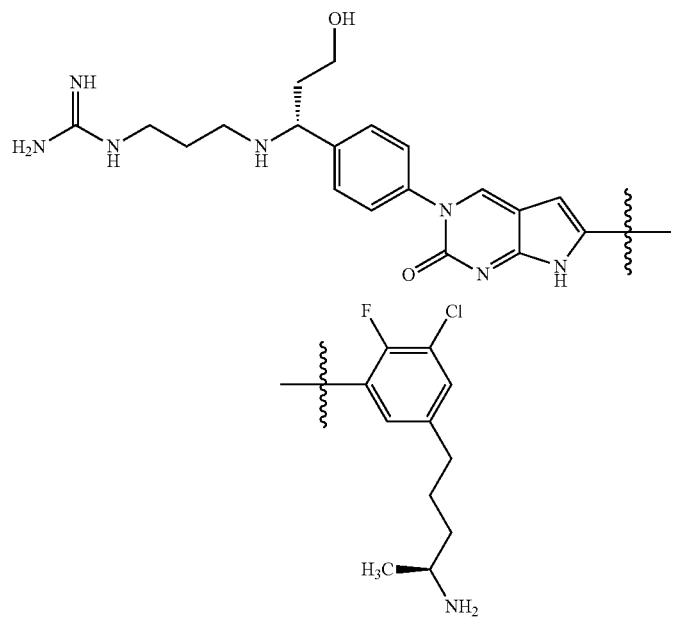

-continued
507
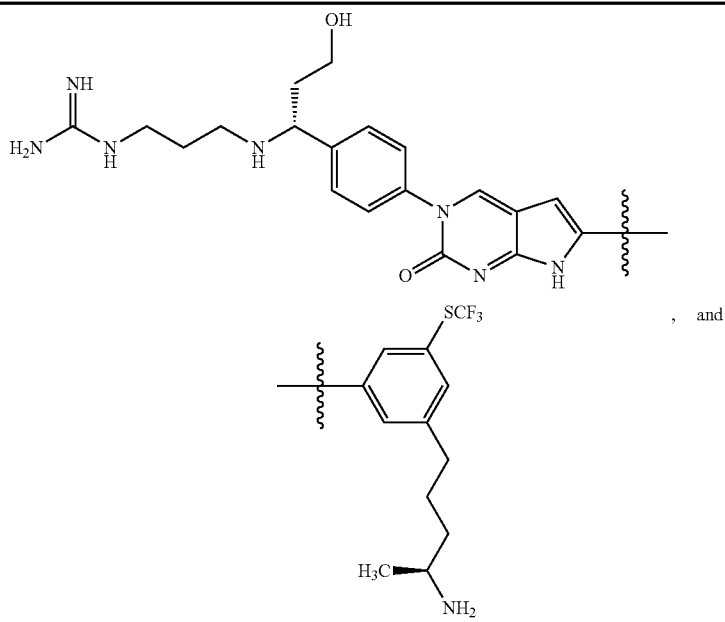
, and
508
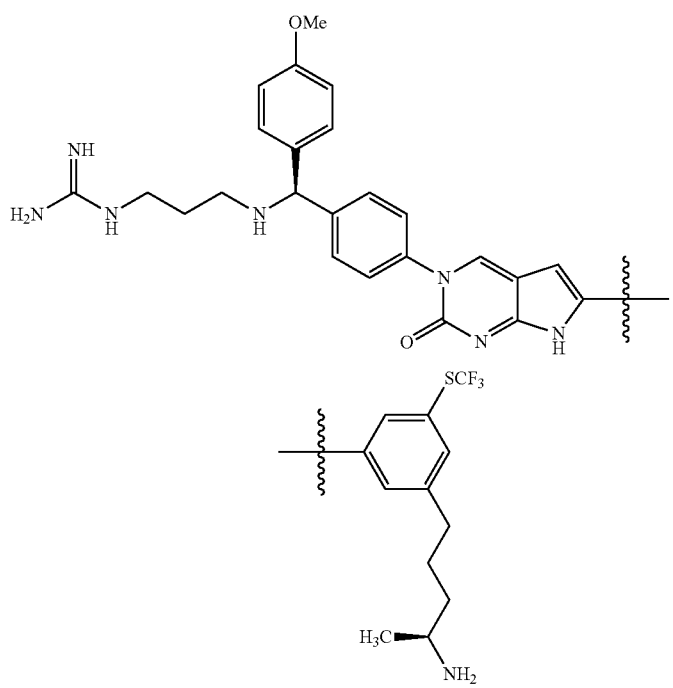
.
17. A pharmaceutical composition comprising a compound according to claim 1 or a tautomer thereof, or a pharmaceutically acceptable salt, ester, or prodrug of said compound or tautomer, and a pharmaceutically acceptable carrier.
* * * * *